US007386398B2

(12) United States Patent
Coulombe et al.

(10) Patent No.: US 7,386,398 B2
(45) Date of Patent: Jun. 10, 2008

(54) HEPATITIS C VIRUS NS5B POLYMERASE INHIBITOR BINDING POCKET

(75) Inventors: René Coulombe, Montréal (CA); Pierre Beaulieu, Laval (CA); Eric Jolicoeur, Laval (CA); George Kukolj, Mont-Royal (CA); Steven Laplante, Bois-des-Filion (CA); Marc-André Poupart, Laval (CA)

(73) Assignee: Boehringer Ingelheim International GmbH, Ingelheim (DE)

( * ) Notice: Subject to any disclaimer, the term of this patent is extended or adjusted under 35 U.S.C. 154(b) by 157 days.

(21) Appl. No.: 10/842,046

(22) Filed: May 7, 2004

(65) Prior Publication Data

US 2005/0003348 A1 Jan. 6, 2005

Related U.S. Application Data

(60) Provisional application No. 60/469,604, filed on May 9, 2003.

(51) Int. Cl.
*G01N 33/48* (2006.01)
*G01N 33/53* (2006.01)
*G06F 19/00* (2006.01)
*G06G 7/58* (2006.01)
*A61K 38/43* (2006.01)

(52) U.S. Cl. .................... 702/19; 702/27; 703/11; 435/4; 435/7.1; 424/94.1

(58) Field of Classification Search ............ 435/4, 435/5, 6, 7.1, 7.6, 7.8, 183; 436/86, 173; 514/1, 2, 183; 702/27; 424/184.1, 228.1; 530/300, 350
See application file for complete search history.

(56) References Cited

U.S. PATENT DOCUMENTS 6,434,489 B1 * 8/2002 Lesburg et al. .............. 702/19
2003/0236251 A1 12/2003 Beaulieu et al.

FOREIGN PATENT DOCUMENTS

EP 1 256 628 A2 11/2002
WO WO 03/007945 A1 1/2003

OTHER PUBLICATIONS

Bowie et al., "Deciphering the Message in Protein Sequences: Tolerance to Amino Acid Substitutions," Science, vol. 247 No. 4948, pp. 1306-1310 (Mar. 1990).*
Bressanelli et al., "Structural analysis of the Hepatitis C Virus RNA polymerase in complex with ribonucleotides," Journal of Virology, vol. 76 No. 7, pp. 2482-3492 (Apr. 2002).*
Definition "drug," Stedman's Online Medical Dictionary, 27th Edition, stedmans.com (Oct. 2004).*
McKercher et al., "Specific inhibitors of HCV polymerase identified using an NS5B with lower affinity for template/primer substrate," Nucleic Acids Research, vol. 32 No. 2, pp. 422-431 (Jan. 2004).*
Zurawski et al., "Definition and spatial location of mouse interleukin-2 residues that interact with its heterotrimeric receptor," The EMBO Journal, vol. 12 No. 13, pp. 5113-5119 (Dec. 1993).*
Patrick Labonte, et al. "Modulation of Hepatitis C Virus RNA-dependent RNA Polymerase Activity by Structure-based Site-directed Mutagenesis", J. Bio. Chem. vol. 277, No. 41, Issue of Oct. 11, pp. 38838-38846, USA, 2002.
Stephane Bressanelli, et al. "Structural Analysis of the Hepatitis C Virus RNA Polymerase in Complex with Ribonucleotides", J. Virology. vol. 76, No. 7, pp. 3482-3492, USA, Apr. 2002.
Hideo Ago, et al. "Crystal Structure of the RNA-dependent RNA Polymerase of Hepatitis C Virus", Structure, vol. 7, No. 11, pp. 1417-1426, USA, Nov. 1999.
Stephane Bressanelli, et al. "Crystal Structure of the RNA-dependent RNA Polymerase of Hepatitis C Virus", PNAS, vol. 96, No. 23, pp. 13034-13039, USA, Nov. 1999.
Charles A. Lesburg, et al. "Crystal Structure of the RNA-dependent RNA Polymerase from Hepatitis C Virus Reveals a Fully Encircled Active Site", Nature Structural Biology, vol. 6, No. 10, pp. 937-943, USA, Oct. 1999.
Licia Tomei, et al. "Mechanism of Action and Antiviral Activity of Benzimidazole-Based Allosteric Inhibitors of the Hepatitis C Virus RNA-Dependent RNA Polymerase" Journal of Virology, vol. 77, No. 24, pp. 13225-13231, USA, Dec. 2003.
Pierre L. Beaulieu, "The discover of finger loop inhibitors of the hepatitis C virus NS5B polymerase: Status and prospects for novel HCV therapeutics", IDRUGS, 2006, vol. 9, No. 1, p. 39.
Pierre L. Beaulieu, "Finger loop inhibitors of the HCV NS5B polymerase: Discovery and prospects for new HCV therapy", Curr. Opin. Drug Discovery & Development, 2006, vol. 9, No. 5, p. 618.
Pierre L. Beaulieu, "Non-nucleoside inhibitors of the HCV NS5B polymerase: Progress in the discovery and development of novel agents for the treatment of HCV infections", Curr. Opin. Investigational Drugs, 2007, vol. 8, No. 8, p. 614.
Stefania Di Marco, et al., "Interdomain Communication in Hepatitis C Virus Polymerase Abolished by Small Molecule Inhibitors Bound to a Novel Allosteric Site", J. Biological Chemistry, 2005, vol. 280, No. 33, p. 29765.
C. Giuliano, et al., "Preclinical pharmacokinetics and metabolism of a potent non-nucleoside inhibitor of the hepatitis C virus NS5B polymerase" Xenobiotica, 2005, vol. 35, No. 10, p. 1035.
Steven Harper, et al., "Development and Preliminary Optimization of Indole-N-Acetamide Inhibitors of Hepatitis C Virus NS5B Polymerase", J. Medicinal Chemistry, 2005, vol. 48, p. 1314.
Steven Harper, et al., "Potent Inhibitors of Subgenomic Hepatitis C Virus RNA Replication through Optimization of Indole-N-Acetamide Allosteric inhibitors of the Viral NS5B polymerase", J. Medicinal Chemistry, 2005, vol. 48, p. 4547.

* cited by examiner

*Primary Examiner*—Zachariah Lucas
(74) *Attorney, Agent, or Firm*—Michael Morris; Mary-Ellen M. Devlin; David Dow

(57) ABSTRACT

The HCV NS5B polymerase, when complexed with certain inhibitors, adopts a conformation in which the finger loop region defined by amino acid residues 18 to 35 is displaced to expose a binding pocket defined generally by amino acid residues 392, 393, 395, 396, 399, 424, 425, 428, 429, 492, 493, 494, 495, 496, 500 and 503. This newly exposed binding pocket defines a novel target in the search of further chemical entities which are capable of binding to HCV NS5B and modulating, or preferably inhibiting, the polymerase activity of HCV NS5B.

15 Claims, 347 Drawing Sheets

Loop movement involves aa 18 to 35

Compound B

FIGURE 4-1 -

```
ATOM      1   CB   SER A  1      -7.482   44.347    4.675  1.00 20.95      A
ATOM      2   OG   SER A  1      -8.639   43.935    5.368  1.00 22.33      A
ATOM      3   C    SER A  1      -6.639   45.584    6.659  1.00 24.85      A
ATOM      4   O    SER A  1      -6.834   45.284    7.834  1.00 27.78      A
ATOM      5   N    SER A  1      -6.050   43.226    6.333  1.00 22.49      A
ATOM      6   CA   SER A  1      -6.314   44.510    5.636  1.00 23.26      A
ATOM      7   N    MET A  2      -6.682   46.835    6.220  1.00 25.16      A
ATOM      8   CA   MET A  2      -6.989   47.929    7.123  1.00 25.47      A
ATOM      9   CB   MET A  2      -6.702   49.270    6.452  1.00 25.93      A
ATOM     10   CG   MET A  2      -5.268   49.453    6.018  1.00 25.40      A
ATOM     11   SD   MET A  2      -4.135   49.394    7.395  1.00 30.56      A
ATOM     12   CE   MET A  2      -4.510   50.930    8.231  1.00 26.74      A
ATOM     13   C    MET A  2      -8.449   47.883    7.542  1.00 25.94      A
ATOM     14   O    MET A  2      -9.345   47.718    6.713  1.00 27.05      A
ATOM     15   N    SER A  3      -8.683   48.027    8.837  1.00 26.53      A
ATOM     16   CA   SER A  3     -10.036   48.020    9.374  1.00 26.62      A
ATOM     17   CB   SER A  3      -9.978   48.204   10.890  1.00 28.68      A
ATOM     18   OG   SER A  3      -9.069   49.236   11.238  1.00 29.50      A
ATOM     19   C    SER A  3     -10.853   49.143    8.743  1.00 26.08      A
ATOM     20   O    SER A  3     -12.023   48.964    8.407  1.00 25.82      A
ATOM     21   N    TYR A  4     -10.218   50.299    8.579  1.00 25.90      A
ATOM     22   CA   TYR A  4     -10.874   51.460    7.994  1.00 25.61      A
ATOM     23   CB   TYR A  4     -11.265   52.448    9.099  1.00 26.26      A
ATOM     24   CG   TYR A  4     -12.349   51.952   10.045  1.00 27.09      A
ATOM     25   CD1  TYR A  4     -13.702   52.163    9.759  1.00 25.48      A
ATOM     26   CE1  TYR A  4     -14.696   51.733   10.624  1.00 24.69      A
ATOM     27   CD2  TYR A  4     -12.023   51.286   11.230  1.00 25.97      A
ATOM     28   CE2  TYR A  4     -13.018   50.847   12.101  1.00 25.83      A
ATOM     29   CZ   TYR A  4     -14.348   51.073   11.791  1.00 25.02      A
ATOM     30   OH   TYR A  4     -15.327   50.613   12.637  1.00 26.07      A
ATOM     31   C    TYR A  4      -9.963   52.160    6.989  1.00 26.35      A
ATOM     32   O    TYR A  4      -8.741   51.976    7.005  1.00 26.86      A
ATOM     33   N    THR A  5     -10.576   52.942    6.103  1.00 25.37      A
ATOM     34   CA   THR A  5      -9.866   53.717    5.091  1.00 24.83      A
ATOM     35   CB   THR A  5      -9.947   53.073    3.709  1.00 23.68      A
ATOM     36   OG1  THR A  5      -8.950   52.058    3.597  1.00 24.30      A
ATOM     37   CG2  THR A  5      -9.725   54.109    2.633  1.00 23.44      A
ATOM     38   C    THR A  5     -10.604   55.037    5.035  1.00 26.41      A
ATOM     39   O    THR A  5     -11.830   55.048    4.926  1.00 27.83      A
ATOM     40   N    TRP A  6      -9.884   56.150    5.095  1.00 25.40      A
ATOM     41   CA   TRP A  6     -10.567   57.434    5.086  1.00 24.78      A
ATOM     42   CB   TRP A  6     -10.302   58.185    6.402  1.00 23.02      A
ATOM     43   CG   TRP A  6     -10.413   57.316    7.625  1.00 20.66      A
ATOM     44   CD2  TRP A  6     -11.609   56.963    8.328  1.00 21.24      A
ATOM     45   CE2  TRP A  6     -11.239   56.083    9.367  1.00 22.39      A
ATOM     46   CE3  TRP A  6     -12.962   57.303    8.182  1.00 20.74      A
ATOM     47   CD1  TRP A  6      -9.397   56.656    8.251  1.00 22.25      A
ATOM     48   NE1  TRP A  6      -9.881   55.914    9.297  1.00 23.35      A
ATOM     49   CZ2  TRP A  6     -12.170   55.539   10.253  1.00 19.48      A
ATOM     50   CZ3  TRP A  6     -13.884   56.765    9.065  1.00 18.77      A
ATOM     51   CH2  TRP A  6     -13.483   55.893   10.086  1.00 19.69      A
ATOM     52   C    TRP A  6     -10.228   58.326    3.906  1.00 24.57      A
ATOM     53   O    TRP A  6      -9.082   58.425    3.486  1.00 25.05      A
ATOM     54   N    THR A  7     -11.254   58.973    3.375  1.00 24.28      A
ATOM     55   CA   THR A  7     -11.103   59.880    2.255  1.00 24.64      A
ATOM     56   CB   THR A  7     -12.460   60.196    1.651  1.00 23.77      A
ATOM     57   OG1  THR A  7     -13.240   60.922    2.609  1.00 20.65      A
ATOM     58   CG2  THR A  7     -13.180   58.899    1.273  1.00 23.50      A
ATOM     59   C    THR A  7     -10.479   61.185    2.754  1.00 26.96      A
ATOM     60   O    THR A  7      -9.567   61.735    2.131  1.00 28.06      A
ATOM     61   N    GLY A  8     -10.972   61.663    3.893  1.00 27.34      A
ATOM     62   CA   GLY A  8     -10.475   62.898    4.467  1.00 27.13      A
ATOM     63   C    GLY A  8     -11.637   63.675    5.059  1.00 28.70      A
ATOM     64   O    GLY A  8     -11.463   64.542    5.926  1.00 27.87      A
ATOM     65   N    ALA A  9     -12.833   63.365    4.569  1.00 29.32      A
ATOM     66   CA   ALA A  9     -14.042   64.003    5.046  1.00 29.34      A
ATOM     67   CB   ALA A  9     -15.240   63.411    4.355  1.00 29.57      A
ATOM     68   C    ALA A  9     -14.106   63.731    6.538  1.00 30.70      A
ATOM     69   O    ALA A  9     -13.482   62.792    7.031  1.00 30.79      A
ATOM     70   N    LEU A 10     -14.864   64.546    7.257  1.00 31.95      A
ATOM     71   CA   LEU A 10     -14.967   64.385    8.696  1.00 32.39      A
ATOM     72   CB   LEU A 10     -14.810   65.743    9.381  1.00 32.52      A
ATOM     73   CG   LEU A 10     -13.597   66.651    9.126  1.00 32.49      A
ATOM     74   CD1  LEU A 10     -13.818   67.963    9.865  1.00 31.26      A
```

FIGURE 4-2-

| | | | | | | | | | | |
|---|---|---|---|---|---|---|---|---|---|---|
| ATOM | 75  | CD2 | LEU | A | 10 | -12.297 | 65.994 | 9.589  | 1.00 33.14 | A |
| ATOM | 76  | C   | LEU | A | 10 | -16.281 | 63.770 | 9.149  | 1.00 33.04 | A |
| ATOM | 77  | O   | LEU | A | 10 | -17.309 | 63.892 | 8.477  | 1.00 33.89 | A |
| ATOM | 78  | N   | ILE | A | 11 | -16.236 | 63.100 | 10.295 | 1.00 32.70 | A |
| ATOM | 79  | CA  | ILE | A | 11 | -17.437 | 62.512 | 10.871 | 1.00 32.81 | A |
| ATOM | 80  | CB  | ILE | A | 11 | -17.098 | 61.472 | 11.957 | 1.00 32.99 | A |
| ATOM | 81  | CG2 | ILE | A | 11 | -18.380 | 60.882 | 12.531 | 1.00 33.47 | A |
| ATOM | 82  | CG1 | ILE | A | 11 | -16.243 | 60.356 | 11.356 | 1.00 31.64 | A |
| ATOM | 83  | CD1 | ILE | A | 11 | -15.621 | 59.444 | 12.389 | 1.00 32.57 | A |
| ATOM | 84  | C   | ILE | A | 11 | -18.157 | 63.712 | 11.485 | 1.00 32.37 | A |
| ATOM | 85  | O   | ILE | A | 11 | -17.693 | 64.315 | 12.447 | 1.00 31.68 | A |
| ATOM | 86  | N   | THR | A | 12 | -19.300 | 64.045 | 10.908 | 1.00 33.52 | A |
| ATOM | 87  | CA  | THR | A | 12 | -20.072 | 65.201 | 11.308 | 1.00 34.79 | A |
| ATOM | 88  | CB  | THR | A | 12 | -20.469 | 65.959 | 10.040 | 1.00 35.99 | A |
| ATOM | 89  | OG1 | THR | A | 12 | -21.210 | 65.082 | 9.176  | 1.00 35.20 | A |
| ATOM | 90  | CG2 | THR | A | 12 | -19.221 | 66.418 | 9.298  | 1.00 33.52 | A |
| ATOM | 91  | C   | THR | A | 12 | -21.325 | 64.923 | 12.139 | 1.00 36.76 | A |
| ATOM | 92  | O   | THR | A | 12 | -21.826 | 63.805 | 12.167 | 1.00 39.35 | A |
| ATOM | 93  | N   | PRO | A | 13 | -21.834 | 65.949 | 12.839 | 1.00 37.78 | A |
| ATOM | 94  | CD  | PRO | A | 13 | -21.008 | 67.105 | 13.208 | 1.00 37.55 | A |
| ATOM | 95  | CA  | PRO | A | 13 | -23.027 | 65.908 | 13.692 | 1.00 39.06 | A |
| ATOM | 96  | CB  | PRO | A | 13 | -22.660 | 66.839 | 14.850 | 1.00 38.87 | A |
| ATOM | 97  | CG  | PRO | A | 13 | -21.134 | 67.119 | 14.674 | 1.00 37.23 | A |
| ATOM | 98  | C   | PRO | A | 13 | -24.251 | 66.442 | 12.949 | 1.00 41.08 | A |
| ATOM | 99  | O   | PRO | A | 13 | -24.104 | 67.141 | 11.951 | 1.00 42.28 | A |
| ATOM | 100 | N   | CYS | A | 14 | -25.451 | 66.127 | 13.436 | 1.00 43.45 | A |
| ATOM | 101 | CA  | CYS | A | 14 | -26.683 | 66.629 | 12.814 | 1.00 45.99 | A |
| ATOM | 102 | CB  | CYS | A | 14 | -27.883 | 65.735 | 13.113 | 1.00 46.57 | A |
| ATOM | 103 | SG  | CYS | A | 14 | -27.650 | 64.015 | 12.798 | 1.00 53.22 | A |
| ATOM | 104 | C   | CYS | A | 14 | -26.968 | 67.958 | 13.469 | 1.00 46.67 | A |
| ATOM | 105 | O   | CYS | A | 14 | -26.884 | 69.021 | 12.854 | 1.00 47.33 | A |
| ATOM | 106 | N   | ALA | A | 15 | -27.315 | 67.859 | 14.745 | 1.00 47.70 | A |
| ATOM | 107 | CA  | ALA | A | 15 | -27.635 | 69.004 | 15.573 | 1.00 47.69 | A |
| ATOM | 108 | CB  | ALA | A | 15 | -28.810 | 68.660 | 16.481 | 1.00 48.35 | A |
| ATOM | 109 | C   | ALA | A | 15 | -26.417 | 69.388 | 16.410 | 1.00 46.91 | A |
| ATOM | 110 | O   | ALA | A | 15 | -25.363 | 68.747 | 16.319 | 1.00 45.80 | A |
| ATOM | 111 | N   | ALA | A | 16 | -26.573 | 70.439 | 17.216 | 1.00 45.43 | A |
| ATOM | 112 | CA  | ALA | A | 16 | -25.507 | 70.913 | 18.091 | 1.00 42.96 | A |
| ATOM | 113 | CB  | ALA | A | 16 | -25.900 | 72.246 | 18.726 | 1.00 42.50 | A |
| ATOM | 114 | C   | ALA | A | 16 | -25.300 | 69.849 | 19.165 | 1.00 41.95 | A |
| ATOM | 115 | O   | ALA | A | 16 | -26.212 | 69.080 | 19.478 | 1.00 40.30 | A |
| ATOM | 116 | N   | GLU | A | 17 | -24.100 | 69.805 | 19.728 | 1.00 40.93 | A |
| ATOM | 117 | CA  | GLU | A | 17 | -23.786 | 68.818 | 20.743 | 1.00 39.98 | A |
| ATOM | 118 | CB  | GLU | A | 17 | -22.618 | 67.951 | 20.271 | 1.00 40.14 | A |
| ATOM | 119 | CG  | GLU | A | 17 | -22.861 | 67.234 | 18.946 | 1.00 38.65 | A |
| ATOM | 120 | CD  | GLU | A | 17 | -21.573 | 66.837 | 18.251 | 1.00 38.29 | A |
| ATOM | 121 | OE1 | GLU | A | 17 | -20.866 | 67.737 | 17.748 | 1.00 37.83 | A |
| ATOM | 122 | OE2 | GLU | A | 17 | -21.265 | 65.629 | 18.212 | 1.00 39.10 | A |
| ATOM | 123 | C   | GLU | A | 17 | -23.437 | 69.458 | 22.077 | 1.00 40.03 | A |
| ATOM | 124 | O   | GLU | A | 17 | -22.506 | 70.252 | 22.180 | 1.00 39.44 | A |
| ATOM | 125 | N   | GLU | A | 18 | -24.195 | 69.107 | 23.104 | 1.00 41.49 | A |
| ATOM | 126 | CA  | GLU | A | 18 | -23.933 | 69.627 | 24.432 | 1.00 42.96 | A |
| ATOM | 127 | CB  | GLU | A | 18 | -25.183 | 69.511 | 25.292 | 1.00 46.08 | A |
| ATOM | 128 | CG  | GLU | A | 18 | -26.479 | 69.777 | 24.533 | 1.00 52.33 | A |
| ATOM | 129 | CD  | GLU | A | 18 | -26.580 | 71.205 | 24.019 | 1.00 55.53 | A |
| ATOM | 130 | OE1 | GLU | A | 18 | -26.495 | 72.146 | 24.846 | 1.00 57.64 | A |
| ATOM | 131 | OE2 | GLU | A | 18 | -26.749 | 71.382 | 22.788 | 1.00 56.42 | A |
| ATOM | 132 | C   | GLU | A | 18 | -22.834 | 68.728 | 24.989 | 1.00 42.31 | A |
| ATOM | 133 | O   | GLU | A | 18 | -22.928 | 67.505 | 24.907 | 1.00 41.40 | A |
| ATOM | 134 | N   | SER | A | 19 | -21.786 | 69.324 | 25.539 | 1.00 41.95 | A |
| ATOM | 135 | CA  | SER | A | 19 | -20.699 | 68.532 | 26.092 | 1.00 41.75 | A |
| ATOM | 136 | CB  | SER | A | 19 | -19.398 | 68.804 | 25.332 | 1.00 41.34 | A |
| ATOM | 137 | OG  | SER | A | 19 | -19.041 | 70.174 | 25.403 | 1.00 42.40 | A |
| ATOM | 138 | C   | SER | A | 19 | -20.490 | 68.812 | 27.574 | 1.00 41.20 | A |
| ATOM | 139 | O   | SER | A | 19 | -19.828 | 68.044 | 28.267 | 1.00 39.91 | A |
| ATOM | 140 | N   | LYS | A | 20 | -21.058 | 69.911 | 28.062 | 1.00 41.89 | A |
| ATOM | 141 | CA  | LYS | A | 20 | -20.903 | 70.264 | 29.466 | 1.00 41.49 | A |
| ATOM | 142 | CB  | LYS | A | 20 | -20.426 | 71.710 | 29.596 | 1.00 41.91 | A |
| ATOM | 143 | CG  | LYS | A | 20 | -18.999 | 71.908 | 29.096 | 1.00 45.69 | A |
| ATOM | 144 | CD  | LYS | A | 20 | -18.553 | 73.355 | 29.179 | 1.00 48.30 | A |
| ATOM | 145 | CE  | LYS | A | 20 | -17.183 | 73.556 | 28.523 | 1.00 50.57 | A |
| ATOM | 146 | NZ  | LYS | A | 20 | -16.739 | 74.996 | 28.530 | 1.00 49.74 | A |
| ATOM | 147 | C   | LYS | A | 20 | -22.176 | 70.048 | 30.270 | 1.00 40.78 | A |
| ATOM | 148 | O   | LYS | A | 20 | -23.289 | 70.152 | 29.745 | 1.00 40.80 | A |
| ATOM | 149 | N   | LEU | A | 21 | -21.991 | 69.725 | 31.546 | 1.00 39.67 | A |
| ATOM | 150 | CA  | LEU | A | 21 | -23.095 | 69.479 | 32.463 | 1.00 38.51 | A |

FIGURE 4- 3 -

```
ATOM    151  CB   LEU A  21     -22.602  68.643  33.642  1.00 36.37           A
ATOM    152  CG   LEU A  21     -23.618  68.399  34.747  1.00 35.03           A
ATOM    153  CD1  LEU A  21     -24.819  67.687  34.163  1.00 37.07           A
ATOM    154  CD2  LEU A  21     -22.987  67.587  35.857  1.00 33.58           A
ATOM    155  C    LEU A  21     -23.658  70.807  32.962  1.00 39.03           A
ATOM    156  O    LEU A  21     -22.938  71.619  33.543  1.00 39.16           A
ATOM    157  N    PRO A  22     -24.957  71.048  32.726  1.00 39.89           A
ATOM    158  CD   PRO A  22     -25.840  70.224  31.879  1.00 41.52           A
ATOM    159  CA   PRO A  22     -25.639  72.281  33.143  1.00 39.54           A
ATOM    160  CB   PRO A  22     -27.059  72.086  32.613  1.00 39.86           A
ATOM    161  CG   PRO A  22     -26.855  71.239  31.390  1.00 41.15           A
ATOM    162  C    PRO A  22     -25.628  72.514  34.653  1.00 39.12           A
ATOM    163  O    PRO A  22     -25.333  71.605  35.433  1.00 39.77           A
ATOM    164  N    ILE A  23     -25.942  73.742  35.051  1.00 37.53           A
ATOM    165  CA   ILE A  23     -26.003  74.106  36.456  1.00 37.15           A
ATOM    166  CB   ILE A  23     -25.407  75.515  36.673  1.00 37.50           A
ATOM    167  CG2  ILE A  23     -25.575  75.959  38.134  1.00 36.43           A
ATOM    168  CG1  ILE A  23     -23.925  75.494  36.281  1.00 37.34           A
ATOM    169  CD1  ILE A  23     -23.203  76.807  36.500  1.00 38.57           A
ATOM    170  C    ILE A  23     -27.486  74.061  36.827  1.00 36.82           A
ATOM    171  O    ILE A  23     -28.147  75.088  36.963  1.00 38.77           A
ATOM    172  N    ASN A  24     -27.993  72.844  36.978  1.00 35.92           A
ATOM    173  CA   ASN A  24     -29.394  72.595  37.281  1.00 35.50           A
ATOM    174  CB   ASN A  24     -29.849  71.425  36.412  1.00 37.27           A
ATOM    175  CG   ASN A  24     -31.320  71.139  36.534  1.00 40.48           A
ATOM    176  OD1  ASN A  24     -31.814  70.822  37.618  1.00 43.45           A
ATOM    177  ND2  ASN A  24     -32.037  71.238  35.415  1.00 39.91           A
ATOM    178  C    ASN A  24     -29.630  72.297  38.769  1.00 34.25           A
ATOM    179  O    ASN A  24     -28.961  71.452  39.358  1.00 33.24           A
ATOM    180  N    PRO A  25     -30.588  72.994  39.397  1.00 32.92           A
ATOM    181  CD   PRO A  25     -31.496  74.018  38.856  1.00 32.36           A
ATOM    182  CA   PRO A  25     -30.856  72.752  40.821  1.00 32.98           A
ATOM    183  CB   PRO A  25     -32.003  73.722  41.136  1.00 30.78           A
ATOM    184  CG   PRO A  25     -32.657  73.943  39.818  1.00 31.80           A
ATOM    185  C    PRO A  25     -31.187  71.295  41.150  1.00 32.54           A
ATOM    186  O    PRO A  25     -30.824  70.793  42.218  1.00 32.16           A
ATOM    187  N    LEU A  26     -31.863  70.624  40.223  1.00 32.31           A
ATOM    188  CA   LEU A  26     -32.236  69.224  40.392  1.00 32.00           A
ATOM    189  CB   LEU A  26     -33.240  68.822  39.316  1.00 32.25           A
ATOM    190  CG   LEU A  26     -34.704  68.772  39.746  1.00 32.38           A
ATOM    191  CD1  LEU A  26     -34.984  69.857  40.757  1.00 31.56           A
ATOM    192  CD2  LEU A  26     -35.587  68.901  38.515  1.00 31.52           A
ATOM    193  C    LEU A  26     -31.028  68.298  40.326  1.00 32.09           A
ATOM    194  O    LEU A  26     -30.848  67.445  41.190  1.00 31.82           A
ATOM    195  N    SER A  27     -30.207  68.456  39.293  1.00 31.10           A
ATOM    196  CA   SER A  27     -29.019  67.625  39.149  1.00 28.36           A
ATOM    197  CB   SER A  27     -28.418  67.808  37.756  1.00 27.66           A
ATOM    198  OG   SER A  27     -27.870  69.108  37.599  1.00 25.09           A
ATOM    199  C    SER A  27     -27.969  68.001  40.195  1.00 27.50           A
ATOM    200  O    SER A  27     -27.220  67.161  40.668  1.00 26.79           A
ATOM    201  N    ASN A  28     -27.926  69.275  40.551  1.00 28.69           A
ATOM    202  CA   ASN A  28     -26.950  69.769  41.506  1.00 29.54           A
ATOM    203  CB   ASN A  28     -26.990  71.292  41.543  1.00 31.61           A
ATOM    204  CG   ASN A  28     -25.876  71.873  42.379  1.00 34.36           A
ATOM    205  OD1  ASN A  28     -24.701  71.746  42.035  1.00 36.32           A
ATOM    206  ND2  ASN A  28     -26.235  72.506  43.490  1.00 34.80           A
ATOM    207  C    ASN A  28     -27.089  69.226  42.929  1.00 29.36           A
ATOM    208  O    ASN A  28     -26.114  69.213  43.688  1.00 26.64           A
ATOM    209  N    SER A  29     -28.291  68.790  43.300  1.00 30.03           A
ATOM    210  CA   SER A  29     -28.494  68.257  44.642  1.00 30.37           A
ATOM    211  CB   SER A  29     -29.973  68.355  45.064  1.00 31.75           A
ATOM    212  OG   SER A  29     -30.830  67.505  44.316  1.00 31.94           A
ATOM    213  C    SER A  29     -28.019  66.818  44.654  1.00 30.32           A
ATOM    214  O    SER A  29     -27.967  66.182  45.703  1.00 32.63           A
ATOM    215  N    LEU A  30     -27.648  66.326  43.473  1.00 29.55           A
ATOM    216  CA   LEU A  30     -27.155  64.962  43.291  1.00 27.59           A
ATOM    217  CB   LEU A  30     -27.874  64.295  42.117  1.00 26.17           A
ATOM    218  CG   LEU A  30     -27.234  63.042  41.506  1.00 25.01           A
ATOM    219  CD1  LEU A  30     -27.157  61.935  42.537  1.00 22.15           A
ATOM    220  CD2  LEU A  30     -28.043  62.603  40.304  1.00 22.76           A
ATOM    221  C    LEU A  30     -25.650  64.912  43.047  1.00 27.58           A
ATOM    222  O    LEU A  30     -24.969  64.047  43.589  1.00 28.98           A
ATOM    223  N    LEU A  31     -25.132  65.831  42.234  1.00 26.72           A
ATOM    224  CA   LEU A  31     -23.701  65.862  41.923  1.00 26.57           A
ATOM    225  CB   LEU A  31     -23.474  65.075  40.632  1.00 24.46           A
ATOM    226  CG   LEU A  31     -22.072  64.739  40.142  1.00 22.76           A
```

FIGURE 4- 4 -

```
ATOM    227  CD1 LEU A  31     -22.121  63.498  39.279  1.00 16.54      A
ATOM    228  CD2 LEU A  31     -21.511  65.923  39.373  1.00 23.10      A
ATOM    229  C   LEU A  31     -23.208  67.314  41.798  1.00 28.06      A
ATOM    230  O   LEU A  31     -23.499  68.001  40.820  1.00 28.00      A
ATOM    231  N   ARG A  32     -22.457  67.770  42.799  1.00 29.61      A
ATOM    232  CA  ARG A  32     -21.961  69.149  42.843  1.00 30.91      A
ATOM    233  CB  ARG A  32     -21.525  69.514  44.273  1.00 33.55      A
ATOM    234  CG  ARG A  32     -22.643  69.951  45.215  1.00 37.30      A
ATOM    235  CD  ARG A  32     -23.710  68.876  45.369  1.00 42.19      A
ATOM    236  NE  ARG A  32     -24.915  69.391  46.017  1.00 45.78      A
ATOM    237  CZ  ARG A  32     -25.077  69.497  47.332  1.00 46.81      A
ATOM    238  NH1 ARG A  32     -24.101  69.115  48.150  1.00 46.00      A
ATOM    239  NH2 ARG A  32     -26.214  69.989  47.824  1.00 46.62      A
ATOM    240  C   ARG A  32     -20.835  69.521  41.890  1.00 29.97      A
ATOM    241  O   ARG A  32     -20.848  70.615  41.337  1.00 30.02      A
ATOM    242  N   HIS A  33     -19.864  68.628  41.714  1.00 30.22      A
ATOM    243  CA  HIS A  33     -18.713  68.879  40.837  1.00 30.26      A
ATOM    244  CB  HIS A  33     -17.551  67.954  41.222  1.00 30.86      A
ATOM    245  CG  HIS A  33     -17.082  68.126  42.636  1.00 32.66      A
ATOM    246  CD2 HIS A  33     -17.330  69.099  43.546  1.00 31.30      A
ATOM    247  ND1 HIS A  33     -16.256  67.217  43.263  1.00 31.65      A
ATOM    248  CE1 HIS A  33     -16.019  67.620  44.497  1.00 30.77      A
ATOM    249  NE2 HIS A  33     -16.659  68.759  44.694  1.00 32.07      A
ATOM    250  C   HIS A  33     -19.059  68.677  39.366  1.00 30.78      A
ATOM    251  O   HIS A  33     -18.454  67.847  38.677  1.00 31.21      A
ATOM    252  N   HIS A  34     -20.019  69.456  38.884  1.00 29.67      A
ATOM    253  CA  HIS A  34     -20.472  69.344  37.514  1.00 30.28      A
ATOM    254  CB  HIS A  34     -21.570  70.375  37.259  1.00 31.59      A
ATOM    255  CG  HIS A  34     -21.130  71.795  37.444  1.00 35.36      A
ATOM    256  CD2 HIS A  34     -21.431  72.702  38.405  1.00 34.60      A
ATOM    257  ND1 HIS A  34     -20.297  72.441  36.552  1.00 34.85      A
ATOM    258  CE1 HIS A  34     -20.110  73.686  36.955  1.00 35.22      A
ATOM    259  NE2 HIS A  34     -20.787  73.870  38.075  1.00 36.06      A
ATOM    260  C   HIS A  34     -19.377  69.438  36.446  1.00 31.28      A
ATOM    261  O   HIS A  34     -19.532  68.888  35.352  1.00 32.38      A
ATOM    262  N   ASN A  35     -18.270  70.108  36.746  1.00 30.52      A
ATOM    263  CA  ASN A  35     -17.198  70.226  35.760  1.00 30.08      A
ATOM    264  CB  ASN A  35     -16.180  71.307  36.177  1.00 31.19      A
ATOM    265  CG  ASN A  35     -16.718  72.734  36.012  1.00 30.35      A
ATOM    266  OD1 ASN A  35     -17.338  73.066  35.003  1.00 29.94      A
ATOM    267  ND2 ASN A  35     -16.461  73.580  36.999  1.00 29.06      A
ATOM    268  C   ASN A  35     -16.460  68.905  35.501  1.00 30.08      A
ATOM    269  O   ASN A  35     -15.623  68.817  34.602  1.00 30.51      A
ATOM    270  N   MET A  36     -16.751  67.877  36.288  1.00 29.38      A
ATOM    271  CA  MET A  36     -16.092  66.595  36.078  1.00 29.29      A
ATOM    272  CB  MET A  36     -15.768  65.940  37.412  1.00 30.50      A
ATOM    273  CG  MET A  36     -14.831  66.716  38.284  1.00 31.98      A
ATOM    274  SD  MET A  36     -14.975  66.087  39.955  1.00 37.33      A
ATOM    275  CE  MET A  36     -14.175  64.483  39.762  1.00 35.98      A
ATOM    276  C   MET A  36     -16.981  65.655  35.260  1.00 28.63      A
ATOM    277  O   MET A  36     -16.655  64.479  35.078  1.00 27.25      A
ATOM    278  N   VAL A  37     -18.101  66.186  34.774  1.00 27.53      A
ATOM    279  CA  VAL A  37     -19.057  65.411  33.990  1.00 25.91      A
ATOM    280  CB  VAL A  37     -20.493  65.505  34.594  1.00 24.52      A
ATOM    281  CG1 VAL A  37     -21.466  64.665  33.790  1.00 22.88      A
ATOM    282  CG2 VAL A  37     -20.486  65.047  36.032  1.00 22.23      A
ATOM    283  C   VAL A  37     -19.101  65.920  32.558  1.00 26.11      A
ATOM    284  O   VAL A  37     -19.560  67.030  32.306  1.00 24.30      A
ATOM    285  N   TYR A  38     -18.614  65.111  31.619  1.00 27.53      A
ATOM    286  CA  TYR A  38     -18.630  65.503  30.212  1.00 27.20      A
ATOM    287  CB  TYR A  38     -17.213  65.722  29.675  1.00 26.48      A
ATOM    288  CG  TYR A  38     -16.363  64.478  29.607  1.00 28.27      A
ATOM    289  CD1 TYR A  38     -15.731  63.976  30.745  1.00 28.52      A
ATOM    290  CE1 TYR A  38     -14.953  62.820  30.690  1.00 28.38      A
ATOM    291  CD2 TYR A  38     -16.196  63.793  28.407  1.00 28.80      A
ATOM    292  CE2 TYR A  38     -15.423  62.634  28.342  1.00 30.15      A
ATOM    293  CZ  TYR A  38     -14.803  62.150  29.488  1.00 29.34      A
ATOM    294  OH  TYR A  38     -14.049  60.994  29.423  1.00 29.22      A
ATOM    295  C   TYR A  38     -19.331  64.482  29.332  1.00 27.78      A
ATOM    296  O   TYR A  38     -19.643  63.357  29.763  1.00 25.88      A
ATOM    297  N   ALA A  39     -19.578  64.903  28.092  1.00 27.73      A
ATOM    298  CA  ALA A  39     -20.231  64.074  27.084  1.00 26.94      A
ATOM    299  CB  ALA A  39     -21.582  64.661  26.708  1.00 23.46      A
ATOM    300  C   ALA A  39     -19.316  64.076  25.878  1.00 26.69      A
ATOM    301  O   ALA A  39     -18.753  65.121  25.540  1.00 28.90      A
ATOM    302  N   THR A  40     -19.140  62.921  25.246  1.00 24.20      A
```

FIGURE 4- 5 -

```
ATOM   303  CA   THR A  40     -18.303  62.861  24.054  1.00 23.52      A
ATOM   304  CB   THR A  40     -18.049  61.428  23.620  1.00 21.67      A
ATOM   305  OG1  THR A  40     -19.307  60.768  23.442  1.00 23.26      A
ATOM   306  CG2  THR A  40     -17.223  60.697  24.647  1.00 20.09      A
ATOM   307  C    THR A  40     -19.064  63.551  22.921  1.00 24.73      A
ATOM   308  O    THR A  40     -20.291  63.644  22.962  1.00 26.42      A
ATOM   309  N    THR A  41     -18.344  64.053  21.924  1.00 24.65      A
ATOM   310  CA   THR A  41     -18.985  64.695  20.780  1.00 26.03      A
ATOM   311  CB   THR A  41     -19.091  66.221  20.929  1.00 26.58      A
ATOM   312  OG1  THR A  41     -17.821  66.816  20.636  1.00 28.07      A
ATOM   313  CG2  THR A  41     -19.521  66.587  22.329  1.00 24.88      A
ATOM   314  C    THR A  41     -18.126  64.409  19.568  1.00 26.47      A
ATOM   315  O    THR A  41     -17.007  63.906  19.714  1.00 25.86      A
ATOM   316  N    SER A  42     -18.645  64.740  18.385  1.00 26.56      A
ATOM   317  CA   SER A  42     -17.933  64.508  17.129  1.00 27.56      A
ATOM   318  CB   SER A  42     -18.738  65.056  15.963  1.00 26.69      A
ATOM   319  OG   SER A  42     -18.642  66.466  15.945  1.00 31.58      A
ATOM   320  C    SER A  42     -16.564  65.177  17.146  1.00 27.34      A
ATOM   321  O    SER A  42     -15.624  64.715  16.506  1.00 26.56      A
ATOM   322  N    ARG A  43     -16.454  66.264  17.901  1.00 28.31      A
ATOM   323  CA   ARG A  43     -15.196  66.995  17.989  1.00 27.85      A
ATOM   324  CB   ARG A  43     -15.293  68.132  19.017  1.00 27.40      A
ATOM   325  CG   ARG A  43     -16.223  69.266  18.617  1.00 27.32      A
ATOM   326  CD   ARG A  43     -15.946  70.500  19.449  1.00 27.75      A
ATOM   327  NE   ARG A  43     -16.281  70.326  20.860  1.00 27.33      A
ATOM   328  CZ   ARG A  43     -17.523  70.224  21.327  1.00 26.79      A
ATOM   329  NH1  ARG A  43     -18.558  70.276  20.493  1.00 24.30      A
ATOM   330  NH2  ARG A  43     -17.729  70.076  22.630  1.00 25.00      A
ATOM   331  C    ARG A  43     -13.987  66.133  18.319  1.00 26.28      A
ATOM   332  O    ARG A  43     -12.866  66.584  18.129  1.00 26.82      A
ATOM   333  N    SER A  44     -14.193  64.913  18.814  1.00 24.09      A
ATOM   334  CA   SER A  44     -13.060  64.051  19.146  1.00 22.31      A
ATOM   335  CB   SER A  44     -13.070  63.666  20.635  1.00 23.11      A
ATOM   336  OG   SER A  44     -14.236  62.948  21.027  1.00 23.44      A
ATOM   337  C    SER A  44     -13.015  62.795  18.295  1.00 22.87      A
ATOM   338  O    SER A  44     -12.144  61.948  18.480  1.00 22.31      A
ATOM   339  N    ALA A  45     -13.941  62.685  17.349  1.00 22.54      A
ATOM   340  CA   ALA A  45     -14.000  61.522  16.477  1.00 23.58      A
ATOM   341  CB   ALA A  45     -14.947  61.797  15.322  1.00 23.70      A
ATOM   342  C    ALA A  45     -12.620  61.166  15.945  1.00 24.26      A
ATOM   343  O    ALA A  45     -12.209  60.011  15.956  1.00 24.85      A
ATOM   344  N    SER A  46     -11.912  62.184  15.481  1.00 26.45      A
ATOM   345  CA   SER A  46     -10.570  62.043  14.924  1.00 28.96      A
ATOM   346  CB   SER A  46      -9.941  63.433  14.790  1.00 29.65      A
ATOM   347  OG   SER A  46      -8.528  63.348  14.767  1.00 32.82      A
ATOM   348  C    SER A  46      -9.640  61.133  15.726  1.00 29.72      A
ATOM   349  O    SER A  46      -8.979  60.252  15.169  1.00 29.52      A
ATOM   350  N    LEU A  47      -9.580  61.360  17.033  1.00 30.61      A
ATOM   351  CA   LEU A  47      -8.726  60.567  17.910  1.00 31.43      A
ATOM   352  CB   LEU A  47      -8.832  61.092  19.342  1.00 31.67      A
ATOM   353  CG   LEU A  47      -8.305  62.524  19.465  1.00 31.65      A
ATOM   354  CD1  LEU A  47      -8.726  63.133  20.773  1.00 28.90      A
ATOM   355  CD2  LEU A  47      -6.793  62.502  19.318  1.00 31.27      A
ATOM   356  C    LEU A  47      -9.106  59.100  17.863  1.00 32.22      A
ATOM   357  O    LEU A  47      -8.240  58.232  17.741  1.00 32.86      A
ATOM   358  N    ARG A  48     -10.409  58.836  17.951  1.00 31.88      A
ATOM   359  CA   ARG A  48     -10.937  57.481  17.922  1.00 31.64      A
ATOM   360  CB   ARG A  48     -12.451  57.518  18.126  1.00 32.49      A
ATOM   361  CG   ARG A  48     -13.093  56.161  18.304  1.00 32.06      A
ATOM   362  CD   ARG A  48     -12.493  55.420  19.488  1.00 36.75      A
ATOM   363  NE   ARG A  48     -13.033  54.066  19.586  1.00 41.78      A
ATOM   364  CZ   ARG A  48     -12.594  53.132  20.425  1.00 42.29      A
ATOM   365  NH1  ARG A  48     -11.590  53.398  21.257  1.00 42.30      A
ATOM   366  NH2  ARG A  48     -13.166  51.932  20.429  1.00 40.55      A
ATOM   367  C    ARG A  48     -10.593  56.789  16.605  1.00 31.78      A
ATOM   368  O    ARG A  48     -10.209  55.616  16.590  1.00 31.13      A
ATOM   369  N    GLN A  49     -10.726  57.515  15.499  1.00 31.01      A
ATOM   370  CA   GLN A  49     -10.399  56.954  14.190  1.00 31.20      A
ATOM   371  CB   GLN A  49     -10.619  57.990  13.095  1.00 31.31      A
ATOM   372  CG   GLN A  49     -12.033  58.471  12.986  1.00 33.71      A
ATOM   373  CD   GLN A  49     -12.187  59.568  11.960  1.00 33.91      A
ATOM   374  OE1  GLN A  49     -11.939  59.365  10.768  1.00 31.66      A
ATOM   375  NE2  GLN A  49     -12.600  60.746  12.418  1.00 34.75      A
ATOM   376  C    GLN A  49      -8.932  56.538  14.176  1.00 30.20      A
ATOM   377  O    GLN A  49      -8.555  55.519  13.592  1.00 28.42      A
ATOM   378  N    LYS A  50      -8.117  57.349  14.834  1.00 29.50      A
```

FIGURE 4- 6 -

```
ATOM    379  CA  LYS A  50      -6.692  57.114  14.904  1.00 30.34           A
ATOM    380  CB  LYS A  50      -6.019  58.306  15.589  1.00 31.70           A
ATOM    381  CG  LYS A  50      -4.647  58.655  15.048  1.00 33.38           A
ATOM    382  CD  LYS A  50      -3.525  57.928  15.771  1.00 36.10           A
ATOM    383  CE  LYS A  50      -2.198  58.177  15.062  1.00 38.45           A
ATOM    384  NZ  LYS A  50      -2.184  59.506  14.356  1.00 40.27           A
ATOM    385  C   LYS A  50      -6.391  55.829  15.656  1.00 29.98           A
ATOM    386  O   LYS A  50      -5.373  55.189  15.410  1.00 31.09           A
ATOM    387  N   LYS A  51      -7.282  55.442  16.563  1.00 29.87           A
ATOM    388  CA  LYS A  51      -7.066  54.231  17.350  1.00 29.63           A
ATOM    389  CB  LYS A  51      -7.645  54.396  18.756  1.00 30.41           A
ATOM    390  CG  LYS A  51      -7.327  53.235  19.684  1.00 32.68           A
ATOM    391  CD  LYS A  51      -7.785  53.537  21.104  1.00 36.36           A
ATOM    392  CE  LYS A  51      -7.243  52.516  22.111  1.00 38.74           A
ATOM    393  NZ  LYS A  51      -7.634  52.866  23.505  1.00 37.32           A
ATOM    394  C   LYS A  51      -7.647  52.976  16.728  1.00 28.59           A
ATOM    395  O   LYS A  51      -7.043  51.911  16.800  1.00 28.94           A
ATOM    396  N   VAL A  52      -8.822  53.107  16.118  1.00 27.85           A
ATOM    397  CA  VAL A  52      -9.509  51.974  15.500  1.00 26.72           A
ATOM    398  CB  VAL A  52     -11.023  52.237  15.417  1.00 23.82           A
ATOM    399  CG1 VAL A  52     -11.551  52.627  16.788  1.00 23.25           A
ATOM    400  CG2 VAL A  52     -11.295  53.335  14.412  1.00 21.63           A
ATOM    401  C   VAL A  52      -9.010  51.623  14.095  1.00 26.99           A
ATOM    402  O   VAL A  52      -9.414  50.608  13.527  1.00 27.38           A
ATOM    403  N   THR A  53      -8.147  52.464  13.533  1.00 26.02           A
ATOM    404  CA  THR A  53      -7.631  52.203  12.199  1.00 25.58           A
ATOM    405  CB  THR A  53      -7.544  53.493  11.351  1.00 23.73           A
ATOM    406  OG1 THR A  53      -8.831  54.115  11.278  1.00 22.88           A
ATOM    407  CG2 THR A  53      -7.080  53.169   9.950  1.00 22.89           A
ATOM    408  C   THR A  53      -6.253  51.561  12.278  1.00 26.03           A
ATOM    409  O   THR A  53      -5.293  52.152  12.772  1.00 27.25           A
ATOM    410  N   PHE A  54      -6.175  50.333  11.790  1.00 25.50           A
ATOM    411  CA  PHE A  54      -4.937  49.597  11.773  1.00 25.44           A
ATOM    412  CB  PHE A  54      -4.512  49.232  13.209  1.00 24.56           A
ATOM    413  CG  PHE A  54      -5.487  48.362  13.939  1.00 24.61           A
ATOM    414  CD1 PHE A  54      -5.531  46.997  13.702  1.00 24.53           A
ATOM    415  CD2 PHE A  54      -6.373  48.914  14.860  1.00 25.39           A
ATOM    416  CE1 PHE A  54      -6.445  46.188  14.369  1.00 25.59           A
ATOM    417  CE2 PHE A  54      -7.293  48.117  15.534  1.00 25.70           A
ATOM    418  CZ  PHE A  54      -7.331  46.751  15.290  1.00 25.74           A
ATOM    419  C   PHE A  54      -5.090  48.356  10.914  1.00 26.94           A
ATOM    420  O   PHE A  54      -6.190  48.025  10.449  1.00 26.00           A
ATOM    421  N   ASP A  55      -3.969  47.688  10.690  1.00 27.26           A
ATOM    422  CA  ASP A  55      -3.942  46.499   9.874  1.00 29.10           A
ATOM    423  CB  ASP A  55      -2.609  46.437   9.149  1.00 31.91           A
ATOM    424  CG  ASP A  55      -2.741  45.879   7.774  1.00 35.21           A
ATOM    425  OD1 ASP A  55      -3.730  46.254   7.109  1.00 39.07           A
ATOM    426  OD2 ASP A  55      -1.869  45.083   7.352  1.00 36.16           A
ATOM    427  C   ASP A  55      -4.128  45.265  10.742  1.00 29.81           A
ATOM    428  O   ASP A  55      -3.484  45.128  11.787  1.00 29.86           A
ATOM    429  N   ARG A  56      -5.001  44.360  10.311  1.00 29.94           A
ATOM    430  CA  ARG A  56      -5.256  43.152  11.090  1.00 30.38           A
ATOM    431  CB  ARG A  56      -6.740  42.748  11.002  1.00 28.00           A
ATOM    432  CG  ARG A  56      -7.725  43.620  11.797  1.00 26.76           A
ATOM    433  CD  ARG A  56      -7.959  44.972  11.145  1.00 24.68           A
ATOM    434  NE  ARG A  56      -8.445  44.849   9.768  1.00 25.09           A
ATOM    435  CZ  ARG A  56      -9.669  44.454   9.426  1.00 24.83           A
ATOM    436  NH1 ARG A  56     -10.555  44.138  10.356  1.00 27.38           A
ATOM    437  NH2 ARG A  56     -10.014  44.368   8.152  1.00 25.72           A
ATOM    438  C   ARG A  56      -4.382  41.938  10.738  1.00 31.72           A
ATOM    439  O   ARG A  56      -4.316  41.493   9.586  1.00 31.92           A
ATOM    440  N   LEU A  57      -3.710  41.406  11.753  1.00 32.06           A
ATOM    441  CA  LEU A  57      -2.873  40.218  11.590  1.00 32.06           A
ATOM    442  CB  LEU A  57      -1.603  40.346  12.454  1.00 32.83           A
ATOM    443  CG  LEU A  57      -0.555  39.225  12.521  1.00 31.99           A
ATOM    444  CD1 LEU A  57       0.691  39.743  13.213  1.00 30.96           A
ATOM    445  CD2 LEU A  57      -1.113  38.022  13.268  1.00 32.49           A
ATOM    446  C   LEU A  57      -3.714  39.028  12.055  1.00 29.73           A
ATOM    447  O   LEU A  57      -4.311  39.083  13.124  1.00 30.62           A
ATOM    448  N   GLN A  58      -3.774  37.964  11.260  1.00 28.15           A
ATOM    449  CA  GLN A  58      -4.553  36.792  11.656  1.00 26.26           A
ATOM    450  CB  GLN A  58      -6.019  36.981  11.278  1.00 25.85           A
ATOM    451  CG  GLN A  58      -6.935  35.891  11.808  1.00 23.49           A
ATOM    452  CD  GLN A  58      -8.399  36.271  11.720  1.00 22.53           A
ATOM    453  OE1 GLN A  58      -8.893  36.656  10.657  1.00 23.32           A
ATOM    454  NE2 GLN A  58      -9.096  36.160  12.836  1.00 20.93           A
```

FIGURE 4- 7 -

```
ATOM   455  C    GLN A  58      -4.053  35.473  11.082  1.00 25.86      A
ATOM   456  O    GLN A  58      -4.035  35.275   9.872  1.00 25.13      A
ATOM   457  N    VAL A  59      -3.649  34.572  11.966  1.00 25.90      A
ATOM   458  CA   VAL A  59      -3.156  33.269  11.558  1.00 26.27      A
ATOM   459  CB   VAL A  59      -1.724  33.029  12.039  1.00 26.98      A
ATOM   460  CG1  VAL A  59      -1.210  31.705  11.490  1.00 25.10      A
ATOM   461  CG2  VAL A  59      -0.838  34.192  11.631  1.00 27.44      A
ATOM   462  C    VAL A  59      -4.028  32.245  12.240  1.00 27.11      A
ATOM   463  O    VAL A  59      -4.089  32.214  13.464  1.00 27.57      A
ATOM   464  N    LEU A  60      -4.691  31.404  11.456  1.00 27.28      A
ATOM   465  CA   LEU A  60      -5.562  30.384  12.019  1.00 28.02      A
ATOM   466  CB   LEU A  60      -6.707  30.084  11.050  1.00 27.34      A
ATOM   467  CG   LEU A  60      -7.623  31.266  10.725  1.00 26.22      A
ATOM   468  CD1  LEU A  60      -8.746  30.805   9.801  1.00 24.17      A
ATOM   469  CD2  LEU A  60      -8.180  31.847  12.019  1.00 24.31      A
ATOM   470  C    LEU A  60      -4.779  29.115  12.286  1.00 29.16      A
ATOM   471  O    LEU A  60      -3.641  28.986  11.845  1.00 32.09      A
ATOM   472  N    ASP A  61      -5.368  28.175  13.018  1.00 29.28      A
ATOM   473  CA   ASP A  61      -4.671  26.922  13.270  1.00 28.69      A
ATOM   474  CB   ASP A  61      -3.657  27.083  14.405  1.00 28.94      A
ATOM   475  CG   ASP A  61      -4.299  27.127  15.758  1.00 29.26      A
ATOM   476  OD1  ASP A  61      -5.301  27.846  15.916  1.00 27.31      A
ATOM   477  OD2  ASP A  61      -3.787  26.441  16.667  1.00 31.08      A
ATOM   478  C    ASP A  61      -5.643  25.787  13.559  1.00 29.17      A
ATOM   479  O    ASP A  61      -6.858  25.992  13.548  1.00 27.94      A
ATOM   480  N    ASP A  62      -5.108  24.589  13.798  1.00 29.43      A
ATOM   481  CA   ASP A  62      -5.942  23.421  14.045  1.00 29.41      A
ATOM   482  CB   ASP A  62      -5.076  22.183  14.248  1.00 31.28      A
ATOM   483  CG   ASP A  62      -4.390  21.734  12.969  1.00 33.08      A
ATOM   484  OD1  ASP A  62      -4.790  22.197  11.881  1.00 34.56      A
ATOM   485  OD2  ASP A  62      -3.458  20.906  13.048  1.00 34.60      A
ATOM   486  C    ASP A  62      -6.886  23.596  15.218  1.00 29.79      A
ATOM   487  O    ASP A  62      -8.038  23.150  15.170  1.00 28.66      A
ATOM   488  N    HIS A  63      -6.406  24.254  16.270  1.00 30.01      A
ATOM   489  CA   HIS A  63      -7.243  24.489  17.439  1.00 28.48      A
ATOM   490  CB   HIS A  63      -6.467  25.243  18.522  1.00 27.81      A
ATOM   491  CG   HIS A  63      -5.590  24.369  19.364  1.00 27.96      A
ATOM   492  CD2  HIS A  63      -4.291  24.492  19.726  1.00 28.21      A
ATOM   493  ND1  HIS A  63      -6.050  23.223  19.978  1.00 28.22      A
ATOM   494  CE1  HIS A  63      -5.074  22.679  20.683  1.00 27.18      A
ATOM   495  NE2  HIS A  63      -3.995  23.430  20.548  1.00 27.95      A
ATOM   496  C    HIS A  63      -8.455  25.302  17.002  1.00 27.92      A
ATOM   497  O    HIS A  63      -9.592  24.957  17.320  1.00 27.51      A
ATOM   498  N    TYR A  64      -8.197  26.373  16.255  1.00 26.59      A
ATOM   499  CA   TYR A  64      -9.254  27.250  15.762  1.00 26.76      A
ATOM   500  CB   TYR A  64      -8.664  28.374  14.926  1.00 27.48      A
ATOM   501  CG   TYR A  64      -9.696  29.311  14.353  1.00 27.60      A
ATOM   502  CD1  TYR A  64     -10.071  30.466  15.034  1.00 27.55      A
ATOM   503  CE1  TYR A  64     -11.016  31.339  14.496  1.00 27.06      A
ATOM   504  CD2  TYR A  64     -10.295  29.050  13.120  1.00 26.42      A
ATOM   505  CE2  TYR A  64     -11.235  29.912  12.578  1.00 23.71      A
ATOM   506  CZ   TYR A  64     -11.591  31.054  13.266  1.00 25.48      A
ATOM   507  OH   TYR A  64     -12.506  31.929  12.723  1.00 25.27      A
ATOM   508  C    TYR A  64     -10.248  26.501  14.908  1.00 26.86      A
ATOM   509  O    TYR A  64     -11.457  26.660  15.059  1.00 28.70      A
ATOM   510  N    ARG A  65      -9.728  25.693  13.995  1.00 27.66      A
ATOM   511  CA   ARG A  65     -10.569  24.913  13.102  1.00 26.12      A
ATOM   512  CB   ARG A  65      -9.725  24.309  11.976  1.00 26.62      A
ATOM   513  CG   ARG A  65      -9.329  25.321  10.891  1.00 26.52      A
ATOM   514  CD   ARG A  65      -8.442  24.697   9.813  1.00 26.10      A
ATOM   515  NE   ARG A  65      -7.109  24.354  10.318  1.00 27.30      A
ATOM   516  CZ   ARG A  65      -6.039  25.147  10.238  1.00 24.66      A
ATOM   517  NH1  ARG A  65      -6.115  26.348   9.665  1.00 21.50      A
ATOM   518  NH2  ARG A  65      -4.888  24.734  10.742  1.00 22.31      A
ATOM   519  C    ARG A  65     -11.332  23.836  13.856  1.00 25.64      A
ATOM   520  O    ARG A  65     -12.451  23.499  13.477  1.00 26.30      A
ATOM   521  N    ASP A  66     -10.761  23.299  14.930  1.00 24.42      A
ATOM   522  CA   ASP A  66     -11.492  22.275  15.681  1.00 24.46      A
ATOM   523  CB   ASP A  66     -10.597  21.575  16.712  1.00 23.85      A
ATOM   524  CG   ASP A  66      -9.485  20.774  16.083  1.00 25.84      A
ATOM   525  OD1  ASP A  66      -9.698  20.167  15.004  1.00 25.70      A
ATOM   526  OD2  ASP A  66      -8.391  20.742  16.687  1.00 27.11      A
ATOM   527  C    ASP A  66     -12.682  22.906  16.418  1.00 24.60      A
ATOM   528  O    ASP A  66     -13.796  22.369  16.407  1.00 21.84      A
ATOM   529  N    VAL A  67     -12.440  24.053  17.061  1.00 24.10      A
ATOM   530  CA   VAL A  67     -13.491  24.733  17.800  1.00 23.79      A
```

FIGURE 4- 8 -

| | | | | | | | | | |
|---|---|---|---|---|---|---|---|---|---|
| ATOM | 531 | CB | VAL A | 67 | -12.917 | 25.914 | 18.609 | 1.00 23.45 | A |
| ATOM | 532 | CG1 | VAL A | 67 | -14.029 | 26.669 | 19.318 | 1.00 23.00 | A |
| ATOM | 533 | CG2 | VAL A | 67 | -11.937 | 25.393 | 19.642 | 1.00 22.92 | A |
| ATOM | 534 | C | VAL A | 67 | -14.582 | 25.198 | 16.835 | 1.00 24.88 | A |
| ATOM | 535 | O | VAL A | 67 | -15.770 | 25.205 | 17.181 | 1.00 23.91 | A |
| ATOM | 536 | N | LEU A | 68 | -14.189 | 25.563 | 15.617 | 1.00 23.59 | A |
| ATOM | 537 | CA | LEU A | 68 | -15.169 | 25.986 | 14.627 | 1.00 23.49 | A |
| ATOM | 538 | CB | LEU A | 68 | -14.473 | 26.458 | 13.353 | 1.00 21.94 | A |
| ATOM | 539 | CG | LEU A | 68 | -15.380 | 26.984 | 12.235 | 1.00 20.36 | A |
| ATOM | 540 | CD1 | LEU A | 68 | -16.448 | 27.909 | 12.811 | 1.00 19.43 | A |
| ATOM | 541 | CD2 | LEU A | 68 | -14.538 | 27.707 | 11.205 | 1.00 16.66 | A |
| ATOM | 542 | C | LEU A | 68 | -16.124 | 24.838 | 14.304 | 1.00 24.92 | A |
| ATOM | 543 | O | LEU A | 68 | -17.340 | 25.013 | 14.332 | 1.00 25.95 | A |
| ATOM | 544 | N | LYS A | 69 | -15.569 | 23.665 | 14.006 | 1.00 26.56 | A |
| ATOM | 545 | CA | LYS A | 69 | -16.368 | 22.474 | 13.694 | 1.00 26.77 | A |
| ATOM | 546 | CB | LYS A | 69 | -15.478 | 21.236 | 13.524 | 1.00 29.85 | A |
| ATOM | 547 | CG | LYS A | 69 | -14.385 | 21.327 | 12.469 | 1.00 32.96 | A |
| ATOM | 548 | CD | LYS A | 69 | -14.926 | 21.292 | 11.045 | 1.00 34.28 | A |
| ATOM | 549 | CE | LYS A | 69 | -13.778 | 21.700 | 10.065 | 1.00 36.95 | A |
| ATOM | 550 | NZ | LYS A | 69 | -12.983 | 19.864 | 10.383 | 1.00 37.55 | A |
| ATOM | 551 | C | LYS A | 69 | -17.353 | 22.180 | 14.812 | 1.00 25.30 | A |
| ATOM | 552 | O | LYS A | 69 | -18.527 | 21.935 | 14.563 | 1.00 27.26 | A |
| ATOM | 553 | N | GLU A | 70 | -16.873 | 22.171 | 16.047 | 1.00 23.99 | A |
| ATOM | 554 | CA | GLU A | 70 | -17.757 | 21.907 | 17.173 | 1.00 24.51 | A |
| ATOM | 555 | CB | GLU A | 70 | -16.997 | 22.029 | 18.484 | 1.00 24.64 | A |
| ATOM | 556 | CG | GLU A | 70 | -16.151 | 20.831 | 18.807 | 1.00 26.36 | A |
| ATOM | 557 | CD | GLU A | 70 | -15.114 | 21.135 | 19.857 | 1.00 30.72 | A |
| ATOM | 558 | OE1 | GLU A | 70 | -15.442 | 21.849 | 20.836 | 1.00 32.61 | A |
| ATOM | 559 | OE2 | GLU A | 70 | -13.968 | 20.655 | 19.704 | 1.00 33.72 | A |
| ATOM | 560 | C | GLU A | 70 | -18.938 | 22.867 | 17.178 | 1.00 24.19 | A |
| ATOM | 561 | O | GLU A | 70 | -20.081 | 22.451 | 17.323 | 1.00 25.03 | A |
| ATOM | 562 | N | MET A | 71 | -18.657 | 24.156 | 17.012 | 1.00 23.15 | A |
| ATOM | 563 | CA | MET A | 71 | -19.706 | 25.168 | 16.991 | 1.00 20.72 | A |
| ATOM | 564 | CB | MET A | 71 | -19.078 | 26.555 | 16.873 | 1.00 20.75 | A |
| ATOM | 565 | CG | MET A | 71 | -18.321 | 26.955 | 18.112 | 1.00 20.19 | A |
| ATOM | 566 | SD | MET A | 71 | -17.300 | 28.379 | 17.861 | 1.00 21.96 | A |
| ATOM | 567 | CE | MET A | 71 | -16.478 | 29.680 | 18.143 | 1.00 20.84 | A |
| ATOM | 568 | C | MET A | 71 | -20.717 | 24.939 | 15.865 | 1.00 19.94 | A |
| ATOM | 569 | O | MET A | 71 | -21.925 | 25.083 | 16.076 | 1.00 17.58 | A |
| ATOM | 570 | N | LYS A | 72 | -20.219 | 24.588 | 14.677 | 1.00 18.54 | A |
| ATOM | 571 | CA | LYS A | 72 | -21.084 | 24.313 | 13.535 | 1.00 18.46 | A |
| ATOM | 572 | CB | LYS A | 72 | -20.242 | 23.943 | 12.312 | 1.00 16.78 | A |
| ATOM | 573 | CG | LYS A | 72 | -19.195 | 24.987 | 11.928 | 1.00 19.38 | A |
| ATOM | 574 | CD | LYS A | 72 | -19.480 | 25.649 | 10.585 | 1.00 17.43 | A |
| ATOM | 575 | CE | LYS A | 72 | -19.248 | 24.693 | 9.425 | 1.00 17.36 | A |
| ATOM | 576 | NZ | LYS A | 72 | -19.618 | 25.272 | 8.106 | 1.00 15.61 | A |
| ATOM | 577 | C | LYS A | 72 | -22.028 | 23.149 | 13.884 | 1.00 19.87 | A |
| ATOM | 578 | O | LYS A | 72 | -23.245 | 23.231 | 13.697 | 1.00 19.65 | A |
| ATOM | 579 | N | ALA A | 73 | -21.464 | 22.068 | 14.409 | 1.00 19.56 | A |
| ATOM | 580 | CA | ALA A | 73 | -22.260 | 20.909 | 14.770 | 1.00 19.67 | A |
| ATOM | 581 | CB | ALA A | 73 | -21.409 | 19.916 | 15.535 | 1.00 18.41 | A |
| ATOM | 582 | C | ALA A | 73 | -23.484 | 21.294 | 15.591 | 1.00 19.58 | A |
| ATOM | 583 | O | ALA A | 73 | -24.578 | 20.790 | 15.357 | 1.00 21.27 | A |
| ATOM | 584 | N | LYS A | 74 | -23.315 | 22.187 | 16.554 | 1.00 19.32 | A |
| ATOM | 585 | CA | LYS A | 74 | -24.450 | 22.587 | 17.364 | 1.00 20.79 | A |
| ATOM | 586 | CB | LYS A | 74 | -23.970 | 23.286 | 18.627 | 1.00 21.44 | A |
| ATOM | 587 | CG | LYS A | 74 | -23.378 | 22.331 | 19.621 | 1.00 22.69 | A |
| ATOM | 588 | CD | LYS A | 74 | -22.897 | 23.057 | 20.850 | 1.00 28.67 | A |
| ATOM | 589 | CE | LYS A | 74 | -22.366 | 22.075 | 21.876 | 1.00 30.35 | A |
| ATOM | 590 | NZ | LYS A | 74 | -23.433 | 21.094 | 22.220 | 1.00 35.10 | A |
| ATOM | 591 | C | LYS A | 74 | -25.390 | 23.489 | 16.577 | 1.00 21.58 | A |
| ATOM | 592 | O | LYS A | 74 | -26.603 | 23.450 | 16.768 | 1.00 21.55 | A |
| ATOM | 593 | N | ALA A | 75 | -24.817 | 24.288 | 15.682 | 1.00 22.14 | A |
| ATOM | 594 | CA | ALA A | 75 | -25.581 | 25.194 | 14.838 | 1.00 22.08 | A |
| ATOM | 595 | CB | ALA A | 75 | -24.663 | 25.854 | 13.838 | 1.00 21.27 | A |
| ATOM | 596 | C | ALA A | 75 | -26.641 | 24.397 | 14.105 | 1.00 22.66 | A |
| ATOM | 597 | O | ALA A | 75 | -27.801 | 24.802 | 14.024 | 1.00 22.82 | A |
| ATOM | 598 | N | SER A | 76 | -26.213 | 23.257 | 13.573 | 1.00 23.53 | A |
| ATOM | 599 | CA | SER A | 76 | -27.065 | 22.346 | 12.826 | 1.00 24.00 | A |
| ATOM | 600 | CB | SER A | 76 | -26.319 | 21.042 | 12.593 | 1.00 23.90 | A |
| ATOM | 601 | OG | SER A | 76 | -25.153 | 21.293 | 11.833 | 1.00 28.66 | A |
| ATOM | 602 | C | SER A | 76 | -28.405 | 22.043 | 13.478 | 1.00 23.89 | A |
| ATOM | 603 | O | SER A | 76 | -29.420 | 21.889 | 12.785 | 1.00 25.73 | A |
| ATOM | 604 | N | THR A | 77 | -28.417 | 21.962 | 14.800 | 1.00 21.54 | A |
| ATOM | 605 | CA | THR A | 77 | -29.646 | 21.647 | 15.507 | 1.00 21.27 | A |
| ATOM | 606 | CB | THR A | 77 | -29.365 | 21.317 | 16.986 | 1.00 22.56 | A |

FIGURE 4-9-

```
ATOM    607  CG1  THR A  77    -28.957  22.508  17.673  1.00 26.12    A
ATOM    608  CG2  THR A  77    -28.262  20.283  17.097  1.00 20.24    A
ATOM    609  C    THR A  77    -30.670  22.777  15.442  1.00 21.51    A
ATOM    610  O    THR A  77    -31.867  22.531  15.613  1.00 21.49    A
ATOM    611  N    VAL A  78    -30.211  24.004  15.189  1.00 20.04    A
ATOM    612  CA   VAL A  78    -31.114  25.157  15.121  1.00 20.54    A
ATOM    613  CB   VAL A  78    -30.355  26.495  15.302  1.00 21.47    A
ATOM    614  CG1  VAL A  78    -31.329  27.653  15.300  1.00 16.76    A
ATOM    615  CG2  VAL A  78    -29.589  26.482  16.592  1.00 23.78    A
ATOM    616  C    VAL A  78    -31.947  25.273  13.843  1.00 20.81    A
ATOM    617  O    VAL A  78    -31.480  24.971  12.739  1.00 20.05    A
ATOM    618  N    LYS A  79    -33.177  25.744  14.031  1.00 21.79    A
ATOM    619  CA   LYS A  79    -34.164  25.945  12.978  1.00 23.69    A
ATOM    620  CB   LYS A  79    -35.293  24.925  13.129  1.00 25.11    A
ATOM    621  CG   LYS A  79    -36.490  25.176  12.233  1.00 29.95    A
ATOM    622  CD   LYS A  79    -37.223  23.875  11.966  1.00 35.76    A
ATOM    623  CE   LYS A  79    -38.067  23.926  10.691  1.00 38.47    A
ATOM    624  NZ   LYS A  79    -38.372  22.523  10.215  1.00 42.10    A
ATOM    625  C    LYS A  79    -34.727  27.347  13.162  1.00 24.37    A
ATOM    626  O    LYS A  79    -35.556  27.570  14.041  1.00 26.03    A
ATOM    627  N    ALA A  80    -34.296  28.285  12.326  1.00 24.24    A
ATOM    628  CA   ALA A  80    -34.741  29.666  12.455  1.00 23.01    A
ATOM    629  CB   ALA A  80    -33.555  30.594  12.283  1.00 21.97    A
ATOM    630  C    ALA A  80    -35.868  30.092  11.522  1.00 24.50    A
ATOM    631  O    ALA A  80    -35.835  29.832  10.310  1.00 23.36    A
ATOM    632  N    LYS A  81    -36.857  30.767  12.104  1.00 24.89    A
ATOM    633  CA   LYS A  81    -38.009  31.262  11.365  1.00 27.54    A
ATOM    634  CB   LYS A  81    -39.227  31.361  12.295  1.00 30.88    A
ATOM    635  CG   LYS A  81    -38.971  32.248  13.517  1.00 37.88    A
ATOM    636  CD   LYS A  81    -40.226  32.590  14.333  1.00 41.11    A
ATOM    637  CE   LYS A  81    -39.853  33.490  15.535  1.00 42.87    A
ATOM    638  NZ   LYS A  81    -41.016  34.180  16.188  1.00 43.85    A
ATOM    639  C    LYS A  81    -37.734  32.644  10.755  1.00 27.67    A
ATOM    640  O    LYS A  81    -36.966  33.440  11.300  1.00 28.21    A
ATOM    641  N    LEU A  82    -38.371  32.911   9.620  1.00 26.35    A
ATOM    642  CA   LEU A  82    -38.253  34.186   8.924  1.00 24.81    A
ATOM    643  CB   LEU A  82    -38.458  33.968   7.428  1.00 23.61    A
ATOM    644  CG   LEU A  82    -38.436  35.149   6.462  1.00 24.67    A
ATOM    645  CD1  LEU A  82    -37.071  35.821   6.442  1.00 24.02    A
ATOM    646  CD2  LEU A  82    -38.785  34.632   5.077  1.00 24.20    A
ATOM    647  C    LEU A  82    -39.361  35.074   9.478  1.00 24.82    A
ATOM    648  O    LEU A  82    -40.518  34.700   9.427  1.00 27.00    A
ATOM    649  N    LEU A  83    -39.016  36.241  10.004  1.00 24.92    A
ATOM    650  CA   LEU A  83    -40.011  37.138  10.578  1.00 25.55    A
ATOM    651  CB   LEU A  83    -39.330  38.173  11.489  1.00 23.63    A
ATOM    652  CG   LEU A  83    -39.587  38.107  13.002  1.00 19.23    A
ATOM    653  CD1  LEU A  83    -39.278  36.741  13.532  1.00 18.74    A
ATOM    654  CD2  LEU A  83    -38.728  39.126  13.704  1.00 20.45    A
ATOM    655  C    LEU A  83    -40.847  37.856   9.528  1.00 28.66    A
ATOM    656  O    LEU A  83    -40.369  38.158   8.434  1.00 30.84    A
ATOM    657  N    SER A  84    -42.103  38.126   9.866  1.00 30.12    A
ATOM    658  CA   SER A  84    -43.011  38.827   8.964  1.00 32.61    A
ATOM    659  CB   SER A  84    -44.453  38.627   9.416  1.00 33.13    A
ATOM    660  OG   SER A  84    -44.662  39.206  10.697  1.00 33.77    A
ATOM    661  C    SER A  84    -42.694  40.314   9.016  1.00 34.28    A
ATOM    662  O    SER A  84    -42.112  40.786   9.993  1.00 33.96    A
ATOM    663  N    ILE A  85    -43.078  41.057   7.980  1.00 35.70    A
ATOM    664  CA   ILE A  85    -42.832  42.497   7.984  1.00 36.02    A
ATOM    665  CB   ILE A  85    -43.462  43.209   6.772  1.00 34.58    A
ATOM    666  CG2  ILE A  85    -43.442  44.706   6.990  1.00 34.25    A
ATOM    667  CG1  ILE A  85    -42.671  42.899   5.512  1.00 34.16    A
ATOM    668  CD1  ILE A  85    -43.145  43.676   4.313  1.00 34.84    A
ATOM    669  C    ILE A  85    -43.446  43.093   9.244  1.00 36.56    A
ATOM    670  O    ILE A  85    -42.841  43.935   9.907  1.00 36.34    A
ATOM    671  N    GLU A  86    -44.652  42.647   9.575  1.00 37.70    A
ATOM    672  CA   GLU A  86    -45.333  43.154  10.758  1.00 39.08    A
ATOM    673  CB   GLU A  86    -46.701  42.479  10.913  1.00 42.68    A
ATOM    674  CG   GLU A  86    -47.779  43.370  11.527  1.00 46.56    A
ATOM    675  CD   GLU A  86    -48.580  42.685  12.635  1.00 49.84    A
ATOM    676  OE1  GLU A  86    -49.649  43.228  13.004  1.00 51.23    A
ATOM    677  OE2  GLU A  86    -48.142  41.621  13.143  1.00 50.49    A
ATOM    678  C    GLU A  86    -44.482  42.912  12.009  1.00 37.72    A
ATOM    679  O    GLU A  86    -44.223  43.844  12.772  1.00 37.11    A
ATOM    680  N    GLU A  87    -44.036  41.669  12.200  1.00 35.93    A
ATOM    681  CA   GLU A  87    -43.216  41.303  13.359  1.00 35.48    A
ATOM    682  CB   GLU A  87    -42.843  39.823  13.306  1.00 36.48    A
```

FIGURE 4- 10 -

```
ATOM    683  CG  GLU A  87     -43.979  38.842  13.482  1.00 37.69       A
ATOM    684  CD  GLU A  87     -43.535  37.415  13.185  1.00 42.19       A
ATOM    685  OE1 GLU A  87     -43.163  37.144  12.020  1.00 42.44       A
ATOM    686  OE2 GLU A  87     -43.542  36.566  14.110  1.00 44.47       A
ATOM    687  C   GLU A  87     -41.930  42.120  13.466  1.00 34.16       A
ATOM    688  O   GLU A  87     -41.608  42.606  14.567  1.00 35.48       A
ATOM    689  N   ALA A  88     -41.191  42.255  12.387  1.00 32.39       A
ATOM    690  CA  ALA A  88     -39.943  43.012  12.387  1.00 30.71       A
ATOM    691  CB  ALA A  88     -39.259  42.884  11.044  1.00 28.57       A
ATOM    692  C   ALA A  88     -40.244  44.474  12.681  1.00 30.41       A
ATOM    693  O   ALA A  88     -39.480  45.168  13.360  1.00 28.74       A
ATOM    694  N   CYS A  89     -41.369  44.932  12.153  1.00 30.18       A
ATOM    695  CA  CYS A  89     -41.811  46.298  12.359  1.00 31.04       A
ATOM    696  CB  CYS A  89     -43.074  46.560  11.535  1.00 30.20       A
ATOM    697  SG  CYS A  89     -42.762  46.994   9.811  1.00 28.28       A
ATOM    698  C   CYS A  89     -42.084  46.594  13.841  1.00 31.88       A
ATOM    699  O   CYS A  89     -41.640  47.613  14.378  1.00 31.92       A
ATOM    700  N   LYS A  90     -42.807  45.698  14.503  1.00 31.24       A
ATOM    701  CA  LYS A  90     -43.133  45.895  15.906  1.00 33.01       A
ATOM    702  CB  LYS A  90     -44.076  44.781  16.378  1.00 35.14       A
ATOM    703  CG  LYS A  90     -44.578  44.963  17.803  1.00 40.06       A
ATOM    704  CD  LYS A  90     -45.419  43.781  18.290  1.00 42.15       A
ATOM    705  CE  LYS A  90     -45.987  44.054  19.686  1.00 42.47       A
ATOM    706  NZ  LYS A  90     -46.637  42.848  20.274  1.00 43.09       A
ATOM    707  C   LYS A  90     -41.878  45.939  16.786  1.00 32.57       A
ATOM    708  O   LYS A  90     -41.931  46.365  17.943  1.00 32.32       A
ATOM    709  N   LEU A  91     -40.750  45.504  16.230  1.00 32.04       A
ATOM    710  CA  LEU A  91     -39.480  45.482  16.956  1.00 30.17       A
ATOM    711  CB  LEU A  91     -38.591  44.360  16.423  1.00 27.88       A
ATOM    712  CG  LEU A  91     -38.947  42.935  16.844  1.00 27.48       A
ATOM    713  CD1 LEU A  91     -38.051  41.951  16.107  1.00 27.34       A
ATOM    714  CD2 LEU A  91     -38.781  42.781  18.343  1.00 25.26       A
ATOM    715  C   LEU A  91     -38.705  46.790  16.898  1.00 30.88       A
ATOM    716  O   LEU A  91     -37.802  47.011  17.698  1.00 31.60       A
ATOM    717  N   THR A  92     -39.056  47.661  15.960  1.00 31.92       A
ATOM    718  CA  THR A  92     -38.353  48.927  15.808  1.00 31.87       A
ATOM    719  CB  THR A  92     -38.715  49.565  14.477  1.00 32.70       A
ATOM    720  OG1 THR A  92     -38.474  48.617  13.432  1.00 32.98       A
ATOM    721  CG2 THR A  92     -37.878  50.822  14.235  1.00 33.69       A
ATOM    722  C   THR A  92     -38.612  49.938  16.920  1.00 32.67       A
ATOM    723  O   THR A  92     -39.756  50.285  17.209  1.00 33.90       A
ATOM    724  N   PRO A  93     -37.542  50.427  17.568  1.00 33.00       A
ATOM    725  CD  PRO A  93     -36.109  50.156  17.367  1.00 32.50       A
ATOM    726  CA  PRO A  93     -37.739  51.402  18.638  1.00 31.98       A
ATOM    727  CB  PRO A  93     -36.315  51.772  19.037  1.00 31.98       A
ATOM    728  CG  PRO A  93     -35.530  50.564  18.688  1.00 30.77       A
ATOM    729  C   PRO A  93     -38.488  52.589  18.063  1.00 32.38       A
ATOM    730  O   PRO A  93     -38.240  52.997  16.927  1.00 29.90       A
ATOM    731  N   PRO A  94     -39.423  53.152  18.838  1.00 35.04       A
ATOM    732  CD  PRO A  94     -39.897  52.694  20.159  1.00 35.68       A
ATOM    733  CA  PRO A  94     -40.204  54.302  18.382  1.00 34.87       A
ATOM    734  CB  PRO A  94     -41.022  54.669  19.619  1.00 32.95       A
ATOM    735  CG  PRO A  94     -41.268  53.336  20.245  1.00 33.44       A
ATOM    736  C   PRO A  94     -39.324  55.451  17.903  1.00 35.46       A
ATOM    737  O   PRO A  94     -39.690  56.176  16.985  1.00 36.99       A
ATOM    738  N   HIS A  95     -38.153  55.606  18.503  1.00 35.13       A
ATOM    739  CA  HIS A  95     -37.288  56.698  18.104  1.00 35.38       A
ATOM    740  CB  HIS A  95     -36.866  57.466  19.343  1.00 37.72       A
ATOM    741  CG  HIS A  95     -38.028  57.996  20.118  1.00 40.60       A
ATOM    742  CD2 HIS A  95     -39.099  58.723  19.722  1.00 40.61       A
ATOM    743  ND1 HIS A  95     -38.214  57.732  21.459  1.00 41.23       A
ATOM    744  CE1 HIS A  95     -39.353  58.270  21.854  1.00 43.00       A
ATOM    745  NE2 HIS A  95     -39.910  58.876  20.819  1.00 43.49       A
ATOM    746  C   HIS A  95     -36.079  56.305  17.276  1.00 35.14       A
ATOM    747  O   HIS A  95     -35.090  57.043  17.228  1.00 35.62       A
ATOM    748  N   SER A  96     -36.163  55.152  16.612  1.00 33.35       A
ATOM    749  CA  SER A  96     -35.075  54.684  15.760  1.00 31.83       A
ATOM    750  CB  SER A  96     -35.444  53.332  15.138  1.00 31.44       A
ATOM    751  OG  SER A  96     -34.325  52.715  14.513  1.00 29.56       A
ATOM    752  C   SER A  96     -34.854  55.734  14.660  1.00 31.55       A
ATOM    753  O   SER A  96     -35.779  56.451  14.279  1.00 31.55       A
ATOM    754  N   ALA A  97     -33.634  55.832  14.150  1.00 29.95       A
ATOM    755  CA  ALA A  97     -33.346  56.803  13.103  1.00 29.64       A
ATOM    756  CB  ALA A  97     -31.880  56.722  12.712  1.00 29.80       A
ATOM    757  C   ALA A  97     -34.222  56.594  11.876  1.00 30.37       A
ATOM    758  O   ALA A  97     -34.410  55.471  11.410  1.00 30.66       A
```

FIGURE 4- 11 -

```
ATOM    759  N    LYS A  98     -34.759  57.684  11.348  1.00 32.14           A
ATOM    760  CA   LYS A  98     -35.613  57.604  10.170  1.00 33.40           A
ATOM    761  CB   LYS A  98     -36.351  58.924   9.953  1.00 33.53           A
ATOM    762  CG   LYS A  98     -35.432  60.084   9.628  1.00 33.55           A
ATOM    763  CD   LYS A  98     -36.203  61.313   9.195  1.00 34.24           A
ATOM    764  CE   LYS A  98     -35.257  62.490   9.038  1.00 35.14           A
ATOM    765  NZ   LYS A  98     -35.975  63.725   8.649  1.00 38.05           A
ATOM    766  C    LYS A  98     -34.790  57.294   8.928  1.00 34.22           A
ATOM    767  O    LYS A  98     -33.588  57.562   8.879  1.00 34.93           A
ATOM    768  N    SER A  99     -35.456  56.734   7.925  1.00 34.32           A
ATOM    769  CA   SER A  99     -34.828  56.377   6.659  1.00 34.74           A
ATOM    770  CB   SER A  99     -35.700  55.353   5.922  1.00 36.68           A
ATOM    771  OG   SER A  99     -35.444  55.349   4.528  1.00 36.43           A
ATOM    772  C    SER A  99     -34.687  57.620   5.809  1.00 34.25           A
ATOM    773  O    SER A  99     -35.385  58.600   6.029  1.00 36.14           A
ATOM    774  N    LYS A 100     -33.785  57.595   4.842  1.00 34.35           A
ATOM    775  CA   LYS A 100     -33.637  58.751   3.978  1.00 36.34           A
ATOM    776  CB   LYS A 100     -32.196  58.874   3.462  1.00 36.39           A
ATOM    777  CG   LYS A 100     -31.700  57.704   2.609  1.00 38.67           A
ATOM    778  CD   LYS A 100     -30.162  57.745   2.414  1.00 40.23           A
ATOM    779  CE   LYS A 100     -29.401  57.522   3.743  1.00 40.36           A
ATOM    780  NZ   LYS A 100     -27.906  57.622   3.645  1.00 36.59           A
ATOM    781  C    LYS A 100     -34.609  58.579   2.816  1.00 37.76           A
ATOM    782  O    LYS A 100     -34.446  59.192   1.762  1.00 40.54           A
ATOM    783  N    PHE A 101     -35.637  57.759   3.021  1.00 36.80           A
ATOM    784  CA   PHE A 101     -36.609  57.499   1.970  1.00 35.94           A
ATOM    785  CB   PHE A 101     -36.561  56.013   1.593  1.00 34.92           A
ATOM    786  CG   PHE A 101     -35.221  55.577   1.059  1.00 33.00           A
ATOM    787  CD1  PHE A 101     -34.806  55.953  -0.218  1.00 32.47           A
ATOM    788  CD2  PHE A 101     -34.335  54.872   1.860  1.00 32.43           A
ATOM    789  CE1  PHE A 101     -33.519  55.640  -0.688  1.00 31.12           A
ATOM    790  CE2  PHE A 101     -33.045  54.556   1.398  1.00 33.48           A
ATOM    791  CZ   PHE A 101     -32.638  54.946   0.118  1.00 30.18           A
ATOM    792  C    PHE A 101     -38.037  57.942   2.296  1.00 37.42           A
ATOM    793  O    PHE A 101     -39.018  57.307   1.876  1.00 37.52           A
ATOM    794  N    GLY A 102     -38.143  59.037   3.044  1.00 37.25           A
ATOM    795  CA   GLY A 102     -39.442  59.594   3.375  1.00 36.31           A
ATOM    796  C    GLY A 102     -40.320  58.867   4.371  1.00 36.85           A
ATOM    797  O    GLY A 102     -41.528  58.743   4.152  1.00 37.79           A
ATOM    798  N    TYR A 103     -39.729  58.382   5.459  1.00 35.32           A
ATOM    799  CA   TYR A 103     -40.496  57.698   6.497  1.00 34.07           A
ATOM    800  CB   TYR A 103     -41.162  56.429   5.945  1.00 31.73           A
ATOM    801  CG   TYR A 103     -40.227  55.295   5.603  1.00 33.19           A
ATOM    802  CD1  TYR A 103     -39.907  54.313   6.547  1.00 32.09           A
ATOM    803  CE1  TYR A 103     -39.075  53.242   6.215  1.00 32.85           A
ATOM    804  CD2  TYR A 103     -39.685  55.179   4.323  1.00 33.12           A
ATOM    805  CE2  TYR A 103     -38.853  54.113   3.982  1.00 32.70           A
ATOM    806  CZ   TYR A 103     -38.555  53.147   4.926  1.00 33.36           A
ATOM    807  OH   TYR A 103     -37.773  52.077   4.551  1.00 32.48           A
ATOM    808  C    TYR A 103     -39.617  57.379   7.702  1.00 34.07           A
ATOM    809  O    TYR A 103     -38.406  57.189   7.568  1.00 34.90           A
ATOM    810  N    GLY A 104     -40.228  57.335   8.881  1.00 32.95           A
ATOM    811  CA   GLY A 104     -39.462  57.067  10.078  1.00 33.76           A
ATOM    812  C    GLY A 104     -39.934  55.929  10.954  1.00 35.25           A
ATOM    813  O    GLY A 104     -40.867  55.188  10.627  1.00 34.62           A
ATOM    814  N    ALA A 105     -39.265  55.802  12.090  1.00 36.66           A
ATOM    815  CA   ALA A 105     -39.560  54.759  13.054  1.00 38.81           A
ATOM    816  CB   ALA A 105     -38.790  55.020  14.338  1.00 39.38           A
ATOM    817  C    ALA A 105     -41.048  54.661  13.346  1.00 39.83           A
ATOM    818  O    ALA A 105     -41.616  53.568  13.360  1.00 39.19           A
ATOM    819  N    LYS A 106     -41.673  55.811  13.576  1.00 41.70           A
ATOM    820  CA   LYS A 106     -43.094  55.857  13.883  1.00 43.02           A
ATOM    821  CB   LYS A 106     -43.537  57.301  14.130  1.00 46.46           A
ATOM    822  CG   LYS A 106     -44.632  57.454  15.205  1.00 49.57           A
ATOM    823  CD   LYS A 106     -44.061  57.426  16.640  1.00 52.36           A
ATOM    824  CE   LYS A 106     -43.354  56.108  16.984  1.00 52.71           A
ATOM    825  NZ   LYS A 106     -44.262  54.923  16.877  1.00 53.66           A
ATOM    826  C    LYS A 106     -43.916  55.253  12.755  1.00 42.74           A
ATOM    827  O    LYS A 106     -44.836  54.481  13.008  1.00 42.95           A
ATOM    828  N    ASP A 107     -43.581  55.605  11.515  1.00 42.24           A
ATOM    829  CA   ASP A 107     -44.287  55.085  10.343  1.00 41.44           A
ATOM    830  CB   ASP A 107     -43.760  55.734   9.071  1.00 40.56           A
ATOM    831  CG   ASP A 107     -43.878  57.219   9.100  1.00 39.40           A
ATOM    832  OD1  ASP A 107     -45.002  57.710   9.326  1.00 41.41           A
ATOM    833  OD2  ASP A 107     -42.851  57.892   8.899  1.00 38.82           A
ATOM    834  C    ASP A 107     -44.127  53.579  10.207  1.00 42.14           A
```

FIGURE 4- 12 -

```
ATOM    835  C   ASP A 107     -45.069  52.877   9.849  1.00 41.75           A
ATOM    836  N   VAL A 108     -42.916  53.095  10.469  1.00 41.54           A
ATOM    837  CA  VAL A 108     -42.632  51.676  10.374  1.00 41.78           A
ATOM    838  CB  VAL A 108     -41.128  51.389  10.614  1.00 42.58           A
ATOM    839  CG1 VAL A 108     -40.915  49.895  10.848  1.00 43.27           A
ATOM    840  CG2 VAL A 108     -40.306  51.846   9.419  1.00 41.20           A
ATOM    841  C   VAL A 108     -43.450  50.885  11.390  1.00 42.34           A
ATOM    842  O   VAL A 108     -44.091  49.890  11.045  1.00 41.78           A
ATOM    843  N   ARG A 109     -43.417  51.327  12.645  1.00 42.82           A
ATOM    844  CA  ARG A 109     -44.146  50.652  13.720  1.00 43.27           A
ATOM    845  CB  ARG A 109     -43.895  51.349  15.058  1.00 43.05           A
ATOM    846  CG  ARG A 109     -42.435  51.467  15.468  1.00 43.50           A
ATOM    847  CD  ARG A 109     -42.324  52.112  16.841  1.00 43.01           A
ATOM    848  NE  ARG A 109     -43.252  51.485  17.775  1.00 43.50           A
ATOM    849  CZ  ARG A 109     -43.215  50.202  18.117  1.00 43.61           A
ATOM    850  NH1 ARG A 109     -42.286  49.402  17.609  1.00 43.81           A
ATOM    851  NH2 ARG A 109     -44.121  49.713  18.951  1.00 43.17           A
ATOM    852  C   ARG A 109     -45.646  50.654  13.451  1.00 43.86           A
ATOM    853  O   ARG A 109     -46.388  49.817  13.976  1.00 43.05           A
ATOM    854  N   ASN A 110     -46.069  51.602  12.617  1.00 43.75           A
ATOM    855  CA  ASN A 110     -47.467  51.789  12.262  1.00 42.60           A
ATOM    856  CB  ASN A 110     -47.766  53.288  12.243  1.00 44.98           A
ATOM    857  CG  ASN A 110     -49.249  53.592  12.231  1.00 48.82           A
ATOM    858  CD1 ASN A 110     -49.906  53.535  11.185  1.00 51.35           A
ATOM    859  ND2 ASN A 110     -49.791  53.916  13.405  1.00 50.84           A
ATOM    860  C   ASN A 110     -47.843  51.159  10.922  1.00 41.43           A
ATOM    861  O   ASN A 110     -48.869  51.494  10.342  1.00 42.35           A
ATOM    862  N   LEU A 111     -47.013  50.252  10.424  1.00 38.99           A
ATOM    863  CA  LEU A 111     -47.299  49.592   9.157  1.00 36.71           A
ATOM    864  CB  LEU A 111     -48.313  48.472   9.380  1.00 35.08           A
ATOM    865  CG  LEU A 111     -47.869  47.361  10.329  1.00 34.17           A
ATOM    866  CD1 LEU A 111     -49.004  46.364  10.521  1.00 33.90           A
ATOM    867  CD2 LEU A 111     -46.641  46.673   9.766  1.00 33.10           A
ATOM    868  C   LEU A 111     -47.815  50.526   8.055  1.00 36.15           A
ATOM    869  O   LEU A 111     -48.620  50.116   7.215  1.00 36.53           A
ATOM    870  N   SER A 112     -47.361  51.774   8.054  1.00 35.00           A
ATOM    871  CA  SER A 112     -47.791  52.712   7.026  1.00 36.02           A
ATOM    872  CB  SER A 112     -47.137  54.082   7.227  1.00 35.83           A
ATOM    873  OG  SER A 112     -46.009  54.250   6.384  1.00 36.32           A
ATOM    874  C   SER A 112     -47.403  52.162   5.652  1.00 36.79           A
ATOM    875  O   SER A 112     -46.399  51.463   5.506  1.00 36.81           A
ATOM    876  N   SER A 113     -48.198  52.497   4.644  1.00 37.80           A
ATOM    877  CA  SER A 113     -47.956  52.029   3.290  1.00 38.94           A
ATOM    878  CB  SER A 113     -49.030  52.560   2.347  1.00 40.76           A
ATOM    879  OG  SER A 113     -48.722  52.203   1.008  1.00 43.46           A
ATOM    880  C   SER A 113     -46.590  52.369   2.713  1.00 39.07           A
ATOM    881  O   SER A 113     -45.868  51.481   2.267  1.00 39.61           A
ATOM    882  N   ARG A 114     -46.222  53.642   2.701  1.00 38.94           A
ATOM    883  CA  ARG A 114     -44.931  53.978   2.130  1.00 39.04           A
ATOM    884  CB  ARG A 114     -44.619  55.470   2.284  1.00 39.68           A
ATOM    885  CG  ARG A 114     -43.222  55.831   1.766  1.00 42.99           A
ATOM    886  CD  ARG A 114     -43.033  57.325   1.637  1.00 45.26           A
ATOM    887  NE  ARG A 114     -43.954  57.861   0.646  1.00 48.75           A
ATOM    888  CZ  ARG A 114     -44.283  59.141   0.545  1.00 50.53           A
ATOM    889  NH1 ARG A 114     -43.759  60.030   1.386  1.00 49.26           A
ATOM    890  NH2 ARG A 114     -45.149  59.524  -0.390  1.00 51.01           A
ATOM    891  C   ARG A 114     -43.801  53.150   2.740  1.00 38.11           A
ATOM    892  O   ARG A 114     -43.031  52.509   2.016  1.00 37.95           A
ATOM    893  N   ALA A 115     -43.709  53.152   4.068  1.00 35.93           A
ATOM    894  CA  ALA A 115     -42.649  52.416   4.751  1.00 34.90           A
ATOM    895  CB  ALA A 115     -42.829  52.512   6.260  1.00 35.12           A
ATOM    896  C   ALA A 115     -42.629  50.962   4.316  1.00 33.83           A
ATOM    897  O   ALA A 115     -41.602  50.450   3.878  1.00 33.14           A
ATOM    898  N   VAL A 116     -43.776  50.308   4.429  1.00 32.94           A
ATOM    899  CA  VAL A 116     -43.894  48.917   4.051  1.00 32.46           A
ATOM    900  CB  VAL A 116     -45.348  48.419   4.210  1.00 31.28           A
ATOM    901  CG1 VAL A 116     -45.463  46.972   3.734  1.00 29.34           A
ATOM    902  CG2 VAL A 116     -45.763  48.522   5.672  1.00 29.84           A
ATOM    903  C   VAL A 116     -43.422  48.654   2.626  1.00 34.03           A
ATOM    904  O   VAL A 116     -42.695  47.697   2.385  1.00 36.17           A
ATOM    905  N   ASN A 117     -43.816  49.500   1.683  1.00 35.42           A
ATOM    906  CA  ASN A 117     -43.409  49.309   0.291  1.00 36.15           A
ATOM    907  CB  ASN A 117     -44.029  50.379  -0.604  1.00 37.94           A
ATOM    908  CG  ASN A 117     -45.543  50.298  -0.631  1.00 40.65           A
ATOM    909  CD1 ASN A 117     -46.120  49.232  -0.880  1.00 39.87           A
ATOM    910  ND2 ASN A 117     -46.199  51.426  -0.372  1.00 43.63           A
```

FIGURE 4- 13 -

```
ATOM    911  C   ASN A 117     -41.903  49.317   0.110  1.00 35.91      A
ATOM    912  O   ASN A 117     -41.352  48.437  -0.565  1.00 35.19      A
ATOM    913  N   HIS A 118     -41.240  50.311   0.708  1.00 35.63      A
ATOM    914  CA  HIS A 118     -39.787  50.417   0.605  1.00 34.43      A
ATOM    915  CB  HIS A 118     -39.277  51.716   1.247  1.00 37.10      A
ATOM    916  CG  HIS A 118     -39.674  52.951   0.492  1.00 42.08      A
ATOM    917  CD2 HIS A 118     -38.927  53.897  -0.129  1.00 42.46      A
ATOM    918  ND1 HIS A 118     -40.991  53.323   0.308  1.00 43.19      A
ATOM    919  CE1 HIS A 118     -41.038  54.444  -0.391  1.00 42.28      A
ATOM    920  NE2 HIS A 118     -39.799  54.814  -0.669  1.00 42.29      A
ATOM    921  C   HIS A 118     -39.142  49.197   1.245  1.00 31.66      A
ATOM    922  O   HIS A 118     -38.214  48.627   0.683  1.00 30.10      A
ATOM    923  N   ILE A 119     -39.637  48.776   2.404  1.00 29.04      A
ATOM    924  CA  ILE A 119     -39.079  47.595   3.037  1.00 28.93      A
ATOM    925  CB  ILE A 119     -39.865  47.230   4.320  1.00 27.00      A
ATOM    926  CG2 ILE A 119     -39.439  45.861   4.839  1.00 25.16      A
ATOM    927  CG1 ILE A 119     -39.600  48.291   5.386  1.00 25.24      A
ATOM    928  CD1 ILE A 119     -40.433  48.138   6.626  1.00 26.35      A
ATOM    929  C   ILE A 119     -39.144  46.442   2.014  1.00 29.82      A
ATOM    930  O   ILE A 119     -38.127  45.799   1.707  1.00 29.90      A
ATOM    931  N   ARG A 120     -40.341  46.208   1.482  1.00 27.58      A
ATOM    932  CA  ARG A 120     -40.565  45.170   0.490  1.00 25.30      A
ATOM    933  CB  ARG A 120     -41.941  45.341  -0.157  1.00 29.62      A
ATOM    934  CG  ARG A 120     -43.128  45.275   0.788  1.00 33.34      A
ATOM    935  CD  ARG A 120     -43.715  43.884   0.859  1.00 37.58      A
ATOM    936  NE  ARG A 120     -44.914  43.865   1.691  1.00 42.17      A
ATOM    937  CZ  ARG A 120     -46.049  44.486   1.382  1.00 44.51      A
ATOM    938  NH1 ARG A 120     -46.142  45.176   0.248  1.00 43.28      A
ATOM    939  NH2 ARG A 120     -47.090  44.424   2.214  1.00 46.13      A
ATOM    940  C   ARG A 120     -39.510  45.230  -0.602  1.00 21.85      A
ATOM    941  O   ARG A 120     -38.962  44.209  -0.997  1.00 19.85      A
ATOM    942  N   SER A 121     -39.229  46.426  -1.099  1.00 19.79      A
ATOM    943  CA  SER A 121     -38.244  46.551  -2.162  1.00 19.61      A
ATOM    944  CB  SER A 121     -38.384  47.897  -2.875  1.00 18.15      A
ATOM    945  OG  SER A 121     -38.369  48.954  -1.955  1.00 19.48      A
ATOM    946  C   SER A 121     -36.819  46.351  -1.686  1.00 18.65      A
ATOM    947  O   SER A 121     -36.033  45.714  -2.385  1.00 18.56      A
ATOM    948  N   VAL A 122     -36.492  46.888  -0.507  1.00 18.75      A
ATOM    949  CA  VAL A 122     -35.159  46.751   0.091  1.00 17.67      A
ATOM    950  CB  VAL A 122     -35.098  47.421   1.485  1.00 16.10      A
ATOM    951  CG1 VAL A 122     -33.926  46.901   2.287  1.00 15.96      A
ATOM    952  CG2 VAL A 122     -34.950  48.906   1.328  1.00 14.82      A
ATOM    953  C   VAL A 122     -34.889  45.262   0.237  1.00 19.33      A
ATOM    954  O   VAL A 122     -33.774  44.777  -0.014  1.00 19.36      A
ATOM    955  N   TRP A 123     -35.934  44.546   0.634  1.00 19.96      A
ATOM    956  CA  TRP A 123     -35.869  43.107   0.800  1.00 21.21      A
ATOM    957  CB  TRP A 123     -37.148  42.594   1.458  1.00 19.40      A
ATOM    958  CG  TRP A 123     -37.152  41.107   1.674  1.00 21.18      A
ATOM    959  CD2 TRP A 123     -36.528  40.387   2.754  1.00 21.52      A
ATOM    960  CE2 TRP A 123     -36.791  39.020   2.551  1.00 20.07      A
ATOM    961  CE3 TRP A 123     -35.772  40.768   3.871  1.00 22.11      A
ATOM    962  CD1 TRP A 123     -37.742  40.166   0.884  1.00 20.88      A
ATOM    963  NE1 TRP A 123     -37.532  38.910   1.403  1.00 19.95      A
ATOM    964  CZ2 TRP A 123     -36.325  38.034   3.424  1.00 18.71      A
ATOM    965  CZ3 TRP A 123     -35.313  39.785   4.731  1.00 20.47      A
ATOM    966  CH2 TRP A 123     -35.592  38.436   4.502  1.00 18.34      A
ATOM    967  C   TRP A 123     -35.694  42.432  -0.549  1.00 22.27      A
ATOM    968  O   TRP A 123     -34.837  41.568  -0.713  1.00 24.97      A
ATOM    969  N   GLU A 124     -36.507  42.828  -1.519  1.00 22.95      A
ATOM    970  CA  GLU A 124     -36.426  42.233  -2.837  1.00 23.55      A
ATOM    971  CB  GLU A 124     -37.532  42.782  -3.735  1.00 26.58      A
ATOM    972  CG  GLU A 124     -37.680  42.015  -5.030  1.00 34.18      A
ATOM    973  CD  GLU A 124     -37.612  40.500  -4.808  1.00 40.55      A
ATOM    974  OE1 GLU A 124     -38.081  40.036  -3.733  1.00 42.33      A
ATOM    975  OE2 GLU A 124     -37.102  39.779  -5.707  1.00 39.96      A
ATOM    976  C   GLU A 124     -35.065  42.487  -3.465  1.00 22.76      A
ATOM    977  O   GLU A 124     -34.637  41.748  -4.355  1.00 21.61      A
ATOM    978  N   ASP A 125     -34.385  43.534  -3.003  1.00 22.66      A
ATOM    979  CA  ASP A 125     -33.059  43.861  -3.525  1.00 22.10      A
ATOM    980  CB  ASP A 125     -32.704  45.322  -3.259  1.00 21.10      A
ATOM    981  CG  ASP A 125     -31.282  45.663  -3.691  1.00 23.56      A
ATOM    982  OD1 ASP A 125     -31.057  45.924  -4.894  1.00 23.33      A
ATOM    983  OD2 ASP A 125     -30.377  45.659  -2.827  1.00 21.51      A
ATOM    984  C   ASP A 125     -32.020  42.961  -2.871  1.00 21.91      A
ATOM    985  O   ASP A 125     -31.017  42.617  -3.484  1.00 22.59      A
ATOM    986  N   LEU A 126     -32.251  42.585  -1.619  1.00 20.90      A
```

FIGURE 4- 14 -

```
ATOM    987  CA   LEU A 126     -31.316  41.706  -0.945  1.00 20.32      A
ATOM    988  CB   LEU A 126     -31.664  41.589   0.535  1.00 20.58      A
ATOM    989  CG   LEU A 126     -31.164  42.775   1.363  1.00 23.65      A
ATOM    990  CD1  LEU A 126     -31.607  42.633   2.820  1.00 20.13      A
ATOM    991  CD2  LEU A 126     -29.633  42.847   1.241  1.00 22.83      A
ATOM    992  C    LEU A 126     -31.357  40.332  -1.596  1.00 21.28      A
ATOM    993  O    LEU A 126     -30.363  39.611  -1.605  1.00 21.03      A
ATOM    994  N    LEU A 127     -32.509  39.973  -2.152  1.00 21.36      A
ATOM    995  CA   LEU A 127     -32.648  38.673  -2.785  1.00 21.89      A
ATOM    996  CB   LEU A 127     -34.121  38.258  -2.831  1.00 22.00      A
ATOM    997  CG   LEU A 127     -34.849  38.086  -1.492  1.00 22.67      A
ATOM    998  CD1  LEU A 127     -36.261  37.600  -1.758  1.00 19.25      A
ATOM    999  CD2  LEU A 127     -34.110  37.089  -0.597  1.00 21.70      A
ATOM   1000  C    LEU A 127     -32.062  38.665  -4.188  1.00 22.20      A
ATOM   1001  O    LEU A 127     -31.838  37.625  -4.675  1.00 21.61      A
ATOM   1002  N    GLU A 128     -32.016  39.827  -4.830  1.00 23.96      A
ATOM   1003  CA   GLU A 128     -31.488  39.915  -6.188  1.00 24.77      A
ATOM   1004  CB   GLU A 128     -32.407  40.774  -7.041  1.00 26.89      A
ATOM   1005  CG   GLU A 128     -33.632  40.012  -7.480  1.00 30.91      A
ATOM   1006  CD   GLU A 128     -34.794  40.913  -7.766  1.00 33.51      A
ATOM   1007  OE1  GLU A 128     -35.920  40.383  -7.879  1.00 37.55      A
ATOM   1008  OE2  GLU A 128     -34.589  42.140  -7.878  1.00 34.24      A
ATOM   1009  C    GLU A 128     -30.068  40.405  -6.335  1.00 23.60      A
ATOM   1010  O    GLU A 128     -29.356  39.955  -7.225  1.00 22.24      A
ATOM   1011  N    ASP A 129     -29.858  41.332  -5.477  1.00 24.26      A
ATOM   1012  CA   ASP A 129     -28.301  41.859  -5.534  1.00 24.15      A
ATOM   1013  CB   ASP A 129     -28.292  43.371  -5.284  1.00 21.02      A
ATOM   1014  CG   ASP A 129     -27.040  44.049  -5.833  1.00 21.86      A
ATOM   1015  OD1  ASP A 129     -25.951  43.444  -5.784  1.00 20.89      A
ATOM   1016  OD2  ASP A 129     -27.134  45.201  -6.307  1.00 20.78      A
ATOM   1017  C    ASP A 129     -27.505  41.144  -4.449  1.00 25.05      A
ATOM   1018  O    ASP A 129     -27.753  41.337  -3.259  1.00 28.08      A
ATOM   1019  N    THR A 130     -26.554  40.313  -4.852  1.00 23.48      A
ATOM   1020  CA   THR A 130     -25.758  39.586  -3.883  1.00 23.17      A
ATOM   1021  CB   THR A 130     -25.570  38.137  -4.321  1.00 22.94      A
ATOM   1022  OG1  THR A 130     -24.862  38.103  -5.566  1.00 19.06      A
ATOM   1023  CG2  THR A 130     -26.918  37.451  -4.470  1.00 20.81      A
ATOM   1024  C    THR A 130     -24.383  40.199  -3.682  1.00 25.30      A
ATOM   1025  O    THR A 130     -23.576  39.665  -2.912  1.00 25.65      A
ATOM   1026  N    GLU A 131     -24.131  41.332  -4.341  1.00 26.43      A
ATOM   1027  CA   GLU A 131     -22.828  41.988  -4.275  1.00 28.31      A
ATOM   1028  CB   GLU A 131     -22.153  41.931  -5.639  1.00 37.86      A
ATOM   1029  CG   GLU A 131     -21.715  40.574  -6.101  1.00 40.78      A
ATOM   1030  CD   GLU A 131     -21.058  40.646  -7.480  1.00 45.86      A
ATOM   1031  OE1  GLU A 131     -20.506  41.730  -7.814  1.00 47.10      A
ATOM   1032  OE2  GLU A 131     -21.083  39.627  -8.216  1.00 46.06      A
ATOM   1033  C    GLU A 131     -22.714  43.430  -3.807  1.00 27.49      A
ATOM   1034  O    GLU A 131     -22.033  43.700  -2.831  1.00 28.85      A
ATOM   1035  N    THR A 132     -23.334  44.350  -4.543  1.00 25.95      A
ATOM   1036  CA   THR A 132     -23.259  45.787  -4.255  1.00 24.94      A
ATOM   1037  CB   THR A 132     -24.450  46.566  -4.887  1.00 27.56      A
ATOM   1038  OG1  THR A 132     -24.775  46.008  -6.172  1.00 29.48      A
ATOM   1039  CG2  THR A 132     -24.078  48.044  -5.056  1.00 24.37      A
ATOM   1040  C    THR A 132     -23.192  46.167  -2.783  1.00 23.31      A
ATOM   1041  O    THR A 132     -24.111  45.874  -2.014  1.00 21.90      A
ATOM   1042  N    PRO A 133     -22.093  46.830  -2.370  1.00 21.76      A
ATOM   1043  CD   PRO A 133     -20.851  47.068  -3.123  1.00 20.73      A
ATOM   1044  CA   PRO A 133     -21.929  47.247  -0.974  1.00 20.88      A
ATOM   1045  CB   PRO A 133     -20.648  48.061  -1.010  1.00 19.74      A
ATOM   1046  CG   PRO A 133     -19.838  47.296  -2.010  1.00 19.97      A
ATOM   1047  C    PRO A 133     -23.121  48.061  -0.557  1.00 20.07      A
ATOM   1048  O    PRO A 133     -23.700  48.768  -1.375  1.00 21.24      A
ATOM   1049  N    ILE A 134     -23.506  47.943   0.704  1.00 19.30      A
ATOM   1050  CA   ILE A 134     -24.652  48.680   1.202  1.00 19.97      A
ATOM   1051  CB   ILE A 134     -25.559  47.749   2.025  1.00 19.62      A
ATOM   1052  CG2  ILE A 134     -26.443  48.553   2.968  1.00 15.99      A
ATOM   1053  CG1  ILE A 134     -26.361  46.857   1.067  1.00 17.54      A
ATOM   1054  CD1  ILE A 134     -27.157  45.760   1.757  1.00 16.52      A
ATOM   1055  C    ILE A 134     -24.218  49.892   2.025  1.00 22.38      A
ATOM   1056  O    ILE A 134     -23.377  49.787   2.920  1.00 24.22      A
ATOM   1057  N    ASP A 135     -24.790  51.047   1.713  1.00 22.75      A
ATOM   1058  CA   ASP A 135     -24.437  52.262   2.414  1.00 24.16      A
ATOM   1059  CB   ASP A 135     -25.152  53.452   1.784  1.00 25.54      A
ATOM   1060  CG   ASP A 135     -24.740  54.769   2.410  1.00 30.13      A
ATOM   1061  OD1  ASP A 135     -23.569  55.179   2.224  1.00 31.12      A
ATOM   1062  OD2  ASP A 135     -25.582  55.387   3.098  1.00 32.19      A
```

FIGURE 4- 15 -

```
ATOM   1063  C   ASP A 135     -24.730  52.243   3.914  1.00 24.94      A
ATOM   1064  O   ASP A 135     -25.746  51.702   4.373  1.00 26.54      A
ATOM   1065  N   THR A 136     -23.822  52.844   4.674  1.00 24.33      A
ATOM   1066  CA  THR A 136     -23.971  52.959   6.118  1.00 23.72      A
ATOM   1067  CB  THR A 136     -23.043  51.998   6.888  1.00 23.71      A
ATOM   1068  OG1 THR A 136     -21.678  52.387   6.688  1.00 22.16      A
ATOM   1069  CG2 THR A 136     -23.244  50.566   6.416  1.00 23.96      A
ATOM   1070  C   THR A 136     -23.593  54.381   6.508  1.00 23.79      A
ATOM   1071  O   THR A 136     -22.777  55.020   5.851  1.00 22.97      A
ATOM   1072  N   THR A 137     -24.209  54.881   7.570  1.00 24.68      A
ATOM   1073  CA  THR A 137     -23.910  56.212   8.056  1.00 24.57      A
ATOM   1074  CB  THR A 137     -25.168  56.933   8.545  1.00 22.50      A
ATOM   1075  OG1 THR A 137     -26.060  57.118   7.444  1.00 23.76      A
ATOM   1076  CG2 THR A 137     -24.815  58.284   9.135  1.00 18.57      A
ATOM   1077  C   THR A 137     -22.986  56.013   9.234  1.00 26.65      A
ATOM   1078  O   THR A 137     -23.115  55.020   9.958  1.00 29.93      A
ATOM   1079  N   ILE A 138     -22.044  56.935   9.414  1.00 27.18      A
ATOM   1080  CA  ILE A 138     -21.116  56.856  10.533  1.00 27.14      A
ATOM   1081  CB  ILE A 138     -19.648  56.730  10.050  1.00 26.97      A
ATOM   1082  CG2 ILE A 138     -19.291  57.893   9.119  1.00 26.51      A
ATOM   1083  CG1 ILE A 138     -18.712  56.646  11.260  1.00 24.63      A
ATOM   1084  CD1 ILE A 138     -17.291  56.265  10.908  1.00 21.59      A
ATOM   1085  C   ILE A 138     -21.297  58.113  11.364  1.00 27.54      A
ATOM   1086  O   ILE A 138     -21.298  59.220  10.832  1.00 28.31      A
ATOM   1087  N   MET A 139     -21.470  57.925  12.670  1.00 28.59      A
ATOM   1088  CA  MET A 139     -21.692  59.025  13.605  1.00 28.15      A
ATOM   1089  CB  MET A 139     -23.156  59.056  14.036  1.00 26.73      A
ATOM   1090  CG  MET A 139     -24.098  59.408  12.926  1.00 28.86      A
ATOM   1091  SD  MET A 139     -23.772  61.087  12.414  1.00 33.49      A
ATOM   1092  CE  MET A 139     -25.180  61.939  13.197  1.00 33.60      A
ATOM   1093  C   MET A 139     -20.842  58.920  14.848  1.00 28.45      A
ATOM   1094  O   MET A 139     -20.371  57.843  15.205  1.00 28.67      A
ATOM   1095  N   ALA A 140     -20.649  60.059  15.504  1.00 30.37      A
ATOM   1096  CA  ALA A 140     -19.895  60.108  16.750  1.00 29.12      A
ATOM   1097  CB  ALA A 140     -19.283  61.486  16.954  1.00 27.19      A
ATOM   1098  C   ALA A 140     -20.961  59.836  17.799  1.00 28.71      A
ATOM   1099  O   ALA A 140     -22.028  60.451  17.786  1.00 27.94      A
ATOM   1100  N   LYS A 141     -20.684  58.893  18.686  1.00 29.52      A
ATOM   1101  CA  LYS A 141     -21.628  58.531  19.727  1.00 29.51      A
ATOM   1102  CB  LYS A 141     -21.308  57.132  20.224  1.00 31.62      A
ATOM   1103  CG  LYS A 141     -22.402  56.483  21.021  1.00 36.98      A
ATOM   1104  CD  LYS A 141     -22.015  55.046  21.324  1.00 40.07      A
ATOM   1105  CE  LYS A 141     -23.181  54.229  21.854  1.00 41.29      A
ATOM   1106  NZ  LYS A 141     -22.771  52.790  21.920  1.00 43.54      A
ATOM   1107  C   LYS A 141     -21.526  59.532  20.865  1.00 28.49      A
ATOM   1108  O   LYS A 141     -20.452  60.077  21.134  1.00 29.35      A
ATOM   1109  N   SER A 142     -22.646  59.792  21.524  1.00 27.44      A
ATOM   1110  CA  SER A 142     -22.656  60.735  22.640  1.00 25.00      A
ATOM   1111  CB  SER A 142     -23.775  61.752  22.464  1.00 23.32      A
ATOM   1112  OG  SER A 142     -23.695  62.743  23.463  1.00 20.94      A
ATOM   1113  C   SER A 142     -22.849  59.997  23.963  1.00 23.81      A
ATOM   1114  O   SER A 142     -23.963  59.597  24.304  1.00 22.39      A
ATOM   1115  N   GLU A 143     -21.756  59.817  24.697  1.00 22.68      A
ATOM   1116  CA  GLU A 143     -21.796  59.128  25.981  1.00 23.49      A
ATOM   1117  CB  GLU A 143     -21.038  57.790  25.911  1.00 23.96      A
ATOM   1118  CG  GLU A 143     -21.549  56.834  24.852  1.00 26.42      A
ATOM   1119  CD  GLU A 143     -20.697  55.576  24.733  1.00 29.47      A
ATOM   1120  OE1 GLU A 143     -19.453  55.691  24.815  1.00 29.37      A
ATOM   1121  OE2 GLU A 143     -21.270  54.478  24.539  1.00 30.45      A
ATOM   1122  C   GLU A 143     -21.179  60.000  27.067  1.00 22.57      A
ATOM   1123  O   GLU A 143     -20.187  60.694  26.834  1.00 22.40      A
ATOM   1124  N   VAL A 144     -21.778  59.951  28.251  1.00 22.30      A
ATOM   1125  CA  VAL A 144     -21.321  60.721  29.404  1.00 21.56      A
ATOM   1126  CB  VAL A 144     -22.527  61.095  30.292  1.00 21.34      A
ATOM   1127  CG1 VAL A 144     -22.065  61.558  31.664  1.00 19.76      A
ATOM   1128  CG2 VAL A 144     -23.355  62.176  29.596  1.00 18.44      A
ATOM   1129  C   VAL A 144     -20.289  59.959  30.242  1.00 23.13      A
ATOM   1130  O   VAL A 144     -20.334  58.728  30.360  1.00 23.49      A
ATOM   1131  N   PHE A 145     -19.353  60.701  30.821  1.00 24.08      A
ATOM   1132  CA  PHE A 145     -18.310  60.110  31.651  1.00 24.18      A
ATOM   1133  CB  PHE A 145     -17.128  59.666  30.792  1.00 22.21      A
ATOM   1134  CG  PHE A 145     -17.410  58.477  29.947  1.00 23.19      A
ATOM   1135  CD1 PHE A 145     -17.478  57.209  30.517  1.00 24.75      A
ATOM   1136  CD2 PHE A 145     -17.618  58.614  28.577  1.00 23.51      A
ATOM   1137  CE1 PHE A 145     -17.750  56.079  29.737  1.00 23.47      A
ATOM   1138  CE2 PHE A 145     -17.892  57.495  27.783  1.00 24.56      A
```

FIGURE 4- 16 -

```
ATOM   1139  CZ   PHE A 145     -17.957  56.222  28.372  1.00 24.07      A
ATOM   1140  C    PHE A 145     -17.816  61.149  32.635  1.00 26.17      A
ATOM   1141  O    PHE A 145     -18.229  62.311  32.578  1.00 26.64      A
ATOM   1142  N    CYS A 146     -16.933  60.717  33.535  1.00 27.24      A
ATOM   1143  CA   CYS A 146     -16.315  61.596  34.514  1.00 28.11      A
ATOM   1144  CB   CYS A 146     -16.424  60.996  35.917  1.00 27.48      A
ATOM   1145  SG   CYS A 146     -15.423  61.833  37.193  1.00 29.19      A
ATOM   1146  C    CYS A 146     -14.844  61.729  34.106  1.00 30.64      A
ATOM   1147  O    CYS A 146     -14.213  60.743  33.704  1.00 29.54      A
ATOM   1148  N    VAL A 147     -14.304  62.945  34.191  1.00 32.77      A
ATOM   1149  CA   VAL A 147     -12.908  63.189  33.834  1.00 34.90      A
ATOM   1150  CB   VAL A 147     -12.488  64.617  34.173  1.00 32.55      A
ATOM   1151  CG1  VAL A 147     -13.353  65.594  33.428  1.00 33.18      A
ATOM   1152  CG2  VAL A 147     -12.594  64.841  35.662  1.00 33.03      A
ATOM   1153  C    VAL A 147     -12.010  62.244  34.616  1.00 38.16      A
ATOM   1154  O    VAL A 147     -12.442  61.633  35.585  1.00 38.21      A
ATOM   1155  N    GLN A 148     -10.751  62.140  34.216  1.00 42.78      A
ATOM   1156  CA   GLN A 148      -9.837  61.251  34.909  1.00 47.81      A
ATOM   1157  CB   GLN A 148      -9.425  60.121  33.964  1.00 49.27      A
ATOM   1158  CG   GLN A 148     -10.595  59.233  33.544  1.00 52.21      A
ATOM   1159  CD   GLN A 148     -10.354  58.492  32.230  1.00 53.77      A
ATOM   1160  OE1  GLN A 148     -10.122  59.110  31.180  1.00 53.91      A
ATOM   1161  NE2  GLN A 148     -10.417  57.161  32.282  1.00 53.67      A
ATOM   1162  C    GLN A 148      -8.601  61.975  35.442  1.00 50.58      A
ATOM   1163  O    GLN A 148      -8.388  63.157  35.165  1.00 50.10      A
ATOM   1164  N    PRO A 149      -7.799  61.285  36.271  1.00 53.59      A
ATOM   1165  CD   PRO A 149      -8.145  60.068  37.032  1.00 54.30      A
ATOM   1166  CA   PRO A 149      -6.585  61.908  36.812  1.00 53.83      A
ATOM   1167  CB   PRO A 149      -6.174  60.949  37.933  1.00 54.39      A
ATOM   1168  CG   PRO A 149      -7.489  60.340  38.366  1.00 54.35      A
ATOM   1169  C    PRO A 149      -5.538  61.965  35.688  1.00 54.07      A
ATOM   1170  O    PRO A 149      -5.354  63.066  35.118  1.00 53.03      A
ATOM   1171  OXT  PRO A 149      -4.948  60.899  35.373  1.00 53.42      A
ATOM   1172  CB   ARG A 154     -11.414  63.640  27.933  1.00 43.41      A
ATOM   1173  CG   ARG A 154     -11.690  64.742  28.917  1.00 46.45      A
ATOM   1174  CD   ARG A 154     -12.550  65.810  28.291  1.00 49.79      A
ATOM   1175  NE   ARG A 154     -12.889  66.845  29.260  1.00 52.69      A
ATOM   1176  CZ   ARG A 154     -13.783  67.803  29.041  1.00 55.35      A
ATOM   1177  NH1  ARG A 154     -14.432  67.857  27.881  1.00 56.90      A
ATOM   1178  NH2  ARG A 154     -14.030  68.708  29.980  1.00 55.64      A
ATOM   1179  C    ARG A 154     -10.902  61.264  27.533  1.00 42.32      A
ATOM   1180  O    ARG A 154      -9.863  61.027  26.921  1.00 43.90      A
ATOM   1181  N    ARG A 154      -9.632  62.534  29.275  1.00 43.26      A
ATOM   1182  CA   ARG A 154     -10.951  62.346  28.590  1.00 43.80      A
ATOM   1183  N    LYS A 155     -12.032  60.604  27.324  1.00 40.07      A
ATOM   1184  CA   LYS A 155     -12.114  59.547  26.331  1.00 38.41      A
ATOM   1185  CB   LYS A 155     -13.054  58.441  26.807  1.00 38.58      A
ATOM   1186  CG   LYS A 155     -12.668  57.822  28.130  1.00 41.40      A
ATOM   1187  CD   LYS A 155     -13.634  56.719  28.536  1.00 40.79      A
ATOM   1188  CE   LYS A 155     -13.181  56.070  29.828  1.00 42.38      A
ATOM   1189  NZ   LYS A 155     -14.184  55.122  30.380  1.00 44.32      A
ATOM   1190  C    LYS A 155     -12.658  60.113  25.028  1.00 36.50      A
ATOM   1191  O    LYS A 155     -13.514  60.994  25.038  1.00 37.12      A
ATOM   1192  N    PRO A 156     -12.147  59.635  23.885  1.00 33.82      A
ATOM   1193  CD   PRO A 156     -10.959  58.784  23.717  1.00 31.39      A
ATOM   1194  CA   PRO A 156     -12.631  60.119  22.588  1.00 31.56      A
ATOM   1195  CB   PRO A 156     -11.527  59.693  21.638  1.00 30.79      A
ATOM   1196  CG   PRO A 156     -11.041  58.432  22.263  1.00 31.79      A
ATOM   1197  C    PRO A 156     -13.949  59.409  22.295  1.00 30.68      A
ATOM   1198  O    PRO A 156     -14.155  58.280  22.748  1.00 31.27      A
ATOM   1199  N    ALA A 157     -14.843  60.052  21.555  1.00 28.16      A
ATOM   1200  CA   ALA A 157     -16.125  59.427  21.245  1.00 27.22      A
ATOM   1201  CB   ALA A 157     -16.971  60.360  20.404  1.00 26.16      A
ATOM   1202  C    ALA A 157     -15.966  58.101  20.514  1.00 27.38      A
ATOM   1203  O    ALA A 157     -15.037  57.929  19.725  1.00 27.57      A
ATOM   1204  N    ARG A 158     -16.859  57.152  20.793  1.00 28.59      A
ATOM   1205  CA   ARG A 158     -16.823  55.874  20.089  1.00 28.54      A
ATOM   1206  CB   ARG A 158     -17.479  54.739  20.919  1.00 30.11      A
ATOM   1207  CG   ARG A 158     -16.525  54.100  21.967  1.00 33.90      A
ATOM   1208  CD   ARG A 158     -16.807  52.602  22.305  1.00 35.97      A
ATOM   1209  NE   ARG A 158     -15.582  51.889  22.737  1.00 40.58      A
ATOM   1210  CZ   ARG A 158     -15.469  50.564  22.899  1.00 40.24      A
ATOM   1211  NH1  ARG A 158     -16.510  49.770  22.674  1.00 43.76      A
ATOM   1212  NH2  ARG A 158     -14.313  50.021  23.264  1.00 33.72      A
ATOM   1213  C    ARG A 158     -17.601  56.161  18.794  1.00 27.37      A
ATOM   1214  O    ARG A 158     -18.424  57.084  18.755  1.00 26.66      A
```

FIGURE 4- 17 -

```
ATOM   1215  N    LEU A 159     -17.320  55.407  17.735  1.00 25.20           A
ATOM   1216  CA   LEU A 159     -17.985  55.614  16.446  1.00 24.37           A
ATOM   1217  CB   LEU A 159     -16.951  55.552  15.311  1.00 23.96           A
ATOM   1218  CG   LEU A 159     -15.890  56.636  15.044  1.00 22.89           A
ATOM   1219  CD1  LEU A 159     -15.968  57.803  16.011  1.00 21.45           A
ATOM   1220  CD2  LEU A 159     -14.544  55.980  15.114  1.00 22.38           A
ATOM   1221  C    LEU A 159     -19.081  54.592  16.142  1.00 24.03           A
ATOM   1222  O    LEU A 159     -18.823  53.392  16.150  1.00 26.49           A
ATOM   1223  N    ILE A 160     -20.296  55.041  15.855  1.00 22.60           A
ATOM   1224  CA   ILE A 160     -21.345  54.084  15.526  1.00 22.31           A
ATOM   1225  CB   ILE A 160     -22.646  54.423  16.226  1.00 24.16           A
ATOM   1226  CG2  ILE A 160     -22.411  54.460  17.726  1.00 26.81           A
ATOM   1227  CG1  ILE A 160     -23.142  55.792  15.776  1.00 25.27           A
ATOM   1228  CD1  ILE A 160     -24.429  56.211  16.450  1.00 26.78           A
ATOM   1229  C    ILE A 160     -21.567  54.048  14.023  1.00 22.70           A
ATOM   1230  O    ILE A 160     -21.489  55.074  13.346  1.00 22.33           A
ATOM   1231  N    VAL A 161     -21.835  52.858  13.500  1.00 23.25           A
ATOM   1232  CA   VAL A 161     -22.049  52.672  12.065  1.00 22.59           A
ATOM   1233  CB   VAL A 161     -20.838  51.958  11.438  1.00 19.60           A
ATOM   1234  CG1  VAL A 161     -21.086  51.684   9.970  1.00 17.94           A
ATOM   1235  CG2  VAL A 161     -19.603  52.804  11.626  1.00 17.16           A
ATOM   1236  C    VAL A 161     -23.306  51.841  11.822  1.00 24.58           A
ATOM   1237  O    VAL A 161     -23.418  50.711  12.315  1.00 24.95           A
ATOM   1238  N    PHE A 162     -24.245  52.385  11.052  1.00 24.90           A
ATOM   1239  CA   PHE A 162     -25.497  51.667  10.790  1.00 25.56           A
ATOM   1240  CB   PHE A 162     -26.551  52.055  11.832  1.00 22.77           A
ATOM   1241  CG   PHE A 162     -26.751  53.544  11.959  1.00 21.05           A
ATOM   1242  CD1  PHE A 162     -25.846  54.328  12.684  1.00 19.85           A
ATOM   1243  CD2  PHE A 162     -27.820  54.170  11.326  1.00 19.03           A
ATOM   1244  CE1  PHE A 162     -26.002  55.706  12.773  1.00 16.56           A
ATOM   1245  CE2  PHE A 162     -27.985  55.550  11.410  1.00 17.23           A
ATOM   1246  CZ   PHE A 162     -27.071  56.317  12.137  1.00 17.59           A
ATOM   1247  C    PHE A 162     -26.064  51.945   9.407  1.00 26.39           A
ATOM   1248  O    PHE A 162     -25.812  53.008   8.830  1.00 29.15           A
ATOM   1249  N    PRO A 163     -26.835  50.988   8.854  1.00 25.80           A
ATOM   1250  CD   PRO A 163     -26.993  49.614   9.360  1.00 26.10           A
ATOM   1251  CA   PRO A 163     -27.456  51.112   7.536  1.00 25.31           A
ATOM   1252  CB   PRO A 163     -27.657  49.666   7.116  1.00 26.42           A
ATOM   1253  CG   PRO A 163     -28.022  49.028   8.397  1.00 25.90           A
ATOM   1254  C    PRO A 163     -28.771  51.824   7.723  1.00 25.11           A
ATOM   1255  O    PRO A 163     -29.144  52.146   8.846  1.00 24.14           A
ATOM   1256  N    ASP A 164     -29.476  52.039   6.619  1.00 26.17           A
ATOM   1257  CA   ASP A 164     -30.755  52.728   6.621  1.00 25.56           A
ATOM   1258  CB   ASP A 164     -31.159  53.018   5.186  1.00 26.80           A
ATOM   1259  CG   ASP A 164     -32.405  53.846   5.096  1.00 29.33           A
ATOM   1260  OD1  ASP A 164     -32.317  55.073   5.323  1.00 28.83           A
ATOM   1261  OD2  ASP A 164     -33.474  53.262   4.808  1.00 33.07           A
ATOM   1262  C    ASP A 164     -31.845  51.914   7.312  1.00 27.28           A
ATOM   1263  O    ASP A 164     -31.817  50.683   7.287  1.00 27.46           A
ATOM   1264  N    LEU A 165     -32.807  52.600   7.928  1.00 27.63           A
ATOM   1265  CA   LEU A 165     -33.890  51.918   8.622  1.00 27.87           A
ATOM   1266  CB   LEU A 165     -34.981  52.912   9.031  1.00 29.29           A
ATOM   1267  CG   LEU A 165     -36.286  52.265   9.532  1.00 30.74           A
ATOM   1268  CD1  LEU A 165     -36.019  51.414  10.766  1.00 31.54           A
ATOM   1269  CD2  LEU A 165     -37.304  53.346   9.845  1.00 32.77           A
ATOM   1270  C    LEU A 165     -34.515  50.802   7.789  1.00 28.33           A
ATOM   1271  O    LEU A 165     -34.915  49.767   8.333  1.00 27.82           A
ATOM   1272  N    GLY A 166     -34.625  51.016   6.477  1.00 27.62           A
ATOM   1273  CA   GLY A 166     -35.199  49.992   5.619  1.00 26.21           A
ATOM   1274  C    GLY A 166     -34.441  48.677   5.740  1.00 25.32           A
ATOM   1275  O    GLY A 166     -35.036  47.608   5.870  1.00 25.12           A
ATOM   1276  N    VAL A 167     -33.115  48.762   5.707  1.00 24.03           A
ATOM   1277  CA   VAL A 167     -32.262  47.589   5.821  1.00 21.35           A
ATOM   1278  CB   VAL A 167     -30.785  47.974   5.564  1.00 19.66           A
ATOM   1279  CG1  VAL A 167     -29.858  46.918   6.100  1.00 18.23           A
ATOM   1280  CG2  VAL A 167     -30.551  48.142   4.069  1.00 17.45           A
ATOM   1281  C    VAL A 167     -32.408  46.937   7.195  1.00 21.23           A
ATOM   1282  O    VAL A 167     -32.515  45.716   7.317  1.00 20.64           A
ATOM   1283  N    ARG A 168     -32.431  47.752   8.235  1.00 21.79           A
ATOM   1284  CA   ARG A 168     -32.561  47.215   9.578  1.00 23.32           A
ATOM   1285  CB   ARG A 168     -32.531  48.354  10.593  1.00 21.24           A
ATOM   1286  CG   ARG A 168     -31.262  49.186  10.482  1.00 19.07           A
ATOM   1287  CD   ARG A 168     -30.970  49.947  11.751  1.00 17.59           A
ATOM   1288  NE   ARG A 168     -31.954  50.983  12.031  1.00 18.26           A
ATOM   1289  CZ   ARG A 168     -31.958  52.196  11.479  1.00 18.07           A
ATOM   1290  NH1  ARG A 168     -31.030  52.547  10.598  1.00 16.79           A
```

FIGURE 4- 18 -

```
ATOM   1291  NH2  ARG A 168     -32.880  53.078  11.836  1.00 16.52      A
ATOM   1292  C    ARG A 168     -33.818  46.356   9.741  1.00 24.76      A
ATOM   1293  O    ARG A 168     -33.769  45.288  10.363  1.00 26.94      A
ATOM   1294  N    VAL A 169     -34.940  46.791   9.179  1.00 24.26      A
ATOM   1295  CA   VAL A 169     -36.160  45.984   9.282  1.00 22.63      A
ATOM   1296  CB   VAL A 169     -37.398  46.729   8.697  1.00 21.09      A
ATOM   1297  CG1  VAL A 169     -38.649  45.874   8.842  1.00 17.46      A
ATOM   1298  CG2  VAL A 169     -37.594  48.047   9.423  1.00 16.34      A
ATOM   1299  C    VAL A 169     -35.948  44.652   8.544  1.00 22.44      A
ATOM   1300  O    VAL A 169     -36.374  43.599   9.014  1.00 20.97      A
ATOM   1301  N    CYS A 170     -35.276  44.692   7.397  1.00 22.93      A
ATOM   1302  CA   CYS A 170     -35.012  43.457   6.659  1.00 24.13      A
ATOM   1303  CB   CYS A 170     -34.411  43.763   5.286  1.00 22.90      A
ATOM   1304  SG   CYS A 170     -35.490  44.689   4.183  1.00 24.89      A
ATOM   1305  C    CYS A 170     -34.066  42.532   7.451  1.00 24.98      A
ATOM   1306  O    CYS A 170     -34.223  41.307   7.427  1.00 24.19      A
ATOM   1307  N    GLU A 171     -33.084  43.108   8.146  1.00 24.51      A
ATOM   1308  CA   GLU A 171     -32.166  42.299   8.936  1.00 23.98      A
ATOM   1309  CB   GLU A 171     -31.188  43.165   9.730  1.00 23.58      A
ATOM   1310  CG   GLU A 171     -30.057  43.827   8.983  1.00 23.56      A
ATOM   1311  CD   GLU A 171     -29.151  44.603   9.939  1.00 25.19      A
ATOM   1312  OE1  GLU A 171     -28.313  43.983  10.630  1.00 22.37      A
ATOM   1313  OE2  GLU A 171     -29.295  45.842  10.015  1.00 28.18      A
ATOM   1314  C    GLU A 171     -32.991  41.506   9.944  1.00 25.58      A
ATOM   1315  O    GLU A 171     -32.820  40.294  10.089  1.00 26.06      A
ATOM   1316  N    LYS A 172     -33.876  42.206  10.655  1.00 25.75      A
ATOM   1317  CA   LYS A 172     -34.710  41.572  11.669  1.00 26.46      A
ATOM   1318  CB   LYS A 172     -35.680  42.584  12.277  1.00 26.33      A
ATOM   1319  CG   LYS A 172     -35.037  43.630  13.144  1.00 27.62      A
ATOM   1320  CD   LYS A 172     -36.021  44.746  13.472  1.00 27.67      A
ATOM   1321  CE   LYS A 172     -35.391  45.809  14.371  1.00 27.65      A
ATOM   1322  NZ   LYS A 172     -34.100  46.317  13.835  1.00 25.85      A
ATOM   1323  C    LYS A 172     -35.499  40.397  11.108  1.00 27.58      A
ATOM   1324  O    LYS A 172     -35.604  39.348  11.758  1.00 28.63      A
ATOM   1325  N    MET A 173     -36.063  40.575   9.912  1.00 26.13      A
ATOM   1326  CA   MET A 173     -36.846  39.520   9.272  1.00 25.91      A
ATOM   1327  CB   MET A 173     -37.461  40.022   7.964  1.00 26.68      A
ATOM   1328  CG   MET A 173     -38.674  40.902   8.153  1.00 28.71      A
ATOM   1329  SD   MET A 173     -39.362  41.443   6.600  1.00 29.74      A
ATOM   1330  CE   MET A 173     -38.339  42.852   6.282  1.00 29.27      A
ATOM   1331  C    MET A 173     -36.021  38.277   8.971  1.00 24.60      A
ATOM   1332  O    MET A 173     -36.483  37.153   9.139  1.00 24.56      A
ATOM   1333  N    ALA A 174     -34.790  38.490   8.538  1.00 22.02      A
ATOM   1334  CA   ALA A 174     -33.929  37.391   8.180  1.00 20.40      A
ATOM   1335  CB   ALA A 174     -33.078  37.809   6.988  1.00 19.25      A
ATOM   1336  C    ALA A 174     -33.035  36.853   9.301  1.00 20.29      A
ATOM   1337  O    ALA A 174     -32.631  35.692   9.259  1.00 18.93      A
ATOM   1338  N    LEU A 175     -32.755  37.665  10.315  1.00 19.46      A
ATOM   1339  CA   LEU A 175     -31.843  37.218  11.350  1.00 20.95      A
ATOM   1340  CB   LEU A 175     -30.491  37.890  11.112  1.00 22.21      A
ATOM   1341  CG   LEU A 175     -29.576  37.304  10.038  1.00 22.26      A
ATOM   1342  CD1  LEU A 175     -28.543  38.330   9.617  1.00 21.83      A
ATOM   1343  CD2  LEU A 175     -28.908  36.069  10.594  1.00 22.36      A
ATOM   1344  C    LEU A 175     -32.213  37.367  12.823  1.00 22.27      A
ATOM   1345  O    LEU A 175     -31.504  36.847  13.690  1.00 22.53      A
ATOM   1346  N    TYR A 176     -33.292  38.077  13.124  1.00 22.05      A
ATOM   1347  CA   TYR A 176     -33.681  38.259  14.519  1.00 21.16      A
ATOM   1348  CB   TYR A 176     -35.021  39.000  14.614  1.00 22.30      A
ATOM   1349  CG   TYR A 176     -35.469  39.232  16.046  1.00 24.78      A
ATOM   1350  CD1  TYR A 176     -34.862  40.209  16.842  1.00 24.42      A
ATOM   1351  CE1  TYR A 176     -35.225  40.375  18.174  1.00 26.42      A
ATOM   1352  CD2  TYR A 176     -36.457  38.428  16.629  1.00 24.98      A
ATOM   1353  CE2  TYR A 176     -36.821  38.584  17.963  1.00 23.86      A
ATOM   1354  CZ   TYR A 176     -36.204  39.557  18.725  1.00 26.82      A
ATOM   1355  OH   TYR A 176     -36.565  39.715  20.042  1.00 30.26      A
ATOM   1356  C    TYR A 176     -33.783  36.925  15.260  1.00 19.07      A
ATOM   1357  O    TYR A 176     -33.284  36.770  16.362  1.00 17.71      A
ATOM   1358  N    ASP A 177     -34.431  35.954  14.647  1.00 20.35      A
ATOM   1359  CA   ASP A 177     -34.575  34.654  15.285  1.00 22.47      A
ATOM   1360  CB   ASP A 177     -35.522  33.766  14.477  1.00 22.99      A
ATOM   1361  CG   ASP A 177     -36.184  32.739  15.328  1.00 22.27      A
ATOM   1362  OD1  ASP A 177     -36.700  33.133  16.390  1.00 27.52      A
ATOM   1363  OD2  ASP A 177     -36.190  31.555  14.952  1.00 25.70      A
ATOM   1364  C    ASP A 177     -33.218  33.968  15.422  1.00 22.97      A
ATOM   1365  O    ASP A 177     -32.905  33.372  16.458  1.00 20.84      A
ATOM   1366  N    VAL A 178     -32.416  34.052  14.366  1.00 22.92      A
```

FIGURE 4- 19 -

```
ATOM   1367  CA   VAL A 178    -31.103  33.441  14.402  1.00 23.34      A
ATOM   1368  CB   VAL A 178    -30.333  33.650  13.079  1.00 22.41      A
ATOM   1369  CG1  VAL A 178    -28.922  33.089  13.204  1.00 19.34      A
ATOM   1370  CG2  VAL A 178    -31.067  32.960  11.939  1.00 21.50      A
ATOM   1371  C    VAL A 178    -30.268  33.999  15.545  1.00 23.93      A
ATOM   1372  O    VAL A 178    -29.709  33.235  16.331  1.00 26.40      A
ATOM   1373  N    VAL A 179    -30.186  35.321  15.650  1.00 22.60      A
ATOM   1374  CA   VAL A 179    -29.384  35.924  16.701  1.00 22.36      A
ATOM   1375  CB   VAL A 179    -29.087  37.400  16.415  1.00 22.94      A
ATOM   1376  CG1  VAL A 179    -28.549  37.554  15.017  1.00 23.13      A
ATOM   1377  CG2  VAL A 179    -30.341  38.237  16.624  1.00 26.45      A
ATOM   1378  C    VAL A 179    -30.002  35.831  18.086  1.00 21.74      A
ATOM   1379  O    VAL A 179    -29.328  36.101  19.074  1.00 22.51      A
ATOM   1380  N    SER A 180    -31.268  35.442  18.165  1.00 21.24      A
ATOM   1381  CA   SER A 180    -31.942  35.330  19.459  1.00 22.67      A
ATOM   1382  CB   SER A 180    -33.416  35.698  19.321  1.00 20.96      A
ATOM   1383  OG   SER A 180    -33.574  37.081  19.067  1.00 21.26      A
ATOM   1384  C    SER A 180    -31.851  33.930  20.041  1.00 24.42      A
ATOM   1385  O    SER A 180    -31.910  33.738  21.253  1.00 27.02      A
ATOM   1386  N    THR A 181    -31.680  32.955  19.162  1.00 25.25      A
ATOM   1387  CA   THR A 181    -31.635  31.569  19.553  1.00 24.17      A
ATOM   1388  CB   THR A 181    -32.786  30.864  18.872  1.00 25.53      A
ATOM   1389  OG1  THR A 181    -34.001  31.470  19.324  1.00 29.37      A
ATOM   1390  CG2  THR A 181    -32.796  29.390  19.180  1.00 25.47      A
ATOM   1391  C    THR A 181    -30.340  30.820  19.276  1.00 24.87      A
ATOM   1392  O    THR A 181    -30.015  29.873  19.994  1.00 27.20      A
ATOM   1393  N    LEU A 182    -29.581  31.231  18.268  1.00 22.37      A
ATOM   1394  CA   LEU A 182    -28.355  30.510  17.960  1.00 21.21      A
ATOM   1395  CB   LEU A 182    -27.887  30.858  16.546  1.00 19.93      A
ATOM   1396  CG   LEU A 182    -26.744  29.982  16.041  1.00 19.20      A
ATOM   1397  CD1  LEU A 182    -26.826  29.822  14.555  1.00 22.27      A
ATOM   1398  CD2  LEU A 182    -25.440  30.596  16.426  1.00 19.98      A
ATOM   1399  C    LEU A 182    -27.189  30.626  18.947  1.00 20.68      A
ATOM   1400  O    LEU A 182    -26.511  29.641  19.216  1.00 20.62      A
ATOM   1401  N    PRO A 183    -26.927  31.821  19.494  1.00 21.65      A
ATOM   1402  CD   PRO A 183    -27.585  33.126  19.311  1.00 21.59      A
ATOM   1403  CA   PRO A 183    -25.804  31.915  20.443  1.00 23.69      A
ATOM   1404  CB   PRO A 183    -25.921  33.339  20.981  1.00 22.05      A
ATOM   1405  CG   PRO A 183    -26.536  34.086  19.824  1.00 23.37      A
ATOM   1406  C    PRO A 183    -25.908  30.863  21.563  1.00 25.87      A
ATOM   1407  O    PRO A 183    -24.926  30.192  21.905  1.00 26.52      A
ATOM   1408  N    GLN A 184    -27.108  30.733  22.119  1.00 25.85      A
ATOM   1409  CA   GLN A 184    -27.391  29.782  23.179  1.00 27.12      A
ATOM   1410  CB   GLN A 184    -28.846  29.929  23.593  1.00 31.68      A
ATOM   1411  CG   GLN A 184    -29.410  28.739  24.373  1.00 35.60      A
ATOM   1412  CD   GLN A 184    -28.845  28.656  25.766  1.00 36.34      A
ATOM   1413  OE1  GLN A 184    -28.798  29.658  26.475  1.00 39.25      A
ATOM   1414  NE2  GLN A 184    -28.424  27.463  26.175  1.00 37.72      A
ATOM   1415  C    GLN A 184    -27.145  28.334  22.756  1.00 26.73      A
ATOM   1416  O    GLN A 184    -26.376  27.598  23.382  1.00 27.78      A
ATOM   1417  N    ALA A 185    -27.824  27.925  21.696  1.00 25.04      A
ATOM   1418  CA   ALA A 185    -27.705  26.574  21.199  1.00 24.18      A
ATOM   1419  CB   ALA A 185    -28.528  26.416  19.930  1.00 23.28      A
ATOM   1420  C    ALA A 185    -26.255  26.226  20.932  1.00 24.59      A
ATOM   1421  O    ALA A 185    -25.845  25.078  21.103  1.00 25.68      A
ATOM   1422  N    VAL A 186    -25.469  27.217  20.527  1.00 24.61      A
ATOM   1423  CA   VAL A 186    -24.064  26.959  20.229  1.00 25.01      A
ATOM   1424  CB   VAL A 186    -23.510  27.941  19.170  1.00 22.30      A
ATOM   1425  CG1  VAL A 186    -22.041  27.659  18.933  1.00 18.57      A
ATOM   1426  CG2  VAL A 186    -24.273  27.800  17.879  1.00 21.63      A
ATOM   1427  C    VAL A 186    -23.113  26.989  21.422  1.00 26.03      A
ATOM   1428  O    VAL A 186    -22.376  26.033  21.645  1.00 26.37      A
ATOM   1429  N    MET A 187    -23.126  28.075  22.187  1.00 26.31      A
ATOM   1430  CA   MET A 187    -22.203  28.202  23.311  1.00 27.29      A
ATOM   1431  CB   MET A 187    -21.841  29.671  23.506  1.00 27.68      A
ATOM   1432  CG   MET A 187    -21.085  30.247  22.337  1.00 27.84      A
ATOM   1433  SD   MET A 187    -20.989  32.022  22.413  1.00 30.44      A
ATOM   1434  CE   MET A 187    -22.450  32.439  21.479  1.00 29.46      A
ATOM   1435  C    MET A 187    -22.661  27.610  24.632  1.00 27.41      A
ATOM   1436  O    MET A 187    -21.887  27.549  25.594  1.00 27.54      A
ATOM   1437  N    GLY A 188    -23.909  27.161  24.687  1.00 26.39      A
ATOM   1438  CA   GLY A 188    -24.398  26.588  25.925  1.00 24.64      A
ATOM   1439  C    GLY A 188    -24.302  27.604  27.042  1.00 23.87      A
ATOM   1440  O    GLY A 188    -24.407  28.809  26.809  1.00 23.88      A
ATOM   1441  N    SER A 189    -24.067  27.125  28.255  1.00 22.71      A
ATOM   1442  CA   SER A 189    -23.994  28.010  29.413  1.00 23.04      A
```

FIGURE 4- 20 -

```
ATOM   1443  CB   SER A 189     -23.839  27.190  30.689  1.00 19.78           A
ATOM   1444  OG   SER A 189     -22.542  26.648  30.757  1.00 24.72           A
ATOM   1445  C    SER A 189     -22.914  29.089  29.373  1.00 22.94           A
ATOM   1446  O    SER A 189     -22.864  29.933  30.268  1.00 24.37           A
ATOM   1447  N    SER A 190     -22.047  29.074  28.363  1.00 22.57           A
ATOM   1448  CA   SER A 190     -21.011  30.101  28.294  1.00 21.98           A
ATOM   1449  CB   SER A 190     -19.832  29.631  27.441  1.00 22.34           A
ATOM   1450  OG   SER A 190     -19.088  28.622  28.100  1.00 22.32           A
ATOM   1451  C    SER A 190     -21.572  31.411  27.741  1.00 22.14           A
ATOM   1452  O    SER A 190     -20.971  32.462  27.906  1.00 21.68           A
ATOM   1453  N    TYR A 191     -22.737  31.348  27.103  1.00 22.57           A
ATOM   1454  CA   TYR A 191     -23.368  32.538  26.540  1.00 22.37           A
ATOM   1455  CB   TYR A 191     -24.459  32.135  25.563  1.00 22.65           A
ATOM   1456  CG   TYR A 191     -25.205  33.288  24.938  1.00 23.53           A
ATOM   1457  CD1  TYR A 191     -24.541  34.252  24.175  1.00 23.33           A
ATOM   1458  CE1  TYR A 191     -25.241  35.286  23.561  1.00 22.48           A
ATOM   1459  CD2  TYR A 191     -26.585  33.392  25.073  1.00 22.37           A
ATOM   1460  CE2  TYR A 191     -27.286  34.417  24.464  1.00 22.82           A
ATOM   1461  CZ   TYR A 191     -26.613  35.355  23.711  1.00 23.37           A
ATOM   1462  OH   TYR A 191     -27.334  36.352  23.093  1.00 26.35           A
ATOM   1463  C    TYR A 191     -23.968  33.386  27.645  1.00 23.83           A
ATOM   1464  O    TYR A 191     -25.053  33.083  28.153  1.00 24.40           A
ATOM   1465  N    GLY A 192     -23.269  34.469  27.981  1.00 24.06           A
ATOM   1466  CA   GLY A 192     -23.696  35.354  29.047  1.00 23.46           A
ATOM   1467  C    GLY A 192     -25.079  35.980  29.059  1.00 23.23           A
ATOM   1468  O    GLY A 192     -25.719  36.038  30.108  1.00 23.84           A
ATOM   1469  N    PHE A 193     -25.550  36.448  27.912  1.00 23.14           A
ATOM   1470  CA   PHE A 193     -26.843  37.128  27.843  1.00 24.32           A
ATOM   1471  CB   PHE A 193     -27.030  37.679  26.431  1.00 22.64           A
ATOM   1472  CG   PHE A 193     -26.104  38.814  26.109  1.00 21.45           A
ATOM   1473  CD1  PHE A 193     -26.183  40.017  26.827  1.00 19.72           A
ATOM   1474  CD2  PHE A 193     -25.144  38.684  25.104  1.00 19.30           A
ATOM   1475  CE1  PHE A 193     -25.328  41.070  26.552  1.00 17.55           A
ATOM   1476  CE2  PHE A 193     -24.277  39.737  24.819  1.00 20.28           A
ATOM   1477  CZ   PHE A 193     -24.370  40.935  25.547  1.00 19.75           A
ATOM   1478  C    PHE A 193     -28.114  36.335  28.307  1.00 25.60           A
ATOM   1479  O    PHE A 193     -29.186  37.005  28.433  1.00 25.09           A
ATOM   1480  N    GLN A 194     -27.993  35.103  28.579  1.00 26.09           A
ATOM   1481  CA   GLN A 194     -29.130  34.315  29.029  1.00 26.31           A
ATOM   1482  CB   GLN A 194     -28.866  32.835  28.765  1.00 25.66           A
ATOM   1483  CG   GLN A 194     -27.667  32.293  29.546  1.00 27.11           A
ATOM   1484  CD   GLN A 194     -27.365  30.846  29.223  1.00 26.30           A
ATOM   1485  OE1  GLN A 194     -28.194  29.973  29.438  1.00 27.55           A
ATOM   1486  NE2  GLN A 194     -26.177  30.588  28.697  1.00 26.14           A
ATOM   1487  C    GLN A 194     -29.372  34.522  30.521  1.00 26.78           A
ATOM   1488  O    GLN A 194     -30.452  34.213  31.032  1.00 28.54           A
ATOM   1489  N    TYR A 195     -28.368  35.051  31.213  1.00 26.97           A
ATOM   1490  CA   TYR A 195     -28.450  35.270  32.654  1.00 27.52           A
ATOM   1491  CB   TYR A 195     -27.101  34.983  33.298  1.00 28.62           A
ATOM   1492  CG   TYR A 195     -26.514  33.641  32.967  1.00 29.25           A
ATOM   1493  CD1  TYR A 195     -27.158  32.471  33.346  1.00 30.45           A
ATOM   1494  CE1  TYR A 195     -26.616  31.230  33.076  1.00 32.07           A
ATOM   1495  CD2  TYR A 195     -25.301  33.541  32.299  1.00 29.48           A
ATOM   1496  CE2  TYR A 195     -24.739  32.300  32.022  1.00 33.49           A
ATOM   1497  CZ   TYR A 195     -25.405  31.143  32.416  1.00 34.05           A
ATOM   1498  OH   TYR A 195     -24.860  29.900  32.161  1.00 33.83           A
ATOM   1499  C    TYR A 195     -28.863  36.668  33.098  1.00 29.10           A
ATOM   1500  O    TYR A 195     -28.418  37.672  32.526  1.00 30.81           A
ATOM   1501  N    SER A 196     -29.706  36.720  34.128  1.00 27.50           A
ATOM   1502  CA   SER A 196     -30.137  37.973  34.730  1.00 26.28           A
ATOM   1503  CB   SER A 196     -31.445  37.771  35.482  1.00 27.84           A
ATOM   1504  OG   SER A 196     -31.271  36.846  36.547  1.00 29.91           A
ATOM   1505  C    SER A 196     -29.016  38.228  35.733  1.00 26.89           A
ATOM   1506  O    SER A 196     -28.298  37.238  36.092  1.00 27.20           A
ATOM   1507  N    PRO A 197     -28.849  39.474  36.209  1.00 27.50           A
ATOM   1508  CD   PRO A 197     -29.642  40.635  35.969  1.00 27.22           A
ATOM   1509  CA   PRO A 197     -27.768  39.731  37.174  1.00 26.03           A
ATOM   1510  CB   PRO A 197     -28.159  41.070  37.774  1.00 24.95           A
ATOM   1511  CG   PRO A 197     -28.760  41.776  36.589  1.00 26.42           A
ATOM   1512  C    PRO A 197     -27.649  38.626  38.216  1.00 27.37           A
ATOM   1513  O    PRO A 197     -26.563  38.084  38.435  1.00 28.14           A
ATOM   1514  N    LYS A 198     -28.768  38.278  38.846  1.00 29.10           A
ATOM   1515  CA   LYS A 198     -28.768  37.217  39.854  1.00 28.21           A
ATOM   1516  CB   LYS A 198     -30.191  36.971  40.358  1.00 31.81           A
ATOM   1517  CG   LYS A 198     -30.300  35.911  41.442  1.00 32.92           A
ATOM   1518  CD   LYS A 198     -31.758  35.672  41.787  1.00 36.46           A
```

FIGURE 4- 21 -

```
ATOM   1519  CE  LYS A 198     -31.923  35.085  43.187  1.00 37.33           A
ATOM   1520  NZ  LYS A 198     -33.366  34.854  43.555  1.00 39.17           A
ATOM   1521  C   LYS A 198     -28.214  35.902  39.299  1.00 26.00           A
ATOM   1522  O   LYS A 198     -27.405  35.239  39.932  1.00 23.87           A
ATOM   1523  N   GLN A 199     -28.660  35.531  38.108  1.00 25.26           A
ATOM   1524  CA  GLN A 199     -28.219  34.284  37.500  1.00 25.98           A
ATOM   1525  CB  GLN A 199     -29.109  33.962  36.298  1.00 23.19           A
ATOM   1526  CG  GLN A 199     -30.581  34.046  36.656  1.00 22.18           A
ATOM   1527  CD  GLN A 199     -31.498  33.769  35.499  1.00 19.29           A
ATOM   1528  OE1 GLN A 199     -31.293  34.259  34.393  1.00 21.26           A
ATOM   1529  NE2 GLN A 199     -32.529  32.993  35.752  1.00 19.96           A
ATOM   1530  C   GLN A 199     -26.748  34.298  37.099  1.00 26.29           A
ATOM   1531  O   GLN A 199     -26.069  33.272  37.190  1.00 26.52           A
ATOM   1532  N   ARG A 200     -26.259  35.454  36.657  1.00 25.72           A
ATOM   1533  CA  ARG A 200     -24.866  35.576  36.262  1.00 25.82           A
ATOM   1534  CB  ARG A 200     -24.604  36.932  35.624  1.00 25.74           A
ATOM   1535  CG  ARG A 200     -23.152  37.121  35.211  1.00 25.99           A
ATOM   1536  CD  ARG A 200     -22.804  38.589  35.061  1.00 26.60           A
ATOM   1537  NE  ARG A 200     -21.442  38.797  34.575  1.00 31.11           A
ATOM   1538  CZ  ARG A 200     -21.023  38.506  33.342  1.00 31.78           A
ATOM   1539  NH1 ARG A 200     -21.869  37.988  32.458  1.00 31.47           A
ATOM   1540  NH2 ARG A 200     -19.773  38.750  32.986  1.00 32.24           A
ATOM   1541  C   ARG A 200     -23.994  35.429  37.501  1.00 27.06           A
ATOM   1542  O   ARG A 200     -22.945  34.782  37.470  1.00 27.97           A
ATOM   1543  N   VAL A 201     -24.424  36.036  38.600  1.00 26.25           A
ATOM   1544  CA  VAL A 201     -23.662  35.934  39.837  1.00 26.34           A
ATOM   1545  CB  VAL A 201     -24.208  36.920  40.890  1.00 25.70           A
ATOM   1546  CG1 VAL A 201     -23.476  36.758  42.200  1.00 24.96           A
ATOM   1547  CG2 VAL A 201     -24.031  38.325  40.378  1.00 26.35           A
ATOM   1548  C   VAL A 201     -23.712  34.495  40.364  1.00 25.26           A
ATOM   1549  O   VAL A 201     -22.762  34.011  40.974  1.00 22.38           A
ATOM   1550  N   GLU A 202     -24.828  33.818  40.116  1.00 25.96           A
ATOM   1551  CA  GLU A 202     -24.988  32.436  40.542  1.00 28.76           A
ATOM   1552  CB  GLU A 202     -26.411  31.940  40.227  1.00 32.57           A
ATOM   1553  CG  GLU A 202     -26.613  30.421  40.382  1.00 37.01           A
ATOM   1554  CD  GLU A 202     -28.084  29.983  40.216  1.00 40.11           A
ATOM   1555  OE1 GLU A 202     -28.866  30.723  39.563  1.00 40.33           A
ATOM   1556  OE2 GLU A 202     -28.446  28.891  40.727  1.00 37.97           A
ATOM   1557  C   GLU A 202     -23.968  31.584  39.803  1.00 28.15           A
ATOM   1558  O   GLU A 202     -23.262  30.774  40.402  1.00 27.44           A
ATOM   1559  N   PHE A 203     -23.886  31.796  38.496  1.00 27.89           A
ATOM   1560  CA  PHE A 203     -22.978  31.044  37.657  1.00 28.47           A
ATOM   1561  CB  PHE A 203     -23.258  31.360  36.186  1.00 29.89           A
ATOM   1562  CG  PHE A 203     -22.355  30.635  35.227  1.00 31.87           A
ATOM   1563  CD1 PHE A 203     -22.384  29.247  35.138  1.00 31.79           A
ATOM   1564  CD2 PHE A 203     -21.459  31.340  34.431  1.00 32.64           A
ATOM   1565  CE1 PHE A 203     -21.534  28.570  34.272  1.00 32.87           A
ATOM   1566  CE2 PHE A 203     -20.599  30.671  33.560  1.00 34.80           A
ATOM   1567  CZ  PHE A 203     -20.637  29.281  33.480  1.00 33.49           A
ATOM   1568  C   PHE A 203     -21.511  31.309  37.989  1.00 28.76           A
ATOM   1569  O   PHE A 203     -20.688  30.396  37.973  1.00 30.47           A
ATOM   1570  N   LEU A 204     -21.176  32.552  38.283  1.00 26.38           A
ATOM   1571  CA  LEU A 204     -19.801  32.877  38.604  1.00 26.11           A
ATOM   1572  CB  LEU A 204     -19.635  34.400  38.650  1.00 25.89           A
ATOM   1573  CG  LEU A 204     -19.673  35.127  37.300  1.00 23.44           A
ATOM   1574  CD1 LEU A 204     -19.842  36.614  37.500  1.00 20.90           A
ATOM   1575  CD2 LEU A 204     -18.404  34.827  36.541  1.00 20.92           A
ATOM   1576  C   LEU A 204     -19.359  32.250  39.934  1.00 27.23           A
ATOM   1577  O   LEU A 204     -18.283  31.657  40.036  1.00 26.90           A
ATOM   1578  N   VAL A 205     -20.194  32.387  40.953  1.00 28.05           A
ATOM   1579  CA  VAL A 205     -19.876  31.845  42.259  1.00 28.38           A
ATOM   1580  CB  VAL A 205     -20.895  32.309  43.309  1.00 28.05           A
ATOM   1581  CG1 VAL A 205     -20.509  31.783  44.671  1.00 26.27           A
ATOM   1582  CG2 VAL A 205     -20.956  33.816  43.328  1.00 27.10           A
ATOM   1583  C   VAL A 205     -19.819  30.322  42.240  1.00 29.08           A
ATOM   1584  O   VAL A 205     -18.843  29.735  42.710  1.00 28.84           A
ATOM   1585  N   ASN A 206     -20.843  29.670  41.702  1.00 29.23           A
ATOM   1586  CA  ASN A 206     -20.796  28.213  41.669  1.00 31.51           A
ATOM   1587  CB  ASN A 206     -22.062  27.620  41.034  1.00 32.82           A
ATOM   1588  CG  ASN A 206     -23.309  27.858  41.883  1.00 37.60           A
ATOM   1589  OD1 ASN A 206     -23.299  27.666  43.108  1.00 38.85           A
ATOM   1590  ND2 ASN A 206     -24.395  28.271  41.232  1.00 39.02           A
ATOM   1591  C   ASN A 206     -19.550  27.736  40.918  1.00 30.88           A
ATOM   1592  O   ASN A 206     -18.871  26.812  41.367  1.00 31.59           A
ATOM   1593  N   THR A 207     -19.240  28.369  39.791  1.00 29.04           A
ATOM   1594  CA  THR A 207     -18.064  27.987  39.018  1.00 29.55           A
```

FIGURE 4- 22 -

```
ATOM   1595  CB   THR A 207     -17.903  28.856  37.738  1.00 29.86      A
ATOM   1596  OG1  THR A 207     -19.037  28.669  36.883  1.00 32.95      A
ATOM   1597  CG2  THR A 207     -16.647  28.464  36.970  1.00 29.18      A
ATOM   1598  C    THR A 207     -16.803  28.139  39.865  1.00 29.56      A
ATOM   1599  O    THR A 207     -16.007  27.210  39.991  1.00 30.10      A
ATOM   1600  N    TRP A 208     -16.627  29.316  40.449  1.00 28.91      A
ATOM   1601  CA   TRP A 208     -15.455  29.577  41.265  1.00 27.44      A
ATOM   1602  CB   TRP A 208     -15.557  30.964  41.904  1.00 26.76      A
ATOM   1603  CG   TRP A 208     -14.288  31.412  42.542  1.00 24.77      A
ATOM   1604  CD2  TRP A 208     -13.178  32.026  41.883  1.00 25.13      A
ATOM   1605  CE2  TRP A 208     -12.176  32.233  42.858  1.00 24.91      A
ATOM   1606  CE3  TRP A 208     -12.930  32.423  40.561  1.00 24.12      A
ATOM   1607  CD1  TRP A 208     -13.931  31.275  43.851  1.00 23.80      A
ATOM   1608  NE1  TRP A 208     -12.663  31.764  44.051  1.00 23.19      A
ATOM   1609  CZ2  TRP A 208     -10.940  32.819  42.552  1.00 23.70      A
ATOM   1610  CZ3  TRP A 208     -11.704  33.006  40.257  1.00 25.52      A
ATOM   1611  CH2  TRP A 208     -10.724  33.197  41.252  1.00 25.28      A
ATOM   1612  C    TRP A 208     -15.328  28.519  42.336  1.00 27.66      A
ATOM   1613  O    TRP A 208     -14.272  27.913  42.497  1.00 26.63      A
ATOM   1614  N    LYS A 209     -16.422  28.298  43.060  1.00 29.19      A
ATOM   1615  CA   LYS A 209     -16.450  27.315  44.138  1.00 29.67      A
ATOM   1616  CB   LYS A 209     -17.792  27.363  44.880  1.00 28.98      A
ATOM   1617  CG   LYS A 209     -18.018  28.619  45.710  1.00 32.45      A
ATOM   1618  CD   LYS A 209     -19.298  28.539  46.573  1.00 34.08      A
ATOM   1619  CE   LYS A 209     -19.439  29.782  47.480  1.00 37.89      A
ATOM   1620  NZ   LYS A 209     -20.623  29.798  48.409  1.00 36.49      A
ATOM   1621  C    LYS A 209     -16.201  25.888  43.665  1.00 29.59      A
ATOM   1622  O    LYS A 209     -15.811  25.041  44.459  1.00 31.57      A
ATOM   1623  N    SER A 210     -16.406  25.613  42.383  1.00 28.00      A
ATOM   1624  CA   SER A 210     -16.222  24.253  41.902  1.00 29.08      A
ATOM   1625  CB   SER A 210     -17.180  23.959  40.758  1.00 28.16      A
ATOM   1626  OG   SER A 210     -16.740  24.590  39.577  1.00 30.47      A
ATOM   1627  C    SER A 210     -14.810  23.928  41.458  1.00 30.11      A
ATOM   1628  O    SER A 210     -14.523  22.802  41.075  1.00 29.53      A
ATOM   1629  N    LYS A 211     -13.925  24.911  41.500  1.00 32.13      A
ATOM   1630  CA   LYS A 211     -12.549  24.667  41.104  1.00 34.20      A
ATOM   1631  CB   LYS A 211     -11.933  25.917  40.461  1.00 34.18      A
ATOM   1632  CG   LYS A 211     -12.651  26.416  39.213  1.00 34.28      A
ATOM   1633  CD   LYS A 211     -12.844  25.315  38.186  1.00 33.76      A
ATOM   1634  CE   LYS A 211     -13.547  25.837  36.944  1.00 32.41      A
ATOM   1635  NZ   LYS A 211     -13.801  24.743  35.963  1.00 32.64      A
ATOM   1636  C    LYS A 211     -11.772  24.305  42.361  1.00 35.63      A
ATOM   1637  O    LYS A 211     -11.906  24.969  43.387  1.00 34.77      A
ATOM   1638  N    LYS A 212     -10.971  23.250  42.285  1.00 36.85      A
ATOM   1639  CA   LYS A 212     -10.175  22.835  43.426  1.00 38.92      A
ATOM   1640  CB   LYS A 212      -9.235  21.705  43.012  1.00 42.68      A
ATOM   1641  CG   LYS A 212      -9.996  20.495  42.425  1.00 49.05      A
ATOM   1642  CD   LYS A 212      -9.100  19.267  42.208  1.00 52.70      A
ATOM   1643  CE   LYS A 212      -9.917  18.025  41.839  1.00 53.99      A
ATOM   1644  NZ   LYS A 212      -9.089  16.775  41.840  1.00 55.37      A
ATOM   1645  C    LYS A 212      -9.405  24.052  43.927  1.00 38.43      A
ATOM   1646  O    LYS A 212      -9.354  24.324  45.127  1.00 37.85      A
ATOM   1647  N    CYS A 213      -8.829  24.793  42.988  1.00 37.47      A
ATOM   1648  CA   CYS A 213      -8.090  26.012  43.293  1.00 36.46      A
ATOM   1649  CB   CYS A 213      -6.596  25.715  43.439  1.00 35.64      A
ATOM   1650  SG   CYS A 213      -5.652  27.111  44.105  1.00 35.13      A
ATOM   1651  C    CYS A 213      -8.338  26.963  42.116  1.00 35.50      A
ATOM   1652  O    CYS A 213      -7.557  27.012  41.159  1.00 35.43      A
ATOM   1653  N    PRO A 214      -9.435  27.735  42.179  1.00 33.71      A
ATOM   1654  CD   PRO A 214     -10.324  27.863  43.344  1.00 33.38      A
ATOM   1655  CA   PRO A 214      -9.836  28.688  41.143  1.00 32.97      A
ATOM   1656  CB   PRO A 214     -11.185  29.185  41.643  1.00 31.91      A
ATOM   1657  CG   PRO A 214     -10.975  29.214  43.098  1.00 31.54      A
ATOM   1658  C    PRO A 214      -8.905  29.844  40.820  1.00 31.72      A
ATOM   1659  O    PRO A 214      -8.392  30.524  41.707  1.00 33.29      A
ATOM   1660  N    MET A 215      -8.695  30.040  39.523  1.00 28.79      A
ATOM   1661  CA   MET A 215      -7.903  31.137  39.008  1.00 26.59      A
ATOM   1662  CB   MET A 215      -6.592  30.663  38.397  1.00 26.75      A
ATOM   1663  CG   MET A 215      -5.732  31.811  37.840  1.00 28.47      A
ATOM   1664  SD   MET A 215      -6.191  32.425  36.180  1.00 28.48      A
ATOM   1665  CE   MET A 215      -5.159  31.385  35.188  1.00 25.61      A
ATOM   1666  C    MET A 215      -8.793  31.695  37.926  1.00 25.52      A
ATOM   1667  O    MET A 215      -9.340  30.944  37.118  1.00 25.63      A
ATOM   1668  N    GLY A 216      -8.969  33.008  37.924  1.00 24.86      A
ATOM   1669  CA   GLY A 216      -9.814  33.609  36.916  1.00 21.71      A
ATOM   1670  C    GLY A 216      -9.193  34.854  36.324  1.00 20.17      A
```

FIGURE 4-23-

```
ATOM   1671  O    GLY A 216      -8.304  35.466  36.916  1.00 20.17           A
ATOM   1672  N    PHE A 217      -9.658  35.224  35.140  1.00 19.24           A
ATOM   1673  CA   PHE A 217      -9.166  36.419  34.482  1.00 18.14           A
ATOM   1674  CB   PHE A 217      -7.815  36.169  33.809  1.00 19.10           A
ATOM   1675  CG   PHE A 217      -7.875  35.250  32.629  1.00 18.44           A
ATOM   1676  CD1  PHE A 217      -7.622  33.887  32.779  1.00 17.55           A
ATOM   1677  CD2  PHE A 217      -8.140  35.749  31.355  1.00 18.74           A
ATOM   1678  CE1  PHE A 217      -7.623  33.040  31.679  1.00 16.91           A
ATOM   1679  CE2  PHE A 217      -8.146  34.906  30.248  1.00 18.15           A
ATOM   1680  CZ   PHE A 217      -7.886  33.553  30.410  1.00 18.16           A
ATOM   1681  C    PHE A 217     -10.119  36.948  33.444  1.00 16.83           A
ATOM   1682  O    PHE A 217     -10.835  36.197  32.799  1.00 16.11           A
ATOM   1683  N    SER A 218     -10.125  38.260  33.301  1.00 16.63           A
ATOM   1684  CA   SER A 218     -10.949  38.907  32.307  1.00 18.34           A
ATOM   1685  CB   SER A 218     -11.483  40.224  32.851  1.00 17.81           A
ATOM   1686  OG   SER A 218     -10.407  41.074  33.177  1.00 18.40           A
ATOM   1687  C    SER A 218      -9.956  39.179  31.181  1.00 20.33           A
ATOM   1688  O    SER A 218      -8.745  39.223  31.415  1.00 21.12           A
ATOM   1689  N    TYR A 219     -10.446  39.323  29.959  1.00 21.26           A
ATOM   1690  CA   TYR A 219      -9.554  39.610  28.846  1.00 23.26           A
ATOM   1691  CB   TYR A 219      -9.372  38.393  27.931  1.00 22.50           A
ATOM   1692  CG   TYR A 219      -8.356  38.634  26.838  1.00 22.43           A
ATOM   1693  CD1  TYR A 219      -6.988  38.557  27.100  1.00 21.07           A
ATOM   1694  CE1  TYR A 219      -6.044  38.802  26.090  1.00 21.27           A
ATOM   1695  CD2  TYR A 219      -8.763  38.965  25.542  1.00 23.49           A
ATOM   1696  CE2  TYR A 219      -7.831  39.215  24.524  1.00 22.31           A
ATOM   1697  CZ   TYR A 219      -6.471  39.132  24.804  1.00 22.39           A
ATOM   1698  OH   TYR A 219      -5.546  39.393  23.811  1.00 18.07           A
ATOM   1699  C    TYR A 219     -10.141  40.760  28.054  1.00 23.75           A
ATOM   1700  O    TYR A 219     -11.274  40.688  27.569  1.00 23.84           A
ATOM   1701  N    ASP A 220      -9.357  41.822  27.936  1.00 24.42           A
ATOM   1702  CA   ASP A 220      -9.781  43.008  27.229  1.00 24.48           A
ATOM   1703  CB   ASP A 220      -9.473  44.232  28.065  1.00 25.09           A
ATOM   1704  CG   ASP A 220      -9.310  45.495  27.354  1.00 27.20           A
ATOM   1705  OD1  ASP A 220     -10.934  45.568  26.808  1.00 26.46           A
ATOM   1706  OD2  ASP A 220      -8.957  46.410  27.341  1.00 30.56           A
ATOM   1707  C    ASP A 220      -9.134  43.154  25.862  1.00 26.32           A
ATOM   1708  O    ASP A 220      -7.944  43.452  25.742  1.00 25.98           A
ATOM   1709  N    THR A 221      -9.942  42.943  24.829  1.00 27.49           A
ATOM   1710  CA   THR A 221      -9.503  43.052  23.450  1.00 24.92           A
ATOM   1711  CB   THR A 221     -10.491  42.331  22.536  1.00 23.80           A
ATOM   1712  OG1  THR A 221     -10.518  40.937  22.878  1.00 22.80           A
ATOM   1713  CG2  THR A 221     -10.095  42.503  21.088  1.00 24.18           A
ATOM   1714  C    THR A 221      -9.431  44.521  23.060  1.00 24.92           A
ATOM   1715  O    THR A 221     -10.388  45.263  23.247  1.00 25.98           A
ATOM   1716  N    ARG A 222      -8.291  44.946  22.531  1.00 27.40           A
ATOM   1717  CA   ARG A 222      -8.121  46.339  22.116  1.00 29.32           A
ATOM   1718  CB   ARG A 222      -6.652  46.621  21.759  1.00 30.80           A
ATOM   1719  CG   ARG A 222      -6.398  48.082  21.415  1.00 34.89           A
ATOM   1720  CD   ARG A 222      -5.166  48.289  20.552  1.00 39.23           A
ATOM   1721  NE   ARG A 222      -5.346  49.454  19.681  1.00 44.73           A
ATOM   1722  CZ   ARG A 222      -4.630  50.576  19.751  1.00 46.58           A
ATOM   1723  NH1  ARG A 222      -3.663  50.695  20.658  1.00 48.24           A
ATOM   1724  NH2  ARG A 222      -4.891  51.585  18.922  1.00 45.57           A
ATOM   1725  C    ARG A 222      -9.000  46.662  20.902  1.00 28.53           A
ATOM   1726  O    ARG A 222      -8.686  46.258  19.783  1.00 29.01           A
ATOM   1727  N    CYS A 223     -10.091  47.389  21.122  1.00 27.99           A
ATOM   1728  CA   CYS A 223     -11.000  47.770  20.034  1.00 30.51           A
ATOM   1729  CB   CYS A 223     -10.310  48.721  19.047  1.00 33.88           A
ATOM   1730  SG   CYS A 223      -9.606  50.242  19.747  1.00 42.46           A
ATOM   1731  C    CYS A 223     -11.478  46.552  19.257  1.00 29.03           A
ATOM   1732  O    CYS A 223     -11.124  46.374  18.087  1.00 29.03           A
ATOM   1733  N    PHE A 224     -12.314  45.740  19.892  1.00 27.76           A
ATOM   1734  CA   PHE A 224     -12.316  44.513  19.278  1.00 26.60           A
ATOM   1735  CB   PHE A 224     -13.829  43.847  20.215  1.00 23.54           A
ATOM   1736  CG   PHE A 224     -14.136  42.418  19.863  1.00 22.83           A
ATOM   1737  CD1  PHE A 224     -15.143  42.110  18.948  1.00 20.63           A
ATOM   1738  CD2  PHE A 224     -13.438  41.373  20.472  1.00 19.99           A
ATOM   1739  CE1  PHE A 224     -15.459  40.784  18.652  1.00 19.67           A
ATOM   1740  CE2  PHE A 224     -13.748  40.037  20.178  1.00 18.95           A
ATOM   1741  CZ   PHE A 224     -14.758  39.744  19.272  1.00 19.81           A
ATOM   1742  C    PHE A 224     -13.405  44.656  17.873  1.00 26.36           A
ATOM   1743  O    PHE A 224     -13.005  43.935  16.957  1.00 25.80           A
ATOM   1744  N    ASP A 225     -14.338  45.585  17.693  1.00 26.55           A
ATOM   1745  CA   ASP A 225     -14.956  45.765  16.383  1.00 26.43           A
ATOM   1746  CB   ASP A 225     -15.922  46.948  16.416  1.00 25.63           A
```

FIGURE 4- 24 -

```
ATOM   1747  CG   ASP A 225    -17.250  46.601  17.061  1.00 28.31      A
ATOM   1748  OD1  ASP A 225    -17.389  45.475  17.602  1.00 27.28      A
ATOM   1749  OD2  ASP A 225    -18.159  47.466  17.029  1.00 29.45      A
ATOM   1750  C    ASP A 225    -13.991  45.919  15.202  1.00 25.50      A
ATOM   1751  O    ASP A 225    -14.243  45.379  14.120  1.00 26.69      A
ATOM   1752  N    SER A 226    -12.895  46.643  15.390  1.00 23.35      A
ATOM   1753  CA   SER A 226    -11.958  46.822  14.295  1.00 24.53      A
ATOM   1754  CB   SER A 226    -11.153  48.106  14.475  1.00 25.64      A
ATOM   1755  OG   SER A 226    -10.498  48.116  15.731  1.00 32.01      A
ATOM   1756  C    SER A 226    -11.025  45.635  14.185  1.00 25.20      A
ATOM   1757  O    SER A 226    -10.252  45.532  13.232  1.00 26.56      A
ATOM   1758  N    THR A 227    -11.086  44.727  15.154  1.00 24.56      A
ATOM   1759  CA   THR A 227    -10.220  43.561  15.087  1.00 24.31      A
ATOM   1760  CB   THR A 227     -9.778  43.045  16.490  1.00 25.01      A
ATOM   1761  OG1  THR A 227    -10.909  42.538  17.207  1.00 25.61      A
ATOM   1762  CG2  THR A 227     -9.131  44.160  17.282  1.00 24.65      A
ATOM   1763  C    THR A 227    -10.910  42.431  14.357  1.00 23.55      A
ATOM   1764  O    THR A 227    -10.274  41.446  14.013  1.00 24.20      A
ATOM   1765  N    VAL A 228    -12.208  42.566  14.122  1.00 23.30      A
ATOM   1766  CA   VAL A 228    -12.954  41.523  13.420  1.00 24.14      A
ATOM   1767  CB   VAL A 228    -14.466  41.671  13.655  1.00 24.84      A
ATOM   1768  CG1  VAL A 228    -15.236  40.687  12.775  1.00 24.67      A
ATOM   1769  CG2  VAL A 228    -14.777  41.441  15.122  1.00 24.58      A
ATOM   1770  C    VAL A 228    -12.673  41.578  11.923  1.00 23.49      A
ATOM   1771  O    VAL A 228    -12.838  42.626  11.292  1.00 23.57      A
ATOM   1772  N    THR A 229    -12.264  40.442  11.362  1.00 23.27      A
ATOM   1773  CA   THR A 229    -11.925  40.343   9.938  1.00 24.09      A
ATOM   1774  CB   THR A 229    -10.724  39.413   9.731  1.00 22.27      A
ATOM   1775  OG1  THR A 229    -11.134  38.054   9.937  1.00 21.23      A
ATOM   1776  CG2  THR A 229     -9.617  39.752  10.708  1.00 21.01      A
ATOM   1777  C    THR A 229    -13.037  39.814   9.033  1.00 25.96      A
ATOM   1778  O    THR A 229    -13.979  39.169   9.499  1.00 27.30      A
ATOM   1779  N    GLU A 230    -12.908  40.076   7.733  1.00 27.58      A
ATOM   1780  CA   GLU A 230    -13.879  39.585   6.755  1.00 28.43      A
ATOM   1781  CB   GLU A 230    -13.423  39.876   5.320  1.00 32.52      A
ATOM   1782  CG   GLU A 230    -12.908  41.295   5.100  1.00 39.60      A
ATOM   1783  CD   GLU A 230    -11.406  41.421   5.370  1.00 42.86      A
ATOM   1784  OE1  GLU A 230    -10.848  40.556   6.101  1.00 41.83      A
ATOM   1785  OE2  GLU A 230    -10.794  42.392   4.854  1.00 42.20      A
ATOM   1786  C    GLU A 230    -13.958  38.075   6.949  1.00 26.10      A
ATOM   1787  O    GLU A 230    -15.030  37.480   6.833  1.00 24.96      A
ATOM   1788  N    SER A 231    -12.812  37.465   7.245  1.00 23.46      A
ATOM   1789  CA   SER A 231    -12.762  36.033   7.483  1.00 21.80      A
ATOM   1790  CB   SER A 231    -11.341  35.585   7.754  1.00 19.25      A
ATOM   1791  OG   SER A 231    -11.338  34.225   8.128  1.00 19.63      A
ATOM   1792  C    SER A 231    -13.633  35.714   8.692  1.00 23.48      A
ATOM   1793  O    SER A 231    -14.421  34.761   8.660  1.00 23.98      A
ATOM   1794  N    ASP A 232    -13.497  36.508   9.756  1.00 22.54      A
ATOM   1795  CA   ASP A 232    -14.305  36.287  10.944  1.00 23.05      A
ATOM   1796  CB   ASP A 232    -14.042  37.345  12.006  1.00 23.01      A
ATOM   1797  CG   ASP A 232    -12.706  37.185  12.667  1.00 25.02      A
ATOM   1798  OD1  ASP A 232    -12.185  36.048  12.682  1.00 25.91      A
ATOM   1799  OD2  ASP A 232    -12.188  38.196  13.186  1.00 24.49      A
ATOM   1800  C    ASP A 232    -15.773  36.354  10.578  1.00 23.55      A
ATOM   1801  O    ASP A 232    -16.563  35.484  10.946  1.00 22.47      A
ATOM   1802  N    ILE A 233    -16.134  37.401   9.851  1.00 23.51      A
ATOM   1803  CA   ILE A 233    -17.513  37.595   9.465  1.00 24.70      A
ATOM   1804  CB   ILE A 233    -17.677  38.979   8.804  1.00 26.00      A
ATOM   1805  CG2  ILE A 233    -19.062  39.143   8.235  1.00 28.26      A
ATOM   1806  CG1  ILE A 233    -17.451  40.063   9.861  1.00 26.57      A
ATOM   1807  CD1  ILE A 233    -17.315  41.460   9.295  1.00 29.39      A
ATOM   1808  C    ILE A 233    -18.042  36.470   8.585  1.00 24.01      A
ATOM   1809  O    ILE A 233    -19.190  36.065   8.736  1.00 24.27      A
ATOM   1810  N    ARG A 234    -17.213  35.951   7.685  1.00 23.54      A
ATOM   1811  CA   ARG A 234    -17.643  34.861   6.818  1.00 22.83      A
ATOM   1812  CB   ARG A 234    -16.664  34.685   5.647  1.00 21.48      A
ATOM   1813  CG   ARG A 234    -16.808  35.760   4.558  1.00 21.18      A
ATOM   1814  CD   ARG A 234    -15.694  35.671   3.507  1.00 26.61      A
ATOM   1815  NE   ARG A 234    -15.394  36.957   2.859  1.00 28.73      A
ATOM   1816  CZ   ARG A 234    -16.023  37.429   1.786  1.00 29.41      A
ATOM   1817  NH1  ARG A 234    -16.992  36.734   1.213  1.00 31.92      A
ATOM   1818  NH2  ARG A 234    -15.691  38.602   1.284  1.00 30.32      A
ATOM   1819  C    ARG A 234    -17.783  33.568   7.628  1.00 23.90      A
ATOM   1820  O    ARG A 234    -18.726  32.797   7.411  1.00 24.66      A
ATOM   1821  N    VAL A 235    -16.856  33.331   8.559  1.00 22.69      A
ATOM   1822  CA   VAL A 235    -16.921  32.149   9.419  1.00 20.57      A
```

FIGURE 4- 25 -

```
ATOM   1823  CB   VAL A 235     -15.680  32.059  10.357  1.00 21.01      A
ATOM   1824  CG1  VAL A 235     -16.028  31.290  11.651  1.00 21.10      A
ATOM   1825  CG2  VAL A 235     -14.540  31.357   9.641  1.00 16.45      A
ATOM   1826  C    VAL A 235     -18.190  32.269  10.266  1.00 20.65      A
ATOM   1827  O    VAL A 235     -18.877  31.296  10.537  1.00 21.87      A
ATOM   1828  N    GLU A 236     -18.487  33.485  10.684  1.00 22.02      A
ATOM   1829  CA   GLU A 236     -19.669  33.763  11.469  1.00 22.86      A
ATOM   1830  CB   GLU A 236     -19.656  35.229  11.849  1.00 24.52      A
ATOM   1831  CG   GLU A 236     -20.935  35.780  12.410  1.00 26.47      A
ATOM   1832  CD   GLU A 236     -20.840  37.290  12.562  1.00 29.78      A
ATOM   1833  OE1  GLU A 236     -21.903  37.955  12.588  1.00 29.70      A
ATOM   1834  OE2  GLU A 236     -19.693  37.804  12.651  1.00 27.90      A
ATOM   1835  C    GLU A 236     -20.899  33.432  10.634  1.00 24.09      A
ATOM   1836  O    GLU A 236     -21.922  33.002  11.167  1.00 26.98      A
ATOM   1837  N    GLU A 237     -20.796  33.618   9.320  1.00 22.92      A
ATOM   1838  CA   GLU A 237     -21.910  33.321   8.425  1.00 20.45      A
ATOM   1839  CB   GLU A 237     -21.702  33.947   7.039  1.00 20.62      A
ATOM   1840  CG   GLU A 237     -22.991  34.006   6.201  1.00 21.78      A
ATOM   1841  CD   GLU A 237     -22.768  33.905   4.691  1.00 22.69      A
ATOM   1842  OE1  GLU A 237     -21.641  34.177   4.228  1.00 21.69      A
ATOM   1843  OE2  GLU A 237     -23.732  33.569   3.965  1.00 19.98      A
ATOM   1844  C    GLU A 237     -22.053  31.819   8.258  1.00 18.56      A
ATOM   1845  O    GLU A 237     -23.153  31.295   8.277  1.00 17.22      A
ATOM   1846  N    SER A 238     -20.935  31.128   8.079  1.00 17.85      A
ATOM   1847  CA   SER A 238     -20.975  29.684   7.891  1.00 18.24      A
ATOM   1848  CB   SER A 238     -19.565  29.098   7.817  1.00 17.55      A
ATOM   1849  OG   SER A 238     -19.025  28.901   9.111  1.00 12.72      A
ATOM   1850  C    SER A 238     -21.721  29.022   9.033  1.00 19.72      A
ATOM   1851  O    SER A 238     -22.277  27.934   8.860  1.00 19.31      A
ATOM   1852  N    ILE A 239     -21.719  29.664  10.202  1.00 20.49      A
ATOM   1853  CA   ILE A 239     -22.422  29.110  11.351  1.00 21.32      A
ATOM   1854  CB   ILE A 239     -21.968  29.749  12.672  1.00 21.34      A
ATOM   1855  CG2  ILE A 239     -22.891  29.286  13.814  1.00 20.32      A
ATOM   1856  CG1  ILE A 239     -20.505  29.373  12.958  1.00 20.30      A
ATOM   1857  CD1  ILE A 239     -19.864  30.138  14.094  1.00 14.39      A
ATOM   1858  C    ILE A 239     -23.900  29.373  11.155  1.00 23.16      A
ATOM   1859  O    ILE A 239     -24.718  28.485  11.338  1.00 26.11      A
ATOM   1860  N    TYR A 240     -24.243  30.597  10.775  1.00 24.54      A
ATOM   1861  CA   TYR A 240     -25.635  30.939  10.543  1.00 22.64      A
ATOM   1862  CB   TYR A 240     -25.769  32.374  10.043  1.00 24.54      A
ATOM   1863  CG   TYR A 240     -25.268  33.426  10.994  1.00 26.06      A
ATOM   1864  CD1  TYR A 240     -25.430  33.284  12.375  1.00 26.38      A
ATOM   1865  CE1  TYR A 240     -25.000  34.277  13.250  1.00 25.23      A
ATOM   1866  CD2  TYR A 240     -24.664  34.588  10.514  1.00 25.39      A
ATOM   1867  CE2  TYR A 240     -24.232  35.581  11.381  1.00 24.65      A
ATOM   1868  CZ   TYR A 240     -24.403  35.414  12.739  1.00 24.36      A
ATOM   1869  OH   TYR A 240     -23.957  36.379  13.586  1.00 28.90      A
ATOM   1870  C    TYR A 240     -26.189  30.025   9.475  1.00 21.37      A
ATOM   1871  O    TYR A 240     -27.361  29.665   9.510  1.00 22.20      A
ATOM   1872  N    GLN A 241     -25.329  29.662   8.527  1.00 20.35      A
ATOM   1873  CA   GLN A 241     -25.710  28.821   7.400  1.00 19.01      A
ATOM   1874  CB   GLN A 241     -24.612  28.832   6.339  1.00 19.39      A
ATOM   1875  CG   GLN A 241     -24.465  30.160   5.619  1.00 20.45      A
ATOM   1876  CD   GLN A 241     -25.681  30.509   4.778  1.00 20.99      A
ATOM   1877  OE1  GLN A 241     -26.641  29.749   4.715  1.00 20.77      A
ATOM   1878  NE2  GLN A 241     -25.639  31.666   4.122  1.00 22.81      A
ATOM   1879  C    GLN A 241     -26.050  27.397   7.761  1.00 18.45      A
ATOM   1880  O    GLN A 241     -26.610  26.675   6.945  1.00 19.35      A
ATOM   1881  N    CYS A 242     -25.713  26.992   8.978  1.00 18.63      A
ATOM   1882  CA   CYS A 242     -26.007  25.645   9.439  1.00 17.28      A
ATOM   1883  CB   CYS A 242     -25.086  25.278  10.587  1.00 15.31      A
ATOM   1884  SG   CYS A 242     -23.424  24.991  10.035  1.00 20.63      A
ATOM   1885  C    CYS A 242     -27.454  25.522   9.884  1.00 17.34      A
ATOM   1886  O    CYS A 242     -27.981  24.419   9.992  1.00 18.33      A
ATOM   1887  N    CYS A 243     -28.097  26.653  10.141  1.00 16.78      A
ATOM   1888  CA   CYS A 243     -29.491  26.644  10.567  1.00 19.21      A
ATOM   1889  CB   CYS A 243     -29.918  28.023  11.065  1.00 17.37      A
ATOM   1890  SG   CYS A 243     -29.092  28.599  12.515  1.00 23.91      A
ATOM   1891  C    CYS A 243     -30.432  26.263   9.429  1.00 20.32      A
ATOM   1892  O    CYS A 243     -30.129  26.459   8.251  1.00 19.99      A
ATOM   1893  N    ASP A 244     -31.580  25.711   9.794  1.00 21.55      A
ATOM   1894  CA   ASP A 244     -32.581  25.374   8.809  1.00 21.18      A
ATOM   1895  CB   ASP A 244     -33.592  24.394   9.397  1.00 19.39      A
ATOM   1896  CG   ASP A 244     -34.665  24.057   8.422  1.00 22.92      A
ATOM   1897  OD1  ASP A 244     -35.706  24.789   8.390  1.00 20.96      A
ATOM   1898  OD2  ASP A 244     -34.504  23.070   7.665  1.00 23.28      A
```

FIGURE 4- 26 -

```
ATOM   1899  C    ASP A 244     -33.217  26.744   8.548  1.00 19.81           A
ATOM   1900  O    ASP A 244     -33.690  27.389   9.477  1.00 21.09           A
ATOM   1901  N    LEU A 245     -33.221  27.187   7.298  1.00 18.20           A
ATOM   1902  CA   LEU A 245     -33.742  28.504   6.975  1.00 19.53           A
ATOM   1903  CB   LEU A 245     -32.576  29.473   6.823  1.00 19.01           A
ATOM   1904  CG   LEU A 245     -31.551  29.579   7.945  1.00 18.13           A
ATOM   1905  CD1  LEU A 245     -30.237  30.100   7.373  1.00 16.59           A
ATOM   1906  CD2  LEU A 245     -32.087  30.483   9.040  1.00 15.50           A
ATOM   1907  C    LEU A 245     -34.563  28.546   5.638  1.00 20.91           A
ATOM   1908  O    LEU A 245     -34.308  27.785   4.754  1.00 22.21           A
ATOM   1909  N    ALA A 246     -35.532  29.455   5.630  1.00 20.85           A
ATOM   1910  CA   ALA A 246     -36.356  29.590   4.435  1.00 21.76           A
ATOM   1911  CB   ALA A 246     -37.546  30.482   4.719  1.00 20.06           A
ATOM   1912  C    ALA A 246     -35.487  30.200   3.341  1.00 23.25           A
ATOM   1913  O    ALA A 246     -34.647  31.051   3.613  1.00 22.64           A
ATOM   1914  N    PRO A 247     -35.670  29.763   2.086  1.00 25.18           A
ATOM   1915  CD   PRO A 247     -36.647  28.764   1.607  1.00 25.65           A
ATOM   1916  CA   PRO A 247     -34.881  30.290   0.969  1.00 25.36           A
ATOM   1917  CB   PRO A 247     -35.716  29.892  -0.247  1.00 26.80           A
ATOM   1918  CG   PRO A 247     -36.203  28.528   0.150  1.00 25.79           A
ATOM   1919  C    PRO A 247     -34.557  31.792   1.003  1.00 25.65           A
ATOM   1920  O    PRO A 247     -33.385  32.175   1.020  1.00 25.41           A
ATOM   1921  N    GLU A 248     -35.573  32.648   1.023  1.00 24.97           A
ATOM   1922  CA   GLU A 248     -35.297  34.080   1.021  1.00 24.92           A
ATOM   1923  CB   GLU A 248     -36.599  34.870   0.983  1.00 25.87           A
ATOM   1924  CG   GLU A 248     -37.544  34.424  -0.105  1.00 25.16           A
ATOM   1925  CD   GLU A 248     -38.513  35.510  -0.493  1.00 27.57           A
ATOM   1926  OE1  GLU A 248     -38.971  36.264   0.397  1.00 25.85           A
ATOM   1927  OE2  GLU A 248     -38.821  35.606  -1.697  1.00 29.68           A
ATOM   1928  C    GLU A 248     -34.454  34.520   2.212  1.00 24.47           A
ATOM   1929  O    GLU A 248     -33.711  35.498   2.137  1.00 24.40           A
ATOM   1930  N    ALA A 249     -34.574  33.794   3.314  1.00 23.95           A
ATOM   1931  CA   ALA A 249     -33.813  34.109   4.515  1.00 22.41           A
ATOM   1932  CB   ALA A 249     -34.370  33.337   5.701  1.00 22.74           A
ATOM   1933  C    ALA A 249     -32.362  33.738   4.286  1.00 21.85           A
ATOM   1934  O    ALA A 249     -31.460  34.482   4.663  1.00 22.35           A
ATOM   1935  N    ARG A 250     -32.140  32.586   3.657  1.00 21.12           A
ATOM   1936  CA   ARG A 250     -30.786  32.116   3.382  1.00 19.80           A
ATOM   1937  CB   ARG A 250     -30.823  30.713   2.774  1.00 19.90           A
ATOM   1938  CG   ARG A 250     -29.473  30.015   2.702  1.00 20.18           A
ATOM   1939  CD   ARG A 250     -29.622  28.564   2.228  1.00 20.93           A
ATOM   1940  NE   ARG A 250     -30.237  27.674   3.218  1.00 21.93           A
ATOM   1941  CZ   ARG A 250     -29.607  27.174   4.284  1.00 23.86           A
ATOM   1942  NH1  ARG A 250     -28.329  27.464   4.522  1.00 20.98           A
ATOM   1943  NH2  ARG A 250     -30.252  26.369   5.119  1.00 22.98           A
ATOM   1944  C    ARG A 250     -30.077  33.082   2.450  1.00 20.12           A
ATOM   1945  O    ARG A 250     -28.874  33.311   2.592  1.00 21.06           A
ATOM   1946  N    GLN A 251     -30.823  33.657   1.507  1.00 19.52           A
ATOM   1947  CA   GLN A 251     -30.251  34.615   0.564  1.00 18.63           A
ATOM   1948  CB   GLN A 251     -31.218  34.890  -0.599  1.00 19.02           A
ATOM   1949  CG   GLN A 251     -30.637  35.684  -1.789  1.00 16.33           A
ATOM   1950  CD   GLN A 251     -29.558  34.915  -2.534  1.00 19.38           A
ATOM   1951  OE1  GLN A 251     -28.372  35.106  -2.295  1.00 21.40           A
ATOM   1952  NE2  GLN A 251     -29.968  34.025  -3.431  1.00 17.96           A
ATOM   1953  C    GLN A 251     -29.986  35.905   1.316  1.00 19.08           A
ATOM   1954  O    GLN A 251     -28.925  36.501   1.166  1.00 20.01           A
ATOM   1955  N    ALA A 252     -30.952  36.334   2.126  1.00 19.38           A
ATOM   1956  CA   ALA A 252     -30.808  37.570   2.903  1.00 19.88           A
ATOM   1957  CB   ALA A 252     -32.049  37.810   3.758  1.00 17.35           A
ATOM   1958  C    ALA A 252     -29.557  37.510   3.783  1.00 20.11           A
ATOM   1959  O    ALA A 252     -28.793  38.474   3.840  1.00 21.82           A
ATOM   1960  N    ILE A 253     -29.339  36.382   4.457  1.00 18.08           A
ATOM   1961  CA   ILE A 253     -28.153  36.232   5.290  1.00 17.92           A
ATOM   1962  CB   ILE A 253     -28.173  34.873   6.029  1.00 15.88           A
ATOM   1963  CG2  ILE A 253     -26.858  34.638   6.761  1.00 12.69           A
ATOM   1964  CG1  ILE A 253     -29.350  34.841   6.998  1.00 13.73           A
ATOM   1965  CD1  ILE A 253     -29.458  33.575   7.798  1.00 10.99           A
ATOM   1966  C    ILE A 253     -26.899  36.323   4.403  1.00 20.28           A
ATOM   1967  O    ILE A 253     -25.915  36.969   4.766  1.00 20.51           A
ATOM   1968  N    ARG A 254     -26.946  35.677   3.237  1.00 21.65           A
ATOM   1969  CA   ARG A 254     -25.831  35.689   2.285  1.00 21.57           A
ATOM   1970  CB   ARG A 254     -26.157  34.771   1.101  1.00 21.20           A
ATOM   1971  CG   ARG A 254     -25.099  34.692  -0.007  1.00 19.84           A
ATOM   1972  CD   ARG A 254     -24.069  33.619   0.238  1.00 19.71           A
ATOM   1973  NE   ARG A 254     -23.027  34.026   1.174  1.00 21.24           A
ATOM   1974  CZ   ARG A 254     -22.046  34.870   0.879  1.00 20.84           A
```

FIGURE 4- 27 -

| | | | | | | | | | |
|---|---|---|---|---|---|---|---|---|---|
| ATOM | 1975 | NH1 | ARG A 254 | -21.972 | 35.402 | -0.330 | 1.00 | 19.85 | A |
| ATOM | 1976 | NH2 | ARG A 254 | -21.133 | 35.176 | 1.790 | 1.00 | 22.48 | A |
| ATOM | 1977 | C | ARG A 254 | -25.529 | 37.103 | 1.767 | 1.00 | 21.49 | A |
| ATOM | 1978 | O | ARG A 254 | -24.394 | 37.567 | 1.845 | 1.00 | 22.50 | A |
| ATOM | 1979 | N | SER A 255 | -26.548 | 37.780 | 1.240 | 1.00 | 20.99 | A |
| ATOM | 1980 | CA | SER A 255 | -26.380 | 39.129 | 0.706 | 1.00 | 20.88 | A |
| ATOM | 1981 | CB | SER A 255 | -27.651 | 39.582 | -0.015 | 1.00 | 20.95 | A |
| ATOM | 1982 | OG | SER A 255 | -27.869 | 38.805 | -1.179 | 1.00 | 23.02 | A |
| ATOM | 1983 | C | SER A 255 | -26.008 | 40.146 | 1.773 | 1.00 | 20.74 | A |
| ATOM | 1984 | O | SER A 255 | -25.224 | 41.057 | 1.518 | 1.00 | 20.84 | A |
| ATOM | 1985 | N | LEU A 256 | -26.561 | 39.999 | 2.968 | 1.00 | 19.73 | A |
| ATOM | 1986 | CA | LEU A 256 | -26.230 | 40.928 | 4.029 | 1.00 | 18.63 | A |
| ATOM | 1987 | CB | LEU A 256 | -27.123 | 40.687 | 5.237 | 1.00 | 18.17 | A |
| ATOM | 1988 | CG | LEU A 256 | -28.589 | 41.100 | 5.034 | 1.00 | 19.68 | A |
| ATOM | 1989 | CD1 | LEU A 256 | -29.429 | 40.636 | 6.204 | 1.00 | 22.12 | A |
| ATOM | 1990 | CD2 | LEU A 256 | -28.676 | 42.596 | 4.891 | 1.00 | 18.61 | A |
| ATOM | 1991 | C | LEU A 256 | -24.760 | 40.769 | 4.409 | 1.00 | 19.74 | A |
| ATOM | 1992 | O | LEU A 256 | -24.064 | 41.749 | 4.687 | 1.00 | 21.32 | A |
| ATOM | 1993 | N | THR A 257 | -24.275 | 39.535 | 4.411 | 1.00 | 19.62 | A |
| ATOM | 1994 | CA | THR A 257 | -22.882 | 39.294 | 4.765 | 1.00 | 19.40 | A |
| ATOM | 1995 | CB | THR A 257 | -22.549 | 37.780 | 4.759 | 1.00 | 18.74 | A |
| ATOM | 1996 | OG1 | THR A 257 | -23.423 | 37.099 | 5.662 | 1.00 | 17.47 | A |
| ATOM | 1997 | CG2 | THR A 257 | -21.112 | 37.539 | 5.202 | 1.00 | 15.09 | A |
| ATOM | 1998 | C | THR A 257 | -21.940 | 40.010 | 3.804 | 1.00 | 20.80 | A |
| ATOM | 1999 | O | THR A 257 | -21.043 | 40.727 | 4.234 | 1.00 | 19.71 | A |
| ATOM | 2000 | N | GLU A 258 | -22.157 | 39.817 | 2.504 | 1.00 | 22.95 | A |
| ATOM | 2001 | CA | GLU A 258 | -21.313 | 40.417 | 1.458 | 1.00 | 25.25 | A |
| ATOM | 2002 | CB | GLU A 258 | -21.558 | 39.728 | 0.103 | 1.00 | 26.99 | A |
| ATOM | 2003 | CG | GLU A 258 | -21.060 | 38.299 | 0.026 | 1.00 | 29.72 | A |
| ATOM | 2004 | CD | GLU A 258 | -19.583 | 38.188 | 0.341 | 1.00 | 30.28 | A |
| ATOM | 2005 | OE1 | GLU A 258 | -18.755 | 38.465 | -0.554 | 1.00 | 28.93 | A |
| ATOM | 2006 | OE2 | GLU A 258 | -19.257 | 37.833 | 1.496 | 1.00 | 28.70 | A |
| ATOM | 2007 | C | GLU A 258 | -21.478 | 41.913 | 1.245 | 1.00 | 24.91 | A |
| ATOM | 2008 | O | GLU A 258 | -20.509 | 42.619 | 0.943 | 1.00 | 25.28 | A |
| ATOM | 2009 | N | ARG A 259 | -22.701 | 42.399 | 1.398 | 1.00 | 22.96 | A |
| ATOM | 2010 | CA | ARG A 259 | -22.967 | 43.801 | 1.152 | 1.00 | 22.92 | A |
| ATOM | 2011 | CB | ARG A 259 | -24.323 | 43.939 | 0.458 | 1.00 | 22.13 | A |
| ATOM | 2012 | CG | ARG A 259 | -24.535 | 42.979 | -0.706 | 1.00 | 20.13 | A |
| ATOM | 2013 | CD | ARG A 259 | -25.986 | 42.946 | -1.158 | 1.00 | 18.03 | A |
| ATOM | 2014 | NE | ARG A 259 | -26.422 | 44.261 | -1.608 | 1.00 | 20.65 | A |
| ATOM | 2015 | CZ | ARG A 259 | -27.661 | 44.559 | -1.976 | 1.00 | 19.65 | A |
| ATOM | 2016 | NH1 | ARG A 259 | -28.602 | 43.629 | -1.950 | 1.00 | 21.22 | A |
| ATOM | 2017 | NH2 | ARG A 259 | -27.957 | 45.789 | -2.365 | 1.00 | 17.00 | A |
| ATOM | 2018 | C | ARG A 259 | -22.927 | 44.684 | 2.390 | 1.00 | 23.89 | A |
| ATOM | 2019 | O | ARG A 259 | -22.792 | 45.904 | 2.273 | 1.00 | 25.28 | A |
| ATOM | 2020 | N | LEU A 260 | -23.027 | 44.087 | 3.575 | 1.00 | 23.48 | A |
| ATOM | 2021 | CA | LEU A 260 | -23.036 | 44.888 | 4.800 | 1.00 | 21.43 | A |
| ATOM | 2022 | CB | LEU A 260 | -24.472 | 44.973 | 5.346 | 1.00 | 18.72 | A |
| ATOM | 2023 | CG | LEU A 260 | -24.687 | 45.753 | 6.650 | 1.00 | 17.21 | A |
| ATOM | 2024 | CD1 | LEU A 260 | -24.223 | 47.178 | 6.463 | 1.00 | 14.86 | A |
| ATOM | 2025 | CD2 | LEU A 260 | -26.160 | 45.710 | 7.066 | 1.00 | 15.44 | A |
| ATOM | 2026 | C | LEU A 260 | -22.106 | 44.475 | 5.936 | 1.00 | 21.14 | A |
| ATOM | 2027 | O | LEU A 260 | -21.315 | 45.283 | 6.422 | 1.00 | 20.71 | A |
| ATOM | 2028 | N | TYR A 261 | -22.192 | 43.222 | 6.360 | 1.00 | 20.71 | A |
| ATOM | 2029 | CA | TYR A 261 | -21.389 | 42.781 | 7.488 | 1.00 | 21.83 | A |
| ATOM | 2030 | CB | TYR A 261 | -21.880 | 41.411 | 7.962 | 1.00 | 21.87 | A |
| ATOM | 2031 | CG | TYR A 261 | -23.357 | 41.392 | 8.326 | 1.00 | 21.96 | A |
| ATOM | 2032 | CD1 | TYR A 261 | -23.980 | 42.516 | 8.876 | 1.00 | 20.22 | A |
| ATOM | 2033 | CE1 | TYR A 261 | -25.329 | 42.500 | 9.201 | 1.00 | 20.56 | A |
| ATOM | 2034 | CD2 | TYR A 261 | -24.130 | 40.249 | 8.117 | 1.00 | 22.00 | A |
| ATOM | 2035 | CE2 | TYR A 261 | -25.479 | 40.221 | 8.445 | 1.00 | 20.70 | A |
| ATOM | 2036 | CZ | TYR A 261 | -26.075 | 41.347 | 8.985 | 1.00 | 22.59 | A |
| ATOM | 2037 | OH | TYR A 261 | -27.412 | 41.305 | 9.315 | 1.00 | 23.57 | A |
| ATOM | 2038 | C | TYR A 261 | -19.869 | 42.787 | 7.343 | 1.00 | 22.65 | A |
| ATOM | 2039 | O | TYR A 261 | -19.181 | 43.252 | 8.247 | 1.00 | 24.05 | A |
| ATOM | 2040 | N | ILE A 262 | -19.333 | 42.296 | 6.223 | 1.00 | 22.63 | A |
| ATOM | 2041 | CA | ILE A 262 | -17.889 | 42.259 | 6.015 | 1.00 | 20.09 | A |
| ATOM | 2042 | CB | ILE A 262 | -17.526 | 41.448 | 4.781 | 1.00 | 18.72 | A |
| ATOM | 2043 | CG2 | ILE A 262 | -18.017 | 40.034 | 4.926 | 1.00 | 18.16 | A |
| ATOM | 2044 | CG1 | ILE A 262 | -18.134 | 42.101 | 3.553 | 1.00 | 18.94 | A |
| ATOM | 2045 | CD1 | ILE A 262 | -17.798 | 41.378 | 2.277 | 1.00 | 21.67 | A |
| ATOM | 2046 | C | ILE A 262 | -17.258 | 43.640 | 5.850 | 1.00 | 20.63 | A |
| ATOM | 2047 | O | ILE A 262 | -16.059 | 43.816 | 6.109 | 1.00 | 22.25 | A |
| ATOM | 2048 | N | GLY A 263 | -18.050 | 44.610 | 5.404 | 1.00 | 19.33 | A |
| ATOM | 2049 | CA | GLY A 263 | -17.539 | 45.958 | 5.225 | 1.00 | 18.24 | A |
| ATOM | 2050 | C | GLY A 263 | -18.421 | 46.768 | 4.296 | 1.00 | 19.47 | A |

FIGURE 4- 28 -

```
ATOM   2051  O    GLY A 263     -19.511  46.326   3.946  1.00 21.23       A
ATOM   2052  N    GLY A 264     -17.957  47.944   3.884  1.00 20.12       A
ATOM   2053  CA   GLY A 264     -18.742  48.779   2.989  1.00 20.95       A
ATOM   2054  C    GLY A 264     -18.395  50.257   3.106  1.00 23.30       A
ATOM   2055  O    GLY A 264     -17.593  50.653   3.963  1.00 25.52       A
ATOM   2056  N    PRO A 265     -18.995  51.114   2.272  1.00 22.13       A
ATOM   2057  CD   PRO A 265     -20.058  50.804   1.306  1.00 22.12       A
ATOM   2058  CA   PRO A 265     -18.727  52.553   2.301  1.00 21.16       A
ATOM   2059  CB   PRO A 265     -19.412  53.037   1.035  1.00 19.98       A
ATOM   2060  CG   PRO A 265     -20.598  52.177   0.973  1.00 20.98       A
ATOM   2061  C    PRO A 265     -19.253  53.257   3.555  1.00 20.47       A
ATOM   2062  O    PRO A 265     -20.251  52.841   4.132  1.00 21.57       A
ATOM   2063  N    LEU A 266     -18.575  54.321   3.974  1.00 19.53       A
ATOM   2064  CA   LEU A 266     -18.997  55.085   5.150  1.00 19.93       A
ATOM   2065  CB   LEU A 266     -17.873  55.117   6.190  1.00 18.20       A
ATOM   2066  CG   LEU A 266     -17.374  53.737   6.626  1.00 18.86       A
ATOM   2067  CD1  LEU A 266     -15.976  53.882   7.226  1.00 17.69       A
ATOM   2068  CD2  LEU A 266     -18.354  53.090   7.607  1.00 15.99       A
ATOM   2069  C    LEU A 266     -19.380  56.517   4.748  1.00 20.43       A
ATOM   2070  O    LEU A 266     -18.604  57.210   4.091  1.00 20.62       A
ATOM   2071  N    THR A 267     -20.576  56.950   5.147  1.00 21.67       A
ATOM   2072  CA   THR A 267     -21.072  58.287   4.820  1.00 23.84       A
ATOM   2073  CB   THR A 267     -22.340  58.196   3.920  1.00 22.92       A
ATOM   2074  OG1  THR A 267     -22.013  57.507   2.704  1.00 20.39       A
ATOM   2075  CG2  THR A 267     -22.886  59.596   3.593  1.00 18.74       A
ATOM   2076  C    THR A 267     -21.412  59.099   6.075  1.00 26.88       A
ATOM   2077  O    THR A 267     -22.091  58.602   6.973  1.00 28.08       A
ATOM   2078  N    ASN A 268     -20.943  60.346   6.142  1.00 29.34       A
ATOM   2079  CA   ASN A 268     -21.242  61.170   7.309  1.00 31.30       A
ATOM   2080  CB   ASN A 268     -20.221  62.309   7.498  1.00 32.99       A
ATOM   2081  CG   ASN A 268     -20.214  63.301   6.328  1.00 35.24       A
ATOM   2082  OD1  ASN A 268     -21.262  63.651   5.778  1.00 34.18       A
ATOM   2083  ND2  ASN A 268     -19.024  63.778   5.970  1.00 34.52       A
ATOM   2084  C    ASN A 268     -22.652  61.723   7.195  1.00 31.50       A
ATOM   2085  O    ASN A 268     -23.364  61.420   6.242  1.00 31.75       A
ATOM   2086  N    SER A 269     -23.050  62.528   8.173  1.00 32.82       A
ATOM   2087  CA   SER A 269     -24.390  63.107   8.213  1.00 33.28       A
ATOM   2088  CB   SER A 269     -24.625  63.744   9.583  1.00 34.02       A
ATOM   2089  OG   SER A 269     -23.613  64.695   9.873  1.00 34.41       A
ATOM   2090  C    SER A 269     -24.683  64.133   7.121  1.00 33.92       A
ATOM   2091  O    SER A 269     -25.837  64.497   6.897  1.00 33.48       A
ATOM   2092  N    LYS A 270     -23.642  64.611   6.451  1.00 34.93       A
ATOM   2093  CA   LYS A 270     -23.831  65.590   5.390  1.00 35.69       A
ATOM   2094  CB   LYS A 270     -22.661  66.579   5.372  1.00 37.32       A
ATOM   2095  CG   LYS A 270     -22.557  67.393   6.654  1.00 40.15       A
ATOM   2096  CD   LYS A 270     -21.538  68.510   6.562  1.00 41.29       A
ATOM   2097  CE   LYS A 270     -21.461  69.250   7.890  1.00 44.61       A
ATOM   2098  NZ   LYS A 270     -20.637  70.506   7.840  1.00 46.72       A
ATOM   2099  C    LYS A 270     -23.974  64.916   4.028  1.00 34.67       A
ATOM   2100  O    LYS A 270     -24.296  65.577   3.035  1.00 35.62       A
ATOM   2101  N    GLY A 271     -23.745  63.605   3.985  1.00 31.51       A
ATOM   2102  CA   GLY A 271     -23.855  62.885   2.734  1.00 29.43       A
ATOM   2103  C    GLY A 271     -22.525  62.733   2.024  1.00 29.42       A
ATOM   2104  O    GLY A 271     -22.468  62.269   0.890  1.00 29.62       A
ATOM   2105  N    GLN A 272     -21.450  63.133   2.689  1.00 30.04       A
ATOM   2106  CA   GLN A 272     -20.125  63.029   2.114  1.00 29.91       A
ATOM   2107  CB   GLN A 272     -19.189  64.042   2.785  1.00 30.60       A
ATOM   2108  CG   GLN A 272     -19.716  65.480   2.724  1.00 32.09       A
ATOM   2109  CD   GLN A 272     -18.813  66.501   3.420  1.00 34.38       A
ATOM   2110  OE1  GLN A 272     -18.566  66.432   4.631  1.00 34.64       A
ATOM   2111  NE2  GLN A 272     -18.329  67.464   2.650  1.00 34.43       A
ATOM   2112  C    GLN A 272     -19.639  61.605   2.330  1.00 30.70       A
ATOM   2113  O    GLN A 272     -20.227  60.858   3.100  1.00 31.20       A
ATOM   2114  N    ASN A 273     -18.561  61.243   1.647  1.00 32.00       A
ATOM   2115  CA   ASN A 273     -17.976  59.909   1.721  1.00 31.71       A
ATOM   2116  CB   ASN A 273     -17.604  59.499   0.292  1.00 31.18       A
ATOM   2117  CG   ASN A 273     -16.886  58.182   0.216  1.00 32.50       A
ATOM   2118  OD1  ASN A 273     -16.521  57.744  -0.867  1.00 33.56       A
ATOM   2119  ND2  ASN A 273     -16.675  57.538   1.357  1.00 34.31       A
ATOM   2120  C    ASN A 273     -16.746  59.913   2.650  1.00 31.68       A
ATOM   2121  O    ASN A 273     -15.670  60.347   2.248  1.00 33.09       A
ATOM   2122  N    CYS A 274     -16.911  59.424   3.892  1.00 31.13       A
ATOM   2123  CA   CYS A 274     -15.826  59.388   4.879  1.00 31.57       A
ATOM   2124  CB   CYS A 274     -16.373  59.107   6.272  1.00 31.03       A
ATOM   2125  SG   CYS A 274     -17.288  60.431   6.973  1.00 40.13       A
ATOM   2126  C    CYS A 274     -14.742  58.367   4.631  1.00 30.35       A
```

FIGURE 4-29-

```
ATOM   2127  O    CYS A 274     -13.562  58.608   4.904  1.00 30.17      A
ATOM   2128  N    GLY A 275     -15.151  57.206   4.146  1.00 29.78      A
ATOM   2129  CA   GLY A 275     -14.183  56.163   3.897  1.00 29.35      A
ATOM   2130  C    GLY A 275     -14.794  54.802   3.670  1.00 27.68      A
ATOM   2131  O    GLY A 275     -15.885  54.676   3.115  1.00 26.49      A
ATOM   2132  N    TYR A 276     -14.091  53.778   4.131  1.00 27.49      A
ATOM   2133  CA   TYR A 276     -14.539  52.415   3.934  1.00 27.16      A
ATOM   2134  CB   TYR A 276     -13.833  51.860   2.705  1.00 25.27      A
ATOM   2135  CG   TYR A 276     -14.538  50.701   2.085  1.00 26.18      A
ATOM   2136  CD1  TYR A 276     -15.503  50.899   1.102  1.00 24.49      A
ATOM   2137  CE1  TYR A 276     -16.172  49.839   0.544  1.00 25.63      A
ATOM   2138  CD2  TYR A 276     -14.262  49.401   2.497  1.00 26.00      A
ATOM   2139  CE2  TYR A 276     -14.927  48.334   1.949  1.00 26.80      A
ATOM   2140  CZ   TYR A 276     -15.864  48.554   0.970  1.00 26.71      A
ATOM   2141  OH   TYR A 276     -16.557  47.481   0.436  1.00 27.73      A
ATOM   2142  C    TYR A 276     -14.268  51.505   5.134  1.00 27.20      A
ATOM   2143  O    TYR A 276     -13.154  51.484   5.667  1.00 27.66      A
ATOM   2144  N    ARG A 277     -15.290  50.742   5.529  1.00 26.70      A
ATOM   2145  CA   ARG A 277     -15.221  49.794   6.653  1.00 25.71      A
ATOM   2146  CB   ARG A 277     -16.565  49.770   7.388  1.00 25.49      A
ATOM   2147  CG   ARG A 277     -16.733  48.657   8.407  1.00 25.51      A
ATOM   2148  CD   ARG A 277     -18.081  48.781   9.108  1.00 26.33      A
ATOM   2149  NE   ARG A 277     -19.206  48.742   8.175  1.00 25.70      A
ATOM   2150  CZ   ARG A 277     -19.870  47.633   7.600  1.00 26.71      A
ATOM   2151  NH1  ARG A 277     -19.116  46.455   7.860  1.00 26.63      A
ATOM   2152  NH2  ARG A 277     -20.687  47.699   6.750  1.00 26.28      A
ATOM   2153  C    ARG A 277     -14.903  48.383   6.170  1.00 25.65      A
ATOM   2154  O    ARG A 277     -15.431  47.944   5.150  1.00 27.94      A
ATOM   2155  N    ARG A 278     -14.034  47.679   6.887  1.00 23.89      A
ATOM   2156  CA   ARG A 278     -13.687  46.301   6.528  1.00 24.02      A
ATOM   2157  CB   ARG A 278     -12.327  46.228   5.823  1.00 23.97      A
ATOM   2158  CG   ARG A 278     -12.397  46.602   4.366  1.00 27.56      A
ATOM   2159  CD   ARG A 278     -11.037  46.487   3.689  1.00 30.83      A
ATOM   2160  NE   ARG A 278     -10.853  47.547   2.697  1.00 33.29      A
ATOM   2161  CZ   ARG A 278     -10.657  48.831   3.004  1.00 34.35      A
ATOM   2162  NH1  ARG A 278     -10.610  49.210   4.284  1.00 33.65      A
ATOM   2163  NH2  ARG A 278     -10.530  49.741   2.037  1.00 31.63      A
ATOM   2164  C    ARG A 278     -13.650  45.447   7.786  1.00 22.45      A
ATOM   2165  O    ARG A 278     -12.939  44.438   7.848  1.00 23.02      A
ATOM   2166  N    CYS A 279     -14.413  45.875   8.787  1.00 19.42      A
ATOM   2167  CA   CYS A 279     -14.486  45.186  10.063  1.00 18.88      A
ATOM   2168  CB   CYS A 279     -13.527  45.825  11.073  1.00 16.88      A
ATOM   2169  SG   CYS A 279     -13.931  47.553  11.427  1.00 18.80      A
ATOM   2170  C    CYS A 279     -15.917  45.314  10.566  1.00 19.76      A
ATOM   2171  O    CYS A 279     -16.791  45.840   9.865  1.00 17.46      A
ATOM   2172  N    ARG A 280     -16.136  44.867  11.799  1.00 19.79      A
ATOM   2173  CA   ARG A 280     -17.456  44.893  12.397  1.00 19.90      A
ATOM   2174  CB   ARG A 280     -17.411  44.346  13.819  1.00 19.57      A
ATOM   2175  CG   ARG A 280     -18.777  44.261  14.484  1.00 19.74      A
ATOM   2176  CD   ARG A 280     -19.566  43.086  13.960  1.00 19.76      A
ATOM   2177  NE   ARG A 280     -19.014  41.817  14.434  1.00 21.22      A
ATOM   2178  CZ   ARG A 280     -19.292  40.626  13.908  1.00 20.14      A
ATOM   2179  NH1  ARG A 280     -20.120  40.516  12.879  1.00 21.13      A
ATOM   2180  NH2  ARG A 280     -18.740  39.538  14.413  1.00 20.26      A
ATOM   2181  C    ARG A 280     -18.079  46.268  12.433  1.00 21.17      A
ATOM   2182  O    ARG A 280     -17.436  47.252  12.812  1.00 21.19      A
ATOM   2183  N    ALA A 281     -19.340  46.319  12.014  1.00 21.95      A
ATOM   2184  CA   ALA A 281     -20.129  47.536  12.034  1.00 21.83      A
ATOM   2185  CB   ALA A 281     -21.137  47.516  10.919  1.00 22.40      A
ATOM   2186  C    ALA A 281     -20.828  47.426  13.384  1.00 22.85      A
ATOM   2187  O    ALA A 281     -21.542  46.462  13.641  1.00 22.30      A
ATOM   2188  N    SER A 282     -20.604  48.405  14.246  1.00 23.99      A
ATOM   2189  CA   SER A 282     -21.173  48.408  15.585  1.00 24.65      A
ATOM   2190  CB   SER A 282     -20.618  49.577  16.366  1.00 24.78      A
ATOM   2191  OG   SER A 282     -21.186  50.765  15.857  1.00 27.13      A
ATOM   2192  C    SER A 282     -22.686  48.513  15.635  1.00 24.33      A
ATOM   2193  O    SER A 282     -23.310  48.136  16.634  1.00 24.72      A
ATOM   2194  N    GLY A 283     -23.279  49.031  14.572  1.00 23.53      A
ATOM   2195  CA   GLY A 283     -24.715  49.205  14.587  1.00 22.38      A
ATOM   2196  C    GLY A 283     -25.601  48.323  13.736  1.00 21.68      A
ATOM   2197  O    GLY A 283     -26.510  48.836  13.089  1.00 22.50      A
ATOM   2198  N    VAL A 284     -25.348  47.018  13.704  1.00 19.52      A
ATOM   2199  CA   VAL A 284     -26.219  46.132  12.946  1.00 19.52      A
ATOM   2200  CB   VAL A 284     -25.492  45.437  11.774  1.00 21.32      A
ATOM   2201  CG1  VAL A 284     -25.129  46.467  10.711  1.00 18.48      A
ATOM   2202  CG2  VAL A 284     -24.253  44.700  12.278  1.00 23.23      A
```

FIGURE 4- 30 -

```
ATOM   2203  C    VAL A 284    -26.795  45.104  13.905  1.00 19.80           A
ATOM   2204  O    VAL A 284    -26.370  45.018  15.060  1.00 20.69           A
ATOM   2205  N    LEU A 285    -27.772  44.340  13.432  1.00 19.51           A
ATOM   2206  CA   LEU A 285    -28.440  43.343  14.254  1.00 19.29           A
ATOM   2207  CB   LEU A 285    -29.635  42.781  13.487  1.00 19.74           A
ATOM   2208  CG   LEU A 285    -30.504  41.737  14.192  1.00 20.07           A
ATOM   2209  CD1  LEU A 285    -31.073  42.322  15.463  1.00 18.55           A
ATOM   2210  CD2  LEU A 285    -31.613  41.283  13.269  1.00 17.21           A
ATOM   2211  C    LEU A 285    -27.542  42.202  14.700  1.00 20.53           A
ATOM   2212  O    LEU A 285    -27.747  41.637  15.772  1.00 21.54           A
ATOM   2213  N    THR A 286    -26.550  41.862  13.882  1.00 21.74           A
ATOM   2214  CA   THR A 286    -25.645  40.752  14.194  1.00 22.28           A
ATOM   2215  CB   THR A 286    -25.170  40.035  12.918  1.00 22.06           A
ATOM   2216  OG1  THR A 286    -24.717  41.010  11.969  1.00 22.80           A
ATOM   2217  CG2  THR A 286    -26.288  39.204  12.320  1.00 24.17           A
ATOM   2218  C    THR A 286    -24.398  41.129  14.962  1.00 22.60           A
ATOM   2219  O    THR A 286    -23.540  40.270  15.184  1.00 22.47           A
ATOM   2220  N    THR A 287    -24.289  42.394  15.362  1.00 21.29           A
ATOM   2221  CA   THR A 287    -23.109  42.860  16.094  1.00 22.24           A
ATOM   2222  CB   THR A 287    -23.226  44.356  16.402  1.00 24.45           A
ATOM   2223  OG1  THR A 287    -23.450  45.068  15.179  1.00 29.81           A
ATOM   2224  CG2  THR A 287    -21.954  44.876  17.061  1.00 22.23           A
ATOM   2225  C    THR A 287    -22.851  42.111  17.404  1.00 20.76           A
ATOM   2226  O    THR A 287    -21.732  41.715  17.686  1.00 18.52           A
ATOM   2227  N    SER A 288    -23.893  41.926  18.203  1.00 21.65           A
ATOM   2228  CA   SER A 288    -23.766  41.231  19.471  1.00 22.23           A
ATOM   2229  CB   SER A 288    -25.040  41.421  20.299  1.00 23.02           A
ATOM   2230  OG   SER A 288    -24.874  40.961  21.628  1.00 24.95           A
ATOM   2231  C    SER A 288    -23.517  39.750  19.239  1.00 22.68           A
ATOM   2232  O    SER A 288    -22.608  39.167  19.822  1.00 23.14           A
ATOM   2233  N    CYS A 289    -24.323  39.148  18.378  1.00 22.52           A
ATOM   2234  CA   CYS A 289    -24.189  37.730  18.086  1.00 23.79           A
ATOM   2235  CB   CYS A 289    -25.291  37.300  17.123  1.00 24.55           A
ATOM   2236  SG   CYS A 289    -25.442  35.529  16.936  1.00 30.37           A
ATOM   2237  C    CYS A 289    -22.820  37.389  17.500  1.00 23.66           A
ATOM   2238  O    CYS A 289    -22.160  36.457  17.949  1.00 24.27           A
ATOM   2239  N    GLY A 290    -22.386  38.148  16.503  1.00 23.69           A
ATOM   2240  CA   GLY A 290    -21.099  37.871  15.897  1.00 22.62           A
ATOM   2241  C    GLY A 290    -19.939  38.029  16.859  1.00 21.83           A
ATOM   2242  O    GLY A 290    -19.044  37.185  16.926  1.00 21.32           A
ATOM   2243  N    ASN A 291    -19.945  39.116  17.613  1.00 21.06           A
ATOM   2244  CA   ASN A 291    -18.867  39.340  18.548  1.00 21.35           A
ATOM   2245  CB   ASN A 291    -18.986  40.723  19.193  1.00 19.69           A
ATOM   2246  CG   ASN A 291    -18.604  41.849  18.236  1.00 18.84           A
ATOM   2247  OD1  ASN A 291    -18.062  41.600  17.162  1.00 15.70           A
ATOM   2248  ND2  ASN A 291    -18.873  43.096  18.633  1.00 19.70           A
ATOM   2249  C    ASN A 291    -18.863  38.248  19.599  1.00 22.14           A
ATOM   2250  O    ASN A 291    -17.802  37.735  19.947  1.00 23.35           A
ATOM   2251  N    THR A 292    -20.034  37.869  20.099  1.00 22.11           A
ATOM   2252  CA   THR A 292    -20.069  36.809  21.105  1.00 21.40           A
ATOM   2253  CB   THR A 292    -21.486  36.568  21.666  1.00 19.64           A
ATOM   2254  OG1  THR A 292    -21.985  37.777  22.247  1.00 19.04           A
ATOM   2255  CG2  THR A 292    -21.448  35.505  22.742  1.00 18.95           A
ATOM   2256  C    THR A 292    -19.550  35.516  20.486  1.00 21.97           A
ATOM   2257  O    THR A 292    -18.745  34.816  21.104  1.00 22.61           A
ATOM   2258  N    LEU A 293    -19.993  35.203  19.267  1.00 20.23           A
ATOM   2259  CA   LEU A 293    -19.536  33.987  18.598  1.00 18.69           A
ATOM   2260  CB   LEU A 293    -20.260  33.770  17.263  1.00 16.81           A
ATOM   2261  CG   LEU A 293    -21.728  33.326  17.268  1.00 18.19           A
ATOM   2262  CD1  LEU A 293    -22.147  33.014  15.839  1.00 19.20           A
ATOM   2263  CD2  LEU A 293    -21.926  32.094  18.146  1.00 16.36           A
ATOM   2264  C    LEU A 293    -18.042  34.020  18.332  1.00 18.40           A
ATOM   2265  O    LEU A 293    -17.313  33.082  18.679  1.00 18.88           A
ATOM   2266  N    THR A 294    -17.594  35.100  17.704  1.00 16.35           A
ATOM   2267  CA   THR A 294    -16.198  35.252  17.358  1.00 15.28           A
ATOM   2268  CB   THR A 294    -15.973  36.551  16.611  1.00 16.04           A
ATOM   2269  OG1  THR A 294    -16.698  36.510  15.378  1.00 17.98           A
ATOM   2270  CG2  THR A 294    -14.497  36.760  16.337  1.00 14.60           A
ATOM   2271  C    THR A 294    -15.313  35.235  18.575  1.00 16.61           A
ATOM   2272  O    THR A 294    -14.316  34.524  18.612  1.00 17.25           A
ATOM   2273  N    CYS A 295    -15.670  36.018  19.581  1.00 18.16           A
ATOM   2274  CA   CYS A 295    -14.861  36.055  20.790  1.00 20.18           A
ATOM   2275  CB   CYS A 295    -15.381  37.113  21.762  1.00 21.99           A
ATOM   2276  SG   CYS A 295    -14.553  37.083  23.368  1.00 21.23           A
ATOM   2277  C    CYS A 295    -14.821  34.704  21.486  1.00 19.89           A
ATOM   2278  O    CYS A 295    -13.800  34.329  22.033  1.00 20.93           A
```

FIGURE 4-31-

```
ATOM   2279  N    TYR A 296     -15.933  33.977  21.472  1.00 19.51      A
ATOM   2280  CA   TYR A 296     -15.985  32.663  22.107  1.00 18.64      A
ATOM   2281  CB   TYR A 296     -17.442  32.152  22.147  1.00 15.55      A
ATOM   2282  CG   TYR A 296     -17.606  30.682  22.484  1.00 12.22      A
ATOM   2283  CD1  TYR A 296     -17.469  29.716  21.505  1.00 12.80      A
ATOM   2284  CE1  TYR A 296     -17.602  28.372  21.798  1.00 14.73      A
ATOM   2285  CD2  TYR A 296     -17.885  30.258  23.784  1.00 13.53      A
ATOM   2286  CE2  TYR A 296     -18.021  28.905  24.095  1.00  9.41      A
ATOM   2287  CZ   TYR A 296     -17.876  27.971  23.091  1.00 13.19      A
ATOM   2288  CH   TYR A 296     -17.983  26.623  23.340  1.00 14.11      A
ATOM   2289  C    TYR A 296     -15.085  31.693  21.347  1.00 20.13      A
ATOM   2290  C    TYR A 296     -14.323  30.926  21.944  1.00 20.15      A
ATOM   2291  N    LEU A 297     -15.174  31.738  20.023  1.00 21.28      A
ATOM   2292  CA   LEU A 297     -14.377  30.862  19.186  1.00 22.69      A
ATOM   2293  CB   LEU A 297     -14.662  31.143  17.711  1.00 22.67      A
ATOM   2294  CG   LEU A 297     -13.687  30.560  16.682  1.00 22.30      A
ATOM   2295  CD1  LEU A 297     -13.559  29.050  16.834  1.00 20.85      A
ATOM   2296  CD2  LEU A 297     -14.197  30.922  15.303  1.00 22.82      A
ATOM   2297  C    LEU A 297     -12.901  31.055  19.477  1.00 23.42      A
ATOM   2298  C    LEU A 297     -12.231  30.133  19.928  1.00 25.13      A
ATOM   2299  N    LYS A 298     -12.403  32.261  19.228  1.00 23.18      A
ATOM   2300  CA   LYS A 298     -11.000  32.571  19.461  1.00 22.81      A
ATOM   2301  CB   LYS A 298     -10.727  34.056  19.179  1.00 21.68      A
ATOM   2302  CG   LYS A 298     -10.973  34.457  17.718  1.00 17.75      A
ATOM   2303  CD   LYS A 298     -10.679  35.921  17.471  1.00 16.98      A
ATOM   2304  CE   LYS A 298     -11.136  36.342  16.087  1.00 18.14      A
ATOM   2305  NZ   LYS A 298     -10.897  37.789  15.854  1.00 17.78      A
ATOM   2306  C    LYS A 298     -10.547  32.202  20.869  1.00 23.05      A
ATOM   2307  C    LYS A 298      -9.556  31.498  21.027  1.00 25.93      A
ATOM   2308  N    ALA A 299     -11.274  32.648  21.887  1.00 22.57      A
ATOM   2309  CA   ALA A 299     -10.912  32.333  23.274  1.00 22.92      A
ATOM   2310  CB   ALA A 299     -11.883  33.022  24.257  1.00 20.31      A
ATOM   2311  C    ALA A 299     -10.855  30.828  23.562  1.00 22.45      A
ATOM   2312  C    ALA A 299      -9.910  30.356  24.190  1.00 23.66      A
ATOM   2313  N    TER A 300     -11.848  30.071  23.108  1.00 21.28      A
ATOM   2314  CA   TER A 300     -11.839  28.634  23.354  1.00 22.20      A
ATOM   2315  CB   TER A 300     -13.064  27.932  22.694  1.00 22.05      A
ATOM   2316  CG1  TER A 300     -14.275  28.476  23.225  1.00 21.60      A
ATOM   2317  CG2  TER A 300     -13.055  26.452  22.979  1.00 17.78      A
ATOM   2318  C    TER A 300     -10.542  28.015  22.817  1.00 23.65      A
ATOM   2319  C    TER A 300      -9.833  27.311  23.542  1.00 22.80      A
ATOM   2320  N    ALA A 301     -10.234  28.292  21.551  1.00 24.45      A
ATOM   2321  CA   ALA A 301      -9.027  27.775  20.909  1.00 24.82      A
ATOM   2322  CB   ALA A 301      -9.033  28.121  19.418  1.00 22.24      A
ATOM   2323  C    ALA A 301      -7.766  28.326  21.580  1.00 25.90      A
ATOM   2324  C    ALA A 301      -6.769  27.610  21.720  1.00 27.42      A
ATOM   2325  N    ALA A 302      -7.793  29.590  21.991  1.00 24.64      A
ATOM   2326  CA   ALA A 302      -6.626  30.145  22.663  1.00 24.74      A
ATOM   2327  CB   ALA A 302      -6.811  31.633  22.950  1.00 22.48      A
ATOM   2328  C    ALA A 302      -6.453  29.372  23.966  1.00 25.98      A
ATOM   2329  C    ALA A 302      -5.339  28.991  24.319  1.00 27.85      A
ATOM   2330  N    CYS A 303      -7.554  29.125  24.676  1.00 25.63      A
ATOM   2331  CA   CYS A 303      -7.476  28.391  25.934  1.00 25.27      A
ATOM   2332  CB   CYS A 303      -8.869  28.148  26.515  1.00 24.41      A
ATOM   2333  SG   CYS A 303      -9.363  29.349  27.766  1.00 25.60      A
ATOM   2334  C    CYS A 303      -6.753  27.062  25.785  1.00 25.70      A
ATOM   2335  C    CYS A 303      -5.993  26.657  26.667  1.00 26.09      A
ATOM   2336  N    ARG A 304      -6.990  26.378  24.672  1.00 25.54      A
ATOM   2337  CA   ARG A 304      -6.337  25.101  24.438  1.00 25.59      A
ATOM   2338  CB   ARG A 304      -6.986  24.404  23.248  1.00 22.04      A
ATOM   2339  CG   ARG A 304      -8.474  24.214  23.416  1.00 19.06      A
ATOM   2340  CD   ARG A 304      -9.058  23.344  22.328  1.00 18.81      A
ATOM   2341  NE   ARG A 304     -10.489  23.115  22.511  1.00 18.28      A
ATOM   2342  CZ   ARG A 304     -11.228  22.343  21.721  1.00 19.86      A
ATOM   2343  NH1  ARG A 304     -10.680  21.717  20.684  1.00 20.04      A
ATOM   2344  NH2  ARG A 304     -12.519  22.189  21.970  1.00 19.26      A
ATOM   2345  C    ARG A 304      -4.849  25.343  24.186  1.00 27.00      A
ATOM   2346  C    ARG A 304      -3.980  24.761  24.842  1.00 28.11      A
ATOM   2347  N    ALA A 305      -4.557  26.231  23.249  1.00 27.15      A
ATOM   2348  CA   ALA A 305      -3.177  26.542  22.929  1.00 27.66      A
ATOM   2349  CB   ALA A 305      -3.134  27.707  21.949  1.00 27.56      A
ATOM   2350  C    ALA A 305      -2.353  26.869  24.182  1.00 27.32      A
ATOM   2351  C    ALA A 305      -1.183  26.503  24.279  1.00 27.59      A
ATOM   2352  N    ALA A 306      -2.969  27.555  25.136  1.00 26.76      A
ATOM   2353  CA   ALA A 306      -2.287  27.946  26.360  1.00 27.43      A
ATOM   2354  CB   ALA A 306      -2.975  29.157  26.966  1.00 28.47      A
```

FIGURE 4- 32 -

```
ATOM   2355  C    ALA A 306      -2.224  26.822  27.385  1.00 27.97           A
ATOM   2356  O    ALA A 306      -1.387  26.843  28.283  1.00 27.64           A
ATOM   2357  N    LYS A 307      -3.113  25.845  27.254  1.00 29.08           A
ATOM   2358  CA   LYS A 307      -3.141  24.715  28.173  1.00 30.81           A
ATOM   2359  CB   LYS A 307      -1.733  24.146  28.370  1.00 32.22           A
ATOM   2360  CG   LYS A 307      -1.315  23.172  27.290  1.00 34.73           A
ATOM   2361  CD   LYS A 307       0.110  23.422  26.817  1.00 37.64           A
ATOM   2362  CE   LYS A 307       0.500  22.389  25.759  1.00 41.53           A
ATOM   2363  NZ   LYS A 307      -0.571  22.234  24.709  1.00 43.97           A
ATOM   2364  C    LYS A 307      -3.757  25.007  29.532  1.00 31.48           A
ATOM   2365  O    LYS A 307      -3.414  24.365  30.522  1.00 30.82           A
ATOM   2366  N    LEU A 308      -4.661  25.977  29.589  1.00 32.59           A
ATOM   2367  CA   LEU A 308      -5.339  26.282  30.839  1.00 33.09           A
ATOM   2368  CB   LEU A 308      -6.223  27.512  30.677  1.00 32.37           A
ATOM   2369  CG   LEU A 308      -5.514  28.867  30.811  1.00 32.54           A
ATOM   2370  CD1  LEU A 308      -4.077  28.778  30.331  1.00 32.03           A
ATOM   2371  CD2  LEU A 308      -6.288  29.913  30.012  1.00 31.33           A
ATOM   2372  C    LEU A 308      -6.168  25.042  31.153  1.00 35.46           A
ATOM   2373  O    LEU A 308      -6.764  24.428  30.265  1.00 33.57           A
ATOM   2374  N    GLN A 309      -6.195  24.660  32.419  1.00 38.49           A
ATOM   2375  CA   GLN A 309      -6.904  23.456  32.796  1.00 40.70           A
ATOM   2376  CB   GLN A 309      -6.090  22.724  33.870  1.00 42.44           A
ATOM   2377  CG   GLN A 309      -5.940  21.217  33.669  1.00 48.24           A
ATOM   2378  CD   GLN A 309      -4.994  20.819  32.516  1.00 50.97           A
ATOM   2379  OE1  GLN A 309      -4.714  19.629  32.316  1.00 51.57           A
ATOM   2380  NE2  GLN A 309      -4.505  21.809  31.762  1.00 51.69           A
ATOM   2381  C    GLN A 309      -8.325  23.693  33.290  1.00 41.46           A
ATOM   2382  O    GLN A 309      -8.572  24.597  34.097  1.00 42.73           A
ATOM   2383  N    ASP A 310      -9.255  22.882  32.782  1.00 40.84           A
ATOM   2384  CA   ASP A 310     -10.656  22.922  33.197  1.00 38.78           A
ATOM   2385  CB   ASP A 310     -10.741  22.391  34.632  1.00 41.02           A
ATOM   2386  CG   ASP A 310     -12.135  21.955  35.018  1.00 42.95           A
ATOM   2387  OD1  ASP A 310     -12.372  21.757  36.229  1.00 43.49           A
ATOM   2388  OD2  ASP A 310     -12.988  21.800  34.118  1.00 44.26           A
ATOM   2389  C    ASP A 310     -11.301  24.309  33.118  1.00 36.56           A
ATOM   2390  O    ASP A 310     -11.959  24.745  34.060  1.00 36.01           A
ATOM   2391  N    CYS A 311     -11.129  24.985  31.987  1.00 34.70           A
ATOM   2392  CA   CYS A 311     -11.673  26.333  31.797  1.00 32.52           A
ATOM   2393  CB   CYS A 311     -11.094  26.959  30.528  1.00 29.86           A
ATOM   2394  SG   CYS A 311      -9.311  27.128  30.535  1.00 31.37           A
ATOM   2395  C    CYS A 311     -13.189  26.420  31.714  1.00 31.44           A
ATOM   2396  O    CYS A 311     -13.837  25.545  31.146  1.00 31.72           A
ATOM   2397  N    THR A 312     -13.750  27.477  32.293  1.00 29.86           A
ATOM   2398  CA   THR A 312     -15.189  27.713  32.230  1.00 28.66           A
ATOM   2399  CB   THR A 312     -15.880  27.586  33.597  1.00 28.90           A
ATOM   2400  OG1  THR A 312     -15.770  26.240  34.069  1.00 26.19           A
ATOM   2401  CG2  THR A 312     -17.364  27.951  33.473  1.00 27.68           A
ATOM   2402  C    THR A 312     -15.279  29.147  31.754  1.00 28.76           A
ATOM   2403  O    THR A 312     -14.745  30.052  32.398  1.00 29.24           A
ATOM   2404  N    MET A 313     -15.950  29.356  30.629  1.00 28.28           A
ATOM   2405  CA   MET A 313     -16.039  30.686  30.049  1.00 28.37           A
ATOM   2406  CB   MET A 313     -15.573  30.643  28.600  1.00 29.33           A
ATOM   2407  CG   MET A 313     -14.288  31.360  28.332  1.00 30.41           A
ATOM   2408  SD   MET A 313     -13.621  30.794  26.763  1.00 35.64           A
ATOM   2409  CE   MET A 313     -14.983  31.208  25.656  1.00 31.13           A
ATOM   2410  C    MET A 313     -17.391  31.348  30.072  1.00 27.68           A
ATOM   2411  O    MET A 313     -18.435  30.685  30.041  1.00 29.16           A
ATOM   2412  N    LEU A 314     -17.349  32.676  30.099  1.00 25.12           A
ATOM   2413  CA   LEU A 314     -18.543  33.501  30.077  1.00 23.63           A
ATOM   2414  CB   LEU A 314     -18.775  34.120  31.452  1.00 22.18           A
ATOM   2415  CG   LEU A 314     -20.211  34.545  31.722  1.00 21.67           A
ATOM   2416  CD1  LEU A 314     -21.109  33.342  31.577  1.00 21.50           A
ATOM   2417  CD2  LEU A 314     -20.327  35.149  33.104  1.00 18.57           A
ATOM   2418  C    LEU A 314     -18.257  34.573  29.024  1.00 23.14           A
ATOM   2419  O    LEU A 314     -17.286  35.320  29.136  1.00 25.15           A
ATOM   2420  N    VAL A 315     -19.080  34.617  27.983  1.00 21.66           A
ATOM   2421  CA   VAL A 315     -18.899  35.574  26.897  1.00 21.00           A
ATOM   2422  CB   VAL A 315     -18.613  34.855  25.540  1.00 22.68           A
ATOM   2423  CG1  VAL A 315     -18.320  35.898  24.441  1.00 25.24           A
ATOM   2424  CG2  VAL A 315     -17.455  33.893  25.678  1.00 21.33           A
ATOM   2425  C    VAL A 315     -20.140  36.438  26.701  1.00 21.05           A
ATOM   2426  O    VAL A 315     -21.263  35.928  26.660  1.00 19.22           A
ATOM   2427  N    ASN A 316     -19.923  37.745  26.582  1.00 20.70           A
ATOM   2428  CA   ASN A 316     -20.991  38.715  26.370  1.00 21.20           A
ATOM   2429  CB   ASN A 316     -21.195  39.604  27.593  1.00 21.82           A
ATOM   2430  CG   ASN A 316     -22.089  38.983  28.626  1.00 21.01           A
```

FIGURE 4-33-

```
ATOM   2431  OD1 ASN A 316     -21.664  38.137  29.411  1.00 21.54        A
ATOM   2432  ND2 ASN A 316     -23.343  39.399  28.633  1.00 20.57        A
ATOM   2433  C   ASN A 316     -20.510  39.594  25.249  1.00 23.20        A
ATOM   2434  O   ASN A 316     -19.933  40.652  25.495  1.00 24.35        A
ATOM   2435  N   GLY A 317     -20.747  39.182  24.015  1.00 23.64        A
ATOM   2436  CA  GLY A 317     -20.263  39.988  22.918  1.00 23.50        A
ATOM   2437  C   GLY A 317     -18.754  39.979  23.007  1.00 22.94        A
ATOM   2438  O   GLY A 317     -18.143  38.912  23.014  1.00 24.93        A
ATOM   2439  N   ASP A 318     -18.152  41.155  23.114  1.00 22.93        A
ATOM   2440  CA  ASP A 318     -16.706  41.252  23.190  1.00 23.17        A
ATOM   2441  CB  ASP A 318     -16.247  42.608  22.631  1.00 24.00        A
ATOM   2442  CG  ASP A 318     -16.553  43.767  23.561  1.00 26.74        A
ATOM   2443  OD1 ASP A 318     -17.692  43.875  24.047  1.00 29.12        A
ATOM   2444  OD2 ASP A 318     -15.650  44.588  23.803  1.00 28.77        A
ATOM   2445  C   ASP A 318     -16.165  41.025  24.603  1.00 23.16        A
ATOM   2446  O   ASP A 318     -14.978  40.771  24.774  1.00 24.95        A
ATOM   2447  N   ASP A 319     -17.027  41.080  25.615  1.00 23.22        A
ATOM   2448  CA  ASP A 319     -16.576  40.869  26.997  1.00 23.49        A
ATOM   2449  CB  ASP A 319     -17.617  41.396  27.990  1.00 25.44        A
ATOM   2450  CG  ASP A 319     -17.010  41.775  29.344  1.00 26.78        A
ATOM   2451  OD1 ASP A 319     -16.572  40.871  30.090  1.00 29.17        A
ATOM   2452  OD2 ASP A 319     -16.967  42.984  29.664  1.00 24.87        A
ATOM   2453  C   ASP A 319     -16.314  39.387  27.249  1.00 23.94        A
ATOM   2454  O   ASP A 319     -17.131  38.532  26.897  1.00 23.55        A
ATOM   2455  N   LEU A 320     -15.171  39.092  27.868  1.00 24.90        A
ATOM   2456  CA  LEU A 320     -14.769  37.716  28.149  1.00 25.32        A
ATOM   2457  CB  LEU A 320     -13.750  37.259  27.096  1.00 25.96        A
ATOM   2458  CG  LEU A 320     -13.036  35.920  27.289  1.00 24.60        A
ATOM   2459  CD1 LEU A 320     -14.022  34.768  27.147  1.00 24.65        A
ATOM   2460  CD2 LEU A 320     -11.943  35.804  26.255  1.00 26.54        A
ATOM   2461  C   LEU A 320     -14.154  37.538  29.529  1.00 25.44        A
ATOM   2462  O   LEU A 320     -13.317  38.333  29.946  1.00 26.36        A
ATOM   2463  N   VAL A 321     -14.568  36.486  30.229  1.00 25.16        A
ATOM   2464  CA  VAL A 321     -14.025  36.180  31.547  1.00 26.25        A
ATOM   2465  CB  VAL A 321     -14.937  36.703  32.696  1.00 25.92        A
ATOM   2466  CG1 VAL A 321     -16.356  36.222  32.514  1.00 25.60        A
ATOM   2467  CG2 VAL A 321     -14.403  36.224  34.029  1.00 26.68        A
ATOM   2468  C   VAL A 321     -13.855  34.667  31.671  1.00 27.37        A
ATOM   2469  O   VAL A 321     -14.765  33.905  31.368  1.00 29.74        A
ATOM   2470  N   VAL A 322     -12.683  34.231  32.107  1.00 27.77        A
ATOM   2471  CA  VAL A 322     -12.422  32.811  32.246  1.00 27.69        A
ATOM   2472  CB  VAL A 322     -11.267  32.358  31.329  1.00 29.29        A
ATOM   2473  CG1 VAL A 322     -11.054  30.855  31.457  1.00 29.14        A
ATOM   2474  CG2 VAL A 322     -11.561  32.733  29.897  1.00 30.79        A
ATOM   2475  C   VAL A 322     -12.025  32.485  33.671  1.00 28.02        A
ATOM   2476  O   VAL A 322     -11.358  33.279  34.334  1.00 27.95        A
ATOM   2477  N   ILE A 323     -12.444  31.308  34.124  1.00 27.61        A
ATOM   2478  CA  ILE A 323     -12.135  30.799  35.454  1.00 26.26        A
ATOM   2479  CB  ILE A 323     -13.383  30.790  36.345  1.00 24.49        A
ATOM   2480  CG2 ILE A 323     -13.060  30.149  37.683  1.00 23.35        A
ATOM   2481  CG1 ILE A 323     -13.880  32.225  36.535  1.00 23.19        A
ATOM   2482  CD1 ILE A 323     -15.150  32.343  37.328  1.00 23.34        A
ATOM   2483  C   ILE A 323     -11.662  29.374  35.216  1.00 27.00        A
ATOM   2484  O   ILE A 323     -12.307  28.621  34.480  1.00 28.40        A
ATOM   2485  N   CYS A 324     -10.544  28.995  35.820  1.00 26.85        A
ATOM   2486  CA  CYS A 324     -10.017  27.653  35.599  1.00 29.24        A
ATOM   2487  CB  CYS A 324      -9.090  27.673  34.380  1.00 29.83        A
ATOM   2488  SG  CYS A 324      -7.684  28.833  34.527  1.00 33.93        A
ATOM   2489  C   CYS A 324      -9.261  27.089  36.796  1.00 30.18        A
ATOM   2490  O   CYS A 324      -9.143  27.737  37.830  1.00 31.28        A
ATOM   2491  N   GLU A 325      -8.757  25.867  36.648  1.00 31.08        A
ATOM   2492  CA  GLU A 325      -7.981  25.233  37.705  1.00 31.60        A
ATOM   2493  CB  GLU A 325      -7.911  23.721  37.489  1.00 33.63        A
ATOM   2494  CG  GLU A 325      -9.163  22.968  37.881  1.00 37.99        A
ATOM   2495  CD  GLU A 325      -9.406  22.975  39.384  1.00 39.54        A
ATOM   2496  OE1 GLU A 325     -10.337  22.274  39.831  1.00 41.50        A
ATOM   2497  OE2 GLU A 325      -8.673  23.677  40.117  1.00 39.95        A
ATOM   2498  C   GLU A 325      -6.571  25.803  37.684  1.00 30.82        A
ATOM   2499  O   GLU A 325      -5.862  25.696  36.686  1.00 30.46        A
ATOM   2500  N   SER A 326      -6.164  26.412  38.785  1.00 30.51        A
ATOM   2501  CA  SER A 326      -4.832  26.985  38.858  1.00 31.06        A
ATOM   2502  CB  SER A 326      -4.684  27.842  40.117  1.00 29.03        A
ATOM   2503  OG  SER A 326      -3.371  28.360  40.216  1.00 27.68        A
ATOM   2504  C   SER A 326      -3.771  25.896  38.871  1.00 33.39        A
ATOM   2505  O   SER A 326      -3.984  24.803  39.406  1.00 34.84        A
ATOM   2506  N   ALA A 327      -2.627  26.191  38.268  1.00 34.78        A
```

FIGURE 4- 34 -

```
ATOM   2507  CA   ALA A 327      -1.520  25.248  38.247  1.00 35.82           A
ATOM   2508  CB   ALA A 327      -0.809  25.301  36.913  1.00 32.74           A
ATOM   2509  C    ALA A 327      -0.605  25.733  39.360  1.00 36.60           A
ATOM   2510  O    ALA A 327      -0.290  25.011  40.297  1.00 40.18           A
ATOM   2511  N    GLY A 328      -0.218  26.991  39.253  1.00 36.88           A
ATOM   2512  CA   GLY A 328       0.635  27.605  40.240  1.00 36.07           A
ATOM   2513  C    GLY A 328       0.833  29.045  39.822  1.00 36.06           A
ATOM   2514  O    GLY A 328       0.674  29.395  38.657  1.00 36.90           A
ATOM   2515  N    THR A 329       1.177  29.890  40.771  1.00 35.94           A
ATOM   2516  CA   THR A 329       1.396  31.289  40.470  1.00 36.59           A
ATOM   2517  CB   THR A 329       2.197  31.953  41.603  1.00 36.11           A
ATOM   2518  OG1  THR A 329       1.402  31.969  42.795  1.00 36.24           A
ATOM   2519  CG2  THR A 329       2.563  33.369  41.239  1.00 37.14           A
ATOM   2520  C    THR A 329       2.121  31.480  39.139  1.00 37.40           A
ATOM   2521  O    THR A 329       1.623  32.178  38.255  1.00 37.39           A
ATOM   2522  N    GLN A 330       3.284  30.844  38.996  1.00 38.98           A
ATOM   2523  CA   GLN A 330       4.094  30.965  37.780  1.00 39.91           A
ATOM   2524  CB   GLN A 330       5.489  30.355  37.991  1.00 42.59           A
ATOM   2525  CG   GLN A 330       6.388  31.117  38.952  1.00 46.42           A
ATOM   2526  CD   GLN A 330       6.668  32.536  38.488  1.00 50.68           A
ATOM   2527  OE1  GLN A 330       5.740  33.290  38.164  1.00 53.24           A
ATOM   2528  NE2  GLN A 330       7.952  32.915  38.462  1.00 52.28           A
ATOM   2529  C    GLN A 330       3.451  30.314  36.570  1.00 38.85           A
ATOM   2530  O    GLN A 330       3.343  30.928  35.507  1.00 38.93           A
ATOM   2531  N    GLU A 331       3.040  29.064  36.728  1.00 37.77           A
ATOM   2532  CA   GLU A 331       2.407  28.349  35.632  1.00 38.74           A
ATOM   2533  CB   GLU A 331       1.879  26.989  36.109  1.00 41.25           A
ATOM   2534  CG   GLU A 331       2.912  26.029  36.711  1.00 43.52           A
ATOM   2535  CD   GLU A 331       3.587  26.579  37.957  1.00 45.33           A
ATOM   2536  OE1  GLU A 331       2.967  27.409  38.653  1.00 45.14           A
ATOM   2537  OE2  GLU A 331       4.736  26.168  38.244  1.00 44.89           A
ATOM   2538  C    GLU A 331       1.249  29.187  35.066  1.00 37.06           A
ATOM   2539  O    GLU A 331       1.179  29.423  33.856  1.00 37.89           A
ATOM   2540  N    ASP A 332       0.356  29.636  35.950  1.00 32.37           A
ATOM   2541  CA   ASP A 332      -0.799  30.445  35.569  1.00 29.79           A
ATOM   2542  CB   ASP A 332      -1.560  30.915  36.818  1.00 30.34           A
ATOM   2543  CG   ASP A 332      -2.338  29.801  37.496  1.00 30.08           A
ATOM   2544  OD1  ASP A 332      -2.142  28.625  37.135  1.00 27.13           A
ATOM   2545  OD2  ASP A 332      -3.143  30.109  38.402  1.00 30.78           A
ATOM   2546  C    ASP A 332      -0.411  31.672  34.751  1.00 28.04           A
ATOM   2547  O    ASP A 332      -1.034  31.973  33.733  1.00 27.25           A
ATOM   2548  N    ALA A 333       0.606  32.390  35.216  1.00 25.76           A
ATOM   2549  CA   ALA A 333       1.074  33.590  34.543  1.00 23.67           A
ATOM   2550  CB   ALA A 333       2.131  34.239  35.368  1.00 22.00           A
ATOM   2551  C    ALA A 333       1.624  33.269  33.155  1.00 25.28           A
ATOM   2552  O    ALA A 333       1.327  33.959  32.172  1.00 24.28           A
ATOM   2553  N    ALA A 334       2.436  32.221  33.079  1.00 24.88           A
ATOM   2554  CA   ALA A 334       3.010  31.822  31.809  1.00 26.46           A
ATOM   2555  CB   ALA A 334       3.995  30.695  32.027  1.00 27.72           A
ATOM   2556  C    ALA A 334       1.904  31.388  30.844  1.00 25.84           A
ATOM   2557  O    ALA A 334       1.969  31.658  29.648  1.00 25.68           A
ATOM   2558  N    ALA A 335       0.888  30.722  31.378  1.00 25.82           A
ATOM   2559  CA   ALA A 335      -0.238  30.251  30.581  1.00 26.78           A
ATOM   2560  CB   ALA A 335      -1.107  29.328  31.423  1.00 23.73           A
ATOM   2561  C    ALA A 335      -1.080  31.413  30.033  1.00 28.38           A
ATOM   2562  O    ALA A 335      -1.434  31.435  28.850  1.00 28.50           A
ATOM   2563  N    LEU A 336      -1.408  32.370  30.898  1.00 29.22           A
ATOM   2564  CA   LEU A 336      -2.199  33.526  30.497  1.00 30.03           A
ATOM   2565  CB   LEU A 336      -2.322  34.514  31.660  1.00 31.23           A
ATOM   2566  CG   LEU A 336      -3.680  35.202  31.842  1.00 32.99           A
ATOM   2567  CD1  LEU A 336      -3.610  36.173  33.012  1.00 31.49           A
ATOM   2568  CD2  LEU A 336      -4.076  35.927  30.572  1.00 32.09           A
ATOM   2569  C    LEU A 336      -1.484  34.190  29.330  1.00 30.06           A
ATOM   2570  O    LEU A 336      -2.082  34.491  28.303  1.00 30.60           A
ATOM   2571  N    ARG A 337      -0.186  34.404  29.498  1.00 30.85           A
ATOM   2572  CA   ARG A 337       0.629  35.016  28.459  1.00 29.64           A
ATOM   2573  CB   ARG A 337       2.080  35.111  28.940  1.00 30.15           A
ATOM   2574  CG   ARG A 337       2.557  36.531  29.191  1.00 32.31           A
ATOM   2575  CD   ARG A 337       3.139  36.712  30.569  1.00 33.08           A
ATOM   2576  NE   ARG A 337       4.094  35.655  30.892  1.00 35.57           A
ATOM   2577  CZ   ARG A 337       4.687  35.512  32.075  1.00 33.38           A
ATOM   2578  NH1  ARG A 337       4.436  36.366  33.058  1.00 32.55           A
ATOM   2579  NH2  ARG A 337       5.502  34.492  32.287  1.00 33.57           A
ATOM   2580  C    ARG A 337       0.538  34.208  27.162  1.00 27.92           A
ATOM   2581  O    ARG A 337       0.443  34.773  26.078  1.00 28.21           A
ATOM   2582  N    ALA A 338       0.560  32.884  27.271  1.00 25.88           A
```

FIGURE 4- 35 -

```
ATOM   2583  CA   ALA A 338     0.460  32.036  26.086  1.00 24.91      A
ATOM   2584  CB   ALA A 338     0.642  30.574  26.466  1.00 22.06      A
ATOM   2585  C    ALA A 338    -0.917  32.254  25.468  1.00 24.29      A
ATOM   2586  O    ALA A 338    -1.073  32.300  24.253  1.00 23.93      A
ATOM   2587  N    PHE A 339    -1.915  32.395  26.329  1.00 23.94      A
ATOM   2588  CA   PHE A 339    -3.279  32.621  25.890  1.00 24.18      A
ATOM   2589  CB   PHE A 339    -4.204  32.717  27.098  1.00 24.11      A
ATOM   2590  CG   PHE A 339    -5.574  33.223  26.774  1.00 23.09      A
ATOM   2591  CD1  PHE A 339    -6.556  32.361  26.315  1.00 25.14      A
ATOM   2592  CD2  PHE A 339    -5.886  34.569  26.942  1.00 22.68      A
ATOM   2593  CE1  PHE A 339    -7.841  32.830  26.029  1.00 26.58      A
ATOM   2594  CE2  PHE A 339    -7.154  35.052  26.660  1.00 23.09      A
ATOM   2595  CZ   PHE A 339    -8.139  34.184  26.204  1.00 25.56      A
ATOM   2596  C    PHE A 339    -3.358  33.913  25.093  1.00 24.56      A
ATOM   2597  O    PHE A 339    -4.047  33.985  24.078  1.00 26.47      A
ATOM   2598  N    THR A 340    -2.653  34.936  25.558  1.00 22.73      A
ATOM   2599  CA   THR A 340    -2.670  36.217  24.876  1.00 21.56      A
ATOM   2600  CB   THR A 340    -2.033  37.301  25.765  1.00 19.09      A
ATOM   2601  OG1  THR A 340    -2.741  37.351  27.010  1.00 17.99      A
ATOM   2602  CG2  THR A 340    -2.100  38.672  25.094  1.00 16.16      A
ATOM   2603  C    THR A 340    -1.971  36.143  23.511  1.00 23.47      A
ATOM   2604  O    THR A 340    -2.368  36.830  22.557  1.00 22.84      A
ATOM   2605  N    GLU A 341    -0.943  35.306  23.405  1.00 22.87      A
ATOM   2606  CA   GLU A 341    -0.257  35.175  22.129  1.00 24.81      A
ATOM   2607  CB   GLU A 341     1.040  34.375  22.294  1.00 27.24      A
ATOM   2608  CG   GLU A 341     2.091  35.100  23.131  1.00 28.48      A
ATOM   2609  CD   GLU A 341     2.337  36.514  22.632  1.00 28.17      A
ATOM   2610  OE1  GLU A 341     2.772  37.375  23.425  1.00 27.54      A
ATOM   2611  OE2  GLU A 341     2.092  36.762  21.436  1.00 30.38      A
ATOM   2612  C    GLU A 341    -1.200  34.485  21.149  1.00 24.82      A
ATOM   2613  O    GLU A 341    -1.198  34.779  19.957  1.00 23.73      A
ATOM   2614  N    ALA A 342    -2.012  33.572  21.670  1.00 24.22      A
ATOM   2615  CA   ALA A 342    -2.974  32.857  20.852  1.00 25.06      A
ATOM   2616  CB   ALA A 342    -3.697  31.833  21.688  1.00 23.00      A
ATOM   2617  C    ALA A 342    -3.968  33.875  20.310  1.00 26.97      A
ATOM   2618  O    ALA A 342    -4.157  33.997  19.095  1.00 29.13      A
ATOM   2619  N    MET A 343    -4.595  34.610  21.225  1.00 26.49      A
ATOM   2620  CA   MET A 343    -5.575  35.621  20.862  1.00 25.97      A
ATOM   2621  CB   MET A 343    -6.060  36.360  22.116  1.00 25.19      A
ATOM   2622  CG   MET A 343    -6.968  35.539  23.021  1.00 24.33      A
ATOM   2623  SD   MET A 343    -8.466  34.954  22.185  1.00 24.58      A
ATOM   2624  CE   MET A 343    -9.663  36.124  22.819  1.00 24.68      A
ATOM   2625  C    MET A 343    -4.996  36.617  19.863  1.00 26.20      A
ATOM   2626  O    MET A 343    -5.638  36.966  18.866  1.00 25.82      A
ATOM   2627  N    THR A 344    -3.776  37.066  20.134  1.00 25.83      A
ATOM   2628  CA   THR A 344    -3.111  38.022  19.266  1.00 26.11      A
ATOM   2629  CB   THR A 344    -1.677  38.315  19.759  1.00 26.79      A
ATOM   2630  OG1  THR A 344    -1.721  38.793  21.111  1.00 28.07      A
ATOM   2631  CG2  THR A 344    -1.023  39.368  18.886  1.00 24.14      A
ATOM   2632  C    THR A 344    -3.052  37.479  17.843  1.00 25.79      A
ATOM   2633  O    THR A 344    -3.367  38.194  16.885  1.00 25.76      A
ATOM   2634  N    ARG A 345    -2.663  36.212  17.712  1.00 24.25      A
ATOM   2635  CA   ARG A 345    -2.569  35.578  16.410  1.00 23.48      A
ATOM   2636  CB   ARG A 345    -1.942  34.195  16.519  1.00 21.97      A
ATOM   2637  CG   ARG A 345    -0.444  34.205  16.645  1.00 19.73      A
ATOM   2638  CD   ARG A 345     0.100  32.804  16.501  1.00 21.56      A
ATOM   2639  NE   ARG A 345    -0.322  31.939  17.596  1.00 22.95      A
ATOM   2640  CZ   ARG A 345     0.246  31.932  18.796  1.00 25.59      A
ATOM   2641  NH1  ARG A 345     1.265  32.742  19.060  1.00 29.54      A
ATOM   2642  NH2  ARG A 345    -0.201  31.121  19.737  1.00 26.25      A
ATOM   2643  C    ARG A 345    -3.926  35.456  15.743  1.00 25.23      A
ATOM   2644  O    ARG A 345    -4.030  35.611  14.523  1.00 26.11      A
ATOM   2645  N    TYR A 346    -4.965  35.164  16.527  1.00 25.19      A
ATOM   2646  CA   TYR A 346    -6.306  35.051  15.959  1.00 24.35      A
ATOM   2647  CB   TYR A 346    -7.266  34.351  16.910  1.00 22.98      A
ATOM   2648  CG   TYR A 346    -6.942  32.909  17.227  1.00 23.34      A
ATOM   2649  CD1  TYR A 346    -6.201  32.118  16.350  1.00 20.53      A
ATOM   2650  CE1  TYR A 346    -5.960  30.780  16.629  1.00 21.26      A
ATOM   2651  CD2  TYR A 346    -7.430  32.320  18.391  1.00 22.54      A
ATOM   2652  CE2  TYR A 346    -7.196  30.986  18.674  1.00 22.58      A
ATOM   2653  CZ   TYR A 346    -6.462  30.223  17.791  1.00 22.53      A
ATOM   2654  OH   TYR A 346    -6.246  28.898  18.081  1.00 23.00      A
ATOM   2655  C    TYR A 346    -6.865  36.429  15.670  1.00 25.32      A
ATOM   2656  O    TYR A 346    -6.038  36.557  15.333  1.00 26.47      A
ATOM   2657  N    SER A 347    -6.028  37.452  15.824  1.00 25.21      A
ATOM   2658  CA   SER A 347    -6.420  38.834  15.584  1.00 26.88      A
```

FIGURE 4- 36 -

```
ATOM   2659  CB  SER A 347      -7.190  38.964  14.278  1.00 25.80      A
ATOM   2660  CG  SER A 347      -7.603  40.304  14.105  1.00 26.41      A
ATOM   2661  C   SER A 347      -7.272  39.433  16.689  1.00 29.30      A
ATOM   2662  O   SER A 347      -8.312  40.041  16.415  1.00 31.99      A
ATOM   2663  N   ALA A 348      -6.838  39.272  17.933  1.00 29.47      A
ATOM   2664  CA  ALA A 348      -7.567  39.820  19.075  1.00 28.53      A
ATOM   2665  CB  ALA A 348      -8.530  38.781  19.624  1.00 28.39      A
ATOM   2666  C   ALA A 348      -6.549  40.225  20.143  1.00 28.12      A
ATOM   2667  O   ALA A 348      -6.540  39.695  21.259  1.00 27.58      A
ATOM   2668  N   PRO A 349      -5.665  41.171  19.803  1.00 27.10      A
ATOM   2669  CD  PRO A 349      -5.718  42.019  18.599  1.00 24.70      A
ATOM   2670  CA  PRO A 349      -4.637  41.646  20.735  1.00 27.73      A
ATOM   2671  CB  PRO A 349      -3.930  42.729  19.930  1.00 26.84      A
ATOM   2672  CG  PRO A 349      -5.048  43.278  19.060  1.00 25.32      A
ATOM   2673  C   PRO A 349      -5.243  42.185  22.040  1.00 28.99      A
ATOM   2674  O   PRO A 349      -6.412  42.566  22.095  1.00 27.16      A
ATOM   2675  N   PRO A 350      -4.453  42.219  23.111  1.00 30.42      A
ATOM   2676  CD  PRO A 350      -3.173  41.533  23.343  1.00 30.32      A
ATOM   2677  CA  PRO A 350      -5.015  42.730  24.360  1.00 32.50      A
ATOM   2678  CB  PRO A 350      -4.168  42.043  25.420  1.00 31.48      A
ATOM   2679  CG  PRO A 350      -2.837  41.943  24.755  1.00 29.98      A
ATOM   2680  C   PRO A 350      -4.940  44.243  24.455  1.00 34.74      A
ATOM   2681  O   PRO A 350      -4.047  44.864  23.898  1.00 35.41      A
ATOM   2682  N   GLY A 351      -5.907  44.835  25.137  1.00 37.84      A
ATOM   2683  CA  GLY A 351      -5.896  46.271  25.321  1.00 40.16      A
ATOM   2684  C   GLY A 351      -5.131  46.405  26.617  1.00 41.98      A
ATOM   2685  O   GLY A 351      -3.975  46.824  26.646  1.00 42.38      A
ATOM   2686  N   ASP A 352      -5.785  46.027  27.703  1.00 43.36      A
ATOM   2687  CA  ASP A 352      -5.136  46.056  29.000  1.00 47.41      A
ATOM   2688  CB  ASP A 352      -6.168  46.268  30.121  1.00 50.15      A
ATOM   2689  CG  ASP A 352      -6.970  47.562  29.952  1.00 53.11      A
ATOM   2690  OD1 ASP A 352      -6.352  48.640  29.770  1.00 53.30      A
ATOM   2691  OD2 ASP A 352      -8.221  47.500  30.009  1.00 54.37      A
ATOM   2692  C   ASP A 352      -4.491  44.681  29.126  1.00 46.38      A
ATOM   2693  O   ASP A 352      -4.997  43.697  28.586  1.00 49.40      A
ATOM   2694  N   PRO A 353      -3.354  44.593  29.812  1.00 43.93      A
ATOM   2695  CD  PRO A 353      -2.523  45.693  30.319  1.00 44.09      A
ATOM   2696  CA  PRO A 353      -2.686  43.294  29.971  1.00 42.50      A
ATOM   2697  CB  PRO A 353      -1.344  43.670  30.593  1.00 44.20      A
ATOM   2698  CG  PRO A 353      -1.149  45.117  30.172  1.00 45.49      A
ATOM   2699  C   PRO A 353      -3.497  42.378  30.891  1.00 40.31      A
ATOM   2700  O   PRO A 353      -3.822  42.760  32.015  1.00 41.35      A
ATOM   2701  N   PRO A 354      -3.836  41.163  30.433  1.00 37.41      A
ATOM   2702  CD  PRO A 354      -3.603  40.567  29.111  1.00 36.39      A
ATOM   2703  CA  PRO A 354      -4.612  40.256  31.282  1.00 36.84      A
ATOM   2704  CB  PRO A 354      -4.954  39.107  30.338  1.00 35.52      A
ATOM   2705  CG  PRO A 354      -3.821  39.102  29.387  1.00 35.34      A
ATOM   2706  C   PRO A 354      -3.875  39.788  32.538  1.00 37.75      A
ATOM   2707  O   PRO A 354      -2.819  39.158  32.457  1.00 37.55      A
ATOM   2708  N   GLN A 355      -4.447  40.109  33.696  1.00 38.48      A
ATOM   2709  CA  GLN A 355      -3.879  39.737  34.988  1.00 38.54      A
ATOM   2710  CB  GLN A 355      -3.930  40.922  35.962  1.00 42.79      A
ATOM   2711  CG  GLN A 355      -3.012  42.062  35.616  1.00 47.33      A
ATOM   2712  CD  GLN A 355      -1.621  41.565  35.278  1.00 51.80      A
ATOM   2713  OE1 GLN A 355      -0.991  40.846  36.071  1.00 52.81      A
ATOM   2714  NE2 GLN A 355      -1.132  41.937  34.094  1.00 52.33      A
ATOM   2715  C   GLN A 355      -4.634  38.582  35.623  1.00 37.27      A
ATOM   2716  O   GLN A 355      -5.860  38.621  35.750  1.00 36.78      A
ATOM   2717  N   PRO A 356      -3.916  37.533  36.036  1.00 35.58      A
ATOM   2718  CD  PRO A 356      -2.488  37.230  35.851  1.00 35.11      A
ATOM   2719  CA  PRO A 356      -4.613  36.409  36.661  1.00 34.53      A
ATOM   2720  CB  PRO A 356      -3.561  35.307  36.647  1.00 34.73      A
ATOM   2721  CG  PRO A 356      -2.286  36.058  36.792  1.00 34.39      A
ATOM   2722  C   PRO A 356      -5.038  36.779  38.078  1.00 34.03      A
ATOM   2723  O   PRO A 356      -4.215  37.239  38.860  1.00 34.24      A
ATOM   2724  N   GLU A 357      -6.319  36.590  38.396  1.00 33.41      A
ATOM   2725  CA  GLU A 357      -6.851  36.886  39.729  1.00 32.49      A
ATOM   2726  CB  GLU A 357      -8.138  37.715  39.639  1.00 33.58      A
ATOM   2727  CG  GLU A 357      -7.980  39.128  39.116  1.00 37.17      A
ATOM   2728  CD  GLU A 357      -6.943  39.925  39.883  1.00 39.30      A
ATOM   2729  OE1 GLU A 357      -6.942  39.856  41.136  1.00 38.55      A
ATOM   2730  OE2 GLU A 357      -6.136  40.626  39.224  1.00 40.71      A
ATOM   2731  C   GLU A 357      -7.151  35.587  40.495  1.00 31.48      A
ATOM   2732  O   GLU A 357      -7.518  34.563  39.900  1.00 30.65      A
ATOM   2733  N   TYR A 358      -7.011  35.642  41.816  1.00 29.12      A
ATOM   2734  CA  TYR A 358      -7.245  34.474  42.654  1.00 27.98      A
```

FIGURE 4- 37 -

```
ATOM   2735  CB  TYR A 358      -5.947  34.075  43.355  1.00 23.75      A
ATOM   2736  CG  TYR A 358      -4.918  33.528  42.399  1.00 21.32      A
ATOM   2737  CD1 TYR A 358      -5.037  32.239  41.889  1.00 21.85      A
ATOM   2738  CE1 TYR A 358      -4.118  31.746  40.946  1.00 21.23      A
ATOM   2739  CD2 TYR A 358      -3.857  34.315  41.952  1.00 19.44      A
ATOM   2740  CE2 TYR A 358      -2.942  33.836  41.023  1.00 18.55      A
ATOM   2741  CZ  TYR A 358      -3.081  32.552  40.525  1.00 19.91      A
ATOM   2742  OH  TYR A 358      -2.192  32.066  39.605  1.00 21.84      A
ATOM   2743  C   TYR A 358      -8.348  34.714  43.673  1.00 30.32      A
ATOM   2744  O   TYR A 358      -8.566  33.900  44.578  1.00 29.94      A
ATOM   2745  N   ASP A 359      -9.038  35.839  43.509  1.00 31.52      A
ATOM   2746  CA  ASP A 359     -10.147  36.226  44.367  1.00 31.95      A
ATOM   2747  CB  ASP A 359      -9.703  37.322  45.338  1.00 35.42      A
ATOM   2748  CG  ASP A 359     -10.874  38.011  46.031  1.00 40.90      A
ATOM   2749  OD1 ASP A 359     -11.966  37.394  46.145  1.00 42.95      A
ATOM   2750  OD2 ASP A 359     -10.689  39.175  46.472  1.00 42.31      A
ATOM   2751  C   ASP A 359     -11.244  36.731  43.440  1.00 32.06      A
ATOM   2752  O   ASP A 359     -11.083  37.759  42.783  1.00 32.71      A
ATOM   2753  N   LEU A 360     -12.352  35.998  43.385  1.00 31.21      A
ATOM   2754  CA  LEU A 360     -13.478  36.333  42.520  1.00 30.24      A
ATOM   2755  CB  LEU A 360     -14.691  35.464  42.880  1.00 28.23      A
ATOM   2756  CG  LEU A 360     -15.919  35.609  41.969  1.00 27.56      A
ATOM   2757  CD1 LEU A 360     -15.528  35.322  40.541  1.00 26.54      A
ATOM   2758  CD2 LEU A 360     -17.012  34.662  42.394  1.00 28.23      A
ATOM   2759  C   LEU A 360     -13.884  37.809  42.544  1.00 30.99      A
ATOM   2760  O   LEU A 360     -14.206  38.399  41.502  1.00 30.91      A
ATOM   2761  N   GLU A 361     -13.866  38.412  43.727  1.00 30.44      A
ATOM   2762  CA  GLU A 361     -14.260  39.803  43.837  1.00 30.39      A
ATOM   2763  CB  GLU A 361     -14.360  40.188  45.310  1.00 32.46      A
ATOM   2764  CG  GLU A 361     -15.534  39.521  46.005  1.00 35.14      A
ATOM   2765  CD  GLU A 361     -15.886  40.179  47.326  1.00 38.68      A
ATOM   2766  OE1 GLU A 361     -15.548  41.374  47.506  1.00 39.18      A
ATOM   2767  OE2 GLU A 361     -16.516  39.506  48.173  1.00 39.93      A
ATOM   2768  C   GLU A 361     -13.349  40.762  43.081  1.00 29.48      A
ATOM   2769  O   GLU A 361     -13.752  41.871  42.740  1.00 28.57      A
ATOM   2770  N   LEU A 362     -12.127  40.327  42.798  1.00 29.54      A
ATOM   2771  CA  LEU A 362     -11.174  41.166  42.074  1.00 30.22      A
ATOM   2772  CB  LEU A 362      -9.746  40.707  42.367  1.00 30.82      A
ATOM   2773  CG  LEU A 362      -9.368  40.888  43.840  1.00 31.16      A
ATOM   2774  CD1 LEU A 362      -7.931  40.450  44.072  1.00 28.86      A
ATOM   2775  CD2 LEU A 362      -9.556  42.346  44.227  1.00 28.81      A
ATOM   2776  C   LEU A 362     -11.414  41.206  40.564  1.00 29.69      A
ATOM   2777  O   LEU A 362     -11.205  42.244  39.924  1.00 30.61      A
ATOM   2778  N   ILE A 363     -11.856  40.088  39.997  1.00 26.81      A
ATOM   2779  CA  ILE A 363     -12.127  40.040  38.572  1.00 24.91      A
ATOM   2780  CB  ILE A 363     -12.518  38.623  38.139  1.00 24.18      A
ATOM   2781  CG2 ILE A 363     -12.868  38.606  36.643  1.00 22.60      A
ATOM   2782  CG1 ILE A 363     -11.368  37.667  38.465  1.00 23.66      A
ATOM   2783  CD1 ILE A 363     -11.651  36.219  38.164  1.00 21.04      A
ATOM   2784  C   ILE A 363     -13.265  41.001  38.214  1.00 25.34      A
ATOM   2785  O   ILE A 363     -14.219  41.162  38.983  1.00 25.89      A
ATOM   2786  N   THR A 364     -13.145  41.653  37.060  1.00 23.12      A
ATOM   2787  CA  THR A 364     -14.170  42.571  36.598  1.00 21.50      A
ATOM   2788  CB  THR A 364     -13.683  44.021  36.572  1.00 20.84      A
ATOM   2789  OG1 THR A 364     -13.279  44.410  37.890  1.00 22.82      A
ATOM   2790  CG2 THR A 364     -14.802  44.951  36.070  1.00 15.73      A
ATOM   2791  C   THR A 364     -14.551  42.194  35.184  1.00 23.32      A
ATOM   2792  O   THR A 364     -13.757  42.370  34.251  1.00 24.92      A
ATOM   2793  N   SER A 365     -15.760  41.668  35.028  1.00 22.68      A
ATOM   2794  CA  SER A 365     -16.265  41.270  33.727  1.00 23.24      A
ATOM   2795  CB  SER A 365     -16.539  39.772  33.696  1.00 26.14      A
ATOM   2796  OG  SER A 365     -17.662  39.459  34.507  1.00 32.49      A
ATOM   2797  C   SER A 365     -17.556  42.028  33.510  1.00 23.11      A
ATOM   2798  O   SER A 365     -18.371  42.151  34.434  1.00 21.66      A
ATOM   2799  N   CYS A 366     -17.740  42.524  32.288  1.00 23.26      A
ATOM   2800  CA  CYS A 366     -18.917  43.306  31.933  1.00 23.97      A
ATOM   2801  CB  CYS A 366     -20.187  42.459  32.006  1.00 25.04      A
ATOM   2802  SG  CYS A 366     -20.486  41.394  30.584  1.00 30.76      A
ATOM   2803  C   CYS A 366     -19.063  44.507  32.856  1.00 23.47      A
ATOM   2804  O   CYS A 366     -20.171  44.892  33.207  1.00 23.42      A
ATOM   2805  N   SER A 367     -17.940  45.092  33.252  1.00 24.09      A
ATOM   2806  CA  SER A 367     -17.954  46.256  34.135  1.00 26.82      A
ATOM   2807  CB  SER A 367     -18.792  47.370  33.501  1.00 25.71      A
ATOM   2808  OG  SER A 367     -18.337  47.657  32.195  1.00 26.94      A
ATOM   2809  C   SER A 367     -18.480  45.983  35.556  1.00 27.65      A
ATOM   2810  O   SER A 367     -18.720  46.924  36.320  1.00 27.50      A
```

FIGURE 4- 38 -

```
ATOM   2811  N    SER A 368   -18.657  44.710  35.906  1.00 26.75      A
ATOM   2812  CA   SER A 368   -19.165  44.353  37.222  1.00 27.75      A
ATOM   2813  CB   SER A 368   -20.552  43.722  37.100  1.00 27.33      A
ATOM   2814  OG   SER A 368   -21.375  44.470  36.234  1.00 27.55      A
ATOM   2815  C    SER A 368   -18.247  43.370  37.917  1.00 28.82      A
ATOM   2816  O    SER A 368   -17.398  42.753  37.286  1.00 31.17      A
ATOM   2817  N    ASN A 369   -18.423  43.232  39.225  1.00 29.56      A
ATOM   2818  CA   ASN A 369   -17.639  42.291  40.017  1.00 30.60      A
ATOM   2819  CB   ASN A 369   -16.472  42.977  40.712  1.00 30.95      A
ATOM   2820  CG   ASN A 369   -16.934  43.967  41.762  1.00 32.53      A
ATOM   2821  OD1  ASN A 369   -17.534  44.989  41.439  1.00 36.97      A
ATOM   2822  ND2  ASN A 369   -16.674  43.661  43.025  1.00 32.37      A
ATOM   2823  C    ASN A 369   -18.571  41.769  41.088  1.00 31.71      A
ATOM   2824  O    ASN A 369   -19.634  42.343  41.346  1.00 31.37      A
ATOM   2825  N    VAL A 370   -18.168  40.682  41.721  1.00 31.53      A
ATOM   2826  CA   VAL A 370   -18.962  40.117  42.785  1.00 32.05      A
ATOM   2827  CB   VAL A 370   -18.695  38.622  42.902  1.00 32.58      A
ATOM   2828  CG1  VAL A 370   -19.427  38.054  44.115  1.00 33.21      A
ATOM   2829  CG2  VAL A 370   -19.135  37.933  41.617  1.00 31.74      A
ATOM   2830  C    VAL A 370   -18.633  40.802  44.116  1.00 32.54      A
ATOM   2831  O    VAL A 370   -17.550  41.348  44.304  1.00 33.90      A
ATOM   2832  N    SER A 371   -19.593  40.797  45.025  1.00 32.29      A
ATOM   2833  CA   SER A 371   -19.405  41.382  46.337  1.00 32.63      A
ATOM   2834  CB   SER A 371   -19.667  42.885  46.304  1.00 33.56      A
ATOM   2835  OG   SER A 371   -19.470  43.456  47.585  1.00 31.66      A
ATOM   2836  C    SER A 371   -20.406  40.676  47.234  1.00 33.12      A
ATOM   2837  O    SER A 371   -21.352  40.062  46.746  1.00 32.23      A
ATOM   2838  N    VAL A 372   -20.212  40.760  48.540  1.00 34.19      A
ATOM   2839  CA   VAL A 372   -21.113  40.068  49.442  1.00 36.74      A
ATOM   2840  CB   VAL A 372   -20.333  39.022  50.265  1.00 36.65      A
ATOM   2841  CG1  VAL A 372   -21.297  38.117  51.005  1.00 39.06      A
ATOM   2842  CG2  VAL A 372   -19.441  38.199  49.342  1.00 38.61      A
ATOM   2843  C    VAL A 372   -21.883  40.970  50.395  1.00 37.69      A
ATOM   2844  O    VAL A 372   -21.452  42.077  50.718  1.00 39.85      A
ATOM   2845  N    ALA A 373   -23.037  40.484  50.835  1.00 37.32      A
ATOM   2846  CA   ALA A 373   -23.877  41.206  51.786  1.00 37.32      A
ATOM   2847  CB   ALA A 373   -24.774  42.201  51.060  1.00 36.64      A
ATOM   2848  C    ALA A 373   -24.712  40.171  52.542  1.00 36.47      A
ATOM   2849  O    ALA A 373   -24.556  38.972  52.333  1.00 36.35      A
ATOM   2850  N    HIS A 374   -25.595  40.625  53.419  1.00 36.14      A
ATOM   2851  CA   HIS A 374   -26.417  39.702  54.184  1.00 37.25      A
ATOM   2852  CB   HIS A 374   -25.929  39.667  55.625  1.00 37.75      A
ATOM   2853  CG   HIS A 374   -24.472  39.354  55.756  1.00 39.65      A
ATOM   2854  CD2  HIS A 374   -23.377  40.144  55.646  1.00 40.30      A
ATOM   2855  ND1  HIS A 374   -24.001  38.078  55.984  1.00 40.07      A
ATOM   2856  CE1  HIS A 374   -22.679  38.096  56.008  1.00 40.00      A
ATOM   2857  NE2  HIS A 374   -22.275  39.337  55.805  1.00 40.87      A
ATOM   2858  C    HIS A 374   -27.864  40.144  54.130  1.00 38.05      A
ATOM   2859  O    HIS A 374   -28.141  41.331  54.022  1.00 38.56      A
ATOM   2860  N    ASP A 375   -28.789  39.191  54.176  1.00 40.53      A
ATOM   2861  CA   ASP A 375   -30.207  39.531  54.143  1.00 43.39      A
ATOM   2862  CB   ASP A 375   -31.028  38.440  53.442  1.00 45.95      A
ATOM   2863  CG   ASP A 375   -30.845  37.072  54.073  1.00 49.22      A
ATOM   2864  OD1  ASP A 375   -30.872  36.982  55.321  1.00 50.68      A
ATOM   2865  OD2  ASP A 375   -30.685  36.084  53.317  1.00 50.85      A
ATOM   2866  C    ASP A 375   -30.707  39.709  55.567  1.00 43.26      A
ATOM   2867  O    ASP A 375   -29.914  39.842  56.503  1.00 42.14      A
ATOM   2868  N    ALA A 376   -32.025  39.710  55.724  1.00 43.54      A
ATOM   2869  CA   ALA A 376   -32.625  39.878  57.035  1.00 43.50      A
ATOM   2870  CB   ALA A 376   -34.130  39.763  56.920  1.00 44.47      A
ATOM   2871  C    ALA A 376   -32.090  38.842  58.022  1.00 43.41      A
ATOM   2872  O    ALA A 376   -31.800  39.161  59.173  1.00 43.52      A
ATOM   2873  N    SER A 377   -31.938  37.608  57.555  1.00 42.65      A
ATOM   2874  CA   SER A 377   -31.463  36.508  58.390  1.00 42.44      A
ATOM   2875  CB   SER A 377   -31.985  35.195  57.827  1.00 43.07      A
ATOM   2876  OG   SER A 377   -33.398  35.225  57.789  1.00 46.85      A
ATOM   2877  C    SER A 377   -29.955  36.399  58.596  1.00 41.90      A
ATOM   2878  O    SER A 377   -29.486  35.511  59.310  1.00 42.31      A
ATOM   2879  N    GLY A 378   -29.193  37.293  57.979  1.00 41.57      A
ATOM   2880  CA   GLY A 378   -27.749  37.250  58.143  1.00 38.60      A
ATOM   2881  C    GLY A 378   -27.088  36.325  57.148  1.00 36.67      A
ATOM   2882  O    GLY A 378   -25.864  36.240  57.084  1.00 35.09      A
ATOM   2883  N    LYS A 379   -27.910  35.624  56.375  1.00 36.96      A
ATOM   2884  CA   LYS A 379   -27.423  34.698  55.361  1.00 37.25      A
ATOM   2885  CB   LYS A 379   -28.615  33.994  54.689  1.00 39.35      A
ATOM   2886  CG   LYS A 379   -28.231  32.894  53.703  1.00 44.82      A
```

FIGURE 4- 39 -

```
ATOM   2887  CD   LYS A 379     -29.439  32.340  52.927  1.00 48.48          A
ATOM   2888  CE   LYS A 379     -30.067  33.396  51.995  1.00 51.49          A
ATOM   2889  NZ   LYS A 379     -31.182  32.849  51.142  1.00 51.53          A
ATOM   2890  C    LYS A 379     -26.634  35.514  54.335  1.00 35.43          A
ATOM   2891  C    LYS A 379     -27.008  36.637  54.008  1.00 33.92          A
ATOM   2892  N    ARG A 380     -25.537  34.956  53.839  1.00 33.98          A
ATOM   2893  CA   ARG A 380     -24.723  35.656  52.857  1.00 33.99          A
ATOM   2894  CB   ARG A 380     -23.335  35.040  52.772  1.00 35.01          A
ATOM   2895  CG   ARG A 380     -22.622  35.021  54.087  1.00 39.62          A
ATOM   2896  CD   ARG A 380     -21.289  34.350  53.948  1.00 43.47          A
ATOM   2897  NE   ARG A 380     -20.481  35.019  52.941  1.00 47.85          A
ATOM   2898  CZ   ARG A 380     -19.243  34.662  52.629  1.00 49.71          A
ATOM   2899  NH1  ARG A 380     -18.674  33.637  53.259  1.00 50.68          A
ATOM   2900  NH2  ARG A 380     -18.579  35.325  51.685  1.00 49.84          A
ATOM   2901  C    ARG A 380     -25.362  35.622  51.482  1.00 32.87          A
ATOM   2902  C    ARG A 380     -25.869  34.589  51.036  1.00 33.47          A
ATOM   2903  N    VAL A 381     -25.340  36.766  50.816  1.00 30.56          A
ATOM   2904  CA   VAL A 381     -25.903  36.878  49.491  1.00 28.55          A
ATOM   2905  CB   VAL A 381     -27.211  37.675  49.504  1.00 28.03          A
ATOM   2906  CG1  VAL A 381     -27.720  37.849  48.090  1.00 25.98          A
ATOM   2907  CG2  VAL A 381     -28.241  36.957  50.350  1.00 27.99          A
ATOM   2908  C    VAL A 381     -24.918  37.566  48.563  1.00 28.60          A
ATOM   2909  C    VAL A 381     -24.550  38.727  48.771  1.00 29.55          A
ATOM   2910  N    TYR A 382     -24.483  36.825  47.549  1.00 26.74          A
ATOM   2911  CA   TYR A 382     -23.564  37.334  46.554  1.00 23.18          A
ATOM   2912  CB   TYR A 382     -22.917  36.168  45.809  1.00 21.49          A
ATOM   2913  CG   TYR A 382     -22.039  35.291  46.667  1.00 22.21          A
ATOM   2914  CD1  TYR A 382     -20.742  35.679  47.014  1.00 23.03          A
ATOM   2915  CE1  TYR A 382     -19.944  34.872  47.826  1.00 23.10          A
ATOM   2916  CD2  TYR A 382     -22.511  34.080  47.153  1.00 22.29          A
ATOM   2917  CE2  TYR A 382     -21.727  33.267  47.963  1.00 23.41          A
ATOM   2918  CZ   TYR A 382     -20.450  33.663  48.299  1.00 25.73          A
ATOM   2919  OH   TYR A 382     -19.696  32.844  49.116  1.00 29.51          A
ATOM   2920  C    TYR A 382     -24.385  38.181  45.586  1.00 22.05          A
ATOM   2921  C    TYR A 382     -25.452  37.766  45.155  1.00 22.11          A
ATOM   2922  N    TYR A 383     -23.906  39.377  45.270  1.00 22.16          A
ATOM   2923  CA   TYR A 383     -24.609  40.239  44.333  1.00 22.45          A
ATOM   2924  CB   TYR A 383     -25.422  41.301  45.070  1.00 22.41          A
ATOM   2925  CG   TYR A 383     -24.613  42.416  45.697  1.00 23.29          A
ATOM   2926  CD1  TYR A 383     -23.829  42.193  46.831  1.00 22.68          A
ATOM   2927  CE1  TYR A 383     -23.113  43.233  47.430  1.00 22.03          A
ATOM   2928  CD2  TYR A 383     -24.661  43.705  45.171  1.00 23.84          A
ATOM   2929  CE2  TYR A 383     -23.954  44.748  45.759  1.00 25.95          A
ATOM   2930  CZ   TYR A 383     -23.179  44.507  46.888  1.00 24.78          A
ATOM   2931  OH   TYR A 383     -22.466  45.548  47.455  1.00 26.56          A
ATOM   2932  C    TYR A 383     -23.611  40.905  43.403  1.00 22.28          A
ATOM   2933  C    TYR A 383     -22.417  40.947  43.689  1.00 22.89          A
ATOM   2934  N    LEU A 384     -24.106  41.434  42.293  1.00 22.37          A
ATOM   2935  CA   LEU A 384     -23.247  42.071  41.305  1.00 21.39          A
ATOM   2936  CB   LEU A 384     -23.722  41.868  39.921  1.00 21.91          A
ATOM   2937  CG   LEU A 384     -22.657  41.599  38.836  1.00 25.65          A
ATOM   2938  CD1  LEU A 384     -21.605  40.576  39.218  1.00 25.43          A
ATOM   2939  CD2  LEU A 384     -23.320  41.220  37.516  1.00 27.34          A
ATOM   2940  C    LEU A 384     -23.217  43.598  41.441  1.00 21.43          A
ATOM   2941  C    LEU A 384     -24.263  44.246  41.506  1.00 21.41          A
ATOM   2942  N    THR A 385     -22.012  44.163  41.484  1.00 21.04          A
ATOM   2943  CA   THR A 385     -21.841  45.603  41.631  1.00 21.29          A
ATOM   2944  CB   THR A 385     -21.572  45.987  43.119  1.00 20.50          A
ATOM   2945  CG1  THR A 385     -21.681  47.410  43.270  1.00 23.52          A
ATOM   2946  CG2  THR A 385     -20.180  45.553  43.561  1.00 18.25          A
ATOM   2947  C    THR A 385     -20.711  46.169  40.756  1.00 23.29          A
ATOM   2948  C    THR A 385     -20.133  45.464  39.926  1.00 23.77          A
ATOM   2949  N    ARG A 386     -20.390  47.445  40.961  1.00 24.11          A
ATOM   2950  CA   ARG A 386     -19.349  48.104  40.180  1.00 24.18          A
ATOM   2951  CB   ARG A 386     -19.805  48.258  38.739  1.00 23.31          A
ATOM   2952  CG   ARG A 386     -21.044  49.140  38.633  1.00 21.66          A
ATOM   2953  CD   ARG A 386     -21.355  49.510  37.212  1.00 19.80          A
ATOM   2954  NE   ARG A 386     -20.496  50.582  36.726  1.00 20.09          A
ATOM   2955  CZ   ARG A 386     -20.304  50.839  35.438  1.00 19.52          A
ATOM   2956  NH1  ARG A 386     -20.908  50.089  34.534  1.00 20.59          A
ATOM   2957  NH2  ARG A 386     -19.529  51.842  35.055  1.00 17.57          A
ATOM   2958  C    ARG A 386     -19.074  49.502  40.704  1.00 24.63          A
ATOM   2959  C    ARG A 386     -19.828  50.037  41.509  1.00 26.14          A
ATOM   2960  N    ASP A 387     -17.991  50.097  40.231  1.00 23.93          A
ATOM   2961  CA   ASP A 387     -17.685  51.450  40.624  1.00 23.93          A
ATOM   2962  CB   ASP A 387     -16.387  51.884  39.973  1.00 24.04          A
```

FIGURE 4- 40 -

```
ATOM   2963  CG   ASP A 387     -16.037  53.294  40.296  1.00 25.92           A
ATOM   2964  OD1  ASP A 387     -16.805  54.190  39.882  1.00 26.71           A
ATOM   2965  OD2  ASP A 387     -15.003  53.506  40.972  1.00 28.07           A
ATOM   2966  C    ASP A 387     -18.870  52.253  40.072  1.00 24.51           A
ATOM   2967  O    ASP A 387     -19.215  52.132  38.893  1.00 23.90           A
ATOM   2968  N    PRO A 388     -19.518  53.071  40.919  1.00 24.67           A
ATOM   2969  CD   PRO A 388     -19.362  53.125  42.384  1.00 25.49           A
ATOM   2970  CA   PRO A 388     -20.671  53.872  40.494  1.00 24.11           A
ATOM   2971  CB   PRO A 388     -21.452  54.040  41.791  1.00 24.85           A
ATOM   2972  CG   PRO A 388     -20.365  54.189  42.790  1.00 25.52           A
ATOM   2973  C    PRO A 388     -20.429  55.208  39.796  1.00 23.38           A
ATOM   2974  O    PRO A 388     -21.390  55.894  39.456  1.00 22.52           A
ATOM   2975  N    THR A 389     -19.170  55.576  39.572  1.00 23.52           A
ATOM   2976  CA   THR A 389     -18.859  56.850  38.915  1.00 23.09           A
ATOM   2977  CB   THR A 389     -17.391  56.951  38.529  1.00 22.16           A
ATOM   2978  OG1  THR A 389     -16.578  56.843  39.701  1.00 25.32           A
ATOM   2979  CG2  THR A 389     -17.131  58.282  37.879  1.00 21.11           A
ATOM   2980  C    THR A 389     -19.659  57.141  37.650  1.00 23.10           A
ATOM   2981  O    THR A 389     -20.424  58.112  37.602  1.00 23.05           A
ATOM   2982  N    THR A 390     -19.470  56.320  36.620  1.00 22.06           A
ATOM   2983  CA   THR A 390     -20.192  56.539  35.376  1.00 21.43           A
ATOM   2984  CB   THR A 390     -19.862  55.462  34.304  1.00 21.90           A
ATOM   2985  OG1  THR A 390     -18.452  55.439  34.051  1.00 18.82           A
ATOM   2986  CG2  THR A 390     -20.569  55.782  33.007  1.00 20.15           A
ATOM   2987  C    THR A 390     -21.694  56.539  35.645  1.00 21.12           A
ATOM   2988  O    THR A 390     -22.392  57.483  35.279  1.00 22.27           A
ATOM   2989  N    PRO A 391     -22.214  55.489  36.301  1.00 20.03           A
ATOM   2990  CD   PRO A 391     -21.607  54.233  36.774  1.00 20.43           A
ATOM   2991  CA   PRO A 391     -23.653  55.493  36.558  1.00 20.89           A
ATOM   2992  CB   PRO A 391     -23.839  54.285  37.474  1.00 20.24           A
ATOM   2993  CG   PRO A 391     -22.817  53.338  36.971  1.00 19.95           A
ATOM   2994  C    PRO A 391     -24.143  56.798  37.190  1.00 21.76           A
ATOM   2995  O    PRO A 391     -25.168  57.352  36.781  1.00 23.84           A
ATOM   2996  N    LEU A 392     -23.413  57.295  38.183  1.00 20.93           A
ATOM   2997  CA   LEU A 392     -23.807  58.530  38.843  1.00 19.96           A
ATOM   2998  CB   LEU A 392     -22.935  58.774  40.075  1.00 18.31           A
ATOM   2999  CG   LEU A 392     -23.264  57.827  41.227  1.00 17.06           A
ATOM   3000  CD1  LEU A 392     -22.262  57.977  42.340  1.00 15.21           A
ATOM   3001  CD2  LEU A 392     -24.656  58.117  41.714  1.00 16.54           A
ATOM   3002  C    LEU A 392     -23.706  59.705  37.878  1.00 20.57           A
ATOM   3003  O    LEU A 392     -24.653  60.497  37.760  1.00 18.66           A
ATOM   3004  N    ALA A 393     -22.569  59.811  37.187  1.00 20.35           A
ATOM   3005  CA   ALA A 393     -22.359  60.893  36.227  1.00 20.75           A
ATOM   3006  CB   ALA A 393     -21.076  60.663  35.460  1.00 18.34           A
ATOM   3007  C    ALA A 393     -23.538  60.983  35.254  1.00 22.32           A
ATOM   3008  O    ALA A 393     -24.039  62.073  34.960  1.00 21.74           A
ATOM   3009  N    ARG A 394     -23.990  59.830  34.770  1.00 22.72           A
ATOM   3010  CA   ARG A 394     -25.092  59.788  33.827  1.00 23.50           A
ATOM   3011  CB   ARG A 394     -25.126  58.427  33.144  1.00 23.60           A
ATOM   3012  CG   ARG A 394     -23.856  58.170  32.368  1.00 21.77           A
ATOM   3013  CD   ARG A 394     -23.839  56.839  31.662  1.00 21.51           A
ATOM   3014  NE   ARG A 394     -22.603  56.738  30.894  1.00 23.32           A
ATOM   3015  CZ   ARG A 394     -22.264  55.705  30.133  1.00 21.65           A
ATOM   3016  NH1  ARG A 394     -23.075  54.660  30.028  1.00 22.52           A
ATOM   3017  NH2  ARG A 394     -21.110  55.725  29.480  1.00 19.08           A
ATOM   3018  C    ARG A 394     -26.433  60.106  34.463  1.00 24.73           A
ATOM   3019  O    ARG A 394     -27.319  60.637  33.803  1.00 26.77           A
ATOM   3020  N    ALA A 395     -26.602  59.782  35.738  1.00 24.44           A
ATOM   3021  CA   ALA A 395     -27.858  60.101  36.398  1.00 24.09           A
ATOM   3022  CB   ALA A 395     -27.867  59.545  37.819  1.00 24.33           A
ATOM   3023  C    ALA A 395     -27.958  61.626  36.421  1.00 24.22           A
ATOM   3024  O    ALA A 395     -28.986  62.201  36.065  1.00 23.49           A
ATOM   3025  N    ALA A 396     -26.869  62.273  36.825  1.00 23.82           A
ATOM   3026  CA   ALA A 396     -26.822  63.726  36.898  1.00 24.85           A
ATOM   3027  CB   ALA A 396     -25.449  64.186  37.331  1.00 24.88           A
ATOM   3028  C    ALA A 396     -27.161  64.333  35.561  1.00 25.09           A
ATOM   3029  O    ALA A 396     -28.031  65.191  35.466  1.00 26.98           A
ATOM   3030  N    TRP A 397     -26.462  63.896  34.526  1.00 25.51           A
ATOM   3031  CA   TRP A 397     -26.712  64.400  33.188  1.00 26.31           A
ATOM   3032  CB   TRP A 397     -25.862  63.628  32.191  1.00 27.97           A
ATOM   3033  CG   TRP A 397     -25.995  64.125  30.815  1.00 30.33           A
ATOM   3034  CD2  TRP A 397     -25.144  65.072  30.179  1.00 32.02           A
ATOM   3035  CE2  TRP A 397     -25.678  65.320  28.895  1.00 32.19           A
ATOM   3036  CE3  TRP A 397     -23.980  65.741  30.571  1.00 32.45           A
ATOM   3037  CD1  TRP A 397     -26.986  63.833  29.920  1.00 31.18           A
ATOM   3038  NE1  TRP A 397     -26.802  64.549  28.761  1.00 32.33           A
```

FIGURE 4- 41 -

| | | | | | | | | | | |
|---|---|---|---|---|---|---|---|---|---|---|
| ATOM | 3039 | CZ2 | TRP | A | 397 | -25.089 | 66.207 | 28.004 | 1.00 32.81 | A |
| ATOM | 3040 | CZ3 | TRP | A | 397 | -23.394 | 66.621 | 29.689 | 1.00 33.97 | A |
| ATOM | 3041 | CH2 | TRP | A | 397 | -23.950 | 66.848 | 28.416 | 1.00 35.37 | A |
| ATOM | 3042 | C | TRP | A | 397 | -28.194 | 64.234 | 32.852 | 1.00 26.14 | A |
| ATOM | 3043 | O | TRP | A | 397 | -28.897 | 65.201 | 32.555 | 1.00 24.99 | A |
| ATOM | 3044 | N | GLU | A | 398 | -28.659 | 62.991 | 32.919 | 1.00 26.38 | A |
| ATOM | 3045 | CA | GLU | A | 398 | -30.045 | 62.649 | 32.633 | 1.00 26.82 | A |
| ATOM | 3046 | CB | GLU | A | 398 | -30.218 | 61.141 | 32.785 | 1.00 26.07 | A |
| ATOM | 3047 | CG | GLU | A | 398 | -29.758 | 60.380 | 31.543 | 1.00 28.56 | A |
| ATOM | 3048 | CD | GLU | A | 398 | -29.295 | 58.953 | 31.816 | 1.00 29.70 | A |
| ATOM | 3049 | OE1 | GLU | A | 398 | -29.946 | 58.236 | 32.609 | 1.00 30.20 | A |
| ATOM | 3050 | OE2 | GLU | A | 398 | -28.274 | 58.549 | 31.214 | 1.00 30.71 | A |
| ATOM | 3051 | C | GLU | A | 398 | -31.043 | 63.407 | 33.509 | 1.00 28.02 | A |
| ATOM | 3052 | O | GLU | A | 398 | -32.246 | 63.403 | 33.253 | 1.00 29.25 | A |
| ATOM | 3053 | N | THR | A | 399 | -30.538 | 64.070 | 34.538 | 1.00 28.57 | A |
| ATOM | 3054 | CA | THR | A | 399 | -31.388 | 64.828 | 35.431 | 1.00 29.11 | A |
| ATOM | 3055 | CB | THR | A | 399 | -30.785 | 64.879 | 36.848 | 1.00 28.48 | A |
| ATOM | 3056 | OG1 | THR | A | 399 | -30.671 | 63.554 | 37.371 | 1.00 25.35 | A |
| ATOM | 3057 | CG2 | THR | A | 399 | -31.665 | 65.710 | 37.775 | 1.00 29.58 | A |
| ATOM | 3058 | C | THR | A | 399 | -31.500 | 66.247 | 34.892 | 1.00 31.87 | A |
| ATOM | 3059 | O | THR | A | 399 | -32.551 | 66.883 | 34.976 | 1.00 32.22 | A |
| ATOM | 3060 | N | ALA | A | 400 | -30.406 | 66.739 | 34.329 | 1.00 34.49 | A |
| ATOM | 3061 | CA | ALA | A | 400 | -30.363 | 68.092 | 33.799 | 1.00 38.42 | A |
| ATOM | 3062 | CB | ALA | A | 400 | -28.923 | 68.595 | 33.819 | 1.00 37.78 | A |
| ATOM | 3063 | C | ALA | A | 400 | -30.941 | 68.206 | 32.389 | 1.00 41.83 | A |
| ATOM | 3064 | O | ALA | A | 400 | -31.420 | 69.268 | 31.989 | 1.00 42.82 | A |
| ATOM | 3065 | N | ARG | A | 401 | -30.890 | 67.108 | 31.641 | 1.00 45.26 | A |
| ATOM | 3066 | CA | ARG | A | 401 | -31.389 | 67.075 | 30.273 | 1.00 48.19 | A |
| ATOM | 3067 | CB | ARG | A | 401 | -30.221 | 67.037 | 29.294 | 1.00 47.49 | A |
| ATOM | 3068 | CG | ARG | A | 401 | -29.304 | 68.227 | 29.329 | 1.00 48.07 | A |
| ATOM | 3069 | CD | ARG | A | 401 | -28.091 | 67.929 | 28.459 | 1.00 51.49 | A |
| ATOM | 3070 | NE | ARG | A | 401 | -27.179 | 69.065 | 28.327 | 1.00 53.08 | A |
| ATOM | 3071 | CZ | ARG | A | 401 | -27.436 | 70.156 | 27.612 | 1.00 51.88 | A |
| ATOM | 3072 | NH1 | ARG | A | 401 | -28.585 | 70.263 | 26.955 | 1.00 50.34 | A |
| ATOM | 3073 | NH2 | ARG | A | 401 | -26.544 | 71.139 | 27.562 | 1.00 50.04 | A |
| ATOM | 3074 | C | ARG | A | 401 | -32.264 | 65.851 | 30.015 | 1.00 51.19 | A |
| ATOM | 3075 | O | ARG | A | 401 | -31.987 | 64.752 | 30.510 | 1.00 51.77 | A |
| ATOM | 3076 | N | HIS | A | 402 | -33.324 | 66.040 | 29.236 | 1.00 54.37 | A |
| ATOM | 3077 | CA | HIS | A | 402 | -34.193 | 64.921 | 28.902 | 1.00 56.24 | A |
| ATOM | 3078 | CB | HIS | A | 402 | -35.563 | 65.409 | 28.421 | 1.00 60.35 | A |
| ATOM | 3079 | CG | HIS | A | 402 | -36.674 | 65.115 | 29.383 | 1.00 66.44 | A |
| ATOM | 3080 | CD2 | HIS | A | 402 | -36.773 | 64.199 | 30.379 | 1.00 68.10 | A |
| ATOM | 3081 | ND1 | HIS | A | 402 | -37.868 | 65.809 | 29.382 | 1.00 69.51 | A |
| ATOM | 3082 | CE1 | HIS | A | 402 | -38.653 | 65.335 | 30.336 | 1.00 70.37 | A |
| ATOM | 3083 | NE2 | HIS | A | 402 | -38.012 | 64.358 | 30.955 | 1.00 70.19 | A |
| ATOM | 3084 | C | HIS | A | 402 | -33.485 | 64.148 | 27.807 | 1.00 54.16 | A |
| ATOM | 3085 | O | HIS | A | 402 | -33.205 | 64.672 | 26.735 | 1.00 53.95 | A |
| ATOM | 3086 | N | THR | A | 403 | -33.163 | 62.902 | 28.098 | 1.00 52.30 | A |
| ATOM | 3087 | CA | THR | A | 403 | -32.479 | 62.073 | 27.132 | 1.00 51.52 | A |
| ATOM | 3088 | CB | THR | A | 403 | -31.193 | 61.491 | 27.746 | 1.00 51.83 | A |
| ATOM | 3089 | OG1 | THR | A | 403 | -31.428 | 61.168 | 29.124 | 1.00 52.11 | A |
| ATOM | 3090 | CG2 | THR | A | 403 | -30.059 | 62.502 | 27.648 | 1.00 50.02 | A |
| ATOM | 3091 | C | THR | A | 403 | -33.399 | 60.958 | 26.649 | 1.00 50.20 | A |
| ATOM | 3092 | O | THR | A | 403 | -34.360 | 60.594 | 27.333 | 1.00 49.57 | A |
| ATOM | 3093 | N | PRO | A | 404 | -33.122 | 60.412 | 25.453 | 1.00 48.95 | A |
| ATOM | 3094 | CD | PRO | A | 404 | -31.947 | 60.743 | 24.631 | 1.00 48.61 | A |
| ATOM | 3095 | CA | PRO | A | 404 | -33.904 | 59.331 | 24.833 | 1.00 47.91 | A |
| ATOM | 3096 | CB | PRO | A | 404 | -33.139 | 59.037 | 23.539 | 1.00 48.97 | A |
| ATOM | 3097 | CG | PRO | A | 404 | -32.407 | 60.329 | 23.259 | 1.00 50.28 | A |
| ATOM | 3098 | C | PRO | A | 404 | -33.948 | 58.108 | 25.744 | 1.00 45.19 | A |
| ATOM | 3099 | O | PRO | A | 404 | -34.984 | 57.464 | 25.904 | 1.00 44.71 | A |
| ATOM | 3100 | N | ILE | A | 405 | -32.797 | 57.795 | 26.327 | 1.00 43.06 | A |
| ATOM | 3101 | CA | ILE | A | 405 | -32.668 | 56.664 | 27.229 | 1.00 41.96 | A |
| ATOM | 3102 | CB | ILE | A | 405 | -31.566 | 55.691 | 26.774 | 1.00 40.55 | A |
| ATOM | 3103 | CG2 | ILE | A | 405 | -31.447 | 54.547 | 27.781 | 1.00 39.14 | A |
| ATOM | 3104 | CG1 | ILE | A | 405 | -31.892 | 55.132 | 25.392 | 1.00 40.07 | A |
| ATOM | 3105 | CD1 | ILE | A | 405 | -33.066 | 54.175 | 25.385 | 1.00 41.75 | A |
| ATOM | 3106 | C | ILE | A | 405 | -32.322 | 57.121 | 28.642 | 1.00 41.93 | A |
| ATOM | 3107 | O | ILE | A | 405 | -31.637 | 58.132 | 28.846 | 1.00 42.71 | A |
| ATOM | 3108 | N | ASN | A | 406 | -32.801 | 56.362 | 29.617 | 1.00 40.32 | A |
| ATOM | 3109 | CA | ASN | A | 406 | -32.541 | 56.673 | 31.003 | 1.00 38.55 | A |
| ATOM | 3110 | CB | ASN | A | 406 | -33.856 | 56.763 | 31.769 | 1.00 39.95 | A |
| ATOM | 3111 | CG | ASN | A | 406 | -34.722 | 57.909 | 31.285 | 1.00 42.02 | A |
| ATOM | 3112 | OD1 | ASN | A | 406 | -34.372 | 59.083 | 31.455 | 1.00 42.94 | A |
| ATOM | 3113 | ND2 | ASN | A | 406 | -35.853 | 57.578 | 30.664 | 1.00 41.88 | A |
| ATOM | 3114 | C | ASN | A | 406 | -31.657 | 55.585 | 31.563 | 1.00 37.09 | A |

FIGURE 4- 42 -

```
ATOM   3115  O    ASN A 406     -32.137  54.570  32.076  1.00 36.15           A
ATOM   3116  N    SER A 407     -30.352  55.791  31.433  1.00 34.44           A
ATOM   3117  CA   SER A 407     -29.398  54.831  31.937  1.00 33.47           A
ATOM   3118  CB   SER A 407     -27.985  55.362  31.763  1.00 33.38           A
ATOM   3119  OG   SER A 407     -27.821  56.553  32.509  1.00 36.11           A
ATOM   3120  C    SER A 407     -29.656  54.573  33.418  1.00 33.87           A
ATOM   3121  O    SER A 407     -29.347  53.500  33.931  1.00 35.54           A
ATOM   3122  N    TRP A 408     -30.232  55.551  34.108  1.00 32.77           A
ATOM   3123  CA   TRP A 408     -30.479  55.387  35.530  1.00 30.87           A
ATOM   3124  CB   TRP A 408     -30.820  56.727  36.171  1.00 29.78           A
ATOM   3125  CG   TRP A 408     -32.108  57.291  35.732  1.00 29.76           A
ATOM   3126  CD2  TRP A 408     -33.394  57.008  36.291  1.00 29.17           A
ATOM   3127  CE2  TRP A 408     -34.334  57.790  35.591  1.00 29.46           A
ATOM   3128  CE3  TRP A 408     -33.844  56.167  37.320  1.00 29.31           A
ATOM   3129  CD1  TRP A 408     -32.311  58.203  34.737  1.00 29.57           A
ATOM   3130  NE1  TRP A 408     -33.648  58.511  34.648  1.00 29.84           A
ATOM   3131  CZ2  TRP A 408     -35.701  57.756  35.889  1.00 28.60           A
ATOM   3132  CZ3  TRP A 408     -35.203  56.132  37.616  1.00 25.23           A
ATOM   3133  CH2  TRP A 408     -36.111  56.921  36.904  1.00 27.68           A
ATOM   3134  C    TRP A 408     -31.566  54.372  35.842  1.00 29.99           A
ATOM   3135  O    TRP A 408     -31.496  53.675  36.858  1.00 30.65           A
ATOM   3136  N    LEU A 409     -32.571  54.277  34.979  1.00 28.86           A
ATOM   3137  CA   LEU A 409     -33.644  53.316  35.210  1.00 27.93           A
ATOM   3138  CB   LEU A 409     -34.821  53.586  34.268  1.00 26.52           A
ATOM   3139  CG   LEU A 409     -36.109  52.783  34.494  1.00 27.09           A
ATOM   3140  CD1  LEU A 409     -36.677  53.073  35.879  1.00 26.69           A
ATOM   3141  CD2  LEU A 409     -37.128  53.142  33.425  1.00 25.51           A
ATOM   3142  C    LEU A 409     -33.086  51.912  34.981  1.00 27.81           A
ATOM   3143  O    LEU A 409     -33.470  50.958  35.656  1.00 27.89           A
ATOM   3144  N    GLY A 410     -32.155  51.809  34.033  1.00 27.17           A
ATOM   3145  CA   GLY A 410     -31.542  50.534  33.720  1.00 24.09           A
ATOM   3146  C    GLY A 410     -30.573  50.111  34.798  1.00 24.46           A
ATOM   3147  O    GLY A 410     -30.494  48.927  35.148  1.00 24.20           A
ATOM   3148  N    ASN A 411     -29.827  51.072  35.336  1.00 24.39           A
ATOM   3149  CA   ASN A 411     -28.867  50.748  36.378  1.00 24.32           A
ATOM   3150  CB   ASN A 411     -27.907  51.912  36.613  1.00 22.12           A
ATOM   3151  CG   ASN A 411     -26.751  51.917  35.621  1.00 24.24           A
ATOM   3152  OD1  ASN A 411     -26.301  50.862  35.166  1.00 23.81           A
ATOM   3153  ND2  ASN A 411     -26.253  53.103  35.296  1.00 24.64           A
ATOM   3154  C    ASN A 411     -29.560  50.330  37.669  1.00 25.43           A
ATOM   3155  O    ASN A 411     -29.081  49.430  38.366  1.00 26.11           A
ATOM   3156  N    ILE A 412     -30.684  50.965  37.994  1.00 24.07           A
ATOM   3157  CA   ILE A 412     -31.408  50.573  39.193  1.00 23.78           A
ATOM   3158  CB   ILE A 412     -32.677  51.427  39.391  1.00 23.95           A
ATOM   3159  CG2  ILE A 412     -33.682  50.686  40.269  1.00 19.59           A
ATOM   3160  CG1  ILE A 412     -32.295  52.780  39.993  1.00 23.47           A
ATOM   3161  CD1  ILE A 412     -33.472  53.711  40.188  1.00 26.33           A
ATOM   3162  C    ILE A 412     -31.809  49.111  39.013  1.00 24.27           A
ATOM   3163  O    ILE A 412     -31.520  48.266  39.851  1.00 25.26           A
ATOM   3164  N    ILE A 413     -32.459  48.821  37.894  1.00 24.62           A
ATOM   3165  CA   ILE A 413     -32.901  47.469  37.593  1.00 24.29           A
ATOM   3166  CB   ILE A 413     -33.621  47.413  36.220  1.00 21.37           A
ATOM   3167  CG2  ILE A 413     -34.000  45.991  35.907  1.00 19.33           A
ATOM   3168  CG1  ILE A 413     -34.874  48.295  36.245  1.00 21.28           A
ATOM   3169  CD1  ILE A 413     -35.686  48.311  34.949  1.00 17.14           A
ATOM   3170  C    ILE A 413     -31.753  46.456  37.597  1.00 25.60           A
ATOM   3171  O    ILE A 413     -31.899  45.352  38.120  1.00 26.35           A
ATOM   3172  N    MET A 414     -30.609  46.823  37.028  1.00 25.27           A
ATOM   3173  CA   MET A 414     -29.484  45.891  36.981  1.00 25.73           A
ATOM   3174  CB   MET A 414     -28.599  46.200  35.771  1.00 27.23           A
ATOM   3175  CG   MET A 414     -29.299  46.070  34.427  1.00 27.06           A
ATOM   3176  SD   MET A 414     -29.912  44.400  34.116  1.00 29.41           A
ATOM   3177  CE   MET A 414     -28.438  43.616  33.476  1.00 25.42           A
ATOM   3178  C    MET A 414     -28.631  45.889  38.251  1.00 24.95           A
ATOM   3179  O    MET A 414     -27.847  44.973  38.485  1.00 24.93           A
ATOM   3180  N    TYR A 415     -28.794  46.909  39.081  1.00 24.42           A
ATOM   3181  CA   TYR A 415     -28.018  46.998  40.301  1.00 22.40           A
ATOM   3182  CB   TYR A 415     -26.989  48.098  40.157  1.00 20.01           A
ATOM   3183  CG   TYR A 415     -25.970  47.767  39.116  1.00 18.45           A
ATOM   3184  CD1  TYR A 415     -24.983  46.820  39.369  1.00 18.64           A
ATOM   3185  CE1  TYR A 415     -24.020  46.501  38.405  1.00 18.97           A
ATOM   3186  CD2  TYR A 415     -25.988  48.392  37.873  1.00 18.28           A
ATOM   3187  CE2  TYR A 415     -25.042  48.085  36.904  1.00 18.39           A
ATOM   3188  CZ   TYR A 415     -24.054  47.141  37.175  1.00 18.49           A
ATOM   3189  OH   TYR A 415     -23.091  46.858  36.232  1.00 17.70           A
ATOM   3190  C    TYR A 415     -28.855  47.236  41.528  1.00 22.51           A
```

FIGURE 4- 43 -

| | | | | | | | | | | |
|---|---|---|---|---|---|---|---|---|---|---|
| ATOM | 3191 | O | TYR | A 415 | -28.346 | 47.704 | 42.544 | 1.00 | 23.70 | A |
| ATOM | 3192 | N | ALA | A 416 | -30.133 | 46.884 | 41.443 | 1.00 | 22.47 | A |
| ATOM | 3193 | CA | ALA | A 416 | -31.052 | 47.063 | 42.560 | 1.00 | 23.88 | A |
| ATOM | 3194 | CB | ALA | A 416 | -32.357 | 46.335 | 42.280 | 1.00 | 23.99 | A |
| ATOM | 3195 | C | ALA | A 416 | -30.501 | 46.622 | 43.916 | 1.00 | 24.49 | A |
| ATOM | 3196 | O | ALA | A 416 | -30.914 | 47.147 | 44.942 | 1.00 | 27.01 | A |
| ATOM | 3197 | N | PRO | A 417 | -29.579 | 45.642 | 43.944 | 1.00 | 24.28 | A |
| ATOM | 3198 | CD | PRO | A 417 | -29.194 | 44.683 | 42.892 | 1.00 | 24.93 | A |
| ATOM | 3199 | CA | PRO | A 417 | -29.053 | 45.216 | 45.242 | 1.00 | 23.88 | A |
| ATOM | 3200 | CB | PRO | A 417 | -28.534 | 43.802 | 44.974 | 1.00 | 22.69 | A |
| ATOM | 3201 | CG | PRO | A 417 | -29.132 | 43.405 | 43.644 | 1.00 | 23.07 | A |
| ATOM | 3202 | C | PRO | A 417 | -27.934 | 46.104 | 45.760 | 1.00 | 24.99 | A |
| ATOM | 3203 | O | PRO | A 417 | -27.739 | 46.220 | 46.973 | 1.00 | 25.67 | A |
| ATOM | 3204 | N | THR | A 418 | -27.193 | 46.725 | 44.848 | 1.00 | 24.36 | A |
| ATOM | 3205 | CA | THR | A 418 | -26.070 | 47.546 | 45.265 | 1.00 | 24.11 | A |
| ATOM | 3206 | CB | THR | A 418 | -25.286 | 48.143 | 44.054 | 1.00 | 23.99 | A |
| ATOM | 3207 | OG1 | THR | A 418 | -26.086 | 49.125 | 43.385 | 1.00 | 23.44 | A |
| ATOM | 3208 | CG2 | THR | A 418 | -24.910 | 47.039 | 43.071 | 1.00 | 21.78 | A |
| ATOM | 3209 | C | THR | A 418 | -26.474 | 48.662 | 46.210 | 1.00 | 24.63 | A |
| ATOM | 3210 | O | THR | A 418 | -27.618 | 49.114 | 46.237 | 1.00 | 24.96 | A |
| ATOM | 3211 | N | LEU | A 419 | -25.500 | 49.072 | 47.003 | 1.00 | 24.85 | A |
| ATOM | 3212 | CA | LEU | A 419 | -25.633 | 50.125 | 47.989 | 1.00 | 24.45 | A |
| ATOM | 3213 | CB | LEU | A 419 | -24.288 | 50.231 | 48.683 | 1.00 | 26.20 | A |
| ATOM | 3214 | CG | LEU | A 419 | -24.182 | 51.143 | 49.920 | 1.00 | 28.81 | A |
| ATOM | 3215 | CD1 | LEU | A 419 | -25.002 | 50.510 | 51.043 | 1.00 | 30.81 | A |
| ATOM | 3216 | CD2 | LEU | A 419 | -22.725 | 51.239 | 50.318 | 1.00 | 31.68 | A |
| ATOM | 3217 | C | LEU | A 419 | -26.029 | 51.446 | 47.341 | 1.00 | 23.69 | A |
| ATOM | 3218 | O | LEU | A 419 | -27.031 | 52.055 | 47.696 | 1.00 | 24.58 | A |
| ATOM | 3219 | N | TRP | A 420 | -25.231 | 51.884 | 46.380 | 1.00 | 22.23 | A |
| ATOM | 3220 | CA | TRP | A 420 | -25.486 | 53.143 | 45.708 | 1.00 | 23.00 | A |
| ATOM | 3221 | CB | TRP | A 420 | -24.334 | 53.455 | 44.767 | 1.00 | 21.96 | A |
| ATOM | 3222 | CG | TRP | A 420 | -23.940 | 52.315 | 43.908 | 1.00 | 22.42 | A |
| ATOM | 3223 | CD2 | TRP | A 420 | -24.327 | 52.102 | 42.552 | 1.00 | 20.89 | A |
| ATOM | 3224 | CE2 | TRP | A 420 | -23.693 | 50.923 | 42.116 | 1.00 | 22.04 | A |
| ATOM | 3225 | CE3 | TRP | A 420 | -25.149 | 52.794 | 41.663 | 1.00 | 19.08 | A |
| ATOM | 3226 | CD1 | TRP | A 420 | -23.114 | 51.282 | 44.238 | 1.00 | 23.33 | A |
| ATOM | 3227 | NE1 | TRP | A 420 | -22.956 | 50.439 | 43.164 | 1.00 | 23.55 | A |
| ATOM | 3228 | CZ2 | TRP | A 420 | -23.854 | 50.424 | 40.824 | 1.00 | 22.17 | A |
| ATOM | 3229 | CZ3 | TRP | A 420 | -25.309 | 52.299 | 40.384 | 1.00 | 20.27 | A |
| ATOM | 3230 | CH2 | TRP | A 420 | -24.665 | 51.125 | 39.974 | 1.00 | 20.37 | A |
| ATOM | 3231 | C | TRP | A 420 | -26.812 | 53.241 | 44.955 | 1.00 | 23.66 | A |
| ATOM | 3232 | O | TRP | A 420 | -27.472 | 54.967 | 44.967 | 1.00 | 24.82 | A |
| ATOM | 3233 | N | ALA | A 421 | -27.204 | 52.158 | 44.300 | 1.00 | 22.69 | A |
| ATOM | 3234 | CA | ALA | A 421 | -28.447 | 52.155 | 43.548 | 1.00 | 22.68 | A |
| ATOM | 3235 | CB | ALA | A 421 | -28.598 | 50.839 | 42.808 | 1.00 | 21.97 | A |
| ATOM | 3236 | C | ALA | A 421 | -29.651 | 52.378 | 44.452 | 1.00 | 23.90 | A |
| ATOM | 3237 | O | ALA | A 421 | -30.576 | 53.113 | 44.106 | 1.00 | 25.07 | A |
| ATOM | 3238 | N | ARG | A 422 | -29.640 | 51.740 | 45.613 | 1.00 | 24.25 | A |
| ATOM | 3239 | CA | ARG | A 422 | -30.751 | 51.859 | 46.537 | 1.00 | 24.27 | A |
| ATOM | 3240 | CB | ARG | A 422 | -30.692 | 50.743 | 47.580 | 1.00 | 25.22 | A |
| ATOM | 3241 | CG | ARG | A 422 | -30.575 | 49.340 | 47.003 | 1.00 | 25.43 | A |
| ATOM | 3242 | CD | ARG | A 422 | -30.325 | 48.313 | 48.102 | 1.00 | 24.35 | A |
| ATOM | 3243 | NE | ARG | A 422 | -31.498 | 48.083 | 48.940 | 1.00 | 24.17 | A |
| ATOM | 3244 | CZ | ARG | A 422 | -31.439 | 47.523 | 50.144 | 1.00 | 23.60 | A |
| ATOM | 3245 | NH1 | ARG | A 422 | -30.266 | 47.152 | 50.635 | 1.00 | 22.69 | A |
| ATOM | 3246 | NH2 | ARG | A 422 | -32.542 | 47.323 | 50.853 | 1.00 | 23.24 | A |
| ATOM | 3247 | C | ARG | A 422 | -30.742 | 53.190 | 47.249 | 1.00 | 24.53 | A |
| ATOM | 3248 | O | ARG | A 422 | -31.735 | 53.915 | 47.254 | 1.00 | 23.68 | A |
| ATOM | 3249 | N | MET | A 423 | -29.604 | 53.513 | 47.848 | 1.00 | 25.03 | A |
| ATOM | 3250 | CA | MET | A 423 | -29.485 | 54.743 | 48.615 | 1.00 | 24.70 | A |
| ATOM | 3251 | CB | MET | A 423 | -28.258 | 54.667 | 49.520 | 1.00 | 23.18 | A |
| ATOM | 3252 | CG | MET | A 423 | -28.359 | 53.558 | 50.538 | 1.00 | 23.26 | A |
| ATOM | 3253 | SD | MET | A 423 | -27.067 | 53.599 | 51.769 | 1.00 | 28.00 | A |
| ATOM | 3254 | CE | MET | A 423 | -27.586 | 55.024 | 52.729 | 1.00 | 24.33 | A |
| ATOM | 3255 | C | MET | A 423 | -29.452 | 56.031 | 47.817 | 1.00 | 23.89 | A |
| ATOM | 3256 | O | MET | A 423 | -29.878 | 57.064 | 48.312 | 1.00 | 23.28 | A |
| ATOM | 3257 | N | ILE | A 424 | -28.955 | 55.933 | 46.588 | 1.00 | 23.46 | A |
| ATOM | 3258 | CA | ILE | A 424 | -28.877 | 57.202 | 45.795 | 1.00 | 22.87 | A |
| ATOM | 3259 | CB | ILE | A 424 | -27.423 | 57.446 | 45.315 | 1.00 | 21.79 | A |
| ATOM | 3260 | CG2 | ILE | A 424 | -27.324 | 58.789 | 44.580 | 1.00 | 16.72 | A |
| ATOM | 3261 | CG1 | ILE | A 424 | -26.480 | 57.405 | 46.529 | 1.00 | 19.30 | A |
| ATOM | 3262 | CD1 | ILE | A 424 | -25.020 | 57.477 | 46.204 | 1.00 | 16.32 | A |
| ATOM | 3263 | C | ILE | A 424 | -29.821 | 57.227 | 44.600 | 1.00 | 24.52 | A |
| ATOM | 3264 | O | ILE | A 424 | -30.767 | 58.021 | 44.570 | 1.00 | 24.47 | A |
| ATOM | 3265 | N | LEU | A 425 | -29.568 | 56.357 | 43.624 | 1.00 | 25.00 | A |
| ATOM | 3266 | CA | LEU | A 425 | -30.391 | 56.303 | 42.426 | 1.00 | 23.56 | A |

FIGURE 4-44-

```
ATOM   3267  CB   LEU A 425     -29.996  55.109  41.568  1.00 23.31           A
ATOM   3268  CG   LEU A 425     -28.640  55.327  40.865  1.00 23.26           A
ATOM   3269  CD1  LEU A 425     -28.419  54.229  39.854  1.00 19.62           A
ATOM   3270  CD2  LEU A 425     -28.610  56.717  40.218  1.00 19.02           A
ATOM   3271  C    LEU A 425     -31.869  56.264  42.722  1.00 23.91           A
ATOM   3272  O    LEU A 425     -32.635  57.025  42.139  1.00 26.09           A
ATOM   3273  N    MET A 426     -32.286  55.387  43.625  1.00 22.96           A
ATOM   3274  CA   MET A 426     -33.697  55.317  43.955  1.00 23.11           A
ATOM   3275  CB   MET A 426     -33.975  54.103  44.838  1.00 21.89           A
ATOM   3276  CG   MET A 426     -33.665  52.780  44.158  1.00 22.99           A
ATOM   3277  SD   MET A 426     -34.375  51.346  45.019  1.00 23.90           A
ATOM   3278  CE   MET A 426     -33.227  50.079  44.591  1.00 21.38           A
ATOM   3279  C    MET A 426     -34.157  56.515  44.637  1.00 23.85           A
ATOM   3280  O    MET A 426     -35.015  57.325  44.112  1.00 24.32           A
ATOM   3281  N    THR A 427     -33.574  56.938  45.767  1.00 23.57           A
ATOM   3282  CA   THR A 427     -33.934  58.150  46.520  1.00 23.43           A
ATOM   3283  CB   THR A 427     -32.856  58.476  47.561  1.00 23.01           A
ATOM   3284  OG1  THR A 427     -32.577  57.299  48.324  1.00 23.75           A
ATOM   3285  CG2  THR A 427     -33.312  59.595  48.492  1.00 21.95           A
ATOM   3286  C    THR A 427     -34.095  59.364  45.595  1.00 25.19           A
ATOM   3287  O    THR A 427     -35.165  59.970  45.509  1.00 23.75           A
ATOM   3288  N    HIS A 428     -33.016  59.691  44.894  1.00 26.39           A
ATOM   3289  CA   HIS A 428     -32.968  60.825  43.985  1.00 27.47           A
ATOM   3290  CB   HIS A 428     -31.623  60.841  43.264  1.00 28.04           A
ATOM   3291  CG   HIS A 428     -31.468  61.984  42.317  1.00 29.64           A
ATOM   3292  CD2  HIS A 428     -31.503  62.032  40.964  1.00 31.18           A
ATOM   3293  ND1  HIS A 428     -31.287  63.281  42.743  1.00 31.15           A
ATOM   3294  CE1  HIS A 428     -31.218  64.080  41.692  1.00 32.01           A
ATOM   3295  NE2  HIS A 428     -31.346  63.348  40.600  1.00 31.57           A
ATOM   3296  C    HIS A 428     -34.078  60.815  42.941  1.00 28.45           A
ATOM   3297  O    HIS A 428     -34.707  61.971  42.787  1.00 28.21           A
ATOM   3298  N    PHE A 429     -34.305  59.821  42.215  1.00 28.66           A
ATOM   3299  CA   PHE A 429     -35.316  59.809  41.162  1.00 28.00           A
ATOM   3300  CB   PHE A 429     -34.993  58.717  40.139  1.00 25.37           A
ATOM   3301  CG   PHE A 429     -33.798  59.040  39.301  1.00 22.13           A
ATOM   3302  CD1  PHE A 429     -33.841  60.090  38.391  1.00 21.89           A
ATOM   3303  CD2  PHE A 429     -32.600  58.376  39.499  1.00 22.47           A
ATOM   3304  CE1  PHE A 429     -32.702  60.489  37.691  1.00 22.97           A
ATOM   3305  CE2  PHE A 429     -31.447  58.762  38.810  1.00 26.06           A
ATOM   3306  CZ   PHE A 429     -31.498  59.828  37.902  1.00 24.65           A
ATOM   3307  C    PHE A 429     -36.753  59.708  41.640  1.00 28.85           A
ATOM   3308  O    PHE A 429     -37.639  60.354  41.076  1.00 29.99           A
ATOM   3309  N    PHE A 430     -37.013  58.914  42.668  1.00 28.76           A
ATOM   3310  CA   PHE A 430     -38.376  58.862  43.149  1.00 29.61           A
ATOM   3311  CB   PHE A 430     -38.575  57.735  44.151  1.00 27.16           A
ATOM   3312  CG   PHE A 430     -38.874  56.432  43.499  1.00 25.77           A
ATOM   3313  CD1  PHE A 430     -37.846  55.590  43.064  1.00 24.72           A
ATOM   3314  CD2  PHE A 430     -40.190  56.067  43.230  1.00 24.66           A
ATOM   3315  CE1  PHE A 430     -38.126  54.401  42.408  1.00 23.17           A
ATOM   3316  CE2  PHE A 430     -40.477  54.882  42.554  1.00 23.05           A
ATOM   3317  CZ   PHE A 430     -39.441  54.050  42.144  1.00 23.43           A
ATOM   3318  C    PHE A 430     -38.689  60.208  43.766  1.00 31.10           A
ATOM   3319  O    PHE A 430     -39.824  60.674  43.723  1.00 32.14           A
ATOM   3320  N    SER A 431     -37.668  60.846  44.323  1.00 33.17           A
ATOM   3321  CA   SER A 431     -37.852  62.161  44.918  1.00 34.02           A
ATOM   3322  CB   SER A 431     -36.527  62.890  45.467  1.00 35.34           A
ATOM   3323  OG   SER A 431     -36.582  64.088  45.690  1.00 38.44           A
ATOM   3324  C    SER A 431     -38.368  63.090  43.833  1.00 33.79           A
ATOM   3325  O    SER A 431     -39.420  63.702  43.983  1.00 34.05           A
ATOM   3326  N    ILE A 432     -37.624  63.176  42.734  1.00 34.58           A
ATOM   3327  CA   ILE A 432     -37.983  64.035  41.605  1.00 35.14           A
ATOM   3328  CB   ILE A 432     -36.850  64.091  40.552  1.00 34.68           A
ATOM   3329  CG2  ILE A 432     -37.330  64.824  39.310  1.00 34.14           A
ATOM   3330  CG1  ILE A 432     -35.620  64.784  41.127  1.00 34.19           A
ATOM   3331  CD1  ILE A 432     -34.437  64.734  40.190  1.00 34.73           A
ATOM   3332  C    ILE A 432     -39.256  63.807  40.872  1.00 36.44           A
ATOM   3333  O    ILE A 432     -39.989  64.458  40.353  1.00 34.94           A
ATOM   3334  N    LEU A 433     -39.517  62.801  40.804  1.00 36.44           A
ATOM   3335  CA   LEU A 433     -40.714  61.848  40.106  1.00 36.90           A
ATOM   3336  CB   LEU A 433     -40.657  60.340  39.837  1.00 36.04           A
ATOM   3337  CG   LEU A 433     -39.668  59.357  38.723  1.00 34.73           A
ATOM   3338  CD1  LEU A 433     -39.737  58.474  38.425  1.00 32.55           A
ATOM   3339  CD2  LEU A 433     -39.984  60.754  37.474  1.00 32.30           A
ATOM   3340  C    LEU A 433     -41.962  62.223  40.886  1.00 37.80           A
ATOM   3341  O    LEU A 433     -43.017  62.448  40.304  1.00 38.55           A
ATOM   3342  N    LEU A 434     -41.841  62.305  42.204  1.00 38.76           A
```

FIGURE 4- 45 -

```
ATOM   3343  CA   LEU A 434     -42.989  62.705  43.030  1.00 39.41      A
ATOM   3344  CB   LEU A 434     -42.634  62.534  44.509  1.00 38.91      A
ATOM   3345  CG   LEU A 434     -42.694  61.103  45.020  1.00 38.96      A
ATOM   3346  CD1  LEU A 434     -42.204  61.018  46.459  1.00 38.12      A
ATOM   3347  CD2  LEU A 434     -44.132  60.628  44.896  1.00 39.85      A
ATOM   3348  C    LEU A 434     -43.249  64.176  42.746  1.00 40.16      A
ATOM   3349  O    LEU A 434     -44.350  64.557  42.359  1.00 41.18      A
ATOM   3350  N    ALA A 435     -42.227  64.997  42.929  1.00 40.54      A
ATOM   3351  CA   ALA A 435     -42.343  66.425  42.710  1.00 42.20      A
ATOM   3352  CB   ALA A 435     -40.970  67.077  42.865  1.00 42.27      A
ATOM   3353  C    ALA A 435     -42.942  66.792  41.352  1.00 43.34      A
ATOM   3354  O    ALA A 435     -43.515  67.869  41.193  1.00 44.86      A
ATOM   3355  N    GLN A 436     -42.815  65.903  40.374  1.00 44.12      A
ATOM   3356  CA   GLN A 436     -43.326  66.186  39.040  1.00 44.57      A
ATOM   3357  CB   GLN A 436     -42.182  66.065  38.027  1.00 44.76      A
ATOM   3358  CG   GLN A 436     -40.877  66.729  38.483  1.00 45.63      A
ATOM   3359  CD   GLN A 436     -39.699  66.430  37.565  1.00 46.56      A
ATOM   3360  OE1  GLN A 436     -39.683  65.410  36.868  1.00 48.46      A
ATOM   3361  NE2  GLN A 436     -38.698  67.308  37.574  1.00 43.58      A
ATOM   3362  C    GLN A 436     -44.470  65.247  38.664  1.00 44.99      A
ATOM   3363  O    GLN A 436     -44.888  65.191  37.507  1.00 44.24      A
ATOM   3364  N    GLU A 437     -44.986  64.524  39.652  1.00 46.30      A
ATOM   3365  CA   GLU A 437     -46.071  63.573  39.424  1.00 48.16      A
ATOM   3366  CB   GLU A 437     -47.420  64.288  39.445  1.00 49.84      A
ATOM   3367  CG   GLU A 437     -47.920  64.628  40.839  1.00 52.21      A
ATOM   3368  CD   GLU A 437     -49.118  65.561  40.817  1.00 54.18      A
ATOM   3369  OE1  GLU A 437     -49.674  65.843  41.900  1.00 55.26      A
ATOM   3370  OE2  GLU A 437     -49.501  66.018  39.716  1.00 55.63      A
ATOM   3371  C    GLU A 437     -45.887  62.832  38.102  1.00 47.95      A
ATOM   3372  O    GLU A 437     -46.733  62.887  37.207  1.00 47.76      A
ATOM   3373  N    GLN A 438     -44.756  62.149  37.985  1.00 46.48      A
ATOM   3374  CA   GLN A 438     -44.455  61.390  36.791  1.00 45.56      A
ATOM   3375  CB   GLN A 438     -43.265  62.005  36.049  1.00 46.64      A
ATOM   3376  CG   GLN A 438     -43.558  63.315  35.324  1.00 48.55      A
ATOM   3377  CD   GLN A 438     -42.332  63.845  34.583  1.00 50.40      A
ATOM   3378  OE1  GLN A 438     -41.325  64.216  35.199  1.00 51.28      A
ATOM   3379  NE2  GLN A 438     -42.407  63.871  33.256  1.00 50.70      A
ATOM   3380  C    GLN A 438     -44.153  59.947  37.163  1.00 44.26      A
ATOM   3381  O    GLN A 438     -43.587  59.204  36.365  1.00 44.41      A
ATOM   3382  N    LEU A 439     -44.537  59.554  38.375  1.00 42.87      A
ATOM   3383  CA   LEU A 439     -44.314  58.188  38.845  1.00 43.10      A
ATOM   3384  CB   LEU A 439     -44.876  57.995  40.257  1.00 41.53      A
ATOM   3385  CG   LEU A 439     -44.136  58.648  41.421  1.00 41.73      A
ATOM   3386  CD1  LEU A 439     -44.761  58.202  42.731  1.00 38.74      A
ATOM   3387  CD2  LEU A 439     -42.662  58.259  41.369  1.00 41.52      A
ATOM   3388  C    LEU A 439     -44.957  57.154  37.928  1.00 44.07      A
ATOM   3389  O    LEU A 439     -44.593  55.974  37.957  1.00 43.34      A
ATOM   3390  N    GLU A 440     -45.908  57.599  37.110  1.00 45.38      A
ATOM   3391  CA   GLU A 440     -46.612  56.696  36.209  1.00 46.80      A
ATOM   3392  CB   GLU A 440     -48.118  56.865  36.369  1.00 50.97      A
ATOM   3393  CG   GLU A 440     -48.594  56.417  37.731  1.00 56.70      A
ATOM   3394  CD   GLU A 440     -50.028  56.794  38.023  1.00 60.79      A
ATOM   3395  OE1  GLU A 440     -50.376  57.977  37.794  1.00 62.13      A
ATOM   3396  OE2  GLU A 440     -50.796  55.914  38.496  1.00 62.97      A
ATOM   3397  C    GLU A 440     -46.235  56.859  34.767  1.00 44.11      A
ATOM   3398  O    GLU A 440     -46.646  56.072  33.928  1.00 44.17      A
ATOM   3399  N    LYS A 441     -45.454  57.886  34.477  1.00 42.92      A
ATOM   3400  CA   LYS A 441     -45.009  58.118  33.115  1.00 42.18      A
ATOM   3401  CB   LYS A 441     -44.446  59.530  32.985  1.00 41.74      A
ATOM   3402  CG   LYS A 441     -43.985  59.903  31.600  1.00 42.28      A
ATOM   3403  CD   LYS A 441     -43.315  61.264  31.634  1.00 43.77      A
ATOM   3404  CE   LYS A 441     -42.787  61.675  30.275  1.00 44.87      A
ATOM   3405  NZ   LYS A 441     -42.002  62.936  30.385  1.00 48.63      A
ATOM   3406  C    LYS A 441     -43.932  57.087  32.787  1.00 42.19      A
ATOM   3407  O    LYS A 441     -42.939  56.960  33.506  1.00 42.84      A
ATOM   3408  N    ALA A 442     -44.138  56.336  31.713  1.00 41.57      A
ATOM   3409  CA   ALA A 442     -43.167  55.328  31.313  1.00 41.67      A
ATOM   3410  CB   ALA A 442     -43.807  54.346  30.342  1.00 39.84      A
ATOM   3411  C    ALA A 442     -41.908  55.946  30.684  1.00 41.47      A
ATOM   3412  O    ALA A 442     -41.982  56.898  29.898  1.00 39.96      A
ATOM   3413  N    LEU A 443     -40.751  55.399  31.044  1.00 41.32      A
ATOM   3414  CA   LEU A 443     -39.483  55.873  30.508  1.00 40.91      A
ATOM   3415  CB   LEU A 443     -38.577  56.372  31.633  1.00 40.91      A
ATOM   3416  CG   LEU A 443     -39.149  57.442  32.561  1.00 41.40      A
ATOM   3417  CD1  LEU A 443     -38.119  57.756  33.631  1.00 41.50      A
ATOM   3418  CD2  LEU A 443     -39.517  58.695  31.774  1.00 39.85      A
```

FIGURE 4- 46 -

```
ATOM   3419  C    LEU A 443     -38.785  54.735  29.778  1.00 39.84           A
ATOM   3420  O    LEU A 443     -38.936  53.572  30.137  1.00 39.25           A
ATOM   3421  N    ASP A 444     -38.025  55.071  28.747  1.00 40.05           A
ATOM   3422  CA   ASP A 444     -37.301  54.053  28.004  1.00 39.81           A
ATOM   3423  CB   ASP A 444     -37.121  54.457  26.529  1.00 40.69           A
ATOM   3424  CG   ASP A 444     -38.440  54.588  25.781  1.00 42.26           A
ATOM   3425  OD1  ASP A 444     -39.424  53.921  26.175  1.00 43.06           A
ATOM   3426  OD2  ASP A 444     -38.489  55.348  24.785  1.00 41.57           A
ATOM   3427  C    ASP A 444     -35.920  53.845  28.622  1.00 39.52           A
ATOM   3428  O    ASP A 444     -35.093  54.755  28.642  1.00 40.02           A
ATOM   3429  N    CYS A 445     -35.672  52.661  29.155  1.00 37.76           A
ATOM   3430  CA   CYS A 445     -34.358  52.381  29.698  1.00 37.90           A
ATOM   3431  CB   CYS A 445     -34.460  51.781  31.093  1.00 38.36           A
ATOM   3432  SG   CYS A 445     -35.284  50.201  31.113  1.00 38.24           A
ATOM   3433  C    CYS A 445     -33.776  51.363  28.725  1.00 38.73           A
ATOM   3434  O    CYS A 445     -34.342  51.134  27.658  1.00 37.71           A
ATOM   3435  N    GLN A 446     -32.666  50.733  29.078  1.00 39.01           A
ATOM   3436  CA   GLN A 446     -32.080  49.772  28.167  1.00 38.69           A
ATOM   3437  CB   GLN A 446     -31.091  50.482  27.250  1.00 41.32           A
ATOM   3438  CG   GLN A 446     -31.234  50.113  25.790  1.00 44.46           A
ATOM   3439  CD   GLN A 446     -30.296  50.911  24.898  1.00 46.57           A
ATOM   3440  OE1  GLN A 446     -29.068  50.742  24.948  1.00 45.53           A
ATOM   3441  NE2  GLN A 446     -30.871  51.794  24.079  1.00 45.59           A
ATOM   3442  C    GLN A 446     -31.386  48.629  28.886  1.00 38.16           A
ATOM   3443  O    GLN A 446     -30.604  48.841  29.817  1.00 37.87           A
ATOM   3444  N    ILE A 447     -31.682  47.415  28.433  1.00 36.97           A
ATOM   3445  CA   ILE A 447     -31.112  46.202  28.990  1.00 34.76           A
ATOM   3446  CB   ILE A 447     -32.197  45.396  29.701  1.00 33.87           A
ATOM   3447  CG2  ILE A 447     -31.605  44.133  30.315  1.00 31.15           A
ATOM   3448  CG1  ILE A 447     -32.845  46.282  30.768  1.00 33.64           A
ATOM   3449  CD1  ILE A 447     -33.988  45.641  31.492  1.00 35.77           A
ATOM   3450  C    ILE A 447     -30.501  45.388  27.852  1.00 35.73           A
ATOM   3451  O    ILE A 447     -31.189  45.034  26.899  1.00 36.13           A
ATOM   3452  N    TYR A 448     -29.203  45.112  27.952  1.00 36.68           A
ATOM   3453  CA   TYR A 448     -28.480  44.358  26.936  1.00 36.50           A
ATOM   3454  CB   TYR A 448     -28.784  42.864  27.032  1.00 37.33           A
ATOM   3455  CG   TYR A 448     -28.323  42.210  28.302  1.00 38.01           A
ATOM   3456  CD1  TYR A 448     -27.191  42.667  28.983  1.00 38.32           A
ATOM   3457  CE1  TYR A 448     -26.737  42.018  30.137  1.00 39.05           A
ATOM   3458  CD2  TYR A 448     -28.991  41.095  28.801  1.00 40.14           A
ATOM   3459  CE2  TYR A 448     -28.548  40.441  29.948  1.00 40.49           A
ATOM   3460  CZ   TYR A 448     -27.423  40.905  30.607  1.00 39.43           A
ATOM   3461  OH   TYR A 448     -26.991  40.234  31.722  1.00 40.55           A
ATOM   3462  C    TYR A 448     -28.811  44.828  25.531  1.00 36.77           A
ATOM   3463  O    TYR A 448     -29.222  44.037  24.679  1.00 34.95           A
ATOM   3464  N    GLY A 449     -28.623  46.120  25.289  1.00 38.04           A
ATOM   3465  CA   GLY A 449     -28.901  46.658  23.973  1.00 38.93           A
ATOM   3466  C    GLY A 449     -30.376  46.875  23.701  1.00 39.54           A
ATOM   3467  O    GLY A 449     -30.745  47.891  23.117  1.00 41.19           A
ATOM   3468  N    ALA A 450     -31.217  45.928  24.109  1.00 38.84           A
ATOM   3469  CA   ALA A 450     -32.657  46.039  23.897  1.00 38.82           A
ATOM   3470  CB   ALA A 450     -33.348  44.734  24.299  1.00 39.97           A
ATOM   3471  C    ALA A 450     -33.275  47.215  24.665  1.00 38.61           A
ATOM   3472  O    ALA A 450     -32.990  47.429  25.842  1.00 36.72           A
ATOM   3473  N    CYS A 451     -34.129  47.969  23.982  1.00 38.46           A
ATOM   3474  CA   CYS A 451     -34.793  49.113  24.577  1.00 37.91           A
ATOM   3475  CB   CYS A 451     -34.991  50.207  23.534  1.00 37.04           A
ATOM   3476  SG   CYS A 451     -35.872  51.655  24.155  1.00 38.78           A
ATOM   3477  C    CYS A 451     -36.143  48.705  25.135  1.00 39.00           A
ATOM   3478  O    CYS A 451     -36.978  48.168  24.409  1.00 39.77           A
ATOM   3479  N    TYR A 452     -36.349  48.968  26.425  1.00 40.91           A
ATOM   3480  CA   TYR A 452     -37.598  48.647  27.121  1.00 41.78           A
ATOM   3481  CB   TYR A 452     -37.314  47.760  28.339  1.00 42.87           A
ATOM   3482  CG   TYR A 452     -36.921  46.343  28.003  1.00 45.51           A
ATOM   3483  CD1  TYR A 452     -37.889  45.385  27.696  1.00 46.56           A
ATOM   3484  CE1  TYR A 452     -37.530  44.089  27.341  1.00 48.07           A
ATOM   3485  CD2  TYR A 452     -35.577  45.969  27.951  1.00 46.60           A
ATOM   3486  CE2  TYR A 452     -35.204  44.682  27.599  1.00 48.05           A
ATOM   3487  CZ   TYR A 452     -36.183  43.744  27.293  1.00 49.40           A
ATOM   3488  OH   TYR A 452     -35.816  42.464  26.933  1.00 50.46           A
ATOM   3489  C    TYR A 452     -38.326  49.906  27.599  1.00 41.85           A
ATOM   3490  O    TYR A 452     -37.703  50.916  27.930  1.00 41.71           A
ATOM   3491  N    SER A 453     -39.652  49.844  27.626  1.00 41.48           A
ATOM   3492  CA   SER A 453     -40.445  50.963  28.107  1.00 41.78           A
ATOM   3493  CB   SER A 453     -41.637  51.218  27.186  1.00 40.49           A
ATOM   3494  OG   SER A 453     -42.258  52.447  27.516  1.00 40.52           A
```

FIGURE 4- 47 -

```
ATOM   3495  C    SER A 453     -40.913  50.515  29.486  1.00 42.94           A
ATOM   3496  O    SER A 453     -41.504  49.442  29.624  1.00 43.47           A
ATOM   3497  N    ILE A 454     -40.647  51.323  30.512  1.00 43.53           A
ATOM   3498  CA   ILE A 454     -41.019  50.940  31.875  1.00 43.07           A
ATOM   3499  CB   ILE A 454     -39.809  50.341  32.608  1.00 40.97           A
ATOM   3500  CG2  ILE A 454     -40.192  49.973  34.029  1.00 40.52           A
ATOM   3501  CG1  ILE A 454     -39.298  49.125  31.843  1.00 39.28           A
ATOM   3502  CD1  ILE A 454     -38.138  48.433  32.508  1.00 41.21           A
ATOM   3503  C    ILE A 454     -41.600  52.022  32.779  1.00 43.88           A
ATOM   3504  O    ILE A 454     -41.172  53.179  32.756  1.00 45.20           A
ATOM   3505  N    GLU A 455     -42.578  51.827  33.587  1.00 43.62           A
ATOM   3506  CA   GLU A 455     -43.184  52.553  34.527  1.00 43.80           A
ATOM   3507  CB   GLU A 455     -44.670  52.249  34.748  1.00 46.02           A
ATOM   3508  CG   GLU A 455     -45.609  52.619  33.600  1.00 48.35           A
ATOM   3509  CD   GLU A 455     -47.081  52.534  34.012  1.00 50.01           A
ATOM   3510  OE1  GLU A 455     -47.541  53.412  34.779  1.00 51.01           A
ATOM   3511  OE2  GLU A 455     -47.774  51.581  33.586  1.00 50.76           A
ATOM   3512  C    GLU A 455     -42.451  52.372  35.844  1.00 42.14           A
ATOM   3513  O    GLU A 455     -42.378  51.262  36.373  1.00 41.90           A
ATOM   3514  N    PRO A 456     -41.897  53.463  36.389  1.00 40.15           A
ATOM   3515  CD   PRO A 456     -41.957  54.821  35.821  1.00 39.87           A
ATOM   3516  CA   PRO A 456     -41.160  53.462  37.658  1.00 38.35           A
ATOM   3517  CB   PRO A 456     -40.999  54.945  37.959  1.00 38.39           A
ATOM   3518  CG   PRO A 456     -40.878  55.536  36.603  1.00 39.32           A
ATOM   3519  C    PRO A 456     -41.928  52.745  38.761  1.00 36.43           A
ATOM   3520  O    PRO A 456     -41.348  52.146  39.655  1.00 35.54           A
ATOM   3521  N    LEU A 457     -43.246  52.811  38.693  1.00 36.67           A
ATOM   3522  CA   LEU A 457     -44.070  52.164  39.694  1.00 36.31           A
ATOM   3523  CB   LEU A 457     -45.518  52.509  39.537  1.00 35.66           A
ATOM   3524  CG   LEU A 457     -45.691  54.082  39.897  1.00 36.34           A
ATOM   3525  CD1  LEU A 457     -47.093  54.499  39.582  1.00 35.67           A
ATOM   3526  CD2  LEU A 457     -45.375  54.307  41.383  1.00 34.56           A
ATOM   3527  C    LEU A 457     -43.991  50.649  39.664  1.00 35.55           A
ATOM   3528  O    LEU A 457     -44.374  49.997  40.627  1.00 36.48           A
ATOM   3529  N    ASP A 458     -43.493  50.082  38.572  1.00 34.64           A
ATOM   3530  CA   ASP A 458     -43.392  48.633  38.482  1.00 35.24           A
ATOM   3531  CB   ASP A 458     -43.475  48.170  37.019  1.00 38.89           A
ATOM   3532  CG   ASP A 458     -44.892  48.226  36.453  1.00 40.50           A
ATOM   3533  OD1  ASP A 458     -45.821  47.685  37.092  1.00 40.16           A
ATOM   3534  OD2  ASP A 458     -45.066  48.804  35.357  1.00 43.70           A
ATOM   3535  C    ASP A 458     -42.111  48.086  39.096  1.00 33.57           A
ATOM   3536  O    ASP A 458     -42.053  46.921  39.489  1.00 33.82           A
ATOM   3537  N    LEU A 459     -41.094  48.936  39.185  1.00 32.06           A
ATOM   3538  CA   LEU A 459     -39.792  48.548  39.711  1.00 30.38           A
ATOM   3539  CB   LEU A 459     -39.024  49.788  40.189  1.00 28.87           A
ATOM   3540  CG   LEU A 459     -38.394  50.610  39.050  1.00 28.11           A
ATOM   3541  CD1  LEU A 459     -37.854  51.926  39.588  1.00 25.37           A
ATOM   3542  CD2  LEU A 459     -37.281  49.797  38.378  1.00 27.60           A
ATOM   3543  C    LEU A 459     -39.787  47.470  40.784  1.00 29.49           A
ATOM   3544  O    LEU A 459     -39.048  46.501  40.671  1.00 30.52           A
ATOM   3545  N    PRO A 460     -40.617  47.612  41.827  1.00 29.35           A
ATOM   3546  CD   PRO A 460     -41.564  48.712  42.081  1.00 28.86           A
ATOM   3547  CA   PRO A 460     -40.683  46.624  42.909  1.00 29.69           A
ATOM   3548  CB   PRO A 460     -41.868  47.109  43.734  1.00 28.65           A
ATOM   3549  CG   PRO A 460     -41.799  48.587  43.566  1.00 27.67           A
ATOM   3550  C    PRO A 460     -40.873  45.191  42.414  1.00 31.03           A
ATOM   3551  O    PRO A 460     -40.143  44.284  42.831  1.00 30.13           A
ATOM   3552  N    GLN A 461     -41.862  44.997  41.538  1.00 31.81           A
ATOM   3553  CA   GLN A 461     -42.155  43.688  40.957  1.00 34.37           A
ATOM   3554  CB   GLN A 461     -43.328  43.775  39.973  1.00 38.81           A
ATOM   3555  CG   GLN A 461     -44.698  44.078  40.563  1.00 44.12           A
ATOM   3556  CD   GLN A 461     -44.936  45.562  40.801  1.00 47.00           A
ATOM   3557  OE1  GLN A 461     -44.330  46.174  41.691  1.00 47.87           A
ATOM   3558  NE2  GLN A 461     -45.825  46.151  39.997  1.00 47.37           A
ATOM   3559  C    GLN A 461     -40.933  43.200  40.180  1.00 34.82           A
ATOM   3560  O    GLN A 461     -40.450  42.076  40.358  1.00 34.43           A
ATOM   3561  N    ILE A 462     -40.459  44.067  39.296  1.00 33.97           A
ATOM   3562  CA   ILE A 462     -39.307  43.784  38.470  1.00 33.76           A
ATOM   3563  CB   ILE A 462     -38.921  45.033  37.662  1.00 33.62           A
ATOM   3564  CG2  ILE A 462     -37.638  44.787  36.885  1.00 34.80           A
ATOM   3565  CG1  ILE A 462     -40.062  45.384  36.707  1.00 32.84           A
ATOM   3566  CD1  ILE A 462     -39.829  46.645  35.909  1.00 32.90           A
ATOM   3567  C    ILE A 462     -38.137  43.347  39.338  1.00 34.07           A
ATOM   3568  O    ILE A 462     -37.595  42.260  39.157  1.00 34.24           A
ATOM   3569  N    ILE A 463     -37.758  44.196  40.285  1.00 34.19           A
ATOM   3570  CA   ILE A 463     -36.649  43.893  41.179  1.00 34.08           A
```

FIGURE 4- 48 -

```
ATOM   3571  CB   ILE A 463     -36.433  45.035  42.212  1.00 31.86      A
ATOM   3572  CG2  ILE A 463     -35.525  44.566  43.333  1.00 28.53      A
ATOM   3573  CG1  ILE A 463     -35.837  46.261  41.508  1.00 29.19      A
ATOM   3574  CD1  ILE A 463     -35.616  47.441  42.403  1.00 26.78      A
ATOM   3575  C    ILE A 463     -36.833  42.567  41.916  1.00 36.27      A
ATOM   3576  O    ILE A 463     -35.892  41.773  42.001  1.00 36.23      A
ATOM   3577  N    GLU A 464     -38.032  42.316  42.443  1.00 37.45      A
ATOM   3578  CA   GLU A 464     -38.266  41.063  43.163  1.00 39.78      A
ATOM   3579  CB   GLU A 464     -39.678  41.016  43.765  1.00 40.89      A
ATOM   3580  CG   GLU A 464     -39.926  39.758  44.606  1.00 41.12      A
ATOM   3581  CD   GLU A 464     -41.385  39.561  44.985  1.00 41.63      A
ATOM   3582  OE1  GLU A 464     -42.252  40.278  44.441  1.00 42.32      A
ATOM   3583  OE2  GLU A 464     -41.670  38.678  45.821  1.00 41.28      A
ATOM   3584  C    GLU A 464     -38.062  39.840  42.264  1.00 40.51      A
ATOM   3585  O    GLU A 464     -37.473  38.840  42.694  1.00 40.10      A
ATOM   3586  N    ARG A 465     -38.545  39.923  41.024  1.00 40.43      A
ATOM   3587  CA   ARG A 465     -38.409  38.820  40.071  1.00 40.75      A
ATOM   3588  CB   ARG A 465     -39.339  39.023  38.867  1.00 42.05      A
ATOM   3589  CG   ARG A 465     -40.816  38.710  39.139  1.00 45.89      A
ATOM   3590  CD   ARG A 465     -41.127  37.206  39.115  1.00 46.98      A
ATOM   3591  NE   ARG A 465     -40.994  36.638  37.768  1.00 49.46      A
ATOM   3592  CZ   ARG A 465     -41.750  36.971  36.719  1.00 48.78      A
ATOM   3593  NH1  ARG A 465     -42.716  37.875  36.843  1.00 48.44      A
ATOM   3594  NH2  ARG A 465     -41.527  36.410  35.536  1.00 47.77      A
ATOM   3595  C    ARG A 465     -36.983  38.588  39.564  1.00 39.71      A
ATOM   3596  O    ARG A 465     -36.547  37.447  39.448  1.00 41.07      A
ATOM   3597  N    LEU A 466     -36.254  39.656  39.266  1.00 37.56      A
ATOM   3598  CA   LEU A 466     -34.892  39.515  38.756  1.00 35.90      A
ATOM   3599  CB   LEU A 466     -34.526  40.725  37.891  1.00 34.83      A
ATOM   3600  CG   LEU A 466     -35.583  41.226  36.910  1.00 34.48      A
ATOM   3601  CD1  LEU A 466     -35.073  42.453  36.192  1.00 31.14      A
ATOM   3602  CD2  LEU A 466     -35.925  40.131  35.929  1.00 33.31      A
ATOM   3603  C    LEU A 466     -33.820  39.364  39.837  1.00 35.86      A
ATOM   3604  O    LEU A 466     -32.674  39.035  39.530  1.00 37.84      A
ATOM   3605  N    HIS A 467     -34.174  39.604  41.092  1.00 34.62      A
ATOM   3606  CA   HIS A 467     -33.194  39.526  42.164  1.00 33.57      A
ATOM   3607  CB   HIS A 467     -32.854  40.929  42.638  1.00 31.65      A
ATOM   3608  CG   HIS A 467     -32.183  41.779  41.608  1.00 31.57      A
ATOM   3609  CD2  HIS A 467     -32.641  42.827  40.882  1.00 31.47      A
ATOM   3610  ND1  HIS A 467     -30.866  41.607  41.243  1.00 31.50      A
ATOM   3611  CE1  HIS A 467     -30.540  42.515  40.339  1.00 31.53      A
ATOM   3612  NE2  HIS A 467     -31.600  43.268  40.103  1.00 30.55      A
ATOM   3613  C    HIS A 467     -33.633  38.712  43.374  1.00 35.82      A
ATOM   3614  O    HIS A 467     -32.805  38.086  44.038  1.00 36.25      A
ATOM   3615  N    GLY A 468     -34.931  38.731  43.665  1.00 37.21      A
ATOM   3616  CA   GLY A 468     -35.446  38.009  44.815  1.00 37.20      A
ATOM   3617  C    GLY A 468     -35.657  39.020  45.923  1.00 37.54      A
ATOM   3618  O    GLY A 468     -35.076  40.098  45.870  1.00 37.93      A
ATOM   3619  N    LEU A 469     -36.465  38.690  46.925  1.00 37.23      A
ATOM   3620  CA   LEU A 469     -36.729  39.631  48.012  1.00 37.02      A
ATOM   3621  CB   LEU A 469     -37.673  39.015  49.058  1.00 35.79      A
ATOM   3622  CG   LEU A 469     -39.168  38.984  48.708  1.00 35.34      A
ATOM   3623  CD1  LEU A 469     -39.968  38.396  49.865  1.00 33.95      A
ATOM   3624  CD2  LEU A 469     -39.642  40.387  48.397  1.00 33.72      A
ATOM   3625  C    LEU A 469     -35.489  40.176  48.716  1.00 36.70      A
ATOM   3626  O    LEU A 469     -35.530  41.270  49.268  1.00 37.64      A
ATOM   3627  N    SER A 470     -34.388  39.435  48.700  1.00 35.94      A
ATOM   3628  CA   SER A 470     -33.184  39.903  49.381  1.00 35.03      A
ATOM   3629  CB   SER A 470     -32.035  38.906  49.200  1.00 35.22      A
ATOM   3630  OG   SER A 470     -31.625  38.842  47.845  1.00 36.88      A
ATOM   3631  C    SER A 470     -32.734  41.276  48.897  1.00 34.28      A
ATOM   3632  O    SER A 470     -31.973  41.956  49.583  1.00 34.57      A
ATOM   3633  N    ALA A 471     -33.204  41.687  47.722  1.00 33.36      A
ATOM   3634  CA   ALA A 471     -32.820  42.982  47.156  1.00 32.35      A
ATOM   3635  CB   ALA A 471     -33.233  43.060  45.701  1.00 30.59      A
ATOM   3636  C    ALA A 471     -33.400  44.165  47.916  1.00 32.09      A
ATOM   3637  O    ALA A 471     -32.998  45.307  47.697  1.00 34.50      A
ATOM   3638  N    PHE A 472     -34.351  43.893  48.801  1.00 31.50      A
ATOM   3639  CA   PHE A 472     -34.981  44.943  49.593  1.00 30.44      A
ATOM   3640  CB   PHE A 472     -36.500  44.803  49.545  1.00 30.10      A
ATOM   3641  CG   PHE A 472     -37.054  44.774  48.164  1.00 29.46      A
ATOM   3642  CD1  PHE A 472     -36.832  45.832  47.290  1.00 29.23      A
ATOM   3643  CD2  PHE A 472     -37.780  43.678  47.726  1.00 29.44      A
ATOM   3644  CE1  PHE A 472     -37.322  45.797  45.993  1.00 29.22      A
ATOM   3645  CE2  PHE A 472     -38.275  43.631  46.432  1.00 30.05      A
ATOM   3646  CZ   PHE A 472     -38.044  44.694  45.563  1.00 29.96      A
```

FIGURE 4- 49 -

```
ATOM   3647  C    PHE A 472     -34.522  44.879  51.042  1.00 30.24           A
ATOM   3648  C    PHE A 472     -34.852  45.750  51.846  1.00 30.03           A
ATOM   3649  N    THR A 473     -33.756  43.848  51.372  1.00 29.66           A
ATOM   3650  CA   THR A 473     -33.278  43.691  52.730  1.00 29.02           A
ATOM   3651  CB   THR A 473     -33.968  42.488  53.406  1.00 30.71           A
ATOM   3652  CG1  THR A 473     -33.638  41.278  52.708  1.00 33.01           A
ATOM   3653  CG2  THR A 473     -35.476  42.678  53.370  1.00 31.83           A
ATOM   3654  C    THR A 473     -31.770  43.538  52.824  1.00 27.18           A
ATOM   3655  C    THR A 473     -31.232  43.404  53.919  1.00 29.03           A
ATOM   3656  N    LEU A 474     -31.081  43.559  51.690  1.00 25.89           A
ATOM   3657  CA   LEU A 474     -29.626  43.427  51.718  1.00 25.42           A
ATOM   3658  CB   LEU A 474     -29.032  43.632  50.325  1.00 23.56           A
ATOM   3659  CG   LEU A 474     -28.153  42.499  49.773  1.00 24.56           A
ATOM   3660  CD1  LEU A 474     -28.862  41.145  49.849  1.00 22.16           A
ATOM   3661  CD2  LEU A 474     -27.794  42.826  48.338  1.00 23.44           A
ATOM   3662  C    LEU A 474     -29.095  44.479  52.681  1.00 25.60           A
ATOM   3663  C    LEU A 474     -29.642  45.584  52.782  1.00 26.18           A
ATOM   3664  N    HIS A 475     -28.045  44.131  53.407  1.00 25.05           A
ATOM   3665  CA   HIS A 475     -27.483  45.046  54.383  1.00 25.42           A
ATOM   3666  CB   HIS A 475     -28.423  45.160  55.590  1.00 25.81           A
ATOM   3667  CG   HIS A 475     -28.285  44.035  56.574  1.00 29.73           A
ATOM   3668  CD2  HIS A 475     -28.919  42.840  56.659  1.00 30.90           A
ATOM   3669  ND1  HIS A 475     -27.366  44.052  57.603  1.00 30.76           A
ATOM   3670  CE1  HIS A 475     -27.439  42.917  58.277  1.00 30.62           A
ATOM   3671  NE2  HIS A 475     -28.373  42.163  57.725  1.00 30.89           A
ATOM   3672  C    HIS A 475     -26.133  44.532  54.848  1.00 24.81           A
ATOM   3673  C    HIS A 475     -25.762  43.392  54.584  1.00 22.42           A
ATOM   3674  N    SER A 476     -25.405  45.378  55.560  1.00 26.11           A
ATOM   3675  CA   SER A 476     -24.107  44.985  56.063  1.00 27.14           A
ATOM   3676  CB   SER A 476     -24.276  43.763  56.976  1.00 27.08           A
ATOM   3677  CG   SER A 476     -23.057  43.393  57.588  1.00 29.41           A
ATOM   3678  C    SER A 476     -23.226  44.656  54.857  1.00 26.90           A
ATOM   3679  C    SER A 476     -22.838  43.505  54.647  1.00 28.43           A
ATOM   3680  N    TYR A 477     -22.924  45.673  54.055  1.00 26.68           A
ATOM   3681  CA   TYR A 477     -22.095  45.476  52.868  1.00 26.03           A
ATOM   3682  CB   TYR A 477     -22.326  46.596  51.844  1.00 23.27           A
ATOM   3683  CG   TYR A 477     -23.711  46.619  51.231  1.00 21.40           A
ATOM   3684  CD1  TYR A 477     -24.815  47.056  51.960  1.00 20.18           A
ATOM   3685  CE1  TYR A 477     -26.092  47.109  51.386  1.00 19.32           A
ATOM   3686  CD2  TYR A 477     -23.914  46.227  49.910  1.00 22.61           A
ATOM   3687  CE2  TYR A 477     -25.196  46.273  49.321  1.00 21.36           A
ATOM   3688  CZ   TYR A 477     -26.277  46.718  50.067  1.00 20.88           A
ATOM   3689  OH   TYR A 477     -27.534  46.784  49.494  1.00 20.58           A
ATOM   3690  C    TYR A 477     -20.622  45.410  53.243  1.00 25.07           A
ATOM   3691  C    TYR A 477     -20.220  45.914  54.275  1.00 25.09           A
ATOM   3692  N    SER A 478     -19.822  44.770  52.404  1.00 26.55           A
ATOM   3693  CA   SER A 478     -18.401  44.639  52.679  1.00 28.25           A
ATOM   3694  CB   SER A 478     -17.745  43.764  51.614  1.00 27.96           A
ATOM   3695  CG   SER A 478     -17.849  44.378  50.345  1.00 27.65           A
ATOM   3696  C    SER A 478     -17.740  46.011  52.704  1.00 29.70           A
ATOM   3697  C    SER A 478     -18.136  46.916  51.972  1.00 30.93           A
ATOM   3698  N    PRO A 479     -16.709  46.180  53.543  1.00 30.71           A
ATOM   3699  CD   PRO A 479     -16.045  45.148  54.357  1.00 31.67           A
ATOM   3700  CA   PRO A 479     -16.004  47.462  53.647  1.00 30.65           A
ATOM   3701  CB   PRO A 479     -14.864  47.157  54.621  1.00 30.46           A
ATOM   3702  CG   PRO A 479     -15.371  45.982  55.413  1.00 31.31           A
ATOM   3703  C    PRO A 479     -15.481  47.934  52.288  1.00 31.00           A
ATOM   3704  C    PRO A 479     -15.644  49.099  51.916  1.00 32.12           A
ATOM   3705  N    GLY A 480     -14.846  47.024  51.556  1.00 30.58           A
ATOM   3706  CA   GLY A 480     -14.312  47.375  50.255  1.00 29.83           A
ATOM   3707  C    GLY A 480     -15.355  48.056  49.395  1.00 30.54           A
ATOM   3708  C    GLY A 480     -15.095  49.099  48.787  1.00 30.73           A
ATOM   3709  N    GLU A 481     -16.547  47.472  49.355  1.00 29.63           A
ATOM   3710  CA   GLU A 481     -17.631  48.023  48.557  1.00 27.74           A
ATOM   3711  CB   GLU A 481     -18.791  47.020  48.515  1.00 25.47           A
ATOM   3712  CG   GLU A 481     -20.050  47.495  47.803  1.00 22.71           A
ATOM   3713  CD   GLU A 481     -19.800  47.949  46.389  1.00 20.73           A
ATOM   3714  CE1  GLU A 481     -18.671  47.762  45.893  1.00 19.76           A
ATOM   3715  CE2  GLU A 481     -20.740  48.489  45.771  1.00 17.94           A
ATOM   3716  C    GLU A 481     -18.080  49.372  49.111  1.00 27.83           A
ATOM   3717  C    GLU A 481     -18.396  50.277  48.353  1.00 27.48           A
ATOM   3718  N    ILE A 482     -18.093  49.512  50.432  1.00 29.33           A
ATOM   3719  CA   ILE A 482     -18.500  50.775  51.052  1.00 31.26           A
ATOM   3720  CB   ILE A 482     -18.624  50.663  52.598  1.00 31.31           A
ATOM   3721  CG2  ILE A 482     -18.956  52.035  53.190  1.00 30.26           A
ATOM   3722  CG1  ILE A 482     -19.714  49.653  52.976  1.00 30.75           A
```

FIGURE 4- 50 -

```
ATOM   3723  CD1 ILE A 482     -19.927  49.524  54.482  1.00 26.95        A
ATOM   3724  C   ILE A 482     -17.494  51.889  50.759  1.00 31.55        A
ATOM   3725  O   ILE A 482     -17.874  53.006  50.399  1.00 31.70        A
ATOM   3726  N   ASN A 483     -16.214  51.580  50.921  1.00 30.76        A
ATOM   3727  CA  ASN A 483     -15.162  52.560  50.685  1.00 31.41        A
ATOM   3728  CB  ASN A 483     -13.798  51.961  51.041  1.00 35.88        A
ATOM   3729  CG  ASN A 483     -13.645  51.702  52.539  1.00 38.90        A
ATOM   3730  OD1 ASN A 483     -14.478  51.034  53.168  1.00 39.61        A
ATOM   3731  ND2 ASN A 483     -12.573  52.234  53.116  1.00 41.79        A
ATOM   3732  C   ASN A 483     -15.150  53.069  49.256  1.00 28.38        A
ATOM   3733  O   ASN A 483     -15.050  54.265  49.019  1.00 28.34        A
ATOM   3734  N   ARG A 484     -15.256  52.158  48.300  1.00 27.54        A
ATOM   3735  CA  ARG A 484     -15.259  52.555  46.901  1.00 25.67        A
ATOM   3736  CB  ARG A 484     -15.427  51.342  45.980  1.00 23.88        A
ATOM   3737  CG  ARG A 484     -15.506  51.715  44.499  1.00 23.06        A
ATOM   3738  CD  ARG A 484     -15.235  50.522  43.585  1.00 22.61        A
ATOM   3739  NE  ARG A 484     -16.353  49.589  43.521  1.00 23.04        A
ATOM   3740  CZ  ARG A 484     -16.306  48.428  42.883  1.00 22.64        A
ATOM   3741  NH1 ARG A 484     -15.197  48.071  42.266  1.00 23.09        A
ATOM   3742  NH2 ARG A 484     -17.361  47.626  42.859  1.00 23.47        A
ATOM   3743  C   ARG A 484     -16.397  53.519  46.684  1.00 25.06        A
ATOM   3744  O   ARG A 484     -16.248  54.533  46.008  1.00 25.65        A
ATOM   3745  N   VAL A 485     -17.540  53.206  47.276  1.00 23.95        A
ATOM   3746  CA  VAL A 485     -18.702  54.061  47.125  1.00 23.12        A
ATOM   3747  CB  VAL A 485     -19.952  53.373  47.692  1.00 20.83        A
ATOM   3748  CG1 VAL A 485     -21.096  54.370  47.841  1.00 20.72        A
ATOM   3749  CG2 VAL A 485     -20.360  52.275  46.754  1.00 19.42        A
ATOM   3750  C   VAL A 485     -18.539  55.445  47.746  1.00 22.45        A
ATOM   3751  O   VAL A 485     -18.797  56.451  47.087  1.00 22.16        A
ATOM   3752  N   ALA A 486     -18.110  55.493  49.004  1.00 22.36        A
ATOM   3753  CA  ALA A 486     -17.933  56.763  49.704  1.00 21.94        A
ATOM   3754  CB  ALA A 486     -17.549  56.514  51.152  1.00 18.39        A
ATOM   3755  C   ALA A 486     -16.859  57.582  49.013  1.00 22.52        A
ATOM   3756  O   ALA A 486     -16.998  58.796  48.835  1.00 21.92        A
ATOM   3757  N   SER A 487     -15.783  56.905  48.632  1.00 22.85        A
ATOM   3758  CA  SER A 487     -14.683  57.554  47.948  1.00 24.36        A
ATOM   3759  CB  SER A 487     -13.653  56.494  47.558  1.00 25.34        A
ATOM   3760  OG  SER A 487     -12.540  57.065  46.904  1.00 30.22        A
ATOM   3761  C   SER A 487     -15.272  58.237  46.703  1.00 25.45        A
ATOM   3762  O   SER A 487     -15.149  59.453  46.508  1.00 24.72        A
ATOM   3763  N   CYS A 488     -15.941  57.439  45.881  1.00 24.37        A
ATOM   3764  CA  CYS A 488     -16.565  57.931  44.678  1.00 24.34        A
ATOM   3765  CB  CYS A 488     -17.441  56.836  44.091  1.00 24.77        A
ATOM   3766  SG  CYS A 488     -18.360  57.331  42.625  1.00 32.18        A
ATOM   3767  C   CYS A 488     -17.404  59.190  44.923  1.00 25.63        A
ATOM   3768  O   CYS A 488     -17.297  60.176  44.183  1.00 26.67        A
ATOM   3769  N   LEU A 489     -18.234  59.160  45.963  1.00 25.01        A
ATOM   3770  CA  LEU A 489     -19.099  60.292  46.279  1.00 24.22        A
ATOM   3771  CB  LEU A 489     -20.001  59.949  47.467  1.00 22.92        A
ATOM   3772  CG  LEU A 489     -20.909  58.734  47.256  1.00 24.37        A
ATOM   3773  CD1 LEU A 489     -21.954  58.692  48.364  1.00 23.91        A
ATOM   3774  CD2 LEU A 489     -21.600  58.305  45.888  1.00 22.93        A
ATOM   3775  C   LEU A 489     -18.321  61.575  46.550  1.00 25.06        A
ATOM   3776  O   LEU A 489     -18.654  62.632  46.016  1.00 23.97        A
ATOM   3777  N   ARG A 490     -17.282  61.480  47.376  1.00 25.94        A
ATOM   3778  CA  ARG A 490     -16.459  62.638  47.689  1.00 26.04        A
ATOM   3779  CB  ARG A 490     -15.306  62.247  48.608  1.00 26.57        A
ATOM   3780  CG  ARG A 490     -15.709  61.351  50.009  1.00 28.76        A
ATOM   3781  CD  ARG A 490     -14.470  61.671  50.879  1.00 31.46        A
ATOM   3782  NE  ARG A 490     -13.895  60.325  50.826  1.00 34.61        A
ATOM   3783  CZ  ARG A 490     -14.326  59.300  51.561  1.00 36.24        A
ATOM   3784  NH1 ARG A 490     -15.340  59.468  52.406  1.00 37.11        A
ATOM   3785  NH2 ARG A 490     -13.740  58.109  51.461  1.00 35.52        A
ATOM   3786  C   ARG A 490     -15.887  63.186  46.391  1.00 26.17        A
ATOM   3787  O   ARG A 490     -15.893  64.390  46.156  1.00 27.43        A
ATOM   3788  N   LYS A 491     -15.395  62.285  45.547  1.00 25.62        A
ATOM   3789  CA  LYS A 491     -14.813  62.664  44.268  1.00 23.49        A
ATOM   3790  CB  LYS A 491     -14.360  61.414  43.504  1.00 23.27        A
ATOM   3791  CG  LYS A 491     -13.789  61.715  42.127  1.00 25.50        A
ATOM   3792  CD  LYS A 491     -13.307  60.465  41.424  1.00 27.41        A
ATOM   3793  CE  LYS A 491     -14.451  59.515  41.100  1.00 30.74        A
ATOM   3794  NZ  LYS A 491     -13.975  58.279  40.402  1.00 33.48        A
ATOM   3795  C   LYS A 491     -15.782  63.478  43.413  1.00 22.36        A
ATOM   3796  O   LYS A 491     -15.481  64.607  43.038  1.00 23.25        A
ATOM   3797  N   LEU A 492     -16.944  62.910  43.111  1.00 20.85        A
ATOM   3798  CA  LEU A 492     -17.940  63.589  42.283  1.00 20.14        A
```

FIGURE 4- 51 -

```
ATOM   3799  CB   LEU A 492     -19.069  62.615  41.898  1.00  20.53      A
ATOM   3800  CG   LEU A 492     -19.030  61.724  40.651  1.00  19.26      A
ATOM   3801  CD1  LEU A 492     -17.682  61.759  39.967  1.00  18.53      A
ATOM   3802  CD2  LEU A 492     -19.392  60.323  41.069  1.00  18.42      A
ATOM   3803  C    LEU A 492     -18.563  64.822  42.933  1.00  19.51      A
ATOM   3804  O    LEU A 492     -19.013  65.736  42.234  1.00  18.71      A
ATOM   3805  N    GLY A 493     -18.605  64.854  44.262  1.00  19.33      A
ATOM   3806  CA   GLY A 493     -19.225  65.987  44.937  1.00  20.45      A
ATOM   3807  C    GLY A 493     -20.689  65.679  45.222  1.00  20.76      A
ATOM   3808  O    GLY A 493     -21.563  66.546  45.161  1.00  20.31      A
ATOM   3809  N    VAL A 494     -20.948  64.413  45.521  1.00  21.56      A
ATOM   3810  CA   VAL A 494     -22.287  63.921  45.816  1.00  22.34      A
ATOM   3811  CB   VAL A 494     -22.473  62.512  45.185  1.00  23.71      A
ATOM   3812  CG1  VAL A 494     -23.821  61.910  45.582  1.00  24.89      A
ATOM   3813  CG2  VAL A 494     -22.343  62.609  43.666  1.00  22.05      A
ATOM   3814  C    VAL A 494     -22.439  63.838  47.337  1.00  23.54      A
ATOM   3815  O    VAL A 494     -21.549  63.340  48.031  1.00  24.43      A
ATOM   3816  N    PRO A 495     -23.562  64.333  47.879  1.00  23.40      A
ATOM   3817  CD   PRO A 495     -24.711  64.959  47.198  1.00  24.85      A
ATOM   3818  CA   PRO A 495     -23.766  64.282  49.334  1.00  22.80      A
ATOM   3819  CB   PRO A 495     -25.230  64.683  49.490  1.00  23.01      A
ATOM   3820  CG   PRO A 495     -25.436  65.648  48.339  1.00  23.82      A
ATOM   3821  C    PRO A 495     -23.468  62.901  49.935  1.00  22.55      A
ATOM   3822  O    PRO A 495     -23.687  61.866  49.304  1.00  20.78      A
ATOM   3823  N    PRO A 496     -22.960  62.870  51.172  1.00  22.25      A
ATOM   3824  CD   PRO A 496     -22.709  63.986  52.098  1.00  22.02      A
ATOM   3825  CA   PRO A 496     -22.649  61.589  51.808  1.00  21.81      A
ATOM   3826  CB   PRO A 496     -21.974  62.014  53.113  1.00  22.08      A
ATOM   3827  CG   PRO A 496     -22.670  63.281  53.444  1.00  21.92      A
ATOM   3828  C    PRO A 496     -23.886  60.728  52.031  1.00  21.45      A
ATOM   3829  O    PRO A 496     -25.009  61.243  52.106  1.00  22.50      A
ATOM   3830  N    LEU A 497     -23.671  59.419  52.140  1.00  20.79      A
ATOM   3831  CA   LEU A 497     -24.757  58.469  52.350  1.00  18.34      A
ATOM   3832  CB   LEU A 497     -24.188  57.078  52.617  1.00  16.88      A
ATOM   3833  CG   LEU A 497     -23.543  56.395  51.402  1.00  19.18      A
ATOM   3834  CD1  LEU A 497     -23.012  55.027  51.803  1.00  14.11      A
ATOM   3835  CD2  LEU A 497     -24.566  56.269  50.256  1.00  16.97      A
ATOM   3836  C    LEU A 497     -25.729  58.858  53.456  1.00  17.83      A
ATOM   3837  O    LEU A 497     -26.925  58.610  53.333  1.00  18.37      A
ATOM   3838  N    ARG A 498     -25.240  59.464  54.533  1.00  18.31      A
ATOM   3839  CA   ARG A 498     -26.155  59.868  55.597  1.00  20.47      A
ATOM   3840  CB   ARG A 498     -25.402  60.474  56.795  1.00  19.81      A
ATOM   3841  CG   ARG A 498     -24.557  61.696  56.490  1.00  21.79      A
ATOM   3842  CD   ARG A 498     -23.735  62.122  57.706  1.00  20.54      A
ATOM   3843  NE   ARG A 498     -22.672  63.042  57.325  1.00  22.15      A
ATOM   3844  CZ   ARG A 498     -22.872  64.298  56.927  1.00  25.53      A
ATOM   3845  NH1  ARG A 498     -24.104  64.797  56.869  1.00  26.24      A
ATOM   3846  NH2  ARG A 498     -21.841  65.051  56.553  1.00  24.15      A
ATOM   3847  C    ARG A 498     -27.194  60.858  55.060  1.00  21.97      A
ATOM   3848  O    ARG A 498     -28.352  60.827  55.476  1.00  23.51      A
ATOM   3849  N    THR A 499     -26.801  61.721  54.127  1.00  21.19      A
ATOM   3850  CA   THR A 499     -27.761  62.660  53.583  1.00  21.42      A
ATOM   3851  CB   THR A 499     -27.083  63.717  52.675  1.00  22.36      A
ATOM   3852  OG1  THR A 499     -26.299  64.605  53.476  1.00  21.88      A
ATOM   3853  CG2  THR A 499     -28.147  64.548  51.932  1.00  22.80      A
ATOM   3854  C    THR A 499     -28.814  61.891  52.790  1.00  22.70      A
ATOM   3855  O    THR A 499     -30.002  62.229  52.828  1.00  22.17      A
ATOM   3856  N    TRP A 500     -28.389  60.848  52.081  1.00  23.24      A
ATOM   3857  CA   TRP A 500     -29.336  60.059  51.302  1.00  23.93      A
ATOM   3858  CB   TRP A 500     -28.597  59.100  50.373  1.00  22.55      A
ATOM   3859  CG   TRP A 500     -27.851  59.812  49.299  1.00  23.04      A
ATOM   3860  CD2  TRP A 500     -28.414  60.528  48.189  1.00  23.75      A
ATOM   3861  CE2  TRP A 500     -27.341  61.111  47.482  1.00  23.40      A
ATOM   3862  CE3  TRP A 500     -29.718  60.734  47.727  1.00  22.26      A
ATOM   3863  CD1  TRP A 500     -26.508  59.978  49.217  1.00  23.06      A
ATOM   3864  NE1  TRP A 500     -26.190  60.759  48.130  1.00  24.06      A
ATOM   3865  CZ2  TRP A 500     -27.529  61.888  46.339  1.00  23.00      A
ATOM   3866  CZ3  TRP A 500     -29.904  61.503  46.593  1.00  23.06      A
ATOM   3867  CH2  TRP A 500     -28.815  62.073  45.911  1.00  23.15      A
ATOM   3868  C    TRP A 500     -30.316  59.290  52.187  1.00  24.66      A
ATOM   3869  O    TRP A 500     -31.464  59.070  51.806  1.00  25.04      A
ATOM   3870  N    ARG A 501     -29.864  58.882  53.366  1.00  25.13      A
ATOM   3871  CA   ARG A 501     -30.729  58.163  54.291  1.00  26.91      A
ATOM   3872  CB   ARG A 501     -29.921  57.758  55.530  1.00  27.96      A
ATOM   3873  CG   ARG A 501     -30.639  56.902  56.566  1.00  28.00      A
ATOM   3874  CD   ARG A 501     -29.612  56.350  57.553  1.00  32.18      A
```

FIGURE 4- 52 -

```
ATOM   3875  NE   ARG A 501     -28.816  57.416  58.180  1.00 38.15           A
ATOM   3876  CZ   ARG A 501     -27.484  57.408  58.307  1.00 39.14           A
ATOM   3877  NH1  ARG A 501     -26.761  56.391  57.852  1.00 39.70           A
ATOM   3878  NH2  ARG A 501     -26.862  58.427  58.884  1.00 40.01           A
ATOM   3879  C    ARG A 501     -31.848  59.132  54.664  1.00 27.32           A
ATOM   3880  O    ARG A 501     -33.032  58.824  54.533  1.00 25.53           A
ATOM   3881  N    HIS A 502     -31.451  60.319  55.110  1.00 28.30           A
ATOM   3882  CA   HIS A 502     -32.398  61.347  55.503  1.00 29.48           A
ATOM   3883  CB   HIS A 502     -31.670  62.654  55.833  1.00 33.16           A
ATOM   3884  CG   HIS A 502     -30.661  62.534  56.933  1.00 36.18           A
ATOM   3885  CD2  HIS A 502     -30.404  61.530  57.808  1.00 37.97           A
ATOM   3886  ND1  HIS A 502     -29.770  63.543  57.233  1.00 36.37           A
ATOM   3887  CE1  HIS A 502     -29.006  63.165  58.245  1.00 39.57           A
ATOM   3888  NE2  HIS A 502     -29.371  61.948  58.614  1.00 38.49           A
ATOM   3889  C    HIS A 502     -33.372  61.601  54.364  1.00 29.29           A
ATOM   3890  O    HIS A 502     -34.582  61.594  54.562  1.00 30.96           A
ATOM   3891  N    ARG A 503     -32.840  61.830  53.168  1.00 28.38           A
ATOM   3892  CA   ARG A 503     -33.676  62.101  52.011  1.00 27.01           A
ATOM   3893  CB   ARG A 503     -32.805  62.376  50.790  1.00 26.10           A
ATOM   3894  CG   ARG A 503     -32.163  63.751  50.768  1.00 26.68           A
ATOM   3895  CD   ARG A 503     -31.189  63.851  49.617  1.00 28.31           A
ATOM   3896  NE   ARG A 503     -30.596  65.172  49.456  1.00 26.56           A
ATOM   3897  CZ   ARG A 503     -29.624  65.431  48.585  1.00 27.86           A
ATOM   3898  NH1  ARG A 503     -29.152  64.451  47.818  1.00 27.33           A
ATOM   3899  NH2  ARG A 503     -29.129  66.657  48.465  1.00 25.91           A
ATOM   3900  C    ARG A 503     -34.628  60.959  51.704  1.00 27.57           A
ATOM   3901  O    ARG A 503     -35.794  61.185  51.385  1.00 26.56           A
ATOM   3902  N    ALA A 504     -34.123  59.732  51.792  1.00 28.30           A
ATOM   3903  CA   ALA A 504     -34.930  58.552  51.512  1.00 28.79           A
ATOM   3904  CB   ALA A 504     -34.079  57.313  51.601  1.00 28.43           A
ATOM   3905  C    ALA A 504     -36.084  58.459  52.493  1.00 30.66           A
ATOM   3906  O    ALA A 504     -37.181  58.015  52.135  1.00 28.67           A
ATOM   3907  N    ARG A 505     -35.832  58.864  53.737  1.00 32.47           A
ATOM   3908  CA   ARG A 505     -36.874  58.838  54.747  1.00 33.57           A
ATOM   3909  CB   ARG A 505     -36.346  59.366  56.078  1.00 35.42           A
ATOM   3910  CG   ARG A 505     -35.686  58.306  56.946  1.00 40.73           A
ATOM   3911  CD   ARG A 505     -35.321  58.857  58.318  1.00 43.69           A
ATOM   3912  NE   ARG A 505     -35.233  57.808  59.335  1.00 47.25           A
ATOM   3913  CZ   ARG A 505     -36.284  57.190  59.872  1.00 47.98           A
ATOM   3914  NH1  ARG A 505     -37.513  57.516  59.488  1.00 47.32           A
ATOM   3915  NH2  ARG A 505     -36.104  56.247  60.795  1.00 48.28           A
ATOM   3916  C    ARG A 505     -38.046  59.692  54.274  1.00 33.81           A
ATOM   3917  O    ARG A 505     -39.202  59.252  54.293  1.00 33.85           A
ATOM   3918  N    SER A 506     -37.747  60.907  53.830  1.00 32.38           A
ATOM   3919  CA   SER A 506     -38.793  61.798  53.364  1.00 32.83           A
ATOM   3920  CB   SER A 506     -38.206  63.163  53.027  1.00 32.98           A
ATOM   3921  OG   SER A 506     -39.201  64.011  52.485  1.00 33.53           A
ATOM   3922  C    SER A 506     -39.534  61.229  52.153  1.00 33.88           A
ATOM   3923  O    SER A 506     -40.758  61.066  52.188  1.00 33.83           A
ATOM   3924  N    VAL A 507     -38.798  60.925  51.085  1.00 33.85           A
ATOM   3925  CA   VAL A 507     -39.407  60.373  49.877  1.00 33.04           A
ATOM   3926  CB   VAL A 507     -38.349  59.944  48.854  1.00 30.86           A
ATOM   3927  CG1  VAL A 507     -39.011  59.306  47.682  1.00 30.04           A
ATOM   3928  CG2  VAL A 507     -37.564  61.144  48.390  1.00 34.26           A
ATOM   3929  C    VAL A 507     -40.291  59.169  50.191  1.00 33.56           A
ATOM   3930  O    VAL A 507     -41.352  59.012  49.598  1.00 34.92           A
ATOM   3931  N    ARG A 508     -39.857  58.325  51.122  1.00 34.29           A
ATOM   3932  CA   ARG A 508     -40.632  57.147  51.498  1.00 35.43           A
ATOM   3933  CB   ARG A 508     -39.860  56.294  52.512  1.00 35.04           A
ATOM   3934  CG   ARG A 508     -40.648  55.116  53.058  1.00 33.84           A
ATOM   3935  CD   ARG A 508     -39.877  54.413  54.161  1.00 36.74           A
ATOM   3936  NE   ARG A 508     -40.769  53.800  55.143  1.00 40.77           A
ATOM   3937  CZ   ARG A 508     -41.112  52.516  55.164  1.00 41.43           A
ATOM   3938  NH1  ARG A 508     -40.636  51.666  54.259  1.00 42.15           A
ATOM   3939  NH2  ARG A 508     -41.951  52.088  56.089  1.00 40.30           A
ATOM   3940  C    ARG A 508     -41.976  57.562  52.094  1.00 35.46           A
ATOM   3941  O    ARG A 508     -43.035  57.143  51.624  1.00 35.30           A
ATOM   3942  N    ALA A 509     -41.919  58.387  53.133  1.00 35.84           A
ATOM   3943  CA   ALA A 509     -43.117  58.865  53.798  1.00 35.15           A
ATOM   3944  CB   ALA A 509     -42.773  60.025  54.704  1.00 34.68           A
ATOM   3945  C    ALA A 509     -44.137  59.294  52.760  1.00 35.79           A
ATOM   3946  O    ALA A 509     -45.273  58.837  52.790  1.00 35.95           A
ATOM   3947  N    LYS A 510     -43.730  60.161  51.834  1.00 36.70           A
ATOM   3948  CA   LYS A 510     -44.634  60.632  50.785  1.00 37.71           A
ATOM   3949  CB   LYS A 510     -43.923  61.595  49.829  1.00 37.23           A
ATOM   3950  CG   LYS A 510     -43.292  62.811  50.468  1.00 37.36           A
```

FIGURE 4- 53 -

```
ATOM   3951  CD   LYS A 510     -42.951  63.844  49.390  1.00 38.11      A
ATOM   3952  CE   LYS A 510     -42.225  65.058  49.950  1.00 38.17      A
ATOM   3953  NZ   LYS A 510     -40.839  64.709  50.375  1.00 38.06      A
ATOM   3954  C    LYS A 510     -45.194  59.466  49.968  1.00 39.03      A
ATOM   3955  O    LYS A 510     -46.406  59.358  49.787  1.00 39.45      A
ATOM   3956  N    LEU A 511     -44.319  58.598  49.466  1.00 39.00      A
ATOM   3957  CA   LEU A 511     -44.777  57.463  48.676  1.00 40.11      A
ATOM   3958  CB   LEU A 511     -43.618  56.509  48.392  1.00 38.88      A
ATOM   3959  CG   LEU A 511     -42.544  57.104  47.477  1.00 38.93      A
ATOM   3960  CD1  LEU A 511     -41.399  56.105  47.317  1.00 37.08      A
ATOM   3961  CD2  LEU A 511     -43.158  57.462  46.125  1.00 37.96      A
ATOM   3962  C    LEU A 511     -45.921  56.715  49.363  1.00 40.79      A
ATOM   3963  O    LEU A 511     -47.007  56.583  48.800  1.00 40.58      A
ATOM   3964  N    LEU A 512     -45.678  56.234  50.578  1.00 41.45      A
ATOM   3965  CA   LEU A 512     -46.699  55.518  51.334  1.00 42.29      A
ATOM   3966  CB   LEU A 512     -46.186  55.225  52.743  1.00 40.36      A
ATOM   3967  CG   LEU A 512     -44.981  54.277  52.799  1.00 41.16      A
ATOM   3968  CD1  LEU A 512     -44.248  54.403  54.128  1.00 40.43      A
ATOM   3969  CD2  LEU A 512     -45.457  52.852  52.580  1.00 40.60      A
ATOM   3970  C    LEU A 512     -48.001  56.327  51.411  1.00 44.59      A
ATOM   3971  O    LEU A 512     -49.095  55.787  51.216  1.00 45.07      A
ATOM   3972  N    SER A 513     -47.878  57.626  51.685  1.00 45.48      A
ATOM   3973  CA   SER A 513     -49.041  58.509  51.797  1.00 45.33      A
ATOM   3974  CB   SER A 513     -48.604  59.975  51.869  1.00 46.89      A
ATOM   3975  OG   SER A 513     -47.847  60.236  53.040  1.00 50.88      A
ATOM   3976  C    SER A 513     -49.989  58.356  50.627  1.00 44.78      A
ATOM   3977  O    SER A 513     -51.202  58.481  50.784  1.00 45.34      A
ATOM   3978  N    GLN A 514     -49.423  58.087  49.455  1.00 43.48      A
ATOM   3979  CA   GLN A 514     -50.198  57.939  48.235  1.00 42.15      A
ATOM   3980  CB   GLN A 514     -49.301  58.201  47.030  1.00 40.21      A
ATOM   3981  CG   GLN A 514     -48.857  59.639  46.937  1.00 41.21      A
ATOM   3982  CD   GLN A 514     -48.334  59.995  45.567  1.00 41.61      A
ATOM   3983  OE1  GLN A 514     -48.636  59.325  44.580  1.00 42.99      A
ATOM   3984  NE2  GLN A 514     -47.564  61.067  45.493  1.00 41.91      A
ATOM   3985  C    GLN A 514     -50.913  56.609  48.050  1.00 42.61      A
ATOM   3986  O    GLN A 514     -51.807  56.501  47.207  1.00 41.96      A
ATOM   3987  N    GLY A 515     -50.533  55.602  48.830  1.00 42.95      A
ATOM   3988  CA   GLY A 515     -51.157  54.299  48.685  1.00 44.38      A
ATOM   3989  C    GLY A 515     -50.879  53.710  47.311  1.00 45.63      A
ATOM   3990  O    GLY A 515     -50.139  54.287  46.515  1.00 46.61      A
ATOM   3991  N    GLY A 516     -51.458  52.548  47.029  1.00 46.70      A
ATOM   3992  CA   GLY A 516     -51.258  51.916  45.736  1.00 46.59      A
ATOM   3993  C    GLY A 516     -49.835  51.489  45.418  1.00 46.92      A
ATOM   3994  O    GLY A 516     -49.018  51.260  46.315  1.00 46.80      A
ATOM   3995  N    ARG A 517     -49.544  51.392  44.121  1.00 46.70      A
ATOM   3996  CA   ARG A 517     -48.232  50.973  43.630  1.00 46.11      A
ATOM   3997  CB   ARG A 517     -48.162  51.136  42.107  1.00 45.46      A
ATOM   3998  CG   ARG A 517     -49.211  50.326  41.355  1.00 44.66      A
ATOM   3999  CD   ARG A 517     -48.729  49.918  39.966  1.00 44.39      A
ATOM   4000  NE   ARG A 517     -48.661  51.018  39.008  1.00 42.68      A
ATOM   4001  CZ   ARG A 517     -48.195  50.882  37.769  1.00 43.84      A
ATOM   4002  NH1  ARG A 517     -47.762  49.696  37.364  1.00 44.27      A
ATOM   4003  NH2  ARG A 517     -48.159  51.918  36.936  1.00 42.84      A
ATOM   4004  C    ARG A 517     -47.084  51.737  44.281  1.00 46.17      A
ATOM   4005  O    ARG A 517     -46.012  51.174  44.543  1.00 45.05      A
ATOM   4006  N    ALA A 518     -47.320  53.023  44.527  1.00 46.14      A
ATOM   4007  CA   ALA A 518     -46.335  53.889  45.148  1.00 45.23      A
ATOM   4008  CB   ALA A 518     -46.811  55.330  45.397  1.00 44.45      A
ATOM   4009  C    ALA A 518     -46.109  53.458  46.593  1.00 45.13      A
ATOM   4010  O    ALA A 518     -44.969  53.282  47.027  1.00 45.58      A
ATOM   4011  N    ALA A 519     -47.197  53.281  47.334  1.00 44.58      A
ATOM   4012  CA   ALA A 519     -47.101  52.870  48.731  1.00 44.96      A
ATOM   4013  CB   ALA A 519     -48.497  52.574  49.291  1.00 44.83      A
ATOM   4014  C    ALA A 519     -46.211  51.631  48.848  1.00 44.60      A
ATOM   4015  O    ALA A 519     -45.595  51.381  49.890  1.00 45.11      A
ATOM   4016  N    THR A 520     -46.151  50.860  47.785  1.00 43.08      A
ATOM   4017  CA   THR A 520     -45.348  49.646  47.725  1.00 41.22      A
ATOM   4018  CB   THR A 520     -45.795  48.741  46.571  1.00 42.62      A
ATOM   4019  OG1  THR A 520     -47.214  48.857  46.411  1.00 43.27      A
ATOM   4020  CG2  THR A 520     -45.436  47.275  46.854  1.00 41.75      A
ATOM   4021  C    THR A 520     -43.890  50.034  47.513  1.00 40.61      A
ATOM   4022  O    THR A 520     -42.997  49.548  48.213  1.00 40.23      A
ATOM   4023  N    CYS A 521     -43.665  50.912  46.534  1.00 38.71      A
ATOM   4024  CA   CYS A 521     -42.330  51.398  46.215  1.00 38.03      A
ATOM   4025  CB   CYS A 521     -42.406  52.567  45.234  1.00 34.45      A
ATOM   4026  SG   CYS A 521     -42.739  52.061  43.548  1.00 33.92      A
```

FIGURE 4- 54 -

```
ATOM   4027  C    CYS A 521     -41.660  51.859  47.490  1.00 36.02      A
ATOM   4028  O    CYS A 521     -40.484  51.586  47.726  1.00 36.89      A
ATOM   4029  N    GLY A 522     -42.422  52.557  48.319  1.00 34.64      A
ATOM   4030  CA   GLY A 522     -41.871  53.036  49.563  1.00 35.23      A
ATOM   4031  C    GLY A 522     -41.619  51.903  50.533  1.00 35.77      A
ATOM   4032  O    GLY A 522     -40.606  51.879  51.229  1.00 36.44      A
ATOM   4033  N    ARG A 523     -42.532  50.943  50.569  1.00 36.31      A
ATOM   4034  CA   ARG A 523     -42.405  49.831  51.496  1.00 37.33      A
ATOM   4035  CB   ARG A 523     -43.708  49.016  51.505  1.00 39.50      A
ATOM   4036  CG   ARG A 523     -43.942  48.215  52.787  1.00 44.11      A
ATOM   4037  CD   ARG A 523     -45.286  47.475  52.773  1.00 47.87      A
ATOM   4038  NE   ARG A 523     -46.419  48.343  52.419  1.00 52.16      A
ATOM   4039  CZ   ARG A 523     -46.938  49.298  53.195  1.00 53.48      A
ATOM   4040  NH1  ARG A 523     -46.436  49.538  54.402  1.00 54.31      A
ATOM   4041  NH2  ARG A 523     -47.976  50.013  52.763  1.00 52.51      A
ATOM   4042  C    ARG A 523     -41.210  48.935  51.183  1.00 36.32      A
ATOM   4043  O    ARG A 523     -40.420  48.611  52.074  1.00 35.20      A
ATOM   4044  N    TYR A 524     -41.067  48.558  49.915  1.00 35.72      A
ATOM   4045  CA   TYR A 524     -39.978  47.680  49.499  1.00 36.02      A
ATOM   4046  CB   TYR A 524     -40.431  46.777  48.349  1.00 37.52      A
ATOM   4047  CG   TYR A 524     -41.513  45.796  48.726  1.00 38.77      A
ATOM   4048  CD1  TYR A 524     -42.841  46.206  48.847  1.00 38.99      A
ATOM   4049  CE1  TYR A 524     -43.839  45.319  49.220  1.00 39.73      A
ATOM   4050  CD2  TYR A 524     -41.207  44.465  48.967  1.00 39.30      A
ATOM   4051  CE2  TYR A 524     -42.199  43.562  49.364  1.00 41.79      A
ATOM   4052  CZ   TYR A 524     -43.518  43.993  49.480  1.00 41.46      A
ATOM   4053  OH   TYR A 524     -44.511  43.105  49.854  1.00 41.16      A
ATOM   4054  C    TYR A 524     -38.666  48.358  49.105  1.00 35.77      A
ATOM   4055  O    TYR A 524     -37.601  47.939  49.557  1.00 37.50      A
ATOM   4056  N    LEU A 525     -38.723  49.391  48.269  1.00 33.40      A
ATOM   4057  CA   LEU A 525     -37.500  50.060  47.849  1.00 31.34      A
ATOM   4058  CB   LEU A 525     -37.773  51.060  46.733  1.00 30.38      A
ATOM   4059  CG   LEU A 525     -38.398  50.501  45.458  1.00 31.32      A
ATOM   4060  CD1  LEU A 525     -38.564  51.622  44.437  1.00 31.40      A
ATOM   4061  CD2  LEU A 525     -37.530  49.386  44.913  1.00 30.77      A
ATOM   4062  C    LEU A 525     -36.818  50.789  48.979  1.00 31.84      A
ATOM   4063  O    LEU A 525     -35.593  50.845  49.030  1.00 33.41      A
ATOM   4064  N    PHE A 526     -37.598  51.335  49.902  1.00 31.67      A
ATOM   4065  CA   PHE A 526     -37.009  52.103  50.989  1.00 31.69      A
ATOM   4066  CB   PHE A 526     -37.594  53.511  50.951  1.00 27.91      A
ATOM   4067  CG   PHE A 526     -37.187  54.277  49.735  1.00 27.23      A
ATOM   4068  CD1  PHE A 526     -35.902  54.800  49.627  1.00 26.46      A
ATOM   4069  CD2  PHE A 526     -38.065  54.445  48.672  1.00 26.20      A
ATOM   4070  CE1  PHE A 526     -35.507  55.479  48.479  1.00 24.27      A
ATOM   4071  CE2  PHE A 526     -37.670  55.123  47.522  1.00 22.88      A
ATOM   4072  CZ   PHE A 526     -36.398  55.636  47.427  1.00 23.56      A
ATOM   4073  C    PHE A 526     -37.058  51.540  52.403  1.00 31.95      A
ATOM   4074  O    PHE A 526     -36.822  52.260  53.370  1.00 32.67      A
ATOM   4075  N    ASN A 527     -37.331  50.251  52.532  1.00 33.14      A
ATOM   4076  CA   ASN A 527     -37.386  49.656  53.852  1.00 34.10      A
ATOM   4077  CB   ASN A 527     -37.799  48.192  53.771  1.00 34.06      A
ATOM   4078  CG   ASN A 527     -38.822  47.834  54.819  1.00 35.63      A
ATOM   4079  OD1  ASN A 527     -39.871  48.482  54.920  1.00 37.58      A
ATOM   4080  ND2  ASN A 527     -38.531  46.809  55.611  1.00 33.88      A
ATOM   4081  C    ASN A 527     -36.034  49.770  54.532  1.00 34.74      A
ATOM   4082  O    ASN A 527     -35.899  49.496  55.716  1.00 35.93      A
ATOM   4083  N    TRP A 528     -35.024  50.189  53.788  1.00 36.26      A
ATOM   4084  CA   TRP A 528     -33.699  50.320  54.373  1.00 37.10      A
ATOM   4085  CB   TRP A 528     -32.628  50.125  53.299  1.00 33.79      A
ATOM   4086  CG   TRP A 528     -32.740  51.113  52.192  1.00 31.57      A
ATOM   4087  CD2  TRP A 528     -32.277  52.468  52.212  1.00 30.18      A
ATOM   4088  CE2  TRP A 528     -32.636  53.050  50.980  1.00 29.40      A
ATOM   4089  CE3  TRP A 528     -31.594  53.247  53.155  1.00 29.69      A
ATOM   4090  CD1  TRP A 528     -33.343  50.931  50.984  1.00 30.84      A
ATOM   4091  NE1  TRP A 528     -33.286  52.092  50.247  1.00 30.68      A
ATOM   4092  CZ2  TRP A 528     -32.336  54.371  50.666  1.00 28.49      A
ATOM   4093  CZ3  TRP A 528     -31.296  54.559  52.843  1.00 29.73      A
ATOM   4094  CH2  TRP A 528     -31.667  55.108  51.606  1.00 29.18      A
ATOM   4095  C    TRP A 528     -33.538  51.688  55.034  1.00 39.01      A
ATOM   4096  O    TRP A 528     -32.604  51.906  55.807  1.00 38.97      A
ATOM   4097  N    ALA A 529     -34.452  52.606  54.725  1.00 41.29      A
ATOM   4098  CA   ALA A 529     -34.406  53.953  55.289  1.00 44.61      A
ATOM   4099  CB   ALA A 529     -35.250  54.913  54.436  1.00 42.82      A
ATOM   4100  C    ALA A 529     -34.882  53.986  56.748  1.00 46.97      A
ATOM   4101  O    ALA A 529     -34.431  54.828  57.532  1.00 47.82      A
ATOM   4102  N    VAL A 530     -35.788  53.073  57.107  1.00 48.67      A
```

FIGURE 4- 55 -

```
ATOM   4103  CA   VAL A 530     -36.319  53.002  58.470  1.00 50.17      A
ATOM   4104  CB   VAL A 530     -37.815  52.635  58.471  1.00 49.77      A
ATOM   4105  CG1  VAL A 530     -38.576  53.537  57.509  1.00 50.57      A
ATOM   4106  CG2  VAL A 530     -37.994  51.172  58.086  1.00 48.98      A
ATOM   4107  C    VAL A 530     -35.588  51.947  59.298  1.00 52.04      A
ATOM   4108  O    VAL A 530     -34.947  51.051  58.752  1.00 52.39      A
ATOM   4109  N    ARG A 531     -35.681  52.054  60.620  1.00 54.57      A
ATOM   4110  CA   ARG A 531     -35.039  51.072  61.491  1.00 56.57      A
ATOM   4111  CB   ARG A 531     -34.296  51.758  62.642  1.00 58.47      A
ATOM   4112  CG   ARG A 531     -32.964  52.352  62.186  1.00 62.65      A
ATOM   4113  CD   ARG A 531     -32.137  51.287  61.452  1.00 65.09      A
ATOM   4114  NE   ARG A 531     -31.147  51.850  60.536  1.00 68.46      A
ATOM   4115  CZ   ARG A 531     -30.455  51.126  59.657  1.00 70.15      A
ATOM   4116  NH1  ARG A 531     -30.653  49.814  59.586  1.00 70.89      A
ATOM   4117  NH2  ARG A 531     -29.573  51.710  58.847  1.00 70.00      A
ATOM   4118  C    ARG A 531     -36.079  50.093  62.013  1.00 56.78      A
ATOM   4119  O    ARG A 531     -35.777  48.926  62.270  1.00 57.23      A
ATOM   4120  N    THR A 532     -37.306  50.577  62.169  1.00 56.01      A
ATOM   4121  CA   THR A 532     -38.403  49.724  62.593  1.00 56.08      A
ATOM   4122  CB   THR A 532     -39.479  50.513  63.374  1.00 55.85      A
ATOM   4123  OG1  THR A 532     -38.969  50.849  64.670  1.00 54.15      A
ATOM   4124  CG2  THR A 532     -40.738  49.684  63.540  1.00 54.51      A
ATOM   4125  C    THR A 532     -38.955  49.211  61.268  1.00 56.07      A
ATOM   4126  O    THR A 532     -40.033  49.597  60.815  1.00 55.56      A
ATOM   4127  N    LYS A 533     -38.170  48.338  60.653  1.00 56.76      A
ATOM   4128  CA   LYS A 533     -38.492  47.760  59.361  1.00 58.77      A
ATOM   4129  CB   LYS A 533     -37.308  46.930  58.867  1.00 58.73      A
ATOM   4130  CG   LYS A 533     -36.010  47.699  58.847  1.00 59.54      A
ATOM   4131  CD   LYS A 533     -35.002  47.052  57.923  1.00 61.15      A
ATOM   4132  CE   LYS A 533     -33.764  47.928  57.775  1.00 61.75      A
ATOM   4133  NZ   LYS A 533     -32.844  47.404  56.730  1.00 61.99      A
ATOM   4134  C    LYS A 533     -39.752  46.913  59.297  1.00 59.67      A
ATOM   4135  O    LYS A 533     -40.181  46.319  60.285  1.00 59.48      A
ATOM   4136  N    LEU A 534     -40.334  46.861  58.105  1.00 60.70      A
ATOM   4137  CA   LEU A 534     -41.530  46.071  57.874  1.00 62.31      A
ATOM   4138  CB   LEU A 534     -42.429  46.758  56.838  1.00 62.22      A
ATOM   4139  CG   LEU A 534     -42.713  48.249  57.068  1.00 62.66      A
ATOM   4140  CD1  LEU A 534     -43.645  48.768  55.973  1.00 60.66      A
ATOM   4141  CD2  LEU A 534     -43.330  48.453  58.455  1.00 61.66      A
ATOM   4142  C    LEU A 534     -41.090  44.703  57.355  1.00 63.29      A
ATOM   4143  O    LEU A 534     -40.025  44.571  56.739  1.00 62.98      A
ATOM   4144  N    LYS A 535     -41.898  43.682  57.622  1.00 63.99      A
ATOM   4145  CA   LYS A 535     -41.583  42.340  57.153  1.00 64.20      A
ATOM   4146  CB   LYS A 535     -42.314  41.281  57.987  1.00 66.23      A
ATOM   4147  CG   LYS A 535     -42.130  41.432  59.496  1.00 68.40      A
ATOM   4148  CD   LYS A 535     -40.674  41.292  59.914  1.00 69.85      A
ATOM   4149  CE   LYS A 535     -40.496  41.638  61.388  1.00 71.38      A
ATOM   4150  NZ   LYS A 535     -39.073  41.514  61.847  1.00 72.48      A
ATOM   4151  C    LYS A 535     -42.061  42.298  55.713  1.00 62.78      A
ATOM   4152  O    LYS A 535     -43.260  42.342  55.439  1.00 62.35      A
ATOM   4153  N    LEU A 536     -41.113  42.235  54.790  1.00 61.63      A
ATOM   4154  CA   LEU A 536     -41.456  42.210  53.384  1.00 60.34      A
ATOM   4155  CB   LEU A 536     -40.310  42.821  52.575  1.00 58.57      A
ATOM   4156  CG   LEU A 536     -40.109  44.267  53.041  1.00 56.31      A
ATOM   4157  CD1  LEU A 536     -38.875  44.865  52.438  1.00 56.70      A
ATOM   4158  CD2  LEU A 536     -41.329  45.073  52.670  1.00 55.76      A
ATOM   4159  C    LEU A 536     -41.798  40.801  52.926  1.00 59.61      A
ATOM   4160  O    LEU A 536     -41.012  39.864  53.062  1.00 59.61      A
ATOM   4161  N    THR A 537     -43.002  40.670  52.395  1.00 59.07      A
ATOM   4162  CA   THR A 537     -43.507  39.399  51.928  1.00 59.53      A
ATOM   4163  CB   THR A 537     -44.873  39.105  52.570  1.00 61.22      A
ATOM   4164  OG1  THR A 537     -45.833  40.077  52.121  1.00 60.98      A
ATOM   4165  CG2  THR A 537     -44.765  39.179  54.092  1.00 60.75      A
ATOM   4166  C    THR A 537     -43.686  39.469  50.424  1.00 58.77      A
ATOM   4167  O    THR A 537     -43.921  40.544  49.873  1.00 58.46      A
ATOM   4168  N    PRO A 538     -43.591  38.319  49.742  1.00 58.41      A
ATOM   4169  CD   PRO A 538     -43.410  36.968  50.304  1.00 57.78      A
ATOM   4170  CA   PRO A 538     -43.747  38.265  48.286  1.00 59.28      A
ATOM   4171  CB   PRO A 538     -44.112  36.807  48.042  1.00 57.76      A
ATOM   4172  CG   PRO A 538     -43.264  36.108  49.058  1.00 58.13      A
ATOM   4173  C    PRO A 538     -44.811  39.236  47.773  1.00 60.35      A
ATOM   4174  O    PRO A 538     -45.842  39.443  48.413  1.00 60.85      A
ATOM   4175  N    ILE A 539     -44.547  39.839  46.622  1.00 61.23      A
ATOM   4176  CA   ILE A 539     -45.487  40.785  46.033  1.00 63.48      A
ATOM   4177  CB   ILE A 539     -44.740  41.969  45.389  1.00 62.83      A
ATOM   4178  CG2  ILE A 539     -45.734  42.943  44.781  1.00 61.99      A
```

FIGURE 4- 56 -

```
ATOM   4179  CG1 ILE A 539     -43.871  42.650  46.447  1.00 62.53       A
ATOM   4180  CD1 ILE A 539     -42.998  43.755  45.921  1.00 63.37       A
ATOM   4181  C   ILE A 539     -46.329  40.079  44.974  1.00 65.74       A
ATOM   4182  O   ILE A 539     -45.813  39.658  43.939  1.00 66.72       A
ATOM   4183  N   PRO A 540     -47.645  39.957  45.213  1.00 67.41       A
ATOM   4184  CD  PRO A 540     -48.362  40.603  46.325  1.00 67.19       A
ATOM   4185  CA  PRO A 540     -48.589  39.296  44.299  1.00 68.70       A
ATOM   4186  CB  PRO A 540     -49.943  39.780  44.800  1.00 68.27       A
ATOM   4187  CG  PRO A 540     -49.710  39.940  46.257  1.00 67.92       A
ATOM   4188  C   PRO A 540     -48.396  39.585  42.807  1.00 70.36       A
ATOM   4189  O   PRO A 540     -47.908  38.738  42.055  1.00 70.15       A
ATOM   4190  N   ALA A 541     -48.786  40.790  42.398  1.00 72.53       A
ATOM   4191  CA  ALA A 541     -48.709  41.233  41.003  1.00 74.81       A
ATOM   4192  CB  ALA A 541     -49.104  42.708  40.925  1.00 74.56       A
ATOM   4193  C   ALA A 541     -47.378  41.013  40.261  1.00 76.33       A
ATOM   4194  O   ALA A 541     -47.287  41.243  39.049  1.00 75.88       A
ATOM   4195  N   ALA A 542     -46.351  40.567  40.977  1.00 77.90       A
ATOM   4196  CA  ALA A 542     -45.044  40.340  40.362  1.00 79.17       A
ATOM   4197  CB  ALA A 542     -43.978  40.149  41.444  1.00 78.56       A
ATOM   4198  C   ALA A 542     -45.049  39.142  39.413  1.00 80.10       A
ATOM   4199  O   ALA A 542     -44.908  39.297  38.196  1.00 80.28       A
ATOM   4200  N   SER A 543     -45.213  37.950  39.981  1.00 80.47       A
ATOM   4201  CA  SER A 543     -45.244  36.715  39.202  1.00 80.01       A
ATOM   4202  CB  SER A 543     -45.597  35.539  40.113  1.00 79.06       A
ATOM   4203  OG  SER A 543     -46.676  35.872  40.977  1.00 78.66       A
ATOM   4204  C   SER A 543     -46.229  36.783  38.020  1.00 79.95       A
ATOM   4205  O   SER A 543     -46.157  35.969  37.094  1.00 80.40       A
ATOM   4206  N   GLN A 544     -47.136  37.758  38.050  1.00 78.96       A
ATOM   4207  CA  GLN A 544     -48.124  37.933  36.986  1.00 77.97       A
ATOM   4208  CB  GLN A 544     -49.334  38.711  37.519  1.00 79.20       A
ATOM   4209  CG  GLN A 544     -50.319  39.192  36.447  1.00 79.88       A
ATOM   4210  CD  GLN A 544     -51.357  40.175  36.995  1.00 80.03       A
ATOM   4211  OE1 GLN A 544     -52.299  40.564  36.292  1.00 78.86       A
ATOM   4212  NE2 GLN A 544     -51.184  40.582  38.255  1.00 79.80       A
ATOM   4213  C   GLN A 544     -47.508  38.701  35.823  1.00 76.73       A
ATOM   4214  O   GLN A 544     -48.095  38.811  34.747  1.00 76.27       A
ATOM   4215  N   LEU A 545     -46.313  39.227  36.066  1.00 75.78       A
ATOM   4216  CA  LEU A 545     -45.571  40.021  35.095  1.00 73.38       A
ATOM   4217  CB  LEU A 545     -44.560  40.903  35.836  1.00 72.88       A
ATOM   4218  CG  LEU A 545     -44.490  42.400  35.553  1.00 71.69       A
ATOM   4219  CD1 LEU A 545     -43.294  42.952  36.312  1.00 71.54       A
ATOM   4220  CD2 LEU A 545     -44.361  42.669  34.065  1.00 71.36       A
ATOM   4221  C   LEU A 545     -44.841  39.151  34.070  1.00 71.88       A
ATOM   4222  O   LEU A 545     -44.189  38.162  34.420  1.00 70.97       A
ATOM   4223  N   ASP A 546     -44.955  39.530  32.803  1.00 69.93       A
ATOM   4224  CA  ASP A 546     -44.303  38.794  31.733  1.00 67.63       A
ATOM   4225  CB  ASP A 546     -45.104  38.938  30.436  1.00 66.95       A
ATOM   4226  CG  ASP A 546     -44.343  38.453  29.229  1.00 66.42       A
ATOM   4227  OD1 ASP A 546     -43.709  37.382  29.320  1.00 66.41       A
ATOM   4228  OD2 ASP A 546     -44.388  39.144  28.189  1.00 67.49       A
ATOM   4229  C   ASP A 546     -42.884  39.321  31.553  1.00 65.88       A
ATOM   4230  O   ASP A 546     -42.676  40.439  31.084  1.00 65.53       A
ATOM   4231  N   LEU A 547     -41.908  38.512  31.944  1.00 63.66       A
ATOM   4232  CA  LEU A 547     -40.519  38.915  31.830  1.00 61.21       A
ATOM   4233  CB  LEU A 547     -39.859  38.948  33.209  1.00 61.39       A
ATOM   4234  CG  LEU A 547     -40.158  40.177  34.079  1.00 61.58       A
ATOM   4235  CD1 LEU A 547     -41.660  40.385  34.234  1.00 60.85       A
ATOM   4236  CD2 LEU A 547     -39.505  39.986  35.443  1.00 62.60       A
ATOM   4237  C   LEU A 547     -39.780  37.972  30.918  1.00 59.26       A
ATOM   4238  O   LEU A 547     -38.556  37.938  30.900  1.00 58.03       A
ATOM   4239  N   SER A 548     -40.533  37.190  30.162  1.00 58.38       A
ATOM   4240  CA  SER A 548     -39.911  36.267  29.230  1.00 57.30       A
ATOM   4241  CB  SER A 548     -40.968  35.417  28.519  1.00 56.68       A
ATOM   4242  OG  SER A 548     -41.801  36.231  27.703  1.00 55.62       A
ATOM   4243  C   SER A 548     -39.196  37.146  28.216  1.00 56.21       A
ATOM   4244  O   SER A 548     -39.591  38.296  27.991  1.00 56.06       A
ATOM   4245  N   GLY A 549     -38.138  36.614  27.619  1.00 54.56       A
ATOM   4246  CA  GLY A 549     -37.402  37.370  26.624  1.00 52.84       A
ATOM   4247  C   GLY A 549     -36.521  38.480  27.163  1.00 51.18       A
ATOM   4248  O   GLY A 549     -35.780  39.096  26.393  1.00 52.59       A
ATOM   4249  N   TRP A 550     -36.588  38.737  28.465  1.00 49.04       A
ATOM   4250  CA  TRP A 550     -35.783  39.791  29.080  1.00 47.25       A
ATOM   4251  CB  TRP A 550     -36.270  40.065  30.499  1.00 49.31       A
ATOM   4252  CG  TRP A 550     -37.266  41.166  30.598  1.00 51.24       A
ATOM   4253  CD2 TRP A 550     -37.184  42.313  31.446  1.00 53.36       A
ATOM   4254  CE2 TRP A 550     -38.349  43.076  31.228  1.00 54.09       A
```

FIGURE 4- 57 -

```
ATOM   4255  CE3 TRP A 550     -36.237  42.770  32.373  1.00 54.70      A
ATOM   4256  CD1 TRP A 550     -38.440  41.274  29.918  1.00 51.77      A
ATOM   4257  NE1 TRP A 550     -39.098  42.419  30.289  1.00 52.80      A
ATOM   4258  CZ2 TRP A 550     -38.599  44.279  31.905  1.00 55.39      A
ATOM   4259  CZ3 TRP A 550     -36.486  43.967  33.048  1.00 55.79      A
ATOM   4260  CH2 TRP A 550     -37.659  44.706  32.808  1.00 55.20      A
ATOM   4261  C   TRP A 550     -34.288  39.481  29.127  1.00 45.60      A
ATOM   4262  O   TRP A 550     -33.442  40.343  28.845  1.00 44.30      A
ATOM   4263  N   PHE A 551     -33.960  38.254  29.498  1.00 42.17      A
ATOM   4264  CA  PHE A 551     -32.566  37.870  29.575  1.00 40.38      A
ATOM   4265  CB  PHE A 551     -32.173  37.661  31.034  1.00 39.15      A
ATOM   4266  CG  PHE A 551     -32.298  38.909  31.860  1.00 38.55      A
ATOM   4267  CD1 PHE A 551     -31.473  40.006  31.612  1.00 37.83      A
ATOM   4268  CD2 PHE A 551     -33.253  39.004  32.866  1.00 38.27      A
ATOM   4269  CE1 PHE A 551     -31.596  41.184  32.354  1.00 37.83      A
ATOM   4270  CE2 PHE A 551     -33.385  40.176  33.616  1.00 38.68      A
ATOM   4271  CZ  PHE A 551     -32.552  41.269  33.357  1.00 38.09      A
ATOM   4272  C   PHE A 551     -32.361  36.625  28.750  1.00 39.43      A
ATOM   4273  O   PHE A 551     -32.075  35.542  29.271  1.00 40.85      A
ATOM   4274  N   VAL A 552     -32.520  36.807  27.444  1.00 36.52      A
ATOM   4275  CA  VAL A 552     -32.380  35.731  26.483  1.00 33.93      A
ATOM   4276  CB  VAL A 552     -33.678  35.582  25.672  1.00 33.90      A
ATOM   4277  CG1 VAL A 552     -33.511  34.546  24.561  1.00 32.08      A
ATOM   4278  CG2 VAL A 552     -34.805  35.212  26.609  1.00 32.75      A
ATOM   4279  C   VAL A 552     -31.216  35.983  25.534  1.00 32.97      A
ATOM   4280  O   VAL A 552     -30.458  35.070  25.217  1.00 32.17      A
ATOM   4281  N   ALA A 553     -31.069  37.222  25.079  1.00 32.16      A
ATOM   4282  CA  ALA A 553     -29.985  37.534  24.155  1.00 32.67      A
ATOM   4283  CB  ALA A 553     -30.363  37.080  22.747  1.00 34.30      A
ATOM   4284  C   ALA A 553     -29.613  39.005  24.132  1.00 31.39      A
ATOM   4285  O   ALA A 553     -30.448  39.861  24.401  1.00 32.65      A
ATOM   4286  N   GLY A 554     -28.355  39.293  23.814  1.00 29.70      A
ATOM   4287  CA  GLY A 554     -27.914  40.676  23.736  1.00 29.26      A
ATOM   4288  C   GLY A 554     -28.242  41.273  22.373  1.00 28.50      A
ATOM   4289  O   GLY A 554     -28.337  40.552  21.374  1.00 28.87      A
ATOM   4290  N   TYR A 555     -28.412  42.588  22.311  1.00 27.49      A
ATOM   4291  CA  TYR A 555     -28.755  43.233  21.047  1.00 27.02      A
ATOM   4292  CB  TYR A 555     -30.268  43.404  20.944  1.00 26.46      A
ATOM   4293  CG  TYR A 555     -31.056  42.118  20.961  1.00 26.77      A
ATOM   4294  CD1 TYR A 555     -31.234  41.372  19.799  1.00 24.75      A
ATOM   4295  CE1 TYR A 555     -31.986  40.206  19.810  1.00 26.49      A
ATOM   4296  CD2 TYR A 555     -31.644  41.660  22.140  1.00 25.25      A
ATOM   4297  CE2 TYR A 555     -32.388  40.501  22.165  1.00 26.27      A
ATOM   4298  CZ  TYR A 555     -32.562  39.775  21.000  1.00 27.67      A
ATOM   4299  OH  TYR A 555     -33.321  38.627  21.039  1.00 26.97      A
ATOM   4300  C   TYR A 555     -28.105  44.600  20.925  1.00 26.83      A
ATOM   4301  O   TYR A 555     -28.699  45.527  20.368  1.00 25.39      A
ATOM   4302  N   SER A 556     -26.890  44.726  21.446  1.00 28.22      A
ATOM   4303  CA  SER A 556     -26.185  46.001  21.396  1.00 30.48      A
ATOM   4304  CB  SER A 556     -24.767  45.842  21.940  1.00 32.20      A
ATOM   4305  OG  SER A 556     -24.102  47.091  21.974  1.00 33.96      A
ATOM   4306  C   SER A 556     -26.128  46.559  19.980  1.00 29.74      A
ATOM   4307  O   SER A 556     -25.608  45.905  19.072  1.00 30.39      A
ATOM   4308  N   GLY A 557     -26.670  47.765  19.802  1.00 28.35      A
ATOM   4309  CA  GLY A 557     -26.669  48.407  18.497  1.00 27.42      A
ATOM   4310  C   GLY A 557     -27.536  47.716  17.461  1.00 27.75      A
ATOM   4311  O   GLY A 557     -27.520  48.086  16.280  1.00 26.39      A
ATOM   4312  N   GLY A 558     -28.305  46.723  17.914  1.00 28.31      A
ATOM   4313  CA  GLY A 558     -29.181  45.959  17.037  1.00 26.90      A
ATOM   4314  C   GLY A 558     -30.513  46.588  16.654  1.00 26.78      A
ATOM   4315  O   GLY A 558     -31.266  46.000  15.876  1.00 27.13      A
ATOM   4316  N   ASP A 559     -30.816  47.767  17.196  1.00 26.01      A
ATOM   4317  CA  ASP A 559     -32.056  48.456  16.868  1.00 25.72      A
ATOM   4318  CB  ASP A 559     -32.053  48.778  15.366  1.00 25.97      A
ATOM   4319  CG  ASP A 559     -33.145  49.750  14.961  1.00 27.50      A
ATOM   4320  OD1 ASP A 559     -33.453  50.682  15.735  1.00 28.64      A
ATOM   4321  OD2 ASP A 559     -33.680  49.594  13.850  1.00 26.19      A
ATOM   4322  C   ASP A 559     -33.257  47.585  17.256  1.00 27.40      A
ATOM   4323  O   ASP A 559     -34.186  47.395  16.473  1.00 28.36      A
ATOM   4324  N   ILE A 560     -33.229  47.060  18.477  1.00 28.15      A
ATOM   4325  CA  ILE A 560     -34.303  46.212  18.971  1.00 29.66      A
ATOM   4326  CB  ILE A 560     -33.760  44.857  19.474  1.00 27.73      A
ATOM   4327  CG2 ILE A 560     -34.871  44.062  20.152  1.00 22.90      A
ATOM   4328  CG1 ILE A 560     -33.145  44.084  18.309  1.00 25.41      A
ATOM   4329  CD1 ILE A 560     -34.073  43.889  17.135  1.00 23.81      A
ATOM   4330  C   ILE A 560     -35.119  46.846  20.096  1.00 33.51      A
```

FIGURE 4- 58 -

```
ATOM   4331  O    ILE A 560     -34.578  47.407  21.049  1.00 33.38      A
ATOM   4332  N    TYR A 561     -36.432  46.724  19.981  1.00 38.65      A
ATOM   4333  CA   TYR A 561     -37.347  47.277  20.965  1.00 44.04      A
ATOM   4334  CB   TYR A 561     -37.836  48.663  20.524  1.00 44.53      A
ATOM   4335  CG   TYR A 561     -38.962  49.232  21.374  1.00 46.35      A
ATOM   4336  CD1  TYR A 561     -38.701  50.146  22.393  1.00 47.98      A
ATOM   4337  CE1  TYR A 561     -39.729  50.641  23.193  1.00 48.79      A
ATOM   4338  CD2  TYR A 561     -40.287  48.831  21.177  1.00 47.51      A
ATOM   4339  CE2  TYR A 561     -41.319  49.313  21.969  1.00 47.58      A
ATOM   4340  CZ   TYR A 561     -41.036  50.215  22.976  1.00 49.44      A
ATOM   4341  OH   TYR A 561     -42.057  50.666  23.782  1.00 50.67      A
ATOM   4342  C    TYR A 561     -38.562  46.393  21.151  1.00 47.76      A
ATOM   4343  O    TYR A 561     -39.498  46.452  20.355  1.00 47.79      A
ATOM   4344  N    HIS A 562     -38.554  45.536  22.160  1.00 52.23      A
ATOM   4345  CA   HIS A 562     -39.762  44.768  22.399  1.00 57.64      A
ATOM   4346  CB   HIS A 562     -39.616  43.256  22.098  1.00 58.50      A
ATOM   4347  CG   HIS A 562     -38.309  42.645  22.496  1.00 61.19      A
ATOM   4348  CD2  HIS A 562     -37.331  42.083  21.746  1.00 62.18      A
ATOM   4349  ND1  HIS A 562     -37.939  42.454  23.810  1.00 63.62      A
ATOM   4350  CE1  HIS A 562     -36.793  41.796  23.852  1.00 63.80      A
ATOM   4351  NE2  HIS A 562     -36.403  41.558  22.613  1.00 62.60      A
ATOM   4352  C    HIS A 562     -40.208  45.056  23.822  1.00 59.45      A
ATOM   4353  O    HIS A 562     -39.599  44.610  24.793  1.00 60.54      A
ATOM   4354  N    SER A 563     -41.266  45.858  23.919  1.00 61.24      A
ATOM   4355  CA   SER A 563     -41.320  46.278  25.197  1.00 63.61      A
ATOM   4356  CB   SER A 563     -41.271  47.663  25.557  1.00 63.65      A
ATOM   4357  OG   SER A 563     -41.790  48.106  26.797  1.00 65.14      A
ATOM   4358  C    SER A 563     -43.351  46.312  25.181  1.00 64.35      A
ATOM   4359  O    SER A 563     -43.911  47.433  25.170  1.00 64.47      A
ATOM   4360  OXT  SER A 563     -43.968  45.219  25.172  1.00 64.70      A
ATOM   4361  CB   SER B   1     -46.252  21.241  -6.638  1.00 23.68      B
ATOM   4362  OG   SER B   1     -44.990  20.596  -6.699  1.00 25.39      B
ATOM   4363  C    SER B   1     -47.210  19.096  -7.447  1.00 25.25      B
ATOM   4364  O    SER B   1     -46.899  17.956  -7.087  1.00 27.50      B
ATOM   4365  N    SER B   1     -47.301  19.671  -5.029  1.00 22.50      B
ATOM   4366  CA   SER B   1     -47.365  20.219  -6.421  1.00 25.06      B
ATOM   4367  N    MET B   2     -47.420  19.415  -8.722  1.00 23.80      B
ATOM   4368  CA   MET B   2     -47.277  18.411  -9.771  1.00 23.17      B
ATOM   4369  CB   MET B   2     -48.037  18.828 -11.034  1.00 21.26      B
ATOM   4370  CG   MET B   2     -49.558  18.792 -10.917  1.00 19.10      B
ATOM   4371  SD   MET B   2     -50.256  17.199 -10.401  1.00 21.33      B
ATOM   4372  CE   MET B   2     -49.990  16.182 -11.846  1.00 14.91      B
ATOM   4373  C    MET B   2     -45.810  18.178 -10.130  1.00 23.48      B
ATOM   4374  O    MET B   2     -45.031  19.117 -10.289  1.00 23.98      B
ATOM   4375  N    SER B   3     -45.436  16.915 -10.257  1.00 22.87      B
ATOM   4376  CA   SER B   3     -44.075  16.570 -10.621  1.00 22.79      B
ATOM   4377  CB   SER B   3     -43.947  15.050 -10.717  1.00 22.98      B
ATOM   4378  OG   SER B   3     -44.885  14.511 -11.642  1.00 23.51      B
ATOM   4379  C    SER B   3     -43.719  17.204 -11.972  1.00 23.87      B
ATOM   4380  O    SER B   3     -42.605  17.700 -12.169  1.00 25.36      B
ATOM   4381  N    TYR B   4     -44.675  17.183 -12.899  1.00 23.53      B
ATOM   4382  CA   TYR B   4     -44.469  17.732 -14.232  1.00 23.38      B
ATOM   4383  CB   TYR B   4     -44.064  16.631 -15.210  1.00 25.93      B
ATOM   4384  CG   TYR B   4     -42.722  16.006 -14.965  1.00 26.96      B
ATOM   4385  CD1  TYR B   4     -41.561  16.626 -15.400  1.00 27.46      B
ATOM   4386  CE1  TYR B   4     -40.322  16.046 -15.178  1.00 26.90      B
ATOM   4387  CD2  TYR B   4     -42.612  14.787 -14.299  1.00 25.22      B
ATOM   4388  CE2  TYR B   4     -41.382  14.204 -14.074  1.00 23.68      B
ATOM   4389  CZ   TYR B   4     -40.243  14.839 -14.514  1.00 24.59      B
ATOM   4390  OH   TYR B   4     -39.015  14.277 -14.274  1.00 25.80      B
ATOM   4391  C    TYR B   4     -45.746  18.348 -14.766  1.00 23.45      B
ATOM   4392  O    TYR B   4     -46.842  18.026 -14.301  1.00 23.88      B
ATOM   4393  N    THR B   5     -45.577  19.221 -15.758  1.00 21.84      B
ATOM   4394  CA   THR B   5     -46.667  19.887 -16.450  1.00 20.28      B
ATOM   4395  CB   THR B   5     -46.818  21.361 -16.045  1.00 17.90      B
ATOM   4396  OG1  THR B   5     -47.167  21.455 -14.660  1.00 14.79      B
ATOM   4397  CG2  THR B   5     -47.915  22.010 -16.878  1.00 15.45      B
ATOM   4398  C    THR B   5     -46.260  19.847 -17.913  1.00 22.54      B
ATOM   4399  O    THR B   5     -45.149  20.256 -18.249  1.00 22.98      B
ATOM   4400  N    TRP B   6     -47.158  19.367 -18.775  1.00 23.48      B
ATOM   4401  CA   TRP B   6     -46.884  19.249 -20.207  1.00 22.07      B
ATOM   4402  CB   TRP B   6     -47.221  17.836 -20.657  1.00 21.29      B
ATOM   4403  CG   TRP B   6     -46.575  16.807 -19.799  1.00 22.80      B
ATOM   4404  CD2  TRP B   6     -45.175  16.515 -19.724  1.00 21.99      B
ATOM   4405  CE2  TRP B   6     -45.009  15.522 -18.737  1.00 20.81      B
ATOM   4406  CE3  TRP B   6     -44.044  17.002 -20.393  1.00 21.23      B
```

FIGURE 4- 59 -

| | | | | | | | | | | |
|---|---|---|---|---|---|---|---|---|---|---|
| ATOM | 4407 | CD1 | TRP | B | 6 | -47.184 | 16.000 | -18.882 | 1.00 21.93 | B |
| ATOM | 4408 | NE1 | TRP | B | 6 | -46.252 | 15.226 | -18.241 | 1.00 20.48 | B |
| ATOM | 4409 | CZ2 | TRP | B | 6 | -43.758 | 15.003 | -18.399 | 1.00 19.37 | B |
| ATOM | 4410 | CZ3 | TRP | B | 6 | -42.804 | 16.490 | -20.059 | 1.00 21.71 | B |
| ATOM | 4411 | CH2 | TRP | B | 6 | -42.671 | 15.497 | -19.067 | 1.00 21.36 | B |
| ATOM | 4412 | C | TRP | B | 6 | -47.655 | 20.249 | -21.064 | 1.00 22.44 | B |
| ATOM | 4413 | O | TRP | B | 6 | -48.781 | 20.604 | -20.736 | 1.00 24.31 | B |
| ATOM | 4414 | N | THR | B | 7 | -47.045 | 20.683 | -22.166 | 1.00 22.20 | B |
| ATOM | 4415 | CA | THR | B | 7 | -47.663 | 21.633 | -23.092 | 1.00 23.11 | B |
| ATOM | 4416 | CB | THR | B | 7 | -46.648 | 22.678 | -23.609 | 1.00 21.59 | B |
| ATOM | 4417 | OG1 | THR | B | 7 | -45.697 | 22.031 | -24.471 | 1.00 20.46 | B |
| ATOM | 4418 | CG2 | THR | B | 7 | -45.931 | 23.347 | -22.462 | 1.00 17.07 | B |
| ATOM | 4419 | C | THR | B | 7 | -48.216 | 20.916 | -24.331 | 1.00 26.23 | B |
| ATOM | 4420 | O | THR | B | 7 | -48.843 | 21.538 | -25.201 | 1.00 28.16 | B |
| ATOM | 4421 | N | GLY | B | 8 | -47.974 | 19.615 | -24.421 | 1.00 27.43 | B |
| ATOM | 4422 | CA | GLY | B | 8 | -48.441 | 18.871 | -25.573 | 1.00 29.43 | B |
| ATOM | 4423 | C | GLY | B | 8 | -47.322 | 18.678 | -26.583 | 1.00 30.19 | B |
| ATOM | 4424 | O | GLY | B | 8 | -47.343 | 17.724 | -27.361 | 1.00 30.13 | B |
| ATOM | 4425 | N | ALA | B | 9 | -46.351 | 19.588 | -26.581 | 1.00 31.52 | B |
| ATOM | 4426 | CA | ALA | B | 9 | -45.216 | 19.486 | -27.495 | 1.00 33.29 | B |
| ATOM | 4427 | CB | ALA | B | 9 | -44.264 | 20.658 | -27.299 | 1.00 33.01 | B |
| ATOM | 4428 | C | ALA | B | 9 | -44.504 | 18.164 | -27.208 | 1.00 34.84 | B |
| ATOM | 4429 | O | ALA | B | 9 | -44.479 | 17.693 | -26.063 | 1.00 33.96 | B |
| ATOM | 4430 | N | LEU | B | 10 | -43.901 | 17.582 | -28.236 | 1.00 36.43 | B |
| ATOM | 4431 | CA | LEU | B | 10 | -43.262 | 16.290 | -28.079 | 1.00 38.04 | B |
| ATOM | 4432 | CB | LEU | B | 10 | -43.354 | 15.513 | -29.388 | 1.00 37.10 | B |
| ATOM | 4433 | CG | LEU | B | 10 | -44.746 | 15.305 | -29.980 | 1.00 35.87 | B |
| ATOM | 4434 | CD1 | LEU | B | 10 | -44.600 | 14.398 | -31.200 | 1.00 33.63 | B |
| ATOM | 4435 | CD2 | LEU | B | 10 | -45.694 | 14.703 | -28.942 | 1.00 33.10 | B |
| ATOM | 4436 | C | LEU | B | 10 | -41.834 | 16.206 | -27.590 | 1.00 39.68 | B |
| ATOM | 4437 | O | LEU | B | 10 | -41.045 | 17.145 | -27.689 | 1.00 39.51 | B |
| ATOM | 4438 | N | ILE | B | 11 | -41.533 | 15.037 | -27.049 | 1.00 42.07 | B |
| ATOM | 4439 | CA | ILE | B | 11 | -40.213 | 14.708 | -26.565 | 1.00 45.11 | B |
| ATOM | 4440 | CB | ILE | B | 11 | -40.305 | 13.671 | -25.435 | 1.00 44.97 | B |
| ATOM | 4441 | CG2 | ILE | B | 11 | -38.933 | 13.110 | -25.104 | 1.00 45.15 | B |
| ATOM | 4442 | CG1 | ILE | B | 11 | -40.938 | 14.338 | -24.214 | 1.00 43.81 | B |
| ATOM | 4443 | CD1 | ILE | B | 11 | -41.206 | 13.409 | -23.075 | 1.00 44.84 | B |
| ATOM | 4444 | C | ILE | B | 11 | -39.628 | 14.108 | -27.824 | 1.00 48.04 | B |
| ATOM | 4445 | O | ILE | B | 11 | -39.912 | 12.961 | -28.174 | 1.00 46.13 | B |
| ATOM | 4446 | N | THR | B | 12 | -38.827 | 14.917 | -28.507 | 1.00 52.66 | B |
| ATOM | 4447 | CA | THR | B | 12 | -38.228 | 14.532 | -29.776 | 1.00 57.14 | B |
| ATOM | 4448 | CB | THR | B | 12 | -38.159 | 15.757 | -30.698 | 1.00 56.47 | B |
| ATOM | 4449 | OG1 | THR | B | 12 | -37.473 | 16.819 | -30.033 | 1.00 56.89 | B |
| ATOM | 4450 | CG2 | THR | B | 12 | -39.571 | 16.226 | -31.070 | 1.00 55.84 | B |
| ATOM | 4451 | C | THR | B | 12 | -36.857 | 13.820 | -29.746 | 1.00 61.70 | B |
| ATOM | 4452 | O | THR | B | 12 | -36.089 | 13.958 | -28.795 | 1.00 62.72 | B |
| ATOM | 4453 | N | PRO | B | 13 | -36.546 | 13.049 | -30.809 | 1.00 66.15 | B |
| ATOM | 4454 | CD | PRO | B | 13 | -37.628 | 12.800 | -31.769 | 1.00 66.95 | B |
| ATOM | 4455 | CA | PRO | B | 13 | -35.379 | 12.216 | -31.162 | 1.00 69.56 | B |
| ATOM | 4456 | CB | PRO | B | 13 | -35.929 | 11.320 | -32.276 | 1.00 69.01 | B |
| ATOM | 4457 | CG | PRO | B | 13 | -37.416 | 11.362 | -32.083 | 1.00 67.51 | B |
| ATOM | 4458 | C | PRO | B | 13 | -34.066 | 12.876 | -31.609 | 1.00 72.85 | B |
| ATOM | 4459 | O | PRO | B | 13 | -33.315 | 13.429 | -30.798 | 1.00 73.19 | B |
| ATOM | 4460 | N | CYS | B | 14 | -33.809 | 12.741 | -32.915 | 1.00 76.55 | B |
| ATOM | 4461 | CA | CYS | B | 14 | -32.637 | 13.253 | -33.635 | 1.00 80.08 | B |
| ATOM | 4462 | CB | CYS | B | 14 | -31.921 | 14.345 | -32.824 | 1.00 80.56 | B |
| ATOM | 4463 | SG | CYS | B | 14 | -30.508 | 15.104 | -33.694 | 1.00 83.26 | B |
| ATOM | 4464 | C | CYS | B | 14 | -31.620 | 12.160 | -34.026 | 1.00 81.54 | B |
| ATOM | 4465 | O | CYS | B | 14 | -30.530 | 12.477 | -34.500 | 1.00 81.43 | B |
| ATOM | 4466 | N | ALA | B | 15 | -31.957 | 10.884 | -33.835 | 1.00 83.75 | B |
| ATOM | 4467 | CA | ALA | B | 15 | -31.025 | 9.795 | -34.175 | 1.00 85.61 | B |
| ATOM | 4468 | CB | ALA | B | 15 | -30.180 | 9.437 | -32.957 | 1.00 84.97 | B |
| ATOM | 4469 | C | ALA | B | 15 | -31.755 | 8.556 | -34.676 | 1.00 86.89 | B |
| ATOM | 4470 | O | ALA | B | 15 | -31.143 | 7.526 | -34.991 | 1.00 87.17 | B |
| ATOM | 4471 | N | ALA | B | 16 | -33.074 | 8.687 | -34.743 | 1.00 88.12 | B |
| ATOM | 4472 | CA | ALA | B | 16 | -33.970 | 7.633 | -35.182 | 1.00 89.15 | B |
| ATOM | 4473 | CB | ALA | B | 16 | -33.211 | 6.521 | -35.895 | 1.00 89.34 | B |
| ATOM | 4474 | C | ALA | B | 16 | -34.688 | 7.085 | -33.966 | 1.00 90.09 | B |
| ATOM | 4475 | O | ALA | B | 16 | -34.910 | 5.879 | -33.842 | 1.00 90.43 | B |
| ATOM | 4476 | N | GLU | B | 17 | -35.033 | 7.981 | -33.052 | 1.00 90.35 | B |
| ATOM | 4477 | CA | GLU | B | 17 | -35.759 | 7.576 | -31.863 | 1.00 90.54 | B |
| ATOM | 4478 | CB | GLU | B | 17 | -35.654 | 8.657 | -30.789 | 1.00 90.09 | B |
| ATOM | 4479 | CG | GLU | B | 17 | -34.620 | 8.409 | -29.716 | 1.00 90.32 | B |
| ATOM | 4480 | CD | GLU | B | 17 | -34.325 | 9.672 | -28.913 | 1.00 90.78 | B |
| ATOM | 4481 | OE1 | GLU | B | 17 | -35.288 | 10.314 | -28.434 | 1.00 91.95 | B |
| ATOM | 4482 | OE2 | GLU | B | 17 | -33.134 | 10.028 | -28.763 | 1.00 90.43 | B |

FIGURE 4- 60 -

```
ATOM   4483   C    GLU B  17    -37.224    7.348 -32.259  1.00 91.03      B
ATOM   4484   O    GLU B  17    -38.078    8.157 -31.845  1.00 91.44      B
ATOM   4485   OXT  GLU B  17    -37.503    6.374 -32.998  1.00 91.22      B
ATOM   4486   CB   MET B  36    -36.334  -11.620 -27.553  1.00 76.38      B
ATOM   4487   CG   MET B  36    -37.372  -12.686 -27.840  1.00 78.04      B
ATOM   4488   SD   MET B  36    -37.157  -14.134 -26.752  1.00 81.54      B
ATOM   4489   CE   MET B  36    -38.400  -13.822 -25.466  1.00 79.74      B
ATOM   4490   C    MET B  36    -35.753   -9.177 -27.576  1.00 73.65      B
ATOM   4491   O    MET B  36    -35.882   -8.943 -26.368  1.00 73.17      B
ATOM   4492   N    MET B  36    -36.335  -10.408 -29.715  1.00 74.87      B
ATOM   4493   CA   MET B  36    -36.588  -10.277 -28.256  1.00 74.97      B
ATOM   4494   N    VAL B  37    -34.909   -8.490 -28.341  1.00 71.96      B
ATOM   4495   CA   VAL B  37    -34.047   -7.451 -27.781  1.00 70.93      B
ATOM   4496   CB   VAL B  37    -32.565   -7.810 -27.996  1.00 70.57      B
ATOM   4497   CG1  VAL B  37    -31.676   -6.715 -27.426  1.00 70.35      B
ATOM   4498   CG2  VAL B  37    -32.252   -9.145 -27.342  1.00 69.89      B
ATOM   4499   C    VAL B  37    -34.330   -6.077 -28.393  1.00 70.82      B
ATOM   4500   O    VAL B  37    -33.966   -5.825 -29.549  1.00 70.37      B
ATOM   4501   N    TYR B  38    -34.969   -5.198 -27.607  1.00 69.95      B
ATOM   4502   CA   TYR B  38    -35.339   -3.850 -28.062  1.00 67.47      B
ATOM   4503   CB   TYR B  38    -36.849   -3.636 -27.890  1.00 67.34      B
ATOM   4504   CG   TYR B  38    -37.290   -3.611 -26.440  1.00 66.87      B
ATOM   4505   CD1  TYR B  38    -37.326   -4.782 -25.679  1.00 66.84      B
ATOM   4506   CE1  TYR B  38    -37.692   -4.756 -24.332  1.00 66.72      B
ATOM   4507   CD2  TYR B  38    -37.637   -2.407 -25.815  1.00 66.52      B
ATOM   4508   CE2  TYR B  38    -38.003   -2.371 -24.464  1.00 66.30      B
ATOM   4509   CZ   TYR B  38    -38.027   -3.551 -23.731  1.00 66.70      B
ATOM   4510   OH   TYR B  38    -38.372   -3.537 -22.398  1.00 66.38      B
ATOM   4511   C    TYR B  38    -34.614   -2.691 -27.373  1.00 65.44      B
ATOM   4512   O    TYR B  38    -34.145   -2.805 -26.238  1.00 63.71      B
ATOM   4513   N    ALA B  39    -34.548   -1.569 -28.082  1.00 64.00      B
ATOM   4514   CA   ALA B  39    -33.931   -0.347 -27.570  1.00 63.10      B
ATOM   4515   CB   ALA B  39    -32.952    0.220 -28.594  1.00 62.31      B
ATOM   4516   C    ALA B  39    -35.065    0.642 -27.324  1.00 62.16      B
ATOM   4517   O    ALA B  39    -35.943    0.304 -28.170  1.00 61.83      B
ATOM   4518   N    THR B  40    -35.064    1.292 -26.167  1.00 61.50      B
ATOM   4519   CA   THR B  40    -36.122    2.248 -25.859  1.00 61.45      B
ATOM   4520   CB   THR B  40    -35.986    2.776 -24.420  1.00 60.62      B
ATOM   4521   OG1  THR B  40    -34.632    3.186 -24.190  1.00 60.30      B
ATOM   4522   CG2  THR B  40    -36.365    1.694 -23.421  1.00 58.74      B
ATOM   4523   C    THR B  40    -36.109    3.414 -26.848  1.00 61.91      B
ATOM   4524   O    THR B  40    -35.057    3.809 -27.348  1.00 61.79      B
ATOM   4525   N    THR B  41    -37.287    3.958 -27.132  1.00 62.64      B
ATOM   4526   CA   THR B  41    -37.407    5.054 -28.087  1.00 62.94      B
ATOM   4527   CB   THR B  41    -37.915    4.524 -29.438  1.00 62.78      B
ATOM   4528   OG1  THR B  41    -38.405    5.615 -30.226  1.00 62.93      B
ATOM   4529   CG2  THR B  41    -39.033    3.503 -29.220  1.00 62.23      B
ATOM   4530   C    THR B  41    -38.345    6.160 -27.607  1.00 62.85      B
ATOM   4531   O    THR B  41    -39.154    5.950 -26.697  1.00 62.90      B
ATOM   4532   N    SER B  42    -38.241    7.332 -28.235  1.00 61.86      B
ATOM   4533   CA   SER B  42    -39.072    8.482 -27.872  1.00 61.44      B
ATOM   4534   CB   SER B  42    -38.601    9.733 -28.621  1.00 59.62      B
ATOM   4535   OG   SER B  42    -38.780    9.589 -30.013  1.00 59.08      B
ATOM   4536   C    SER B  42    -40.563    8.255 -28.142  1.00 61.79      B
ATOM   4537   O    SER B  42    -41.420    9.004 -27.659  1.00 61.76      B
ATOM   4538   N    ARG B  43    -40.865    7.213 -28.909  1.00 61.44      B
ATOM   4539   CA   ARG B  43    -42.243    6.887 -29.245  1.00 60.59      B
ATOM   4540   CB   ARG B  43    -42.254    5.869 -30.395  1.00 61.88      B
ATOM   4541   CG   ARG B  43    -41.514    6.380 -31.643  1.00 63.82      B
ATOM   4542   CD   ARG B  43    -41.763    5.545 -32.904  1.00 65.47      B
ATOM   4543   NE   ARG B  43    -40.721    4.551 -33.153  1.00 66.79      B
ATOM   4544   CZ   ARG B  43    -40.591    3.408 -32.488  1.00 68.42      B
ATOM   4545   NH1  ARG B  43    -41.447    3.100 -31.519  1.00 69.56      B
ATOM   4546   NH2  ARG B  43    -39.600    2.573 -32.793  1.00 68.06      B
ATOM   4547   C    ARG B  43    -43.007    6.367 -28.017  1.00 59.47      B
ATOM   4548   O    ARG B  43    -44.220    6.575 -27.892  1.00 59.27      B
ATOM   4549   N    SER B  44    -42.289    5.718 -27.101  1.00 57.37      B
ATOM   4550   CA   SER B  44    -42.903    5.189 -25.880  1.00 54.99      B
ATOM   4551   CB   SER B  44    -42.256    3.867 -25.466  1.00 55.14      B
ATOM   4552   OG   SER B  44    -41.001    4.093 -24.841  1.00 53.04      B
ATOM   4553   C    SER B  44    -42.722    6.186 -24.740  1.00 53.66      B
ATOM   4554   O    SER B  44    -43.037    5.886 -23.583  1.00 52.44      B
ATOM   4555   N    ALA B  45    -42.193    7.362 -25.076  1.00 51.08      B
ATOM   4556   CA   ALA B  45    -41.959    8.414 -24.095  1.00 49.14      B
ATOM   4557   CB   ALA B  45    -41.244    9.584 -24.755  1.00 49.11      B
ATOM   4558   C    ALA B  45    -43.274    8.879 -23.464  1.00 47.72      B
```

FIGURE 4- 61 -

```
ATOM   4559  O   ALA B  45     -43.375   9.033 -22.243  1.00 47.20      B
ATOM   4560  N   SER B  46     -44.273   9.106 -24.305  1.00 45.50      B
ATOM   4561  CA  SER B  46     -45.585   9.531 -23.830  1.00 42.96      B
ATOM   4562  CB  SER B  46     -46.606   9.409 -24.959  1.00 42.58      B
ATOM   4563  OG  SER B  46     -47.928   9.443 -24.454  1.00 41.61      B
ATOM   4564  C   SER B  46     -45.992   8.627 -22.679  1.00 42.28      B
ATOM   4565  O   SER B  46     -46.386   9.084 -21.609  1.00 41.64      B
ATOM   4566  N   LEU B  47     -45.869   7.330 -22.918  1.00 41.74      B
ATOM   4567  CA  LEU B  47     -46.222   6.321 -21.944  1.00 41.12      B
ATOM   4568  CB  LEU B  47     -45.811   4.954 -22.476  1.00 43.20      B
ATOM   4569  CG  LEU B  47     -46.285   3.763 -21.656  1.00 44.36      B
ATOM   4570  CD1 LEU B  47     -47.781   3.879 -21.398  1.00 45.20      B
ATOM   4571  CD2 LEU B  47     -45.954   2.483 -22.405  1.00 46.57      B
ATOM   4572  C   LEU B  47     -45.583   6.560 -20.580  1.00 41.00      B
ATOM   4573  O   LEU B  47     -46.238   6.400 -19.542  1.00 41.61      B
ATOM   4574  N   ARG B  48     -44.312   6.950 -20.589  1.00 39.05      B
ATOM   4575  CA  ARG B  48     -43.557   7.205 -19.365  1.00 38.35      B
ATOM   4576  CB  ARG B  48     -42.063   7.265 -19.713  1.00 38.23      B
ATOM   4577  CG  ARG B  48     -41.173   8.060 -18.780  1.00 37.97      B
ATOM   4578  CD  ARG B  48     -41.091   7.491 -17.372  1.00 39.99      B
ATOM   4579  NE  ARG B  48     -40.729   6.080 -17.343  1.00 41.95      B
ATOM   4580  CZ  ARG B  48     -40.296   5.430 -16.262  1.00 44.71      B
ATOM   4581  NH1 ARG B  48     -40.144   6.055 -15.092  1.00 42.96      B
ATOM   4582  NH2 ARG B  48     -40.047   4.127 -16.346  1.00 47.12      B
ATOM   4583  C   ARG B  48     -44.004   8.474 -18.623  1.00 38.43      B
ATOM   4584  O   ARG B  48     -44.150   8.473 -17.387  1.00 37.38      B
ATOM   4585  N   GLN B  49     -44.233   9.544 -19.378  1.00 36.66      B
ATOM   4586  CA  GLN B  49     -44.657  10.810 -18.795  1.00 36.95      B
ATOM   4587  CB  GLN B  49     -44.922  11.826 -19.900  1.00 36.26      B
ATOM   4588  CG  GLN B  49     -43.834  11.898 -20.946  1.00 36.17      B
ATOM   4589  CD  GLN B  49     -44.178  12.840 -22.072  1.00 35.82      B
ATOM   4590  OE1 GLN B  49     -44.187  14.058 -21.897  1.00 35.28      B
ATOM   4591  NE2 GLN B  49     -44.476  12.280 -23.240  1.00 37.70      B
ATOM   4592  C   GLN B  49     -45.931  10.615 -17.979  1.00 37.70      B
ATOM   4593  O   GLN B  49     -46.189  11.332 -17.008  1.00 37.21      B
ATOM   4594  N   LYS B  50     -46.725   9.634 -18.383  1.00 37.26      B
ATOM   4595  CA  LYS B  50     -47.977   9.352 -17.708  1.00 38.38      B
ATOM   4596  CB  LYS B  50     -48.805   8.381 -18.559  1.00 39.51      B
ATOM   4597  CG  LYS B  50     -50.303   8.357 -18.269  1.00 38.95      B
ATOM   4598  CD  LYS B  50     -50.652   7.434 -17.127  1.00 39.43      B
ATOM   4599  CE  LYS B  50     -52.158   7.227 -17.041  1.00 40.33      B
ATOM   4600  NZ  LYS B  50     -52.512   6.172 -16.038  1.00 41.12      B
ATOM   4601  C   LYS B  50     -47.699   8.758 -16.340  1.00 38.93      B
ATOM   4602  O   LYS B  50     -48.416   9.033 -15.378  1.00 39.51      B
ATOM   4603  N   LYS B  51     -46.642   7.957 -16.248  1.00 39.27      B
ATOM   4604  CA  LYS B  51     -46.305   7.315 -14.985  1.00 38.26      B
ATOM   4605  CB  LYS B  51     -45.440   6.078 -15.216  1.00 39.35      B
ATOM   4606  CG  LYS B  51     -45.213   5.266 -13.940  1.00 41.97      B
ATOM   4607  CD  LYS B  51     -44.153   4.204 -14.134  1.00 44.95      B
ATOM   4608  CE  LYS B  51     -44.004   3.332 -12.889  1.00 46.29      B
ATOM   4609  NZ  LYS B  51     -42.861   2.360 -13.003  1.00 46.62      B
ATOM   4610  C   LYS B  51     -45.583   8.228 -14.018  1.00 37.15      B
ATOM   4611  O   LYS B  51     -45.754   8.108 -12.811  1.00 38.29      B
ATOM   4612  N   VAL B  52     -44.763   9.132 -14.538  1.00 35.50      B
ATOM   4613  CA  VAL B  52     -44.022  10.030 -13.662  1.00 33.88      B
ATOM   4614  CB  VAL B  52     -42.623  10.358 -14.234  1.00 32.97      B
ATOM   4615  CG1 VAL B  52     -41.893   9.075 -14.577  1.00 30.24      B
ATOM   4616  CG2 VAL B  52     -42.743  11.258 -15.448  1.00 31.14      B
ATOM   4617  C   VAL B  52     -44.743  11.340 -13.388  1.00 32.86      B
ATOM   4618  O   VAL B  52     -44.241  12.181 -12.653  1.00 33.41      B
ATOM   4619  N   THR B  53     -45.921  11.517 -13.968  1.00 31.49      B
ATOM   4620  CA  THR B  53     -46.659  12.754 -13.756  1.00 31.20      B
ATOM   4621  CB  THR B  53     -47.284  13.276 -15.082  1.00 31.07      B
ATOM   4622  OG1 THR B  53     -46.251  13.505 -16.048  1.00 29.61      B
ATOM   4623  CG2 THR B  53     -48.039  14.573 -14.841  1.00 27.60      B
ATOM   4624  C   THR B  53     -47.762  12.611 -12.710  1.00 30.92      B
ATOM   4625  O   THR B  53     -48.827  12.048 -12.972  1.00 31.76      B
ATOM   4626  N   PHE B  54     -47.501  13.133 -11.522  1.00 30.28      B
ATOM   4627  CA  PHE B  54     -48.479  13.073 -10.452  1.00 30.54      B
ATOM   4628  CB  PHE B  54     -48.445  11.693  -9.787  1.00 29.91      B
ATOM   4629  CG  PHE B  54     -47.098  11.304  -9.247  1.00 30.01      B
ATOM   4630  CD1 PHE B  54     -46.685  11.731  -7.996  1.00 30.41      B
ATOM   4631  CD2 PHE B  54     -46.244  10.493  -9.992  1.00 31.37      B
ATOM   4632  CE1 PHE B  54     -45.441  11.351  -7.490  1.00 31.08      B
ATOM   4633  CE2 PHE B  54     -45.003  10.110  -9.498  1.00 29.95      B
ATOM   4634  CZ  PHE B  54     -44.603  10.541  -8.242  1.00 30.74      B
```

FIGURE 4-62-

```
ATOM   4635  C    PHE B  54     -48.236  14.171  -9.426  1.00 30.76      B
ATOM   4636  O    PHE B  54     -47.271  14.928  -9.529  1.00 30.65      B
ATOM   4637  N    ASP B  55     -49.124  14.255  -8.442  1.00 31.19      B
ATOM   4638  CA   ASP B  55     -49.018  15.260  -7.389  1.00 29.85      B
ATOM   4639  CB   ASP B  55     -50.408  15.770  -7.013  1.00 29.64      B
ATOM   4640  CG   ASP B  55     -50.364  17.055  -6.214  1.00 30.60      B
ATOM   4641  OD1  ASP B  55     -49.253  17.541  -5.920  1.00 31.01      B
ATOM   4642  OD2  ASP B  55     -51.444  17.586  -5.881  1.00 30.97      B
ATOM   4643  C    ASP B  55     -48.354  14.675  -6.153  1.00 28.70      B
ATOM   4644  O    ASP B  55     -48.773  13.631  -5.657  1.00 26.99      B
ATOM   4645  N    ARG B  56     -47.303  15.336  -5.677  1.00 27.94      B
ATOM   4646  CA   ARG B  56     -46.620  14.889  -4.480  1.00 27.81      B
ATOM   4647  CB   ARG B  56     -45.146  15.285  -4.486  1.00 25.49      B
ATOM   4648  CG   ARG B  56     -44.289  14.562  -5.489  1.00 24.98      B
ATOM   4649  CD   ARG B  56     -44.604  15.022  -6.895  1.00 25.61      B
ATOM   4650  NE   ARG B  56     -44.386  16.454  -7.085  1.00 23.83      B
ATOM   4651  CZ   ARG B  56     -43.192  17.028  -7.183  1.00 23.65      B
ATOM   4652  NH1  ARG B  56     -42.085  16.294  -7.109  1.00 20.11      B
ATOM   4653  NH2  ARG B  56     -43.108  18.342  -7.364  1.00 22.84      B
ATOM   4654  C    ARG B  56     -47.321  15.636  -3.369  1.00 29.64      B
ATOM   4655  O    ARG B  56     -47.552  16.836  -3.492  1.00 30.86      B
ATOM   4656  N    LEU B  57     -47.674  14.931  -2.299  1.00 30.79      B
ATOM   4657  CA   LEU B  57     -48.342  15.554  -1.164  1.00 32.28      B
ATOM   4658  CB   LEU B  57     -49.817  15.145  -1.158  1.00 35.02      B
ATOM   4659  CG   LEU B  57     -50.823  16.071  -0.464  1.00 38.41      B
ATOM   4660  CD1  LEU B  57     -50.763  17.486  -1.069  1.00 38.28      B
ATOM   4661  CD2  LEU B  57     -52.223  15.477  -0.617  1.00 38.23      B
ATOM   4662  C    LEU B  57     -47.612  15.070   0.097  1.00 32.21      B
ATOM   4663  O    LEU B  57     -48.102  14.229   0.857  1.00 33.45      B
ATOM   4664  N    GLN B  58     -46.425  15.630   0.299  1.00 30.76      B
ATOM   4665  CA   GLN B  58     -45.630  15.283   1.397  1.00 29.11      B
ATOM   4666  CB   GLN B  58     -44.131  15.725   0.986  1.00 27.37      B
ATOM   4667  CG   GLN B  58     -42.999  15.347   1.888  1.00 26.33      B
ATOM   4668  CD   GLN B  58     -41.675  15.801   1.309  1.00 26.95      B
ATOM   4669  OE1  GLN B  58     -41.526  16.953   0.898  1.00 25.02      B
ATOM   4670  NE2  GLN B  58     -40.707  14.901   1.270  1.00 27.17      B
ATOM   4671  C    GLN B  58     -45.895  15.845   2.775  1.00 29.50      B
ATOM   4672  O    GLN B  58     -46.380  16.968   2.893  1.00 28.89      B
ATOM   4673  N    VAL B  59     -45.659  15.046   3.815  1.00 30.63      B
ATOM   4674  CA   VAL B  59     -45.941  15.439   5.203  1.00 31.12      B
ATOM   4675  CB   VAL B  59     -47.279  14.827   5.724  1.00 31.62      B
ATOM   4676  CG1  VAL B  59     -47.507  15.258   7.168  1.00 27.78      B
ATOM   4677  CG2  VAL B  59     -48.465  15.264   4.841  1.00 30.48      B
ATOM   4678  C    VAL B  59     -44.822  14.937   6.119  1.00 30.90      B
ATOM   4679  O    VAL B  59     -44.660  13.736   6.280  1.00 31.76      B
ATOM   4680  N    LEU B  60     -44.077  15.848   6.737  1.00 31.05      B
ATOM   4681  CA   LEU B  60     -42.971  15.461   7.612  1.00 32.69      B
ATOM   4682  CB   LEU B  60     -41.788  16.405   7.391  1.00 32.81      B
ATOM   4683  CG   LEU B  60     -41.449  16.669   5.925  1.00 33.96      B
ATOM   4684  CD1  LEU B  60     -40.608  17.934   5.809  1.00 32.41      B
ATOM   4685  CD2  LEU B  60     -40.743  15.458   5.343  1.00 33.11      B
ATOM   4686  C    LEU B  60     -43.312  15.438   9.103  1.00 33.75      B
ATOM   4687  O    LEU B  60     -44.287  16.050   9.531  1.00 34.37      B
ATOM   4688  N    ASP B  61     -42.491  14.730   9.883  1.00 34.83      B
ATOM   4689  CA   ASP B  61     -42.672  14.613  11.331  1.00 34.33      B
ATOM   4690  CB   ASP B  61     -43.263  13.251  11.697  1.00 34.68      B
ATOM   4691  CG   ASP B  61     -42.550  12.098  11.016  1.00 34.76      B
ATOM   4692  OD1  ASP B  61     -41.306  12.087  10.982  1.00 36.22      B
ATOM   4693  OD2  ASP B  61     -43.242  11.188  10.523  1.00 36.40      B
ATOM   4694  C    ASP B  61     -41.367  14.807  12.099  1.00 35.65      B
ATOM   4695  O    ASP B  61     -40.356  15.242  11.539  1.00 35.62      B
ATOM   4696  N    ASP B  62     -41.387  14.469  13.386  1.00 36.10      B
ATOM   4697  CA   ASP B  62     -40.202  14.643  14.211  1.00 35.88      B
ATOM   4698  CB   ASP B  62     -40.573  14.585  15.689  1.00 37.45      B
ATOM   4699  CG   ASP B  62     -41.263  15.846  16.155  1.00 39.44      B
ATOM   4700  OD1  ASP B  62     -40.739  16.942  15.872  1.00 40.87      B
ATOM   4701  OD2  ASP B  62     -42.322  15.748  16.808  1.00 41.78      B
ATOM   4702  C    ASP B  62     -39.065  13.676  13.930  1.00 35.08      B
ATOM   4703  O    ASP B  62     -37.906  13.994  14.196  1.00 34.94      B
ATOM   4704  N    HIS B  63     -39.382  12.498  13.405  1.00 33.62      B
ATOM   4705  CA   HIS B  63     -38.339  11.532  13.098  1.00 32.66      B
ATOM   4706  CB   HIS B  63     -38.945  10.179  12.751  1.00 34.03      B
ATOM   4707  CG   HIS B  63     -39.354   9.384  13.948  1.00 37.06      B
ATOM   4708  CD2  HIS B  63     -40.543   8.834  14.293  1.00 37.58      B
ATOM   4709  ND1  HIS B  63     -38.475   9.065  14.961  1.00 37.55      B
ATOM   4710  CE1  HIS B  63     -39.105   8.352  15.876  1.00 38.05      B
```

FIGURE 4- 63 -

```
ATOM   4711  NE2 HIS B  63     -40.361   8.198  15.495  1.00 37.25      B
ATOM   4712  C   HIS B  63     -37.540  12.066  11.928  1.00 32.32      B
ATOM   4713  O   HIS B  63     -36.311  11.970  11.900  1.00 30.95      B
ATOM   4714  N   TYR B  64     -38.256  12.637  10.966  1.00 31.67      B
ATOM   4715  CA  TYR B  64     -37.641  13.219   9.789  1.00 31.25      B
ATOM   4716  CB  TYR B  64     -38.721  13.754   8.844  1.00 31.92      B
ATOM   4717  CG  TYR B  64     -38.195  14.393   7.569  1.00 32.70      B
ATOM   4718  CD1 TYR B  64     -37.919  13.626   6.439  1.00 31.62      B
ATOM   4719  CE1 TYR B  64     -37.435  14.214   5.273  1.00 31.89      B
ATOM   4720  CD2 TYR B  64     -37.968  15.770   7.497  1.00 32.60      B
ATOM   4721  CE2 TYR B  64     -37.482  16.367   6.330  1.00 31.73      B
ATOM   4722  CZ  TYR B  64     -37.220  15.587   5.226  1.00 31.56      B
ATOM   4723  OH  TYR B  64     -36.753  16.172   4.075  1.00 31.72      B
ATOM   4724  C   TYR B  64     -36.761  14.368  10.262  1.00 31.03      B
ATOM   4725  O   TYR B  64     -35.573  14.422   9.960  1.00 31.87      B
ATOM   4726  N   ARG B  65     -37.351  15.282  11.022  1.00 30.80      B
ATOM   4727  CA  ARG B  65     -36.608  16.431  11.511  1.00 31.18      B
ATOM   4728  CB  ARG B  65     -37.553  17.410  12.221  1.00 31.44      B
ATOM   4729  CG  ARG B  65     -38.434  18.198  11.249  1.00 32.81      B
ATOM   4730  CD  ARG B  65     -39.309  19.207  11.969  1.00 36.41      B
ATOM   4731  NE  ARG B  65     -40.341  18.563  12.785  1.00 37.40      B
ATOM   4732  CZ  ARG B  65     -41.575  18.291  12.367  1.00 36.96      B
ATOM   4733  NH1 ARG B  65     -41.950  18.608  11.132  1.00 35.51      B
ATOM   4734  NH2 ARG B  65     -42.433  17.697  13.189  1.00 36.42      B
ATOM   4735  C   ARG B  65     -35.474  16.001  12.420  1.00 30.65      B
ATOM   4736  O   ARG B  65     -34.445  16.668  12.509  1.00 32.22      B
ATOM   4737  N   ASP B  66     -35.656  14.871  13.082  1.00 29.93      B
ATOM   4738  CA  ASP B  66     -34.638  14.348  13.974  1.00 30.36      B
ATOM   4739  CB  ASP B  66     -35.208  13.185  14.776  1.00 32.50      B
ATOM   4740  CG  ASP B  66     -35.701  13.600  16.134  1.00 33.23      B
ATOM   4741  OD1 ASP B  66     -36.196  14.740  16.261  1.00 32.66      B
ATOM   4742  OD2 ASP B  66     -35.600  12.768  17.066  1.00 35.13      B
ATOM   4743  C   ASP B  66     -33.405  13.869  13.213  1.00 30.24      B
ATOM   4744  O   ASP B  66     -32.275  14.188  13.592  1.00 30.89      B
ATOM   4745  N   VAL B  67     -33.625  13.099  12.147  1.00 28.50      B
ATOM   4746  CA  VAL B  67     -32.525  12.554  11.351  1.00 25.20      B
ATOM   4747  CB  VAL B  67     -33.034  11.473  10.348  1.00 24.83      B
ATOM   4748  CG1 VAL B  67     -31.891  10.970   9.484  1.00 21.01      B
ATOM   4749  CG2 VAL B  67     -33.661  10.310  11.114  1.00 21.64      B
ATOM   4750  C   VAL B  67     -31.775  13.635  10.593  1.00 23.91      B
ATOM   4751  O   VAL B  67     -30.539  13.615  10.535  1.00 21.45      B
ATOM   4752  N   LEU B  68     -32.524  14.577  10.021  1.00 23.61      B
ATOM   4753  CA  LEU B  68     -31.922  15.673   9.261  1.00 23.30      B
ATOM   4754  CB  LEU B  68     -32.992  16.667   8.803  1.00 20.46      B
ATOM   4755  CG  LEU B  68     -32.598  17.879   7.946  1.00 17.31      B
ATOM   4756  CD1 LEU B  68     -31.750  17.482   6.762  1.00 17.18      B
ATOM   4757  CD2 LEU B  68     -33.857  18.547   7.467  1.00 15.82      B
ATOM   4758  C   LEU B  68     -30.890  16.373  10.125  1.00 24.13      B
ATOM   4759  O   LEU B  68     -29.733  16.529   9.716  1.00 25.85      B
ATOM   4760  N   LYS B  69     -31.293  16.773  11.326  1.00 22.91      B
ATOM   4761  CA  LYS B  69     -30.359  17.431  12.229  1.00 24.90      B
ATOM   4762  CB  LYS B  69     -31.033  17.708  13.574  1.00 25.39      B
ATOM   4763  CG  LYS B  69     -32.164  18.698  13.493  1.00 25.72      B
ATOM   4764  CD  LYS B  69     -32.792  18.894  14.842  1.00 28.10      B
ATOM   4765  CE  LYS B  69     -33.891  19.939  14.783  1.00 30.95      B
ATOM   4766  NZ  LYS B  69     -34.476  20.203  16.133  1.00 32.44      B
ATOM   4767  C   LYS B  69     -29.090  16.594  12.444  1.00 24.31      B
ATOM   4768  O   LYS B  69     -27.986  17.114  12.453  1.00 23.27      B
ATOM   4769  N   GLU B  70     -29.252  15.289  12.611  1.00 26.68      B
ATOM   4770  CA  GLU B  70     -28.108  14.405  12.826  1.00 26.82      B
ATOM   4771  CB  GLU B  70     -28.605  12.990  13.139  1.00 27.21      B
ATOM   4772  CG  GLU B  70     -29.186  12.848  14.545  1.00 29.10      B
ATOM   4773  CD  GLU B  70     -29.945  11.539  14.752  1.00 34.68      B
ATOM   4774  OE1 GLU B  70     -29.461  10.473  14.302  1.00 34.64      B
ATOM   4775  OE2 GLU B  70     -31.032  11.576  15.380  1.00 37.74      B
ATOM   4776  C   GLU B  70     -27.223  14.412  11.591  1.00 26.18      B
ATOM   4777  O   GLU B  70     -26.003  14.568  11.674  1.00 24.91      B
ATOM   4778  N   MET B  71     -27.851  14.261  10.436  1.00 26.47      B
ATOM   4779  CA  MET B  71     -27.104  14.263   9.194  1.00 26.96      B
ATOM   4780  CB  MET B  71     -28.058  14.064   8.027  1.00 28.04      B
ATOM   4781  CG  MET B  71     -28.717  12.708   7.985  1.00 25.80      B
ATOM   4782  SD  MET B  71     -29.907  12.740   6.651  1.00 29.64      B
ATOM   4783  CE  MET B  71     -28.969  12.076   5.298  1.00 26.00      B
ATOM   4784  C   MET B  71     -26.334  15.572   9.025  1.00 25.88      B
ATOM   4785  O   MET B  71     -25.175  15.570   8.614  1.00 25.19      B
ATOM   4786  N   LYS B  72     -26.987  16.685   9.351  1.00 24.73      B
```

FIGURE 4- 64 -

```
ATOM   4787  CA   LYS B  72     -26.376  18.009   9.234  1.00 23.10      B
ATOM   4788  CB   LYS B  72     -27.413  19.092   9.550  1.00 19.09      B
ATOM   4789  CG   LYS B  72     -28.582  19.120   8.603  1.00 17.45      B
ATOM   4790  CD   LYS B  72     -29.502  20.312   8.866  1.00 15.87      B
ATOM   4791  CE   LYS B  72     -28.870  21.614   8.446  1.00 13.81      B
ATOM   4792  NZ   LYS B  72     -29.725  22.773   8.777  1.00 12.83      B
ATOM   4793  C    LYS B  72     -25.138  18.221  10.126  1.00 22.74      B
ATOM   4794  O    LYS B  72     -24.137  18.770   9.680  1.00 20.94      B
ATOM   4795  N    ALA B  73     -25.211  17.800  11.386  1.00 23.48      B
ATOM   4796  CA   ALA B  73     -24.092  17.974  12.305  1.00 24.20      B
ATOM   4797  CB   ALA B  73     -24.429  17.379  13.650  1.00 21.16      B
ATOM   4798  C    ALA B  73     -22.842  17.315  11.731  1.00 26.33      B
ATOM   4799  O    ALA B  73     -21.727  17.812  11.912  1.00 27.33      B
ATOM   4800  N    LYS B  74     -23.034  16.197  11.033  1.00 27.26      B
ATOM   4801  CA   LYS B  74     -21.926  15.481  10.416  1.00 27.24      B
ATOM   4802  CB   LYS B  74     -22.346  14.080  10.000  1.00 29.34      B
ATOM   4803  CG   LYS B  74     -22.459  13.066  11.116  1.00 32.45      B
ATOM   4804  CD   LYS B  74     -22.841  11.734  10.488  1.00 38.25      B
ATOM   4805  CE   LYS B  74     -22.838  10.561  11.454  1.00 40.62      B
ATOM   4806  NZ   LYS B  74     -23.280   9.323  10.718  1.00 43.65      B
ATOM   4807  C    LYS B  74     -21.443  16.222   9.184  1.00 27.72      B
ATOM   4808  O    LYS B  74     -20.257  16.195   8.871  1.00 29.65      B
ATOM   4809  N    ALA B  75     -22.359  16.874   8.473  1.00 27.55      B
ATOM   4810  CA   ALA B  75     -21.983  17.626   7.280  1.00 27.08      B
ATOM   4811  CB   ALA B  75     -23.229  18.079   6.533  1.00 27.92      B
ATOM   4812  C    ALA B  75     -21.132  18.836   7.673  1.00 26.53      B
ATOM   4813  O    ALA B  75     -20.281  19.284   6.905  1.00 24.61      B
ATOM   4814  N    SER B  76     -21.369  19.335   8.885  1.00 27.44      B
ATOM   4815  CA   SER B  76     -20.666  20.493   9.450  1.00 29.73      B
ATOM   4816  CB   SER B  76     -21.132  20.737  10.888  1.00 31.51      B
ATOM   4817  OG   SER B  76     -22.438  21.289  10.914  1.00 37.18      B
ATOM   4818  C    SER B  76     -19.151  20.377   9.456  1.00 29.57      B
ATOM   4819  O    SER B  76     -18.437  21.378   9.304  1.00 29.39      B
ATOM   4820  N    THR B  77     -18.675  19.151   9.648  1.00 28.58      B
ATOM   4821  CA   THR B  77     -17.252  18.845   9.696  1.00 27.31      B
ATOM   4822  CB   THR B  77     -17.035  17.375  10.153  1.00 28.88      B
ATOM   4823  OG1  THR B  77     -17.404  16.482   9.092  1.00 30.52      B
ATOM   4824  CG2  THR B  77     -17.902  17.049  11.365  1.00 27.22      B
ATOM   4825  C    THR B  77     -16.559  19.031   8.336  1.00 26.88      B
ATOM   4826  O    THR B  77     -15.356  19.282   8.283  1.00 26.67      B
ATOM   4827  N    VAL B  78     -17.325  18.916   7.249  1.00 25.34      B
ATOM   4828  CA   VAL B  78     -16.804  19.014   5.883  1.00 23.65      B
ATOM   4829  CB   VAL B  78     -17.832  18.456   4.866  1.00 21.39      B
ATOM   4830  CG1  VAL B  78     -17.260  18.500   3.478  1.00 18.26      B
ATOM   4831  CG2  VAL B  78     -18.206  17.048   5.219  1.00 19.38      B
ATOM   4832  C    VAL B  78     -16.371  20.389   5.372  1.00 25.42      B
ATOM   4833  O    VAL B  78     -17.095  21.368   5.526  1.00 26.26      B
ATOM   4834  N    LYS B  79     -15.186  20.447   4.756  1.00 26.69      B
ATOM   4835  CA   LYS B  79     -14.670  21.686   4.168  1.00 27.82      B
ATOM   4836  CB   LYS B  79     -13.334  22.102   4.780  1.00 28.45      B
ATOM   4837  CG   LYS B  79     -12.760  23.365   4.125  1.00 30.62      B
ATOM   4838  CD   LYS B  79     -11.531  23.881   4.851  1.00 32.63      B
ATOM   4839  CE   LYS B  79     -10.956  25.145   4.195  1.00 35.01      B
ATOM   4840  NZ   LYS B  79      -9.933  25.849   5.061  1.00 34.36      B
ATOM   4841  C    LYS B  79     -14.479  21.471   2.673  1.00 27.52      B
ATOM   4842  O    LYS B  79     -13.413  21.069   2.219  1.00 26.91      B
ATOM   4843  N    ALA B  80     -15.532  21.738   1.914  1.00 28.65      B
ATOM   4844  CA   ALA B  80     -15.512  21.566   0.472  1.00 28.61      B
ATOM   4845  CB   ALA B  80     -16.934  21.496  -0.058  1.00 29.21      B
ATOM   4846  C    ALA B  80     -14.775  22.710  -0.179  1.00 28.27      B
ATOM   4847  O    ALA B  80     -14.859  23.843   0.275  1.00 29.25      B
ATOM   4848  N    LYS B  81     -14.066  22.401  -1.255  1.00 29.43      B
ATOM   4849  CA   LYS B  81     -13.301  23.392  -1.991  1.00 32.94      B
ATOM   4850  CB   LYS B  81     -11.895  22.876  -2.277  1.00 38.35      B
ATOM   4851  CG   LYS B  81     -10.910  22.948  -1.120  1.00 46.30      B
ATOM   4852  CD   LYS B  81      -9.686  22.090  -1.460  1.00 50.65      B
ATOM   4853  CE   LYS B  81      -8.557  22.223  -0.448  1.00 52.59      B
ATOM   4854  NZ   LYS B  81      -7.450  21.272  -0.794  1.00 53.97      B
ATOM   4855  C    LYS B  81     -13.938  23.758  -3.321  1.00 32.21      B
ATOM   4856  O    LYS B  81     -14.729  23.012  -3.886  1.00 32.49      B
ATOM   4857  N    LEU B  82     -13.553  24.924  -3.813  1.00 31.55      B
ATOM   4858  CA   LEU B  82     -14.016  25.455  -5.082  1.00 29.74      B
ATOM   4859  CB   LEU B  82     -13.977  26.983  -5.004  1.00 28.83      B
ATOM   4860  CG   LEU B  82     -14.503  27.819  -6.160  1.00 28.44      B
ATOM   4861  CD1  LEU B  82     -15.924  27.404  -6.482  1.00 29.39      B
ATOM   4862  CD2  LEU B  82     -14.439  29.283  -5.781  1.00 25.91      B
```

FIGURE 4- 65 -

```
ATOM   4863  C   LEU B  82     -13.061  24.940  -6.169  1.00 30.26      B
ATOM   4864  O   LEU B  82     -11.841  25.021  -6.022  1.00 30.34      B
ATOM   4865  N   LEU B  83     -13.606  24.396  -7.251  1.00 31.21      B
ATOM   4866  CA  LEU B  83     -12.776  23.882  -8.333  1.00 30.76      B
ATOM   4867  CB  LEU B  83     -13.493  22.761  -9.081  1.00 29.95      B
ATOM   4868  CG  LEU B  83     -12.994  21.341  -8.798  1.00 30.62      B
ATOM   4869  CD1 LEU B  83     -13.337  20.968  -7.374  1.00 28.61      B
ATOM   4870  CD2 LEU B  83     -13.619  20.356  -9.788  1.00 28.98      B
ATOM   4871  C   LEU B  83     -12.418  24.975  -9.318  1.00 32.65      B
ATOM   4872  O   LEU B  83     -13.195  25.895  -9.544  1.00 33.33      B
ATOM   4873  N   SER B  84     -11.226  24.883  -9.898  1.00 34.61      B
ATOM   4874  CA  SER B  84     -10.786  25.866 -10.885  1.00 34.90      B
ATOM   4875  CB  SER B  84      -9.294  25.707 -11.165  1.00 34.73      B
ATOM   4876  OG  SER B  84      -9.017  24.402 -11.649  1.00 33.52      B
ATOM   4877  C   SER B  84     -11.550  25.571 -12.162  1.00 35.27      B
ATOM   4878  O   SER B  84     -11.977  24.433 -12.382  1.00 34.32      B
ATOM   4879  N   ILE B  85     -11.728  26.587 -12.996  1.00 35.62      B
ATOM   4880  CA  ILE B  85     -12.421  26.387 -14.258  1.00 37.18      B
ATOM   4881  CB  ILE B  85     -12.335  27.639 -15.149  1.00 36.44      B
ATOM   4882  CG2 ILE B  85     -12.841  27.331 -16.549  1.00 34.24      B
ATOM   4883  CG1 ILE B  85     -13.148  28.763 -14.504  1.00 38.37      B
ATOM   4884  CD1 ILE B  85     -13.187  30.056 -15.296  1.00 39.76      B
ATOM   4885  C   ILE B  85     -11.732  25.223 -14.956  1.00 38.34      B
ATOM   4886  O   ILE B  85     -12.376  24.267 -15.403  1.00 38.17      B
ATOM   4887  N   GLU B  86     -10.410  25.298 -15.020  1.00 39.25      B
ATOM   4888  CA  GLU B  86      -9.635  24.256 -15.661  1.00 40.68      B
ATOM   4889  CB  GLU B  86      -8.150  24.513 -15.488  1.00 43.54      B
ATOM   4890  CG  GLU B  86      -7.312  23.635 -16.386  1.00 49.55      B
ATOM   4891  CD  GLU B  86      -5.837  23.884 -16.220  1.00 51.64      B
ATOM   4892  OE1 GLU B  86      -5.440  25.070 -16.243  1.00 52.11      B
ATOM   4893  OE2 GLU B  86      -5.081  22.897 -16.073  1.00 53.55      B
ATOM   4894  C   GLU B  86      -9.972  22.894 -15.095  1.00 40.25      B
ATOM   4895  O   GLU B  86     -10.278  21.966 -15.841  1.00 40.24      B
ATOM   4896  N   GLU B  87      -9.913  22.774 -13.772  1.00 40.65      B
ATOM   4897  CA  GLU B  87     -10.226  21.511 -13.106  1.00 41.01      B
ATOM   4898  CB  GLU B  87     -10.198  21.677 -11.591  1.00 43.30      B
ATOM   4899  CG  GLU B  87      -8.839  21.438 -10.971  1.00 46.74      B
ATOM   4900  CD  GLU B  87      -8.913  21.327  -9.460  1.00 48.00      B
ATOM   4901  OE1 GLU B  87      -9.079  22.376  -8.787  1.00 48.92      B
ATOM   4902  OE2 GLU B  87      -8.819  20.183  -8.957  1.00 46.45      B
ATOM   4903  C   GLU B  87     -11.591  20.993 -13.507  1.00 40.01      B
ATOM   4904  O   GLU B  87     -11.776  19.793 -13.711  1.00 39.44      B
ATOM   4905  N   ALA B  88     -12.549  21.908 -13.601  1.00 38.77      B
ATOM   4906  CA  ALA B  88     -13.903  21.555 -13.974  1.00 36.80      B
ATOM   4907  CB  ALA B  88     -14.806  22.754 -13.825  1.00 37.58      B
ATOM   4908  C   ALA B  88     -13.910  21.030 -15.410  1.00 36.48      B
ATOM   4909  O   ALA B  88     -14.582  20.116 -15.755  1.00 36.99      B
ATOM   4910  N   CYS B  89     -13.150  21.759 -16.254  1.00 35.91      B
ATOM   4911  CA  CYS B  89     -13.109  21.335 -17.650  1.00 35.51      B
ATOM   4912  CB  CYS B  89     -12.296  22.414 -18.436  1.00 34.24      B
ATOM   4913  SG  CYS B  89     -13.192  23.993 -18.690  1.00 32.72      B
ATOM   4914  C   CYS B  89     -12.563  19.930 -17.866  1.00 36.05      B
ATOM   4915  O   CYS B  89     -13.094  19.215 -18.676  1.00 36.23      B
ATOM   4916  N   LYS B  90     -11.516  19.633 -17.126  1.00 37.07      B
ATOM   4917  CA  LYS B  90     -10.898  18.322 -17.262  1.00 37.97      B
ATOM   4918  CB  LYS B  90      -9.598  18.254 -16.460  1.00 40.61      B
ATOM   4919  CG  LYS B  90      -8.995  16.865 -16.438  1.00 46.19      B
ATOM   4920  CD  LYS B  90      -7.545  16.821 -16.065  1.00 49.99      B
ATOM   4921  CE  LYS B  90      -6.951  15.468 -16.440  1.00 52.03      B
ATOM   4922  NZ  LYS B  90      -5.531  15.336 -16.015  1.00 55.58      B
ATOM   4923  C   LYS B  90     -11.803  17.161 -16.855  1.00 37.76      B
ATOM   4924  O   LYS B  90     -11.648  16.036 -17.348  1.00 37.45      B
ATOM   4925  N   LEU B  91     -12.744  17.431 -15.954  1.00 36.83      B
ATOM   4926  CA  LEU B  91     -13.675  16.411 -15.439  1.00 34.41      B
ATOM   4927  CB  LEU B  91     -14.364  16.880 -14.218  1.00 32.72      B
ATOM   4928  CG  LEU B  91     -13.591  16.768 -12.913  1.00 31.33      B
ATOM   4929  CD1 LEU B  91     -14.335  17.505 -11.822  1.00 32.20      B
ATOM   4930  CD2 LEU B  91     -13.435  15.316 -12.544  1.00 30.42      B
ATOM   4931  C   LEU B  91     -14.739  16.054 -16.520  1.00 34.93      B
ATOM   4932  O   LEU B  91     -15.380  15.020 -16.406  1.00 36.25      B
ATOM   4933  N   THR B  92     -14.915  16.905 -17.526  1.00 36.09      B
ATOM   4934  CA  THR B  92     -15.916  16.704 -18.578  1.00 36.82      B
ATOM   4935  CB  THR B  92     -16.095  17.994 -19.399  1.00 35.48      B
ATOM   4936  OG1 THR B  92     -16.163  19.115 -18.517  1.00 35.30      B
ATOM   4937  CG2 THR B  92     -17.376  17.930 -20.212  1.00 35.19      B
ATOM   4938  C   THR B  92     -15.671  15.564 -19.587  1.00 37.96      B
```

FIGURE 4- 66 -

| | | | | | | | | | | |
|---|---|---|---|---|---|---|---|---|---|---|
| ATOM | 4939 | O | THR | B | 92 | -14.624 | 15.495 | -20.223 | 1.00 37.50 | B |
| ATOM | 4940 | N | PRO | B | 93 | -16.650 | 14.660 | -19.753 | 1.00 39.82 | B |
| ATOM | 4941 | CD | PRO | B | 93 | -17.925 | 14.514 | -19.029 | 1.00 40.47 | B |
| ATOM | 4942 | CA | PRO | B | 93 | -16.468 | 13.566 | -20.712 | 1.00 40.62 | B |
| ATOM | 4943 | CB | PRO | B | 93 | -17.792 | 12.807 | -20.630 | 1.00 40.73 | B |
| ATOM | 4944 | CG | PRO | B | 93 | -18.227 | 13.039 | -19.219 | 1.00 41.32 | B |
| ATOM | 4945 | C | PRO | B | 93 | -16.240 | 14.167 | -22.098 | 1.00 41.07 | B |
| ATOM | 4946 | O | PRO | B | 93 | -16.809 | 15.207 | -22.430 | 1.00 41.72 | B |
| ATOM | 4947 | N | PRO | B | 94 | -15.406 | 13.519 | -22.922 | 1.00 42.03 | B |
| ATOM | 4948 | CD | PRO | B | 94 | -14.556 | 12.380 | -22.548 | 1.00 43.13 | B |
| ATOM | 4949 | CA | PRO | B | 94 | -15.083 | 13.974 | -24.278 | 1.00 41.81 | B |
| ATOM | 4950 | CB | PRO | B | 94 | -13.982 | 13.014 | -24.714 | 1.00 41.75 | B |
| ATOM | 4951 | CG | PRO | B | 94 | -13.358 | 12.595 | -23.428 | 1.00 42.74 | B |
| ATOM | 4952 | C | PRO | B | 94 | -16.249 | 13.975 | -25.257 | 1.00 41.63 | B |
| ATOM | 4953 | O | PRO | B | 94 | -16.246 | 14.732 | -26.220 | 1.00 42.45 | B |
| ATOM | 4954 | N | HIS | B | 95 | -17.244 | 13.129 | -25.037 | 1.00 41.33 | B |
| ATOM | 4955 | CA | HIS | B | 95 | -18.369 | 13.115 | -25.958 | 1.00 42.66 | B |
| ATOM | 4956 | CB | HIS | B | 95 | -18.658 | 11.689 | -26.443 | 1.00 47.20 | B |
| ATOM | 4957 | CG | HIS | B | 95 | -17.675 | 11.182 | -27.456 | 1.00 51.67 | B |
| ATOM | 4958 | CD2 | HIS | B | 95 | -17.684 | 11.239 | -28.811 | 1.00 52.41 | B |
| ATOM | 4959 | ND1 | HIS | B | 95 | -16.500 | 10.548 | -27.107 | 1.00 52.93 | B |
| ATOM | 4960 | CE1 | HIS | B | 95 | -15.828 | 10.237 | -28.203 | 1.00 54.09 | B |
| ATOM | 4961 | NE2 | HIS | B | 95 | -16.524 | 10.646 | -29.249 | 1.00 54.00 | B |
| ATOM | 4962 | C | HIS | B | 95 | -19.628 | 13.740 | -25.358 | 1.00 41.73 | B |
| ATOM | 4963 | O | HIS | B | 95 | -20.732 | 13.601 | -25.902 | 1.00 40.85 | B |
| ATOM | 4964 | N | SER | B | 96 | -19.448 | 14.433 | -24.235 | 1.00 40.03 | B |
| ATOM | 4965 | CA | SER | B | 96 | -20.543 | 15.118 | -23.551 | 1.00 37.26 | B |
| ATOM | 4966 | CB | SER | B | 96 | -19.960 | 15.998 | -22.431 | 1.00 37.08 | B |
| ATOM | 4967 | OG | SER | B | 96 | -20.971 | 16.599 | -21.635 | 1.00 37.53 | B |
| ATOM | 4968 | C | SER | B | 96 | -21.319 | 15.975 | -24.574 | 1.00 35.94 | B |
| ATOM | 4969 | O | SER | B | 96 | -20.764 | 16.377 | -25.602 | 1.00 34.13 | B |
| ATOM | 4970 | N | ALA | B | 97 | -22.596 | 16.242 | -24.302 | 1.00 34.81 | B |
| ATOM | 4971 | CA | ALA | B | 97 | -23.435 | 17.046 | -25.204 | 1.00 33.91 | B |
| ATOM | 4972 | CB | ALA | B | 97 | -24.845 | 17.149 | -24.657 | 1.00 31.33 | B |
| ATOM | 4973 | C | ALA | B | 97 | -22.867 | 18.441 | -25.403 | 1.00 35.23 | B |
| ATOM | 4974 | O | ALA | B | 97 | -22.623 | 19.164 | -24.438 | 1.00 36.53 | B |
| ATOM | 4975 | N | LYS | B | 98 | -22.663 | 18.828 | -26.656 | 1.00 36.02 | B |
| ATOM | 4976 | CA | LYS | B | 98 | -22.105 | 20.141 | -26.952 | 1.00 36.28 | B |
| ATOM | 4977 | CB | LYS | B | 98 | -21.941 | 20.319 | -28.464 | 1.00 37.76 | B |
| ATOM | 4978 | CG | LYS | B | 98 | -23.245 | 20.344 | -29.238 | 1.00 36.35 | B |
| ATOM | 4979 | CD | LYS | B | 98 | -23.003 | 20.705 | -30.685 | 1.00 36.84 | B |
| ATOM | 4980 | CE | LYS | B | 98 | -24.302 | 20.851 | -31.446 | 1.00 37.33 | B |
| ATOM | 4981 | NZ | LYS | B | 98 | -24.074 | 21.478 | -32.781 | 1.00 40.20 | B |
| ATOM | 4982 | C | LYS | B | 98 | -22.990 | 21.248 | -26.403 | 1.00 36.27 | B |
| ATOM | 4983 | O | LYS | B | 98 | -24.138 | 21.004 | -26.014 | 1.00 35.18 | B |
| ATOM | 4984 | N | SER | B | 99 | -22.452 | 22.465 | -26.372 | 1.00 35.46 | B |
| ATOM | 4985 | CA | SER | B | 99 | -23.201 | 23.608 | -25.875 | 1.00 35.08 | B |
| ATOM | 4986 | CB | SER | B | 99 | -22.285 | 24.668 | -25.301 | 1.00 33.25 | B |
| ATOM | 4987 | OG | SER | B | 99 | -23.037 | 25.846 | -25.079 | 1.00 26.89 | B |
| ATOM | 4988 | C | SER | B | 99 | -24.023 | 24.274 | -26.945 | 1.00 36.78 | B |
| ATOM | 4989 | O | SER | B | 99 | -23.659 | 24.282 | -28.116 | 1.00 38.66 | B |
| ATOM | 4990 | N | LYS | B | 100 | -25.130 | 24.862 | -26.523 | 1.00 37.62 | B |
| ATOM | 4991 | CA | LYS | B | 100 | -26.017 | 25.566 | -27.429 | 1.00 37.92 | B |
| ATOM | 4992 | CB | LYS | B | 100 | -27.272 | 25.990 | -26.652 | 1.00 41.32 | B |
| ATOM | 4993 | CG | LYS | B | 100 | -28.265 | 26.831 | -27.429 | 1.00 46.05 | B |
| ATOM | 4994 | CD | LYS | B | 100 | -29.435 | 27.289 | -26.549 | 1.00 47.98 | B |
| ATOM | 4995 | CE | LYS | B | 100 | -30.464 | 28.064 | -27.389 | 1.00 50.56 | B |
| ATOM | 4996 | NZ | LYS | B | 100 | -31.529 | 28.735 | -26.579 | 1.00 51.75 | B |
| ATOM | 4997 | C | LYS | B | 100 | -25.282 | 26.798 | -27.965 | 1.00 35.96 | B |
| ATOM | 4998 | O | LYS | B | 100 | -25.691 | 27.400 | -28.961 | 1.00 35.24 | B |
| ATOM | 4999 | N | PHE | B | 101 | -24.178 | 27.142 | -27.304 | 1.00 33.60 | B |
| ATOM | 5000 | CA | PHE | B | 101 | -23.403 | 28.325 | -27.647 | 1.00 32.14 | B |
| ATOM | 5001 | CB | PHE | B | 101 | -23.025 | 29.066 | -26.363 | 1.00 31.99 | B |
| ATOM | 5002 | CG | PHE | B | 101 | -24.207 | 29.588 | -25.611 | 1.00 32.25 | B |
| ATOM | 5003 | CD1 | PHE | B | 101 | -24.842 | 30.760 | -26.017 | 1.00 32.51 | B |
| ATOM | 5004 | CD2 | PHE | B | 101 | -24.741 | 28.869 | -24.547 | 1.00 31.29 | B |
| ATOM | 5005 | CE1 | PHE | B | 101 | -26.001 | 31.209 | -25.379 | 1.00 32.41 | B |
| ATOM | 5006 | CE2 | PHE | B | 101 | -25.895 | 29.306 | -23.905 | 1.00 32.16 | B |
| ATOM | 5007 | CZ | PHE | B | 101 | -26.529 | 30.480 | -24.323 | 1.00 31.71 | B |
| ATOM | 5008 | C | PHE | B | 101 | -22.167 | 28.163 | -28.503 | 1.00 31.13 | B |
| ATOM | 5009 | O | PHE | B | 101 | -21.217 | 28.914 | -28.343 | 1.00 30.92 | B |
| ATOM | 5010 | N | GLY | B | 102 | -22.160 | 27.179 | -29.391 | 1.00 31.25 | B |
| ATOM | 5011 | CA | GLY | B | 102 | -21.020 | 27.012 | -30.280 | 1.00 30.89 | B |
| ATOM | 5012 | C | GLY | B | 102 | -19.713 | 26.402 | -29.809 | 1.00 30.80 | B |
| ATOM | 5013 | O | GLY | B | 102 | -18.641 | 26.912 | -30.136 | 1.00 30.69 | B |
| ATOM | 5014 | N | TYR | B | 103 | -19.790 | 25.320 | -29.046 | 1.00 30.89 | B |

FIGURE 4- 67 -

```
ATOM   5015  CA   TYR B 103    -18.592  24.624 -28.595  1.00 32.66      B
ATOM   5016  CB   TYR B 103    -17.784  25.479 -27.610  1.00 33.88      B
ATOM   5017  CG   TYR B 103    -18.439  25.737 -26.276  1.00 35.35      B
ATOM   5018  CD1  TYR B 103    -18.321  24.820 -25.223  1.00 34.59      B
ATOM   5019  CE1  TYR B 103    -18.945  25.050 -23.998  1.00 33.52      B
ATOM   5020  CD2  TYR B 103    -19.196  26.890 -26.067  1.00 35.37      B
ATOM   5021  CE2  TYR B 103    -19.826  27.125 -24.845  1.00 34.62      B
ATOM   5022  CZ   TYR B 103    -19.695  26.204 -23.822  1.00 33.57      B
ATOM   5023  OH   TYR B 103    -20.323  26.448 -22.626  1.00 34.71      B
ATOM   5024  C    TYR B 103    -19.008  23.299 -27.975  1.00 33.83      B
ATOM   5025  O    TYR B 103    -20.183  23.113 -27.635  1.00 34.73      B
ATOM   5026  N    GLY B 104    -18.061  22.373 -27.855  1.00 32.65      B
ATOM   5027  CA   GLY B 104    -18.380  21.071 -27.302  1.00 33.24      B
ATOM   5028  C    GLY B 104    -17.405  20.573 -26.254  1.00 34.96      B
ATOM   5029  O    GLY B 104    -16.492  21.290 -25.840  1.00 34.63      B
ATOM   5030  N    ALA B 105    -17.603  19.334 -25.818  1.00 35.69      B
ATOM   5031  CA   ALA B 105    -16.739  18.740 -24.807  1.00 37.15      B
ATOM   5032  CB   ALA B 105    -17.006  17.249 -24.707  1.00 37.47      B
ATOM   5033  C    ALA B 105    -15.298  18.980 -25.201  1.00 38.12      B
ATOM   5034  O    ALA B 105    -14.473  19.419 -24.389  1.00 36.56      B
ATOM   5035  N    LYS B 106    -15.025  18.684 -26.470  1.00 39.44      B
ATOM   5036  CA   LYS B 106    -13.709  18.834 -27.075  1.00 39.87      B
ATOM   5037  CB   LYS B 106    -13.848  18.689 -28.593  1.00 43.35      B
ATOM   5038  CG   LYS B 106    -12.559  18.458 -29.360  1.00 48.40      B
ATOM   5039  CD   LYS B 106    -12.182  16.980 -29.388  1.00 53.36      B
ATOM   5040  CE   LYS B 106    -10.972  16.731 -30.311  1.00 56.45      B
ATOM   5041  NZ   LYS B 106     -9.780  17.573 -29.937  1.00 56.83      B
ATOM   5042  C    LYS B 106    -13.109  20.205 -26.726  1.00 38.97      B
ATOM   5043  O    LYS B 106    -12.009  20.294 -26.173  1.00 37.11      B
ATOM   5044  N    ASP B 107    -13.844  21.270 -27.038  1.00 37.48      B
ATOM   5045  CA   ASP B 107    -13.375  22.622 -26.770  1.00 37.46      B
ATOM   5046  CB   ASP B 107    -14.278  23.633 -27.479  1.00 37.38      B
ATOM   5047  CG   ASP B 107    -14.303  23.431 -28.984  1.00 38.73      B
ATOM   5048  OD1  ASP B 107    -13.210  23.412 -29.598  1.00 39.58      B
ATOM   5049  OD2  ASP B 107    -15.409  23.286 -29.550  1.00 38.30      B
ATOM   5050  C    ASP B 107    -13.259  22.957 -25.279  1.00 38.16      B
ATOM   5051  O    ASP B 107    -12.438  23.796 -24.889  1.00 39.26      B
ATOM   5052  N    VAL B 108    -14.069  22.306 -24.446  1.00 36.70      B
ATOM   5053  CA   VAL B 108    -14.011  22.545 -23.011  1.00 34.84      B
ATOM   5054  CB   VAL B 108    -15.233  21.922 -22.278  1.00 34.66      B
ATOM   5055  CG1  VAL B 108    -15.041  21.987 -20.765  1.00 32.96      B
ATOM   5056  CG2  VAL B 108    -16.496  22.666 -22.655  1.00 33.23      B
ATOM   5057  C    VAL B 108    -12.722  21.946 -22.452  1.00 34.78      B
ATOM   5058  O    VAL B 108    -11.972  22.614 -21.738  1.00 34.85      B
ATOM   5059  N    ARG B 109    -12.452  20.691 -22.791  1.00 34.71      B
ATOM   5060  CA   ARG B 109    -11.246  20.035 -22.294  1.00 35.52      B
ATOM   5061  CB   ARG B 109    -11.171  18.590 -22.788  1.00 34.00      B
ATOM   5062  CG   ARG B 109    -12.357  17.738 -22.402  1.00 32.63      B
ATOM   5063  CD   ARG B 109    -12.226  16.309 -22.919  1.00 35.36      B
ATOM   5064  NE   ARG B 109    -11.166  15.565 -22.245  1.00 35.91      B
ATOM   5065  CZ   ARG B 109    -11.108  15.370 -20.932  1.00 37.35      B
ATOM   5066  NH1  ARG B 109    -12.050  15.860 -20.139  1.00 39.67      B
ATOM   5067  NH2  ARG B 109    -10.096  14.699 -20.405  1.00 39.48      B
ATOM   5068  C    ARG B 109     -9.985  20.784 -22.712  1.00 36.40      B
ATOM   5069  O    ARG B 109     -9.044  20.886 -21.930  1.00 37.52      B
ATOM   5070  N    ASN B 110     -9.967  21.312 -23.935  1.00 36.37      B
ATOM   5071  CA   ASN B 110     -8.800  22.049 -24.419  1.00 38.72      B
ATOM   5072  CB   ASN B 110     -8.693  21.950 -25.943  1.00 41.31      B
ATOM   5073  CG   ASN B 110     -8.360  20.541 -26.413  1.00 45.36      B
ATOM   5074  OD1  ASN B 110     -7.374  19.938 -25.963  1.00 47.58      B
ATOM   5075  ND2  ASN B 110     -9.176  20.008 -27.324  1.00 45.14      B
ATOM   5076  C    ASN B 110     -8.798  23.520 -24.007  1.00 38.21      B
ATOM   5077  O    ASN B 110     -7.989  24.307 -24.497  1.00 37.99      B
ATOM   5078  N    LEU B 111     -9.701  23.883 -23.104  1.00 36.54      B
ATOM   5079  CA   LEU B 111     -9.796  25.254 -22.620  1.00 34.98      B
ATOM   5080  CB   LEU B 111     -8.599  25.565 -21.714  1.00 35.04      B
ATOM   5081  CG   LEU B 111     -8.210  24.528 -20.652  1.00 36.25      B
ATOM   5082  CD1  LEU B 111     -7.238  25.172 -19.666  1.00 35.28      B
ATOM   5083  CD2  LEU B 111     -9.445  24.023 -19.912  1.00 36.53      B
ATOM   5084  C    LEU B 111     -9.867  26.292 -23.747  1.00 33.52      B
ATOM   5085  O    LEU B 111     -9.144  27.289 -23.723  1.00 32.20      B
ATOM   5086  N    SER B 112    -10.751  26.077 -24.717  1.00 32.36      B
ATOM   5087  CA   SER B 112    -10.863  27.009 -25.831  1.00 33.42      B
ATOM   5088  CB   SER B 112    -11.482  26.318 -27.046  1.00 32.17      B
ATOM   5089  OG   SER B 112    -12.895  26.337 -26.986  1.00 32.00      B
ATOM   5090  C    SER B 112    -11.675  28.254 -25.484  1.00 35.61      B
```

FIGURE 4- 68 -

```
ATOM   5091  O    SER B 112     -12.908  28.232 -25.479  1.00 37.95           B
ATOM   5092  N    SER B 113     -10.967  29.343 -25.208  1.00 36.15           B
ATOM   5093  CA   SER B 113     -11.571  30.625 -24.849  1.00 37.97           B
ATOM   5094  CB   SER B 113     -10.919  31.752 -25.651  1.00 37.97           B
ATOM   5095  OG   SER B 113     -11.178  31.598 -27.029  1.00 40.79           B
ATOM   5096  C    SER B 113     -13.090  30.730 -24.985  1.00 38.02           B
ATOM   5097  O    SER B 113     -13.795  30.781 -23.977  1.00 39.50           B
ATOM   5098  N    ARG B 114     -13.596  30.767 -26.216  1.00 37.69           B
ATOM   5099  CA   ARG B 114     -15.040  30.883 -26.426  1.00 38.12           B
ATOM   5100  CB   ARG B 114     -15.435  30.388 -27.815  1.00 35.36           B
ATOM   5101  CG   ARG B 114     -16.950  30.288 -27.998  1.00 36.93           B
ATOM   5102  CD   ARG B 114     -17.369  30.415 -29.455  1.00 37.09           B
ATOM   5103  NE   ARG B 114     -18.815  30.351 -29.634  1.00 37.55           B
ATOM   5104  CZ   ARG B 114     -19.468  30.920 -30.647  1.00 39.74           B
ATOM   5105  NH1  ARG B 114     -18.802  31.601 -31.569  1.00 39.37           B
ATOM   5106  NH2  ARG B 114     -20.789  30.807 -30.749  1.00 39.54           B
ATOM   5107  C    ARG B 114     -15.835  30.114 -25.374  1.00 39.60           B
ATOM   5108  O    ARG B 114     -16.846  30.608 -24.864  1.00 39.60           B
ATOM   5109  N    ALA B 115     -15.366  28.909 -25.056  1.00 39.72           B
ATOM   5110  CA   ALA B 115     -16.010  28.058 -24.065  1.00 39.27           B
ATOM   5111  CB   ALA B 115     -15.595  26.608 -24.278  1.00 39.55           B
ATOM   5112  C    ALA B 115     -15.651  28.497 -22.647  1.00 38.61           B
ATOM   5113  O    ALA B 115     -16.522  28.577 -21.774  1.00 38.06           B
ATOM   5114  N    VAL B 116     -14.369  28.769 -22.417  1.00 37.22           B
ATOM   5115  CA   VAL B 116     -13.926  29.199 -21.098  1.00 36.81           B
ATOM   5116  CB   VAL B 116     -12.410  29.406 -21.034  1.00 35.64           B
ATOM   5117  CG1  VAL B 116     -12.000  29.742 -19.610  1.00 34.83           B
ATOM   5118  CG2  VAL B 116     -11.700  28.167 -21.505  1.00 36.00           B
ATOM   5119  C    VAL B 116     -14.581  30.522 -20.754  1.00 37.22           B
ATOM   5120  O    VAL B 116     -15.062  30.730 -19.644  1.00 37.66           B
ATOM   5121  N    ASN B 117     -14.602  31.426 -21.716  1.00 37.47           B
ATOM   5122  CA   ASN B 117     -15.197  32.717 -21.468  1.00 38.32           B
ATOM   5123  CB   ASN B 117     -14.747  33.710 -22.546  1.00 40.83           B
ATOM   5124  CG   ASN B 117     -13.226  33.910 -22.553  1.00 41.85           B
ATOM   5125  OD1  ASN B 117     -12.630  34.335 -21.551  1.00 42.11           B
ATOM   5126  ND2  ASN B 117     -12.594  33.595 -23.682  1.00 41.57           B
ATOM   5127  C    ASN B 117     -16.715  32.611 -21.377  1.00 37.58           B
ATOM   5128  O    ASN B 117     -17.358  33.455 -20.755  1.00 39.64           B
ATOM   5129  N    HIS B 118     -17.300  31.580 -21.978  1.00 35.65           B
ATOM   5130  CA   HIS B 118     -18.745  31.421 -21.867  1.00 34.78           B
ATOM   5131  CB   HIS B 118     -19.319  30.477 -22.926  1.00 34.90           B
ATOM   5132  CG   HIS B 118     -20.772  30.170 -22.718  1.00 35.63           B
ATOM   5133  CD2  HIS B 118     -21.879  30.935 -22.889  1.00 35.80           B
ATOM   5134  ND1  HIS B 118     -21.213  28.974 -22.192  1.00 35.88           B
ATOM   5135  CE1  HIS B 118     -22.527  29.016 -22.046  1.00 35.43           B
ATOM   5136  NE2  HIS B 118     -22.955  30.195 -22.461  1.00 34.66           B
ATOM   5137  C    HIS B 118     -19.040  30.850 -20.492  1.00 34.73           B
ATOM   5138  O    HIS B 118     -20.007  31.246 -19.843  1.00 35.59           B
ATOM   5139  N    ILE B 119     -18.209  29.909 -20.053  1.00 33.06           B
ATOM   5140  CA   ILE B 119     -18.380  29.309 -18.739  1.00 31.47           B
ATOM   5141  CB   ILE B 119     -17.351  28.215 -18.486  1.00 29.95           B
ATOM   5142  CG2  ILE B 119     -17.387  27.815 -17.018  1.00 27.71           B
ATOM   5143  CG1  ILE B 119     -17.634  27.026 -19.413  1.00 29.32           B
ATOM   5144  CD1  ILE B 119     -16.511  26.034 -19.496  1.00 27.36           B
ATOM   5145  C    ILE B 119     -18.227  30.376 -17.670  1.00 31.91           B
ATOM   5146  O    ILE B 119     -19.056  30.466 -16.768  1.00 33.88           B
ATOM   5147  N    ARG B 120     -17.164  31.174 -17.762  1.00 31.22           B
ATOM   5148  CA   ARG B 120     -16.947  32.253 -16.805  1.00 30.11           B
ATOM   5149  CB   ARG B 120     -15.789  33.156 -17.235  1.00 33.89           B
ATOM   5150  CG   ARG B 120     -14.388  32.581 -17.153  1.00 40.57           B
ATOM   5151  CD   ARG B 120     -13.386  33.738 -17.014  1.00 44.87           B
ATOM   5152  NE   ARG B 120     -11.996  33.299 -16.924  1.00 49.07           B
ATOM   5153  CZ   ARG B 120     -11.180  33.182 -17.969  1.00 52.73           B
ATOM   5154  NH1  ARG B 120     -11.609  33.472 -19.195  1.00 53.89           B
ATOM   5155  NH2  ARG B 120      -9.928  32.781 -17.789  1.00 53.49           B
ATOM   5156  C    ARG B 120     -18.215  33.097 -16.812  1.00 28.34           B
ATOM   5157  O    ARG B 120     -18.641  33.621 -15.782  1.00 27.11           B
ATOM   5158  N    SER B 121     -18.795  33.223 -18.004  1.00 25.59           B
ATOM   5159  CA   SER B 121     -20.003  33.992 -18.236  1.00 23.58           B
ATOM   5160  CB   SER B 121     -20.308  34.022 -19.744  1.00 25.49           B
ATOM   5161  OG   SER B 121     -21.481  34.759 -20.061  1.00 29.10           B
ATOM   5162  C    SER B 121     -21.165  33.382 -17.470  1.00 22.60           B
ATOM   5163  O    SER B 121     -21.856  34.071 -16.721  1.00 21.97           B
ATOM   5164  N    VAL B 122     -21.374  32.082 -17.653  1.00 21.39           B
ATOM   5165  CA   VAL B 122     -22.464  31.393 -16.981  1.00 18.09           B
ATOM   5166  CB   VAL B 122     -22.531  29.906 -17.380  1.00 14.59           B
```

FIGURE 4- 69 -

| | | | | | | | | | | |
|---|---|---|---|---|---|---|---|---|---|---|
| ATOM | 5167 | CG1 | VAL | B | 122 | -23.552 | 29.183 | -16.532 | 1.00 12.51 | B |
| ATOM | 5168 | CG2 | VAL | B | 122 | -22.915 | 29.783 | -18.831 | 1.00 10.21 | B |
| ATOM | 5169 | C | VAL | B | 122 | -22.329 | 31.489 | -15.481 | 1.00 19.39 | B |
| ATOM | 5170 | O | VAL | B | 122 | -23.334 | 31.517 | -14.766 | 1.00 20.60 | B |
| ATOM | 5171 | N | TRP | B | 123 | -21.086 | 31.551 | -15.007 | 1.00 20.44 | B |
| ATOM | 5172 | CA | TRP | B | 123 | -20.802 | 31.633 | -13.571 | 1.00 20.42 | B |
| ATOM | 5173 | CB | TRP | B | 123 | -19.344 | 31.236 | -13.310 | 1.00 20.13 | B |
| ATOM | 5174 | CG | TRP | B | 123 | -18.924 | 31.320 | -11.849 | 1.00 22.26 | B |
| ATOM | 5175 | CD2 | TRP | B | 123 | -18.945 | 30.264 | -10.884 | 1.00 20.26 | B |
| ATOM | 5176 | CE2 | TRP | B | 123 | -18.454 | 30.795 | -9.671 | 1.00 22.29 | B |
| ATOM | 5177 | CE3 | TRP | B | 123 | -19.330 | 28.921 | -10.926 | 1.00 21.39 | B |
| ATOM | 5178 | CD1 | TRP | B | 123 | -18.437 | 32.420 | -11.195 | 1.00 21.85 | B |
| ATOM | 5179 | NE1 | TRP | B | 123 | -18.152 | 32.112 | -9.891 | 1.00 20.56 | B |
| ATOM | 5180 | CZ2 | TRP | B | 123 | -18.335 | 30.021 | -8.501 | 1.00 24.67 | B |
| ATOM | 5181 | CZ3 | TRP | B | 123 | -19.212 | 28.146 | -9.761 | 1.00 22.73 | B |
| ATOM | 5182 | CH2 | TRP | B | 123 | -18.718 | 28.702 | -8.567 | 1.00 23.61 | B |
| ATOM | 5183 | C | TRP | B | 123 | -21.117 | 33.000 | -12.955 | 1.00 19.63 | B |
| ATOM | 5184 | O | TRP | B | 123 | -21.711 | 33.080 | -11.860 | 1.00 18.48 | B |
| ATOM | 5185 | N | GLU | B | 124 | -20.717 | 34.073 | -13.626 | 1.00 20.42 | B |
| ATOM | 5186 | CA | GLU | B | 124 | -21.016 | 35.397 | -13.122 | 1.00 21.19 | B |
| ATOM | 5187 | CB | GLU | B | 124 | -20.503 | 36.477 | -14.075 | 1.00 26.21 | B |
| ATOM | 5188 | CG | GLU | B | 124 | -18.992 | 36.497 | -14.301 | 1.00 33.79 | B |
| ATOM | 5189 | CD | GLU | B | 124 | -18.202 | 36.438 | -13.005 | 1.00 38.82 | B |
| ATOM | 5190 | OE1 | GLU | B | 124 | -18.571 | 37.162 | -12.046 | 1.00 41.01 | B |
| ATOM | 5191 | OE2 | GLU | B | 124 | -17.205 | 35.670 | -12.953 | 1.00 42.18 | B |
| ATOM | 5192 | C | GLU | B | 124 | -22.538 | 35.481 | -13.021 | 1.00 20.62 | B |
| ATOM | 5193 | O | GLU | B | 124 | -23.070 | 36.098 | -12.101 | 1.00 20.82 | B |
| ATOM | 5194 | N | ASP | B | 125 | -23.237 | 34.844 | -13.958 | 1.00 18.69 | B |
| ATOM | 5195 | CA | ASP | B | 125 | -24.698 | 34.858 | -13.955 | 1.00 17.87 | B |
| ATOM | 5196 | CB | ASP | B | 125 | -25.248 | 34.181 | -15.210 | 1.00 18.11 | B |
| ATOM | 5197 | CG | ASP | B | 125 | -26.759 | 34.315 | -15.327 | 1.00 18.38 | B |
| ATOM | 5198 | OD1 | ASP | B | 125 | -27.225 | 35.399 | -15.713 | 1.00 19.85 | B |
| ATOM | 5199 | OD2 | ASP | B | 125 | -27.439 | 33.346 | -15.020 | 1.00 17.26 | B |
| ATOM | 5200 | C | ASP | B | 125 | -25.294 | 34.178 | -12.722 | 1.00 18.71 | B |
| ATOM | 5201 | O | ASP | B | 125 | -26.365 | 34.549 | -12.263 | 1.00 20.08 | B |
| ATOM | 5202 | N | LEU | B | 126 | -24.624 | 33.163 | -12.196 | 1.00 18.89 | B |
| ATOM | 5203 | CA | LEU | B | 126 | -25.137 | 32.501 | -11.010 | 1.00 18.10 | B |
| ATOM | 5204 | CB | LEU | B | 126 | -24.350 | 31.227 | -10.731 | 1.00 17.06 | B |
| ATOM | 5205 | CG | LEU | B | 126 | -24.629 | 30.095 | -11.713 | 1.00 17.30 | B |
| ATOM | 5206 | CD1 | LEU | B | 126 | -23.790 | 28.884 | -11.354 | 1.00 18.59 | B |
| ATOM | 5207 | CD2 | LEU | B | 126 | -26.116 | 29.755 | -11.677 | 1.00 14.18 | B |
| ATOM | 5208 | C | LEU | B | 126 | -25.030 | 33.445 | -9.820 | 1.00 18.82 | B |
| ATOM | 5209 | O | LEU | B | 126 | -25.820 | 33.368 | -8.891 | 1.00 17.76 | B |
| ATOM | 5210 | N | LEU | B | 127 | -24.052 | 34.343 | -9.861 | 1.00 20.16 | B |
| ATOM | 5211 | CA | LEU | B | 127 | -23.847 | 35.294 | -8.779 | 1.00 21.92 | B |
| ATOM | 5212 | CB | LEU | B | 127 | -22.370 | 35.695 | -8.692 | 1.00 21.18 | B |
| ATOM | 5213 | CG | LEU | B | 127 | -21.301 | 34.590 | -8.721 | 1.00 22.83 | B |
| ATOM | 5214 | CD1 | LEU | B | 127 | -19.900 | 35.206 | -8.684 | 1.00 18.95 | B |
| ATOM | 5215 | CD2 | LEU | B | 127 | -21.505 | 33.646 | -7.548 | 1.00 22.94 | B |
| ATOM | 5216 | C | LEU | B | 127 | -24.694 | 36.541 | -8.990 | 1.00 23.26 | B |
| ATOM | 5217 | O | LEU | B | 127 | -25.059 | 37.220 | -8.031 | 1.00 24.25 | B |
| ATOM | 5218 | N | GLU | B | 128 | -25.015 | 36.839 | -10.243 | 1.00 23.80 | B |
| ATOM | 5219 | CA | GLU | B | 128 | -25.796 | 38.026 | -10.553 | 1.00 23.62 | B |
| ATOM | 5220 | CB | GLU | B | 128 | -25.364 | 38.584 | -11.906 | 1.00 24.43 | B |
| ATOM | 5221 | CG | GLU | B | 128 | -23.985 | 39.213 | -11.919 | 1.00 25.59 | B |
| ATOM | 5222 | CD | GLU | B | 128 | -23.941 | 40.496 | -11.137 | 1.00 28.52 | B |
| ATOM | 5223 | OE1 | GLU | B | 128 | -24.973 | 41.195 | -11.085 | 1.00 31.60 | B |
| ATOM | 5224 | OE2 | GLU | B | 128 | -22.875 | 40.820 | -10.583 | 1.00 31.09 | B |
| ATOM | 5225 | C | GLU | B | 128 | -27.300 | 37.809 | -10.555 | 1.00 24.09 | B |
| ATOM | 5226 | O | GLU | B | 128 | -28.060 | 38.745 | -10.305 | 1.00 26.52 | B |
| ATOM | 5227 | N | ASP | B | 129 | -27.726 | 36.581 | -10.840 | 1.00 24.11 | B |
| ATOM | 5228 | CA | ASP | B | 129 | -29.147 | 36.229 | -10.910 | 1.00 22.46 | B |
| ATOM | 5229 | CB | ASP | B | 129 | -29.504 | 35.822 | -12.342 | 1.00 22.05 | B |
| ATOM | 5230 | CG | ASP | B | 129 | -30.999 | 35.679 | -12.555 | 1.00 23.61 | B |
| ATOM | 5231 | OD1 | ASP | B | 129 | -31.698 | 35.150 | -11.659 | 1.00 25.92 | B |
| ATOM | 5232 | OD2 | ASP | B | 129 | -31.480 | 36.086 | -13.632 | 1.00 22.46 | B |
| ATOM | 5233 | C | ASP | B | 129 | -29.471 | 35.073 | -9.958 | 1.00 22.00 | B |
| ATOM | 5234 | O | ASP | B | 129 | -28.911 | 33.980 | -10.063 | 1.00 20.81 | B |
| ATOM | 5235 | N | THR | B | 130 | -30.398 | 35.309 | -9.040 | 1.00 20.99 | B |
| ATOM | 5236 | CA | THR | B | 130 | -30.760 | 34.296 | -8.065 | 1.00 21.00 | B |
| ATOM | 5237 | CB | THR | B | 130 | -30.774 | 34.886 | -6.642 | 1.00 20.41 | B |
| ATOM | 5238 | OG1 | THR | B | 130 | -31.694 | 35.983 | -6.607 | 1.00 19.88 | B |
| ATOM | 5239 | CG2 | THR | B | 130 | -29.336 | 35.372 | -6.220 | 1.00 16.94 | B |
| ATOM | 5240 | C | THR | B | 130 | -32.132 | 33.686 | -8.300 | 1.00 22.98 | B |
| ATOM | 5241 | O | THR | B | 130 | -32.558 | 32.840 | -7.520 | 1.00 24.88 | B |
| ATOM | 5242 | N | GLU | B | 131 | -32.832 | 34.077 | -9.360 | 1.00 23.17 | B |

FIGURE 4-70-

```
ATOM   5243  CA   GLU B 131     -34.166  33.527  -9.540  1.00 24.68      B
ATOM   5244  CB   GLU B 131     -35.212  34.613  -9.295  1.00 27.45      B
ATOM   5245  CG   GLU B 131     -34.974  35.468  -8.066  1.00 35.98      B
ATOM   5246  CD   GLU B 131     -35.773  36.775  -8.107  1.00 40.16      B
ATOM   5247  OE1  GLU B 131     -35.788  37.426  -9.184  1.00 42.18      B
ATOM   5248  OE2  GLU B 131     -36.375  37.153  -7.068  1.00 39.93      B
ATOM   5249  C    GLU B 131     -34.491  32.855 -10.861  1.00 23.94      B
ATOM   5250  O    GLU B 131     -35.004  31.738 -10.877  1.00 25.31      B
ATOM   5251  N    THR B 132     -34.216  33.538 -11.964  1.00 21.89      B
ATOM   5252  CA   THR B 132     -34.543  33.017 -13.289  1.00 20.25      B
ATOM   5253  CB   THR B 132     -33.848  33.801 -14.403  1.00 17.61      B
ATOM   5254  OG1  THR B 132     -33.745  35.181 -14.031  1.00 17.88      B
ATOM   5255  CG2  THR B 132     -34.661  33.695 -15.678  1.00 12.77      B
ATOM   5256  C    THR B 132     -34.239  31.549 -13.526  1.00 21.20      B
ATOM   5257  O    THR B 132     -33.092  31.110 -13.396  1.00 22.45      B
ATOM   5258  N    PRO B 133     -35.274  30.768 -13.878  1.00 19.95      B
ATOM   5259  CD   PRO B 133     -36.705  31.113 -13.827  1.00 17.34      B
ATOM   5260  CA   PRO B 133     -35.101  29.340 -14.141  1.00 19.10      B
ATOM   5261  CB   PRO B 133     -36.509  28.891 -14.510  1.00 18.63      B
ATOM   5262  CG   PRO B 133     -37.353  29.758 -13.646  1.00 17.10      B
ATOM   5263  C    PRO B 133     -34.115  29.123 -15.276  1.00 18.79      B
ATOM   5264  O    PRO B 133     -34.070  29.896 -16.232  1.00 17.29      B
ATOM   5265  N    ILE B 134     -33.318  28.071 -15.152  1.00 19.03      B
ATOM   5266  CA   ILE B 134     -32.327  27.731 -16.160  1.00 19.71      B
ATOM   5267  CB   ILE B 134     -31.055  27.164 -15.485  1.00 20.61      B
ATOM   5268  CG2  ILE B 134     -30.196  26.431 -16.495  1.00 19.45      B
ATOM   5269  CG1  ILE B 134     -30.302  28.318 -14.799  1.00 22.58      B
ATOM   5270  CD1  ILE B 134     -29.198  27.902 -13.837  1.00 20.58      B
ATOM   5271  C    ILE B 134     -32.929  26.714 -17.115  1.00 19.69      B
ATOM   5272  O    ILE B 134     -33.637  25.802 -16.701  1.00 20.32      B
ATOM   5273  N    ASP B 135     -32.665  26.869 -18.402  1.00 20.28      B
ATOM   5274  CA   ASP B 135     -33.235  25.938 -19.356  1.00 21.47      B
ATOM   5275  CB   ASP B 135     -33.033  26.434 -20.795  1.00 23.35      B
ATOM   5276  CG   ASP B 135     -33.898  25.671 -21.795  1.00 29.12      B
ATOM   5277  OD1  ASP B 135     -34.919  25.084 -21.357  1.00 30.20      B
ATOM   5278  OD2  ASP B 135     -33.576  25.661 -23.009  1.00 30.84      B
ATOM   5279  C    ASP B 135     -32.664  24.537 -19.202  1.00 20.18      B
ATOM   5280  O    ASP B 135     -31.554  24.360 -18.698  1.00 19.94      B
ATOM   5281  N    THR B 136     -33.466  23.552 -19.606  1.00 19.91      B
ATOM   5282  CA   THR B 136     -33.096  22.133 -19.580  1.00 18.57      B
ATOM   5283  CB   THR B 136     -33.608  21.384 -18.324  1.00 14.86      B
ATOM   5284  OG1  THR B 136     -35.018  21.576 -18.196  1.00 13.45      B
ATOM   5285  CG2  THR B 136     -32.893  21.856 -17.075  1.00 14.33      B
ATOM   5286  C    THR B 136     -33.676  21.421 -20.804  1.00 19.76      B
ATOM   5287  O    THR B 136     -34.744  21.776 -21.320  1.00 19.13      B
ATOM   5288  N    THR B 137     -32.948  20.413 -21.259  1.00 20.66      B
ATOM   5289  CA   THR B 137     -33.336  19.622 -22.409  1.00 20.93      B
ATOM   5290  CB   THR B 137     -32.122  19.362 -23.333  1.00 20.28      B
ATOM   5291  OG1  THR B 137     -31.737  20.584 -23.972  1.00 16.31      B
ATOM   5292  CG2  THR B 137     -32.461  18.313 -24.387  1.00 18.83      B
ATOM   5293  C    THR B 137     -33.845  18.290 -21.902  1.00 23.09      B
ATOM   5294  O    THR B 137     -33.193  17.653 -21.070  1.00 22.58      B
ATOM   5295  N    ILE B 138     -35.014  17.881 -22.382  1.00 25.15      B
ATOM   5296  CA   ILE B 138     -35.576  16.602 -21.983  1.00 28.09      B
ATOM   5297  CB   ILE B 138     -37.054  16.736 -21.531  1.00 26.41      B
ATOM   5298  CG2  ILE B 138     -37.864  17.409 -22.594  1.00 26.14      B
ATOM   5299  CG1  ILE B 138     -37.629  15.353 -21.209  1.00 26.64      B
ATOM   5300  CD1  ILE B 138     -38.978  15.389 -20.515  1.00 27.75      B
ATOM   5301  C    ILE B 138     -35.472  15.688 -23.189  1.00 29.97      B
ATOM   5302  O    ILE B 138     -35.634  16.131 -24.314  1.00 31.27      B
ATOM   5303  N    MET B 139     -35.172  14.418 -22.963  1.00 33.68      B
ATOM   5304  CA   MET B 139     -35.046  13.481 -24.069  1.00 37.12      B
ATOM   5305  CB   MET B 139     -33.600  13.418 -24.564  1.00 38.52      B
ATOM   5306  CG   MET B 139     -33.051  14.713 -25.108  1.00 41.37      B
ATOM   5307  SD   MET B 139     -32.421  14.473 -26.783  1.00 48.40      B
ATOM   5308  CE   MET B 139     -31.113  13.199 -26.447  1.00 46.56      B
ATOM   5309  C    MET B 139     -35.457  12.094 -23.633  1.00 38.13      B
ATOM   5310  O    MET B 139     -35.459  11.787 -22.443  1.00 37.58      B
ATOM   5311  N    ALA B 140     -35.813  11.260 -24.601  1.00 39.79      B
ATOM   5312  CA   ALA B 140     -36.179   9.887 -24.302  1.00 40.58      B
ATOM   5313  CB   ALA B 140     -37.089   9.340 -25.378  1.00 38.74      B
ATOM   5314  C    ALA B 140     -34.839   9.176 -24.319  1.00 41.38      B
ATOM   5315  O    ALA B 140     -34.109   9.274 -25.300  1.00 41.74      B
ATOM   5316  N    LYS B 141     -34.500   8.482 -23.239  1.00 43.66      B
ATOM   5317  CA   LYS B 141     -33.214   7.795 -23.181  1.00 47.34      B
ATOM   5318  CB   LYS B 141     -32.863   7.423 -21.740  1.00 47.41      B
```

FIGURE 4- 71 -

```
ATOM   5319  CG   LYS B 141     -31.475    6.840  -21.608  1.00 49.27      B
ATOM   5320  CD   LYS B 141     -31.262    6.144  -20.265  1.00 52.61      B
ATOM   5321  CE   LYS B 141     -31.041    7.119  -19.104  1.00 52.68      B
ATOM   5322  NZ   LYS B 141     -30.773    6.378  -17.833  1.00 50.97      B
ATOM   5323  C    LYS B 141     -33.207    6.537  -24.035  1.00 48.91      B
ATOM   5324  O    LYS B 141     -34.260    5.991  -24.350  1.00 49.74      B
ATOM   5325  N    SER B 142     -32.016    6.076  -24.404  1.00 51.38      B
ATOM   5326  CA   SER B 142     -31.879    4.871  -25.219  1.00 53.48      B
ATOM   5327  CB   SER B 142     -31.018    5.162  -26.454  1.00 55.00      B
ATOM   5328  OG   SER B 142     -30.880    4.008  -27.271  1.00 57.04      B
ATOM   5329  C    SER B 142     -31.255    3.729  -24.422  1.00 53.98      B
ATOM   5330  O    SER B 142     -30.069    3.758  -24.100  1.00 52.01      B
ATOM   5331  N    GLU B 143     -32.069    2.727  -24.106  1.00 56.30      B
ATOM   5332  CA   GLU B 143     -31.613    1.561  -23.355  1.00 58.28      B
ATOM   5333  CB   GLU B 143     -32.144    1.612  -21.923  1.00 58.62      B
ATOM   5334  CG   GLU B 143     -31.742    2.872  -21.179  1.00 59.54      B
ATOM   5335  CD   GLU B 143     -31.866    2.747  -19.670  1.00 59.80      B
ATOM   5336  OE1  GLU B 143     -32.983    2.482  -19.166  1.00 59.61      B
ATOM   5337  OE2  GLU B 143     -30.833    2.925  -18.990  1.00 60.17      B
ATOM   5338  C    GLU B 143     -32.074    0.274  -24.029  1.00 59.73      B
ATOM   5339  O    GLU B 143     -33.150    0.228  -24.630  1.00 59.94      B
ATOM   5340  N    VAL B 144     -31.254   -0.768  -23.924  1.00 61.54      B
ATOM   5341  CA   VAL B 144     -31.565   -2.061  -24.535  1.00 63.19      B
ATOM   5342  CB   VAL B 144     -30.335   -2.616  -25.282  1.00 62.38      B
ATOM   5343  CG1  VAL B 144     -30.643   -3.990  -25.833  1.00 62.08      B
ATOM   5344  CG2  VAL B 144     -29.936   -1.663  -26.403  1.00 61.96      B
ATOM   5345  C    VAL B 144     -32.060   -3.100  -23.524  1.00 64.36      B
ATOM   5346  O    VAL B 144     -31.429   -3.325  -22.491  1.00 63.29      B
ATOM   5347  N    PHE B 145     -33.194   -3.727  -23.840  1.00 66.57      B
ATOM   5348  CA   PHE B 145     -33.803   -4.740  -22.972  1.00 68.60      B
ATOM   5349  CB   PHE B 145     -34.986   -4.141  -22.192  1.00 67.54      B
ATOM   5350  CG   PHE B 145     -34.587   -3.097  -21.186  1.00 67.89      B
ATOM   5351  CD1  PHE B 145     -33.763   -3.424  -20.114  1.00 68.05      B
ATOM   5352  CD2  PHE B 145     -35.021   -1.779  -21.317  1.00 68.45      B
ATOM   5353  CE1  PHE B 145     -33.369   -2.450  -19.181  1.00 67.58      B
ATOM   5354  CE2  PHE B 145     -34.635   -0.796  -20.391  1.00 68.63      B
ATOM   5355  CZ   PHE B 145     -33.806   -1.134  -19.321  1.00 67.71      B
ATOM   5356  C    PHE B 145     -34.289   -5.961  -23.755  1.00 70.05      B
ATOM   5357  O    PHE B 145     -34.099   -6.060  -24.972  1.00 69.21      B
ATOM   5358  N    CYS B 146     -34.919   -6.886  -23.032  1.00 71.90      B
ATOM   5359  CA   CYS B 146     -35.456   -8.115  -23.607  1.00 73.93      B
ATOM   5360  CB   CYS B 146     -34.684   -9.326  -23.074  1.00 74.26      B
ATOM   5361  SG   CYS B 146     -35.146  -10.907  -23.831  1.00 75.43      B
ATOM   5362  C    CYS B 146     -36.939   -8.236  -23.254  1.00 75.37      B
ATOM   5363  O    CYS B 146     -37.318   -8.149  -22.084  1.00 75.25      B
ATOM   5364  N    VAL B 147     -37.764   -8.444  -24.277  1.00 77.11      B
ATOM   5365  CA   VAL B 147     -39.210   -8.548  -24.110  1.00 78.44      B
ATOM   5366  CB   VAL B 147     -39.927   -8.734  -25.488  1.00 77.71      B
ATOM   5367  CG1  VAL B 147     -39.258   -7.870  -26.543  1.00 77.21      B
ATOM   5368  CG2  VAL B 147     -39.915  -10.198  -25.915  1.00 76.79      B
ATOM   5369  C    VAL B 147     -39.644   -9.685  -23.186  1.00 79.91      B
ATOM   5370  O    VAL B 147     -39.101  -10.787  -23.240  1.00 80.46      B
ATOM   5371  N    GLN B 148     -40.614   -9.408  -22.319  1.00 81.30      B
ATOM   5372  CA   GLN B 148     -41.152  -10.418  -21.407  1.00 82.55      B
ATOM   5373  CB   GLN B 148     -41.516   -9.781  -20.059  1.00 83.10      B
ATOM   5374  CG   GLN B 148     -42.415  -10.656  -19.200  1.00 85.08      B
ATOM   5375  CD   GLN B 148     -42.637  -10.090  -17.812  1.00 86.57      B
ATOM   5376  OE1  GLN B 148     -42.704   -8.869  -17.628  1.00 87.09      B
ATOM   5377  NE2  GLN B 148     -42.771  -10.974  -16.825  1.00 86.79      B
ATOM   5378  C    GLN B 148     -42.394  -11.086  -22.031  1.00 82.83      B
ATOM   5379  O    GLN B 148     -42.296  -12.265  -22.442  1.00 82.28      B
ATOM   5380  OXT  GLN B 148     -43.450  -10.418  -22.120  1.00 83.43      B
ATOM   5381  C    GLY B 153     -43.550   -5.654  -21.797  1.00 66.26      B
ATOM   5382  O    GLY B 153     -42.596   -6.427  -21.905  1.00 66.14      B
ATOM   5383  N    GLY B 153     -44.930   -7.597  -20.945  1.00 67.21      B
ATOM   5384  CA   GLY B 153     -44.891   -6.130  -21.256  1.00 66.70      B
ATOM   5385  N    ARG B 154     -43.481   -4.371  -22.139  1.00 65.84      B
ATOM   5386  CA   ARG B 154     -42.262   -3.766  -22.675  1.00 65.48      B
ATOM   5387  CB   ARG B 154     -42.357   -3.660  -24.197  1.00 66.09      B
ATOM   5388  CG   ARG B 154     -41.228   -2.887  -24.838  1.00 67.15      B
ATOM   5389  CD   ARG B 154     -41.300   -2.988  -26.350  1.00 68.70      B
ATOM   5390  NE   ARG B 154     -40.952   -4.324  -26.826  1.00 69.84      B
ATOM   5391  CZ   ARG B 154     -40.936   -4.678  -28.107  1.00 70.58      B
ATOM   5392  NH1  ARG B 154     -41.252   -3.792  -29.045  1.00 70.99      B
ATOM   5393  NH2  ARG B 154     -40.596   -5.916  -28.448  1.00 70.79      B
ATOM   5394  C    ARG B 154     -42.087   -2.379  -22.063  1.00 64.16      B
```

FIGURE 4- 72 -

```
ATOM   5395  O   ARG B 154    -42.971  -1.532 -22.179  1.00 65.49      B
ATOM   5396  N   LYS B 155    -40.943  -2.138 -21.429  1.00 61.43      B
ATOM   5397  CA  LYS B 155    -40.712  -0.857 -20.769  1.00 58.86      B
ATOM   5398  CB  LYS B 155    -39.634  -1.010 -19.693  1.00 59.42      B
ATOM   5399  CG  LYS B 155    -38.326  -1.630 -20.162  1.00 58.85      B
ATOM   5400  CD  LYS B 155    -37.476  -2.043 -18.955  1.00 58.25      B
ATOM   5401  CE  LYS B 155    -38.224  -3.033 -18.055  1.00 56.89      B
ATOM   5402  NZ  LYS B 155    -37.403  -3.498 -16.911  1.00 55.27      B
ATOM   5403  C   LYS B 155    -40.391   0.344 -21.648  1.00 56.97      B
ATOM   5404  O   LYS B 155    -39.587   0.256 -22.576  1.00 56.93      B
ATOM   5405  N   PRO B 156    -41.036   1.490 -21.361  1.00 54.85      B
ATOM   5406  CD  PRO B 156    -42.048   1.659 -20.299  1.00 54.22      B
ATOM   5407  CA  PRO B 156    -40.849   2.742 -22.097  1.00 52.43      B
ATOM   5408  CB  PRO B 156    -42.060   3.569 -21.684  1.00 52.61      B
ATOM   5409  CG  PRO B 156    -42.229   3.170 -20.249  1.00 53.43      B
ATOM   5410  C   PRO B 156    -39.538   3.386 -21.672  1.00 50.44      B
ATOM   5411  O   PRO B 156    -39.022   3.106 -20.589  1.00 49.49      B
ATOM   5412  N   ALA B 157    -39.008   4.250 -22.527  1.00 48.15      B
ATOM   5413  CA  ALA B 157    -37.753   4.918 -22.245  1.00 45.54      B
ATOM   5414  CB  ALA B 157    -37.344   5.773 -23.426  1.00 44.84      B
ATOM   5415  C   ALA B 157    -37.875   5.780 -21.014  1.00 43.96      B
ATOM   5416  O   ALA B 157    -38.961   6.248 -20.681  1.00 44.16      B
ATOM   5417  N   ARG B 158    -36.756   5.967 -20.327  1.00 42.63      B
ATOM   5418  CA  ARG B 158    -36.729   6.830 -19.159  1.00 40.97      B
ATOM   5419  CB  ARG B 158    -35.584   6.445 -18.213  1.00 41.89      B
ATOM   5420  CG  ARG B 158    -35.806   5.120 -17.482  1.00 44.89      B
ATOM   5421  CD  ARG B 158    -35.151   5.092 -16.099  1.00 48.00      B
ATOM   5422  NE  ARG B 158    -35.908   4.257 -15.157  1.00 53.54      B
ATOM   5423  CZ  ARG B 158    -36.170   4.597 -13.891  1.00 56.32      B
ATOM   5424  NH1 ARG B 158    -36.863   3.732 -13.100  1.00 55.72      B
ATOM   5425  NH2 ARG B 158    -35.739   5.761 -13.414  1.00 58.30      B
ATOM   5426  C   ARG B 158    -36.510   8.236 -19.717  1.00 39.30      B
ATOM   5427  O   ARG B 158    -36.073   8.398 -20.857  1.00 40.08      B
ATOM   5428  N   LEU B 159    -36.828   9.255 -18.934  1.00 36.65      B
ATOM   5429  CA  LEU B 159    -36.647  10.618 -19.404  1.00 34.09      B
ATOM   5430  CB  LEU B 159    -37.855  11.469 -19.020  1.00 34.00      B
ATOM   5431  CG  LEU B 159    -39.206  10.865 -19.426  1.00 35.92      B
ATOM   5432  CD1 LEU B 159    -40.326  11.739 -18.985  1.00 35.85      B
ATOM   5433  CD2 LEU B 159    -39.257  10.630 -20.935  1.00 33.47      B
ATOM   5434  C   LEU B 159    -35.390  11.217 -18.803  1.00 32.39      B
ATOM   5435  O   LEU B 159    -35.083  10.994 -17.637  1.00 33.19      B
ATOM   5436  N   ILE B 160    -34.636  11.957 -19.600  1.00 30.75      B
ATOM   5437  CA  ILE B 160    -33.441  12.587 -19.072  1.00 29.74      B
ATOM   5438  CB  ILE B 160    -32.173  12.083 -19.772  1.00 30.65      B
ATOM   5439  CG2 ILE B 160    -31.989  10.599 -19.488  1.00 31.09      B
ATOM   5440  CG1 ILE B 160    -32.275  12.324 -21.274  1.00 31.77      B
ATOM   5441  CD1 ILE B 160    -31.056  11.868 -22.035  1.00 33.91      B
ATOM   5442  C   ILE B 160    -33.576  14.089 -19.244  1.00 28.55      B
ATOM   5443  O   ILE B 160    -33.916  14.575 -20.323  1.00 27.68      B
ATOM   5444  N   VAL B 161    -33.341  14.814 -18.157  1.00 27.13      B
ATOM   5445  CA  VAL B 161    -33.435  16.267 -18.154  1.00 26.11      B
ATOM   5446  CB  VAL B 161    -34.478  16.727 -17.110  1.00 26.01      B
ATOM   5447  CG1 VAL B 161    -34.494  18.244 -16.999  1.00 24.02      B
ATOM   5448  CG2 VAL B 161    -35.853  16.197 -17.502  1.00 22.84      B
ATOM   5449  C   VAL B 161    -32.059  16.816 -17.803  1.00 25.53      B
ATOM   5450  O   VAL B 161    -31.492  16.470 -16.766  1.00 26.31      B
ATOM   5451  N   PHE B 162    -31.508  17.657 -18.665  1.00 24.12      B
ATOM   5452  CA  PHE B 162    -30.183  18.191 -18.391  1.00 24.80      B
ATOM   5453  CB  PHE B 162    -29.126  17.263 -19.005  1.00 25.35      B
ATOM   5454  CG  PHE B 162    -29.145  17.240 -20.504  1.00 25.50      B
ATOM   5455  CD1 PHE B 162    -30.098  16.492 -21.193  1.00 28.29      B
ATOM   5456  CD2 PHE B 162    -28.247  18.013 -21.233  1.00 23.95      B
ATOM   5457  CE1 PHE B 162    -30.159  16.520 -22.593  1.00 26.60      B
ATOM   5458  CE2 PHE B 162    -28.299  18.049 -22.621  1.00 24.80      B
ATOM   5459  CZ  PHE B 162    -29.257  17.302 -23.302  1.00 25.92      B
ATOM   5460  C   PHE B 162    -29.971  19.631 -18.892  1.00 23.35      B
ATOM   5461  O   PHE B 162    -30.546  20.039 -19.906  1.00 24.26      B
ATOM   5462  N   PRO B 163    -29.142  20.418 -18.176  1.00 20.01      B
ATOM   5463  CD  PRO B 163    -28.505  20.110 -16.883  1.00 19.21      B
ATOM   5464  CA  PRO B 163    -28.866  21.797 -18.559  1.00 17.37      B
ATOM   5465  CB  PRO B 163    -28.530  22.441 -17.233  1.00 16.01      B
ATOM   5466  CG  PRO B 163    -27.727  21.374 -16.585  1.00 16.57      B
ATOM   5467  C   PRO B 163    -27.707  21.849 -19.548  1.00 17.34      B
ATOM   5468  O   PRO B 163    -27.001  20.851 -19.748  1.00 16.05      B
ATOM   5469  N   ASP B 164    -27.523  23.017 -20.157  1.00 17.74      B
ATOM   5470  CA  ASP B 164    -26.469  23.242 -21.134  1.00 16.04      B
```

FIGURE 4- 73 -

```
ATOM   5471  CB   ASP B 164     -26.534  24.681 -21.635  1.00 14.81        B
ATOM   5472  CG   ASP B 164     -25.684  24.910 -22.866  1.00 18.32        B
ATOM   5473  OD1  ASP B 164     -26.120  24.559 -23.996  1.00 19.54        B
ATOM   5474  OD2  ASP B 164     -24.565  25.440 -22.719  1.00 21.33        B
ATOM   5475  C    ASP B 164     -25.076  22.965 -20.552  1.00 17.90        B
ATOM   5476  O    ASP B 164     -24.858  23.041 -19.333  1.00 14.62        B
ATOM   5477  N    LEU B 165     -24.150  22.639 -21.452  1.00 19.75        B
ATOM   5478  CA   LEU B 165     -22.768  22.339 -21.122  1.00 19.73        B
ATOM   5479  CB   LEU B 165     -21.963  22.276 -22.419  1.00 20.30        B
ATOM   5480  CG   LEU B 165     -20.476  21.949 -22.321  1.00 21.32        B
ATOM   5481  CD1  LEU B 165     -20.268  20.677 -21.528  1.00 20.22        B
ATOM   5482  CD2  LEU B 165     -19.915  21.799 -23.712  1.00 22.12        B
ATOM   5483  C    LEU B 165     -22.176  23.387 -20.176  1.00 20.10        B
ATOM   5484  O    LEU B 165     -21.595  23.051 -19.136  1.00 18.78        B
ATOM   5485  N    GLY B 166     -22.323  24.655 -20.543  1.00 19.63        B
ATOM   5486  CA   GLY B 166     -21.796  25.723 -19.714  1.00 21.44        B
ATOM   5487  C    GLY B 166     -22.185  25.579 -18.254  1.00 21.12        B
ATOM   5488  O    GLY B 166     -21.338  25.642 -17.369  1.00 22.71        B
ATOM   5489  N    VAL B 167     -23.473  25.393 -17.999  1.00 21.67        B
ATOM   5490  CA   VAL B 167     -23.968  25.238 -16.638  1.00 21.73        B
ATOM   5491  CB   VAL B 167     -25.517  25.117 -16.625  1.00 22.62        B
ATOM   5492  CG1  VAL B 167     -26.011  24.732 -15.227  1.00 21.35        B
ATOM   5493  CG2  VAL B 167     -26.145  26.432 -17.068  1.00 21.41        B
ATOM   5494  C    VAL B 167     -23.378  23.982 -16.000  1.00 22.00        B
ATOM   5495  O    VAL B 167     -22.981  23.993 -14.831  1.00 22.57        B
ATOM   5496  N    ARG B 168     -23.333  22.899 -16.774  1.00 21.24        B
ATOM   5497  CA   ARG B 168     -22.813  21.637 -16.287  1.00 20.12        B
ATOM   5498  CB   ARG B 168     -22.839  20.573 -17.393  1.00 20.89        B
ATOM   5499  CG   ARG B 168     -24.238  20.140 -17.855  1.00 20.25        B
ATOM   5500  CD   ARG B 168     -24.227  18.759 -18.529  1.00 16.92        B
ATOM   5501  NE   ARG B 168     -23.427  18.693 -19.751  1.00 20.69        B
ATOM   5502  CZ   ARG B 168     -23.819  19.127 -20.953  1.00 23.69        B
ATOM   5503  NH1  ARG B 168     -25.019  19.673 -21.132  1.00 22.83        B
ATOM   5504  NH2  ARG B 168     -23.009  19.005 -21.994  1.00 21.32        B
ATOM   5505  C    ARG B 168     -21.402  21.795 -15.753  1.00 21.57        B
ATOM   5506  O    ARG B 168     -21.040  21.175 -14.750  1.00 21.28        B
ATOM   5507  N    VAL B 169     -20.595  22.621 -16.409  1.00 21.71        B
ATOM   5508  CA   VAL B 169     -19.230  22.816 -15.936  1.00 22.68        B
ATOM   5509  CB   VAL B 169     -18.350  23.541 -16.994  1.00 22.41        B
ATOM   5510  CG1  VAL B 169     -16.939  23.732 -16.460  1.00 20.87        B
ATOM   5511  CG2  VAL B 169     -18.298  22.725 -18.285  1.00 20.68        B
ATOM   5512  C    VAL B 169     -19.246  23.630 -14.641  1.00 24.45        B
ATOM   5513  O    VAL B 169     -18.508  23.331 -13.698  1.00 25.41        B
ATOM   5514  N    CYS B 170     -20.093  24.653 -14.576  1.00 24.64        B
ATOM   5515  CA   CYS B 170     -20.149  25.467 -13.368  1.00 24.28        B
ATOM   5516  CB   CYS B 170     -21.062  26.666 -13.580  1.00 23.67        B
ATOM   5517  SG   CYS B 170     -20.388  27.839 -14.776  1.00 25.50        B
ATOM   5518  C    CYS B 170     -20.592  24.669 -12.158  1.00 24.37        B
ATOM   5519  O    CYS B 170     -20.152  24.931 -11.045  1.00 25.21        B
ATOM   5520  N    GLU B 171     -21.458  23.687 -12.370  1.00 24.94        B
ATOM   5521  CA   GLU B 171     -21.917  22.853 -11.266  1.00 25.39        B
ATOM   5522  CB   GLU B 171     -22.896  21.794 -11.745  1.00 27.25        B
ATOM   5523  CG   GLU B 171     -24.155  22.267 -12.418  1.00 28.03        B
ATOM   5524  CD   GLU B 171     -25.066  21.088 -12.706  1.00 29.13        B
ATOM   5525  OE1  GLU B 171     -25.700  20.584 -11.755  1.00 29.71        B
ATOM   5526  OE2  GLU B 171     -25.129  20.643 -13.873  1.00 28.59        B
ATOM   5527  C    GLU B 171     -20.722  22.122 -10.673  1.00 25.78        B
ATOM   5528  O    GLU B 171     -20.658  21.882  -9.468  1.00 25.23        B
ATOM   5529  N    LYS B 172     -19.784  21.746 -11.539  1.00 26.83        B
ATOM   5530  CA   LYS B 172     -18.587  21.032 -11.107  1.00 27.54        B
ATOM   5531  CB   LYS B 172     -17.773  20.534 -12.308  1.00 28.00        B
ATOM   5532  CG   LYS B 172     -18.416  19.414 -13.115  1.00 30.51        B
ATOM   5533  CD   LYS B 172     -17.511  18.988 -14.273  1.00 32.25        B
ATOM   5534  CE   LYS B 172     -18.124  17.873 -15.122  1.00 32.06        B
ATOM   5535  NZ   LYS B 172     -19.217  18.373 -16.001  1.00 35.83        B
ATOM   5536  C    LYS B 172     -17.713  21.931 -10.247  1.00 27.87        B
ATOM   5537  O    LYS B 172     -17.202  21.503  -9.209  1.00 29.34        B
ATOM   5538  N    MET B 173     -17.544  23.179 -10.672  1.00 26.93        B
ATOM   5539  CA   MET B 173     -16.715  24.108  -9.919  1.00 26.03        B
ATOM   5540  CB   MET B 173     -16.610  25.453 -10.639  1.00 25.64        B
ATOM   5541  CG   MET B 173     -15.895  25.372 -11.975  1.00 26.83        B
ATOM   5542  SD   MET B 173     -15.637  26.965 -12.777  1.00 31.13        B
ATOM   5543  CE   MET B 173     -17.207  27.219 -13.558  1.00 28.21        B
ATOM   5544  C    MET B 173     -17.261  24.326  -8.528  1.00 25.37        B
ATOM   5545  O    MET B 173     -16.509  24.347  -7.549  1.00 25.31        B
ATOM   5546  N    ALA B 174     -18.576  24.459  -8.433  1.00 24.41        B
```

FIGURE 4- 74 -

```
ATOM   5547  CA   ALA B 174     -19.201   24.718   -7.146  1.00 23.26      B
ATOM   5548  CB   ALA B 174     -20.387   25.643   -7.348  1.00 21.85      B
ATOM   5549  C    ALA B 174     -19.625   23.509   -6.308  1.00 23.27      B
ATOM   5550  O    ALA B 174     -19.708   23.618   -5.087  1.00 23.92      B
ATOM   5551  N    LEU B 175     -19.883   22.359   -6.926  1.00 21.07      B
ATOM   5552  CA   LEU B 175     -20.339   21.224   -6.129  1.00 21.17      B
ATOM   5553  CB   LEU B 175     -21.846   21.039   -6.329  1.00 16.83      B
ATOM   5554  CG   LEU B 175     -22.786   22.064   -5.701  1.00 16.50      B
ATOM   5555  CD1  LEU B 175     -24.069   22.153   -6.511  1.00 14.62      B
ATOM   5556  CD2  LEU B 175     -23.064   21.674   -4.256  1.00 15.23      B
ATOM   5557  C    LEU B 175     -19.645   19.873   -6.316  1.00 22.65      B
ATOM   5558  O    LEU B 175     -20.034   18.896   -5.666  1.00 20.12      B
ATOM   5559  N    TYR B 176     -18.636   19.805   -7.185  1.00 22.92      B
ATOM   5560  CA   TYR B 176     -17.947   18.544   -7.402  1.00 23.87      B
ATOM   5561  CB   TYR B 176     -16.848   18.672   -8.453  1.00 24.76      B
ATOM   5562  CG   TYR B 176     -16.137   17.354   -8.677  1.00 27.26      B
ATOM   5563  CD1  TYR B 176     -16.807   16.260   -9.239  1.00 27.46      B
ATOM   5564  CE1  TYR B 176     -16.189   15.017   -9.356  1.00 27.58      B
ATOM   5565  CD2  TYR B 176     -14.828   17.168   -8.247  1.00 26.97      B
ATOM   5566  CE2  TYR B 176     -14.206   15.929   -8.361  1.00 27.41      B
ATOM   5567  CZ   TYR B 176     -14.889   14.863   -8.910  1.00 27.80      B
ATOM   5568  OH   TYR B 176     -14.271   13.640   -8.985  1.00 30.75      B
ATOM   5569  C    TYR B 176     -17.327   18.028   -6.116  1.00 24.46      B
ATOM   5570  O    TYR B 176     -17.532   16.875   -5.735  1.00 24.67      B
ATOM   5571  N    ASP B 177     -16.555   18.875   -5.449  1.00 25.12      B
ATOM   5572  CA   ASP B 177     -15.926   18.473   -4.202  1.00 25.18      B
ATOM   5573  CB   ASP B 177     -15.153   19.639   -3.601  1.00 27.06      B
ATOM   5574  CG   ASP B 177     -14.101   19.190   -2.616  1.00 28.94      B
ATOM   5575  OD1  ASP B 177     -14.025   17.971   -2.353  1.00 30.00      B
ATOM   5576  OD2  ASP B 177     -13.346   20.055   -2.108  1.00 30.18      B
ATOM   5577  C    ASP B 177     -17.025   18.031   -3.247  1.00 23.50      B
ATOM   5578  O    ASP B 177     -16.955   16.962   -2.657  1.00 23.15      B
ATOM   5579  N    VAL B 178     -18.059   18.848   -3.120  1.00 24.26      B
ATOM   5580  CA   VAL B 178     -19.157   18.518   -2.227  1.00 25.20      B
ATOM   5581  CB   VAL B 178     -20.301   19.541   -2.326  1.00 24.09      B
ATOM   5582  CG1  VAL B 178     -21.314   19.268   -1.236  1.00 22.00      B
ATOM   5583  CG2  VAL B 178     -19.757   20.958   -2.202  1.00 24.11      B
ATOM   5584  C    VAL B 178     -19.738   17.130   -2.484  1.00 27.82      B
ATOM   5585  O    VAL B 178     -19.755   16.296   -1.571  1.00 29.73      B
ATOM   5586  N    VAL B 179     -20.213   16.872   -3.708  1.00 27.78      B
ATOM   5587  CA   VAL B 179     -20.808   15.571   -4.031  1.00 26.64      B
ATOM   5588  CB   VAL B 179     -21.462   15.574   -5.425  1.00 26.91      B
ATOM   5589  CG1  VAL B 179     -22.464   16.705   -5.520  1.00 25.38      B
ATOM   5590  CG2  VAL B 179     -20.394   15.674   -6.517  1.00 26.75      B
ATOM   5591  C    VAL B 179     -19.852   14.376   -3.956  1.00 27.49      B
ATOM   5592  O    VAL B 179     -20.290   13.226   -3.982  1.00 29.57      B
ATOM   5593  N    SER B 180     -18.556   14.642   -3.850  1.00 26.99      B
ATOM   5594  CA   SER B 180     -17.565   13.578   -3.767  1.00 27.55      B
ATOM   5595  CB   SER B 180     -16.303   13.954   -4.541  1.00 25.84      B
ATOM   5596  OG   SER B 180     -16.582   14.133   -5.911  1.00 25.76      B
ATOM   5597  C    SER B 180     -17.162   13.303   -2.335  1.00 29.14      B
ATOM   5598  O    SER B 180     -16.592   12.250   -2.037  1.00 31.93      B
ATOM   5599  N    THR B 181     -17.460   14.241   -1.443  1.00 29.19      B
ATOM   5600  CA   THR B 181     -17.064   14.097   -0.046  1.00 28.69      B
ATOM   5601  CB   THR B 181     -16.144   15.267    0.366  1.00 29.09      B
ATOM   5602  OG1  THR B 181     -14.963   15.251   -0.439  1.00 28.37      B
ATOM   5603  CG2  THR B 181     -15.738   15.144    1.820  1.00 31.71      B
ATOM   5604  C    THR B 181     -18.174   14.006    0.996  1.00 27.95      B
ATOM   5605  O    THR B 181     -18.118   13.183    1.898  1.00 29.76      B
ATOM   5606  N    LEU B 182     -19.173   14.865    0.880  1.00 26.54      B
ATOM   5607  CA   LEU B 182     -20.251   14.905    1.849  1.00 23.31      B
ATOM   5608  CB   LEU B 182     -21.202   16.041    1.465  1.00 18.68      B
ATOM   5609  CG   LEU B 182     -22.297   16.406    2.447  1.00 15.69      B
ATOM   5610  CD1  LEU B 182     -22.627   17.855    2.325  1.00 19.26      B
ATOM   5611  CD2  LEU B 182     -23.510   15.570    2.169  1.00 16.91      B
ATOM   5612  C    LEU B 182     -21.003   13.583    2.081  1.00 24.44      B
ATOM   5613  O    LEU B 182     -21.200   13.178    3.230  1.00 24.14      B
ATOM   5614  N    PRO B 183     -21.421   12.885    1.007  1.00 25.29      B
ATOM   5615  CD   PRO B 183     -21.158   13.173   -0.415  1.00 25.94      B
ATOM   5616  CA   PRO B 183     -22.150   11.612    1.160  1.00 26.00      B
ATOM   5617  CB   PRO B 183     -22.118   11.019   -0.247  1.00 25.49      B
ATOM   5618  CG   PRO B 183     -22.119   12.227   -1.123  1.00 27.26      B
ATOM   5619  C    PRO B 183     -21.513   10.665    2.183  1.00 27.13      B
ATOM   5620  O    PRO B 183     -22.178   10.160    3.087  1.00 26.75      B
ATOM   5621  N    GLN B 184     -20.217   10.425    2.021  1.00 27.65      B
ATOM   5622  CA   GLN B 184     -19.469    9.555    2.911  1.00 27.70      B
```

FIGURE 4-75-

```
ATOM   5623  CB   GLN B 184     -18.031    9.474    2.429  1.00 30.94        B
ATOM   5624  CG   GLN B 184     -17.102    8.723    3.358  1.00 36.84        B
ATOM   5625  CD   GLN B 184     -16.890    7.282    2.929  1.00 40.18        B
ATOM   5626  CE1  GLN B 184     -16.645    7.002    1.745  1.00 42.24        B
ATOM   5627  NE2  GLN B 184     -16.966    6.357    3.891  1.00 40.50        B
ATOM   5628  C    GLN B 184     -19.490   10.101    4.330  1.00 26.82        B
ATOM   5629  O    GLN B 184     -19.778    9.384    5.293  1.00 25.95        B
ATOM   5630  N    ALA B 185     -19.173   11.383    4.439  1.00 25.08        B
ATOM   5631  CA   ALA B 185     -19.126   12.081    5.716  1.00 25.79        B
ATOM   5632  CB   ALA B 185     -18.725   13.536    5.478  1.00 25.38        B
ATOM   5633  C    ALA B 185     -20.429   12.028    6.521  1.00 25.71        B
ATOM   5634  O    ALA B 185     -20.407   11.973    7.752  1.00 25.06        B
ATOM   5635  N    VAL B 186     -21.558   12.041    5.822  1.00 25.70        B
ATOM   5636  CA   VAL B 186     -22.859   12.033    6.474  1.00 25.81        B
ATOM   5637  CB   VAL B 186     -23.902   12.813    5.626  1.00 24.38        B
ATOM   5638  CG1  VAL B 186     -25.257   12.802    6.300  1.00 19.98        B
ATOM   5639  CG2  VAL B 186     -23.432   14.246    5.423  1.00 23.87        B
ATOM   5640  C    VAL B 186     -23.407   10.643    6.757  1.00 27.72        B
ATOM   5641  O    VAL B 186     -23.919   10.387    7.852  1.00 28.26        B
ATOM   5642  N    MET B 187     -23.282    9.743    5.788  1.00 28.82        B
ATOM   5643  CA   MET B 187     -23.816    8.391    5.938  1.00 30.88        B
ATOM   5644  CB   MET B 187     -24.613    8.043    4.680  1.00 31.56        B
ATOM   5645  CG   MET B 187     -25.747    9.028    4.390  1.00 32.91        B
ATOM   5646  SD   MET B 187     -26.194    9.102    2.640  1.00 34.63        B
ATOM   5647  CE   MET B 187     -26.578    7.404    2.322  1.00 36.55        B
ATOM   5648  C    MET B 187     -22.793    7.284    6.241  1.00 31.86        B
ATOM   5649  O    MET B 187     -23.166    6.139    6.512  1.00 32.58        B
ATOM   5650  N    GLY B 188     -21.509    7.621    6.195  1.00 32.19        B
ATOM   5651  CA   GLY B 188     -20.484    6.632    6.470  1.00 31.82        B
ATOM   5652  C    GLY B 188     -20.704    5.283    5.811  1.00 32.13        B
ATOM   5653  O    GLY B 188     -20.963    5.202    4.612  1.00 32.70        B
ATOM   5654  N    SER B 189     -20.611    4.221    6.604  1.00 32.74        B
ATOM   5655  CA   SER B 189     -20.767    2.851    6.105  1.00 33.04        B
ATOM   5656  CB   SER B 189     -20.856    1.868    7.274  1.00 32.83        B
ATOM   5657  OG   SER B 189     -22.121    1.960    7.910  1.00 34.06        B
ATOM   5658  C    SER B 189     -21.966    2.608    5.191  1.00 32.88        B
ATOM   5659  O    SER B 189     -21.898    1.773    4.289  1.00 33.09        B
ATOM   5660  N    SER B 190     -23.063    3.318    5.433  1.00 31.77        B
ATOM   5661  CA   SER B 190     -24.267    3.145    4.628  1.00 32.05        B
ATOM   5662  CB   SER B 190     -25.469    3.754    5.352  1.00 32.65        B
ATOM   5663  OG   SER B 190     -25.716    3.084    6.576  1.00 35.24        B
ATOM   5664  C    SER B 190     -24.199    3.705    3.206  1.00 31.95        B
ATOM   5665  O    SER B 190     -25.089    3.442    2.399  1.00 33.19        B
ATOM   5666  N    TYR B 191     -23.169    4.482    2.891  1.00 30.96        B
ATOM   5667  CA   TYR B 191     -23.053    5.031    1.548  1.00 31.78        B
ATOM   5668  CB   TYR B 191     -22.076    6.209    1.534  1.00 32.80        B
ATOM   5669  CG   TYR B 191     -21.920    6.899    0.190  1.00 31.97        B
ATOM   5670  CD1  TYR B 191     -23.026    7.344   -0.520  1.00 31.58        B
ATOM   5671  CE1  TYR B 191     -22.885    7.996   -1.738  1.00 31.19        B
ATOM   5672  CD2  TYR B 191     -20.656    7.128   -0.355  1.00 32.75        B
ATOM   5673  CE2  TYR B 191     -20.503    7.786   -1.571  1.00 31.65        B
ATOM   5674  CZ   TYR B 191     -21.624    8.214   -2.258  1.00 32.67        B
ATOM   5675  OH   TYR B 191     -21.489    8.849   -3.477  1.00 34.43        B
ATOM   5676  C    TYR B 191     -22.557    3.910    0.652  1.00 32.88        B
ATOM   5677  O    TYR B 191     -21.431    3.432    0.804  1.00 34.60        B
ATOM   5678  N    GLY B 192     -23.405    3.486   -0.279  1.00 33.27        B
ATOM   5679  CA   GLY B 192     -23.042    2.400   -1.167  1.00 34.02        B
ATOM   5680  C    GLY B 192     -21.859    2.592   -2.101  1.00 35.29        B
ATOM   5681  O    GLY B 192     -20.972    1.740   -2.164  1.00 35.24        B
ATOM   5682  N    PHE B 193     -21.826    3.713   -2.813  1.00 36.35        B
ATOM   5683  CA   PHE B 193     -20.769    3.966   -3.791  1.00 37.03        B
ATOM   5684  CB   PHE B 193     -21.077    5.255   -4.543  1.00 35.55        B
ATOM   5685  CG   PHE B 193     -22.391    5.226   -5.258  1.00 35.57        B
ATOM   5686  CD1  PHE B 193     -22.611    4.322   -6.289  1.00 34.49        B
ATOM   5687  CD2  PHE B 193     -23.415    6.099   -4.902  1.00 36.33        B
ATOM   5688  CE1  PHE B 193     -23.827    4.286   -6.959  1.00 33.64        B
ATOM   5689  CE2  PHE B 193     -24.639    6.072   -5.567  1.00 35.24        B
ATOM   5690  CZ   PHE B 193     -24.843    5.161   -6.598  1.00 35.27        B
ATOM   5691  C    PHE B 193     -19.325    3.981   -3.319  1.00 37.51        B
ATOM   5692  O    PHE B 193     -18.411    4.127   -4.130  1.00 37.24        B
ATOM   5693  N    GLN B 194     -19.101    3.822   -2.023  1.00 39.33        B
ATOM   5694  CA   GLN B 194     -17.729    3.823   -1.528  1.00 41.71        B
ATOM   5695  CB   GLN B 194     -17.671    4.306   -0.082  1.00 41.01        B
ATOM   5696  CG   GLN B 194     -18.127    3.282    0.918  1.00 40.81        B
ATOM   5697  CD   GLN B 194     -17.871    3.731    2.330  1.00 41.80        B
ATOM   5698  CE1  GLN B 194     -16.751    4.104    2.674  1.00 41.98        B
```

FIGURE 4- 76 -

```
ATOM   5699  NE2 GLN B 194     -18.907   3.694   3.165  1.00 42.10      B
ATOM   5700  C   GLN B 194     -17.163   2.415  -1.590  1.00 43.36      B
ATOM   5701  O   GLN B 194     -15.988   2.192  -1.287  1.00 43.99      B
ATOM   5702  N   TYR B 195     -18.011   1.471  -1.990  1.00 43.80      B
ATOM   5703  CA  TYR B 195     -17.630   0.070  -2.066  1.00 43.07      B
ATOM   5704  CB  TYR B 195     -18.686  -0.783  -1.383  1.00 41.34      B
ATOM   5705  CG  TYR B 195     -18.964  -0.442   0.053  1.00 41.20      B
ATOM   5706  CD1 TYR B 195     -17.964  -0.534   1.020  1.00 40.19      B
ATOM   5707  CE1 TYR B 195     -18.244  -0.316   2.363  1.00 40.01      B
ATOM   5708  CD2 TYR B 195     -20.254  -0.111   0.463  1.00 41.91      B
ATOM   5709  CE2 TYR B 195     -20.549   0.108   1.803  1.00 42.56      B
ATOM   5710  CZ  TYR B 195     -19.540  -0.002   2.750  1.00 42.38      B
ATOM   5711  OH  TYR B 195     -19.847   0.165   4.082  1.00 45.04      B
ATOM   5712  C   TYR B 195     -17.428  -0.502  -3.461  1.00 44.56      B
ATOM   5713  O   TYR B 195     -18.161  -0.184  -4.395  1.00 45.04      B
ATOM   5714  N   SER B 196     -16.428  -1.368  -3.588  1.00 46.44      B
ATOM   5715  CA  SER B 196     -16.167  -2.052  -4.850  1.00 46.37      B
ATOM   5716  CB  SER B 196     -14.681  -2.381  -5.002  1.00 44.33      B
ATOM   5717  OG  SER B 196     -14.293  -3.404  -4.105  1.00 42.58      B
ATOM   5718  C   SER B 196     -16.981  -3.341  -4.698  1.00 47.90      B
ATOM   5719  O   SER B 196     -17.306  -3.754  -3.572  1.00 47.07      B
ATOM   5720  N   PRO B 197     -17.311  -4.002  -5.316  1.00 48.88      B
ATOM   5721  CD  PRO B 197     -16.737  -3.805  -7.158  1.00 48.64      B
ATOM   5722  CA  PRO B 197     -18.098  -5.241  -5.770  1.00 49.37      B
ATOM   5723  CB  PRO B 197     -17.809  -5.875  -7.120  1.00 49.23      B
ATOM   5724  CG  PRO B 197     -17.620  -4.684  -8.004  1.00 48.75      B
ATOM   5725  C   PRO B 197     -17.739  -6.160  -4.605  1.00 50.27      B
ATOM   5726  O   PRO B 197     -18.622  -6.636  -3.882  1.00 49.31      B
ATOM   5727  N   LYS B 198     -16.443  -6.407  -4.425  1.00 51.39      B
ATOM   5728  CA  LYS B 198     -15.990  -7.264  -3.337  1.00 52.32      B
ATOM   5729  CB  LYS B 198     -14.477  -7.470  -3.400  1.00 53.33      B
ATOM   5730  CG  LYS B 198     -13.936  -8.282  -2.233  1.00 55.35      B
ATOM   5731  CD  LYS B 198     -12.432  -8.509  -2.314  1.00 57.91      B
ATOM   5732  CE  LYS B 198     -11.948  -9.358  -1.125  1.00 59.42      B
ATOM   5733  NZ  LYS B 198     -10.468  -9.625  -1.116  1.00 59.96      B
ATOM   5734  C   LYS B 198     -16.344  -6.654  -1.986  1.00 52.07      B
ATOM   5735  O   LYS B 198     -16.824  -7.340  -1.078  1.00 51.98      B
ATOM   5736  N   GLN B 199     -16.110  -5.355  -1.864  1.00 50.73      B
ATOM   5737  CA  GLN B 199     -16.372  -4.656  -0.620  1.00 50.55      B
ATOM   5738  CB  GLN B 199     -15.742  -3.270  -0.698  1.00 50.41      B
ATOM   5739  CG  GLN B 199     -14.325  -3.360  -1.240  1.00 49.93      B
ATOM   5740  CD  GLN B 199     -13.551  -2.081  -1.128  1.00 48.80      B
ATOM   5741  OE1 GLN B 199     -13.980  -1.031  -1.614  1.00 48.32      B
ATOM   5742  NE2 GLN B 199     -12.386  -2.159  -0.493  1.00 48.71      B
ATOM   5743  C   GLN B 199     -17.856  -4.581  -0.290  1.00 50.36      B
ATOM   5744  O   GLN B 199     -18.249  -4.650   0.879  1.00 49.83      B
ATOM   5745  N   ARG B 200     -18.685  -4.451  -1.319  1.00 49.54      B
ATOM   5746  CA  ARG B 200     -20.119  -4.388  -1.099  1.00 48.82      B
ATOM   5747  CB  ARG B 200     -20.856  -4.158  -2.423  1.00 48.43      B
ATOM   5748  CG  ARG B 200     -22.361  -4.033  -2.273  1.00 47.04      B
ATOM   5749  CD  ARG B 200     -23.055  -3.952  -3.619  1.00 47.60      B
ATOM   5750  NE  ARG B 200     -24.509  -3.859  -3.473  1.00 46.81      B
ATOM   5751  CZ  ARG B 200     -25.158  -2.785  -3.032  1.00 45.14      B
ATOM   5752  NH1 ARG B 200     -24.485  -1.693  -2.690  1.00 44.90      B
ATOM   5753  NH2 ARG B 200     -26.480  -2.809  -2.928  1.00 43.45      B
ATOM   5754  C   ARG B 200     -20.569  -5.706  -0.475  1.00 49.16      B
ATOM   5755  O   ARG B 200     -21.197  -5.720   0.584  1.00 48.47      B
ATOM   5756  N   VAL B 201     -20.232  -6.815  -1.130  1.00 49.79      B
ATOM   5757  CA  VAL B 201     -20.620  -8.131  -0.630  1.00 51.03      B
ATOM   5758  CB  VAL B 201     -19.928  -9.283  -1.402  1.00 52.26      B
ATOM   5759  CG1 VAL B 201     -20.405 -10.620  -0.859  1.00 51.68      B
ATOM   5760  CG2 VAL B 201     -20.220  -9.181  -2.889  1.00 54.03      B
ATOM   5761  C   VAL B 201     -20.232  -8.268   0.831  1.00 50.33      B
ATOM   5762  O   VAL B 201     -21.037  -8.699   1.664  1.00 49.53      B
ATOM   5763  N   GLU B 202     -18.990  -7.891   1.125  1.00 49.63      B
ATOM   5764  CA  GLU B 202     -18.463  -7.980   2.473  1.00 49.36      B
ATOM   5765  CB  GLU B 202     -17.049  -7.407   2.540  1.00 50.68      B
ATOM   5766  CG  GLU B 202     -16.577  -7.201   3.972  1.00 52.88      B
ATOM   5767  CD  GLU B 202     -15.163  -6.660   4.071  1.00 53.96      B
ATOM   5768  OE1 GLU B 202     -14.827  -5.736   3.293  1.00 54.66      B
ATOM   5769  OE2 GLU B 202     -14.399  -7.151   4.938  1.00 54.15      B
ATOM   5770  C   GLU B 202     -19.340  -7.273   3.486  1.00 48.60      B
ATOM   5771  O   GLU B 202     -19.740  -7.869   4.484  1.00 49.62      B
ATOM   5772  N   PHE B 203     -19.646  -6.007   3.231  1.00 47.42      B
ATOM   5773  CA  PHE B 203     -20.475  -5.241   4.151  1.00 46.35      B
ATOM   5774  CB  PHE B 203     -20.679  -3.816   3.619  1.00 44.74      B
```

FIGURE 4- 77 -

```
ATOM   5775  CG   PHE B 203     -21.463  -2.925   4.547  1.00 43.64      B
ATOM   5776  CD1  PHE B 203     -20.932  -2.530   5.766  1.00 42.59      B
ATOM   5777  CD2  PHE B 203     -22.743  -2.491   4.200  1.00 42.83      B
ATOM   5778  CE1  PHE B 203     -21.665  -1.714   6.630  1.00 43.44      B
ATOM   5779  CE2  PHE B 203     -23.473  -1.680   5.052  1.00 41.55      B
ATOM   5780  CZ   PHE B 203     -22.941  -1.290   6.270  1.00 42.42      B
ATOM   5781  C    PHE B 203     -21.830  -5.922   4.371  1.00 46.20      B
ATOM   5782  O    PHE B 203     -22.318  -6.003   5.496  1.00 47.19      B
ATOM   5783  N    LEU B 204     -22.435  -6.425   3.303  1.00 45.21      B
ATOM   5784  CA   LEU B 204     -23.727  -7.067   3.442  1.00 44.39      B
ATOM   5785  CB   LEU B 204     -24.322  -7.365   2.066  1.00 41.98      B
ATOM   5786  CG   LEU B 204     -24.814  -6.141   1.284  1.00 38.89      B
ATOM   5787  CD1  LEU B 204     -25.450  -6.588  -0.012  1.00 37.07      B
ATOM   5788  CD2  LEU B 204     -25.822  -5.359   2.107  1.00 36.00      B
ATOM   5789  C    LEU B 204     -23.697  -8.329   4.301  1.00 45.84      B
ATOM   5790  O    LEU B 204     -24.398  -8.405   5.313  1.00 46.38      B
ATOM   5791  N    VAL B 205     -22.889  -9.317   3.926  1.00 47.11      B
ATOM   5792  CA   VAL B 205     -22.835 -10.548   4.720  1.00 47.44      B
ATOM   5793  CB   VAL B 205     -21.814 -11.562   4.163  1.00 47.02      B
ATOM   5794  CG1  VAL B 205     -21.590 -12.686   5.173  1.00 45.83      B
ATOM   5795  CG2  VAL B 205     -22.328 -12.134   2.850  1.00 45.60      B
ATOM   5796  C    VAL B 205     -22.484 -10.236   6.165  1.00 47.77      B
ATOM   5797  O    VAL B 205     -23.148 -10.708   7.086  1.00 47.45      B
ATOM   5798  N    ASN B 206     -21.437  -9.443   6.358  1.00 48.91      B
ATOM   5799  CA   ASN B 206     -21.028  -9.057   7.699  1.00 49.76      B
ATOM   5800  CB   ASN B 206     -19.892  -8.040   7.657  1.00 48.32      B
ATOM   5801  CG   ASN B 206     -18.538  -8.692   7.551  1.00 48.00      B
ATOM   5802  OD1  ASN B 206     -18.258  -9.668   8.245  1.00 48.00      B
ATOM   5803  ND2  ASN B 206     -17.681  -8.151   6.693  1.00 47.49      B
ATOM   5804  C    ASN B 206     -22.208  -8.442   8.428  1.00 51.49      B
ATOM   5805  O    ASN B 206     -22.460  -8.752   9.594  1.00 51.95      B
ATOM   5806  N    THR B 207     -22.935  -7.569   7.737  1.00 52.94      B
ATOM   5807  CA   THR B 207     -24.084  -6.921   8.345  1.00 55.04      B
ATOM   5808  CB   THR B 207     -24.744  -5.889   7.387  1.00 54.35      B
ATOM   5809  OG1  THR B 207     -23.818  -4.833   7.109  1.00 51.78      B
ATOM   5810  CG2  THR B 207     -25.999  -5.290   8.025  1.00 52.83      B
ATOM   5811  C    THR B 207     -25.108  -7.977   8.728  1.00 57.28      B
ATOM   5812  O    THR B 207     -25.731  -7.892   9.786  1.00 58.32      B
ATOM   5813  N    TRP B 208     -25.271  -8.983   7.875  1.00 59.44      B
ATOM   5814  CA   TRP B 208     -26.238 -10.039   8.151  1.00 62.19      B
ATOM   5815  CB   TRP B 208     -26.395 -10.950   6.924  1.00 63.65      B
ATOM   5816  CG   TRP B 208     -27.544 -11.909   7.047  1.00 65.34      B
ATOM   5817  CD2  TRP B 208     -28.888 -11.695   6.600  1.00 66.17      B
ATOM   5818  CE2  TRP B 208     -29.641 -12.824   6.992  1.00 66.42      B
ATOM   5819  CE3  TRP B 208     -29.530 -10.656   5.914  1.00 65.83      B
ATOM   5820  CD1  TRP B 208     -27.537 -13.123   7.667  1.00 65.67      B
ATOM   5821  NE1  TRP B 208     -28.791 -13.679   7.641  1.00 65.58      B
ATOM   5822  CZ2  TRP B 208     -31.008 -12.946   6.717  1.00 66.74      B
ATOM   5823  CZ3  TRP B 208     -30.887 -10.777   5.641  1.00 66.32      B
ATOM   5824  CH2  TRP B 208     -31.610 -11.916   6.044  1.00 67.04      B
ATOM   5825  C    TRP B 208     -25.837 -10.862   9.379  1.00 63.29      B
ATOM   5826  O    TRP B 208     -26.688 -11.187  10.219  1.00 63.76      B
ATOM   5827  N    LYS B 209     -24.547 -11.185   9.488  1.00 63.69      B
ATOM   5828  CA   LYS B 209     -24.035 -11.969  10.614  1.00 63.64      B
ATOM   5829  CB   LYS B 209     -22.588 -12.383  10.358  1.00 63.58      B
ATOM   5830  CG   LYS B 209     -22.435 -13.375   9.228  1.00 64.94      B
ATOM   5831  CD   LYS B 209     -21.007 -13.874   9.129  1.00 65.83      B
ATOM   5832  CE   LYS B 209     -20.889 -14.982   8.101  1.00 67.01      B
ATOM   5833  NZ   LYS B 209     -19.491 -15.491   8.001  1.00 68.14      B
ATOM   5834  C    LYS B 209     -24.114 -11.232  11.946  1.00 63.56      B
ATOM   5835  O    LYS B 209     -24.517 -11.806  12.959  1.00 64.18      B
ATOM   5836  N    SER B 210     -23.729  -9.962  11.946  1.00 63.15      B
ATOM   5837  CA   SER B 210     -23.763  -9.165  13.165  1.00 62.60      B
ATOM   5838  CB   SER B 210     -23.381  -7.717  12.857  1.00 61.76      B
ATOM   5839  OG   SER B 210     -24.279  -7.154  11.922  1.00 61.19      B
ATOM   5840  C    SER B 210     -25.134  -9.194  13.841  1.00 62.80      B
ATOM   5841  O    SER B 210     -25.232  -9.001  15.051  1.00 62.44      B
ATOM   5842  N    LYS B 211     -26.186  -9.431  13.058  1.00 63.39      B
ATOM   5843  CA   LYS B 211     -27.550  -9.480  13.586  1.00 63.93      B
ATOM   5844  CB   LYS B 211     -28.581  -9.228  12.475  1.00 63.69      B
ATOM   5845  CG   LYS B 211     -28.305  -8.016  11.583  1.00 62.95      B
ATOM   5846  CD   LYS B 211     -28.307  -6.712  12.364  1.00 60.72      B
ATOM   5847  CE   LYS B 211     -28.043  -5.531  11.458  1.00 57.48      B
ATOM   5848  NZ   LYS B 211     -28.028  -4.267  12.236  1.00 56.63      B
ATOM   5849  C    LYS B 211     -27.823 -10.844  14.200  1.00 64.77      B
ATOM   5850  O    LYS B 211     -27.388 -11.872  13.679  1.00 64.63      B
```

FIGURE 4- 78 -

```
ATOM   5851  N   LYS B 212     -28.568 -10.851  15.306  1.00 65.78      B
ATOM   5852  CA  LYS B 212     -28.915 -12.102  15.975  1.00 66.43      B
ATOM   5853  CB  LYS B 212     -29.639 -11.824  17.295  1.00 67.60      B
ATOM   5854  CG  LYS B 212     -28.799 -11.068  18.309  1.00 68.84      B
ATOM   5855  CD  LYS B 212     -29.517 -10.937  19.644  1.00 70.32      B
ATOM   5856  CE  LYS B 212     -28.617 -10.279  20.691  1.00 70.76      B
ATOM   5857  NZ  LYS B 212     -29.221 -10.312  22.059  1.00 70.84      B
ATOM   5858  C   LYS B 212     -29.817 -12.892  15.034  1.00 66.13      B
ATOM   5859  O   LYS B 212     -29.367 -13.836  14.389  1.00 66.83      B
ATOM   5860  N   CYS B 213     -31.087 -12.501  14.962  1.00 65.25      B
ATOM   5861  CA  CYS B 213     -32.049 -13.139  14.067  1.00 64.54      B
ATOM   5862  CB  CYS B 213     -33.350 -13.473  14.813  1.00 65.19      B
ATOM   5863  SG  CYS B 213     -34.515 -14.562  13.913  1.00 65.25      B
ATOM   5864  C   CYS B 213     -32.318 -12.111  12.962  1.00 63.96      B
ATOM   5865  O   CYS B 213     -33.255 -11.308  13.049  1.00 63.52      B
ATOM   5866  N   PRO B 214     -31.484 -12.118  11.907  1.00 62.72      B
ATOM   5867  CD  PRO B 214     -30.402 -13.077  11.630  1.00 61.97      B
ATOM   5868  CA  PRO B 214     -31.638 -11.176  10.793  1.00 62.17      B
ATOM   5869  CB  PRO B 214     -30.535 -11.598   9.818  1.00 61.24      B
ATOM   5870  CG  PRO B 214     -30.341 -13.037  10.123  1.00 61.80      B
ATOM   5871  C   PRO B 214     -33.007 -11.121  10.131  1.00 61.17      B
ATOM   5872  O   PRO B 214     -33.889 -11.939  10.399  1.00 62.40      B
ATOM   5873  N   MET B 215     -33.159 -10.114   9.280  1.00 58.50      B
ATOM   5874  CA  MET B 215     -34.369  -9.859   8.516  1.00 55.98      B
ATOM   5875  CB  MET B 215     -35.511  -9.410   9.420  1.00 55.48      B
ATOM   5876  CG  MET B 215     -36.830  -9.229   8.685  1.00 56.24      B
ATOM   5877  SD  MET B 215     -36.854  -7.868   7.473  1.00 56.74      B
ATOM   5878  CE  MET B 215     -37.925  -6.681   8.339  1.00 54.13      B
ATOM   5879  C   MET B 215     -33.975  -8.725   7.593  1.00 54.75      B
ATOM   5880  O   MET B 215     -33.378  -7.743   8.032  1.00 54.19      B
ATOM   5881  N   GLY B 216     -34.290  -8.862   6.314  1.00 52.92      B
ATOM   5882  CA  GLY B 216     -33.917  -7.820   5.386  1.00 51.38      B
ATOM   5883  C   GLY B 216     -34.832  -7.685   4.196  1.00 49.83      B
ATOM   5884  O   GLY B 216     -35.475  -8.642   3.775  1.00 50.03      B
ATOM   5885  N   PHE B 217     -34.886  -6.477   3.653  1.00 47.80      B
ATOM   5886  CA  PHE B 217     -35.715  -6.209   2.495  1.00 44.94      B
ATOM   5887  CB  PHE B 217     -37.114  -5.763   2.927  1.00 44.79      B
ATOM   5888  CG  PHE B 217     -37.116  -4.560   3.853  1.00 43.74      B
ATOM   5889  CD1 PHE B 217     -36.900  -4.749   5.218  1.00 44.00      B
ATOM   5890  CD2 PHE B 217     -37.316  -3.294   3.357  1.00 42.77      B
ATOM   5891  CE1 PHE B 217     -36.884  -3.652   6.081  1.00 43.60      B
ATOM   5892  CE2 PHE B 217     -37.301  -2.194   4.206  1.00 42.47      B
ATOM   5893  CZ  PHE B 217     -37.085  -2.371   5.572  1.00 42.94      B
ATOM   5894  C   PHE B 217     -35.082  -5.129   1.647  1.00 42.60      B
ATOM   5895  O   PHE B 217     -34.128  -4.475   2.053  1.00 42.27      B
ATOM   5896  N   SER B 218     -35.615  -4.968   0.451  1.00 40.67      B
ATOM   5897  CA  SER B 218     -35.139  -3.957  -0.462  1.00 38.60      B
ATOM   5898  CB  SER B 218     -34.776  -4.568  -1.810  1.00 37.87      B
ATOM   5899  OG  SER B 218     -35.903  -5.207  -2.408  1.00 37.63      B
ATOM   5900  C   SER B 218     -36.343  -3.047  -0.598  1.00 38.39      B
ATOM   5901  O   SER B 218     -37.478  -3.477  -0.375  1.00 38.14      B
ATOM   5902  N   TYR B 219     -36.109  -1.785  -0.923  1.00 38.29      B
ATOM   5903  CA  TYR B 219     -37.220  -0.867  -1.078  1.00 37.89      B
ATOM   5904  CB  TYR B 219     -37.226   0.188   0.024  1.00 37.70      B
ATOM   5905  CG  TYR B 219     -38.531   0.951   0.106  1.00 35.80      B
ATOM   5906  CD1 TYR B 219     -39.648   0.399   0.733  1.00 34.33      B
ATOM   5907  CE1 TYR B 219     -40.851   1.078   0.776  1.00 34.25      B
ATOM   5908  CD2 TYR B 219     -38.657   2.210  -0.475  1.00 34.79      B
ATOM   5909  CE2 TYR B 219     -39.854   2.900  -0.444  1.00 34.57      B
ATOM   5910  CZ  TYR B 219     -40.951   2.333   0.179  1.00 35.92      B
ATOM   5911  OH  TYR B 219     -42.154   3.009   0.168  1.00 35.02      B
ATOM   5912  C   TYR B 219     -37.117  -0.204  -2.430  1.00 39.14      B
ATOM   5913  O   TYR B 219     -36.175   0.539  -2.723  1.00 40.22      B
ATOM   5914  N   ASP B 220     -38.095  -0.500  -3.265  1.00 39.64      B
ATOM   5915  CA  ASP B 220     -38.135   0.045  -4.599  1.00 39.75      B
ATOM   5916  CB  ASP B 220     -38.587  -1.039  -5.569  1.00 40.70      B
ATOM   5917  CG  ASP B 220     -39.098  -0.475  -6.871  1.00 43.08      B
ATOM   5918  OD1 ASP B 220     -38.275   0.070  -7.641  1.00 44.04      B
ATOM   5919  OD2 ASP B 220     -40.328  -0.571  -7.115  1.00 43.48      B
ATOM   5920  C   ASP B 220     -39.105   1.213  -4.607  1.00 39.95      B
ATOM   5921  O   ASP B 220     -40.322   1.030  -4.520  1.00 40.51      B
ATOM   5922  N   THR B 221     -38.564   2.421  -4.691  1.00 39.69      B
ATOM   5923  CA  THR B 221     -39.410   3.597  -4.711  1.00 39.55      B
ATOM   5924  CB  THR B 221     -38.642   4.856  -4.306  1.00 39.25      B
ATOM   5925  OG1 THR B 221     -37.882   4.594  -3.118  1.00 40.22      B
ATOM   5926  CG2 THR B 221     -39.614   5.994  -4.038  1.00 37.95      B
```

FIGURE 4- 79 -

```
ATOM   5927  C    THR B 221     -39.960   3.776  -6.114  1.00 40.79      B
ATOM   5928  O    THR B 221     -39.237   3.653  -7.106  1.00 41.74      B
ATOM   5929  N    ARG B 222     -41.252   4.058  -6.191  1.00 41.69      B
ATOM   5930  CA   ARG B 222     -41.917   4.249  -7.468  1.00 41.66      B
ATOM   5931  CB   ARG B 222     -43.430   4.271  -7.254  1.00 43.44      B
ATOM   5932  CG   ARG B 222     -44.252   4.537  -8.495  1.00 44.74      B
ATOM   5933  CD   ARG B 222     -45.702   4.676  -8.116  1.00 46.49      B
ATOM   5934  NE   ARG B 222     -46.539   5.027  -9.255  1.00 51.07      B
ATOM   5935  CZ   ARG B 222     -46.373   6.115 -10.001  1.00 53.75      B
ATOM   5936  NH1  ARG B 222     -45.386   6.964  -9.727  1.00 56.35      B
ATOM   5937  NH2  ARG B 222     -47.202   6.361 -11.010  1.00 52.50      B
ATOM   5938  C    ARG B 222     -41.463   5.554  -8.092  1.00 40.28      B
ATOM   5939  O    ARG B 222     -41.810   6.620  -7.600  1.00 41.69      B
ATOM   5940  N    CYS B 223     -40.688   5.468  -9.170  1.00 39.44      B
ATOM   5941  CA   CYS B 223     -40.192   6.658  -9.869  1.00 38.34      B
ATOM   5942  CB   CYS B 223     -41.323   7.308 -10.656  1.00 40.10      B
ATOM   5943  SG   CYS B 223     -42.138   6.199 -11.796  1.00 45.91      B
ATOM   5944  C    CYS B 223     -39.629   7.675  -8.887  1.00 36.65      B
ATOM   5945  O    CYS B 223     -40.152   8.787  -8.765  1.00 36.22      B
ATOM   5946  N    PHE B 224     -38.553   7.293  -8.204  1.00 34.12      B
ATOM   5947  CA   PHE B 224     -37.933   8.141  -7.199  1.00 31.58      B
ATOM   5948  CB   PHE B 224     -36.563   7.581  -6.808  1.00 31.66      B
ATOM   5949  CG   PHE B 224     -35.990   8.209  -5.564  1.00 33.20      B
ATOM   5950  CD1  PHE B 224     -35.458   9.503  -5.595  1.00 31.38      B
ATOM   5951  CD2  PHE B 224     -36.047   7.535  -4.336  1.00 31.45      B
ATOM   5952  CE1  PHE B 224     -34.998  10.119  -4.424  1.00 29.79      B
ATOM   5953  CE2  PHE B 224     -35.589   8.145  -3.159  1.00 29.83      B
ATOM   5954  CZ   PHE B 224     -35.067   9.439  -3.205  1.00 30.04      B
ATOM   5955  C    PHE B 224     -37.797   9.609  -7.584  1.00 30.65      B
ATOM   5956  O    PHE B 224     -38.241  10.490  -6.851  1.00 28.97      B
ATOM   5957  N    ASP B 225     -37.193   9.878  -8.734  1.00 30.70      B
ATOM   5958  CA   ASP B 225     -37.000  11.252  -9.158  1.00 29.81      B
ATOM   5959  CB   ASP B 225     -36.335  11.299 -10.537  1.00 30.36      B
ATOM   5960  CG   ASP B 225     -34.889  10.836 -10.494  1.00 33.35      B
ATOM   5961  OD1  ASP B 225     -34.399  10.547  -9.381  1.00 35.25      B
ATOM   5962  OD2  ASP B 225     -34.234  10.760 -11.559  1.00 34.98      B
ATOM   5963  C    ASP B 225     -38.271  12.075  -9.149  1.00 28.41      B
ATOM   5964  O    ASP B 225     -38.283  13.194  -8.633  1.00 29.04      B
ATOM   5965  N    SER B 226     -39.348  11.537  -9.701  1.00 27.89      B
ATOM   5966  CA   SER B 226     -40.585  12.303  -9.725  1.00 28.39      B
ATOM   5967  CB   SER B 226     -41.651  11.597 -10.567  1.00 29.94      B
ATOM   5968  OG   SER B 226     -41.878  10.277 -10.110  1.00 35.92      B
ATOM   5969  C    SER B 226     -41.101  12.536  -8.320  1.00 27.25      B
ATOM   5970  O    SER B 226     -41.823  13.495  -8.074  1.00 27.31      B
ATOM   5971  N    THR B 227     -40.713  11.676  -7.387  1.00 27.68      B
ATOM   5972  CA   THR B 227     -41.183  11.836  -6.022  1.00 27.79      B
ATOM   5973  CB   THR B 227     -41.142  10.513  -5.243  1.00 29.27      B
ATOM   5974  OG1  THR B 227     -39.792  10.207  -4.872  1.00 31.35      B
ATOM   5975  CG2  THR B 227     -41.702   9.389  -6.093  1.00 30.42      B
ATOM   5976  C    THR B 227     -40.398  12.874  -5.241  1.00 27.00      B
ATOM   5977  O    THR B 227     -40.855  13.309  -4.188  1.00 28.47      B
ATOM   5978  N    VAL B 228     -39.224  13.268  -5.737  1.00 26.42      B
ATOM   5979  CA   VAL B 228     -38.412  14.279  -5.048  1.00 25.54      B
ATOM   5980  CB   VAL B 228     -36.982  14.365  -5.635  1.00 25.62      B
ATOM   5981  CG1  VAL B 228     -36.245  15.567  -5.063  1.00 23.01      B
ATOM   5982  CG2  VAL B 228     -36.222  13.104  -5.295  1.00 24.29      B
ATOM   5983  C    VAL B 228     -39.094  15.647  -5.135  1.00 25.24      B
ATOM   5984  O    VAL B 228     -39.371  16.155  -6.227  1.00 25.50      B
ATOM   5985  N    THR B 229     -39.348  16.233  -3.969  1.00 24.31      B
ATOM   5986  CA   THR B 229     -40.047  17.515  -3.849  1.00 22.82      B
ATOM   5987  CB   THR B 229     -40.947  17.494  -2.616  1.00 20.04      B
ATOM   5988  OG1  THR B 229     -40.133  17.477  -1.437  1.00 16.03      B
ATOM   5989  CG2  THR B 229     -41.820  16.259  -2.629  1.00 17.39      B
ATOM   5990  C    THR B 229     -39.175  18.765  -3.744  1.00 24.33      B
ATOM   5991  O    THR B 229     -37.989  18.697  -3.426  1.00 24.58      B
ATOM   5992  N    GLU B 230     -39.779  19.917  -4.001  1.00 25.36      B
ATOM   5993  CA   GLU B 230     -39.049  21.171  -3.904  1.00 26.88      B
ATOM   5994  CB   GLU B 230     -39.981  22.363  -4.159  1.00 29.09      B
ATOM   5995  CG   GLU B 230     -40.675  22.345  -5.511  1.00 32.43      B
ATOM   5996  CD   GLU B 230     -42.017  21.634  -5.467  1.00 35.24      B
ATOM   5997  OE1  GLU B 230     -42.103  20.532  -4.862  1.00 36.17      B
ATOM   5998  OE2  GLU B 230     -42.982  22.183  -6.044  1.00 35.06      B
ATOM   5999  C    GLU B 230     -38.480  21.259  -2.491  1.00 25.90      B
ATOM   6000  O    GLU B 230     -37.381  21.772  -2.263  1.00 25.63      B
ATOM   6001  N    SER B 231     -39.243  20.738  -1.541  1.00 24.29      B
ATOM   6002  CA   SER B 231     -38.830  20.754  -0.156  1.00 22.81      B
```

FIGURE 4-80-

```
ATOM   6003  CB   SER B 231     -39.977  20.267   0.719  1.00 20.49      B
ATOM   6004  OG   SER B 231     -39.598  20.242   2.076  1.00 18.36      B
ATOM   6005  C    SER B 231     -37.595  19.873   0.029  1.00 24.01      B
ATOM   6006  O    SER B 231     -36.629  20.290   0.665  1.00 25.37      B
ATOM   6007  N    ASP B 232     -37.622  18.665  -0.534  1.00 22.90      B
ATOM   6008  CA   ASP B 232     -36.491  17.749  -0.421  1.00 22.68      B
ATOM   6009  CB   ASP B 232     -36.757  16.450  -1.186  1.00 23.61      B
ATOM   6010  CG   ASP B 232     -37.882  15.638  -0.590  1.00 26.72      B
ATOM   6011  OD1  ASP B 232     -38.018  15.625   0.660  1.00 24.14      B
ATOM   6012  OD2  ASP B 232     -38.616  14.995  -1.378  1.00 27.31      B
ATOM   6013  C    ASP B 232     -35.201  18.361  -0.958  1.00 21.99      B
ATOM   6014  O    ASP B 232     -34.133  18.228  -0.354  1.00 20.73      B
ATOM   6015  N    ILE B 233     -35.313  19.020  -2.106  1.00 20.97      B
ATOM   6016  CA   ILE B 233     -34.178  19.653  -2.757  1.00 20.24      B
ATOM   6017  CB   ILE B 233     -34.581  20.015  -4.217  1.00 18.35      B
ATOM   6018  CG2  ILE B 233     -33.550  20.904  -4.903  1.00 14.51      B
ATOM   6019  CG1  ILE B 233     -34.739  18.713  -5.001  1.00 14.92      B
ATOM   6020  CD1  ILE B 233     -35.617  18.831  -6.224  1.00 12.96      B
ATOM   6021  C    ILE B 233     -33.672  20.857  -1.933  1.00 21.80      B
ATOM   6022  O    ILE B 233     -32.468  21.134  -1.895  1.00 22.06      B
ATOM   6023  N    ARG B 234     -34.573  21.548  -1.243  1.00 21.53      B
ATOM   6024  CA   ARG B 234     -34.155  22.665  -0.400  1.00 21.34      B
ATOM   6025  CB   ARG B 234     -35.335  23.598  -0.116  1.00 21.32      B
ATOM   6026  CG   ARG B 234     -35.420  24.737  -1.105  1.00 22.34      B
ATOM   6027  CD   ARG B 234     -36.767  25.390  -1.080  1.00 26.50      B
ATOM   6028  NE   ARG B 234     -36.926  26.358  -2.165  1.00 29.20      B
ATOM   6029  CZ   ARG B 234     -38.078  26.578  -2.792  1.00 27.52      B
ATOM   6030  NH1  ARG B 234     -39.161  25.897  -2.441  1.00 29.98      B
ATOM   6031  NH2  ARG B 234     -38.154  27.474  -3.762  1.00 26.45      B
ATOM   6032  C    ARG B 234     -33.544  22.162   0.909  1.00 20.81      B
ATOM   6033  O    ARG B 234     -32.665  22.807   1.481  1.00 21.08      B
ATOM   6034  N    VAL B 235     -34.010  21.011   1.378  1.00 20.04      B
ATOM   6035  CA   VAL B 235     -33.484  20.412   2.600  1.00 20.93      B
ATOM   6036  CB   VAL B 235     -34.326  19.200   3.054  1.00 20.19      B
ATOM   6037  CG1  VAL B 235     -33.576  18.410   4.099  1.00 21.38      B
ATOM   6038  CG2  VAL B 235     -35.650  19.660   3.603  1.00 19.54      B
ATOM   6039  C    VAL B 235     -32.039  19.924   2.263  1.00 21.75      B
ATOM   6040  O    VAL B 235     -31.140  20.129   3.013  1.00 21.92      B
ATOM   6041  N    GLU B 236     -31.931  19.264   1.120  1.00 22.70      B
ATOM   6042  CA   GLU B 236     -30.707  18.759   0.649  1.00 23.77      B
ATOM   6043  CB   GLU B 236     -30.904  18.205  -0.756  1.00 24.79      B
ATOM   6044  CG   GLU B 236     -29.656  17.951  -1.559  1.00 25.93      B
ATOM   6045  CD   GLU B 236     -29.985  17.374  -2.923  1.00 29.61      B
ATOM   6046  OE1  GLU B 236     -29.102  17.423  -3.813  1.00 31.11      B
ATOM   6047  OE2  GLU B 236     -31.125  16.866  -3.103  1.00 28.65      B
ATOM   6048  C    GLU B 236     -29.725  19.937   0.654  1.00 25.12      B
ATOM   6049  O    GLU B 236     -28.571  19.813   1.083  1.00 25.08      B
ATOM   6050  N    GLU B 237     -30.198  21.092   0.200  1.00 23.15      B
ATOM   6051  CA   GLU B 237     -29.355  22.267   0.178  1.00 22.47      B
ATOM   6052  CB   GLU B 237     -30.085  23.464  -0.407  1.00 23.00      B
ATOM   6053  CG   GLU B 237     -29.135  24.529  -0.900  1.00 23.19      B
ATOM   6054  CD   GLU B 237     -29.710  25.911  -0.797  1.00 25.59      B
ATOM   6055  OE1  GLU B 237     -30.905  26.082  -1.111  1.00 25.15      B
ATOM   6056  OE2  GLU B 237     -28.958  26.827  -0.409  1.00 26.48      B
ATOM   6057  C    GLU B 237     -28.918  22.620   1.589  1.00 23.82      B
ATOM   6058  O    GLU B 237     -27.742  22.902   1.816  1.00 24.75      B
ATOM   6059  N    SER B 238     -29.852  22.624   2.537  1.00 21.97      B
ATOM   6060  CA   SER B 238     -29.436  22.958   3.896  1.00 20.50      B
ATOM   6061  CB   SER B 238     -30.676  22.790   4.831  1.00 21.00      B
ATOM   6062  OG   SER B 238     -30.947  21.425   5.078  1.00 20.61      B
ATOM   6063  C    SER B 238     -28.341  22.047   4.327  1.00 21.85      B
ATOM   6064  O    SER B 238     -27.534  22.412   5.189  1.00 21.75      B
ATOM   6065  N    ILE B 239     -28.258  20.861   3.734  1.00 20.90      B
ATOM   6066  CA   ILE B 239     -27.164  19.971   4.092  1.00 22.90      B
ATOM   6067  CB   ILE B 239     -27.435  18.502   3.691  1.00 21.00      B
ATOM   6068  CG2  ILE B 239     -26.211  17.646   4.033  1.00 18.83      B
ATOM   6069  CG1  ILE B 239     -28.653  17.969   4.455  1.00 20.79      B
ATOM   6070  CD1  ILE B 239     -29.107  16.593   4.024  1.00 18.82      B
ATOM   6071  C    ILE B 239     -25.876  20.457   3.428  1.00 24.22      B
ATOM   6072  O    ILE B 239     -24.852  20.568   4.079  1.00 28.20      B
ATOM   6073  N    TYR B 240     -25.915  20.759   2.138  1.00 24.26      B
ATOM   6074  CA   TYR B 240     -24.717  21.253   1.478  1.00 23.43      B
ATOM   6075  CB   TYR B 240     -25.002  21.569   0.011  1.00 23.86      B
ATOM   6076  CG   TYR B 240     -25.483  20.397  -0.795  1.00 23.46      B
ATOM   6077  CD1  TYR B 240     -24.992  19.117  -0.554  1.00 23.87      B
ATOM   6078  CE1  TYR B 240     -25.391  18.038  -1.331  1.00 26.60      B
```

FIGURE 4- 81 -

```
ATOM   6079  CD2 TYR B 240     -26.394  20.573  -1.836  1.00 24.06      B
ATOM   6080  CE2 TYR B 240     -26.804  19.500  -2.626  1.00 24.86      B
ATOM   6081  CZ  TYR B 240     -26.295  18.236  -2.368  1.00 27.01      B
ATOM   6082  OH  TYR B 240     -26.657  17.177  -3.162  1.00 29.35      B
ATOM   6083  C   TYR B 240     -24.197  22.524   2.155  1.00 23.54      B
ATOM   6084  O   TYR B 240     -22.995  22.663   2.356  1.00 23.83      B
ATOM   6085  N   GLN B 241     -25.104  23.445   2.490  1.00 22.29      B
ATOM   6086  CA  GLN B 241     -24.754  24.719   3.119  1.00 20.85      B
ATOM   6087  CB  GLN B 241     -25.989  25.610   3.231  1.00 22.02      B
ATOM   6088  CG  GLN B 241     -26.535  26.147   1.913  1.00 22.64      B
ATOM   6089  CD  GLN B 241     -25.622  27.170   1.267  1.00 23.67      B
ATOM   6090  OE1 GLN B 241     -24.658  27.627   1.874  1.00 25.29      B
ATOM   6091  NE2 GLN B 241     -25.934  27.546   0.035  1.00 22.68      B
ATOM   6092  C   GLN B 241     -24.114  24.587   4.500  1.00 22.39      B
ATOM   6093  O   GLN B 241     -23.792  25.600   5.150  1.00 22.08      B
ATOM   6094  N   CYS B 242     -23.937  23.352   4.958  1.00 20.83      B
ATOM   6095  CA  CYS B 242     -23.299  23.125   6.244  1.00 19.52      B
ATOM   6096  CB  CYS B 242     -23.814  21.840   6.875  1.00 18.89      B
ATOM   6097  SG  CYS B 242     -25.372  22.063   7.732  1.00 24.51      B
ATOM   6098  C   CYS B 242     -21.788  23.050   6.088  1.00 19.01      B
ATOM   6099  O   CYS B 242     -21.054  23.205   7.061  1.00 18.68      B
ATOM   6100  N   CYS B 243     -21.332  22.816   4.862  1.00 18.46      B
ATOM   6101  CA  CYS B 243     -19.909  22.715   4.569  1.00 21.22      B
ATOM   6102  CB  CYS B 243     -19.689  22.152   3.160  1.00 20.34      B
ATOM   6103  SG  CYS B 243     -20.460  20.556   2.841  1.00 24.56      B
ATOM   6104  C   CYS B 243     -19.260  24.090   4.645  1.00 22.57      B
ATOM   6105  O   CYS B 243     -19.955  25.102   4.674  1.00 23.21      B
ATOM   6106  N   ASP B 244     -17.930  24.118   4.694  1.00 22.46      B
ATOM   6107  CA  ASP B 244     -17.201  25.373   4.714  1.00 23.35      B
ATOM   6108  CB  ASP B 244     -15.855  25.215   5.427  1.00 22.79      B
ATOM   6109  CG  ASP B 244     -15.070  26.515   5.486  1.00 22.48      B
ATOM   6110  OD1 ASP B 244     -14.469  26.923   4.469  1.00 22.31      B
ATOM   6111  OD2 ASP B 244     -15.069  27.147   6.559  1.00 22.91      B
ATOM   6112  C   ASP B 244     -16.989  25.681   3.233  1.00 24.69      B
ATOM   6113  O   ASP B 244     -16.121  25.093   2.574  1.00 26.69      B
ATOM   6114  N   LEU B 245     -17.786  26.607   2.714  1.00 24.38      B
ATOM   6115  CA  LEU B 245     -17.734  26.952   1.302  1.00 24.07      B
ATOM   6116  CB  LEU B 245     -19.144  26.889   0.726  1.00 21.21      B
ATOM   6117  CG  LEU B 245     -19.839  25.550   0.923  1.00 18.49      B
ATOM   6118  CD1 LEU B 245     -21.320  25.728   0.786  1.00 21.24      B
ATOM   6119  CD2 LEU B 245     -19.317  24.557  -0.072  1.00 18.12      B
ATOM   6120  C   LEU B 245     -17.145  28.312   0.987  1.00 23.24      B
ATOM   6121  O   LEU B 245     -17.162  29.219   1.811  1.00 23.79      B
ATOM   6122  N   ALA B 246     -16.612  28.440  -0.219  1.00 22.79      B
ATOM   6123  CA  ALA B 246     -16.072  29.715  -0.657  1.00 23.23      B
ATOM   6124  CB  ALA B 246     -15.284  29.538  -1.945  1.00 20.84      B
ATOM   6125  C   ALA B 246     -17.291  30.629  -0.896  1.00 23.71      B
ATOM   6126  O   ALA B 246     -18.365  30.164  -1.323  1.00 22.45      B
ATOM   6127  N   PRO B 247     -17.151  31.936  -0.615  1.00 22.42      B
ATOM   6128  CD  PRO B 247     -16.009  32.692  -0.079  1.00 21.06      B
ATOM   6129  CA  PRO B 247     -18.282  32.831  -0.829  1.00 22.25      B
ATOM   6130  CB  PRO B 247     -17.632  34.205  -0.765  1.00 20.76      B
ATOM   6131  CG  PRO B 247     -16.655  34.013   0.302  1.00 19.17      B
ATOM   6132  C   PRO B 247     -19.036  32.574  -2.129  1.00 22.43      B
ATOM   6133  O   PRO B 247     -20.246  32.373  -2.108  1.00 24.40      B
ATOM   6134  N   GLU B 248     -18.340  32.550  -3.257  1.00 22.02      B
ATOM   6135  CA  GLU B 248     -19.041  32.337  -4.508  1.00 22.69      B
ATOM   6136  CB  GLU B 248     -18.138  32.715  -5.673  1.00 23.99      B
ATOM   6137  CG  GLU B 248     -17.750  34.176  -5.661  1.00 24.07      B
ATOM   6138  CD  GLU B 248     -17.085  34.607  -6.941  1.00 26.12      B
ATOM   6139  OE1 GLU B 248     -16.744  33.719  -7.756  1.00 25.39      B
ATOM   6140  OE2 GLU B 248     -16.901  35.833  -7.130  1.00 28.35      B
ATOM   6141  C   GLU B 248     -19.588  30.920  -4.667  1.00 23.59      B
ATOM   6142  O   GLU B 248     -20.535  30.693  -5.420  1.00 25.19      B
ATOM   6143  N   ALA B 249     -19.005  29.965  -3.957  1.00 23.15      B
ATOM   6144  CA  ALA B 249     -19.489  28.599  -4.037  1.00 21.33      B
ATOM   6145  CB  ALA B 249     -18.498  27.664  -3.400  1.00 20.82      B
ATOM   6146  C   ALA B 249     -20.807  28.571  -3.278  1.00 22.03      B
ATOM   6147  O   ALA B 249     -21.816  28.051  -3.748  1.00 21.54      B
ATOM   6148  N   ARG B 250     -20.804  29.160  -2.095  1.00 22.59      B
ATOM   6149  CA  ARG B 250     -22.014  29.181  -1.302  1.00 23.29      B
ATOM   6150  CB  ARG B 250     -21.776  29.955  -0.008  1.00 23.90      B
ATOM   6151  CG  ARG B 250     -22.879  29.790   1.013  1.00 26.71      B
ATOM   6152  CD  ARG B 250     -22.503  30.402   2.355  1.00 25.86      B
ATOM   6153  NE  ARG B 250     -21.427  29.684   3.029  1.00 24.74      B
ATOM   6154  CZ  ARG B 250     -21.587  28.590   3.766  1.00 25.75      B
```

FIGURE 4- 82 -

```
ATOM   6155  NH1 ARG B 250     -22.791  28.059   3.939  1.00 24.65           B
ATOM   6156  NH2 ARG B 250     -20.532  28.040   4.351  1.00 26.82           B
ATOM   6157  C   ARG B 250     -23.162  29.802  -2.086  1.00 23.70           B
ATOM   6158  O   ARG B 250     -24.294  29.338  -1.993  1.00 23.39           B
ATOM   6159  N   GLN B 251     -22.873  30.838  -2.873  1.00 24.22           B
ATOM   6160  CA  GLN B 251     -23.918  31.504  -3.654  1.00 23.62           B
ATOM   6161  CB  GLN B 251     -23.482  32.899  -4.086  1.00 22.35           B
ATOM   6162  CG  GLN B 251     -24.550  33.628  -4.911  1.00 22.26           B
ATOM   6163  CD  GLN B 251     -25.758  34.032  -4.083  1.00 23.37           B
ATOM   6164  OE1 GLN B 251     -26.901  33.740  -4.434  1.00 24.45           B
ATOM   6165  NE2 GLN B 251     -25.509  34.710  -2.981  1.00 22.19           B
ATOM   6166  C   GLN B 251     -24.329  30.720  -4.894  1.00 24.81           B
ATOM   6167  O   GLN B 251     -25.510  30.693  -5.252  1.00 23.72           B
ATOM   6168  N   ALA B 252     -23.353  30.103  -5.558  1.00 24.34           B
ATOM   6169  CA  ALA B 252     -23.634  29.315  -6.754  1.00 22.92           B
ATOM   6170  CB  ALA B 252     -22.339  28.777  -7.351  1.00 20.58           B
ATOM   6171  C   ALA B 252     -24.566  28.164  -6.391  1.00 21.61           B
ATOM   6172  O   ALA B 252     -25.487  27.836  -7.142  1.00 21.86           B
ATOM   6173  N   ILE B 253     -24.322  27.558  -5.235  1.00 19.63           B
ATOM   6174  CA  ILE B 253     -25.139  26.442  -4.774  1.00 19.39           B
ATOM   6175  CB  ILE B 253     -24.523  25.825  -3.480  1.00 19.31           B
ATOM   6176  CG2 ILE B 253     -25.524  24.929  -2.785  1.00 18.94           B
ATOM   6177  CG1 ILE B 253     -23.255  25.044  -3.844  1.00 18.20           B
ATOM   6178  CD1 ILE B 253     -22.313  24.791  -2.688  1.00 17.19           B
ATOM   6179  C   ILE B 253     -26.576  26.908  -4.535  1.00 18.09           B
ATOM   6180  O   ILE B 253     -27.530  26.216  -4.886  1.00 15.97           B
ATOM   6181  N   ARG B 254     -26.707  28.096  -3.948  1.00 18.29           B
ATOM   6182  CA  ARG B 254     -28.000  28.720  -3.647  1.00 17.48           B
ATOM   6183  CB  ARG B 254     -27.736  30.049  -2.941  1.00 14.88           B
ATOM   6184  CG  ARG B 254     -28.946  30.822  -2.498  1.00 17.07           B
ATOM   6185  CD  ARG B 254     -29.520  30.271  -1.207  1.00 19.99           B
ATOM   6186  NE  ARG B 254     -30.420  29.135  -1.397  1.00 18.20           B
ATOM   6187  CZ  ARG B 254     -31.671  29.247  -1.828  1.00 19.52           B
ATOM   6188  NH1 ARG B 254     -32.180  30.443  -2.113  1.00 20.65           B
ATOM   6189  NH2 ARG B 254     -32.416  28.162  -1.981  1.00 19.68           B
ATOM   6190  C   ARG B 254     -28.807  28.953  -4.944  1.00 18.01           B
ATOM   6191  O   ARG B 254     -29.986  28.607  -5.033  1.00 18.58           B
ATOM   6192  N   SER B 255     -28.150  29.528  -5.947  1.00 17.36           B
ATOM   6193  CA  SER B 255     -28.769  29.822  -7.230  1.00 15.85           B
ATOM   6194  CB  SER B 255     -27.831  30.692  -8.059  1.00 14.50           B
ATOM   6195  OG  SER B 255     -27.682  31.964  -7.459  1.00 14.64           B
ATOM   6196  C   SER B 255     -29.155  28.586  -8.030  1.00 16.93           B
ATOM   6197  O   SER B 255     -30.251  28.502  -8.576  1.00 16.90           B
ATOM   6198  N   LEU B 256     -28.244  27.631  -8.117  1.00 17.49           B
ATOM   6199  CA  LEU B 256     -28.520  26.409  -8.850  1.00 17.00           B
ATOM   6200  CB  LEU B 256     -27.295  25.506  -8.850  1.00 15.32           B
ATOM   6201  CG  LEU B 256     -26.057  26.089  -9.526  1.00 14.53           B
ATOM   6202  CD1 LEU B 256     -24.866  25.247  -9.142  1.00 12.79           B
ATOM   6203  CD2 LEU B 256     -26.246  26.136 -11.026  1.00  8.28           B
ATOM   6204  C   LEU B 256     -29.683  25.676  -8.212  1.00 19.19           B
ATOM   6205  O   LEU B 256     -30.395  24.935  -8.890  1.00 22.16           B
ATOM   6206  N   THR B 257     -29.875  25.877  -6.911  1.00 18.81           B
ATOM   6207  CA  THR B 257     -30.958  25.219  -6.203  1.00 19.00           B
ATOM   6208  CB  THR B 257     -30.843  25.441  -4.675  1.00 19.61           B
ATOM   6209  OG1 THR B 257     -29.693  24.752  -4.171  1.00 19.75           B
ATOM   6210  CG2 THR B 257     -32.072  24.914  -3.960  1.00 17.63           B
ATOM   6211  C   THR B 257     -32.296  25.760  -6.690  1.00 21.08           B
ATOM   6212  O   THR B 257     -33.163  25.000  -7.117  1.00 22.65           B
ATOM   6213  N   GLU B 258     -32.461  27.077  -6.641  1.00 21.12           B
ATOM   6214  CA  GLU B 258     -33.712  27.696  -7.071  1.00 21.71           B
ATOM   6215  CB  GLU B 258     -33.796  29.131  -6.535  1.00 21.80           B
ATOM   6216  CG  GLU B 258     -33.841  29.260  -5.010  1.00 21.94           B
ATOM   6217  CD  GLU B 258     -35.006  28.513  -4.375  1.00 21.31           B
ATOM   6218  OE1 GLU B 258     -36.100  28.509  -4.966  1.00 20.92           B
ATOM   6219  OE2 GLU B 258     -34.833  27.946  -3.275  1.00 21.93           B
ATOM   6220  C   GLU B 258     -33.924  27.729  -8.585  1.00 21.79           B
ATOM   6221  O   GLU B 258     -35.043  27.573  -9.064  1.00 22.13           B
ATOM   6222  N   ARG B 259     -32.842  27.920  -9.334  1.00 22.11           B
ATOM   6223  CA  ARG B 259     -32.912  28.043 -10.788  1.00 21.26           B
ATOM   6224  CB  ARG B 259     -31.836  29.035 -11.255  1.00 20.53           B
ATOM   6225  CG  ARG B 259     -31.956  30.418 -10.628  1.00 19.76           B
ATOM   6226  CD  ARG B 259     -30.779  31.297 -11.004  1.00 19.00           B
ATOM   6227  NE  ARG B 259     -30.677  31.457 -12.450  1.00 20.99           B
ATOM   6228  CZ  ARG B 259     -29.772  32.212 -13.064  1.00 19.53           B
ATOM   6229  NH1 ARG B 259     -28.877  32.892 -12.364  1.00 19.84           B
ATOM   6230  NH2 ARG B 259     -29.755  32.277 -14.383  1.00 16.70           B
```

FIGURE 4- 83 -

```
ATOM   6231  C    ARG B 259     -32.822  26.766 -11.627  1.00 22.01      B
ATOM   6232  O    ARG B 259     -33.202  26.767 -12.811  1.00 22.35      B
ATOM   6233  N    LEU B 260     -32.337  25.677 -11.036  1.00 20.38      B
ATOM   6234  CA   LEU B 260     -32.202  24.440 -11.796  1.00 19.20      B
ATOM   6235  CB   LEU B 260     -30.734  24.226 -12.170  1.00 18.83      B
ATOM   6236  CG   LEU B 260     -30.378  23.023 -13.051  1.00 18.68      B
ATOM   6237  CD1  LEU B 260     -30.915  23.249 -14.453  1.00 19.35      B
ATOM   6238  CD2  LEU B 260     -28.874  22.837 -13.081  1.00 16.29      B
ATOM   6239  C    LEU B 260     -32.713  23.219 -11.047  1.00 19.95      B
ATOM   6240  O    LEU B 260     -33.562  22.475 -11.548  1.00 19.96      B
ATOM   6241  N    TYR B 261     -32.204  23.030  -9.833  1.00 18.71      B
ATOM   6242  CA   TYR B 261     -32.559  21.885  -9.010  1.00 15.35      B
ATOM   6243  CB   TYR B 261     -31.637  21.831  -7.806  1.00 13.81      B
ATOM   6244  CG   TYR B 261     -30.171  21.790  -8.173  1.00 12.93      B
ATOM   6245  CD1  TYR B 261     -29.743  21.181  -9.346  1.00 13.36      B
ATOM   6246  CE1  TYR B 261     -28.388  21.118  -9.672  1.00 13.47      B
ATOM   6247  CD2  TYR B 261     -29.206  22.336  -7.331  1.00 12.97      B
ATOM   6248  CE2  TYR B 261     -27.857  22.274  -7.648  1.00 11.39      B
ATOM   6249  CZ   TYR B 261     -27.452  21.665  -8.816  1.00 12.37      B
ATOM   6250  OH   TYR B 261     -26.101  21.591  -9.115  1.00 14.01      B
ATOM   6251  C    TYR B 261     -34.003  21.692  -8.564  1.00 15.77      B
ATOM   6252  O    TYR B 261     -34.449  20.560  -8.539  1.00 17.32      B
ATOM   6253  N    ILE B 262     -34.745  22.742  -8.208  1.00 16.34      B
ATOM   6254  CA   ILE B 262     -36.139  22.528  -7.792  1.00 18.02      B
ATOM   6255  CB   ILE B 262     -36.695  23.657  -6.869  1.00 18.41      B
ATOM   6256  CG2  ILE B 262     -36.001  23.642  -5.526  1.00 20.49      B
ATOM   6257  CG1  ILE B 262     -36.556  25.003  -7.550  1.00 17.70      B
ATOM   6258  CD1  ILE B 262     -36.984  26.147  -6.692  1.00 20.99      B
ATOM   6259  C    ILE B 262     -37.075  22.426  -8.993  1.00 19.22      B
ATOM   6260  O    ILE B 262     -38.282  22.198  -8.839  1.00 20.28      B
ATOM   6261  N    GLY B 263     -36.529  22.602 -10.191  1.00 19.27      B
ATOM   6262  CA   GLY B 263     -37.362  22.500 -11.373  1.00 20.47      B
ATOM   6263  C    GLY B 263     -37.034  23.582 -12.373  1.00 21.14      B
ATOM   6264  O    GLY B 263     -36.065  24.309 -12.196  1.00 22.13      B
ATOM   6265  N    GLY B 264     -37.847  23.695 -13.418  1.00 21.73      B
ATOM   6266  CA   GLY B 264     -37.614  24.694 -14.442  1.00 21.13      B
ATOM   6267  C    GLY B 264     -38.206  24.216 -15.744  1.00 21.31      B
ATOM   6268  O    GLY B 264     -38.718  23.102 -15.801  1.00 23.09      B
ATOM   6269  N    PRO B 265     -38.137  25.016 -16.816  1.00 21.16      B
ATOM   6270  CD   PRO B 265     -37.473  26.325 -16.873  1.00 20.26      B
ATOM   6271  CA   PRO B 265     -38.681  24.662 -18.136  1.00 21.39      B
ATOM   6272  CB   PRO B 265     -38.559  25.965 -18.909  1.00 18.74      B
ATOM   6273  CG   PRO B 265     -37.312  26.527 -18.367  1.00 20.47      B
ATOM   6274  C    PRO B 265     -38.008  23.491 -18.864  1.00 21.74      B
ATOM   6275  O    PRO B 265     -36.791  23.342 -18.840  1.00 21.67      B
ATOM   6276  N    LEU B 266     -38.827  22.675 -19.524  1.00 23.36      B
ATOM   6277  CA   LEU B 266     -38.354  21.510 -20.270  1.00 23.52      B
ATOM   6278  CB   LEU B 266     -39.246  20.301 -19.945  1.00 23.76      B
ATOM   6279  CG   LEU B 266     -39.316  19.854 -18.480  1.00 23.68      B
ATOM   6280  CD1  LEU B 266     -40.532  18.974 -18.279  1.00 24.97      B
ATOM   6281  CD2  LEU B 266     -38.047  19.123 -18.089  1.00 21.73      B
ATOM   6282  C    LEU B 266     -38.365  21.774 -21.782  1.00 22.57      B
ATOM   6283  O    LEU B 266     -39.391  22.117 -22.347  1.00 21.55      B
ATOM   6284  N    THR B 267     -37.221  21.611 -22.435  1.00 23.37      B
ATOM   6285  CA   THR B 267     -37.140  21.837 -23.875  1.00 24.51      B
ATOM   6286  CB   THR B 267     -36.112  22.940 -24.215  1.00 22.79      B
ATOM   6287  OG1  THR B 267     -36.462  24.150 -23.531  1.00 23.41      B
ATOM   6288  CG2  THR B 267     -36.098  23.200 -25.707  1.00 19.01      B
ATOM   6289  C    THR B 267     -36.755  20.584 -24.660  1.00 25.86      B
ATOM   6290  O    THR B 267     -35.766  19.922 -24.329  1.00 25.31      B
ATOM   6291  N    ASN B 268     -37.535  20.263 -25.696  1.00 26.77      B
ATOM   6292  CA   ASN B 268     -37.227  19.102 -26.520  1.00 28.74      B
ATOM   6293  CB   ASN B 268     -38.446  18.654 -27.364  1.00 28.44      B
ATOM   6294  CG   ASN B 268     -38.925  19.718 -28.366  1.00 30.72      B
ATOM   6295  OD1  ASN B 268     -38.165  20.591 -28.805  1.00 27.75      B
ATOM   6296  ND2  ASN B 268     -40.197  19.622 -28.748  1.00 28.89      B
ATOM   6297  C    ASN B 268     -36.036  19.438 -27.422  1.00 29.89      B
ATOM   6298  O    ASN B 268     -35.627  20.592 -27.524  1.00 28.99      B
ATOM   6299  N    SER B 269     -35.463  18.430 -28.060  1.00 32.11      B
ATOM   6300  CA   SER B 269     -34.328  18.662 -28.938  1.00 33.36      B
ATOM   6301  CB   SER B 269     -33.895  17.347 -29.593  1.00 34.42      B
ATOM   6302  OG   SER B 269     -34.960  16.758 -30.333  1.00 36.37      B
ATOM   6303  C    SER B 269     -34.625  19.707 -30.015  1.00 34.36      B
ATOM   6304  O    SER B 269     -33.699  20.308 -30.551  1.00 35.83      B
ATOM   6305  N    LYS B 270     -35.901  19.930 -30.335  1.00 34.96      B
ATOM   6306  CA   LYS B 270     -36.271  20.922 -31.357  1.00 35.75      B
```

FIGURE 4- 84 -

```
ATOM   6307  CB  LYS B 270     -37.681  20.662 -31.897  1.00 38.44      B
ATOM   6308  CG  LYS B 270     -37.828  19.610 -32.979  1.00 41.32      B
ATOM   6309  CD  LYS B 270     -39.237  19.730 -33.567  1.00 45.92      B
ATOM   6310  CE  LYS B 270     -39.757  18.412 -34.155  1.00 49.48      B
ATOM   6311  NZ  LYS B 270     -41.250  18.435 -34.378  1.00 49.94      B
ATOM   6312  C   LYS B 270     -36.239  22.381 -30.882  1.00 34.49      B
ATOM   6313  O   LYS B 270     -36.295  23.304 -31.692  1.00 34.31      B
ATOM   6314  N   GLY B 271     -36.173  22.596 -29.577  1.00 33.27      B
ATOM   6315  CA  GLY B 271     -36.170  23.955 -29.077  1.00 30.61      B
ATOM   6316  C   GLY B 271     -37.588  24.369 -28.731  1.00 29.80      B
ATOM   6317  O   GLY B 271     -37.901  25.561 -28.640  1.00 29.25      B
ATOM   6318  N   GLN B 272     -38.453  23.374 -28.550  1.00 28.56      B
ATOM   6319  CA  GLN B 272     -39.843  23.626 -28.202  1.00 26.99      B
ATOM   6320  CB  GLN B 272     -40.776  22.773 -29.055  1.00 25.18      B
ATOM   6321  CG  GLN B 272     -40.653  23.027 -30.534  1.00 26.26      B
ATOM   6322  CD  GLN B 272     -41.534  22.105 -31.352  1.00 27.88      B
ATOM   6323  OE1 GLN B 272     -41.353  20.887 -31.355  1.00 27.17      B
ATOM   6324  NE2 GLN B 272     -42.501  22.685 -32.050  1.00 29.85      B
ATOM   6325  C   GLN B 272     -40.092  23.337 -26.728  1.00 26.39      B
ATOM   6326  O   GLN B 272     -39.530  22.408 -26.143  1.00 25.19      B
ATOM   6327  N   ASN B 273     -40.946  24.156 -26.144  1.00 25.04      B
ATOM   6328  CA  ASN B 273     -41.305  24.045 -24.751  1.00 25.74      B
ATOM   6329  CB  ASN B 273     -41.960  25.345 -24.316  1.00 24.98      B
ATOM   6330  CG  ASN B 273     -42.293  25.363 -22.861  1.00 26.05      B
ATOM   6331  OD1 ASN B 273     -42.907  26.301 -22.388  1.00 29.10      B
ATOM   6332  ND2 ASN B 273     -41.889  24.328 -22.132  1.00 26.07      B
ATOM   6333  C   ASN B 273     -42.249  22.880 -24.499  1.00 26.42      B
ATOM   6334  O   ASN B 273     -43.406  22.907 -24.898  1.00 30.01      B
ATOM   6335  N   CYS B 274     -41.760  21.861 -23.820  1.00 26.33      B
ATOM   6336  CA  CYS B 274     -42.576  20.706 -23.528  1.00 27.22      B
ATOM   6337  CB  CYS B 274     -41.699  19.472 -23.397  1.00 28.13      B
ATOM   6338  SG  CYS B 274     -40.959  19.036 -24.928  1.00 36.39      B
ATOM   6339  C   CYS B 274     -43.371  20.870 -22.260  1.00 26.82      B
ATOM   6340  O   CYS B 274     -44.445  20.238 -22.121  1.00 29.77      B
ATOM   6341  N   GLY B 275     -42.836  21.640 -21.325  1.00 25.99      B
ATOM   6342  CA  GLY B 275     -43.523  21.831 -20.071  1.00 25.48      B
ATOM   6343  C   GLY B 275     -42.603  22.271 -18.959  1.00 26.18      B
ATOM   6344  O   GLY B 275     -41.540  22.843 -19.203  1.00 26.76      B
ATOM   6345  N   TYR B 276     -43.004  21.987 -17.727  1.00 25.21      B
ATOM   6346  CA  TYR B 276     -42.230  22.407 -16.577  1.00 23.92      B
ATOM   6347  CB  TYR B 276     -43.037  23.422 -15.777  1.00 23.19      B
ATOM   6348  CG  TYR B 276     -42.188  24.374 -14.988  1.00 24.73      B
ATOM   6349  CD1 TYR B 276     -41.657  25.519 -15.587  1.00 24.41      B
ATOM   6350  CE1 TYR B 276     -40.819  26.376 -14.888  1.00 23.61      B
ATOM   6351  CD2 TYR B 276     -41.866  24.109 -13.658  1.00 24.51      B
ATOM   6352  CE2 TYR B 276     -41.032  24.961 -12.947  1.00 26.04      B
ATOM   6353  CZ  TYR B 276     -40.511  26.093 -13.568  1.00 25.93      B
ATOM   6354  OH  TYR B 276     -39.691  26.939 -12.859  1.00 25.73      B
ATOM   6355  C   TYR B 276     -41.889  21.227 -15.688  1.00 24.32      B
ATOM   6356  O   TYR B 276     -42.556  20.199 -15.744  1.00 26.40      B
ATOM   6357  N   ARG B 277     -40.860  21.387 -14.860  1.00 22.79      B
ATOM   6358  CA  ARG B 277     -40.434  20.337 -13.945  1.00 22.27      B
ATOM   6359  CB  ARG B 277     -39.039  19.827 -14.330  1.00 21.28      B
ATOM   6360  CG  ARG B 277     -38.419  18.847 -13.333  1.00 23.15      B
ATOM   6361  CD  ARG B 277     -36.992  18.466 -13.729  1.00 22.81      B
ATOM   6362  NE  ARG B 277     -36.173  19.650 -14.006  1.00 23.96      B
ATOM   6363  CZ  ARG B 277     -35.425  20.298 -13.112  1.00 20.38      B
ATOM   6364  NH1 ARG B 277     -35.356  19.899 -11.849  1.00 15.24      B
ATOM   6365  NH2 ARG B 277     -34.754  21.367 -13.495  1.00 19.95      B
ATOM   6366  C   ARG B 277     -40.410  20.845 -12.506  1.00 23.13      B
ATOM   6367  O   ARG B 277     -40.024  21.988 -12.250  1.00 21.86      B
ATOM   6368  N   ARG B 278     -40.824  19.993 -11.570  1.00 23.45      B
ATOM   6369  CA  ARG B 278     -40.826  20.360 -10.163  1.00 24.13      B
ATOM   6370  CB  ARG B 278     -42.235  20.709  -9.703  1.00 23.92      B
ATOM   6371  CG  ARG B 278     -42.902  21.710 -10.616  1.00 24.43      B
ATOM   6372  CD  ARG B 278     -44.054  22.428  -9.956  1.00 21.15      B
ATOM   6373  NE  ARG B 278     -44.700  23.290 -10.930  1.00 22.71      B
ATOM   6374  CZ  ARG B 278     -45.396  22.838 -11.967  1.00 22.25      B
ATOM   6375  NH1 ARG B 278     -45.542  21.528 -12.156  1.00 22.00      B
ATOM   6376  NH2 ARG B 278     -45.927  23.691 -12.828  1.00 20.10      B
ATOM   6377  C   ARG B 278     -40.273  19.233  -9.311  1.00 25.29      B
ATOM   6378  O   ARG B 278     -40.562  19.143  -8.115  1.00 26.28      B
ATOM   6379  N   CYS B 279     -39.473  18.376  -9.936  1.00 24.56      B
ATOM   6380  CA  CYS B 279     -38.863  17.249  -9.240  1.00 24.76      B
ATOM   6381  CB  CYS B 279     -39.657  15.963  -9.518  1.00 25.76      B
ATOM   6382  SG  CYS B 279     -39.654  15.431 -11.250  1.00 21.50      B
```

FIGURE 4- 85 -

```
ATOM   6383  C    CYS B 279     -37.403  17.059  -9.670  1.00 24.32      B
ATOM   6384  O    CYS B 279     -36.840  17.886 -10.382  1.00 24.59      B
ATOM   6385  N    ARG B 280     -36.800  15.955  -9.248  1.00 22.33      B
ATOM   6386  CA   ARG B 280     -35.417  15.678  -9.584  1.00 21.95      B
ATOM   6387  CB   ARG B 280     -34.988  14.349  -8.959  1.00 21.54      B
ATOM   6388  CG   ARG B 280     -33.530  13.986  -9.208  1.00 21.68      B
ATOM   6389  CD   ARG B 280     -32.606  14.831  -8.355  1.00 21.63      B
ATOM   6390  NE   ARG B 280     -32.593  14.395  -6.957  1.00 23.05      B
ATOM   6391  CZ   ARG B 280     -32.270  15.179  -5.930  1.00 23.57      B
ATOM   6392  NH1  ARG B 280     -31.941  16.447  -6.152  1.00 21.43      B
ATOM   6393  NH2  ARG B 280     -32.269  14.701  -4.686  1.00 19.94      B
ATOM   6394  C    ARG B 280     -35.131  15.639 -11.082  1.00 22.64      B
ATOM   6395  O    ARG B 280     -35.847  15.004 -11.851  1.00 23.36      B
ATOM   6396  N    ALA B 281     -34.077  16.338 -11.489  1.00 22.89      B
ATOM   6397  CA   ALA B 281     -33.638  16.336 -12.880  1.00 23.13      B
ATOM   6398  CB   ALA B 281     -33.051  17.680 -13.253  1.00 22.22      B
ATOM   6399  C    ALA B 281     -32.551  15.258 -12.917  1.00 24.11      B
ATOM   6400  O    ALA B 281     -31.557  15.342 -12.199  1.00 24.21      B
ATOM   6401  N    SER B 282     -32.749  14.237 -13.736  1.00 24.86      B
ATOM   6402  CA   SER B 282     -31.798  13.135 -13.833  1.00 24.84      B
ATOM   6403  CB   SER B 282     -32.322  12.099 -14.819  1.00 24.79      B
ATOM   6404  OG   SER B 282     -32.569  12.700 -16.083  1.00 28.64      B
ATOM   6405  C    SER B 282     -30.390  13.530 -14.256  1.00 25.10      B
ATOM   6406  O    SER B 282     -29.424  12.852 -13.899  1.00 25.61      B
ATOM   6407  N    GLY B 283     -30.276  14.623 -15.007  1.00 24.69      B
ATOM   6408  CA   GLY B 283     -28.979  15.044 -15.499  1.00 24.86      B
ATOM   6409  C    GLY B 283     -28.214  16.197 -14.865  1.00 26.23      B
ATOM   6410  O    GLY B 283     -27.555  16.960 -15.583  1.00 27.70      B
ATOM   6411  N    VAL B 284     -28.291  16.353 -13.547  1.00 24.35      B
ATOM   6412  CA   VAL B 284     -27.531  17.407 -12.886  1.00 24.40      B
ATOM   6413  CB   VAL B 284     -28.419  18.328 -12.012  1.00 25.38      B
ATOM   6414  CG1  VAL B 284     -29.321  19.151 -12.911  1.00 25.14      B
ATOM   6415  CG2  VAL B 284     -29.225  17.508 -10.995  1.00 23.47      B
ATOM   6416  C    VAL B 284     -26.487  16.713 -12.015  1.00 23.84      B
ATOM   6417  O    VAL B 284     -26.622  15.529 -11.712  1.00 25.48      B
ATOM   6418  N    LEU B 285     -25.452  17.435 -11.608  1.00 21.36      B
ATOM   6419  CA   LEU B 285     -24.415  16.818 -10.812  1.00 21.92      B
ATOM   6420  CB   LEU B 285     -23.245  17.776 -10.652  1.00 19.45      B
ATOM   6421  CG   LEU B 285     -21.977  17.066 -10.189  1.00 18.93      B
ATOM   6422  CD1  LEU B 285     -21.875  15.724 -10.886  1.00 17.00      B
ATOM   6423  CD2  LEU B 285     -20.764  17.925 -10.491  1.00 19.13      B
ATOM   6424  C    LEU B 285     -24.876  16.349  -9.438  1.00 24.11      B
ATOM   6425  O    LEU B 285     -24.231  15.506  -8.806  1.00 25.97      B
ATOM   6426  N    THR B 286     -26.003  16.873  -8.976  1.00 23.58      B
ATOM   6427  CA   THR B 286     -26.478  16.508  -7.655  1.00 23.12      B
ATOM   6428  CB   THR B 286     -27.116  17.733  -6.966  1.00 23.82      B
ATOM   6429  OG1  THR B 286     -28.174  18.256  -7.783  1.00 25.37      B
ATOM   6430  CG2  THR B 286     -26.073  18.811  -6.762  1.00 24.45      B
ATOM   6431  C    THR B 286     -27.446  15.335  -7.616  1.00 22.55      B
ATOM   6432  O    THR B 286     -27.835  14.892  -6.534  1.00 20.46      B
ATOM   6433  N    THR B 287     -27.824  14.824  -8.785  1.00 21.19      B
ATOM   6434  CA   THR B 287     -28.762  13.708  -8.837  1.00 21.66      B
ATOM   6435  CB   THR B 287     -28.948  13.188 -10.280  1.00 20.59      B
ATOM   6436  OG1  THR B 287     -29.530  14.213 -11.088  1.00 24.14      B
ATOM   6437  CG2  THR B 287     -29.869  12.008 -10.299  1.00 18.91      B
ATOM   6438  C    THR B 287     -28.364  12.532  -7.936  1.00 21.38      B
ATOM   6439  O    THR B 287     -29.161  12.075  -7.114  1.00 20.47      B
ATOM   6440  N    SER B 288     -27.138  12.044  -8.072  1.00 21.41      B
ATOM   6441  CA   SER B 288     -26.723  10.916  -7.255  1.00 22.59      B
ATOM   6442  CB   SER B 288     -25.408  10.344  -7.759  1.00 22.61      B
ATOM   6443  OG   SER B 288     -25.192   9.078  -7.169  1.00 26.26      B
ATOM   6444  C    SER B 288     -26.590  11.256  -5.776  1.00 23.28      B
ATOM   6445  O    SER B 288     -27.174  10.588  -4.920  1.00 24.12      B
ATOM   6446  N    CYS B 289     -25.828  12.293  -5.470  1.00 23.35      B
ATOM   6447  CA   CYS B 289     -25.642  12.679  -4.080  1.00 25.42      B
ATOM   6448  CB   CYS B 289     -24.689  13.861  -4.001  1.00 26.09      B
ATOM   6449  SG   CYS B 289     -24.505  14.448  -2.341  1.00 30.73      B
ATOM   6450  C    CYS B 289     -26.949  13.021  -3.353  1.00 25.77      B
ATOM   6451  O    CYS B 289     -27.177  12.583  -2.223  1.00 25.68      B
ATOM   6452  N    GLY B 290     -27.797  13.810  -4.009  1.00 27.03      B
ATOM   6453  CA   GLY B 290     -29.069  14.204  -3.431  1.00 26.57      B
ATOM   6454  C    GLY B 290     -30.032  13.047  -3.256  1.00 27.92      B
ATOM   6455  O    GLY B 290     -30.747  12.972  -2.252  1.00 27.98      B
ATOM   6456  N    ASN B 291     -30.069  12.141  -4.229  1.00 28.41      B
ATOM   6457  CA   ASN B 291     -30.961  10.995  -4.121  1.00 27.97      B
ATOM   6458  CB   ASN B 291     -31.016  10.223  -5.437  1.00 28.19      B
```

FIGURE 4- 86 -

```
ATOM   6459  CG   ASN B 291     -31.804  10.956  -6.505  1.00 30.30      B
ATOM   6460  OD1  ASN B 291     -32.311  12.049  -6.269  1.00 31.35      B
ATOM   6461  ND2  ASN B 291     -31.913  10.358  -7.683  1.00 29.72      B
ATOM   6462  C    ASN B 291     -30.464  10.106  -3.001  1.00 27.26      B
ATOM   6463  O    ASN B 291     -31.243   9.653  -2.167  1.00 27.38      B
ATOM   6464  N    THR B 292     -29.162   9.868  -2.965  1.00 25.83      B
ATOM   6465  CA   THR B 292     -28.615   9.034  -1.911  1.00 26.01      B
ATOM   6466  CB   THR B 292     -27.102   8.872  -2.050  1.00 25.27      B
ATOM   6467  OG1  THR B 292     -26.815   8.212  -3.286  1.00 26.62      B
ATOM   6468  CG2  THR B 292     -26.549   8.048  -0.910  1.00 23.00      B
ATOM   6469  C    THR B 292     -28.920   9.637  -0.554  1.00 26.24      B
ATOM   6470  O    THR B 292     -29.334   8.927   0.362  1.00 28.58      B
ATOM   6471  N    LEU B 293     -28.727  10.948  -0.431  1.00 24.80      B
ATOM   6472  CA   LEU B 293     -28.972  11.646   0.826  1.00 23.19      B
ATOM   6473  CB   LEU B 293     -28.433  13.075   0.760  1.00 22.68      B
ATOM   6474  CG   LEU B 293     -26.929  13.302   0.892  1.00 21.66      B
ATOM   6475  CD1  LEU B 293     -26.591  14.711   0.451  1.00 22.16      B
ATOM   6476  CD2  LEU B 293     -26.498  13.069   2.323  1.00 19.60      B
ATOM   6477  C    LEU B 293     -30.442  11.699   1.185  1.00 22.92      B
ATOM   6478  O    LEU B 293     -30.805  11.555   2.343  1.00 23.37      B
ATOM   6479  N    THR B 294     -31.289  11.924   0.191  1.00 23.36      B
ATOM   6480  CA   THR B 294     -32.721  12.014   0.425  1.00 22.82      B
ATOM   6481  CB   THR B 294     -33.408  12.651  -0.790  1.00 21.91      B
ATOM   6482  OG1  THR B 294     -32.881  13.969  -0.966  1.00 24.42      B
ATOM   6483  CG2  THR B 294     -34.916  12.747  -0.593  1.00 19.62      B
ATOM   6484  C    THR B 294     -33.340  10.655   0.744  1.00 23.43      B
ATOM   6485  O    THR B 294     -34.251  10.560   1.571  1.00 22.13      B
ATOM   6486  N    CYS B 295     -32.840   9.606   0.098  1.00 23.91      B
ATOM   6487  CA   CYS B 295     -33.344   8.256   0.330  1.00 24.88      B
ATOM   6488  CB   CYS B 295     -32.710   7.292  -0.664  1.00 25.94      B
ATOM   6489  SG   CYS B 295     -33.330   5.603  -0.590  1.00 25.59      B
ATOM   6490  C    CYS B 295     -32.961   7.864   1.748  1.00 25.68      B
ATOM   6491  O    CYS B 295     -33.797   7.431   2.552  1.00 23.15      B
ATOM   6492  N    TYR B 296     -31.681   8.034   2.052  1.00 26.30      B
ATOM   6493  CA   TYR B 296     -31.172   7.720   3.375  1.00 26.20      B
ATOM   6494  CB   TYR B 296     -29.697   8.127   3.453  1.00 25.82      B
ATOM   6495  CG   TYR B 296     -29.087   8.022   4.825  1.00 29.06      B
ATOM   6496  CD1  TYR B 296     -29.455   8.903   5.843  1.00 29.97      B
ATOM   6497  CE1  TYR B 296     -28.895   8.811   7.109  1.00 30.97      B
ATOM   6498  CD2  TYR B 296     -28.140   7.046   5.114  1.00 30.15      B
ATOM   6499  CE2  TYR B 296     -27.570   6.948   6.381  1.00 29.87      B
ATOM   6500  CZ   TYR B 296     -27.953   7.830   7.367  1.00 30.39      B
ATOM   6501  OH   TYR B 296     -27.389   7.732   8.613  1.00 32.24      B
ATOM   6502  C    TYR B 296     -32.019   8.429   4.439  1.00 26.10      B
ATOM   6503  O    TYR B 296     -32.573   7.783   5.327  1.00 26.73      B
ATOM   6504  N    LEU B 297     -32.140   9.748   4.335  1.00 25.57      B
ATOM   6505  CA   LEU B 297     -32.921  10.511   5.302  1.00 26.99      B
ATOM   6506  CB   LEU B 297     -33.032  11.983   4.869  1.00 25.10      B
ATOM   6507  CG   LEU B 297     -34.015  12.907   5.617  1.00 23.84      B
ATOM   6508  CD1  LEU B 297     -33.748  12.916   7.115  1.00 22.85      B
ATOM   6509  CD2  LEU B 297     -33.896  14.306   5.059  1.00 23.73      B
ATOM   6510  C    LEU B 297     -34.317   9.920   5.483  1.00 28.61      B
ATOM   6511  O    LEU B 297     -34.713   9.573   6.607  1.00 31.00      B
ATOM   6512  N    LYS B 298     -35.059   9.798   4.393  1.00 28.49      B
ATOM   6513  CA   LYS B 298     -36.413   9.260   4.456  1.00 27.90      B
ATOM   6514  CB   LYS B 298     -37.042   9.268   3.056  1.00 25.50      B
ATOM   6515  CG   LYS B 298     -37.251  10.686   2.522  1.00 23.68      B
ATOM   6516  CD   LYS B 298     -37.960  10.747   1.175  1.00 21.57      B
ATOM   6517  CE   LYS B 298     -38.274  12.188   0.801  1.00 18.55      B
ATOM   6518  NZ   LYS B 298     -38.959  12.316  -0.517  1.00 18.43      B
ATOM   6519  C    LYS B 298     -36.446   7.859   5.065  1.00 27.99      B
ATOM   6520  O    LYS B 298     -37.191   7.602   5.999  1.00 27.57      B
ATOM   6521  N    ALA B 299     -35.621   6.961   4.551  1.00 29.28      B
ATOM   6522  CA   ALA B 299     -35.586   5.595   5.065  1.00 31.37      B
ATOM   6523  CB   ALA B 299     -34.581   4.764   4.271  1.00 31.80      B
ATOM   6524  C    ALA B 299     -35.249   5.545   6.559  1.00 32.34      B
ATOM   6525  O    ALA B 299     -36.034   5.014   7.355  1.00 31.10      B
ATOM   6526  N    THR B 300     -34.092   6.093   6.941  1.00 33.06      B
ATOM   6527  CA   THR B 300     -33.691   6.087   8.351  1.00 32.72      B
ATOM   6528  CB   THR B 300     -32.452   6.982   8.626  1.00 30.57      B
ATOM   6529  OG1  THR B 300     -31.287   6.407   8.029  1.00 30.14      B
ATOM   6530  CG2  THR B 300     -32.217   7.104  10.118  1.00 27.43      B
ATOM   6531  C    THR B 300     -34.834   6.584   9.237  1.00 33.73      B
ATOM   6532  O    THR B 300     -35.110   6.000  10.285  1.00 33.54      B
ATOM   6533  N    ALA B 301     -35.497   7.658   8.815  1.00 33.61      B
ATOM   6534  CA   ALA B 301     -36.599   8.197   9.595  1.00 34.97      B
```

FIGURE 4- 87 -

```
ATOM   6535  CB  ALA B 301    -37.067    9.515    9.008  1.00 34.73       B
ATOM   6536  C   ALA B 301    -37.743    7.191    9.606  1.00 36.72       B
ATOM   6537  O   ALA B 301    -38.314    6.893   10.661  1.00 37.61       B
ATOM   6538  N   ALA B 302    -38.068    6.665    8.430  1.00 36.87       B
ATOM   6539  CA  ALA B 302    -39.142    5.698    8.305  1.00 37.18       B
ATOM   6540  CB  ALA B 302    -39.267    5.235    6.872  1.00 36.08       B
ATOM   6541  C   ALA B 302    -38.891    4.503    9.219  1.00 38.85       B
ATOM   6542  O   ALA B 302    -39.832    3.973    9.820  1.00 40.89       B
ATOM   6543  N   CYS B 303    -37.636    4.070    9.325  1.00 38.13       B
ATOM   6544  CA  CYS B 303    -37.317    2.942   10.195  1.00 37.59       B
ATOM   6545  CB  CYS B 303    -35.836    2.597   10.103  1.00 38.23       B
ATOM   6546  SG  CYS B 303    -35.397    1.759    8.585  1.00 42.19       B
ATOM   6547  C   CYS B 303    -37.687    3.264   11.639  1.00 37.91       B
ATOM   6548  O   CYS B 303    -38.227    2.426   12.359  1.00 37.58       B
ATOM   6549  N   ARG B 304    -37.401    4.487   12.064  1.00 37.69       B
ATOM   6550  CA  ARG B 304    -37.733    4.888   13.416  1.00 38.03       B
ATOM   6551  CB  ARG B 304    -37.140    6.263   13.730  1.00 36.02       B
ATOM   6552  CG  ARG B 304    -35.630    6.279   13.688  1.00 33.31       B
ATOM   6553  CD  ARG B 304    -35.091    7.551   14.271  1.00 31.54       B
ATOM   6554  NE  ARG B 304    -33.654    7.677   14.071  1.00 31.42       B
ATOM   6555  CZ  ARG B 304    -32.961    8.761   14.405  1.00 32.28       B
ATOM   6556  NH1 ARG B 304    -33.583    9.801   14.957  1.00 29.78       B
ATOM   6557  NH2 ARG B 304    -31.653    8.812   14.178  1.00 31.08       B
ATOM   6558  C   ARG B 304    -39.247    4.914   13.596  1.00 39.14       B
ATOM   6559  O   ARG B 304    -39.743    4.674   14.690  1.00 41.50       B
ATOM   6560  N   ALA B 305    -39.981    5.204   12.528  1.00 39.09       B
ATOM   6561  CA  ALA B 305    -41.432    5.239   12.620  1.00 39.56       B
ATOM   6562  CB  ALA B 305    -42.016    5.903   11.401  1.00 39.12       B
ATOM   6563  C   ALA B 305    -41.984    3.828   12.755  1.00 41.22       B
ATOM   6564  O   ALA B 305    -43.004    3.617   13.403  1.00 41.68       B
ATOM   6565  N   ALA B 306    -41.303    2.863   12.145  1.00 42.59       B
ATOM   6566  CA  ALA B 306    -41.735    1.469   12.194  1.00 44.67       B
ATOM   6567  CB  ALA B 306    -41.290    0.746   10.933  1.00 43.79       B
ATOM   6568  C   ALA B 306    -41.181    0.757   13.424  1.00 47.00       B
ATOM   6569  O   ALA B 306    -41.636   -0.325   13.799  1.00 48.06       B
ATOM   6570  N   LYS B 307    -40.185    1.373   14.045  1.00 48.95       B
ATOM   6571  CA  LYS B 307    -39.552    0.817   15.231  1.00 49.29       B
ATOM   6572  CB  LYS B 307    -40.603    0.530   16.313  1.00 49.84       B
ATOM   6573  CG  LYS B 307    -41.570    1.685   16.576  1.00 50.58       B
ATOM   6574  CD  LYS B 307    -42.105    1.658   17.997  1.00 49.75       B
ATOM   6575  CE  LYS B 307    -40.970    1.892   18.985  1.00 50.48       B
ATOM   6576  NZ  LYS B 307    -41.385    1.740   20.408  1.00 52.11       B
ATOM   6577  C   LYS B 307    -38.746   -0.450   14.930  1.00 48.91       B
ATOM   6578  O   LYS B 307    -38.642   -1.341   15.770  1.00 50.54       B
ATOM   6579  N   LEU B 308    -38.179   -0.539   13.732  1.00 48.44       B
ATOM   6580  CA  LEU B 308    -37.357   -1.697   13.381  1.00 49.62       B
ATOM   6581  CB  LEU B 308    -36.950   -1.630   11.907  1.00 47.59       B
ATOM   6582  CG  LEU B 308    -38.098   -1.571   10.897  1.00 45.13       B
ATOM   6583  CD1 LEU B 308    -37.557   -1.241    9.531  1.00 43.55       B
ATOM   6584  CD2 LEU B 308    -38.823   -2.894   10.872  1.00 45.24       B
ATOM   6585  C   LEU B 308    -36.112   -1.632   14.279  1.00 50.98       B
ATOM   6586  O   LEU B 308    -35.572   -0.550   14.515  1.00 51.35       B
ATOM   6587  N   GLN B 309    -35.653   -2.771   14.786  1.00 51.64       B
ATOM   6588  CA  GLN B 309    -34.493   -2.751   15.668  1.00 53.04       B
ATOM   6589  CB  GLN B 309    -34.639   -3.821   16.754  1.00 55.63       B
ATOM   6590  CG  GLN B 309    -35.800   -3.551   17.700  1.00 58.79       B
ATOM   6591  CD  GLN B 309    -35.737   -2.156   18.334  1.00 60.91       B
ATOM   6592  OE1 GLN B 309    -35.685   -1.131   17.638  1.00 59.69       B
ATOM   6593  NE2 GLN B 309    -35.751   -2.117   19.665  1.00 62.57       B
ATOM   6594  C   GLN B 309    -33.171   -2.912   14.947  1.00 52.73       B
ATOM   6595  O   GLN B 309    -33.095   -3.598   13.921  1.00 53.04       B
ATOM   6596  N   ASP B 310    -32.133   -2.280   15.491  1.00 51.60       B
ATOM   6597  CA  ASP B 310    -30.803   -2.341   14.902  1.00 52.24       B
ATOM   6598  CB  ASP B 310    -30.035   -3.536   15.470  1.00 55.31       B
ATOM   6599  CG  ASP B 310    -29.586   -3.317   16.910  1.00 59.11       B
ATOM   6600  OD1 ASP B 310    -30.376   -2.749   17.702  1.00 59.24       B
ATOM   6601  OD2 ASP B 310    -28.448   -3.730   17.248  1.00 60.51       B
ATOM   6602  C   ASP B 310    -30.852   -2.453   13.380  1.00 50.77       B
ATOM   6603  O   ASP B 310    -30.647   -3.537   12.835  1.00 50.77       B
ATOM   6604  N   CYS B 311    -31.133   -1.343   12.699  1.00 48.73       B
ATOM   6605  CA  CYS B 311    -31.195   -1.339   11.236  1.00 46.63       B
ATOM   6606  CB  CYS B 311    -32.274   -0.366   10.729  1.00 44.67       B
ATOM   6607  SG  CYS B 311    -33.980   -0.665   11.274  1.00 43.18       B
ATOM   6608  C   CYS B 311    -29.853   -0.914   10.644  1.00 45.93       B
ATOM   6609  O   CYS B 311    -29.178   -0.055   11.191  1.00 46.22       B
ATOM   6610  N   THR B 312    -29.464   -1.521    9.530  1.00 45.02       B
```

FIGURE 4- 88 -

```
ATCM   6611  CA   THR  B  312    -28.224   -1.143    8.865   1.00  44.83       B
ATCM   6612  CB   THR  B  312    -27.117   -2.189    9.062   1.00  44.70       B
ATCM   6613  OG1  THR  B  312    -26.641   -2.114   10.409   1.00  46.49       B
ATCM   6614  CG2  THR  B  312    -25.960   -1.938    8.097   1.00  41.78       B
ATCM   6615  C    THR  B  312    -28.509   -0.987    7.382   1.00  45.05       B
ATCM   6616  O    THR  B  312    -28.683   -1.975    6.661   1.00  45.45       B
ATCM   6617  N    MET  B  313    -28.554    0.257    6.924   1.00  43.75       B
ATCM   6618  CA   MET  B  313    -28.848    0.501    5.527   1.00  43.02       B
ATCM   6619  CB   MET  B  313    -29.733    1.731    5.386   1.00  44.77       B
ATCM   6620  CG   MET  B  313    -31.005    1.657    6.204   1.00  46.97       B
ATCM   6621  SD   MET  B  313    -32.070    3.042    5.825   1.00  49.75       B
ATCM   6622  CE   MET  B  313    -30.920    4.409    5.984   1.00  48.57       B
ATCM   6623  C    MET  B  313    -27.652    0.659    4.613   1.00  41.23       B
ATCM   6624  O    MET  B  313    -26.536    0.944    5.037   1.00  41.04       B
ATCM   6625  N    LEU  B  314    -27.921    0.444    3.337   1.00  40.03       B
ATCM   6626  CA   LEU  B  314    -26.943    0.591    2.285   1.00  39.23       B
ATCM   6627  CB   LEU  B  314    -26.443   -0.773    1.817   1.00  37.96       B
ATCM   6628  CG   LEU  B  314    -25.322   -0.729    0.777   1.00  37.09       B
ATCM   6629  CD1  LEU  B  314    -24.122   -0.024    1.373   1.00  37.89       B
ATCM   6630  CD2  LEU  B  314    -24.945   -2.135    0.347   1.00  34.82       B
ATCM   6631  C    LEU  B  314    -27.757    1.287    1.192   1.00  39.71       B
ATCM   6632  O    LEU  B  314    -28.688    0.710    0.623   1.00  39.57       B
ATCM   6633  N    VAL  B  315    -27.429    2.546    0.937   1.00  39.35       B
ATCM   6634  CA   VAL  B  315    -28.145    3.324   -0.058   1.00  38.18       B
ATCM   6635  CB   VAL  B  315    -28.647    4.655    0.551   1.00  39.01       B
ATCM   6636  CG1  VAL  B  315    -29.440    5.452   -0.480   1.00  37.93       B
ATCM   6637  CG2  VAL  B  315    -29.483    4.374    1.794   1.00  39.28       B
ATCM   6638  C    VAL  B  315    -27.265    3.651   -1.250   1.00  38.40       B
ATCM   6639  O    VAL  B  315    -26.115    4.070   -1.092   1.00  38.30       B
ATCM   6640  N    ASN  B  316    -27.803    3.433   -2.442   1.00  37.37       B
ATCM   6641  CA   ASN  B  316    -27.109    3.753   -3.680   1.00  37.79       B
ATCM   6642  CB   ASN  B  316    -26.761    2.496   -4.480   1.00  38.31       B
ATCM   6643  CG   ASN  B  316    -25.569    1.756   -3.918   1.00  37.60       B
ATCM   6644  OD1  ASN  B  316    -25.652    1.100   -2.875   1.00  38.29       B
ATCM   6645  ND2  ASN  B  316    -24.446    1.862   -4.604   1.00  37.50       B
ATCM   6646  C    ASN  B  316    -28.080    4.602   -4.473   1.00  37.73       B
ATCM   6647  O    ASN  B  316    -28.958    4.079   -5.147   1.00  38.18       B
ATCM   6648  N    GLY  B  317    -27.933    5.916   -4.383   1.00  37.72       B
ATCM   6649  CA   GLY  B  317    -28.845    6.781   -5.096   1.00  38.29       B
ATCM   6650  C    GLY  B  317    -30.237    6.537   -4.554   1.00  38.88       B
ATCM   6651  O    GLY  B  317    -30.516    6.820   -3.391   1.00  39.87       B
ATCM   6652  N    ASP  B  318    -31.115    5.991   -5.385   1.00  39.03       B
ATCM   6653  CA   ASP  B  318    -32.479    5.722   -4.951   1.00  39.79       B
ATCM   6654  CB   ASP  B  318    -33.469    6.109   -6.056   1.00  40.99       B
ATCM   6655  CG   ASP  B  318    -33.531    5.081   -7.166   1.00  41.99       B
ATCM   6656  OD1  ASP  B  318    -32.469    4.705   -7.700   1.00  41.08       B
ATCM   6657  OD2  ASP  B  318    -34.652    4.649   -7.503   1.00  45.00       B
ATCM   6658  C    ASP  B  318    -32.649    4.245   -4.609   1.00  38.36       B
ATCM   6659  O    ASP  B  318    -33.759    3.795   -4.331   1.00  37.19       B
ATCM   6660  N    ASP  B  319    -31.541    3.504   -4.629   1.00  38.16       B
ATCM   6661  CA   ASP  B  319    -31.543    2.067   -4.344   1.00  37.61       B
ATCM   6662  CB   ASP  B  319    -30.534    1.355   -5.244   1.00  39.96       B
ATCM   6663  CG   ASP  B  319    -30.942   -0.068   -5.558   1.00  43.16       B
ATCM   6664  OD1  ASP  B  319    -30.695   -0.970   -4.721   1.00  44.75       B
ATCM   6665  OD2  ASP  B  319    -31.529   -0.279   -6.643   1.00  45.55       B
ATCM   6666  C    ASP  B  319    -31.215    1.817   -2.884   1.00  36.10       B
ATCM   6667  O    ASP  B  319    -30.115    2.105   -2.419   1.00  36.05       B
ATCM   6668  N    LEU  B  320    -32.179    1.244   -2.180   1.00  34.82       B
ATCM   6669  CA   LEU  B  320    -32.060    1.008   -0.758   1.00  35.29       B
ATCM   6670  CB   LEU  B  320    -33.057    1.920   -0.058   1.00  33.71       B
ATCM   6671  CG   LEU  B  320    -33.423    1.610    1.382   1.00  33.61       B
ATCM   6672  CD1  LEU  B  320    -32.280    2.000    2.285   1.00  32.82       B
ATCM   6673  CD2  LEU  B  320    -34.687    2.374    1.737   1.00  34.61       B
ATCM   6674  C    LEU  B  320    -32.272   -0.434   -0.306   1.00  36.54       B
ATCM   6675  O    LEU  B  320    -33.034   -1.187   -0.904   1.00  36.00       B
ATCM   6676  N    VAL  B  321    -31.594   -0.797    0.777   1.00  38.28       B
ATCM   6677  CA   VAL  B  321    -31.686   -2.137    1.348   1.00  39.33       B
ATCM   6678  CB   VAL  B  321    -30.656   -3.096    0.705   1.00  38.61       B
ATCM   6679  CG1  VAL  B  321    -29.249   -2.553    0.893   1.00  36.37       B
ATCM   6680  CG2  VAL  B  321    -30.784   -4.479    1.322   1.00  38.08       B
ATCM   6681  C    VAL  B  321    -31.434   -2.078    2.854   1.00  40.35       B
ATCM   6682  O    VAL  B  321    -30.407   -1.575    3.299   1.00  40.43       B
ATCM   6683  N    VAL  B  322    -32.375   -2.601    3.632   1.00  41.45       B
ATCM   6684  CA   VAL  B  322    -32.265   -2.597    5.084   1.00  42.88       B
ATCM   6685  CB   VAL  B  322    -33.552   -2.054    5.721   1.00  42.47       B
ATCM   6686  CG1  VAL  B  322    -33.363   -1.894    7.218   1.00  42.45       B
```

FIGURE 4- 89 -

```
ATOM   6687  CG2 VAL B 322     -33.940   -0.756   5.069  1.00 42.74      B
ATOM   6688  C   VAL B 322     -32.021   -3.988   5.673  1.00 44.44      B
ATOM   6689  O   VAL B 322     -32.675   -4.955   5.287  1.00 45.88      B
ATOM   6690  N   ILE B 323     -31.075   -4.087   6.598  1.00 45.27      B
ATOM   6691  CA  ILE B 323     -30.797   -5.353   7.268  1.00 47.01      B
ATOM   6692  CB  ILE B 323     -29.372   -5.859   6.976  1.00 45.60      B
ATOM   6693  CG2 ILE B 323     -28.960   -6.907   7.990  1.00 45.69      B
ATOM   6694  CG1 ILE B 323     -29.339   -6.469   5.576  1.00 45.50      B
ATOM   6695  CD1 ILE B 323     -27.999   -7.034   5.176  1.00 44.73      B
ATOM   6696  C   ILE B 323     -30.982   -5.050   8.744  1.00 49.37      B
ATOM   6697  O   ILE B 323     -30.327   -4.160   9.289  1.00 48.25      B
ATOM   6698  N   CYS B 324     -31.885   -5.781   9.390  1.00 52.12      B
ATOM   6699  CA  CYS B 324     -32.183   -5.517  10.791  1.00 55.13      B
ATOM   6700  CB  CYS B 324     -33.398   -4.614  10.864  1.00 54.98      B
ATOM   6701  SG  CYS B 324     -34.783   -5.357  10.002  1.00 56.13      B
ATOM   6702  C   CYS B 324     -32.435   -6.713  11.697  1.00 56.90      B
ATOM   6703  O   CYS B 324     -32.538   -7.854  11.253  1.00 57.77      B
ATOM   6704  N   GLU B 325     -32.558   -6.406  12.985  1.00 59.16      B
ATOM   6705  CA  GLU B 325     -32.806   -7.392  14.027  1.00 60.53      B
ATOM   6706  CB  GLU B 325     -32.398   -6.809  15.384  1.00 61.11      B
ATOM   6707  CG  GLU B 325     -32.319   -7.833  16.488  1.00 63.86      B
ATOM   6708  CD  GLU B 325     -31.294   -8.912  16.187  1.00 64.68      B
ATOM   6709  OE1 GLU B 325     -30.084   -8.584  16.105  1.00 65.21      B
ATOM   6710  OE2 GLU B 325     -31.705  -10.083  16.024  1.00 64.48      B
ATOM   6711  C   GLU B 325     -34.294   -7.756  14.028  1.00 60.40      B
ATOM   6712  O   GLU B 325     -35.138   -6.961  14.438  1.00 59.45      B
ATOM   6713  N   SER B 326     -34.605   -8.961  13.564  1.00 61.56      B
ATOM   6714  CA  SER B 326     -35.990   -9.412  13.494  1.00 63.07      B
ATOM   6715  CB  SER B 326     -36.094  -10.750  12.765  1.00 62.41      B
ATOM   6716  OG  SER B 326     -37.424  -11.235  12.820  1.00 60.35      B
ATOM   6717  C   SER B 326     -36.655   -9.560  14.847  1.00 63.98      B
ATOM   6718  O   SER B 326     -35.987   -9.770  15.857  1.00 64.26      B
ATOM   6719  N   ALA B 327     -37.981   -9.445  14.847  1.00 64.83      B
ATOM   6720  CA  ALA B 327     -38.780   -9.591  16.056  1.00 66.15      B
ATOM   6721  CB  ALA B 327     -39.599   -8.341  16.310  1.00 64.91      B
ATOM   6722  C   ALA B 327     -39.699  -10.787  15.841  1.00 67.39      B
ATOM   6723  O   ALA B 327     -40.135  -11.431  16.796  1.00 68.62      B
ATOM   6724  N   GLY B 328     -39.982  -11.079  14.575  1.00 67.86      B
ATOM   6725  CA  GLY B 328     -40.835  -12.203  14.245  1.00 68.15      B
ATOM   6726  C   GLY B 328     -41.707  -11.998  13.021  1.00 68.80      B
ATOM   6727  O   GLY B 328     -42.329  -10.946  12.858  1.00 69.14      B
ATOM   6728  N   THR B 329     -41.739  -13.017  12.164  1.00 68.76      B
ATOM   6729  CA  THR B 329     -42.534  -13.019  10.937  1.00 68.90      B
ATOM   6730  CB  THR B 329     -43.113  -14.426  10.670  1.00 68.20      B
ATOM   6731  OG1 THR B 329     -42.045  -15.362  10.491  1.00 68.14      B
ATOM   6732  CG2 THR B 329     -43.985  -14.419   9.431  1.00 68.03      B
ATOM   6733  C   THR B 329     -43.706  -12.047  11.032  1.00 70.13      B
ATOM   6734  O   THR B 329     -43.797  -11.060  10.299  1.00 70.39      B
ATOM   6735  N   GLN B 330     -44.596  -12.349  11.967  1.00 70.84      B
ATOM   6736  CA  GLN B 330     -45.794  -11.565  12.217  1.00 70.90      B
ATOM   6737  CB  GLN B 330     -46.495  -12.099  13.474  1.00 72.81      B
ATOM   6738  CG  GLN B 330     -46.374  -13.619  13.655  1.00 75.26      B
ATOM   6739  CD  GLN B 330     -45.047  -14.056  14.285  1.00 76.24      B
ATOM   6740  OE1 GLN B 330     -43.975  -13.562  13.925  1.00 77.75      B
ATOM   6741  NE2 GLN B 330     -45.121  -15.001  15.223  1.00 75.86      B
ATOM   6742  C   GLN B 330     -45.503  -10.080  12.391  1.00 69.09      B
ATOM   6743  O   GLN B 330     -46.145   -9.235  11.771  1.00 68.43      B
ATOM   6744  N   GLU B 331     -44.529   -9.781  13.243  1.00 67.71      B
ATOM   6745  CA  GLU B 331     -44.141   -8.407  13.551  1.00 66.85      B
ATOM   6746  CB  GLU B 331     -43.176   -8.391  14.733  1.00 68.14      B
ATOM   6747  CG  GLU B 331     -43.746   -8.962  16.014  1.00 69.90      B
ATOM   6748  CD  GLU B 331     -42.729   -9.825  16.737  1.00 71.34      B
ATOM   6749  OE1 GLU B 331     -42.419  -10.918  16.211  1.00 71.62      B
ATOM   6750  OE2 GLU B 331     -42.234   -9.412  17.813  1.00 71.83      B
ATOM   6751  C   GLU B 331     -43.501   -7.667  12.392  1.00 64.58      B
ATOM   6752  O   GLU B 331     -43.902   -6.552  12.056  1.00 64.57      B
ATOM   6753  N   ASP B 332     -42.488   -8.281  11.800  1.00 61.78      B
ATOM   6754  CA  ASP B 332     -41.798   -7.671  10.683  1.00 58.93      B
ATOM   6755  CB  ASP B 332     -40.799   -8.655  10.091  1.00 56.81      B
ATOM   6756  CG  ASP B 332     -39.894   -9.253  11.139  1.00 55.71      B
ATOM   6757  OD1 ASP B 332     -39.728   -8.626  12.213  1.00 53.76      B
ATOM   6758  OD2 ASP B 332     -39.343  -10.344  10.884  1.00 54.93      B
ATOM   6759  C   ASP B 332     -42.791   -7.222   9.618  1.00 58.69      B
ATOM   6760  O   ASP B 332     -42.792   -6.058   9.215  1.00 58.62      B
ATOM   6761  N   ALA B 333     -43.638   -8.140   9.163  1.00 58.10      B
ATOM   6762  CA  ALA B 333     -44.627   -7.801   8.145  1.00 57.41      B
```

FIGURE 4- 90 -

```
ATOM   6763  CB   ALA B 333     -45.669   -8.909    8.028  1.00 57.52      B
ATOM   6764  C    ALA B 333     -45.301   -6.493    8.533  1.00 56.87      B
ATOM   6765  O    ALA B 333     -45.467   -5.593    7.701  1.00 57.63      B
ATOM   6766  N    ALA B 334     -45.678   -6.403    9.808  1.00 55.18      B
ATOM   6767  CA   ALA B 334     -46.338   -5.223   10.353  1.00 53.89      B
ATOM   6768  CB   ALA B 334     -46.745   -5.477   11.803  1.00 52.09      B
ATOM   6769  C    ALA B 334     -45.410   -4.016   10.273  1.00 53.27      B
ATOM   6770  O    ALA B 334     -45.786   -2.962    9.760  1.00 53.15      B
ATOM   6771  N    ALA B 335     -44.194   -4.184   10.780  1.00 52.80      B
ATOM   6772  CA   ALA B 335     -43.202   -3.117   10.773  1.00 53.17      B
ATOM   6773  CB   ALA B 335     -41.923   -3.584   11.475  1.00 52.01      B
ATOM   6774  C    ALA B 335     -42.895   -2.664    9.344  1.00 53.56      B
ATOM   6775  O    ALA B 335     -42.797   -1.460    9.075  1.00 53.64      B
ATOM   6776  N    LEU B 336     -42.743   -3.623    8.430  1.00 52.90      B
ATOM   6777  CA   LEU B 336     -42.463   -3.288    7.039  1.00 52.43      B
ATOM   6778  CB   LEU B 336     -42.255   -4.551    6.199  1.00 52.91      B
ATOM   6779  CG   LEU B 336     -41.638   -4.279    4.825  1.00 53.09      B
ATOM   6780  CD1  LEU B 336     -40.305   -3.585    5.011  1.00 53.97      B
ATOM   6781  CD2  LEU B 336     -41.439   -5.565    4.067  1.00 53.44      B
ATOM   6782  C    LEU B 336     -43.644   -2.486    6.498  1.00 52.04      B
ATOM   6783  O    LEU B 336     -43.472   -1.551    5.711  1.00 53.03      B
ATOM   6784  N    ARG B 337     -44.848   -2.852    6.918  1.00 50.63      B
ATOM   6785  CA   ARG B 337     -46.021   -2.115    6.485  1.00 49.59      B
ATOM   6786  CB   ARG B 337     -47.306   -2.803    6.958  1.00 51.48      B
ATOM   6787  CG   ARG B 337     -47.801   -3.931    6.043  1.00 52.40      B
ATOM   6788  CD   ARG B 337     -49.299   -4.232    6.282  1.00 53.65      B
ATOM   6789  NE   ARG B 337     -49.541   -4.916    7.554  1.00 53.55      B
ATOM   6790  CZ   ARG B 337     -49.108   -6.143    7.837  1.00 53.19      B
ATOM   6791  NH1  ARG B 337     -48.412   -6.834    6.938  1.00 51.98      B
ATOM   6792  NH2  ARG B 337     -49.363   -6.676    9.023  1.00 52.07      B
ATOM   6793  C    ARG B 337     -45.931   -0.702    7.062  1.00 48.03      B
ATOM   6794  O    ARG B 337     -46.303    0.270    6.406  1.00 49.32      B
ATOM   6795  N    ALA B 338     -45.423   -0.594    8.287  1.00 45.72      B
ATOM   6796  CA   ALA B 338     -45.264    0.701    8.947  1.00 43.57      B
ATOM   6797  CB   ALA B 338     -44.802    0.503   10.391  1.00 42.56      B
ATOM   6798  C    ALA B 338     -44.242    1.543    8.190  1.00 42.19      B
ATOM   6799  O    ALA B 338     -44.453    2.726    7.935  1.00 41.35      B
ATOM   6800  N    PHE B 339     -43.132    0.911    7.836  1.00 41.12      B
ATOM   6801  CA   PHE B 339     -42.058    1.567    7.112  1.00 41.04      B
ATOM   6802  CB   PHE B 339     -40.956    0.559    6.823  1.00 40.16      B
ATOM   6803  CG   PHE B 339     -39.829    1.110    5.995  1.00 39.61      B
ATOM   6804  CD1  PHE B 339     -38.757    1.754    6.601  1.00 38.10      B
ATOM   6805  CD2  PHE B 339     -39.822    0.946    4.609  1.00 38.78      B
ATOM   6806  CE1  PHE B 339     -37.688    2.219    5.846  1.00 38.43      B
ATOM   6807  CE2  PHE B 339     -38.760    1.408    3.842  1.00 38.97      B
ATOM   6808  CZ   PHE B 339     -37.685    2.047    4.465  1.00 39.28      B
ATOM   6809  C    PHE B 339     -42.527    2.163    5.790  1.00 41.72      B
ATOM   6810  O    PHE B 339     -42.067    3.236    5.375  1.00 41.28      B
ATOM   6811  N    THR B 340     -43.439    1.459    5.128  1.00 40.80      B
ATOM   6812  CA   THR B 340     -43.939    1.906    3.842  1.00 40.15      B
ATOM   6813  CB   THR B 340     -44.625    0.759    3.115  1.00 40.36      B
ATOM   6814  OG1  THR B 340     -43.784   -0.401    3.167  1.00 39.33      B
ATOM   6815  CG2  THR B 340     -44.874    1.132    1.661  1.00 40.53      B
ATOM   6816  C    THR B 340     -44.896    3.085    3.961  1.00 40.09      B
ATOM   6817  O    THR B 340     -45.005    3.903    3.048  1.00 39.21      B
ATOM   6818  N    GLU B 341     -45.588    3.172    5.089  1.00 40.47      B
ATOM   6819  CA   GLU B 341     -46.523    4.264    5.319  1.00 41.67      B
ATOM   6820  CB   GLU B 341     -47.391    3.979    6.536  1.00 45.20      B
ATOM   6821  CG   GLU B 341     -48.322    2.805    6.398  1.00 50.58      B
ATOM   6822  CD   GLU B 341     -48.872    2.380    7.752  1.00 55.00      B
ATOM   6823  OE1  GLU B 341     -49.291    3.275    8.530  1.00 56.17      B
ATOM   6824  OE2  GLU B 341     -48.886    1.158    8.038  1.00 56.57      B
ATOM   6825  C    GLU B 341     -45.767    5.562    5.559  1.00 40.40      B
ATOM   6826  O    GLU B 341     -46.177    6.629    5.091  1.00 40.72      B
ATOM   6827  N    ALA B 342     -44.676    5.470    6.316  1.00 37.74      B
ATOM   6828  CA   ALA B 342     -43.865    6.641    6.603  1.00 35.30      B
ATOM   6829  CB   ALA B 342     -42.822    6.317    7.667  1.00 33.67      B
ATOM   6830  C    ALA B 342     -43.200    7.095    5.302  1.00 33.64      B
ATOM   6831  O    ALA B 342     -43.316    8.255    4.922  1.00 32.14      B
ATOM   6832  N    MET B 343     -42.518    6.183    4.613  1.00 32.38      B
ATOM   6833  CA   MET B 343     -41.878    6.543    3.353  1.00 32.61      B
ATOM   6834  CB   MET B 343     -41.260    5.316    2.679  1.00 31.87      B
ATOM   6835  CG   MET B 343     -40.000    4.793    3.340  1.00 31.84      B
ATOM   6836  SD   MET B 343     -38.579    5.884    3.177  1.00 31.20      B
ATOM   6837  CE   MET B 343     -37.699    5.075    1.868  1.00 31.35      B
ATOM   6838  C    MET B 343     -42.914    7.174    2.422  1.00 32.27      B
```

FIGURE 4-91-

```
ATOM   6839  O    MET B 343     -42.621   8.134   1.701  1.00 33.27      B
ATOM   6840  N    THR B 344     -44.128   6.641   2.442  1.00 31.31      B
ATOM   6841  CA   THR B 344     -45.188   7.187   1.603  1.00 31.05      B
ATOM   6842  CB   THR B 344     -46.446   6.297   1.621  1.00 29.28      B
ATOM   6843  OG1  THR B 344     -46.140   5.030   1.022  1.00 26.09      B
ATOM   6844  CG2  THR B 344     -47.579   6.960   0.851  1.00 25.39      B
ATOM   6845  C    THR B 344     -45.556   8.584   2.083  1.00 31.53      B
ATOM   6846  O    THR B 344     -45.839   9.474   1.282  1.00 31.05      B
ATOM   6847  N    ARG B 345     -45.549   8.781   3.394  1.00 32.53      B
ATOM   6848  CA   ARG B 345     -45.874  10.091   3.923  1.00 34.25      B
ATOM   6849  CB   ARG B 345     -46.010  10.048   5.448  1.00 34.73      B
ATOM   6850  CG   ARG B 345     -47.378   9.625   5.938  1.00 35.98      B
ATOM   6851  CD   ARG B 345     -47.603  10.040   7.391  1.00 37.77      B
ATOM   6852  NE   ARG B 345     -46.664   9.386   8.300  1.00 38.88      B
ATOM   6853  CZ   ARG B 345     -46.674   8.085   8.567  1.00 38.87      B
ATOM   6854  NH1  ARG B 345     -47.580   7.298   7.997  1.00 38.81      B
ATOM   6855  NH2  ARG B 345     -45.773   7.570   9.394  1.00 40.15      B
ATOM   6856  C    ARG B 345     -44.792  11.088   3.531  1.00 35.53      B
ATOM   6857  O    ARG B 345     -45.076  12.276   3.341  1.00 35.69      B
ATOM   6858  N    TYR B 346     -43.559  10.594   3.405  1.00 35.60      B
ATOM   6859  CA   TYR B 346     -42.409  11.423   3.050  1.00 35.67      B
ATOM   6860  CB   TYR B 346     -41.711  10.767   3.520  1.00 34.51      B
ATOM   6861  CG   TYR B 346     -41.052  10.517   5.004  1.00 34.86      B
ATOM   6862  CD1  TYR B 346     -41.867  11.233   5.883  1.00 33.80      B
ATOM   6863  CE1  TYR B 346     -41.788  11.039   7.256  1.00 34.94      B
ATOM   6864  CD2  TYR B 346     -40.150   9.594   5.541  1.00 34.09      B
ATOM   6865  CE2  TYR B 346     -40.061   9.394   6.918  1.00 33.51      B
ATOM   6866  CZ   TYR B 346     -40.883  10.122   7.768  1.00 34.49      B
ATOM   6867  OH   TYR B 346     -40.802   9.952   9.133  1.00 35.99      B
ATOM   6868  C    TYR B 346     -42.307  11.677   1.557  1.00 36.84      B
ATOM   6869  O    TYR B 346     -41.334  12.267   1.089  1.00 37.54      B
ATOM   6870  N    SER B 347     -43.304  11.220   0.814  1.00 36.47      B
ATOM   6871  CA   SER B 347     -43.315  11.402  -0.622  1.00 37.32      B
ATOM   6872  CB   SER B 347     -42.924  12.831  -0.976  1.00 36.05      B
ATOM   6873  OG   SER B 347     -42.812  12.980  -2.377  1.00 36.31      B
ATOM   6874  C    SER B 347     -42.377  10.424  -1.324  1.00 39.79      B
ATOM   6875  O    SER B 347     -41.557  10.817  -2.160  1.00 41.55      B
ATOM   6876  N    ALA B 348     -42.497   9.147  -0.974  1.00 39.67      B
ATOM   6877  CA   ALA B 348     -41.685   8.107  -1.588  1.00 39.27      B
ATOM   6878  CB   ALA B 348     -40.360   7.971  -0.855  1.00 37.95      B
ATOM   6879  C    ALA B 348     -42.442   6.777  -1.578  1.00 39.91      B
ATOM   6880  O    ALA B 348     -42.025   5.808  -0.940  1.00 39.91      B
ATOM   6881  N    PRO B 349     -43.586   6.721  -2.273  1.00 39.96      B
ATOM   6882  CD   PRO B 349     -44.265   7.800  -3.009  1.00 40.83      B
ATOM   6883  CA   PRO B 349     -44.363   5.478  -2.312  1.00 39.80      B
ATOM   6884  CB   PRO B 349     -45.633   5.880  -3.066  1.00 40.61      B
ATOM   6885  CG   PRO B 349     -45.172   7.025  -3.937  1.00 41.78      B
ATOM   6886  C    PRO B 349     -43.585   4.361  -3.001  1.00 39.12      B
ATOM   6887  O    PRO B 349     -42.697   4.616  -3.819  1.00 38.47      B
ATOM   6888  N    PRO B 350     -43.913   3.103  -2.672  1.00 39.18      B
ATOM   6889  CD   PRO B 350     -44.833   2.720  -1.584  1.00 38.40      B
ATOM   6890  CA   PRO B 350     -43.256   1.919  -3.236  1.00 37.87      B
ATOM   6891  CB   PRO B 350     -43.507   0.866  -2.172  1.00 38.60      B
ATOM   6892  CG   PRO B 350     -44.895   1.216  -1.714  1.00 37.83      B
ATOM   6893  C    PRO B 350     -43.739   1.454  -4.598  1.00 36.81      B
ATOM   6894  O    PRO B 350     -44.919   1.544  -4.915  1.00 34.96      B
ATOM   6895  N    GLY B 351     -42.806   0.951  -5.397  1.00 37.96      B
ATOM   6896  CA   GLY B 351     -43.160   0.429  -6.699  1.00 39.64      B
ATOM   6897  C    GLY B 351     -43.848  -0.884  -6.398  1.00 41.24      B
ATOM   6898  O    GLY B 351     -45.048  -1.038  -6.585  1.00 41.17      B
ATOM   6899  N    ASP B 352     -43.080  -1.843  -5.911  1.00 43.92      B
ATOM   6900  CA   ASP B 352     -43.653  -3.128  -5.546  1.00 47.86      B
ATOM   6901  CB   ASP B 352     -42.831  -4.270  -6.130  1.00 49.51      B
ATOM   6902  CG   ASP B 352     -42.462  -4.032  -7.567  1.00 52.21      B
ATOM   6903  OD1  ASP B 352     -43.391  -3.816  -8.380  1.00 53.29      B
ATOM   6904  OD2  ASP B 352     -41.247  -4.055  -7.875  1.00 53.51      B
ATOM   6905  C    ASP B 352     -43.595  -3.200  -4.033  1.00 48.54      B
ATOM   6906  O    ASP B 352     -42.616  -2.766  -3.426  1.00 49.49      B
ATOM   6907  N    PRO B 353     -44.641  -3.730  -3.395  1.00 48.96      B
ATOM   6908  CD   PRO B 353     -45.936  -4.235  -3.877  1.00 49.37      B
ATOM   6909  CA   PRO B 353     -44.561  -3.794  -1.935  1.00 49.07      B
ATOM   6910  CB   PRO B 353     -45.842  -4.535  -1.553  1.00 49.14      B
ATOM   6911  CG   PRO B 353     -46.794  -4.130  -2.630  1.00 49.18      B
ATOM   6912  C    PRO B 353     -43.293  -4.550  -1.510  1.00 48.50      B
ATOM   6913  O    PRO B 353     -42.936  -5.580  -2.099  1.00 47.47      B
ATOM   6914  N    PRO B 354     -42.585  -4.032  -0.499  1.00 47.36      B
```

FIGURE 4- 92 -

```
ATOM   6915  CD   PRO B 354     -42.876  -2.822   0.284  1.00 46.87      B
ATOM   6916  CA   PRO B 354     -41.364  -4.677  -0.018  1.00 48.62      B
ATOM   6917  CB   PRO B 354     -40.777  -3.637   0.916  1.00 47.77      B
ATOM   6918  CG   PRO B 354     -42.000  -3.021   1.496  1.00 48.00      B
ATOM   6919  C    PRO B 354     -41.698  -5.974   0.702  1.00 49.50      B
ATOM   6920  O    PRO B 354     -42.726  -6.080   1.363  1.00 49.69      B
ATOM   6921  N    GLN B 355     -40.826  -6.961   0.569  1.00 50.53      B
ATOM   6922  CA   GLN B 355     -41.047  -8.248   1.199  1.00 50.84      B
ATOM   6923  CB   GLN B 355     -41.200  -9.329   0.129  1.00 54.15      B
ATOM   6924  CG   GLN B 355     -42.444  -9.168  -0.719  1.00 59.06      B
ATOM   6925  CD   GLN B 355     -43.660  -8.794   0.123  1.00 61.95      B
ATOM   6926  OE1  GLN B 355     -43.946  -9.428   1.146  1.00 62.53      B
ATOM   6927  NE2  GLN B 355     -44.380  -7.759  -0.303  1.00 63.47      B
ATOM   6928  C    GLN B 355     -39.910  -8.622   2.123  1.00 49.65      B
ATOM   6929  O    GLN B 355     -38.762  -8.726   1.687  1.00 50.52      B
ATOM   6930  N    PRO B 356     -40.206  -8.827   3.417  1.00 48.45      B
ATOM   6931  CD   PRO B 356     -41.486  -8.699   4.132  1.00 47.66      B
ATOM   6932  CA   PRO B 356     -39.129  -9.198   4.338  1.00 48.53      B
ATOM   6933  CB   PRO B 356     -39.839  -9.286   5.694  1.00 48.09      B
ATOM   6934  CG   PRO B 356     -41.256  -9.570   5.330  1.00 47.83      B
ATOM   6935  C    PRO B 356     -38.453 -10.505   3.930  1.00 48.13      B
ATOM   6936  O    PRO B 356     -39.081 -11.404   3.389  1.00 47.78      B
ATOM   6937  N    GLU B 357     -37.157 -10.588   4.172  1.00 49.09      B
ATOM   6938  CA   GLU B 357     -36.404 -11.779   3.830  1.00 50.66      B
ATOM   6939  CB   GLU B 357     -35.473 -11.493   2.653  1.00 52.19      B
ATOM   6940  CG   GLU B 357     -36.200 -11.185   1.360  1.00 54.31      B
ATOM   6941  CD   GLU B 357     -37.192 -12.270   0.980  1.00 54.95      B
ATOM   6942  OE1  GLU B 357     -36.856 -13.470   1.108  1.00 55.71      B
ATOM   6943  OE2  GLU B 357     -38.306 -11.919   0.542  1.00 56.29      B
ATOM   6944  C    GLU B 357     -35.594 -12.258   5.030  1.00 50.70      B
ATOM   6945  O    GLU B 357     -35.220 -11.468   5.907  1.00 50.70      B
ATOM   6946  N    TYR B 358     -35.326 -13.557   5.064  1.00 49.65      B
ATOM   6947  CA   TYR B 358     -34.574 -14.138   6.159  1.00 49.66      B
ATOM   6948  CB   TYR B 358     -35.503 -15.024   6.974  1.00 47.09      B
ATOM   6949  CG   TYR B 358     -36.676 -14.248   7.533  1.00 44.64      B
ATOM   6950  CD1  TYR B 358     -36.537 -13.455   8.672  1.00 43.62      B
ATOM   6951  CE1  TYR B 358     -37.611 -12.712   9.173  1.00 42.52      B
ATOM   6952  CD2  TYR B 358     -37.919 -14.280   6.906  1.00 44.38      B
ATOM   6953  CE2  TYR B 358     -38.996 -13.540   7.398  1.00 43.27      B
ATOM   6954  CZ   TYR B 358     -38.835 -12.762   8.528  1.00 42.53      B
ATOM   6955  OH   TYR B 358     -39.897 -12.036   9.008  1.00 43.88      B
ATOM   6956  C    TYR B 358     -33.391 -14.905   5.599  1.00 50.85      B
ATOM   6957  O    TYR B 358     -32.605 -15.504   6.328  1.00 50.46      B
ATOM   6958  N    ASP B 359     -33.281 -14.846   4.279  1.00 52.12      B
ATOM   6959  CA   ASP B 359     -32.205 -15.467   3.523  1.00 53.94      B
ATOM   6960  CB   ASP B 359     -32.791 -16.368   2.436  1.00 56.63      B
ATOM   6961  CG   ASP B 359     -31.729 -17.056   1.599  1.00 58.73      B
ATOM   6962  OD1  ASP B 359     -30.614 -16.500   1.447  1.00 60.55      B
ATOM   6963  OD2  ASP B 359     -32.027 -18.155   1.078  1.00 59.74      B
ATOM   6964  C    ASP B 359     -31.539 -14.258   2.878  1.00 54.43      B
ATOM   6965  O    ASP B 359     -32.231 -13.371   2.390  1.00 54.30      B
ATOM   6966  N    LEU B 360     -30.213 -14.208   2.868  1.00 55.08      B
ATOM   6967  CA   LEU B 360     -29.527 -13.063   2.273  1.00 55.15      B
ATOM   6968  CB   LEU B 360     -28.072 -13.008   2.741  1.00 55.17      B
ATOM   6969  CG   LEU B 360     -27.313 -11.740   2.358  1.00 54.70      B
ATOM   6970  CD1  LEU B 360     -27.937 -10.589   3.112  1.00 55.46      B
ATOM   6971  CD2  LEU B 360     -25.835 -11.859   2.697  1.00 54.32      B
ATOM   6972  C    LEU B 360     -29.564 -13.119   0.751  1.00 55.50      B
ATOM   6973  O    LEU B 360     -29.749 -12.102   0.078  1.00 55.66      B
ATOM   6974  N    GLU B 361     -29.383 -14.318   0.215  1.00 55.85      B
ATOM   6975  CA   GLU B 361     -29.387 -14.521  -1.225  1.00 55.77      B
ATOM   6976  CB   GLU B 361     -29.161 -16.000  -1.547  1.00 56.94      B
ATOM   6977  CG   GLU B 361     -27.916 -16.608  -0.932  1.00 59.09      B
ATOM   6978  CD   GLU B 361     -27.553 -17.949  -1.563  1.00 59.95      B
ATOM   6979  OE1  GLU B 361     -27.407 -18.001  -2.807  1.00 59.04      B
ATOM   6980  OE2  GLU B 361     -27.422 -18.945  -0.819  1.00 60.29      B
ATOM   6981  C    GLU B 361     -30.704 -14.073  -1.858  1.00 55.09      B
ATOM   6982  O    GLU B 361     -30.742 -13.691  -3.029  1.00 53.73      B
ATOM   6983  N    LEU B 362     -31.776 -14.117  -1.070  1.00 54.70      B
ATOM   6984  CA   LEU B 362     -33.112 -13.760  -1.545  1.00 55.02      B
ATOM   6985  CB   LEU B 362     -34.167 -14.568  -0.790  1.00 55.14      B
ATOM   6986  CG   LEU B 362     -34.351 -15.992  -1.306  1.00 54.72      B
ATOM   6987  CD1  LEU B 362     -35.306 -16.756  -0.409  1.00 55.40      B
ATOM   6988  CD2  LEU B 362     -34.872 -15.933  -2.729  1.00 53.93      B
ATOM   6989  C    LEU B 362     -33.482 -12.290  -1.489  1.00 55.20      B
ATOM   6990  O    LEU B 362     -34.647 -11.940  -1.297  1.00 55.62      B
```

FIGURE 4- 93 -

```
ATOM   6991  N    ILE B 363     -32.488 -11.433  -1.656  1.00 54.87      B
ATOM   6992  CA   ILE B 363     -32.708  -9.999  -1.654  1.00 53.74      B
ATOM   6993  CB   ILE B 363     -32.114  -9.344  -0.383  1.00 52.76      B
ATOM   6994  CG2  ILE B 363     -32.283  -7.832  -0.442  1.00 52.15      B
ATOM   6995  CG1  ILE B 363     -32.797  -9.912   0.864  1.00 52.10      B
ATOM   6996  CD1  ILE B 363     -32.227  -9.392   2.174  1.00 50.97      B
ATOM   6997  C    ILE B 363     -32.002  -9.454  -2.888  1.00 54.14      B
ATOM   6998  O    ILE B 363     -30.848  -9.797  -3.146  1.00 54.06      B
ATOM   6999  N    THR B 364     -32.698  -8.636  -3.670  1.00 54.86      B
ATOM   7000  CA   THR B 364     -32.077  -8.055  -4.851  1.00 56.10      B
ATOM   7001  CB   THR B 364     -32.860  -8.388  -6.134  1.00 56.48      B
ATOM   7002  OG1  THR B 364     -33.027  -9.808  -6.231  1.00 57.50      B
ATOM   7003  CG2  THR B 364     -32.094  -7.898  -7.369  1.00 55.82      B
ATOM   7004  C    THR B 364     -31.928  -6.538  -4.727  1.00 56.40      B
ATOM   7005  O    THR B 364     -32.905  -5.786  -4.774  1.00 56.52      B
ATOM   7006  N    SER B 365     -30.683  -6.107  -4.551  1.00 56.19      B
ATOM   7007  CA   SER B 365     -30.354  -4.699  -4.429  1.00 57.01      B
ATOM   7008  CB   SER B 365     -29.639  -4.435  -3.106  1.00 57.43      B
ATOM   7009  OG   SER B 365     -29.285  -3.067  -2.992  1.00 59.50      B
ATOM   7010  C    SER B 365     -29.454  -4.295  -5.595  1.00 57.18      B
ATOM   7011  O    SER B 365     -28.552  -5.040  -5.988  1.00 56.99      B
ATOM   7012  N    CYS B 366     -29.703  -3.110  -6.142  1.00 57.22      B
ATOM   7013  CA   CYS B 366     -28.925  -2.606  -7.266  1.00 56.84      B
ATOM   7014  CB   CYS B 366     -27.509  -2.250  -6.817  1.00 56.38      B
ATOM   7015  SG   CYS B 366     -27.460  -0.782  -5.791  1.00 57.69      B
ATOM   7016  C    CYS B 366     -28.864  -3.629  -8.382  1.00 56.34      B
ATOM   7017  O    CYS B 366     -27.810  -3.849  -8.985  1.00 55.72      B
ATOM   7018  N    SER B 367     -29.997  -4.264  -8.651  1.00 55.39      B
ATOM   7019  CA   SER B 367     -30.042  -5.254  -9.706  1.00 56.17      B
ATOM   7020  CB   SER B 367     -29.616  -4.606 -11.029  1.00 55.61      B
ATOM   7021  OG   SER B 367     -30.369  -3.438 -11.301  1.00 54.28      B
ATOM   7022  C    SER B 367     -29.089  -6.403  -9.368  1.00 56.49      B
ATOM   7023  O    SER B 367     -28.519  -7.029 -10.262  1.00 56.52      B
ATOM   7024  N    SER B 368     -28.905  -6.667  -8.078  1.00 55.80      B
ATOM   7025  CA   SER B 368     -28.006  -7.735  -7.655  1.00 55.45      B
ATOM   7026  CB   SER B 368     -26.603  -7.185  -7.397  1.00 54.39      B
ATOM   7027  OG   SER B 368     -25.955  -6.849  -8.606  1.00 54.11      B
ATOM   7028  C    SER B 368     -28.468  -8.471  -6.411  1.00 56.02      B
ATOM   7029  O    SER B 368     -29.051  -7.886  -5.503  1.00 56.24      B
ATOM   7030  N    ASN B 369     -28.204  -9.770  -6.388  1.00 56.73      B
ATOM   7031  CA   ASN B 369     -28.543 -10.611  -5.249  1.00 56.39      B
ATOM   7032  CB   ASN B 369     -29.494 -11.750  -5.650  1.00 56.26      B
ATOM   7033  CG   ASN B 369     -28.851 -12.749  -6.610  1.00 56.64      B
ATOM   7034  OD1  ASN B 369     -28.733 -12.495  -7.809  1.00 56.13      B
ATOM   7035  ND2  ASN B 369     -28.424 -13.890  -6.076  1.00 57.25      B
ATOM   7036  C    ASN B 369     -27.211 -11.196  -4.824  1.00 56.15      B
ATOM   7037  O    ASN B 369     -26.232 -11.120  -5.571  1.00 55.96      B
ATOM   7038  N    VAL B 370     -27.165 -11.760  -3.626  1.00 56.12      B
ATOM   7039  CA   VAL B 370     -25.938 -12.375  -3.143  1.00 55.70      B
ATOM   7040  CB   VAL B 370     -25.748 -12.162  -1.620  1.00 55.79      B
ATOM   7041  CG1  VAL B 370     -24.516 -12.911  -1.137  1.00 55.60      B
ATOM   7042  CG2  VAL B 370     -25.603 -10.683  -1.317  1.00 54.73      B
ATOM   7043  C    VAL B 370     -26.058 -13.864  -3.435  1.00 55.36      B
ATOM   7044  O    VAL B 370     -27.155 -14.425  -3.397  1.00 54.64      B
ATOM   7045  N    SER B 371     -24.932 -14.496  -3.746  1.00 55.43      B
ATOM   7046  CA   SER B 371     -24.918 -15.923  -4.040  1.00 55.11      B
ATOM   7047  CB   SER B 371     -25.096 -16.153  -5.551  1.00 55.65      B
ATOM   7048  OG   SER B 371     -25.345 -17.520  -5.847  1.00 55.49      B
ATOM   7049  C    SER B 371     -23.594 -16.518  -3.559  1.00 54.32      B
ATOM   7050  O    SER B 371     -22.639 -15.793  -3.285  1.00 53.16      B
ATOM   7051  N    VAL B 372     -23.535 -17.840  -3.466  1.00 54.30      B
ATOM   7052  CA   VAL B 372     -22.318 -18.495  -3.005  1.00 54.17      B
ATOM   7053  CB   VAL B 372     -22.629 -19.418  -1.814  1.00 51.56      B
ATOM   7054  CG1  VAL B 372     -21.345 -19.803  -1.104  1.00 49.18      B
ATOM   7055  CG2  VAL B 372     -23.606 -18.724  -0.869  1.00 49.14      B
ATOM   7056  C    VAL B 372     -21.623 -19.302  -4.105  1.00 55.82      B
ATOM   7057  O    VAL B 372     -22.167 -19.491  -5.199  1.00 55.88      B
ATOM   7058  N    ALA B 373     -20.410 -19.755  -3.803  1.00 57.11      B
ATOM   7059  CA   ALA B 373     -19.601 -20.554  -4.719  1.00 58.88      B
ATOM   7060  CB   ALA B 373     -19.086 -19.693  -5.878  1.00 58.56      B
ATOM   7061  C    ALA B 373     -18.428 -21.139  -3.931  1.00 60.35      B
ATOM   7062  O    ALA B 373     -18.381 -21.027  -2.702  1.00 60.01      B
ATOM   7063  N    HIS B 374     -17.482 -21.756  -4.634  1.00 61.79      B
ATOM   7064  CA   HIS B 374     -16.328 -22.353  -3.974  1.00 62.54      B
ATOM   7065  CB   HIS B 374     -16.553 -23.851  -3.778  1.00 60.90      B
ATOM   7066  CG   HIS B 374     -17.500 -24.171  -2.665  1.00 59.94      B
```

FIGURE 4- 94 -

```
ATOM   7067  CD2 HIS B 374     -18.792 -24.577  -2.678  1.00 59.79      B
ATOM   7068  ND1 HIS B 374     -17.150 -24.052  -1.337  1.00 59.81      B
ATOM   7069  CE1 HIS B 374     -18.185 -24.371  -0.579  1.00 59.49      B
ATOM   7070  NE2 HIS B 374     -19.195 -24.693  -1.368  1.00 59.42      B
ATOM   7071  C   HIS B 374     -15.047 -22.127  -4.741  1.00 64.61      B
ATOM   7072  O   HIS B 374     -15.025 -22.194  -5.969  1.00 65.37      B
ATOM   7073  N   ASP B 375     -13.979 -21.852  -4.002  1.00 66.74      B
ATOM   7074  CA  ASP B 375     -12.669 -21.617  -4.594  1.00 69.27      B
ATOM   7075  CB  ASP B 375     -11.893 -20.585  -3.778  1.00 71.15      B
ATOM   7076  CG  ASP B 375     -11.479 -21.115  -2.407  1.00 72.56      B
ATOM   7077  OD1 ASP B 375     -12.343 -21.657  -1.673  1.00 71.33      B
ATOM   7078  OD2 ASP B 375     -10.281 -20.980  -2.069  1.00 73.97      B
ATOM   7079  C   ASP B 375     -11.907 -22.930  -4.583  1.00 70.41      B
ATOM   7080  O   ASP B 375     -12.416 -23.947  -4.097  1.00 70.19      B
ATOM   7081  N   ALA B 376     -10.686 -22.902  -5.109  1.00 71.29      B
ATOM   7082  CA  ALA B 376      -9.853 -24.098  -5.159  1.00 72.41      B
ATOM   7083  CB  ALA B 376      -8.400 -23.717  -5.448  1.00 72.80      B
ATOM   7084  C   ALA B 376      -9.963 -24.810  -3.817  1.00 73.03      B
ATOM   7085  O   ALA B 376     -10.486 -25.926  -3.731  1.00 72.87      B
ATOM   7086  N   SER B 377      -9.484 -24.136  -2.774  1.00 73.74      B
ATOM   7087  CA  SER B 377      -9.516 -24.649  -1.405  1.00 73.94      B
ATOM   7088  CB  SER B 377      -9.418 -23.485  -0.409  1.00 74.45      B
ATOM   7089  OG  SER B 377      -8.473 -22.514  -0.838  1.00 74.76      B
ATOM   7090  C   SER B 377     -10.823 -25.399  -1.157  1.00 73.96      B
ATOM   7091  O   SER B 377     -10.834 -26.510  -0.614  1.00 74.50      B
ATOM   7092  N   GLY B 378     -11.924 -24.777  -1.568  1.00 73.06      B
ATOM   7093  CA  GLY B 378     -13.228 -25.381  -1.385  1.00 72.07      B
ATOM   7094  C   GLY B 378     -14.020 -24.624  -0.341  1.00 71.07      B
ATOM   7095  O   GLY B 378     -15.039 -25.107   0.153  1.00 70.67      B
ATOM   7096  N   LYS B 379     -13.548 -23.429   0.001  1.00 70.50      B
ATOM   7097  CA  LYS B 379     -14.226 -22.599   0.990  1.00 68.86      B
ATOM   7098  CB  LYS B 379     -13.213 -21.678   1.690  1.00 69.09      B
ATOM   7099  CG  LYS B 379     -13.831 -20.739   2.718  1.00 69.21      B
ATOM   7100  CD  LYS B 379     -14.373 -21.486   3.928  1.00 69.90      B
ATOM   7101  CE  LYS B 379     -14.907 -20.504   4.969  1.00 71.11      B
ATOM   7102  NZ  LYS B 379     -15.387 -21.155   6.227  1.00 71.82      B
ATOM   7103  C   LYS B 379     -15.316 -21.767   0.310  1.00 67.43      B
ATOM   7104  O   LYS B 379     -15.180 -21.366  -0.852  1.00 65.77      B
ATOM   7105  N   ARG B 380     -16.399 -21.526   1.043  1.00 66.88      B
ATOM   7106  CA  ARG B 380     -17.526 -20.743   0.544  1.00 65.90      B
ATOM   7107  CB  ARG B 380     -18.625 -20.664   1.610  1.00 67.93      B
ATOM   7108  CG  ARG B 380     -19.059 -22.014   2.144  1.00 71.41      B
ATOM   7109  CD  ARG B 380     -19.720 -21.892   3.505  1.00 75.22      B
ATOM   7110  NE  ARG B 380     -21.129 -21.516   3.424  1.00 78.35      B
ATOM   7111  CZ  ARG B 380     -21.934 -21.393   4.479  1.00 79.46      B
ATOM   7112  NH1 ARG B 380     -21.469 -21.612   5.707  1.00 78.96      B
ATOM   7113  NH2 ARG B 380     -23.211 -21.068   4.306  1.00 79.52      B
ATOM   7114  C   ARG B 380     -17.044 -19.337   0.215  1.00 64.30      B
ATOM   7115  O   ARG B 380     -16.448 -18.666   1.058  1.00 64.44      B
ATOM   7116  N   VAL B 381     -17.293 -18.895  -1.011  1.00 62.12      B
ATOM   7117  CA  VAL B 381     -16.889 -17.559  -1.432  1.00 58.77      B
ATOM   7118  CB  VAL B 381     -15.830 -17.608  -2.552  1.00 58.49      B
ATOM   7119  CG1 VAL B 381     -15.503 -16.196  -3.048  1.00 55.90      B
ATOM   7120  CG2 VAL B 381     -14.577 -18.298  -2.034  1.00 58.07      B
ATOM   7121  C   VAL B 381     -18.106 -16.813  -1.936  1.00 57.06      B
ATOM   7122  O   VAL B 381     -18.680 -17.161  -2.967  1.00 56.79      B
ATOM   7123  N   TYR B 382     -18.510 -15.797  -1.189  1.00 55.52      B
ATOM   7124  CA  TYR B 382     -19.659 -15.001  -1.572  1.00 53.75      B
ATOM   7125  CB  TYR B 382     -20.176 -14.232  -0.371  1.00 51.09      B
ATOM   7126  CG  TYR B 382     -20.702 -15.133   0.711  1.00 49.77      B
ATOM   7127  CD1 TYR B 382     -22.032 -15.533   0.720  1.00 48.76      B
ATOM   7128  CE1 TYR B 382     -22.524 -16.362   1.721  1.00 49.40      B
ATOM   7129  CD2 TYR B 382     -19.869 -15.589   1.728  1.00 49.68      B
ATOM   7130  CE2 TYR B 382     -20.350 -16.420   2.730  1.00 49.84      B
ATOM   7131  CZ  TYR B 382     -21.678 -16.803   2.726  1.00 49.63      B
ATOM   7132  OH  TYR B 382     -22.156 -17.617   3.731  1.00 50.39      B
ATOM   7133  C   TYR B 382     -19.247 -14.047  -2.677  1.00 53.82      B
ATOM   7134  O   TYR B 382     -18.097 -13.605  -2.733  1.00 53.69      B
ATOM   7135  N   TYR B 383     -20.188 -13.756  -3.566  1.00 53.80      B
ATOM   7136  CA  TYR B 383     -19.944 -12.862  -4.682  1.00 53.65      B
ATOM   7137  CB  TYR B 383     -19.327 -13.622  -5.862  1.00 54.98      B
ATOM   7138  CG  TYR B 383     -20.205 -14.712  -6.459  1.00 56.20      B
ATOM   7139  CD1 TYR B 383     -20.666 -15.774  -5.675  1.00 56.67      B
ATOM   7140  CE1 TYR B 383     -21.466 -16.784  -6.218  1.00 55.99      B
ATOM   7141  CD2 TYR B 383     -20.566 -14.686  -7.811  1.00 56.16      B
ATOM   7142  CE2 TYR B 383     -21.366 -15.694  -8.365  1.00 56.64      B
```

FIGURE 4- 95 -

```
ATOM   7143  CZ   TYR B 383     -21.811 -16.737  -7.559  1.00 55.69      B
ATOM   7144  OH   TYR B 383     -22.607 -17.722  -8.093  1.00 54.62      B
ATOM   7145  C    TYR B 383     -21.265 -12.243  -5.097  1.00 53.44      B
ATOM   7146  O    TYR B 383     -22.337 -12.757  -4.756  1.00 53.58      B
ATOM   7147  N    LEU B 384     -21.184 -11.137  -5.827  1.00 51.37      B
ATOM   7148  CA   LEU B 384     -22.375 -10.446  -6.275  1.00 49.25      B
ATOM   7149  CB   LEU B 384     -22.175  -8.940  -6.159  1.00 50.20      B
ATOM   7150  CG   LEU B 384     -23.483  -8.194  -5.928  1.00 51.86      B
ATOM   7151  CD1  LEU B 384     -23.833  -8.301  -4.449  1.00 52.23      B
ATOM   7152  CD2  LEU B 384     -23.346  -6.738  -6.342  1.00 52.86      B
ATOM   7153  C    LEU B 384     -22.704 -10.810  -7.718  1.00 47.89      B
ATOM   7154  O    LEU B 384     -21.831 -10.785  -8.589  1.00 46.57      B
ATOM   7155  N    THR B 385     -23.972 -11.133  -7.967  1.00 46.20      B
ATOM   7156  CA   THR B 385     -24.427 -11.511  -9.304  1.00 44.71      B
ATOM   7157  CB   THR B 385     -24.391 -13.056  -9.479  1.00 43.67      B
ATOM   7158  OG1  THR B 385     -24.939 -13.415 -10.753  1.00 42.91      B
ATOM   7159  CG2  THR B 385     -25.194 -13.729  -8.382  1.00 42.52      B
ATOM   7160  C    THR B 385     -25.847 -11.004  -9.590  1.00 43.55      B
ATOM   7161  O    THR B 385     -26.417 -10.258  -8.793  1.00 42.03      B
ATOM   7162  N    ARG B 386     -26.404 -11.419 -10.729  1.00 43.20      B
ATOM   7163  CA   ARG B 386     -27.751 -11.020 -11.134  1.00 43.34      B
ATOM   7164  CB   ARG B 386     -27.784  -9.523 -11.445  1.00 43.77      B
ATOM   7165  CG   ARG B 386     -26.805  -9.080 -12.535  1.00 44.27      B
ATOM   7166  CD   ARG B 386     -27.170  -7.707 -13.080  1.00 44.60      B
ATOM   7167  NE   ARG B 386     -28.417  -7.739 -13.845  1.00 45.20      B
ATOM   7168  CZ   ARG B 386     -29.059  -6.660 -14.289  1.00 44.92      B
ATOM   7169  NH1  ARG B 386     -28.587  -5.446 -14.049  1.00 43.80      B
ATOM   7170  NH2  ARG B 386     -30.176  -6.796 -14.989  1.00 45.23      B
ATOM   7171  C    ARG B 386     -28.239 -11.773 -12.368  1.00 43.36      B
ATOM   7172  O    ARG B 386     -27.466 -12.467 -13.024  1.00 43.38      B
ATOM   7173  N    ASP B 387     -29.529 -11.630 -12.674  1.00 42.64      B
ATOM   7174  CA   ASP B 387     -30.118 -12.249 -13.855  1.00 42.39      B
ATOM   7175  CB   ASP B 387     -31.614 -11.943 -13.928  1.00 44.89      B
ATOM   7176  CG   ASP B 387     -32.318 -12.711 -15.045  1.00 48.22      B
ATOM   7177  OD1  ASP B 387     -31.804 -12.703 -16.187  1.00 49.38      B
ATOM   7178  OD2  ASP B 387     -33.387 -13.318 -14.780  1.00 47.88      B
ATOM   7179  C    ASP B 387     -29.403 -11.592 -15.034  1.00 42.07      B
ATOM   7180  O    ASP B 387     -29.631 -10.425 -15.339  1.00 41.36      B
ATOM   7181  N    PRO B 388     -28.545 -12.348 -15.724  1.00 41.73      B
ATOM   7182  CD   PRO B 388     -28.438 -13.806 -15.546  1.00 42.32      B
ATOM   7183  CA   PRO B 388     -27.746 -11.915 -16.874  1.00 42.19      B
ATOM   7184  CB   PRO B 388     -26.852 -13.118 -17.125  1.00 41.82      B
ATOM   7185  CG   PRO B 388     -27.776 -14.243 -16.836  1.00 41.95      B
ATOM   7186  C    PRO B 388     -28.462 -11.478 -18.148  1.00 43.54      B
ATOM   7187  O    PRO B 388     -27.802 -11.076 -19.112  1.00 44.59      B
ATOM   7188  N    THR B 389     -29.791 -11.544 -18.166  1.00 43.35      B
ATOM   7189  CA   THR B 389     -30.531 -11.172 -19.368  1.00 43.07      B
ATOM   7190  CB   THR B 389     -32.054 -11.219 -19.140  1.00 43.08      B
ATOM   7191  OG1  THR B 389     -32.415 -12.506 -18.626  1.00 44.14      B
ATOM   7192  CG2  THR B 389     -32.801 -10.990 -20.455  1.00 40.77      B
ATOM   7193  C    THR B 389     -30.161  -9.796 -19.906  1.00 43.81      B
ATOM   7194  O    THR B 389     -29.480  -9.687 -20.932  1.00 43.75      B
ATOM   7195  N    THR B 390     -30.605  -8.748 -19.218  1.00 43.71      B
ATOM   7196  CA   THR B 390     -30.321  -7.391 -19.659  1.00 43.31      B
ATOM   7197  CB   THR B 390     -30.735  -6.360 -18.596  1.00 42.97      B
ATOM   7198  OG1  THR B 390     -32.103  -6.579 -18.220  1.00 41.31      B
ATOM   7199  CG2  THR B 390     -30.581  -4.951 -19.148  1.00 39.81      B
ATOM   7200  C    THR B 390     -28.833  -7.243 -19.965  1.00 44.33      B
ATOM   7201  O    THR B 390     -28.451  -6.724 -21.012  1.00 44.12      B
ATOM   7202  N    PRO B 391     -27.969  -7.701 -19.050  1.00 44.79      B
ATOM   7203  CD   PRO B 391     -28.215  -8.218 -17.692  1.00 44.15      B
ATOM   7204  CA   PRO B 391     -26.535  -7.583 -19.313  1.00 45.70      B
ATOM   7205  CB   PRO B 391     -25.920  -8.385 -18.175  1.00 44.67      B
ATOM   7206  CG   PRO B 391     -26.852  -8.080 -17.045  1.00 44.54      B
ATOM   7207  C    PRO B 391     -26.169  -8.135 -20.696  1.00 47.47      B
ATOM   7208  O    PRO B 391     -25.628  -7.411 -21.530  1.00 48.24      B
ATOM   7209  N    LEU B 392     -26.490  -9.404 -20.943  1.00 48.88      B
ATOM   7210  CA   LEU B 392     -26.185 -10.050 -22.222  1.00 50.06      B
ATOM   7211  CB   LEU B 392     -26.590 -11.529 -22.187  1.00 50.29      B
ATOM   7212  CG   LEU B 392     -25.956 -12.407 -21.107  1.00 50.05      B
ATOM   7213  CD1  LEU B 392     -26.222 -13.862 -21.420  1.00 48.60      B
ATOM   7214  CD2  LEU B 392     -24.453 -12.147 -21.051  1.00 51.21      B
ATOM   7215  C    LEU B 392     -26.846  -9.391 -23.430  1.00 51.23      B
ATOM   7216  O    LEU B 392     -26.196  -9.164 -24.454  1.00 50.97      B
ATOM   7217  N    ALA B 393     -28.142  -9.106 -23.311  1.00 52.75      B
ATOM   7218  CA   ALA B 393     -28.900  -8.474 -24.389  1.00 53.52      B
```

FIGURE 4- 96 -

```
ATOM   7219  CB   ALA B 393     -30.318  -8.165 -23.923  1.00 52.90      B
ATOM   7220  C    ALA B 393     -28.213  -7.196 -24.861  1.00 53.80      B
ATOM   7221  O    ALA B 393     -28.138  -6.931 -26.060  1.00 53.81      B
ATOM   7222  N    ARG B 394     -27.715  -6.401 -23.920  1.00 54.52      B
ATOM   7223  CA   ARG B 394     -27.029  -5.171 -24.295  1.00 56.11      B
ATOM   7224  CB   ARG B 394     -26.818  -4.267 -23.072  1.00 54.59      B
ATOM   7225  CG   ARG B 394     -28.092  -3.560 -22.639  1.00 53.18      B
ATOM   7226  CD   ARG B 394     -27.949  -2.761 -21.348  1.00 52.91      B
ATOM   7227  NE   ARG B 394     -29.245  -2.199 -20.966  1.00 53.19      B
ATOM   7228  CZ   ARG B 394     -29.488  -1.521 -19.848  1.00 53.10      B
ATOM   7229  NH1  ARG B 394     -28.522  -1.301 -18.967  1.00 53.23      B
ATOM   7230  NH2  ARG B 394     -30.712  -1.071 -19.605  1.00 52.78      B
ATOM   7231  C    ARG B 394     -25.699  -5.534 -24.942  1.00 57.71      B
ATOM   7232  O    ARG B 394     -25.352  -5.023 -26.013  1.00 58.08      B
ATOM   7233  N    ALA B 395     -24.971  -6.438 -24.293  1.00 59.20      B
ATOM   7234  CA   ALA B 395     -23.685  -6.897 -24.799  1.00 60.51      B
ATOM   7235  CB   ALA B 395     -23.229  -8.128 -24.024  1.00 60.81      B
ATOM   7236  C    ALA B 395     -23.824  -7.230 -26.278  1.00 61.55      B
ATOM   7237  O    ALA B 395     -22.976  -6.857 -27.087  1.00 61.71      B
ATOM   7238  N    ALA B 396     -24.909  -7.927 -26.615  1.00 62.92      B
ATOM   7239  CA   ALA B 396     -25.190  -8.332 -27.991  1.00 64.22      B
ATOM   7240  CB   ALA B 396     -26.434  -9.212 -28.039  1.00 63.65      B
ATOM   7241  C    ALA B 396     -25.391  -7.116 -28.874  1.00 65.65      B
ATOM   7242  O    ALA B 396     -24.744  -6.970 -29.912  1.00 66.69      B
ATOM   7243  N    TRP B 397     -26.289  -6.242 -28.435  1.00 67.00      B
ATOM   7244  CA   TRP B 397     -26.624  -5.022 -29.151  1.00 68.53      B
ATOM   7245  CB   TRP B 397     -27.587  -4.197 -28.296  1.00 68.71      B
ATOM   7246  CG   TRP B 397     -28.174  -3.012 -28.997  1.00 69.95      B
ATOM   7247  CD2  TRP B 397     -29.451  -2.952 -29.650  1.00 70.00      B
ATOM   7248  CE2  TRP B 397     -29.593  -1.646 -30.170  1.00 69.38      B
ATOM   7249  CE3  TRP B 397     -30.488  -3.878 -29.846  1.00 69.70      B
ATOM   7250  CD1  TRP B 397     -27.608  -1.774 -29.145  1.00 69.15      B
ATOM   7251  NE1  TRP B 397     -28.457  -0.949 -29.849  1.00 69.60      B
ATOM   7252  CZ2  TRP B 397     -30.731  -1.240 -30.872  1.00 69.28      B
ATOM   7253  CZ3  TRP B 397     -31.620  -3.474 -30.544  1.00 70.13      B
ATOM   7254  CH2  TRP B 397     -31.732  -2.163 -31.049  1.00 69.88      B
ATOM   7255  C    TRP B 397     -25.413  -4.164 -29.542  1.00 69.95      B
ATOM   7256  O    TRP B 397     -25.440  -3.465 -30.557  1.00 70.03      B
ATOM   7257  N    GLU B 398     -24.351  -4.221 -28.745  1.00 71.41      B
ATOM   7258  CA   GLU B 398     -23.156  -3.427 -29.009  1.00 72.92      B
ATOM   7259  CB   GLU B 398     -22.412  -3.203 -27.706  1.00 71.82      B
ATOM   7260  CG   GLU B 398     -23.334  -2.672 -26.646  1.00 72.08      B
ATOM   7261  CD   GLU B 398     -22.763  -2.804 -25.269  1.00 72.38      B
ATOM   7262  OE1  GLU B 398     -22.124  -3.845 -24.997  1.00 72.90      B
ATOM   7263  OE2  GLU B 398     -22.970  -1.877 -24.457  1.00 72.87      B
ATOM   7264  C    GLU B 398     -22.233  -4.051 -30.043  1.00 74.71      B
ATOM   7265  O    GLU B 398     -21.393  -3.369 -30.636  1.00 74.48      B
ATOM   7266  N    THR B 399     -22.394  -5.352 -30.258  1.00 77.06      B
ATOM   7267  CA   THR B 399     -21.583  -6.060 -31.237  1.00 79.31      B
ATOM   7268  CB   THR B 399     -21.607  -7.591 -30.998  1.00 79.04      B
ATOM   7269  OG1  THR B 399     -20.960  -7.886 -29.755  1.00 79.59      B
ATOM   7270  CG2  THR B 399     -20.687  -8.327 -32.130  1.00 78.69      B
ATOM   7271  C    THR B 399     -22.118  -5.766 -32.631  1.00 81.00      B
ATOM   7272  O    THR B 399     -21.365  -5.387 -33.533  1.00 81.00      B
ATOM   7273  N    ALA B 400     -23.430  -5.921 -32.784  1.00 82.55      B
ATOM   7274  CA   ALA B 400     -24.102  -5.701 -34.061  1.00 84.33      B
ATOM   7275  CB   ALA B 400     -25.494  -6.337 -34.024  1.00 83.77      B
ATOM   7276  C    ALA B 400     -24.208  -4.242 -34.546  1.00 85.80      B
ATOM   7277  O    ALA B 400     -24.488  -4.007 -35.721  1.00 85.49      B
ATOM   7278  N    ARG B 401     -23.990  -3.266 -33.663  1.00 87.49      B
ATOM   7279  CA   ARG B 401     -24.080  -1.860 -34.073  1.00 89.65      B
ATOM   7280  CB   ARG B 401     -25.279  -1.178 -33.412  1.00 89.41      B
ATOM   7281  CG   ARG B 401     -25.680   0.128 -34.093  1.00 89.92      B
ATOM   7282  CD   ARG B 401     -26.721  -0.068 -35.200  1.00 90.25      B
ATOM   7283  NE   ARG B 401     -26.321  -1.016 -36.243  1.00 90.69      B
ATOM   7284  CZ   ARG B 401     -27.099  -1.378 -37.264  1.00 90.66      B
ATOM   7285  NH1  ARG B 401     -28.323  -0.872 -37.388  1.00 91.04      B
ATOM   7286  NH2  ARG B 401     -26.659  -2.251 -38.162  1.00 90.28      B
ATOM   7287  C    ARG B 401     -22.800  -1.051 -33.809  1.00 91.44      B
ATOM   7288  O    ARG B 401     -21.700  -1.621 -33.851  1.00 91.69      B
ATOM   7289  N    HIS B 402     -22.910   0.254 -33.512  1.00 93.22      B
ATOM   7290  CA   HIS B 402     -21.676   1.031 -33.317  1.00 94.63      B
ATOM   7291  CB   HIS B 402     -21.763   2.461 -33.925  1.00 95.62      B
ATOM   7292  CG   HIS B 402     -22.949   3.276 -33.509  1.00 96.97      B
ATOM   7293  CD2  HIS B 402     -23.049   4.332 -32.665  1.00 97.09      B
ATOM   7294  ND1  HIS B 402     -24.192   3.134 -34.091  1.00 97.25      B
```

FIGURE 4- 97 -

```
ATOM   7295  CE1 HIS B 402     -25.003   4.070 -33.631  1.00 96.83          B
ATOM   7296  NE2 HIS B 402     -24.334   4.811 -32.765  1.00 97.03          B
ATOM   7297  C   HIS B 402     -20.841   1.079 -32.026  1.00 95.15          B
ATOM   7298  O   HIS B 402     -20.796   0.090 -31.291  1.00 94.77          B
ATOM   7299  N   THR B 403     -20.218   2.222 -31.718  1.00 95.80          B
ATOM   7300  CA  THR B 403     -19.200   2.181 -30.671  1.00 95.95          B
ATOM   7301  CB  THR B 403     -17.868   2.607 -31.349  1.00 96.29          B
ATOM   7302  OG1 THR B 403     -18.120   3.630 -32.328  1.00 96.12          B
ATOM   7303  CG2 THR B 403     -17.227   1.381 -32.032  1.00 95.84          B
ATOM   7304  C   THR B 403     -19.025   2.548 -29.194  1.00 95.76          B
ATOM   7305  O   THR B 403     -18.031   3.187 -28.813  1.00 94.88          B
ATOM   7306  N   PRO B 404     -20.009   2.229 -28.353  1.00 96.04          B
ATOM   7307  CD  PRO B 404     -21.472   2.334 -28.494  1.00 95.80          B
ATOM   7308  CA  PRO B 404     -19.593   2.596 -26.998  1.00 95.70          B
ATOM   7309  CB  PRO B 404     -20.906   2.796 -26.251  1.00 95.83          B
ATOM   7310  CG  PRO B 404     -21.845   3.210 -27.315  1.00 95.52          B
ATOM   7311  C   PRO B 404     -19.012   1.184 -26.720  1.00 95.57          B
ATOM   7312  O   PRO B 404     -18.963   0.357 -27.638  1.00 95.83          B
ATOM   7313  N   ILE B 405     -18.568   0.876 -25.512  1.00 95.00          B
ATOM   7314  CA  ILE B 405     -18.068  -0.478 -25.245  1.00 94.18          B
ATOM   7315  CB  ILE B 405     -16.523  -0.562 -25.397  1.00 94.87          B
ATOM   7316  CG2 ILE B 405     -15.963  -1.778 -24.679  1.00 95.04          B
ATOM   7317  CG1 ILE B 405     -16.169  -0.702 -26.887  1.00 95.76          B
ATOM   7318  CD1 ILE B 405     -16.749  -1.966 -27.574  1.00 95.79          B
ATOM   7319  C   ILE B 405     -18.530  -0.808 -23.842  1.00 93.47          B
ATOM   7320  O   ILE B 405     -18.144  -1.801 -23.211  1.00 93.15          B
ATOM   7321  N   ASN B 406     -19.400   0.074 -23.383  1.00 92.25          B
ATOM   7322  CA  ASN B 406     -20.016  -0.011 -22.084  1.00 90.48          B
ATOM   7323  CB  ASN B 406     -21.048   1.121 -21.975  1.00 92.23          B
ATOM   7324  CG  ASN B 406     -21.784   1.357 -23.297  1.00 93.06          B
ATOM   7325  OD1 ASN B 406     -21.916   0.433 -24.109  1.00 92.92          B
ATOM   7326  ND2 ASN B 406     -22.265   2.584 -23.517  1.00 93.57          B
ATOM   7327  C   ASN B 406     -20.684  -1.379 -21.874  1.00 88.20          B
ATOM   7328  O   ASN B 406     -20.509  -2.323 -22.656  1.00 87.43          B
ATOM   7329  N   SER B 407     -21.455  -1.448 -20.797  1.00 85.57          B
ATOM   7330  CA  SER B 407     -22.188  -2.633 -20.396  1.00 82.51          B
ATOM   7331  CB  SER B 407     -23.419  -2.824 -21.288  1.00 81.67          B
ATOM   7332  OG  SER B 407     -23.060  -3.285 -22.570  1.00 81.72          B
ATOM   7333  C   SER B 407     -21.308  -3.883 -20.394  1.00 80.84          B
ATOM   7334  O   SER B 407     -20.692  -4.192 -19.375  1.00 80.63          B
ATOM   7335  N   TRP B 408     -21.209  -4.587 -21.519  1.00 77.93          B
ATOM   7336  CA  TRP B 408     -20.399  -5.799 -21.530  1.00 74.87          B
ATOM   7337  CB  TRP B 408     -20.125  -6.294 -22.964  1.00 74.84          B
ATOM   7338  CG  TRP B 408     -19.014  -5.624 -23.733  1.00 75.03          B
ATOM   7339  CD2 TRP B 408     -17.614  -5.931 -23.660  1.00 74.79          B
ATOM   7340  CE2 TRP B 408     -16.953  -5.087 -24.586  1.00 74.66          B
ATOM   7341  CE3 TRP B 408     -16.852  -6.837 -22.903  1.00 74.82          B
ATOM   7342  CD1 TRP B 408     -19.141  -4.633 -24.670  1.00 74.67          B
ATOM   7343  NE1 TRP B 408     -17.908  -4.308 -25.187  1.00 74.50          B
ATOM   7344  CZ2 TRP B 408     -15.565  -5.121 -24.776  1.00 74.27          B
ATOM   7345  CZ3 TRP B 408     -15.471  -6.871 -23.092  1.00 74.20          B
ATOM   7346  CH2 TRP B 408     -14.844  -6.016 -24.023  1.00 74.04          B
ATOM   7347  C   TRP B 408     -19.096  -5.612 -20.756  1.00 72.68          B
ATOM   7348  O   TRP B 408     -18.864  -6.294 -19.755  1.00 73.02          B
ATOM   7349  N   LEU B 409     -18.267  -4.669 -21.139  1.00 70.17          B
ATOM   7350  CA  LEU B 409     -16.999  -4.425 -20.518  1.00 67.26          B
ATOM   7351  CB  LEU B 409     -16.284  -3.220 -21.143  1.00 66.67          B
ATOM   7352  CG  LEU B 409     -14.927  -2.860 -20.533  1.00 65.53          B
ATOM   7353  CD1 LEU B 409     -14.055  -4.106 -20.431  1.00 65.82          B
ATOM   7354  CD2 LEU B 409     -14.254  -1.799 -21.382  1.00 65.42          B
ATOM   7355  C   LEU B 409     -17.263  -4.179 -19.040  1.00 65.13          B
ATOM   7356  O   LEU B 409     -16.772  -4.908 -18.176  1.00 64.95          B
ATOM   7357  N   GLY B 410     -18.059  -3.156 -18.758  1.00 62.91          B
ATOM   7358  CA  GLY B 410     -18.381  -2.840 -17.381  1.00 60.37          B
ATOM   7359  C   GLY B 410     -18.903  -4.055 -16.647  1.00 58.65          B
ATOM   7360  O   GLY B 410     -18.412  -4.395 -15.567  1.00 58.33          B
ATOM   7361  N   ASN B 411     -19.896  -4.713 -17.244  1.00 57.09          B
ATOM   7362  CA  ASN B 411     -20.502  -5.902 -16.658  1.00 55.21          B
ATOM   7363  CB  ASN B 411     -21.487  -6.555 -17.631  1.00 53.99          B
ATOM   7364  CG  ASN B 411     -22.902  -6.009 -17.496  1.00 53.04          B
ATOM   7365  OD1 ASN B 411     -23.403  -5.785 -16.381  1.00 49.12          B
ATOM   7366  ND2 ASN B 411     -23.564  -5.813 -18.636  1.00 52.85          B
ATOM   7367  C   ASN B 411     -19.451  -6.919 -16.254  1.00 54.81          B
ATOM   7368  O   ASN B 411     -19.511  -7.471 -15.155  1.00 54.28          B
ATOM   7369  N   ILE B 412     -18.493  -7.169 -17.142  1.00 54.35          B
ATOM   7370  CA  ILE B 412     -17.428  -8.119 -16.848  1.00 55.05          B
```

FIGURE 4- 98 -

```
ATOM   7371  CB  ILE B 412     -16.449  -8.257 -13.032  1.00 55.58      B
ATOM   7372  CG2 ILE B 412     -15.201  -9.018 -17.593  1.00 55.35      B
ATOM   7373  CG1 ILE B 412     -17.121  -8.994 -19.191  1.00 56.05      B
ATOM   7374  CD1 ILE B 412     -16.179  -9.265 -20.352  1.00 54.75      B
ATOM   7375  C   ILE B 412     -16.645  -7.638 -15.629  1.00 56.10      B
ATOM   7376  O   ILE B 412     -16.544  -8.335 -14.614  1.00 55.34      B
ATOM   7377  N   ILE B 413     -16.089  -6.437 -15.741  1.00 56.54      B
ATOM   7378  CA  ILE B 413     -15.316  -5.857 -14.658  1.00 56.44      B
ATOM   7379  CB  ILE B 413     -14.999  -4.378 -14.926  1.00 56.67      B
ATOM   7380  CG2 ILE B 413     -14.187  -3.808 -13.771  1.00 56.48      B
ATOM   7381  CG1 ILE B 413     -14.229  -4.242 -16.243  1.00 57.44      B
ATOM   7382  CD1 ILE B 413     -13.909  -2.810 -16.618  1.00 56.20      B
ATOM   7383  C   ILE B 413     -16.073  -5.949 -13.343  1.00 56.43      B
ATOM   7384  O   ILE B 413     -15.525  -6.389 -12.338  1.00 57.02      B
ATOM   7385  N   MET B 414     -17.340  -5.548 -13.362  1.00 55.71      B
ATOM   7386  CA  MET B 414     -18.164  -5.562 -12.156  1.00 55.50      B
ATOM   7387  CB  MET B 414     -19.355  -4.603 -12.325  1.00 55.92      B
ATOM   7388  CG  MET B 414     -18.969  -3.122 -12.510  1.00 56.41      B
ATOM   7389  SD  MET B 414     -17.937  -2.429 -11.164  1.00 56.10      B
ATOM   7390  CE  MET B 414     -19.152  -2.328  -9.810  1.00 52.43      B
ATOM   7391  C   MET B 414     -18.679  -6.931 -11.704  1.00 55.03      B
ATOM   7392  O   MET B 414     -18.881  -7.152 -10.512  1.00 54.02      B
ATOM   7393  N   TYR B 415     -18.892  -7.852 -12.639  1.00 55.20      B
ATOM   7394  CA  TYR B 415     -19.403  -9.177 -12.280  1.00 55.03      B
ATOM   7395  CB  TYR B 415     -20.744  -9.424 -12.971  1.00 52.56      B
ATOM   7396  CG  TYR B 415     -21.865  -8.556 -12.439  1.00 50.60      B
ATOM   7397  CD1 TYR B 415     -22.502  -8.859 -11.235  1.00 50.04      B
ATOM   7398  CE1 TYR B 415     -23.544  -8.061 -10.748  1.00 48.86      B
ATOM   7399  CD2 TYR B 415     -22.292  -7.433 -13.143  1.00 50.20      B
ATOM   7400  CE2 TYR B 415     -23.329  -6.631 -12.668  1.00 49.24      B
ATOM   7401  CZ  TYR B 415     -23.952  -6.950 -11.475  1.00 48.82      B
ATOM   7402  OH  TYR B 415     -25.001  -6.174 -11.036  1.00 48.10      B
ATOM   7403  C   TYR B 415     -18.448 -10.317 -12.601  1.00 55.84      B
ATOM   7404  O   TYR B 415     -18.854 -11.480 -12.648  1.00 55.75      B
ATOM   7405  N   ALA B 416     -17.179  -9.966 -12.797  1.00 56.91      B
ATOM   7406  CA  ALA B 416     -16.113 -10.913 -13.120  1.00 57.29      B
ATOM   7407  CB  ALA B 416     -14.766 -10.299 -12.764  1.00 57.66      B
ATOM   7408  C   ALA B 416     -16.246 -12.287 -12.458  1.00 58.01      B
ATOM   7409  O   ALA B 416     -15.929 -13.311 -13.067  1.00 57.96      B
ATOM   7410  N   PRO B 417     -16.699 -12.328 -11.195  1.00 58.65      B
ATOM   7411  CD  PRO B 417     -16.762 -11.207 -10.246  1.00 58.48      B
ATOM   7412  CA  PRO B 417     -16.861 -13.605 -10.483  1.00 59.41      B
ATOM   7413  CB  PRO B 417     -17.033 -13.171  -9.026  1.00 59.87      B
ATOM   7414  CG  PRO B 417     -16.326 -11.868  -8.974  1.00 59.80      B
ATOM   7415  C   PRO B 417     -18.052 -14.451 -10.944  1.00 59.08      B
ATOM   7416  O   PRO B 417     -18.083 -15.660 -10.716  1.00 58.54      B
ATOM   7417  N   THR B 418     -19.032 -13.821 -11.583  1.00 58.59      B
ATOM   7418  CA  THR B 418     -20.216 -14.551 -12.016  1.00 58.58      B
ATOM   7419  CB  THR B 418     -21.343 -13.615 -12.468  1.00 58.29      B
ATOM   7420  OG1 THR B 418     -21.080 -13.175 -13.804  1.00 58.02      B
ATOM   7421  CG2 THR B 418     -21.458 -12.413 -11.535  1.00 59.42      B
ATOM   7422  C   THR B 418     -19.969 -15.531 -13.149  1.00 58.38      B
ATOM   7423  O   THR B 418     -19.133 -15.305 -14.027  1.00 57.95      B
ATOM   7424  N   LEU B 419     -20.728 -16.623 -13.105  1.00 57.99      B
ATOM   7425  CA  LEU B 419     -20.677 -17.690 -14.095  1.00 56.48      B
ATOM   7426  CB  LEU B 419     -21.859 -18.635 -13.884  1.00 57.18      B
ATOM   7427  CG  LEU B 419     -21.889 -19.931 -14.689  1.00 57.91      B
ATOM   7428  CD1 LEU B 419     -20.873 -20.907 -14.095  1.00 58.86      B
ATOM   7429  CD2 LEU B 419     -23.285 -20.526 -14.639  1.00 57.17      B
ATOM   7430  C   LEU B 419     -20.759 -17.094 -15.499  1.00 55.65      B
ATOM   7431  O   LEU B 419     -19.809 -17.180 -16.277  1.00 56.46      B
ATOM   7432  N   TRP B 420     -21.900 -16.484 -15.808  1.00 53.54      B
ATOM   7433  CA  TRP B 420     -22.121 -15.878 -17.114  1.00 52.71      B
ATOM   7434  CB  TRP B 420     -23.450 -15.104 -17.147  1.00 50.60      B
ATOM   7435  CG  TRP B 420     -23.768 -14.346 -15.900  1.00 46.84      B
ATOM   7436  CD2 TRP B 420     -23.717 -12.929 -15.722  1.00 44.98      B
ATOM   7437  CE2 TRP B 420     -24.092 -12.664 -14.388  1.00 44.82      B
ATOM   7438  CE3 TRP B 420     -23.390 -11.856 -16.559  1.00 43.60      B
ATOM   7439  CD1 TRP B 420     -24.160 -14.868 -14.702  1.00 46.11      B
ATOM   7440  NE1 TRP B 420     -24.357 -13.866 -13.788  1.00 44.70      B
ATOM   7441  CZ2 TRP B 420     -24.149 -11.365 -13.869  1.00 44.91      B
ATOM   7442  CZ3 TRP B 420     -23.446 -10.565 -16.043  1.00 42.93      B
ATOM   7443  CH2 TRP B 420     -23.822 -10.333 -14.711  1.00 43.75      B
ATOM   7444  C   TRP B 420     -21.001 -14.961 -17.579  1.00 53.47      B
ATOM   7445  O   TRP B 420     -20.485 -15.119 -18.687  1.00 54.31      B
ATOM   7446  N   ALA B 421     -20.628 -14.002 -16.740  1.00 53.92      B
```

FIGURE 4- 99 -

```
ATOM   7447  CA   ALA B 421     -19.574 -13.061 -17.092  1.00 53.80      B
ATOM   7448  CB   ALA B 421     -19.273 -12.151 -15.919  1.00 53.88      B
ATOM   7449  C    ALA B 421     -18.307 -13.785 -17.519  1.00 54.77      B
ATOM   7450  O    ALA B 421     -17.627 -13.354 -18.453  1.00 55.06      B
ATOM   7451  N    ARG B 422     -18.003 -14.892 -16.841  1.00 54.99      B
ATOM   7452  CA   ARG B 422     -16.804 -15.676 -17.134  1.00 55.58      B
ATOM   7453  CB   ARG B 422     -16.460 -16.582 -15.950  1.00 54.06      B
ATOM   7454  CG   ARG B 422     -16.359 -15.892 -14.602  1.00 53.26      B
ATOM   7455  CD   ARG B 422     -15.979 -16.899 -13.517  1.00 51.34      B
ATOM   7456  NE   ARG B 422     -14.628 -17.409 -13.727  1.00 50.48      B
ATOM   7457  CZ   ARG B 422     -14.084 -18.411 -13.046  1.00 49.83      B
ATOM   7458  NH1  ARG B 422     -14.779 -19.025 -12.099  1.00 48.20      B
ATOM   7459  NH2  ARG B 422     -12.838 -18.795 -13.313  1.00 49.74      B
ATOM   7460  C    ARG B 422     -16.929 -16.543 -18.392  1.00 56.87      B
ATOM   7461  O    ARG B 422     -16.231 -16.328 -19.390  1.00 56.58      B
ATOM   7462  N    MET B 423     -17.823 -17.525 -18.328  1.00 57.78      B
ATOM   7463  CA   MET B 423     -18.044 -18.452 -19.428  1.00 58.71      B
ATOM   7464  CB   MET B 423     -19.010 -19.556 -18.996  1.00 59.28      B
ATOM   7465  CG   MET B 423     -18.470 -20.484 -17.931  1.00 59.44      B
ATOM   7466  SD   MET B 423     -19.643 -21.801 -17.537  1.00 61.94      B
ATOM   7467  CE   MET B 423     -19.084 -23.146 -18.655  1.00 59.81      B
ATOM   7468  C    MET B 423     -18.558 -17.836 -20.722  1.00 59.21      B
ATOM   7469  O    MET B 423     -18.086 -18.179 -21.804  1.00 60.06      B
ATOM   7470  N    ILE B 424     -19.525 -16.933 -20.623  1.00 58.89      B
ATOM   7471  CA   ILE B 424     -20.091 -16.330 -21.822  1.00 59.05      B
ATOM   7472  CB   ILE B 424     -21.584 -15.987 -21.617  1.00 59.75      B
ATOM   7473  CG2  ILE B 424     -22.211 -15.569 -22.945  1.00 58.18      B
ATOM   7474  CG1  ILE B 424     -22.320 -17.196 -21.036  1.00 59.19      B
ATOM   7475  CD1  ILE B 424     -23.773 -16.933 -20.738  1.00 60.36      B
ATOM   7476  C    ILE B 424     -19.373 -15.077 -22.310  1.00 59.14      B
ATOM   7477  O    ILE B 424     -18.611 -15.128 -23.280  1.00 58.46      B
ATOM   7478  N    LEU B 425     -19.628 -13.957 -21.633  1.00 59.84      B
ATOM   7479  CA   LEU B 425     -19.047 -12.664 -21.992  1.00 60.45      B
ATOM   7480  CB   LEU B 425     -19.341 -11.627 -20.905  1.00 59.95      B
ATOM   7481  CG   LEU B 425     -20.773 -11.090 -20.884  1.00 59.95      B
ATOM   7482  CD1  LEU B 425     -20.859  -9.909 -19.917  1.00 59.10      B
ATOM   7483  CD2  LEU B 425     -21.179 -10.654 -22.282  1.00 59.06      B
ATOM   7484  C    LEU B 425     -17.556 -12.649 -22.315  1.00 61.19      B
ATOM   7485  O    LEU B 425     -17.158 -12.153 -23.368  1.00 61.23      B
ATOM   7486  N    MET B 426     -16.726 -13.171 -21.420  1.00 62.15      B
ATOM   7487  CA   MET B 426     -15.294 -13.186 -21.691  1.00 63.41      B
ATOM   7488  CB   MET B 426     -14.530 -13.787 -20.517  1.00 62.81      B
ATOM   7489  CG   MET B 426     -14.854 -13.126 -19.202  1.00 62.93      B
ATOM   7490  SD   MET B 426     -13.693 -13.574 -17.926  1.00 63.00      B
ATOM   7491  CE   MET B 426     -13.706 -12.100 -16.912  1.00 63.19      B
ATOM   7492  C    MET B 426     -15.032 -13.999 -22.951  1.00 64.59      B
ATOM   7493  O    MET B 426     -14.516 -13.484 -23.944  1.00 65.44      B
ATOM   7494  N    THR B 427     -15.400 -15.272 -22.909  1.00 65.21      B
ATOM   7495  CA   THR B 427     -15.208 -16.142 -24.055  1.00 65.69      B
ATOM   7496  CB   THR B 427     -16.041 -17.419 -23.916  1.00 64.79      B
ATOM   7497  OG1  THR B 427     -15.718 -18.064 -22.679  1.00 64.39      B
ATOM   7498  CG2  THR B 427     -15.745 -18.370 -25.066  1.00 65.10      B
ATOM   7499  C    THR B 427     -15.599 -15.450 -25.358  1.00 66.93      B
ATOM   7500  O    THR B 427     -14.790 -15.343 -26.278  1.00 66.78      B
ATOM   7501  N    HIS B 428     -16.835 -14.964 -25.423  1.00 68.01      B
ATOM   7502  CA   HIS B 428     -17.331 -14.314 -26.632  1.00 70.25      B
ATOM   7503  CB   HIS B 428     -18.788 -13.879 -26.458  1.00 71.72      B
ATOM   7504  CG   HIS B 428     -19.362 -13.205 -27.669  1.00 73.09      B
ATOM   7505  CD2  HIS B 428     -19.575 -11.895 -27.943  1.00 73.35      B
ATOM   7506  ND1  HIS B 428     -19.763 -13.901 -28.791  1.00 73.29      B
ATOM   7507  CE1  HIS B 428     -20.199 -13.049 -29.703  1.00 73.27      B
ATOM   7508  NE2  HIS B 428     -20.095 -11.826 -29.213  1.00 73.74      B
ATOM   7509  C    HIS B 428     -16.526 -13.109 -27.083  1.00 71.06      B
ATOM   7510  O    HIS B 428     -15.844 -13.158 -28.107  1.00 71.05      B
ATOM   7511  N    PHE B 429     -16.629 -12.019 -26.327  1.00 72.30      B
ATOM   7512  CA   PHE B 429     -15.926 -10.783 -26.653  1.00 73.46      B
ATOM   7513  CB   PHE B 429     -16.215  -9.715 -25.591  1.00 73.24      B
ATOM   7514  CG   PHE B 429     -17.485  -8.950 -25.848  1.00 72.71      B
ATOM   7515  CD1  PHE B 429     -17.530  -7.973 -26.837  1.00 71.34      B
ATOM   7516  CD2  PHE B 429     -18.649  -9.245 -25.147  1.00 72.72      B
ATOM   7517  CE1  PHE B 429     -18.713  -7.301 -27.131  1.00 71.11      B
ATOM   7518  CE2  PHE B 429     -19.840  -8.579 -25.433  1.00 72.50      B
ATOM   7519  CZ   PHE B 429     -19.871  -7.603 -26.431  1.00 71.91      B
ATOM   7520  C    PHE B 429     -14.425 -10.948 -26.860  1.00 74.33      B
ATOM   7521  O    PHE B 429     -13.826 -10.233 -27.668  1.00 74.17      B
ATOM   7522  N    PHE B 430     -13.810 -11.882 -26.142  1.00 75.25      B
```

FIGURE 4- 100 -

```
ATOM   7523  CA   PHE B 430     -12.384 -12.104 -26.336  1.00 77.04      B
ATOM   7524  CB   PHE B 430     -11.804 -13.013 -25.248  1.00 78.01      B
ATOM   7525  CG   PHE B 430     -11.086 -12.266 -24.151  1.00 78.63      B
ATOM   7526  CD1  PHE B 430     -11.798 -11.612 -23.146  1.00 78.99      B
ATOM   7527  CD2  PHE B 430      -9.696 -12.207 -24.132  1.00 78.46      B
ATOM   7528  CE1  PHE B 430     -11.129 -10.911 -22.136  1.00 78.96      B
ATOM   7529  CE2  PHE B 430      -9.019 -11.509 -23.129  1.00 78.62      B
ATOM   7530  CZ   PHE B 430      -9.737 -10.860 -22.128  1.00 78.91      B
ATOM   7531  C    PHE B 430     -12.186 -12.729 -27.715  1.00 77.50      B
ATOM   7532  O    PHE B 430     -11.103 -12.581 -28.317  1.00 78.00      B
ATOM   7533  N    SER B 431     -13.181 -13.429 -28.214  1.00 77.63      B
ATOM   7534  CA   SER B 431     -13.093 -14.040 -29.532  1.00 77.21      B
ATOM   7535  CB   SER B 431     -14.304 -14.938 -29.803  1.00 76.60      B
ATOM   7536  CG   SER B 431     -14.296 -16.072 -28.953  1.00 76.92      B
ATOM   7537  C    SER B 431     -13.070 -12.900 -30.529  1.00 77.68      B
ATOM   7538  O    SER B 431     -12.081 -12.696 -31.232  1.00 78.15      B
ATOM   7539  N    ILE B 432     -14.163 -12.141 -30.565  1.00 78.34      B
ATOM   7540  CA   ILE B 432     -14.287 -11.005 -31.471  1.00 78.96      B
ATOM   7541  CB   ILE B 432     -15.637 -10.281 -31.265  1.00 78.65      B
ATOM   7542  CG2  ILE B 432     -15.792  -9.162 -32.281  1.00 78.17      B
ATOM   7543  CG1  ILE B 432     -16.786 -11.284 -31.425  1.00 79.11      B
ATOM   7544  CD1  ILE B 432     -18.170 -10.675 -31.284  1.00 79.44      B
ATOM   7545  C    ILE B 432     -13.134 -10.013 -31.280  1.00 79.71      B
ATOM   7546  O    ILE B 432     -12.984  -9.078 -32.071  1.00 79.20      B
ATOM   7547  N    LEU B 433     -12.343 -10.223 -30.229  1.00 80.77      B
ATOM   7548  CA   LEU B 433     -11.198  -9.358 -29.954  1.00 81.81      B
ATOM   7549  CB   LEU B 433     -10.723  -9.505 -28.500  1.00 81.61      B
ATOM   7550  CG   LEU B 433     -11.236  -8.463 -27.499  1.00 81.77      B
ATOM   7551  CD1  LEU B 433     -10.588  -8.714 -26.145  1.00 81.95      B
ATOM   7552  CD2  LEU B 433     -10.902  -7.048 -27.986  1.00 81.01      B
ATOM   7553  C    LEU B 433     -10.051  -9.681 -30.902  1.00 82.16      B
ATOM   7554  O    LEU B 433      -9.899  -9.026 -31.936  1.00 82.37      B
ATOM   7555  N    LEU B 434      -9.252 -10.691 -30.554  1.00 82.40      B
ATOM   7556  CA   LEU B 434      -8.123 -11.089 -31.392  1.00 82.45      B
ATOM   7557  CB   LEU B 434      -7.498 -12.404 -30.897  1.00 81.58      B
ATOM   7558  CG   LEU B 434      -8.252 -13.317 -29.927  1.00 80.64      B
ATOM   7559  CD1  LEU B 434      -7.481 -14.623 -29.747  1.00 80.32      B
ATOM   7560  CD2  LEU B 434      -8.412 -12.617 -28.589  1.00 80.17      B
ATOM   7561  C    LEU B 434      -8.595 -11.246 -32.832  1.00 82.73      B
ATOM   7562  O    LEU B 434      -7.811 -11.123 -33.774  1.00 82.60      B
ATOM   7563  N    ALA B 435      -9.891 -11.499 -32.990  1.00 83.07      B
ATOM   7564  CA   ALA B 435     -10.489 -11.657 -34.306  1.00 83.67      B
ATOM   7565  CB   ALA B 435     -11.965 -12.038 -34.168  1.00 83.18      B
ATOM   7566  C    ALA B 435     -10.353 -10.351 -35.087  1.00 84.15      B
ATOM   7567  O    ALA B 435     -10.781 -10.261 -36.236  1.00 84.01      B
ATOM   7568  N    GLN B 436      -9.760  -9.341 -34.455  1.00 84.93      B
ATOM   7569  CA   GLN B 436      -9.563  -8.034 -35.080  1.00 86.13      B
ATOM   7570  CB   GLN B 436     -10.803  -7.159 -34.875  1.00 86.06      B
ATOM   7571  CG   GLN B 436     -12.119  -7.893 -35.084  1.00 87.44      B
ATOM   7572  CD   GLN B 436     -13.319  -6.968 -35.072  1.00 88.34      B
ATOM   7573  CE1  GLN B 436     -13.368  -6.011 -34.296  1.00 88.86      B
ATOM   7574  NE2  GLN B 436     -14.305  -7.258 -35.926  1.00 88.89      B
ATOM   7575  C    GLN B 436      -8.341  -7.344 -34.469  1.00 86.81      B
ATOM   7576  O    GLN B 436      -8.031  -6.196 -34.791  1.00 86.38      B
ATOM   7577  N    GLU B 437      -7.665  -8.063 -33.579  1.00 88.42      B
ATOM   7578  CA   GLU B 437      -6.468  -7.579 -32.891  1.00 90.23      B
ATOM   7579  CB   GLU B 437      -5.399  -7.181 -33.924  1.00 90.76      B
ATOM   7580  CG   GLU B 437      -4.013  -6.923 -33.330  1.00 91.27      B
ATOM   7581  CD   GLU B 437      -3.543  -8.070 -32.439  1.00 91.82      B
ATOM   7582  CE1  GLU B 437      -3.438  -9.213 -32.940  1.00 91.66      B
ATOM   7583  CE2  GLU B 437      -3.286  -7.829 -31.236  1.00 92.11      B
ATOM   7584  C    GLU B 437      -6.733  -6.411 -31.926  1.00 91.14      B
ATOM   7585  O    GLU B 437      -5.821  -5.647 -31.595  1.00 91.19      B
ATOM   7586  N    GLN B 438      -7.975  -6.285 -31.460  1.00 92.03      B
ATOM   7587  CA   GLN B 438      -8.350  -5.199 -30.551  1.00 92.20      B
ATOM   7588  CB   GLN B 438      -9.846  -4.914 -30.670  1.00 92.42      B
ATOM   7589  CG   GLN B 438     -10.289  -4.522 -32.073  1.00 93.31      B
ATOM   7590  CD   GLN B 438     -11.733  -4.128 -32.161  1.00 93.66      B
ATOM   7591  CE1  GLN B 438     -12.625  -4.912 -31.817  1.00 92.67      B
ATOM   7592  NE2  GLN B 438     -11.988  -2.905 -32.627  1.00 93.99      B
ATOM   7593  C    GLN B 438      -7.996  -5.422 -29.082  1.00 92.49      B
ATOM   7594  O    GLN B 438      -8.536  -4.750 -28.200  1.00 92.71      B
ATOM   7595  N    LEU B 439      -7.084  -6.355 -28.819  1.00 92.58      B
ATOM   7596  CA   LEU B 439      -6.662  -6.649 -27.449  1.00 92.23      B
ATOM   7597  CB   LEU B 439      -5.684  -7.831 -27.433  1.00 92.43      B
ATOM   7598  CG   LEU B 439      -6.222  -9.180 -27.925  1.00 92.83      B
```

FIGURE 4- 101 -

```
ATOM   7599  CD1 LEJ B 439      -5.067 -10.160 -28.130  1.00 92.84           B
ATOM   7600  CD2 LEJ B 439      -7.235  -9.722 -26.919  1.00 92.22           B
ATOM   7601  C   LEJ B 439      -5.986  -5.415 -26.876  1.00 91.93           B
ATOM   7602  O   LEJ B 439      -5.645  -5.357 -25.692  1.00 91.24           B
ATOM   7603  N   GLJ B 440      -5.809  -4.421 -27.737  1.00 92.26           B
ATOM   7604  CA  GLJ B 440      -5.164  -3.173 -27.357  1.00 92.85           B
ATOM   7605  CB  GLJ B 440      -4.277  -2.688 -28.509  1.00 93.72           B
ATOM   7606  CG  GLJ B 440      -3.454  -3.796 -29.170  1.00 95.11           B
ATOM   7607  CD  GLJ B 440      -2.261  -4.248 -28.323  1.00 95.84           B
ATOM   7608  OE1 GLJ B 440      -1.293  -3.459 -28.175  1.00 95.34           B
ATOM   7609  OE2 GLJ B 440      -2.296  -5.391 -27.808  1.00 96.31           B
ATOM   7610  C   GLJ B 440      -6.189  -2.091 -27.011  1.00 92.60           B
ATOM   7611  O   GLJ B 440      -6.427  -1.787 -25.836  1.00 92.29           B
ATOM   7612  N   LYS B 441      -6.790  -1.529 -28.056  1.00 92.13           B
ATOM   7613  CA  LYS B 441      -7.773  -0.461 -27.945  1.00 92.33           B
ATOM   7614  CB  LYS B 441      -8.844  -0.623 -29.036  1.00 92.62           B
ATOM   7615  CG  LYS B 441      -9.899   0.484 -29.024  1.00 93.71           B
ATOM   7616  CD  LYS B 441     -11.067   0.211 -29.984  1.00 94.26           B
ATOM   7617  CE  LYS B 441     -10.669   0.321 -31.457  1.00 94.82           B
ATOM   7618  NZ  LYS B 441     -11.832   0.027 -32.360  1.00 93.96           B
ATOM   7619  C   LYS B 441      -8.466  -0.310 -26.580  1.00 92.69           B
ATOM   7620  O   LYS B 441      -9.360  -1.088 -26.228  1.00 93.03           B
ATOM   7621  N   ALA B 442      -8.040   0.698 -25.816  1.00 92.16           B
ATOM   7622  CA  ALA B 442      -8.627   0.992 -24.508  1.00 90.52           B
ATOM   7623  CB  ALA B 442      -7.762   1.992 -23.750  1.00 90.17           B
ATOM   7624  C   ALA B 442      -9.998   1.592 -24.804  1.00 89.48           B
ATOM   7625  O   ALA B 442     -10.121   2.470 -25.657  1.00 89.23           B
ATOM   7626  N   LEJ B 443     -11.027   1.119 -24.107  1.00 88.22           B
ATOM   7627  CA  LEJ B 443     -12.384   1.600 -24.354  1.00 86.51           B
ATOM   7628  CB  LEJ B 443     -13.139   0.546 -25.158  1.00 87.12           B
ATOM   7629  CG  LEJ B 443     -12.458   0.291 -26.503  1.00 88.00           B
ATOM   7630  CD1 LEJ B 443     -12.696  -1.148 -26.961  1.00 88.16           B
ATOM   7631  CD2 LEJ B 443     -12.973   1.311 -27.518  1.00 88.39           B
ATOM   7632  C   LEJ B 443     -13.183   1.991 -23.115  1.00 84.73           B
ATOM   7633  O   LEJ B 443     -13.142   1.319 -22.085  1.00 84.70           B
ATOM   7634  N   ASP B 444     -13.921   3.090 -23.253  1.00 82.70           B
ATOM   7635  CA  ASP B 444     -14.750   3.673 -22.195  1.00 80.10           B
ATOM   7636  CB  ASP B 444     -15.403   4.963 -22.721  1.00 80.28           B
ATOM   7637  CG  ASP B 444     -14.517   5.706 -23.719  1.00 80.39           B
ATOM   7638  OD1 ASP B 444     -13.522   6.345 -23.299  1.00 80.09           B
ATOM   7639  OD2 ASP B 444     -14.814   5.633 -24.932  1.00 79.76           B
ATOM   7640  C   ASP B 444     -15.843   2.758 -21.637  1.00 77.56           B
ATOM   7641  O   ASP B 444     -16.463   1.987 -22.368  1.00 77.80           B
ATOM   7642  N   CYS B 445     -16.073   2.856 -20.333  1.00 74.21           B
ATOM   7643  CA  CYS B 445     -17.114   2.076 -19.678  1.00 71.51           B
ATOM   7644  CB  CYS B 445     -16.601   0.677 -19.306  1.00 70.49           B
ATOM   7645  SG  CYS B 445     -15.437   0.569 -17.928  1.00 67.13           B
ATOM   7646  C   CYS B 445     -17.608   2.829 -18.441  1.00 70.43           B
ATOM   7647  O   CYS B 445     -16.877   3.632 -17.855  1.00 70.20           B
ATOM   7648  N   GLN B 446     -18.852   2.573 -18.056  1.00 68.63           B
ATOM   7649  CA  GLN B 446     -19.452   3.243 -16.910  1.00 67.70           B
ATOM   7650  CB  GLN B 446     -20.945   3.465 -17.169  1.00 67.78           B
ATOM   7651  CG  GLN B 446     -21.249   4.450 -18.293  1.00 68.61           B
ATOM   7652  CD  GLN B 446     -21.410   5.883 -17.792  1.00 68.51           B
ATOM   7653  OE1 GLN B 446     -22.389   6.213 -17.113  1.00 67.99           B
ATOM   7654  NE2 GLN B 446     -20.445   6.739 -18.123  1.00 68.43           B
ATOM   7655  C   GLN B 446     -19.285   2.494 -15.594  1.00 66.52           B
ATOM   7656  O   GLN B 446     -19.274   1.266 -15.563  1.00 66.87           B
ATOM   7657  N   ILE B 447     -19.143   3.248 -14.509  1.00 64.93           B
ATOM   7658  CA  ILE B 447     -19.030   2.680 -13.167  1.00 63.80           B
ATOM   7659  CB  ILE B 447     -17.573   2.405 -12.751  1.00 63.49           B
ATOM   7660  CG2 ILE B 447     -17.531   2.022 -11.272  1.00 63.10           B
ATOM   7661  CG1 ILE B 447     -17.004   1.267 -13.596  1.00 63.31           B
ATOM   7662  CD1 ILE B 447     -15.595   0.866 -13.216  1.00 62.22           B
ATOM   7663  C   ILE B 447     -19.648   3.669 -12.189  1.00 63.76           B
ATOM   7664  O   ILE B 447     -18.987   4.596 -11.713  1.00 62.56           B
ATOM   7665  N   TYR B 448     -20.927   3.456 -11.894  1.00 64.18           B
ATOM   7666  CA  TYR B 448     -21.669   4.338 -11.011  1.00 65.16           B
ATOM   7667  CB  TYR B 448     -21.016   4.388  -9.626  1.00 64.06           B
ATOM   7668  CG  TYR B 448     -21.033   3.073  -8.870  1.00 63.93           B
ATOM   7669  CD1 TYR B 448     -22.163   2.243  -8.886  1.00 62.94           B
ATOM   7670  CE1 TYR B 448     -22.202   1.055  -8.147  1.00 61.25           B
ATOM   7671  CD2 TYR B 448     -19.938   2.678  -8.095  1.00 64.34           B
ATOM   7672  CE2 TYR B 448     -19.968   1.493  -7.355  1.00 63.51           B
ATOM   7673  CZ  TYR B 448     -21.099   0.687  -7.385  1.00 62.47           B
ATOM   7674  OH  TYR B 448     -21.108  -0.482  -6.653  1.00 62.71           B
```

FIGURE 4- 102 -

```
ATOM   7675  C   TYR B 448   -21.675   5.730 -11.657  1.00 66.44           B
ATOM   7676  O   TYR B 448   -21.286   6.728 -11.046  1.00 66.64           B
ATOM   7677  N   GLY B 449   -22.107   5.770 -12.914  1.00 67.27           B
ATOM   7678  CA  GLY B 449   -22.166   7.016 -13.653  1.00 68.44           B
ATOM   7679  C   GLY B 449   -20.808   7.568 -14.036  1.00 69.58           B
ATOM   7680  O   GLY B 449   -20.685   8.318 -15.003  1.00 70.29           B
ATOM   7681  N   ALA B 450   -19.784   7.192 -13.279  1.00 70.95           B
ATOM   7682  CA  ALA B 450   -18.431   7.669 -13.531  1.00 72.87           B
ATOM   7683  CB  ALA B 450   -17.574   7.515 -12.263  1.00 72.46           B
ATOM   7684  C   ALA B 450   -17.765   6.956 -14.703  1.00 74.06           B
ATOM   7685  O   ALA B 450   -17.371   5.797 -14.594  1.00 74.30           B
ATOM   7686  N   CYS B 451   -17.637   7.666 -15.819  1.00 75.97           B
ATOM   7687  CA  CYS B 451   -17.005   7.126 -17.017  1.00 78.30           B
ATOM   7688  CB  CYS B 451   -17.286   8.026 -18.224  1.00 78.74           B
ATOM   7689  SG  CYS B 451   -16.290   7.596 -19.686  1.00 81.84           B
ATOM   7690  C   CYS B 451   -15.491   6.975 -16.862  1.00 79.05           B
ATOM   7691  O   CYS B 451   -14.827   7.798 -16.233  1.00 78.93           B
ATOM   7692  N   TYR B 452   -14.958   5.907 -17.444  1.00 80.42           B
ATOM   7693  CA  TYR B 452   -13.529   5.632 -17.413  1.00 81.95           B
ATOM   7694  CB  TYR B 452   -13.230   4.437 -16.496  1.00 80.30           B
ATOM   7695  CG  TYR B 452   -13.390   4.743 -15.019  1.00 79.28           B
ATOM   7696  CD1 TYR B 452   -12.585   5.697 -14.388  1.00 79.27           B
ATOM   7697  CE1 TYR B 452   -12.744   5.993 -13.024  1.00 78.87           B
ATOM   7698  CD2 TYR B 452   -14.355   4.090 -14.254  1.00 79.21           B
ATOM   7699  CE2 TYR B 452   -14.524   4.375 -12.896  1.00 78.48           B
ATOM   7700  CZ  TYR B 452   -13.719   5.325 -12.289  1.00 78.43           B
ATOM   7701  OH  TYR B 452   -13.899   5.610 -10.956  1.00 77.41           B
ATOM   7702  C   TYR B 452   -13.078   5.344 -18.846  1.00 83.63           B
ATOM   7703  O   TYR B 452   -13.442   6.073 -19.770  1.00 83.99           B
ATOM   7704  N   SER B 453   -12.292   4.284 -19.021  1.00 85.29           B
ATOM   7705  CA  SER B 453   -11.773   3.864 -20.331  1.00 87.20           B
ATOM   7706  CB  SER B 453   -11.308   5.076 -21.153  1.00 87.34           B
ATOM   7707  OG  SER B 453   -10.983   4.696 -22.482  1.00 87.59           B
ATOM   7708  C   SER B 453   -10.598   2.903 -20.098  1.00 87.90           B
ATOM   7709  O   SER B 453    -9.445   3.320 -19.969  1.00 88.72           B
ATOM   7710  N   ILE B 454   -10.901   1.610 -20.062  1.00 87.73           B
ATOM   7711  CA  ILE B 454    -9.896   0.592 -19.789  1.00 87.99           B
ATOM   7712  CB  ILE B 454   -10.425  -0.354 -18.688  1.00 87.97           B
ATOM   7713  CG2 ILE B 454    -9.322  -1.302 -18.216  1.00 87.56           B
ATOM   7714  CG1 ILE B 454   -10.959   0.484 -17.520  1.00 88.19           B
ATOM   7715  CD1 ILE B 454   -11.852  -0.272 -16.562  1.00 88.38           B
ATOM   7716  C   ILE B 454    -9.453  -0.235 -20.992  1.00 88.52           B
ATOM   7717  O   ILE B 454   -10.061  -0.188 -22.063  1.00 88.65           B
ATOM   7718  N   GLU B 455    -8.369  -0.982 -20.794  1.00 88.76           B
ATOM   7719  CA  GLU B 455    -7.814  -1.860 -21.815  1.00 89.23           B
ATOM   7720  CB  GLU B 455    -6.285  -1.814 -21.816  1.00 89.91           B
ATOM   7721  CG  GLU B 455    -5.633  -0.472 -22.094  1.00 90.37           B
ATOM   7722  CD  GLU B 455    -4.133  -0.625 -22.342  1.00 90.96           B
ATOM   7723  OE1 GLU B 455    -3.487  -1.404 -21.600  1.00 91.32           B
ATOM   7724  OE2 GLU B 455    -3.601   0.026 -23.272  1.00 90.79           B
ATOM   7725  C   GLU B 455    -8.242  -3.283 -21.473  1.00 89.28           B
ATOM   7726  O   GLU B 455    -8.422  -3.619 -20.302  1.00 89.47           B
ATOM   7727  N   PRO B 456    -8.409  -4.142 -22.486  1.00 89.24           B
ATOM   7728  CD  PRO B 456    -8.444  -3.871 -23.933  1.00 89.70           B
ATOM   7729  CA  PRO B 456    -8.818  -5.520 -22.200  1.00 88.73           B
ATOM   7730  CB  PRO B 456    -9.000  -6.125 -23.591  1.00 89.34           B
ATOM   7731  CG  PRO B 456    -9.394  -4.943 -24.428  1.00 89.74           B
ATOM   7732  C   PRO B 456    -7.769  -6.274 -21.393  1.00 88.02           B
ATOM   7733  O   PRO B 456    -8.095  -6.972 -20.422  1.00 87.96           B
ATOM   7734  N   LEU B 457    -6.507  -6.118 -21.770  1.00 87.33           B
ATOM   7735  CA  LEU B 457    -5.399  -6.801 -21.102  1.00 86.52           B
ATOM   7736  CB  LEU B 457    -4.070  -6.369 -21.719  1.00 87.00           B
ATOM   7737  CG  LEU B 457    -4.004  -6.504 -23.239  1.00 88.05           B
ATOM   7738  CD1 LEU B 457    -2.656  -5.974 -23.729  1.00 88.70           B
ATOM   7739  CD2 LEU B 457    -4.212  -7.965 -23.641  1.00 87.60           B
ATOM   7740  C   LEU B 457    -5.327  -6.614 -19.591  1.00 85.41           B
ATOM   7741  O   LEU B 457    -4.876  -7.509 -18.876  1.00 84.58           B
ATOM   7742  N   ASP B 458    -5.775  -5.460 -19.107  1.00 84.06           B
ATOM   7743  CA  ASP B 458    -5.734  -5.163 -17.677  1.00 83.56           B
ATOM   7744  CB  ASP B 458    -5.975  -3.667 -17.452  1.00 83.76           B
ATOM   7745  CG  ASP B 458    -4.780  -2.820 -17.846  1.00 84.39           B
ATOM   7746  OD1 ASP B 458    -3.697  -3.013 -17.241  1.00 83.42           B
ATOM   7747  OD2 ASP B 458    -4.919  -1.969 -18.755  1.00 84.16           B
ATOM   7748  C   ASP B 458    -6.695  -5.961 -16.791  1.00 83.07           B
ATOM   7749  O   ASP B 458    -6.401  -6.221 -15.616  1.00 83.02           B
ATOM   7750  N   LEU B 459    -7.835  -6.350 -17.359  1.00 81.68           B
```

FIGURE 4- 103 -

```
ATOM   7751  CA   LEU B 459      -8.863   -7.094  -16.632  1.00 79.74           B
ATOM   7752  CB   LEU B 459      -9.778   -7.831  -17.618  1.00 79.57           B
ATOM   7753  CG   LEU B 459     -10.461   -6.992  -18.697  1.00 79.20           B
ATOM   7754  CD1  LEU B 459     -11.282   -7.913  -19.584  1.00 78.67           B
ATOM   7755  CD2  LEU B 459     -11.346   -5.923  -18.064  1.00 79.68           B
ATOM   7756  C    LEU B 459      -8.354   -8.091  -15.588  1.00 78.71           B
ATOM   7757  O    LEU B 459      -8.785   -8.062  -14.436  1.00 78.25           B
ATOM   7758  N    PRO B 460      -7.433   -8.990  -15.976  1.00 77.48           B
ATOM   7759  CD   PRO B 460      -6.814   -9.153  -17.304  1.00 76.53           B
ATOM   7760  CA   PRO B 460      -6.904   -9.982  -15.030  1.00 76.88           B
ATOM   7761  CB   PRO B 460      -5.746  -10.605  -15.806  1.00 76.31           B
ATOM   7762  CG   PRO B 460      -6.239  -10.550  -17.214  1.00 76.12           B
ATOM   7763  C    PRO B 460      -6.465   -9.414  -13.674  1.00 76.79           B
ATOM   7764  O    PRO B 460      -6.901   -9.382  -12.619  1.00 76.06           B
ATOM   7765  N    GLN B 461      -5.600   -8.404  -13.715  1.00 76.49           B
ATOM   7766  CA   GLN B 461      -5.089   -7.770  -12.502  1.00 75.93           B
ATOM   7767  CB   GLN B 461      -3.959   -6.793  -12.855  1.00 76.81           B
ATOM   7768  CG   GLN B 461      -2.919   -7.352  -13.838  1.00 77.75           B
ATOM   7769  CD   GLN B 461      -3.150   -6.893  -15.283  1.00 78.15           B
ATOM   7770  OE1  GLN B 461      -2.967   -5.712  -15.619  1.00 77.64           B
ATOM   7771  NE2  GLN B 461      -3.559   -7.827  -16.141  1.00 77.45           B
ATOM   7772  C    GLN B 461      -6.206   -7.031  -11.766  1.00 75.29           B
ATOM   7773  O    GLN B 461      -6.411   -7.224  -10.561  1.00 74.84           B
ATOM   7774  N    ILE B 462      -6.926   -6.186  -12.501  1.00 74.68           B
ATOM   7775  CA   ILE B 462      -8.039   -5.412  -11.944  1.00 73.38           B
ATOM   7776  CB   ILE B 462      -8.834   -4.698  -13.048  1.00 72.41           B
ATOM   7777  CG2  ILE B 462     -10.000   -3.947  -12.431  1.00 71.66           B
ATOM   7778  CG1  ILE B 462      -7.912   -3.767  -13.838  1.00 71.82           B
ATOM   7779  CD1  ILE B 462      -8.594   -3.085  -15.005  1.00 72.01           B
ATOM   7780  C    ILE B 462      -9.013   -6.306  -11.186  1.00 72.95           B
ATOM   7781  O    ILE B 462      -9.348   -6.040  -10.029  1.00 73.12           B
ATOM   7782  N    ILE B 463      -9.466   -7.364  -11.855  1.00 71.90           B
ATOM   7783  CA   ILE B 463     -10.403   -8.307  -11.260  1.00 70.84           B
ATOM   7784  CB   ILE B 463     -10.648   -9.519  -12.184  1.00 69.91           B
ATOM   7785  CG2  ILE B 463     -11.495  -10.570  -11.463  1.00 68.70           B
ATOM   7786  CG1  ILE B 463     -11.344   -9.051  -13.465  1.00 68.40           B
ATOM   7787  CD1  ILE B 463     -11.640  -10.156  -14.441  1.00 67.56           B
ATOM   7788  C    ILE B 463      -9.931   -8.801   -9.902  1.00 71.13           B
ATOM   7789  O    ILE B 463     -10.734   -8.925   -8.976  1.00 71.03           B
ATOM   7790  N    GLU B 464      -8.636   -9.072   -9.772  1.00 72.24           B
ATOM   7791  CA   GLU B 464      -8.113   -9.544   -8.496  1.00 74.07           B
ATOM   7792  CB   GLU B 464      -6.660  -10.001   -8.619  1.00 75.20           B
ATOM   7793  CG   GLU B 464      -6.036  -10.285   -7.258  1.00 77.24           B
ATOM   7794  CD   GLU B 464      -4.566  -10.658   -7.327  1.00 79.19           B
ATOM   7795  OE1  GLU B 464      -4.257  -11.843   -7.590  1.00 79.90           B
ATOM   7796  OE2  GLU B 464      -3.718   -9.760   -7.120  1.00 80.78           B
ATOM   7797  C    GLU B 464      -8.196   -8.473   -7.409  1.00 74.83           B
ATOM   7798  O    GLU B 464      -8.683   -8.734   -6.312  1.00 74.50           B
ATOM   7799  N    ARG B 465      -7.719   -7.266   -7.700  1.00 75.19           B
ATOM   7800  CA   ARG B 465      -7.771   -6.221   -6.691  1.00 75.15           B
ATOM   7801  CB   ARG B 465      -7.101   -4.941   -7.184  1.00 76.83           B
ATOM   7802  CG   ARG B 465      -6.903   -3.919   -6.072  1.00 79.32           B
ATOM   7803  CD   ARG B 465      -6.000   -2.769   -6.503  1.00 80.92           B
ATOM   7804  NE   ARG B 465      -5.816   -1.792   -5.433  1.00 82.69           B
ATOM   7805  CZ   ARG B 465      -5.060   -0.702   -5.534  1.00 84.08           B
ATOM   7806  NH1  ARG B 465      -4.414   -0.450   -6.664  1.00 84.40           B
ATOM   7807  NH2  ARG B 465      -4.954    0.137   -4.507  1.00 84.57           B
ATOM   7808  C    ARG B 465      -9.219   -5.942   -6.302  1.00 74.69           B
ATOM   7809  O    ARG B 465      -9.513   -5.668   -5.133  1.00 75.31           B
ATOM   7810  N    LEU B 466     -10.122   -6.029   -7.279  1.00 73.00           B
ATOM   7811  CA   LEU B 466     -11.547   -5.802   -7.036  1.00 70.49           B
ATOM   7812  CB   LEU B 466     -12.297   -5.550   -8.350  1.00 70.13           B
ATOM   7813  CG   LEU B 466     -12.015   -4.275   -9.145  1.00 70.46           B
ATOM   7814  CD1  LEU B 466     -12.970   -4.181  -10.331  1.00 69.00           B
ATOM   7815  CD2  LEU B 466     -12.192   -3.071   -8.240  1.00 71.19           B
ATOM   7816  C    LEU B 466     -12.205   -6.985   -6.326  1.00 69.36           B
ATOM   7817  O    LEU B 466     -12.363   -6.980   -5.101  1.00 69.54           B
ATOM   7818  N    HIS B 467     -12.572   -7.994   -7.117  1.00 67.27           B
ATOM   7819  CA   HIS B 467     -13.246   -9.203   -6.638  1.00 64.65           B
ATOM   7820  CB   HIS B 467     -13.843   -9.935   -7.820  1.00 59.18           B
ATOM   7821  CG   HIS B 467     -14.649   -9.048   -8.705  1.00 54.08           B
ATOM   7822  CD2  HIS B 467     -14.329   -8.413   -9.856  1.00 51.76           B
ATOM   7823  ND1  HIS B 467     -15.942   -8.661   -8.407  1.00 50.90           B
ATOM   7824  CE1  HIS B 467     -16.386   -7.859   -9.340  1.00 50.98           B
ATOM   7825  NE2  HIS B 467     -15.426   -7.679  -10.229  1.00 51.31           B
ATOM   7826  C    HIS B 467     -12.318  -10.126   -5.883  1.00 66.20           B
```

FIGURE 4- 104 -

```
ATOM   7827  O   HIS B 467     -12.751 -11.106  -5.269  1.00 65.92      B
ATOM   7828  N   GLY B 468     -11.032  -9.812  -5.958  1.00 67.95      B
ATOM   7829  CA  GLY B 468     -10.030 -10.581  -5.250  1.00 69.16      B
ATOM   7830  C   GLY B 468      -9.836 -12.046  -5.575  1.00 69.41      B
ATOM   7831  O   GLY B 468     -10.788 -12.821  -5.681  1.00 70.73      B
ATOM   7832  N   LEU B 469      -8.569 -12.398  -5.755  1.00 68.97      B
ATOM   7833  CA  LEU B 469      -8.116 -13.762  -6.007  1.00 68.37      B
ATOM   7834  CB  LEU B 469      -7.579 -14.317  -4.679  1.00 69.43      B
ATOM   7835  CG  LEU B 469      -7.661 -13.346  -3.477  1.00 69.74      B
ATOM   7836  CD1 LEU B 469      -7.420 -14.092  -2.154  1.00 69.22      B
ATOM   7837  CD2 LEU B 469      -6.636 -12.214  -3.656  1.00 69.02      B
ATOM   7838  C   LEU B 469      -9.119 -14.760  -6.615  1.00 67.41      B
ATOM   7839  O   LEU B 469      -9.114 -15.015  -7.825  1.00 65.99      B
ATOM   7840  N   SER B 470      -9.961 -15.319  -5.744  1.00 66.45      B
ATOM   7841  CA  SER B 470     -10.988 -16.316  -6.075  1.00 65.82      B
ATOM   7842  CB  SER B 470     -11.907 -16.521  -4.864  1.00 66.14      B
ATOM   7843  OG  SER B 470     -12.736 -15.388  -4.654  1.00 64.51      B
ATOM   7844  C   SER B 470     -11.877 -16.098  -7.304  1.00 65.13      B
ATOM   7845  O   SER B 470     -12.650 -16.930  -7.671  1.00 64.05      B
ATOM   7846  N   ALA B 471     -11.784 -14.937  -7.936  1.00 64.95      B
ATOM   7847  CA  ALA B 471     -12.611 -14.664  -9.107  1.00 64.29      B
ATOM   7848  CB  ALA B 471     -12.601 -13.167  -9.410  1.00 64.98      B
ATOM   7849  C   ALA B 471     -12.163 -15.459 -10.340  1.00 63.95      B
ATOM   7850  O   ALA B 471     -12.658 -15.239 -11.449  1.00 64.07      B
ATOM   7851  N   PHE B 472     -11.226 -16.381 -10.142  1.00 62.82      B
ATOM   7852  CA  PHE B 472     -10.716 -17.207 -11.235  1.00 62.09      B
ATOM   7853  CB  PHE B 472      -9.267 -16.845 -11.559  1.00 62.16      B
ATOM   7854  CG  PHE B 472      -9.033 -15.391 -11.831  1.00 62.18      B
ATOM   7855  CD1 PHE B 472      -9.653 -14.762 -12.906  1.00 62.70      B
ATOM   7856  CD2 PHE B 472      -8.154 -14.661 -11.044  1.00 62.65      B
ATOM   7857  CE1 PHE B 472      -9.387 -13.424 -13.200  1.00 61.93      B
ATOM   7858  CE2 PHE B 472      -7.882 -13.325 -11.328  1.00 62.39      B
ATOM   7859  CZ  PHE B 472      -8.499 -12.707 -12.409  1.00 62.14      B
ATOM   7860  C   PHE B 472     -10.751 -18.687 -10.859  1.00 61.28      B
ATOM   7861  O   PHE B 472     -10.478 -19.557 -11.686  1.00 60.97      B
ATOM   7862  N   THR B 473     -11.077 -18.972  -9.607  1.00 60.27      B
ATOM   7863  CA  THR B 473     -11.107 -20.350  -9.155  1.00 59.72      B
ATOM   7864  CB  THR B 473      -9.952 -20.615  -8.147  1.00 60.34      B
ATOM   7865  OG1 THR B 473     -10.282 -20.063  -6.865  1.00 59.58      B
ATOM   7866  CG2 THR B 473      -8.651 -19.968  -8.649  1.00 59.51      B
ATOM   7867  C   THR B 473     -12.443 -20.707  -8.516  1.00 59.19      B
ATOM   7868  O   THR B 473     -12.511 -21.547  -7.617  1.00 58.71      B
ATOM   7869  N   LEU B 474     -13.514 -20.069  -8.970  1.00 58.64      B
ATOM   7870  CA  LEU B 474     -14.814 -20.377  -8.405  1.00 58.64      B
ATOM   7871  CB  LEU B 474     -15.696 -19.125  -8.324  1.00 58.11      B
ATOM   7872  CG  LEU B 474     -15.222 -18.034  -7.298  1.00 58.99      B
ATOM   7873  CD1 LEU B 474     -16.200 -16.915  -7.235  1.00 58.97      B
ATOM   7874  CD2 LEU B 474     -15.088 -18.737  -5.926  1.00 58.15      B
ATOM   7875  C   LEU B 474     -15.491 -21.462  -9.216  1.00 59.08      B
ATOM   7876  O   LEU B 474     -15.437 -21.473 -10.445  1.00 58.38      B
ATOM   7877  N   HIS B 475     -16.104 -22.392  -8.500  1.00 59.65      B
ATOM   7878  CA  HIS B 475     -16.812 -23.507  -9.105  1.00 60.96      B
ATOM   7879  CB  HIS B 475     -15.881 -24.705  -9.283  1.00 60.06      B
ATOM   7880  CG  HIS B 475     -15.434 -25.297  -7.986  1.00 60.11      B
ATOM   7881  CD2 HIS B 475     -15.838 -26.408  -7.327  1.00 60.01      B
ATOM   7882  ND1 HIS B 475     -14.532 -24.667  -7.156  1.00 60.62      B
ATOM   7883  CE1 HIS B 475     -14.401 -25.362  -6.041  1.00 61.48      B
ATOM   7884  NE2 HIS B 475     -15.184 -26.423  -6.118  1.00 61.76      B
ATOM   7885  C   HIS B 475     -17.887 -23.874  -8.091  1.00 62.46      B
ATOM   7886  O   HIS B 475     -17.963 -23.277  -7.009  1.00 62.89      B
ATOM   7887  N   SER B 476     -18.697 -24.871  -8.435  1.00 63.25      B
ATOM   7888  CA  SER B 476     -19.766 -25.334  -7.559  1.00 63.84      B
ATOM   7889  CB  SER B 476     -19.189 -25.790  -6.212  1.00 64.65      B
ATOM   7890  OG  SER B 476     -20.190 -26.373  -5.393  1.00 65.62      B
ATOM   7891  C   SER B 476     -20.780 -24.210  -7.351  1.00 63.62      B
ATOM   7892  O   SER B 476     -21.253 -23.962  -6.232  1.00 63.18      B
ATOM   7893  N   TYR B 477     -21.097 -23.521  -8.442  1.00 62.69      B
ATOM   7894  CA  TYR B 477     -22.058 -22.436  -8.381  1.00 62.18      B
ATOM   7895  CB  TYR B 477     -22.219 -21.776  -9.751  1.00 63.07      B
ATOM   7896  CG  TYR B 477     -21.066 -20.880 -10.153  1.00 63.76      B
ATOM   7897  CD1 TYR B 477     -19.916 -21.404 -10.745  1.00 63.32      B
ATOM   7898  CE1 TYR B 477     -18.853 -20.574 -11.111  1.00 63.11      B
ATOM   7899  CD2 TYR B 477     -21.127 -19.500  -9.933  1.00 64.21      B
ATOM   7900  CE2 TYR B 477     -20.074 -18.662 -10.290  1.00 63.96      B
ATOM   7901  CZ  TYR B 477     -18.943 -19.205 -10.880  1.00 63.97      B
ATOM   7902  OH  TYR B 477     -17.915 -18.373 -11.247  1.00 64.44      B
```

FIGURE 4- 105 -

```
ATOM   7903  C    TYR B 477     -23.403 -22.973  -7.913  1.00 61.42      B
ATOM   7904  O    TYR B 477     -23.732 -24.133  -8.140  1.00 60.81      B
ATOM   7905  N    SER B 478     -24.175 -22.116  -7.254  1.00 61.02      B
ATOM   7906  CA   SER B 478     -25.492 -22.489  -6.756  1.00 58.86      B
ATOM   7907  CB   SER B 478     -26.192 -21.274  -6.163  1.00 58.05      B
ATOM   7908  OG   SER B 478     -27.565 -21.558  -5.955  1.00 57.45      B
ATOM   7909  C    SER B 478     -26.406 -23.081  -7.825  1.00 58.21      B
ATOM   7910  O    SER B 478     -26.325 -22.721  -9.001  1.00 57.33      B
ATOM   7911  N    PRO B 479     -27.295 -24.003  -7.425  1.00 57.33      B
ATOM   7912  CD   PRO B 479     -27.409 -24.685  -6.125  1.00 56.98      B
ATOM   7913  CA   PRO B 479     -28.204 -24.598  -8.405  1.00 56.72      B
ATOM   7914  CB   PRO B 479     -28.996 -25.603  -7.575  1.00 56.52      B
ATOM   7915  CG   PRO B 479     -28.009 -26.011  -6.525  1.00 56.67      B
ATOM   7916  C    PRO B 479     -29.083 -23.487  -8.963  1.00 55.96      B
ATOM   7917  O    PRO B 479     -29.059 -23.200 -10.160  1.00 55.56      B
ATOM   7918  N    GLY B 480     -29.842 -22.852  -8.074  1.00 55.09      B
ATOM   7919  CA   GLY B 480     -30.714 -21.769  -8.487  1.00 55.08      B
ATOM   7920  C    GLY B 480     -30.020 -20.815  -9.440  1.00 55.12      B
ATOM   7921  O    GLY B 480     -30.607 -20.392 -10.438  1.00 56.07      B
ATOM   7922  N    GLU B 481     -28.762 -20.496  -9.131  1.00 54.64      B
ATOM   7923  CA   GLU B 481     -27.939 -19.583  -9.926  1.00 53.53      B
ATOM   7924  CB   GLU B 481     -26.657 -19.234  -9.153  1.00 51.57      B
ATOM   7925  CG   GLU B 481     -25.731 -18.219  -9.844  1.00 49.77      B
ATOM   7926  CD   GLU B 481     -26.409 -16.890 -10.158  1.00 47.32      B
ATOM   7927  OE1  GLU B 481     -27.220 -16.419  -9.328  1.00 45.91      B
ATOM   7928  OE2  GLU B 481     -26.113 -16.311 -11.226  1.00 44.38      B
ATOM   7929  C    GLU B 481     -27.582 -20.166 -11.295  1.00 53.90      B
ATOM   7930  O    GLU B 481     -27.709 -19.486 -12.322  1.00 51.78      B
ATOM   7931  N    ILE B 482     -27.130 -21.423 -11.294  1.00 54.76      B
ATOM   7932  CA   ILE B 482     -26.763 -22.127 -12.524  1.00 54.19      B
ATOM   7933  CB   ILE B 482     -26.328 -23.584 -12.250  1.00 53.97      B
ATOM   7934  CG2  ILE B 482     -26.123 -24.313 -13.565  1.00 53.24      B
ATOM   7935  CG1  ILE B 482     -25.047 -23.615 -11.413  1.00 54.10      B
ATOM   7936  CD1  ILE B 482     -24.593 -25.019 -11.052  1.00 53.46      B
ATOM   7937  C    ILE B 482     -27.973 -22.178 -13.435  1.00 54.14      B
ATOM   7938  O    ILE B 482     -27.867 -22.034 -14.653  1.00 53.51      B
ATOM   7939  N    ASN B 483     -29.138 -22.387 -12.826  1.00 54.46      B
ATOM   7940  CA   ASN B 483     -30.381 -22.461 -13.568  1.00 55.76      B
ATOM   7941  CB   ASN B 483     -31.519 -22.893 -12.648  1.00 58.31      B
ATOM   7942  CG   ASN B 483     -31.319 -24.289 -12.108  1.00 60.48      B
ATOM   7943  OD1  ASN B 483     -30.986 -25.212 -12.862  1.00 60.53      B
ATOM   7944  ND2  ASN B 483     -31.522 -24.461 -10.796  1.00 61.82      B
ATOM   7945  C    ASN B 483     -30.723 -21.138 -14.220  1.00 55.29      B
ATOM   7946  O    ASN B 483     -30.885 -21.072 -15.438  1.00 56.09      B
ATOM   7947  N    ARG B 484     -30.825 -20.084 -13.418  1.00 53.93      B
ATOM   7948  CA   ARG B 484     -31.156 -18.778 -13.967  1.00 52.54      B
ATOM   7949  CB   ARG B 484     -30.910 -17.680 -12.928  1.00 51.98      B
ATOM   7950  CG   ARG B 484     -31.273 -16.286 -13.430  1.00 52.49      B
ATOM   7951  CD   ARG B 484     -31.354 -15.263 -12.307  1.00 52.75      B
ATOM   7952  NE   ARG B 484     -30.145 -15.239 -11.490  1.00 53.88      B
ATOM   7953  CZ   ARG B 484     -29.893 -14.326 -10.555  1.00 55.13      B
ATOM   7954  NH1  ARG B 484     -30.779 -13.360 -10.321  1.00 55.20      B
ATOM   7955  NH2  ARG B 484     -28.773 -14.378  -9.853  1.00 55.85      B
ATOM   7956  C    ARG B 484     -30.358 -18.499 -15.245  1.00 51.58      B
ATOM   7957  O    ARG B 484     -30.893 -17.956 -16.213  1.00 51.70      B
ATOM   7958  N    VAL B 485     -29.086 -18.895 -15.260  1.00 50.36      B
ATOM   7959  CA   VAL B 485     -28.236 -18.674 -16.433  1.00 49.80      B
ATOM   7960  CB   VAL B 485     -26.750 -19.055 -16.153  1.00 48.53      B
ATOM   7961  CG1  VAL B 485     -25.874 -18.692 -17.356  1.00 45.56      B
ATOM   7962  CG2  VAL B 485     -26.255 -18.343 -14.907  1.00 46.99      B
ATOM   7963  C    VAL B 485     -28.733 -19.485 -17.628  1.00 50.27      B
ATOM   7964  O    VAL B 485     -29.113 -18.918 -18.652  1.00 49.51      B
ATOM   7965  N    ALA B 486     -28.726 -20.810 -17.490  1.00 51.48      B
ATOM   7966  CA   ALA B 486     -29.174 -21.705 -18.560  1.00 51.98      B
ATOM   7967  CB   ALA B 486     -29.265 -23.128 -18.044  1.00 50.32      B
ATOM   7968  C    ALA B 486     -30.522 -21.259 -19.136  1.00 52.94      B
ATOM   7969  O    ALA B 486     -30.680 -21.145 -20.358  1.00 53.11      B
ATOM   7970  N    SER B 487     -31.489 -21.001 -18.261  1.00 53.10      B
ATOM   7971  CA   SER B 487     -32.791 -20.549 -18.720  1.00 54.33      B
ATOM   7972  CB   SER B 487     -33.674 -20.160 -17.536  1.00 54.70      B
ATOM   7973  OG   SER B 487     -32.960 -20.267 -16.318  1.00 55.70      B
ATOM   7974  C    SER B 487     -32.587 -19.342 -19.625  1.00 56.00      B
ATOM   7975  O    SER B 487     -33.024 -19.344 -20.775  1.00 56.68      B
ATOM   7976  N    CYS B 488     -31.905 -18.324 -19.102  1.00 56.95      B
ATOM   7977  CA   CYS B 488     -31.642 -17.100 -19.852  1.00 57.23      B
ATOM   7978  CB   CYS B 488     -30.743 -16.161 -19.040  1.00 57.99      B
```

FIGURE 4- 106 -

```
ATOM   7979  SG   CYS B 488    -30.476 -14.509 -19.788  1.00 60.12      B
ATOM   7980  C    CYS B 488    -30.992 -17.400 -21.197  1.00 57.24      B
ATOM   7981  O    CYS B 488    -31.393 -16.841 -22.219  1.00 57.03      B
ATOM   7982  N    LEU B 489    -29.986 -18.273 -21.195  1.00 57.47      B
ATOM   7983  CA   LEU B 489    -29.303 -18.640 -22.432  1.00 57.35      B
ATOM   7984  CB   LEU B 489    -28.198 -19.665 -22.167  1.00 56.47      B
ATOM   7985  CG   LEU B 489    -26.901 -19.075 -21.609  1.00 56.40      B
ATOM   7986  CD1  LEU B 489    -25.885 -20.174 -21.367  1.00 56.21      B
ATOM   7987  CD2  LEU B 489    -26.352 -18.052 -22.595  1.00 56.49      B
ATOM   7988  C    LEU B 489    -30.329 -19.210 -23.395  1.00 58.04      B
ATOM   7989  O    LEU B 489    -30.271 -18.962 -24.603  1.00 57.53      B
ATOM   7990  N    ARG B 490    -31.274 -19.970 -22.852  1.00 58.58      B
ATOM   7991  CA   ARG B 490    -32.334 -20.543 -23.662  1.00 59.05      B
ATOM   7992  CB   ARG B 490    -33.122 -21.577 -22.860  1.00 59.79      B
ATOM   7993  CG   ARG B 490    -32.546 -22.976 -22.948  1.00 59.87      B
ATOM   7994  CD   ARG B 490    -33.501 -23.991 -22.330  1.00 60.22      B
ATOM   7995  NE   ARG B 490    -33.392 -24.080 -20.874  1.00 58.66      B
ATOM   7996  CZ   ARG B 490    -32.303 -24.502 -20.232  1.00 57.37      B
ATOM   7997  NH1  ARG B 490    -31.221 -24.865 -20.914  1.00 55.70      B
ATOM   7998  NH2  ARG B 490    -32.307 -24.593 -18.911  1.00 56.48      B
ATOM   7999  C    ARG B 490    -33.270 -19.442 -24.160  1.00 59.14      B
ATOM   8000  O    ARG B 490    -33.455 -19.286 -25.368  1.00 59.56      B
ATOM   8001  N    LYS B 491    -33.847 -18.676 -23.234  1.00 58.71      B
ATOM   8002  CA   LYS B 491    -34.754 -17.594 -23.605  1.00 58.52      B
ATOM   8003  CB   LYS B 491    -35.103 -16.713 -22.400  1.00 59.15      B
ATOM   8004  CG   LYS B 491    -35.819 -15.404 -22.796  1.00 59.76      B
ATOM   8005  CD   LYS B 491    -36.303 -14.581 -21.592  1.00 59.46      B
ATOM   8006  CE   LYS B 491    -35.149 -14.027 -20.760  1.00 58.88      B
ATOM   8007  NZ   LYS B 491    -35.638 -13.226 -19.600  1.00 57.41      B
ATOM   8008  C    LYS B 491    -34.156 -16.716 -24.688  1.00 58.45      B
ATOM   8009  O    LYS B 491    -34.812 -16.411 -25.682  1.00 58.19      B
ATOM   8010  N    LEU B 492    -32.910 -16.301 -24.492  1.00 58.71      B
ATOM   8011  CA   LEU B 492    -32.251 -15.448 -25.468  1.00 59.49      B
ATOM   8012  CB   LEU B 492    -30.992 -14.812 -24.861  1.00 58.41      B
ATOM   8013  CG   LEU B 492    -31.097 -13.328 -24.483  1.00 56.75      B
ATOM   8014  CD1  LEU B 492    -32.348 -13.074 -23.656  1.00 57.22      B
ATOM   8015  CD2  LEU B 492    -29.864 -12.921 -23.706  1.00 55.72      B
ATOM   8016  C    LEU B 492    -31.898 -16.224 -26.731  1.00 60.41      B
ATOM   8017  O    LEU B 492    -31.841 -15.656 -27.823  1.00 61.14      B
ATOM   8018  N    GLY B 493    -31.679 -17.526 -26.582  1.00 60.81      B
ATOM   8019  CA   GLY B 493    -31.325 -18.344 -27.730  1.00 61.41      B
ATOM   8020  C    GLY B 493    -29.827 -18.340 -27.971  1.00 61.35      B
ATOM   8021  O    GLY B 493    -29.362 -18.087 -29.080  1.00 61.68      B
ATOM   8022  N    VAL B 494    -29.073 -18.627 -26.917  1.00 60.36      B
ATOM   8023  CA   VAL B 494    -27.618 -18.654 -26.976  1.00 59.49      B
ATOM   8024  CB   VAL B 494    -27.017 -17.670 -25.938  1.00 59.21      B
ATOM   8025  CG1  VAL B 494    -25.491 -17.704 -25.978  1.00 57.90      B
ATOM   8026  CG2  VAL B 494    -27.547 -16.272 -26.199  1.00 58.15      B
ATOM   8027  C    VAL B 494    -27.108 -20.056 -26.867  1.00 59.53      B
ATOM   8028  O    VAL B 494    -27.719 -20.793 -25.895  1.00 58.97      B
ATOM   8029  N    PRO B 495    -25.989 -20.454 -27.287  1.00 59.73      B
ATOM   8030  CD   PRO B 495    -25.260 -19.794 -28.386  1.00 60.00      B
ATOM   8031  CA   PRO B 495    -25.446 -21.789 -27.020  1.00 60.72      B
ATOM   8032  CB   PRO B 495    -24.100 -21.756 -27.737  1.00 60.13      B
ATOM   8033  CG   PRO B 495    -24.418 -20.930 -28.952  1.00 60.25      B
ATOM   8034  C    PRO B 495    -25.314 -22.026 -25.508  1.00 61.69      B
ATOM   8035  O    PRO B 495    -24.930 -21.121 -24.760  1.00 61.74      B
ATOM   8036  N    PRO B 496    -25.642 -23.245 -25.043  1.00 62.10      B
ATOM   8037  CD   PRO B 496    -25.959 -24.437 -25.847  1.00 61.71      B
ATOM   8038  CA   PRO B 496    -25.560 -23.589 -23.620  1.00 62.31      B
ATOM   8039  CB   PRO B 496    -26.112 -25.009 -23.574  1.00 62.46      B
ATOM   8040  CG   PRO B 496    -25.653 -25.564 -24.881  1.00 62.92      B
ATOM   8041  C    PRO B 496    -24.133 -23.507 -23.108  1.00 62.31      B
ATOM   8042  O    PRO B 496    -23.179 -23.553 -23.887  1.00 62.60      B
ATOM   8043  N    LEU B 497    -23.998 -23.385 -21.793  1.00 62.63      B
ATOM   8044  CA   LEU B 497    -22.690 -23.271 -21.160  1.00 62.18      B
ATOM   8045  CB   LEU B 497    -22.799 -23.617 -19.669  1.00 60.19      B
ATOM   8046  CG   LEU B 497    -23.659 -22.653 -18.839  1.00 58.93      B
ATOM   8047  CD1  LEU B 497    -23.593 -23.024 -17.362  1.00 56.95      B
ATOM   8048  CD2  LEU B 497    -23.161 -21.230 -19.037  1.00 58.12      B
ATOM   8049  C    LEU B 497    -21.639 -24.149 -21.827  1.00 63.20      B
ATOM   8050  O    LEU B 497    -20.499 -23.725 -22.032  1.00 62.06      B
ATOM   8051  N    ARG B 498    -22.041 -25.367 -22.177  1.00 65.17      B
ATOM   8052  CA   ARG B 498    -21.148 -26.326 -22.814  1.00 66.71      B
ATOM   8053  CB   ARG B 498    -21.917 -27.596 -23.162  1.00 69.19      B
ATOM   8054  CG   ARG B 498    -22.570 -28.250 -21.958  1.00 72.91      B
```

FIGURE 4-107-

```
ATOM   8055  CD   ARG B 498     -21.526 -28.686 -20.936  1.00 75.95           B
ATOM   8056  NE   ARG B 498     -22.103 -29.522 -19.887  1.00 77.45           B
ATOM   8057  CZ   ARG B 498     -21.391 -30.260 -19.043  1.00 78.58           B
ATOM   8058  NH1  ARG B 498     -20.062 -30.270 -19.120  1.00 79.84           B
ATOM   8059  NH2  ARG B 498     -22.009 -30.999 -18.128  1.00 78.74           B
ATOM   8060  C    ARG B 498     -20.497 -25.765 -24.069  1.00 66.42           B
ATOM   8061  O    ARG B 498     -19.275 -25.680 -24.157  1.00 67.11           B
ATOM   8062  N    THR B 499     -21.312 -25.380 -25.040  1.00 65.91           B
ATOM   8063  CA   THR B 499     -20.782 -24.835 -26.276  1.00 66.07           B
ATOM   8064  CB   THR B 499     -21.922 -24.383 -27.215  1.00 67.34           B
ATOM   8065  OG1  THR B 499     -22.680 -25.533 -27.616  1.00 68.02           B
ATOM   8066  CG2  THR B 499     -21.357 -23.698 -28.467  1.00 68.08           B
ATOM   8067  C    THR B 499     -19.825 -23.679 -26.000  1.00 65.70           B
ATOM   8068  O    THR B 499     -18.922 -23.410 -26.797  1.00 66.01           B
ATOM   8069  N    TRP B 500     -20.015 -22.995 -24.874  1.00 65.06           B
ATOM   8070  CA   TRP B 500     -19.121 -21.897 -24.511  1.00 64.75           B
ATOM   8071  CB   TRP B 500     -19.771 -20.953 -23.490  1.00 61.72           B
ATOM   8072  CG   TRP B 500     -20.800 -20.053 -24.085  1.00 58.55           B
ATOM   8073  CD2  TRP B 500     -20.573 -19.017 -25.044  1.00 56.88           B
ATOM   8074  CE2  TRP B 500     -21.834 -18.465 -25.370  1.00 56.47           B
ATOM   8075  CE3  TRP B 500     -19.426 -18.502 -25.665  1.00 56.23           B
ATOM   8076  CD1  TRP B 500     -22.150 -20.085 -23.866  1.00 57.62           B
ATOM   8077  NE1  TRP B 500     -22.779 -19.134 -24.636  1.00 56.28           B
ATOM   8078  CZ2  TRP B 500     -21.982 -17.420 -26.292  1.00 56.36           B
ATOM   8079  CZ3  TRP B 500     -19.573 -17.460 -26.585  1.00 56.74           B
ATOM   8080  CH2  TRP B 500     -20.846 -16.932 -26.888  1.00 55.82           B
ATOM   8081  C    TRP B 500     -17.853 -22.503 -23.916  1.00 66.62           B
ATOM   8082  O    TRP B 500     -16.750 -21.999 -24.135  1.00 67.38           B
ATOM   8083  N    ARG B 501     -18.022 -23.589 -23.163  1.00 67.71           B
ATOM   8084  CA   ARG B 501     -16.895 -24.284 -22.547  1.00 68.98           B
ATOM   8085  CB   ARG B 501     -17.392 -25.486 -21.735  1.00 69.07           B
ATOM   8086  CG   ARG B 501     -16.288 -26.294 -21.087  1.00 68.65           B
ATOM   8087  CD   ARG B 501     -16.833 -27.412 -20.208  1.00 69.86           B
ATOM   8088  NE   ARG B 501     -15.742 -28.228 -19.674  1.00 71.52           B
ATOM   8089  CZ   ARG B 501     -14.803 -27.783 -18.841  1.00 72.06           B
ATOM   8090  NH1  ARG B 501     -14.815 -26.521 -18.432  1.00 72.77           B
ATOM   8091  NH2  ARG B 501     -13.840 -28.596 -18.424  1.00 71.86           B
ATOM   8092  C    ARG B 501     -15.947 -24.755 -23.648  1.00 70.27           B
ATOM   8093  O    ARG B 501     -14.730 -24.826 -23.461  1.00 70.44           B
ATOM   8094  N    HIS B 502     -16.512 -25.071 -24.806  1.00 71.71           B
ATOM   8095  CA   HIS B 502     -15.699 -25.517 -25.925  1.00 73.75           B
ATOM   8096  CB   HIS B 502     -16.576 -26.107 -27.036  1.00 75.28           B
ATOM   8097  CG   HIS B 502     -15.827 -26.988 -27.988  1.00 76.78           B
ATOM   8098  CD2  HIS B 502     -15.123 -26.695 -29.109  1.00 77.01           B
ATOM   8099  ND1  HIS B 502     -15.699 -28.348 -27.798  1.00 77.42           B
ATOM   8100  CE1  HIS B 502     -14.949 -28.856 -28.761  1.00 77.99           B
ATOM   8101  NE2  HIS B 502     -14.586 -27.874 -29.568  1.00 78.05           B
ATOM   8102  C    HIS B 502     -14.935 -24.314 -26.470  1.00 74.30           B
ATOM   8103  O    HIS B 502     -13.704 -24.318 -26.540  1.00 73.94           B
ATOM   8104  N    ARG B 503     -15.681 -23.282 -26.849  1.00 74.81           B
ATOM   8105  CA   ARG B 503     -15.092 -22.068 -27.396  1.00 75.92           B
ATOM   8106  CB   ARG B 503     -16.193 -21.062 -27.736  1.00 75.87           B
ATOM   8107  CG   ARG B 503     -17.197 -21.597 -28.747  1.00 76.55           B
ATOM   8108  CD   ARG B 503     -18.219 -20.551 -29.164  1.00 76.56           B
ATOM   8109  NE   ARG B 503     -19.254 -21.130 -30.016  1.00 76.45           B
ATOM   8110  CZ   ARG B 503     -20.330 -20.478 -30.445  1.00 77.30           B
ATOM   8111  NH1  ARG B 503     -20.528 -19.207 -30.107  1.00 76.96           B
ATOM   8112  NH2  ARG B 503     -21.216 -21.101 -31.212  1.00 77.67           B
ATOM   8113  C    ARG B 503     -14.099 -21.444 -26.426  1.00 76.59           B
ATOM   8114  O    ARG B 503     -13.080 -20.880 -26.837  1.00 75.80           B
ATOM   8115  N    ALA B 504     -14.402 -21.557 -25.135  1.00 77.96           B
ATOM   8116  CA   ALA B 504     -13.548 -21.008 -24.087  1.00 79.04           B
ATOM   8117  CB   ALA B 504     -14.170 -21.256 -22.726  1.00 78.41           B
ATOM   8118  C    ALA B 504     -12.147 -21.605 -24.136  1.00 80.09           B
ATOM   8119  O    ALA B 504     -11.185 -20.991 -23.672  1.00 80.59           B
ATOM   8120  N    ARG B 505     -12.035 -22.803 -24.703  1.00 80.90           B
ATOM   8121  CA   ARG B 505     -10.746 -23.469 -24.814  1.00 80.62           B
ATOM   8122  CB   ARG B 505     -10.947 -24.979 -24.970  1.00 80.81           B
ATOM   8123  CG   ARG B 505     -11.874 -25.582 -23.912  1.00 81.50           B
ATOM   8124  CD   ARG B 505     -11.590 -27.069 -23.677  1.00 82.40           B
ATOM   8125  NE   ARG B 505     -10.216 -27.297 -23.216  1.00 82.81           B
ATOM   8126  CZ   ARG B 505      -9.770 -28.441 -22.701  1.00 82.74           B
ATOM   8127  NH1  ARG B 505     -10.587 -29.479 -22.572  1.00 83.29           B
ATOM   8128  NH2  ARG B 505      -8.504 -28.550 -22.312  1.00 82.33           B
ATOM   8129  C    ARG B 505      -9.944 -22.900 -25.989  1.00 80.86           B
ATOM   8130  O    ARG B 505      -8.754 -22.628 -25.850  1.00 80.64           B
```

FIGURE 4- 108 -

```
ATOM   8131  N    SER B 506    -10.604 -22.711 -27.132  1.00 81.73      B
ATOM   8132  CA   SER B 506     -9.966 -22.153 -28.328  1.00 82.50      B
ATOM   8133  CB   SER B 506    -10.956 -22.108 -29.502  1.00 82.50      B
ATOM   8134  OG   SER B 506    -10.602 -21.101 -30.447  1.00 80.81      B
ATOM   8135  C    SER B 506     -9.460 -20.739 -28.061  1.00 83.68      B
ATOM   8136  O    SER B 506     -8.373 -20.360 -28.504  1.00 83.87      B
ATOM   8137  N    VAL B 507    -10.266 -19.955 -27.352  1.00 84.69      B
ATOM   8138  CA   VAL B 507     -9.895 -18.586 -27.024  1.00 85.35      B
ATOM   8139  CB   VAL B 507    -10.957 -17.907 -26.116  1.00 85.86      B
ATOM   8140  CG1  VAL B 507    -10.549 -16.458 -25.822  1.00 86.23      B
ATOM   8141  CG2  VAL B 507    -12.327 -17.954 -26.793  1.00 85.83      B
ATOM   8142  C    VAL B 507     -8.556 -18.624 -26.298  1.00 84.95      B
ATOM   8143  O    VAL B 507     -7.569 -18.045 -26.760  1.00 85.25      B
ATOM   8144  N    ARG B 508     -8.533 -19.325 -25.170  1.00 84.53      B
ATOM   8145  CA   ARG B 508     -7.326 -19.466 -24.367  1.00 84.90      B
ATOM   8146  CB   ARG B 508     -7.489 -20.625 -23.381  1.00 84.51      B
ATOM   8147  CG   ARG B 508     -6.289 -20.849 -22.477  1.00 84.40      B
ATOM   8148  CD   ARG B 508     -6.395 -22.199 -21.801  1.00 84.93      B
ATOM   8149  NE   ARG B 508     -6.130 -22.124 -20.368  1.00 85.10      B
ATOM   8150  CZ   ARG B 508     -6.327 -23.132 -19.525  1.00 85.39      B
ATOM   8151  NH1  ARG B 508     -6.789 -24.237 -19.983  1.00 84.44      B
ATOM   8152  NH2  ARG B 508     -6.075 -22.980 -18.227  1.00 86.34      B
ATOM   8153  C    ARG B 508     -6.106 -19.729 -25.251  1.00 85.26      B
ATOM   8154  O    ARG B 508     -5.188 -18.904 -25.330  1.00 85.54      B
ATOM   8155  N    ALA B 509     -6.116 -20.885 -25.913  1.00 84.74      B
ATOM   8156  CA   ALA B 509     -5.030 -21.302 -26.790  1.00 83.86      B
ATOM   8157  CB   ALA B 509     -5.470 -22.500 -27.615  1.00 83.57      B
ATOM   8158  C    ALA B 509     -4.553 -20.179 -27.706  1.00 83.69      B
ATOM   8159  O    ALA B 509     -3.398 -19.757 -27.627  1.00 83.40      B
ATOM   8160  N    LYS B 510     -5.444 -19.694 -28.566  1.00 83.73      B
ATOM   8161  CA   LYS B 510     -5.108 -18.619 -29.496  1.00 84.36      B
ATOM   8162  CB   LYS B 510     -6.372 -18.098 -30.167  1.00 83.14      B
ATOM   8163  CG   LYS B 510     -7.092 -19.144 -31.021  1.00 81.26      B
ATOM   8164  CD   LYS B 510     -8.043 -18.506 -32.021  1.00 79.65      B
ATOM   8165  CE   LYS B 510     -8.724 -19.559 -32.884  1.00 78.22      B
ATOM   8166  NZ   LYS B 510     -9.466 -18.959 -34.031  1.00 76.74      B
ATOM   8167  C    LYS B 510     -4.383 -17.458 -28.809  1.00 85.94      B
ATOM   8168  O    LYS B 510     -3.453 -16.871 -29.375  1.00 86.20      B
ATOM   8169  N    LEU B 511     -4.809 -17.145 -27.586  1.00 87.27      B
ATOM   8170  CA   LEU B 511     -4.221 -16.060 -26.800  1.00 88.20      B
ATOM   8171  CB   LEU B 511     -5.222 -15.564 -25.755  1.00 87.87      B
ATOM   8172  CG   LEU B 511     -6.346 -14.637 -26.218  1.00 88.26      B
ATOM   8173  CD1  LEU B 511     -7.255 -14.362 -25.022  1.00 88.09      B
ATOM   8174  CD2  LEU B 511     -5.772 -13.329 -26.761  1.00 87.68      B
ATOM   8175  C    LEU B 511     -2.917 -16.438 -26.098  1.00 89.05      B
ATOM   8176  O    LEU B 511     -2.012 -15.609 -25.961  1.00 89.25      B
ATOM   8177  N    LEU B 512     -2.830 -17.637 -25.645  1.00 89.71      B
ATOM   8178  CA   LEU B 512     -1.639 -18.174 -24.964  1.00 89.67      B
ATOM   8179  CB   LEU B 512     -1.877 -19.589 -24.431  1.00 88.12      B
ATOM   8180  CG   LEU B 512     -1.373 -19.798 -23.005  1.00 86.90      B
ATOM   8181  CD1  LEU B 512     -2.024 -18.779 -22.074  1.00 86.47      B
ATOM   8182  CD2  LEU B 512     -1.684 -21.210 -22.564  1.00 85.84      B
ATOM   8183  C    LEU B 512     -0.469 -18.163 -25.948  1.00 90.79      B
ATOM   8184  O    LEU B 512      0.688 -18.036 -25.546  1.00 90.71      B
ATOM   8185  N    SER B 513     -0.792 -18.290 -27.238  1.00 91.95      B
ATOM   8186  CA   SER B 513      0.198 -18.270 -28.317  1.00 92.92      B
ATOM   8187  CB   SER B 513     -0.491 -18.499 -29.672  1.00 92.90      B
ATOM   8188  OG   SER B 513     -1.600 -19.382 -29.565  1.00 93.37      B
ATOM   8189  C    SER B 513      0.835 -16.875 -28.292  1.00 94.09      B
ATOM   8190  O    SER B 513      1.986 -16.691 -28.694  1.00 93.91      B
ATOM   8191  N    GLN B 514      0.055 -15.911 -27.804  1.00 95.50      B
ATOM   8192  CA   GLN B 514      0.488 -14.524 -27.687  1.00 95.98      B
ATOM   8193  CB   GLN B 514     -0.723 -13.589 -27.587  1.00 96.02      B
ATOM   8194  CG   GLN B 514     -0.396 -12.115 -27.747  1.00 95.77      B
ATOM   8195  CD   GLN B 514     -0.911 -11.542 -29.063  1.00 95.50      B
ATOM   8196  OE1  GLN B 514     -1.499 -12.256 -29.880  1.00 94.97      B
ATOM   8197  NE2  GLN B 514     -0.693 -10.245 -29.269  1.00 95.06      B
ATOM   8198  C    GLN B 514      1.357 -14.400 -26.445  1.00 96.50      B
ATOM   8199  O    GLN B 514      1.063 -14.962 -25.388  1.00 95.97      B
ATOM   8200  N    GLY B 515      2.434 -13.646 -26.594  1.00 97.50      B
ATOM   8201  CA   GLY B 515      3.361 -13.474 -25.500  1.00 98.39      B
ATOM   8202  C    GLY B 515      3.068 -12.237 -24.621  1.00 98.87      B
ATOM   8203  O    GLY B 515      2.838 -11.177 -25.096  1.00 99.23      B
ATOM   8204  N    GLY B 516      3.069 -12.518 -23.319  1.00 98.98      B
ATOM   8205  CA   GLY B 516      2.831 -11.418 -22.418  1.00 98.92      B
ATOM   8206  C    GLY B 516      1.405 -11.315 -21.939  1.00 98.80      B
```

FIGURE 4- 109 -

```
ATOM   3207  O    GLY B 516      0.867 -12.271 -21.378  1.00 98.84      B
ATOM   3208  N    ARG B 517      0.807 -10.144 -22.169  1.00 98.49      B
ATOM   3209  CA   ARG B 517     -0.563  -9.825 -21.752  1.00 97.94      B
ATOM   3210  CB   ARG B 517     -1.071  -8.554 -22.464  1.00 98.39      B
ATOM   3211  CG   ARG B 517     -0.008  -7.502 -22.765  1.00 98.55      B
ATOM   3212  CD   ARG B 517      0.882  -7.933 -23.931  1.00 98.25      B
ATOM   3213  NE   ARG B 517      2.291  -7.932 -23.554  1.00 97.92      B
ATOM   3214  CZ   ARG B 517      2.958  -6.847 -23.175  1.00 98.16      B
ATOM   3215  NH1  ARG B 517      2.342  -5.672 -23.124  1.00 97.97      B
ATOM   3216  NH2  ARG B 517      4.242  -6.939 -22.854  1.00 98.37      B
ATOM   3217  C    ARG B 517     -1.559 -10.958 -21.998  1.00 97.33      B
ATOM   3218  O    ARG B 517     -2.063 -11.576 -21.053  1.00 96.34      B
ATOM   3219  N    ALA B 518     -1.850 -11.206 -23.273  1.00 97.02      B
ATOM   3220  CA   ALA B 518     -2.788 -12.252 -23.666  1.00 96.70      B
ATOM   3221  CB   ALA B 518     -2.640 -12.563 -25.154  1.00 96.44      B
ATOM   3222  C    ALA B 518     -2.560 -13.513 -22.842  1.00 96.29      B
ATOM   3223  O    ALA B 518     -3.469 -13.991 -22.160  1.00 96.39      B
ATOM   3224  N    ALA B 519     -1.338 -14.040 -22.904  1.00 96.05      B
ATOM   3225  CA   ALA B 519     -0.969 -15.246 -22.162  1.00 95.95      B
ATOM   3226  CB   ALA B 519      0.563 -15.351 -22.039  1.00 95.69      B
ATOM   3227  C    ALA B 519     -1.606 -15.190 -20.779  1.00 95.48      B
ATOM   3228  O    ALA B 519     -2.203 -16.163 -20.312  1.00 95.11      B
ATOM   3229  N    THR B 520     -1.487 -14.025 -20.146  1.00 95.48      B
ATOM   3230  CA   THR B 520     -2.040 -13.789 -18.814  1.00 95.49      B
ATOM   3231  CB   THR B 520     -1.659 -12.386 -18.288  1.00 95.89      B
ATOM   3232  OG1  THR B 520     -0.319 -12.072 -18.690  1.00 96.10      B
ATOM   3233  CG2  THR B 520     -1.747 -12.348 -16.751  1.00 95.97      B
ATOM   3234  C    THR B 520     -3.566 -13.897 -18.846  1.00 95.07      B
ATOM   3235  O    THR B 520     -4.161 -14.671 -18.089  1.00 94.91      B
ATOM   3236  N    CYS B 521     -4.193 -13.108 -19.717  1.00 93.90      B
ATOM   3237  CA   CYS B 521     -5.644 -13.135 -19.855  1.00 92.35      B
ATOM   3238  CB   CYS B 521     -6.082 -12.366 -21.119  1.00 91.99      B
ATOM   3239  SG   CYS B 521     -5.911 -10.541 -21.051  1.00 90.89      B
ATOM   3240  C    CYS B 521     -6.093 -14.596 -19.938  1.00 92.03      B
ATOM   3241  O    CYS B 521     -6.820 -15.085 -19.074  1.00 92.13      B
ATOM   3242  N    GLY B 522     -5.631 -15.291 -20.973  1.00 91.57      B
ATOM   3243  CA   GLY B 522     -5.982 -16.687 -21.164  1.00 91.25      B
ATOM   3244  C    GLY B 522     -5.773 -17.573 -19.946  1.00 91.07      B
ATOM   3245  O    GLY B 522     -6.646 -18.368 -19.590  1.00 91.64      B
ATOM   3246  N    ARG B 523     -4.616 -17.439 -19.303  1.00 90.45      B
ATOM   3247  CA   ARG B 523     -4.280 -18.241 -18.124  1.00 89.80      B
ATOM   3248  CB   ARG B 523     -2.872 -17.888 -17.628  1.00 90.91      B
ATOM   3249  CG   ARG B 523     -2.486 -18.593 -16.338  1.00 91.87      B
ATOM   3250  CD   ARG B 523     -1.198 -18.023 -15.753  1.00 92.43      B
ATOM   3251  NE   ARG B 523     -0.859 -18.621 -14.462  1.00 92.96      B
ATOM   3252  CZ   ARG B 523      0.073 -18.147 -13.637  1.00 93.37      B
ATOM   3253  NH1  ARG B 523      0.763 -17.064 -13.967  1.00 93.56      B
ATOM   3254  NH2  ARG B 523      0.313 -18.749 -12.477  1.00 93.43      B
ATOM   3255  C    ARG B 523     -5.265 -18.106 -16.959  1.00 88.74      B
ATOM   3256  O    ARG B 523     -5.867 -19.096 -16.534  1.00 87.87      B
ATOM   3257  N    TYR B 524     -5.417 -16.880 -16.452  1.00 87.68      B
ATOM   3258  CA   TYR B 524     -6.304 -16.590 -15.321  1.00 86.39      B
ATOM   3259  CB   TYR B 524     -5.951 -15.229 -14.696  1.00 87.00      B
ATOM   3260  CG   TYR B 524     -4.675 -15.244 -13.889  1.00 88.62      B
ATOM   3261  CD1  TYR B 524     -3.426 -15.256 -14.514  1.00 88.97      B
ATOM   3262  CE1  TYR B 524     -2.250 -15.323 -13.768  1.00 89.27      B
ATOM   3263  CD2  TYR B 524     -4.717 -15.294 -12.495  1.00 89.23      B
ATOM   3264  CE2  TYR B 524     -3.551 -15.362 -11.742  1.00 89.61      B
ATOM   3265  CZ   TYR B 524     -2.319 -15.379 -12.381  1.00 89.48      B
ATOM   3266  OH   TYR B 524     -1.163 -15.471 -11.635  1.00 89.62      B
ATOM   3267  C    TYR B 524     -7.797 -16.607 -15.632  1.00 84.89      B
ATOM   3268  O    TYR B 524     -8.577 -17.287 -14.953  1.00 84.89      B
ATOM   3269  N    LEU B 525     -8.194 -15.853 -16.650  1.00 82.70      B
ATOM   3270  CA   LEU B 525     -9.598 -15.766 -17.031  1.00 80.88      B
ATOM   3271  CB   LEU B 525     -9.770 -14.810 -18.211  1.00 79.90      B
ATOM   3272  CG   LEU B 525     -9.273 -13.379 -18.033  1.00 79.56      B
ATOM   3273  CD1  LEU B 525     -9.649 -12.579 -19.269  1.00 79.57      B
ATOM   3274  CD2  LEU B 525     -9.889 -12.753 -16.786  1.00 80.27      B
ATOM   3275  C    LEU B 525    -10.222 -17.105 -17.399  1.00 80.39      B
ATOM   3276  O    LEU B 525    -11.326 -17.425 -16.952  1.00 80.15      B
ATOM   3277  N    PHE B 526     -9.504 -17.889 -18.200  1.00 79.14      B
ATOM   3278  CA   PHE B 526    -10.013 -19.172 -18.670  1.00 77.69      B
ATOM   3279  CB   PHE B 526     -9.888 -19.205 -20.189  1.00 75.14      B
ATOM   3280  CG   PHE B 526    -10.407 -17.958 -20.860  1.00 73.19      B
ATOM   3281  CD1  PHE B 526    -11.738 -17.578 -20.721  1.00 71.88      B
ATOM   3282  CD2  PHE B 526     -9.566 -17.164 -21.634  1.00 71.86      B
```

FIGURE 4- 110 -

```
ATOM   8283  CE1 PHE B 526     -12.223 -16.429 -21.343  1.00 70.78           B
ATOM   8284  CE2 PHE B 526     -10.045 -16.011 -22.260  1.00 70.31           B
ATOM   8285  CZ  PHE B 526     -11.374 -15.644 -22.115  1.00 70.02           B
ATOM   8286  C   PHE B 526      -9.365 -20.409 -18.055  1.00 78.36           B
ATOM   8287  O   PHE B 526      -9.079 -21.386 -18.744  1.00 78.60           B
ATOM   8288  N   ASN B 527      -9.156 -20.366 -16.746  1.00 79.30           B
ATOM   8289  CA  ASN B 527      -8.554 -21.480 -16.026  1.00 80.29           B
ATOM   8290  CB  ASN B 527      -7.730 -20.943 -14.850  1.00 79.83           B
ATOM   8291  CG  ASN B 527      -7.069 -22.042 -14.041  1.00 79.24           B
ATOM   8292  OD1 ASN B 527      -6.264 -22.825 -14.563  1.00 78.09           B
ATOM   8293  ND2 ASN B 527      -7.407 -22.106 -12.750  1.00 78.48           B
ATOM   8294  C   ASN B 527      -9.663 -22.414 -15.530  1.00 81.29           B
ATOM   8295  O   ASN B 527      -9.429 -23.323 -14.731  1.00 81.47           B
ATOM   8296  N   TRP B 528     -10.875 -22.182 -16.021  1.00 82.58           B
ATOM   8297  CA  TRP B 528     -12.031 -22.994 -15.641  1.00 83.86           B
ATOM   8298  CB  TRP B 528     -13.218 -22.096 -15.281  1.00 83.49           B
ATOM   8299  CG  TRP B 528     -13.576 -21.118 -16.374  1.00 83.05           B
ATOM   8300  CD2 TRP B 528     -14.427 -21.361 -17.503  1.00 82.62           B
ATOM   8301  CE2 TRP B 528     -14.459 -20.170 -18.267  1.00 82.28           B
ATOM   8302  CE3 TRP B 528     -15.165 -22.469 -17.946  1.00 82.03           B
ATOM   8303  CD1 TRP B 528     -13.138 -19.828 -16.497  1.00 82.73           B
ATOM   8304  NE1 TRP B 528     -13.665 -19.252 -17.631  1.00 81.88           B
ATOM   8305  CZ2 TRP B 528     -15.201 -20.056 -19.447  1.00 81.90           B
ATOM   8306  CZ3 TRP B 528     -15.903 -22.354 -19.122  1.00 81.78           B
ATOM   8307  CH2 TRP B 528     -15.915 -21.154 -19.858  1.00 81.66           B
ATOM   8308  C   TRP B 528     -12.449 -23.929 -16.776  1.00 84.63           B
ATOM   8309  O   TRP B 528     -13.127 -24.938 -16.551  1.00 84.38           B
ATOM   8310  N   ALA B 529     -12.038 -23.583 -17.995  1.00 85.60           B
ATOM   8311  CA  ALA B 529     -12.372 -24.372 -19.179  1.00 87.13           B
ATOM   8312  CB  ALA B 529     -12.275 -23.499 -20.435  1.00 86.82           B
ATOM   8313  C   ALA B 529     -11.502 -25.617 -19.348  1.00 87.98           B
ATOM   8314  O   ALA B 529     -11.416 -26.168 -20.446  1.00 87.83           B
ATOM   8315  N   VAL B 530     -10.867 -26.057 -18.262  1.00 89.33           B
ATOM   8316  CA  VAL B 530     -10.005 -27.238 -18.298  1.00 90.37           B
ATOM   8317  CB  VAL B 530      -8.577 -26.887 -18.787  1.00 89.51           B
ATOM   8318  CG1 VAL B 530      -8.626 -26.342 -20.199  1.00 89.36           B
ATOM   8319  CG2 VAL B 530      -7.933 -25.884 -17.839  1.00 88.82           B
ATOM   8320  C   VAL B 530      -9.840 -27.975 -16.963  1.00 91.75           B
ATOM   8321  O   VAL B 530      -9.836 -27.363 -15.890  1.00 91.60           B
ATOM   8322  N   ARG B 531      -9.715 -29.299 -17.050  1.00 93.34           B
ATOM   8323  CA  ARG B 531      -9.482 -30.145 -15.885  1.00 94.20           B
ATOM   8324  CB  ARG B 531     -10.145 -31.514 -16.065  1.00 94.81           B
ATOM   8325  CG  ARG B 531     -11.663 -31.441 -16.130  1.00 96.79           B
ATOM   8326  CD  ARG B 531     -12.303 -32.821 -16.263  1.00 98.50           B
ATOM   8327  NE  ARG B 531     -13.751 -32.726 -16.458  1.00103.24           B
ATOM   8328  CZ  ARG B 531     -14.564 -33.769 -16.623  1.00101.18           B
ATOM   8329  NH1 ARG B 531     -14.080 -35.006 -16.614  1.00101.18           B
ATOM   8330  NH2 ARG B 531     -15.866 -33.575 -16.810  1.00101.96           B
ATOM   8331  C   ARG B 531      -7.965 -30.278 -15.896  1.00 94.23           B
ATOM   8332  O   ARG B 531      -7.403 -31.340 -15.633  1.00 94.04           B
ATOM   8333  N   THR B 532      -7.326 -29.162 -16.241  1.00 94.66           B
ATOM   8334  CA  THR B 532      -5.874 -29.045 -16.340  1.00 94.90           B
ATOM   8335  CB  THR B 532      -5.465 -28.322 -17.666  1.00 94.13           B
ATOM   8336  OG1 THR B 532      -5.839 -29.128 -18.794  1.00 93.57           B
ATOM   8337  CG2 THR B 532      -3.962 -28.063 -17.702  1.00 93.46           B
ATOM   8338  C   THR B 532      -5.334 -28.249 -15.152  1.00 95.09           B
ATOM   8339  O   THR B 532      -4.598 -28.783 -14.319  1.00 95.50           B
ATOM   8340  N   LYS B 533      -5.715 -26.975 -15.092  1.00 94.88           B
ATOM   8341  CA  LYS B 533      -5.306 -26.054 -14.030  1.00 93.94           B
ATOM   8342  CB  LYS B 533      -5.226 -26.780 -12.677  1.00 92.53           B
ATOM   8343  CG  LYS B 533      -6.516 -27.458 -12.243  1.00 91.29           B
ATOM   8344  CD  LYS B 533      -6.335 -28.182 -10.918  1.00 90.13           B
ATOM   8345  CE  LYS B 533      -7.637 -28.801 -10.411  1.00 88.90           B
ATOM   8346  NZ  LYS B 533      -7.453 -29.510  -9.101  1.00 86.66           B
ATOM   8347  C   LYS B 533      -3.970 -25.351 -14.304  1.00 93.73           B
ATOM   8348  O   LYS B 533      -3.342 -25.542 -15.349  1.00 92.81           B
ATOM   8349  N   LEU B 534      -3.563 -24.531 -13.340  1.00 93.80           B
ATOM   8350  CA  LEU B 534      -2.317 -23.772 -13.386  1.00 94.20           B
ATOM   8351  CB  LEU B 534      -2.216 -22.954 -14.678  1.00 93.30           B
ATOM   8352  CG  LEU B 534      -0.938 -22.114 -14.817  1.00 93.20           B
ATOM   8353  CD1 LEU B 534       0.308 -23.008 -14.724  1.00 92.26           B
ATOM   8354  CD2 LEU B 534      -0.964 -21.374 -16.144  1.00 92.87           B
ATOM   8355  C   LEU B 534      -2.269 -22.835 -12.180  1.00 94.51           B
ATOM   8356  O   LEU B 534      -2.792 -21.720 -12.230  1.00 94.58           B
ATOM   8357  N   LYS B 535      -1.646 -23.309 -11.101  1.00 94.86           B
ATOM   8358  CA  LYS B 535      -1.506 -22.560  -9.848  1.00 94.79           B
```

FIGURE 4- 111 -

```
ATOM   8359  CB   LYS B 535     -0.332 -23.120  -9.030  1.00 94.66      B
ATOM   8360  CG   LYS B 535     -0.523 -24.571  -8.591  1.00 94.27      B
ATOM   8361  CD   LYS B 535      0.641 -25.084  -7.758  1.00 93.40      B
ATOM   8362  CE   LYS B 535      0.432 -26.539  -7.376  1.00 92.66      B
ATOM   8363  NZ   LYS B 535      1.558 -27.085  -6.567  1.00 92.00      B
ATOM   8364  C    LYS B 535     -1.344 -21.047 -10.036  1.00 94.73      B
ATOM   8365  O    LYS B 535     -0.236 -20.532 -10.219  1.00 94.43      B
ATOM   8366  N    LEU B 536     -2.476 -20.349  -9.974  1.00 94.29      B
ATOM   8367  CA   LEU B 536     -2.524 -18.901 -10.131  1.00 93.62      B
ATOM   8368  CB   LEU B 536     -3.979 -18.427 -10.245  1.00 93.90      B
ATOM   8369  CG   LEU B 536     -5.051 -19.379 -10.792  1.00 93.95      B
ATOM   8370  CD1  LEU B 536     -5.305 -20.513  -9.791  1.00 94.35      B
ATOM   8371  CD2  LEU B 536     -6.340 -18.600 -11.023  1.00 93.57      B
ATOM   8372  C    LEU B 536     -1.878 -18.255  -8.913  1.00 93.36      B
ATOM   8373  O    LEU B 536     -2.278 -18.525  -7.782  1.00 93.08      B
ATOM   8374  N    THR B 537     -0.881 -17.405  -9.149  1.00 92.90      B
ATOM   8375  CA   THR B 537     -0.175 -16.719  -8.069  1.00 92.13      B
ATOM   8376  CB   THR B 537      1.344 -17.020  -8.118  1.00 92.08      B
ATOM   8377  OG1  THR B 537      1.909 -16.471  -9.316  1.00 91.76      B
ATOM   8378  CG2  THR B 537      1.584 -18.529  -8.097  1.00 91.85      B
ATOM   8379  C    THR B 537     -0.393 -15.206  -8.161  1.00 92.10      B
ATOM   8380  O    THR B 537     -0.061 -14.583  -9.172  1.00 91.91      B
ATOM   8381  N    PRO B 538     -0.953 -14.598  -7.099  1.00 91.80      B
ATOM   8382  CD   PRO B 538     -1.140 -15.222  -5.775  1.00 91.43      B
ATOM   8383  CA   PRO B 538     -1.232 -13.157  -7.033  1.00 91.50      B
ATOM   8384  CB   PRO B 538     -1.163 -12.871  -5.540  1.00 91.36      B
ATOM   8385  CG   PRO B 538     -1.782 -14.100  -4.965  1.00 91.09      B
ATOM   8386  C    PRO B 538     -0.272 -12.291  -7.852  1.00 91.79      B
ATOM   8387  O    PRO B 538      0.748 -11.818  -7.356  1.00 91.78      B
ATOM   8388  N    ILE B 539     -0.627 -12.098  -9.116  1.00 92.21      B
ATOM   8389  CA   ILE B 539      0.154 -11.315 -10.070  1.00 92.85      B
ATOM   8390  CB   ILE B 539     -0.613 -11.227 -11.410  1.00 92.35      B
ATOM   8391  CG2  ILE B 539     -0.012 -12.200 -12.412  1.00 92.28      B
ATOM   8392  CG1  ILE B 539     -2.102 -11.515 -11.172  1.00 91.65      B
ATOM   8393  CD1  ILE B 539     -2.913 -11.743 -12.436  1.00 91.82      B
ATOM   8394  C    ILE B 539      0.561  -9.902  -9.615  1.00 94.12      B
ATOM   8395  O    ILE B 539      0.132  -9.430  -8.558  1.00 94.24      B
ATOM   8396  N    PRO B 540      1.413  -9.216 -10.410  1.00 95.43      B
ATOM   8397  CD   PRO B 540      2.145  -9.739 -11.580  1.00 95.56      B
ATOM   8398  CA   PRO B 540      1.880  -7.858 -10.089  1.00 95.65      B
ATOM   8399  CB   PRO B 540      2.776  -7.514 -11.279  1.00 95.39      B
ATOM   8400  CG   PRO B 540      3.366  -8.838 -11.623  1.00 95.06      B
ATOM   8401  C    PRO B 540      0.748  -6.849  -9.900  1.00 95.96      B
ATOM   8402  O    PRO B 540      0.202  -6.729  -8.803  1.00 95.57      B
ATOM   8403  N    ALA B 541      0.405  -6.136 -10.973  1.00 96.80      B
ATOM   8404  CA   ALA B 541     -0.662  -5.133 -10.949  1.00 97.53      B
ATOM   8405  CB   ALA B 541     -1.210  -4.914 -12.365  1.00 97.21      B
ATOM   8406  C    ALA B 541     -1.788  -5.533  -9.986  1.00 98.10      B
ATOM   8407  O    ALA B 541     -2.712  -6.272 -10.340  1.00 97.78      B
ATOM   8408  N    ALA B 542     -1.675  -5.026  -8.762  1.00 98.65      B
ATOM   8409  CA   ALA B 542     -2.606  -5.288  -7.664  1.00 99.00      B
ATOM   8410  CB   ALA B 542     -2.564  -6.768  -7.282  1.00 98.50      B
ATOM   8411  C    ALA B 542     -2.053  -4.422  -6.534  1.00 99.32      B
ATOM   8412  O    ALA B 542     -2.739  -3.549  -5.999  1.00100.12      B
ATOM   8413  N    SER B 543     -0.787  -4.663  -6.201  1.00 99.14      B
ATOM   8414  CA   SER B 543     -0.077  -3.893  -5.181  1.00 98.80      B
ATOM   8415  CB   SER B 543      1.053  -4.729  -4.566  1.00 98.65      B
ATOM   8416  OG   SER B 543      0.602  -6.029  -4.224  1.00 98.64      B
ATOM   8417  C    SER B 543      0.529  -2.712  -5.943  1.00 98.57      B
ATOM   8418  O    SER B 543      1.411  -1.999  -5.449  1.00 98.33      B
ATOM   8419  N    GLN B 544      0.039  -2.523  -7.173  1.00 97.79      B
ATOM   8420  CA   GLN B 544      0.524  -1.468  -8.058  1.00 97.23      B
ATOM   8421  CB   GLN B 544      1.649  -2.012  -8.942  1.00 97.15      B
ATOM   8422  CG   GLN B 544      2.730  -2.783  -8.205  1.00 96.56      B
ATOM   8423  CD   GLN B 544      3.689  -3.455  -9.156  1.00 96.06      B
ATOM   8424  OE1  GLN B 544      3.277  -4.225 -10.024  1.00 96.25      B
ATOM   8425  NE2  GLN B 544      4.978  -3.172  -8.999  1.00 95.86      B
ATOM   8426  C    GLN B 544     -0.556  -0.878  -8.970  1.00 96.81      B
ATOM   8427  O    GLN B 544     -0.270   0.016  -9.773  1.00 96.80      B
ATOM   8428  N    LEU B 545     -1.787  -1.371  -8.856  1.00 95.73      B
ATOM   8429  CA   LEU B 545     -2.870  -0.870  -9.699  1.00 94.51      B
ATOM   8430  CB   LEU B 545     -4.128  -1.739  -9.544  1.00 93.92      B
ATOM   8431  CG   LEU B 545     -4.123  -3.050 -10.345  1.00 93.73      B
ATOM   8432  CD1  LEU B 545     -5.342  -3.896  -9.979  1.00 92.94      B
ATOM   8433  CD2  LEU B 545     -4.119  -2.732 -11.845  1.00 93.12      B
ATOM   8434  C    LEU B 545     -3.217   0.598  -9.466  1.00 94.11      B
```

FIGURE 4- 112 -

```
ATOM   8435  O    LEU B 545      -3.390   1.052  -8.335  1.00 93.76      B
ATOM   8436  N    ASP B 546      -3.309   1.333 -10.567  1.00 93.66      B
ATOM   8437  CA   ASP B 546      -3.635   2.755 -10.544  1.00 93.29      B
ATOM   8438  CB   ASP B 546      -3.284   3.371 -11.899  1.00 92.39      B
ATOM   8439  CG   ASP B 546      -3.559   2.418 -13.053  1.00 92.34      B
ATOM   8440  OD1  ASP B 546      -4.732   2.014 -13.225  1.00 91.99      B
ATOM   8441  OD2  ASP B 546      -2.604   2.061 -13.781  1.00 92.64      B
ATOM   8442  C    ASP B 546      -5.118   2.972 -10.228  1.00 93.19      B
ATOM   8443  O    ASP B 546      -5.795   3.777 -10.873  1.00 92.88      B
ATOM   8444  N    LEU B 547      -5.611   2.244  -9.227  1.00 92.88      B
ATOM   8445  CA   LEU B 547      -7.010   2.323  -8.804  1.00 92.31      B
ATOM   8446  CB   LEU B 547      -7.327   1.199  -7.811  1.00 91.51      B
ATOM   8447  CG   LEU B 547      -8.483   0.281  -8.213  1.00 91.07      B
ATOM   8448  CD1  LEU B 547      -8.232  -0.253  -9.624  1.00 91.49      B
ATOM   8449  CD2  LEU B 547      -8.615  -0.862  -7.215  1.00 90.68      B
ATOM   8450  C    LEU B 547      -7.370   3.670  -8.178  1.00 92.13      B
ATOM   8451  O    LEU B 547      -7.711   3.746  -6.993  1.00 92.33      B
ATOM   8452  N    SER B 548      -7.294   4.722  -8.992  1.00 91.48      B
ATOM   8453  CA   SER B 548      -7.596   6.096  -8.574  1.00 90.53      B
ATOM   8454  CB   SER B 548      -7.724   7.003  -9.813  1.00 90.16      B
ATOM   8455  OG   SER B 548      -8.724   6.525 -10.704  1.00 89.28      B
ATOM   8456  C    SER B 548      -8.861   6.221  -7.707  1.00 89.84      B
ATOM   8457  O    SER B 548      -8.901   5.764  -6.553  1.00 89.81      B
ATOM   8458  N    GLY B 549      -9.985   6.864  -8.260  1.00 88.50      B
ATOM   8459  CA   GLY B 549     -11.132   7.037  -7.537  1.00 86.79      B
ATOM   8460  C    GLY B 549     -12.241   6.208  -8.153  1.00 85.59      B
ATOM   8461  O    GLY B 549     -13.234   6.749  -8.655  1.00 85.81      B
ATOM   8462  N    TRP B 550     -12.072   4.888  -8.118  1.00 83.54      B
ATOM   8463  CA   TRP B 550     -13.068   3.989  -8.688  1.00 81.50      B
ATOM   8464  CB   TRP B 550     -12.496   2.585  -8.893  1.00 83.10      B
ATOM   8465  CG   TRP B 550     -11.407   2.496  -9.905  1.00 84.51      B
ATOM   8466  CD2  TRP B 550     -11.522   2.008 -11.243  1.00 85.05      B
ATOM   8467  CE2  TRP B 550     -10.236   2.076 -11.822  1.00 85.62      B
ATOM   8468  CE3  TRP B 550     -12.587   1.518 -12.010  1.00 85.56      B
ATOM   8469  CD1  TRP B 550     -10.099   2.836  -9.731  1.00 85.17      B
ATOM   8470  NE1  TRP B 550      -9.387   2.585 -10.877  1.00 85.93      B
ATOM   8471  CZ2  TRP B 550      -9.983   1.672 -13.135  1.00 86.64      B
ATOM   8472  CZ3  TRP B 550     -12.335   1.114 -13.319  1.00 86.52      B
ATOM   8473  CH2  TRP B 550     -11.040   1.195 -13.867  1.00 86.81      B
ATOM   8474  C    TRP B 550     -14.287   3.877  -7.799  1.00 79.06      B
ATOM   8475  O    TRP B 550     -15.430   4.010  -8.257  1.00 78.64      B
ATOM   8476  N    PHE B 551     -14.037   3.631  -6.521  1.00 75.36      B
ATOM   8477  CA   PHE B 551     -15.127   3.465  -5.587  1.00 72.43      B
ATOM   8478  CB   PHE B 551     -15.104   2.034  -5.073  1.00 71.51      B
ATOM   8479  CG   PHE B 551     -15.204   1.029  -6.180  1.00 70.21      B
ATOM   8480  CD1  PHE B 551     -16.417   0.792  -6.812  1.00 69.89      B
ATOM   8481  CD2  PHE B 551     -14.065   0.412  -6.676  1.00 70.27      B
ATOM   8482  CE1  PHE B 551     -16.493  -0.040  -7.929  1.00 69.54      B
ATOM   8483  CE2  PHE B 551     -14.130  -0.420  -7.791  1.00 69.98      B
ATOM   8484  CZ   PHE B 551     -15.346  -0.644  -8.419  1.00 69.30      B
ATOM   8485  C    PHE B 551     -15.104   4.495  -4.483  1.00 70.65      B
ATOM   8486  O    PHE B 551     -14.835   4.210  -3.313  1.00 70.47      B
ATOM   8487  N    VAL B 552     -15.409   5.713  -4.913  1.00 68.31      B
ATOM   8488  CA   VAL B 552     -15.458   6.836  -4.060  1.00 66.24      B
ATOM   8489  CB   VAL B 552     -14.528   7.981  -4.611  1.00 66.11      B
ATOM   8490  CG1  VAL B 552     -14.667   9.262  -3.795  1.00 65.46      B
ATOM   8491  CG2  VAL B 552     -13.100   7.475  -4.605  1.00 66.76      B
ATOM   8492  C    VAL B 552     -16.878   7.437  -3.980  1.00 64.27      B
ATOM   8493  O    VAL B 552     -17.439   7.571  -2.889  1.00 63.37      B
ATOM   8494  N    ALA B 553     -17.459   7.743  -5.137  1.00 61.84      B
ATOM   8495  CA   ALA B 553     -18.801   8.302  -5.181  1.00 60.06      B
ATOM   8496  CB   ALA B 553     -18.734   9.734  -4.850  1.00 59.96      B
ATOM   8497  C    ALA B 553     -19.508   8.102  -6.524  1.00 59.20      B
ATOM   8498  O    ALA B 553     -18.870   8.079  -7.581  1.00 58.67      B
ATOM   8499  N    GLY B 554     -20.832   7.969  -6.470  1.00 57.32      B
ATOM   8500  CA   GLY B 554     -21.610   7.739  -7.682  1.00 55.92      B
ATOM   8501  C    GLY B 554     -21.774   9.103  -8.419  1.00 55.32      B
ATOM   8502  O    GLY B 554     -21.833  10.162  -7.795  1.00 56.25      B
ATOM   8503  N    TYR B 555     -21.842   9.041  -9.744  1.00 54.09      B
ATOM   8504  CA   TYR B 555     -21.995  10.240 -10.565  1.00 52.91      B
ATOM   8505  CB   TYR B 555     -20.645  10.659 -11.155  1.00 52.19      B
ATOM   8506  CG   TYR B 555     -19.588  10.942 -10.115  1.00 52.52      B
ATOM   8507  CD1  TYR B 555     -19.686  12.056  -9.275  1.00 51.51      B
ATOM   8508  CE1  TYR B 555     -18.725  12.302  -8.292  1.00 51.35      B
ATOM   8509  CD2  TYR B 555     -18.501  10.080  -9.949  1.00 51.60      B
ATOM   8510  CE2  TYR B 555     -17.538  10.314  -8.971  1.00 51.64      B
```

FIGURE 4- 113 -

```
ATOM   8511  CZ   TYR B 555     -17.654  11.426  -8.145  1.00 51.53      B
ATOM   8512  OH   TYR B 555     -16.703  11.652  -7.174  1.00 49.78      B
ATOM   8513  C    TYR B 555     -22.968   9.971 -11.701  1.00 52.49      B
ATOM   8514  O    TYR B 555     -22.874  10.585 -12.767  1.00 51.73      B
ATOM   8515  N    SER B 556     -23.903   9.054 -11.475  1.00 52.23      B
ATOM   8516  CA   SER B 556     -24.866   8.706 -12.512  1.00 52.19      B
ATOM   8517  CB   SER B 556     -25.866   7.666 -11.992  1.00 52.55      B
ATOM   8518  OG   SER B 556     -26.594   7.093 -13.069  1.00 50.11      B
ATOM   8519  C    SER B 556     -25.602   9.947 -12.990  1.00 51.51      B
ATOM   8520  O    SER B 556     -26.379  10.534 -12.241  1.00 50.33      B
ATOM   8521  N    GLY B 557     -25.345  10.339 -14.238  1.00 51.42      B
ATOM   8522  CA   GLY B 557     -25.986  11.516 -14.804  1.00 51.55      B
ATOM   8523  C    GLY B 557     -25.270  12.809 -14.447  1.00 52.06      B
ATOM   8524  O    GLY B 557     -25.729  13.908 -14.765  1.00 51.65      B
ATOM   8525  N    GLY B 558     -24.128  12.674 -13.787  1.00 52.55      B
ATOM   8526  CA   GLY B 558     -23.367  13.838 -13.385  1.00 53.96      B
ATOM   8527  C    GLY B 558     -22.411  14.387 -14.428  1.00 55.08      B
ATOM   8528  O    GLY B 558     -21.687  15.338 -14.146  1.00 56.32      B
ATOM   8529  N    ASP B 559     -22.384  13.800 -15.621  1.00 55.28      B
ATOM   8530  CA   ASP B 559     -21.493  14.296 -16.666  1.00 55.18      B
ATOM   8531  CB   ASP B 559     -21.920  15.731 -17.037  1.00 54.15      B
ATOM   8532  CG   ASP B 559     -21.181  16.285 -18.245  1.00 54.33      B
ATOM   8533  OD1  ASP B 559     -21.128  15.596 -19.287  1.00 54.53      B
ATOM   8534  OD2  ASP B 559     -20.666  17.422 -18.158  1.00 54.95      B
ATOM   8535  C    ASP B 559     -20.038  14.259 -16.170  1.00 55.99      B
ATOM   8536  O    ASP B 559     -19.261  15.187 -16.416  1.00 57.34      B
ATOM   8537  N    ILE B 560     -19.675  13.184 -15.471  1.00 56.04      B
ATOM   8538  CA   ILE B 560     -18.322  13.024 -14.936  1.00 56.21      B
ATOM   8539  CB   ILE B 560     -18.357  12.534 -13.461  1.00 55.22      B
ATOM   8540  CG2  ILE B 560     -16.944  12.281 -12.942  1.00 54.41      B
ATOM   8541  CG1  ILE B 560     -19.048  13.581 -12.584  1.00 52.99      B
ATOM   8542  CD1  ILE B 560     -18.335  14.906 -12.519  1.00 52.03      B
ATOM   8543  C    ILE B 560     -17.473  12.066 -15.776  1.00 57.61      B
ATOM   8544  O    ILE B 560     -17.961  11.067 -16.297  1.00 55.46      B
ATOM   8545  N    TYR B 561     -16.188  12.392 -15.883  1.00 61.19      B
ATOM   8546  CA   TYR B 561     -15.231  11.623 -16.669  1.00 64.69      B
ATOM   8547  CB   TYR B 561     -14.996  12.321 -18.018  1.00 66.59      B
ATOM   8548  CG   TYR B 561     -14.026  11.616 -18.950  1.00 69.59      B
ATOM   8549  CD1  TYR B 561     -14.445  10.545 -19.747  1.00 70.33      B
ATOM   8550  CE1  TYR B 561     -13.554   9.882 -20.599  1.00 71.19      B
ATOM   8551  CD2  TYR B 561     -12.686  12.010 -19.028  1.00 70.57      B
ATOM   8552  CE2  TYR B 561     -11.785  11.355 -19.873  1.00 71.96      B
ATOM   8553  CZ   TYR B 561     -12.224  10.292 -20.656  1.00 72.68      B
ATOM   8554  OH   TYR B 561     -11.335   9.643 -21.489  1.00 74.04      B
ATOM   8555  C    TYR B 561     -13.895  11.501 -15.946  1.00 66.57      B
ATOM   8556  O    TYR B 561     -12.951  12.221 -16.266  1.00 67.40      B
ATOM   8557  N    HIS B 562     -13.802  10.603 -14.973  1.00 68.65      B
ATOM   8558  CA   HIS B 562     -12.540  10.434 -14.263  1.00 71.28      B
ATOM   8559  CB   HIS B 562     -12.732   9.555 -13.029  1.00 71.94      B
ATOM   8560  CG   HIS B 562     -13.398  10.257 -11.885  1.00 72.11      B
ATOM   8561  CD2  HIS B 562     -13.869  11.521 -11.768  1.00 72.16      B
ATOM   8562  ND1  HIS B 562     -13.625   9.650 -10.669  1.00 72.31      B
ATOM   8563  CE1  HIS B 562     -14.205  10.510  -9.851  1.00 72.54      B
ATOM   8564  NE2  HIS B 562     -14.365  11.652 -10.493  1.00 71.74      B
ATOM   8565  C    HIS B 562     -11.505   9.812 -15.195  1.00 72.97      B
ATOM   8566  O    HIS B 562     -11.797   8.840 -15.888  1.00 73.36      B
ATOM   8567  N    SER B 563     -10.299  10.378 -15.214  1.00 75.53      B
ATOM   8568  CA   SER B 563      -9.219   9.879 -16.077  1.00 77.13      B
ATOM   8569  CB   SER B 563      -8.992  10.851 -17.250  1.00 77.92      B
ATOM   8570  OG   SER B 563      -8.684  12.163 -16.796  1.00 77.68      B
ATOM   8571  C    SER B 563      -7.887   9.640 -15.345  1.00 77.50      B
ATOM   8572  O    SER B 563      -7.469   8.462 -15.238  1.00 77.02      B
ATOM   8573  OXT  SER B 563      -7.277  10.633 -14.889  1.00 78.15      B
ATOM   8574  OH2  WAT S   1     -23.181  47.630  46.595  1.00 20.28      S
ATOM   8575  OH2  WAT S   2     -28.571  24.452   6.488  1.00 15.98      S
ATOM   8576  OH2  WAT S   3     -21.765  47.737   4.285  1.00 12.26      S
ATOM   8577  OH2  WAT S   4     -11.569  40.014  17.279  1.00 11.52      S
ATOM   8578  OH2  WAT S   5     -17.080  27.282   8.155  1.00 11.95      S
ATOM   8579  OH2  WAT S   6     -16.315  39.382  39.899  1.00 19.75      S
ATOM   8580  OH2  WAT S   7     -18.774  50.916  14.438  1.00 15.60      S
ATOM   8581  OH2  WAT S   8       0.039  36.208  33.137  1.00 13.00      S
ATOM   8582  OH2  WAT S   9     -15.956  34.423  13.420  1.00 13.63      S
ATOM   8583  OH2  WAT S  10     -29.158  33.182  21.795  1.00 24.58      S
ATOM   8584  OH2  WAT S  11     -29.373  21.245 -22.071  1.00 20.23      S
ATOM   8585  OH2  WAT S  12      -8.120  21.767  19.466  1.00 27.41      S
ATOM   8586  OH2  WAT S  13     -36.352   2.696  -5.764  1.00 20.34      S
```

FIGURE 4-114 -

```
ATOM   8587  OH2 WAT S  14    -23.068  24.070  28.133  1.00 17.55      S
ATOM   8588  OH2 WAT S  15     -7.189  40.438  33.462  1.00 25.61      S
ATOM   8589  OH2 WAT S  16    -19.666  50.553   6.107  1.00 29.57      S
ATOM   8590  OH2 WAT S  17    -16.839  45.340  45.411  1.00 14.96      S
ATOM   8591  OH2 WAT S  18    -38.630  17.636   2.535  1.00 21.59      S
ATOM   8592  OH2 WAT S  19     -7.960 -19.506  -5.261  1.00 33.84      S
ATOM   8593  OH2 WAT S  20    -32.154  21.928   7.467  1.00 16.73      S
ATOM   8594  OH2 WAT S  21    -35.188  48.503  51.369  1.00 34.30      S
ATOM   8595  OH2 WAT S  22    -22.401  36.677 -17.576  1.00 17.86      S
ATOM   8596  OH2 WAT S  23     -0.706  38.464  31.006  1.00 23.32      S
ATOM   8597  OH2 WAT S  24    -25.799  38.047  21.261  1.00 18.14      S
ATOM   8598  OH2 WAT S  25    -31.206  38.232  -8.482  1.00 19.65      S
ATOM   8599  OH2 WAT S  26    -12.343  27.066  -2.345  1.00 15.27      S
ATOM   8600  OH2 WAT S  27    -36.608  15.103 -14.539  1.00 22.68      S
ATOM   8601  OH2 WAT S  28    -15.558  33.274  -3.512  1.00 32.27      S
ATOM   8602  OH2 WAT S  29    -17.173  53.773  32.141  1.00 29.41      S
ATOM   8603  OH2 WAT S  30    -13.421  33.841  14.081  1.00 35.29      S
ATOM   8604  OH2 WAT S  31    -35.930  48.773  12.325  1.00 36.34      S
ATOM   8605  OH2 WAT S  32     -9.728  38.169   6.801  1.00 22.49      S
ATOM   8606  OH2 WAT S  33    -28.800  46.965  -6.203  1.00 26.20      S
ATOM   8607  OH2 WAT S  34      1.517  36.551  18.860  1.00 19.44      S
ATOM   8608  OH2 WAT S  35    -20.921  31.168  51.051  1.00 23.94      S
ATOM   8609  OH2 WAT S  36    -26.605  40.177  17.721  1.00 27.12      S
ATOM   8610  OH2 WAT S  37    -21.061  44.053  49.377  1.00 34.09      S
ATOM   8611  OH2 WAT S  38    -28.012  38.439  19.424  1.00 13.89      S
ATOM   8612  OH2 WAT S  39    -26.159  70.842  38.084  1.00 27.31      S
ATOM   8613  OH2 WAT S  40     -8.339  39.307  35.519  1.00 21.93      S
ATOM   8614  OH2 WAT S  41      2.758  34.243  17.544  1.00 31.48      S
ATOM   8615  OH2 WAT S  42    -16.136  43.836  47.588  1.00 21.33      S
ATOM   8616  OH2 WAT S  43    -13.474  57.076  42.910  1.00 34.44      S
ATOM   8617  OH2 WAT S  44    -34.094  15.488   0.945  1.00 45.62      S
ATOM   8618  OH2 WAT S  45    -34.141  24.261 -14.573  1.00 28.00      S
ATOM   8619  OH2 WAT S  46    -22.950  39.657  10.872  1.00 38.20      S
ATOM   8620  OH2 WAT S  47    -27.578   2.651   8.308  1.00 31.95      S
ATOM   8621  OH2 WAT S  48    -29.484  49.589  19.131  1.00 24.24      S
ATOM   8622  OH2 WAT S  49    -24.213  53.870  33.359  1.00 13.24      S
ATOM   8623  OH2 WAT S  50    -43.916  13.178 -26.102  1.00 24.36      S
ATOM   8624  OH2 WAT S  51    -18.949  50.257  44.232  1.00 20.76      S
ATOM   8625  OH2 WAT S  52    -40.220  -2.679  -2.036  1.00 18.45      S
ATOM   8626  OH2 WAT S  53    -26.654  39.434  -7.744  1.00 30.58      S
ATOM   8627  OH2 WAT S  54    -21.562  26.379   6.469  1.00 32.75      S
ATOM   8628  OH2 WAT S  55    -38.475  32.011   1.390  1.00 19.27      S
ATOM   8629  OH2 WAT S  56    -15.884  53.042  18.458  1.00 21.38      S
ATOM   8630  OH2 WAT S  57    -29.418 -16.631  -7.896  1.00 28.45      S
ATOM   8631  OH2 WAT S  58    -17.833  45.197   1.213  1.00 23.26      S
ATOM   8632  OH2 WAT S  59    -31.262  29.275 -18.994  1.00 18.69      S
ATOM   8633  OH2 WAT S  60    -48.050  21.667  -9.625  1.00 30.30      S
ATOM   8634  OH2 WAT S  61    -23.394  36.323  -2.436  1.00 17.79      S
ATOM   8635  OH2 WAT S  62    -20.115  43.912  10.837  1.00 25.17      S
ATOM   8636  OH2 WAT S  63    -36.251  10.430  16.106  1.00 35.09      S
ATOM   8637  OH2 WAT S  64    -22.620   1.003 -12.915  1.00 25.86      S
ATOM   8638  OH2 WAT S  65    -19.981  63.538  50.509  1.00 31.39      S
ATOM   8639  C1  BI  I   1    -24.197 -17.114 -30.702  1.00 80.00      I
ATOM   8640  C2  BI  I   1    -25.564 -16.682 -30.639  1.00 81.40      I
ATOM   8641  C3  BI  I   1    -25.931 -15.556 -29.826  1.00 82.30      I
ATOM   8642  C4  BI  I   1    -24.930 -14.866 -29.086  1.00 82.23      I
ATOM   8643  C5  BI  I   1    -23.560 -15.302 -29.152  1.00 81.73      I
ATOM   8644  C6  BI  I   1    -23.199 -16.418 -29.956  1.00 81.31      I
ATOM   8645  N7  BI  I   1    -27.165 -14.933 -29.589  1.00 82.50      I
ATOM   8646  C8  BI  I   1    -26.968 -13.853 -28.698  1.00 81.63      I
ATOM   8647  C9  BI  I   1    -25.591 -13.785 -28.372  1.00 81.70      I
ATOM   8648  C10 BI  I   1    -24.918 -12.752 -27.431  1.00 80.87      I
ATOM   8649  C11 BI  I   1    -24.419 -13.396 -26.108  1.00 80.44      I
ATOM   8650  C12 BI  I   1    -23.698 -12.382 -25.197  1.00 80.23      I
ATOM   8651  C13 BI  I   1    -22.545 -11.657 -25.920  1.00 79.60      I
ATOM   8652  C14 BI  I   1    -22.988 -11.019 -27.247  1.00 79.15      I
ATOM   8653  C15 BI  I   1    -23.754 -11.999 -28.158  1.00 80.08      I
ATOM   8654  C16 BI  I   1    -27.999 -12.952 -28.197  1.00 80.62      I
ATOM   8655  C17 BI  I   1    -28.859 -12.130 -28.963  1.00 80.60      I
ATOM   8656  C18 BI  I   1    -29.660 -11.459 -28.062  1.00 80.50      I
ATOM   8657  O19 BI  I   1    -29.342 -11.821 -26.783  1.00 79.95      I
ATOM   8658  C20 BI  I   1    -28.330 -12.731 -26.873  1.00 80.43      I
ATOM   8659  C21 BI  I   1    -23.807 -18.303 -31.562  1.00 78.68      I
ATOM   8660  O22 BI  I   1    -22.583 -18.648 -31.590  1.00 76.82      I
ATOM   8661  O23 BI  I   1    -24.722 -18.900 -32.215  1.00 77.79      I
ATOM   8662  C24 BI  I   1    -28.455 -15.363 -30.192  1.00 83.42      I
```

FIGURE 4-115-

```
ATOM   8663  C25  BI  I   1     -28.716  -14.699  -31.566  1.00  84.61           I
ATOM   8664  O26  BI  I   1     -27.779  -14.225  -32.229  1.00  83.17           I
ATOM   8665  N27  BI  I   1     -30.069  -14.636  -32.050  1.00  85.96           I
ATOM   8666  C28  BI  I   1     -31.210  -15.215  -31.275  1.00  86.92           I
ATOM   8667  C29  BI  I   1     -32.418  -14.252  -31.193  1.00  88.44           I
ATOM   8668  C30  BI  I   1     -32.750  -13.582  -32.550  1.00  88.67           I
ATOM   8669  C31  BI  I   1     -31.509  -12.978  -33.236  1.00  88.08           I
ATOM   8670  C32  BI  I   1     -30.353  -13.990  -33.357  1.00  86.78           I
ATOM   8671  C33  BI  I   1     -33.847  -12.494  -32.393  1.00  88.96           I
ATOM   8672  O34  BI  I   1     -33.724  -11.630  -31.464  1.00  89.42           I
ATOM   8673  O35  BI  I   1     -34.815  -12.509  -33.214  1.00  88.60           I
ATOM   8674  S    SO4 S 101     -11.150   50.072   23.239  1.00  89.61           S
ATOM   8675  O1   SO4 S 101     -10.249   51.220   22.991  1.00  89.47           S
ATOM   8676  O2   SO4 S 101     -11.956   50.320   24.455  1.00  89.55           S
ATOM   8677  O3   SO4 S 101     -12.062   49.885   22.081  1.00  89.00           S
ATOM   8678  O4   SO4 S 101     -10.336   48.849   23.440  1.00  89.75           S
ATOM   8679  S    SO4 S 102     -21.138   43.824   21.804  1.00  73.22           S
ATOM   8680  O1   SO4 S 102     -19.861   44.554   21.915  1.00  73.85           S
ATOM   8681  O2   SO4 S 102     -21.669   43.534   23.151  1.00  73.71           S
ATOM   8682  O3   SO4 S 102     -22.127   44.635   21.057  1.00  73.58           S
ATOM   8683  O4   SO4 S 102     -20.898   42.559   21.085  1.00  73.37           S
ATOM   8684  S    SO4 S 103     -39.281    3.031  -11.466  1.00  94.04           S
ATOM   8685  O1   SO4 S 103     -38.563    4.289  -11.162  1.00  93.99           S
ATOM   8686  O2   SO4 S 103     -39.947    2.522  -10.243  1.00  94.46           S
ATOM   8687  O3   SO4 S 103     -40.309    3.265  -12.512  1.00  93.25           S
ATOM   8688  O4   SO4 S 103     -38.309    2.020  -11.939  1.00  94.05           S
END
```

FIGURE 5-1-

| | | | | | | | | | | |
|---|---|---|---|---|---|---|---|---|---|---|
| ATOM | 1 | CB | SER | A | 1 | -7.308 | 44.263 | 4.785 | 1.00 32.17 | A |
| ATOM | 2 | CG | SER | A | 1 | -8.477 | 43.883 | 5.490 | 1.00 33.66 | A |
| ATOM | 3 | C | SER | A | 1 | -6.491 | 45.581 | 6.726 | 1.00 33.83 | A |
| ATOM | 4 | C | SER | A | 1 | -6.804 | 45.323 | 7.879 | 1.00 34.74 | A |
| ATOM | 5 | N | SER | A | 1 | -5.931 | 43.225 | 6.546 | 1.00 35.92 | A |
| ATOM | 6 | CA | SER | A | 1 | -6.152 | 44.467 | 5.757 | 1.00 33.74 | A |
| ATOM | 7 | N | MET | A | 2 | -6.421 | 46.822 | 6.268 | 1.00 34.02 | A |
| ATOM | 8 | CA | MET | A | 2 | -6.747 | 47.942 | 7.130 | 1.00 33.81 | A |
| ATOM | 9 | CB | MET | A | 2 | -6.570 | 49.260 | 6.385 | 1.00 33.94 | A |
| ATOM | 10 | CG | MET | A | 2 | -5.141 | 49.555 | 6.027 | 1.00 33.42 | A |
| ATOM | 11 | SD | MET | A | 2 | -4.094 | 49.441 | 7.472 | 1.00 40.73 | A |
| ATOM | 12 | CE | MET | A | 2 | -4.562 | 50.914 | 8.372 | 1.00 35.00 | A |
| ATOM | 13 | C | MET | A | 2 | -8.182 | 47.830 | 7.603 | 1.00 34.31 | A |
| ATOM | 14 | C | MET | A | 2 | -9.093 | 47.595 | 6.811 | 1.00 35.54 | A |
| ATOM | 15 | N | SER | A | 3 | -8.380 | 47.992 | 8.904 | 1.00 34.78 | A |
| ATOM | 16 | CA | SER | A | 3 | -9.714 | 47.927 | 9.479 | 1.00 34.32 | A |
| ATOM | 17 | CB | SER | A | 3 | -9.627 | 48.093 | 10.999 | 1.00 34.22 | A |
| ATOM | 18 | CG | SER | A | 3 | -9.065 | 49.350 | 11.334 | 1.00 36.29 | A |
| ATOM | 19 | C | SER | A | 3 | -10.535 | 49.063 | 8.868 | 1.00 33.41 | A |
| ATOM | 20 | C | SER | A | 3 | -11.727 | 48.922 | 8.610 | 1.00 32.47 | A |
| ATOM | 21 | N | TYR | A | 4 | -9.872 | 50.188 | 8.625 | 1.00 33.49 | A |
| ATOM | 22 | CA | TYR | A | 4 | -10.524 | 51.357 | 8.049 | 1.00 34.47 | A |
| ATOM | 23 | CB | TYR | A | 4 | -10.934 | 52.326 | 9.161 | 1.00 33.68 | A |
| ATOM | 24 | CG | TYR | A | 4 | -12.073 | 51.845 | 10.030 | 1.00 35.72 | A |
| ATOM | 25 | CD1 | TYR | A | 4 | -13.400 | 52.005 | 9.626 | 1.00 34.60 | A |
| ATOM | 26 | CE1 | TYR | A | 4 | -14.445 | 51.579 | 10.425 | 1.00 34.05 | A |
| ATOM | 27 | CD2 | TYR | A | 4 | -11.828 | 51.235 | 11.263 | 1.00 34.68 | A |
| ATOM | 28 | CE2 | TYR | A | 4 | -12.874 | 50.797 | 12.065 | 1.00 32.44 | A |
| ATOM | 29 | CZ | TYR | A | 4 | -14.175 | 50.973 | 11.642 | 1.00 33.27 | A |
| ATOM | 30 | OH | TYR | A | 4 | -15.211 | 50.531 | 12.432 | 1.00 35.84 | A |
| ATOM | 31 | C | TYR | A | 4 | -9.630 | 52.105 | 7.056 | 1.00 35.31 | A |
| ATOM | 32 | C | TYR | A | 4 | -8.401 | 51.998 | 7.090 | 1.00 35.08 | A |
| ATOM | 33 | N | THR | A | 5 | -10.275 | 52.854 | 6.169 | 1.00 35.26 | A |
| ATOM | 34 | CA | THR | A | 5 | -9.604 | 53.683 | 5.179 | 1.00 34.29 | A |
| ATOM | 35 | CB | THR | A | 5 | -9.646 | 53.064 | 3.803 | 1.00 33.16 | A |
| ATOM | 36 | CG1 | THR | A | 5 | -8.652 | 52.040 | 3.717 | 1.00 35.42 | A |
| ATOM | 37 | CG2 | THR | A | 5 | -9.378 | 54.113 | 2.756 | 1.00 33.79 | A |
| ATOM | 38 | C | THR | A | 5 | -10.392 | 54.982 | 5.142 | 1.00 36.05 | A |
| ATOM | 39 | C | THR | A | 5 | -11.618 | 54.962 | 5.072 | 1.00 37.55 | A |
| ATOM | 40 | N | TRP | A | 6 | -9.704 | 56.114 | 5.181 | 1.00 36.14 | A |
| ATOM | 41 | CA | TRP | A | 6 | -10.410 | 57.386 | 5.179 | 1.00 35.86 | A |
| ATOM | 42 | CB | TRP | A | 6 | -10.727 | 58.132 | 6.484 | 1.00 33.22 | A |
| ATOM | 43 | CG | TRP | A | 6 | -10.224 | 57.238 | 7.683 | 1.00 33.15 | A |
| ATOM | 44 | CD2 | TRP | A | 6 | -11.415 | 56.874 | 8.393 | 1.00 33.00 | A |
| ATOM | 45 | CE2 | TRP | A | 6 | -11.034 | 55.989 | 9.419 | 1.00 33.89 | A |
| ATOM | 46 | CE3 | TRP | A | 6 | -12.768 | 57.215 | 8.264 | 1.00 33.18 | A |
| ATOM | 47 | CD1 | TRP | A | 6 | -9.201 | 56.575 | 8.290 | 1.00 33.09 | A |
| ATOM | 48 | NE1 | TRP | A | 6 | -9.676 | 55.822 | 9.334 | 1.00 34.18 | A |
| ATOM | 49 | CZ2 | TRP | A | 6 | -11.960 | 55.432 | 10.308 | 1.00 32.64 | A |
| ATOM | 50 | CZ3 | TRP | A | 6 | -13.685 | 56.662 | 9.151 | 1.00 30.67 | A |
| ATOM | 51 | CH2 | TRP | A | 6 | -13.275 | 55.784 | 10.158 | 1.00 30.95 | A |
| ATOM | 52 | C | TRP | A | 6 | -10.100 | 58.275 | 3.983 | 1.00 35.46 | A |
| ATOM | 53 | C | TRP | A | 6 | -8.964 | 58.360 | 3.521 | 1.00 35.59 | A |
| ATOM | 54 | N | THR | A | 7 | -11.135 | 58.931 | 3.482 | 1.00 34.58 | A |
| ATOM | 55 | CA | THR | A | 7 | -10.995 | 59.812 | 2.343 | 1.00 35.33 | A |
| ATOM | 56 | CB | THR | A | 7 | -12.357 | 60.145 | 1.743 | 1.00 34.91 | A |
| ATOM | 57 | CG1 | THR | A | 7 | -13.142 | 60.822 | 2.735 | 1.00 32.64 | A |
| ATOM | 58 | CG2 | THR | A | 7 | -13.068 | 58.876 | 1.271 | 1.00 32.06 | A |
| ATOM | 59 | C | THR | A | 7 | -10.368 | 61.118 | 2.814 | 1.00 37.63 | A |
| ATOM | 60 | C | THR | A | 7 | -9.585 | 61.746 | 2.098 | 1.00 38.17 | A |
| ATOM | 61 | N | GLY | A | 8 | -10.729 | 61.518 | 4.025 | 1.00 37.40 | A |
| ATOM | 62 | CA | GLY | A | 8 | -10.220 | 62.754 | 4.580 | 1.00 38.06 | A |
| ATOM | 63 | C | GLY | A | 8 | -11.365 | 63.563 | 5.160 | 1.00 39.70 | A |
| ATOM | 64 | C | GLY | A | 8 | -11.168 | 64.372 | 6.073 | 1.00 40.12 | A |
| ATOM | 65 | N | ALA | A | 9 | -12.567 | 63.347 | 4.622 | 1.00 39.36 | A |
| ATOM | 66 | CA | ALA | A | 9 | -13.756 | 64.037 | 5.099 | 1.00 38.55 | A |
| ATOM | 67 | CB | ALA | A | 9 | -14.959 | 63.602 | 4.307 | 1.00 38.68 | A |
| ATOM | 68 | C | ALA | A | 9 | -13.952 | 63.719 | 6.580 | 1.00 40.04 | A |
| ATOM | 69 | C | ALA | A | 9 | -13.564 | 62.657 | 7.069 | 1.00 39.72 | A |
| ATOM | 70 | N | LEU | A | 10 | -14.580 | 64.637 | 7.295 | 1.00 40.25 | A |
| ATOM | 71 | CA | LEU | A | 10 | -14.759 | 64.451 | 8.721 | 1.00 39.87 | A |
| ATOM | 72 | CB | LEU | A | 10 | -14.633 | 65.806 | 9.420 | 1.00 39.76 | A |
| ATOM | 73 | CG | LEU | A | 10 | -13.375 | 66.642 | 9.167 | 1.00 39.01 | A |
| ATOM | 74 | CD1 | LEU | A | 10 | -13.443 | 67.872 | 10.059 | 1.00 36.61 | A |
| ATOM | 75 | CD2 | LEU | A | 10 | -12.107 | 65.833 | 9.445 | 1.00 37.67 | A |
| ATOM | 76 | C | LEU | A | 10 | -16.048 | 63.791 | 9.177 | 1.00 39.24 | A |

FIGURE 5-2 -

```
ATOM     77  C   LEU A  10     -17.086  63.893   8.525  1.00 39.38      A
ATOM     78  N   ILE A  11     -15.965  63.099  10.308  1.00 38.14      A
ATOM     79  CA  ILE A  11     -17.147  62.488  10.890  1.00 38.98      A
ATOM     80  CB  ILE A  11     -16.786  61.495  12.017  1.00 36.94      A
ATOM     81  CG2 ILE A  11     -18.050  60.973  12.672  1.00 34.95      A
ATOM     82  CG1 ILE A  11     -15.989  60.327  11.442  1.00 35.63      A
ATOM     83  CD1 ILE A  11     -15.284  59.496  12.496  1.00 37.37      A
ATOM     84  C   ILE A  11     -17.887  63.703  11.465  1.00 40.00      A
ATOM     85  C   ILE A  11     -17.385  64.389  12.350  1.00 40.60      A
ATOM     86  N   THR A  12     -19.079  63.967  10.952  1.00 41.68      A
ATOM     87  CA  THR A  12     -19.835  65.134  11.363  1.00 43.73      A
ATOM     88  CB  THR A  12     -20.206  65.945  10.116  1.00 43.24      A
ATOM     89  CG1 THR A  12     -20.990  65.127   9.235  1.00 44.68      A
ATOM     90  CG2 THR A  12     -18.951  66.375   9.381  1.00 40.09      A
ATOM     91  C   THR A  12     -21.106  64.852  12.152  1.00 46.73      A
ATOM     92  C   THR A  12     -21.635  63.743  12.118  1.00 49.33      A
ATOM     93  N   PRO A  13     -21.608  65.863  12.884  1.00 48.80      A
ATOM     94  CD  PRO A  13     -20.842  67.061  13.248  1.00 48.72      A
ATOM     95  CA  PRO A  13     -22.825  65.787  13.702  1.00 49.75      A
ATOM     96  CB  PRO A  13     -22.495  66.662  14.919  1.00 48.87      A
ATOM     97  CG  PRO A  13     -21.058  67.102  14.724  1.00 48.55      A
ATOM     98  C   PRO A  13     -23.995  66.379  12.924  1.00 51.28      A
ATOM     99  C   PRO A  13     -23.780  67.125  11.971  1.00 51.66      A
ATOM    100  N   CYS A  14     -25.222  66.057  13.325  1.00 53.51      A
ATOM    101  CA  CYS A  14     -26.399  66.613  12.658  1.00 57.37      A
ATOM    102  CB  CYS A  14     -27.626  65.720  12.824  1.00 57.92      A
ATOM    103  SG  CYS A  14     -27.288  63.983  12.990  1.00 63.15      A
ATOM    104  C   CYS A  14     -26.693  67.923  13.364  1.00 58.82      A
ATOM    105  C   CYS A  14     -26.558  69.010  12.793  1.00 60.30      A
ATOM    106  N   ALA A  15     -27.095  67.794  14.625  1.00 59.40      A
ATOM    107  CA  ALA A  15     -27.426  68.936  15.459  1.00 59.71      A
ATOM    108  CB  ALA A  15     -28.706  68.650  16.248  1.00 59.27      A
ATOM    109  C   ALA A  15     -26.276  69.245  16.413  1.00 59.57      A
ATOM    110  C   ALA A  15     -25.255  68.547  16.419  1.00 58.58      A
ATOM    111  N   ALA A  16     -26.459  70.299  17.209  1.00 58.89      A
ATOM    112  CA  ALA A  16     -25.470  70.736  18.190  1.00 57.61      A
ATOM    113  CB  ALA A  16     -26.011  71.937  18.980  1.00 58.01      A
ATOM    114  C   ALA A  16     -25.136  69.594  19.143  1.00 56.01      A
ATOM    115  C   ALA A  16     -25.865  68.605  19.225  1.00 53.85      A
ATOM    116  N   GLU A  17     -24.032  69.739  19.866  1.00 55.18      A
ATOM    117  CA  GLU A  17     -23.614  68.715  20.805  1.00 54.60      A
ATOM    118  CB  GLU A  17     -22.402  67.962  20.257  1.00 54.84      A
ATOM    119  CG  GLU A  17     -22.680  67.162  18.992  1.00 53.25      A
ATOM    120  CD  GLU A  17     -21.411  66.763  18.270  1.00 53.44      A
ATOM    121  CE1 GLU A  17     -20.704  67.666  17.769  1.00 52.07      A
ATOM    122  CE2 GLU A  17     -21.117  65.552  18.206  1.00 54.54      A
ATOM    123  C   GLU A  17     -23.275  69.308  22.156  1.00 54.61      A
ATOM    124  C   GLU A  17     -22.309  70.059  22.295  1.00 53.67      A
ATOM    125  N   GLU A  18     -24.085  68.968  23.151  1.00 55.53      A
ATOM    126  CA  GLU A  18     -23.860  69.437  24.509  1.00 56.79      A
ATOM    127  CB  GLU A  18     -25.124  69.259  25.343  1.00 61.33      A
ATOM    128  CG  GLU A  18     -26.397  69.681  24.629  1.00 67.21      A
ATOM    129  CD  GLU A  18     -26.350  71.124  24.172  1.00 70.13      A
ATOM    130  CE1 GLU A  18     -26.303  72.029  25.038  1.00 70.85      A
ATOM    131  CE2 GLU A  18     -26.354  71.347  22.940  1.00 71.98      A
ATOM    132  C   GLU A  18     -22.751  68.562  25.075  1.00 55.12      A
ATOM    133  C   GLU A  18     -22.816  67.339  24.977  1.00 53.51      A
ATOM    134  N   SER A  19     -21.736  69.182  25.661  1.00 54.58      A
ATOM    135  CA  SER A  19     -20.622  68.426  26.218  1.00 54.85      A
ATOM    136  CB  SER A  19     -19.326  68.792  25.494  1.00 55.86      A
ATOM    137  CG  SER A  19     -19.036  70.173  25.645  1.00 56.95      A
ATOM    138  C   SER A  19     -20.452  68.688  27.706  1.00 53.86      A
ATOM    139  C   SER A  19     -19.937  67.851  28.442  1.00 53.84      A
ATOM    140  N   LYS A  20     -20.886  69.860  28.145  1.00 53.58      A
ATOM    141  CA  LYS A  20     -20.762  70.217  29.544  1.00 52.21      A
ATOM    142  CB  LYS A  20     -20.319  71.672  29.667  1.00 52.05      A
ATOM    143  CG  LYS A  20     -18.911  71.881  29.125  1.00 55.70      A
ATOM    144  CD  LYS A  20     -18.390  73.289  29.342  1.00 58.18      A
ATOM    145  CE  LYS A  20     -17.026  73.457  28.682  1.00 60.63      A
ATOM    146  NZ  LYS A  20     -16.534  74.873  28.694  1.00 60.53      A
ATOM    147  C   LYS A  20     -22.046  69.978  30.315  1.00 51.45      A
ATOM    148  C   LYS A  20     -23.145  70.150  29.789  1.00 52.16      A
ATOM    149  N   LEU A  21     -21.889  69.546  31.561  1.00 50.39      A
ATOM    150  CA  LEU A  21     -23.015  69.286  32.441  1.00 47.88      A
ATOM    151  CB  LEU A  21     -22.547  68.444  33.619  1.00 46.19      A
ATOM    152  CG  LEU A  21     -23.561  68.228  34.733  1.00 46.56      A
```

FIGURE 5-3-

```
ATOM    153  CD1  LEU A  21    -24.825  67.596  34.171  1.00 46.58      A
ATOM    154  CD2  LEU A  21    -22.936  67.355  35.804  1.00 45.22      A
ATOM    155  C    LEU A  21    -23.567  70.621  32.936  1.00 47.33      A
ATOM    156  O    LEU A  21    -22.857  71.395  33.577  1.00 47.04      A
ATOM    157  N    PRO A  22    -24.840  70.913  32.634  1.00 47.47      A
ATOM    158  CD   PRO A  22    -25.747  70.045  31.858  1.00 48.73      A
ATOM    159  CA   PRO A  22    -25.515  72.153  33.034  1.00 47.77      A
ATOM    160  CB   PRO A  22    -26.936  71.975  32.489  1.00 48.43      A
ATOM    161  CG   PRO A  22    -26.760  71.033  31.332  1.00 48.12      A
ATOM    162  C    PRO A  22    -25.529  72.376  34.546  1.00 47.58      A
ATOM    163  O    PRO A  22    -25.309  71.443  35.324  1.00 48.95      A
ATOM    164  N    ILE A  23    -25.790  73.617  34.951  1.00 46.10      A
ATOM    165  CA   ILE A  23    -25.868  73.978  36.364  1.00 45.43      A
ATOM    166  CB   ILE A  23    -25.255  75.379  36.610  1.00 45.78      A
ATOM    167  CG2  ILE A  23    -25.396  75.779  38.083  1.00 45.20      A
ATOM    168  CG1  ILE A  23    -23.784  75.376  36.183  1.00 45.06      A
ATOM    169  CD1  ILE A  23    -23.057  76.679  36.449  1.00 45.11      A
ATOM    170  C    ILE A  23    -27.355  73.981  36.738  1.00 45.57      A
ATOM    171  O    ILE A  23    -27.981  75.033  36.854  1.00 47.64      A
ATOM    172  N    ASN A  24    -27.907  72.786  36.920  1.00 44.69      A
ATOM    173  CA   ASN A  24    -29.318  72.604  37.238  1.00 44.37      A
ATOM    174  CB   ASN A  24    -29.862  71.482  36.352  1.00 47.34      A
ATOM    175  CG   ASN A  24    -31.322  71.198  36.592  1.00 50.44      A
ATOM    176  OD1  ASN A  24    -31.718  70.806  37.690  1.00 54.60      A
ATOM    177  ND2  ASN A  24    -32.137  71.387  35.561  1.00 49.63      A
ATOM    178  C    ASN A  24    -29.554  72.273  38.714  1.00 43.13      A
ATOM    179  O    ASN A  24    -28.873  71.422  39.285  1.00 44.58      A
ATOM    180  N    PRO A  25    -30.529  72.937  39.352  1.00 40.17      A
ATOM    181  CD   PRO A  25    -31.461  73.947  38.834  1.00 38.87      A
ATOM    182  CA   PRO A  25    -30.794  72.656  40.768  1.00 39.97      A
ATOM    183  CB   PRO A  25    -31.974  73.582  41.094  1.00 37.41      A
ATOM    184  CG   PRO A  25    -32.620  73.815  39.782  1.00 38.22      A
ATOM    185  C    PRO A  25    -31.076  71.179  41.067  1.00 39.94      A
ATOM    186  O    PRO A  25    -30.552  70.618  42.033  1.00 40.27      A
ATOM    187  N    LEU A  26    -31.890  70.553  40.224  1.00 39.24      A
ATOM    188  CA   LEU A  26    -32.239  69.144  40.377  1.00 38.95      A
ATOM    189  CB   LEU A  26    -33.261  68.755  39.321  1.00 38.99      A
ATOM    190  CG   LEU A  26    -34.710  68.713  39.781  1.00 37.75      A
ATOM    191  CD1  LEU A  26    -34.950  69.679  40.925  1.00 38.11      A
ATOM    192  CD2  LEU A  26    -35.579  69.036  38.589  1.00 37.67      A
ATOM    193  C    LEU A  26    -31.049  68.190  40.297  1.00 39.32      A
ATOM    194  O    LEU A  26    -30.928  67.268  41.102  1.00 39.45      A
ATOM    195  N    SER A  27    -30.181  68.393  39.314  1.00 38.67      A
ATOM    196  CA   SER A  27    -29.005  67.545  39.169  1.00 36.40      A
ATOM    197  CB   SER A  27    -28.400  67.723  37.779  1.00 36.04      A
ATOM    198  OG   SER A  27    -28.034  69.083  37.558  1.00 36.43      A
ATOM    199  C    SER A  27    -27.958  67.900  40.222  1.00 35.70      A
ATOM    200  O    SER A  27    -27.202  67.048  40.674  1.00 35.04      A
ATOM    201  N    ASN A  28    -27.929  69.167  40.621  1.00 36.84      A
ATOM    202  CA   ASN A  28    -26.947  69.635  41.587  1.00 37.93      A
ATOM    203  CB   ASN A  28    -26.930  71.166  41.632  1.00 37.90      A
ATOM    204  CG   ASN A  28    -25.773  71.708  42.458  1.00 38.71      A
ATOM    205  OD1  ASN A  28    -24.607  71.456  42.154  1.00 38.79      A
ATOM    206  ND2  ASN A  28    -26.090  72.451  43.511  1.00 37.98      A
ATOM    207  C    ASN A  28    -27.119  69.083  42.998  1.00 39.08      A
ATOM    208  O    ASN A  28    -26.154  69.053  43.773  1.00 38.61      A
ATOM    209  N    SER A  29    -28.331  68.659  43.352  1.00 39.15      A
ATOM    210  CA   SER A  29    -28.530  68.107  44.686  1.00 40.44      A
ATOM    211  CB   SER A  29    -30.017  68.091  45.069  1.00 40.66      A
ATOM    212  OG   SER A  29    -30.765  67.185  44.281  1.00 42.15      A
ATOM    213  C    SER A  29    -27.958  66.695  44.683  1.00 40.37      A
ATOM    214  O    SER A  29    -27.768  66.083  45.736  1.00 41.98      A
ATOM    215  N    LEU A  30    -27.653  66.202  43.482  1.00 39.96      A
ATOM    216  CA   LEU A  30    -27.094  64.865  43.277  1.00 38.24      A
ATOM    217  CB   LEU A  30    -27.729  64.222  42.045  1.00 38.64      A
ATOM    218  CG   LEU A  30    -27.078  62.938  41.529  1.00 39.67      A
ATOM    219  CD1  LEU A  30    -27.285  61.824  42.532  1.00 39.59      A
ATOM    220  CD2  LEU A  30    -27.682  62.552  40.202  1.00 39.68      A
ATOM    221  C    LEU A  30    -25.575  64.827  43.109  1.00 37.43      A
ATOM    222  O    LEU A  30    -24.909  63.967  43.684  1.00 37.50      A
ATOM    223  N    LEU A  31    -25.032  65.747  42.316  1.00 35.79      A
ATOM    224  CA   LEU A  31    -23.593  65.782  42.053  1.00 35.29      A
ATOM    225  CB   LEU A  31    -23.319  64.940  40.803  1.00 32.00      A
ATOM    226  CG   LEU A  31    -21.925  64.590  40.292  1.00 30.56      A
ATOM    227  CD1  LEU A  31    -21.997  63.290  39.492  1.00 24.56      A
ATOM    228  CD2  LEU A  31    -21.387  65.728  39.442  1.00 28.81      A
```

FIGURE 5- 4 -

```
ATOM   229  C    LEU A  31     -23.137  67.233  41.873  1.00  36.89      A
ATOM   230  O    LEU A  31     -23.411  67.864  40.856  1.00  37.13      A
ATOM   231  N    ARG A  32     -22.441  67.757  42.877  1.00  38.44      A
ATOM   232  CA   ARG A  32     -21.986  69.149  42.870  1.00  38.98      A
ATOM   233  CB   ARG A  32     -21.614  69.591  44.298  1.00  40.54      A
ATOM   234  CG   ARG A  32     -22.795  69.906  45.217  1.00  41.06      A
ATOM   235  CD   ARG A  32     -23.750  68.718  45.368  1.00  44.15      A
ATOM   236  NE   ARG A  32     -24.962  69.092  46.094  1.00  45.67      A
ATOM   237  CZ   ARG A  32     -25.036  69.220  47.416  1.00  45.96      A
ATOM   238  NH1  ARG A  32     -23.964  68.991  48.167  1.00  43.40      A
ATOM   239  NH2  ARG A  32     -26.179  69.597  47.980  1.00  44.96      A
ATOM   240  C    ARG A  32     -20.638  69.488  41.931  1.00  39.34      A
ATOM   241  O    ARG A  32     -20.821  70.571  41.352  1.00  39.07      A
ATOM   242  N    HIS A  33     -19.879  68.575  41.793  1.00  40.53      A
ATOM   243  CA   HIS A  33     -18.717  68.784  40.927  1.00  41.09      A
ATOM   244  CB   HIS A  33     -17.594  67.836  41.353  1.00  40.86      A
ATOM   245  CG   HIS A  33     -17.114  68.062  42.756  1.00  42.03      A
ATOM   246  CD2  HIS A  33     -17.350  69.073  43.627  1.00  40.85      A
ATOM   247  ND1  HIS A  33     -16.270  67.185  43.406  1.00  40.02      A
ATOM   248  CE1  HIS A  33     -16.009  67.645  44.615  1.00  40.25      A
ATOM   249  NE2  HIS A  33     -16.652  68.789  44.775  1.00  40.94      A
ATOM   250  C    HIS A  33     -19.049  68.571  39.443  1.00  42.09      A
ATOM   251  O    HIS A  33     -18.463  67.711  38.780  1.00  41.94      A
ATOM   252  N    HIS A  34     -19.971  69.381  38.927  1.00  42.62      A
ATOM   253  CA   HIS A  34     -20.419  69.276  37.546  1.00  44.96      A
ATOM   254  CB   HIS A  34     -21.537  70.291  37.296  1.00  47.60      A
ATOM   255  CG   HIS A  34     -21.120  71.713  37.493  1.00  51.02      A
ATOM   256  CD2  HIS A  34     -21.491  72.631  38.418  1.00  52.02      A
ATOM   257  ND1  HIS A  34     -20.224  72.348  36.660  1.00  52.45      A
ATOM   258  CE1  HIS A  34     -20.063  73.597  37.062  1.00  52.74      A
ATOM   259  NE2  HIS A  34     -20.821  73.794  38.126  1.00  53.13      A
ATOM   260  C    HIS A  34     -19.356  69.389  36.446  1.00  45.40      A
ATOM   261  O    HIS A  34     -19.558  68.884  35.339  1.00  45.37      A
ATOM   262  N    ASN A  35     -18.228  70.029  36.730  1.00  45.24      A
ATOM   263  CA   ASN A  35     -17.185  70.150  35.716  1.00  45.53      A
ATOM   264  CB   ASN A  35     -16.227  71.297  36.062  1.00  45.70      A
ATOM   265  CG   ASN A  35     -16.917  72.652  36.057  1.00  45.69      A
ATOM   266  OD1  ASN A  35     -17.689  72.965  35.151  1.00  43.72      A
ATOM   267  ND2  ASN A  35     -16.635  73.463  37.067  1.00  46.37      A
ATOM   268  C    ASN A  35     -16.397  68.851  35.498  1.00  45.90      A
ATOM   269  O    ASN A  35     -15.513  68.782  34.640  1.00  46.85      A
ATOM   270  N    MET A  36     -16.706  67.816  36.267  1.00  44.29      A
ATOM   271  CA   MET A  36     -16.011  66.553  36.086  1.00  43.84      A
ATOM   272  CB   MET A  36     -15.746  65.902  37.436  1.00  45.33      A
ATOM   273  CG   MET A  36     -14.738  66.630  38.282  1.00  45.95      A
ATOM   274  SD   MET A  36     -14.803  65.990  39.954  1.00  48.69      A
ATOM   275  CE   MET A  36     -13.808  64.487  39.768  1.00  45.12      A
ATOM   276  C    MET A  36     -16.840  65.615  35.209  1.00  42.54      A
ATOM   277  O    MET A  36     -16.408  64.505  34.876  1.00  41.35      A
ATOM   278  N    VAL A  37     -18.033  66.074  34.838  1.00  40.96      A
ATOM   279  CA   VAL A  37     -18.943  65.294  34.005  1.00  39.38      A
ATOM   280  CB   VAL A  37     -20.389  65.348  34.543  1.00  37.40      A
ATOM   281  CG1  VAL A  37     -21.302  64.499  33.672  1.00  34.76      A
ATOM   282  CG2  VAL A  37     -20.426  64.880  35.983  1.00  36.47      A
ATOM   283  C    VAL A  37     -18.964  65.841  32.590  1.00  39.38      A
ATOM   284  O    VAL A  37     -19.380  66.974  32.371  1.00  40.42      A
ATOM   285  N    TYR A  38     -18.512  65.044  31.628  1.00  39.75      A
ATOM   286  CA   TYR A  38     -18.521  65.484  30.235  1.00  39.37      A
ATOM   287  CB   TYR A  38     -17.100  65.736  29.720  1.00  37.31      A
ATOM   288  CG   TYR A  38     -16.243  64.499  29.650  1.00  37.19      A
ATOM   289  CD1  TYR A  38     -15.699  63.941  30.808  1.00  36.23      A
ATOM   290  CE1  TYR A  38     -14.937  62.782  30.754  1.00  36.76      A
ATOM   291  CD2  TYR A  38     -16.000  63.863  28.430  1.00  35.15      A
ATOM   292  CE2  TYR A  38     -15.242  62.700  28.366  1.00  34.49      A
ATOM   293  CZ   TYR A  38     -14.714  62.163  29.533  1.00  36.75      A
ATOM   294  OH   TYR A  38     -13.983  60.995  29.501  1.00  37.20      A
ATOM   295  C    TYR A  38     -19.193  64.448  29.347  1.00  39.96      A
ATOM   296  O    TYR A  38     -19.513  63.334  29.785  1.00  39.64      A
ATOM   297  N    ALA A  39     -19.412  64.828  28.097  1.00  40.02      A
ATOM   298  CA   ALA A  39     -20.035  63.942  27.127  1.00  40.54      A
ATOM   299  CB   ALA A  39     -21.431  64.430  26.798  1.00  39.67      A
ATOM   300  C    ALA A  39     -19.171  63.981  25.887  1.00  40.28      A
ATOM   301  O    ALA A  39     -18.748  65.064  25.471  1.00  41.76      A
ATOM   302  N    THR A  40     -18.883  62.815  25.310  1.00  37.90      A
ATOM   303  CA   THR A  40     -18.086  62.782  24.085  1.00  36.87      A
ATOM   304  CB   THR A  40     -17.764  61.354  23.665  1.00  35.13      A
```

FIGURE 5-5-

```
ATOM    305  OG1  THR A   40     -18.981  60.605  23.594  1.00 36.93      A
ATOM    306  CG2  THR A   40     -16.815  60.706  24.652  1.00 32.37      A
ATOM    307  C    THR A   40     -18.887  63.438  22.955  1.00 37.03      A
ATOM    308  O    THR A   40     -20.120  63.470  22.991  1.00 36.78      A
ATOM    309  N    THR A   41     -18.186  63.980  21.966  1.00 37.57      A
ATOM    310  CA   THR A   41     -18.837  64.623  20.825  1.00 38.68      A
ATOM    311  CB   THR A   41     -18.903  66.163  20.972  1.00 39.40      A
ATOM    312  OG1  THR A   41     -17.599  66.722  20.752  1.00 40.20      A
ATOM    313  CG2  THR A   41     -19.395  66.554  22.364  1.00 37.28      A
ATOM    314  C    THR A   41     -17.992  64.304  19.607  1.00 39.84      A
ATOM    315  O    THR A   41     -16.914  63.723  19.739  1.00 40.43      A
ATOM    316  N    SER A   42     -18.464  64.689  18.424  1.00 40.66      A
ATOM    317  CA   SER A   42     -17.719  64.419  17.192  1.00 39.79      A
ATOM    318  CB   SER A   42     -18.484  64.937  15.994  1.00 37.35      A
ATOM    319  OG   SER A   42     -18.555  66.341  16.070  1.00 39.62      A
ATOM    320  C    SER A   42     -16.353  65.089  17.221  1.00 40.16      A
ATOM    321  O    SER A   42     -15.413  64.627  16.578  1.00 41.37      A
ATOM    322  N    ARG A   43     -16.244  66.173  17.980  1.00 39.91      A
ATOM    323  CA   ARG A   43     -14.991  66.906  18.066  1.00 40.01      A
ATOM    324  CB   ARG A   43     -15.118  68.061  19.064  1.00 40.58      A
ATOM    325  CG   ARG A   43     -16.090  69.131  18.613  1.00 42.30      A
ATOM    326  CD   ARG A   43     -15.879  70.419  19.375  1.00 44.72      A
ATOM    327  NE   ARG A   43     -16.382  70.363  20.746  1.00 47.47      A
ATOM    328  CZ   ARG A   43     -17.669  70.268  21.070  1.00 47.72      A
ATOM    329  NH1  ARG A   43     -18.598  70.211  20.117  1.00 44.40      A
ATOM    330  NH2  ARG A   43     -18.028  70.252  22.350  1.00 47.16      A
ATOM    331  C    ARG A   43     -13.778  66.053  18.412  1.00 39.04      A
ATOM    332  O    ARG A   43     -12.644  66.477  18.194  1.00 38.05      A
ATOM    333  N    SER A   44     -13.999  64.857  18.948  1.00 37.51      A
ATOM    334  CA   SER A   44     -12.871  64.002  19.290  1.00 35.90      A
ATOM    335  CB   SER A   44     -12.913  63.611  20.775  1.00 36.76      A
ATOM    336  OG   SER A   44     -14.060  62.850  21.115  1.00 37.72      A
ATOM    337  C    SER A   44     -12.807  62.754  18.422  1.00 35.21      A
ATOM    338  O    SER A   44     -11.939  61.904  18.617  1.00 35.63      A
ATOM    339  N    ALA A   45     -13.715  62.658  17.456  1.00 33.81      A
ATOM    340  CA   ALA A   45     -13.771  61.512  16.547  1.00 34.27      A
ATOM    341  CB   ALA A   45     -14.733  61.807  15.402  1.00 34.62      A
ATOM    342  C    ALA A   45     -12.395  61.172  15.990  1.00 34.11      A
ATOM    343  O    ALA A   45     -11.975  60.018  15.967  1.00 32.26      A
ATOM    344  N    SER A   46     -11.706  62.205  15.534  1.00 36.08      A
ATOM    345  CA   SER A   46     -10.374  62.079  14.970  1.00 36.81      A
ATOM    346  CB   SER A   46      -9.758  63.473  14.880  1.00 37.25      A
ATOM    347  OG   SER A   46      -8.399  63.401  14.500  1.00 40.51      A
ATOM    348  C    SER A   46      -9.474  61.160  15.798  1.00 37.63      A
ATOM    349  O    SER A   46      -8.767  60.299  15.262  1.00 36.53      A
ATOM    350  N    LEU A   47      -9.509  61.350  17.114  1.00 39.34      A
ATOM    351  CA   LEU A   47      -8.687  60.565  18.036  1.00 40.40      A
ATOM    352  CB   LEU A   47      -8.809  61.138  19.442  1.00 40.83      A
ATOM    353  CG   LEU A   47      -8.209  62.543  19.488  1.00 41.54      A
ATOM    354  CD1  LEU A   47      -8.690  63.299  20.706  1.00 38.89      A
ATOM    355  CD2  LEU A   47      -6.705  62.413  19.456  1.00 39.19      A
ATOM    356  C    LEU A   47      -9.038  59.094  18.051  1.00 40.30      A
ATOM    357  O    LEU A   47      -8.154  58.247  18.158  1.00 40.63      A
ATOM    358  N    ARG A   48     -10.331  58.802  17.943  1.00 40.29      A
ATOM    359  CA   ARG A   48     -10.830  57.431  17.938  1.00 40.66      A
ATOM    360  CB   ARG A   48     -12.355  57.431  18.095  1.00 41.46      A
ATOM    361  CG   ARG A   48     -12.971  56.064  18.291  1.00 42.44      A
ATOM    362  CD   ARG A   48     -12.432  55.364  19.540  1.00 47.08      A
ATOM    363  NE   ARG A   48     -12.938  53.992  19.628  1.00 52.17      A
ATOM    364  CZ   ARG A   48     -12.463  53.051  20.443  1.00 51.49      A
ATOM    365  NH1  ARG A   48     -11.451  53.327  21.260  1.00 50.45      A
ATOM    366  NH2  ARG A   48     -12.999  51.830  20.432  1.00 46.45      A
ATOM    367  C    ARG A   48     -10.437  56.746  16.631  1.00 41.04      A
ATOM    368  O    ARG A   48     -10.041  55.573  16.615  1.00 40.01      A
ATOM    369  N    GLN A   49     -10.539  57.493  15.537  1.00 40.61      A
ATOM    370  CA   GLN A   49     -10.197  56.966  14.230  1.00 40.46      A
ATOM    371  CB   GLN A   49     -10.379  58.042  13.164  1.00 38.84      A
ATOM    372  CG   GLN A   49     -11.771  58.614  13.132  1.00 41.24      A
ATOM    373  CD   GLN A   49     -11.975  59.579  11.997  1.00 41.34      A
ATOM    374  OE1  GLN A   49     -12.009  59.190  10.833  1.00 42.46      A
ATOM    375  NE2  GLN A   49     -12.111  60.851  12.329  1.00 44.02      A
ATOM    376  C    GLN A   49      -8.759  56.497  14.234  1.00 40.51      A
ATOM    377  O    GLN A   49      -8.442  55.394  13.792  1.00 41.03      A
ATOM    378  N    LYS A   50      -7.885  57.342  14.754  1.00 41.08      A
ATOM    379  CA   LYS A   50      -6.473  57.020  14.788  1.00 41.03      A
ATOM    380  CB   LYS A   50      -5.694  58.175  15.416  1.00 42.77      A
```

FIGURE 5- 6 -

| | | | | | | | | | | |
|---|---|---|---|---|---|---|---|---|---|---|
| ATOM | 381 | CG | LYS A | 50 | -4.228 | 58.221 | 15.017 | 1.00 | 46.06 | A |
| ATOM | 382 | CD | LYS A | 50 | -3.312 | 57.663 | 16.094 | 1.00 | 48.55 | A |
| ATOM | 383 | CE | LYS A | 50 | -1.861 | 57.736 | 15.637 | 1.00 | 50.90 | A |
| ATOM | 384 | NZ | LYS A | 50 | -1.581 | 59.048 | 14.984 | 1.00 | 54.44 | A |
| ATOM | 385 | C | LYS A | 50 | -6.207 | 55.735 | 15.544 | 1.00 | 39.51 | A |
| ATOM | 386 | O | LYS A | 50 | -5.252 | 55.026 | 15.244 | 1.00 | 40.21 | A |
| ATOM | 387 | N | LYS A | 51 | -7.069 | 55.418 | 16.504 | 1.00 | 39.20 | A |
| ATOM | 388 | CA | LYS A | 51 | -6.878 | 54.219 | 17.314 | 1.00 | 39.14 | A |
| ATOM | 389 | CB | LYS A | 51 | -7.367 | 54.460 | 18.747 | 1.00 | 40.19 | A |
| ATOM | 390 | CG | LYS A | 51 | -7.057 | 53.306 | 19.702 | 1.00 | 42.05 | A |
| ATOM | 391 | CD | LYS A | 51 | -7.458 | 53.642 | 21.130 | 1.00 | 42.00 | A |
| ATOM | 392 | CE | LYS A | 51 | -7.042 | 52.551 | 22.107 | 1.00 | 42.04 | A |
| ATOM | 393 | NZ | LYS A | 51 | -7.525 | 52.853 | 23.485 | 1.00 | 41.39 | A |
| ATOM | 394 | C | LYS A | 51 | -7.533 | 52.958 | 16.775 | 1.00 | 38.22 | A |
| ATOM | 395 | O | LYS A | 51 | -7.021 | 51.857 | 16.977 | 1.00 | 40.46 | A |
| ATOM | 396 | N | VAL A | 52 | -8.659 | 53.112 | 16.091 | 1.00 | 35.55 | A |
| ATOM | 397 | CA | VAL A | 52 | -9.371 | 51.962 | 15.553 | 1.00 | 33.46 | A |
| ATOM | 398 | CB | VAL A | 52 | -10.899 | 52.226 | 15.528 | 1.00 | 30.28 | A |
| ATOM | 399 | CG1 | VAL A | 52 | -11.380 | 52.630 | 16.923 | 1.00 | 25.56 | A |
| ATOM | 400 | CG2 | VAL A | 52 | -11.226 | 53.319 | 14.527 | 1.00 | 25.75 | A |
| ATOM | 401 | C | VAL A | 52 | -8.893 | 51.598 | 14.148 | 1.00 | 35.27 | A |
| ATOM | 402 | O | VAL A | 52 | -9.313 | 50.592 | 13.580 | 1.00 | 38.11 | A |
| ATOM | 403 | N | THR A | 53 | -8.014 | 52.422 | 13.589 | 1.00 | 34.13 | A |
| ATOM | 404 | CA | THR A | 53 | -7.495 | 52.178 | 12.252 | 1.00 | 31.84 | A |
| ATOM | 405 | CB | THR A | 53 | -7.328 | 53.486 | 11.452 | 1.00 | 29.80 | A |
| ATOM | 406 | OG1 | THR A | 53 | -8.579 | 54.182 | 11.371 | 1.00 | 28.22 | A |
| ATOM | 407 | CG2 | THR A | 53 | -6.833 | 53.182 | 10.060 | 1.00 | 25.32 | A |
| ATOM | 408 | C | THR A | 53 | -6.130 | 51.528 | 12.359 | 1.00 | 33.39 | A |
| ATOM | 409 | O | THR A | 53 | -5.198 | 52.106 | 12.917 | 1.00 | 35.61 | A |
| ATOM | 410 | N | PHE A | 54 | -6.015 | 50.321 | 11.833 | 1.00 | 32.25 | A |
| ATOM | 411 | CA | PHE A | 54 | -4.758 | 49.612 | 11.856 | 1.00 | 31.83 | A |
| ATOM | 412 | CB | PHE A | 54 | -4.346 | 49.259 | 13.295 | 1.00 | 32.12 | A |
| ATOM | 413 | CG | PHE A | 54 | -5.357 | 48.436 | 14.051 | 1.00 | 32.14 | A |
| ATOM | 414 | CD1 | PHE A | 54 | -5.410 | 47.052 | 13.895 | 1.00 | 32.09 | A |
| ATOM | 415 | CD2 | PHE A | 54 | -6.269 | 49.049 | 14.909 | 1.00 | 32.86 | A |
| ATOM | 416 | CE1 | PHE A | 54 | -6.351 | 46.285 | 14.591 | 1.00 | 32.22 | A |
| ATOM | 417 | CE2 | PHE A | 54 | -7.213 | 48.295 | 15.609 | 1.00 | 34.40 | A |
| ATOM | 418 | CZ | PHE A | 54 | -7.257 | 46.907 | 15.447 | 1.00 | 33.08 | A |
| ATOM | 419 | C | PHE A | 54 | -4.873 | 48.369 | 11.001 | 1.00 | 33.10 | A |
| ATOM | 420 | O | PHE A | 54 | -5.969 | 47.981 | 10.580 | 1.00 | 31.01 | A |
| ATOM | 421 | N | ASP A | 55 | -3.730 | 47.753 | 10.741 | 1.00 | 33.62 | A |
| ATOM | 422 | CA | ASP A | 55 | -3.688 | 46.572 | 9.911 | 1.00 | 35.51 | A |
| ATOM | 423 | CB | ASP A | 55 | -2.390 | 46.588 | 9.112 | 1.00 | 36.74 | A |
| ATOM | 424 | CG | ASP A | 55 | -2.376 | 45.570 | 8.016 | 1.00 | 40.49 | A |
| ATOM | 425 | OD1 | ASP A | 55 | -3.469 | 45.078 | 7.655 | 1.00 | 44.06 | A |
| ATOM | 426 | OD2 | ASP A | 55 | -1.275 | 45.264 | 7.508 | 1.00 | 42.40 | A |
| ATOM | 427 | C | ASP A | 55 | -3.807 | 45.316 | 10.769 | 1.00 | 36.53 | A |
| ATOM | 428 | O | ASP A | 55 | -3.065 | 45.145 | 11.740 | 1.00 | 37.32 | A |
| ATOM | 429 | N | ARG A | 56 | -4.758 | 44.451 | 10.415 | 1.00 | 36.48 | A |
| ATOM | 430 | CA | ARG A | 56 | -5.003 | 43.216 | 11.162 | 1.00 | 36.62 | A |
| ATOM | 431 | CB | ARG A | 56 | -6.474 | 42.792 | 11.049 | 1.00 | 34.87 | A |
| ATOM | 432 | CG | ARG A | 56 | -7.464 | 43.616 | 11.855 | 1.00 | 36.84 | A |
| ATOM | 433 | CD | ARG A | 56 | -7.767 | 44.934 | 11.187 | 1.00 | 37.72 | A |
| ATOM | 434 | NE | ARG A | 56 | -8.378 | 44.738 | 9.875 | 1.00 | 37.65 | A |
| ATOM | 435 | CZ | ARG A | 56 | -9.622 | 44.316 | 9.684 | 1.00 | 38.25 | A |
| ATOM | 436 | NH1 | ARG A | 56 | -10.396 | 44.047 | 10.726 | 1.00 | 40.59 | A |
| ATOM | 437 | NH2 | ARG A | 56 | -10.090 | 44.154 | 8.453 | 1.00 | 38.46 | A |
| ATOM | 438 | C | ARG A | 56 | -4.134 | 42.028 | 10.761 | 1.00 | 37.49 | A |
| ATOM | 439 | O | ARG A | 56 | -3.980 | 41.717 | 9.580 | 1.00 | 39.81 | A |
| ATOM | 440 | N | LEU A | 57 | -3.585 | 41.355 | 11.764 | 1.00 | 37.44 | A |
| ATOM | 441 | CA | LEU A | 57 | -2.753 | 40.171 | 11.549 | 1.00 | 37.02 | A |
| ATOM | 442 | CB | LEU A | 57 | -1.440 | 40.301 | 12.352 | 1.00 | 37.38 | A |
| ATOM | 443 | CG | LEU A | 57 | -0.475 | 39.135 | 12.624 | 1.00 | 37.53 | A |
| ATOM | 444 | CD1 | LEU A | 57 | 0.772 | 39.683 | 13.301 | 1.00 | 36.94 | A |
| ATOM | 445 | CD2 | LEU A | 57 | -1.119 | 38.081 | 13.524 | 1.00 | 37.63 | A |
| ATOM | 446 | C | LEU A | 57 | -3.555 | 38.966 | 12.036 | 1.00 | 35.17 | A |
| ATOM | 447 | O | LEU A | 57 | -4.112 | 38.998 | 13.129 | 1.00 | 34.35 | A |
| ATOM | 448 | N | GLN A | 58 | -3.620 | 37.910 | 11.235 | 1.00 | 34.25 | A |
| ATOM | 449 | CA | GLN A | 58 | -4.351 | 36.720 | 11.655 | 1.00 | 33.54 | A |
| ATOM | 450 | CB | GLN A | 58 | -5.819 | 36.849 | 11.258 | 1.00 | 33.39 | A |
| ATOM | 451 | CG | GLN A | 58 | -6.731 | 35.761 | 11.806 | 1.00 | 32.23 | A |
| ATOM | 452 | CD | GLN A | 58 | -8.190 | 36.140 | 11.681 | 1.00 | 32.01 | A |
| ATOM | 453 | OE1 | GLN A | 58 | -8.653 | 36.536 | 10.610 | 1.00 | 33.05 | A |
| ATOM | 454 | NE2 | GLN A | 58 | -8.923 | 36.022 | 12.777 | 1.00 | 30.56 | A |
| ATOM | 455 | C | GLN A | 58 | -3.773 | 35.421 | 11.102 | 1.00 | 33.93 | A |
| ATOM | 456 | O | GLN A | 58 | -3.581 | 35.283 | 9.902 | 1.00 | 34.95 | A |

FIGURE 5-7-

```
ATOM    457  N    VAL A   59      -3.490  34.476  11.991  1.00 34.22           A
ATOM    458  CA   VAL A   59      -2.951  33.188  11.595  1.00 35.13           A
ATOM    459  CB   VAL A   59      -1.496  33.023  12.058  1.00 35.72           A
ATOM    460  CG1  VAL A   59      -0.953  31.680  11.582  1.00 33.78           A
ATOM    461  CG2  VAL A   59      -0.648  34.167  11.533  1.00 36.61           A
ATOM    462  C    VAL A   59      -3.788  32.130  12.286  1.00 36.32           A
ATOM    463  O    VAL A   59      -3.739  32.004  13.504  1.00 38.80           A
ATOM    464  N    LEU A   60      -4.556  31.372  11.517  1.00 36.24           A
ATOM    465  CA   LEU A   60      -5.406  30.343  12.100  1.00 37.08           A
ATOM    466  CB   LEU A   60      -6.600  30.058  11.193  1.00 35.26           A
ATOM    467  CG   LEU A   60      -7.533  31.232  10.938  1.00 34.02           A
ATOM    468  CD1  LEU A   60      -8.728  30.745  10.139  1.00 32.04           A
ATOM    469  CD2  LEU A   60      -7.962  31.844  12.269  1.00 32.56           A
ATOM    470  C    LEU A   60      -4.637  29.060  12.316  1.00 38.86           A
ATOM    471  O    LEU A   60      -3.589  28.847  11.700  1.00 41.10           A
ATOM    472  N    ASP A   61      -5.155  28.198  13.185  1.00 38.62           A
ATOM    473  CA   ASP A   61      -4.489  26.935  13.449  1.00 38.06           A
ATOM    474  CB   ASP A   61      -3.524  27.086  14.625  1.00 38.08           A
ATOM    475  CG   ASP A   61      -4.230  27.194  15.955  1.00 39.64           A
ATOM    476  OD1  ASP A   61      -5.332  27.764  16.012  1.00 37.50           A
ATOM    477  OD2  ASP A   61      -3.664  26.713  16.956  1.00 43.18           A
ATOM    478  C    ASP A   61      -5.488  25.816  13.710  1.00 38.77           A
ATOM    479  O    ASP A   61      -6.703  26.034  13.706  1.00 37.18           A
ATOM    480  N    ASP A   62      -4.961  24.614  13.920  1.00 38.68           A
ATOM    481  CA   ASP A   62      -5.786  23.444  14.161  1.00 38.42           A
ATOM    482  CB   ASP A   62      -4.891  22.226  14.389  1.00 38.33           A
ATOM    483  CG   ASP A   62      -4.383  21.633  13.083  1.00 40.30           A
ATOM    484  OD1  ASP A   62      -4.463  22.329  12.041  1.00 40.18           A
ATOM    485  OD2  ASP A   62      -3.904  20.475  13.091  1.00 41.28           A
ATOM    486  C    ASP A   62      -6.734  23.648  15.328  1.00 38.64           A
ATOM    487  O    ASP A   62      -7.915  23.279  15.260  1.00 36.74           A
ATOM    488  N    HIS A   63      -6.224  24.248  16.398  1.00 38.61           A
ATOM    489  CA   HIS A   63      -7.061  24.495  17.560  1.00 38.12           A
ATOM    490  CB   HIS A   63      -6.260  25.238  18.634  1.00 37.05           A
ATOM    491  CG   HIS A   63      -5.327  24.359  19.407  1.00 38.77           A
ATOM    492  CD2  HIS A   63      -3.989  24.431  19.606  1.00 41.17           A
ATOM    493  ND1  HIS A   63      -5.760  23.266  20.126  1.00 39.72           A
ATOM    494  CE1  HIS A   63      -4.731  22.704  20.736  1.00 40.45           A
ATOM    495  NE2  HIS A   63      -3.644  23.391  20.437  1.00 41.12           A
ATOM    496  C    HIS A   63      -8.296  25.304  17.133  1.00 37.44           A
ATOM    497  O    HIS A   63      -9.435  24.960  17.477  1.00 36.97           A
ATOM    498  N    TYR A   64      -8.062  26.362  16.362  1.00 34.88           A
ATOM    499  CA   TYR A   64      -9.139  27.218  15.889  1.00 34.12           A
ATOM    500  CB   TYR A   64      -8.573  28.320  15.001  1.00 34.58           A
ATOM    501  CG   TYR A   64      -9.601  29.272  14.430  1.00 34.52           A
ATOM    502  CD1  TYR A   64      -9.987  30.414  15.129  1.00 34.34           A
ATOM    503  CE1  TYR A   64     -10.921  31.302  14.594  1.00 34.42           A
ATOM    504  CD2  TYR A   64     -10.181  29.038  13.179  1.00 33.52           A
ATOM    505  CE2  TYR A   64     -11.116  29.918  12.638  1.00 31.61           A
ATOM    506  CZ   TYR A   64     -11.481  31.046  13.347  1.00 33.99           A
ATOM    507  OH   TYR A   64     -12.401  31.927  12.821  1.00 35.12           A
ATOM    508  C    TYR A   64     -10.154  26.416  15.092  1.00 34.40           A
ATOM    509  O    TYR A   64     -11.361  26.496  15.325  1.00 33.66           A
ATOM    510  N    ARG A   65      -9.650  25.634  14.147  1.00 35.99           A
ATOM    511  CA   ARG A   65     -10.512  24.840  13.293  1.00 34.97           A
ATOM    512  CB   ARG A   65      -9.720  24.333  12.092  1.00 33.97           A
ATOM    513  CG   ARG A   65      -9.368  25.480  11.136  1.00 35.44           A
ATOM    514  CD   ARG A   65      -8.604  25.003   9.922  1.00 34.18           A
ATOM    515  NE   ARG A   65      -7.293  24.497  10.298  1.00 35.47           A
ATOM    516  CZ   ARG A   65      -6.160  25.185  10.194  1.00 34.91           A
ATOM    517  NH1  ARG A   65      -6.161  26.426   9.714  1.00 33.52           A
ATOM    518  NH2  ARG A   65      -5.024  24.620  10.573  1.00 35.45           A
ATOM    519  C    ARG A   65     -11.219  23.716  14.022  1.00 35.23           A
ATOM    520  O    ARG A   65     -12.325  23.336  13.643  1.00 35.85           A
ATOM    521  N    ASP A   66     -10.617  23.184  15.077  1.00 34.34           A
ATOM    522  CA   ASP A   66     -11.309  22.136  15.805  1.00 34.44           A
ATOM    523  CB   ASP A   66     -10.384  21.462  16.821  1.00 35.81           A
ATOM    524  CG   ASP A   66      -9.218  20.738  16.169  1.00 39.21           A
ATOM    525  OD1  ASP A   66      -9.384  20.198  15.042  1.00 38.83           A
ATOM    526  OD2  ASP A   66      -8.136  20.697  16.800  1.00 40.14           A
ATOM    527  C    ASP A   66     -12.485  22.800  16.528  1.00 35.37           A
ATOM    528  O    ASP A   66     -13.626  22.331  16.451  1.00 34.41           A
ATOM    529  N    VAL A   67     -12.209  23.910  17.214  1.00 34.84           A
ATOM    530  CA   VAL A   67     -13.258  24.613  17.944  1.00 33.04           A
ATOM    531  CB   VAL A   67     -12.681  25.822  18.737  1.00 31.64           A
ATOM    532  CG1  VAL A   67     -13.802  26.673  19.301  1.00 30.39           A
```

FIGURE 5- 8 -

| | | | | | | | | | | |
|---|---|---|---|---|---|---|---|---|---|---|
| ATOM | 533 | CG2 | VAL | A | 67 | -11.840 | 25.319 | 19.886 | 1.00 30.39 | A |
| ATOM | 534 | C | VAL | A | 67 | -14.381 | 25.065 | 17.007 | 1.00 32.38 | A |
| ATOM | 535 | O | VAL | A | 67 | -15.555 | 25.002 | 17.372 | 1.00 32.04 | A |
| ATOM | 536 | N | LEU | A | 68 | -14.028 | 25.510 | 15.804 | 1.00 30.99 | A |
| ATOM | 537 | CA | LEU | A | 68 | -15.039 | 25.936 | 14.839 | 1.00 30.39 | A |
| ATOM | 538 | CB | LEU | A | 68 | -14.379 | 26.541 | 13.598 | 1.00 26.55 | A |
| ATOM | 539 | CG | LEU | A | 68 | -15.283 | 26.917 | 12.418 | 1.00 23.12 | A |
| ATOM | 540 | CD1 | LEU | A | 68 | -16.462 | 27.730 | 12.894 | 1.00 19.31 | A |
| ATOM | 541 | CD2 | LEU | A | 68 | -14.462 | 27.692 | 11.388 | 1.00 17.19 | A |
| ATOM | 542 | C | LEU | A | 68 | -15.927 | 24.756 | 14.436 | 1.00 32.11 | A |
| ATOM | 543 | O | LEU | A | 68 | -17.142 | 24.896 | 14.333 | 1.00 33.68 | A |
| ATOM | 544 | N | LYS | A | 69 | -15.327 | 23.589 | 14.218 | 1.00 33.49 | A |
| ATOM | 545 | CA | LYS | A | 69 | -16.101 | 22.400 | 13.850 | 1.00 33.80 | A |
| ATOM | 546 | CB | LYS | A | 69 | -15.181 | 21.214 | 13.576 | 1.00 35.41 | A |
| ATOM | 547 | CG | LYS | A | 69 | -14.136 | 21.441 | 12.495 | 1.00 37.40 | A |
| ATOM | 548 | CD | LYS | A | 69 | -14.542 | 20.845 | 11.170 | 1.00 38.96 | A |
| ATOM | 549 | CE | LYS | A | 69 | -13.373 | 20.878 | 10.193 | 1.00 44.38 | A |
| ATOM | 550 | NZ | LYS | A | 69 | -12.159 | 20.142 | 10.688 | 1.00 47.19 | A |
| ATOM | 551 | C | LYS | A | 69 | -17.041 | 22.030 | 14.991 | 1.00 33.38 | A |
| ATOM | 552 | O | LYS | A | 69 | -18.181 | 21.644 | 14.765 | 1.00 35.43 | A |
| ATOM | 553 | N | GLU | A | 70 | -16.561 | 22.133 | 16.222 | 1.00 32.56 | A |
| ATOM | 554 | CA | GLU | A | 70 | -17.405 | 21.805 | 17.367 | 1.00 33.32 | A |
| ATOM | 555 | CB | GLU | A | 70 | -16.612 | 21.935 | 18.665 | 1.00 33.49 | A |
| ATOM | 556 | CG | GLU | A | 70 | -15.673 | 20.788 | 18.947 | 1.00 35.72 | A |
| ATOM | 557 | CD | GLU | A | 70 | -14.608 | 21.170 | 19.952 | 1.00 42.16 | A |
| ATOM | 558 | OE1 | GLU | A | 70 | -14.932 | 21.904 | 20.915 | 1.00 44.24 | A |
| ATOM | 559 | OE2 | GLU | A | 70 | -13.444 | 20.739 | 19.784 | 1.00 45.79 | A |
| ATOM | 560 | C | GLU | A | 70 | -18.641 | 22.705 | 17.423 | 1.00 31.90 | A |
| ATOM | 561 | O | GLU | A | 70 | -19.753 | 22.234 | 17.656 | 1.00 31.99 | A |
| ATOM | 562 | N | MET | A | 71 | -18.436 | 23.997 | 17.199 | 1.00 30.09 | A |
| ATOM | 563 | CA | MET | A | 71 | -19.517 | 24.975 | 17.226 | 1.00 29.14 | A |
| ATOM | 564 | CB | MET | A | 71 | -18.930 | 26.387 | 17.157 | 1.00 29.66 | A |
| ATOM | 565 | CG | MET | A | 71 | -17.988 | 26.727 | 18.298 | 1.00 26.83 | A |
| ATOM | 566 | SD | MET | A | 71 | -17.212 | 28.329 | 18.064 | 1.00 30.19 | A |
| ATOM | 567 | CE | MET | A | 71 | -18.551 | 29.368 | 18.390 | 1.00 29.16 | A |
| ATOM | 568 | C | MET | A | 71 | -20.510 | 24.773 | 16.082 | 1.00 28.58 | A |
| ATOM | 569 | O | MET | A | 71 | -21.718 | 24.884 | 16.265 | 1.00 27.73 | A |
| ATOM | 570 | N | LYS | A | 72 | -19.993 | 24.489 | 14.894 | 1.00 28.96 | A |
| ATOM | 571 | CA | LYS | A | 72 | -20.846 | 24.260 | 13.735 | 1.00 28.91 | A |
| ATOM | 572 | CB | LYS | A | 72 | -19.992 | 23.962 | 12.495 | 1.00 28.81 | A |
| ATOM | 573 | CG | LYS | A | 72 | -19.135 | 25.135 | 12.032 | 1.00 28.90 | A |
| ATOM | 574 | CD | LYS | A | 72 | -19.504 | 25.595 | 10.636 | 1.00 27.75 | A |
| ATOM | 575 | CE | LYS | A | 72 | -19.027 | 24.619 | 9.585 | 1.00 27.08 | A |
| ATOM | 576 | NZ | LYS | A | 72 | -19.275 | 25.117 | 8.206 | 1.00 27.16 | A |
| ATOM | 577 | C | LYS | A | 72 | -21.783 | 23.090 | 14.008 | 1.00 28.10 | A |
| ATOM | 578 | O | LYS | A | 72 | -22.957 | 23.127 | 13.652 | 1.00 28.97 | A |
| ATOM | 579 | N | ALA | A | 73 | -21.253 | 22.060 | 14.655 | 1.00 28.11 | A |
| ATOM | 580 | CA | ALA | A | 73 | -22.015 | 20.865 | 14.972 | 1.00 27.92 | A |
| ATOM | 581 | CB | ALA | A | 73 | -21.140 | 19.886 | 15.716 | 1.00 26.94 | A |
| ATOM | 582 | C | ALA | A | 73 | -23.242 | 21.198 | 15.796 | 1.00 28.41 | A |
| ATOM | 583 | O | ALA | A | 73 | -24.317 | 20.627 | 15.593 | 1.00 29.15 | A |
| ATOM | 584 | N | LYS | A | 74 | -23.086 | 22.124 | 16.728 | 1.00 27.93 | A |
| ATOM | 585 | CA | LYS | A | 74 | -24.206 | 22.518 | 17.561 | 1.00 30.24 | A |
| ATOM | 586 | CB | LYS | A | 74 | -23.694 | 23.250 | 18.797 | 1.00 30.69 | A |
| ATOM | 587 | CG | LYS | A | 74 | -22.925 | 22.340 | 19.724 | 1.00 30.29 | A |
| ATOM | 588 | CD | LYS | A | 74 | -22.522 | 23.020 | 21.004 | 1.00 35.53 | A |
| ATOM | 589 | CE | LYS | A | 74 | -22.040 | 21.980 | 22.000 | 1.00 40.13 | A |
| ATOM | 590 | NZ | LYS | A | 74 | -23.080 | 20.899 | 22.193 | 1.00 44.24 | A |
| ATOM | 591 | C | LYS | A | 74 | -25.158 | 23.404 | 16.767 | 1.00 31.80 | A |
| ATOM | 592 | O | LYS | A | 74 | -26.378 | 23.319 | 16.916 | 1.00 33.07 | A |
| ATOM | 593 | N | ALA | A | 75 | -24.585 | 24.246 | 15.914 | 1.00 32.61 | A |
| ATOM | 594 | CA | ALA | A | 75 | -25.358 | 25.152 | 15.081 | 1.00 33.15 | A |
| ATOM | 595 | CB | ALA | A | 75 | -24.433 | 25.956 | 14.205 | 1.00 33.84 | A |
| ATOM | 596 | C | ALA | A | 75 | -26.323 | 24.365 | 14.221 | 1.00 33.75 | A |
| ATOM | 597 | O | ALA | A | 75 | -27.432 | 24.820 | 13.951 | 1.00 34.79 | A |
| ATOM | 598 | N | SER | A | 76 | -25.889 | 23.180 | 13.799 | 1.00 33.09 | A |
| ATOM | 599 | CA | SER | A | 76 | -26.691 | 22.294 | 12.963 | 1.00 32.33 | A |
| ATOM | 600 | CB | SER | A | 76 | -25.932 | 21.000 | 12.701 | 1.00 33.89 | A |
| ATOM | 601 | OG | SER | A | 76 | -24.733 | 21.260 | 12.003 | 1.00 36.21 | A |
| ATOM | 602 | C | SER | A | 76 | -28.041 | 21.941 | 13.563 | 1.00 31.87 | A |
| ATOM | 603 | O | SER | A | 76 | -28.992 | 21.656 | 12.838 | 1.00 31.72 | A |
| ATOM | 604 | N | THR | A | 77 | -28.131 | 21.959 | 14.886 | 1.00 30.84 | A |
| ATOM | 605 | CA | THR | A | 77 | -29.376 | 21.600 | 15.544 | 1.00 29.98 | A |
| ATOM | 606 | CB | THR | A | 77 | -29.146 | 21.224 | 17.013 | 1.00 30.82 | A |
| ATOM | 607 | OG1 | THR | A | 77 | -28.892 | 22.417 | 17.766 | 1.00 32.43 | A |
| ATOM | 608 | CG2 | THR | A | 77 | -27.972 | 20.263 | 17.155 | 1.00 27.15 | A |

FIGURE 5-9-

```
ATOM    609  C    THR A  77     -30.412  22.711  15.521  1.00 29.60      A
ATOM    610  O    THR A  77     -31.578  22.479  15.831  1.00 29.80      A
ATOM    611  N    VAL A  78     -29.998  23.912  15.148  1.00 29.24      A
ATOM    612  CA   VAL A  78     -30.914  25.046  15.133  1.00 29.51      A
ATOM    613  CB   VAL A  78     -30.132  26.359  15.302  1.00 27.83      A
ATOM    614  CG1  VAL A  78     -31.070  27.509  15.436  1.00 26.87      A
ATOM    615  CG2  VAL A  78     -29.245  26.273  16.512  1.00 29.86      A
ATOM    616  C    VAL A  78     -31.805  25.174  13.891  1.00 31.13      A
ATOM    617  O    VAL A  78     -31.385  24.873  12.767  1.00 29.85      A
ATOM    618  N    LYS A  79     -33.035  25.636  14.115  1.00 32.34      A
ATOM    619  CA   LYS A  79     -34.008  25.859  13.051  1.00 35.12      A
ATOM    620  CB   LYS A  79     -35.153  24.851  13.138  1.00 37.13      A
ATOM    621  CG   LYS A  79     -36.201  25.027  12.045  1.00 42.40      A
ATOM    622  CD   LYS A  79     -37.150  23.852  12.037  1.00 49.08      A
ATOM    623  CE   LYS A  79     -37.964  23.745  10.752  1.00 52.10      A
ATOM    624  NZ   LYS A  79     -38.553  22.353  10.647  1.00 55.54      A
ATOM    625  C    LYS A  79     -34.567  27.261  13.220  1.00 34.97      A
ATOM    626  O    LYS A  79     -35.417  27.481  14.074  1.00 36.52      A
ATOM    627  N    ALA A  80     -34.099  28.202  12.405  1.00 35.24      A
ATOM    628  CA   ALA A  80     -34.539  29.593  12.498  1.00 33.96      A
ATOM    629  CB   ALA A  80     -33.356  30.513  12.273  1.00 33.53      A
ATOM    630  C    ALA A  80     -35.674  29.970  11.550  1.00 34.72      A
ATOM    631  O    ALA A  80     -35.701  29.563  10.390  1.00 34.86      A
ATOM    632  N    LYS A  81     -36.605  30.771  12.060  1.00 36.28      A
ATOM    633  CA   LYS A  81     -37.758  31.221  11.292  1.00 37.15      A
ATOM    634  CB   LYS A  81     -39.016  31.260  12.169  1.00 40.69      A
ATOM    635  CG   LYS A  81     -38.926  32.274  13.313  1.00 46.95      A
ATOM    636  CD   LYS A  81     -40.230  32.415  14.102  1.00 51.15      A
ATOM    637  CE   LYS A  81     -40.052  33.415  15.256  1.00 55.56      A
ATOM    638  NZ   LYS A  81     -41.298  33.701  16.022  1.00 56.00      A
ATOM    639  C    LYS A  81     -37.505  32.612  10.750  1.00 36.76      A
ATOM    640  O    LYS A  81     -36.785  33.409  11.341  1.00 38.37      A
ATOM    641  N    LEU A  82     -38.113  32.891   9.611  1.00 36.25      A
ATOM    642  CA   LEU A  82     -38.003  34.181   8.953  1.00 34.86      A
ATOM    643  CB   LEU A  82     -38.266  33.980   7.464  1.00 32.98      A
ATOM    644  CG   LEU A  82     -38.155  35.101   6.444  1.00 33.02      A
ATOM    645  CD1  LEU A  82     -36.721  35.597   6.293  1.00 33.62      A
ATOM    646  CD2  LEU A  82     -38.646  34.540   5.129  1.00 32.82      A
ATOM    647  C    LEU A  82     -39.101  35.023   9.590  1.00 35.63      A
ATOM    648  O    LEU A  82     -40.212  34.540   9.785  1.00 37.27      A
ATOM    649  N    LEU A  83     -38.809  36.268   9.931  1.00 35.05      A
ATOM    650  CA   LEU A  83     -39.831  37.100  10.553  1.00 35.13      A
ATOM    651  CB   LEU A  83     -39.180  38.148  11.471  1.00 32.50      A
ATOM    652  CG   LEU A  83     -39.220  37.979  13.003  1.00 29.44      A
ATOM    653  CD1  LEU A  83     -38.904  36.563  13.421  1.00 27.25      A
ATOM    654  CD2  LEU A  83     -38.226  38.933  13.627  1.00 28.16      A
ATOM    655  C    LEU A  83     -40.692  37.785   9.498  1.00 36.97      A
ATOM    656  O    LEU A  83     -40.230  38.066   8.394  1.00 39.02      A
ATOM    657  N    SER A  84     -41.953  38.030   9.836  1.00 37.88      A
ATOM    658  CA   SER A  84     -42.879  38.709   8.937  1.00 40.06      A
ATOM    659  CB   SER A  84     -44.301  38.543   9.444  1.00 40.19      A
ATOM    660  OG   SER A  84     -44.452  39.167  10.713  1.00 41.35      A
ATOM    661  C    SER A  84     -42.532  40.193   8.969  1.00 43.08      A
ATOM    662  O    SER A  84     -41.944  40.668   9.946  1.00 45.20      A
ATOM    663  N    ILE A  85     -42.893  40.933   7.929  1.00 43.78      A
ATOM    664  CA   ILE A  85     -42.594  42.363   7.951  1.00 44.94      A
ATOM    665  CB   ILE A  85     -43.145  43.097   6.721  1.00 43.29      A
ATOM    666  CG2  ILE A  85     -43.026  44.595   6.911  1.00 42.17      A
ATOM    667  CG1  ILE A  85     -42.345  42.692   5.487  1.00 45.02      A
ATOM    668  CD1  ILE A  85     -42.647  43.515   4.256  1.00 45.82      A
ATOM    669  C    ILE A  85     -43.200  42.979   9.205  1.00 46.61      A
ATOM    670  O    ILE A  85     -42.600  43.851   9.827  1.00 47.68      A
ATOM    671  N    GLU A  86     -44.382  42.508   9.587  1.00 47.97      A
ATOM    672  CA   GLU A  86     -45.049  43.035  10.772  1.00 49.52      A
ATOM    673  CB   GLU A  86     -46.408  42.350  10.975  1.00 53.54      A
ATOM    674  CG   GLU A  86     -47.485  43.243  11.596  1.00 58.20      A
ATOM    675  CD   GLU A  86     -48.282  42.557  12.704  1.00 63.48      A
ATOM    676  OE1  GLU A  86     -49.336  43.102  13.111  1.00 65.52      A
ATOM    677  OE2  GLU A  86     -47.853  41.478  13.182  1.00 65.11      A
ATOM    678  C    GLU A  86     -44.167  42.818  12.001  1.00 48.04      A
ATOM    679  O    GLU A  86     -43.786  43.777  12.672  1.00 46.46      A
ATOM    680  N    GLU A  87     -43.836  41.556  12.278  1.00 47.41      A
ATOM    681  CA   GLU A  87     -42.995  41.193  13.422  1.00 46.34      A
ATOM    682  CB   GLU A  87     -42.615  39.708  13.350  1.00 47.94      A
ATOM    683  CG   GLU A  87     -43.756  38.721  13.516  1.00 51.27      A
ATOM    684  CD   GLU A  87     -43.312  37.273  13.294  1.00 55.09      A
```

FIGURE 5- 10 -

```
ATOM    685  OE1 GLU A  87     -42.878  36.941  12.167  1.00 56.59      A
ATOM    686  OE2 GLU A  87     -43.391  36.461  14.245  1.00 56.58      A
ATOM    687  C   GLU A  87     -41.709  42.033  13.507  1.00 44.49      A
ATOM    688  O   GLU A  87     -41.344  42.511  14.581  1.00 43.71      A
ATOM    689  N   ALA A  88     -41.023  42.201  12.377  1.00 42.29      A
ATOM    690  CA  ALA A  88     -39.784  42.968  12.347  1.00 41.01      A
ATOM    691  CB  ALA A  88     -39.077  42.764  11.033  1.00 39.96      A
ATOM    692  C   ALA A  88     -40.038  44.445  12.570  1.00 40.89      A
ATOM    693  O   ALA A  88     -39.215  45.147  13.151  1.00 41.63      A
ATOM    694  N   CYS A  89     -41.180  44.925  12.104  1.00 40.50      A
ATOM    695  CA  CYS A  89     -41.512  46.323  12.281  1.00 40.64      A
ATOM    696  CB  CYS A  89     -42.756  46.671  11.462  1.00 39.94      A
ATOM    697  SG  CYS A  89     -42.469  46.891   9.693  1.00 39.41      A
ATOM    698  C   CYS A  89     -41.760  46.630  13.761  1.00 41.47      A
ATOM    699  O   CYS A  89     -41.312  47.653  14.286  1.00 40.82      A
ATOM    700  N   LYS A  90     -42.467  45.728  14.429  1.00 40.66      A
ATOM    701  CA  LYS A  90     -42.805  45.912  15.827  1.00 42.24      A
ATOM    702  CB  LYS A  90     -43.816  44.844  16.252  1.00 44.49      A
ATOM    703  CG  LYS A  90     -44.464  45.114  17.595  1.00 52.45      A
ATOM    704  CD  LYS A  90     -45.219  43.901  18.134  1.00 56.00      A
ATOM    705  CE  LYS A  90     -45.822  44.201  19.504  1.00 56.83      A
ATOM    706  NZ  LYS A  90     -46.473  42.999  20.095  1.00 58.77      A
ATOM    707  C   LYS A  90     -41.562  45.868  16.717  1.00 42.66      A
ATOM    708  O   LYS A  90     -41.615  46.195  17.905  1.00 43.23      A
ATOM    709  N   LEU A  91     -40.440  45.456  16.142  1.00 43.07      A
ATOM    710  CA  LEU A  91     -39.196  45.393  16.891  1.00 41.90      A
ATOM    711  CB  LEU A  91     -38.303  44.271  16.353  1.00 41.02      A
ATOM    712  CG  LEU A  91     -38.661  42.830  16.741  1.00 41.67      A
ATOM    713  CD1 LEU A  91     -37.797  41.855  15.945  1.00 42.24      A
ATOM    714  CD2 LEU A  91     -38.452  42.621  18.237  1.00 38.51      A
ATOM    715  C   LEU A  91     -38.471  46.728  16.789  1.00 42.19      A
ATOM    716  O   LEU A  91     -37.689  47.087  17.658  1.00 43.73      A
ATOM    717  N   THR A  92     -38.744  47.473  15.728  1.00 42.51      A
ATOM    718  CA  THR A  92     -38.096  48.756  15.523  1.00 42.73      A
ATOM    719  CB  THR A  92     -38.569  49.381  14.214  1.00 41.90      A
ATOM    720  OG1 THR A  92     -38.465  48.412  13.166  1.00 40.24      A
ATOM    721  CG2 THR A  92     -37.732  50.598  13.864  1.00 40.97      A
ATOM    722  C   THR A  92     -38.382  49.728  16.662  1.00 45.91      A
ATOM    723  O   THR A  92     -39.537  49.966  17.015  1.00 47.25      A
ATOM    724  N   PRO A  93     -37.328  50.293  17.273  1.00 48.17      A
ATOM    725  CD  PRO A  93     -35.894  49.975  17.173  1.00 48.36      A
ATOM    726  CA  PRO A  93     -37.576  51.238  18.367  1.00 48.74      A
ATOM    727  CB  PRO A  93     -36.175  51.546  18.890  1.00 47.61      A
ATOM    728  CG  PRO A  93     -35.409  50.306  18.561  1.00 47.80      A
ATOM    729  C   PRO A  93     -38.270  52.487  17.829  1.00 49.72      A
ATOM    730  O   PRO A  93     -37.927  52.986  16.755  1.00 47.12      A
ATOM    731  N   PRO A  94     -39.259  53.001  18.575  1.00 51.89      A
ATOM    732  CD  PRO A  94     -39.757  52.453  19.853  1.00 53.25      A
ATOM    733  CA  PRO A  94     -40.016  54.196  18.194  1.00 52.73      A
ATOM    734  CB  PRO A  94     -40.860  54.474  19.435  1.00 51.04      A
ATOM    735  CG  PRO A  94     -41.117  53.099  19.973  1.00 51.32      A
ATOM    736  C   PRO A  94     -39.131  55.391  17.816  1.00 53.43      A
ATOM    737  O   PRO A  94     -39.508  56.215  16.984  1.00 54.96      A
ATOM    738  N   HIS A  95     -37.953  55.490  18.414  1.00 52.36      A
ATOM    739  CA  HIS A  95     -37.090  56.613  18.105  1.00 52.42      A
ATOM    740  CB  HIS A  95     -36.631  57.275  19.401  1.00 56.67      A
ATOM    741  CG  HIS A  95     -37.753  57.872  20.191  1.00 60.74      A
ATOM    742  CD2 HIS A  95     -38.852  58.559  19.795  1.00 61.99      A
ATOM    743  ND1 HIS A  95     -37.840  57.766  21.564  1.00 61.80      A
ATOM    744  CE1 HIS A  95     -38.947  58.357  21.978  1.00 63.61      A
ATOM    745  NE2 HIS A  95     -39.580  58.845  20.925  1.00 63.95      A
ATOM    746  C   HIS A  95     -35.894  56.239  17.250  1.00 51.12      A
ATOM    747  O   HIS A  95     -34.940  57.008  17.143  1.00 50.27      A
ATOM    748  N   SER A  96     -35.955  55.058  16.639  1.00 48.95      A
ATOM    749  CA  SER A  96     -34.887  54.575  15.767  1.00 45.53      A
ATOM    750  CB  SER A  96     -35.294  53.232  15.153  1.00 44.93      A
ATOM    751  OG  SER A  96     -34.267  52.693  14.344  1.00 44.67      A
ATOM    752  C   SER A  96     -34.668  55.615  14.673  1.00 44.83      A
ATOM    753  O   SER A  96     -35.611  56.272  14.240  1.00 44.17      A
ATOM    754  N   ALA A  97     -33.430  55.779  14.228  1.00 44.27      A
ATOM    755  CA  ALA A  97     -33.141  56.766  13.194  1.00 44.29      A
ATOM    756  CB  ALA A  97     -31.672  56.743  12.852  1.00 44.37      A
ATOM    757  C   ALA A  97     -33.963  56.533  11.938  1.00 45.78      A
ATOM    758  O   ALA A  97     -34.003  55.427  11.397  1.00 45.83      A
ATOM    759  N   LYS A  98     -34.611  57.591  11.467  1.00 47.33      A
ATOM    760  CA  LYS A  98     -35.435  57.512  10.270  1.00 47.46      A
```

FIGURE 5- 11 -

```
ATOM    761  CB   LYS A  98     -36.131  58.846  10.021  1.00 48.67      A
ATOM    762  CG   LYS A  98     -35.160  59.939   9.783  1.00 50.30      A
ATOM    763  CD   LYS A  98     -35.858  61.195   9.173  1.00 52.84      A
ATOM    764  CE   LYS A  98     -34.908  62.382   9.069  1.00 54.52      A
ATOM    765  NZ   LYS A  98     -35.558  63.570   8.444  1.00 56.51      A
ATOM    766  C    LYS A  98     -34.610  57.158   9.045  1.00 47.24      A
ATOM    767  O    LYS A  98     -33.386  57.312   9.031  1.00 47.03      A
ATOM    768  N    SER A  99     -35.307  56.697   8.015  1.00 47.52      A
ATOM    769  CA   SER A  99     -34.697  56.319   6.749  1.00 47.89      A
ATOM    770  CB   SER A  99     -35.601  55.326   6.013  1.00 49.40      A
ATOM    771  OG   SER A  99     -35.212  55.139   4.656  1.00 50.04      A
ATOM    772  C    SER A  99     -34.507  57.544   5.877  1.00 47.21      A
ATOM    773  O    SER A  99     -35.202  58.542   6.045  1.00 47.95      A
ATOM    774  N    LYS A 100     -33.568  57.478   4.943  1.00 46.96      A
ATOM    775  CA   LYS A 100     -33.362  58.608   4.054  1.00 47.74      A
ATOM    776  CB   LYS A 100     -31.896  58.702   3.613  1.00 47.01      A
ATOM    777  CG   LYS A 100     -31.398  57.546   2.753  1.00 49.83      A
ATOM    778  CD   LYS A 100     -29.877  57.632   2.495  1.00 50.89      A
ATOM    779  CE   LYS A 100     -29.072  57.570   3.807  1.00 50.89      A
ATOM    780  NZ   LYS A 100     -27.593  57.658   3.612  1.00 47.61      A
ATOM    781  C    LYS A 100     -34.275  58.410   2.849  1.00 48.48      A
ATOM    782  O    LYS A 100     -33.987  58.893   1.757  1.00 50.52      A
ATOM    783  N    PHE A 101     -35.389  57.712   3.060  1.00 47.25      A
ATOM    784  CA   PHE A 101     -36.331  57.439   1.984  1.00 47.34      A
ATOM    785  CB   PHE A 101     -36.290  55.947   1.638  1.00 47.47      A
ATOM    786  CG   PHE A 101     -34.966  55.497   1.078  1.00 48.04      A
ATOM    787  CD1  PHE A 101     -34.556  55.900  -0.186  1.00 47.72      A
ATOM    788  CD2  PHE A 101     -34.112  54.700   1.828  1.00 48.48      A
ATOM    789  CE1  PHE A 101     -33.311  55.521  -0.691  1.00 47.39      A
ATOM    790  CE2  PHE A 101     -32.865  54.319   1.326  1.00 48.25      A
ATOM    791  CZ   PHE A 101     -32.466  54.732   0.065  1.00 46.42      A
ATOM    792  C    PHE A 101     -37.773  57.876   2.263  1.00 48.26      A
ATOM    793  O    PHE A 101     -38.731  57.235   1.813  1.00 47.95      A
ATOM    794  N    GLY A 102     -37.925  58.962   3.014  1.00 48.98      A
ATOM    795  CA   GLY A 102     -39.248  59.485   3.304  1.00 49.73      A
ATOM    796  C    GLY A 102     -40.134  58.770   4.309  1.00 50.55      A
ATOM    797  O    GLY A 102     -41.355  58.634   4.115  1.00 52.78      A
ATOM    798  N    TYR A 103     -39.544  58.252   5.379  1.00 48.36      A
ATOM    799  CA   TYR A 103     -40.319  57.585   6.418  1.00 46.79      A
ATOM    800  CB   TYR A 103     -40.993  56.320   5.878  1.00 45.56      A
ATOM    801  CG   TYR A 103     -40.054  55.138   5.546  1.00 45.65      A
ATOM    802  CD1  TYR A 103     -39.722  54.221   6.502  1.00 45.22      A
ATOM    803  CE1  TYR A 103     -38.864  53.164   6.189  1.00 43.86      A
ATOM    804  CD2  TYR A 103     -39.499  55.071   4.270  1.00 45.39      A
ATOM    805  CE2  TYR A 103     -38.640  54.019   3.951  1.00 44.76      A
ATOM    806  CZ   TYR A 103     -38.334  53.073   4.913  1.00 43.93      A
ATOM    807  OH   TYR A 103     -37.514  52.031   4.585  1.00 45.33      A
ATOM    808  C    TYR A 103     -39.390  57.262   7.573  1.00 46.66      A
ATOM    809  O    TYR A 103     -38.176  57.158   7.385  1.00 47.85      A
ATOM    810  N    GLY A 104     -39.955  57.124   8.768  1.00 45.08      A
ATOM    811  CA   GLY A 104     -39.137  56.844   9.927  1.00 44.07      A
ATOM    812  C    GLY A 104     -39.694  55.782  10.842  1.00 45.32      A
ATOM    813  O    GLY A 104     -40.698  55.131  10.538  1.00 45.14      A
ATOM    814  N    ALA A 105     -39.023  55.621  11.975  1.00 46.02      A
ATOM    815  CA   ALA A 105     -39.393  54.636  12.978  1.00 47.89      A
ATOM    816  CB   ALA A 105     -38.735  54.984  14.299  1.00 47.54      A
ATOM    817  C    ALA A 105     -40.895  54.511  13.170  1.00 49.00      A
ATOM    818  O    ALA A 105     -41.456  53.426  13.030  1.00 49.36      A
ATOM    819  N    LYS A 106     -41.539  55.627  13.491  1.00 50.55      A
ATOM    820  CA   LYS A 106     -42.975  55.641  13.723  1.00 52.19      A
ATOM    821  CB   LYS A 106     -43.443  57.065  14.032  1.00 55.42      A
ATOM    822  CG   LYS A 106     -44.563  57.155  15.073  1.00 59.28      A
ATOM    823  CD   LYS A 106     -44.013  57.333  16.506  1.00 63.84      A
ATOM    824  CE   LYS A 106     -43.285  56.091  17.039  1.00 65.08      A
ATOM    825  NZ   LYS A 106     -44.213  54.954  17.355  1.00 67.21      A
ATOM    826  C    LYS A 106     -43.755  55.092  12.531  1.00 51.73      A
ATOM    827  O    LYS A 106     -44.707  54.342  12.707  1.00 52.54      A
ATOM    828  N    ASP A 107     -43.359  55.467  11.321  1.00 51.18      A
ATOM    829  CA   ASP A 107     -44.040  54.986  10.123  1.00 51.31      A
ATOM    830  CB   ASP A 107     -43.452  55.653   8.893  1.00 53.86      A
ATOM    831  CG   ASP A 107     -43.427  57.150   9.012  1.00 54.58      A
ATOM    832  OD1  ASP A 107     -44.513  57.750   9.165  1.00 55.22      A
ATOM    833  OD2  ASP A 107     -42.319  57.720   8.956  1.00 55.06      A
ATOM    834  C    ASP A 107     -43.860  53.483   9.999  1.00 51.22      A
ATOM    835  O    ASP A 107     -44.758  52.760   9.555  1.00 49.68      A
ATOM    836  N    VAL A 108     -42.672  53.030  10.377  1.00 50.31      A
```

FIGURE 5- 12 -

```
ATOM    837  CA   VAL A 108     -42.340  51.621  10.341  1.00 49.62      A
ATOM    838  CB   VAL A 108     -40.836  51.412  10.662  1.00 49.80      A
ATOM    839  CG1  VAL A 108     -40.557  49.947  10.993  1.00 51.24      A
ATOM    840  CG2  VAL A 108     -39.997  51.843   9.477  1.00 48.38      A
ATOM    841  C    VAL A 108     -43.196  50.859  11.354  1.00 49.24      A
ATOM    842  O    VAL A 108     -43.933  49.939  10.991  1.00 47.87      A
ATOM    843  N    ARG A 109     -43.098  51.247  12.623  1.00 49.52      A
ATOM    844  CA   ARG A 109     -43.851  50.585  13.689  1.00 50.84      A
ATOM    845  CB   ARG A 109     -43.681  51.328  15.018  1.00 49.85      A
ATOM    846  CG   ARG A 109     -42.270  51.356  15.586  1.00 50.79      A
ATOM    847  CD   ARG A 109     -42.278  51.914  17.008  1.00 51.54      A
ATOM    848  NE   ARG A 109     -43.246  51.194  17.832  1.00 52.15      A
ATOM    849  CZ   ARG A 109     -43.129  49.914  18.167  1.00 51.75      A
ATOM    850  NH1  ARG A 109     -42.077  49.219  17.758  1.00 53.08      A
ATOM    851  NH2  ARG A 109     -44.075  49.318  18.877  1.00 50.66      A
ATOM    852  C    ARG A 109     -45.332  50.532  13.358  1.00 51.28      A
ATOM    853  O    ARG A 109     -46.066  49.660  13.836  1.00 49.24      A
ATOM    854  N    ASN A 110     -45.742  51.473  12.514  1.00 52.93      A
ATOM    855  CA   ASN A 110     -47.128  51.639  12.108  1.00 53.78      A
ATOM    856  CB   ASN A 110     -47.424  53.129  12.043  1.00 54.63      A
ATOM    857  CG   ASN A 110     -48.860  53.440  12.333  1.00 58.65      A
ATOM    858  OD1  ASN A 110     -49.710  53.413  11.435  1.00 60.96      A
ATOM    859  ND2  ASN A 110     -49.157  53.720  13.606  1.00 58.11      A
ATOM    860  C    ASN A 110     -47.521  50.985  10.791  1.00 54.15      A
ATOM    861  O    ASN A 110     -48.568  51.298  10.232  1.00 55.96      A
ATOM    862  N    LEU A 111     -46.691  50.075  10.299  1.00 54.19      A
ATOM    863  CA   LEU A 111     -46.966  49.394   9.038  1.00 52.61      A
ATOM    864  CB   LEU A 111     -47.983  48.276   9.265  1.00 51.25      A
ATOM    865  CG   LEU A 111     -47.523  47.199  10.252  1.00 52.28      A
ATOM    866  CD1  LEU A 111     -48.599  46.143  10.403  1.00 52.43      A
ATOM    867  CD2  LEU A 111     -46.233  46.566   9.760  1.00 53.12      A
ATOM    868  C    LEU A 111     -47.465  50.345   7.949  1.00 51.74      A
ATOM    869  O    LEU A 111     -48.265  49.953   7.098  1.00 52.16      A
ATOM    870  N    SER A 112     -46.988  51.589   7.972  1.00 50.20      A
ATOM    871  CA   SER A 112     -47.396  52.575   6.977  1.00 50.65      A
ATOM    872  CB   SER A 112     -46.690  53.908   7.204  1.00 49.79      A
ATOM    873  OG   SER A 112     -45.682  54.109   6.226  1.00 49.64      A
ATOM    874  C    SER A 112     -47.064  52.079   5.577  1.00 52.26      A
ATOM    875  O    SER A 112     -46.008  51.495   5.342  1.00 53.25      A
ATOM    876  N    SER A 113     -47.968  52.334   4.644  1.00 54.10      A
ATOM    877  CA   SER A 113     -47.780  51.902   3.271  1.00 54.71      A
ATOM    878  CB   SER A 113     -48.856  52.507   2.378  1.00 56.09      A
ATOM    879  OG   SER A 113     -48.621  52.146   1.031  1.00 58.71      A
ATOM    880  C    SER A 113     -46.414  52.242   2.692  1.00 54.45      A
ATOM    881  O    SER A 113     -45.705  51.364   2.209  1.00 55.45      A
ATOM    882  N    ARG A 114     -46.033  53.510   2.726  1.00 53.40      A
ATOM    883  CA   ARG A 114     -44.750  53.862   2.155  1.00 52.34      A
ATOM    884  CB   ARG A 114     -44.474  55.354   2.305  1.00 53.21      A
ATOM    885  CG   ARG A 114     -43.105  55.744   1.775  1.00 56.33      A
ATOM    886  CD   ARG A 114     -42.959  57.235   1.672  1.00 59.58      A
ATOM    887  NE   ARG A 114     -43.923  57.774   0.727  1.00 63.65      A
ATOM    888  CZ   ARG A 114     -44.211  59.064   0.618  1.00 66.13      A
ATOM    889  NH1  ARG A 114     -43.601  59.946   1.405  1.00 66.05      A
ATOM    890  NH2  ARG A 114     -45.111  59.467  -0.274  1.00 66.62      A
ATOM    891  C    ARG A 114     -43.592  53.065   2.742  1.00 51.32      A
ATOM    892  O    ARG A 114     -42.836  52.440   1.997  1.00 50.75      A
ATOM    893  N    ALA A 115     -43.458  53.079   4.069  1.00 49.91      A
ATOM    894  CA   ALA A 115     -42.365  52.366   4.736  1.00 48.07      A
ATOM    895  CB   ALA A 115     -42.521  52.438   6.246  1.00 48.12      A
ATOM    896  C    ALA A 115     -42.327  50.921   4.297  1.00 46.63      A
ATOM    897  O    ALA A 115     -41.287  50.414   3.873  1.00 45.57      A
ATOM    898  N    VAL A 116     -43.477  50.269   4.396  1.00 44.97      A
ATOM    899  CA   VAL A 116     -43.602  48.876   4.012  1.00 44.62      A
ATOM    900  CB   VAL A 116     -45.054  48.396   4.178  1.00 42.67      A
ATOM    901  CG1  VAL A 116     -45.190  46.963   3.696  1.00 41.85      A
ATOM    902  CG2  VAL A 116     -45.457  48.496   5.644  1.00 40.93      A
ATOM    903  C    VAL A 116     -43.124  48.586   2.589  1.00 45.45      A
ATOM    904  O    VAL A 116     -42.387  47.629   2.371  1.00 45.72      A
ATOM    905  N    ASN A 117     -43.523  49.404   1.621  1.00 47.29      A
ATOM    906  CA   ASN A 117     -43.103  49.170   0.235  1.00 47.64      A
ATOM    907  CB   ASN A 117     -43.758  50.173  -0.710  1.00 48.86      A
ATOM    908  CG   ASN A 117     -45.263  50.088  -0.686  1.00 50.80      A
ATOM    909  OD1  ASN A 117     -45.838  49.029  -0.399  1.00 51.16      A
ATOM    910  ND2  ASN A 117     -45.920  51.201  -1.000  1.00 52.73      A
ATOM    911  C    ASN A 117     -41.593  49.224   0.049  1.00 47.63      A
ATOM    912  O    ASN A 117     -41.023  48.397  -0.675  1.00 45.83      A
```

FIGURE 5-13-

```
ATOM    913  N    HIS A 118     -40.951  50.205   0.685  1.00 47.28      A
ATOM    914  CA   HIS A 118     -39.503  50.337   0.596  1.00 46.77      A
ATOM    915  CB   HIS A 118     -39.040  51.638   1.256  1.00 49.56      A
ATOM    916  CG   HIS A 118     -39.420  52.866   0.484  1.00 55.11      A
ATOM    917  CD2  HIS A 118     -38.660  53.806  -0.130  1.00 55.34      A
ATOM    918  ND1  HIS A 118     -40.733  53.234   0.263  1.00 56.56      A
ATOM    919  CE1  HIS A 118     -40.763  54.348  -0.449  1.00 55.04      A
ATOM    920  NE2  HIS A 118     -39.519  54.716  -0.700  1.00 55.49      A
ATOM    921  C    HIS A 118     -38.853  49.122   1.255  1.00 44.53      A
ATOM    922  O    HIS A 118     -37.883  48.576   0.734  1.00 43.99      A
ATOM    923  N    ILE A 119     -39.396  48.689   2.388  1.00 41.53      A
ATOM    924  CA   ILE A 119     -38.864  47.513   3.063  1.00 40.84      A
ATOM    925  CB   ILE A 119     -39.691  47.178   4.335  1.00 38.92      A
ATOM    926  CG2  ILE A 119     -39.311  45.811   4.875  1.00 37.80      A
ATOM    927  CG1  ILE A 119     -39.434  48.234   5.408  1.00 38.11      A
ATOM    928  CD1  ILE A 119     -40.285  48.070   6.648  1.00 37.75      A
ATOM    929  C    ILE A 119     -38.914  46.342   2.065  1.00 41.47      A
ATOM    930  O    ILE A 119     -37.904  45.661   1.827  1.00 40.57      A
ATOM    931  N    ARG A 120     -40.093  46.136   1.476  1.00 41.29      A
ATOM    932  CA   ARG A 120     -40.311  45.084   0.485  1.00 41.26      A
ATOM    933  CB   ARG A 120     -41.676  45.246  -0.198  1.00 44.76      A
ATOM    934  CG   ARG A 120     -42.902  45.254   0.712  1.00 50.36      A
ATOM    935  CD   ARG A 120     -43.463  43.859   0.939  1.00 55.05      A
ATOM    936  NE   ARG A 120     -44.722  43.891   1.688  1.00 60.39      A
ATOM    937  CZ   ARG A 120     -45.859  44.419   1.234  1.00 62.52      A
ATOM    938  NH1  ARG A 120     -45.907  44.966   0.021  1.00 61.93      A
ATOM    939  NH2  ARG A 120     -46.951  44.401   1.995  1.00 63.14      A
ATOM    940  C    ARG A 120     -39.243  45.155  -0.600  1.00 39.14      A
ATOM    941  O    ARG A 120     -38.632  44.146  -0.953  1.00 38.64      A
ATOM    942  N    SER A 121     -39.026  46.355  -1.128  1.00 36.67      A
ATOM    943  CA   SER A 121     -38.053  46.535  -2.194  1.00 36.19      A
ATOM    944  CB   SER A 121     -38.190  47.926  -2.828  1.00 35.45      A
ATOM    945  OG   SER A 121     -37.592  48.912  -2.014  1.00 39.05      A
ATOM    946  C    SER A 121     -36.626  46.319  -1.719  1.00 34.14      A
ATOM    947  O    SER A 121     -35.808  45.792  -2.469  1.00 35.41      A
ATOM    948  N    VAL A 122     -36.323  46.726  -0.488  1.00 32.07      A
ATOM    949  CA   VAL A 122     -34.980  46.540   0.060  1.00 30.76      A
ATOM    950  CB   VAL A 122     -34.840  47.192   1.446  1.00 30.38      A
ATOM    951  CG1  VAL A 122     -33.713  46.533   2.240  1.00 29.78      A
ATOM    952  CG2  VAL A 122     -34.540  48.655   1.286  1.00 27.27      A
ATOM    953  C    VAL A 122     -34.710  45.045   0.187  1.00 32.04      A
ATOM    954  O    VAL A 122     -33.604  44.564  -0.105  1.00 31.53      A
ATOM    955  N    TRP A 123     -35.737  44.317   0.620  1.00 31.75      A
ATOM    956  CA   TRP A 123     -35.645  42.877   0.776  1.00 31.04      A
ATOM    957  CB   TRP A 123     -36.917  42.339   1.396  1.00 27.34      A
ATOM    958  CG   TRP A 123     -36.865  40.868   1.636  1.00 27.81      A
ATOM    959  CD2  TRP A 123     -36.265  40.202   2.754  1.00 27.20      A
ATOM    960  CE2  TRP A 123     -36.505  38.827   2.598  1.00 27.90      A
ATOM    961  CE3  TRP A 123     -35.502  40.632   3.844  1.00 28.44      A
ATOM    962  CD1  TRP A 123     -37.449  39.894   0.882  1.00 27.32      A
ATOM    963  NE1  TRP A 123     -37.249  38.666   1.458  1.00 27.64      A
ATOM    964  CZ2  TRP A 123     -36.072  37.885   3.531  1.00 29.29      A
ATOM    965  CZ3  TRP A 123     -35.069  39.698   4.764  1.00 26.82      A
ATOM    966  CH2  TRP A 123     -35.333  38.340   4.591  1.00 28.62      A
ATOM    967  C    TRP A 123     -35.424  42.203  -0.566  1.00 32.56      A
ATOM    968  O    TRP A 123     -34.590  41.302  -0.697  1.00 34.95      A
ATOM    969  N    GLU A 124     -36.175  42.643  -1.565  1.00 33.45      A
ATOM    970  CA   GLU A 124     -36.054  42.078  -2.891  1.00 33.84      A
ATOM    971  CB   GLU A 124     -37.068  42.712  -3.828  1.00 36.45      A
ATOM    972  CG   GLU A 124     -37.156  42.013  -5.168  1.00 44.20      A
ATOM    973  CD   GLU A 124     -37.324  40.509  -5.011  1.00 49.38      A
ATOM    974  OE1  GLU A 124     -37.967  40.096  -4.009  1.00 52.93      A
ATOM    975  OE2  GLU A 124     -36.825  39.751  -5.883  1.00 47.35      A
ATOM    976  C    GLU A 124     -34.652  42.305  -3.426  1.00 33.58      A
ATOM    977  O    GLU A 124     -34.097  41.445  -4.110  1.00 34.36      A
ATOM    978  N    ASP A 125     -34.073  43.461  -3.112  1.00 32.23      A
ATOM    979  CA   ASP A 125     -32.726  43.772  -3.575  1.00 31.84      A
ATOM    980  CB   ASP A 125     -32.397  45.242  -3.311  1.00 30.18      A
ATOM    981  CG   ASP A 125     -30.968  45.596  -3.695  1.00 33.74      A
ATOM    982  OD1  ASP A 125     -30.693  45.796  -4.896  1.00 35.04      A
ATOM    983  OD2  ASP A 125     -30.107  45.662  -2.793  1.00 34.61      A
ATOM    984  C    ASP A 125     -31.699  42.866  -2.884  1.00 31.97      A
ATOM    985  O    ASP A 125     -30.666  42.525  -3.465  1.00 32.03      A
ATOM    986  N    LEU A 126     -31.984  42.482  -1.644  1.00 30.68      A
ATOM    987  CA   LEU A 126     -31.087  41.612  -0.911  1.00 29.39      A
ATOM    988  CB   LEU A 126     -31.520  41.504   0.548  1.00 29.47      A
```

FIGURE 5-14-

```
ATOM    989  CG   LEU A 126     -31.067  42.622   1.494  1.00 28.46      A
ATOM    990  CD1  LEU A 126     -31.644  42.401   2.888  1.00 25.25      A
ATOM    991  CD2  LEU A 126     -29.548  42.647   1.538  1.00 26.22      A
ATOM    992  C    LEU A 126     -31.101  40.234  -1.539  1.00 30.59      A
ATOM    993  O    LEU A 126     -30.127  39.499  -1.450  1.00 31.86      A
ATOM    994  N    LEU A 127     -32.207  39.890  -2.187  1.00 30.02      A
ATOM    995  CA   LEU A 127     -32.347  38.582  -2.816  1.00 29.77      A
ATOM    996  CB   LEU A 127     -33.320  38.160  -2.868  1.00 27.16      A
ATOM    997  CG   LEU A 127     -34.600  37.938  -1.572  1.00 25.00      A
ATOM    998  CD1  LEU A 127     -35.990  37.471  -1.928  1.00 22.68      A
ATOM    999  CD2  LEU A 127     -33.906  36.899  -0.689  1.00 25.47      A
ATOM   1000  C    LEU A 127     -31.304  38.540  -4.224  1.00 31.28      A
ATOM   1001  O    LEU A 127     -31.452  37.476  -4.718  1.00 33.33      A
ATOM   1002  N    GLU A 128     -31.740  39.699  -4.869  1.00 33.73      A
ATOM   1003  CA   GLU A 128     -31.275  39.785  -6.252  1.00 34.45      A
ATOM   1004  CB   GLU A 128     -32.195  40.726  -7.023  1.00 38.45      A
ATOM   1005  CG   GLU A 128     -33.600  40.171  -7.165  1.00 45.88      A
ATOM   1006  CD   GLU A 128     -34.590  41.178  -7.719  1.00 50.49      A
ATOM   1007  OE1  GLU A 128     -35.723  40.760  -8.045  1.00 54.12      A
ATOM   1008  OE2  GLU A 128     -34.248  42.380  -7.817  1.00 51.93      A
ATOM   1009  C    GLU A 128     -29.826  40.214  -6.420  1.00 32.22      A
ATOM   1010  O    GLU A 128     -29.117  39.691  -7.278  1.00 29.54      A
ATOM   1011  N    ASP A 129     -29.397  41.169  -5.601  1.00 31.14      A
ATOM   1012  CA   ASP A 129     -28.031  41.670  -5.639  1.00 30.88      A
ATOM   1013  CB   ASP A 129     -28.026  43.181  -5.410  1.00 29.97      A
ATOM   1014  CG   ASP A 129     -26.734  43.841  -5.856  1.00 30.53      A
ATOM   1015  OD1  ASP A 129     -25.656  43.234  -5.680  1.00 29.62      A
ATOM   1016  OD2  ASP A 129     -26.796  44.981  -6.367  1.00 29.57      A
ATOM   1017  C    ASP A 129     -27.266  40.975  -4.513  1.00 31.60      A
ATOM   1018  O    ASP A 129     -27.619  41.107  -3.349  1.00 33.54      A
ATOM   1019  N    THR A 130     -26.224  40.231  -4.856  1.00 31.21      A
ATOM   1020  CA   THR A 130     -25.432  39.524  -3.856  1.00 31.59      A
ATOM   1021  CB   THR A 130     -25.190  38.076  -4.293  1.00 31.24      A
ATOM   1022  OG1  THR A 130     -24.411  38.063  -5.501  1.00 29.16      A
ATOM   1023  CG2  THR A 130     -26.501  37.379  -4.545  1.00 29.85      A
ATOM   1024  C    THR A 130     -24.055  40.147  -3.626  1.00 33.87      A
ATOM   1025  O    THR A 130     -23.250  39.590  -2.882  1.00 33.14      A
ATOM   1026  N    GLU A 131     -23.791  41.303  -4.235  1.00 36.22      A
ATOM   1027  CA   GLU A 131     -22.467  41.910  -4.138  1.00 39.19      A
ATOM   1028  CB   GLU A 131     -21.733  41.770  -5.468  1.00 42.45      A
ATOM   1029  CG   GLU A 131     -21.474  40.369  -5.958  1.00 51.23      A
ATOM   1030  CD   GLU A 131     -20.752  40.391  -7.301  1.00 56.21      A
ATOM   1031  OE1  GLU A 131     -20.049  41.400  -7.576  1.00 58.42      A
ATOM   1032  OE2  GLU A 131     -20.875  39.408  -8.071  1.00 56.17      A
ATOM   1033  C    GLU A 131     -22.327  43.369  -3.758  1.00 39.04      A
ATOM   1034  O    GLU A 131     -21.491  43.715  -2.931  1.00 40.95      A
ATOM   1035  N    THR A 132     -23.103  44.229  -4.401  1.00 37.01      A
ATOM   1036  CA   THR A 132     -22.988  45.661  -4.171  1.00 35.19      A
ATOM   1037  CB   THR A 132     -24.106  46.423  -4.896  1.00 36.43      A
ATOM   1038  OG1  THR A 132     -24.276  45.886  -6.221  1.00 35.50      A
ATOM   1039  CG2  THR A 132     -23.745  47.904  -4.981  1.00 33.37      A
ATOM   1040  C    THR A 132     -22.959  46.086  -2.711  1.00 33.57      A
ATOM   1041  O    THR A 132     -23.936  45.906  -1.978  1.00 33.33      A
ATOM   1042  N    PRO A 133     -21.826  46.656  -2.268  1.00 31.42      A
ATOM   1043  CD   PRO A 133     -20.591  46.896  -3.027  1.00 30.11      A
ATOM   1044  CA   PRO A 133     -21.672  47.109  -0.884  1.00 30.63      A
ATOM   1045  CB   PRO A 133     -20.404  47.936  -0.937  1.00 28.83      A
ATOM   1046  CG   PRO A 133     -19.590  47.170  -1.926  1.00 30.24      A
ATOM   1047  C    PRO A 133     -22.878  47.926  -0.506  1.00 30.26      A
ATOM   1048  O    PRO A 133     -23.471  48.583  -1.354  1.00 32.96      A
ATOM   1049  N    ILE A 134     -23.253  47.874   0.760  1.00 28.44      A
ATOM   1050  CA   ILE A 134     -24.408  48.616   1.210  1.00 28.63      A
ATOM   1051  CB   ILE A 134     -25.327  47.701   2.031  1.00 28.76      A
ATOM   1052  CG2  ILE A 134     -26.353  48.513   2.816  1.00 25.18      A
ATOM   1053  CG1  ILE A 134     -25.987  46.692   1.089  1.00 27.62      A
ATOM   1054  CD1  ILE A 134     -26.883  45.674   1.795  1.00 26.53      A
ATOM   1055  C    ILE A 134     -23.984  49.824   2.022  1.00 30.34      A
ATOM   1056  O    ILE A 134     -23.207  49.710   2.960  1.00 33.07      A
ATOM   1057  N    ASP A 135     -24.505  50.986   1.660  1.00 30.58      A
ATOM   1058  CA   ASP A 135     -24.160  52.209   2.356  1.00 32.89      A
ATOM   1059  CB   ASP A 135     -24.920  53.389   1.752  1.00 35.68      A
ATOM   1060  CG   ASP A 135     -24.626  54.696   2.465  1.00 40.96      A
ATOM   1061  OD1  ASP A 135     -23.478  55.188   2.352  1.00 42.33      A
ATOM   1062  OD2  ASP A 135     -25.538  55.225   3.149  1.00 43.20      A
ATOM   1063  C    ASP A 135     -24.436  52.155   3.854  1.00 32.92      A
ATOM   1064  O    ASP A 135     -25.373  51.494   4.307  1.00 33.42      A
```

FIGURE 5- 15 -

```
ATOM   1065  N   THR A 136     -23.607  52.865   4.614  1.00 32.46      A
ATOM   1066  CA  THR A 136     -23.757  52.955   6.059  1.00 32.15      A
ATOM   1067  CB  THR A 136     -22.808  51.990   6.819  1.00 32.39      A
ATOM   1068  OG1 THR A 136     -21.459  52.473   6.743  1.00 30.53      A
ATOM   1069  CG2 THR A 136     -22.864  50.582   6.229  1.00 31.10      A
ATOM   1070  C   THR A 136     -23.394  54.381   6.443  1.00 32.61      A
ATOM   1071  O   THR A 136     -22.651  55.043   5.732  1.00 33.18      A
ATOM   1072  N   THR A 137     -23.935  54.854   7.556  1.00 33.30      A
ATOM   1073  CA  THR A 137     -23.648  56.192   8.045  1.00 33.98      A
ATOM   1074  CB  THR A 137     -24.930  56.893   8.552  1.00 34.15      A
ATOM   1075  OG1 THR A 137     -25.865  57.012   7.475  1.00 35.71      A
ATOM   1076  CG2 THR A 137     -24.617  58.276   9.101  1.00 31.43      A
ATOM   1077  C   THR A 137     -22.714  55.983   9.223  1.00 36.80      A
ATOM   1078  O   THR A 137     -22.794  54.955   9.902  1.00 39.38      A
ATOM   1079  N   ILE A 138     -21.825  56.939   9.468  1.00 37.14      A
ATOM   1080  CA  ILE A 138     -20.904  56.823  10.591  1.00 36.64      A
ATOM   1081  CB  ILE A 138     -19.438  56.689  10.104  1.00 35.85      A
ATOM   1082  CG2 ILE A 138     -19.084  57.856   9.207  1.00 32.64      A
ATOM   1083  CG1 ILE A 138     -18.490  56.568  11.305  1.00 35.43      A
ATOM   1084  CD1 ILE A 138     -17.034  56.283  10.930  1.00 32.09      A
ATOM   1085  C   ILE A 138     -21.076  58.060  11.461  1.00 37.01      A
ATOM   1086  O   ILE A 138     -21.022  59.184  10.970  1.00 38.35      A
ATOM   1087  N   MET A 139     -21.304  57.842  12.752  1.00 37.17      A
ATOM   1088  CA  MET A 139     -21.515  58.934  13.693  1.00 36.51      A
ATOM   1089  CB  MET A 139     -22.968  58.954  14.158  1.00 36.34      A
ATOM   1090  CG  MET A 139     -23.963  59.251  13.061  1.00 38.57      A
ATOM   1091  SD  MET A 139     -23.712  60.904  12.410  1.00 45.82      A
ATOM   1092  CE  MET A 139     -24.916  61.841  13.369  1.00 41.97      A
ATOM   1093  C   MET A 139     -20.631  58.850  14.916  1.00 36.43      A
ATOM   1094  O   MET A 139     -20.154  57.782  15.279  1.00 37.03      A
ATOM   1095  N   ALA A 140     -20.405  60.002  15.536  1.00 37.80      A
ATOM   1096  CA  ALA A 140     -19.625  60.075  16.759  1.00 37.35      A
ATOM   1097  CB  ALA A 140     -19.050  61.456  16.936  1.00 37.23      A
ATOM   1098  C   ALA A 140     -20.658  59.788  17.842  1.00 38.87      A
ATOM   1099  O   ALA A 140     -21.706  60.434  17.908  1.00 37.77      A
ATOM   1100  N   LYS A 141     -20.371  58.796  18.674  1.00 40.89      A
ATOM   1101  CA  LYS A 141     -21.283  58.405  19.733  1.00 40.92      A
ATOM   1102  CB  LYS A 141     -20.944  56.987  20.188  1.00 43.55      A
ATOM   1103  CG  LYS A 141     -22.076  56.247  20.880  1.00 46.10      A
ATOM   1104  CD  LYS A 141     -21.682  54.799  21.116  1.00 46.10      A
ATOM   1105  CE  LYS A 141     -22.766  54.021  21.838  1.00 47.01      A
ATOM   1106  NZ  LYS A 141     -22.309  52.619  22.048  1.00 47.29      A
ATOM   1107  C   LYS A 141     -21.163  59.383  20.887  1.00 40.91      A
ATOM   1108  O   LYS A 141     -20.059  59.793  21.253  1.00 41.72      A
ATOM   1109  N   SER A 142     -22.307  59.762  21.445  1.00 39.65      A
ATOM   1110  CA  SER A 142     -22.362  60.698  22.567  1.00 37.38      A
ATOM   1111  CB  SER A 142     -23.493  61.696  22.348  1.00 37.21      A
ATOM   1112  OG  SER A 142     -23.684  62.492  23.497  1.00 36.32      A
ATOM   1113  C   SER A 142     -22.590  59.972  23.890  1.00 36.00      A
ATOM   1114  O   SER A 142     -23.712  59.577  24.202  1.00 35.06      A
ATOM   1115  N   GLU A 143     -21.525  59.800  24.665  1.00 34.68      A
ATOM   1116  CA  GLU A 143     -21.620  59.117  25.952  1.00 34.99      A
ATOM   1117  CB  GLU A 143     -20.917  57.754  25.898  1.00 35.33      A
ATOM   1118  CG  GLU A 143     -21.389  56.835  24.788  1.00 38.22      A
ATOM   1119  CD  GLU A 143     -20.551  55.570  24.679  1.00 39.82      A
ATOM   1120  OE1 GLU A 143     -19.316  55.689  24.617  1.00 43.04      A
ATOM   1121  OE2 GLU A 143     -21.114  54.457  24.641  1.00 42.03      A
ATOM   1122  C   GLU A 143     -20.991  59.959  27.061  1.00 35.32      A
ATOM   1123  O   GLU A 143     -19.969  60.627  26.858  1.00 33.49      A
ATOM   1124  N   VAL A 144     -21.616  59.908  28.234  1.00 35.53      A
ATOM   1125  CA  VAL A 144     -21.167  60.651  29.402  1.00 36.31      A
ATOM   1126  CB  VAL A 144     -22.379  61.056  30.273  1.00 36.09      A
ATOM   1127  CG1 VAL A 144     -21.916  61.489  31.665  1.00 34.05      A
ATOM   1128  CG2 VAL A 144     -23.155  62.178  29.578  1.00 34.97      A
ATOM   1129  C   VAL A 144     -20.172  59.881  30.265  1.00 36.87      A
ATOM   1130  O   VAL A 144     -20.280  58.666  30.433  1.00 37.74      A
ATOM   1131  N   PHE A 145     -19.203  60.604  30.812  1.00 36.81      A
ATOM   1132  CA  PHE A 145     -18.190  60.011  31.670  1.00 38.00      A
ATOM   1133  CB  PHE A 145     -17.005  59.534  30.837  1.00 36.58      A
ATOM   1134  CG  PHE A 145     -17.334  58.428  29.899  1.00 36.82      A
ATOM   1135  CD1 PHE A 145     -17.460  57.123  30.362  1.00 39.19      A
ATOM   1136  CD2 PHE A 145     -17.532  58.684  28.546  1.00 37.31      A
ATOM   1137  CE1 PHE A 145     -17.783  56.073  29.488  1.00 36.70      A
ATOM   1138  CE2 PHE A 145     -17.854  57.649  27.662  1.00 36.39      A
ATOM   1139  CZ  PHE A 145     -17.979  56.339  28.139  1.00 36.05      A
ATOM   1140  C   PHE A 145     -17.706  61.071  32.655  1.00 40.11      A
```

FIGURE 5-16-

```
ATOM   1141  O    PHE A 145     -18.081  62.247  32.546  1.00 40.28           A
ATOM   1142  N    CYS A 146     -16.879  60.642  33.611  1.00 40.76           A
ATOM   1143  CA   CYS A 146     -16.279  61.528  34.612  1.00 41.35           A
ATOM   1144  CB   CYS A 146     -16.376  60.890  36.005  1.00 41.48           A
ATOM   1145  SG   CYS A 146     -15.521  61.776  37.348  1.00 42.72           A
ATOM   1146  C    CYS A 146     -14.807  61.694  34.208  1.00 42.46           A
ATOM   1147  O    CYS A 146     -14.195  60.739  33.719  1.00 43.00           A
ATOM   1148  N    VAL A 147     -14.241  62.888  34.389  1.00 42.85           A
ATOM   1149  CA   VAL A 147     -12.836  63.110  34.029  1.00 44.70           A
ATOM   1150  CB   VAL A 147     -12.352  64.530  34.387  1.00 41.41           A
ATOM   1151  CG1  VAL A 147     -12.975  65.543  33.460  1.00 39.95           A
ATOM   1152  CG2  VAL A 147     -12.688  64.837  35.838  1.00 41.04           A
ATOM   1153  C    VAL A 147     -11.937  62.136  34.769  1.00 49.26           A
ATOM   1154  O    VAL A 147     -12.344  61.520  35.751  1.00 50.31           A
ATOM   1155  N    GLN A 148     -10.697  62.021  34.317  1.00 54.63           A
ATOM   1156  CA   GLN A 148      -9.753  61.112  34.946  1.00 60.93           A
ATOM   1157  CB   GLN A 148      -9.354  60.028  33.951  1.00 62.56           A
ATOM   1158  CG   GLN A 148     -10.532  59.256  33.400  1.00 66.18           A
ATOM   1159  CD   GLN A 148     -10.173  58.460  32.162  1.00 68.44           A
ATOM   1160  OE1  GLN A 148      -9.707  59.019  31.163  1.00 69.91           A
ATOM   1161  NE2  GLN A 148     -10.386  57.148  32.219  1.00 69.03           A
ATOM   1162  C    GLN A 148      -8.496  61.817  35.444  1.00 64.15           A
ATOM   1163  O    GLN A 148      -8.222  62.966  35.084  1.00 64.37           A
ATOM   1164  N    PRO A 149      -7.726  61.138  36.312  1.00 67.02           A
ATOM   1165  CD   PRO A 149      -8.139  59.972  37.120  1.00 66.47           A
ATOM   1166  CA   PRO A 149      -6.488  61.729  36.836  1.00 67.97           A
ATOM   1167  CB   PRO A 149      -6.152  60.827  38.029  1.00 68.10           A
ATOM   1168  CG   PRO A 149      -7.511  60.280  38.451  1.00 66.14           A
ATOM   1169  C    PRO A 149      -5.393  61.697  35.744  1.00 69.08           A
ATOM   1170  O    PRO A 149      -5.043  62.784  35.224  1.00 69.35           A
ATOM   1171  OXT  PRO A 149      -4.917  60.584  35.403  1.00 67.74           A
ATOM   1172  CB   ARG A 154     -11.491  63.612  27.868  1.00 53.33           A
ATOM   1173  CG   ARG A 154     -11.868  64.674  28.860  1.00 57.87           A
ATOM   1174  CD   ARG A 154     -12.615  65.807  28.205  1.00 60.74           A
ATOM   1175  NE   ARG A 154     -12.391  66.851  29.184  1.00 66.93           A
ATOM   1176  CZ   ARG A 154     -13.606  67.943  28.935  1.00 69.68           A
ATOM   1177  NH1  ARG A 154     -14.123  68.138  27.728  1.00 72.62           A
ATOM   1178  NH2  ARG A 154     -13.814  68.835  29.895  1.00 70.23           A
ATOM   1179  C    ARG A 154     -10.760  61.295  27.481  1.00 51.42           A
ATOM   1180  O    ARG A 154      -9.760  61.143  26.785  1.00 52.83           A
ATOM   1181  N    ARG A 154      -9.497  62.760  29.082  1.00 51.89           A
ATOM   1182  CA   ARG A 154     -10.829  62.399  28.512  1.00 52.71           A
ATOM   1183  N    LYS A 155     -11.835  60.520  27.396  1.00 49.61           A
ATOM   1184  CA   LYS A 155     -11.930  59.431  26.438  1.00 47.87           A
ATOM   1185  CB   LYS A 155     -12.887  58.345  26.942  1.00 48.34           A
ATOM   1186  CG   LYS A 155     -12.543  57.745  28.291  1.00 50.69           A
ATOM   1187  CD   LYS A 155     -13.575  56.699  28.708  1.00 50.72           A
ATOM   1188  CE   LYS A 155     -13.198  56.072  30.047  1.00 53.43           A
ATOM   1189  NZ   LYS A 155     -14.167  55.036  30.519  1.00 54.16           A
ATOM   1190  C    LYS A 155     -12.506  60.023  25.159  1.00 47.17           A
ATOM   1191  O    LYS A 155     -13.356  60.920  25.208  1.00 47.03           A
ATOM   1192  N    PRO A 156     -12.029  59.564  23.995  1.00 45.62           A
ATOM   1193  CD   PRO A 156     -10.784  58.822  23.744  1.00 44.35           A
ATOM   1194  CA   PRO A 156     -12.580  60.111  22.750  1.00 44.27           A
ATOM   1195  CB   PRO A 156     -11.471  59.854  21.741  1.00 44.14           A
ATOM   1196  CG   PRO A 156     -10.847  58.597  22.258  1.00 45.24           A
ATOM   1197  C    PRO A 156     -13.866  59.355  22.424  1.00 43.61           A
ATOM   1198  O    PRO A 156     -14.046  58.213  22.863  1.00 42.92           A
ATOM   1199  N    ALA A 157     -14.763  59.988  21.674  1.00 41.72           A
ATOM   1200  CA   ALA A 157     -16.028  59.353  21.318  1.00 40.47           A
ATOM   1201  CB   ALA A 157     -16.857  60.293  20.464  1.00 39.15           A
ATOM   1202  C    ALA A 157     -15.836  58.034  20.582  1.00 39.42           A
ATOM   1203  O    ALA A 157     -14.860  57.857  19.859  1.00 38.93           A
ATOM   1204  N    ARG A 158     -16.756  57.097  20.786  1.00 39.92           A
ATOM   1205  CA   ARG A 158     -16.679  55.827  20.076  1.00 40.64           A
ATOM   1206  CB   ARG A 158     -17.360  54.688  20.873  1.00 42.18           A
ATOM   1207  CG   ARG A 158     -16.506  54.118  22.034  1.00 43.54           A
ATOM   1208  CD   ARG A 158     -16.816  52.632  22.378  1.00 44.94           A
ATOM   1209  NE   ARG A 158     -15.656  51.942  22.983  1.00 48.78           A
ATOM   1210  CZ   ARG A 158     -15.367  50.641  22.835  1.00 49.75           A
ATOM   1211  NH1  ARG A 158     -16.148  49.858  22.100  1.00 52.54           A
ATOM   1212  NH2  ARG A 158     -14.291  50.113  23.409  1.00 43.98           A
ATOM   1213  C    ARG A 158     -17.403  56.091  18.749  1.00 40.08           A
ATOM   1214  O    ARG A 158     -18.144  57.065  18.630  1.00 40.16           A
ATOM   1215  N    LEU A 159     -17.172  55.256  17.743  1.00 38.56           A
ATOM   1216  CA   LEU A 159     -17.326  55.442  16.451  1.00 36.28           A
```

FIGURE 5- 17 -

```
ATOM   1217  CB   LEU A 159     -16.806  55.359  15.310  1.00 35.98      A
ATOM   1218  CG   LEU A 159     -15.761  56.455  15.071  1.00 36.51      A
ATOM   1219  CD1  LEU A 159     -15.906  57.601  16.082  1.00 36.81      A
ATOM   1220  CD2  LEU A 159     -14.389  55.819  15.128  1.00 32.46      A
ATOM   1221  C    LEU A 159     -18.900  54.393  16.199  1.00 35.70      A
ATOM   1222  O    LEU A 159     -18.661  53.199  16.364  1.00 35.86      A
ATOM   1223  N    ILE A 160     -20.087  54.832  15.804  1.00 34.64      A
ATOM   1224  CA   ILE A 160     -21.138  53.885  15.490  1.00 33.82      A
ATOM   1225  CB   ILE A 160     -22.436  54.228  16.209  1.00 33.09      A
ATOM   1226  CG2  ILE A 160     -22.264  53.999  17.688  1.00 33.92      A
ATOM   1227  CG1  ILE A 160     -22.809  55.682  15.947  1.00 34.72      A
ATOM   1228  CD1  ILE A 160     -24.124  56.116  16.593  1.00 33.51      A
ATOM   1229  C    ILE A 160     -21.350  53.898  13.985  1.00 34.49      A
ATOM   1230  O    ILE A 160     -21.249  54.936  13.340  1.00 37.00      A
ATOM   1231  N    VAL A 161     -21.618  52.732  13.419  1.00 34.40      A
ATOM   1232  CA   VAL A 161     -21.834  52.614  11.986  1.00 32.55      A
ATOM   1233  CB   VAL A 161     -20.635  51.898  11.333  1.00 30.42      A
ATOM   1234  CG1  VAL A 161     -20.890  51.646   9.846  1.00 31.10      A
ATOM   1235  CG2  VAL A 161     -19.400  52.740  11.510  1.00 26.73      A
ATOM   1236  C    VAL A 161     -23.122  51.823  11.788  1.00 34.28      A
ATOM   1237  O    VAL A 161     -23.297  50.747  12.368  1.00 34.82      A
ATOM   1238  N    PHE A 162     -24.034  52.350  10.975  1.00 34.41      A
ATOM   1239  CA   PHE A 162     -25.302  51.664  10.769  1.00 33.86      A
ATOM   1240  CB   PHE A 162     -26.300  52.070  11.855  1.00 32.47      A
ATOM   1241  CG   PHE A 162     -26.513  53.562  11.963  1.00 31.20      A
ATOM   1242  CD1  PHE A 162     -25.636  54.353  12.700  1.00 31.11      A
ATOM   1243  CD2  PHE A 162     -27.568  54.179  11.299  1.00 28.71      A
ATOM   1244  CE1  PHE A 162     -25.814  55.736  12.773  1.00 28.52      A
ATOM   1245  CE2  PHE A 162     -27.747  55.554  11.370  1.00 26.43      A
ATOM   1246  CZ   PHE A 162     -26.867  56.331  12.105  1.00 26.39      A
ATOM   1247  C    PHE A 162     -25.937  51.923   9.419  1.00 33.95      A
ATOM   1248  O    PHE A 162     -25.872  53.041   8.900  1.00 36.09      A
ATOM   1249  N    PRO A 163     -26.578  50.889   8.841  1.00 32.13      A
ATOM   1250  CD   PRO A 163     -26.643  49.518   9.374  1.00 31.15      A
ATOM   1251  CA   PRO A 163     -27.252  50.960   7.544  1.00 31.31      A
ATOM   1252  CB   PRO A 163     -27.441  49.498   7.182  1.00 32.53      A
ATOM   1253  CG   PRO A 163     -27.718  48.893   8.517  1.00 32.28      A
ATOM   1254  C    PRO A 163     -28.575  51.675   7.715  1.00 30.72      A
ATOM   1255  O    PRO A 163     -28.987  51.954   8.841  1.00 26.94      A
ATOM   1256  N    ASP A 164     -29.246  51.947   6.597  1.00 31.79      A
ATOM   1257  CA   ASP A 164     -30.526  52.649   6.602  1.00 32.99      A
ATOM   1258  CB   ASP A 164     -30.946  52.977   5.167  1.00 32.91      A
ATOM   1259  CG   ASP A 164     -32.072  53.991   5.105  1.00 34.71      A
ATOM   1260  OD1  ASP A 164     -31.808  55.184   5.355  1.00 36.53      A
ATOM   1261  OD2  ASP A 164     -33.221  53.599   4.818  1.00 34.32      A
ATOM   1262  C    ASP A 164     -31.638  51.852   7.287  1.00 33.95      A
ATOM   1263  O    ASP A 164     -31.676  50.625   7.212  1.00 32.82      A
ATOM   1264  N    LEU A 165     -32.547  52.561   7.946  1.00 35.12      A
ATOM   1265  CA   LEU A 165     -33.654  51.912   8.634  1.00 37.21      A
ATOM   1266  CB   LEU A 165     -34.738  52.938   8.981  1.00 38.60      A
ATOM   1267  CG   LEU A 165     -36.082  52.406   9.509  1.00 39.64      A
ATOM   1268  CD1  LEU A 165     -35.871  51.429  10.662  1.00 39.58      A
ATOM   1269  CD2  LEU A 165     -36.941  53.586   9.958  1.00 40.06      A
ATOM   1270  C    LEU A 165     -34.268  50.785   7.810  1.00 38.25      A
ATOM   1271  O    LEU A 165     -34.708  49.774   8.366  1.00 39.18      A
ATOM   1272  N    GLY A 166     -34.309  50.969   6.489  1.00 37.59      A
ATOM   1273  CA   GLY A 166     -34.876  49.957   5.615  1.00 34.78      A
ATOM   1274  C    GLY A 166     -34.147  48.635   5.758  1.00 34.35      A
ATOM   1275  O    GLY A 166     -34.759  47.603   6.022  1.00 36.96      A
ATOM   1276  N    VAL A 167     -32.831  48.665   5.581  1.00 32.94      A
ATOM   1277  CA   VAL A 167     -32.016  47.469   5.709  1.00 30.90      A
ATOM   1278  CB   VAL A 167     -30.527  47.793   5.471  1.00 28.66      A
ATOM   1279  CG1  VAL A 167     -29.674  46.681   5.975  1.00 29.18      A
ATOM   1280  CG2  VAL A 167     -30.267  47.997   3.998  1.00 26.77      A
ATOM   1281  C    VAL A 167     -32.185  46.865   7.108  1.00 31.89      A
ATOM   1282  O    VAL A 167     -32.294  45.646   7.265  1.00 32.13      A
ATOM   1283  N    ARG A 168     -32.217  47.723   8.121  1.00 32.68      A
ATOM   1284  CA   ARG A 168     -32.362  47.263   9.494  1.00 32.30      A
ATOM   1285  CB   ARG A 168     -32.387  48.452  10.453  1.00 31.43      A
ATOM   1286  CG   ARG A 168     -31.073  49.230  10.468  1.00 31.56      A
ATOM   1287  CD   ARG A 168     -30.860  49.968  11.789  1.00 31.26      A
ATOM   1288  NE   ARG A 168     -31.855  51.010  12.023  1.00 33.74      A
ATOM   1289  CZ   ARG A 168     -31.825  52.223  11.474  1.00 34.40      A
ATOM   1290  NH1  ARG A 168     -30.842  52.570  10.647  1.00 34.01      A
ATOM   1291  NH2  ARG A 168     -32.780  53.097  11.760  1.00 33.85      A
ATOM   1292  C    ARG A 168     -33.597  46.394   9.688  1.00 33.41      A
```

FIGURE 5-18 -

```
ATOM   1293  O    ARG A 168     -33.533  45.365  10.371  1.00 36.87           A
ATOM   1294  N    VAL A 169     -34.715  46.776   9.082  1.00 32.04           A
ATOM   1295  CA   VAL A 169     -35.927  45.977   9.218  1.00 31.15           A
ATOM   1296  CB   VAL A 169     -37.146  46.708   8.623  1.00 30.91           A
ATOM   1297  CG1  VAL A 169     -38.406  45.879   8.824  1.00 26.84           A
ATOM   1298  CG2  VAL A 169     -37.308  48.067   9.293  1.00 28.81           A
ATOM   1299  C    VAL A 169     -35.731  44.629   8.520  1.00 32.12           A
ATOM   1300  O    VAL A 169     -36.236  43.603   8.975  1.00 31.83           A
ATOM   1301  N    CYS A 170     -34.983  44.628   7.421  1.00 32.56           A
ATOM   1302  CA   CYS A 170     -34.713  43.385   6.703  1.00 33.06           A
ATOM   1303  CB   CYS A 170     -34.106  43.674   5.339  1.00 32.13           A
ATOM   1304  SG   CYS A 170     -35.253  44.424   4.220  1.00 34.12           A
ATOM   1305  C    CYS A 170     -33.768  42.482   7.493  1.00 32.82           A
ATOM   1306  O    CYS A 170     -33.857  41.254   7.418  1.00 32.52           A
ATOM   1307  N    GLU A 171     -32.851  43.088   8.239  1.00 32.76           A
ATOM   1308  CA   GLU A 171     -31.925  42.299   9.043  1.00 32.62           A
ATOM   1309  CB   GLU A 171     -30.954  43.190   9.827  1.00 31.71           A
ATOM   1310  CG   GLU A 171     -29.858  43.842   9.033  1.00 31.76           A
ATOM   1311  CD   GLU A 171     -28.880  44.592   9.937  1.00 34.72           A
ATOM   1312  OE1  GLU A 171     -28.077  43.941  10.637  1.00 32.38           A
ATOM   1313  OE2  GLU A 171     -28.921  45.840   9.962  1.00 38.60           A
ATOM   1314  C    GLU A 171     -32.748  41.496  10.039  1.00 32.10           A
ATOM   1315  O    GLU A 171     -32.537  40.294  10.198  1.00 31.95           A
ATOM   1316  N    LYS A 172     -33.688  42.167  10.704  1.00 31.24           A
ATOM   1317  CA   LYS A 172     -34.521  41.503  11.699  1.00 32.80           A
ATOM   1318  CB   LYS A 172     -35.506  42.499  12.332  1.00 34.57           A
ATOM   1319  CG   LYS A 172     -34.854  43.539  13.235  1.00 36.44           A
ATOM   1320  CD   LYS A 172     -35.802  44.689  13.560  1.00 38.20           A
ATOM   1321  CE   LYS A 172     -35.160  45.705  14.505  1.00 38.38           A
ATOM   1322  NZ   LYS A 172     -33.936  46.352  13.950  1.00 40.94           A
ATOM   1323  C    LYS A 172     -35.287  40.325  11.098  1.00 33.19           A
ATOM   1324  O    LYS A 172     -35.357  39.250  11.701  1.00 32.28           A
ATOM   1325  N    MET A 173     -35.854  40.522   9.908  1.00 32.19           A
ATOM   1326  CA   MET A 173     -36.615  39.458   9.256  1.00 31.57           A
ATOM   1327  CB   MET A 173     -37.209  39.943   7.932  1.00 32.61           A
ATOM   1328  CG   MET A 173     -38.437  40.829   8.078  1.00 33.63           A
ATOM   1329  SD   MET A 173     -39.141  41.257   6.480  1.00 36.32           A
ATOM   1330  CE   MET A 173     -38.148  42.684   6.013  1.00 34.07           A
ATOM   1331  C    MET A 173     -35.785  38.213   8.992  1.00 31.06           A
ATOM   1332  O    MET A 173     -36.247  37.088   9.204  1.00 30.70           A
ATOM   1333  N    ALA A 174     -34.556  38.421   8.535  1.00 29.25           A
ATOM   1334  CA   ALA A 174     -33.673  37.317   8.210  1.00 28.14           A
ATOM   1335  CB   ALA A 174     -32.800  37.710   7.024  1.00 25.80           A
ATOM   1336  C    ALA A 174     -32.789  36.818   9.357  1.00 29.13           A
ATOM   1337  O    ALA A 174     -32.356  35.666   9.354  1.00 28.14           A
ATOM   1338  N    LEU A 175     -32.537  37.651  10.357  1.00 28.95           A
ATOM   1339  CA   LEU A 175     -31.640  37.203  11.406  1.00 30.37           A
ATOM   1340  CB   LEU A 175     -30.288  37.898  11.212  1.00 30.02           A
ATOM   1341  CG   LEU A 175     -29.417  37.314  10.093  1.00 29.68           A
ATOM   1342  CD1  LEU A 175     -28.404  38.343   9.627  1.00 30.12           A
ATOM   1343  CD2  LEU A 175     -28.715  36.056  10.603  1.00 26.66           A
ATOM   1344  C    LEU A 175     -32.070  37.306  12.863  1.00 30.46           A
ATOM   1345  O    LEU A 175     -31.434  36.721  13.736  1.00 30.78           A
ATOM   1346  N    TYR A 176     -33.143  38.029  13.141  1.00 31.22           A
ATOM   1347  CA   TYR A 176     -33.581  38.162  14.521  1.00 29.97           A
ATOM   1348  CB   TYR A 176     -34.947  38.861  14.596  1.00 28.46           A
ATOM   1349  CG   TYR A 176     -35.368  39.132  16.018  1.00 30.13           A
ATOM   1350  CD1  TYR A 176     -34.804  40.178  16.741  1.00 31.44           A
ATOM   1351  CE1  TYR A 176     -35.096  40.356  18.086  1.00 32.23           A
ATOM   1352  CD2  TYR A 176     -36.242  38.273  16.679  1.00 28.69           A
ATOM   1353  CE2  TYR A 176     -36.534  38.436  18.015  1.00 28.92           A
ATOM   1354  CZ   TYR A 176     -35.959  39.477  18.719  1.00 32.15           A
ATOM   1355  OF   TYR A 176     -36.236  39.631  20.063  1.00 34.08           A
ATOM   1356  C    TYR A 176     -33.638  36.799  15.227  1.00 29.57           A
ATOM   1357  O    TYR A 176     -33.057  36.615  16.298  1.00 29.69           A
ATOM   1358  N    ASP A 177     -34.315  35.831  14.631  1.00 29.13           A
ATOM   1359  CA   ASP A 177     -34.401  34.534  15.278  1.00 30.10           A
ATOM   1360  CB   ASP A 177     -35.320  33.614  14.485  1.00 31.77           A
ATOM   1361  CG   ASP A 177     -36.030  32.626  15.368  1.00 33.64           A
ATOM   1362  OD1  ASP A 177     -36.323  32.991  16.530  1.00 37.51           A
ATOM   1363  OD2  ASP A 177     -36.305  31.501  14.909  1.00 35.05           A
ATOM   1364  C    ASP A 177     -33.019  33.895  15.459  1.00 30.17           A
ATOM   1365  O    ASP A 177     -32.683  33.403  16.543  1.00 28.89           A
ATOM   1366  N    VAL A 178     -32.217  33.914  14.400  1.00 29.77           A
ATOM   1367  CA   VAL A 178     -30.876  33.348  14.457  1.00 27.53           A
ATOM   1368  CB   VAL A 178     -30.114  33.595  13.143  1.00 26.26           A
```

FIGURE 5- 19 -

```
ATOM   1369  CG1 VAL A 178     -28.664  33.184  13.288  1.00 23.54      7
ATOM   1370  CG2 VAL A 178     -30.766  32.799  12.019  1.00 25.83      7
ATOM   1371  C   VAL A 178     -30.069  33.925  15.617  1.00 28.31      7
ATOM   1372  O   VAL A 178     -29.553  33.175  16.460  1.00 29.62      7
ATOM   1373  N   VAL A 179     -29.965  35.248  15.680  1.00 26.40      7
ATOM   1374  CA  VAL A 179     -29.202  35.864  16.750  1.00 25.82      7
ATOM   1375  CB  VAL A 179     -28.904  37.329  16.459  1.00 25.81      7
ATOM   1376  CG1 VAL A 179     -28.230  37.443  15.114  1.00 24.67      7
ATOM   1377  CG2 VAL A 179     -30.178  38.161  16.535  1.00 24.38      7
ATOM   1378  C   VAL A 179     -29.842  35.773  18.132  1.00 27.73      7
ATOM   1379  O   VAL A 179     -29.178  36.029  19.136  1.00 29.06      7
ATOM   1380  N   SER A 180     -31.116  35.401  18.198  1.00 28.48      7
ATOM   1381  CA  SER A 180     -31.789  35.287  19.488  1.00 29.36      7
ATOM   1382  CB  SER A 180     -33.254  35.697  19.363  1.00 29.31      7
ATOM   1383  OG  SER A 180     -33.383  37.015  18.867  1.00 32.67      7
ATOM   1384  C   SER A 180     -31.734  33.858  20.003  1.00 31.44      7
ATOM   1385  O   SER A 180     -31.931  33.609  21.187  1.00 32.97      7
ATOM   1386  N   THR A 181     -31.432  32.921  19.111  1.00 33.39      7
ATOM   1387  CA  THR A 181     -31.418  31.512  19.460  1.00 32.48      7
ATOM   1388  CB  THR A 181     -32.522  30.838  18.699  1.00 34.59      7
ATOM   1389  OG1 THR A 181     -33.740  31.550  18.948  1.00 40.19      7
ATOM   1390  CG2 THR A 181     -32.669  29.415  19.117  1.00 37.72      7
ATOM   1391  C   THR A 181     -30.131  30.728  19.238  1.00 31.99      7
ATOM   1392  O   THR A 181     -29.849  29.795  19.985  1.00 33.64      7
ATOM   1393  N   LEU A 182     -29.346  31.098  18.231  1.00 30.24      7
ATOM   1394  CA  LEU A 182     -28.116  30.365  17.932  1.00 29.21      7
ATOM   1395  CB  LEU A 182     -27.586  30.763  16.554  1.00 28.63      7
ATOM   1396  CG  LEU A 182     -26.465  29.854  16.066  1.00 27.94      7
ATOM   1397  CD1 LEU A 182     -26.666  29.545  14.630  1.00 32.05      7
ATOM   1398  CD2 LEU A 182     -25.148  30.510  16.267  1.00 30.25      7
ATOM   1399  C   LEU A 182     -26.988  30.470  18.954  1.00 27.87      7
ATOM   1400  O   LEU A 182     -26.349  29.472  19.284  1.00 27.50      7
ATOM   1401  N   PRO A 183     -26.710  31.683  19.453  1.00 28.53      7
ATOM   1402  CD  PRO A 183     -27.431  32.949  19.239  1.00 27.37      7
ATOM   1403  CA  PRO A 183     -25.637  31.849  20.441  1.00 28.83      7
ATOM   1404  CB  PRO A 183     -25.870  33.263  20.957  1.00 26.51      7
ATOM   1405  CG  PRO A 183     -26.475  33.951  19.777  1.00 26.12      7
ATOM   1406  C   PRO A 183     -25.767  30.804  21.560  1.00 30.40      7
ATOM   1407  O   PRO A 183     -24.807  30.108  21.909  1.00 28.86      7
ATOM   1408  N   GLN A 184     -26.978  30.714  22.101  1.00 31.37      7
ATOM   1409  CA  GLN A 184     -27.315  29.798  23.169  1.00 33.21      7
ATOM   1410  CB  GLN A 184     -28.779  30.013  23.552  1.00 39.94      7
ATOM   1411  CG  GLN A 184     -29.394  28.893  24.396  1.00 46.81      7
ATOM   1412  CD  GLN A 184     -28.608  28.640  25.660  1.00 49.94      7
ATOM   1413  OE1 GLN A 184     -28.292  29.575  26.397  1.00 54.60      7
ATOM   1414  NE2 GLN A 184     -28.285  27.376  25.922  1.00 52.08      7
ATOM   1415  C   GLN A 184     -27.084  28.329  22.814  1.00 32.48      7
ATOM   1416  O   GLN A 184     -26.458  27.585  23.566  1.00 32.92      7
ATOM   1417  N   ALA A 185     -27.598  27.910  21.668  1.00 30.47      7
ATOM   1418  CA  ALA A 185     -27.455  26.531  21.244  1.00 29.05      7
ATOM   1419  CB  ALA A 185     -28.229  26.295  19.959  1.00 27.30      7
ATOM   1420  C   ALA A 185     -26.002  26.173  21.038  1.00 29.66      7
ATOM   1421  O   ALA A 185     -25.568  25.046  21.314  1.00 30.52      7
ATOM   1422  N   VAL A 186     -25.222  27.131  20.558  1.00 29.15      7
ATOM   1423  CA  VAL A 186     -23.819  26.866  20.299  1.00 30.84      7
ATOM   1424  CB  VAL A 186     -23.242  27.851  19.250  1.00 30.01      7
ATOM   1425  CG1 VAL A 186     -21.782  27.528  18.980  1.00 28.00      7
ATOM   1426  CG2 VAL A 186     -24.037  27.766  17.958  1.00 30.07      7
ATOM   1427  C   VAL A 186     -22.924  26.904  21.531  1.00 32.37      7
ATOM   1428  O   VAL A 186     -22.220  25.935  21.832  1.00 32.35      7
ATOM   1429  N   MET A 187     -22.955  28.015  22.253  1.00 32.58      7
ATOM   1430  CA  MET A 187     -22.084  28.159  23.402  1.00 32.94      7
ATOM   1431  CB  MET A 187     -21.719  29.626  23.566  1.00 34.15      7
ATOM   1432  CG  MET A 187     -20.900  30.137  22.402  1.00 35.83      7
ATOM   1433  SD  MET A 187     -20.810  31.909  22.343  1.00 36.81      7
ATOM   1434  CE  MET A 187     -22.292  32.252  21.429  1.00 35.07      7
ATOM   1435  C   MET A 187     -22.562  27.591  24.716  1.00 33.07      7
ATOM   1436  O   MET A 187     -21.804  27.553  25.686  1.00 34.12      7
ATOM   1437  N   GLY A 188     -23.805  27.135  24.764  1.00 31.32      7
ATOM   1438  CA  GLY A 188     -24.290  26.577  26.012  1.00 30.20      7
ATOM   1439  C   GLY A 188     -24.080  27.537  27.164  1.00 29.59      7
ATOM   1440  O   GLY A 188     -24.030  28.748  26.963  1.00 32.17      7
ATOM   1441  N   SER A 189     -23.924  27.008  28.369  1.00 28.68      7
ATOM   1442  CA  SER A 189     -23.759  27.851  29.555  1.00 29.26      7
ATOM   1443  CB  SER A 189     -23.381  26.996  30.763  1.00 27.50      7
ATOM   1444  OG  SER A 189     -22.083  26.458  30.602  1.00 29.47      7
```

FIGURE 5-20 -

```
ATOM   1445  C    SER A 189     -22.764  29.010  29.432  1.00 30.18      A
ATOM   1446  C    SER A 189     -22.835  29.962  30.209  1.00 31.51      A
ATOM   1447  N    SER A 190     -21.843  28.944  28.474  1.00 29.08      A
ATOM   1448  CA   SER A 190     -20.868  30.015  28.320  1.00 28.14      A
ATOM   1449  CB   SER A 190     -19.691  29.548  27.468  1.00 30.22      A
ATOM   1450  CG   SER A 190     -18.768  28.804  28.248  1.00 33.89      A
ATOM   1451  C    SER A 190     -21.433  31.312  27.747  1.00 27.09      A
ATOM   1452  C    SER A 190     -20.806  32.353  27.859  1.00 26.14      A
ATOM   1453  N    TYR A 191     -22.610  31.254  27.137  1.00 26.84      A
ATOM   1454  CA   TYR A 191     -23.230  32.451  26.579  1.00 27.04      A
ATOM   1455  CB   TYR A 191     -24.388  32.055  25.657  1.00 26.88      A
ATOM   1456  CG   TYR A 191     -25.083  33.211  24.970  1.00 27.75      A
ATOM   1457  CD1  TYR A 191     -24.360  34.172  24.264  1.00 28.52      A
ATOM   1458  CE1  TYR A 191     -24.999  35.241  23.638  1.00 27.62      A
ATOM   1459  CD2  TYR A 191     -26.463  33.348  25.023  1.00 28.73      A
ATOM   1460  CE2  TYR A 191     -27.112  34.418  24.393  1.00 29.17      A
ATOM   1461  CZ   TYR A 191     -26.373  35.355  23.710  1.00 28.37      A
ATOM   1462  CH   TYR A 191     -27.016  36.398  23.083  1.00 29.81      A
ATOM   1463  C    TYR A 191     -23.737  33.271  27.764  1.00 28.47      A
ATOM   1464  C    TYR A 191     -24.623  32.828  28.481  1.00 31.15      A
ATOM   1465  N    GLY A 192     -23.185  34.466  27.963  1.00 27.85      A
ATOM   1466  CA   GLY A 192     -23.579  35.289  29.094  1.00 28.41      A
ATOM   1467  C    GLY A 192     -24.919  36.014  29.103  1.00 29.49      A
ATOM   1468  C    GLY A 192     -25.484  36.233  30.174  1.00 29.81      A
ATOM   1469  N    PHE A 193     -25.435  36.389  27.937  1.00 29.29      A
ATOM   1470  CA   PHE A 193     -26.703  37.110  27.859  1.00 29.32      A
ATOM   1471  CB   PHE A 193     -26.892  37.664  26.453  1.00 28.40      A
ATOM   1472  CG   PHE A 193     -25.958  38.784  26.118  1.00 29.16      A
ATOM   1473  CD1  PHE A 193     -26.041  39.998  26.798  1.00 25.71      A
ATOM   1474  CD2  PHE A 193     -24.983  38.624  25.132  1.00 29.13      A
ATOM   1475  CE1  PHE A 193     -25.181  41.037  26.508  1.00 25.39      A
ATOM   1476  CE2  PHE A 193     -24.110  39.663  24.831  1.00 30.08      A
ATOM   1477  CZ   PHE A 193     -24.211  40.878  25.523  1.00 29.09      A
ATOM   1478  C    PHE A 193     -27.960  36.343  28.263  1.00 31.47      A
ATOM   1479  C    PHE A 193     -29.057  36.907  28.288  1.00 31.94      A
ATOM   1480  N    GLN A 194     -27.807  35.068  28.603  1.00 32.60      A
ATOM   1481  CA   GLN A 194     -28.942  34.250  29.017  1.00 34.13      A
ATOM   1482  CB   GLN A 194     -28.638  32.770  28.759  1.00 34.02      A
ATOM   1483  CG   GLN A 194     -27.401  32.255  29.518  1.00 34.39      A
ATOM   1484  CD   GLN A 194     -27.168  30.763  29.340  1.00 33.77      A
ATOM   1485  CE1  GLN A 194     -27.973  29.952  29.772  1.00 36.58      A
ATOM   1486  NE2  GLN A 194     -26.066  30.400  28.698  1.00 32.88      A
ATOM   1487  C    GLN A 194     -29.212  34.450  30.514  1.00 35.32      A
ATOM   1488  C    GLN A 194     -30.288  34.102  31.013  1.00 36.58      A
ATOM   1489  N    TYR A 195     -28.229  35.017  31.210  1.00 34.39      A
ATOM   1490  CA   TYR A 195     -28.315  35.237  32.653  1.00 33.85      A
ATOM   1491  CB   TYR A 195     -26.963  34.958  33.315  1.00 32.05      A
ATOM   1492  CG   TYR A 195     -26.348  33.625  32.973  1.00 30.95      A
ATOM   1493  CD1  TYR A 195     -27.011  32.443  33.263  1.00 30.65      A
ATOM   1494  CE1  TYR A 195     -26.459  31.206  32.961  1.00 31.44      A
ATOM   1495  CD2  TYR A 195     -25.100  33.547  32.351  1.00 29.83      A
ATOM   1496  CE2  TYR A 195     -24.534  32.312  32.034  1.00 32.18      A
ATOM   1497  CZ   TYR A 195     -25.227  31.139  32.344  1.00 32.55      A
ATOM   1498  CH   TYR A 195     -24.711  29.898  32.027  1.00 32.05      A
ATOM   1499  C    TYR A 195     -28.733  36.629  33.091  1.00 34.73      A
ATOM   1500  C    TYR A 195     -28.266  37.635  32.548  1.00 36.73      A
ATOM   1501  N    SER A 196     -29.613  36.675  34.088  1.00 34.70      A
ATOM   1502  CA   SER A 196     -30.047  37.933  34.688  1.00 34.31      A
ATOM   1503  CB   SER A 196     -31.341  37.741  35.460  1.00 33.56      A
ATOM   1504  CG   SER A 196     -31.110  36.900  36.581  1.00 36.32      A
ATOM   1505  C    SER A 196     -28.917  38.157  35.690  1.00 33.81      A
ATOM   1506  C    SER A 196     -28.198  37.212  36.020  1.00 34.41      A
ATOM   1507  N    PRO A 197     -28.754  39.384  36.204  1.00 32.85      A
ATOM   1508  CD   PRO A 197     -29.594  40.580  36.028  1.00 34.05      A
ATOM   1509  CA   PRO A 197     -27.676  39.638  37.165  1.00 32.06      A
ATOM   1510  CB   PRO A 197     -28.084  40.963  37.788  1.00 31.86      A
ATOM   1511  CG   PRO A 197     -28.736  41.672  36.639  1.00 32.33      A
ATOM   1512  C    PRO A 197     -27.521  38.519  38.189  1.00 33.54      A
ATOM   1513  C    PRO A 197     -26.445  37.924  38.307  1.00 32.96      A
ATOM   1514  N    LYS A 198     -28.600  38.217  38.913  1.00 34.32      A
ATOM   1515  CA   LYS A 198     -28.567  37.152  39.927  1.00 35.34      A
ATOM   1516  CB   LYS A 198     -29.981  36.869  40.441  1.00 37.71      A
ATOM   1517  CG   LYS A 198     -30.058  36.023  41.705  1.00 37.30      A
ATOM   1518  CD   LYS A 198     -31.515  35.796  42.079  1.00 42.44      A
ATOM   1519  CE   LYS A 198     -31.699  35.231  43.489  1.00 44.84      A
ATOM   1520  NZ   LYS A 198     -33.153  34.950  43.792  1.00 46.50      A
```

FIGURE 5- 21 -

| | | | | | | | | | | |
|---|---|---|---|---|---|---|---|---|---|---|
| ATOM | 1521 | C | LYS | A | 198 | -27.986 | 35.864 | 39.347 | 1.00 33.63 | A |
| ATOM | 1522 | O | LYS | A | 198 | -27.064 | 35.274 | 39.896 | 1.00 33.50 | A |
| ATOM | 1523 | N | GLN | A | 199 | -28.529 | 35.445 | 38.217 | 1.00 32.67 | A |
| ATOM | 1524 | CA | GLN | A | 199 | -28.087 | 34.228 | 37.567 | 1.00 32.66 | A |
| ATOM | 1525 | CB | GLN | A | 199 | -28.943 | 33.986 | 36.334 | 1.00 31.02 | A |
| ATOM | 1526 | CG | GLN | A | 199 | -30.403 | 34.005 | 36.687 | 1.00 30.24 | A |
| ATOM | 1527 | CD | GLN | A | 199 | -31.293 | 33.776 | 35.517 | 1.00 28.33 | A |
| ATOM | 1528 | OE1 | GLN | A | 199 | -31.142 | 34.408 | 34.474 | 1.00 33.66 | A |
| ATOM | 1529 | NE2 | GLN | A | 199 | -32.245 | 32.881 | 35.677 | 1.00 26.28 | A |
| ATOM | 1530 | C | GLN | A | 199 | -26.618 | 34.219 | 37.203 | 1.00 33.04 | A |
| ATOM | 1531 | O | GLN | A | 199 | -25.961 | 33.180 | 37.310 | 1.00 33.64 | A |
| ATOM | 1532 | N | ARG | A | 200 | -26.103 | 35.368 | 36.777 | 1.00 32.64 | A |
| ATOM | 1533 | CA | ARG | A | 200 | -24.700 | 35.471 | 36.400 | 1.00 33.12 | A |
| ATOM | 1534 | CB | ARG | A | 200 | -24.435 | 36.829 | 35.763 | 1.00 31.20 | A |
| ATOM | 1535 | CG | ARG | A | 200 | -23.019 | 37.039 | 35.279 | 1.00 30.88 | A |
| ATOM | 1536 | CD | ARG | A | 200 | -22.731 | 38.535 | 35.036 | 1.00 31.68 | A |
| ATOM | 1537 | NE | ARG | A | 200 | -21.354 | 38.756 | 34.601 | 1.00 33.92 | A |
| ATOM | 1538 | CZ | ARG | A | 200 | -20.900 | 38.475 | 33.381 | 1.00 35.26 | A |
| ATOM | 1539 | NH1 | ARG | A | 200 | -21.716 | 37.972 | 32.462 | 1.00 35.56 | A |
| ATOM | 1540 | NH2 | ARG | A | 200 | -19.621 | 38.663 | 33.089 | 1.00 36.19 | A |
| ATOM | 1541 | C | ARG | A | 200 | -23.846 | 35.296 | 37.653 | 1.00 35.35 | A |
| ATOM | 1542 | O | ARG | A | 200 | -22.851 | 34.556 | 37.655 | 1.00 35.77 | A |
| ATOM | 1543 | N | VAL | A | 201 | -24.249 | 35.970 | 38.726 | 1.00 36.44 | A |
| ATOM | 1544 | CA | VAL | A | 201 | -23.527 | 35.875 | 39.993 | 1.00 37.68 | A |
| ATOM | 1545 | CB | VAL | A | 201 | -24.207 | 36.716 | 41.081 | 1.00 36.96 | A |
| ATOM | 1546 | CG1 | VAL | A | 201 | -23.474 | 36.564 | 42.379 | 1.00 37.48 | A |
| ATOM | 1547 | CG2 | VAL | A | 201 | -24.213 | 38.163 | 40.669 | 1.00 41.01 | A |
| ATOM | 1548 | C | VAL | A | 201 | -23.485 | 34.420 | 40.447 | 1.00 36.57 | A |
| ATOM | 1549 | O | VAL | A | 201 | -22.468 | 33.933 | 40.954 | 1.00 33.92 | A |
| ATOM | 1550 | N | GLU | A | 202 | -24.610 | 33.739 | 40.255 | 1.00 36.87 | A |
| ATOM | 1551 | CA | GLU | A | 202 | -24.744 | 32.337 | 40.618 | 1.00 37.98 | A |
| ATOM | 1552 | CB | GLU | A | 202 | -26.163 | 31.850 | 40.296 | 1.00 40.38 | A |
| ATOM | 1553 | CG | GLU | A | 202 | -26.404 | 30.352 | 40.521 | 1.00 45.51 | A |
| ATOM | 1554 | CD | GLU | A | 202 | -27.872 | 29.957 | 40.336 | 1.00 49.28 | A |
| ATOM | 1555 | OE1 | GLU | A | 202 | -28.662 | 30.801 | 39.845 | 1.00 49.65 | A |
| ATOM | 1556 | OE2 | GLU | A | 202 | -28.233 | 28.804 | 40.678 | 1.00 50.34 | A |
| ATOM | 1557 | C | GLU | A | 202 | -23.728 | 31.517 | 39.840 | 1.00 36.99 | A |
| ATOM | 1558 | O | GLU | A | 202 | -22.953 | 30.750 | 40.419 | 1.00 34.78 | A |
| ATOM | 1559 | N | PHE | A | 203 | -23.728 | 31.706 | 38.523 | 1.00 35.48 | A |
| ATOM | 1560 | CA | PHE | A | 203 | -22.828 | 30.976 | 37.659 | 1.00 34.79 | A |
| ATOM | 1561 | CB | PHE | A | 203 | -23.105 | 31.317 | 36.204 | 1.00 36.10 | A |
| ATOM | 1562 | CG | PHE | A | 203 | -22.240 | 30.567 | 35.235 | 1.00 37.42 | A |
| ATOM | 1563 | CD1 | PHE | A | 203 | -22.412 | 29.198 | 35.046 | 1.00 36.54 | A |
| ATOM | 1564 | CD2 | PHE | A | 203 | -21.228 | 31.219 | 34.538 | 1.00 37.35 | A |
| ATOM | 1565 | CE1 | PHE | A | 203 | -21.599 | 28.488 | 34.177 | 1.00 35.69 | A |
| ATOM | 1566 | CE2 | PHE | A | 203 | -20.407 | 30.515 | 33.667 | 1.00 38.54 | A |
| ATOM | 1567 | CZ | PHE | A | 203 | -20.592 | 29.141 | 33.488 | 1.00 37.33 | A |
| ATOM | 1568 | C | PHE | A | 203 | -21.368 | 31.257 | 37.972 | 1.00 34.95 | A |
| ATOM | 1569 | O | PHE | A | 203 | -20.536 | 30.359 | 37.911 | 1.00 35.51 | A |
| ATOM | 1570 | N | LEU | A | 204 | -21.046 | 32.501 | 38.297 | 1.00 33.95 | A |
| ATOM | 1571 | CA | LEU | A | 204 | -19.664 | 32.839 | 38.601 | 1.00 32.84 | A |
| ATOM | 1572 | CB | LEU | A | 204 | -19.502 | 34.360 | 38.703 | 1.00 31.57 | A |
| ATOM | 1573 | CG | LEU | A | 204 | -19.558 | 35.155 | 37.394 | 1.00 31.90 | A |
| ATOM | 1574 | CD1 | LEU | A | 204 | -19.435 | 36.636 | 37.668 | 1.00 30.23 | A |
| ATOM | 1575 | CD2 | LEU | A | 204 | -18.431 | 34.704 | 36.488 | 1.00 30.20 | A |
| ATOM | 1576 | C | LEU | A | 204 | -19.192 | 32.180 | 39.894 | 1.00 33.29 | A |
| ATOM | 1577 | O | LEU | A | 204 | -18.122 | 31.576 | 39.946 | 1.00 32.58 | A |
| ATOM | 1578 | N | VAL | A | 205 | -20.005 | 32.298 | 40.934 | 1.00 34.22 | A |
| ATOM | 1579 | CA | VAL | A | 205 | -19.676 | 31.745 | 42.233 | 1.00 34.59 | A |
| ATOM | 1580 | CB | VAL | A | 205 | -20.650 | 32.262 | 43.300 | 1.00 33.96 | A |
| ATOM | 1581 | CG1 | VAL | A | 205 | -20.514 | 31.457 | 44.584 | 1.00 33.43 | A |
| ATOM | 1582 | CG2 | VAL | A | 205 | -20.357 | 33.729 | 43.572 | 1.00 32.79 | A |
| ATOM | 1583 | C | VAL | A | 205 | -19.656 | 30.229 | 42.243 | 1.00 36.41 | A |
| ATOM | 1584 | O | VAL | A | 205 | -18.724 | 29.626 | 42.780 | 1.00 36.85 | A |
| ATOM | 1585 | N | ASN | A | 206 | -20.669 | 29.601 | 41.662 | 1.00 36.88 | A |
| ATOM | 1586 | CA | ASN | A | 206 | -20.671 | 28.150 | 41.634 | 1.00 39.02 | A |
| ATOM | 1587 | CB | ASN | A | 206 | -21.945 | 27.611 | 40.976 | 1.00 41.18 | A |
| ATOM | 1588 | CG | ASN | A | 206 | -23.143 | 27.653 | 41.914 | 1.00 45.62 | A |
| ATOM | 1589 | OD1 | ASN | A | 206 | -23.033 | 27.300 | 43.091 | 1.00 48.87 | A |
| ATOM | 1590 | ND2 | ASN | A | 206 | -24.294 | 28.077 | 41.398 | 1.00 48.60 | A |
| ATOM | 1591 | C | ASN | A | 206 | -19.435 | 27.657 | 40.887 | 1.00 39.38 | A |
| ATOM | 1592 | O | ASN | A | 206 | -18.758 | 26.727 | 41.332 | 1.00 40.68 | A |
| ATOM | 1593 | N | THR | A | 207 | -19.130 | 28.298 | 39.764 | 1.00 38.14 | A |
| ATOM | 1594 | CA | THR | A | 207 | -17.977 | 27.921 | 38.964 | 1.00 37.44 | A |
| ATOM | 1595 | CB | THR | A | 207 | -17.839 | 28.815 | 37.706 | 1.00 37.53 | A |
| ATOM | 1596 | OG1 | THR | A | 207 | -18.984 | 28.635 | 36.862 | 1.00 37.19 | A |

FIGURE 5- 22 -

```
ATOM   1597  CG2 THR A 207     -16.574  28.457  36.921  1.00 35.16      A
ATOM   1598  C   THR A 207     -16.713  28.053  39.792  1.00 38.73      A
ATOM   1599  O   THR A 207     -15.901  27.126  39.860  1.00 39.37      A
ATOM   1600  N   TRP A 208     -16.557  29.209  40.429  1.00 38.79      A
ATOM   1601  CA  TRP A 208     -15.378  29.481  41.241  1.00 38.43      A
ATOM   1602  CB  TRP A 208     -15.455  30.895  41.816  1.00 37.71      A
ATOM   1603  CG  TRP A 208     -14.207  31.344  42.506  1.00 34.99      A
ATOM   1604  CD2 TRP A 208     -13.063  31.945  41.890  1.00 34.96      A
ATOM   1605  CE2 TRP A 208     -12.119  32.189  42.914  1.00 33.58      A
ATOM   1606  CE3 TRP A 208     -12.744  32.305  40.571  1.00 34.59      A
ATOM   1607  CD1 TRP A 208     -13.924  31.248  43.833  1.00 32.76      A
ATOM   1608  NE1 TRP A 208     -12.671  31.754  44.089  1.00 33.29      A
ATOM   1609  CZ2 TRP A 208     -10.869  32.775  42.662  1.00 32.84      A
ATOM   1610  CZ3 TRP A 208     -11.494  32.892  40.319  1.00 36.13      A
ATOM   1611  CH2 TRP A 208     -10.576  33.119  41.365  1.00 33.20      A
ATOM   1612  C   TRP A 208     -15.241  28.472  42.357  1.00 39.72      A
ATOM   1613  O   TRP A 208     -14.139  27.995  42.638  1.00 39.96      A
ATOM   1614  N   LYS A 209     -16.368  28.143  42.981  1.00 40.63      A
ATOM   1615  CA  LYS A 209     -16.388  27.183  44.078  1.00 42.10      A
ATOM   1616  CB  LYS A 209     -17.715  27.268  44.841  1.00 42.25      A
ATOM   1617  CG  LYS A 209     -17.839  28.479  45.756  1.00 45.37      A
ATOM   1618  CD  LYS A 209     -19.128  28.452  46.595  1.00 46.65      A
ATOM   1619  CE  LYS A 209     -19.176  29.627  47.584  1.00 48.32      A
ATOM   1620  NZ  LYS A 209     -20.394  29.636  48.456  1.00 49.29      A
ATOM   1621  C   LYS A 209     -16.164  25.738  43.632  1.00 42.64      A
ATOM   1622  O   LYS A 209     -15.874  24.871  44.458  1.00 44.36      A
ATOM   1623  N   SER A 210     -16.282  25.465  42.338  1.00 41.24      A
ATOM   1624  CA  SER A 210     -16.105  24.097  41.868  1.00 41.14      A
ATOM   1625  CB  SER A 210     -16.976  23.841  40.648  1.00 40.29      A
ATOM   1626  OG  SER A 210     -16.377  24.440  39.515  1.00 43.00      A
ATOM   1627  C   SER A 210     -14.662  23.778  41.514  1.00 41.44      A
ATOM   1628  O   SER A 210     -14.325  22.630  41.248  1.00 42.51      A
ATOM   1629  N   LYS A 211     -13.806  24.789  41.491  1.00 41.62      A
ATOM   1630  CA  LYS A 211     -12.408  24.548  41.168  1.00 42.22      A
ATOM   1631  CB  LYS A 211     -11.769  25.806  40.567  1.00 42.77      A
ATOM   1632  CG  LYS A 211     -12.519  26.399  39.373  1.00 43.79      A
ATOM   1633  CD  LYS A 211     -12.642  25.417  38.220  1.00 41.68      A
ATOM   1634  CE  LYS A 211     -13.489  25.996  37.104  1.00 39.91      A
ATOM   1635  NZ  LYS A 211     -13.649  25.019  35.987  1.00 42.01      A
ATOM   1636  C   LYS A 211     -11.691  24.172  42.459  1.00 42.11      A
ATOM   1637  O   LYS A 211     -11.968  24.741  43.510  1.00 40.32      A
ATOM   1638  N   LYS A 212     -10.780  23.210  42.383  1.00 42.60      A
ATOM   1639  CA  LYS A 212     -10.045  22.798  43.568  1.00 45.02      A
ATOM   1640  CB  LYS A 212      -9.086  21.652  43.219  1.00 49.73      A
ATOM   1641  CG  LYS A 212      -9.822  20.445  42.596  1.00 55.68      A
ATOM   1642  CD  LYS A 212      -8.981  19.162  42.531  1.00 58.78      A
ATOM   1643  CE  LYS A 212      -9.819  17.983  42.012  1.00 60.45      A
ATOM   1644  NZ  LYS A 212      -9.097  16.673  42.031  1.00 60.64      A
ATOM   1645  C   LYS A 212      -9.303  24.020  44.085  1.00 43.99      A
ATOM   1646  O   LYS A 212      -9.302  24.311  45.278  1.00 42.63      A
ATOM   1647  N   CYS A 213      -8.685  24.738  43.160  1.00 44.58      A
ATOM   1648  CA  CYS A 213      -7.973  25.964  43.472  1.00 44.54      A
ATOM   1649  CB  CYS A 213      -6.486  25.696  43.672  1.00 43.67      A
ATOM   1650  SG  CYS A 213      -5.616  27.162  44.262  1.00 44.92      A
ATOM   1651  C   CYS A 213      -8.201  26.871  42.258  1.00 45.03      A
ATOM   1652  O   CYS A 213      -7.443  26.834  41.281  1.00 45.75      A
ATOM   1653  N   PRO A 214      -9.256  27.699  42.308  1.00 43.99      A
ATOM   1654  CD  PRO A 214     -10.152  27.900  43.461  1.00 44.09      A
ATOM   1655  CA  PRO A 214      -9.609  28.613  41.220  1.00 43.35      A
ATOM   1656  CB  PRO A 214     -10.972  29.149  41.653  1.00 42.60      A
ATOM   1657  CG  PRO A 214     -10.823  29.225  43.131  1.00 42.60      A
ATOM   1658  C   PRO A 214      -8.639  29.738  40.897  1.00 42.24      A
ATOM   1659  O   PRO A 214      -8.019  30.326  41.782  1.00 43.30      A
ATOM   1660  N   MET A 215      -8.517  30.003  39.601  1.00 39.88      A
ATOM   1661  CA  MET A 215      -7.709  31.081  39.071  1.00 37.25      A
ATOM   1662  CB  MET A 215      -6.435  30.572  38.420  1.00 37.59      A
ATOM   1663  CG  MET A 215      -5.499  31.691  37.918  1.00 39.20      A
ATOM   1664  SD  MET A 215      -5.957  32.498  36.345  1.00 37.98      A
ATOM   1665  CE  MET A 215      -5.223  31.388  35.205  1.00 35.67      A
ATOM   1666  C   MET A 215      -8.627  31.625  38.007  1.00 38.20      A
ATOM   1667  O   MET A 215      -9.231  30.859  37.248  1.00 38.74      A
ATOM   1668  N   GLY A 216      -8.769  32.940  37.960  1.00 36.90      A
ATOM   1669  CA  GLY A 216      -9.639  33.509  36.960  1.00 35.03      A
ATOM   1670  C   GLY A 216      -9.036  34.762  36.388  1.00 34.42      A
ATOM   1671  O   GLY A 216      -8.156  35.363  36.997  1.00 35.95      A
ATOM   1672  N   PHE A 217      -9.500  35.153  35.211  1.00 32.68      A
```

FIGURE 5- 23 -

```
ATOM   1673  CA  PHE A 217      -9.004  36.359  34.583  1.00 31.82           A
ATOM   1674  CB  PHE A 217      -7.651  36.108  33.894  1.00 31.82           A
ATOM   1675  CG  PHE A 217      -7.707  35.142  32.728  1.00 31.24           A
ATOM   1676  CD1 PHE A 217      -7.378  33.799  32.901  1.00 30.23           A
ATOM   1677  CD2 PHE A 217      -8.047  35.586  31.445  1.00 31.28           A
ATOM   1678  CE1 PHE A 217      -7.384  32.917  31.820  1.00 28.55           A
ATOM   1679  CE2 PHE A 217      -8.057  34.704  30.354  1.00 28.42           A
ATOM   1680  CZ  PHE A 217      -7.723  33.372  30.545  1.00 29.39           A
ATOM   1681  C   PHE A 217      -9.982  36.903  33.564  1.00 30.98           A
ATOM   1682  O   PHE A 217     -10.734  36.156  32.946  1.00 31.55           A
ATOM   1683  N   SER A 218      -9.991  38.217  33.421  1.00 29.22           A
ATOM   1684  CA  SER A 218     -10.828  38.844  32.428  1.00 30.66           A
ATOM   1685  CB  SER A 218     -11.448  40.126  32.980  1.00 30.43           A
ATOM   1686  OG  SER A 218     -10.451  41.027  33.403  1.00 33.62           A
ATOM   1687  C   SER A 218      -9.831  39.156  31.306  1.00 31.60           A
ATOM   1688  O   SER A 218      -8.630  39.288  31.551  1.00 30.66           A
ATOM   1689  N   TYR A 219     -10.304  39.234  30.073  1.00 31.98           A
ATOM   1690  CA  TYR A 219      -9.403  39.535  28.973  1.00 32.41           A
ATOM   1691  CB  TYR A 219      -9.186  38.314  28.094  1.00 32.13           A
ATOM   1692  CG  TYR A 219      -8.191  38.554  26.992  1.00 33.48           A
ATOM   1693  CD1 TYR A 219      -6.824  38.410  27.216  1.00 33.98           A
ATOM   1694  CE1 TYR A 219      -5.899  38.629  26.190  1.00 34.25           A
ATOM   1695  CD2 TYR A 219      -8.613  38.926  25.717  1.00 35.01           A
ATOM   1696  CE2 TYR A 219      -7.699  39.147  24.688  1.00 34.32           A
ATOM   1697  CZ  TYR A 219      -6.346  38.996  24.930  1.00 34.00           A
ATOM   1698  OH  TYR A 219      -5.445  39.212  23.910  1.00 33.34           A
ATOM   1699  C   TYR A 219     -10.003  40.651  28.153  1.00 32.58           A
ATOM   1700  O   TYR A 219     -11.093  40.513  27.604  1.00 32.25           A
ATOM   1701  N   ASP A 220      -9.281  41.762  28.084  1.00 34.21           A
ATOM   1702  CA  ASP A 220      -9.736  42.931  27.353  1.00 34.41           A
ATOM   1703  CB  ASP A 220      -9.455  44.180  28.168  1.00 35.15           A
ATOM   1704  CG  ASP A 220      -9.718  45.433  27.398  1.00 37.63           A
ATOM   1705  OD1 ASP A 220     -10.762  45.492  26.720  1.00 38.65           A
ATOM   1706  OD2 ASP A 220      -8.884  46.363  27.475  1.00 42.34           A
ATOM   1707  C   ASP A 220      -9.095  43.066  25.986  1.00 36.09           A
ATOM   1708  O   ASP A 220      -7.901  43.357  25.866  1.00 35.78           A
ATOM   1709  N   THR A 221      -9.901  42.849  24.952  1.00 36.88           A
ATOM   1710  CA  THR A 221      -9.432  42.956  23.576  1.00 36.34           A
ATOM   1711  CB  THR A 221     -10.406  42.239  22.622  1.00 34.76           A
ATOM   1712  OG1 THR A 221     -10.462  40.848  22.957  1.00 32.17           A
ATOM   1713  CG2 THR A 221      -9.960  42.398  21.190  1.00 36.30           A
ATOM   1714  C   THR A 221      -9.336  44.435  23.189  1.00 37.09           A
ATOM   1715  O   THR A 221     -10.276  45.207  23.401  1.00 37.60           A
ATOM   1716  N   ARG A 222      -8.199  44.840  22.637  1.00 38.01           A
ATOM   1717  CA  ARG A 222      -8.039  46.230  22.234  1.00 38.22           A
ATOM   1718  CB  ARG A 222      -6.579  46.519  21.861  1.00 40.25           A
ATOM   1719  CG  ARG A 222      -6.332  47.978  21.503  1.00 44.84           A
ATOM   1720  CD  ARG A 222      -4.954  48.246  20.918  1.00 47.56           A
ATOM   1721  NE  ARG A 222      -5.076  49.235  19.846  1.00 56.27           A
ATOM   1722  CZ  ARG A 222      -4.515  50.444  19.842  1.00 59.48           A
ATOM   1723  NH1 ARG A 222      -3.761  50.846  20.865  1.00 60.74           A
ATOM   1724  NH2 ARG A 222      -4.731  51.262  18.814  1.00 59.17           A
ATOM   1725  C   ARG A 222      -8.941  46.540  21.038  1.00 37.08           A
ATOM   1726  O   ARG A 222      -8.691  46.075  19.931  1.00 37.08           A
ATOM   1727  N   CYS A 223      -9.998  47.310  21.268  1.00 36.67           A
ATOM   1728  CA  CYS A 223     -10.916  47.701  20.196  1.00 39.18           A
ATOM   1729  CB  CYS A 223     -10.238  48.697  19.251  1.00 42.30           A
ATOM   1730  SG  CYS A 223      -9.605  50.181  20.058  1.00 49.83           A
ATOM   1731  C   CYS A 223     -11.396  46.517  19.382  1.00 38.06           A
ATOM   1732  O   CYS A 223     -11.142  46.433  18.166  1.00 37.15           A
ATOM   1733  N   PHE A 224     -12.116  45.626  20.056  1.00 36.06           A
ATOM   1734  CA  PHE A 224     -12.636  44.405  19.452  1.00 34.11           A
ATOM   1735  CB  PHE A 224     -13.652  43.764  20.402  1.00 31.11           A
ATOM   1736  CG  PHE A 224     -13.971  42.346  20.065  1.00 30.66           A
ATOM   1737  CD1 PHE A 224     -14.889  42.042  19.068  1.00 29.31           A
ATOM   1738  CD2 PHE A 224     -13.324  41.304  20.723  1.00 29.81           A
ATOM   1739  CE1 PHE A 224     -15.153  40.720  18.728  1.00 29.12           A
ATOM   1740  CE2 PHE A 224     -13.582  39.972  20.389  1.00 26.70           A
ATOM   1741  CZ  PHE A 224     -14.495  39.681  19.395  1.00 27.89           A
ATOM   1742  C   PHE A 224     -13.235  44.530  18.042  1.00 33.51           A
ATOM   1743  O   PHE A 224     -12.841  43.788  17.143  1.00 32.12           A
ATOM   1744  N   ASP A 225     -14.169  45.457  17.842  1.00 33.12           A
ATOM   1745  CA  ASP A 225     -14.802  45.616  16.529  1.00 33.83           A
ATOM   1746  CB  ASP A 225     -15.749  46.815  16.519  1.00 30.91           A
ATOM   1747  CG  ASP A 225     -17.052  46.536  17.230  1.00 30.53           A
ATOM   1748  OD1 ASP A 225     -17.258  45.384  17.668  1.00 29.42           A
```

FIGURE 5- 24 -

```
ATOM   1749  OD2 ASP A 225     -17.873  47.473  17.344  1.00 29.44           A
ATOM   1750  C   ASP A 225     -13.842  45.741  15.352  1.00 34.25           A
ATOM   1751  O   ASP A 225     -14.005  45.062  14.331  1.00 35.56           A
ATOM   1752  N   SER A 226     -12.842  46.601  15.489  1.00 33.18           A
ATOM   1753  CA  SER A 226     -11.887  46.796  14.413  1.00 32.95           A
ATOM   1754  CB  SER A 226     -11.081  48.072  14.640  1.00 35.70           A
ATOM   1755  OG  SER A 226     -10.493  48.063  15.931  1.00 44.14           A
ATOM   1756  C   SER A 226     -10.955  45.609  14.285  1.00 31.97           A
ATOM   1757  O   SER A 226     -10.230  45.497  13.295  1.00 33.63           A
ATOM   1758  N   THR A 227     -10.961  44.712  15.268  1.00 29.38           A
ATOM   1759  CA  THR A 227     -10.084  43.551  15.165  1.00 27.94           A
ATOM   1760  CB  THR A 227      -9.614  43.014  16.543  1.00 25.75           A
ATOM   1761  OG1 THR A 227     -10.687  42.341  17.201  1.00 27.33           A
ATOM   1762  CG2 THR A 227      -9.137  44.148  17.404  1.00 28.14           A
ATOM   1763  C   THR A 227     -10.738  42.413  14.413  1.00 26.92           A
ATOM   1764  O   THR A 227     -10.056  41.479  14.000  1.00 27.64           A
ATOM   1765  N   VAL A 228     -12.053  42.487  14.240  1.00 25.50           A
ATOM   1766  CA  VAL A 228     -12.780  41.441  13.526  1.00 27.13           A
ATOM   1767  CB  VAL A 228     -14.309  41.565  13.756  1.00 29.40           A
ATOM   1768  CG1 VAL A 228     -15.049  40.565  12.885  1.00 30.49           A
ATOM   1769  CG2 VAL A 228     -14.634  41.331  15.219  1.00 27.91           A
ATOM   1770  C   VAL A 228     -12.469  41.531  12.030  1.00 26.34           A
ATOM   1771  O   VAL A 228     -12.696  42.560  11.400  1.00 26.25           A
ATOM   1772  N   THR A 229     -11.953  40.445  11.473  1.00 26.02           A
ATOM   1773  CA  THR A 229     -11.558  40.402  10.067  1.00 26.52           A
ATOM   1774  CB  THR A 229     -10.399  39.448   9.870  1.00 24.42           A
ATOM   1775  OG1 THR A 229     -10.872  38.117  10.084  1.00 23.27           A
ATOM   1776  CG2 THR A 229      -9.276  39.737  10.849  1.00 22.32           A
ATOM   1777  C   THR A 229     -12.653  39.924   9.122  1.00 29.26           A
ATOM   1778  O   THR A 229     -13.690  39.422   9.559  1.00 31.28           A
ATOM   1779  N   GLU A 230     -12.404  40.064   7.821  1.00 30.35           A
ATOM   1780  CA  GLU A 230     -13.359  39.607   6.815  1.00 32.42           A
ATOM   1781  CB  GLU A 230     -12.856  39.918   5.399  1.00 37.12           A
ATOM   1782  CG  GLU A 230     -12.556  41.408   5.155  1.00 43.83           A
ATOM   1783  CD  GLU A 230     -11.097  41.784   5.440  1.00 47.20           A
ATOM   1784  OE1 GLU A 230     -10.489  41.212   6.385  1.00 48.89           A
ATOM   1785  OE2 GLU A 230     -10.565  42.662   4.721  1.00 45.47           A
ATOM   1786  C   GLU A 230     -13.532  38.094   6.983  1.00 30.72           A
ATOM   1787  O   GLU A 230     -14.617  37.554   6.772  1.00 28.78           A
ATOM   1788  N   SER A 231     -12.455  37.420   7.380  1.00 28.15           A
ATOM   1789  CA  SER A 231     -12.500  35.983   7.594  1.00 26.71           A
ATOM   1790  CB  SER A 231     -11.098  35.437   7.819  1.00 23.97           A
ATOM   1791  OG  SER A 231     -11.117  34.020   7.897  1.00 21.75           A
ATOM   1792  C   SER A 231     -13.379  35.626   8.795  1.00 29.80           A
ATOM   1793  O   SER A 231     -14.102  34.616   8.764  1.00 30.72           A
ATOM   1794  N   ASP A 232     -13.310  36.441   9.851  1.00 28.85           A
ATOM   1795  CA  ASP A 232     -14.113  36.204  11.048  1.00 29.14           A
ATOM   1796  CB  ASP A 232     -13.767  37.218  12.145  1.00 30.77           A
ATOM   1797  CG  ASP A 232     -12.448  36.971  12.781  1.00 33.60           A
ATOM   1798  OD1 ASP A 232     -12.039  35.791  12.861  1.00 35.31           A
ATOM   1799  OD2 ASP A 232     -11.812  37.953  13.211  1.00 34.51           A
ATOM   1800  C   ASP A 232     -15.593  36.312  10.725  1.00 29.57           A
ATOM   1801  O   ASP A 232     -16.412  35.524  11.198  1.00 29.81           A
ATOM   1802  N   ILE A 233     -15.931  37.308   9.921  1.00 28.98           A
ATOM   1803  CA  ILE A 233     -17.306  37.513   9.545  1.00 29.40           A
ATOM   1804  CB  ILE A 233     -17.461  38.906   8.910  1.00 29.17           A
ATOM   1805  CG2 ILE A 233     -18.818  39.053   8.239  1.00 28.49           A
ATOM   1806  CG1 ILE A 233     -17.294  39.956  10.013  1.00 28.79           A
ATOM   1807  CD1 ILE A 233     -17.376  41.370   9.537  1.00 31.17           A
ATOM   1808  C   ILE A 233     -17.802  36.392   8.630  1.00 29.70           A
ATOM   1809  O   ILE A 233     -18.959  35.980   8.715  1.00 31.03           A
ATOM   1810  N   ARG A 234     -16.929  35.876   7.773  1.00 29.02           A
ATOM   1811  CA  ARG A 234     -17.327  34.793   6.892  1.00 28.23           A
ATOM   1812  CB  ARG A 234     -16.305  34.607   5.768  1.00 28.93           A
ATOM   1813  CG  ARG A 234     -16.439  35.624   4.643  1.00 27.69           A
ATOM   1814  CD  ARG A 234     -15.249  35.551   3.702  1.00 35.61           A
ATOM   1815  NE  ARG A 234     -15.072  36.795   2.939  1.00 40.17           A
ATOM   1816  CZ  ARG A 234     -15.878  37.190   1.956  1.00 40.18           A
ATOM   1817  NH1 ARG A 234     -16.912  36.440   1.604  1.00 43.26           A
ATOM   1818  NH2 ARG A 234     -15.669  38.337   1.339  1.00 40.19           A
ATOM   1819  C   ARG A 234     -17.468  33.513   7.709  1.00 29.06           A
ATOM   1820  O   ARG A 234     -18.434  32.757   7.494  1.00 29.46           A
ATOM   1821  N   VAL A 235     -16.580  33.281   8.656  1.00 27.67           A
ATOM   1822  CA  VAL A 235     -16.663  32.110   9.526  1.00 25.83           A
ATOM   1823  CB  VAL A 235     -15.416  32.014  10.431  1.00 24.84           A
ATOM   1824  CG1 VAL A 235     -15.713  31.136  11.664  1.00 22.71           A
```

FIGURE 5- 25 -

```
ATOM   1825  CG2 VAL A 235     -14.253  31.439   9.635  1.00 21.07      A
ATOM   1826  C   VAL A 235     -17.923  32.203  10.400  1.00 26.89      A
ATOM   1827  O   VAL A 235     -18.523  31.203  10.779  1.00 28.61      A
ATOM   1828  N   GLU A 236     -18.320  33.420  10.720  1.00 27.69      A
ATOM   1829  CA  GLU A 236     -19.499  33.653  11.523  1.00 28.34      A
ATOM   1830  CB  GLU A 236     -19.510  35.125  11.902  1.00 30.95      A
ATOM   1831  CG  GLU A 236     -20.809  35.696  12.388  1.00 37.14      A
ATOM   1832  CD  GLU A 236     -20.708  37.214  12.557  1.00 41.23      A
ATOM   1833  OE1 GLU A 236     -21.767  37.900  12.558  1.00 41.56      A
ATOM   1834  OE2 GLU A 236     -19.557  37.710  12.684  1.00 40.45      A
ATOM   1835  C   GLU A 236     -20.706  33.271  10.673  1.00 30.36      A
ATOM   1836  O   GLU A 236     -21.678  32.679  11.160  1.00 30.57      A
ATOM   1837  N   GLU A 237     -20.634  33.587   9.382  1.00 31.06      A
ATOM   1838  CA  GLU A 237     -21.729  33.254   8.473  1.00 29.35      A
ATOM   1839  CB  GLU A 237     -21.499  33.853   7.085  1.00 30.54      A
ATOM   1840  CG  GLU A 237     -22.751  33.892   6.195  1.00 31.12      A
ATOM   1841  CD  GLU A 237     -22.425  33.823   4.703  1.00 31.25      A
ATOM   1842  OE1 GLU A 237     -21.310  34.241   4.321  1.00 32.66      A
ATOM   1843  OE2 GLU A 237     -23.282  33.363   3.914  1.00 27.40      A
ATOM   1844  C   GLU A 237     -21.816  31.743   8.348  1.00 28.51      A
ATOM   1845  O   GLU A 237     -22.899  31.178   8.431  1.00 28.99      A
ATOM   1846  N   SER A 238     -20.671  31.092   8.161  1.00 25.94      A
ATOM   1847  CA  SER A 238     -20.647  29.644   8.010  1.00 26.08      A
ATOM   1848  CB  SER A 238     -19.205  29.112   7.989  1.00 23.81      A
ATOM   1849  OG  SER A 238     -18.712  28.844   9.286  1.00 19.79      A
ATOM   1850  C   SER A 238     -21.437  28.992   9.136  1.00 27.81      A
ATOM   1851  O   SER A 238     -22.061  27.949   8.942  1.00 27.45      A
ATOM   1852  N   ILE A 239     -21.418  29.614  10.313  1.00 29.36      A
ATOM   1853  CA  ILE A 239     -22.159  29.082  11.453  1.00 29.65      A
ATOM   1854  CB  ILE A 239     -21.701  29.715  12.782  1.00 29.60      A
ATOM   1855  CG2 ILE A 239     -22.718  29.413  13.878  1.00 30.33      A
ATOM   1856  CG1 ILE A 239     -20.320  29.176  13.165  1.00 27.60      A
ATOM   1857  CD1 ILE A 239     -19.654  29.951  14.271  1.00 27.49      A
ATOM   1858  C   ILE A 239     -23.656  29.311  11.278  1.00 30.47      A
ATOM   1859  O   ILE A 239     -24.439  28.396  11.500  1.00 31.82      A
ATOM   1860  N   TYR A 240     -24.063  30.520  10.886  1.00 31.13      A
ATOM   1861  CA  TYR A 240     -25.488  30.785  10.682  1.00 30.75      A
ATOM   1862  CB  TYR A 240     -25.740  32.213  10.208  1.00 32.51      A
ATOM   1863  CG  TYR A 240     -25.197  33.296  11.113  1.00 34.87      A
ATOM   1864  CD1 TYR A 240     -25.273  33.170  12.501  1.00 35.42      A
ATOM   1865  CE1 TYR A 240     -24.774  34.160  13.337  1.00 34.20      A
ATOM   1866  CD2 TYR A 240     -24.609  34.452  10.583  1.00 33.19      A
ATOM   1867  CE2 TYR A 240     -24.109  35.444  11.413  1.00 32.23      A
ATOM   1868  CZ  TYR A 240     -24.196  35.285  12.787  1.00 32.89      A
ATOM   1869  OH  TYR A 240     -23.695  36.242  13.623  1.00 36.49      A
ATOM   1870  C   TYR A 240     -26.009  29.841   9.611  1.00 30.42      A
ATOM   1871  O   TYR A 240     -27.145  29.386   9.673  1.00 31.28      A
ATOM   1872  N   GLN A 241     -25.153  29.545   8.636  1.00 30.54      A
ATOM   1873  CA  GLN A 241     -25.489  28.670   7.519  1.00 28.77      A
ATOM   1874  CB  GLN A 241     -24.365  28.701   6.493  1.00 28.32      A
ATOM   1875  CG  GLN A 241     -24.212  30.050   5.800  1.00 29.54      A
ATOM   1876  CD  GLN A 241     -25.397  30.384   4.925  1.00 29.37      A
ATOM   1877  OE1 GLN A 241     -26.324  29.593   4.804  1.00 32.55      A
ATOM   1878  NE2 GLN A 241     -25.371  31.555   4.301  1.00 30.72      A
ATOM   1879  C   GLN A 241     -25.802  27.226   7.903  1.00 28.67      A
ATOM   1880  O   GLN A 241     -26.374  26.478   7.108  1.00 30.07      A
ATOM   1881  N   CYS A 242     -25.435  26.827   9.113  1.00 27.17      A
ATOM   1882  CA  CYS A 242     -25.724  25.475   9.555  1.00 26.62      A
ATOM   1883  CB  CYS A 242     -24.774  25.070  10.678  1.00 24.56      A
ATOM   1884  SG  CYS A 242     -23.064  24.916  10.137  1.00 30.69      A
ATOM   1885  C   CYS A 242     -27.178  25.384  10.025  1.00 26.78      A
ATOM   1886  O   CYS A 242     -27.702  24.291  10.240  1.00 25.95      A
ATOM   1887  N   CYS A 243     -27.833  26.533  10.175  1.00 25.88      A
ATOM   1888  CA  CYS A 243     -29.227  26.550  10.608  1.00 27.97      A
ATOM   1889  CB  CYS A 243     -29.651  27.961  11.006  1.00 25.74      A
ATOM   1890  SG  CYS A 243     -28.994  28.562  12.541  1.00 31.74      A
ATOM   1891  C   CYS A 243     -30.163  26.091   9.497  1.00 29.79      A
ATOM   1892  O   CYS A 243     -29.800  26.103   8.325  1.00 30.96      A
ATOM   1893  N   ASP A 244     -31.368  25.673   9.865  1.00 30.71      A
ATOM   1894  CA  ASP A 244     -32.344  25.312   8.850  1.00 29.31      A
ATOM   1895  CB  ASP A 244     -33.389  24.345   9.405  1.00 27.33      A
ATOM   1896  CG  ASP A 244     -34.382  23.897   8.345  1.00 30.81      A
ATOM   1897  OD1 ASP A 244     -35.495  24.474   8.265  1.00 29.77      A
ATOM   1898  OD2 ASP A 244     -34.036  22.973   7.570  1.00 32.04      A
ATOM   1899  C   ASP A 244     -32.952  26.692   8.557  1.00 27.67      A
ATOM   1900  O   ASP A 244     -33.368  27.385   9.475  1.00 27.79      A
```

FIGURE 5- 26 -

```
ATOM   1901  N    LEU A 245     -32.988   27.092    7.292  1.00 26.21      A
ATOM   1902  CA   LEU A 245     -33.482   28.418    6.943  1.00 25.71      A
ATOM   1903  CB   LEU A 245     -32.283   29.336    6.723  1.00 23.91      A
ATOM   1904  CG   LEU A 245     -31.300   29.496    7.879  1.00 24.02      A
ATOM   1905  CD1  LEU A 245     -29.923   29.911    7.363  1.00 20.37      A
ATOM   1906  CD2  LEU A 245     -31.854   30.537    8.837  1.00 21.80      A
ATOM   1907  C    LEU A 245     -34.356   28.480    5.694  1.00 25.66      A
ATOM   1908  O    LEU A 245     -34.168   27.710    4.760  1.00 25.35      A
ATOM   1909  N    ALA A 246     -35.303   29.415    5.672  1.00 26.70      A
ATOM   1910  CA   ALA A 246     -36.158   29.588    4.493  1.00 28.01      A
ATOM   1911  CB   ALA A 246     -37.233   30.612    4.787  1.00 26.97      A
ATOM   1912  C    ALA A 246     -35.230   30.087    3.386  1.00 28.41      A
ATOM   1913  O    ALA A 246     -34.319   30.864    3.650  1.00 27.12      A
ATOM   1914  N    PRO A 247     -35.450   29.653    2.133  1.00 30.12      A
ATOM   1915  CD   PRO A 247     -36.593   28.867    1.633  1.00 30.53      A
ATOM   1916  CA   PRO A 247     -34.599   30.076    1.013  1.00 30.35      A
ATOM   1917  CB   PRO A 247     -35.431   29.701   -0.214  1.00 31.64      A
ATOM   1918  CG   PRO A 247     -36.141   28.485    0.222  1.00 29.81      A
ATOM   1919  C    PRO A 247     -34.210   31.551    1.015  1.00 31.02      A
ATOM   1920  O    PRO A 247     -33.019   31.887    0.972  1.00 30.64      A
ATOM   1921  N    GLU A 248     -35.209   32.429    1.072  1.00 31.37      A
ATOM   1922  CA   GLU A 248     -34.948   33.867    1.059  1.00 32.09      A
ATOM   1923  CB   GLU A 248     -36.265   34.638    1.004  1.00 33.88      A
ATOM   1924  CG   GLU A 248     -37.203   34.153   -0.076  1.00 33.44      A
ATOM   1925  CD   GLU A 248     -38.114   35.240   -0.569  1.00 35.88      A
ATOM   1926  OE1  GLU A 248     -38.429   36.157    0.221  1.00 37.06      A
ATOM   1927  OE2  GLU A 248     -38.523   35.171   -1.743  1.00 36.82      A
ATOM   1928  C    GLU A 248     -34.121   34.335    2.254  1.00 30.93      A
ATOM   1929  O    GLU A 248     -33.392   35.318    2.164  1.00 33.19      A
ATOM   1930  N    ALA A 249     -34.241   33.628    3.370  1.00 29.36      A
ATOM   1931  CA   ALA A 249     -33.482   33.952    4.572  1.00 28.49      A
ATOM   1932  CB   ALA A 249     -33.995   33.143    5.743  1.00 25.77      A
ATOM   1933  C    ALA A 249     -32.023   33.621    4.329  1.00 28.54      A
ATOM   1934  O    ALA A 249     -31.132   34.408    4.634  1.00 29.37      A
ATOM   1935  N    ARG A 250     -31.789   32.437    3.777  1.00 28.65      A
ATOM   1936  CA   ARG A 250     -30.445   31.976    3.483  1.00 27.41      A
ATOM   1937  CB   ARG A 250     -30.507   30.560    2.915  1.00 26.74      A
ATOM   1938  CG   ARG A 250     -29.165   29.858    2.790  1.00 27.36      A
ATOM   1939  CD   ARG A 250     -29.348   28.429    2.276  1.00 28.94      A
ATOM   1940  NE   ARG A 250     -29.854   27.498    3.289  1.00 28.86      A
ATOM   1941  CZ   ARG A 250     -29.148   27.074    4.340  1.00 28.77      A
ATOM   1942  NH1  ARG A 250     -27.904   27.496    4.524  1.00 27.36      A
ATOM   1943  NH2  ARG A 250     -29.675   26.216    5.202  1.00 26.11      A
ATOM   1944  C    ARG A 250     -29.782   32.936    2.505  1.00 28.68      A
ATOM   1945  O    ARG A 250     -28.581   33.197    2.592  1.00 28.39      A
ATOM   1946  N    GLN A 251     -30.567   33.475    1.575  1.00 29.13      A
ATOM   1947  CA   GLN A 251     -30.019   34.412    0.599  1.00 29.45      A
ATOM   1948  CB   GLN A 251     -30.980   34.618   -0.579  1.00 30.42      A
ATOM   1949  CG   GLN A 251     -30.393   35.442   -1.735  1.00 29.52      A
ATOM   1950  CD   GLN A 251     -29.228   34.734   -2.427  1.00 31.06      A
ATOM   1951  OE1  GLN A 251     -28.069   35.101   -2.252  1.00 30.77      A
ATOM   1952  NE2  GLN A 251     -29.540   33.709   -3.210  1.00 31.56      A
ATOM   1953  C    GLN A 251     -29.795   35.745    1.292  1.00 29.51      A
ATOM   1954  O    GLN A 251     -28.756   36.384    1.107  1.00 29.26      A
ATOM   1955  N    ALA A 252     -30.777   36.164    2.091  1.00 28.20      A
ATOM   1956  CA   ALA A 252     -30.673   37.432    2.805  1.00 27.25      A
ATOM   1957  CB   ALA A 252     -31.918   37.673    3.626  1.00 25.69      A
ATOM   1958  C    ALA A 252     -29.429   37.438    3.695  1.00 26.63      A
ATOM   1959  O    ALA A 252     -28.734   38.447    3.779  1.00 27.49      A
ATOM   1960  N    ILE A 253     -29.140   36.312    4.340  1.00 24.32      A
ATOM   1961  CA   ILE A 253     -27.971   36.223    5.199  1.00 24.22      A
ATOM   1962  CB   ILE A 253     -27.980   34.915    6.015  1.00 23.34      A
ATOM   1963  CG2  ILE A 253     -26.635   34.708    6.725  1.00 19.98      A
ATOM   1964  CG1  ILE A 253     -29.128   34.949    7.013  1.00 20.46      A
ATOM   1965  CD1  ILE A 253     -29.199   33.724    7.841  1.00 18.71      A
ATOM   1966  C    ILE A 253     -26.700   36.283    4.353  1.00 26.12      A
ATOM   1967  O    ILE A 253     -25.727   36.947    4.721  1.00 27.75      A
ATOM   1968  N    ARG A 254     -26.707   35.588    3.222  1.00 26.64      A
ATOM   1969  CA   ARG A 254     -25.555   35.576    2.313  1.00 27.87      A
ATOM   1970  CB   ARG A 254     -25.835   34.641    1.130  1.00 27.07      A
ATOM   1971  CG   ARG A 254     -24.715   34.511    0.090  1.00 25.53      A
ATOM   1972  CD   ARG A 254     -23.693   33.454    0.454  1.00 27.18      A
ATOM   1973  NE   ARG A 254     -22.602   33.950    1.290  1.00 27.69      A
ATOM   1974  CZ   ARG A 254     -21.712   34.845    0.883  1.00 27.74      A
ATOM   1975  NH1  ARG A 254     -21.798   35.336   -0.346  1.00 28.54      A
ATOM   1976  NH2  ARG A 254     -20.737   35.238    1.692  1.00 25.98      A
```

FIGURE 5- 27 -

```
ATOM   1977  C   ARG A 254     -25.271  36.998   1.812  1.00 27.61      A
ATOM   1978  O   ARG A 254     -24.156  37.495   1.931  1.00 30.97      A
ATOM   1979  N   SER A 255     -26.288  37.645   1.253  1.00 26.73      A
ATOM   1980  CA  SER A 255     -26.157  38.999   0.734  1.00 26.32      A
ATOM   1981  CB  SER A 255     -27.481  39.451   0.129  1.00 24.87      A
ATOM   1982  OG  SER A 255     -27.815  38.652  -0.987  1.00 23.72      A
ATOM   1983  C   SER A 255     -25.730  39.995   1.805  1.00 27.53      A
ATOM   1984  O   SER A 255     -24.867  40.846   1.574  1.00 27.63      A
ATOM   1985  N   LEU A 256     -26.344  39.892   2.977  1.00 27.81      A
ATOM   1986  CA  LEU A 256     -26.022  40.783   4.078  1.00 27.35      A
ATOM   1987  CB  LEU A 256     -26.976  40.513   5.243  1.00 24.38      A
ATOM   1988  CG  LEU A 256     -28.377  41.091   4.972  1.00 24.20      A
ATOM   1989  CD1 LEU A 256     -29.363  40.710   6.083  1.00 23.05      A
ATOM   1990  CD2 LEU A 256     -28.270  42.599   4.872  1.00 20.73      A
ATOM   1991  C   LEU A 256     -24.556  40.651   4.506  1.00 28.14      A
ATOM   1992  O   LEU A 256     -23.893  41.647   4.827  1.00 28.28      A
ATOM   1993  N   THR A 257     -24.044  39.425   4.495  1.00 28.93      A
ATOM   1994  CA  THR A 257     -22.652  39.187   4.861  1.00 29.00      A
ATOM   1995  CB  THR A 257     -22.335  37.671   4.873  1.00 29.43      A
ATOM   1996  OG1 THR A 257     -23.077  37.044   5.922  1.00 29.58      A
ATOM   1997  CG2 THR A 257     -20.855  37.419   5.115  1.00 26.06      A
ATOM   1998  C   THR A 257     -21.719  39.904   3.885  1.00 29.85      A
ATOM   1999  O   THR A 257     -20.887  40.707   4.302  1.00 30.12      A
ATOM   2000  N   GLU A 258     -21.875  39.626   2.591  1.00 30.82      A
ATOM   2001  CA  GLU A 258     -21.044  40.239   1.533  1.00 32.93      A
ATOM   2002  CB  GLU A 258     -21.307  39.583   0.168  1.00 34.85      A
ATOM   2003  CG  GLU A 258     -20.766  38.188   0.008  1.00 37.71      A
ATOM   2004  CD  GLU A 258     -19.307  38.096   0.393  1.00 38.02      A
ATOM   2005  OE1 GLU A 258     -18.447  38.585  -0.374  1.00 36.95      A
ATOM   2006  OE2 GLU A 258     -19.034  37.543   1.479  1.00 36.13      A
ATOM   2007  C   GLU A 258     -21.208  41.745   1.336  1.00 31.61      A
ATOM   2008  O   GLU A 258     -20.246  42.444   1.018  1.00 32.17      A
ATOM   2009  N   ARG A 259     -22.424  42.241   1.507  1.00 28.83      A
ATOM   2010  CA  ARG A 259     -22.682  43.645   1.253  1.00 29.25      A
ATOM   2011  CB  ARG A 259     -24.014  43.778   0.520  1.00 27.69      A
ATOM   2012  CG  ARG A 259     -24.074  42.909  -0.727  1.00 28.42      A
ATOM   2013  CD  ARG A 259     -25.482  42.766  -1.274  1.00 26.44      A
ATOM   2014  NE  ARG A 259     -26.034  44.061  -1.638  1.00 26.78      A
ATOM   2015  CZ  ARG A 259     -27.310  44.275  -1.920  1.00 24.69      A
ATOM   2016  NH1 ARG A 259     -28.177  43.275  -1.892  1.00 27.10      A
ATOM   2017  NH2 ARG A 259     -27.719  45.495  -2.202  1.00 22.35      A
ATOM   2018  C   ARG A 259     -22.681  44.566   2.453  1.00 29.13      A
ATOM   2019  O   ARG A 259     -22.566  45.778   2.293  1.00 30.92      A
ATOM   2020  N   LEU A 260     -22.804  44.013   3.664  1.00 29.48      A
ATOM   2021  CA  LEU A 260     -22.849  44.855   4.856  1.00 27.66      A
ATOM   2022  CB  LEU A 260     -24.278  44.909   5.403  1.00 25.73      A
ATOM   2023  CG  LEU A 260     -24.517  45.791   6.632  1.00 25.31      A
ATOM   2024  CD1 LEU A 260     -24.189  47.238   6.302  1.00 27.50      A
ATOM   2025  CD2 LEU A 260     -25.968  45.657   7.086  1.00 25.31      A
ATOM   2026  C   LEU A 260     -21.909  44.467   5.980  1.00 27.47      A
ATOM   2027  O   LEU A 260     -21.087  45.277   6.423  1.00 27.59      A
ATOM   2028  N   TYR A 261     -22.018  43.226   6.437  1.00 26.51      A
ATOM   2029  CA  TYR A 261     -21.198  42.777   7.551  1.00 26.96      A
ATOM   2030  CB  TYR A 261     -21.680  41.402   8.024  1.00 25.45      A
ATOM   2031  CG  TYR A 261     -23.151  41.394   8.422  1.00 24.63      A
ATOM   2032  CD1 TYR A 261     -23.765  42.537   8.948  1.00 22.34      A
ATOM   2033  CE1 TYR A 261     -25.105  42.539   9.287  1.00 22.99      A
ATOM   2034  CD2 TYR A 261     -23.930  40.249   8.255  1.00 25.58      A
ATOM   2035  CE2 TYR A 261     -25.273  40.238   8.591  1.00 24.83      A
ATOM   2036  CZ  TYR A 261     -25.855  41.384   9.104  1.00 26.60      A
ATOM   2037  OH  TYR A 261     -27.191  41.366   9.422  1.00 27.13      A
ATOM   2038  C   TYR A 261     -19.679  42.782   7.368  1.00 28.68      A
ATOM   2039  O   TYR A 261     -18.970  43.289   8.231  1.00 30.72      A
ATOM   2040  N   ILE A 262     -19.171  42.245   6.263  1.00 30.08      A
ATOM   2041  CA  ILE A 262     -17.722  42.216   6.051  1.00 30.27      A
ATOM   2042  CB  ILE A 262     -17.345  41.396   4.804  1.00 30.15      A
ATOM   2043  CG2 ILE A 262     -17.804  39.968   4.952  1.00 27.57      A
ATOM   2044  CG1 ILE A 262     -17.995  42.008   3.575  1.00 30.95      A
ATOM   2045  CD1 ILE A 262     -17.598  41.315   2.309  1.00 35.20      A
ATOM   2046  C   ILE A 262     -17.106  43.609   5.902  1.00 30.46      A
ATOM   2047  O   ILE A 262     -15.903  43.788   6.117  1.00 28.82      A
ATOM   2048  N   GLY A 263     -17.933  44.587   5.534  1.00 30.57      A
ATOM   2049  CA  GLY A 263     -17.448  45.945   5.363  1.00 30.18      A
ATOM   2050  C   GLY A 263     -18.249  46.757   4.363  1.00 31.18      A
ATOM   2051  O   GLY A 263     -19.293  46.311   3.891  1.00 32.08      A
ATOM   2052  N   GLY A 264     -17.764  47.951   4.035  1.00 31.10      A
```

FIGURE 5-28 -

```
ATOM   2053  CA   GLY A 264     -18.464  48.791   3.079  1.00 31.93      A
ATOM   2054  C    GLY A 264     -18.153  50.277   3.205  1.00 33.94      A
ATOM   2055  O    GLY A 264     -17.412  50.704   4.101  1.00 35.12      A
ATOM   2056  N    PRO A 265     -18.717  51.102   2.314  1.00 33.02      A
ATOM   2057  CD   PRO A 265     -19.725  50.754   1.300  1.00 31.54      A
ATOM   2058  CA   PRO A 265     -18.486  52.548   2.346  1.00 31.68      A
ATOM   2059  CB   PRO A 265     -19.230  53.032   1.109  1.00 30.71      A
ATOM   2060  CG   PRO A 265     -20.378  52.087   1.044  1.00 31.23      A
ATOM   2061  C    PRO A 265     -19.021  53.196   3.623  1.00 31.37      A
ATOM   2062  O    PRO A 265     -19.988  52.718   4.209  1.00 31.54      A
ATOM   2063  N    LEU A 266     -18.380  54.284   4.044  1.00 31.37      A
ATOM   2064  CA   LEU A 266     -18.787  55.032   5.235  1.00 29.32      A
ATOM   2065  CB   LEU A 266     -17.632  55.113   6.237  1.00 26.81      A
ATOM   2066  CG   LEU A 266     -17.138  53.763   6.753  1.00 26.14      A
ATOM   2067  CD1  LEU A 266     -15.807  53.942   7.444  1.00 25.77      A
ATOM   2068  CD2  LEU A 266     -18.169  53.154   7.686  1.00 24.43      A
ATOM   2069  C    LEU A 266     -19.185  56.433   4.802  1.00 29.27      A
ATOM   2070  O    LEU A 266     -18.456  57.088   4.062  1.00 29.53      A
ATOM   2071  N    THR A 267     -20.338  56.894   5.268  1.00 29.94      A
ATOM   2072  CA   THR A 267     -20.830  58.220   4.903  1.00 32.57      A
ATOM   2073  CB   THR A 267     -22.079  58.094   3.985  1.00 31.23      A
ATOM   2074  OG1  THR A 267     -21.703  57.427   2.768  1.00 28.11      A
ATOM   2075  CG2  THR A 267     -22.679  59.476   3.675  1.00 25.36      A
ATOM   2076  C    THR A 267     -21.186  59.045   6.141  1.00 34.94      A
ATOM   2077  O    THR A 267     -21.870  58.551   7.036  1.00 36.02      A
ATOM   2078  N    ASN A 268     -20.721  60.293   6.205  1.00 36.49      A
ATOM   2079  CA   ASN A 268     -21.029  61.120   7.364  1.00 39.27      A
ATOM   2080  CB   ASN A 268     -20.005  62.255   7.539  1.00 42.45      A
ATOM   2081  CG   ASN A 268     -19.974  63.222   6.361  1.00 44.61      A
ATOM   2082  OD1  ASN A 268     -21.008  63.557   5.777  1.00 43.84      A
ATOM   2083  ND2  ASN A 268     -18.779  63.693   6.025  1.00 42.80      A
ATOM   2084  C    ASN A 268     -22.433  61.685   7.254  1.00 39.57      A
ATOM   2085  O    ASN A 268     -23.129  61.439   6.270  1.00 39.87      A
ATOM   2086  N    SER A 269     -22.848  62.435   8.269  1.00 40.91      A
ATOM   2087  CA   SER A 269     -24.190  63.018   8.300  1.00 42.85      A
ATOM   2088  CB   SER A 269     -24.447  63.663   9.665  1.00 43.04      A
ATOM   2089  OG   SER A 269     -23.481  64.664   9.935  1.00 41.61      A
ATOM   2090  C    SER A 269     -24.429  64.052   7.204  1.00 44.16      A
ATOM   2091  O    SER A 269     -25.562  64.468   6.966  1.00 43.73      A
ATOM   2092  N    LYS A 270     -23.356  64.477   6.550  1.00 45.56      A
ATOM   2093  CA   LYS A 270     -23.464  65.450   5.486  1.00 45.67      A
ATOM   2094  CB   LYS A 270     -22.246  66.389   5.496  1.00 46.39      A
ATOM   2095  CG   LYS A 270     -22.203  67.321   6.698  1.00 46.59      A
ATOM   2096  CD   LYS A 270     -21.150  68.385   6.524  1.00 47.56      A
ATOM   2097  CE   LYS A 270     -21.299  69.454   7.582  1.00 49.55      A
ATOM   2098  NZ   LYS A 270     -20.404  70.617   7.322  1.00 49.82      A
ATOM   2099  C    LYS A 270     -23.584  64.773   4.136  1.00 45.72      A
ATOM   2100  O    LYS A 270     -23.680  65.437   3.103  1.00 47.16      A
ATOM   2101  N    GLY A 271     -23.579  63.443   4.147  1.00 44.01      A
ATOM   2102  CA   GLY A 271     -23.694  62.696   2.903  1.00 42.28      A
ATOM   2103  C    GLY A 271     -22.398  62.631   2.126  1.00 42.08      A
ATOM   2104  O    GLY A 271     -22.398  62.322   0.936  1.00 40.84      A
ATOM   2105  N    GLN A 272     -21.294  62.932   2.801  1.00 42.50      A
ATOM   2106  CA   GLN A 272     -19.976  62.900   2.184  1.00 42.62      A
ATOM   2107  CB   GLN A 272     -19.081  63.977   2.809  1.00 42.78      A
ATOM   2108  CG   GLN A 272     -19.643  65.392   2.656  1.00 44.22      A
ATOM   2109  CD   GLN A 272     -18.799  66.462   3.343  1.00 45.13      A
ATOM   2110  OE1  GLN A 272     -18.629  66.459   4.566  1.00 45.48      A
ATOM   2111  NE2  GLN A 272     -18.275  67.387   2.554  1.00 45.86      A
ATOM   2112  C    GLN A 272     -19.384  61.513   2.407  1.00 43.23      A
ATOM   2113  O    GLN A 272     -19.837  60.777   3.280  1.00 44.78      A
ATOM   2114  N    ASN A 273     -18.379  61.157   1.617  1.00 42.63      A
ATOM   2115  CA   ASN A 273     -17.734  59.851   1.717  1.00 42.00      A
ATOM   2116  CB   ASN A 273     -17.239  59.446   0.328  1.00 41.11      A
ATOM   2117  CG   ASN A 273     -16.756  58.021   0.269  1.00 43.06      A
ATOM   2118  OD1  ASN A 273     -16.156  57.606  -0.718  1.00 43.11      A
ATOM   2119  ND2  ASN A 273     -17.019  57.257   1.320  1.00 45.53      A
ATOM   2120  C    ASN A 273     -16.561  59.909   2.704  1.00 42.33      A
ATOM   2121  O    ASN A 273     -15.549  60.529   2.403  1.00 44.26      A
ATOM   2122  N    CYS A 274     -16.689  59.263   3.863  1.00 42.41      A
ATOM   2123  CA   CYS A 274     -15.627  59.271   4.883  1.00 42.53      A
ATOM   2124  CB   CYS A 274     -16.208  59.042   6.279  1.00 42.43      A
ATOM   2125  SG   CYS A 274     -17.030  60.451   7.005  1.00 50.72      A
ATOM   2126  C    CYS A 274     -14.522  58.243   4.678  1.00 41.71      A
ATOM   2127  O    CYS A 274     -13.373  58.476   5.052  1.00 41.96      A
ATOM   2128  N    GLY A 275     -14.874  57.099   4.109  1.00 40.71      A
```

FIGURE 5- 29 -

```
ATOM   2129  CA   GLY A 275     -13.888  56.059   3.899  1.00 38.23       A
ATOM   2130  C    GLY A 275     -14.494  54.682   3.683  1.00 37.45       A
ATOM   2131  O    GLY A 275     -15.555  54.542   3.069  1.00 35.17       A
ATOM   2132  N    TYR A 276     -13.830  53.658   4.208  1.00 36.73       A
ATOM   2133  CA   TYR A 276     -14.302  52.293   4.028  1.00 35.94       A
ATOM   2134  CB   TYR A 276     -13.611  51.684   2.813  1.00 34.57       A
ATOM   2135  CG   TYR A 276     -14.372  50.572   2.167  1.00 34.56       A
ATOM   2136  CD1  TYR A 276     -15.359  50.844   1.225  1.00 34.31       A
ATOM   2137  CE1  TYR A 276     -16.067  49.822   0.609  1.00 36.30       A
ATOM   2138  CD2  TYR A 276     -14.107  49.242   2.489  1.00 36.18       A
ATOM   2139  CE2  TYR A 276     -14.812  48.203   1.878  1.00 37.27       A
ATOM   2140  CZ   TYR A 276     -15.790  48.503   0.938  1.00 37.42       A
ATOM   2141  OH   TYR A 276     -16.486  47.490   0.321  1.00 38.38       A
ATOM   2142  C    TYR A 276     -14.030  51.413   5.241  1.00 35.37       A
ATOM   2143  O    TYR A 276     -12.920  51.428   5.789  1.00 35.83       A
ATOM   2144  N    ARG A 277     -15.044  50.639   5.634  1.00 33.43       A
ATOM   2145  CA   ARG A 277     -14.966  49.718   6.770  1.00 32.41       A
ATOM   2146  CB   ARG A 277     -16.278  49.744   7.557  1.00 32.09       A
ATOM   2147  CG   ARG A 277     -16.425  48.634   8.595  1.00 31.93       A
ATOM   2148  CD   ARG A 277     -17.786  48.712   9.264  1.00 32.54       A
ATOM   2149  NE   ARG A 277     -18.862  48.674   8.280  1.00 33.94       A
ATOM   2150  CZ   ARG A 277     -19.404  47.562   7.790  1.00 33.67       A
ATOM   2151  NH1  ARG A 277     -18.983  46.376   8.197  1.00 33.19       A
ATOM   2152  NH2  ARG A 277     -20.360  47.640   6.872  1.00 34.44       A
ATOM   2153  C    ARG A 277     -14.711  48.292   6.298  1.00 32.75       A
ATOM   2154  O    ARG A 277     -15.384  47.814   5.389  1.00 35.27       A
ATOM   2155  N    ARG A 278     -13.742  47.616   6.907  1.00 32.13       A
ATOM   2156  CA   ARG A 278     -13.430  46.228   6.554  1.00 31.78       A
ATOM   2157  CB   ARG A 278     -12.105  46.131   5.790  1.00 32.03       A
ATOM   2158  CG   ARG A 278     -12.170  46.745   4.425  1.00 34.90       A
ATOM   2159  CD   ARG A 278     -10.891  46.541   3.662  1.00 40.29       A
ATOM   2160  NE   ARG A 278     -10.694  47.609   2.682  1.00 47.02       A
ATOM   2161  CZ   ARG A 278     -10.397  48.868   3.007  1.00 48.67       A
ATOM   2162  NH1  ARG A 278     -10.263  49.203   4.286  1.00 49.23       A
ATOM   2163  NH2  ARG A 278     -10.235  49.793   2.062  1.00 48.51       A
ATOM   2164  C    ARG A 278     -13.350  45.410   7.832  1.00 31.46       A
ATOM   2165  O    ARG A 278     -12.599  44.434   7.927  1.00 30.39       A
ATOM   2166  N    CYS A 279     -14.131  45.839   8.819  1.00 30.66       A
ATOM   2167  CA   CYS A 279     -14.187  45.186  10.118  1.00 30.21       A
ATOM   2168  CB   CYS A 279     -13.259  45.886  11.112  1.00 27.67       A
ATOM   2169  SG   CYS A 279     -13.740  47.601  11.467  1.00 30.31       A
ATOM   2170  C    CYS A 279     -15.632  45.281  10.595  1.00 29.65       A
ATOM   2171  O    CYS A 279     -16.505  45.729   9.849  1.00 29.04       A
ATOM   2172  N    ARG A 280     -15.870  44.880  11.839  1.00 28.17       A
ATOM   2173  CA   ARG A 280     -17.207  44.884  12.405  1.00 27.12       A
ATOM   2174  CB   ARG A 280     -17.204  44.309  13.819  1.00 26.19       A
ATOM   2175  CG   ARG A 280     -18.586  44.305  14.475  1.00 26.96       A
ATOM   2176  CD   ARG A 280     -19.430  43.144  13.997  1.00 25.78       A
ATOM   2177  NE   ARG A 280     -18.858  41.887  14.458  1.00 28.29       A
ATOM   2178  CZ   ARG A 280     -19.149  40.693  13.959  1.00 28.73       A
ATOM   2179  NH1  ARG A 280     -20.017  40.572  12.971  1.00 33.46       A
ATOM   2180  NH2  ARG A 280     -18.558  39.617  14.445  1.00 30.46       A
ATOM   2181  C    ARG A 280     -17.862  46.234  12.471  1.00 27.13       A
ATOM   2182  O    ARG A 280     -17.250  47.205  12.907  1.00 27.52       A
ATOM   2183  N    ALA A 281     -19.117  46.275  12.036  1.00 28.20       A
ATOM   2184  CA   ALA A 281     -19.929  47.480  12.094  1.00 29.34       A
ATOM   2185  CB   ALA A 281     -21.017  47.437  11.048  1.00 30.71       A
ATOM   2186  C    ALA A 281     -20.541  47.380  13.492  1.00 31.00       A
ATOM   2187  O    ALA A 281     -21.027  46.319  13.883  1.00 31.30       A
ATOM   2188  N    SER A 282     -20.522  48.468  14.249  1.00 30.83       A
ATOM   2189  CA   SER A 282     -21.051  48.413  15.595  1.00 30.58       A
ATOM   2190  CB   SER A 282     -20.480  49.550  16.431  1.00 30.05       A
ATOM   2191  OG   SER A 282     -21.042  50.781  16.031  1.00 32.64       A
ATOM   2192  C    SER A 282     -22.563  48.478  15.643  1.00 31.63       A
ATOM   2193  O    SER A 282     -23.173  48.029  16.616  1.00 33.07       A
ATOM   2194  N    GLY A 283     -23.171  49.027  14.597  1.00 31.03       A
ATOM   2195  CA   GLY A 283     -24.615  49.165  14.592  1.00 29.97       A
ATOM   2196  C    GLY A 283     -25.444  48.275  13.687  1.00 30.39       A
ATOM   2197  O    GLY A 283     -26.330  48.772  12.978  1.00 31.99       A
ATOM   2198  N    VAL A 284     -25.165  46.973  13.683  1.00 27.67       A
ATOM   2199  CA   VAL A 284     -25.951  46.045  12.878  1.00 26.20       A
ATOM   2200  CB   VAL A 284     -25.120  45.364  11.767  1.00 27.00       A
ATOM   2201  CG1  VAL A 284     -24.848  46.356  10.651  1.00 24.46       A
ATOM   2202  CG2  VAL A 284     -23.813  44.808  12.331  1.00 27.49       A
ATOM   2203  C    VAL A 284     -26.537  45.006  13.827  1.00 28.03       A
ATOM   2204  O    VAL A 284     -26.145  44.931  14.994  1.00 29.70       A
```

FIGURE 5- 30 -

```
ATOM   2205  N    LEU A 285     -27.486  44.220  13.340  1.00 27.28      A
ATOM   2206  CA   LEU A 285     -28.146  43.231  14.173  1.00 27.20      A
ATOM   2207  CB   LEU A 285     -29.337  42.647  13.404  1.00 26.58      A
ATOM   2208  CG   LEU A 285     -30.219  41.604  14.099  1.00 27.93      A
ATOM   2209  CD1  LEU A 285     -30.869  42.224  15.324  1.00 26.04      A
ATOM   2210  CD2  LEU A 285     -31.281  41.092  13.133  1.00 25.06      A
ATOM   2211  C    LEU A 285     -27.225  42.106  14.646  1.00 28.95      A
ATOM   2212  O    LEU A 285     -27.326  41.642  15.781  1.00 29.43      A
ATOM   2213  N    THR A 286     -26.315  41.681  13.781  1.00 29.03      A
ATOM   2214  CA   THR A 286     -25.425  40.574  14.106  1.00 29.55      A
ATOM   2215  CB   THR A 286     -24.937  39.877  12.822  1.00 29.97      A
ATOM   2216  OG1  THR A 286     -24.438  40.870  11.915  1.00 34.03      A
ATOM   2217  CG2  THR A 286     -26.069  39.107  12.151  1.00 28.52      A
ATOM   2218  C    THR A 286     -24.194  40.948  14.903  1.00 29.62      A
ATOM   2219  O    THR A 286     -23.331  40.101  15.106  1.00 29.40      A
ATOM   2220  N    THR A 287     -24.102  42.199  15.349  1.00 28.91      A
ATOM   2221  CA   THR A 287     -22.925  42.652  16.093  1.00 29.84      A
ATOM   2222  CB   THR A 287     -22.989  44.151  16.369  1.00 31.88      A
ATOM   2223  OG1  THR A 287     -23.248  44.839  15.145  1.00 36.26      A
ATOM   2224  CG2  THR A 287     -21.667  44.646  16.950  1.00 31.89      A
ATOM   2225  C    THR A 287     -22.681  41.951  17.426  1.00 29.57      A
ATOM   2226  O    THR A 287     -21.566  41.541  17.717  1.00 29.39      A
ATOM   2227  N    SER A 288     -23.716  41.833  18.245  1.00 30.88      A
ATOM   2228  CA   SER A 288     -23.576  41.175  19.532  1.00 31.59      A
ATOM   2229  CB   SER A 288     -24.843  41.382  20.371  1.00 33.23      A
ATOM   2230  OG   SER A 288     -24.660  40.961  21.713  1.00 33.36      A
ATOM   2231  C    SER A 288     -23.322  39.685  19.329  1.00 31.50      A
ATOM   2232  O    SER A 288     -22.390  39.121  19.896  1.00 32.86      A
ATOM   2233  N    CYS A 289     -24.152  39.061  18.505  1.00 30.51      A
ATOM   2234  CA   CYS A 289     -24.048  37.637  18.229  1.00 31.37      A
ATOM   2235  CB   CYS A 289     -25.210  37.199  17.333  1.00 31.41      A
ATOM   2236  SG   CYS A 289     -25.256  35.428  16.992  1.00 33.62      A
ATOM   2237  C    CYS A 289     -22.725  37.276  17.567  1.00 31.64      A
ATOM   2238  O    CYS A 289     -22.099  36.270  17.906  1.00 31.45      A
ATOM   2239  N    GLY A 290     -22.305  38.101  16.617  1.00 31.95      A
ATOM   2240  CA   GLY A 290     -21.062  37.845  15.920  1.00 31.51      A
ATOM   2241  C    GLY A 290     -19.880  37.947  16.855  1.00 32.76      A
ATOM   2242  O    GLY A 290     -19.023  37.060  16.883  1.00 34.05      A
ATOM   2243  N    ASN A 291     -19.835  39.024  17.631  1.00 31.95      A
ATOM   2244  CA   ASN A 291     -18.742  39.223  18.564  1.00 31.89      A
ATOM   2245  CB   ASN A 291     -18.827  40.605  19.220  1.00 32.40      A
ATOM   2246  CG   ASN A 291     -18.459  41.735  18.261  1.00 33.43      A
ATOM   2247  OD1  ASN A 291     -17.837  41.505  17.215  1.00 31.33      A
ATOM   2248  ND2  ASN A 291     -18.827  42.964  18.623  1.00 31.23      A
ATOM   2249  C    ASN A 291     -18.692  38.146  19.635  1.00 32.19      A
ATOM   2250  O    ASN A 291     -17.609  37.691  19.992  1.00 34.40      A
ATOM   2251  N    THR A 292     -19.847  37.730  20.152  1.00 30.68      A
ATOM   2252  CA   THR A 292     -19.855  36.690  21.183  1.00 28.98      A
ATOM   2253  CB   THR A 292     -21.269  36.383  21.729  1.00 27.63      A
ATOM   2254  OG1  THR A 292     -21.901  37.586  22.172  1.00 26.78      A
ATOM   2255  CG2  THR A 292     -21.174  35.429  22.893  1.00 26.66      A
ATOM   2256  C    THR A 292     -19.326  35.398  20.581  1.00 29.08      A
ATOM   2257  O    THR A 292     -18.552  34.680  21.215  1.00 29.39      A
ATOM   2258  N    LEU A 293     -19.747  35.108  19.352  1.00 27.23      A
ATOM   2259  CA   LEU A 293     -19.314  33.891  18.685  1.00 27.26      A
ATOM   2260  CB   LEU A 293     -20.101  33.656  17.389  1.00 25.95      A
ATOM   2261  CG   LEU A 293     -21.534  33.118  17.474  1.00 26.99      A
ATOM   2262  CD1  LEU A 293     -22.145  33.111  16.081  1.00 28.27      A
ATOM   2263  CD2  LEU A 293     -21.552  31.707  18.068  1.00 25.40      A
ATOM   2264  C    LEU A 293     -17.837  33.939  18.373  1.00 27.04      A
ATOM   2265  O    LEU A 293     -17.114  32.995  18.677  1.00 28.65      A
ATOM   2266  N    THR A 294     -17.391  35.036  17.767  1.00 25.84      A
ATOM   2267  CA   THR A 294     -15.992  35.192  17.400  1.00 24.49      A
ATOM   2268  CB   THR A 294     -15.751  36.520  16.699  1.00 23.26      A
ATOM   2269  OG1  THR A 294     -16.513  36.561  15.493  1.00 25.92      A
ATOM   2270  CG2  THR A 294     -14.294  36.678  16.355  1.00 21.27      A
ATOM   2271  C    THR A 294     -15.086  35.139  18.609  1.00 26.38      A
ATOM   2272  O    THR A 294     -14.085  34.434  18.608  1.00 27.10      A
ATOM   2273  N    CYS A 295     -15.440  35.904  19.636  1.00 27.55      A
ATOM   2274  CA   CYS A 295     -14.661  35.961  20.864  1.00 28.51      A
ATOM   2275  CB   CYS A 295     -15.238  37.017  21.802  1.00 29.89      A
ATOM   2276  SG   CYS A 295     -14.421  37.094  23.403  1.00 32.57      A
ATOM   2277  C    CYS A 295     -14.633  34.620  21.574  1.00 29.04      A
ATOM   2278  O    CYS A 295     -13.636  34.262  22.193  1.00 30.25      A
ATOM   2279  N    TYR A 296     -15.737  33.888  21.499  1.00 28.38      A
ATOM   2280  CA   TYR A 296     -15.818  32.579  22.126  1.00 28.53      A
```

FIGURE 5- 31 -

```
ATOM   2281  CD   TYR A 296     -17.275  32.092  22.139  1.00 27.63      A
ATOM   2282  CG   TYR A 296     -17.455  30.643  22.541  1.00 25.96      A
ATOM   2283  CD1  TYR A 296     -17.402  29.633  21.595  1.00 25.31      A
ATOM   2284  CE1  TYR A 296     -17.541  28.302  21.956  1.00 26.02      A
ATOM   2285  CD2  TYR A 296     -17.655  30.283  23.878  1.00 25.96      A
ATOM   2286  CE2  TYR A 296     -17.797  28.949  24.255  1.00 23.98      A
ATOM   2287  CZ   TYR A 296     -17.739  27.964  23.285  1.00 25.74      A
ATOM   2288  OE   TYR A 296     -17.877  26.637  23.625  1.00 26.65      A
ATOM   2289  C    TYR A 296     -14.937  31.577  21.386  1.00 29.94      A
ATOM   2290  O    TYR A 296     -14.238  30.772  22.006  1.00 31.78      A
ATOM   2291  N    LEU A 297     -14.968  31.629  20.057  1.00 29.88      A
ATOM   2292  CA   LEU A 297     -14.181  30.711  19.254  1.00 29.77      A
ATOM   2293  CB   LEU A 297     -14.490  30.900  17.771  1.00 28.81      A
ATOM   2294  CG   LEU A 297     -13.479  30.380  16.738  1.00 26.18      A
ATOM   2295  CD1  LEU A 297     -13.201  28.896  16.916  1.00 23.31      A
ATOM   2296  CD2  LEU A 297     -14.046  30.648  15.364  1.00 24.34      A
ATOM   2297  C    LEU A 297     -12.704  30.916  19.500  1.00 31.34      A
ATOM   2298  O    LEU A 297     -11.975  29.969  19.771  1.00 33.45      A
ATOM   2299  N    LYS A 298     -12.263  32.162  19.417  1.00 32.16      A
ATOM   2300  CA   LYS A 298     -10.861  32.471  19.622  1.00 31.56      A
ATOM   2301  CB   LYS A 298     -10.612  33.940  19.303  1.00 28.53      A
ATOM   2302  CG   LYS A 298     -10.925  34.310  17.856  1.00 26.07      A
ATOM   2303  CD   LYS A 298     -10.586  35.767  17.591  1.00 28.40      A
ATOM   2304  CE   LYS A 298     -10.904  36.182  16.173  1.00 27.65      A
ATOM   2305  NZ   LYS A 298     -10.738  37.652  16.005  1.00 25.00      A
ATOM   2306  C    LYS A 298     -10.375  32.139  21.030  1.00 33.01      A
ATOM   2307  O    LYS A 298      -9.313  31.537  21.202  1.00 35.23      A
ATOM   2308  N    ALA A 299     -11.160  32.512  22.035  1.00 34.11      A
ATOM   2309  CA   ALA A 299     -10.794  32.263  23.431  1.00 33.21      A
ATOM   2310  CB   ALA A 299     -11.802  32.950  24.369  1.00 30.37      A
ATOM   2311  C    ALA A 299     -10.700  30.771  23.761  1.00 32.66      A
ATOM   2312  O    ALA A 299      -9.791  30.339  24.466  1.00 33.45      A
ATOM   2313  N    THR A 300     -11.640  29.987  23.247  1.00 31.34      A
ATOM   2314  CA   THR A 300     -11.646  28.559  23.509  1.00 30.28      A
ATOM   2315  CB   THR A 300     -12.870  27.897  22.864  1.00 30.10      A
ATOM   2316  OG1  THR A 300     -14.059  28.498  23.387  1.00 31.89      A
ATOM   2317  CG2  THR A 300     -12.898  26.417  23.160  1.00 25.91      A
ATOM   2318  C    THR A 300     -10.376  27.900  22.980  1.00 30.76      A
ATOM   2319  O    THR A 300      -9.715  27.135  23.691  1.00 29.25      A
ATOM   2320  N    ALA A 301     -10.040  28.208  21.729  1.00 30.07      A
ATOM   2321  CA   ALA A 301      -8.857  27.651  21.091  1.00 29.54      A
ATOM   2322  CB   ALA A 301      -8.835  28.015  19.613  1.00 28.41      A
ATOM   2323  C    ALA A 301      -7.617  28.185  21.796  1.00 30.58      A
ATOM   2324  O    ALA A 301      -6.676  27.425  22.070  1.00 32.53      A
ATOM   2325  N    ALA A 302      -7.615  29.480  22.101  1.00 27.87      A
ATOM   2326  CA   ALA A 302      -6.482  30.064  22.803  1.00 28.65      A
ATOM   2327  CB   ALA A 302      -6.703  31.554  23.037  1.00 26.39      A
ATOM   2328  C    ALA A 302      -6.284  29.338  24.143  1.00 30.56      A
ATOM   2329  O    ALA A 302      -5.155  29.081  24.549  1.00 32.75      A
ATOM   2330  N    CYS A 303      -7.367  29.001  24.834  1.00 29.06      A
ATOM   2331  CA   CYS A 303      -7.218  28.303  26.097  1.00 30.04      A
ATOM   2332  CB   CYS A 303      -8.578  28.020  26.724  1.00 29.99      A
ATOM   2333  SG   CYS A 303      -9.259  29.408  27.621  1.00 34.80      A
ATOM   2334  C    CYS A 303      -6.479  26.994  25.875  1.00 31.33      A
ATOM   2335  O    CYS A 303      -5.624  26.596  26.667  1.00 33.11      A
ATOM   2336  N    ARG A 304      -6.815  26.319  24.788  1.00 32.04      A
ATOM   2337  CA   ARG A 304      -6.177  25.059  24.476  1.00 30.66      A
ATOM   2338  CB   ARG A 304      -6.873  24.417  23.288  1.00 28.02      A
ATOM   2339  CG   ARG A 304      -8.324  24.094  23.571  1.00 26.16      A
ATOM   2340  CD   ARG A 304      -8.919  23.291  22.455  1.00 24.89      A
ATOM   2341  NE   ARG A 304     -10.345  23.074  22.634  1.00 24.97      A
ATOM   2342  CZ   ARG A 304     -11.075  22.314  21.826  1.00 27.58      A
ATOM   2343  NF1  ARG A 304     -10.500  21.713  20.793  1.00 28.19      A
ATOM   2344  NE2  ARG A 304     -12.368  22.131  22.058  1.00 28.13      A
ATOM   2345  C    ARG A 304      -4.711  25.312  24.173  1.00 32.44      A
ATOM   2346  O    ARG A 304      -3.830  24.681  24.747  1.00 32.48      A
ATOM   2347  N    ALA A 305      -4.446  26.249  23.276  1.00 33.27      A
ATOM   2348  CA   ALA A 305      -3.070  26.553  22.938  1.00 34.90      A
ATOM   2349  CB   ALA A 305      -3.006  27.791  22.053  1.00 35.72      A
ATOM   2350  C    ALA A 305      -2.260  26.779  24.209  1.00 36.25      A
ATOM   2351  O    ALA A 305      -1.149  26.275  24.330  1.00 37.54      A
ATOM   2352  N    ALA A 306      -2.831  27.522  25.157  1.00 36.28      A
ATOM   2353  CA   ALA A 306      -2.157  27.845  26.409  1.00 36.42      A
ATOM   2354  CB   ALA A 306      -2.728  29.122  26.985  1.00 35.37      A
ATOM   2355  C    ALA A 306      -2.201  26.742  27.459  1.00 38.09      A
ATOM   2356  O    ALA A 306      -1.516  26.829  28.474  1.00 38.81      A
```

FIGURE 5- 32 -

```
ATOM   2357  N    LYS A 307      -3.013  25.717  27.237  1.00 39.24           A
ATOM   2358  CA   LYS A 307      -3.085  24.608  28.179  1.00 40.43           A
ATOM   2359  CB   LYS A 307      -1.693  24.017  28.394  1.00 42.06           A
ATOM   2360  CG   LYS A 307      -1.258  23.082  27.293  1.00 44.84           A
ATOM   2361  CD   LYS A 307       0.085  23.473  26.720  1.00 48.80           A
ATOM   2362  CE   LYS A 307       0.578  22.391  25.767  1.00 53.35           A
ATOM   2363  NZ   LYS A 307      -0.473  22.030  24.764  1.00 56.58           A
ATOM   2364  C    LYS A 307      -3.700  24.926  29.531  1.00 41.28           A
ATOM   2365  O    LYS A 307      -3.416  24.252  30.527  1.00 40.04           A
ATOM   2366  N    LEU A 308      -4.539  25.952  29.577  1.00 42.21           A
ATOM   2367  CA   LEU A 308      -5.202  26.289  30.820  1.00 42.56           A
ATOM   2368  CB   LEU A 308      -6.083  27.516  30.624  1.00 41.65           A
ATOM   2369  CG   LEU A 308      -5.367  28.862  30.799  1.00 41.02           A
ATOM   2370  CD1  LEU A 308      -3.919  28.750  30.414  1.00 40.15           A
ATOM   2371  CD2  LEU A 308      -6.069  29.918  29.954  1.00 41.97           A
ATOM   2372  C    LEU A 308      -6.024  25.062  31.187  1.00 44.77           A
ATOM   2373  O    LEU A 308      -6.661  24.447  30.329  1.00 43.47           A
ATOM   2374  N    GLN A 309      -6.000  24.702  32.463  1.00 47.82           A
ATOM   2375  CA   GLN A 309      -6.698  23.511  32.924  1.00 49.53           A
ATOM   2376  CB   GLN A 309      -5.918  22.892  34.088  1.00 52.25           A
ATOM   2377  CG   GLN A 309      -5.762  21.378  34.016  1.00 59.78           A
ATOM   2378  CD   GLN A 309      -4.925  20.907  32.818  1.00 64.55           A
ATOM   2379  OE1  GLN A 309      -4.661  19.705  32.665  1.00 66.69           A
ATOM   2380  NE2  GLN A 309      -4.508  21.850  31.966  1.00 65.55           A
ATOM   2381  C    GLN A 309      -8.149  23.703  33.340  1.00 49.03           A
ATOM   2382  O    GLN A 309      -8.478  24.640  34.069  1.00 49.38           A
ATOM   2383  N    ASP A 310      -9.004  22.802  32.860  1.00 47.54           A
ATOM   2384  CA   ASP A 310     -10.428  22.791  33.198  1.00 46.27           A
ATOM   2385  CB   ASP A 310     -10.600  22.145  34.579  1.00 49.91           A
ATOM   2386  CG   ASP A 310     -12.053  21.853  34.923  1.00 52.47           A
ATOM   2387  OD1  ASP A 310     -12.329  21.604  36.116  1.00 54.17           A
ATOM   2388  OD2  ASP A 310     -12.912  21.861  34.014  1.00 52.45           A
ATOM   2389  C    ASP A 310     -11.081  24.174  33.185  1.00 44.03           A
ATOM   2390  O    ASP A 310     -11.666  24.605  34.182  1.00 42.71           A
ATOM   2391  N    CYS A 311     -10.994  24.847  32.040  1.00 42.20           A
ATOM   2392  CA   CYS A 311     -11.547  26.191  31.862  1.00 40.29           A
ATOM   2393  CB   CYS A 311     -11.004  26.819  30.583  1.00 39.17           A
ATOM   2394  SG   CYS A 311      -9.261  27.102  30.578  1.00 41.78           A
ATOM   2395  C    CYS A 311     -13.062  26.322  31.808  1.00 38.66           A
ATOM   2396  O    CYS A 311     -13.759  25.456  31.279  1.00 37.93           A
ATOM   2397  N    THR A 312     -13.559  27.428  32.348  1.00 36.61           A
ATOM   2398  CA   THR A 312     -14.983  27.730  32.303  1.00 36.40           A
ATOM   2399  CB   THR A 312     -15.679  27.525  33.656  1.00 35.80           A
ATOM   2400  OG1  THR A 312     -15.572  26.152  34.046  1.00 38.38           A
ATOM   2401  CG2  THR A 312     -17.146  27.865  33.538  1.00 34.41           A
ATOM   2402  C    THR A 312     -15.082  29.192  31.890  1.00 35.64           A
ATOM   2403  O    THR A 312     -14.620  30.073  32.607  1.00 37.69           A
ATOM   2404  N    MET A 313     -15.676  29.441  30.729  1.00 34.86           A
ATOM   2405  CA   MET A 313     -15.801  30.793  30.185  1.00 34.63           A
ATOM   2406  CB   MET A 313     -15.312  30.835  28.739  1.00 36.29           A
ATOM   2407  CG   MET A 313     -13.842  31.061  28.549  1.00 39.13           A
ATOM   2408  SD   MET A 313     -13.379  30.594  26.875  1.00 44.31           A
ATOM   2409  CE   MET A 313     -14.838  31.148  25.947  1.00 39.18           A
ATOM   2410  C    MET A 313     -17.200  31.358  30.177  1.00 33.90           A
ATOM   2411  O    MET A 313     -18.189  30.626  30.134  1.00 34.35           A
ATOM   2412  N    LEU A 314     -17.255  32.682  30.173  1.00 31.54           A
ATOM   2413  CA   LEU A 314     -18.500  33.415  30.123  1.00 29.62           A
ATOM   2414  CB   LEU A 314     -18.801  34.038  31.482  1.00 29.14           A
ATOM   2415  CG   LEU A 314     -20.255  34.435  31.711  1.00 30.53           A
ATOM   2416  CD1  LEU A 314     -21.126  33.190  31.575  1.00 31.96           A
ATOM   2417  CD2  LEU A 314     -20.422  35.059  33.098  1.00 30.68           A
ATOM   2418  C    LEU A 314     -18.226  34.495  29.083  1.00 29.65           A
ATOM   2419  O    LEU A 314     -17.255  35.245  29.207  1.00 29.71           A
ATOM   2420  N    VAL A 315     -19.057  34.558  28.046  1.00 29.36           A
ATOM   2421  CA   VAL A 315     -18.861  35.542  26.987  1.00 29.55           A
ATOM   2422  CB   VAL A 315     -18.533  34.867  25.612  1.00 31.72           A
ATOM   2423  CG1  VAL A 315     -18.148  35.936  24.587  1.00 32.19           A
ATOM   2424  CG2  VAL A 315     -17.410  33.849  25.761  1.00 28.45           A
ATOM   2425  C    VAL A 315     -20.085  36.413  26.782  1.00 29.50           A
ATOM   2426  O    VAL A 315     -21.208  35.910  26.748  1.00 27.65           A
ATOM   2427  N    ASN A 316     -19.848  37.719  26.653  1.00 29.32           A
ATOM   2428  CA   ASN A 316     -20.891  38.712  26.412  1.00 29.91           A
ATOM   2429  CB   ASN A 316     -21.146  39.571  27.648  1.00 29.89           A
ATOM   2430  CG   ASN A 316     -21.889  38.837  28.733  1.00 30.49           A
ATOM   2431  OD1  ASN A 316     -21.329  37.978  29.415  1.00 30.41           A
ATOM   2432  ND2  ASN A 316     -23.162  39.178  28.907  1.00 30.22           A
```

FIGURE 5- 33 -

```
ATOM   2433  C    ASN A 316    -20.375  39.616  25.305  1.00 31.02      A
ATOM   2434  O    ASN A 316    -19.938  40.740  25.558  1.00 32.39      A
ATOM   2435  N    GLY A 317    -20.420  39.137  24.073  1.00 30.67      A
ATOM   2436  CA   GLY A 317    -19.906  39.950  22.994  1.00 31.82      A
ATOM   2437  C    GLY A 317    -18.398  39.986  23.109  1.00 32.49      A
ATOM   2438  O    GLY A 317    -17.756  38.941  23.153  1.00 34.41      A
ATOM   2439  N    ASP A 318    -17.818  41.174  23.180  1.00 33.71      A
ATOM   2440  CA   ASP A 318    -16.369  41.280  23.282  1.00 33.41      A
ATOM   2441  CB   ASP A 318    -15.893  42.648  22.778  1.00 32.38      A
ATOM   2442  CG   ASP A 318    -16.395  43.795  23.629  1.00 33.99      A
ATOM   2443  OD1  ASP A 318    -17.580  43.793  24.004  1.00 39.21      A
ATOM   2444  OD2  ASP A 318    -15.614  44.716  23.918  1.00 35.91      A
ATOM   2445  C    ASP A 318    -15.863  41.050  24.696  1.00 33.40      A
ATOM   2446  O    ASP A 318    -14.666  40.859  24.894  1.00 35.87      A
ATOM   2447  N    ASP A 319    -16.757  41.053  25.681  1.00 32.72      A
ATOM   2448  CA   ASP A 319    -16.329  40.855  27.065  1.00 32.17      A
ATOM   2449  CB   ASP A 319    -17.367  41.408  28.043  1.00 34.50      A
ATOM   2450  CG   ASP A 319    -16.744  41.891  29.350  1.00 36.13      A
ATOM   2451  OD1  ASP A 319    -16.318  41.037  30.160  1.00 38.85      A
ATOM   2452  OD2  ASP A 319    -16.673  43.128  29.561  1.00 35.54      A
ATOM   2453  C    ASP A 319    -16.099  39.383  27.320  1.00 31.79      A
ATOM   2454  O    ASP A 319    -16.918  38.547  26.951  1.00 33.08      A
ATOM   2455  N    LEU A 320    -14.973  39.076  27.957  1.00 32.09      A
ATOM   2456  CA   LEU A 320    -14.573  37.704  28.248  1.00 30.79      A
ATOM   2457  CB   LEU A 320    -13.543  37.257  27.216  1.00 29.45      A
ATOM   2458  CG   LEU A 320    -12.782  35.957  27.445  1.00 29.60      A
ATOM   2459  CD1  LEU A 320    -13.719  34.768  27.247  1.00 30.19      A
ATOM   2460  CD2  LEU A 320    -11.615  35.892  26.464  1.00 30.09      A
ATOM   2461  C    LEU A 320    -13.974  37.529  29.638  1.00 31.93      A
ATOM   2462  O    LEU A 320    -13.162  38.346  30.082  1.00 32.57      A
ATOM   2463  N    VAL A 321    -14.388  36.464  30.320  1.00 30.72      A
ATOM   2464  CA   VAL A 321    -13.862  36.151  31.639  1.00 30.99      A
ATOM   2465  CB   VAL A 321    -14.804  36.622  32.777  1.00 30.60      A
ATOM   2466  CG1  VAL A 321    -16.173  36.003  32.637  1.00 31.47      A
ATOM   2467  CG2  VAL A 321    -14.211  36.243  34.104  1.00 30.57      A
ATOM   2468  C    VAL A 321    -13.669  34.643  31.708  1.00 31.54      A
ATOM   2469  O    VAL A 321    -14.522  33.881  31.257  1.00 32.25      A
ATOM   2470  N    VAL A 322    -12.540  34.214  32.259  1.00 31.58      A
ATOM   2471  CA   VAL A 322    -12.235  32.792  32.359  1.00 32.28      A
ATOM   2472  CB   VAL A 322    -11.068  32.405  31.416  1.00 32.49      A
ATOM   2473  CG1  VAL A 322    -10.826  30.899  31.463  1.00 31.55      A
ATOM   2474  CG2  VAL A 322    -11.368  32.861  30.015  1.00 32.09      A
ATOM   2475  C    VAL A 322    -11.830  32.389  33.771  1.00 32.62      A
ATOM   2476  O    VAL A 322    -11.089  33.111  34.442  1.00 33.21      A
ATOM   2477  N    ILE A 323    -12.316  31.226  34.202  1.00 32.50      A
ATOM   2478  CA   ILE A 323    -12.013  30.658  35.519  1.00 32.03      A
ATOM   2479  CB   ILE A 323    -13.279  30.591  36.399  1.00 30.45      A
ATOM   2480  CG2  ILE A 323    -12.980  29.869  37.698  1.00 31.20      A
ATOM   2481  CG1  ILE A 323    -13.781  32.004  36.690  1.00 28.81      A
ATOM   2482  CD1  ILE A 323    -15.120  32.043  37.379  1.00 28.64      A
ATOM   2483  C    ILE A 323    -11.514  29.248  35.244  1.00 32.91      A
ATOM   2484  O    ILE A 323    -12.160  28.490  34.523  1.00 34.85      A
ATOM   2485  N    CYS A 324    -10.370  28.887  35.806  1.00 33.82      A
ATOM   2486  CA   CYS A 324     -9.816  27.557  35.561  1.00 35.77      A
ATOM   2487  CB   CYS A 324     -8.860  27.635  34.374  1.00 38.27      A
ATOM   2488  SG   CYS A 324     -7.463  28.770  34.677  1.00 42.94      A
ATOM   2489  C    CYS A 324     -9.069  27.001  36.775  1.00 35.89      A
ATOM   2490  O    CYS A 324     -8.959  27.668  37.799  1.00 35.98      A
ATOM   2491  N    GLU A 325     -8.565  25.775  36.661  1.00 36.00      A
ATOM   2492  CA   GLU A 325     -7.802  25.175  37.749  1.00 36.63      A
ATOM   2493  CB   GLU A 325     -7.712  23.656  37.588  1.00 37.81      A
ATOM   2494  CG   GLU A 325     -8.961  22.888  37.989  1.00 41.32      A
ATOM   2495  CD   GLU A 325     -9.225  22.932  39.486  1.00 43.49      A
ATOM   2496  OE1  GLU A 325    -10.195  22.277  39.933  1.00 44.41      A
ATOM   2497  OE2  GLU A 325     -8.469  23.619  40.214  1.00 43.47      A
ATOM   2498  C    GLU A 325     -6.395  25.755  37.749  1.00 36.88      A
ATOM   2499  O    GLU A 325     -5.680  25.693  36.748  1.00 36.75      A
ATOM   2500  N    SER A 326     -5.997  26.322  38.877  1.00 37.96      A
ATOM   2501  CA   SER A 326     -4.669  26.904  38.996  1.00 39.36      A
ATOM   2502  CB   SER A 326     -4.554  27.667  40.309  1.00 37.45      A
ATOM   2503  OG   SER A 326     -3.315  28.339  40.366  1.00 39.45      A
ATOM   2504  C    SER A 326     -3.575  25.838  38.935  1.00 40.89      A
ATOM   2505  O    SER A 326     -3.721  24.752  39.495  1.00 41.65      A
ATOM   2506  N    ALA A 327     -2.480  26.154  38.253  1.00 41.31      A
ATOM   2507  CA   ALA A 327     -1.357  25.230  38.133  1.00 40.98      A
ATOM   2508  CB   ALA A 327     -0.925  25.127  36.684  1.00 38.10      A
```

FIGURE 5- 34 -

```
ATOM   2509  C    ALA A 327     -0.205  25.756  38.987  1.00 42.29           A
ATOM   2510  O    ALA A 327      0.853  25.139  39.085  1.00 42.08           A
ATOM   2511  N    GLY A 328     -0.431  26.905  39.609  1.00 43.57           A
ATOM   2512  CA   GLY A 328      0.589  27.521  40.429  1.00 44.19           A
ATOM   2513  C    GLY A 328      0.835  28.934  39.934  1.00 46.17           A
ATOM   2514  O    GLY A 328      0.711  29.220  38.745  1.00 47.44           A
ATOM   2515  N    THR A 329      1.188  29.820  40.853  1.00 47.14           A
ATOM   2516  CA   THR A 329      1.445  31.213  40.540  1.00 47.15           A
ATOM   2517  CB   THR A 329      2.178  31.893  41.705  1.00 47.46           A
ATOM   2518  OG1  THR A 329      1.339  31.872  42.868  1.00 47.05           A
ATOM   2519  CG2  THR A 329      2.523  33.337  41.355  1.00 48.03           A
ATOM   2520  C    THR A 329      2.245  31.423  39.263  1.00 48.30           A
ATOM   2521  O    THR A 329      1.776  32.094  38.341  1.00 48.65           A
ATOM   2522  N    GLN A 330      3.448  30.854  39.214  1.00 49.80           A
ATOM   2523  CA   GLN A 330      4.325  30.995  38.052  1.00 50.41           A
ATOM   2524  CB   GLN A 330      5.636  30.344  38.317  1.00 54.01           A
ATOM   2525  CG   GLN A 330      6.563  31.087  39.308  1.00 59.93           A
ATOM   2526  CD   GLN A 330      6.892  32.501  38.856  1.00 64.55           A
ATOM   2527  OE1  GLN A 330      6.001  33.355  38.734  1.00 66.86           A
ATOM   2528  NE2  GLN A 330      8.178  32.759  38.602  1.00 65.46           A
ATOM   2529  C    GLN A 330      3.735  30.391  36.796  1.00 49.05           A
ATOM   2530  O    GLN A 330      3.777  30.997  35.730  1.00 49.32           A
ATOM   2531  N    GLU A 331      3.197  29.186  36.928  1.00 48.11           A
ATOM   2532  CA   GLU A 331      2.600  28.482  35.805  1.00 48.02           A
ATOM   2533  CB   GLU A 331      2.090  27.112  36.253  1.00 50.13           A
ATOM   2534  CG   GLU A 331      3.136  26.209  36.895  1.00 53.12           A
ATOM   2535  CD   GLU A 331      3.769  26.834  38.122  1.00 55.53           A
ATOM   2536  OE1  GLU A 331      3.026  27.429  38.930  1.00 55.17           A
ATOM   2537  OE2  GLU A 331      5.006  26.726  38.282  1.00 57.89           A
ATOM   2538  C    GLU A 331      1.443  29.290  35.223  1.00 47.20           A
ATOM   2539  O    GLU A 331      1.391  29.528  34.012  1.00 47.16           A
ATOM   2540  N    ASP A 332      0.520  29.705  36.091  1.00 44.25           A
ATOM   2541  CA   ASP A 332     -0.645  30.482  35.674  1.00 42.88           A
ATOM   2542  CB   ASP A 332     -1.468  30.926  36.894  1.00 43.66           A
ATOM   2543  CG   ASP A 332     -2.211  29.776  37.572  1.00 44.64           A
ATOM   2544  OD1  ASP A 332     -2.051  28.608  37.160  1.00 43.51           A
ATOM   2545  OD2  ASP A 332     -2.964  30.052  38.534  1.00 46.19           A
ATOM   2546  C    ASP A 332     -0.223  31.723  34.887  1.00 41.97           A
ATOM   2547  O    ASP A 332     -0.809  32.049  33.853  1.00 41.41           A
ATOM   2548  N    ALA A 333      0.792  32.419  35.386  1.00 39.41           A
ATOM   2549  CA   ALA A 333      1.266  33.622  34.733  1.00 37.60           A
ATOM   2550  CB   ALA A 333      2.385  34.226  35.534  1.00 35.80           A
ATOM   2551  C    ALA A 333      1.739  33.323  33.318  1.00 38.76           A
ATOM   2552  O    ALA A 333      1.408  34.046  32.377  1.00 39.96           A
ATOM   2553  N    ALA A 334      2.520  32.258  33.170  1.00 36.99           A
ATOM   2554  CA   ALA A 334      3.039  31.873  31.866  1.00 36.10           A
ATOM   2555  CB   ALA A 334      4.044  30.758  32.029  1.00 33.40           A
ATOM   2556  C    ALA A 334      1.896  31.423  30.956  1.00 35.97           A
ATOM   2557  O    ALA A 334      1.864  31.732  29.765  1.00 34.72           A
ATOM   2558  N    ALA A 335      0.963  30.679  31.533  1.00 35.72           A
ATOM   2559  CA   ALA A 335     -0.192  30.186  30.801  1.00 34.37           A
ATOM   2560  CB   ALA A 335     -1.028  29.303  31.712  1.00 30.45           A
ATOM   2561  C    ALA A 335     -1.037  31.347  30.265  1.00 35.12           A
ATOM   2562  O    ALA A 335     -1.547  31.298  29.141  1.00 34.40           A
ATOM   2563  N    LEU A 336     -1.193  32.397  31.066  1.00 36.03           A
ATOM   2564  CA   LEU A 336     -1.978  33.541  30.638  1.00 37.77           A
ATOM   2565  CB   LEU A 336     -2.175  34.513  31.802  1.00 38.63           A
ATOM   2566  CG   LEU A 336     -3.564  35.152  31.893  1.00 39.45           A
ATOM   2567  CD1  LEU A 336     -3.613  36.132  33.057  1.00 36.29           A
ATOM   2568  CD2  LEU A 336     -3.891  35.840  30.582  1.00 39.01           A
ATOM   2569  C    LEU A 336     -1.231  34.243  29.477  1.00 37.41           A
ATOM   2570  O    LEU A 336     -1.925  34.727  28.551  1.00 37.74           A
ATOM   2571  N    ARG A 337      0.045  34.288  29.546  1.00 37.94           A
ATOM   2572  CA   ARG A 337      0.870  34.906  28.515  1.00 37.72           A
ATOM   2573  CB   ARG A 337      2.333  34.898  28.962  1.00 38.40           A
ATOM   2574  CG   ARG A 337      2.947  36.260  29.121  1.00 40.92           A
ATOM   2575  CD   ARG A 337      3.482  36.480  30.513  1.00 43.23           A
ATOM   2576  NE   ARG A 337      4.372  35.404  30.933  1.00 47.07           A
ATOM   2577  CZ   ARG A 337      5.039  35.390  32.085  1.00 46.98           A
ATOM   2578  NH1  ARG A 337      4.924  36.400  32.936  1.00 46.97           A
ATOM   2579  NH2  ARG A 337      5.807  34.354  32.392  1.00 48.60           A
ATOM   2580  C    ARG A 337      0.709  34.097  27.224  1.00 37.16           A
ATOM   2581  O    ARG A 337      0.633  34.648  26.126  1.00 38.46           A
ATOM   2582  N    ALA A 338      0.659  32.781  27.364  1.00 35.09           A
ATOM   2583  CA   ALA A 338      0.436  31.919  26.208  1.00 34.55           A
ATOM   2584  CB   ALA A 338      0.553  30.458  26.633  1.00 32.13           A
```

FIGURE 5- 35 -

```
ATOM   2585  C    ALA A 338      -0.880  32.237  25.604  1.00 33.71      A
ATOM   2586  O    ALA A 338      -0.999  32.527  24.418  1.00 34.71      A
ATOM   2587  N    PHE A 339      -1.907  32.194  26.443  1.00 32.85      A
ATOM   2588  CA   PHE A 339      -3.263  32.482  26.010  1.00 31.62      A
ATOM   2589  CB   PHE A 339      -4.188  32.592  27.223  1.00 30.21      A
ATOM   2590  CG   PHE A 339      -5.559  33.081  26.886  1.00 26.75      A
ATOM   2591  CD1  PHE A 339      -6.567  32.186  26.562  1.00 28.33      A
ATOM   2592  CD2  PHE A 339      -5.837  34.442  26.866  1.00 25.79      A
ATOM   2593  CE1  PHE A 339      -7.835  32.640  26.203  1.00 26.78      A
ATOM   2594  CE2  PHE A 339      -7.094  34.911  26.508  1.00 24.92      A
ATOM   2595  CZ   PHE A 339      -8.100  34.009  26.183  1.00 25.62      A
ATOM   2596  C    PHE A 339      -3.302  33.788  25.231  1.00 31.44      A
ATOM   2597  O    PHE A 339      -3.983  33.895  24.217  1.00 32.67      A
ATOM   2598  N    THR A 340      -2.566  34.781  25.707  1.00 30.76      A
ATOM   2599  CA   THR A 340      -2.562  36.077  25.054  1.00 30.52      A
ATOM   2600  CB   THR A 340      -1.918  37.140  25.963  1.00 28.14      A
ATOM   2601  OG1  THR A 340      -2.618  37.163  27.212  1.00 27.49      A
ATOM   2602  CG2  THR A 340      -2.008  38.530  25.329  1.00 25.06      A
ATOM   2603  C    THR A 340      -1.873  36.060  23.696  1.00 32.06      A
ATOM   2604  O    THR A 340      -2.290  36.772  22.779  1.00 31.96      A
ATOM   2605  N    GLU A 341      -0.825  35.255  23.550  1.00 32.58      A
ATOM   2606  CA   GLU A 341      -0.140  35.203  22.267  1.00 34.09      A
ATOM   2607  CB   GLU A 341       1.210  34.491  22.394  1.00 35.00      A
ATOM   2608  CG   GLU A 341       2.199  35.212  23.311  1.00 36.43      A
ATOM   2609  CD   GLU A 341       2.468  36.649  22.876  1.00 36.93      A
ATOM   2610  OE1  GLU A 341       2.687  37.513  23.753  1.00 35.98      A
ATOM   2611  OE2  GLU A 341       2.468  36.918  21.657  1.00 39.04      A
ATOM   2612  C    GLU A 341      -1.046  34.479  21.282  1.00 35.21      A
ATOM   2613  O    GLU A 341      -1.068  34.797  20.095  1.00 37.65      A
ATOM   2614  N    ALA A 342      -1.809  33.516  21.782  1.00 33.39      A
ATOM   2615  CA   ALA A 342      -2.731  32.781  20.937  1.00 34.15      A
ATOM   2616  CB   ALA A 342      -3.418  31.698  21.747  1.00 33.02      A
ATOM   2617  C    ALA A 342      -3.763  33.767  20.382  1.00 35.38      A
ATOM   2618  O    ALA A 342      -3.979  33.340  19.173  1.00 37.88      A
ATOM   2619  N    MET A 343      -4.391  34.529  21.275  1.00 35.02      A
ATOM   2620  CA   MET A 343      -5.400  35.514  20.893  1.00 34.24      A
ATOM   2621  CB   MET A 343      -5.937  36.251  22.132  1.00 33.06      A
ATOM   2622  CG   MET A 343      -6.826  35.428  23.056  1.00 32.06      A
ATOM   2623  SD   MET A 343      -8.429  34.990  22.333  1.00 31.85      A
ATOM   2624  CE   MET A 343      -9.405  36.401  22.840  1.00 31.59      A
ATOM   2625  C    MET A 343      -4.842  36.542  19.914  1.00 34.64      A
ATOM   2626  O    MET A 343      -5.524  36.946  18.964  1.00 35.20      A
ATOM   2627  N    THR A 344      -3.605  36.971  20.154  1.00 33.85      A
ATOM   2628  CA   THR A 344      -2.967  37.969  19.303  1.00 31.92      A
ATOM   2629  CB   THR A 344      -1.583  38.357  19.866  1.00 31.05      A
ATOM   2630  OG1  THR A 344      -1.748  38.902  21.180  1.00 32.28      A
ATOM   2631  CG2  THR A 344      -0.914  39.398  18.982  1.00 26.47      A
ATOM   2632  C    THR A 344      -2.832  37.429  17.883  1.00 31.78      A
ATOM   2633  O    THR A 344      -2.997  38.161  16.906  1.00 31.92      A
ATOM   2634  N    ARG A 345      -2.544  36.135  17.782  1.00 30.91      A
ATOM   2635  CA   ARG A 345      -2.407  35.483  16.497  1.00 30.38      A
ATOM   2636  CB   ARG A 345      -1.809  34.091  16.656  1.00 28.40      A
ATOM   2637  CG   ARG A 345      -0.320  34.074  16.717  1.00 25.66      A
ATOM   2638  CD   ARG A 345       0.152  32.657  16.641  1.00 24.28      A
ATOM   2639  NE   ARG A 345      -0.178  31.901  17.839  1.00 27.43      A
ATOM   2640  CZ   ARG A 345       0.582  31.862  18.926  1.00 29.46      A
ATOM   2641  NH1  ARG A 345       1.723  32.536  18.965  1.00 32.23      A
ATOM   2642  NH2  ARG A 345       0.210  31.146  19.971  1.00 30.76      A
ATOM   2643  C    ARG A 345      -3.764  35.359  15.835  1.00 32.53      A
ATOM   2644  O    ARG A 345      -3.864  35.445  14.607  1.00 35.37      A
ATOM   2645  N    TYR A 346      -4.803  35.129  16.637  1.00 31.48      A
ATOM   2646  CA   TYR A 346      -6.145  35.013  16.086  1.00 31.15      A
ATOM   2647  CB   TYR A 346      -7.099  34.328  17.060  1.00 30.44      A
ATOM   2648  CG   TYR A 346      -6.803  32.876  17.340  1.00 30.51      A
ATOM   2649  CD1  TYR A 346      -6.201  32.063  16.382  1.00 29.35      A
ATOM   2650  CE1  TYR A 346      -6.010  30.708  16.617  1.00 29.96      A
ATOM   2651  CD2  TYR A 346      -7.200  32.293  18.545  1.00 30.82      A
ATOM   2652  CE2  TYR A 346      -7.017  30.940  18.787  1.00 29.88      A
ATOM   2653  CZ   TYR A 346      -6.427  30.156  17.819  1.00 30.58      A
ATOM   2654  OH   TYR A 346      -6.300  28.313  18.048  1.00 33.38      A
ATOM   2655  C    TYR A 346      -6.698  36.388  15.752  1.00 31.84      A
ATOM   2656  O    TYR A 346      -7.815  36.500  15.255  1.00 32.84      A
ATOM   2657  N    SER A 347      -5.918  37.427  16.039  1.00 31.92      A
ATOM   2658  CA   SER A 347      -6.316  38.799  15.763  1.00 33.66      A
ATOM   2659  CB   SER A 347      -7.030  38.907  14.419  1.00 32.62      A
ATOM   2660  OG   SER A 347      -7.549  40.212  14.236  1.00 33.36      A
```

FIGURE 5-36-

```
ATOM   2661  C    SER A 347      -7.226  39.341  16.837  1.00 36.22           A
ATOM   2662  O    SER A 347      -8.304  39.878  16.553  1.00 39.36           A
ATOM   2663  N    ALA A 348      -6.792  39.189  18.077  1.00 36.97           A
ATOM   2664  CA   ALA A 348      -7.540  39.680  19.224  1.00 35.84           A
ATOM   2665  CB   ALA A 348      -8.435  38.589  19.769  1.00 35.74           A
ATOM   2666  C    ALA A 348      -6.509  40.113  20.268  1.00 35.14           A
ATOM   2667  O    ALA A 348      -6.482  39.611  21.393  1.00 34.31           A
ATOM   2668  N    PRO A 349      -5.626  41.050  19.884  1.00 33.85           A
ATOM   2669  CD   PRO A 349      -5.668  41.806  18.619  1.00 32.10           A
ATOM   2670  CA   PRO A 349      -4.580  41.571  20.768  1.00 34.39           A
ATOM   2671  CB   PRO A 349      -3.870  42.596  19.886  1.00 33.35           A
ATOM   2672  CG   PRO A 349      -4.965  43.089  18.990  1.00 32.03           A
ATOM   2673  C    PRO A 349      -5.167  42.186  22.044  1.00 34.92           A
ATOM   2674  O    PRO A 349      -6.272  42.734  22.041  1.00 35.68           A
ATOM   2675  N    PRO A 350      -4.431  42.109  23.153  1.00 35.37           A
ATOM   2676  CD   PRO A 350      -3.151  41.422  23.374  1.00 35.76           A
ATOM   2677  CA   PRO A 350      -4.943  42.671  24.400  1.00 36.99           A
ATOM   2678  CB   PRO A 350      -4.076  42.006  25.451  1.00 36.23           A
ATOM   2679  CG   PRO A 350      -2.768  41.904  24.749  1.00 36.04           A
ATOM   2680  C    PRO A 350      -4.862  44.176  24.484  1.00 38.91           A
ATOM   2681  O    PRO A 350      -4.061  44.801  23.797  1.00 39.89           A
ATOM   2682  N    GLY A 351      -5.730  44.749  25.310  1.00 40.79           A
ATOM   2683  CA   GLY A 351      -5.715  46.179  25.537  1.00 42.19           A
ATOM   2684  C    GLY A 351      -4.887  46.207  26.799  1.00 43.62           A
ATOM   2685  O    GLY A 351      -3.658  46.144  26.740  1.00 43.40           A
ATOM   2686  N    ASP A 352      -5.551  46.270  27.947  1.00 46.12           A
ATOM   2687  CA   ASP A 352      -4.831  46.231  29.216  1.00 48.95           A
ATOM   2688  CB   ASP A 352      -5.796  46.368  30.406  1.00 52.68           A
ATOM   2689  CG   ASP A 352      -6.768  47.547  30.260  1.00 56.15           A
ATOM   2690  OD1  ASP A 352      -6.315  48.693  30.018  1.00 56.48           A
ATOM   2691  OD2  ASP A 352      -7.994  47.323  30.401  1.00 57.73           A
ATOM   2692  C    ASP A 352      -4.256  44.814  29.184  1.00 48.09           A
ATOM   2693  O    ASP A 352      -4.752  43.965  28.447  1.00 50.37           A
ATOM   2694  N    PRO A 353      -3.199  44.537  29.952  1.00 46.29           A
ATOM   2695  CD   PRO A 353      -2.214  45.468  30.515  1.00 46.66           A
ATOM   2696  CA   PRO A 353      -2.663  43.166  29.903  1.00 43.52           A
ATOM   2697  CB   PRO A 353      -1.199  43.346  30.296  1.00 45.80           A
ATOM   2698  CG   PRO A 353      -0.932  44.841  30.050  1.00 47.26           A
ATOM   2699  C    PRO A 353      -3.402  42.270  30.883  1.00 41.15           A
ATOM   2700  O    PRO A 353      -3.631  42.664  32.019  1.00 42.59           A
ATOM   2701  N    PRO A 354      -3.795  41.057  30.462  1.00 38.86           A
ATOM   2702  CD   PRO A 354      -3.563  40.417  29.159  1.00 36.88           A
ATOM   2703  CA   PRO A 354      -4.514  40.148  31.363  1.00 38.87           A
ATOM   2704  CB   PRO A 354      -4.860  38.973  30.456  1.00 36.40           A
ATOM   2705  CG   PRO A 354      -3.737  38.958  29.492  1.00 36.34           A
ATOM   2706  C    PRO A 354      -3.704  39.727  32.593  1.00 39.93           A
ATOM   2707  O    PRO A 354      -2.561  39.287  32.477  1.00 41.58           A
ATOM   2708  N    GLN A 355      -4.305  39.866  33.768  1.00 40.41           A
ATOM   2709  CA   GLN A 355      -3.647  39.508  35.019  1.00 42.95           A
ATOM   2710  CB   GLN A 355      -3.593  40.714  35.965  1.00 48.04           A
ATOM   2711  CG   GLN A 355      -2.694  41.847  35.508  1.00 54.38           A
ATOM   2712  CD   GLN A 355      -1.299  41.362  35.124  1.00 59.48           A
ATOM   2713  OE1  GLN A 355      -0.649  40.622  35.878  1.00 61.17           A
ATOM   2714  NE2  GLN A 355      -0.829  41.781  33.947  1.00 60.01           A
ATOM   2715  C    GLN A 355      -4.397  38.387  35.721  1.00 41.76           A
ATOM   2716  O    GLN A 355      -5.618  38.442  35.857  1.00 41.96           A
ATOM   2717  N    PRO A 356      -3.679  37.352  36.179  1.00 40.75           A
ATOM   2718  CD   PRO A 356      -2.265  36.989  35.970  1.00 39.03           A
ATOM   2719  CA   PRO A 356      -4.397  36.275  36.859  1.00 40.32           A
ATOM   2720  CB   PRO A 356      -3.368  35.147  36.893  1.00 38.52           A
ATOM   2721  CG   PRO A 356      -2.077  35.866  36.957  1.00 36.03           A
ATOM   2722  C    PRO A 356      -4.842  36.718  38.247  1.00 41.22           A
ATOM   2723  O    PRO A 356      -4.089  37.378  38.953  1.00 42.15           A
ATOM   2724  N    GLU A 357      -6.076  36.380  38.617  1.00 41.37           A
ATOM   2725  CA   GLU A 357      -6.623  36.727  39.932  1.00 39.87           A
ATOM   2726  CB   GLU A 357      -7.911  37.543  39.806  1.00 38.87           A
ATOM   2727  CG   GLU A 357      -7.747  38.951  39.285  1.00 41.04           A
ATOM   2728  CD   GLU A 357      -6.795  39.782  40.120  1.00 43.69           A
ATOM   2729  OE1  GLU A 357      -6.870  39.719  41.365  1.00 45.27           A
ATOM   2730  OE2  GLU A 357      -5.975  40.514  39.533  1.00 45.53           A
ATOM   2731  C    GLU A 357      -6.939  35.440  40.674  1.00 39.81           A
ATOM   2732  O    GLU A 357      -7.269  34.425  40.058  1.00 41.68           A
ATOM   2733  N    TYR A 358      -6.840  35.480  41.995  1.00 38.66           A
ATOM   2734  CA   TYR A 358      -7.114  34.305  42.803  1.00 37.29           A
ATOM   2735  CB   TYR A 358      -5.827  33.819  43.462  1.00 35.20           A
ATOM   2736  CG   TYR A 358      -4.766  33.395  42.468  1.00 33.28           A
```

FIGURE 5- 37 -

```
ATOM   2737  CD1 TYR A 358      -4.797  32.133  41.874  1.00 34.25           A
ATOM   2738  CE1 TYR A 358      -3.831  31.753  40.926  1.00 33.36           A
ATOM   2739  CD2 TYR A 358      -3.749  34.266  42.097  1.00 31.97           A
ATOM   2740  CE2 TYR A 358      -2.788  33.898  41.163  1.00 33.55           A
ATOM   2741  CZ  TYR A 358      -2.835  32.646  40.583  1.00 33.92           A
ATOM   2742  OH  TYR A 358      -1.884  32.301  39.655  1.00 39.14           A
ATOM   2743  C   TYR A 358      -8.179  34.617  43.847  1.00 38.80           A
ATOM   2744  O   TYR A 358      -8.331  33.895  44.831  1.00 39.16           A
ATOM   2745  N   ASP A 359      -8.915  35.702  43.604  1.00 40.03           A
ATOM   2746  CA  ASP A 359     -10.008  36.159  44.457  1.00 40.68           A
ATOM   2747  CB  ASP A 359      -9.544  37.280  45.387  1.00 44.19           A
ATOM   2748  CG  ASP A 359     -10.707  37.981  46.091  1.00 50.62           A
ATOM   2749  OD1 ASP A 359     -11.793  37.356  46.225  1.00 52.11           A
ATOM   2750  OD2 ASP A 359     -10.529  39.153  46.521  1.00 51.83           A
ATOM   2751  C   ASP A 359     -11.105  36.681  43.540  1.00 40.54           A
ATOM   2752  O   ASP A 359     -10.985  37.771  42.983  1.00 41.99           A
ATOM   2753  N   LEU A 360     -12.170  35.900  43.388  1.00 38.65           A
ATOM   2754  CA  LEU A 360     -13.280  36.255  42.515  1.00 37.16           A
ATOM   2755  CB  LEU A 360     -14.512  35.403  42.843  1.00 34.33           A
ATOM   2756  CG  LEU A 360     -15.746  35.715  41.987  1.00 33.41           A
ATOM   2757  CD1 LEU A 360     -15.501  35.253  40.569  1.00 31.53           A
ATOM   2758  CD2 LEU A 360     -16.978  35.036  42.548  1.00 33.44           A
ATOM   2759  C   LEU A 360     -13.679  37.725  42.541  1.00 38.52           A
ATOM   2760  O   LEU A 360     -13.937  38.325  41.496  1.00 40.08           A
ATOM   2761  N   GLU A 361     -13.735  38.313  43.725  1.00 38.37           A
ATOM   2762  CA  GLU A 361     -14.148  39.698  43.821  1.00 38.88           A
ATOM   2763  CB  GLU A 361     -14.254  40.108  45.283  1.00 41.41           A
ATOM   2764  CG  GLU A 361     -15.394  39.434  46.010  1.00 45.34           A
ATOM   2765  CD  GLU A 361     -15.694  40.086  47.349  1.00 49.20           A
ATOM   2766  OE1 GLU A 361     -15.181  41.207  47.605  1.00 48.86           A
ATOM   2767  OE2 GLU A 361     -16.456  39.476  48.133  1.00 50.72           A
ATOM   2768  C   GLU A 361     -13.263  40.680  43.078  1.00 38.42           A
ATOM   2769  O   GLU A 361     -13.696  41.782  42.754  1.00 39.28           A
ATOM   2770  N   LEU A 362     -12.029  40.287  42.798  1.00 38.80           A
ATOM   2771  CA  LEU A 362     -11.099  41.175  42.107  1.00 38.69           A
ATOM   2772  CB  LEU A 362      -9.659  40.801  42.461  1.00 38.66           A
ATOM   2773  CG  LEU A 362      -9.319  40.944  43.954  1.00 38.41           A
ATOM   2774  CD1 LEU A 362      -7.849  40.621  44.181  1.00 36.78           A
ATOM   2775  CD2 LEU A 362      -9.634  42.356  44.424  1.00 34.04           A
ATOM   2776  C   LEU A 362     -11.291  41.189  40.596  1.00 38.51           A
ATOM   2777  O   LEU A 362     -11.014  42.191  39.932  1.00 39.49           A
ATOM   2778  N   ILE A 363     -11.774  40.082  40.051  1.00 36.92           A
ATOM   2779  CA  ILE A 363     -12.017  40.003  38.623  1.00 34.66           A
ATOM   2780  CB  ILE A 363     -12.392  38.583  38.220  1.00 32.82           A
ATOM   2781  CG2 ILE A 363     -12.687  38.517  36.717  1.00 30.36           A
ATOM   2782  CG1 ILE A 363     -11.271  37.636  38.636  1.00 30.34           A
ATOM   2783  CD1 ILE A 363     -11.535  36.210  38.271  1.00 27.68           A
ATOM   2784  C   ILE A 363     -13.170  40.931  38.249  1.00 36.62           A
ATOM   2785  O   ILE A 363     -14.169  41.007  38.970  1.00 38.06           A
ATOM   2786  N   THR A 364     -13.024  41.639  37.131  1.00 35.63           A
ATOM   2787  CA  THR A 364     -14.060  42.543  36.653  1.00 35.06           A
ATOM   2788  CB  THR A 364     -13.563  43.985  36.584  1.00 34.07           A
ATOM   2789  CG1 THR A 364     -13.099  44.386  37.876  1.00 35.40           A
ATOM   2790  CG2 THR A 364     -14.689  44.912  36.115  1.00 30.34           A
ATOM   2791  C   THR A 364     -14.478  42.128  35.250  1.00 36.96           A
ATOM   2792  O   THR A 364     -13.672  42.180  34.320  1.00 38.95           A
ATOM   2793  N   SER A 365     -15.734  41.722  35.102  1.00 36.40           A
ATOM   2794  CA  SER A 365     -16.260  41.294  33.813  1.00 37.31           A
ATOM   2795  CB  SER A 365     -16.517  39.795  33.821  1.00 39.30           A
ATOM   2796  OG  SER A 365     -17.601  39.490  34.682  1.00 42.24           A
ATOM   2797  C   SER A 365     -17.568  42.021  33.559  1.00 38.58           A
ATOM   2798  O   SER A 365     -18.442  42.069  34.433  1.00 37.83           A
ATOM   2799  N   CYS A 366     -17.704  42.573  32.357  1.00 39.07           A
ATOM   2800  CA  CYS A 366     -18.889  43.336  31.992  1.00 38.72           A
ATOM   2801  CB  CYS A 366     -20.153  42.487  32.102  1.00 39.26           A
ATOM   2802  SG  CYS A 366     -20.428  41.397  30.692  1.00 44.15           A
ATOM   2803  C   CYS A 366     -18.999  44.534  32.914  1.00 38.30           A
ATOM   2804  O   CYS A 366     -20.092  44.944  33.281  1.00 38.21           A
ATOM   2805  N   SER A 367     -17.849  45.079  33.296  1.00 38.56           A
ATOM   2806  CA  SER A 367     -17.789  46.243  34.174  1.00 38.61           A
ATOM   2807  CB  SER A 367     -18.560  47.395  33.541  1.00 35.54           A
ATOM   2808  OG  SER A 367     -18.012  47.707  32.277  1.00 38.06           A
ATOM   2809  C   SER A 367     -18.320  45.996  35.586  1.00 39.45           A
ATOM   2810  O   SER A 367     -18.550  46.948  36.336  1.00 40.52           A
ATOM   2811  N   SER A 368     -18.507  44.730  35.950  1.00 38.21           A
ATOM   2812  CA  SER A 368     -19.026  44.396  37.266  1.00 37.92           A
```

FIGURE 5- 38 -

```
ATOM   2813  CB   SER A 368     -20.439  43.824  37.137  1.00 38.71      A
ATOM   2814  OG   SER A 368     -21.282  44.728  36.450  1.00 38.69      A
ATOM   2815  C    SER A 368     -18.152  43.388  37.984  1.00 37.13      A
ATOM   2816  O    SER A 368     -17.293  42.756  37.377  1.00 38.66      A
ATOM   2817  N    ASN A 369     -18.370  43.252  39.285  1.00 35.85      A
ATOM   2818  CA   ASN A 369     -17.634  42.286  40.085  1.00 35.98      A
ATOM   2819  CB   ASN A 369     -16.420  42.914  40.760  1.00 36.49      A
ATOM   2820  CG   ASN A 369     -16.804  43.900  41.839  1.00 38.17      A
ATOM   2821  OD1  ASN A 369     -17.241  45.013  41.555  1.00 40.40      A
ATOM   2822  ND2  ASN A 369     -16.658  43.487  43.089  1.00 37.52      A
ATOM   2823  C    ASN A 369     -18.567  41.760  41.154  1.00 35.59      A
ATOM   2824  O    ASN A 369     -19.628  42.323  41.402  1.00 36.06      A
ATOM   2825  N    VAL A 370     -18.169  40.662  41.774  1.00 35.26      A
ATOM   2826  CA   VAL A 370     -18.953  40.063  42.833  1.00 35.65      A
ATOM   2827  CB   VAL A 370     -18.686  38.540  42.910  1.00 36.90      A
ATOM   2828  CG1  VAL A 370     -19.436  37.920  44.099  1.00 34.14      A
ATOM   2829  CG2  VAL A 370     -19.097  37.883  41.593  1.00 34.75      A
ATOM   2830  C    VAL A 370     -18.585  40.708  44.175  1.00 37.13      A
ATOM   2831  O    VAL A 370     -17.441  41.111  44.398  1.00 37.83      A
ATOM   2832  N    SER A 371     -19.570  40.822  45.056  1.00 36.88      A
ATOM   2833  CA   SER A 371     -19.357  41.374  46.383  1.00 36.43      A
ATOM   2834  CB   SER A 371     -19.643  42.872  46.397  1.00 35.26      A
ATOM   2835  OG   SER A 371     -19.627  43.363  47.722  1.00 34.82      A
ATOM   2836  C    SER A 371     -20.326  40.629  47.292  1.00 37.47      A
ATOM   2837  O    SER A 371     -21.252  39.985  46.805  1.00 36.68      A
ATOM   2838  N    VAL A 372     -20.126  40.710  48.602  1.00 39.09      A
ATOM   2839  CA   VAL A 372     -20.997  39.991  49.519  1.00 39.53      A
ATOM   2840  CB   VAL A 372     -20.197  39.012  50.406  1.00 39.69      A
ATOM   2841  CG1  VAL A 372     -21.095  37.866  50.845  1.00 41.49      A
ATOM   2842  CG2  VAL A 372     -18.990  38.480  49.657  1.00 42.03      A
ATOM   2843  C    VAL A 372     -21.762  40.920  50.432  1.00 39.50      A
ATOM   2844  O    VAL A 372     -21.314  42.016  50.739  1.00 41.40      A
ATOM   2845  N    ALA A 373     -22.932  40.468  50.856  1.00 40.06      A
ATOM   2846  CA   ALA A 373     -23.780  41.224  51.770  1.00 40.70      A
ATOM   2847  CB   ALA A 373     -24.673  42.190  51.002  1.00 38.10      A
ATOM   2848  C    ALA A 373     -24.620  40.188  52.517  1.00 41.10      A
ATOM   2849  O    ALA A 373     -24.546  38.999  52.218  1.00 39.53      A
ATOM   2850  N    HIS A 374     -25.410  40.626  53.487  1.00 41.54      A
ATOM   2851  CA   HIS A 374     -26.218  39.690  54.245  1.00 43.22      A
ATOM   2852  CB   HIS A 374     -25.738  39.677  55.692  1.00 43.21      A
ATOM   2853  CG   HIS A 374     -24.282  39.359  55.830  1.00 44.36      A
ATOM   2854  CD2  HIS A 374     -23.181  40.116  55.609  1.00 45.78      A
ATOM   2855  ND1  HIS A 374     -23.821  38.101  56.158  1.00 45.36      A
ATOM   2856  CE1  HIS A 374     -22.500  38.095  56.130  1.00 45.51      A
ATOM   2857  NE2  HIS A 374     -22.086  39.306  55.799  1.00 47.52      A
ATOM   2858  C    HIS A 374     -27.670  40.095  54.159  1.00 44.63      A
ATOM   2859  O    HIS A 374     -27.967  41.270  54.007  1.00 46.28      A
ATOM   2860  N    ASP A 375     -28.574  39.124  54.221  1.00 47.11      A
ATOM   2861  CA   ASP A 375     -29.998  39.431  54.158  1.00 49.90      A
ATOM   2862  CB   ASP A 375     -30.783  38.331  53.429  1.00 52.27      A
ATOM   2863  CG   ASP A 375     -30.652  36.972  54.090  1.00 55.54      A
ATOM   2864  OD1  ASP A 375     -30.768  36.893  55.334  1.00 57.79      A
ATOM   2865  OD2  ASP A 375     -30.445  35.977  53.360  1.00 57.34      A
ATOM   2866  C    ASP A 375     -30.531  39.585  55.571  1.00 50.54      A
ATOM   2867  O    ASP A 375     -29.758  39.629  56.531  1.00 48.49      A
ATOM   2868  N    ALA A 376     -31.852  39.663  55.691  1.00 51.50      A
ATOM   2869  CA   ALA A 376     -32.485  39.816  56.988  1.00 53.22      A
ATOM   2870  CB   ALA A 376     -33.968  39.584  56.852  1.00 53.41      A
ATOM   2871  C    ALA A 376     -31.895  38.843  58.010  1.00 55.06      A
ATOM   2872  O    ALA A 376     -31.445  39.248  59.085  1.00 55.28      A
ATOM   2873  N    SER A 377     -31.881  37.561  57.656  1.00 56.35      A
ATOM   2874  CA   SER A 377     -31.379  36.502  58.534  1.00 57.44      A
ATOM   2875  CB   SER A 377     -31.777  35.144  57.970  1.00 58.23      A
ATOM   2876  OG   SER A 377     -33.132  35.156  57.568  1.00 62.30      A
ATOM   2877  C    SER A 377     -29.877  36.495  58.781  1.00 57.34      A
ATOM   2878  O    SER A 377     -29.396  35.826  59.700  1.00 58.65      A
ATOM   2879  N    GLY A 378     -29.129  37.215  57.959  1.00 57.04      A
ATOM   2880  CA   GLY A 378     -27.689  37.233  58.134  1.00 55.35      A
ATOM   2881  C    GLY A 378     -27.012  36.734  57.182  1.00 53.91      A
ATOM   2882  O    GLY A 378     -25.797  36.072  57.243  1.00 53.46      A
ATOM   2883  N    LYS A 379     -27.802  35.670  56.300  1.00 52.89      A
ATOM   2884  CA   LYS A 379     -27.261  34.730  55.327  1.00 51.48      A
ATOM   2885  CB   LYS A 379     -28.404  34.003  54.600  1.00 53.69      A
ATOM   2886  CG   LYS A 379     -27.946  32.825  53.744  1.00 58.05      A
ATOM   2887  CD   LYS A 379     -29.084  32.184  52.947  1.00 61.60      A
ATOM   2888  CE   LYS A 379     -29.587  33.098  51.829  1.00 64.92      A
```

FIGURE 5- 39 -

```
ATOM   2889  NZ   LYS A 379     -30.658  32.453  50.993  1.00 66.74      A
ATOM   2890  C    LYS A 379     -26.435  35.546  54.336  1.00 48.23      A
ATOM   2891  O    LYS A 379     -26.788  36.680  54.033  1.00 45.29      A
ATOM   2892  N    ARG A 380     -25.332  34.983  53.850  1.00 46.11      A
ATOM   2893  CA   ARG A 380     -24.490  35.690  52.892  1.00 44.65      A
ATOM   2894  CB   ARG A 380     -23.116  35.051  52.800  1.00 46.29      A
ATOM   2895  CG   ARG A 380     -22.424  34.926  54.124  1.00 51.70      A
ATOM   2896  CD   ARG A 380     -21.092  34.273  53.944  1.00 55.11      A
ATOM   2897  NE   ARG A 380     -20.269  35.032  53.015  1.00 59.90      A
ATOM   2898  CZ   ARG A 380     -19.073  34.634  52.601  1.00 62.49      A
ATOM   2899  NH1  ARG A 380     -18.573  33.485  53.045  1.00 64.05      A
ATOM   2900  NH2  ARG A 380     -18.379  35.376  51.745  1.00 62.25      A
ATOM   2901  C    ARG A 380     -25.122  35.679  51.513  1.00 42.89      A
ATOM   2902  O    ARG A 380     -25.664  34.668  51.071  1.00 42.37      A
ATOM   2903  N    VAL A 381     -25.053  36.816  50.837  1.00 40.62      A
ATOM   2904  CA   VAL A 381     -25.615  36.929  49.513  1.00 38.08      A
ATOM   2905  CB   VAL A 381     -26.940  37.674  49.523  1.00 37.09      A
ATOM   2906  CG1  VAL A 381     -27.417  37.871  48.096  1.00 31.90      A
ATOM   2907  CG2  VAL A 381     -27.965  36.886  50.326  1.00 36.37      A
ATOM   2908  C    VAL A 381     -24.691  37.619  48.528  1.00 39.48      A
ATOM   2909  O    VAL A 381     -24.393  38.820  48.638  1.00 38.82      A
ATOM   2910  N    TYR A 382     -24.240  36.825  47.564  1.00 38.28      A
ATOM   2911  CA   TYR A 382     -23.370  37.297  46.512  1.00 35.58      A
ATOM   2912  CB   TYR A 382     -22.772  36.100  45.778  1.00 34.48      A
ATOM   2913  CG   TYR A 382     -21.878  35.245  46.640  1.00 35.96      A
ATOM   2914  CD1  TYR A 382     -20.572  35.629  46.925  1.00 36.97      A
ATOM   2915  CE1  TYR A 382     -19.755  34.852  47.742  1.00 39.77      A
ATOM   2916  CD2  TYR A 382     -22.347  34.060  47.193  1.00 38.51      A
ATOM   2917  CE2  TYR A 382     -21.541  33.271  48.016  1.00 39.60      A
ATOM   2918  CZ   TYR A 382     -20.249  33.669  48.288  1.00 41.56      A
ATOM   2919  OH   TYR A 382     -19.459  32.885  49.111  1.00 44.25      A
ATOM   2920  C    TYR A 382     -24.252  38.120  45.585  1.00 34.45      A
ATOM   2921  O    TYR A 382     -25.381  37.740  45.301  1.00 34.39      A
ATOM   2922  N    TYR A 383     -23.751  39.265  45.146  1.00 34.13      A
ATOM   2923  CA   TYR A 383     -24.506  40.125  44.244  1.00 34.03      A
ATOM   2924  CB   TYR A 383     -25.368  41.138  45.021  1.00 33.05      A
ATOM   2925  CG   TYR A 383     -24.597  42.228  45.739  1.00 32.70      A
ATOM   2926  CD1  TYR A 383     -23.847  41.946  46.886  1.00 33.35      A
ATOM   2927  CE1  TYR A 383     -23.113  42.949  47.540  1.00 32.96      A
ATOM   2928  CD2  TYR A 383     -24.604  43.539  45.262  1.00 33.35      A
ATOM   2929  CE2  TYR A 383     -23.880  44.546  45.905  1.00 35.11      A
ATOM   2930  CZ   TYR A 383     -23.133  44.242  47.039  1.00 34.46      A
ATOM   2931  OH   TYR A 383     -22.372  45.222  47.637  1.00 37.04      A
ATOM   2932  C    TYR A 383     -23.508  40.846  43.365  1.00 33.76      A
ATOM   2933  O    TYR A 383     -22.326  40.904  43.687  1.00 34.46      A
ATOM   2934  N    LEU A 384     -23.988  41.401  42.261  1.00 33.97      A
ATOM   2935  CA   LEU A 384     -23.116  42.087  41.323  1.00 32.71      A
ATOM   2936  CB   LEU A 384     -23.543  41.726  39.907  1.00 36.27      A
ATOM   2937  CG   LEU A 384     -22.424  41.519  38.889  1.00 40.51      A
ATOM   2938  CD1  LEU A 384     -21.433  40.475  39.392  1.00 38.56      A
ATOM   2939  CD2  LEU A 384     -23.050  41.081  37.574  1.00 42.81      A
ATOM   2940  C    LEU A 384     -23.122  43.595  41.508  1.00 31.58      A
ATOM   2941  O    LEU A 384     -24.178  44.227  41.546  1.00 30.59      A
ATOM   2942  N    THR A 385     -21.932  44.171  41.611  1.00 30.53      A
ATOM   2943  CA   THR A 385     -21.798  45.609  41.806  1.00 31.56      A
ATOM   2944  CB   THR A 385     -21.489  45.935  43.304  1.00 31.79      A
ATOM   2945  OG1  THR A 385     -21.546  47.352  43.513  1.00 33.73      A
ATOM   2946  CG2  THR A 385     -20.113  45.416  43.700  1.00 30.03      A
ATOM   2947  C    THR A 385     -20.692  46.176  40.904  1.00 32.35      A
ATOM   2948  O    THR A 385     -20.181  45.477  40.031  1.00 32.81      A
ATOM   2949  N    ARG A 386     -20.332  47.440  41.108  1.00 31.89      A
ATOM   2950  CA   ARG A 386     -19.291  48.072  40.302  1.00 31.88      A
ATOM   2951  CB   ARG A 386     -19.724  48.163  38.841  1.00 29.72      A
ATOM   2952  CG   ARG A 386     -20.936  49.063  38.631  1.00 29.70      A
ATOM   2953  CD   ARG A 386     -21.124  49.455  37.185  1.00 28.79      A
ATOM   2954  NE   ARG A 386     -20.330  50.627  36.822  1.00 29.99      A
ATOM   2955  CZ   ARG A 386     -19.998  50.941  35.572  1.00 29.04      A
ATOM   2956  NH1  ARG A 386     -20.390  50.167  34.572  1.00 24.89      A
ATOM   2957  NH2  ARG A 386     -19.275  52.024  35.321  1.00 28.31      A
ATOM   2958  C    ARG A 386     -19.006  49.488  40.778  1.00 33.38      A
ATOM   2959  O    ARG A 386     -19.816  50.089  41.487  1.00 33.64      A
ATOM   2960  N    ASP A 387     -17.847  50.016  40.389  1.00 33.71      A
ATOM   2961  CA   ASP A 387     -17.513  51.387  40.730  1.00 33.83      A
ATOM   2962  CB   ASP A 387     -16.208  51.799  40.061  1.00 33.95      A
ATOM   2963  CG   ASP A 387     -15.882  53.254  40.282  1.00 36.96      A
ATOM   2964  OD1  ASP A 387     -16.668  54.111  39.820  1.00 38.65      A
```

FIGURE 5- 40 -

```
ATOM   2965  OD2 ASP A 387     -14.845  53.543  40.922  1.00 38.35      A
ATOM   2966  C   ASP A 387     -18.686  52.154  40.121  1.00 34.25      A
ATOM   2967  O   ASP A 387     -18.947  52.040  38.922  1.00 34.12      A
ATOM   2968  N   PRO A 388     -19.417  52.927  40.945  1.00 33.68      A
ATOM   2969  CD  PRO A 388     -19.195  53.031  42.398  1.00 33.85      A
ATOM   2970  CA  PRO A 388     -20.584  53.723  40.550  1.00 33.05      A
ATOM   2971  CB  PRO A 388     -21.325  53.889  41.870  1.00 33.38      A
ATOM   2972  CG  PRO A 388     -20.198  54.098  42.818  1.00 33.91      A
ATOM   2973  C   PRO A 388     -20.351  55.069  39.867  1.00 31.92      A
ATOM   2974  O   PRO A 388     -21.305  55.812  39.641  1.00 31.44      A
ATOM   2975  N   THR A 389     -19.104  55.387  39.534  1.00 31.02      A
ATOM   2976  CA  THR A 389     -18.814  56.670  38.901  1.00 29.74      A
ATOM   2977  CB  THR A 389     -17.334  56.838  38.593  1.00 29.35      A
ATOM   2978  OG1 THR A 389     -16.588  56.768  39.812  1.00 30.48      A
ATOM   2979  CG2 THR A 389     -17.097  58.193  37.946  1.00 27.07      A
ATOM   2980  C   THR A 389     -19.575  56.953  37.618  1.00 28.89      A
ATOM   2981  O   THR A 389     -20.292  57.945  37.530  1.00 27.49      A
ATOM   2982  N   THR A 390     -19.414  56.098  36.615  1.00 28.32      A
ATOM   2983  CA  THR A 390     -20.111  56.336  35.366  1.00 28.26      A
ATOM   2984  CB  THR A 390     -19.779  55.268  34.290  1.00 29.31      A
ATOM   2985  OG1 THR A 390     -18.367  55.054  34.242  1.00 28.60      A
ATOM   2986  CG2 THR A 390     -20.217  55.755  32.911  1.00 27.77      A
ATOM   2987  C   THR A 390     -21.608  56.369  35.618  1.00 27.50      A
ATOM   2988  O   THR A 390     -22.274  57.307  35.215  1.00 29.24      A
ATOM   2989  N   PRO A 391     -22.158  55.354  36.301  1.00 28.47      A
ATOM   2990  CD  PRO A 391     -21.561  54.094  36.787  1.00 28.67      A
ATOM   2991  CA  PRO A 391     -23.603  55.371  36.557  1.00 28.87      A
ATOM   2992  CB  PRO A 391     -23.794  54.184  37.497  1.00 27.38      A
ATOM   2993  CG  PRO A 391     -22.778  53.212  36.984  1.00 28.05      A
ATOM   2994  C   PRO A 391     -24.091  56.692  37.166  1.00 29.62      A
ATOM   2995  O   PRO A 391     -25.103  57.257  36.739  1.00 30.44      A
ATOM   2996  N   LEU A 392     -23.356  57.187  38.155  1.00 29.53      A
ATOM   2997  CA  LEU A 392     -23.715  58.428  38.820  1.00 28.80      A
ATOM   2998  CB  LEU A 392     -22.822  58.643  40.045  1.00 26.36      A
ATOM   2999  CG  LEU A 392     -23.064  57.655  41.187  1.00 25.51      A
ATOM   3000  CD1 LEU A 392     -21.964  57.779  42.234  1.00 24.65      A
ATOM   3001  CD2 LEU A 392     -24.438  57.914  41.791  1.00 22.48      A
ATOM   3002  C   LEU A 392     -23.606  59.619  37.881  1.00 29.97      A
ATOM   3003  O   LEU A 392     -24.511  60.449  37.821  1.00 31.30      A
ATOM   3004  N   ALA A 393     -22.501  59.704  37.148  1.00 30.32      A
ATOM   3005  CA  ALA A 393     -22.293  60.809  36.219  1.00 31.10      A
ATOM   3006  CB  ALA A 393     -21.015  60.593  35.444  1.00 30.06      A
ATOM   3007  C   ALA A 393     -23.477  60.924  35.257  1.00 33.13      A
ATOM   3008  O   ALA A 393     -24.018  62.016  35.027  1.00 32.46      A
ATOM   3009  N   ARG A 394     -23.880  59.786  34.701  1.00 32.69      A
ATOM   3010  CA  ARG A 394     -24.990  59.762  33.772  1.00 33.01      A
ATOM   3011  CB  ARG A 394     -25.032  58.407  33.089  1.00 33.19      A
ATOM   3012  CG  ARG A 394     -23.747  58.145  32.357  1.00 32.79      A
ATOM   3013  CD  ARG A 394     -23.724  56.813  31.673  1.00 33.00      A
ATOM   3014  NE  ARG A 394     -22.510  56.702  30.879  1.00 34.51      A
ATOM   3015  CZ  ARG A 394     -22.195  55.647  30.142  1.00 32.84      A
ATOM   3016  NH1 ARG A 394     -23.017  54.603  30.105  1.00 30.06      A
ATOM   3017  NH2 ARG A 394     -21.065  55.645  29.441  1.00 30.68      A
ATOM   3018  C   ARG A 394     -26.309  60.062  34.470  1.00 34.31      A
ATOM   3019  O   ARG A 394     -27.221  60.637  33.874  1.00 34.40      A
ATOM   3020  N   ALA A 395     -26.414  59.678  35.736  1.00 33.56      A
ATOM   3021  CA  ALA A 395     -27.628  59.951  36.479  1.00 33.22      A
ATOM   3022  CB  ALA A 395     -27.522  59.383  37.879  1.00 32.53      A
ATOM   3023  C   ALA A 395     -27.802  61.468  36.524  1.00 34.29      A
ATOM   3024  O   ALA A 395     -28.896  61.987  36.286  1.00 33.65      A
ATOM   3025  N   ALA A 396     -26.713  62.178  36.806  1.00 34.09      A
ATOM   3026  CA  ALA A 396     -26.762  63.634  36.880  1.00 35.61      A
ATOM   3027  CB  ALA A 396     -25.444  64.180  37.381  1.00 34.80      A
ATOM   3028  C   ALA A 396     -27.082  64.227  35.521  1.00 36.88      A
ATOM   3029  O   ALA A 396     -27.990  65.039  35.384  1.00 39.40      A
ATOM   3030  N   TRP A 397     -26.332  63.830  34.508  1.00 37.91      A
ATOM   3031  CA  TRP A 397     -26.584  64.338  33.175  1.00 37.80      A
ATOM   3032  CB  TRP A 397     -25.650  63.661  32.189  1.00 38.44      A
ATOM   3033  CG  TRP A 397     -25.825  64.126  30.801  1.00 39.13      A
ATOM   3034  CD2 TRP A 397     -24.990  65.052  30.112  1.00 39.80      A
ATOM   3035  CE2 TRP A 397     -25.551  65.245  28.830  1.00 41.57      A
ATOM   3036  CE3 TRP A 397     -23.818  65.738  30.452  1.00 37.97      A
ATOM   3037  CD1 TRP A 397     -26.837  63.798  29.938  1.00 39.50      A
ATOM   3038  NE1 TRP A 397     -26.679  64.467  28.751  1.00 40.61      A
ATOM   3039  CZ2 TRP A 397     -24.983  66.106  27.889  1.00 41.31      A
ATOM   3040  CZ3 TRP A 397     -23.256  66.587  29.526  1.00 40.37      A
```

FIGURE 5- 41 -

```
ATOM   3041  CH2  TRP A 397     -23.837  66.764  28.253  1.00 42.15      A
ATOM   3042  C    TRP A 397     -28.038  64.087  32.771  1.00 38.32      A
ATOM   3043  O    TRP A 397     -28.712  64.985  32.283  1.00 38.15      A
ATOM   3044  N    GLU A 398     -28.521  62.866  32.984  1.00 39.39      A
ATOM   3045  CA   GLU A 398     -29.894  62.504  32.628  1.00 40.50      A
ATOM   3046  CB   GLU A 398     -30.083  60.989  32.767  1.00 38.80      A
ATOM   3047  CG   GLU A 398     -29.470  60.216  31.603  1.00 40.99      A
ATOM   3048  CD   GLU A 398     -29.096  58.778  31.944  1.00 42.08      A
ATOM   3049  OE1  GLU A 398     -29.874  58.107  32.654  1.00 43.65      A
ATOM   3050  OE2  GLU A 398     -28.024  58.318  31.484  1.00 42.05      A
ATOM   3051  C    GLU A 398     -30.941  63.254  33.451  1.00 41.28      A
ATOM   3052  O    GLU A 398     -32.131  63.264  33.116  1.00 42.67      A
ATOM   3053  N    THR A 399     -30.486  63.897  34.518  1.00 40.28      A
ATOM   3054  CA   THR A 399     -31.365  64.654  35.384  1.00 40.28      A
ATOM   3055  CB   THR A 399     -30.820  64.697  36.809  1.00 40.23      A
ATOM   3056  OG1  THR A 399     -30.650  63.365  37.295  1.00 40.79      A
ATOM   3057  CG2  THR A 399     -31.772  65.457  37.717  1.00 42.61      A
ATOM   3058  C    THR A 399     -31.769  66.086  34.887  1.00 41.47      A
ATOM   3059  O    THR A 399     -32.523  66.707  34.980  1.00 38.92      A
ATOM   3060  N    ALA A 400     -30.358  66.601  34.365  1.00 44.18      A
ATOM   3061  CA   ALA A 400     -30.289  67.970  33.868  1.00 48.18      A
ATOM   3062  CB   ALA A 400     -28.841  68.449  33.891  1.00 46.30      A
ATOM   3063  C    ALA A 400     -30.869  68.152  32.465  1.00 51.86      A
ATOM   3064  O    ALA A 400     -31.382  69.225  32.137  1.00 52.61      A
ATOM   3065  N    ARG A 401     -30.778  67.108  31.643  1.00 55.65      A
ATOM   3066  CA   ARG A 401     -31.275  67.142  30.269  1.00 59.04      A
ATOM   3067  CB   ARG A 401     -30.108  67.133  29.289  1.00 58.44      A
ATOM   3068  CG   ARG A 401     -29.196  68.324  29.373  1.00 60.98      A
ATOM   3069  CD   ARG A 401     -27.882  67.990  28.688  1.00 65.88      A
ATOM   3070  NE   ARG A 401     -27.006  69.151  28.540  1.00 69.59      A
ATOM   3071  CZ   ARG A 401     -27.258  70.185  27.743  1.00 69.48      A
ATOM   3072  NH1  ARG A 401     -28.368  70.212  27.010  1.00 69.19      A
ATOM   3073  NH2  ARG A 401     -26.397  71.194  27.679  1.00 68.29      A
ATOM   3074  C    ARG A 401     -32.149  65.932  29.971  1.00 61.88      A
ATOM   3075  O    ARG A 401     -31.880  64.829  30.456  1.00 62.58      A
ATOM   3076  N    HIS A 402     -33.197  66.131  29.177  1.00 64.48      A
ATOM   3077  CA   HIS A 402     -34.049  65.010  28.817  1.00 66.12      A
ATOM   3078  CB   HIS A 402     -35.419  65.488  28.328  1.00 69.50      A
ATOM   3079  CG   HIS A 402     -36.508  65.323  29.350  1.00 74.44      A
ATOM   3080  CD2  HIS A 402     -36.609  64.492  30.417  1.00 75.60      A
ATOM   3081  ND1  HIS A 402     -37.668  66.071  29.339  1.00 76.04      A
ATOM   3082  CE1  HIS A 402     -38.434  65.710  30.355  1.00 76.63      A
ATOM   3083  NE2  HIS A 402     -37.814  64.753  31.025  1.00 76.61      A
ATOM   3084  C    HIS A 402     -33.306  64.235  27.743  1.00 64.93      A
ATOM   3085  O    HIS A 402     -32.882  64.790  26.735  1.00 64.74      A
ATOM   3086  N    THR A 403     -33.121  62.949  28.000  1.00 64.33      A
ATOM   3087  CA   THR A 403     -32.400  62.067  27.101  1.00 63.33      A
ATOM   3088  CB   THR A 403     -31.152  61.527  27.809  1.00 63.22      A
ATOM   3089  OG1  THR A 403     -31.456  61.305  29.192  1.00 62.13      A
ATOM   3090  CG2  THR A 403     -30.008  62.522  27.701  1.00 62.82      A
ATOM   3091  C    THR A 403     -33.256  60.898  26.597  1.00 63.04      A
ATOM   3092  O    THR A 403     -34.174  60.436  27.281  1.00 62.43      A
ATOM   3093  N    PRO A 404     -32.955  60.403  25.386  1.00 62.71      A
ATOM   3094  CD   PRO A 404     -31.847  60.858  24.526  1.00 62.94      A
ATOM   3095  CA   PRO A 404     -33.680  59.290  24.759  1.00 61.62      A
ATOM   3096  CB   PRO A 404     -32.915  59.068  23.452  1.00 63.07      A
ATOM   3097  CG   PRO A 404     -32.311  60.422  23.164  1.00 63.22      A
ATOM   3098  C    PRO A 404     -33.707  58.031  25.618  1.00 59.27      A
ATOM   3099  O    PRO A 404     -34.715  57.325  25.677  1.00 60.10      A
ATOM   3100  N    ILE A 405     -32.585  57.750  26.270  1.00 56.75      A
ATOM   3101  CA   ILE A 405     -32.468  56.574  27.122  1.00 53.55      A
ATOM   3102  CB   ILE A 405     -31.359  55.620  26.606  1.00 52.93      A
ATOM   3103  CG2  ILE A 405     -31.197  54.448  27.554  1.00 52.58      A
ATOM   3104  CG1  ILE A 405     -31.708  55.113  25.205  1.00 51.91      A
ATOM   3105  CD1  ILE A 405     -32.945  54.248  25.156  1.00 53.27      A
ATOM   3106  C    ILE A 405     -32.136  56.979  28.554  1.00 51.83      A
ATOM   3107  O    ILE A 405     -31.359  57.913  28.784  1.00 52.93      A
ATOM   3108  N    ASN A 406     -32.730  56.272  29.511  1.00 48.49      A
ATOM   3109  CA   ASN A 406     -32.497  56.537  30.925  1.00 45.10      A
ATOM   3110  CB   ASN A 406     -33.826  56.647  31.665  1.00 44.45      A
ATOM   3111  CG   ASN A 406     -34.630  57.841  31.217  1.00 45.61      A
ATOM   3112  OD1  ASN A 406     -34.235  58.987  31.439  1.00 47.49      A
ATOM   3113  ND2  ASN A 406     -35.759  57.585  30.568  1.00 46.30      A
ATOM   3114  C    ASN A 406     -31.633  55.449  31.555  1.00 43.52      A
ATOM   3115  O    ASN A 406     -32.145  54.458  32.087  1.00 43.27      A
ATOM   3116  N    SER A 407     -30.327  55.639  31.485  1.00 40.65      A
```

FIGURE 5- 42 -

```
ATOM   3117  CA   SER A 407     -29.408  54.673  32.047  1.00 38.74           A
ATOM   3118  CB   SER A 407     -27.976  55.160  31.894  1.00 37.07           A
ATOM   3119  OG   SER A 407     -27.714  56.196  32.824  1.00 41.07           A
ATOM   3120  C    SER A 407     -29.691  54.442  33.526  1.00 39.24           A
ATOM   3121  O    SER A 407     -29.539  53.329  34.021  1.00 40.77           A
ATOM   3122  N    TRP A 408     -30.105  55.480  34.244  1.00 38.19           A
ATOM   3123  CA   TRP A 408     -30.345  55.301  35.669  1.00 37.12           A
ATOM   3124  CB   TRP A 408     -30.793  56.604  36.317  1.00 36.18           A
ATOM   3125  CG   TRP A 408     -32.046  57.158  35.791  1.00 36.23           A
ATOM   3126  CD2  TRP A 408     -33.362  56.915  36.297  1.00 35.82           A
ATOM   3127  CE2  TRP A 408     -34.252  57.705  35.542  1.00 35.89           A
ATOM   3128  CE3  TRP A 408     -33.875  56.103  37.316  1.00 35.45           A
ATOM   3129  CD1  TRP A 408     -32.181  58.053  34.776  1.00 37.15           A
ATOM   3130  NE1  TRP A 408     -33.506  58.394  34.621  1.00 37.72           A
ATOM   3131  CZ2  TRP A 408     -35.626  57.714  35.776  1.00 34.56           A
ATOM   3132  CZ3  TRP A 408     -35.233  56.108  37.548  1.00 35.00           A
ATOM   3133  CH2  TRP A 408     -36.097  56.911  36.779  1.00 35.62           A
ATOM   3134  C    TRP A 408     -31.353  54.211  35.969  1.00 35.99           A
ATOM   3135  O    TRP A 408     -31.145  53.385  36.866  1.00 35.16           A
ATOM   3136  N    LEU A 409     -32.440  54.213  35.207  1.00 35.17           A
ATOM   3137  CA   LEU A 409     -33.502  53.233  35.363  1.00 34.39           A
ATOM   3138  CB   LEU A 409     -34.673  53.591  34.450  1.00 33.91           A
ATOM   3139  CG   LEU A 409     -35.862  52.637  34.456  1.00 33.12           A
ATOM   3140  CD1  LEU A 409     -36.338  52.428  35.881  1.00 32.20           A
ATOM   3141  CD2  LEU A 409     -36.965  53.214  33.575  1.00 31.73           A
ATOM   3142  C    LEU A 409     -32.954  51.860  35.007  1.00 34.62           A
ATOM   3143  O    LEU A 409     -33.307  50.854  35.632  1.00 35.31           A
ATOM   3144  N    GLY A 410     -32.088  51.830  33.994  1.00 33.83           A
ATOM   3145  CA   GLY A 410     -31.470  50.586  33.581  1.00 29.85           A
ATOM   3146  C    GLY A 410     -30.530  50.113  34.675  1.00 30.90           A
ATOM   3147  O    GLY A 410     -30.455  48.907  34.962  1.00 30.42           A
ATOM   3148  N    ASN A 411     -29.818  51.055  35.302  1.00 31.11           A
ATOM   3149  CA   ASN A 411     -28.888  50.706  36.378  1.00 31.68           A
ATOM   3150  CB   ASN A 411     -27.917  51.849  36.668  1.00 29.74           A
ATOM   3151  CG   ASN A 411     -26.725  51.842  35.729  1.00 30.29           A
ATOM   3152  OD1  ASN A 411     -26.197  50.782  35.387  1.00 29.34           A
ATOM   3153  ND2  ASN A 411     -26.288  53.024  35.313  1.00 30.82           A
ATOM   3154  C    ASN A 411     -29.601  50.286  37.657  1.00 33.34           A
ATOM   3155  O    ASN A 411     -29.108  49.417  38.385  1.00 33.17           A
ATOM   3156  N    ILE A 412     -30.755  50.885  37.944  1.00 33.21           A
ATOM   3157  CA   ILE A 412     -31.487  50.475  39.134  1.00 34.05           A
ATOM   3158  CB   ILE A 412     -32.820  51.251  39.308  1.00 33.63           A
ATOM   3159  CG2  ILE A 412     -33.725  50.525  40.296  1.00 30.53           A
ATOM   3160  CG1  ILE A 412     -32.538  52.663  39.812  1.00 34.88           A
ATOM   3161  CD1  ILE A 412     -33.776  53.404  40.270  1.00 38.72           A
ATOM   3162  C    ILE A 412     -31.808  48.992  38.967  1.00 34.58           A
ATOM   3163  O    ILE A 412     -31.513  48.169  39.828  1.00 36.58           A
ATOM   3164  N    ILE A 413     -32.391  48.659  37.827  1.00 34.27           A
ATOM   3165  CA   ILE A 413     -32.771  47.293  37.547  1.00 33.92           A
ATOM   3166  CB   ILE A 413     -33.478  47.219  36.181  1.00 32.77           A
ATOM   3167  CG2  ILE A 413     -33.826  45.782  35.851  1.00 30.54           A
ATOM   3168  CG1  ILE A 413     -34.733  48.095  36.217  1.00 33.06           A
ATOM   3169  CD1  ILE A 413     -35.536  48.094  34.942  1.00 33.52           A
ATOM   3170  C    ILE A 413     -31.612  46.290  37.598  1.00 35.86           A
ATOM   3171  O    ILE A 413     -31.766  45.192  38.148  1.00 35.96           A
ATOM   3172  N    MET A 414     -30.454  46.657  37.051  1.00 35.09           A
ATOM   3173  CA   MET A 414     -29.318  45.733  37.043  1.00 35.58           A
ATOM   3174  CB   MET A 414     -28.381  46.056  35.869  1.00 37.88           A
ATOM   3175  CG   MET A 414     -29.027  45.956  34.485  1.00 39.91           A
ATOM   3176  SD   MET A 414     -29.745  44.323  34.125  1.00 43.28           A
ATOM   3177  CE   MET A 414     -28.279  43.390  33.611  1.00 39.56           A
ATOM   3178  C    MET A 414     -28.518  45.727  38.345  1.00 35.39           A
ATOM   3179  O    MET A 414     -27.812  44.762  38.667  1.00 34.14           A
ATOM   3180  N    TYR A 415     -28.641  46.800  39.112  1.00 35.37           A
ATOM   3181  CA   TYR A 415     -27.897  46.889  40.355  1.00 34.62           A
ATOM   3182  CB   TYR A 415     -26.866  48.002  40.227  1.00 33.86           A
ATOM   3183  CG   TYR A 415     -25.848  47.694  39.159  1.00 34.58           A
ATOM   3184  CD1  TYR A 415     -24.819  46.778  39.397  1.00 36.33           A
ATOM   3185  CE1  TYR A 415     -23.868  46.480  38.413  1.00 34.97           A
ATOM   3186  CD2  TYR A 415     -25.910  48.304  37.905  1.00 33.93           A
ATOM   3187  CE2  TYR A 415     -24.967  48.012  36.912  1.00 32.86           A
ATOM   3188  CZ   TYR A 415     -23.947  47.099  37.175  1.00 34.02           A
ATOM   3189  OH   TYR A 415     -23.001  46.802  36.214  1.00 32.96           A
ATOM   3190  C    TYR A 415     -28.768  47.084  41.582  1.00 32.94           A
ATOM   3191  O    TYR A 415     -28.277  47.461  42.647  1.00 33.72           A
ATOM   3192  N    ALA A 416     -30.055  46.791  41.434  1.00 30.51           A
```

FIGURE 5-43-

```
ATOM   3193  CA   ALA A 416     -30.998  46.927  42.537  1.00 31.51       A
ATOM   3194  CB   ALA A 416     -32.247  46.122  42.245  1.00 31.05       A
ATOM   3195  C    ALA A 416     -30.418  46.515  43.892  1.00 31.38       A
ATOM   3196  O    ALA A 416     -30.773  47.075  44.913  1.00 32.00       A
ATOM   3197  N    PRO A 417     -29.526  45.518  43.916  1.00 32.36       A
ATOM   3198  CD   PRO A 417     -29.349  44.462  42.906  1.00 32.64       A
ATOM   3199  CA   PRO A 417     -28.948  45.094  45.196  1.00 33.19       A
ATOM   3200  CB   PRO A 417     -28.440  43.683  44.899  1.00 32.13       A
ATOM   3201  CG   PRO A 417     -29.277  43.239  43.753  1.00 31.92       A
ATOM   3202  C    PRO A 417     -27.822  45.967  45.735  1.00 33.30       A
ATOM   3203  O    PRO A 417     -27.515  45.919  46.927  1.00 34.32       A
ATOM   3204  N    THR A 418     -27.200  46.761  44.877  1.00 32.01       A
ATOM   3205  CA   THR A 418     -26.084  47.556  45.347  1.00 32.55       A
ATOM   3206  CB   THR A 418     -25.315  48.218  44.200  1.00 32.25       A
ATOM   3207  OG1  THR A 418     -26.178  49.119  43.508  1.00 32.45       A
ATOM   3208  CG2  THR A 418     -24.766  47.169  43.240  1.00 31.35       A
ATOM   3209  C    THR A 418     -26.438  48.625  46.345  1.00 32.93       A
ATOM   3210  O    THR A 418     -27.583  49.039  46.471  1.00 34.12       A
ATOM   3211  N    LEU A 419     -25.408  49.054  47.056  1.00 33.52       A
ATOM   3212  CA   LEU A 419     -25.489  50.081  48.073  1.00 33.12       A
ATOM   3213  CB   LEU A 419     -24.124  50.212  48.719  1.00 34.78       A
ATOM   3214  CG   LEU A 419     -23.998  51.080  49.945  1.00 37.88       A
ATOM   3215  CD1  LEU A 419     -24.760  50.423  51.084  1.00 40.24       A
ATOM   3216  CD2  LEU A 419     -22.533  51.230  50.299  1.00 39.24       A
ATOM   3217  C    LEU A 419     -25.879  51.415  47.447  1.00 33.71       A
ATOM   3218  O    LEU A 419     -26.816  52.083  47.887  1.00 34.96       A
ATOM   3219  N    TRP A 420     -25.154  51.796  46.403  1.00 32.38       A
ATOM   3220  CA   TRP A 420     -25.401  53.059  45.726  1.00 31.85       A
ATOM   3221  CB   TRP A 420     -24.239  53.364  44.782  1.00 29.53       A
ATOM   3222  CG   TRP A 420     -23.848  52.192  43.931  1.00 27.93       A
ATOM   3223  CD2  TRP A 420     -24.196  51.979  42.564  1.00 25.23       A
ATOM   3224  CE2  TRP A 420     -23.645  50.744  42.182  1.00 25.44       A
ATOM   3225  CE3  TRP A 420     -24.925  52.713  41.626  1.00 23.83       A
ATOM   3226  CD1  TRP A 420     -23.119  51.108  44.313  1.00 26.80       A
ATOM   3227  NE1  TRP A 420     -22.991  50.233  43.270  1.00 26.30       A
ATOM   3228  CZ2  TRP A 420     -23.795  50.225  40.897  1.00 26.67       A
ATOM   3229  CZ3  TRP A 420     -25.075  52.202  40.355  1.00 24.56       A
ATOM   3230  CH2  TRP A 420     -24.514  50.968  39.998  1.00 26.24       A
ATOM   3231  C    TRP A 420     -26.726  53.137  44.962  1.00 33.02       A
ATOM   3232  O    TRP A 420     -27.388  54.188  44.949  1.00 35.83       A
ATOM   3233  N    ALA A 421     -27.192  52.041  44.329  1.00 30.87       A
ATOM   3234  CA   ALA A 421     -28.363  52.038  43.566  1.00 30.68       A
ATOM   3235  CB   ALA A 421     -28.487  50.747  42.765  1.00 31.02       A
ATOM   3236  C    ALA A 421     -29.578  52.208  44.465  1.00 31.12       A
ATOM   3237  O    ALA A 421     -30.543  52.872  44.106  1.00 32.44       A
ATOM   3238  N    ARG A 422     -29.540  51.605  45.642  1.00 31.79       A
ATOM   3239  CA   ARG A 422     -30.666  51.720  46.547  1.00 32.11       A
ATOM   3240  CB   ARG A 422     -30.610  50.608  47.593  1.00 31.89       A
ATOM   3241  CG   ARG A 422     -30.603  49.207  47.004  1.00 29.83       A
ATOM   3242  CD   ARG A 422     -30.311  48.159  48.061  1.00 30.30       A
ATOM   3243  NE   ARG A 422     -31.408  47.999  49.018  1.00 32.29       A
ATOM   3244  CZ   ARG A 422     -31.281  47.387  50.192  1.00 31.62       A
ATOM   3245  NH1  ARG A 422     -30.102  46.888  50.541  1.00 31.90       A
ATOM   3246  NH2  ARG A 422     -32.324  47.268  51.014  1.00 30.73       A
ATOM   3247  C    ARG A 422     -30.650  53.080  47.232  1.00 33.79       A
ATOM   3248  O    ARG A 422     -31.614  53.847  47.155  1.00 35.37       A
ATOM   3249  N    MET A 423     -29.538  53.393  47.884  1.00 35.14       A
ATOM   3250  CA   MET A 423     -29.430  54.652  48.611  1.00 34.73       A
ATOM   3251  CB   MET A 423     -28.222  54.608  49.534  1.00 32.70       A
ATOM   3252  CG   MET A 423     -28.338  53.513  50.557  1.00 31.00       A
ATOM   3253  SD   MET A 423     -26.957  53.500  51.677  1.00 34.46       A
ATOM   3254  CE   MET A 423     -27.449  54.798  52.811  1.00 30.99       A
ATOM   3255  C    MET A 423     -29.386  55.913  47.770  1.00 34.24       A
ATOM   3256  O    MET A 423     -29.896  56.946  48.192  1.00 34.29       A
ATOM   3257  N    ILE A 424     -28.798  55.842  46.580  1.00 33.75       A
ATOM   3258  CA   ILE A 424     -28.716  57.040  45.756  1.00 33.33       A
ATOM   3259  CB   ILE A 424     -27.267  57.258  45.255  1.00 31.09       A
ATOM   3260  CG2  ILE A 424     -27.173  58.573  44.499  1.00 26.03       A
ATOM   3261  CG1  ILE A 424     -26.315  57.257  46.465  1.00 31.12       A
ATOM   3262  CD1  ILE A 424     -24.830  57.265  46.156  1.00 28.07       A
ATOM   3263  C    ILE A 424     -29.690  57.086  44.578  1.00 35.12       A
ATOM   3264  O    ILE A 424     -30.618  57.902  44.569  1.00 34.51       A
ATOM   3265  N    LEU A 425     -29.494  56.203  43.600  1.00 35.17       A
ATOM   3266  CA   LEU A 425     -30.345  56.179  42.414  1.00 33.72       A
ATOM   3267  CB   LEU A 425     -29.934  55.020  41.501  1.00 32.85       A
ATOM   3268  CG   LEU A 425     -28.550  55.247  40.867  1.00 32.20       A
```

FIGURE 5- 44 -

```
ATOM   3269  CD1 LEU A 425     -28.203  54.106  39.939  1.00 31.49          A
ATOM   3270  CD2 LEU A 425     -28.549  56.565  40.100  1.00 28.71          A
ATOM   3271  C   LEU A 425     -31.831  56.116  42.732  1.00 34.38          A
ATOM   3272  O   LEU A 425     -32.630  56.852  42.147  1.00 35.33          A
ATOM   3273  N   MET A 426     -32.214  55.250  43.660  1.00 33.77          A
ATOM   3274  CA  MET A 426     -33.618  55.156  44.020  1.00 34.14          A
ATOM   3275  CB  MET A 426     -33.854  53.932  44.916  1.00 31.68          A
ATOM   3276  CG  MET A 426     -33.713  52.614  44.165  1.00 32.47          A
ATOM   3277  SD  MET A 426     -34.288  51.145  45.067  1.00 35.96          A
ATOM   3278  CE  MET A 426     -33.136  49.887  44.532  1.00 31.57          A
ATOM   3279  C   MET A 426     -34.128  56.447  44.688  1.00 34.84          A
ATOM   3280  O   MET A 426     -35.027  57.106  44.162  1.00 35.46          A
ATOM   3281  N   THR A 427     -33.549  56.822  45.825  1.00 35.85          A
ATOM   3282  CA  THR A 427     -33.982  58.031  46.531  1.00 35.73          A
ATOM   3283  CB  THR A 427     -32.964  58.461  47.596  1.00 33.68          A
ATOM   3284  OG1 THR A 427     -32.613  57.342  48.413  1.00 33.84          A
ATOM   3285  CG2 THR A 427     -33.554  59.547  48.462  1.00 31.51          A
ATOM   3286  C   THR A 427     -34.165  59.213  45.581  1.00 37.84          A
ATOM   3287  O   THR A 427     -35.275  59.702  45.360  1.00 38.09          A
ATOM   3288  N   HIS A 428     -33.047  59.659  45.025  1.00 38.67          A
ATOM   3289  CA  HIS A 428     -33.001  60.782  44.109  1.00 39.67          A
ATOM   3290  CB  HIS A 428     -31.657  60.775  43.390  1.00 40.74          A
ATOM   3291  CG  HIS A 428     -31.519  61.858  42.377  1.00 41.37          A
ATOM   3292  CD2 HIS A 428     -31.422  61.810  41.028  1.00 42.90          A
ATOM   3293  ND1 HIS A 428     -31.519  63.192  42.718  1.00 43.20          A
ATOM   3294  CE1 HIS A 428     -31.429  63.922  41.620  1.00 45.77          A
ATOM   3295  NE2 HIS A 428     -31.368  63.108  40.581  1.00 45.16          A
ATOM   3296  C   HIS A 428     -34.117  60.840  43.069  1.00 40.66          A
ATOM   3297  O   HIS A 428     -34.907  61.793  43.032  1.00 40.76          A
ATOM   3298  N   PHE A 429     -34.165  59.823  42.217  1.00 40.41          A
ATOM   3299  CA  PHE A 429     -35.153  59.768  41.155  1.00 40.83          A
ATOM   3300  CB  PHE A 429     -34.801  58.645  40.174  1.00 39.95          A
ATOM   3301  CG  PHE A 429     -33.611  58.968  39.321  1.00 39.24          A
ATOM   3302  CD1 PHE A 429     -33.696  59.955  38.340  1.00 38.77          A
ATOM   3303  CD2 PHE A 429     -32.379  58.361  39.554  1.00 38.62          A
ATOM   3304  CE1 PHE A 429     -32.565  60.346  37.613  1.00 38.00          A
ATOM   3305  CE2 PHE A 429     -31.244  58.748  38.834  1.00 38.57          A
ATOM   3306  CZ  PHE A 429     -31.339  59.740  37.862  1.00 37.96          A
ATOM   3307  C   PHE A 429     -36.589  59.649  41.625  1.00 41.59          A
ATOM   3308  O   PHE A 429     -37.474  60.287  41.056  1.00 42.05          A
ATOM   3309  N   PHE A 430     -36.849  58.844  42.648  1.00 41.37          A
ATOM   3310  CA  PHE A 430     -38.222  58.766  43.106  1.00 42.65          A
ATOM   3311  CB  PHE A 430     -38.407  57.645  44.116  1.00 41.63          A
ATOM   3312  CG  PHE A 430     -38.770  56.344  43.479  1.00 40.64          A
ATOM   3313  CD1 PHE A 430     -37.799  55.563  42.860  1.00 39.52          A
ATOM   3314  CD2 PHE A 430     -40.095  55.926  43.437  1.00 39.01          A
ATOM   3315  CE1 PHE A 430     -38.143  54.385  42.204  1.00 39.03          A
ATOM   3316  CE2 PHE A 430     -40.449  54.752  42.785  1.00 38.71          A
ATOM   3317  CZ  PHE A 430     -39.469  53.980  42.168  1.00 39.82          A
ATOM   3318  C   PHE A 430     -38.591  60.112  43.695  1.00 44.31          A
ATOM   3319  O   PHE A 430     -39.721  60.575  43.557  1.00 45.45          A
ATOM   3320  N   SER A 431     -37.617  60.755  44.325  1.00 45.36          A
ATOM   3321  CA  SER A 431     -37.830  62.075  44.901  1.00 46.07          A
ATOM   3322  CB  SER A 431     -36.527  62.591  45.521  1.00 46.22          A
ATOM   3323  OG  SER A 431     -36.531  64.004  45.637  1.00 48.93          A
ATOM   3324  C   SER A 431     -38.300  63.023  43.797  1.00 45.79          A
ATOM   3325  O   SER A 431     -39.271  63.759  43.967  1.00 44.68          A
ATOM   3326  N   ILE A 432     -37.610  62.995  42.663  1.00 45.88          A
ATOM   3327  CA  ILE A 432     -37.963  63.857  41.539  1.00 46.55          A
ATOM   3328  CB  ILE A 432     -36.808  63.938  40.503  1.00 45.09          A
ATOM   3329  CG2 ILE A 432     -37.307  64.554  39.203  1.00 44.51          A
ATOM   3330  CG1 ILE A 432     -35.658  64.763  41.071  1.00 43.30          A
ATOM   3331  CD1 ILE A 432     -34.484  64.881  40.140  1.00 43.75          A
ATOM   3332  C   ILE A 432     -39.246  63.434  40.810  1.00 47.51          A
ATOM   3333  O   ILE A 432     -39.988  64.287  40.319  1.00 47.38          A
ATOM   3334  N   LEU A 433     -39.514  62.133  40.730  1.00 47.52          A
ATOM   3335  CA  LEU A 433     -40.721  61.691  40.042  1.00 49.07          A
ATOM   3336  CB  LEU A 433     -40.700  60.178  39.790  1.00 47.40          A
ATOM   3337  CG  LEU A 433     -39.689  59.719  38.731  1.00 47.23          A
ATOM   3338  CD1 LEU A 433     -39.842  58.229  38.474  1.00 45.04          A
ATOM   3339  CD2 LEU A 433     -39.899  60.496  37.445  1.00 45.30          A
ATOM   3340  C   LEU A 433     -41.964  62.081  40.828  1.00 50.65          A
ATOM   3341  O   LEU A 433     -43.046  62.228  40.258  1.00 50.72          A
ATOM   3342  N   LEU A 434     -41.812  62.249  42.138  1.00 51.84          A
ATOM   3343  CA  LEU A 434     -42.936  62.652  42.975  1.00 52.72          A
ATOM   3344  CB  LEU A 434     -42.603  62.459  44.455  1.00 52.80          A
```

FIGURE 5- 45 -

```
ATOM   3345  CG   LEU A 434     -42.725  61.026  44.958  1.00 52.14      A
ATOM   3346  CD1  LEU A 434     -42.154  60.889  46.361  1.00 51.31      A
ATOM   3347  CD2  LEU A 434     -44.190  60.640  44.922  1.00 52.74      A
ATOM   3348  C    LEU A 434     -43.219  64.121  42.712  1.00 53.16      A
ATOM   3349  O    LEU A 434     -44.329  64.503  42.348  1.00 53.64      A
ATOM   3350  N    ALA A 435     -42.190  64.937  42.884  1.00 53.13      A
ATOM   3351  CA   ALA A 435     -42.299  66.371  42.685  1.00 54.95      A
ATOM   3352  CB   ALA A 435     -40.933  67.012  42.875  1.00 53.63      A
ATOM   3353  C    ALA A 435     -42.867  66.752  41.319  1.00 56.79      A
ATOM   3354  O    ALA A 435     -43.408  67.844  41.145  1.00 58.30      A
ATOM   3355  N    GLN A 436     -42.744  65.857  40.350  1.00 57.72      A
ATOM   3356  CA   GLN A 436     -43.234  66.139  39.011  1.00 58.86      A
ATOM   3357  CB   GLN A 436     -42.085  66.002  38.014  1.00 60.51      A
ATOM   3358  CG   GLN A 436     -40.790  66.624  38.523  1.00 63.62      A
ATOM   3359  CD   GLN A 436     -39.617  66.424  37.583  1.00 64.91      A
ATOM   3360  OE1  GLN A 436     -39.376  65.318  37.094  1.00 65.35      A
ATOM   3361  NE2  GLN A 436     -38.870  67.496  37.337  1.00 64.77      A
ATOM   3362  C    GLN A 436     -44.354  65.178  38.664  1.00 59.46      A
ATOM   3363  O    GLN A 436     -44.789  65.104  37.517  1.00 59.97      A
ATOM   3364  N    GLU A 437     -44.818  64.447  39.672  1.00 60.44      A
ATOM   3365  CA   GLU A 437     -45.890  63.473  39.503  1.00 62.28      A
ATOM   3366  CB   GLU A 437     -47.246  64.165  39.613  1.00 64.24      A
ATOM   3367  CG   GLU A 437     -47.683  64.413  41.041  1.00 67.80      A
ATOM   3368  CD   GLU A 437     -48.729  65.502  41.144  1.00 70.76      A
ATOM   3369  OE1  GLU A 437     -49.261  65.703  42.258  1.00 72.23      A
ATOM   3370  OE2  GLU A 437     -49.010  66.160  40.116  1.00 71.58      A
ATOM   3371  C    GLU A 437     -45.799  62.709  38.192  1.00 61.81      A
ATOM   3372  O    GLU A 437     -46.697  62.766  37.357  1.00 61.90      A
ATOM   3373  N    GLN A 438     -44.700  61.991  38.015  1.00 61.63      A
ATOM   3374  CA   GLN A 438     -44.510  61.210  36.810  1.00 60.81      A
ATOM   3375  CB   GLN A 438     -43.412  61.831  35.951  1.00 61.31      A
ATOM   3376  CG   GLN A 438     -43.772  63.211  35.432  1.00 62.98      A
ATOM   3377  CD   GLN A 438     -42.683  63.815  34.569  1.00 65.68      A
ATOM   3378  OE1  GLN A 438     -41.511  63.875  34.967  1.00 67.45      A
ATOM   3379  NE2  GLN A 438     -43.061  64.276  33.383  1.00 65.69      A
ATOM   3380  C    GLN A 438     -44.184  59.764  37.156  1.00 60.00      A
ATOM   3381  O    GLN A 438     -43.652  59.026  36.332  1.00 60.34      A
ATOM   3382  N    LEU A 439     -44.520  59.365  38.380  1.00 59.28      A
ATOM   3383  CA   LEU A 439     -44.288  58.000  38.836  1.00 59.60      A
ATOM   3384  CB   LEU A 439     -44.833  57.800  40.254  1.00 58.21      A
ATOM   3385  CG   LEU A 439     -44.065  58.434  41.417  1.00 59.17      A
ATOM   3386  CD1  LEU A 439     -44.721  58.060  42.738  1.00 57.80      A
ATOM   3387  CD2  LEU A 439     -42.623  57.957  41.396  1.00 57.93      A
ATOM   3388  C    LEU A 439     -44.959  56.991  37.912  1.00 61.18      A
ATOM   3389  O    LEU A 439     -44.654  55.795  37.954  1.00 61.70      A
ATOM   3390  N    GLU A 440     -45.874  57.472  37.074  1.00 62.62      A
ATOM   3391  CA   GLU A 440     -46.593  56.591  36.164  1.00 63.69      A
ATOM   3392  CB   GLU A 440     -48.099  56.820  36.286  1.00 67.51      A
ATOM   3393  CG   GLU A 440     -48.654  56.346  37.614  1.00 73.49      A
ATOM   3394  CD   GLU A 440     -50.098  56.741  37.832  1.00 76.89      A
ATOM   3395  OE1  GLU A 440     -50.389  57.955  37.761  1.00 78.41      A
ATOM   3396  OE2  GLU A 440     -50.933  55.839  38.083  1.00 78.49      A
ATOM   3397  C    GLU A 440     -46.167  56.765  34.731  1.00 61.25      A
ATOM   3398  O    GLU A 440     -46.580  56.002  33.865  1.00 60.59      A
ATOM   3399  N    LYS A 441     -45.349  57.775  34.480  1.00 59.67      A
ATOM   3400  CA   LYS A 441     -44.871  58.010  33.134  1.00 59.39      A
ATOM   3401  CB   LYS A 441     -44.280  59.411  33.020  1.00 59.81      A
ATOM   3402  CG   LYS A 441     -43.824  59.773  31.619  1.00 61.59      A
ATOM   3403  CD   LYS A 441     -43.166  61.145  31.585  1.00 63.22      A
ATOM   3404  CE   LYS A 441     -42.705  61.491  30.176  1.00 65.73      A
ATOM   3405  NZ   LYS A 441     -41.973  62.794  30.103  1.00 69.04      A
ATOM   3406  C    LYS A 441     -43.807  56.961  32.814  1.00 59.60      A
ATOM   3407  O    LYS A 441     -42.781  56.866  33.493  1.00 60.73      A
ATOM   3408  N    ALA A 442     -44.065  56.159  31.788  1.00 58.01      A
ATOM   3409  CA   ALA A 442     -43.123  55.131  31.387  1.00 56.63      A
ATOM   3410  CB   ALA A 442     -43.779  54.193  30.389  1.00 55.30      A
ATOM   3411  C    ALA A 442     -41.886  55.785  30.769  1.00 56.28      A
ATOM   3412  O    ALA A 442     -41.991  56.778  30.047  1.00 55.70      A
ATOM   3413  N    LEU A 443     -40.716  55.224  31.060  1.00 55.21      A
ATOM   3414  CA   LEU A 443     -39.458  55.741  30.533  1.00 53.88      A
ATOM   3415  CB   LEU A 443     -38.605  56.262  31.687  1.00 54.44      A
ATOM   3416  CG   LEU A 443     -39.268  57.357  32.527  1.00 55.68      A
ATOM   3417  CD1  LEU A 443     -38.563  57.469  33.864  1.00 56.71      A
ATOM   3418  CD2  LEU A 443     -39.230  58.685  31.779  1.00 54.46      A
ATOM   3419  C    LEU A 443     -38.709  54.633  29.789  1.00 52.81      A
ATOM   3420  O    LEU A 443     -38.854  53.459  30.116  1.00 52.52      A
```

FIGURE 5-46-

```
ATOM   3421  N    ASP A 444     -37.918  54.996  28.786  1.00 51.92      A
ATOM   3422  CA   ASP A 444     -37.159  53.997  28.041  1.00 51.32      A
ATOM   3423  CB   ASP A 444     -36.930  54.426  26.583  1.00 53.22      A
ATOM   3424  CG   ASP A 444     -38.219  54.617  25.800  1.00 56.32      A
ATOM   3425  OD1  ASP A 444     -39.166  53.815  25.930  1.00 57.79      A
ATOM   3426  OD2  ASP A 444     -38.271  55.566  24.980  1.00 56.18      A
ATOM   3427  C    ASP A 444     -35.787  53.782  28.669  1.00 49.93      A
ATOM   3428  O    ASP A 444     -35.032  54.727  28.868  1.00 49.91      A
ATOM   3429  N    CYS A 445     -35.461  52.543  28.988  1.00 48.09      A
ATOM   3430  CA   CYS A 445     -34.139  52.254  29.525  1.00 47.44      A
ATOM   3431  CB   CYS A 445     -34.217  51.783  30.974  1.00 47.79      A
ATOM   3432  SG   CYS A 445     -34.918  50.146  31.154  1.00 46.33      A
ATOM   3433  C    CYS A 445     -33.588  51.138  28.639  1.00 47.68      A
ATOM   3434  O    CYS A 445     -34.290  50.629  27.765  1.00 45.24      A
ATOM   3435  N    GLN A 446     -32.342  50.746  28.858  1.00 47.76      A
ATOM   3436  CA   GLN A 446     -31.768  49.708  28.030  1.00 48.22      A
ATOM   3437  CB   GLN A 446     -30.712  50.320  27.111  1.00 49.73      A
ATOM   3438  CG   GLN A 446     -30.942  50.005  25.645  1.00 55.11      A
ATOM   3439  CD   GLN A 446     -30.007  50.772  24.727  1.00 57.77      A
ATOM   3440  OE1  GLN A 446     -28.782  50.669  24.847  1.00 57.52      A
ATOM   3441  NE2  GLN A 446     -30.582  51.546  23.801  1.00 56.53      A
ATOM   3442  C    GLN A 446     -31.170  48.540  28.801  1.00 47.60      A
ATOM   3443  O    GLN A 446     -30.463  48.727  29.790  1.00 47.53      A
ATOM   3444  N    ILE A 447     -31.464  47.332  28.331  1.00 46.52      A
ATOM   3445  CA   ILE A 447     -30.953  46.112  28.935  1.00 45.69      A
ATOM   3446  CB   ILE A 447     -32.076  45.315  29.597  1.00 46.02      A
ATOM   3447  CG2  ILE A 447     -31.512  44.043  30.233  1.00 45.53      A
ATOM   3448  CG1  ILE A 447     -32.764  46.193  30.641  1.00 44.97      A
ATOM   3449  CD1  ILE A 447     -33.914  45.526  31.322  1.00 46.83      A
ATOM   3450  C    ILE A 447     -30.297  45.260  27.852  1.00 46.02      A
ATOM   3451  O    ILE A 447     -30.958  44.802  26.920  1.00 45.10      A
ATOM   3452  N    TYR A 448     -28.989  45.057  27.930  1.00 47.04      A
ATOM   3453  CA   TYR A 448     -28.223  44.277  27.012  1.00 46.50      A
ATOM   3454  CB   TYR A 448     -28.532  42.793  27.130  1.00 47.03      A
ATOM   3455  CG   TYR A 448     -28.059  42.161  28.406  1.00 47.89      A
ATOM   3456  CD1  TYR A 448     -26.901  42.604  29.042  1.00 47.05      A
ATOM   3457  CE1  TYR A 448     -26.428  41.970  30.194  1.00 49.29      A
ATOM   3458  CD2  TYR A 448     -28.738  41.071  28.949  1.00 49.35      A
ATOM   3459  CE2  TYR A 448     -28.276  40.431  30.090  1.00 50.77      A
ATOM   3460  CZ   TYR A 448     -27.122  40.882  30.707  1.00 50.59      A
ATOM   3461  OH   TYR A 448     -26.665  40.224  31.825  1.00 53.95      A
ATOM   3462  C    TYR A 448     -28.513  44.721  25.593  1.00 46.48      A
ATOM   3463  O    TYR A 448     -28.866  43.910  24.731  1.00 44.69      A
ATOM   3464  N    GLY A 449     -28.372  46.021  25.367  1.00 47.02      A
ATOM   3465  CA   GLY A 449     -28.596  46.573  24.049  1.00 47.72      A
ATOM   3466  C    GLY A 449     -30.039  46.798  23.658  1.00 47.95      A
ATOM   3467  O    GLY A 449     -30.318  47.696  22.861  1.00 49.90      A
ATOM   3468  N    ALA A 450     -30.957  46.000  24.199  1.00 46.58      A
ATOM   3469  CA   ALA A 450     -32.365  46.152  23.855  1.00 46.74      A
ATOM   3470  CB   ALA A 450     -33.101  44.849  24.107  1.00 47.70      A
ATOM   3471  C    ALA A 450     -33.045  47.305  24.607  1.00 47.70      A
ATOM   3472  O    ALA A 450     -32.773  47.551  25.781  1.00 46.18      A
ATOM   3473  N    CYS A 451     -33.936  48.007  23.913  1.00 47.98      A
ATOM   3474  CA   CYS A 451     -34.647  49.129  24.501  1.00 48.99      A
ATOM   3475  CB   CYS A 451     -34.868  50.213  23.449  1.00 48.93      A
ATOM   3476  SG   CYS A 451     -35.585  51.735  24.106  1.00 51.24      A
ATOM   3477  C    CYS A 451     -35.987  48.691  25.081  1.00 49.92      A
ATOM   3478  O    CYS A 451     -36.813  48.121  24.375  1.00 50.39      A
ATOM   3479  N    TYR A 452     -36.186  48.972  26.370  1.00 51.63      A
ATOM   3480  CA   TYR A 452     -37.407  48.623  27.104  1.00 52.23      A
ATOM   3481  CB   TYR A 452     -37.063  47.707  28.296  1.00 52.58      A
ATOM   3482  CG   TYR A 452     -36.664  46.300  27.916  1.00 54.64      A
ATOM   3483  CD1  TYR A 452     -37.627  45.321  27.687  1.00 56.67      A
ATOM   3484  CE1  TYR A 452     -37.270  44.031  27.315  1.00 58.38      A
ATOM   3485  CD2  TYR A 452     -35.323  45.952  27.767  1.00 56.49      A
ATOM   3486  CE2  TYR A 452     -34.953  44.668  27.394  1.00 58.58      A
ATOM   3487  CZ   TYR A 452     -35.932  43.712  27.168  1.00 59.86      A
ATOM   3488  OH   TYR A 452     -35.574  42.441  26.783  1.00 61.89      A
ATOM   3489  C    TYR A 452     -38.133  49.858  27.655  1.00 52.86      A
ATOM   3490  O    TYR A 452     -37.502  50.792  28.159  1.00 52.89      A
ATOM   3491  N    SER A 453     -39.460  49.852  27.560  1.00 53.30      A
ATOM   3492  CA   SER A 453     -40.279  50.944  28.082  1.00 53.28      A
ATOM   3493  CB   SER A 453     -41.445  51.241  27.147  1.00 52.60      A
ATOM   3494  OG   SER A 453     -42.228  52.295  27.670  1.00 54.38      A
ATOM   3495  C    SER A 453     -40.808  50.473  29.430  1.00 53.63      A
ATOM   3496  O    SER A 453     -41.516  49.472  29.502  1.00 54.21      A
```

FIGURE 5- 47 -

```
ATOM   3497  N    ILE A 454     -40.478  51.197  30.495  1.00 53.99       A
ATOM   3498  CA   ILE A 454     -40.882  50.787  31.834  1.00 53.53       A
ATOM   3499  CB   ILE A 454     -39.685  50.153  32.558  1.00 52.47       A
ATOM   3500  CG2  ILE A 454     -40.072  49.742  33.960  1.00 52.21       A
ATOM   3501  CG1  ILE A 454     -39.173  48.970  31.740  1.00 52.26       A
ATOM   3502  CD1  ILE A 454     -38.004  48.249  32.358  1.00 53.39       A
ATOM   3503  C    ILE A 454     -41.446  51.876  32.736  1.00 54.31       A
ATOM   3504  O    ILE A 454     -40.983  53.020  32.732  1.00 53.91       A
ATOM   3505  N    GLU A 455     -42.452  51.506  33.518  1.00 54.69       A
ATOM   3506  CA   GLU A 455     -43.040  52.443  34.458  1.00 56.32       A
ATOM   3507  CB   GLU A 455     -44.522  52.160  34.687  1.00 59.31       A
ATOM   3508  CG   GLU A 455     -45.435  52.370  33.507  1.00 61.94       A
ATOM   3509  CD   GLU A 455     -46.871  52.060  33.880  1.00 65.41       A
ATOM   3510  OE1  GLU A 455     -47.473  52.857  34.635  1.00 67.70       A
ATOM   3511  OE2  GLU A 455     -47.391  51.010  33.438  1.00 66.51       A
ATOM   3512  C    GLU A 455     -42.304  52.244  35.778  1.00 55.15       A
ATOM   3513  O    GLU A 455     -42.195  51.122  36.280  1.00 54.26       A
ATOM   3514  N    PRO A 456     -41.791  53.335  36.356  1.00 53.46       A
ATOM   3515  CD   PRO A 456     -41.820  54.697  35.801  1.00 53.29       A
ATOM   3516  CA   PRO A 456     -41.060  53.305  37.622  1.00 52.48       A
ATOM   3517  CB   PRO A 456     -40.886  54.779  37.939  1.00 52.75       A
ATOM   3518  CG   PRO A 456     -40.721  55.372  36.575  1.00 53.14       A
ATOM   3519  C    PRO A 456     -41.820  52.569  38.712  1.00 51.65       A
ATOM   3520  O    PRO A 456     -41.231  51.889  39.548  1.00 51.70       A
ATOM   3521  N    LEU A 457     -43.136  52.704  38.700  1.00 51.18       A
ATOM   3522  CA   LEU A 457     -43.953  52.046  39.701  1.00 51.02       A
ATOM   3523  CB   LEU A 457     -45.406  52.492  39.554  1.00 52.65       A
ATOM   3524  CG   LEU A 457     -45.659  53.951  39.940  1.00 53.07       A
ATOM   3525  CD1  LEU A 457     -47.060  54.353  39.555  1.00 52.55       A
ATOM   3526  CD2  LEU A 457     -45.446  54.125  41.435  1.00 53.24       A
ATOM   3527  C    LEU A 457     -43.857  50.523  39.652  1.00 50.33       A
ATOM   3528  O    LEU A 457     -44.191  49.852  40.625  1.00 50.63       A
ATOM   3529  N    ASP A 458     -43.394  49.972  38.534  1.00 49.05       A
ATOM   3530  CA   ASP A 458     -43.271  48.521  38.424  1.00 48.16       A
ATOM   3531  CB   ASP A 458     -43.357  48.074  36.961  1.00 52.10       A
ATOM   3532  CG   ASP A 458     -44.783  48.033  36.437  1.00 54.68       A
ATOM   3533  OD1  ASP A 458     -45.664  47.484  37.140  1.00 55.49       A
ATOM   3534  OD2  ASP A 458     -45.016  48.538  35.316  1.00 57.43       A
ATOM   3535  C    ASP A 458     -41.970  47.992  39.007  1.00 45.34       A
ATOM   3536  O    ASP A 458     -41.829  46.795  39.252  1.00 45.41       A
ATOM   3537  N    LEU A 459     -41.025  48.891  39.236  1.00 43.26       A
ATOM   3538  CA   LEU A 459     -39.721  48.514  39.751  1.00 41.66       A
ATOM   3539  CB   LEU A 459     -38.968  49.756  40.215  1.00 39.91       A
ATOM   3540  CG   LEU A 459     -38.416  50.569  39.034  1.00 40.11       A
ATOM   3541  CD1  LEU A 459     -37.861  51.898  39.517  1.00 38.06       A
ATOM   3542  CD2  LEU A 459     -37.331  49.753  38.316  1.00 40.08       A
ATOM   3543  C    LEU A 459     -39.696  47.450  40.829  1.00 42.28       A
ATOM   3544  O    LEU A 459     -38.868  46.546  40.774  1.00 43.94       A
ATOM   3545  N    PRO A 460     -40.605  47.523  41.813  1.00 42.37       A
ATOM   3546  CD   PRO A 460     -41.595  48.580  42.076  1.00 42.84       A
ATOM   3547  CA   PRO A 460     -40.628  46.524  42.886  1.00 41.65       A
ATOM   3548  CB   PRO A 460     -41.772  47.004  43.773  1.00 42.17       A
ATOM   3549  CG   PRO A 460     -41.764  48.479  43.570  1.00 41.05       A
ATOM   3550  C    PRO A 460     -40.838  45.090  42.396  1.00 42.01       A
ATOM   3551  O    PRO A 460     -40.150  44.168  42.842  1.00 39.96       A
ATOM   3552  N    GLN A 461     -41.793  44.903  41.488  1.00 42.88       A
ATOM   3553  CA   GLN A 461     -42.067  43.577  40.949  1.00 45.00       A
ATOM   3554  CB   GLN A 461     -43.273  43.590  40.007  1.00 48.75       A
ATOM   3555  CG   GLN A 461     -44.596  44.017  40.620  1.00 52.27       A
ATOM   3556  CD   GLN A 461     -44.760  45.517  40.648  1.00 54.04       A
ATOM   3557  OE1  GLN A 461     -44.133  46.210  41.451  1.00 55.23       A
ATOM   3558  NE2  GLN A 461     -45.601  46.034  39.756  1.00 54.74       A
ATOM   3559  C    GLN A 461     -40.854  43.138  40.153  1.00 45.04       A
ATOM   3560  O    GLN A 461     -40.313  42.046  40.350  1.00 45.31       A
ATOM   3561  N    ILE A 462     -40.435  44.004  39.239  1.00 43.79       A
ATOM   3562  CA   ILE A 462     -39.286  43.716  38.404  1.00 42.84       A
ATOM   3563  CB   ILE A 462     -38.873  44.953  37.597  1.00 41.32       A
ATOM   3564  CG2  ILE A 462     -37.590  44.668  36.841  1.00 42.50       A
ATOM   3565  CG1  ILE A 462     -39.998  45.332  36.630  1.00 40.35       A
ATOM   3566  CD1  ILE A 462     -39.761  46.616  35.852  1.00 39.48       A
ATOM   3567  C    ILE A 462     -38.117  43.258  39.258  1.00 42.76       A
ATOM   3568  O    ILE A 462     -37.609  42.151  39.091  1.00 43.61       A
ATOM   3569  N    ILE A 463     -37.706  44.110  40.188  1.00 42.32       A
ATOM   3570  CA   ILE A 463     -36.589  43.794  41.057  1.00 42.88       A
ATOM   3571  CB   ILE A 463     -36.338  44.935  42.078  1.00 41.90       A
ATOM   3572  CG2  ILE A 463     -35.312  44.504  43.130  1.00 39.33       A
```

FIGURE 5- 48 -

```
ATOM   3573  CG1 ILE A 463     -35.868  46.186  41.328  1.00 37.72           A
ATOM   3574  CD1 ILE A 463     -35.482  47.326  42.213  1.00 37.01           A
ATOM   3575  C   ILE A 463     -36.751  42.465  41.786  1.00 45.18           A
ATOM   3576  O   ILE A 463     -35.811  41.669  41.834  1.00 45.32           A
ATOM   3577  N   GLU A 464     -37.928  42.203  42.347  1.00 47.21           A
ATOM   3578  CA  GLU A 464     -38.115  40.936  43.057  1.00 48.79           A
ATOM   3579  CB  GLU A 464     -39.506  40.843  43.688  1.00 50.36           A
ATOM   3580  CG  GLU A 464     -39.865  39.414  44.094  1.00 52.24           A
ATOM   3581  CD  GLU A 464     -41.150  39.321  44.879  1.00 54.27           A
ATOM   3582  OE1 GLU A 464     -42.132  39.993  44.496  1.00 56.53           A
ATOM   3583  OE2 GLU A 464     -41.182  38.564  45.872  1.00 54.29           A
ATOM   3584  C   GLU A 464     -37.914  39.734  42.143  1.00 48.44           A
ATOM   3585  O   GLU A 464     -37.220  38.775  42.506  1.00 46.63           A
ATOM   3586  N   ARG A 465     -38.533  39.789  40.967  1.00 47.67           A
ATOM   3587  CA  ARG A 465     -38.429  38.708  39.998  1.00 48.78           A
ATOM   3588  CB  ARG A 465     -39.350  38.975  38.797  1.00 49.69           A
ATOM   3589  CG  ARG A 465     -40.818  38.598  39.019  1.00 52.31           A
ATOM   3590  CD  ARG A 465     -41.038  37.077  38.994  1.00 53.70           A
ATOM   3591  NE  ARG A 465     -40.775  36.500  37.671  1.00 54.48           A
ATOM   3592  CZ  ARG A 465     -41.486  36.573  36.573  1.00 52.91           A
ATOM   3593  NH1 ARG A 465     -42.524  37.590  36.617  1.00 51.12           A
ATOM   3594  NH2 ARG A 465     -41.140  36.212  35.418  1.00 52.35           A
ATOM   3595  C   ARG A 465     -36.996  38.478  39.507  1.00 48.80           A
ATOM   3596  O   ARG A 465     -36.567  37.334  39.357  1.00 49.38           A
ATOM   3597  N   LEU A 466     -36.249  39.553  39.274  1.00 46.99           A
ATOM   3598  CA  LEU A 466     -34.889  39.410  38.777  1.00 45.58           A
ATOM   3599  CB  LEU A 466     -34.516  40.645  37.958  1.00 46.51           A
ATOM   3600  CG  LEU A 466     -35.469  41.051  36.828  1.00 46.75           A
ATOM   3601  CD1 LEU A 466     -34.978  42.316  36.141  1.00 42.05           A
ATOM   3602  CD2 LEU A 466     -35.575  39.912  35.834  1.00 46.90           A
ATOM   3603  C   LEU A 466     -33.809  39.170  39.835  1.00 45.68           A
ATOM   3604  O   LEU A 466     -32.758  38.613  39.527  1.00 47.29           A
ATOM   3605  N   HIS A 467     -34.058  39.574  41.076  1.00 44.45           A
ATOM   3606  CA  HIS A 467     -33.054  39.428  42.130  1.00 42.99           A
ATOM   3607  CB  HIS A 467     -32.601  40.808  42.606  1.00 40.37           A
ATOM   3608  CG  HIS A 467     -32.012  41.673  41.534  1.00 38.35           A
ATOM   3609  CD2 HIS A 467     -32.515  42.749  40.880  1.00 37.16           A
ATOM   3610  ND1 HIS A 467     -30.729  41.507  41.062  1.00 37.59           A
ATOM   3611  CE1 HIS A 467     -30.465  42.445  40.169  1.00 37.31           A
ATOM   3612  NE2 HIS A 467     -31.533  43.213  40.041  1.00 35.59           A
ATOM   3613  C   HIS A 467     -33.512  38.649  43.359  1.00 44.23           A
ATOM   3614  O   HIS A 467     -32.704  38.011  44.030  1.00 43.63           A
ATOM   3615  N   GLY A 468     -34.805  38.715  43.661  1.00 45.84           A
ATOM   3616  CA  GLY A 468     -35.322  38.036  44.837  1.00 46.84           A
ATOM   3617  C   GLY A 468     -35.628  39.089  45.885  1.00 47.58           A
ATOM   3618  O   GLY A 468     -35.278  40.249  45.697  1.00 49.16           A
ATOM   3619  N   LEU A 469     -36.265  38.708  46.987  1.00 47.33           A
ATOM   3620  CA  LEU A 469     -36.605  39.681  48.024  1.00 46.83           A
ATOM   3621  CB  LEU A 469     -37.595  39.075  49.030  1.00 45.45           A
ATOM   3622  CG  LEU A 469     -39.045  38.910  48.562  1.00 46.44           A
ATOM   3623  CD1 LEU A 469     -39.847  38.155  49.610  1.00 45.38           A
ATOM   3624  CD2 LEU A 469     -39.660  40.282  48.292  1.00 45.52           A
ATOM   3625  C   LEU A 469     -35.396  40.235  48.773  1.00 47.21           A
ATOM   3626  O   LEU A 469     -35.476  41.308  49.372  1.00 47.70           A
ATOM   3627  N   SER A 470     -34.279  39.514  48.739  1.00 46.37           A
ATOM   3628  CA  SER A 470     -33.078  39.958  49.437  1.00 45.05           A
ATOM   3629  CB  SER A 470     -31.961  38.943  49.257  1.00 46.26           A
ATOM   3630  OG  SER A 470     -31.546  38.923  47.902  1.00 49.01           A
ATOM   3631  C   SER A 470     -32.613  41.298  48.892  1.00 44.18           A
ATOM   3632  O   SER A 470     -31.861  42.020  49.544  1.00 44.04           A
ATOM   3633  N   ALA A 471     -33.055  41.628  47.685  1.00 42.37           A
ATOM   3634  CA  ALA A 471     -32.666  42.889  47.071  1.00 41.08           A
ATOM   3635  CB  ALA A 471     -33.145  42.937  45.637  1.00 40.63           A
ATOM   3636  C   ALA A 471     -33.219  44.077  47.845  1.00 39.69           A
ATOM   3637  O   ALA A 471     -32.814  45.211  47.620  1.00 40.93           A
ATOM   3638  N   PHE A 472     -34.144  43.815  48.758  1.00 39.45           A
ATOM   3639  CA  PHE A 472     -34.746  44.878  49.554  1.00 38.51           A
ATOM   3640  CB  PHE A 472     -36.266  44.806  49.495  1.00 38.09           A
ATOM   3641  CG  PHE A 472     -36.815  44.754  48.107  1.00 38.96           A
ATOM   3642  CD1 PHE A 472     -36.577  45.793  47.210  1.00 38.58           A
ATOM   3643  CD2 PHE A 472     -37.590  43.674  47.700  1.00 37.78           A
ATOM   3644  CE1 PHE A 472     -37.108  45.763  45.917  1.00 40.13           A
ATOM   3645  CE2 PHE A 472     -38.125  43.632  46.414  1.00 40.39           A
ATOM   3646  CZ  PHE A 472     -37.884  44.681  45.518  1.00 40.44           A
ATOM   3647  C   PHE A 472     -34.328  44.779  51.000  1.00 38.46           A
ATOM   3648  O   PHE A 472     -34.685  45.633  51.805  1.00 39.66           A
```

FIGURE 5- 49 -

```
ATOM   3649  N    THR A 473     -33.565  43.744  51.328  1.00 37.97      A
ATOM   3650  CA   THR A 473     -33.132  43.550  52.698  1.00 37.64      A
ATOM   3651  CB   THR A 473     -33.832  42.328  53.325  1.00 38.61      A
ATOM   3652  OG1  THR A 473     -33.263  41.123  52.798  1.00 39.88      A
ATOM   3653  CG2  THR A 473     -35.321  42.354  52.997  1.00 36.67      A
ATOM   3654  C    THR A 473     -31.630  43.373  52.851  1.00 36.96      A
ATOM   3655  O    THR A 473     -31.141  43.174  53.962  1.00 38.63      A
ATOM   3656  N    LEU A 474     -30.893  43.435  51.749  1.00 36.25      A
ATOM   3657  CA   LEU A 474     -29.445  43.282  51.835  1.00 35.10      A
ATOM   3658  CB   LEU A 474     -28.801  43.415  50.453  1.00 32.34      A
ATOM   3659  CG   LEU A 474     -28.134  42.163  49.857  1.00 32.36      A
ATOM   3660  CD1  LEU A 474     -28.998  40.908  50.040  1.00 28.95      A
ATOM   3661  CD2  LEU A 474     -27.869  42.419  48.371  1.00 30.31      A
ATOM   3662  C    LEU A 474     -28.932  44.358  52.784  1.00 35.54      A
ATOM   3663  O    LEU A 474     -29.499  45.452  52.871  1.00 35.19      A
ATOM   3664  N    HIS A 475     -27.882  44.024  53.524  1.00 35.86      A
ATOM   3665  CA   HIS A 475     -27.300  44.938  54.488  1.00 36.74      A
ATOM   3666  CB   HIS A 475     -28.224  45.084  55.713  1.00 37.44      A
ATOM   3667  CG   HIS A 475     -28.208  43.905  56.643  1.00 42.87      A
ATOM   3668  CD2  HIS A 475     -29.065  42.864  56.779  1.00 43.06      A
ATOM   3669  ND1  HIS A 475     -27.213  43.706  57.582  1.00 43.41      A
ATOM   3670  CE1  HIS A 475     -27.459  42.595  58.254  1.00 43.29      A
ATOM   3671  NE2  HIS A 475     -28.576  42.064  57.787  1.00 44.80      A
ATOM   3672  C    HIS A 475     -25.940  44.417  54.920  1.00 36.33      A
ATOM   3673  O    HIS A 475     -25.560  43.289  54.595  1.00 35.06      A
ATOM   3674  N    SER A 476     -25.213  45.245  55.658  1.00 36.68      A
ATOM   3675  CA   SER A 476     -23.902  44.858  56.135  1.00 38.00      A
ATOM   3676  CB   SER A 476     -24.026  43.640  57.057  1.00 39.87      A
ATOM   3677  OG   SER A 476     -22.795  43.350  57.698  1.00 44.01      A
ATOM   3678  C    SER A 476     -23.042  44.526  54.923  1.00 37.34      A
ATOM   3679  O    SER A 476     -22.628  43.384  54.729  1.00 38.74      A
ATOM   3680  N    TYR A 477     -22.789  45.536  54.101  1.00 36.57      A
ATOM   3681  CA   TYR A 477     -21.982  45.357  52.903  1.00 35.28      A
ATOM   3682  CB   TYR A 477     -22.209  46.524  51.930  1.00 31.72      A
ATOM   3683  CG   TYR A 477     -23.603  46.582  51.336  1.00 29.29      A
ATOM   3684  CD1  TYR A 477     -24.682  47.071  52.069  1.00 27.36      A
ATOM   3685  CE1  TYR A 477     -25.967  47.139  51.511  1.00 27.88      A
ATOM   3686  CD2  TYR A 477     -23.839  46.154  50.031  1.00 29.87      A
ATOM   3687  CE2  TYR A 477     -25.117  46.213  49.459  1.00 29.64      A
ATOM   3688  CZ   TYR A 477     -26.178  46.710  50.202  1.00 30.33      A
ATOM   3689  OH   TYR A 477     -27.434  46.796  49.623  1.00 29.53      A
ATOM   3690  C    TYR A 477     -20.504  45.250  53.265  1.00 35.07      A
ATOM   3691  O    TYR A 477     -20.086  45.708  54.320  1.00 35.36      A
ATOM   3692  N    SER A 478     -19.719  44.633  52.393  1.00 36.42      A
ATOM   3693  CA   SER A 478     -18.296  44.486  52.647  1.00 37.63      A
ATOM   3694  CB   SER A 478     -17.635  43.673  51.532  1.00 37.47      A
ATOM   3695  OG   SER A 478     -17.796  44.299  50.275  1.00 37.09      A
ATOM   3696  C    SER A 478     -17.678  45.873  52.730  1.00 38.95      A
ATOM   3697  O    SER A 478     -18.164  46.812  52.111  1.00 40.04      A
ATOM   3698  N    PRO A 479     -16.592  46.020  53.499  1.00 40.13      A
ATOM   3699  CD   PRO A 479     -15.928  44.975  54.294  1.00 39.81      A
ATOM   3700  CA   PRO A 479     -15.915  47.311  53.662  1.00 39.50      A
ATOM   3701  CB   PRO A 479     -14.812  47.005  54.670  1.00 39.75      A
ATOM   3702  CG   PRO A 479     -15.334  45.784  55.410  1.00 40.68      A
ATOM   3703  C    PRO A 479     -15.349  47.850  52.360  1.00 40.06      A
ATOM   3704  O    PRO A 479     -15.387  49.046  52.111  1.00 43.15      A
ATOM   3705  N    GLY A 480     -14.809  46.967  51.533  1.00 40.14      A
ATOM   3706  CA   GLY A 480     -14.247  47.411  50.271  1.00 38.83      A
ATOM   3707  C    GLY A 480     -15.285  48.060  49.372  1.00 38.56      A
ATOM   3708  O    GLY A 480     -15.002  49.046  48.689  1.00 39.16      A
ATOM   3709  N    GLU A 481     -16.493  47.509  49.375  1.00 36.50      A
ATOM   3710  CA   GLU A 481     -17.568  48.035  48.552  1.00 34.99      A
ATOM   3711  CB   GLU A 481     -18.732  47.028  48.523  1.00 32.01      A
ATOM   3712  CG   GLU A 481     -19.983  47.454  47.754  1.00 29.62      A
ATOM   3713  CD   GLU A 481     -19.706  47.885  46.326  1.00 28.70      A
ATOM   3714  OE1  GLU A 481     -18.594  47.649  45.820  1.00 29.00      A
ATOM   3715  OE2  GLU A 481     -20.614  48.460  45.699  1.00 27.44      A
ATOM   3716  C    GLU A 481     -18.000  49.382  49.118  1.00 35.62      A
ATOM   3717  O    GLU A 481     -18.170  50.344  48.375  1.00 36.25      A
ATOM   3718  N    ILE A 482     -18.151  49.454  50.437  1.00 36.47      A
ATOM   3719  CA   ILE A 482     -18.552  50.698  51.095  1.00 37.97      A
ATOM   3720  CB   ILE A 482     -18.684  50.521  52.633  1.00 37.02      A
ATOM   3721  CG2  ILE A 482     -18.933  51.874  53.299  1.00 35.11      A
ATOM   3722  CG1  ILE A 482     -19.830  49.559  52.952  1.00 35.52      A
ATOM   3723  CD1  ILE A 482     -19.989  49.272  54.436  1.00 31.78      A
ATOM   3724  C    ILE A 482     -17.531  51.804  50.335  1.00 39.39      A
```

FIGURE 5- 50 -

```
ATOM   3725  O   ILE A 482     -17.890  52.922  50.468  1.00 39.52      A
ATOM   3726  N   ASN A 483     -16.258  51.484  51.026  1.00 40.21      A
ATOM   3727  CA  ASN A 483     -15.198  52.455  50.818  1.00 42.65      A
ATOM   3728  CB  ASN A 483     -13.850  51.859  51.229  1.00 45.70      A
ATOM   3729  CG  ASN A 483     -13.750  51.641  52.732  1.00 49.79      A
ATOM   3730  OD1 ASN A 483     -14.559  50.927  53.326  1.00 51.69      A
ATOM   3731  ND2 ASN A 483     -12.758  52.265  53.354  1.00 52.92      A
ATOM   3732  C   ASN A 483     -15.146  52.951  49.380  1.00 42.27      A
ATOM   3733  O   ASN A 483     -14.979  54.151  49.142  1.00 43.98      A
ATOM   3734  N   ARG A 484     -15.291  52.045  48.419  1.00 39.79      A
ATOM   3735  CA  ARG A 484     -15.269  52.465  47.028  1.00 37.36      A
ATOM   3736  CB  ARG A 484     -15.403  51.275  46.081  1.00 37.96      A
ATOM   3737  CG  ARG A 484     -15.555  51.707  44.624  1.00 38.16      A
ATOM   3738  CD  ARG A 484     -15.302  50.568  43.655  1.00 36.70      A
ATOM   3739  NE  ARG A 484     -16.427  49.650  43.572  1.00 34.99      A
ATOM   3740  CZ  ARG A 484     -16.366  48.476  42.964  1.00 32.78      A
ATOM   3741  NH1 ARG A 484     -15.233  48.092  42.398  1.00 31.80      A
ATOM   3742  NH2 ARG A 484     -17.432  47.694  42.919  1.00 31.90      A
ATOM   3743  C   ARG A 484     -16.413  53.426  46.786  1.00 36.24      A
ATOM   3744  O   ARG A 484     -16.247  54.440  46.115  1.00 36.88      A
ATOM   3745  N   VAL A 485     -17.580  53.108  47.333  1.00 34.84      A
ATOM   3746  CA  VAL A 485     -18.732  53.977  47.158  1.00 34.25      A
ATOM   3747  CB  VAL A 485     -20.005  53.366  47.756  1.00 32.46      A
ATOM   3748  CG1 VAL A 485     -21.141  54.375  47.676  1.00 30.90      A
ATOM   3749  CG2 VAL A 485     -20.374  52.115  47.007  1.00 31.06      A
ATOM   3750  C   VAL A 485     -18.515  55.347  47.794  1.00 34.90      A
ATOM   3751  O   VAL A 485     -18.700  56.374  47.143  1.00 35.75      A
ATOM   3752  N   ALA A 486     -18.127  55.353  49.068  1.00 35.02      A
ATOM   3753  CA  ALA A 486     -17.891  56.593  49.807  1.00 34.39      A
ATOM   3754  CB  ALA A 486     -17.435  56.275  51.219  1.00 32.27      A
ATOM   3755  C   ALA A 486     -16.839  57.435  49.109  1.00 34.32      A
ATOM   3756  O   ALA A 486     -17.002  58.639  48.928  1.00 34.16      A
ATOM   3757  N   SER A 487     -15.749  56.781  48.735  1.00 34.20      A
ATOM   3758  CA  SER A 487     -14.653  57.435  48.051  1.00 33.71      A
ATOM   3759  CB  SER A 487     -13.605  56.392  47.679  1.00 34.60      A
ATOM   3760  OG  SER A 487     -12.607  56.958  46.860  1.00 40.58      A
ATOM   3761  C   SER A 487     -15.180  58.124  46.801  1.00 33.41      A
ATOM   3762  O   SER A 487     -14.934  59.310  46.564  1.00 32.46      A
ATOM   3763  N   CYS A 488     -15.927  57.367  46.010  1.00 32.28      A
ATOM   3764  CA  CYS A 488     -16.496  57.878  44.781  1.00 33.26      A
ATOM   3765  CB  CYS A 488     -17.380  56.811  44.159  1.00 34.06      A
ATOM   3766  SG  CYS A 488     -18.160  57.345  42.646  1.00 39.11      A
ATOM   3767  C   CYS A 488     -17.297  59.170  44.978  1.00 33.76      A
ATOM   3768  O   CYS A 488     -17.026  60.183  44.326  1.00 33.47      A
ATOM   3769  N   LEU A 489     -18.282  59.129  45.872  1.00 34.05      A
ATOM   3770  CA  LEU A 489     -19.120  60.293  46.157  1.00 33.82      A
ATOM   3771  CB  LEU A 489     -20.071  59.994  47.318  1.00 33.67      A
ATOM   3772  CG  LEU A 489     -20.843  58.675  47.283  1.00 36.05      A
ATOM   3773  CD1 LEU A 489     -21.973  58.726  48.319  1.00 35.54      A
ATOM   3774  CD2 LEU A 489     -21.410  58.438  45.895  1.00 36.80      A
ATOM   3775  C   LEU A 489     -18.290  61.536  46.493  1.00 33.53      A
ATOM   3776  O   LEU A 489     -18.575  62.638  46.007  1.00 31.45      A
ATOM   3777  N   ARG A 490     -17.272  61.367  47.331  1.00 33.04      A
ATOM   3778  CA  ARG A 490     -16.434  62.495  47.689  1.00 33.67      A
ATOM   3779  CB  ARG A 490     -15.303  62.053  48.616  1.00 34.78      A
ATOM   3780  CG  ARG A 490     -15.779  61.619  50.008  1.00 37.97      A
ATOM   3781  CD  ARG A 490     -14.631  61.594  51.016  1.00 37.55      A
ATOM   3782  NE  ARG A 490     -13.817  60.382  50.940  1.00 40.66      A
ATOM   3783  CZ  ARG A 490     -14.167  59.217  51.483  1.00 41.81      A
ATOM   3784  NH1 ARG A 490     -15.322  59.121  52.137  1.00 44.49      A
ATOM   3785  NH2 ARG A 490     -13.362  58.160  51.396  1.00 37.96      A
ATOM   3786  C   ARG A 490     -15.873  63.091  46.406  1.00 34.50      A
ATOM   3787  O   ARG A 490     -15.986  64.292  46.171  1.00 36.73      A
ATOM   3788  N   LYS A 491     -15.305  62.232  45.565  1.00 34.79      A
ATOM   3789  CA  LYS A 491     -14.715  62.632  44.288  1.00 32.97      A
ATOM   3790  CB  LYS A 491     -14.213  61.388  43.539  1.00 31.34      A
ATOM   3791  CG  LYS A 491     -13.713  61.667  42.135  1.00 31.91      A
ATOM   3792  CD  LYS A 491     -13.175  60.425  41.438  1.00 32.44      A
ATOM   3793  CE  LYS A 491     -14.283  59.491  40.963  1.00 36.79      A
ATOM   3794  NZ  LYS A 491     -13.764  58.360  40.118  1.00 36.86      A
ATOM   3795  C   LYS A 491     -15.676  63.417  43.390  1.00 32.85      A
ATOM   3796  O   LYS A 491     -15.341  64.490  42.893  1.00 33.47      A
ATOM   3797  N   LEU A 492     -16.870  62.875  43.189  1.00 31.81      A
ATOM   3798  CA  LEU A 492     -17.870  63.508  42.334  1.00 30.65      A
ATOM   3799  CB  LEU A 492     -18.949  62.480  41.953  1.00 29.47      A
ATOM   3800  CG  LEU A 492     -18.901  61.665  40.656  1.00 26.73      A
```

FIGURE 5- 51 -

```
ATOM   3801  CD1 LEU A 492     -17.543  61.720  40.001  1.00 24.46           A
ATOM   3802  CD2 LEU A 492     -19.295  60.245  40.985  1.00 24.62           A
ATOM   3803  C   LEU A 492     -18.556  64.728  42.945  1.00 30.46           A
ATOM   3804  O   LEU A 492     -19.126  65.544  42.220  1.00 30.60           A
ATOM   3805  N   GLY A 493     -18.515  64.852  44.269  1.00 30.34           A
ATOM   3806  CA  GLY A 493     -19.190  65.969  44.912  1.00 31.69           A
ATOM   3807  C   GLY A 493     -20.649  65.628  45.218  1.00 33.01           A
ATOM   3808  O   GLY A 493     -21.525  66.500  45.263  1.00 32.22           A
ATOM   3809  N   VAL A 494     -20.903  64.339  45.428  1.00 32.53           A
ATOM   3810  CA  VAL A 494     -22.230  63.823  45.739  1.00 30.97           A
ATOM   3811  CB  VAL A 494     -22.392  62.418  45.103  1.00 33.24           A
ATOM   3812  CG1 VAL A 494     -23.760  61.828  45.428  1.00 34.95           A
ATOM   3813  CG2 VAL A 494     -22.174  62.511  43.599  1.00 30.39           A
ATOM   3814  C   VAL A 494     -22.360  63.724  47.270  1.00 32.97           A
ATOM   3815  O   VAL A 494     -21.462  63.210  47.947  1.00 34.00           A
ATOM   3816  N   PRO A 495     -23.469  64.224  47.840  1.00 33.28           A
ATOM   3817  CD  PRO A 495     -24.621  64.877  47.192  1.00 32.18           A
ATOM   3818  CA  PRO A 495     -23.653  64.161  49.297  1.00 30.09           A
ATOM   3819  CB  PRO A 495     -25.108  64.571  49.472  1.00 31.80           A
ATOM   3820  CG  PRO A 495     -25.297  65.564  48.357  1.00 32.54           A
ATOM   3821  C   PRO A 495     -23.363  62.770  49.868  1.00 30.51           A
ATOM   3822  O   PRO A 495     -23.662  61.761  49.233  1.00 30.87           A
ATOM   3823  N   PRO A 496     -22.770  62.698  51.073  1.00 31.61           A
ATOM   3824  CD  PRO A 496     -22.446  63.801  51.993  1.00 28.53           A
ATOM   3825  CA  PRO A 496     -22.454  61.402  51.692  1.00 28.34           A
ATOM   3826  CB  PRO A 496     -21.793  61.799  53.016  1.00 28.46           A
ATOM   3827  CG  PRO A 496     -22.453  63.100  53.342  1.00 28.55           A
ATOM   3828  C   PRO A 496     -23.695  60.549  51.895  1.00 28.59           A
ATOM   3829  O   PRO A 496     -24.819  61.051  51.803  1.00 29.15           A
ATOM   3830  N   LEU A 497     -23.492  59.268  52.181  1.00 27.99           A
ATOM   3831  CA  LEU A 497     -24.610  58.361  52.376  1.00 28.81           A
ATOM   3832  CB  LEU A 497     -24.100  56.939  52.597  1.00 29.39           A
ATOM   3833  CG  LEU A 497     -23.432  56.316  51.342  1.00 32.23           A
ATOM   3834  CD1 LEU A 497     -22.804  54.996  51.688  1.00 30.08           A
ATOM   3835  CD2 LEU A 497     -24.572  56.135  50.276  1.00 28.86           A
ATOM   3836  C   LEU A 497     -25.576  58.751  53.491  1.00 30.02           A
ATOM   3837  O   LEU A 497     -26.768  58.499  53.380  1.00 31.61           A
ATOM   3838  N   ARG A 498     -25.038  59.360  54.565  1.00 31.87           A
ATOM   3839  CA  ARG A 498     -25.997  59.768  55.629  1.00 32.94           A
ATOM   3840  CB  ARG A 498     -25.239  60.432  56.791  1.00 33.09           A
ATOM   3841  CG  ARG A 498     -24.290  61.554  56.413  1.00 33.28           A
ATOM   3842  CD  ARG A 498     -23.483  62.041  57.628  1.00 33.03           A
ATOM   3843  NE  ARG A 498     -22.568  63.116  57.259  1.00 34.74           A
ATOM   3844  CZ  ARG A 498     -22.967  64.307  56.819  1.00 37.63           A
ATOM   3845  NH1 ARG A 498     -24.265  64.573  56.708  1.00 38.49           A
ATOM   3846  NH2 ARG A 498     -22.075  65.222  56.456  1.00 37.30           A
ATOM   3847  C   ARG A 498     -27.063  60.714  55.073  1.00 34.05           A
ATOM   3848  O   ARG A 498     -28.242  60.613  55.434  1.00 36.07           A
ATOM   3849  N   THR A 499     -26.663  61.615  54.179  1.00 32.85           A
ATOM   3850  CA  THR A 499     -27.614  62.544  53.587  1.00 32.34           A
ATOM   3851  CB  THR A 499     -26.922  63.579  52.683  1.00 33.03           A
ATOM   3852  OG1 THR A 499     -26.140  64.473  53.489  1.00 31.07           A
ATOM   3853  CG2 THR A 499     -27.967  64.382  51.892  1.00 29.72           A
ATOM   3854  C   THR A 499     -28.651  61.806  52.756  1.00 33.89           A
ATOM   3855  O   THR A 499     -29.815  62.212  52.707  1.00 35.60           A
ATOM   3856  N   TRP A 500     -28.234  60.729  52.095  1.00 33.98           A
ATOM   3857  CA  TRP A 500     -29.163  59.958  51.279  1.00 34.35           A
ATOM   3858  CB  TRP A 500     -28.401  58.989  50.368  1.00 31.83           A
ATOM   3859  CG  TRP A 500     -27.639  59.718  49.272  1.00 31.43           A
ATOM   3860  CD2 TRP A 500     -28.292  60.443  48.192  1.00 30.87           A
ATOM   3861  CE2 TRP A 500     -27.251  61.082  47.484  1.00 32.31           A
ATOM   3862  CE3 TRP A 500     -29.609  60.612  47.753  1.00 29.44           A
ATOM   3863  CD1 TRP A 500     -26.347  59.934  49.171  1.00 32.13           A
ATOM   3864  NE1 TRP A 500     -26.075  60.756  48.103  1.00 33.02           A
ATOM   3865  CZ2 TRP A 500     -27.437  61.886  46.368  1.00 31.91           A
ATOM   3866  CZ3 TRP A 500     -29.843  61.404  46.646  1.00 29.68           A
ATOM   3867  CH2 TRP A 500     -28.786  62.033  45.964  1.00 30.43           A
ATOM   3868  C   TRP A 500     -30.175  59.219  52.150  1.00 36.00           A
ATOM   3869  O   TRP A 500     -31.354  59.122  51.800  1.00 37.29           A
ATOM   3870  N   ARG A 501     -29.720  58.717  53.293  1.00 36.66           A
ATOM   3871  CA  ARG A 501     -30.603  58.018  54.216  1.00 37.52           A
ATOM   3872  CB  ARG A 501     -29.812  57.561  55.446  1.00 37.88           A
ATOM   3873  CG  ARG A 501     -30.550  56.616  56.390  1.00 40.47           A
ATOM   3874  CD  ARG A 501     -29.575  55.984  57.392  1.00 44.58           A
ATOM   3875  NE  ARG A 501     -28.804  56.998  58.125  1.00 51.43           A
ATOM   3876  CZ  ARG A 501     -27.470  57.023  58.233  1.00 52.74           A
```

FIGURE 5- 52 -

```
ATOM   3877  NH1 ARG A 501     -26.719  56.086  57.660  1.00 53.03       A
ATOM   3878  NH2 ARG A 501     -26.875  58.005  58.900  1.00 53.61       A
ATOM   3879  C   ARG A 501     -31.702  58.999  54.619  1.00 37.48       A
ATOM   3880  O   ARG A 501     -32.882  58.673  54.580  1.00 35.95       A
ATOM   3881  N   HIS A 502     -31.305  60.213  54.983  1.00 38.23       A
ATOM   3882  CA  HIS A 502     -32.267  61.231  55.387  1.00 40.10       A
ATOM   3883  CB  HIS A 502     -31.540  62.531  55.749  1.00 43.20       A
ATOM   3884  CG  HIS A 502     -30.607  62.400  56.913  1.00 46.56       A
ATOM   3885  CD2 HIS A 502     -30.364  61.363  57.754  1.00 48.03       A
ATOM   3886  ND1 HIS A 502     -29.789  63.429  57.329  1.00 47.23       A
ATOM   3887  CE1 HIS A 502     -29.082  63.033  58.375  1.00 49.73       A
ATOM   3888  NE2 HIS A 502     -29.412  61.783  58.654  1.00 48.47       A
ATOM   3889  C   HIS A 502     -33.296  61.501  54.286  1.00 39.88       A
ATOM   3890  O   HIS A 502     -34.508  61.471  54.530  1.00 39.55       A
ATOM   3891  N   ARG A 503     -32.815  61.759  53.073  1.00 38.46       A
ATOM   3892  CA  ARG A 503     -33.709  62.029  51.959  1.00 37.43       A
ATOM   3893  CB  ARG A 503     -32.902  62.316  50.700  1.00 36.69       A
ATOM   3894  CG  ARG A 503     -32.146  63.618  50.762  1.00 37.81       A
ATOM   3895  CD  ARG A 503     -31.399  63.864  49.476  1.00 39.04       A
ATOM   3896  NE  ARG A 503     -30.593  65.081  49.509  1.00 39.52       A
ATOM   3897  CZ  ARG A 503     -29.722  65.405  48.557  1.00 39.50       A
ATOM   3898  NH1 ARG A 503     -29.562  64.597  47.520  1.00 40.48       A
ATOM   3899  NH2 ARG A 503     -29.005  66.521  48.639  1.00 37.33       A
ATOM   3900  C   ARG A 503     -34.682  60.885  51.694  1.00 37.30       A
ATOM   3901  O   ARG A 503     -35.866  61.117  51.451  1.00 34.95       A
ATOM   3902  N   ALA A 504     -34.183  59.653  51.744  1.00 38.12       A
ATOM   3903  CA  ALA A 504     -35.017  58.475  51.500  1.00 39.49       A
ATOM   3904  CB  ALA A 504     -34.170  57.219  51.560  1.00 37.16       A
ATOM   3905  C   ALA A 504     -36.166  58.390  52.510  1.00 42.06       A
ATOM   3906  O   ALA A 504     -37.301  58.040  52.158  1.00 41.54       A
ATOM   3907  N   ARG A 505     -35.872  58.707  53.768  1.00 43.47       A
ATOM   3908  CA  ARG A 505     -36.892  58.680  54.805  1.00 44.38       A
ATOM   3909  CB  ARG A 505     -36.313  59.195  56.122  1.00 45.57       A
ATOM   3910  CG  ARG A 505     -35.791  58.109  57.041  1.00 48.03       A
ATOM   3911  CD  ARG A 505     -35.404  58.681  58.394  1.00 51.74       A
ATOM   3912  NE  ARG A 505     -35.208  57.639  59.402  1.00 55.83       A
ATOM   3913  CZ  ARG A 505     -36.194  56.952  59.970  1.00 57.36       A
ATOM   3914  NH1 ARG A 505     -37.455  57.198  59.631  1.00 57.30       A
ATOM   3915  NH2 ARG A 505     -35.922  56.018  60.877  1.00 59.70       A
ATOM   3916  C   ARG A 505     -38.088  59.539  54.384  1.00 45.11       A
ATOM   3917  O   ARG A 505     -39.248  59.176  54.608  1.00 43.97       A
ATOM   3918  N   SER A 506     -37.793  60.677  53.762  1.00 45.69       A
ATOM   3919  CA  SER A 506     -38.830  61.593  53.309  1.00 46.90       A
ATOM   3920  CB  SER A 506     -38.213  62.948  52.959  1.00 47.42       A
ATOM   3921  OG  SER A 506     -39.161  63.793  52.336  1.00 48.54       A
ATOM   3922  C   SER A 506     -39.562  61.030  52.098  1.00 47.72       A
ATOM   3923  O   SER A 506     -40.793  60.983  52.074  1.00 49.52       A
ATOM   3924  N   VAL A 507     -38.798  60.608  51.095  1.00 47.05       A
ATOM   3925  CA  VAL A 507     -39.366  60.039  49.881  1.00 45.64       A
ATOM   3926  CB  VAL A 507     -38.267  59.474  48.973  1.00 44.24       A
ATOM   3927  CG1 VAL A 507     -38.882  58.835  47.762  1.00 45.38       A
ATOM   3928  CG2 VAL A 507     -37.328  60.575  48.559  1.00 45.60       A
ATOM   3929  C   VAL A 507     -40.333  58.912  50.230  1.00 45.91       A
ATOM   3930  O   VAL A 507     -41.488  58.911  49.803  1.00 46.36       A
ATOM   3931  N   ARG A 508     -39.849  57.951  51.008  1.00 45.77       A
ATOM   3932  CA  ARG A 508     -40.664  56.815  51.419  1.00 46.33       A
ATOM   3933  CB  ARG A 508     -39.904  55.976  52.444  1.00 45.78       A
ATOM   3934  CG  ARG A 508     -40.744  54.933  53.126  1.00 44.53       A
ATOM   3935  CD  ARG A 508     -39.915  54.203  54.140  1.00 45.45       A
ATOM   3936  NE  ARG A 508     -40.744  53.673  55.213  1.00 49.36       A
ATOM   3937  CZ  ARG A 508     -41.058  52.392  55.357  1.00 50.83       A
ATOM   3938  NH1 ARG A 508     -40.615  51.482  54.494  1.00 50.75       A
ATOM   3939  NH2 ARG A 508     -41.813  52.023  56.378  1.00 51.72       A
ATOM   3940  C   ARG A 508     -41.971  57.297  52.021  1.00 45.72       A
ATOM   3941  O   ARG A 508     -43.054  56.912  51.585  1.00 46.43       A
ATOM   3942  N   ALA A 509     -41.852  58.144  53.032  1.00 45.08       A
ATOM   3943  CA  ALA A 509     -43.010  58.700  53.701  1.00 44.38       A
ATOM   3944  CB  ALA A 509     -42.578  59.844  54.587  1.00 43.97       A
ATOM   3945  C   ALA A 509     -44.038  59.179  52.676  1.00 44.30       A
ATOM   3946  O   ALA A 509     -45.193  58.775  52.722  1.00 43.61       A
ATOM   3947  N   LYS A 510     -43.623  60.034  51.746  1.00 44.79       A
ATOM   3948  CA  LYS A 510     -44.548  60.531  50.732  1.00 46.05       A
ATOM   3949  CB  LYS A 510     -43.860  61.535  49.810  1.00 45.05       A
ATOM   3950  CG  LYS A 510     -43.184  62.693  50.504  1.00 44.98       A
ATOM   3951  CD  LYS A 510     -43.016  63.854  49.533  1.00 47.16       A
ATOM   3952  CE  LYS A 510     -42.238  65.008  50.138  1.00 46.52       A
```

FIGURE 5- 53 -

| | | | | | | | | | | |
|---|---|---|---|---|---|---|---|---|---|---|
| ATOM | 3953 | NZ | LYS | A | 510 | -40.813 | 64.630 | 50.334 | 1.00 50.09 | A |
| ATOM | 3954 | C | LYS | A | 510 | -45.126 | 59.395 | 49.883 | 1.00 48.42 | A |
| ATOM | 3955 | O | LYS | A | 510 | -46.325 | 59.366 | 49.625 | 1.00 50.02 | A |
| ATOM | 3956 | N | LEU | A | 511 | -44.276 | 58.470 | 49.442 | 1.00 49.11 | A |
| ATOM | 3957 | CA | LEU | A | 511 | -44.738 | 57.349 | 48.632 | 1.00 50.06 | A |
| ATOM | 3958 | CB | LEU | A | 511 | -43.585 | 56.398 | 48.310 | 1.00 48.99 | A |
| ATOM | 3959 | CG | LEU | A | 511 | -42.525 | 56.884 | 47.323 | 1.00 48.38 | A |
| ATOM | 3960 | CD1 | LEU | A | 511 | -41.529 | 55.757 | 47.096 | 1.00 46.67 | A |
| ATOM | 3961 | CD2 | LEU | A | 511 | -43.173 | 57.308 | 46.000 | 1.00 45.24 | A |
| ATOM | 3962 | C | LEU | A | 511 | -45.839 | 56.570 | 49.337 | 1.00 51.65 | A |
| ATOM | 3963 | O | LEU | A | 511 | -46.896 | 56.319 | 48.761 | 1.00 52.71 | A |
| ATOM | 3964 | N | LEU | A | 512 | -45.586 | 56.151 | 50.581 | 1.00 52.82 | A |
| ATOM | 3965 | CA | LEU | A | 512 | -46.572 | 55.438 | 51.350 | 1.00 54.35 | A |
| ATOM | 3966 | CB | LEU | A | 512 | -46.052 | 55.179 | 52.764 | 1.00 52.52 | A |
| ATOM | 3967 | CG | LEU | A | 512 | -44.878 | 54.201 | 52.831 | 1.00 54.10 | A |
| ATOM | 3968 | CD1 | LEU | A | 512 | -44.256 | 54.218 | 54.220 | 1.00 54.52 | A |
| ATOM | 3969 | CD2 | LEU | A | 512 | -45.362 | 52.800 | 52.476 | 1.00 54.13 | A |
| ATOM | 3970 | C | LEU | A | 512 | -47.905 | 56.151 | 51.410 | 1.00 56.15 | A |
| ATOM | 3971 | O | LEU | A | 512 | -48.963 | 55.579 | 51.246 | 1.00 56.94 | A |
| ATOM | 3972 | N | SER | A | 513 | -47.847 | 57.490 | 51.635 | 1.00 57.60 | A |
| ATOM | 3973 | CA | SER | A | 513 | -49.048 | 58.320 | 51.718 | 1.00 58.88 | A |
| ATOM | 3974 | CB | SER | A | 513 | -48.681 | 59.803 | 51.744 | 1.00 60.33 | A |
| ATOM | 3975 | OG | SER | A | 513 | -47.864 | 60.111 | 52.859 | 1.00 66.44 | A |
| ATOM | 3976 | C | SER | A | 513 | -49.963 | 58.094 | 50.539 | 1.00 58.92 | A |
| ATOM | 3977 | O | SER | A | 513 | -51.181 | 58.077 | 50.683 | 1.00 60.24 | A |
| ATOM | 3978 | N | GLN | A | 514 | -49.364 | 57.925 | 49.368 | 1.00 58.72 | A |
| ATOM | 3979 | CA | GLN | A | 514 | -50.115 | 57.732 | 48.136 | 1.00 57.64 | A |
| ATOM | 3980 | CB | GLN | A | 514 | -49.191 | 57.953 | 46.939 | 1.00 58.06 | A |
| ATOM | 3981 | CG | GLN | A | 514 | -48.656 | 59.365 | 46.857 | 1.00 58.98 | A |
| ATOM | 3982 | CD | GLN | A | 514 | -48.026 | 59.667 | 45.520 | 1.00 60.05 | A |
| ATOM | 3983 | OE1 | GLN | A | 514 | -48.343 | 59.035 | 44.510 | 1.00 61.23 | A |
| ATOM | 3984 | NE2 | GLN | A | 514 | -47.145 | 60.652 | 45.497 | 1.00 60.87 | A |
| ATOM | 3985 | C | GLN | A | 514 | -50.814 | 56.390 | 47.994 | 1.00 56.33 | A |
| ATOM | 3986 | O | GLN | A | 514 | -51.715 | 56.250 | 47.174 | 1.00 54.91 | A |
| ATOM | 3987 | N | GLY | A | 515 | -50.400 | 55.408 | 48.789 | 1.00 56.43 | A |
| ATOM | 3988 | CA | GLY | A | 515 | -51.000 | 54.091 | 48.696 | 1.00 57.67 | A |
| ATOM | 3989 | C | GLY | A | 515 | -50.846 | 53.513 | 47.297 | 1.00 59.20 | A |
| ATOM | 3990 | O | GLY | A | 515 | -50.295 | 54.153 | 46.404 | 1.00 60.10 | A |
| ATOM | 3991 | N | GLY | A | 516 | -51.331 | 52.295 | 47.098 | 1.00 60.42 | A |
| ATOM | 3992 | CA | GLY | A | 516 | -51.237 | 51.678 | 45.790 | 1.00 60.84 | A |
| ATOM | 3993 | C | GLY | A | 516 | -49.831 | 51.238 | 45.444 | 1.00 61.73 | A |
| ATOM | 3994 | O | GLY | A | 516 | -49.056 | 50.863 | 46.326 | 1.00 61.94 | A |
| ATOM | 3995 | N | ARG | A | 517 | -49.496 | 51.289 | 44.156 | 1.00 61.60 | A |
| ATOM | 3996 | CA | ARG | A | 517 | -48.173 | 50.892 | 43.705 | 1.00 60.86 | A |
| ATOM | 3997 | CB | ARG | A | 517 | -48.064 | 51.008 | 42.183 | 1.00 60.47 | A |
| ATOM | 3998 | CG | ARG | A | 517 | -49.028 | 50.102 | 41.434 | 1.00 58.96 | A |
| ATOM | 3999 | CD | ARG | A | 517 | -48.457 | 49.642 | 40.104 | 1.00 58.66 | A |
| ATOM | 4000 | NE | ARG | A | 517 | -48.454 | 50.670 | 39.064 | 1.00 57.26 | A |
| ATOM | 4001 | CZ | ARG | A | 517 | -47.924 | 50.483 | 37.858 | 1.00 56.80 | A |
| ATOM | 4002 | NH1 | ARG | A | 517 | -47.365 | 49.319 | 37.570 | 1.00 55.99 | A |
| ATOM | 4003 | NH2 | ARG | A | 517 | -47.958 | 51.441 | 36.937 | 1.00 55.86 | A |
| ATOM | 4004 | C | ARG | A | 517 | -47.102 | 51.728 | 44.378 | 1.00 60.90 | A |
| ATOM | 4005 | O | ARG | A | 517 | -46.083 | 51.202 | 44.844 | 1.00 60.96 | A |
| ATOM | 4006 | N | ALA | A | 518 | -47.344 | 53.032 | 44.431 | 1.00 59.54 | A |
| ATOM | 4007 | CA | ALA | A | 518 | -46.407 | 53.951 | 45.053 | 1.00 58.33 | A |
| ATOM | 4008 | CB | ALA | A | 518 | -46.982 | 55.352 | 45.058 | 1.00 58.58 | A |
| ATOM | 4009 | C | ALA | A | 518 | -46.108 | 53.503 | 46.478 | 1.00 58.14 | A |
| ATOM | 4010 | O | ALA | A | 518 | -44.951 | 53.436 | 46.889 | 1.00 58.16 | A |
| ATOM | 4011 | N | ALA | A | 519 | -47.153 | 53.192 | 47.235 | 1.00 57.07 | A |
| ATOM | 4012 | CA | ALA | A | 519 | -46.961 | 52.761 | 48.615 | 1.00 56.73 | A |
| ATOM | 4013 | CB | ALA | A | 519 | -48.312 | 52.492 | 49.274 | 1.00 57.17 | A |
| ATOM | 4014 | C | ALA | A | 519 | -46.083 | 51.503 | 48.685 | 1.00 55.17 | A |
| ATOM | 4015 | O | ALA | A | 519 | -45.378 | 51.280 | 49.670 | 1.00 54.91 | A |
| ATOM | 4016 | N | THR | A | 520 | -46.130 | 50.701 | 47.634 | 1.00 53.12 | A |
| ATOM | 4017 | CA | THR | A | 520 | -45.338 | 49.483 | 47.597 | 1.00 51.50 | A |
| ATOM | 4018 | CB | THR | A | 520 | -45.804 | 48.565 | 46.466 | 1.00 52.98 | A |
| ATOM | 4019 | OG1 | THR | A | 520 | -47.236 | 48.535 | 46.446 | 1.00 53.54 | A |
| ATOM | 4020 | CG2 | THR | A | 520 | -45.280 | 47.152 | 46.675 | 1.00 52.60 | A |
| ATOM | 4021 | C | THR | A | 520 | -43.884 | 49.857 | 47.368 | 1.00 50.10 | A |
| ATOM | 4022 | O | THR | A | 520 | -42.988 | 49.315 | 48.012 | 1.00 48.67 | A |
| ATOM | 4023 | N | CYS | A | 521 | -43.659 | 50.791 | 46.444 | 1.00 48.81 | A |
| ATOM | 4024 | CA | CYS | A | 521 | -42.310 | 51.252 | 46.131 | 1.00 47.18 | A |
| ATOM | 4025 | CB | CYS | A | 521 | -42.344 | 52.411 | 45.127 | 1.00 46.87 | A |
| ATOM | 4026 | SG | CYS | A | 521 | -42.611 | 51.921 | 43.412 | 1.00 46.61 | A |
| ATOM | 4027 | C | CYS | A | 521 | -41.634 | 51.716 | 47.402 | 1.00 45.86 | A |
| ATOM | 4028 | O | CYS | A | 521 | -40.479 | 51.387 | 47.665 | 1.00 44.99 | A |

FIGURE 5- 54 -

```
ATOM   4029  N    GLY A 522     -42.370  52.485  48.190  1.00  45.13      A
ATOM   4030  CA   GLY A 522     -41.823  52.985  49.429  1.00  46.79      A
ATOM   4031  C    GLY A 522     -41.607  51.881  50.440  1.00  47.53      A
ATOM   4032  O    GLY A 522     -40.627  51.896  51.173  1.00  48.50      A
ATOM   4033  N    ARG A 523     -42.512  50.910  50.474  1.00  49.33      A
ATOM   4034  CA   ARG A 523     -42.405  49.817  51.433  1.00  51.09      A
ATOM   4035  CB   ARG A 523     -43.720  49.018  51.476  1.00  54.46      A
ATOM   4036  CG   ARG A 523     -43.832  48.045  52.658  1.00  60.65      A
ATOM   4037  CD   ARG A 523     -45.182  47.320  52.697  1.00  65.13      A
ATOM   4038  NE   ARG A 523     -46.313  48.226  52.469  1.00  70.96      A
ATOM   4039  CZ   ARG A 523     -46.697  49.202  53.292  1.00  73.03      A
ATOM   4040  NH1  ARG A 523     -46.048  49.422  54.431  1.00  73.71      A
ATOM   4041  NH2  ARG A 523     -47.737  49.969  52.971  1.00  73.05      A
ATOM   4042  C    ARG A 523     -41.242  48.881  51.132  1.00  49.75      A
ATOM   4043  O    ARG A 523     -40.509  48.476  52.040  1.00  48.82      A
ATOM   4044  N    TYR A 524     -41.068  48.558  49.854  1.00  48.56      A
ATOM   4045  CA   TYR A 524     -40.013  47.643  49.440  1.00  48.29      A
ATOM   4046  CB   TYR A 524     -40.486  46.794  48.244  1.00  49.34      A
ATOM   4047  CG   TYR A 524     -41.538  45.757  48.605  1.00  49.45      A
ATOM   4048  CD1  TYR A 524     -42.891  46.090  48.664  1.00  48.06      A
ATOM   4049  CE1  TYR A 524     -43.849  45.150  49.058  1.00  48.72      A
ATOM   4050  CD2  TYR A 524     -41.167  44.458  48.946  1.00  49.63      A
ATOM   4051  CE2  TYR A 524     -42.112  43.517  49.343  1.00  51.14      A
ATOM   4052  CZ   TYR A 524     -43.457  43.869  49.401  1.00  51.11      A
ATOM   4053  OH   TYR A 524     -44.392  42.930  49.819  1.00  48.32      A
ATOM   4054  C    TYR A 524     -38.665  48.278  49.116  1.00  47.16      A
ATOM   4055  O    TYR A 524     -37.641  47.852  49.649  1.00  47.70      A
ATOM   4056  N    LEU A 525     -38.658  49.293  48.256  1.00  44.80      A
ATOM   4057  CA   LEU A 525     -37.413  49.944  47.858  1.00  42.49      A
ATOM   4058  CB   LEU A 525     -37.660  50.917  46.706  1.00  40.01      A
ATOM   4059  CG   LEU A 525     -38.246  50.357  45.412  1.00  37.99      A
ATOM   4060  CD1  LEU A 525     -38.614  51.506  44.490  1.00  38.31      A
ATOM   4061  CD2  LEU A 525     -37.253  49.429  44.755  1.00  37.05      A
ATOM   4062  C    LEU A 525     -36.714  50.696  48.974  1.00  43.26      A
ATOM   4063  O    LEU A 525     -35.488  50.734  49.017  1.00  44.32      A
ATOM   4064  N    PHE A 526     -37.486  51.286  49.882  1.00  43.55      A
ATOM   4065  CA   PHE A 526     -36.903  52.073  50.969  1.00  43.37      A
ATOM   4066  CB   PHE A 526     -37.532  53.463  50.936  1.00  40.62      A
ATOM   4067  CG   PHE A 526     -37.248  54.191  49.662  1.00  41.24      A
ATOM   4068  CD1  PHE A 526     -36.005  54.776  49.445  1.00  40.40      A
ATOM   4069  CD2  PHE A 526     -38.189  54.227  48.641  1.00  41.78      A
ATOM   4070  CE1  PHE A 526     -35.697  55.369  48.227  1.00  39.41      A
ATOM   4071  CE2  PHE A 526     -37.887  54.822  47.413  1.00  41.51      A
ATOM   4072  CZ   PHE A 526     -36.641  55.398  47.211  1.00  39.73      A
ATOM   4073  C    PHE A 526     -36.939  51.488  52.384  1.00  41.00      A
ATOM   4074  O    PHE A 526     -36.626  52.168  53.356  1.00  43.23      A
ATOM   4075  N    ASN A 527     -37.285  50.215  52.499  1.00  45.67      A
ATOM   4076  CA   ASN A 527     -37.333  49.585  53.805  1.00  47.29      A
ATOM   4077  CB   ASN A 527     -37.650  48.098  53.664  1.00  46.56      A
ATOM   4078  CG   ASN A 527     -38.604  47.624  54.718  1.00  47.36      A
ATOM   4079  OD1  ASN A 527     -39.630  48.268  54.961  1.00  49.20      A
ATOM   4080  ND2  ASN A 527     -38.287  46.503  55.356  1.00  45.67      A
ATOM   4081  C    ASN A 527     -36.003  49.758  54.528  1.00  48.26      A
ATOM   4082  O    ASN A 527     -35.921  49.662  55.752  1.00  49.62      A
ATOM   4083  N    TRP A 528     -34.956  49.027  53.766  1.00  49.09      A
ATOM   4084  CA   TRP A 528     -33.638  50.189  54.354  1.00  49.95      A
ATOM   4085  CB   TRP A 528     -32.575  50.051  53.267  1.00  47.40      A
ATOM   4086  CG   TRP A 528     -32.734  51.063  52.186  1.00  45.06      A
ATOM   4087  CD2  TRP A 528     -32.215  52.397  52.187  1.00  44.14      A
ATOM   4088  CE2  TRP A 528     -32.662  53.022  51.001  1.00  44.11      A
ATOM   4089  CE3  TRP A 528     -31.423  53.129  53.084  1.00  42.40      A
ATOM   4090  CD1  TRP A 528     -33.448  50.930  51.028  1.00  44.55      A
ATOM   4091  NE1  TRP A 528     -33.409  52.105  50.308  1.00  44.18      A
ATOM   4092  CZ2  TRP A 528     -32.333  54.338  50.684  1.00  42.92      A
ATOM   4093  CZ3  TRP A 528     -31.097  54.433  52.768  1.00  41.96      A
ATOM   4094  CH2  TRP A 528     -31.555  55.027  51.578  1.00  43.08      A
ATOM   4095  C    TRP A 528     -33.470  51.530  55.067  1.00  51.41      A
ATOM   4096  O    TRP A 528     -32.540  51.708  55.852  1.00  50.66      A
ATOM   4097  N    ALA A 529     -34.370  52.470  54.794  1.00  53.39      A
ATOM   4098  CA   ALA A 529     -34.292  53.737  55.398  1.00  56.07      A
ATOM   4099  CB   ALA A 529     -35.055  54.807  54.536  1.00  54.06      A
ATOM   4100  C    ALA A 529     -34.795  53.850  56.839  1.00  58.59      A
ATOM   4101  O    ALA A 529     -34.322  54.670  57.629  1.00  60.14      A
ATOM   4102  N    VAL A 530     -35.744  52.977  57.176  1.00  60.88      A
ATOM   4103  CA   VAL A 530     -36.325  52.920  58.522  1.00  62.74      A
ATOM   4104  CB   VAL A 530     -37.806  52.524  58.463  1.00  63.02      A
```

FIGURE 5- 55 -

```
ATOM   4105  CG1  VAL A 530     -38.548  53.430  57.502  1.00 63.60       A
ATOM   4106  CG2  VAL A 530     -37.942  51.078  58.028  1.00 61.88       A
ATOM   4107  C    VAL A 530     -35.615  51.893  59.394  1.00 65.11       A
ATOM   4108  O    VAL A 530     -34.949  50.996  58.879  1.00 65.72       A
ATOM   4109  N    ARG A 531     -35.755  52.013  60.712  1.00 68.36       A
ATOM   4110  CA   ARG A 531     -35.116  51.043  61.605  1.00 70.73       A
ATOM   4111  CB   ARG A 531     -34.413  51.746  62.772  1.00 74.00       A
ATOM   4112  CG   ARG A 531     -33.068  52.341  62.353  1.00 79.78       A
ATOM   4113  CD   ARG A 531     -32.242  51.290  61.592  1.00 83.98       A
ATOM   4114  NE   ARG A 531     -31.181  51.856  60.759  1.00 87.18       A
ATOM   4115  CZ   ARG A 531     -30.573  51.189  59.779  1.00 89.06       A
ATOM   4116  NH1  ARG A 531     -30.925  49.935  59.512  1.00 89.63       A
ATOM   4117  NH2  ARG A 531     -29.617  51.773  59.063  1.00 89.43       A
ATOM   4118  C    ARG A 531     -36.112  50.010  62.104  1.00 69.94       A
ATOM   4119  O    ARG A 531     -35.757  48.858  62.364  1.00 68.71       A
ATOM   4120  N    THR A 532     -37.364  50.430  62.228  1.00 69.91       A
ATOM   4121  CA   THR A 532     -38.420  49.523  62.635  1.00 70.28       A
ATOM   4122  CB   THR A 532     -39.525  50.263  63.393  1.00 69.67       A
ATOM   4123  OG1  THR A 532     -38.956  50.906  64.539  1.00 69.43       A
ATOM   4124  CG2  THR A 532     -40.594  49.292  63.851  1.00 69.27       A
ATOM   4125  C    THR A 532     -38.946  48.996  61.306  1.00 70.21       A
ATOM   4126  O    THR A 532     -40.065  49.292  60.890  1.00 69.42       A
ATOM   4127  N    LYS A 533     -38.092  48.222  60.643  1.00 71.80       A
ATOM   4128  CA   LYS A 533     -38.378  47.644  59.335  1.00 73.83       A
ATOM   4129  CB   LYS A 533     -37.162  46.848  58.847  1.00 73.17       A
ATOM   4130  CG   LYS A 533     -35.900  47.689  58.704  1.00 73.20       A
ATOM   4131  CD   LYS A 533     -34.819  46.939  57.951  1.00 73.35       A
ATOM   4132  CE   LYS A 533     -33.670  47.854  57.551  1.00 71.96       A
ATOM   4133  NZ   LYS A 533     -32.740  47.151  56.624  1.00 69.48       A
ATOM   4134  C    LYS A 533     -39.616  46.765  59.269  1.00 74.76       A
ATOM   4135  O    LYS A 533     -39.967  46.088  60.239  1.00 75.08       A
ATOM   4136  N    LEU A 534     -40.270  46.786  58.110  1.00 75.07       A
ATOM   4137  CA   LEU A 534     -41.470  45.991  57.877  1.00 75.67       A
ATOM   4138  CB   LEU A 534     -42.344  46.650  56.807  1.00 74.33       A
ATOM   4139  CG   LEU A 534     -42.574  48.156  56.961  1.00 74.65       A
ATOM   4140  CD1  LEU A 534     -43.537  48.636  55.890  1.00 72.33       A
ATOM   4141  CD2  LEU A 534     -43.127  48.458  58.347  1.00 73.95       A
ATOM   4142  C    LEU A 534     -41.054  44.604  57.400  1.00 76.54       A
ATOM   4143  O    LEU A 534     -39.939  44.416  56.903  1.00 76.97       A
ATOM   4144  N    LYS A 535     -41.943  43.631  57.566  1.00 76.75       A
ATOM   4145  CA   LYS A 535     -41.657  42.270  57.131  1.00 76.20       A
ATOM   4146  CB   LYS A 535     -42.452  41.258  57.963  1.00 78.13       A
ATOM   4147  CG   LYS A 535     -42.152  41.318  59.461  1.00 80.69       A
ATOM   4148  CD   LYS A 535     -40.668  41.077  59.747  1.00 82.68       A
ATOM   4149  CE   LYS A 535     -40.342  41.275  61.225  1.00 83.83       A
ATOM   4150  NZ   LYS A 535     -38.886  41.117  61.514  1.00 84.09       A
ATOM   4151  C    LYS A 535     -42.075  42.207  55.678  1.00 74.13       A
ATOM   4152  O    LYS A 535     -43.260  42.254  55.360  1.00 74.20       A
ATOM   4153  N    LEU A 536     -41.096  42.120  54.791  1.00 72.16       A
ATOM   4154  CA   LEU A 536     -41.392  42.080  53.373  1.00 70.55       A
ATOM   4155  CB   LEU A 536     -40.224  42.681  52.593  1.00 67.92       A
ATOM   4156  CG   LEU A 536     -40.043  44.147  52.982  1.00 65.66       A
ATOM   4157  CD1  LEU A 536     -38.868  44.735  52.249  1.00 66.28       A
ATOM   4158  CD2  LEU A 536     -41.311  44.915  52.663  1.00 64.43       A
ATOM   4159  C    LEU A 536     -41.745  40.688  52.864  1.00 70.08       A
ATOM   4160  O    LEU A 536     -40.961  39.743  52.958  1.00 69.71       A
ATOM   4161  N    THR A 537     -42.954  40.582  52.332  1.00 69.83       A
ATOM   4162  CA   THR A 537     -43.466  39.330  51.807  1.00 70.70       A
ATOM   4163  CB   THR A 537     -44.849  39.003  52.399  1.00 72.44       A
ATOM   4164  OG1  THR A 537     -45.766  40.064  52.086  1.00 72.35       A
ATOM   4165  CG2  THR A 537     -44.754  38.832  53.910  1.00 71.63       A
ATOM   4166  C    THR A 537     -43.620  39.437  50.302  1.00 69.70       A
ATOM   4167  O    THR A 537     -43.785  40.529  49.764  1.00 68.91       A
ATOM   4168  N    PRO A 538     -43.585  38.295  49.607  1.00 69.07       A
ATOM   4169  CD   PRO A 538     -43.436  36.939  50.166  1.00 68.99       A
ATOM   4170  CA   PRO A 538     -43.721  38.245  48.151  1.00 69.57       A
ATOM   4171  CB   PRO A 538     -44.049  36.780  47.895  1.00 68.26       A
ATOM   4172  CG   PRO A 538     -43.208  36.095  48.922  1.00 69.21       A
ATOM   4173  C    PRO A 538     -44.793  39.187  47.624  1.00 69.80       A
ATOM   4174  O    PRO A 538     -45.885  39.257  48.170  1.00 70.81       A
ATOM   4175  N    ILE A 539     -44.471  39.923  46.569  1.00 70.54       A
ATOM   4176  CA   ILE A 539     -45.428  40.845  45.978  1.00 72.87       A
ATOM   4177  CB   ILE A 539     -44.723  42.023  45.284  1.00 71.95       A
ATOM   4178  CG2  ILE A 539     -45.754  42.961  44.681  1.00 69.10       A
ATOM   4179  CG1  ILE A 539     -43.833  42.755  46.290  1.00 72.56       A
ATOM   4180  CD1  ILE A 539     -43.041  43.905  45.704  1.00 72.94       A
```

FIGURE 5- 56 -

```
ATOM   4181  C    ILE A 539     -46.244  40.082  44.945  1.00 75.71      A
ATOM   4182  O    ILE A 539     -45.700  39.555  43.976  1.00 76.50      A
ATOM   4183  N    PRO A 540     -47.568  40.015  45.138  1.00 77.74      A
ATOM   4184  CD   PRO A 540     -48.319  40.623  46.251  1.00 77.74      A
ATOM   4185  CA   PRO A 540     -48.471  39.308  44.225  1.00 79.42      A
ATOM   4186  CB   PRO A 540     -49.848  39.735  44.718  1.00 79.44      A
ATOM   4187  CG   PRO A 540     -49.633  39.888  46.187  1.00 78.65      A
ATOM   4188  C    PRO A 540     -48.276  39.591  42.732  1.00 81.09      A
ATOM   4189  O    PRO A 540     -47.831  38.722  41.984  1.00 81.29      A
ATOM   4190  N    ALA A 541     -48.609  40.806  42.307  1.00 82.72      A
ATOM   4191  CA   ALA A 541     -48.511  41.201  40.902  1.00 84.18      A
ATOM   4192  CB   ALA A 541     -48.894  42.670  40.763  1.00 83.86      A
ATOM   4193  C    ALA A 541     -47.160  40.949  40.221  1.00 85.47      A
ATOM   4194  O    ALA A 541     -47.022  41.168  39.015  1.00 85.17      A
ATOM   4195  N    ALA A 542     -46.173  40.482  40.980  1.00 86.94      A
ATOM   4196  CA   ALA A 542     -44.841  40.227  40.429  1.00 88.79      A
ATOM   4197  CB   ALA A 542     -43.847  39.968  41.563  1.00 88.21      A
ATOM   4198  C    ALA A 542     -44.787  39.080  39.417  1.00 89.67      A
ATOM   4199  O    ALA A 542     -44.565  39.306  38.226  1.00 89.56      A
ATOM   4200  N    SER A 543     -44.977  37.853  39.896  1.00 90.50      A
ATOM   4201  CA   SER A 543     -44.943  36.670  39.034  1.00 91.15      A
ATOM   4202  CB   SER A 543     -45.153  35.408  39.878  1.00 91.38      A
ATOM   4203  OG   SER A 543     -46.288  35.540  40.717  1.00 92.58      A
ATOM   4204  C    SER A 543     -45.961  36.711  37.883  1.00 90.78      A
ATOM   4205  O    SER A 543     -45.901  35.893  36.961  1.00 90.84      A
ATOM   4206  N    GLN A 544     -46.890  37.662  37.941  1.00 90.17      A
ATOM   4207  CA   GLN A 544     -47.901  37.823  36.897  1.00 89.53      A
ATOM   4208  CB   GLN A 544     -49.085  38.645  37.424  1.00 90.96      A
ATOM   4209  CG   GLN A 544     -50.129  38.992  36.355  1.00 93.07      A
ATOM   4210  CD   GLN A 544     -51.077  40.118  36.771  1.00 93.75      A
ATOM   4211  OE1  GLN A 544     -51.945  40.530  35.995  1.00 92.44      A
ATOM   4212  NE2  GLN A 544     -50.911  40.619  37.995  1.00 93.76      A
ATOM   4213  C    GLN A 544     -47.262  38.561  35.724  1.00 88.22      A
ATOM   4214  O    GLN A 544     -47.795  38.586  34.615  1.00 87.71      A
ATOM   4215  N    LEU A 545     -46.108  39.161  35.995  1.00 87.49      A
ATOM   4216  CA   LEU A 545     -45.353  39.933  35.012  1.00 85.51      A
ATOM   4217  CB   LEU A 545     -44.302  40.778  35.735  1.00 84.44      A
ATOM   4218  CG   LEU A 545     -44.200  42.264  35.412  1.00 82.91      A
ATOM   4219  CD1  LEU A 545     -42.944  42.801  36.078  1.00 81.51      A
ATOM   4220  CD2  LEU A 545     -44.151  42.484  33.905  1.00 82.94      A
ATOM   4221  C    LEU A 545     -44.661  39.058  33.960  1.00 84.33      A
ATOM   4222  O    LEU A 545     -44.032  38.047  34.286  1.00 84.07      A
ATOM   4223  N    ASP A 546     -44.773  39.461  32.698  1.00 82.53      A
ATOM   4224  CA   ASP A 546     -44.149  38.721  31.609  1.00 80.90      A
ATOM   4225  CB   ASP A 546     -44.962  38.878  30.322  1.00 80.92      A
ATOM   4226  CG   ASP A 546     -44.216  38.383  29.099  1.00 81.12      A
ATOM   4227  OD1  ASP A 546     -43.595  37.300  29.174  1.00 80.36      A
ATOM   4228  OD2  ASP A 546     -44.260  39.075  28.059  1.00 81.62      A
ATOM   4229  C    ASP A 546     -42.726  39.211  31.387  1.00 78.93      A
ATOM   4230  O    ASP A 546     -42.502  40.252  30.767  1.00 79.02      A
ATOM   4231  N    LEU A 547     -41.764  38.455  31.900  1.00 76.15      A
ATOM   4232  CA   LEU A 547     -40.371  38.829  31.762  1.00 73.72      A
ATOM   4233  CB   LEU A 547     -39.683  38.806  33.118  1.00 74.72      A
ATOM   4234  CG   LEU A 547     -39.865  40.067  33.960  1.00 75.24      A
ATOM   4235  CD1  LEU A 547     -41.334  40.443  34.051  1.00 75.80      A
ATOM   4236  CD2  LEU A 547     -39.283  39.819  35.342  1.00 76.26      A
ATOM   4237  C    LEU A 547     -39.632  37.929  30.808  1.00 71.60      A
ATOM   4238  O    LEU A 547     -38.425  38.050  30.649  1.00 71.01      A
ATOM   4239  N    SER A 548     -40.349  37.011  30.178  1.00 70.33      A
ATOM   4240  CA   SER A 548     -39.708  36.120  29.227  1.00 68.17      A
ATOM   4241  CB   SER A 548     -40.734  35.184  28.578  1.00 67.78      A
ATOM   4242  OG   SER A 548     -41.744  35.918  27.907  1.00 68.62      A
ATOM   4243  C    SER A 548     -39.103  37.040  28.183  1.00 66.90      A
ATOM   4244  O    SER A 548     -39.659  38.103  27.890  1.00 67.61      A
ATOM   4245  N    GLY A 549     -37.957  36.648  27.642  1.00 63.92      A
ATOM   4246  CA   GLY A 549     -37.310  37.465  26.635  1.00 61.32      A
ATOM   4247  C    GLY A 549     -36.476  38.589  27.215  1.00 59.04      A
ATOM   4248  O    GLY A 549     -35.884  39.375  26.475  1.00 60.10      A
ATOM   4249  N    TRP A 550     -36.418  38.669  28.538  1.00 55.84      A
ATOM   4250  CA   TRP A 550     -35.647  39.716  29.189  1.00 53.44      A
ATOM   4251  CB   TRP A 550     -36.208  39.994  30.576  1.00 53.59      A
ATOM   4252  CG   TRP A 550     -37.118  41.165  30.588  1.00 54.15      A
ATOM   4253  CD2  TRP A 550     -37.018  42.309  31.432  1.00 54.12      A
ATOM   4254  CE2  TRP A 550     -38.071  43.177  31.079  1.00 55.40      A
ATOM   4255  CE3  TRP A 550     -36.140  42.687  32.452  1.00 54.39      A
ATOM   4256  CD1  TRP A 550     -38.197  41.372  29.782  1.00 53.23      A
```

FIGURE 5- 57 -

```
ATOM   4257  NE1  TRP A 550     -38.774  42.579  30.067  1.00 53.46           A
ATOM   4258  CZ2  TRP A 550     -38.274  44.407  31.717  1.00 56.17           A
ATOM   4259  CZ3  TRP A 550     -36.340  43.906  33.087  1.00 55.92           A
ATOM   4260  CH2  TRP A 550     -37.400  44.753  32.715  1.00 56.07           A
ATOM   4261  C    TRP A 550     -34.162  39.410  29.292  1.00 52.14           A
ATOM   4262  O    TRP A 550     -33.324  40.315  29.258  1.00 52.73           A
ATOM   4263  N    PHE A 551     -33.825  38.139  29.419  1.00 48.07           A
ATOM   4264  CA   PHE A 551     -32.431  37.795  29.511  1.00 46.21           A
ATOM   4265  CB   PHE A 551     -32.053  37.582  30.968  1.00 45.78           A
ATOM   4266  CG   PHE A 551     -32.135  38.835  31.784  1.00 44.06           A
ATOM   4267  CD1  PHE A 551     -31.243  39.875  31.565  1.00 43.94           A
ATOM   4268  CD2  PHE A 551     -33.114  38.986  32.755  1.00 44.14           A
ATOM   4269  CE1  PHE A 551     -31.319  41.051  32.295  1.00 43.34           A
ATOM   4270  CE2  PHE A 551     -33.201  40.158  33.492  1.00 44.41           A
ATOM   4271  CZ   PHE A 551     -32.297  41.194  33.262  1.00 44.21           A
ATOM   4272  C    PHE A 551     -32.159  36.575  28.670  1.00 46.63           A
ATOM   4273  O    PHE A 551     -31.735  35.524  29.163  1.00 47.71           A
ATOM   4274  N    VAL A 552     -32.411  36.741  27.377  1.00 44.27           A
ATOM   4275  CA   VAL A 552     -32.204  35.685  26.415  1.00 41.41           A
ATOM   4276  CB   VAL A 552     -33.463  35.479  25.563  1.00 41.54           A
ATOM   4277  CG1  VAL A 552     -33.223  34.402  24.515  1.00 40.49           A
ATOM   4278  CG2  VAL A 552     -34.615  35.102  26.453  1.00 40.77           A
ATOM   4279  C    VAL A 552     -31.030  35.989  25.499  1.00 40.32           A
ATOM   4280  O    VAL A 552     -30.192  35.124  25.257  1.00 40.45           A
ATOM   4281  N    ALA A 553     -30.953  37.213  24.992  1.00 38.47           A
ATOM   4282  CA   ALA A 553     -29.861  37.548  24.086  1.00 39.13           A
ATOM   4283  CB   ALA A 553     -30.234  37.136  22.667  1.00 38.43           A
ATOM   4284  C    ALA A 553     -29.447  39.011  24.094  1.00 38.46           A
ATOM   4285  O    ALA A 553     -30.235  39.881  24.439  1.00 39.95           A
ATOM   4286  N    GLY A 554     -28.201  39.269  23.713  1.00 37.14           A
ATOM   4287  CA   GLY A 554     -27.710  40.632  23.644  1.00 37.04           A
ATOM   4288  C    GLY A 554     -28.022  41.241  22.280  1.00 37.27           A
ATOM   4289  O    GLY A 554     -28.037  40.546  21.258  1.00 36.70           A
ATOM   4290  N    TYR A 555     -28.270  42.545  22.250  1.00 36.40           A
ATOM   4291  CA   TYR A 555     -28.599  43.213  20.996  1.00 36.06           A
ATOM   4292  CB   TYR A 555     -30.114  43.372  20.869  1.00 35.45           A
ATOM   4293  CG   TYR A 555     -30.890  42.076  20.896  1.00 35.42           A
ATOM   4294  CD1  TYR A 555     -31.137  41.362  19.724  1.00 32.53           A
ATOM   4295  CE1  TYR A 555     -31.893  40.198  19.747  1.00 33.79           A
ATOM   4296  CD2  TYR A 555     -31.411  41.583  22.094  1.00 33.90           A
ATOM   4297  CE2  TYR A 555     -32.161  40.418  22.128  1.00 32.75           A
ATOM   4298  CZ   TYR A 555     -32.404  39.732  20.957  1.00 33.44           A
ATOM   4299  OH   TYR A 555     -33.175  38.594  20.990  1.00 32.92           A
ATOM   4300  C    TYR A 555     -27.960  44.586  20.911  1.00 35.95           A
ATOM   4301  O    TYR A 555     -28.520  45.494  20.306  1.00 34.73           A
ATOM   4302  N    SER A 556     -26.796  44.742  21.529  1.00 38.20           A
ATOM   4303  CA   SER A 556     -26.099  46.027  21.506  1.00 40.59           A
ATOM   4304  CB   SER A 556     -24.714  45.883  22.143  1.00 40.51           A
ATOM   4305  OG   SER A 556     -23.957  47.066  21.962  1.00 43.38           A
ATOM   4306  C    SER A 556     -25.961  46.577  20.078  1.00 39.85           A
ATOM   4307  O    SER A 556     -25.301  45.977  19.230  1.00 39.41           A
ATOM   4308  N    GLY A 557     -26.592  47.719  19.825  1.00 39.70           A
ATOM   4309  CA   GLY A 557     -26.532  48.320  18.503  1.00 39.01           A
ATOM   4310  C    GLY A 557     -27.358  47.563  17.480  1.00 39.16           A
ATOM   4311  O    GLY A 557     -27.196  47.763  16.279  1.00 41.14           A
ATOM   4312  N    GLY A 558     -28.257  46.705  17.955  1.00 38.91           A
ATOM   4313  CA   GLY A 558     -29.094  45.915  17.063  1.00 38.15           A
ATOM   4314  C    GLY A 558     -30.421  46.527  16.638  1.00 37.48           A
ATOM   4315  O    GLY A 558     -31.170  45.913  15.872  1.00 36.67           A
ATOM   4316  N    ASP A 559     -30.716  47.727  17.134  1.00 37.32           A
ATOM   4317  CA   ASP A 559     -31.951  48.420  16.793  1.00 36.41           A
ATOM   4318  CB   ASP A 559     -31.970  48.664  15.283  1.00 36.66           A
ATOM   4319  CG   ASP A 559     -33.005  49.687  14.867  1.00 39.13           A
ATOM   4320  OD1  ASP A 559     -33.290  50.611  15.662  1.00 39.17           A
ATOM   4321  OD2  ASP A 559     -33.518  49.578  13.735  1.00 39.14           A
ATOM   4322  C    ASP A 559     -33.171  47.601  17.236  1.00 36.67           A
ATOM   4323  O    ASP A 559     -34.185  47.553  16.548  1.00 37.42           A
ATOM   4324  N    ILE A 560     -33.064  46.965  18.396  1.00 36.70           A
ATOM   4325  CA   ILE A 560     -34.136  46.131  18.918  1.00 38.66           A
ATOM   4326  CB   ILE A 560     -33.574  44.800  19.473  1.00 36.60           A
ATOM   4327  CG2  ILE A 560     -34.679  43.991  20.156  1.00 33.38           A
ATOM   4328  CG1  ILE A 560     -32.956  43.996  18.342  1.00 34.51           A
ATOM   4329  CD1  ILE A 560     -33.946  43.600  17.284  1.00 38.35           A
ATOM   4330  C    ILE A 560     -34.957  46.804  20.012  1.00 43.04           A
ATOM   4331  O    ILE A 560     -34.425  47.496  20.881  1.00 43.01           A
ATOM   4332  N    TYR A 561     -36.260  46.567  19.972  1.00 48.01           A
```

FIGURE 5- 58 -

```
ATOM   4333  CA   TYR A 561     -37.176  47.147  20.934  1.00 54.93     A
ATOM   4334  CB   TYR A 561     -37.573  48.559  20.497  1.00 56.69     A
ATOM   4335  CG   TYR A 561     -38.684  49.181  21.318  1.00 58.27     A
ATOM   4336  CD1  TYR A 561     -38.399  50.002  22.400  1.00 59.77     A
ATOM   4337  CE1  TYR A 561     -39.420  50.579  23.149  1.00 62.68     A
ATOM   4338  CD2  TYR A 561     -40.024  48.949  21.005  1.00 59.61     A
ATOM   4339  CE2  TYR A 561     -41.050  49.513  21.746  1.00 60.75     A
ATOM   4340  CZ   TYR A 561     -40.745  50.328  22.816  1.00 62.94     A
ATOM   4341  OH   TYR A 561     -41.762  50.890  23.556  1.00 64.62     A
ATOM   4342  C    TYR A 561     -38.436  46.315  21.065  1.00 59.19     A
ATOM   4343  O    TYR A 561     -39.349  46.421  20.240  1.00 59.59     A
ATOM   4344  N    HIS A 562     -38.486  45.455  22.068  1.00 64.02     A
ATOM   4345  CA   HIS A 562     -39.705  44.699  22.279  1.00 69.33     A
ATOM   4346  CB   HIS A 562     -39.562  43.200  21.931  1.00 70.30     A
ATOM   4347  CG   HIS A 562     -38.247  42.593  22.297  1.00 71.05     A
ATOM   4348  CD2  HIS A 562     -37.267  42.069  21.524  1.00 71.82     A
ATOM   4349  ND1  HIS A 562     -37.843  42.412  23.602  1.00 73.81     A
ATOM   4350  CE1  HIS A 562     -36.671  41.800  23.617  1.00 74.63     A
ATOM   4351  NE2  HIS A 562     -36.299  41.581  22.368  1.00 72.98     A
ATOM   4352  C    HIS A 562     -40.094  44.927  23.721  1.00 71.45     A
ATOM   4353  O    HIS A 562     -39.525  44.345  24.644  1.00 72.63     A
ATOM   4354  N    SER A 563     -41.051  45.831  23.895  1.00 74.06     A
ATOM   4355  CA   SER A 563     -41.537  46.198  25.212  1.00 77.31     A
ATOM   4356  CB   SER A 563     -40.969  47.568  25.596  1.00 77.14     A
ATOM   4357  OG   SER A 563     -41.273  47.873  26.944  1.00 79.65     A
ATOM   4358  C    SER A 563     -43.069  46.224  25.264  1.00 78.04     A
ATOM   4359  O    SER A 563     -43.630  47.310  25.531  1.00 78.23     A
ATOM   4360  OXT  SER A 563     -43.688  45.157  25.037  1.00 78.79     A
ATOM   4361  CB   SER B   1     -45.690  21.142  -6.797  1.00 32.54     B
ATOM   4362  OG   SER B   1     -44.445  20.462  -6.715  1.00 34.22     B
ATOM   4363  C    SER B   1     -46.743  19.070  -7.664  1.00 34.31     B
ATOM   4364  O    SER B   1     -46.447  17.919  -7.324  1.00 36.15     B
ATOM   4365  N    SER B   1     -46.891  19.626  -5.232  1.00 31.74     B
ATOM   4366  CA   SER B   1     -46.866  20.178  -6.625  1.00 33.39     B
ATOM   4367  N    MET B   2     -46.963  19.408  -8.932  1.00 33.34     B
ATOM   4368  CA   MET B   2     -46.842  18.398  -9.979  1.00 33.36     B
ATOM   4369  CB   MET B   2     -47.562  18.838 -11.258  1.00 31.97     B
ATOM   4370  CG   MET B   2     -49.095  18.802 -11.197  1.00 33.27     B
ATOM   4371  SD   MET B   2     -49.847  17.227 -10.676  1.00 36.21     B
ATOM   4372  CE   MET B   2     -49.143  16.067 -11.823  1.00 32.55     B
ATOM   4373  C    MET B   2     -45.368  18.152 -10.290  1.00 33.06     B
ATOM   4374  O    MET B   2     -44.585  19.093 -10.430  1.00 33.63     B
ATOM   4375  N    SER B   3     -44.987  16.886 -10.384  1.00 31.13     B
ATOM   4376  CA   SER B   3     -43.612  16.543 -10.707  1.00 30.80     B
ATOM   4377  CB   SER B   3     -43.457  15.026 -10.750  1.00 30.72     B
ATOM   4378  OG   SER B   3     -44.293  14.449 -11.750  1.00 29.83     B
ATOM   4379  C    SER B   3     -43.258  17.127 -12.085  1.00 32.67     B
ATOM   4380  O    SER B   3     -42.139  17.614 -12.314  1.00 32.14     B
ATOM   4381  N    TYR B   4     -44.231  17.081 -12.995  1.00 31.54     B
ATOM   4382  CA   TYR B   4     -44.041  17.564 -14.352  1.00 31.49     B
ATOM   4383  CB   TYR B   4     -43.703  16.391 -15.284  1.00 32.86     B
ATOM   4384  CG   TYR B   4     -42.331  15.803 -15.073  1.00 33.57     B
ATOM   4385  CD1  TYR B   4     -41.209  16.389 -15.645  1.00 32.35     B
ATOM   4386  CE1  TYR B   4     -39.946  15.870 -15.423  1.00 32.34     B
ATOM   4387  CD2  TYR B   4     -42.149  14.676 -14.272  1.00 33.48     B
ATOM   4388  CE2  TYR B   4     -40.888  14.154 -14.046  1.00 31.48     B
ATOM   4389  CZ   TYR B   4     -39.795  14.757 -14.622  1.00 31.65     B
ATOM   4390  OH   TYR B   4     -38.539  14.258 -14.386  1.00 33.78     B
ATOM   4391  C    TYR B   4     -45.276  18.260 -14.893  1.00 31.38     B
ATOM   4392  O    TYR B   4     -46.388  18.024 -14.432  1.00 31.37     B
ATOM   4393  N    THR B   5     -45.054  19.114 -15.885  1.00 30.27     B
ATOM   4394  CA   THR B   5     -46.110  19.843 -16.552  1.00 29.95     B
ATOM   4395  CB   THR B   5     -46.164  21.299 -16.125  1.00 28.94     B
ATOM   4396  OG1  THR B   5     -46.414  21.378 -14.719  1.00 30.42     B
ATOM   4397  CG2  THR B   5     -47.282  22.005 -16.873  1.00 28.51     B
ATOM   4398  C    THR B   5     -45.725  19.801 -18.013  1.00 30.72     B
ATOM   4399  O    THR B   5     -44.634  20.239 -18.367  1.00 31.96     B
ATOM   4400  N    TRP B   6     -46.611  19.285 -18.860  1.00 29.25     B
ATOM   4401  CA   TRP B   6     -46.304  19.172 -20.279  1.00 26.82     B
ATOM   4402  CB   TRP B   6     -46.568  17.750 -20.735  1.00 25.17     B
ATOM   4403  CG   TRP B   6     -45.934  16.752 -19.845  1.00 27.05     B
ATOM   4404  CD2  TRP B   6     -44.538  16.440 -19.768  1.00 27.79     B
ATOM   4405  CE2  TRP B   6     -44.385  15.467 -18.755  1.00 27.57     B
ATOM   4406  CE3  TRP B   6     -43.402  16.884 -20.461  1.00 25.44     B
ATOM   4407  CD1  TRP B   6     -46.552  15.986 -18.901  1.00 27.44     B
ATOM   4408  NE1  TRP B   6     -45.628  15.211 -18.240  1.00 28.78     B
```

FIGURE 5- 59 -

```
ATOM   4409  CZ2 TRP B   6     -43.142  14.939 -18.410  1.00 27.30      B
ATOM   4410  CZ3 TRP B   6     -42.170  16.364 -20.118  1.00 24.68      B
ATOM   4411  CH2 TRP B   6     -42.048  15.396 -19.102  1.00 27.71      B
ATOM   4412  C   TRP B   6     -47.073  20.145 -21.155  1.00 26.69      B
ATOM   4413  O   TRP B   6     -48.244  20.403 -20.916  1.00 27.42      B
ATOM   4414  N   THR B   7     -46.406  20.674 -22.178  1.00 25.90      B
ATOM   4415  CA  THR B   7     -47.016  21.633 -23.089  1.00 26.44      B
ATOM   4416  CB  THR B   7     -45.978  22.639 -23.651  1.00 25.27      B
ATOM   4417  OG1 THR B   7     -44.993  21.928 -24.413  1.00 25.08      B
ATOM   4418  CG2 THR B   7     -45.299  23.402 -22.544  1.00 19.92      B
ATOM   4419  C   THR B   7     -47.645  20.939 -24.289  1.00 29.65      B
ATOM   4420  O   THR B   7     -48.511  21.504 -24.963  1.00 28.49      B
ATOM   4421  N   GLY B   8     -47.193  19.723 -24.568  1.00 32.23      B
ATOM   4422  CA  GLY B   8     -47.718  19.007 -25.713  1.00 35.15      B
ATOM   4423  C   GLY B   8     -46.623  18.720 -26.723  1.00 36.04      B
ATOM   4424  O   GLY B   8     -46.706  17.739 -27.461  1.00 35.53      B
ATOM   4425  N   ALA B   9     -45.601  19.573 -26.754  1.00 37.64      B
ATOM   4426  CA  ALA B   9     -44.471  19.387 -27.667  1.00 39.75      B
ATOM   4427  CB  ALA B   9     -43.453  20.506 -27.505  1.00 39.47      B
ATOM   4428  C   ALA B   9     -43.818  18.052 -27.354  1.00 41.08      B
ATOM   4429  O   ALA B   9     -43.824  17.606 -26.207  1.00 39.97      B
ATOM   4430  N   LEU B  10     -43.242  17.430 -28.376  1.00 43.90      B
ATOM   4431  CA  LEU B  10     -42.622  16.122 -28.230  1.00 45.76      B
ATOM   4432  CB  LEU B  10     -42.597  15.393 -29.575  1.00 45.95      B
ATOM   4433  CG  LEU B  10     -43.847  15.282 -30.441  1.00 46.79      B
ATOM   4434  CD1 LEU B  10     -43.548  14.315 -31.591  1.00 43.00      B
ATOM   4435  CD2 LEU B  10     -45.031  14.804 -29.604  1.00 45.61      B
ATOM   4436  C   LEU B  10     -41.212  16.072 -27.681  1.00 47.36      B
ATOM   4437  O   LEU B  10     -40.427  17.017 -27.788  1.00 45.94      B
ATOM   4438  N   ILE B  11     -40.906  14.926 -27.096  1.00 50.67      B
ATOM   4439  CA  ILE B  11     -39.588  14.656 -26.582  1.00 54.75      B
ATOM   4440  CB  ILE B  11     -39.650  13.644 -25.438  1.00 54.39      B
ATOM   4441  CG2 ILE B  11     -38.250  13.226 -25.026  1.00 55.02      B
ATOM   4442  CG1 ILE B  11     -40.411  14.267 -24.267  1.00 53.81      B
ATOM   4443  CD1 ILE B  11     -40.570  13.355 -23.086  1.00 55.28      B
ATOM   4444  C   ILE B  11     -39.016  14.028 -27.835  1.00 58.22      B
ATOM   4445  O   ILE B  11     -39.193  12.834 -28.082  1.00 58.37      B
ATOM   4446  N   THR B  12     -38.367  14.863 -28.642  1.00 62.99      B
ATOM   4447  CA  THR B  12     -37.801  14.454 -29.921  1.00 67.61      B
ATOM   4448  CB  THR B  12     -37.657  15.671 -30.849  1.00 65.97      B
ATOM   4449  OG1 THR B  12     -36.740  16.610 -30.277  1.00 64.98      B
ATOM   4450  CG2 THR B  12     -39.005  16.345 -31.041  1.00 65.30      B
ATOM   4451  C   THR B  12     -36.471  13.703 -29.899  1.00 72.98      B
ATOM   4452  O   THR B  12     -35.693  13.811 -28.947  1.00 72.97      B
ATOM   4453  N   PRO B  13     -36.205  12.921 -30.967  1.00 77.95      B
ATOM   4454  CD  PRO B  13     -37.224  12.605 -31.983  1.00 78.32      B
ATOM   4455  CA  PRO B  13     -35.006  12.101 -31.191  1.00 81.77      B
ATOM   4456  CB  PRO B  13     -35.435  11.160 -32.318  1.00 81.01      B
ATOM   4457  CG  PRO B  13     -36.932  11.169 -32.259  1.00 79.46      B
ATOM   4458  C   PRO B  13     -33.800  12.936 -31.610  1.00 85.77      B
ATOM   4459  O   PRO B  13     -33.495  13.956 -30.995  1.00 86.33      B
ATOM   4460  N   CYS B  14     -33.134  12.476 -32.670  1.00 90.42      B
ATOM   4461  CA  CYS B  14     -31.961  13.129 -33.256  1.00 95.07      B
ATOM   4462  CB  CYS B  14     -31.170  13.904 -32.196  1.00 95.87      B
ATOM   4463  SG  CYS B  14     -29.745  14.804 -32.851  1.00 99.06      B
ATOM   4464  C   CYS B  14     -31.032  12.113 -33.922  1.00 97.27      B
ATOM   4465  O   CYS B  14     -30.229  12.468 -34.789  1.00 97.60      B
ATOM   4466  N   ALA B  15     -31.148  10.849 -33.521  1.00 99.87      B
ATOM   4467  CA  ALA B  15     -30.296   9.793 -34.067  1.00102.19      B
ATOM   4468  CB  ALA B  15     -29.294   9.341 -33.002  1.00101.69      B
ATOM   4469  C   ALA B  15     -31.082   8.589 -34.583  1.00103.67      B
ATOM   4470  O   ALA B  15     -30.499   7.537 -34.855  1.00104.59      B
ATOM   4471  N   ALA B  16     -32.397   8.760 -34.715  1.00104.77      B
ATOM   4472  CA  ALA B  16     -33.320   7.724 -35.185  1.00105.80      B
ATOM   4473  CB  ALA B  16     -32.590   6.663 -36.035  1.00105.34      B
ATOM   4474  C   ALA B  16     -34.039   7.056 -34.013  1.00106.81      B
ATOM   4475  O   ALA B  16     -34.139   5.826 -33.953  1.00107.61      B
ATOM   4476  N   GLU B  17     -34.528   7.879 -33.082  1.00106.85      B
ATOM   4477  CA  GLU B  17     -35.270   7.399 -31.915  1.00106.63      B
ATOM   4478  CB  GLU B  17     -35.175   8.402 -30.755  1.00106.03      B
ATOM   4479  CG  GLU B  17     -33.927   8.288 -29.891  1.00106.21      B
ATOM   4480  CD  GLU B  17     -33.823   9.407 -28.860  1.00106.39      B
ATOM   4481  OE1 GLU B  17     -34.797   9.622 -28.107  1.00106.61      B
ATOM   4482  OE2 GLU B  17     -32.765  10.071 -28.798  1.00106.03      B
ATOM   4483  C   GLU B  17     -36.742   7.203 -32.291  1.00106.78      B
ATOM   4484  O   GLU B  17     -37.585   7.966 -31.776  1.00107.14      B
```

FIGURE 5- 60 -

```
ATOM   4485  OXT GLU B  17     -37.038   6.297 -33.103  1.00106.39      B
ATOM   4486  CB  MET B  36     -35.705 -11.696 -27.960  1.00 89.55      B
ATOM   4487  CG  MET B  36     -36.849 -12.702 -27.846  1.00 91.70      B
ATOM   4488  SD  MET B  36     -36.518 -13.851 -26.463  1.00 95.67      B
ATOM   4489  CE  MET B  36     -37.785 -13.352 -25.265  1.00 94.38      B
ATOM   4490  C   MET B  36     -35.288  -9.235 -28.044  1.00 86.85      B
ATOM   4491  O   MET B  36     -35.567  -8.950 -26.880  1.00 85.81      B
ATOM   4492  N   MET B  36     -35.631 -10.594 -30.193  1.00 86.55      B
ATOM   4493  CA  MET B  36     -36.002 -10.411 -28.745  1.00 88.07      B
ATOM   4494  N   VAL B  37     -34.393  -8.540 -28.744  1.00 85.40      B
ATOM   4495  CA  VAL B  37     -33.646  -7.445 -28.125  1.00 83.86      B
ATOM   4496  CB  VAL B  37     -32.155  -7.777 -28.119  1.00 83.91      B
ATOM   4497  CG1 VAL B  37     -31.420  -6.811 -27.217  1.00 83.58      B
ATOM   4498  CG2 VAL B  37     -31.958  -9.205 -27.674  1.00 82.85      B
ATOM   4499  C   VAL B  37     -33.822  -6.055 -28.728  1.00 82.47      B
ATOM   4500  O   VAL B  37     -33.385  -5.761 -29.831  1.00 81.14      B
ATOM   4501  N   TYR B  38     -34.411  -5.178 -27.926  1.00 82.24      B
ATOM   4502  CA  TYR B  38     -34.723  -3.801 -28.301  1.00 80.51      B
ATOM   4503  CB  TYR B  38     -36.199  -3.552 -28.055  1.00 80.79      B
ATOM   4504  CG  TYR B  38     -36.573  -3.620 -26.590  1.00 80.51      B
ATOM   4505  CD1 TYR B  38     -36.627  -4.840 -25.910  1.00 80.72      B
ATOM   4506  CE1 TYR B  38     -36.992  -4.896 -24.543  1.00 80.85      B
ATOM   4507  CD2 TYR B  38     -36.882  -2.461 -25.885  1.00 80.09      B
ATOM   4508  CE2 TYR B  38     -37.240  -2.503 -24.541  1.00 80.75      B
ATOM   4509  CZ  TYR B  38     -37.298  -3.720 -23.875  1.00 80.99      B
ATOM   4510  OH  TYR B  38     -37.696  -3.745 -22.559  1.00 80.34      B
ATOM   4511  C   TYR B  38     -33.962  -2.702 -27.547  1.00 79.53      B
ATOM   4512  O   TYR B  38     -33.416  -2.915 -26.468  1.00 77.91      B
ATOM   4513  N   ALA B  39     -33.933  -1.520 -28.151  1.00 79.48      B
ATOM   4514  CA  ALA B  39     -33.284  -0.347 -27.578  1.00 79.42      B
ATOM   4515  CB  ALA B  39     -32.235   0.190 -28.537  1.00 79.49      B
ATOM   4516  C   ALA B  39     -34.405   0.665 -27.394  1.00 78.83      B
ATOM   4517  O   ALA B  39     -35.154   0.931 -28.331  1.00 78.04      B
ATOM   4518  N   THR B  40     -34.537   1.207 -26.186  1.00 78.51      B
ATOM   4519  CA  THR B  40     -35.597   2.171 -25.912  1.00 78.61      B
ATOM   4520  CB  THR B  40     -35.546   2.675 -24.457  1.00 77.00      B
ATOM   4521  OG1 THR B  40     -34.232   3.162 -24.163  1.00 76.98      B
ATOM   4522  CG2 THR B  40     -35.896   1.554 -23.502  1.00 76.09      B
ATOM   4523  C   THR B  40     -35.486   3.359 -26.859  1.00 79.67      B
ATOM   4524  O   THR B  40     -34.384   3.783 -27.217  1.00 80.16      B
ATOM   4525  N   THR B  41     -36.634   3.882 -27.278  1.00 80.14      B
ATOM   4526  CA  THR B  41     -36.674   5.020 -28.191  1.00 80.48      B
ATOM   4527  CB  THR B  41     -37.268   4.609 -29.547  1.00 80.04      B
ATOM   4528  OG1 THR B  41     -38.239   3.569 -29.345  1.00 79.93      B
ATOM   4529  CG2 THR B  41     -36.165   4.145 -30.487  1.00 78.86      B
ATOM   4530  C   THR B  41     -37.510   6.156 -27.616  1.00 81.00      B
ATOM   4531  O   THR B  41     -38.011   6.050 -26.493  1.00 81.77      B
ATOM   4532  N   SER B  42     -37.670   7.229 -28.391  1.00 80.13      B
ATOM   4533  CA  SER B  42     -38.448   8.381 -27.946  1.00 78.97      B
ATOM   4534  CB  SER B  42     -37.948   9.663 -28.619  1.00 78.06      B
ATOM   4535  OG  SER B  42     -38.128   9.613 -30.018  1.00 76.62      B
ATOM   4536  C   SER B  42     -39.930   8.188 -28.242  1.00 78.64      B
ATOM   4537  O   SER B  42     -40.759   9.013 -27.857  1.00 79.47      B
ATOM   4538  N   ARG B  43     -40.263   7.096 -28.922  1.00 77.43      B
ATOM   4539  CA  ARG B  43     -41.652   6.809 -29.251  1.00 75.79      B
ATOM   4540  CB  ARG B  43     -41.714   5.795 -30.403  1.00 76.77      B
ATOM   4541  CG  ARG B  43     -41.015   6.292 -31.674  1.00 77.59      B
ATOM   4542  CD  ARG B  43     -41.226   5.377 -32.886  1.00 78.61      B
ATOM   4543  NE  ARG B  43     -40.139   4.421 -33.113  1.00 78.70      B
ATOM   4544  CZ  ARG B  43     -39.972   3.284 -32.442  1.00 79.93      B
ATOM   4545  NH1 ARG B  43     -40.823   2.936 -31.481  1.00 81.13      B
ATOM   4546  NH2 ARG B  43     -38.954   2.485 -32.741  1.00 79.11      B
ATOM   4547  C   ARG B  43     -42.405   6.295 -28.013  1.00 74.10      B
ATOM   4548  O   ARG B  43     -43.590   6.591 -27.831  1.00 74.21      B
ATOM   4549  N   SER B  44     -41.708   5.547 -27.156  1.00 71.01      B
ATOM   4550  CA  SER B  44     -42.307   5.008 -25.929  1.00 68.15      B
ATOM   4551  CB  SER B  44     -41.637   3.687 -25.532  1.00 68.16      B
ATOM   4552  OG  SER B  44     -40.265   3.878 -25.217  1.00 66.26      B
ATOM   4553  C   SER B  44     -42.141   6.001 -24.786  1.00 66.20      B
ATOM   4554  O   SER B  44     -42.380   5.673 -23.621  1.00 64.84      B
ATOM   4555  N   ALA B  45     -41.726   7.215 -25.133  1.00 63.66      B
ATOM   4556  CA  ALA B  45     -41.507   8.268 -24.156  1.00 62.02      B
ATOM   4557  CB  ALA B  45     -40.842   9.455 -24.827  1.00 60.91      B
ATOM   4558  C   ALA B  45     -42.794   8.708 -23.457  1.00 61.03      B
ATOM   4559  O   ALA B  45     -42.839   8.813 -22.228  1.00 60.97      B
ATOM   4560  N   SER B  46     -43.839   8.967 -24.236  1.00 59.30      B
```

FIGURE 5- 61 -

```
ATOM   4561  CA   SER B  46     -45.110    9.395 -23.665  1.00 57.35      B
ATOM   4562  CB   SER B  46     -46.188    9.445 -24.750  1.00 56.92      B
ATOM   4563  OG   SER B  46     -47.460    9.729 -24.189  1.00 56.23      B
ATOM   4564  C    SER B  46     -45.536    8.426 -22.569  1.00 56.52      B
ATOM   4565  O    SER B  46     -46.071    8.821 -21.532  1.00 54.81      B
ATOM   4566  N    LEU B  47     -45.279    7.149 -22.815  1.00 56.07      B
ATOM   4567  CA   LEU B  47     -45.632    6.089 -21.889  1.00 56.02      B
ATOM   4568  CB   LEU B  47     -45.252    4.754 -22.520  1.00 59.41      B
ATOM   4569  CG   LEU B  47     -45.580    3.468 -21.774  1.00 63.18      B
ATOM   4570  CD1  LEU B  47     -46.972    3.556 -21.148  1.00 63.49      B
ATOM   4571  CD2  LEU B  47     -45.474    2.301 -22.759  1.00 63.75      B
ATOM   4572  C    LEU B  47     -44.953    6.265 -20.532  1.00 54.99      B
ATOM   4573  O    LEU B  47     -45.550    5.998 -19.482  1.00 53.39      B
ATOM   4574  N    ARG B  48     -43.707    6.729 -20.565  1.00 52.99      B
ATOM   4575  CA   ARG B  48     -42.924    6.957 -19.356  1.00 51.51      B
ATOM   4576  CB   ARG B  48     -41.434    6.964 -19.725  1.00 50.57      B
ATOM   4577  CG   ARG B  48     -40.501    7.759 -18.824  1.00 50.31      B
ATOM   4578  CD   ARG B  48     -40.458    7.284 -17.330  1.00 52.11      B
ATOM   4579  NE   ARG B  48     -40.347    5.838 -17.244  1.00 54.01      B
ATOM   4580  CZ   ARG B  48     -39.916    5.213 -16.149  1.00 55.96      B
ATOM   4581  NH1  ARG B  48     -39.530    5.899 -15.077  1.00 52.75      B
ATOM   4582  NH2  ARG B  48     -39.900    3.886 -16.119  1.00 58.90      B
ATOM   4583  C    ARG B  48     -43.340    8.255 -18.640  1.00 51.02      B
ATOM   4584  O    ARG B  48     -43.413    8.292 -17.405  1.00 50.80      B
ATOM   4585  N    GLN B  49     -43.630    9.302 -19.414  1.00 48.40      B
ATOM   4586  CA   GLN B  49     -44.051   10.591 -18.859  1.00 47.31      B
ATOM   4587  CB   GLN B  49     -44.378   11.569 -19.983  1.00 46.24      B
ATOM   4588  CG   GLN B  49     -43.253   11.766 -20.967  1.00 47.59      B
ATOM   4589  CD   GLN B  49     -43.633   12.680 -22.111  1.00 47.89      B
ATOM   4590  OE1  GLN B  49     -43.836   13.882 -21.929  1.00 47.81      B
ATOM   4591  NE2  GLN B  49     -43.737   12.109 -23.304  1.00 48.98      B
ATOM   4592  C    GLN B  49     -45.292   10.404 -18.003  1.00 47.30      B
ATOM   4593  O    GLN B  49     -45.428   10.979 -16.922  1.00 46.44      B
ATOM   4594  N    LYS B  50     -46.202    9.596 -18.524  1.00 47.73      B
ATOM   4595  CA   LYS B  50     -47.451    9.277 -17.861  1.00 48.15      B
ATOM   4596  CB   LYS B  50     -48.204    8.231 -18.702  1.00 49.88      B
ATOM   4597  CG   LYS B  50     -49.715    8.153 -18.510  1.00 50.13      B
ATOM   4598  CD   LYS B  50     -50.118    7.364 -17.279  1.00 50.49      B
ATOM   4599  CE   LYS B  50     -51.621    7.103 -17.236  1.00 52.02      B
ATOM   4600  NZ   LYS B  50     -52.047    6.167 -16.199  1.00 54.96      B
ATOM   4601  C    LYS B  50     -47.115    8.712 -16.487  1.00 47.73      B
ATOM   4602  O    LYS B  50     -47.757    9.045 -15.490  1.00 48.24      B
ATOM   4603  N    LYS B  51     -46.083    7.873 -16.442  1.00 46.84      B
ATOM   4604  CA   LYS B  51     -45.681    7.232 -15.200  1.00 45.81      B
ATOM   4605  CB   LYS B  51     -44.764    6.036 -15.477  1.00 47.82      B
ATOM   4606  CG   LYS B  51     -44.404    5.302 -14.192  1.00 50.78      B
ATOM   4607  CD   LYS B  51     -43.637    4.017 -14.413  1.00 53.36      B
ATOM   4608  CE   LYS B  51     -43.577    3.221 -13.107  1.00 54.67      B
ATOM   4609  NZ   LYS B  51     -42.683    2.033 -13.195  1.00 55.38      B
ATOM   4610  C    LYS B  51     -45.000    8.113 -14.171  1.00 43.53      B
ATOM   4611  O    LYS B  51     -45.189    7.914 -12.969  1.00 43.25      B
ATOM   4612  N    VAL B  52     -44.198    9.068 -14.632  1.00 40.96      B
ATOM   4613  CA   VAL B  52     -43.466    9.945 -13.724  1.00 38.53      B
ATOM   4614  CB   VAL B  52     -42.084   10.270 -14.287  1.00 37.13      B
ATOM   4615  CG1  VAL B  52     -41.326    8.983 -14.537  1.00 35.79      B
ATOM   4616  CG2  VAL B  52     -42.214   11.072 -15.562  1.00 34.04      B
ATOM   4617  C    VAL B  52     -44.175   11.251 -13.404  1.00 38.49      B
ATOM   4618  O    VAL B  52     -43.690   12.054 -12.606  1.00 38.43      B
ATOM   4619  N    THR B  53     -45.331   11.454 -14.021  1.00 37.38      B
ATOM   4620  CA   THR B  53     -46.098   12.669 -13.801  1.00 36.37      B
ATOM   4621  CB   THR B  53     -46.754   13.149 -15.108  1.00 34.36      B
ATOM   4622  OG1  THR B  53     -45.750   13.294 -16.118  1.00 33.78      B
ATOM   4623  CG2  THR B  53     -47.450   14.482 -14.895  1.00 32.23      B
ATOM   4624  C    THR B  53     -47.184   12.489 -12.749  1.00 35.93      B
ATOM   4625  O    THR B  53     -48.191   11.827 -12.979  1.00 36.89      B
ATOM   4626  N    PHE B  54     -46.981   13.090 -11.591  1.00 35.22      B
ATOM   4627  CA   PHE B  54     -47.969   12.987 -10.540  1.00 35.70      B
ATOM   4628  CB   PHE B  54     -47.941   11.581  -9.924  1.00 34.51      B
ATOM   4629  CG   PHE B  54     -46.626   11.205  -9.299  1.00 36.40      B
ATOM   4630  CD1  PHE B  54     -46.345   11.534  -7.978  1.00 35.17      B
ATOM   4631  CD2  PHE B  54     -45.664   10.516 -10.033  1.00 37.51      B
ATOM   4632  CE1  PHE B  54     -45.131   11.176  -7.390  1.00 34.51      B
ATOM   4633  CE2  PHE B  54     -44.452   10.157  -9.455  1.00 36.98      B
ATOM   4634  CZ   PHE B  54     -44.137   10.490  -8.126  1.00 35.53      B
ATOM   4635  C    PHE B  54     -47.716   14.055  -9.492  1.00 36.19      B
ATOM   4636  O    PHE B  54     -46.690   14.728  -9.515  1.00 36.35      B
```

FIGURE 5- 62 -

```
ATOM   4637  N    ASP B  55     -48.664  14.222  -8.582  1.00 37.76      B
ATOM   4638  CA   ASP B  55     -48.524  15.219  -7.538  1.00 38.61      B
ATOM   4639  CB   ASP B  55     -49.890  15.818  -7.206  1.00 39.14      B
ATOM   4640  CG   ASP B  55     -49.795  17.020  -6.287  1.00 41.38      B
ATOM   4641  OD1  ASP B  55     -48.670  17.415  -5.914  1.00 42.50      B
ATOM   4642  OD2  ASP B  55     -50.864  17.575  -5.935  1.00 43.16      B
ATOM   4643  C    ASP B  55     -47.907  14.595  -6.291  1.00 38.29      B
ATOM   4644  O    ASP B  55     -48.344  13.536  -5.848  1.00 37.30      B
ATOM   4645  N    ARG B  56     -46.873  15.245  -5.755  1.00 37.62      B
ATOM   4646  CA   ARG B  56     -46.207  14.776  -4.548  1.00 37.08      B
ATOM   4647  CB   ARG B  56     -44.713  15.096  -4.566  1.00 34.39      B
ATOM   4648  CG   ARG B  56     -43.887  14.328  -5.579  1.00 35.01      B
ATOM   4649  CD   ARG B  56     -44.161  14.792  -7.002  1.00 33.69      B
ATOM   4650  NE   ARG B  56     -43.933  16.227  -7.191  1.00 31.21      B
ATOM   4651  CZ   ARG B  56     -42.739  16.805  -7.248  1.00 28.66      B
ATOM   4652  NH1  ARG B  56     -41.635  16.080  -7.134  1.00 26.02      B
ATOM   4653  NH2  ARG B  56     -42.654  18.117  -7.427  1.00 29.01      B
ATOM   4654  C    ARG B  56     -46.842  15.522  -3.392  1.00 38.91      B
ATOM   4655  O    ARG B  56     -46.920  16.746  -3.419  1.00 40.25      B
ATOM   4656  N    LEU B  57     -47.306  14.790  -2.383  1.00 40.34      B
ATOM   4657  CA   LEU B  57     -47.920  15.417  -1.222  1.00 41.47      B
ATOM   4658  CB   LEU B  57     -49.406  15.084  -1.181  1.00 43.10      B
ATOM   4659  CG   LEU B  57     -50.291  16.223  -0.676  1.00 45.92      B
ATOM   4660  CD1  LEU B  57     -50.089  17.466  -1.537  1.00 47.23      B
ATOM   4661  CD2  LEU B  57     -51.745  15.779  -0.716  1.00 47.27      B
ATOM   4662  C    LEU B  57     -47.194  14.895   0.020  1.00 41.48      B
ATOM   4663  O    LEU B  57     -47.610  13.933   0.661  1.00 44.03      B
ATOM   4664  N    GLN B  58     -46.106  15.573   0.349  1.00 39.60      B
ATOM   4665  CA   GLN B  58     -45.216  15.219   1.445  1.00 37.90      B
ATOM   4666  CB   GLN B  58     -43.827  15.718   1.039  1.00 36.46      B
ATOM   4667  CG   GLN B  58     -42.659  15.321   1.869  1.00 34.45      B
ATOM   4668  CD   GLN B  58     -41.378  15.897   1.290  1.00 36.37      B
ATOM   4669  OE1  GLN B  58     -41.310  17.086   0.959  1.00 34.51      B
ATOM   4670  NE2  GLN B  58     -40.356  15.062   1.167  1.00 36.18      B
ATOM   4671  C    GLN B  58     -45.611  15.748   2.830  1.00 36.87      B
ATOM   4672  O    GLN B  58     -46.129  16.850   2.959  1.00 36.69      B
ATOM   4673  N    VAL B  59     -45.365  14.944   3.862  1.00 36.67      B
ATOM   4674  CA   VAL B  59     -45.659  15.325   5.247  1.00 37.33      B
ATOM   4675  CB   VAL B  59     -46.974  14.689   5.784  1.00 36.49      B
ATOM   4676  CG1  VAL B  59     -47.163  15.082   7.235  1.00 33.36      B
ATOM   4677  CG2  VAL B  59     -48.174  15.141   4.964  1.00 35.36      B
ATOM   4678  C    VAL B  59     -44.527  14.831   6.146  1.00 37.87      B
ATOM   4679  O    VAL B  59     -44.363  13.627   6.335  1.00 38.99      B
ATOM   4680  N    LEU B  60     -43.763  15.754   6.715  1.00 37.58      B
ATOM   4681  CA   LEU B  60     -42.644  15.385   7.582  1.00 39.44      B
ATOM   4682  CB   LEU B  60     -41.487  16.375   7.361  1.00 37.47      B
ATOM   4683  CG   LEU B  60     -41.192  16.673   5.881  1.00 37.81      B
ATOM   4684  CD1  LEU B  60     -40.483  18.008   5.734  1.00 33.80      B
ATOM   4685  CD2  LEU B  60     -40.367  15.537   5.285  1.00 36.21      B
ATOM   4686  C    LEU B  60     -43.035  15.344   9.070  1.00 40.41      B
ATOM   4687  O    LEU B  60     -43.971  16.022   9.492  1.00 41.24      B
ATOM   4688  N    ASP B  61     -42.318  14.542   9.858  1.00 41.17      B
ATOM   4689  CA   ASP B  61     -42.580  14.428  11.291  1.00 41.17      B
ATOM   4690  CB   ASP B  61     -43.121  13.043  11.633  1.00 39.10      B
ATOM   4691  CG   ASP B  61     -42.285  11.931  11.042  1.00 40.41      B
ATOM   4692  OD1  ASP B  61     -41.065  12.134  10.865  1.00 40.08      B
ATOM   4693  OD2  ASP B  61     -42.849  10.849  10.764  1.00 39.99      B
ATOM   4694  C    ASP B  61     -41.309  14.688  12.097  1.00 42.70      B
ATOM   4695  O    ASP B  61     -40.360  15.284  11.589  1.00 43.03      B
ATOM   4696  N    ASP B  62     -41.289  14.236  13.350  1.00 42.74      B
ATOM   4697  CA   ASP B  62     -40.126  14.449  14.199  1.00 41.58      B
ATOM   4698  CB   ASP B  62     -40.496  14.298  15.672  1.00 42.88      B
ATOM   4699  CG   ASP B  62     -41.237  15.501  16.215  1.00 45.99      B
ATOM   4700  OD1  ASP B  62     -41.149  16.582  15.597  1.00 48.16      B
ATOM   4701  OD2  ASP B  62     -41.896  15.371  17.273  1.00 48.69      B
ATOM   4702  C    ASP B  62     -38.950  13.532  13.891  1.00 41.64      B
ATOM   4703  O    ASP B  62     -37.794  13.919  14.083  1.00 41.74      B
ATOM   4704  N    HIS B  63     -39.228  12.317  13.431  1.00 40.98      B
ATOM   4705  CA   HIS B  63     -38.147  11.386  13.128  1.00 40.40      B
ATOM   4706  CB   HIS B  63     -38.692  10.007  12.766  1.00 42.71      B
ATOM   4707  CG   HIS B  63     -39.162   9.217  13.948  1.00 47.45      B
ATOM   4708  CD2  HIS B  63     -40.350   8.623  14.210  1.00 48.50      B
ATOM   4709  ND1  HIS B  63     -38.354   8.950  15.032  1.00 49.26      B
ATOM   4710  CE1  HIS B  63     -39.024   8.225  15.910  1.00 49.15      B
ATOM   4711  NE2  HIS B  63     -40.237   8.013  15.436  1.00 49.60      B
ATOM   4712  C    HIS B  63     -37.327  11.922  11.980  1.00 39.44      B
```

FIGURE 5- 63 -

```
ATOM   4713  O    HIS B  63     -36.106   11.791   11.957  1.00 38.87           B
ATOM   4714  N    TYR B  64     -38.012   12.536   11.027  1.00 38.44           B
ATOM   4715  CA   TYR B  64     -37.355   13.098    9.865  1.00 38.25           B
ATOM   4716  CB   TYR B  64     -38.404   13.607    8.872  1.00 38.64           B
ATOM   4717  CG   TYR B  64     -37.842   14.311    7.657  1.00 39.41           B
ATOM   4718  CD1  TYR B  64     -37.423   13.591    6.538  1.00 39.70           B
ATOM   4719  CE1  TYR B  64     -36.922   14.243    5.409  1.00 40.19           B
ATOM   4720  CD2  TYR B  64     -37.739   15.704    7.620  1.00 39.10           B
ATOM   4721  CE2  TYR B  64     -37.234   16.364    6.497  1.00 39.33           B
ATOM   4722  CZ   TYR B  64     -36.830   15.630    5.395  1.00 38.96           B
ATOM   4723  OH   TYR B  64     -36.346   16.277    4.281  1.00 38.55           B
ATOM   4724  C    TYR B  64     -36.464   14.244   10.316  1.00 37.87           B
ATOM   4725  O    TYR B  64     -35.264   14.268   10.023  1.00 37.28           B
ATOM   4726  N    ARG B  65     -37.060   15.185   11.041  1.00 36.70           B
ATOM   4727  CA   ARG B  65     -36.336   16.346   11.525  1.00 37.26           B
ATOM   4728  CB   ARG B  65     -37.302   17.292   12.241  1.00 38.54           B
ATOM   4729  CG   ARG B  65     -38.243   18.017   11.270  1.00 41.36           B
ATOM   4730  CD   ARG B  65     -39.095   19.045   11.973  1.00 44.39           B
ATOM   4731  NE   ARG B  65     -40.149   18.414   12.759  1.00 47.77           B
ATOM   4732  CZ   ARG B  65     -41.340   18.083   12.272  1.00 48.25           B
ATOM   4733  NH1  ARG B  65     -41.623   18.331   11.000  1.00 49.09           B
ATOM   4734  NH2  ARG B  65     -42.242   17.500   13.054  1.00 47.38           B
ATOM   4735  C    ARG B  65     -35.180   15.947   12.425  1.00 37.36           B
ATOM   4736  O    ARG B  65     -34.139   16.613   12.458  1.00 37.78           B
ATOM   4737  N    ASP B  66     -35.365   14.845   13.142  1.00 37.05           B
ATOM   4738  CA   ASP B  66     -34.339   14.325   14.033  1.00 37.17           B
ATOM   4739  CB   ASP B  66     -34.886   13.153   14.851  1.00 39.65           B
ATOM   4740  CG   ASP B  66     -35.628   13.591   16.088  1.00 41.30           B
ATOM   4741  OD1  ASP B  66     -35.970   14.794   16.187  1.00 40.71           B
ATOM   4742  OD2  ASP B  66     -35.870   12.713   16.954  1.00 41.01           B
ATOM   4743  C    ASP B  66     -33.125   13.834   13.247  1.00 36.44           B
ATOM   4744  O    ASP B  66     -31.984   14.185   13.566  1.00 36.08           B
ATOM   4745  N    VAL B  67     -33.378   13.008   12.229  1.00 33.41           B
ATOM   4746  CA   VAL B  67     -32.307   12.438   11.420  1.00 30.49           B
ATOM   4747  CB   VAL B  67     -32.848   11.338   10.463  1.00 29.81           B
ATOM   4748  CG1  VAL B  67     -31.762   10.893    9.503  1.00 26.59           B
ATOM   4749  CG2  VAL B  67     -33.335   10.139   11.269  1.00 28.56           B
ATOM   4750  C    VAL B  67     -31.563   13.491   10.613  1.00 30.10           B
ATOM   4751  O    VAL B  67     -30.348   13.376   10.395  1.00 27.51           B
ATOM   4752  N    LEU B  68     -32.291   14.518   10.180  1.00 29.31           B
ATOM   4753  CA   LEU B  68     -31.686   15.581    9.394  1.00 28.33           B
ATOM   4754  CB   LEU B  68     -32.750   16.555    8.898  1.00 24.70           B
ATOM   4755  CG   LEU B  68     -32.300   17.800    8.129  1.00 23.34           B
ATOM   4756  CD1  LEU B  68     -31.279   17.454    7.068  1.00 22.45           B
ATOM   4757  CD2  LEU B  68     -33.523   18.455    7.509  1.00 18.53           B
ATOM   4758  C    LEU B  68     -30.658   16.298   10.239  1.00 29.56           B
ATOM   4759  O    LEU B  68     -29.512   16.461    9.829  1.00 31.78           B
ATOM   4760  N    LYS B  69     -31.054   16.710   11.431  1.00 29.69           B
ATOM   4761  CA   LYS B  69     -30.116   17.397   12.304  1.00 30.21           B
ATOM   4762  CB   LYS B  69     -30.781   17.748   13.632  1.00 29.25           B
ATOM   4763  CG   LYS B  69     -31.895   18.733   13.519  1.00 28.53           B
ATOM   4764  CD   LYS B  69     -32.355   19.096   14.890  1.00 31.22           B
ATOM   4765  CE   LYS B  69     -33.527   20.040   14.845  1.00 34.27           B
ATOM   4766  NZ   LYS B  69     -34.050   20.255   16.217  1.00 37.17           B
ATOM   4767  C    LYS B  69     -28.881   16.544   12.575  1.00 29.84           B
ATOM   4768  O    LYS B  69     -27.782   17.064   12.728  1.00 29.65           B
ATOM   4769  N    GLU B  70     -29.064   15.231   12.643  1.00 32.38           B
ATOM   4770  CA   GLU B  70     -27.949   14.325   12.917  1.00 33.35           B
ATOM   4771  CB   GLU B  70     -28.470   12.916   13.229  1.00 33.75           B
ATOM   4772  CG   GLU B  70     -29.062   12.745   14.644  1.00 34.26           B
ATOM   4773  CD   GLU B  70     -29.812   11.411   14.836  1.00 38.07           B
ATOM   4774  OE1  GLU B  70     -29.435   10.403   14.192  1.00 36.10           B
ATOM   4775  OE2  GLU B  70     -30.775   11.368   15.647  1.00 38.45           B
ATOM   4776  C    GLU B  70     -27.014   14.296   11.727  1.00 33.26           B
ATOM   4777  O    GLU B  70     -25.795   14.321   11.877  1.00 33.58           B
ATOM   4778  N    MET B  71     -27.596   14.264   10.536  1.00 34.29           B
ATOM   4779  CA   MET B  71     -26.807   14.239    9.313  1.00 34.32           B
ATOM   4780  CB   MET B  71     -27.712   13.990    8.112  1.00 34.83           B
ATOM   4781  CG   MET B  71     -28.342   12.616    8.072  1.00 33.13           B
ATOM   4782  SD   MET B  71     -29.640   12.616    6.842  1.00 36.62           B
ATOM   4783  CE   MET B  71     -28.754   12.221    5.416  1.00 31.48           B
ATOM   4784  C    MET B  71     -26.080   15.563    9.136  1.00 34.22           B
ATOM   4785  O    MET B  71     -24.948   15.604    8.656  1.00 34.60           B
ATOM   4786  N    LYS B  72     -26.734   16.649    9.526  1.00 33.11           B
ATOM   4787  CA   LYS B  72     -26.133   17.966    9.395  1.00 32.22           B
ATOM   4788  CB   LYS B  72     -27.180   19.050    9.638  1.00 30.28           B
```

FIGURE 5- 64 -

```
ATOM   4789  CG   LYS B  72    -28.224  19.123   8.538  1.00 28.25      B
ATOM   4790  CD   LYS B  72    -29.216  20.256   8.757  1.00 27.66      B
ATOM   4791  CE   LYS B  72    -28.540  21.605   8.711  1.00 25.55      B
ATOM   4792  NZ   LYS B  72    -29.523  22.726   8.692  1.00 27.01      B
ATOM   4793  C    LYS B  72    -24.932  18.170  10.310  1.00 32.14      B
ATOM   4794  O    LYS B  72    -23.942  18.771   9.900  1.00 31.52      B
ATOM   4795  N    ALA B  73    -24.998  17.664  11.536  1.00 32.69      B
ATOM   4796  CA   ALA B  73    -23.870  17.816  12.448  1.00 32.80      B
ATOM   4797  CB   ALA B  73    -24.176  17.170  13.779  1.00 28.71      B
ATOM   4798  C    ALA B  73    -22.635  17.181  11.828  1.00 34.18      B
ATOM   4799  O    ALA B  73    -21.534  17.729  11.917  1.00 36.35      B
ATOM   4800  N    LYS B  74    -22.823  16.038  11.177  1.00 34.60      B
ATOM   4801  CA   LYS B  74    -21.705  15.347  10.562  1.00 34.94      B
ATOM   4802  CB   LYS B  74    -22.099  13.919  10.174  1.00 36.45      B
ATOM   4803  CG   LYS B  74    -22.366  13.002  11.380  1.00 40.08      B
ATOM   4804  CD   LYS B  74    -22.231  11.510  11.008  1.00 44.02      B
ATOM   4805  CE   LYS B  74    -20.762  11.041  10.923  1.00 46.69      B
ATOM   4806  NZ   LYS B  74    -20.582   9.755  10.146  1.00 46.93      B
ATOM   4807  C    LYS B  74    -21.185  16.126   9.365  1.00 35.60      B
ATOM   4808  O    LYS B  74    -19.973  16.207   9.158  1.00 36.30      B
ATOM   4809  N    ALA B  75    -22.096  16.732   8.602  1.00 35.72      B
ATOM   4810  CA   ALA B  75    -21.713  17.525   7.427  1.00 35.31      B
ATOM   4811  CB   ALA B  75    -22.963  17.997   6.665  1.00 34.86      B
ATOM   4812  C    ALA B  75    -20.880  18.732   7.354  1.00 34.58      B
ATOM   4813  O    ALA B  75    -20.035  19.214   7.097  1.00 34.08      B
ATOM   4814  N    SER B  76    -21.128  19.196   9.078  1.00 33.73      B
ATOM   4815  CA   SER B  76    -20.443  20.345   9.656  1.00 34.06      B
ATOM   4816  CB   SER B  76    -20.918  20.580  11.082  1.00 36.51      B
ATOM   4817  OG   SER B  76    -22.257  21.032  11.088  1.00 44.07      B
ATOM   4818  C    SER B  76    -18.940  20.220   9.681  1.00 33.19      B
ATOM   4819  O    SER B  76    -18.237  21.227   9.638  1.00 30.80      B
ATOM   4820  N    THR B  77    -18.456  18.983   9.758  1.00 32.61      B
ATOM   4821  CA   THR B  77    -17.026  18.708   9.812  1.00 32.32      B
ATOM   4822  CB   THR B  77    -16.749  17.237  10.234  1.00 33.21      B
ATOM   4823  OG1  THR B  77    -16.979  16.357   9.125  1.00 33.77      B
ATOM   4824  CG2  THR B  77    -17.670  16.825  11.370  1.00 31.41      B
ATOM   4825  C    THR B  77    -16.338  18.957   8.477  1.00 32.23      B
ATOM   4826  O    THR B  77    -15.171  19.338   8.438  1.00 33.54      B
ATOM   4827  N    VAL B  78    -17.077  18.763   7.390  1.00 31.88      B
ATOM   4828  CA   VAL B  78    -16.559  18.916   6.029  1.00 31.09      B
ATOM   4829  CB   VAL B  78    -17.610  18.417   4.996  1.00 29.21      B
ATOM   4830  CG1  VAL B  78    -17.059  18.511   3.600  1.00 24.52      B
ATOM   4831  CG2  VAL B  78    -18.021  16.996   5.313  1.00 26.49      B
ATOM   4832  C    VAL B  78    -16.115  20.320   5.606  1.00 32.14      B
ATOM   4833  O    VAL B  78    -16.739  21.314   5.959  1.00 31.58      B
ATOM   4834  N    LYS B  79    -15.020  20.372   4.853  1.00 33.63      B
ATOM   4835  CA   LYS B  79    -14.480  21.614   4.302  1.00 37.02      B
ATOM   4836  CB   LYS B  79    -13.155  22.022   4.957  1.00 38.41      B
ATOM   4837  CG   LYS B  79    -12.485  23.183   4.204  1.00 41.36      B
ATOM   4838  CD   LYS B  79    -11.297  23.777   4.942  1.00 45.95      B
ATOM   4839  CE   LYS B  79    -10.697  24.960   4.172  1.00 47.38      B
ATOM   4840  NZ   LYS B  79     -9.660  25.699   4.968  1.00 48.01      B
ATOM   4841  C    LYS B  79    -14.227  21.353   2.820  1.00 37.17      B
ATOM   4842  O    LYS B  79    -13.202  20.792   2.448  1.00 37.62      B
ATOM   4843  N    ALA B  80    -15.163  21.766   1.980  1.00 37.18      B
ATOM   4844  CA   ALA B  80    -15.046  21.540   0.554  1.00 37.26      B
ATOM   4845  CB   ALA B  80    -16.422  21.405  -0.059  1.00 36.48      B
ATOM   4846  C    ALA B  80    -14.302  22.673  -0.095  1.00 37.20      B
ATOM   4847  O    ALA B  80    -14.386  23.804   0.363  1.00 37.54      B
ATOM   4848  N    LYS B  81    -13.588  22.364  -1.170  1.00 38.16      B
ATOM   4849  CA   LYS B  81    -12.822  23.363  -1.888  1.00 40.87      B
ATOM   4850  CB   LYS B  81    -11.404  22.864  -2.133  1.00 46.89      B
ATOM   4851  CG   LYS B  81    -10.520  22.858  -0.885  1.00 56.40      B
ATOM   4852  CD   LYS B  81     -9.222  22.082  -1.146  1.00 62.47      B
ATOM   4853  CE   LYS B  81     -8.301  22.071   0.077  1.00 65.66      B
ATOM   4854  NZ   LYS B  81     -7.093  21.212  -0.144  1.00 67.08      B
ATOM   4855  C    LYS B  81    -13.454  23.746  -3.212  1.00 40.14      B
ATOM   4856  O    LYS B  81    -14.275  23.028  -3.765  1.00 40.05      B
ATOM   4857  N    LEU B  82    -13.055  24.905  -3.707  1.00 40.28      B
ATOM   4858  CA   LEU B  82    -13.553  25.430  -4.966  1.00 38.36      B
ATOM   4859  CB   LEU B  82    -13.571  26.961  -4.901  1.00 35.96      B
ATOM   4860  CG   LEU B  82    -14.327  27.724  -5.983  1.00 33.09      B
ATOM   4861  CD1  LEU B  82    -15.742  27.225  -6.042  1.00 33.66      B
ATOM   4862  CD2  LEU B  82    -14.308  29.202  -5.675  1.00 30.72      B
ATOM   4863  C    LEU B  82    -12.609  24.961  -6.058  1.00 38.01      B
ATOM   4864  O    LEU B  82    -11.411  25.234  -6.005  1.00 38.58      B
```

FIGURE 5- 65 -

```
ATOM   4865  N    LEU B  83     -13.144  24.246  -7.038  1.00 38.67      B
ATOM   4866  CA   LEU B  83     -12.334  23.746  -8.138  1.00 39.08      B
ATOM   4867  CB   LEU B  83     -13.095  22.668  -8.901  1.00 37.33      B
ATOM   4868  CG   LEU B  83     -12.613  21.231  -8.723  1.00 37.37      B
ATOM   4869  CD1  LEU B  83     -12.691  20.835  -7.276  1.00 37.74      B
ATOM   4870  CD2  LEU B  83     -13.465  20.309  -9.565  1.00 37.16      B
ATOM   4871  C    LEU B  83     -11.938  24.858  -9.098  1.00 40.50      B
ATOM   4872  O    LEU B  83     -12.684  25.806  -9.309  1.00 40.66      B
ATOM   4873  N    SER B  84     -10.748  24.747  -9.670  1.00 42.44      B
ATOM   4874  CA   SER B  84     -10.280  25.741 -10.629  1.00 43.66      B
ATOM   4875  CB   SER B  84      -8.784  25.572 -10.863  1.00 44.30      B
ATOM   4876  OG   SER B  84      -8.521  24.280 -11.387  1.00 42.17      B
ATOM   4877  C    SER B  84     -11.012  25.452 -11.930  1.00 44.08      B
ATOM   4878  O    SER B  84     -11.405  24.307 -12.173  1.00 43.43      B
ATOM   4879  N    ILE B  85     -11.198  26.470 -12.766  1.00 44.90      B
ATOM   4880  CA   ILE B  85     -11.869  26.257 -14.045  1.00 46.35      B
ATOM   4881  CB   ILE B  85     -11.804  27.496 -14.948  1.00 45.37      B
ATOM   4882  CG2  ILE B  85     -12.174  27.123 -16.370  1.00 43.99      B
ATOM   4883  CG1  ILE B  85     -12.756  28.569 -14.425  1.00 47.35      B
ATOM   4884  CD1  ILE B  85     -12.746  29.856 -15.236  1.00 48.59      B
ATOM   4885  C    ILE B  85     -11.152  25.121 -14.756  1.00 48.78      B
ATOM   4886  O    ILE B  85     -11.777  24.189 -15.270  1.00 48.53      B
ATOM   4887  N    GLU B  86      -9.827  25.199 -14.770  1.00 50.49      B
ATOM   4888  CA   GLU B  86      -9.037  24.176 -15.414  1.00 51.89      B
ATOM   4889  CB   GLU B  86      -7.549  24.442 -15.210  1.00 54.23      B
ATOM   4890  CG   GLU B  86      -6.674  23.607 -16.130  1.00 59.87      B
ATOM   4891  CD   GLU B  86      -5.187  23.816 -15.904  1.00 62.17      B
ATOM   4892  OE1  GLU B  86      -4.709  24.961 -16.056  1.00 62.62      B
ATOM   4893  OE2  GLU B  86      -4.496  22.827 -15.579  1.00 64.10      B
ATOM   4894  C    GLU B  86      -9.406  22.811 -14.853  1.00 51.77      B
ATOM   4895  O    GLU B  86      -9.713  21.892 -15.609  1.00 53.45      B
ATOM   4896  N    GLU B  87      -9.395  22.675 -13.531  1.00 52.21      B
ATOM   4897  CA   GLU B  87      -9.727  21.393 -12.903  1.00 52.36      B
ATOM   4898  CB   GLU B  87      -9.706  21.506 -11.384  1.00 54.76      B
ATOM   4899  CG   GLU B  87      -8.338  21.416 -10.767  1.00 58.44      B
ATOM   4900  CD   GLU B  87      -8.402  21.510  -9.262  1.00 60.42      B
ATOM   4901  OE1  GLU B  87      -8.792  22.589  -8.748  1.00 60.58      B
ATOM   4902  OE2  GLU B  87      -8.072  20.499  -8.604  1.00 60.59      B
ATOM   4903  C    GLU B  87     -11.083  20.860 -13.309  1.00 50.79      B
ATOM   4904  O    GLU B  87     -11.241  19.668 -13.559  1.00 50.03      B
ATOM   4905  N    ALA B  88     -12.071  21.745 -13.352  1.00 49.51      B
ATOM   4906  CA   ALA B  88     -13.412  21.331 -13.723  1.00 46.94      B
ATOM   4907  CB   ALA B  88     -14.393  22.461 -13.491  1.00 46.85      B
ATOM   4908  C    ALA B  88     -13.418  20.918 -15.178  1.00 44.87      B
ATOM   4909  O    ALA B  88     -14.084  19.964 -15.552  1.00 45.14      B
ATOM   4910  N    CYS B  89     -12.664  21.637 -15.999  1.00 44.26      B
ATOM   4911  CA   CYS B  89     -12.604  21.326 -17.414  1.00 43.59      B
ATOM   4912  CB   CYS B  89     -11.711  22.336 -18.138  1.00 42.63      B
ATOM   4913  SG   CYS B  89     -12.550  23.888 -18.630  1.00 41.52      B
ATOM   4914  C    CYS B  89     -12.103  19.908 -17.649  1.00 44.88      B
ATOM   4915  O    CYS B  89     -12.681  19.160 -18.441  1.00 44.95      B
ATOM   4916  N    LYS B  90     -11.045  19.531 -16.939  1.00 46.90      B
ATOM   4917  CA   LYS B  90     -10.452  18.204 -17.083  1.00 48.53      B
ATOM   4918  CB   LYS B  90      -9.166  18.113 -16.267  1.00 50.42      B
ATOM   4919  CG   LYS B  90      -8.361  16.863 -16.568  1.00 57.51      B
ATOM   4920  CD   LYS B  90      -7.119  16.740 -15.680  1.00 61.75      B
ATOM   4921  CE   LYS B  90      -6.330  15.469 -15.999  1.00 63.68      B
ATOM   4922  NZ   LYS B  90      -5.210  15.243 -15.038  1.00 64.71      B
ATOM   4923  C    LYS B  90     -11.389  17.059 -16.692  1.00 48.70      B
ATOM   4924  O    LYS B  90     -11.331  15.981 -17.282  1.00 48.92      B
ATOM   4925  N    LEU B  91     -12.243  17.287 -15.698  1.00 48.18      B
ATOM   4926  CA   LEU B  91     -13.190  16.271 -15.246  1.00 47.17      B
ATOM   4927  CB   LEU B  91     -13.868  16.710 -13.951  1.00 48.69      B
ATOM   4928  CG   LEU B  91     -13.157  16.558 -12.608  1.00 50.07      B
ATOM   4929  CD1  LEU B  91     -13.952  17.288 -11.526  1.00 50.96      B
ATOM   4930  CD2  LEU B  91     -13.032  15.086 -12.261  1.00 49.85      B
ATOM   4931  C    LEU B  91     -14.276  15.984 -16.271  1.00 46.99      B
ATOM   4932  O    LEU B  91     -15.051  15.055 -16.100  1.00 47.68      B
ATOM   4933  N    THR B  92     -14.329  16.780 -17.333  1.00 47.48      B
ATOM   4934  CA   THR B  92     -15.341  16.629 -18.381  1.00 47.28      B
ATOM   4935  CB   THR B  92     -15.466  17.919 -19.192  1.00 47.36      B
ATOM   4936  OG1  THR B  92     -15.712  19.012 -18.301  1.00 49.95      B
ATOM   4937  CG2  THR B  92     -16.603  17.807 -20.205  1.00 46.36      B
ATOM   4938  C    THR B  92     -15.126  15.498 -19.388  1.00 47.21      B
ATOM   4939  O    THR B  92     -14.103  15.444 -20.058  1.00 46.98      B
ATOM   4940  N    PRO B  93     -16.107  14.591 -19.523  1.00 47.51      B
```

FIGURE 5- 66 -

```
ATOM   4941  CD   PRO B  93     -17.355  14.459 -18.750  1.00 47.93      B
ATOM   4942  CA   PRO B  93     -15.968  13.489 -20.478  1.00 46.58      B
ATOM   4943  CB   PRO B  93     -17.323  12.791 -20.396  1.00 47.84      B
ATOM   4944  CG   PRO B  93     -17.713  12.999 -18.969  1.00 48.87      B
ATOM   4945  C    PRO B  93     -15.688  14.039 -21.873  1.00 46.05      B
ATOM   4946  O    PRO B  93     -16.165  15.118 -22.230  1.00 45.20      B
ATOM   4947  N    PRO B  94     -14.904  13.303 -22.675  1.00 46.19      B
ATOM   4948  CD   PRO B  94     -14.116  12.153 -22.208  1.00 46.35      B
ATOM   4949  CA   PRO B  94     -14.513  13.657 -24.042  1.00 46.67      B
ATOM   4950  CB   PRO B  94     -13.506  12.575 -24.401  1.00 45.76      B
ATOM   4951  CG   PRO B  94     -12.904  12.240 -23.088  1.00 45.92      B
ATOM   4952  C    PRO B  94     -15.646  13.734 -25.054  1.00 47.80      B
ATOM   4953  O    PRO B  94     -15.562  14.493 -26.020  1.00 48.46      B
ATOM   4954  N    HIS B  95     -16.696  12.947 -24.857  1.00 48.40      B
ATOM   4955  CA   HIS B  95     -17.808  12.994 -25.794  1.00 50.12      B
ATOM   4956  CB   HIS B  95     -18.150  11.592 -26.311  1.00 55.33      B
ATOM   4957  CG   HIS B  95     -17.151  11.043 -27.289  1.00 59.98      B
ATOM   4958  CD2  HIS B  95     -17.130  11.059 -28.644  1.00 61.07      B
ATOM   4959  ND1  HIS B  95     -16.000  10.390 -26.895  1.00 59.95      B
ATOM   4960  CE1  HIS B  95     -15.317  10.026 -27.966  1.00 61.68      B
ATOM   4961  NE2  HIS B  95     -15.980  10.420 -29.040  1.00 62.34      B
ATOM   4962  C    HIS B  95     -19.046  13.654 -25.197  1.00 48.68      B
ATOM   4963  O    HIS B  95     -20.139  13.586 -25.769  1.00 47.51      B
ATOM   4964  N    SER B  96     -18.863  14.298 -24.046  1.00 46.78      B
ATOM   4965  CA   SER B  96     -19.946  15.003 -23.368  1.00 44.99      B
ATOM   4966  CB   SER B  96     -19.356  15.849 -22.239  1.00 44.30      B
ATOM   4967  OG   SER B  96     -20.367  16.497 -21.493  1.00 46.87      B
ATOM   4968  C    SER B  96     -20.688  15.894 -24.384  1.00 43.99      B
ATOM   4969  O    SER B  96     -20.080  16.397 -25.334  1.00 44.57      B
ATOM   4970  N    ALA B  97     -21.993  16.085 -24.196  1.00 41.72      B
ATOM   4971  CA   ALA B  97     -22.787  16.902 -25.123  1.00 39.27      B
ATOM   4972  CB   ALA B  97     -24.223  16.965 -24.667  1.00 36.58      B
ATOM   4973  C    ALA B  97     -22.248  18.316 -25.292  1.00 39.47      B
ATOM   4974  O    ALA B  97     -22.033  19.036 -24.316  1.00 38.64      B
ATOM   4975  N    LYS B  98     -22.039  18.713 -26.542  1.00 39.66      B
ATOM   4976  CA   LYS B  98     -21.525  20.041 -26.836  1.00 39.68      B
ATOM   4977  CB   LYS B  98     -21.352  20.216 -28.342  1.00 40.64      B
ATOM   4978  CG   LYS B  98     -22.654  20.168 -29.128  1.00 41.90      B
ATOM   4979  CD   LYS B  98     -22.426  20.549 -30.585  1.00 43.41      B
ATOM   4980  CE   LYS B  98     -23.736  20.740 -31.324  1.00 43.75      B
ATOM   4981  NZ   LYS B  98     -23.521  21.456 -32.616  1.00 46.64      B
ATOM   4982  C    LYS B  98     -22.458  21.127 -26.307  1.00 39.71      B
ATOM   4983  O    LYS B  98     -23.639  20.878 -26.036  1.00 40.17      B
ATOM   4984  N    SER B  99     -21.920  22.333 -26.164  1.00 37.46      B
ATOM   4985  CA   SER B  99     -22.694  23.464 -25.683  1.00 36.37      B
ATOM   4986  CB   SER B  99     -21.797  24.485 -24.977  1.00 36.50      B
ATOM   4987  OG   SER B  99     -22.417  25.764 -24.942  1.00 28.42      B
ATOM   4988  C    SER B  99     -23.409  24.173 -26.807  1.00 37.42      B
ATOM   4989  O    SER B  99     -22.897  24.293 -27.921  1.00 38.91      B
ATOM   4990  N    LYS B 100     -24.596  24.657 -26.479  1.00 38.44      B
ATOM   4991  CA   LYS B 100     -25.451  25.401 -27.386  1.00 39.59      B
ATOM   4992  CB   LYS B 100     -26.703  25.820 -26.603  1.00 42.48      B
ATOM   4993  CG   LYS B 100     -27.597  26.839 -27.277  1.00 49.24      B
ATOM   4994  CD   LYS B 100     -28.802  27.199 -26.402  1.00 53.58      B
ATOM   4995  CE   LYS B 100     -29.757  28.142 -27.151  1.00 58.21      B
ATOM   4996  NZ   LYS B 100     -30.911  28.631 -26.329  1.00 59.35      B
ATOM   4997  C    LYS B 100     -24.710  26.637 -27.921  1.00 39.05      B
ATOM   4998  O    LYS B 100     -25.113  27.236 -28.920  1.00 37.98      B
ATOM   4999  N    PHE B 101     -23.607  26.986 -27.262  1.00 39.34      B
ATOM   5000  CA   PHE B 101     -22.832  28.173 -27.606  1.00 40.01      B
ATOM   5001  CB   PHE B 101     -22.485  28.924 -26.324  1.00 39.79      B
ATOM   5002  CG   PHE B 101     -23.684  29.447 -25.591  1.00 39.57      B
ATOM   5003  CD1  PHE B 101     -24.332  30.603 -26.024  1.00 39.71      B
ATOM   5004  CD2  PHE B 101     -24.192  28.766 -24.491  1.00 39.23      B
ATOM   5005  CE1  PHE B 101     -25.468  31.081 -25.369  1.00 39.11      B
ATOM   5006  CE2  PHE B 101     -25.325  29.232 -23.830  1.00 39.51      B
ATOM   5007  CZ   PHE B 101     -25.967  30.393 -24.273  1.00 39.68      B
ATOM   5008  C    PHE B 101     -21.574  29.028 -28.447  1.00 40.93      B
ATOM   5009  O    PHE B 101     -20.654  28.830 -28.317  1.00 40.41      B
ATOM   5010  N    GLY B 102     -21.509  27.006 -29.291  1.00 41.59      B
ATOM   5011  CA   GLY B 102     -20.354  26.880 -30.157  1.00 40.27      B
ATOM   5012  C    GLY B 102     -19.070  26.247 -29.666  1.00 40.24      B
ATOM   5013  O    GLY B 102     -17.986  26.653 -30.088  1.00 40.61      B
ATOM   5014  N    TYR B 103     -19.174  25.263 -28.783  1.00 39.54      B
ATOM   5015  CA   TYR B 103     -17.992  24.555 -28.312  1.00 38.72      B
ATOM   5016  CB   TYR B 103     -17.199  25.417 -27.321  1.00 39.63      B
```

FIGURE 5- 67 -

```
ATOM   5017  CG   TYR B 103     -17.890   25.703  -26.016  1.00 40.43      B
ATOM   5018  CD1  TYR B 103     -17.885   24.766  -24.982  1.00 40.26      B
ATOM   5019  CE1  TYR B 103     -18.543   25.017  -23.788  1.00 40.36      B
ATOM   5020  CD2  TYR B 103     -18.569   26.903  -25.820  1.00 40.33      B
ATOM   5021  CE2  TYR B 103     -19.233   27.165  -24.627  1.00 40.36      B
ATOM   5022  CZ   TYR B 103     -19.218   26.217  -23.618  1.00 40.39      B
ATOM   5023  OH   TYR B 103     -19.901   26.456  -22.450  1.00 39.51      B
ATOM   5024  C    TYR B 103     -18.408   23.221  -27.695  1.00 39.08      B
ATOM   5025  O    TYR B 103     -19.543   23.064  -27.262  1.00 40.24      B
ATOM   5026  N    GLY B 104     -17.500   22.251  -27.684  1.00 39.13      B
ATOM   5027  CA   GLY B 104     -17.818   20.947  -27.129  1.00 38.24      B
ATOM   5028  C    GLY B 104     -16.816   20.466  -26.098  1.00 39.06      B
ATOM   5029  O    GLY B 104     -15.823   21.136  -25.815  1.00 38.69      B
ATOM   5030  N    ALA B 105     -17.077   19.295  -25.529  1.00 39.70      B
ATOM   5031  CA   ALA B 105     -16.194   18.740  -24.519  1.00 40.86      B
ATOM   5032  CB   ALA B 105     -16.561   17.290  -24.247  1.00 41.15      B
ATOM   5033  C    ALA B 105     -14.756   18.841  -24.997  1.00 42.67      B
ATOM   5034  O    ALA B 105     -13.851   19.125  -24.213  1.00 41.72      B
ATOM   5035  N    LYS B 106     -14.560   18.613  -26.295  1.00 45.42      B
ATOM   5036  CA   LYS B 106     -13.236   18.676  -26.906  1.00 47.68      B
ATOM   5037  CB   LYS B 106     -13.358   18.536  -28.426  1.00 52.13      B
ATOM   5038  CG   LYS B 106     -12.035   18.337  -29.173  1.00 57.52      B
ATOM   5039  CD   LYS B 106     -11.628   16.867  -29.185  1.00 63.82      B
ATOM   5040  CE   LYS B 106     -10.458   16.584  -30.152  1.00 66.23      B
ATOM   5041  NZ   LYS B 106      -9.131   17.060  -29.654  1.00 67.16      B
ATOM   5042  C    LYS B 106     -12.589   20.018  -26.562  1.00 47.26      B
ATOM   5043  O    LYS B 106     -11.454   20.078  -26.080  1.00 46.18      B
ATOM   5044  N    ASP B 107     -13.327   21.097  -26.801  1.00 46.14      B
ATOM   5045  CA   ASP B 107     -12.828   22.438  -26.524  1.00 45.93      B
ATOM   5046  CB   ASP B 107     -13.739   23.463  -27.197  1.00 45.84      B
ATOM   5047  CG   ASP B 107     -13.842   23.244  -28.694  1.00 46.85      B
ATOM   5048  OD1  ASP B 107     -12.803   23.363  -29.386  1.00 47.45      B
ATOM   5049  OD2  ASP B 107     -14.957   22.945  -29.177  1.00 46.25      B
ATOM   5050  C    ASP B 107     -12.678   22.756  -25.031  1.00 45.58      B
ATOM   5051  O    ASP B 107     -11.804   23.532  -24.643  1.00 45.07      B
ATOM   5052  N    VAL B 108     -13.521   22.154  -24.197  1.00 45.13      B
ATOM   5053  CA   VAL B 108     -13.459   22.387  -22.759  1.00 44.84      B
ATOM   5054  CB   VAL B 108     -14.647   21.707  -22.034  1.00 43.84      B
ATOM   5055  CG1  VAL B 108     -14.534   21.926  -20.535  1.00 41.41      B
ATOM   5056  CG2  VAL B 108     -15.970   22.249  -22.562  1.00 41.68      B
ATOM   5057  C    VAL B 108     -12.152   21.836  -22.179  1.00 46.70      B
ATOM   5058  O    VAL B 108     -11.420   22.535  -21.460  1.00 46.24      B
ATOM   5059  N    ARG B 109     -11.863   20.578  -22.507  1.00 46.61      B
ATOM   5060  CA   ARG B 109     -10.665   19.903  -22.027  1.00 47.16      B
ATOM   5061  CB   ARG B 109     -10.666   18.449  -22.496  1.00 46.93      B
ATOM   5062  CG   ARG B 109     -11.916   17.679  -22.096  1.00 48.38      B
ATOM   5063  CD   ARG B 109     -11.909   16.243  -22.614  1.00 49.58      B
ATOM   5064  NE   ARG B 109     -10.881   15.421  -21.978  1.00 50.96      B
ATOM   5065  CZ   ARG B 109     -10.770   15.236  -20.664  1.00 51.98      B
ATOM   5066  NH1  ARG B 109     -11.624   15.817  -19.832  1.00 54.04      B
ATOM   5067  NH2  ARG B 109      -9.807   14.465  -20.178  1.00 52.85      B
ATOM   5068  C    ARG B 109      -9.390   20.590  -22.488  1.00 48.28      B
ATOM   5069  O    ARG B 109      -8.368   20.538  -21.808  1.00 49.98      B
ATOM   5070  N    ASN B 110      -9.440   21.233  -23.647  1.00 48.85      B
ATOM   5071  CA   ASN B 110      -8.263   21.927  -24.145  1.00 49.08      B
ATOM   5072  CB   ASN B 110      -8.239   21.911  -25.673  1.00 50.84      B
ATOM   5073  CG   ASN B 110      -8.038   20.513  -26.239  1.00 53.04      B
ATOM   5074  OD1  ASN B 110      -7.153   19.776  -25.803  1.00 53.45      B
ATOM   5075  ND2  ASN B 110      -8.855   20.147  -27.220  1.00 54.09      B
ATOM   5076  C    ASN B 110      -8.204   23.363  -23.647  1.00 48.76      B
ATOM   5077  O    ASN B 110      -7.245   24.075  -23.929  1.00 50.18      B
ATOM   5078  N    LEU B 111      -9.229   23.781  -22.907  1.00 47.00      B
ATOM   5079  CA   LEU B 111      -9.304   25.135  -22.371  1.00 45.78      B
ATOM   5080  CB   LEU B 111      -8.098   25.428  -21.482  1.00 45.16      B
ATOM   5081  CG   LEU B 111      -7.707   24.373  -20.452  1.00 46.86      B
ATOM   5082  CD1  LEU B 111      -6.519   24.887  -19.652  1.00 47.84      B
ATOM   5083  CD2  LEU B 111      -8.878   24.072  -19.532  1.00 47.28      B
ATOM   5084  C    LEU B 111      -9.368   26.191  -23.473  1.00 45.58      B
ATOM   5085  O    LEU B 111      -8.804   27.274  -23.331  1.00 44.28      B
ATOM   5086  N    SER B 112     -10.057   25.881  -24.564  1.00 46.63      B
ATOM   5087  CA   SER B 112     -10.165   26.819  -25.673  1.00 48.37      B
ATOM   5088  CB   SER B 112     -10.878   26.176  -26.861  1.00 47.88      B
ATOM   5089  OG   SER B 112     -12.281   26.199  -26.680  1.00 47.93      B
ATOM   5090  C    SER B 112     -10.933   28.050  -25.235  1.00 49.71      B
ATOM   5091  O    SER B 112     -12.086   27.961  -24.831  1.00 51.68      B
ATOM   5092  N    SER B 113     -10.281   29.200  -25.323  1.00 50.82      B
```

FIGURE 5- 68 -

```
ATOM   5093  CA   SER B 113    -10.874  30.474 -24.937  1.00 51.54      B
ATOM   5094  CB   SER B 113    -10.232  31.588 -25.754  1.00 51.85      B
ATOM   5095  OG   SER B 113    -10.013  31.150 -27.082  1.00 55.17      B
ATOM   5096  C    SER B 113    -12.397  30.574 -25.037  1.00 50.63      B
ATOM   5097  O    SER B 113    -13.073  30.737 -24.023  1.00 51.72      B
ATOM   5098  N    ARG B 114    -12.941  30.477 -26.245  1.00 49.36      B
ATOM   5099  CA   ARG B 114    -14.387  30.583 -26.412  1.00 48.85      B
ATOM   5100  CB   ARG B 114    -14.814  30.054 -27.778  1.00 47.46      B
ATOM   5101  CG   ARG B 114    -16.326  29.989 -27.954  1.00 48.59      B
ATOM   5102  CD   ARG B 114    -16.730  30.234 -29.397  1.00 50.39      B
ATOM   5103  NE   ARG B 114    -18.175  30.175 -29.608  1.00 50.72      B
ATOM   5104  CZ   ARG B 114    -18.809  30.845 -30.569  1.00 51.94      B
ATOM   5105  NH1  ARG B 114    -18.123  31.624 -31.394  1.00 52.44      B
ATOM   5106  NH2  ARG B 114    -20.127  30.742 -30.711  1.00 51.85      B
ATOM   5107  C    ARG B 114    -15.159  29.851 -25.317  1.00 49.29      B
ATOM   5108  O    ARG B 114    -16.149  30.368 -24.791  1.00 50.34      B
ATOM   5109  N    ALA B 115    -14.702  28.653 -24.972  1.00 47.35      B
ATOM   5110  CA   ALA B 115    -15.355  27.865 -23.938  1.00 46.22      B
ATOM   5111  CB   ALA B 115    -14.934  26.413 -24.051  1.00 46.87      B
ATOM   5112  C    ALA B 115    -15.042  28.385 -22.539  1.00 45.35      B
ATOM   5113  O    ALA B 115    -15.952  28.640 -21.746  1.00 46.85      B
ATOM   5114  N    VAL B 116    -13.757  28.533 -22.235  1.00 42.76      B
ATOM   5115  CA   VAL B 116    -13.341  29.013 -20.925  1.00 41.41      B
ATOM   5116  CB   VAL B 116    -11.826  29.231 -20.855  1.00 39.92      B
ATOM   5117  CG1  VAL B 116    -11.443  29.787 -19.506  1.00 38.25      B
ATOM   5118  CG2  VAL B 116    -11.116  27.933 -21.088  1.00 41.32      B
ATOM   5119  C    VAL B 116    -14.006  30.322 -20.561  1.00 41.37      B
ATOM   5120  O    VAL B 116    -14.493  30.492 -19.447  1.00 42.31      B
ATOM   5121  N    ASN B 117    -14.029  31.254 -21.501  1.00 40.76      B
ATOM   5122  CA   ASN B 117    -14.627  32.545 -21.230  1.00 40.09      B
ATOM   5123  CB   ASN B 117    -14.173  33.559 -22.287  1.00 41.41      B
ATOM   5124  CG   ASN B 117    -12.657  33.816 -22.230  1.00 42.72      B
ATOM   5125  OD1  ASN B 117    -12.128  34.291 -21.212  1.00 41.65      B
ATOM   5126  ND2  ASN B 117    -11.957  33.489 -23.317  1.00 40.39      B
ATOM   5127  C    ASN B 117    -16.145  32.480 -21.106  1.00 39.23      B
ATOM   5128  O    ASN B 117    -16.736  33.294 -20.398  1.00 40.94      B
ATOM   5129  N    HIS B 118    -16.779  31.517 -21.772  1.00 37.62      B
ATOM   5130  CA   HIS B 118    -18.227  31.362 -21.655  1.00 35.97      B
ATOM   5131  CB   HIS B 118    -18.787  30.464 -22.748  1.00 35.21      B
ATOM   5132  CG   HIS B 118    -20.226  30.100 -22.538  1.00 35.17      B
ATOM   5133  CD2  HIS B 118    -21.365  30.800 -22.762  1.00 34.91      B
ATOM   5134  ND1  HIS B 118    -20.620  28.893 -21.998  1.00 34.74      B
ATOM   5135  CE1  HIS B 118    -21.937  28.864 -21.903  1.00 34.55      B
ATOM   5136  NE2  HIS B 118    -22.413  30.010 -22.361  1.00 34.92      B
ATOM   5137  C    HIS B 118    -18.554  30.739 -20.293  1.00 37.19      B
ATOM   5138  O    HIS B 118    -19.594  31.032 -19.687  1.00 36.19      B
ATOM   5139  N    ILE B 119    -17.666  29.863 -19.828  1.00 35.65      B
ATOM   5140  CA   ILE B 119    -17.831  29.219 -18.537  1.00 34.48      B
ATOM   5141  CB   ILE B 119    -16.782  28.122 -18.337  1.00 32.85      B
ATOM   5142  CG2  ILE B 119    -16.789  27.646 -16.898  1.00 29.67      B
ATOM   5143  CG1  ILE B 119    -17.064  26.963 -19.301  1.00 31.72      B
ATOM   5144  CD1  ILE B 119    -15.966  25.915 -19.345  1.00 29.00      B
ATOM   5145  C    ILE B 119    -17.685  30.277 -17.446  1.00 36.14      B
ATOM   5146  O    ILE B 119    -18.521  30.366 -16.555  1.00 37.30      B
ATOM   5147  N    ARG B 120    -16.621  31.074 -17.514  1.00 37.93      B
ATOM   5148  CA   ARG B 120    -16.413  32.142 -16.541  1.00 38.51      B
ATOM   5149  CB   ARG B 120    -15.233  33.037 -16.936  1.00 43.28      B
ATOM   5150  CG   ARG B 120    -13.827  32.450 -16.821  1.00 48.50      B
ATOM   5151  CD   ARG B 120    -12.820  33.589 -16.555  1.00 51.30      B
ATOM   5152  NE   ARG B 120    -11.430  33.147 -16.581  1.00 56.05      B
ATOM   5153  CZ   ARG B 120    -10.717  32.984 -17.693  1.00 59.48      B
ATOM   5154  NH1  ARG B 120    -11.263  33.234 -18.881  1.00 60.00      B
ATOM   5155  NH2  ARG B 120     -9.458  32.563 -17.621  1.00 61.02      B
ATOM   5156  C    ARG B 120    -17.672  32.995 -16.590  1.00 37.93      B
ATOM   5157  O    ARG B 120    -18.107  33.570 -15.593  1.00 37.60      B
ATOM   5158  N    SER B 121    -18.232  33.082 -17.790  1.00 36.95      B
ATOM   5159  CA   SER B 121    -19.435  33.846 -18.045  1.00 35.69      B
ATOM   5160  CB   SER B 121    -19.724  33.856 -19.546  1.00 36.67      B
ATOM   5161  OG   SER B 121    -20.904  34.568 -19.860  1.00 39.92      B
ATOM   5162  C    SER B 121    -20.597  33.227 -17.293  1.00 34.56      B
ATOM   5163  O    SER B 121    -21.308  33.914 -16.567  1.00 35.45      B
ATOM   5164  N    VAL B 122    -20.788  31.924 -17.465  1.00 33.76      B
ATOM   5165  CA   VAL B 122    -21.876  31.227 -16.794  1.00 30.17      B
ATOM   5166  CB   VAL B 122    -21.947  29.744 -17.215  1.00 26.71      B
ATOM   5167  CG1  VAL B 122    -22.989  29.008 -16.397  1.00 23.07      B
ATOM   5168  CG2  VAL B 122    -22.312  29.656 -18.681  1.00 22.74      B
```

FIGURE 5- 69 -

```
ATOM   5169  C    VAL B 122     -21.735  31.319 -15.290  1.00 30.67       B
ATOM   5170  O    VAL B 122     -22.731  31.376 -14.575  1.00 32.74       B
ATOM   5171  N    TRP B 123     -20.497  31.341 -14.810  1.00 31.86       B
ATOM   5172  CA   TRP B 123     -20.235  31.439 -13.377  1.00 31.90       B
ATOM   5173  CB   TRP B 123     -18.760  31.145 -13.103  1.00 30.95       B
ATOM   5174  CG   TRP B 123     -18.385  31.184 -11.653  1.00 30.37       B
ATOM   5175  CD2  TRP B 123     -18.458  30.104 -10.717  1.00 29.68       B
ATOM   5176  CE2  TRP B 123     -18.002  30.597  -9.475  1.00 30.83       B
ATOM   5177  CE3  TRP B 123     -18.886  28.773 -10.799  1.00 30.55       B
ATOM   5178  CD1  TRP B 123     -17.893  32.250 -10.967  1.00 30.05       B
ATOM   5179  NE1  TRP B 123     -17.655  31.909  -9.659  1.00 30.26       B
ATOM   5180  CZ2  TRP B 123     -17.936  29.797  -8.325  1.00 31.32       B
ATOM   5181  CZ3  TRP B 123     -18.825  27.974  -9.650  1.00 31.63       B
ATOM   5182  CH2  TRP B 123     -18.361  28.495  -8.430  1.00 30.72       B
ATOM   5183  C    TRP B 123     -20.632  32.821 -12.839  1.00 32.70       B
ATOM   5184  O    TRP B 123     -21.324  32.922 -11.822  1.00 33.78       B
ATOM   5185  N    GLU B 124     -20.218  33.887 -13.513  1.00 32.71       B
ATOM   5186  CA   GLU B 124     -20.597  35.212 -13.052  1.00 35.50       B
ATOM   5187  CB   GLU B 124     -20.130  36.298 -14.025  1.00 40.92       B
ATOM   5188  CG   GLU B 124     -18.622  36.441 -14.163  1.00 49.19       B
ATOM   5189  CD   GLU B 124     -17.911  36.411 -12.815  1.00 56.48       B
ATOM   5190  OE1  GLU B 124     -18.374  37.109 -11.876  1.00 56.97       B
ATOM   5191  OE2  GLU B 124     -16.885  35.689 -12.700  1.00 60.53       B
ATOM   5192  C    GLU B 124     -22.116  35.283 -12.907  1.00 35.29       B
ATOM   5193  O    GLU B 124     -22.624  35.792 -11.909  1.00 36.82       B
ATOM   5194  N    ASP B 125     -22.840  34.764 -13.897  1.00 33.76       B
ATOM   5195  CA   ASP B 125     -24.308  34.775 -13.879  1.00 30.95       B
ATOM   5196  CB   ASP B 125     -24.857  34.195 -15.184  1.00 29.18       B
ATOM   5197  CG   ASP B 125     -26.367  34.299 -15.279  1.00 29.92       B
ATOM   5198  OD1  ASP B 125     -26.873  35.393 -15.615  1.00 33.38       B
ATOM   5199  OD2  ASP B 125     -27.052  33.290 -15.000  1.00 25.01       B
ATOM   5200  C    ASP B 125     -24.909  34.010 -12.690  1.00 30.08       B
ATOM   5201  O    ASP B 125     -26.039  34.262 -12.288  1.00 30.37       B
ATOM   5202  N    LEU B 126     -24.171  33.060 -12.133  1.00 29.89       B
ATOM   5203  CA   LEU B 126     -24.686  32.331 -10.984  1.00 29.98       B
ATOM   5204  CB   LEU B 126     -23.865  31.075 -10.737  1.00 29.85       B
ATOM   5205  CG   LEU B 126     -24.108  29.911 -11.687  1.00 30.80       B
ATOM   5206  CD1  LEU B 126     -23.157  28.788 -11.320  1.00 30.85       B
ATOM   5207  CD2  LEU B 126     -25.572  29.447 -11.582  1.00 28.89       B
ATOM   5208  C    LEU B 126     -24.606  33.247  -9.765  1.00 30.91       B
ATOM   5209  O    LEU B 126     -25.378  33.108  -8.813  1.00 29.17       B
ATOM   5210  N    LEU B 127     -23.670  34.192  -9.813  1.00 29.80       B
ATOM   5211  CA   LEU B 127     -23.482  35.131  -8.723  1.00 29.89       B
ATOM   5212  CB   LEU B 127     -22.018  35.540  -8.623  1.00 28.22       B
ATOM   5213  CG   LEU B 127     -20.966  34.433  -8.606  1.00 30.33       B
ATOM   5214  CD1  LEU B 127     -19.572  35.083  -8.563  1.00 24.30       B
ATOM   5215  CD2  LEU B 127     -21.202  33.494  -7.409  1.00 26.61       B
ATOM   5216  C    LEU B 127     -24.310  36.376  -8.926  1.00 30.76       B
ATOM   5217  O    LEU B 127     -24.642  37.056  -7.964  1.00 34.61       B
ATOM   5218  N    GLU B 128     -24.636  36.672 -10.179  1.00 31.24       B
ATOM   5219  CA   GLU B 128     -25.402  37.861 -10.532  1.00 30.75       B
ATOM   5220  CB   GLU B 128     -24.946  38.392 -11.888  1.00 31.76       B
ATOM   5221  CG   GLU B 128     -23.587  39.048 -11.894  1.00 35.07       B
ATOM   5222  CD   GLU B 128     -23.589  40.317 -11.099  1.00 37.63       B
ATOM   5223  OE1  GLU B 128     -24.555  41.091 -11.234  1.00 39.71       B
ATOM   5224  OE2  GLU B 128     -22.634  40.549 -10.339  1.00 41.78       B
ATOM   5225  C    GLU B 128     -26.901  37.654 -10.593  1.00 32.13       B
ATOM   5226  O    GLU B 128     -27.664  38.627 -10.565  1.00 35.43       B
ATOM   5227  N    ASP B 129     -27.327  36.399 -10.688  1.00 30.80       B
ATOM   5228  CA   ASP B 129     -28.746  36.077 -10.794  1.00 30.84       B
ATOM   5229  CB   ASP B 129     -29.064  35.665 -12.232  1.00 32.30       B
ATOM   5230  CG   ASP B 129     -30.555  35.471 -12.482  1.00 34.93       B
ATOM   5231  OD1  ASP B 129     -31.279  35.012 -11.561  1.00 34.71       B
ATOM   5232  OD2  ASP B 129     -30.994  35.758 -13.622  1.00 33.54       B
ATOM   5233  C    ASP B 129     -29.037  34.915  -9.871  1.00 31.92       B
ATOM   5234  O    ASP B 129     -28.381  33.881  -9.962  1.00 32.97       B
ATOM   5235  N    THR B 130     -30.020  35.070  -8.992  1.00 31.57       B
ATOM   5236  CA   THR B 130     -30.360  34.003  -8.054  1.00 31.72       B
ATOM   5237  CB   THR B 130     -30.379  34.516  -6.587  1.00 30.80       B
ATOM   5238  OG1  THR B 130     -31.372  35.538  -6.459  1.00 29.33       B
ATOM   5239  CG2  THR B 130     -29.036  35.090  -6.171  1.00 28.24       B
ATOM   5240  C    THR B 130     -31.740  33.416  -8.320  1.00 34.71       B
ATOM   5241  O    THR B 130     -32.167  32.520  -7.603  1.00 36.49       B
ATOM   5242  N    GLU B 131     -32.439  33.894  -9.346  1.00 36.85       B
ATOM   5243  CA   GLU B 131     -33.795  33.412  -9.579  1.00 37.83       B
ATOM   5244  CB   GLU B 131     -34.782  34.546  -9.300  1.00 40.39       B
```

FIGURE 5- 70 -

```
ATOM   5245  CG   GLU B 131     -34.488   35.308   -8.024  1.00 47.70      B
ATOM   5246  CD   GLU B 131     -35.261   36.617   -7.935  1.00 51.22      B
ATOM   5247  OE1  GLU B 131     -35.311   37.344   -8.956  1.00 54.85      B
ATOM   5248  OE2  GLU B 131     -35.802   36.924   -6.846  1.00 50.81      B
ATOM   5249  C    GLU B 131     -34.147   32.807  -10.931  1.00 37.06      B
ATOM   5250  O    GLU B 131     -34.884   31.826  -10.993  1.00 36.80      B
ATOM   5251  N    THR B 132     -33.640   33.387  -12.011  1.00 35.48      B
ATOM   5252  CA   THR B 132     -33.987   32.900  -13.343  1.00 33.86      B
ATOM   5253  CB   THR B 132     -33.264   33.681  -14.424  1.00 32.62      B
ATOM   5254  OG1  THR B 132     -33.162   35.051  -14.025  1.00 32.59      B
ATOM   5255  CG2  THR B 132     -34.053   33.614  -15.707  1.00 28.12      B
ATOM   5256  C    THR B 132     -33.736   31.421  -13.582  1.00 33.61      B
ATOM   5257  O    THR B 132     -32.593   30.956  -13.541  1.00 34.46      B
ATOM   5258  N    PRO B 133     -34.811   30.656  -13.842  1.00 31.57      B
ATOM   5259  CD   PRO B 133     -36.234   31.027  -13.888  1.00 26.98      B
ATOM   5260  CA   PRO B 133     -34.642   29.223  -14.082  1.00 28.94      B
ATOM   5261  CB   PRO B 133     -36.042   28.769  -14.478  1.00 27.40      B
ATOM   5262  CG   PRO B 133     -36.908   29.690  -13.678  1.00 28.16      B
ATOM   5263  C    PRO B 133     -33.624   28.998  -15.177  1.00 26.75      B
ATOM   5264  O    PRO B 133     -33.547   29.769  -16.122  1.00 25.17      B
ATOM   5265  N    ILE B 134     -32.830   27.952  -15.013  1.00 26.95      B
ATOM   5266  CA   ILE B 134     -31.814   27.602  -15.976  1.00 27.44      B
ATOM   5267  CB   ILE B 134     -30.564   27.019  -15.270  1.00 28.40      B
ATOM   5268  CG2  ILE B 134     -29.653   26.341  -16.284  1.00 27.34      B
ATOM   5269  CG1  ILE B 134     -29.836   28.138  -14.509  1.00 27.16      B
ATOM   5270  CD1  ILE B 134     -28.528   27.710  -13.860  1.00 24.60      B
ATOM   5271  C    ILE B 134     -32.431   26.577  -16.900  1.00 28.43      B
ATOM   5272  O    ILE B 134     -33.084   25.638  -16.455  1.00 29.48      B
ATOM   5273  N    ASP B 135     -32.231   26.764  -18.192  1.00 30.01      B
ATOM   5274  CA   ASP B 135     -32.792   25.853  -19.170  1.00 32.18      B
ATOM   5275  CB   ASP B 135     -32.567   26.414  -20.572  1.00 34.16      B
ATOM   5276  CG   ASP B 135     -33.388   25.705  -21.620  1.00 38.84      B
ATOM   5277  OD1  ASP B 135     -34.400   25.073  -21.237  1.00 42.25      B
ATOM   5278  OD2  ASP B 135     -33.037   25.794  -22.821  1.00 38.23      B
ATOM   5279  C    ASP B 135     -32.177   24.465  -19.057  1.00 32.51      B
ATOM   5280  O    ASP B 135     -31.052   24.321  -18.571  1.00 33.19      B
ATOM   5281  N    THR B 136     -32.938   23.455  -19.489  1.00 32.54      B
ATOM   5282  CA   THR B 136     -32.512   22.047  -19.496  1.00 31.76      B
ATOM   5283  CB   THR B 136     -32.996   21.253  -18.260  1.00 29.31      B
ATOM   5284  OG1  THR B 136     -34.425   21.141  -18.290  1.00 28.63      B
ATOM   5285  CG2  THR B 136     -32.553   21.933  -16.978  1.00 28.87      B
ATOM   5286  C    THR B 136     -33.079   21.330  -20.724  1.00 32.45      B
ATOM   5287  O    THR B 136     -34.155   21.673  -21.228  1.00 32.09      B
ATOM   5288  N    THR B 137     -32.340   20.334  -21.199  1.00 32.55      B
ATOM   5289  CA   THR B 137     -32.746   19.540  -22.350  1.00 32.09      B
ATOM   5290  CB   THR B 137     -31.542   19.205  -23.262  1.00 32.01      B
ATOM   5291  OG1  THR B 137     -31.117   20.381  -23.953  1.00 29.81      B
ATOM   5292  CG2  THR B 137     -31.912   18.135  -24.270  1.00 29.79      B
ATOM   5293  C    THR B 137     -33.299   18.229  -21.833  1.00 33.14      B
ATOM   5294  O    THR B 137     -32.674   17.590  -20.992  1.00 31.15      B
ATOM   5295  N    ILE B 138     -34.478   17.838  -22.311  1.00 36.69      B
ATOM   5296  CA   ILE B 138     -35.053   16.559  -21.899  1.00 38.13      B
ATOM   5297  CB   ILE B 138     -36.550   16.648  -21.512  1.00 35.16      B
ATOM   5298  CG2  ILE B 138     -37.367   17.236  -22.649  1.00 33.41      B
ATOM   5299  CG1  ILE B 138     -37.045   15.239  -21.153  1.00 35.36      B
ATOM   5300  CD1  ILE B 138     -38.419   15.167  -20.536  1.00 35.80      B
ATOM   5301  C    ILE B 138     -34.893   15.614  -23.078  1.00 39.96      B
ATOM   5302  O    ILE B 138     -34.919   16.048  -24.219  1.00 39.99      B
ATOM   5303  N    MET B 139     -34.704   14.330  -22.802  1.00 43.66      B
ATOM   5304  CA   MET B 139     -34.522   13.357  -23.866  1.00 46.84      B
ATOM   5305  CB   MET B 139     -33.065   13.315  -24.316  1.00 49.03      B
ATOM   5306  CG   MET B 139     -32.518   14.624  -24.806  1.00 54.35      B
ATOM   5307  SD   MET B 139     -31.916   14.444  -26.473  1.00 62.04      B
ATOM   5308  CE   MET B 139     -30.400   13.515  -26.135  1.00 59.74      B
ATOM   5309  C    MET B 139     -34.895   11.971  -23.417  1.00 47.91      B
ATOM   5310  O    MET B 139     -34.783   11.639  -22.240  1.00 48.34      B
ATOM   5311  N    ALA B 140     -35.333   11.164  -24.374  1.00 50.22      B
ATOM   5312  CA   ALA B 140     -35.685    9.781  -24.112  1.00 52.17      B
ATOM   5313  CB   ALA B 140     -36.569    9.255  -25.219  1.00 51.28      B
ATOM   5314  C    ALA B 140     -34.340    9.070  -24.124  1.00 53.42      B
ATOM   5315  O    ALA B 140     -33.560    9.249  -25.057  1.00 53.01      B
ATOM   5316  N    LYS B 141     -34.047    8.285  -23.094  1.00 55.70      B
ATOM   5317  CA   LYS B 141     -32.761    7.603  -23.065  1.00 59.38      B
ATOM   5318  CB   LYS B 141     -32.344    7.233  -21.640  1.00 60.26      B
ATOM   5319  CG   LYS B 141     -30.872    6.842  -21.558  1.00 62.55      B
ATOM   5320  CD   LYS B 141     -30.499    6.171  -20.241  1.00 66.13      B
```

FIGURE 5-71 -

```
ATOM   5321  CE   LYS B 141     -30.595   7.109 -19.045  1.00 66.71           B
ATOM   5322  NZ   LYS B 141     -30.254   6.395 -17.783  1.00 64.95           B
ATOM   5323  C    LYS B 141     -32.787   6.347 -23.912  1.00 62.07           B
ATOM   5324  O    LYS B 141     -33.841   5.751 -24.131  1.00 62.94           B
ATOM   5325  N    SER B 142     -31.616   5.946 -24.391  1.00 64.78           B
ATOM   5326  CA   SER B 142     -31.508   4.755 -25.218  1.00 66.61           B
ATOM   5327  CB   SER B 142     -30.685   5.063 -26.466  1.00 66.89           B
ATOM   5328  OG   SER B 142     -30.846   4.045 -27.437  1.00 69.65           B
ATOM   5329  C    SER B 142     -30.853   3.629 -24.428  1.00 67.70           B
ATOM   5330  O    SER B 142     -29.678   3.711 -24.067  1.00 67.75           B
ATOM   5331  N    GLU B 143     -31.623   2.585 -24.150  1.00 69.03           B
ATOM   5332  CA   GLU B 143     -31.111   1.445 -23.406  1.00 70.92           B
ATOM   5333  CB   GLU B 143     -31.580   1.508 -21.949  1.00 70.70           B
ATOM   5334  CG   GLU B 143     -31.165   2.792 -21.248  1.00 70.92           B
ATOM   5335  CD   GLU B 143     -31.424   2.778 -19.753  1.00 70.84           B
ATOM   5336  OE1  GLU B 143     -32.585   2.559 -19.337  1.00 71.00           B
ATOM   5337  OE2  GLU B 143     -30.456   3.001 -18.996  1.00 70.01           B
ATOM   5338  C    GLU B 143     -31.587   0.161 -24.056  1.00 72.27           B
ATOM   5339  O    GLU B 143     -32.651   0.129 -24.668  1.00 72.28           B
ATOM   5340  N    VAL B 144     -30.791  -0.894 -23.927  1.00 74.34           B
ATOM   5341  CA   VAL B 144     -31.139  -2.182 -24.515  1.00 76.49           B
ATOM   5342  CB   VAL B 144     -29.923  -2.806 -25.232  1.00 75.72           B
ATOM   5343  CG1  VAL B 144     -30.340  -4.074 -25.940  1.00 75.58           B
ATOM   5344  CG2  VAL B 144     -29.335  -1.814 -26.223  1.00 75.46           B
ATOM   5345  C    VAL B 144     -31.646  -3.157 -23.456  1.00 77.86           B
ATOM   5346  O    VAL B 144     -31.124  -3.195 -22.342  1.00 77.31           B
ATOM   5347  N    PHE B 145     -32.668  -3.934 -23.817  1.00 80.09           B
ATOM   5348  CA   PHE B 145     -33.276  -4.922 -22.920  1.00 82.43           B
ATOM   5349  CB   PHE B 145     -34.423  -4.288 -22.119  1.00 81.48           B
ATOM   5350  CG   PHE B 145     -33.978  -3.235 -21.144  1.00 81.20           B
ATOM   5351  CD1  PHE B 145     -33.262  -3.582 -20.002  1.00 80.49           B
ATOM   5352  CD2  PHE B 145     -34.253  -1.891 -21.380  1.00 80.99           B
ATOM   5353  CE1  PHE B 145     -32.829  -2.604 -19.106  1.00 80.25           B
ATOM   5354  CE2  PHE B 145     -33.823  -0.906 -20.490  1.00 81.19           B
ATOM   5355  CZ   PHE B 145     -33.108  -1.263 -19.352  1.00 80.01           B
ATOM   5356  C    PHE B 145     -33.816  -6.120 -23.706  1.00 84.25           B
ATOM   5357  O    PHE B 145     -33.662  -6.193 -24.927  1.00 84.22           B
ATOM   5358  N    CYS B 146     -34.453  -7.049 -22.994  1.00 86.37           B
ATOM   5359  CA   CYS B 146     -35.028  -8.251 -23.596  1.00 88.17           B
ATOM   5360  CB   CYS B 146     -34.294  -9.493 -23.085  1.00 88.06           B
ATOM   5361  SG   CYS B 146     -34.936 -11.067 -23.704  1.00 88.39           B
ATOM   5362  C    CYS B 146     -36.517  -8.350 -23.259  1.00 90.07           B
ATOM   5363  O    CYS B 146     -36.901  -8.350 -22.088  1.00 89.20           B
ATOM   5364  N    VAL B 147     -37.347  -8.437 -24.296  1.00 93.06           B
ATOM   5365  CA   VAL B 147     -38.798  -8.520 -24.137  1.00 95.81           B
ATOM   5366  CB   VAL B 147     -39.497  -8.699 -25.514  1.00 95.47           B
ATOM   5367  CG1  VAL B 147     -38.901  -7.731 -26.522  1.00 95.08           B
ATOM   5368  CG2  VAL B 147     -39.353 -10.133 -26.005  1.00 94.83           B
ATOM   5369  C    VAL B 147     -39.217  -9.670 -23.221  1.00 97.88           B
ATOM   5370  O    VAL B 147     -38.606 -10.737 -23.240  1.00 98.77           B
ATOM   5371  N    GLN B 148     -40.252  -9.443 -22.414  1.00100.08           B
ATOM   5372  CA   GLN B 148     -40.763 -10.473 -21.509  1.00102.18           B
ATOM   5373  CB   GLN B 148     -41.082  -9.882 -20.131  1.00103.22           B
ATOM   5374  CG   GLN B 148     -42.129 -10.689 -19.354  1.00105.22           B
ATOM   5375  CD   GLN B 148     -42.372 -10.168 -17.947  1.00106.38           B
ATOM   5376  OE1  GLN B 148     -42.442  -8.957 -17.722  1.00106.93           B
ATOM   5377  NE2  GLN B 148     -42.520 -11.088 -16.992  1.00105.82           B
ATOM   5378  C    GLN B 148     -42.026 -11.115 -22.087  1.00103.12           B
ATOM   5379  O    GLN B 148     -42.052 -12.358 -22.218  1.00103.31           B
ATOM   5380  OXT  GLN B 148     -42.978 -10.364 -22.394  1.00104.50           B
ATOM   5381  C    GLY B 153     -43.083  -5.767 -21.873  1.00 85.17           B
ATOM   5382  O    GLY B 153     -42.191  -6.614 -21.996  1.00 85.25           B
ATOM   5383  N    GLY B 153     -44.620  -7.613 -21.085  1.00 85.94           B
ATOM   5384  CA   GLY B 153     -44.451  -6.146 -21.325  1.00 85.41           B
ATOM   5385  N    ARG B 154     -42.926  -4.485 -22.201  1.00 83.79           B
ATOM   5386  CA   ARG B 154     -41.682  -3.937 -22.748  1.00 82.16           B
ATOM   5387  CB   ARG B 154     -41.761  -3.895 -24.274  1.00 82.25           B
ATOM   5388  CG   ARG B 154     -40.675  -3.075 -24.928  1.00 83.52           B
ATOM   5389  CD   ARG B 154     -40.794  -3.135 -26.441  1.00 85.38           B
ATOM   5390  NE   ARG B 154     -40.367  -4.425 -26.978  1.00 86.20           B
ATOM   5391  CZ   ARG B 154     -40.451  -4.765 -28.260  1.00 85.98           B
ATOM   5392  NH1  ARG B 154     -40.951  -3.912 -29.144  1.00 85.64           B
ATOM   5393  NH2  ARG B 154     -40.026  -5.956 -28.659  1.00 86.52           B
ATOM   5394  C    ARG B 154     -41.488  -2.527 -22.191  1.00 80.21           B
ATOM   5395  O    ARG B 154     -42.288  -1.633 -22.462  1.00 81.00           B
ATOM   5396  N    LYS B 155     -40.418  -2.321 -21.431  1.00 77.21           B
```

FIGURE 5- 72 -

```
ATOM   5397  CA  LYS B 155     -40.185  -1.024 -20.804  1.00 73.91      B
ATOM   5398  CB  LYS B 155     -39.127  -1.153 -19.707  1.00 73.97      B
ATOM   5399  CG  LYS B 155     -37.762  -1.590 -20.187  1.00 73.72      B
ATOM   5400  CD  LYS B 155     -36.886  -1.957 -19.000  1.00 74.37      B
ATOM   5401  CE  LYS B 155     -37.517  -3.077 -18.176  1.00 73.35      B
ATOM   5402  NZ  LYS B 155     -36.637  -3.513 -17.062  1.00 73.70      B
ATOM   5403  C   LYS B 155     -39.843   0.166 -21.689  1.00 70.83      B
ATOM   5404  O   LYS B 155     -39.029   0.073 -22.611  1.00 69.52      B
ATOM   5405  N   PRO B 156     -40.495   1.309 -21.415  1.00 68.08      B
ATOM   5406  CD  PRO B 156     -41.670   1.412 -20.528  1.00 66.82      B
ATOM   5407  CA  PRO B 156     -40.293   2.557 -22.148  1.00 65.53      B
ATOM   5408  CB  PRO B 156     -41.549   3.364 -21.811  1.00 65.95      B
ATOM   5409  CG  PRO B 156     -41.877   2.906 -20.433  1.00 66.34      B
ATOM   5410  C   PRO B 156     -39.009   3.229 -21.675  1.00 62.82      B
ATOM   5411  O   PRO B 156     -38.474   2.899 -20.614  1.00 61.63      B
ATOM   5412  N   ALA B 157     -38.526   4.175 -22.468  1.00 60.18      B
ATOM   5413  CA  ALA B 157     -37.296   4.875 -22.156  1.00 57.71      B
ATOM   5414  CB  ALA B 157     -36.872   5.712 -23.341  1.00 58.84      B
ATOM   5415  C   ALA B 157     -37.414   5.755 -20.936  1.00 55.77      B
ATOM   5416  O   ALA B 157     -38.485   6.277 -20.633  1.00 55.89      B
ATOM   5417  N   ARG B 158     -36.301   5.900 -20.229  1.00 53.14      B
ATOM   5418  CA  ARG B 158     -36.256   6.765 -19.069  1.00 50.64      B
ATOM   5419  CB  ARG B 158     -35.139   6.338 -18.119  1.00 51.65      B
ATOM   5420  CG  ARG B 158     -35.533   5.209 -17.186  1.00 56.02      B
ATOM   5421  CD  ARG B 158     -34.440   4.895 -16.167  1.00 58.56      B
ATOM   5422  NE  ARG B 158     -34.970   4.192 -14.994  1.00 62.65      B
ATOM   5423  CZ  ARG B 158     -35.771   4.740 -14.076  1.00 65.06      B
ATOM   5424  NH1 ARG B 158     -36.196   4.012 -13.048  1.00 64.42      B
ATOM   5425  NH2 ARG B 158     -36.143   6.017 -14.174  1.00 65.70      B
ATOM   5426  C   ARG B 158     -35.970   8.147 -19.635  1.00 48.57      B
ATOM   5427  O   ARG B 158     -35.532   8.283 -20.775  1.00 48.22      B
ATOM   5428  N   LEU B 159     -36.228   9.181 -18.856  1.00 46.58      B
ATOM   5429  CA  LEU B 159     -35.969  10.524 -19.341  1.00 44.46      B
ATOM   5430  CB  LEU B 159     -37.078  11.465 -18.892  1.00 44.43      B
ATOM   5431  CG  LEU B 159     -38.502  11.044 -19.241  1.00 44.91      B
ATOM   5432  CD1 LEU B 159     -39.457  12.127 -18.763  1.00 44.19      B
ATOM   5433  CD2 LEU B 159     -38.635  10.823 -20.743  1.00 44.22      B
ATOM   5434  C   LEU B 159     -34.651  11.045 -18.807  1.00 42.58      B
ATOM   5435  O   LEU B 159     -34.195  10.641 -17.740  1.00 43.74      B
ATOM   5436  N   ILE B 160     -34.013  11.921 -19.563  1.00 40.64      B
ATOM   5437  CA  ILE B 160     -32.783  12.521 -19.076  1.00 40.03      B
ATOM   5438  CB  ILE B 160     -31.525  12.048 -19.840  1.00 39.68      B
ATOM   5439  CG2 ILE B 160     -31.326  10.553 -19.638  1.00 39.52      B
ATOM   5440  CG1 ILE B 160     -31.650  12.378 -21.319  1.00 41.05      B
ATOM   5441  CD1 ILE B 160     -30.416  11.999 -22.119  1.00 44.85      B
ATOM   5442  C   ILE B 160     -32.963  14.018 -19.235  1.00 38.50      B
ATOM   5443  O   ILE B 160     -33.396  14.498 -20.283  1.00 37.96      B
ATOM   5444  N   VAL B 161     -32.674  14.742 -18.163  1.00 36.29      B
ATOM   5445  CA  VAL B 161     -32.789  16.188 -18.147  1.00 34.40      B
ATOM   5446  CB  VAL B 161     -33.796  16.642 -17.071  1.00 33.88      B
ATOM   5447  CG1 VAL B 161     -33.843  18.161 -16.998  1.00 32.52      B
ATOM   5448  CG2 VAL B 161     -35.162  16.064 -17.376  1.00 31.22      B
ATOM   5449  C   VAL B 161     -31.409  16.706 -17.779  1.00 33.74      B
ATOM   5450  O   VAL B 161     -30.813  16.247 -16.804  1.00 33.88      B
ATOM   5451  N   PHE B 162     -30.881  17.638 -18.555  1.00 31.87      B
ATOM   5452  CA  PHE B 162     -29.573  18.168 -18.216  1.00 33.55      B
ATOM   5453  CB  PHE B 162     -28.472  17.225 -18.709  1.00 33.42      B
ATOM   5454  CG  PHE B 162     -28.447  17.073 -20.189  1.00 33.30      B
ATOM   5455  CD1 PHE B 162     -29.283  16.165 -20.819  1.00 34.61      B
ATOM   5456  CD2 PHE B 162     -27.645  17.899 -20.964  1.00 33.24      B
ATOM   5457  CE1 PHE B 162     -29.326  16.091 -22.213  1.00 35.55      B
ATOM   5458  CE2 PHE B 162     -27.681  17.835 -22.347  1.00 32.58      B
ATOM   5459  CZ  PHE B 162     -28.521  16.932 -22.973  1.00 33.51      B
ATOM   5460  C   PHE B 162     -29.342  19.569 -18.778  1.00 32.59      B
ATOM   5461  O   PHE B 162     -29.849  19.920 -19.850  1.00 33.90      B
ATOM   5462  N   PRO B 163     -28.573  20.391 -18.045  1.00 30.09      B
ATOM   5463  CD  PRO B 163     -28.064  20.112 -16.691  1.00 28.64      B
ATOM   5464  CA  PRO B 163     -28.254  21.758 -18.447  1.00 29.07      B
ATOM   5465  CB  PRO B 163     -27.787  22.386 -17.149  1.00 28.46      B
ATOM   5466  CG  PRO B 163     -27.093  21.229 -16.481  1.00 28.28      B
ATOM   5467  C   PRO B 163     -27.164  21.765 -19.512  1.00 29.75      B
ATOM   5468  O   PRO B 163     -26.594  20.720 -19.835  1.00 27.43      B
ATOM   5469  N   ASP B 164     -26.880  22.953 -20.045  1.00 30.60      B
ATOM   5470  CA  ASP B 164     -25.867  23.122 -21.070  1.00 29.65      B
ATOM   5471  CB  ASP B 164     -25.883  24.548 -21.615  1.00 31.37      B
ATOM   5472  CG  ASP B 164     -25.041  24.703 -22.883  1.00 34.41      B
```

FIGURE 5- 73 -

```
ATOM   5473  OD1 ASP B 164     -25.494  24.269 -23.964  1.00 35.19      B
ATOM   5474  OD2 ASP B 164     -23.921  25.250 -22.799  1.00 34.61      B
ATOM   5475  C   ASP B 164     -24.495  22.826 -20.492  1.00 31.11      B
ATOM   5476  O   ASP B 164     -24.294  22.853 -19.273  1.00 29.50      B
ATOM   5477  N   LEU B 165     -23.554  22.552 -21.390  1.00 31.99      B
ATOM   5478  CA  LEU B 165     -22.180  22.239 -21.021  1.00 32.27      B
ATOM   5479  CB  LEU B 165     -21.328  22.153 -22.289  1.00 31.34      B
ATOM   5480  CG  LEU B 165     -19.866  21.743 -22.138  1.00 31.98      B
ATOM   5481  CD1 LEU B 165     -19.755  20.469 -21.328  1.00 30.92      B
ATOM   5482  CD2 LEU B 165     -19.265  21.552 -23.520  1.00 32.82      B
ATOM   5483  C   LEU B 165     -21.572  23.253 -20.045  1.00 31.29      B
ATOM   5484  O   LEU B 165     -21.028  22.876 -19.005  1.00 31.32      B
ATOM   5485  N   GLY B 166     -21.669  24.534 -20.383  1.00 29.77      B
ATOM   5486  CA  GLY B 166     -21.113  25.562 -19.521  1.00 31.88      B
ATOM   5487  C   GLY B 166     -21.570  25.421 -18.079  1.00 31.60      B
ATOM   5488  O   GLY B 166     -20.767  25.473 -17.141  1.00 31.28      B
ATOM   5489  N   VAL B 167     -22.873  25.248 -17.903  1.00 30.62      B
ATOM   5490  CA  VAL B 167     -23.434  25.086 -16.578  1.00 30.02      B
ATOM   5491  CB  VAL B 167     -24.981  24.982 -16.644  1.00 30.55      B
ATOM   5492  CG1 VAL B 167     -25.550  24.574 -15.281  1.00 30.08      B
ATOM   5493  CG2 VAL B 167     -25.570  26.324 -17.082  1.00 27.81      B
ATOM   5494  C   VAL B 167     -22.862  23.827 -15.934  1.00 30.44      B
ATOM   5495  O   VAL B 167     -22.487  23.840 -14.762  1.00 31.39      B
ATOM   5496  N   ARG B 168     -22.780  22.745 -16.704  1.00 30.48      B
ATOM   5497  CA  ARG B 168     -22.268  21.488 -16.178  1.00 29.69      B
ATOM   5498  CB  ARG B 168     -22.278  20.391 -17.253  1.00 30.55      B
ATOM   5499  CG  ARG B 168     -23.698  19.920 -17.685  1.00 31.12      B
ATOM   5500  CD  ARG B 168     -23.688  18.535 -18.352  1.00 29.42      B
ATOM   5501  NE  ARG B 168     -22.874  18.487 -19.567  1.00 31.60      B
ATOM   5502  CZ  ARG B 168     -23.268  18.910 -20.767  1.00 32.65      B
ATOM   5503  NH1 ARG B 168     -24.483  19.417 -20.952  1.00 31.76      B
ATOM   5504  NH2 ARG B 168     -22.432  18.843 -21.789  1.00 33.13      B
ATOM   5505  C   ARG B 168     -20.872  21.658 -15.620  1.00 31.23      B
ATOM   5506  O   ARG B 168     -20.526  21.045 -14.601  1.00 31.31      B
ATOM   5507  N   VAL B 169     -20.066  22.495 -16.265  1.00 31.13      B
ATOM   5508  CA  VAL B 169     -18.706  22.708 -15.774  1.00 32.62      B
ATOM   5509  CB  VAL B 169     -17.809  23.398 -16.841  1.00 32.38      B
ATOM   5510  CG1 VAL B 169     -16.412  23.631 -16.284  1.00 30.97      B
ATOM   5511  CG2 VAL B 169     -17.715  22.529 -18.081  1.00 31.81      B
ATOM   5512  C   VAL B 169     -18.701  23.535 -14.483  1.00 32.85      B
ATOM   5513  O   VAL B 169     -17.888  23.304 -13.595  1.00 34.77      B
ATOM   5514  N   CYS B 170     -19.617  24.488 -14.368  1.00 32.36      B
ATOM   5515  CA  CYS B 170     -19.671  25.314 -13.173  1.00 31.02      B
ATOM   5516  CB  CYS B 170     -20.599  26.500 -13.384  1.00 28.96      B
ATOM   5517  SG  CYS B 170     -20.005  27.648 -14.632  1.00 30.19      B
ATOM   5518  C   CYS B 170     -20.131  24.506 -11.984  1.00 31.43      B
ATOM   5519  O   CYS B 170     -19.712  24.753 -10.852  1.00 33.58      B
ATOM   5520  N   GLU B 171     -20.994  23.534 -12.233  1.00 31.92      B
ATOM   5521  CA  GLU B 171     -21.477  22.703 -11.145  1.00 32.38      B
ATOM   5522  CB  GLU B 171     -22.413  21.617 -11.655  1.00 32.98      B
ATOM   5523  CG  GLU B 171     -23.687  22.091 -12.316  1.00 34.10      B
ATOM   5524  CD  GLU B 171     -24.592  20.919 -12.651  1.00 35.71      B
ATOM   5525  OE1 GLU B 171     -25.111  20.284 -11.705  1.00 35.21      B
ATOM   5526  OE2 GLU B 171     -24.770  20.619 -13.852  1.00 36.24      B
ATOM   5527  C   GLU B 171     -20.278  22.031 -10.510  1.00 32.19      B
ATOM   5528  O   GLU B 171     -20.197  21.886  -9.287  1.00 32.21      B
ATOM   5529  N   LYS B 172     -19.336  21.624 -11.351  1.00 32.08      B
ATOM   5530  CA  LYS B 172     -18.167  20.940 -10.847  1.00 32.79      B
ATOM   5531  CB  LYS B 172     -17.320  20.386 -11.997  1.00 32.85      B
ATOM   5532  CG  LYS B 172     -18.041  19.341 -12.840  1.00 33.00      B
ATOM   5533  CD  LYS B 172     -17.076  18.580 -13.721  1.00 35.88      B
ATOM   5534  CE  LYS B 172     -17.786  17.648 -14.700  1.00 36.46      B
ATOM   5535  NZ  LYS B 172     -18.346  18.390 -15.861  1.00 40.09      B
ATOM   5536  C   LYS B 172     -17.357  21.857  -9.961  1.00 33.56      B
ATOM   5537  O   LYS B 172     -17.017  21.482  -8.839  1.00 35.00      B
ATOM   5538  N   MET B 173     -17.073  23.065 -10.435  1.00 32.65      B
ATOM   5539  CA  MET B 173     -16.290  24.000  -9.635  1.00 33.15      B
ATOM   5540  CB  MET B 173     -16.178  25.353 -10.329  1.00 34.14      B
ATOM   5541  CG  MET B 173     -15.342  25.335 -11.591  1.00 36.77      B
ATOM   5542  SD  MET B 173     -15.277  26.971 -12.352  1.00 42.34      B
ATOM   5543  CE  MET B 173     -16.790  26.981 -13.310  1.00 38.70      B
ATOM   5544  C   MET B 173     -16.865  24.215  -8.247  1.00 32.55      B
ATOM   5545  O   MET B 173     -16.127  24.307  -7.272  1.00 32.84      B
ATOM   5546  N   ALA B 174     -18.186  24.272  -8.152  1.00 32.58      B
ATOM   5547  CA  ALA B 174     -18.833  24.523  -6.869  1.00 31.50      B
ATOM   5548  CB  ALA B 174     -20.073  25.372  -7.091  1.00 29.66      B
```

FIGURE 5-74-

| | | | | | | | | | | |
|---|---|---|---|---|---|---|---|---|---|---|
| ATOM | 5549 | C | ALA | B | 174 | -19.203 | 23.307 | -6.031 | 1.00 31.96 | B |
| ATOM | 5550 | O | ALA | B | 174 | -19.210 | 23.388 | -4.802 | 1.00 32.39 | B |
| ATOM | 5551 | N | LEU | B | 175 | -19.494 | 22.175 | -6.665 | 1.00 30.92 | B |
| ATOM | 5552 | CA | LEU | B | 175 | -19.918 | 21.026 | -5.880 | 1.00 30.73 | B |
| ATOM | 5553 | CB | LEU | B | 175 | -21.422 | 20.826 | -6.088 | 1.00 27.88 | B |
| ATOM | 5554 | CG | LEU | B | 175 | -22.276 | 21.938 | -5.478 | 1.00 27.58 | B |
| ATOM | 5555 | CD1 | LEU | B | 175 | -23.570 | 22.133 | -6.256 | 1.00 24.63 | B |
| ATOM | 5556 | CD2 | LEU | B | 175 | -22.548 | 21.585 | -4.019 | 1.00 27.95 | B |
| ATOM | 5557 | C | LEU | B | 175 | -19.185 | 19.699 | -6.060 | 1.00 31.08 | B |
| ATOM | 5558 | O | LEU | B | 175 | -19.447 | 18.751 | -5.317 | 1.00 29.56 | B |
| ATOM | 5559 | N | TYR | B | 176 | -18.271 | 19.620 | -7.021 | 1.00 30.91 | B |
| ATOM | 5560 | CA | TYR | B | 176 | -17.554 | 18.369 | -7.224 | 1.00 31.90 | B |
| ATOM | 5561 | CB | TYR | B | 176 | -16.419 | 18.521 | -8.242 | 1.00 31.35 | B |
| ATOM | 5562 | CG | TYR | B | 176 | -15.722 | 17.201 | -8.499 | 1.00 33.02 | B |
| ATOM | 5563 | CD1 | TYR | B | 176 | -16.355 | 16.181 | -9.212 | 1.00 34.32 | B |
| ATOM | 5564 | CE1 | TYR | B | 176 | -15.765 | 14.928 | -9.358 | 1.00 34.59 | B |
| ATOM | 5565 | CD2 | TYR | B | 176 | -14.475 | 16.932 | -7.947 | 1.00 33.97 | B |
| ATOM | 5566 | CE2 | TYR | B | 176 | -13.881 | 15.688 | -8.086 | 1.00 33.11 | B |
| ATOM | 5567 | CZ | TYR | B | 176 | -14.531 | 14.693 | -8.785 | 1.00 34.43 | B |
| ATOM | 5568 | OH | TYR | B | 176 | -13.958 | 13.452 | -8.869 | 1.00 36.19 | B |
| ATOM | 5569 | C | TYR | B | 176 | -16.975 | 17.863 | -5.907 | 1.00 33.18 | B |
| ATOM | 5570 | O | TYR | B | 176 | -17.271 | 16.743 | -5.475 | 1.00 33.30 | B |
| ATOM | 5571 | N | ASP | B | 177 | -16.149 | 18.693 | -5.274 | 1.00 33.53 | B |
| ATOM | 5572 | CA | ASP | B | 177 | -15.529 | 18.341 | -4.005 | 1.00 33.55 | B |
| ATOM | 5573 | CB | ASP | B | 177 | -14.797 | 19.561 | -3.447 | 1.00 38.51 | B |
| ATOM | 5574 | CG | ASP | B | 177 | -13.693 | 19.200 | -2.450 | 1.00 42.11 | B |
| ATOM | 5575 | OD1 | ASP | B | 177 | -13.609 | 18.032 | -2.006 | 1.00 41.03 | B |
| ATOM | 5576 | OD2 | ASP | B | 177 | -12.901 | 20.111 | -2.105 | 1.00 46.96 | B |
| ATOM | 5577 | C | ASP | B | 177 | -16.628 | 17.897 | -3.037 | 1.00 32.18 | B |
| ATOM | 5578 | O | ASP | B | 177 | -16.556 | 16.823 | -2.444 | 1.00 30.80 | B |
| ATOM | 5579 | N | VAL | B | 178 | -17.661 | 18.722 | -2.906 | 1.00 32.59 | B |
| ATOM | 5580 | CA | VAL | B | 178 | -18.773 | 18.422 | -2.009 | 1.00 32.43 | B |
| ATOM | 5581 | CB | VAL | B | 178 | -19.913 | 19.458 | -2.132 | 1.00 31.77 | B |
| ATOM | 5582 | CG1 | VAL | B | 178 | -20.991 | 19.149 | -1.117 | 1.00 30.45 | B |
| ATOM | 5583 | CG2 | VAL | B | 178 | -19.385 | 20.863 | -1.933 | 1.00 29.42 | B |
| ATOM | 5584 | C | VAL | B | 178 | -19.391 | 17.045 | -2.240 | 1.00 34.91 | B |
| ATOM | 5585 | O | VAL | B | 178 | -19.492 | 16.244 | -1.301 | 1.00 36.86 | B |
| ATOM | 5586 | N | VAL | B | 179 | -19.810 | 16.763 | -3.474 | 1.00 34.19 | B |
| ATOM | 5587 | CA | VAL | B | 179 | -20.439 | 15.478 | -3.766 | 1.00 34.73 | B |
| ATOM | 5588 | CB | VAL | B | 179 | -21.143 | 15.479 | -5.133 | 1.00 33.49 | B |
| ATOM | 5589 | CG1 | VAL | B | 179 | -22.122 | 16.620 | -5.210 | 1.00 32.47 | B |
| ATOM | 5590 | CG2 | VAL | B | 179 | -20.119 | 15.564 | -6.255 | 1.00 35.83 | B |
| ATOM | 5591 | C | VAL | B | 179 | -19.493 | 14.283 | -3.727 | 1.00 37.20 | B |
| ATOM | 5592 | O | VAL | B | 179 | -19.943 | 13.138 | -3.768 | 1.00 39.84 | B |
| ATOM | 5593 | N | SER | B | 180 | -18.193 | 14.538 | -3.640 | 1.00 37.95 | B |
| ATOM | 5594 | CA | SER | B | 180 | -17.220 | 13.452 | -3.597 | 1.00 39.40 | B |
| ATOM | 5595 | CB | SER | B | 180 | -16.017 | 13.787 | -4.466 | 1.00 39.36 | B |
| ATOM | 5596 | OG | SER | B | 180 | -16.419 | 14.055 | -5.789 | 1.00 44.54 | B |
| ATOM | 5597 | C | SER | B | 180 | -16.723 | 13.241 | -2.187 | 1.00 39.89 | B |
| ATOM | 5598 | O | SER | B | 180 | -16.040 | 12.260 | -1.896 | 1.00 39.96 | B |
| ATOM | 5599 | N | THR | B | 181 | -17.087 | 14.163 | -1.310 | 1.00 40.33 | B |
| ATOM | 5600 | CA | THR | B | 181 | -16.619 | 14.139 | 0.064 | 1.00 39.07 | B |
| ATOM | 5601 | CB | THR | B | 181 | -15.843 | 15.438 | 0.335 | 1.00 38.73 | B |
| ATOM | 5602 | OG1 | THR | B | 181 | -14.663 | 15.453 | -0.470 | 1.00 39.91 | B |
| ATOM | 5603 | CG2 | THR | B | 181 | -15.464 | 15.555 | 1.783 | 1.00 41.21 | B |
| ATOM | 5604 | C | THR | B | 181 | -17.671 | 13.987 | 1.148 | 1.00 38.43 | B |
| ATOM | 5605 | O | THR | B | 181 | -17.517 | 13.196 | 2.071 | 1.00 39.59 | B |
| ATOM | 5606 | N | LEU | B | 182 | -18.733 | 14.768 | 1.031 | 1.00 37.64 | B |
| ATOM | 5607 | CA | LEU | B | 182 | -19.794 | 14.802 | 2.021 | 1.00 35.40 | B |
| ATOM | 5608 | CB | LEU | B | 182 | -20.750 | 15.939 | 1.638 | 1.00 32.82 | B |
| ATOM | 5609 | CG | LEU | B | 182 | -21.936 | 16.294 | 2.514 | 1.00 30.16 | B |
| ATOM | 5610 | CD1 | LEU | B | 182 | -22.189 | 17.770 | 2.434 | 1.00 32.58 | B |
| ATOM | 5611 | CD2 | LEU | B | 182 | -23.140 | 15.529 | 2.058 | 1.00 29.93 | B |
| ATOM | 5612 | C | LEU | B | 182 | -20.547 | 13.498 | 2.311 | 1.00 35.30 | B |
| ATOM | 5613 | O | LEU | B | 182 | -20.634 | 13.091 | 3.464 | 1.00 35.54 | B |
| ATOM | 5614 | N | PRO | B | 183 | -21.080 | 12.818 | 1.278 | 1.00 35.68 | B |
| ATOM | 5615 | CD | PRO | B | 183 | -20.862 | 13.090 | -0.155 | 1.00 35.77 | B |
| ATOM | 5616 | CA | PRO | B | 183 | -21.825 | 11.557 | 1.462 | 1.00 36.21 | B |
| ATOM | 5617 | CB | PRO | B | 183 | -21.884 | 10.977 | 0.048 | 1.00 35.17 | B |
| ATOM | 5618 | CG | PRO | B | 183 | -21.898 | 12.197 | -0.818 | 1.00 35.23 | B |
| ATOM | 5619 | C | PRO | B | 183 | -21.161 | 10.584 | 2.441 | 1.00 36.82 | B |
| ATOM | 5620 | O | PRO | B | 183 | -21.797 | 10.055 | 3.356 | 1.00 35.80 | B |
| ATOM | 5621 | N | GLN | B | 184 | -19.879 | 10.335 | 2.222 | 1.00 36.56 | B |
| ATOM | 5622 | CA | GLN | B | 184 | -19.125 | 9.446 | 3.079 | 1.00 37.84 | B |
| ATOM | 5623 | CB | GLN | B | 184 | -17.891 | 9.349 | 2.573 | 1.00 41.54 | B |
| ATOM | 5624 | CG | GLN | B | 184 | -16.754 | 8.585 | 3.488 | 1.00 46.37 | B |

FIGURE 5- 75 -

```
ATOM   5625  CD   GLN B 184     -16.701   7.121   3.141  1.00 49.88      B
ATOM   5626  OE1  GLN B 184     -16.398   6.756   1.999  1.00 53.32      B
ATOM   5627  NE2  GLN B 184     -16.996   6.265   4.117  1.00 51.44      B
ATOM   5628  C    GLN B 184     -19.115   9.998   4.500  1.00 37.29      B
ATOM   5629  O    GLN B 184     -19.336   9.268   5.468  1.00 37.06      B
ATOM   5630  N    ALA B 185     -18.851  11.295   4.612  1.00 35.73      B
ATOM   5631  CA   ALA B 185     -18.775  11.964   5.907  1.00 36.20      B
ATOM   5632  CB   ALA B 185     -18.291  13.397   5.718  1.00 36.03      B
ATOM   5633  C    ALA B 185     -20.080  11.963   6.694  1.00 36.13      B
ATOM   5634  O    ALA B 185     -20.069  11.973   7.926  1.00 35.00      B
ATOM   5635  N    VAL B 186     -21.197  11.947   5.979  1.00 35.94      B
ATOM   5636  CA   VAL B 186     -22.505  11.968   6.606  1.00 37.00      B
ATOM   5637  CB   VAL B 186     -23.512  12.758   5.722  1.00 34.89      B
ATOM   5638  CG1  VAL B 186     -24.898  12.756   6.341  1.00 30.56      B
ATOM   5639  CG2  VAL B 186     -23.023  14.182   5.540  1.00 32.76      B
ATOM   5640  C    VAL B 186     -23.067  10.574   6.887  1.00 40.66      B
ATOM   5641  O    VAL B 186     -23.600  10.315   7.969  1.00 42.44      B
ATOM   5642  N    MET B 187     -22.924   9.664   5.930  1.00 42.57      B
ATOM   5643  CA   MET B 187     -23.477   8.324   6.089  1.00 44.60      B
ATOM   5644  CB   MET B 187     -24.191   7.950   4.793  1.00 45.84      B
ATOM   5645  CG   MET B 187     -25.343   8.904   4.478  1.00 48.13      B
ATOM   5646  SD   MET B 187     -25.787   8.978   2.732  1.00 50.10      B
ATOM   5647  CE   MET B 187     -26.360   7.336   2.494  1.00 51.94      B
ATOM   5648  C    MET B 187     -22.520   7.208   6.523  1.00 45.33      B
ATOM   5649  O    MET B 187     -22.956   6.115   6.892  1.00 47.62      B
ATOM   5650  N    GLY B 188     -21.221   7.474   6.496  1.00 44.40      B
ATOM   5651  CA   GLY B 188     -20.282   6.452   6.910  1.00 42.13      B
ATOM   5652  C    GLY B 188     -20.429   5.170   6.124  1.00 41.43      B
ATOM   5653  O    GLY B 188     -20.659   5.206   4.922  1.00 41.80      B
ATOM   5654  N    SER B 189     -20.309   4.034   6.804  1.00 41.57      B
ATOM   5655  CA   SER B 189     -20.401   2.725   6.153  1.00 40.98      B
ATOM   5656  CB   SER B 189     -20.341   1.605   7.199  1.00 38.89      B
ATOM   5657  OG   SER B 189     -21.494   1.605   8.021  1.00 36.32      B
ATOM   5658  C    SER B 189     -21.624   2.510   5.255  1.00 41.36      B
ATOM   5659  O    SER B 189     -21.559   1.728   4.315  1.00 42.70      B
ATOM   5660  N    SER B 190     -22.735   3.188   5.542  1.00 41.48      B
ATOM   5661  CA   SER B 190     -23.947   3.049   4.732  1.00 40.89      B
ATOM   5662  CB   SER B 190     -25.134   3.714   5.422  1.00 40.44      B
ATOM   5663  OG   SER B 190     -25.479   3.030   6.610  1.00 44.20      B
ATOM   5664  C    SER B 190     -23.824   3.627   3.321  1.00 40.72      B
ATOM   5665  O    SER B 190     -24.676   3.373   2.478  1.00 42.51      B
ATOM   5666  N    TYR B 191     -22.788   4.415   3.057  1.00 39.70      B
ATOM   5667  CA   TYR B 191     -22.622   4.972   1.724  1.00 39.45      B
ATOM   5668  CB   TYR B 191     -21.550   6.059   1.711  1.00 37.56      B
ATOM   5669  CG   TYR B 191     -21.433   6.770   0.381  1.00 35.44      B
ATOM   5670  CD1  TYR B 191     -22.562   7.285  -0.257  1.00 34.40      B
ATOM   5671  CE1  TYR B 191     -22.462   7.953  -1.472  1.00 33.25      B
ATOM   5672  CD2  TYR B 191     -20.198   6.945  -0.234  1.00 34.00      B
ATOM   5673  CE2  TYR B 191     -20.089   7.617  -1.450  1.00 33.49      B
ATOM   5674  CZ   TYR B 191     -21.224   8.115  -2.061  1.00 33.72      B
ATOM   5675  OH   TYR B 191     -21.120   8.773  -3.266  1.00 36.72      B
ATOM   5676  C    TYR B 191     -22.201   3.831   0.830  1.00 41.01      B
ATOM   5677  O    TYR B 191     -21.141   3.253   1.018  1.00 43.56      B
ATOM   5678  N    GLY B 192     -23.029   3.497  -0.145  1.00 42.46      B
ATOM   5679  CA   GLY B 192     -22.698   2.388  -1.017  1.00 44.61      B
ATOM   5680  C    GLY B 192     -21.479   2.557  -1.906  1.00 46.10      B
ATOM   5681  O    GLY B 192     -20.561   1.734  -1.884  1.00 46.85      B
ATOM   5682  N    PHE B 193     -21.462   3.637  -2.675  1.00 46.42      B
ATOM   5683  CA   PHE B 193     -20.390   3.905  -3.625  1.00 46.54      B
ATOM   5684  CB   PHE B 193     -20.670   5.229  -4.328  1.00 45.75      B
ATOM   5685  CG   PHE B 193     -21.999   5.259  -5.016  1.00 45.98      B
ATOM   5686  CD1  PHE B 193     -22.276   4.365  -6.045  1.00 45.22      B
ATOM   5687  CD2  PHE B 193     -22.991   6.149  -4.615  1.00 47.01      B
ATOM   5688  CE1  PHE B 193     -23.522   4.346  -6.663  1.00 44.57      B
ATOM   5689  CE2  PHE B 193     -24.245   6.140  -5.229  1.00 46.57      B
ATOM   5690  CZ   PHE B 193     -24.508   5.235  -6.256  1.00 45.34      B
ATOM   5691  C    PHE B 193     -18.948   3.876  -3.152  1.00 46.34      B
ATOM   5692  O    PHE B 193     -18.041   3.990  -3.965  1.00 46.59      B
ATOM   5693  N    GLN B 194     -18.724   3.709  -1.857  1.00 48.78      B
ATOM   5694  CA   GLN B 194     -17.355   3.681  -1.335  1.00 51.14      B
ATOM   5695  CB   GLN B 194     -17.322   4.198   0.101  1.00 50.14      B
ATOM   5696  CG   GLN B 194     -17.989   3.248   1.065  1.00 51.01      B
ATOM   5697  CD   GLN B 194     -17.783   3.632   2.505  1.00 52.05      B
ATOM   5698  OE1  GLN B 194     -16.649   3.731   2.978  1.00 53.32      B
ATOM   5699  NE2  GLN B 194     -18.880   3.847   3.221  1.00 53.20      B
ATOM   5700  C    GLN B 194     -16.780   2.269  -1.347  1.00 52.80      B
```

FIGURE 5- 76 -

```
ATOM   5701  C    GLN B 194    -15.611   2.062  -1.004  1.00 53.43      B
ATOM   5702  N    TYR B 195    -17.605   1.302  -1.740  1.00 53.67      B
ATOM   5703  CA   TYR B 195    -17.194  -0.099  -1.755  1.00 53.07      B
ATOM   5704  CB   TYR B 195    -18.262  -0.959  -1.094  1.00 49.65      B
ATOM   5705  CG   TYR B 195    -18.547  -0.646   0.345  1.00 48.25      B
ATOM   5706  CD1  TYR B 195    -17.545  -0.729   1.313  1.00 47.74      B
ATOM   5707  CE1  TYR B 195    -17.833  -0.514   2.661  1.00 47.98      B
ATOM   5708  CD2  TYR B 195    -19.839  -0.335   0.757  1.00 47.04      B
ATOM   5709  CE2  TYR B 195    -20.134  -0.119   2.095  1.00 47.29      B
ATOM   5710  CZ   TYR B 195    -19.131  -0.210   3.042  1.00 47.61      B
ATOM   5711  OH   TYR B 195    -19.432   0.004   4.368  1.00 50.15      B
ATOM   5712  C    TYR B 195    -16.922  -0.710  -3.116  1.00 53.76      B
ATOM   5713  O    TYR B 195    -17.602  -0.402  -4.097  1.00 54.63      B
ATOM   5714  N    SER B 196    -15.930  -1.593  -3.164  1.00 54.87      B
ATOM   5715  CA   SER B 196    -15.619  -2.315  -4.394  1.00 55.26      B
ATOM   5716  CB   SER B 196    -14.153  -2.738  -4.440  1.00 55.51      B
ATOM   5717  OG   SER B 196    -13.926  -3.869  -3.614  1.00 58.14      B
ATOM   5718  C    SER B 196    -16.492  -3.554  -4.227  1.00 55.39      B
ATOM   5719  O    SER B 196    -16.769  -3.969  -3.096  1.00 53.88      B
ATOM   5720  N    PRO B 197    -16.934  -4.162  -5.338  1.00 55.48      B
ATOM   5721  CD   PRO B 197    -16.494  -3.916  -6.721  1.00 55.28      B
ATOM   5722  CA   PRO B 197    -17.783  -5.358  -5.265  1.00 55.93      B
ATOM   5723  CB   PRO B 197    -17.569  -5.999  -6.623  1.00 54.78      B
ATOM   5724  CG   PRO B 197    -17.434  -4.797  -7.511  1.00 54.55      B
ATOM   5725  C    PRO B 197    -17.424  -6.285  -4.097  1.00 57.53      B
ATOM   5726  O    PRO B 197    -18.286  -6.635  -3.285  1.00 57.25      B
ATOM   5727  N    LYS B 198    -16.153  -6.672  -4.006  1.00 59.02      B
ATOM   5728  CA   LYS B 198    -15.714  -7.535  -2.916  1.00 60.50      B
ATOM   5729  CB   LYS B 198    -14.196  -7.721  -2.953  1.00 61.81      B
ATOM   5730  CG   LYS B 198    -13.653  -8.538  -1.825  1.00 63.74      B
ATOM   5731  CD   LYS B 198    -12.135  -8.750  -1.885  1.00 66.73      B
ATOM   5732  CE   LYS B 198    -11.625  -9.598  -0.708  1.00 68.93      B
ATOM   5733  NZ   LYS B 198    -10.139  -9.795  -0.699  1.00 69.77      B
ATOM   5734  C    LYS B 198    -16.110  -6.890  -1.590  1.00 61.35      B
ATOM   5735  O    LYS B 198    -16.773  -7.508  -0.752  1.00 61.53      B
ATOM   5736  N    GLN B 199    -15.706  -5.635  -1.417  1.00 60.92      B
ATOM   5737  CA   GLN B 199    -15.997  -4.880  -0.203  1.00 60.42      B
ATOM   5738  CB   GLN B 199    -15.426  -3.469  -0.341  1.00 60.95      B
ATOM   5739  CG   GLN B 199    -13.982  -3.489  -0.817  1.00 61.86      B
ATOM   5740  CD   GLN B 199    -13.374  -2.118  -0.946  1.00 61.75      B
ATOM   5741  OE1  GLN B 199    -13.915  -1.249  -1.636  1.00 61.37      B
ATOM   5742  NE2  GLN B 199    -12.231  -1.913  -0.290  1.00 61.13      B
ATOM   5743  C    GLN B 199    -17.493  -4.823   0.109  1.00 59.53      B
ATOM   5744  O    GLN B 199    -17.901  -4.993   1.262  1.00 58.21      B
ATOM   5745  N    ARG B 200    -18.304  -4.588  -0.919  1.00 58.29      B
ATOM   5746  CA   ARG B 200    -19.748  -4.517  -0.735  1.00 58.05      B
ATOM   5747  CB   ARG B 200    -20.458  -4.273  -2.081  1.00 57.39      B
ATOM   5748  CG   ARG B 200    -21.977  -4.091  -1.968  1.00 55.64      B
ATOM   5749  CD   ARG B 200    -22.681  -3.967  -3.327  1.00 54.73      B
ATOM   5750  NE   ARG B 200    -24.141  -3.969  -3.177  1.00 54.00      B
ATOM   5751  CZ   ARG B 200    -24.874  -2.930  -2.776  1.00 53.09      B
ATOM   5752  NH1  ARG B 200    -24.298  -1.771  -2.489  1.00 53.49      B
ATOM   5753  NH2  ARG B 200    -26.186  -3.059  -2.627  1.00 51.05      B
ATOM   5754  C    ARG B 200    -20.229  -5.826  -0.119  1.00 59.02      B
ATOM   5755  O    ARG B 200    -20.897  -5.829   0.922  1.00 59.21      B
ATOM   5756  N    VAL B 201    -19.877  -6.939  -0.759  1.00 59.63      B
ATOM   5757  CA   VAL B 201    -20.279  -8.256  -0.272  1.00 60.36      B
ATOM   5758  CB   VAL B 201    -19.648  -9.390  -1.107  1.00 60.42      B
ATOM   5759  CG1  VAL B 201    -20.156 -10.726  -0.615  1.00 60.47      B
ATOM   5760  CG2  VAL B 201    -19.979  -9.212  -2.574  1.00 61.68      B
ATOM   5761  C    VAL B 201    -19.843  -8.435   1.177  1.00 60.52      B
ATOM   5762  O    VAL B 201    -20.583  -8.980   2.001  1.00 60.44      B
ATOM   5763  N    GLU B 202    -18.635  -7.976   1.480  1.00 59.69      B
ATOM   5764  CA   GLU B 202    -18.111  -8.088   2.825  1.00 60.14      B
ATOM   5765  CB   GLU B 202    -16.700  -7.504   2.903  1.00 61.76      B
ATOM   5766  CG   GLU B 202    -16.174  -7.396   4.332  1.00 65.08      B
ATOM   5767  CD   GLU B 202    -14.733  -6.924   4.402  1.00 67.09      B
ATOM   5768  OE1  GLU B 202    -14.393  -5.958   3.683  1.00 67.88      B
ATOM   5769  OE2  GLU B 202    -13.947  -7.511   5.181  1.00 66.78      B
ATOM   5770  C    GLU B 202    -19.016  -7.370   3.811  1.00 60.76      B
ATOM   5771  O    GLU B 202    -19.400  -7.938   4.839  1.00 61.30      B
ATOM   5772  N    PHE B 203    -19.362  -6.122   3.496  1.00 59.85      B
ATOM   5773  CA   PHE B 203    -20.216  -5.337   4.378  1.00 58.06      B
ATOM   5774  CB   PHE B 203    -20.432  -3.934   3.813  1.00 55.50      B
ATOM   5775  CG   PHE B 203    -21.146  -3.008   4.760  1.00 54.68      B
ATOM   5776  CD1  PHE B 203    -20.524  -2.567   5.920  1.00 54.09      B
```

FIGURE 5-77-

```
ATOM   5777  CD2 PHE B 203     -22.455  -2.602   4.509  1.00 54.58      B
ATOM   5778  CE1 PHE B 203     -21.191  -1.737   6.818  1.00 54.42      B
ATOM   5779  CE2 PHE B 203     -23.129  -1.774   5.400  1.00 53.64      B
ATOM   5780  CZ  PHE B 203     -22.495  -1.342   6.558  1.00 54.15      B
ATOM   5781  C   PHE B 203     -21.567  -6.023   4.581  1.00 58.25      B
ATOM   5782  O   PHE B 203     -22.067  -6.129   5.705  1.00 57.54      B
ATOM   5783  N   LEU B 204     -22.154  -6.496   3.489  1.00 57.58      B
ATOM   5784  CA  LEU B 204     -23.441  -7.164   3.576  1.00 57.70      B
ATOM   5785  CB  LEU B 204     -23.925  -7.560   2.184  1.00 57.05      B
ATOM   5786  CG  LEU B 204     -24.402  -6.401   1.305  1.00 56.85      B
ATOM   5787  CD1 LEU B 204     -24.753  -6.928  -0.075  1.00 55.03      B
ATOM   5788  CD2 LEU B 204     -25.612  -5.709   1.950  1.00 53.76      B
ATOM   5789  C   LEU B 204     -23.395  -8.393   4.470  1.00 57.85      B
ATOM   5790  O   LEU B 204     -24.111  -8.471   5.468  1.00 58.35      B
ATOM   5791  N   VAL B 205     -22.545  -9.350   4.118  1.00 58.30      B
ATOM   5792  CA  VAL B 205     -22.445 -10.577   4.900  1.00 57.97      B
ATOM   5793  CB  VAL B 205     -21.380 -11.529   4.322  1.00 57.37      B
ATOM   5794  CG1 VAL B 205     -21.216 -12.734   5.230  1.00 56.12      B
ATOM   5795  CG2 VAL B 205     -21.795 -11.977   2.927  1.00 55.90      B
ATOM   5796  C   VAL B 205     -22.138 -10.303   6.362  1.00 57.90      B
ATOM   5797  O   VAL B 205     -22.799 -10.849   7.245  1.00 57.12      B
ATOM   5798  N   ASN B 206     -21.142  -9.459   6.619  1.00 58.55      B
ATOM   5799  CA  ASN B 206     -20.786  -9.127   7.992  1.00 59.14      B
ATOM   5800  CB  ASN B 206     -19.615  -8.147   8.026  1.00 59.37      B
ATOM   5801  CG  ASN B 206     -18.284  -8.828   7.818  1.00 60.26      B
ATOM   5802  OD1 ASN B 206     -18.022  -9.880   8.399  1.00 60.88      B
ATOM   5803  ND2 ASN B 206     -17.426  -8.226   6.999  1.00 60.76      B
ATOM   5804  C   ASN B 206     -21.971  -8.529   8.742  1.00 59.61      B
ATOM   5805  O   ASN B 206     -22.216  -8.871   9.896  1.00 59.62      B
ATOM   5806  N   THR B 207     -22.704  -7.636   8.088  1.00 60.40      B
ATOM   5807  CA  THR B 207     -23.852  -7.017   8.726  1.00 62.25      B
ATOM   5808  CB  THR B 207     -24.535  -5.974   7.794  1.00 62.79      B
ATOM   5809  OG1 THR B 207     -23.634  -4.888   7.544  1.00 62.20      B
ATOM   5810  CG2 THR B 207     -25.810  -5.427   8.435  1.00 60.83      B
ATOM   5811  C   THR B 207     -24.850  -8.109   9.086  1.00 63.83      B
ATOM   5812  O   THR B 207     -25.319  -8.184  10.221  1.00 63.99      B
ATOM   5813  N   TRP B 208     -25.164  -8.965   8.121  1.00 65.86      B
ATOM   5814  CA  TRP B 208     -26.110 -10.050   8.357  1.00 68.64      B
ATOM   5815  CB  TRP B 208     -26.229 -10.927   7.101  1.00 69.74      B
ATOM   5816  CG  TRP B 208     -27.336 -11.937   7.182  1.00 70.60      B
ATOM   5817  CD2 TRP B 208     -28.690 -11.765   6.744  1.00 71.15      B
ATOM   5818  CE2 TRP B 208     -29.396 -12.938   7.090  1.00 70.82      B
ATOM   5819  CE3 TRP B 208     -29.383 -10.721   6.116  1.00 70.22      B
ATOM   5820  CD1 TRP B 208     -27.273 -13.180   7.742  1.00 70.85      B
ATOM   5821  NE1 TRP B 208     -28.505 -13.789   7.690  1.00 70.85      B
ATOM   5822  CZ2 TRP B 208     -30.754 -13.111   6.806  1.00 69.74      B
ATOM   5823  CZ3 TRP B 208     -30.734 -10.894   5.837  1.00 70.55      B
ATOM   5824  CH2 TRP B 208     -31.406 -12.077   6.192  1.00 69.57      B
ATOM   5825  C   TRP B 208     -25.687 -10.894   9.568  1.00 69.92      B
ATOM   5826  O   TRP B 208     -26.506 -11.199  10.442  1.00 69.61      B
ATOM   5827  N   LYS B 209     -24.406 -11.255   9.621  1.00 70.85      B
ATOM   5828  CA  LYS B 209     -23.871 -12.055  10.720  1.00 71.50      B
ATOM   5829  CB  LYS B 209     -22.406 -12.396  10.466  1.00 71.93      B
ATOM   5830  CG  LYS B 209     -22.162 -13.283   9.267  1.00 73.32      B
ATOM   5831  CD  LYS B 209     -20.696 -13.663   9.219  1.00 75.92      B
ATOM   5832  CE  LYS B 209     -20.437 -14.784   8.238  1.00 77.34      B
ATOM   5833  NZ  LYS B 209     -19.071 -15.343   8.433  1.00 78.26      B
ATOM   5834  C   LYS B 209     -23.978 -11.343  12.062  1.00 71.61      B
ATOM   5835  O   LYS B 209     -24.471 -11.908  13.034  1.00 71.64      B
ATOM   5836  N   SER B 210     -23.512 -10.100  12.107  1.00 71.79      B
ATOM   5837  CA  SER B 210     -23.540  -9.308  13.330  1.00 72.32      B
ATOM   5838  CB  SER B 210     -23.102  -7.877  13.032  1.00 71.72      B
ATOM   5839  OG  SER B 210     -24.002  -7.250  12.139  1.00 72.05      B
ATOM   5840  C   SER B 210     -24.902  -9.285  14.019  1.00 73.23      B
ATOM   5841  O   SER B 210     -24.992  -8.990  15.209  1.00 73.30      B
ATOM   5842  N   LYS B 211     -25.961  -9.591  13.276  1.00 74.87      B
ATOM   5843  CA  LYS B 211     -27.307  -9.600  13.847  1.00 76.56      B
ATOM   5844  CB  LYS B 211     -28.357  -9.326  12.762  1.00 75.35      B
ATOM   5845  CG  LYS B 211     -28.054  -8.146  11.842  1.00 74.10      B
ATOM   5846  CD  LYS B 211     -28.139  -6.805  12.557  1.00 71.22      B
ATOM   5847  CE  LYS B 211     -27.853  -5.666  11.597  1.00 67.99      B
ATOM   5848  NZ  LYS B 211     -28.004  -4.351  12.257  1.00 67.40      B
ATOM   5849  C   LYS B 211     -27.583 -10.968  14.467  1.00 78.47      B
ATOM   5850  O   LYS B 211     -27.063 -11.986  13.998  1.00 79.52      B
ATOM   5851  N   LYS B 212     -28.393 -10.991  15.522  1.00 79.37      B
ATOM   5852  CA  LYS B 212     -28.741 -12.247  16.180  1.00 79.58      B
```

FIGURE 5- 78 -

```
ATOM   5853  CB   LYS B 212     -29.475 -11.971  17.491  1.00 80.94      3
ATOM   5854  CG   LYS B 212     -28.661 -11.148  18.464  1.00 83.21      3
ATOM   5855  CD   LYS B 212     -29.400 -10.977  19.805  1.00 84.72      3
ATOM   5856  CE   LYS B 212     -28.550 -10.235  20.830  1.00 85.42      3
ATOM   5857  NZ   LYS B 212     -29.204 -10.211  22.172  1.00 85.94      3
ATOM   5858  C    LYS B 212     -29.633 -13.017  15.214  1.00 79.57      3
ATOM   5859  O    LYS B 212     -29.188 -13.975  14.583  1.00 81.02      3
ATOM   5860  N    CYS B 213     -30.892 -12.602  15.103  1.00 78.55      3
ATOM   5861  CA   CYS B 213     -31.820 -13.226  14.164  1.00 76.45      3
ATOM   5862  CB   CYS B 213     -33.140 -13.613  14.842  1.00 76.64      3
ATOM   5863  SG   CYS B 213     -34.262 -14.580  13.767  1.00 75.74      3
ATOM   5864  C    CYS B 213     -32.074 -12.159  13.105  1.00 75.22      3
ATOM   5865  O    CYS B 213     -32.985 -11.338  13.237  1.00 74.74      3
ATOM   5866  N    PRO B 214     -31.257 -12.155  12.041  1.00 73.67      3
ATOM   5867  CD   PRO B 214     -30.263 -13.188  11.707  1.00 73.09      3
ATOM   5868  CA   PRO B 214     -31.373 -11.188  10.948  1.00 72.47      3
ATOM   5869  CB   PRO B 214     -30.268 -11.617   9.987  1.00 72.10      3
ATOM   5870  CG   PRO B 214     -30.201 -13.086  10.203  1.00 72.40      3
ATOM   5871  C    PRO B 214     -32.727 -11.134  10.271  1.00 71.18      3
ATOM   5872  O    PRO B 214     -33.618 -11.935  10.546  1.00 72.34      3
ATOM   5873  N    MET B 215     -32.858 -10.161   9.381  1.00 68.91      3
ATOM   5874  CA   MET B 215     -34.066  -9.934   8.607  1.00 66.07      3
ATOM   5875  CB   MET B 215     -35.222  -9.499   9.501  1.00 66.10      3
ATOM   5876  CG   MET B 215     -36.533  -9.327   8.757  1.00 67.69      3
ATOM   5877  SD   MET B 215     -36.529  -8.002   7.518  1.00 69.21      3
ATOM   5878  CE   MET B 215     -37.232  -6.645   8.492  1.00 66.67      3
ATOM   5879  C    MET B 215     -33.681  -8.802   7.682  1.00 64.42      3
ATOM   5880  O    MET B 215     -33.169  -7.773   8.129  1.00 64.24      3
ATOM   5881  N    GLY B 216     -33.914  -8.990   6.392  1.00 62.03      3
ATOM   5882  CA   GLY B 216     -33.548  -7.957   5.450  1.00 60.34      3
ATOM   5883  C    GLY B 216     -34.558  -7.739   4.355  1.00 58.64      3
ATOM   5884  O    GLY B 216     -35.474  -8.535   4.163  1.00 58.97      3
ATOM   5885  N    PHE B 217     -34.386  -6.638   3.638  1.00 56.83      3
ATOM   5886  CA   PHE B 217     -35.271  -6.298   2.540  1.00 54.48      3
ATOM   5887  CB   PHE B 217     -36.662  -5.906   3.053  1.00 55.54      3
ATOM   5888  CG   PHE B 217     -36.664  -4.701   3.957  1.00 56.40      3
ATOM   5889  CD1  PHE B 217     -36.307  -4.818   5.297  1.00 56.89      3
ATOM   5890  CD2  PHE B 217     -37.020  -3.449   3.465  1.00 57.17      3
ATOM   5891  CE1  PHE B 217     -36.301  -3.707   6.135  1.00 57.84      3
ATOM   5892  CE2  PHE B 217     -37.017  -2.330   4.290  1.00 58.26      3
ATOM   5893  CZ   PHE B 217     -36.658  -2.457   5.631  1.00 58.89      3
ATOM   5894  C    PHE B 217     -34.684  -5.141   1.770  1.00 51.88      3
ATOM   5895  O    PHE B 217     -33.886  -4.371   2.292  1.00 51.42      3
ATOM   5896  N    SER B 218     -35.076  -5.039   0.513  1.00 49.51      3
ATOM   5897  CA   SER B 218     -34.623  -3.962  -0.334  1.00 47.13      3
ATOM   5898  CB   SER B 218     -34.183  -4.512  -1.691  1.00 47.49      3
ATOM   5899  OG   SER B 218     -35.256  -5.144  -2.368  1.00 48.89      3
ATOM   5900  C    SER B 218     -35.862  -3.104  -0.473  1.00 45.74      3
ATOM   5901  O    SER B 218     -36.972  -3.594  -0.270  1.00 46.00      3
ATOM   5902  N    TYR B 219     -35.691  -1.826  -0.778  1.00 44.39      3
ATOM   5903  CA   TYR B 219     -36.847  -0.961  -0.931  1.00 44.02      3
ATOM   5904  CB   TYR B 219     -36.921   0.069   0.196  1.00 43.34      3
ATOM   5905  CG   TYR B 219     -38.215   0.856   0.204  1.00 43.12      3
ATOM   5906  CD1  TYR B 219     -39.361   0.350   0.806  1.00 42.32      3
ATOM   5907  CE1  TYR B 219     -40.556   1.054   0.777  1.00 44.04      3
ATOM   5908  CD2  TYR B 219     -38.297   2.095  -0.424  1.00 44.70      3
ATOM   5909  CE2  TYR B 219     -39.483   2.809  -0.461  1.00 43.91      3
ATOM   5910  CZ   TYR B 219     -40.611   2.285   0.133  1.00 45.28      3
ATOM   5911  OH   TYR B 219     -41.799   2.985   0.060  1.00 45.93      3
ATOM   5912  C    TYR B 219     -36.773  -0.259  -2.268  1.00 45.05      3
ATOM   5913  O    TYR B 219     -35.886   0.557  -2.521  1.00 46.17      3
ATOM   5914  N    ASP B 220     -37.715  -0.602  -3.126  1.00 45.95      3
ATOM   5915  CA   ASP B 220     -37.792  -0.033  -4.455  1.00 46.73      3
ATOM   5916  CB   ASP B 220     -38.259  -1.110  -5.434  1.00 48.12      3
ATOM   5917  CG   ASP B 220     -38.704  -0.547  -6.774  1.00 50.81      3
ATOM   5918  OD1  ASP B 220     -37.852  -0.020  -7.528  1.00 52.28      3
ATOM   5919  OD2  ASP B 220     -39.916  -0.643  -7.078  1.00 51.64      3
ATOM   5920  C    ASP B 220     -38.775   1.123  -4.423  1.00 47.09      3
ATOM   5921  O    ASP B 220     -39.972   0.927  -4.201  1.00 47.79      3
ATOM   5922  N    THR B 221     -38.263   2.333  -4.622  1.00 46.34      3
ATOM   5923  CA   THR B 221     -39.112   3.511  -4.631  1.00 45.05      3
ATOM   5924  CB   THR B 221     -38.318   4.773  -4.264  1.00 45.09      3
ATOM   5925  OG1  THR B 221     -37.646   4.572  -3.013  1.00 44.38      3
ATOM   5926  CG2  THR B 221     -39.251   5.970  -4.155  1.00 44.72      3
ATOM   5927  C    THR B 221     -39.658   3.650  -6.047  1.00 46.11      3
ATOM   5928  O    THR B 221     -38.978   3.345  -7.024  1.00 47.39      3
```

FIGURE 5-79-

```
ATOM   5929  N    ARG B 222     -40.892   4.107  -6.161  1.00 47.30      B
ATOM   5930  CA   ARG B 222     -41.517   4.255  -7.462  1.00 47.05      B
ATOM   5931  CB   ARG B 222     -43.035   4.276  -7.287  1.00 48.35      B
ATOM   5932  CG   ARG B 222     -43.809   4.476  -8.566  1.00 50.58      B
ATOM   5933  CD   ARG B 222     -45.281   4.649  -8.267  1.00 52.59      B
ATOM   5934  NE   ARG B 222     -46.052   4.907  -9.477  1.00 57.08      B
ATOM   5935  CZ   ARG B 222     -45.852   5.947 -10.279  1.00 60.31      B
ATOM   5936  NH1  ARG B 222     -44.899   6.828  -9.995  1.00 63.62      B
ATOM   5937  NH2  ARG B 222     -46.602   6.109 -11.362  1.00 59.66      B
ATOM   5938  C    ARG B 222     -41.062   5.522  -8.167  1.00 46.34      B
ATOM   5939  O    ARG B 222     -41.579   6.600  -7.888  1.00 48.49      B
ATOM   5940  N    CYS B 223     -40.107   5.397  -9.081  1.00 44.45      B
ATOM   5941  CA   CYS B 223     -39.607   6.557  -9.820  1.00 43.84      B
ATOM   5942  CB   CYS B 223     -40.728   7.175 -10.656  1.00 45.35      B
ATOM   5943  SG   CYS B 223     -41.630   6.021 -11.686  1.00 50.57      B
ATOM   5944  C    CYS B 223     -39.045   7.632  -8.383  1.00 42.58      B
ATOM   5945  O    CYS B 223     -39.463   8.792  -8.924  1.00 40.95      B
ATOM   5946  N    PHE B 224     -38.087   7.234  -8.054  1.00 41.01      B
ATOM   5947  CA   PHE B 224     -37.455   8.113  -7.084  1.00 38.39      B
ATOM   5948  CB   PHE B 224     -36.117   7.501  -6.653  1.00 36.03      B
ATOM   5949  CG   PHE B 224     -35.569   8.073  -5.381  1.00 35.51      B
ATOM   5950  CD1  PHE B 224     -34.908   9.302  -5.379  1.00 34.44      B
ATOM   5951  CD2  PHE B 224     -35.728   7.391  -4.176  1.00 33.31      B
ATOM   5952  CE1  PHE B 224     -34.410   9.841  -4.197  1.00 32.68      B
ATOM   5953  CE2  PHE B 224     -35.234   7.921  -2.987  1.00 31.00      B
ATOM   5954  CZ   PHE B 224     -34.575   9.148  -2.997  1.00 32.29      B
ATOM   5955  C    PHE B 224     -37.258   9.577  -7.545  1.00 37.56      B
ATOM   5956  O    PHE B 224     -37.721  10.515  -6.886  1.00 36.31      B
ATOM   5957  N    ASP B 225     -36.536   9.775  -8.674  1.00 36.05      B
ATOM   5958  CA   ASP B 225     -36.345  11.125  -9.159  1.00 34.89      B
ATOM   5959  CB   ASP B 225     -35.731  11.081 -10.557  1.00 34.80      B
ATOM   5960  CG   ASP B 225     -34.267  10.683 -10.534  1.00 37.09      B
ATOM   5961  OD1  ASP B 225     -33.717  10.495  -9.424  1.00 37.18      B
ATOM   5962  OD2  ASP B 225     -33.661  10.569 -11.622  1.00 34.69      B
ATOM   5963  C    ASP B 225     -37.580  12.013  -9.162  1.00 34.71      B
ATOM   5964  O    ASP B 225     -37.526  13.167  -8.731  1.00 35.45      B
ATOM   5965  N    SER B 226     -38.699  11.487  -9.635  1.00 35.28      B
ATOM   5966  CA   SER B 226     -39.919  12.285  -9.682  1.00 37.25      B
ATOM   5967  CB   SER B 226     -40.947  11.642 -10.613  1.00 38.74      B
ATOM   5968  OG   SER B 226     -41.279  10.333 -10.176  1.00 43.09      B
ATOM   5969  C    SER B 226     -40.523  12.466  -8.300  1.00 37.68      B
ATOM   5970  O    SER B 226     -41.368  13.336  -8.092  1.00 38.45      B
ATOM   5971  N    THR B 227     -40.088  11.653  -7.347  1.00 37.49      B
ATOM   5972  CA   THR B 227     -40.625  11.773  -6.004  1.00 37.27      B
ATOM   5973  CB   THR B 227     -40.624  10.424  -5.260  1.00 37.22      B
ATOM   5974  OG1  THR B 227     -39.284  10.015  -4.973  1.00 36.00      B
ATOM   5975  CG2  THR B 227     -41.302   9.372  -6.114  1.00 39.60      B
ATOM   5976  C    THR B 227     -39.878  12.800  -5.176  1.00 36.90      B
ATOM   5977  O    THR B 227     -40.369  13.212  -4.124  1.00 38.18      B
ATOM   5978  N    VAL B 228     -38.697  13.213  -5.643  1.00 35.14      B
ATOM   5979  CA   VAL B 228     -37.911  14.219  -4.923  1.00 33.26      B
ATOM   5980  CB   VAL B 228     -36.484  14.348  -5.500  1.00 32.84      B
ATOM   5981  CG1  VAL B 228     -35.745  15.480  -4.807  1.00 30.62      B
ATOM   5982  CG2  VAL B 228     -35.731  13.036  -5.299  1.00 30.45      B
ATOM   5983  C    VAL B 228     -38.639  15.551  -5.031  1.00 31.15      B
ATOM   5984  O    VAL B 228     -38.941  16.011  -6.118  1.00 32.46      B
ATOM   5985  N    THR B 229     -38.922  16.164  -3.892  1.00 30.23      B
ATOM   5986  CA   THR B 229     -39.667  17.420  -3.854  1.00 29.36      B
ATOM   5987  CB   THR B 229     -40.647  17.398  -2.672  1.00 26.07      B
ATOM   5988  OG1  THR B 229     -39.912  17.330  -1.443  1.00 25.24      B
ATOM   5989  CG2  THR B 229     -41.529  16.182  -2.754  1.00 23.09      B
ATOM   5990  C    THR B 229     -38.802  18.674  -3.738  1.00 30.32      B
ATOM   5991  O    THR B 229     -37.616  18.586  -3.420  1.00 30.48      B
ATOM   5992  N    GLU B 230     -39.395  19.838  -4.007  1.00 30.17      B
ATOM   5993  CA   GLU B 230     -38.665  21.093  -3.880  1.00 31.76      B
ATOM   5994  CB   GLU B 230     -39.587  22.299  -4.087  1.00 35.72      B
ATOM   5995  CG   GLU B 230     -40.134  22.437  -5.499  1.00 38.97      B
ATOM   5996  CD   GLU B 230     -41.449  21.716  -5.679  1.00 43.20      B
ATOM   5997  OE1  GLU B 230     -41.604  20.604  -5.113  1.00 45.45      B
ATOM   5998  OE2  GLU B 230     -42.323  22.262  -6.392  1.00 42.16      B
ATOM   5999  C    GLU B 230     -38.101  21.133  -2.467  1.00 30.91      B
ATOM   6000  O    GLU B 230     -36.976  21.575  -2.236  1.00 31.86      B
ATOM   6001  N    SER B 231     -38.899  20.677  -1.517  1.00 29.42      B
ATOM   6002  CA   SER B 231     -38.455  20.646  -0.146  1.00 28.89      B
ATOM   6003  CB   SER B 231     -39.568  20.122   0.751  1.00 29.51      B
ATOM   6004  OG   SER B 231     -39.098  19.932   2.074  1.00 27.67      B
```

FIGURE 5-80-

```
ATOM   6005  C    SER B 231     -37.220  19.761   0.000  1.00 30.13       B
ATOM   6006  O    SER B 231     -36.239  20.170   0.616  1.00 30.12       B
ATOM   6007  N    ASP B 232     -37.268  18.555  -0.567  1.00 30.10       B
ATOM   6008  CA   ASP B 232     -36.146  17.623  -0.473  1.00 31.56       B
ATOM   6009  CB   ASP B 232     -36.425  16.350  -1.271  1.00 32.89       B
ATOM   6010  CG   ASP B 232     -37.572  15.560  -0.712  1.00 34.31       B
ATOM   6011  OD1  ASP B 232     -37.738  15.577   0.526  1.00 36.40       B
ATOM   6012  OD2  ASP B 232     -38.291  14.913  -1.502  1.00 33.83       B
ATOM   6013  C    ASP B 232     -34.840  18.222  -0.969  1.00 32.56       B
ATOM   6014  O    ASP B 232     -33.792  18.085  -0.331  1.00 33.37       B
ATOM   6015  N    ILE B 233     -34.911  18.880  -2.117  1.00 31.66       B
ATOM   6016  CA   ILE B 233     -33.746  19.498  -2.712  1.00 31.13       B
ATOM   6017  CB   ILE B 233     -34.074  19.870  -4.166  1.00 29.88       B
ATOM   6018  CG2  ILE B 233     -33.059  20.838  -4.736  1.00 27.90       B
ATOM   6019  CG1  ILE B 233     -34.115  18.585  -4.985  1.00 27.16       B
ATOM   6020  CD1  ILE B 233     -34.989  18.677  -6.190  1.00 29.47       B
ATOM   6021  C    ILE B 233     -33.244  20.696  -1.891  1.00 32.12       B
ATOM   6022  O    ILE B 233     -32.044  20.995  -1.886  1.00 31.66       B
ATOM   6023  N    ARG B 234     -34.149  21.370  -1.186  1.00 31.28       B
ATOM   6024  CA   ARG B 234     -33.740  22.494  -0.348  1.00 31.59       B
ATOM   6025  CB   ARG B 234     -34.913  23.429  -0.087  1.00 30.69       B
ATOM   6026  CG   ARG B 234     -35.038  24.483  -1.136  1.00 30.28       B
ATOM   6027  CD   ARG B 234     -36.333  25.214  -1.020  1.00 31.95       B
ATOM   6028  NE   ARG B 234     -36.491  26.163  -2.115  1.00 33.54       B
ATOM   6029  CZ   ARG B 234     -37.641  26.380  -2.743  1.00 32.49       B
ATOM   6030  NH1  ARG B 234     -38.731  25.712  -2.384  1.00 32.09       B
ATOM   6031  NH2  ARG B 234     -37.701  27.265  -3.727  1.00 30.78       B
ATOM   6032  C    ARG B 234     -33.163  21.993   0.972  1.00 31.55       B
ATOM   6033  O    ARG B 234     -32.270  22.621   1.547  1.00 31.90       B
ATOM   6034  N    VAL B 235     -33.686  20.868   1.452  1.00 31.15       B
ATOM   6035  CA   VAL B 235     -33.195  20.261   2.681  1.00 30.99       B
ATOM   6036  CB   VAL B 235     -34.069  19.060   3.099  1.00 31.69       B
ATOM   6037  CG1  VAL B 235     -33.312  18.150   4.064  1.00 29.77       B
ATOM   6038  CG2  VAL B 235     -35.357  19.571   3.744  1.00 30.51       B
ATOM   6039  C    VAL B 235     -31.798  19.783   2.343  1.00 31.49       B
ATOM   6040  O    VAL B 235     -30.860  19.960   3.112  1.00 32.51       B
ATOM   6041  N    GLU B 236     -31.670  19.183   1.170  1.00 31.80       B
ATOM   6042  CA   GLU B 236     -30.389  18.696   0.692  1.00 33.14       B
ATOM   6043  CB   GLU B 236     -30.583  18.155  -0.722  1.00 34.08       B
ATOM   6044  CG   GLU B 236     -29.332  17.746  -1.454  1.00 36.29       B
ATOM   6045  CD   GLU B 236     -29.646  17.226  -2.848  1.00 39.82       B
ATOM   6046  OE1  GLU B 236     -28.733  17.236  -3.709  1.00 41.89       B
ATOM   6047  OE2  GLU B 236     -30.807  16.804  -3.077  1.00 38.43       B
ATOM   6048  C    GLU B 236     -29.365  19.847   0.713  1.00 34.14       B
ATOM   6049  O    GLU B 236     -28.242  19.705   1.220  1.00 34.37       B
ATOM   6050  N    GLU B 237     -29.765  20.995   0.179  1.00 32.57       B
ATOM   6051  CA   GLU B 237     -28.887  22.150   0.160  1.00 31.86       B
ATOM   6052  CB   GLU B 237     -29.601  23.376  -0.398  1.00 33.03       B
ATOM   6053  CG   GLU B 237     -28.654  24.478  -0.842  1.00 34.48       B
ATOM   6054  CD   GLU B 237     -29.280  25.343  -0.773  1.00 35.87       B
ATOM   6055  OE1  GLU B 237     -30.509  25.942  -0.941  1.00 37.23       B
ATOM   6056  OE2  GLU B 237     -28.538  26.321  -0.560  1.00 36.99       B
ATOM   6057  C    GLU B 237     -28.424  22.483   1.562  1.00 31.47       B
ATOM   6058  O    GLU B 237     -27.259  22.795   1.767  1.00 33.34       B
ATOM   6059  N    SER B 238     -29.341  22.425   2.525  1.00 30.95       B
ATOM   6060  CA   SER B 238     -29.005  22.758   3.901  1.00 29.06       B
ATOM   6061  CB   SER B 238     -30.240  22.660   4.796  1.00 30.02       B
ATOM   6062  OG   SER B 238     -30.640  21.321   4.985  1.00 33.11       B
ATOM   6063  C    SER B 238     -27.901  21.851   4.409  1.00 28.66       B
ATOM   6064  O    SER B 238     -27.131  22.214   5.299  1.00 27.87       B
ATOM   6065  N    ILE B 239     -27.805  20.665   3.838  1.00 27.89       B
ATOM   6066  CA   ILE B 239     -26.746  19.783   4.272  1.00 29.41       B
ATOM   6067  CB   ILE B 239     -27.016  18.327   3.850  1.00 28.14       B
ATOM   6068  CG2  ILE B 239     -25.917  17.419   4.391  1.00 26.20       B
ATOM   6069  CG1  ILE B 239     -28.383  17.898   4.390  1.00 26.44       B
ATOM   6070  CD1  ILE B 239     -28.754  16.488   4.099  1.00 24.27       B
ATOM   6071  C    ILE B 239     -25.436  20.292   3.664  1.00 30.69       B
ATOM   6072  O    ILE B 239     -24.427  20.375   4.351  1.00 33.28       B
ATOM   6073  N    TYR B 240     -25.459  20.653   2.385  1.00 29.97       B
ATOM   6074  CA   TYR B 240     -24.264  21.159   1.723  1.00 28.78       B
ATOM   6075  CB   TYR B 240     -24.542  21.448   0.247  1.00 29.34       B
ATOM   6076  CG   TYR B 240     -25.071  20.277  -0.552  1.00 31.85       B
ATOM   6077  CD1  TYR B 240     -24.683  18.965  -0.259  1.00 32.75       B
ATOM   6078  CE1  TYR B 240     -25.114  17.391  -1.050  1.00 33.14       B
ATOM   6079  CD2  TYR B 240     -25.904  20.484  -1.650  1.00 31.23       B
ATOM   6080  CE2  TYR B 240     -26.335  19.421  -2.444  1.00 31.46       B
```

FIGURE 5- 81 -

```
ATOM   6081  CZ   TYR B 240     -25.935  18.132  -2.139  1.00 32.13           B
ATOM   6082  OH   TYR B 240     -26.338  17.089  -2.935  1.00 33.42           B
ATOM   6083  C    TYR B 240     -23.776  22.443   2.379  1.00 29.06           B
ATOM   6084  O    TYR B 240     -22.576  22.639   2.553  1.00 29.14           B
ATOM   6085  N    GLN B 241     -24.714  23.318   2.733  1.00 28.24           B
ATOM   6086  CA   GLN B 241     -24.393  24.594   3.353  1.00 27.60           B
ATOM   6087  CB   GLN B 241     -25.660  25.427   3.483  1.00 28.19           B
ATOM   6088  CG   GLN B 241     -26.216  25.909   2.143  1.00 31.28           B
ATOM   6089  CD   GLN B 241     -25.310  26.926   1.459  1.00 32.10           B
ATOM   6090  OE1  GLN B 241     -24.283  27.327   2.036  1.00 35.41           B
ATOM   6091  NE2  GLN B 241     -25.691  27.350   0.261  1.00 30.17           B
ATOM   6092  C    GLN B 241     -23.687  24.480   4.706  1.00 29.43           B
ATOM   6093  O    GLN B 241     -23.160  25.471   5.231  1.00 29.75           B
ATOM   6094  N    CYS B 242     -23.662  23.277   5.270  1.00 27.96           B
ATOM   6095  CA   CYS B 242     -22.985  23.069   6.539  1.00 27.42           B
ATOM   6096  CB   CYS B 242     -23.471  21.781   7.205  1.00 28.77           B
ATOM   6097  SG   CYS B 242     -25.151  21.898   7.884  1.00 33.59           B
ATOM   6098  C    CYS B 242     -21.478  23.007   6.309  1.00 26.95           B
ATOM   6099  O    CYS B 242     -20.683  23.166   7.235  1.00 26.58           B
ATOM   6100  N    CYS B 243     -21.083  22.787   5.065  1.00 25.99           B
ATOM   6101  CA   CYS B 243     -19.669  22.726   4.739  1.00 27.75           B
ATOM   6102  CB   CYS B 243     -19.465  22.206   3.313  1.00 26.31           B
ATOM   6103  SG   CYS B 243     -19.929  20.504   3.025  1.00 33.47           B
ATOM   6104  C    CYS B 243     -19.025  24.102   4.827  1.00 28.58           B
ATOM   6105  O    CYS B 243     -19.699  25.130   4.795  1.00 28.16           B
ATOM   6106  N    ASP B 244     -17.706  24.112   4.951  1.00 31.27           B
ATOM   6107  CA   ASP B 244     -16.980  25.362   4.950  1.00 31.78           B
ATOM   6108  CB   ASP B 244     -15.612  25.214   5.607  1.00 31.84           B
ATOM   6109  CG   ASP B 244     -14.818  26.506   5.576  1.00 32.38           B
ATOM   6110  OD1  ASP B 244     -14.217  26.838   4.526  1.00 30.55           B
ATOM   6111  OD2  ASP B 244     -14.814  27.198   6.614  1.00 34.07           B
ATOM   6112  C    ASP B 244     -16.804  25.592   3.455  1.00 32.15           B
ATOM   6113  O    ASP B 244     -16.060  24.871   2.790  1.00 32.91           B
ATOM   6114  N    LEU B 245     -17.503  26.582   2.922  1.00 31.50           B
ATOM   6115  CA   LEU B 245     -17.417  26.851   1.501  1.00 30.91           B
ATOM   6116  CB   LEU B 245     -18.805  26.738   0.878  1.00 28.27           B
ATOM   6117  CG   LEU B 245     -19.442  25.383   1.147  1.00 27.74           B
ATOM   6118  CD1  LEU B 245     -20.942  25.490   1.001  1.00 28.35           B
ATOM   6119  CD2  LEU B 245     -18.853  24.346   0.209  1.00 26.86           B
ATOM   6120  C    LEU B 245     -16.837  28.214   1.181  1.00 30.22           B
ATOM   6121  O    LEU B 245     -16.901  29.139   1.986  1.00 29.21           B
ATOM   6122  N    ALA B 246     -16.256  28.319  -0.005  1.00 29.43           B
ATOM   6123  CA   ALA B 246     -15.712  29.583  -0.457  1.00 31.00           B
ATOM   6124  CB   ALA B 246     -14.993  29.387  -1.793  1.00 29.63           B
ATOM   6125  C    ALA B 246     -16.942  30.483  -0.640  1.00 31.69           B
ATOM   6126  O    ALA B 246     -18.036  29.988  -0.934  1.00 33.68           B
ATOM   6127  N    PRO B 247     -16.793  31.806  -0.467  1.00 30.23           B
ATOM   6128  CD   PRO B 247     -15.654  32.595   0.018  1.00 28.26           B
ATOM   6129  CA   PRO B 247     -17.969  32.664  -0.648  1.00 31.12           B
ATOM   6130  CB   PRO B 247     -17.384  34.072  -0.539  1.00 27.21           B
ATOM   6131  CG   PRO B 247     -16.333  33.889   0.451  1.00 27.66           B
ATOM   6132  C    PRO B 247     -18.714  32.430  -1.975  1.00 31.26           B
ATOM   6133  O    PRO B 247     -19.932  32.249  -1.987  1.00 30.81           B
ATOM   6134  N    GLU B 248     -17.989  32.416  -3.087  1.00 31.24           B
ATOM   6135  CA   GLU B 248     -18.642  32.222  -4.373  1.00 33.04           B
ATOM   6136  CB   GLU B 248     -17.671  32.491  -5.520  1.00 33.92           B
ATOM   6137  CG   GLU B 248     -16.931  33.791  -5.400  1.00 32.40           B
ATOM   6138  CD   GLU B 248     -16.570  34.364  -6.737  1.00 34.54           B
ATOM   6139  OE1  GLU B 248     -16.340  33.579  -7.687  1.00 34.74           B
ATOM   6140  OE2  GLU B 248     -16.510  35.605  -6.833  1.00 35.83           B
ATOM   6141  C    GLU B 248     -19.213  30.819  -4.509  1.00 33.88           B
ATOM   6142  O    GLU B 248     -20.240  30.614  -5.161  1.00 36.35           B
ATOM   6143  N    ALA B 249     -18.548  29.846  -3.903  1.00 32.41           B
ATOM   6144  CA   ALA B 249     -19.036  28.485  -3.974  1.00 30.94           B
ATOM   6145  CB   ALA B 249     -18.046  27.546  -3.320  1.00 30.59           B
ATOM   6146  C    ALA B 249     -20.371  28.453  -3.242  1.00 30.43           B
ATOM   6147  O    ALA B 249     -21.347  27.873  -3.709  1.00 30.30           B
ATOM   6148  N    ARG B 250     -20.421  29.107  -2.094  1.00 28.91           B
ATOM   6149  CA   ARG B 250     -21.646  29.120  -1.328  1.00 29.27           B
ATOM   6150  CB   ARG B 250     -21.450  29.920  -0.047  1.00 27.70           B
ATOM   6151  CG   ARG B 250     -22.413  29.362   1.056  1.00 27.09           B
ATOM   6152  CD   ARG B 250     -22.143  30.385   2.315  1.00 26.52           B
ATOM   6153  NE   ARG B 250     -21.103  29.836   3.186  1.00 23.21           B
ATOM   6154  CZ   ARG B 250     -21.220  28.705   3.869  1.00 21.87           B
ATOM   6155  NH1  ARG B 250     -22.329  27.990   3.777  1.00 21.30           B
ATOM   6156  NH2  ARG B 250     -20.242  28.309   4.669  1.00 19.82           B
```

FIGURE 5- 82 -

```
ATOM   6157  C   ARG B 250     -22.770  29.719  -2.165  1.00 30.92       B
ATOM   6158  O   ARG B 250     -23.881  29.186  -2.212  1.00 32.05       B
ATOM   6159  N   GLN B 251     -22.479  30.819  -2.849  1.00 31.65       B
ATOM   6160  CA  GLN B 251     -23.497  31.466  -3.658  1.00 32.03       B
ATOM   6161  CB  GLN B 251     -23.016  32.819  -4.155  1.00 30.88       B
ATOM   6162  CG  GLN B 251     -24.092  33.530  -4.936  1.00 29.84       B
ATOM   6163  CD  GLN B 251     -25.289  33.833  -4.073  1.00 32.63       B
ATOM   6164  OE1 GLN B 251     -25.426  33.529  -4.434  1.00 35.03       B
ATOM   6165  NE2 GLN B 251     -25.041  34.436  -2.916  1.00 32.73       B
ATOM   6166  C   GLN B 251     -23.896  30.622  -4.861  1.00 33.45       B
ATOM   6167  O   GLN B 251     -25.067  30.580  -5.247  1.00 32.98       B
ATOM   6168  N   ALA B 252     -22.912  29.963  -5.462  1.00 33.16       B
ATOM   6169  CA  ALA B 252     -23.162  29.129  -6.626  1.00 32.43       B
ATOM   6170  CB  ALA B 252     -21.856  28.555  -7.142  1.00 31.38       B
ATOM   6171  C   ALA B 252     -24.130  28.013  -6.252  1.00 31.33       B
ATOM   6172  O   ALA B 252     -25.080  27.718  -6.983  1.00 32.30       B
ATOM   6173  N   ILE B 253     -23.892  27.399  -5.103  1.00 29.92       B
ATOM   6174  CA  ILE B 253     -24.751  26.323  -4.634  1.00 28.12       B
ATOM   6175  CB  ILE B 253     -24.144  25.687  -3.356  1.00 27.44       B
ATOM   6176  CG2 ILE B 253     -25.108  24.692  -2.743  1.00 26.78       B
ATOM   6177  CG1 ILE B 253     -22.830  24.988  -3.725  1.00 26.32       B
ATOM   6178  CD1 ILE B 253     -21.961  24.610  -2.558  1.00 25.76       B
ATOM   6179  C   ILE B 253     -26.170  26.852  -4.383  1.00 27.27       B
ATOM   6180  O   ILE B 253     -27.152  26.195  -4.718  1.00 25.22       B
ATOM   6181  N   ARG B 254     -26.266  28.056  -3.819  1.00 27.27       B
ATOM   6182  CA  ARG B 254     -27.552  28.686  -3.532  1.00 26.18       B
ATOM   6183  CB  ARG B 254     -27.326  30.046  -2.879  1.00 23.44       B
ATOM   6184  CG  ARG B 254     -28.588  30.800  -2.515  1.00 23.88       B
ATOM   6185  CD  ARG B 254     -29.233  30.262  -1.248  1.00 26.34       B
ATOM   6186  NE  ARG B 254     -30.068  29.076  -1.436  1.00 26.77       B
ATOM   6187  CZ  ARG B 254     -31.354  29.113  -1.769  1.00 26.97       B
ATOM   6188  NH1 ARG B 254     -31.955  30.280  -1.956  1.00 28.34       B
ATOM   6189  NH2 ARG B 254     -32.045  27.988  -1.899  1.00 24.50       B
ATOM   6190  C   ARG B 254     -28.344  28.866  -4.829  1.00 27.35       B
ATOM   6191  O   ARG B 254     -29.467  28.390  -4.954  1.00 29.59       B
ATOM   6192  N   SER B 255     -27.746  29.559  -5.791  1.00 27.05       B
ATOM   6193  CA  SER B 255     -28.379  29.808  -7.075  1.00 25.73       B
ATOM   6194  CB  SER B 255     -27.476  30.685  -7.931  1.00 25.65       B
ATOM   6195  OG  SER B 255     -27.308  31.961  -7.330  1.00 25.39       B
ATOM   6196  C   SER B 255     -28.726  28.527  -7.827  1.00 27.00       B
ATOM   6197  O   SER B 255     -29.884  28.311  -8.196  1.00 28.78       B
ATOM   6198  N   LEU B 256     -27.736  27.677  -8.068  1.00 25.48       B
ATOM   6199  CA  LEU B 256     -28.006  26.424  -8.769  1.00 24.98       B
ATOM   6200  CB  LEU B 256     -26.796  25.491  -8.698  1.00 23.22       B
ATOM   6201  CG  LEU B 256     -25.510  25.936  -9.386  1.00 21.18       B
ATOM   6202  CD1 LEU B 256     -24.380  25.012  -8.972  1.00 20.02       B
ATOM   6203  CD2 LEU B 256     -25.705  25.925 -10.875  1.00 16.51       B
ATOM   6204  C   LEU B 256     -29.209  25.713  -8.153  1.00 26.02       B
ATOM   6205  O   LEU B 256     -30.022  25.124  -8.870  1.00 28.90       B
ATOM   6206  N   THR B 257     -29.312  25.758  -6.827  1.00 25.21       B
ATOM   6207  CA  THR B 257     -30.410  25.113  -6.125  1.00 25.98       B
ATOM   6208  CB  THR B 257     -30.293  25.311  -4.590  1.00 26.71       B
ATOM   6209  OG1 THR B 257     -29.158  24.587  -4.103  1.00 27.50       B
ATOM   6210  CG2 THR B 257     -31.543  24.798  -3.869  1.00 24.00       B
ATOM   6211  C   THR B 257     -31.747  25.661  -6.599  1.00 27.44       B
ATOM   6212  O   THR B 257     -32.627  24.902  -7.006  1.00 30.59       B
ATOM   6213  N   GLU B 258     -31.899  26.979  -6.561  1.00 27.81       B
ATOM   6214  CA  GLU B 258     -33.153  27.607  -6.976  1.00 29.78       B
ATOM   6215  CB  GLU B 258     -33.226  29.047  -6.443  1.00 32.77       B
ATOM   6216  CG  GLU B 258     -33.357  29.167  -4.927  1.00 35.11       B
ATOM   6217  CD  GLU B 258     -34.522  28.369  -4.371  1.00 36.34       B
ATOM   6218  OE1 GLU B 258     -35.590  28.354  -5.015  1.00 36.48       B
ATOM   6219  OE2 GLU B 258     -34.372  27.766  -3.284  1.00 38.10       B
ATOM   6220  C   GLU B 258     -33.404  27.633  -8.489  1.00 29.29       B
ATOM   6221  O   GLU B 258     -34.532  27.443  -8.929  1.00 26.53       B
ATOM   6222  N   ARG B 259     -32.350  27.857  -9.273  1.00 29.03       B
ATOM   6223  CA  ARG B 259     -32.467  27.956 -10.729  1.00 26.95       B
ATOM   6224  CB  ARG B 259     -31.412  28.930 -11.266  1.00 25.71       B
ATOM   6225  CG  ARG B 259     -31.542  30.323 -10.711  1.00 26.50       B
ATOM   6226  CD  ARG B 259     -30.343  31.161 -11.070  1.00 28.25       B
ATOM   6227  NE  ARG B 259     -30.234  31.332 -12.512  1.00 31.35       B
ATOM   6228  CZ  ARG B 259     -29.292  32.047 -13.116  1.00 29.98       B
ATOM   6229  NH1 ARG B 259     -28.362  32.671 -12.409  1.00 29.63       B
ATOM   6230  NH2 ARG B 259     -29.274  32.121 -14.433  1.00 28.78       B
ATOM   6231  C   ARG B 259     -32.371  26.662 -11.512  1.00 26.26       B
ATOM   6232  O   ARG B 259     -32.780  26.607 -12.679  1.00 26.42       B
```

FIGURE 5- 83 -

```
ATOM   6233  N    LEU B 260     -31.843  25.616 -10.890  1.00 24.55      B
ATOM   6234  CA   LEU B 260     -31.681  24.365 -11.609  1.00 23.43      B
ATOM   6235  CB   LEU B 260     -30.204  24.164 -11.949  1.00 21.40      B
ATOM   6236  CG   LEU B 260     -29.824  22.922 -12.761  1.00 19.88      B
ATOM   6237  CD1  LEU B 260     -30.489  22.968 -14.133  1.00 17.70      B
ATOM   6238  CD2  LEU B 260     -28.306  22.859 -12.901  1.00 16.76      B
ATOM   6239  C    LEU B 260     -32.190  23.139 -10.879  1.00 25.78      B
ATOM   6240  O    LEU B 260     -33.089  22.443 -11.354  1.00 25.85      B
ATOM   6241  N    TYR B 261     -31.624  22.879  -9.710  1.00 26.60      B
ATOM   6242  CA   TYR B 261     -32.000  21.703  -8.964  1.00 26.51      B
ATOM   6243  CB   TYR B 261     -31.065  21.562  -7.767  1.00 26.57      B
ATOM   6244  CG   TYR B 261     -29.598  21.535  -8.173  1.00 28.75      B
ATOM   6245  CD1  TYR B 261     -29.203  20.982  -9.394  1.00 29.65      B
ATOM   6246  CE1  TYR B 261     -27.859  20.924  -9.758  1.00 30.64      B
ATOM   6247  CD2  TYR B 261     -28.601  22.033  -7.326  1.00 29.21      B
ATOM   6248  CE2  TYR B 261     -27.259  21.977  -7.680  1.00 28.03      B
ATOM   6249  CZ   TYR B 261     -26.895  21.420  -8.896  1.00 31.44      B
ATOM   6250  OH   TYR B 261     -25.565  21.338  -9.245  1.00 34.76      B
ATOM   6251  C    TYR B 261     -33.467  21.515  -8.557  1.00 28.57      B
ATOM   6252  O    TYR B 261     -33.965  20.398  -8.652  1.00 29.94      B
ATOM   6253  N    ILE B 262     -34.181  22.556  -8.125  1.00 29.53      B
ATOM   6254  CA   ILE B 262     -35.583  22.328  -7.743  1.00 30.68      B
ATOM   6255  CB   ILE B 262     -36.140  23.411  -6.786  1.00 30.16      B
ATOM   6256  CG2  ILE B 262     -35.415  23.358  -5.467  1.00 32.39      B
ATOM   6257  CG1  ILE B 262     -36.046  24.788  -7.430  1.00 29.40      B
ATOM   6258  CD1  ILE B 262     -36.672  25.872  -6.593  1.00 26.57      B
ATOM   6259  C    ILE B 262     -36.539  22.241  -8.929  1.00 31.29      B
ATOM   6260  O    ILE B 262     -37.734  21.957  -8.762  1.00 32.23      B
ATOM   6261  N    GLY B 263     -36.025  22.489 -10.127  1.00 30.18      B
ATOM   6262  CA   GLY B 263     -36.882  22.415 -11.291  1.00 29.47      B
ATOM   6263  C    GLY B 263     -36.575  23.486 -12.305  1.00 29.83      B
ATOM   6264  O    GLY B 263     -35.575  24.191 -12.197  1.00 29.46      B
ATOM   6265  N    GLY B 264     -37.444  23.617 -13.297  1.00 30.30      B
ATOM   6266  CA   GLY B 264     -37.224  24.611 -14.326  1.00 29.47      B
ATOM   6267  C    GLY B 264     -37.774  24.124 -15.641  1.00 29.95      B
ATOM   6268  O    GLY B 264     -38.322  23.027 -15.712  1.00 31.35      B
ATOM   6269  N    PRO B 265     -37.637  24.913 -16.710  1.00 30.34      B
ATOM   6270  CD   PRO B 265     -36.957  26.216 -16.757  1.00 29.08      B
ATOM   6271  CA   PRO B 265     -38.140  24.538 -18.036  1.00 31.01      B
ATOM   6272  CB   PRO B 265     -37.977  25.826 -18.833  1.00 28.73      B
ATOM   6273  CG   PRO B 265     -36.760  26.414 -18.242  1.00 28.84      B
ATOM   6274  C    PRO B 265     -37.432  23.349 -18.688  1.00 32.25      B
ATOM   6275  O    PRO B 265     -36.248  23.098 -18.451  1.00 33.45      B
ATOM   6276  N    LEU B 266     -38.186  22.617 -19.503  1.00 32.59      B
ATOM   6277  CA   LEU B 266     -37.692  21.445 -20.220  1.00 31.78      B
ATOM   6278  CB   LEU B 266     -38.552  20.221 -19.881  1.00 29.06      B
ATOM   6279  CG   LEU B 266     -38.505  19.598 -18.483  1.00 29.41      B
ATOM   6280  CD1  LEU B 266     -39.717  18.719 -18.266  1.00 28.43      B
ATOM   6281  CD2  LEU B 266     -37.235  18.785 -18.323  1.00 28.61      B
ATOM   6282  C    LEU B 266     -37.766  21.721 -21.729  1.00 32.80      B
ATOM   6283  O    LEU B 266     -38.825  22.060 -22.249  1.00 32.97      B
ATOM   6284  N    THR B 267     -36.641  21.572 -22.425  1.00 33.74      B
ATOM   6285  CA   THR B 267     -36.589  21.815 -23.869  1.00 33.64      B
ATOM   6286  CB   THR B 267     -35.578  22.938 -24.197  1.00 33.21      B
ATOM   6287  OG1  THR B 267     -35.768  24.035 -23.296  1.00 33.58      B
ATOM   6288  CG2  THR B 267     -35.778  23.435 -25.602  1.00 31.69      B
ATOM   6289  C    THR B 267     -36.168  20.562 -24.636  1.00 34.74      B
ATOM   6290  O    THR B 267     -35.216  19.884 -24.235  1.00 34.64      B
ATOM   6291  N    ASN B 268     -36.877  20.246 -25.724  1.00 35.45      B
ATOM   6292  CA   ASN B 268     -36.525  19.075 -26.532  1.00 36.88      B
ATOM   6293  CB   ASN B 268     -37.726  18.565 -27.356  1.00 36.56      B
ATOM   6294  CG   ASN B 268     -38.166  19.540 -28.448  1.00 38.26      B
ATOM   6295  OD1  ASN B 268     -37.469  20.503 -28.774  1.00 38.32      B
ATOM   6296  ND2  ASN B 268     -39.327  19.277 -29.027  1.00 35.15      B
ATOM   6297  C    ASN B 268     -35.358  19.417 -27.459  1.00 37.27      B
ATOM   6298  O    ASN B 268     -35.003  20.581 -27.620  1.00 35.35      B
ATOM   6299  N    SER B 269     -34.754  18.402 -28.060  1.00 39.31      B
ATOM   6300  CA   SER B 269     -33.628  18.634 -28.950  1.00 42.08      B
ATOM   6301  CB   SER B 269     -33.153  17.313 -29.536  1.00 42.64      B
ATOM   6302  OG   SER B 269     -34.208  16.684 -30.241  1.00 48.39      B
ATOM   6303  C    SER B 269     -33.936  19.619 -30.080  1.00 44.35      B
ATOM   6304  O    SER B 269     -33.015  20.120 -30.735  1.00 46.40      B
ATOM   6305  N    LYS B 270     -35.216  19.901 -30.315  1.00 45.52      B
ATOM   6306  CA   LYS B 270     -35.606  20.842 -31.370  1.00 47.22      B
ATOM   6307  CB   LYS B 270     -37.011  20.536 -31.879  1.00 51.42      B
ATOM   6308  CG   LYS B 270     -37.144  19.423 -32.895  1.00 56.24      B
```

FIGURE 5- 84 -

```
ATOM   6309  CD   LYS B 270     -38.574  19.449 -33.435  1.00 60.18      B
ATOM   6310  CE   LYS B 270     -38.850  18.357 -34.456  1.00 62.24      B
ATOM   6311  NZ   LYS B 270     -40.286  18.402 -34.880  1.00 64.30      B
ATOM   6312  C    LYS B 270     -35.600  22.302 -30.913  1.00 46.88      B
ATOM   6313  O    LYS B 270     -35.799  23.212 -31.719  1.00 46.02      B
ATOM   6314  N    GLY B 271     -35.396  22.521 -29.617  1.00 46.55      B
ATOM   6315  CA   GLY B 271     -35.401  23.872 -29.087  1.00 44.63      B
ATOM   6316  C    GLY B 271     -36.814  24.273 -28.701  1.00 43.92      B
ATOM   6317  O    GLY B 271     -37.107  25.452 -28.510  1.00 44.85      B
ATOM   6318  N    GLN B 272     -37.692  23.283 -28.574  1.00 42.76      B
ATOM   6319  CA   GLN B 272     -39.086  23.529 -28.230  1.00 41.77      B
ATOM   6320  CB   GLN B 272     -39.991  22.702 -29.129  1.00 42.33      B
ATOM   6321  CG   GLN B 272     -39.942  23.120 -30.566  1.00 45.01      B
ATOM   6322  CD   GLN B 272     -40.772  22.225 -31.438  1.00 45.38      B
ATOM   6323  OE1  GLN B 272     -40.490  21.035 -31.578  1.00 43.45      B
ATOM   6324  NE2  GLN B 272     -41.810  22.791 -32.031  1.00 48.22      B
ATOM   6325  C    GLN B 272     -39.444  23.246 -26.781  1.00 40.35      B
ATOM   6326  O    GLN B 272     -39.044  22.229 -26.207  1.00 38.77      B
ATOM   6327  N    ASN B 273     -40.226  24.151 -26.209  1.00 37.51      B
ATOM   6328  CA   ASN B 273     -40.652  24.029 -24.834  1.00 37.64      B
ATOM   6329  CB   ASN B 273     -41.365  25.305 -24.411  1.00 37.29      B
ATOM   6330  CG   ASN B 273     -41.696  25.317 -22.946  1.00 38.28      B
ATOM   6331  OD1  ASN B 273     -42.361  26.224 -22.468  1.00 37.70      B
ATOM   6332  ND2  ASN B 273     -41.227  24.305 -22.215  1.00 40.26      B
ATOM   6333  C    ASN B 273     -41.574  22.831 -24.632  1.00 37.85      B
ATOM   6334  O    ASN B 273     -42.663  22.782 -25.190  1.00 39.45      B
ATOM   6335  N    CYS B 274     -41.135  21.877 -23.818  1.00 38.41      B
ATOM   6336  CA   CYS B 274     -41.902  20.671 -23.542  1.00 38.55      B
ATOM   6337  CB   CYS B 274     -40.977  19.475 -23.392  1.00 37.56      B
ATOM   6338  SG   CYS B 274     -40.306  18.881 -24.921  1.00 46.30      B
ATOM   6339  C    CYS B 274     -42.725  20.771 -22.286  1.00 39.63      B
ATOM   6340  O    CYS B 274     -43.783  20.151 -22.181  1.00 43.11      B
ATOM   6341  N    GLY B 275     -42.228  21.529 -21.318  1.00 38.91      B
ATOM   6342  CA   GLY B 275     -42.944  21.664 -20.071  1.00 37.42      B
ATOM   6343  C    GLY B 275     -42.058  22.158 -18.954  1.00 37.31      B
ATOM   6344  O    GLY B 275     -41.082  22.870 -19.190  1.00 38.79      B
ATOM   6345  N    TYR B 276     -42.394  21.776 -17.730  1.00 35.31      B
ATOM   6346  CA   TYR B 276     -41.635  22.213 -16.578  1.00 33.28      B
ATOM   6347  CB   TYR B 276     -42.429  23.274 -15.826  1.00 32.11      B
ATOM   6348  CG   TYR B 276     -41.583  24.231 -15.033  1.00 32.74      B
ATOM   6349  CD1  TYR B 276     -40.959  25.319 -15.653  1.00 32.85      B
ATOM   6350  CE1  TYR B 276     -40.175  26.214 -14.927  1.00 32.95      B
ATOM   6351  CD2  TYR B 276     -41.400  24.055 -13.663  1.00 32.43      B
ATOM   6352  CE2  TYR B 276     -40.618  24.943 -12.925  1.00 33.95      B
ATOM   6353  CZ   TYR B 276     -40.011  26.020 -13.561  1.00 34.74      B
ATOM   6354  OH   TYR B 276     -39.256  26.905 -12.824  1.00 34.99      B
ATOM   6355  C    TYR B 276     -41.390  21.020 -15.672  1.00 33.59      B
ATOM   6356  O    TYR B 276     -42.169  20.063 -15.670  1.00 34.70      B
ATOM   6357  N    ARG B 277     -40.310  21.086 -14.900  1.00 32.09      B
ATOM   6358  CA   ARG B 277     -39.942  20.020 -13.976  1.00 30.36      B
ATOM   6359  CB   ARG B 277     -38.531  19.509 -14.309  1.00 28.53      B
ATOM   6360  CG   ARG B 277     -37.885  18.624 -13.233  1.00 30.06      B
ATOM   6361  CD   ARG B 277     -36.461  18.228 -13.622  1.00 30.98      B
ATOM   6362  NE   ARG B 277     -35.657  19.412 -13.917  1.00 33.62      B
ATOM   6363  CZ   ARG B 277     -34.984  20.127 -13.021  1.00 31.52      B
ATOM   6364  NH1  ARG B 277     -34.986  19.786 -11.741  1.00 27.35      B
ATOM   6365  NH2  ARG B 277     -34.335  21.215 -13.407  1.00 31.66      B
ATOM   6366  C    ARG B 277     -39.979  20.564 -12.549  1.00 30.85      B
ATOM   6367  O    ARG B 277     -39.658  21.732 -12.317  1.00 30.75      B
ATOM   6368  N    ARG B 278     -40.379  19.725 -11.599  1.00 30.01      B
ATOM   6369  CA   ARG B 278     -40.421  20.141 -10.206  1.00 29.54      B
ATOM   6370  CB   ARG B 278     -41.846  20.516  -9.806  1.00 29.47      B
ATOM   6371  CG   ARG B 278     -42.446  21.590 -10.709  1.00 28.27      B
ATOM   6372  CD   ARG B 278     -43.678  22.242 -10.094  1.00 28.70      B
ATOM   6373  NE   ARG B 278     -44.311  23.138 -11.054  1.00 29.52      B
ATOM   6374  CZ   ARG B 278     -44.983  22.729 -12.123  1.00 27.38      B
ATOM   6375  NH1  ARG B 278     -45.130  21.433 -12.366  1.00 27.69      B
ATOM   6376  NH2  ARG B 278     -45.462  23.616 -12.975  1.00 25.48      B
ATOM   6377  C    ARG B 278     -39.890  19.023  -9.325  1.00 30.61      B
ATOM   6378  O    ARG B 278     -40.247  18.911  -8.152  1.00 30.21      B
ATOM   6379  N    CYS B 279     -39.028  18.200  -9.918  1.00 31.32      B
ATOM   6380  CA   CYS B 279     -38.397  17.072  -9.238  1.00 32.67      B
ATOM   6381  CB   CYS B 279     -39.135  15.765  -9.559  1.00 32.82      B
ATOM   6382  SG   CYS B 279     -39.264  15.399 -11.325  1.00 35.79      B
ATOM   6383  C    CYS B 279     -36.939  16.943  -9.672  1.00 32.28      B
ATOM   6384  O    CYS B 279     -36.417  17.789 -10.393  1.00 33.98      B
```

FIGURE 5- 85 -

```
ATOM   6385  N   ARG B 280     -36.292  15.869  -9.243  1.00 30.59      B
ATOM   6386  CA  ARG B 280     -34.899  15.630  -9.579  1.00 29.82      B
ATOM   6387  CB  ARG B 280     -34.450  14.321  -8.933  1.00 29.74      B
ATOM   6388  CG  ARG B 280     -33.028  13.910  -9.246  1.00 28.13      B
ATOM   6389  CD  ARG B 280     -32.059  14.658  -8.366  1.00 29.35      B
ATOM   6390  NE  ARG B 280     -32.141  14.236  -6.970  1.00 28.96      B
ATOM   6391  CZ  ARG B 280     -31.990  15.058  -5.936  1.00 29.19      B
ATOM   6392  NH1 ARG B 280     -31.760  16.346  -6.150  1.00 24.83      B
ATOM   6393  NH2 ARG B 280     -32.043  14.591  -4.690  1.00 28.19      B
ATOM   6394  C   ARG B 280     -34.615  15.558 -11.082  1.00 30.71      B
ATOM   6395  O   ARG B 280     -35.324  14.894 -11.824  1.00 31.49      B
ATOM   6396  N   ALA B 281     -33.585  16.263 -11.533  1.00 31.83      B
ATOM   6397  CA  ALA B 281     -33.164  16.188 -12.931  1.00 31.28      B
ATOM   6398  CB  ALA B 281     -32.509  17.486 -13.369  1.00 30.91      B
ATOM   6399  C   ALA B 281     -32.125  15.060 -12.871  1.00 31.54      B
ATOM   6400  O   ALA B 281     -31.345  14.979 -11.922  1.00 31.80      B
ATOM   6401  N   SER B 282     -32.110  14.178 -13.856  1.00 30.86      B
ATOM   6402  CA  SER B 282     -31.163  13.075 -13.803  1.00 30.75      B
ATOM   6403  CB  SER B 282     -31.626  11.947 -14.716  1.00 31.33      B
ATOM   6404  OG  SER B 282     -31.606  12.362 -16.068  1.00 34.61      B
ATOM   6405  C   SER B 282     -29.750  13.466 -14.191  1.00 30.64      B
ATOM   6406  O   SER B 282     -28.792  12.825 -13.768  1.00 29.42      B
ATOM   6407  N   GLY B 283     -29.631  14.526 -14.985  1.00 30.78      B
ATOM   6408  CA  GLY B 283     -28.335  14.963 -15.462  1.00 30.43      B
ATOM   6409  C   GLY B 283     -27.625  16.140 -14.822  1.00 32.62      B
ATOM   6410  O   GLY B 283     -26.991  16.925 -15.526  1.00 35.35      B
ATOM   6411  N   VAL B 284     -27.722  16.288 -13.506  1.00 31.55      B
ATOM   6412  CA  VAL B 284     -27.008  17.363 -12.828  1.00 31.69      B
ATOM   6413  CB  VAL B 284     -27.943  16.245 -11.954  1.00 32.53      B
ATOM   6414  CG1 VAL B 284     -28.812  19.109 -12.856  1.00 30.13      B
ATOM   6415  CG2 VAL B 284     -28.796  17.378 -11.030  1.00 30.08      B
ATOM   6416  C   VAL B 284     -25.971  16.671 -11.958  1.00 31.68      B
ATOM   6417  O   VAL B 284     -26.085  15.481 -11.691  1.00 33.40      B
ATOM   6418  N   LEU B 285     -24.960  17.400 -11.515  1.00 30.77      B
ATOM   6419  CA  LEU B 285     -23.910  16.795 -10.715  1.00 30.65      B
ATOM   6420  CB  LEU B 285     -22.777  17.797 -10.528  1.00 30.30      B
ATOM   6421  CG  LEU B 285     -21.494  17.214  -9.950  1.00 31.37      B
ATOM   6422  CD1 LEU B 285     -20.991  16.155 -10.889  1.00 30.95      B
ATOM   6423  CD2 LEU B 285     -20.441  18.303  -9.767  1.00 31.81      B
ATOM   6424  C   LEU B 285     -24.372  16.291  -9.349  1.00 31.77      B
ATOM   6425  O   LEU B 285     -23.753  15.403  -8.768  1.00 32.56      B
ATOM   6426  N   THR B 286     -25.471  16.840  -8.847  1.00 31.37      B
ATOM   6427  CA  THR B 286     -25.960  16.458  -7.528  1.00 31.32      B
ATOM   6428  CB  THR B 286     -26.635  17.662  -6.835  1.00 32.34      B
ATOM   6429  OG1 THR B 286     -27.710  18.149  -7.650  1.00 33.39      B
ATOM   6430  CG2 THR B 286     -25.627  18.777  -6.620  1.00 33.50      B
ATOM   6431  C   THR B 286     -26.926  15.282  -7.461  1.00 29.51      B
ATOM   6432  O   THR B 286     -27.337  14.881  -6.376  1.00 28.90      B
ATOM   6433  N   THR B 287     -27.279  14.711  -8.601  1.00 29.24      B
ATOM   6434  CA  THR B 287     -28.238  13.612  -8.599  1.00 29.50      B
ATOM   6435  CB  THR B 287     -28.506  13.094 -10.024  1.00 27.97      B
ATOM   6436  OG1 THR B 287     -29.032  14.153 -10.827  1.00 30.00      B
ATOM   6437  CG2 THR B 287     -29.515  11.978  -9.994  1.00 26.19      B
ATOM   6438  C   THR B 287     -27.875  12.421  -7.719  1.00 28.34      B
ATOM   6439  O   THR B 287     -28.699  11.935  -6.955  1.00 28.72      B
ATOM   6440  N   SER B 288     -26.646  11.950  -7.813  1.00 28.45      B
ATOM   6441  CA  SER B 288     -26.265  10.793  -7.027  1.00 30.17      B
ATOM   6442  CB  SER B 288     -24.942  10.233  -7.534  1.00 29.00      B
ATOM   6443  OG  SER B 288     -24.689   8.979  -6.936  1.00 34.50      B
ATOM   6444  C   SER B 288     -26.162  11.115  -5.544  1.00 31.29      B
ATOM   6445  O   SER B 288     -26.798  10.477  -4.704  1.00 31.61      B
ATOM   6446  N   CYS B 289     -25.355  12.112  -5.229  1.00 32.25      B
ATOM   6447  CA  CYS B 289     -25.161  12.528  -3.853  1.00 34.14      B
ATOM   6448  CB  CYS B 289     -24.217  13.721  -3.820  1.00 35.03      B
ATOM   6449  SG  CYS B 289     -24.148  14.492  -2.226  1.00 38.19      B
ATOM   6450  C   CYS B 289     -26.473  12.896  -3.160  1.00 34.49      B
ATOM   6451  O   CYS B 289     -26.705  12.509  -2.016  1.00 34.41      B
ATOM   6452  N   GLY B 290     -27.316  13.651  -3.866  1.00 35.29      B
ATOM   6453  CA  GLY B 290     -28.594  14.087  -3.332  1.00 34.21      B
ATOM   6454  C   GLY B 290     -29.575  12.947  -3.181  1.00 35.82      B
ATOM   6455  O   GLY B 290     -30.288  12.847  -2.174  1.00 35.01      B
ATOM   6456  N   ASN B 291     -29.629  12.080  -4.188  1.00 35.21      B
ATOM   6457  CA  ASN B 291     -30.524  10.945  -4.110  1.00 33.78      B
ATOM   6458  CB  ASN B 291     -30.524  10.162  -5.415  1.00 32.97      B
ATOM   6459  CG  ASN B 291     -31.458  10.765  -6.438  1.00 36.65      B
ATOM   6460  OD1 ASN B 291     -32.280  11.616  -6.105  1.00 40.35      B
```

FIGURE 5- 86 -

```
ATOM   6461  ND2 ASN B 291     -31.351   10.325   -7.683  1.00 37.24           B
ATOM   6462  C   ASN B 291     -30.097   10.062   -2.957  1.00 33.69           B
ATOM   6463  O   ASN B 291     -30.931    9.630   -2.173  1.00 34.41           B
ATOM   6464  N   THR B 292     -28.797    9.816   -2.838  1.00 32.89           B
ATOM   6465  CA  THR B 292     -28.292    8.984   -1.757  1.00 32.56           B
ATOM   6466  CB  THR B 292     -26.768    8.831   -1.809  1.00 33.20           B
ATOM   6467  OG1 THR B 292     -26.386    8.236   -3.053  1.00 37.49           B
ATOM   6468  CG2 THR B 292     -26.297    7.937   -0.689  1.00 32.25           B
ATOM   6469  C   THR B 292     -28.642    9.578   -0.408  1.00 32.37           B
ATOM   6470  O   THR B 292     -29.134    8.875    0.476  1.00 34.36           B
ATOM   6471  N   LEU B 293     -28.380   10.871   -0.243  1.00 30.30           B
ATOM   6472  CA  LEU B 293     -28.665   11.529    1.023  1.00 28.89           B
ATOM   6473  CB  LEU B 293     -28.128   12.966    1.023  1.00 27.32           B
ATOM   6474  CG  LEU B 293     -26.600   13.155    1.055  1.00 27.76           B
ATOM   6475  CD1 LEU B 293     -26.213   14.526    0.493  1.00 24.63           B
ATOM   6476  CD2 LEU B 293     -26.101   12.992    2.489  1.00 25.67           B
ATOM   6477  C   LEU B 293     -30.157   11.530    1.270  1.00 29.55           B
ATOM   6478  O   LEU B 293     -30.607   11.189    2.356  1.00 30.60           B
ATOM   6479  N   THR B 294     -30.929   11.894    0.250  1.00 30.62           B
ATOM   6480  CA  THR B 294     -32.385   11.954    0.371  1.00 30.58           B
ATOM   6481  CB  THR B 294     -33.013   12.476   -0.931  1.00 29.95           B
ATOM   6482  OG1 THR B 294     -32.608   13.832   -1.129  1.00 30.15           B
ATOM   6483  CG2 THR B 294     -34.535   12.411   -0.867  1.00 27.38           B
ATOM   6484  C   THR B 294     -33.012   10.606    0.724  1.00 31.27           B
ATOM   6485  O   THR B 294     -33.946   10.529    1.522  1.00 32.73           B
ATOM   6486  N   CYS B 295     -32.496    9.546    0.124  1.00 30.81           B
ATOM   6487  CA  CYS B 295     -32.999    8.212    0.382  1.00 32.48           B
ATOM   6488  CB  CYS B 295     -32.331    7.224   -0.565  1.00 31.98           B
ATOM   6489  SG  CYS B 295     -33.091    5.609   -0.570  1.00 33.47           B
ATOM   6490  C   CYS B 295     -32.673    7.839    1.824  1.00 34.28           B
ATOM   6491  O   CYS B 295     -33.554    7.454    2.604  1.00 33.53           B
ATOM   6492  N   TYR B 296     -31.392    7.961    2.160  1.00 34.53           B
ATOM   6493  CA  TYR B 296     -30.894    7.654    3.491  1.00 34.05           B
ATOM   6494  CB  TYR B 296     -29.401    7.997    3.570  1.00 34.44           B
ATOM   6495  CG  TYR B 296     -28.797    7.882    4.948  1.00 36.51           B
ATOM   6496  CD1 TYR B 296     -29.034    8.855    5.918  1.00 37.26           B
ATOM   6497  CE1 TYR B 296     -28.492    8.743    7.198  1.00 39.73           B
ATOM   6498  CD2 TYR B 296     -28.000    6.792    5.291  1.00 37.52           B
ATOM   6499  CE2 TYR B 296     -27.449    6.671    6.572  1.00 38.87           B
ATOM   6500  CZ  TYR B 296     -27.701    7.648    7.518  1.00 39.76           B
ATOM   6501  OH  TYR B 296     -27.167    7.529    8.785  1.00 42.09           B
ATOM   6502  C   TYR B 296     -31.680    8.397    4.566  1.00 34.59           B
ATOM   6503  O   TYR B 296     -32.090    7.800    5.560  1.00 35.80           B
ATOM   6504  N   LEU B 297     -31.898    9.691    4.374  1.00 33.72           B
ATOM   6505  CA  LEU B 297     -32.633   10.467    5.358  1.00 35.45           B
ATOM   6506  CB  LEU B 297     -32.754   11.932    4.910  1.00 35.19           B
ATOM   6507  CG  LEU B 297     -33.794   12.844    5.586  1.00 31.50           B
ATOM   6508  CD1 LEU B 297     -33.573   12.936    7.097  1.00 30.06           B
ATOM   6509  CD2 LEU B 297     -33.712   14.202    4.938  1.00 28.55           B
ATOM   6510  C   LEU B 297     -34.019    9.883    5.594  1.00 37.38           B
ATOM   6511  O   LEU B 297     -34.400    9.590    6.731  1.00 38.48           B
ATOM   6512  N   LYS B 298     -34.776    9.717    4.517  1.00 38.44           B
ATOM   6513  CA  LYS B 298     -36.126    9.176    4.627  1.00 38.76           B
ATOM   6514  CB  LYS B 298     -36.809    9.201    3.254  1.00 37.00           B
ATOM   6515  CG  LYS B 298     -37.147   10.610    2.778  1.00 34.21           B
ATOM   6516  CD  LYS B 298     -37.667   10.651    1.342  1.00 31.01           B
ATOM   6517  CE  LYS B 298     -37.959   12.095    0.925  1.00 28.08           B
ATOM   6518  NZ  LYS B 298     -38.396   12.260   -0.501  1.00 24.58           B
ATOM   6519  C   LYS B 298     -36.134    7.763    5.205  1.00 38.99           B
ATOM   6520  O   LYS B 298     -36.874    7.477    6.137  1.00 39.22           B
ATOM   6521  N   ALA B 299     -35.304    6.887    4.654  1.00 39.16           B
ATOM   6522  CA  ALA B 299     -35.234    5.508    5.124  1.00 40.43           B
ATOM   6523  CB  ALA B 299     -34.214    4.735    4.302  1.00 40.34           B
ATOM   6524  C   ALA B 299     -34.878    5.419    6.610  1.00 42.22           B
ATOM   6525  O   ALA B 299     -35.562    4.735    7.374  1.00 42.24           B
ATOM   6526  N   THR B 300     -33.803    6.093    7.024  1.00 42.22           B
ATOM   6527  CA  THR B 300     -33.413    6.053    8.428  1.00 40.60           B
ATOM   6528  CB  THR B 300     -32.212    6.957    8.740  1.00 38.50           B
ATOM   6529  OG1 THR B 300     -31.056    6.507    8.032  1.00 37.29           B
ATOM   6530  CG2 THR B 300     -31.926    6.923   10.229  1.00 36.16           B
ATOM   6531  C   THR B 300     -34.563    6.524    9.310  1.00 41.38           B
ATOM   6532  O   THR B 300     -34.866    5.895   10.324  1.00 42.18           B
ATOM   6533  N   ALA B 301     -35.194    7.634    8.927  1.00 39.83           B
ATOM   6534  CA  ALA B 301     -36.298    8.180    9.705  1.00 39.93           B
ATOM   6535  CB  ALA B 301     -36.768    9.493    9.108  1.00 37.51           B
ATOM   6536  C   ALA B 301     -37.440    7.178    9.735  1.00 41.15           B
```

FIGURE 5-87-

```
ATOM   6537  O    ALA B 301   -38.026    6.913   10.783  1.00  42.33    B
ATOM   6538  N    ALA B 302   -37.749    6.616    8.574  1.00  42.24    B
ATOM   6539  CA   ALA B 302   -38.813    5.638    8.468  1.00  41.66    B
ATOM   6540  CB   ALA B 302   -38.927    5.148    7.037  1.00  39.42    B
ATOM   6541  C    ALA B 302   -38.558    4.464    9.414  1.00  42.79    B
ATOM   6542  O    ALA B 302   -39.481    3.991   10.078  1.00  44.57    B
ATOM   6543  N    CYS B 303   -37.316    3.990    9.486  1.00  42.69    B
ATOM   6544  CA   CYS B 303   -37.014    2.874   10.374  1.00  43.53    B
ATOM   6545  CB   CYS B 303   -35.533    2.519   10.312  1.00  43.63    B
ATOM   6546  SG   CYS B 303   -35.065    1.773    8.734  1.00  49.72    B
ATOM   6547  C    CYS B 303   -37.426    3.214   11.796  1.00  43.63    B
ATOM   6548  O    CYS B 303   -38.080    2.419   12.464  1.00  44.14    B
ATOM   6549  N    ARG B 304   -37.066    4.404   12.254  1.00  44.25    B
ATOM   6550  CA   ARG B 304   -37.442    4.821   13.592  1.00  45.25    B
ATOM   6551  CB   ARG B 304   -36.876    6.211   13.899  1.00  43.16    B
ATOM   6552  CG   ARG B 304   -35.362    6.236   13.848  1.00  41.18    B
ATOM   6553  CD   ARG B 304   -34.796    7.530   14.359  1.00  39.63    B
ATOM   6554  NE   ARG B 304   -33.354    7.586   14.149  1.00  40.60    B
ATOM   6555  CZ   ARG B 304   -32.610    8.662   14.390  1.00  42.73    B
ATOM   6556  NH1  ARG B 304   -33.176    9.773   14.851  1.00  43.84    B
ATOM   6557  NH2  ARG B 304   -31.302    8.636   14.164  1.00  42.15    B
ATOM   6558  C    ARG B 304   -38.964    4.827   13.705  1.00  46.89    B
ATOM   6559  O    ARG B 304   -39.515    4.463   14.741  1.00  49.59    B
ATOM   6560  N    ALA B 305   -39.641    5.225   12.632  1.00  46.98    B
ATOM   6561  CA   ALA B 305   -41.094    5.269   12.629  1.00  47.63    B
ATOM   6562  CB   ALA B 305   -41.587    5.949   11.373  1.00  45.91    B
ATOM   6563  C    ALA B 305   -41.679    3.865   12.727  1.00  49.47    B
ATOM   6564  O    ALA B 305   -42.744    3.673   13.304  1.00  50.39    B
ATOM   6565  N    ALA B 306   -40.975    2.985   12.168  1.00  50.54    B
ATOM   6566  CA   ALA B 306   -41.435    1.500   12.184  1.00  52.07    B
ATOM   6567  CB   ALA B 306   -41.002    0.790   10.905  1.00  50.79    B
ATOM   6568  C    ALA B 306   -40.904    0.750   13.402  1.00  54.15    B
ATOM   6569  O    ALA B 306   -41.386   -0.329   13.743  1.00  53.79    B
ATOM   6570  N    LYS B 307   -39.898    1.324   14.048  1.00  56.49    B
ATOM   6571  CA   LYS B 307   -39.305    0.721   15.233  1.00  58.52    B
ATOM   6572  CB   LYS B 307   -40.401    0.350   16.243  1.00  59.31    B
ATOM   6573  CG   LYS B 307   -41.383    1.478   16.536  1.00  61.24    B
ATOM   6574  CD   LYS B 307   -41.849    1.453   17.979  1.00  61.05    B
ATOM   6575  CE   LYS B 307   -40.678    1.688   18.920  1.00  62.59    B
ATOM   6576  NZ   LYS B 307   -41.083    1.685   20.355  1.00  64.64    B
ATOM   6577  C    LYS B 307   -38.436   -0.507   14.945  1.00  59.09    B
ATOM   6578  O    LYS B 307   -38.167   -1.306   15.843  1.00  60.03    B
ATOM   6579  N    LEU B 308   -37.998   -0.667   13.703  1.00  59.04    B
ATOM   6580  CA   LEU B 308   -37.143   -1.797   13.365  1.00  60.00    B
ATOM   6581  CB   LEU B 308   -36.754   -1.722   11.868  1.00  59.41    B
ATOM   6582  CG   LEU B 308   -37.928   -1.798   10.908  1.00  58.13    B
ATOM   6583  CD1  LEU B 308   -37.472   -1.422    9.519  1.00  56.81    B
ATOM   6584  CD2  LEU B 308   -38.499   -3.204   10.920  1.00  58.62    B
ATOM   6585  C    LEU B 308   -35.897   -1.726   14.258  1.00  61.34    B
ATOM   6586  O    LEU B 308   -35.294   -0.667   14.400  1.00  61.81    B
ATOM   6587  N    GLN B 309   -35.515   -2.845   14.864  1.00  62.85    B
ATOM   6588  CA   GLN B 309   -34.355   -2.864   15.754  1.00  64.36    B
ATOM   6589  CB   GLN B 309   -34.479   -4.013   16.764  1.00  67.39    B
ATOM   6590  CG   GLN B 309   -35.742   -3.967   17.619  1.00  70.15    B
ATOM   6591  CD   GLN B 309   -35.892   -2.654   18.382  1.00  72.94    B
ATOM   6592  OE1  GLN B 309   -36.023   -1.579   17.782  1.00  72.28    B
ATOM   6593  NE2  GLN B 309   -35.872   -2.736   19.713  1.00  73.33    B
ATOM   6594  C    GLN B 309   -33.037   -2.996   15.010  1.00  63.77    B
ATOM   6595  O    GLN B 309   -32.984   -3.597   13.940  1.00  63.93    B
ATOM   6596  N    ASP B 310   -31.977   -2.438   15.590  1.00  62.51    B
ATOM   6597  CA   ASP B 310   -30.648   -2.498   14.996  1.00  62.66    B
ATOM   6598  CB   ASP B 310   -29.890   -3.723   15.513  1.00  65.96    B
ATOM   6599  CG   ASP B 310   -29.299   -3.508   16.889  1.00  69.49    B
ATOM   6600  OD1  ASP B 310   -30.013   -2.961   17.761  1.00  71.08    B
ATOM   6601  OD2  ASP B 310   -28.126   -3.897   17.099  1.00  70.48    B
ATOM   6602  C    ASP B 310   -30.673   -2.555   13.481  1.00  61.72    B
ATOM   6603  O    ASP B 310   -30.469   -3.617   12.898  1.00  62.35    B
ATOM   6604  N    CYS B 311   -30.926   -1.422   12.839  1.00  60.41    B
ATOM   6605  CA   CYS B 311   -30.948   -1.387   11.381  1.00  58.27    B
ATOM   6606  CB   CYS B 311   -31.948   -0.350   10.870  1.00  56.84    B
ATOM   6607  SG   CYS B 311   -33.659   -0.702   11.222  1.00  54.86    B
ATOM   6608  C    CYS B 311   -29.579   -1.028   10.832  1.00  56.94    B
ATOM   6609  O    CYS B 311   -28.840   -0.265   11.439  1.00  56.43    B
ATOM   6610  N    THR B 312   -29.242   -1.594    9.683  1.00  56.74    B
ATOM   6611  CA   THR B 312   -27.982   -1.283    9.019  1.00  57.30    B
ATOM   6612  CB   THR B 312   -26.953   -2.412    9.139  1.00  58.10    B
```

FIGURE 5- 88 -

```
ATOM   6613  OG1 THR B 312     -26.518   -2.519   10.502  1.00 60.61       B
ATOM   6614  CG2 THR B 312     -25.753   -2.127    8.240  1.00 57.69       B
ATOM   6615  C   THR B 312     -28.330   -1.087    7.556  1.00 56.00       B
ATOM   6616  O   THR B 312     -28.765   -2.027    6.885  1.00 55.32       B
ATOM   6617  N   MET B 313     -28.152    0.136    7.069  1.00 54.42       B
ATOM   6618  CA  MET B 313     -28.487    0.430    5.693  1.00 52.54       B
ATOM   6619  CB  MET B 313     -29.307    1.710    5.600  1.00 54.23       B
ATOM   6620  CG  MET B 313     -30.545    1.741    6.456  1.00 57.94       B
ATOM   6621  SD  MET B 313     -31.630    3.044    5.882  1.00 61.15       B
ATOM   6622  CE  MET B 313     -30.419    4.304    5.413  1.00 58.24       B
ATOM   6623  C   MET B 313     -27.315    0.574    4.759  1.00 50.47       B
ATOM   6624  O   MET B 313     -26.209    0.929    5.156  1.00 49.96       B
ATOM   6625  N   LEU B 314     -27.589    0.286    3.499  1.00 48.23       B
ATOM   6626  CA  LEU B 314     -26.616    0.422    2.448  1.00 47.00       B
ATOM   6627  CB  LEU B 314     -26.139   -0.939    1.964  1.00 46.04       B
ATOM   6628  CG  LEU B 314     -25.003   -0.838    0.945  1.00 46.68       B
ATOM   6629  CD1 LEU B 314     -23.838   -0.080    1.562  1.00 46.36       B
ATOM   6630  CD2 LEU B 314     -24.570   -2.227    0.513  1.00 46.92       B
ATOM   6631  C   LEU B 314     -27.417    1.138    1.373  1.00 46.55       B
ATOM   6632  O   LEU B 314     -28.394    0.603    0.846  1.00 46.66       B
ATOM   6633  N   VAL B 315     -27.020    2.367    1.078  1.00 45.62       B
ATOM   6634  CA  VAL B 315     -27.724    3.167    0.097  1.00 45.02       B
ATOM   6635  CB  VAL B 315     -28.217    4.479    0.721  1.00 45.99       B
ATOM   6636  CG1 VAL B 315     -29.003    5.287   -0.304  1.00 45.24       B
ATOM   6637  CG2 VAL B 315     -29.058    4.178    1.953  1.00 46.52       B
ATOM   6638  C   VAL B 315     -26.861    3.521   -1.089  1.00 44.90       B
ATOM   6639  O   VAL B 315     -25.708    3.913   -0.938  1.00 45.08       B
ATOM   6640  N   ASN B 316     -27.436    3.376   -2.272  1.00 44.15       B
ATOM   6641  CA  ASN B 316     -26.754    3.710   -3.504  1.00 44.37       B
ATOM   6642  CB  ASN B 316     -26.386    2.450   -4.283  1.00 45.47       B
ATOM   6643  CG  ASN B 316     -25.221    1.705   -3.662  1.00 45.68       B
ATOM   6644  OD1 ASN B 316     -25.354    1.061   -2.612  1.00 46.26       B
ATOM   6645  ND2 ASN B 316     -24.061    1.803   -4.303  1.00 44.51       B
ATOM   6646  C   ASN B 316     -27.736    4.540   -4.292  1.00 44.48       B
ATOM   6647  O   ASN B 316     -28.584    4.006   -4.998  1.00 45.10       B
ATOM   6648  N   GLY B 317     -27.628    5.856   -4.164  1.00 44.63       B
ATOM   6649  CA  GLY B 317     -28.556    6.712   -4.860  1.00 44.14       B
ATOM   6650  C   GLY B 317     -29.936    6.395   -4.316  1.00 45.93       B
ATOM   6651  O   GLY B 317     -30.199    6.577   -3.126  1.00 46.89       B
ATOM   6652  N   ASP B 318     -30.813    5.889   -5.172  1.00 46.37       B
ATOM   6653  CA  ASP B 318     -32.174    5.571   -4.758  1.00 47.58       B
ATOM   6654  CB  ASP B 318     -33.148    5.901   -5.890  1.00 48.33       B
ATOM   6655  CG  ASP B 318     -32.953    5.006   -7.096  1.00 50.26       B
ATOM   6656  OD1 ASP B 318     -31.810    4.557   -7.335  1.00 49.19       B
ATOM   6657  OD2 ASP B 318     -33.942    4.759   -7.813  1.00 52.14       B
ATOM   6658  C   ASP B 318     -32.283    4.102   -4.403  1.00 46.99       B
ATOM   6659  O   ASP B 318     -33.362    3.611   -4.072  1.00 45.12       B
ATOM   6660  N   ASP B 319     -31.151    3.413   -4.470  1.00 48.09       B
ATOM   6661  CA  ASP B 319     -31.085    1.988   -4.176  1.00 49.50       B
ATOM   6662  CB  ASP B 319     -29.973    1.354   -5.001  1.00 52.19       B
ATOM   6663  CG  ASP B 319     -30.315   -0.041   -5.451  1.00 54.84       B
ATOM   6664  OD1 ASP B 319     -30.334   -0.960   -4.596  1.00 55.07       B
ATOM   6665  OD2 ASP B 319     -30.573   -0.206   -6.666  1.00 57.43       B
ATOM   6666  C   ASP B 319     -30.843    1.740   -2.693  1.00 49.52       B
ATOM   6667  O   ASP B 319     -29.783    2.068   -2.156  1.00 48.57       B
ATOM   6668  N   LEU B 320     -31.832    1.133   -2.046  1.00 50.10       B
ATOM   6669  CA  LEU B 320     -31.777    0.866   -0.619  1.00 50.35       B
ATOM   6670  CB  LEU B 320     -32.832    1.717    0.082  1.00 49.52       B
ATOM   6671  CG  LEU B 320     -33.047    1.423    1.562  1.00 49.85       B
ATOM   6672  CD1 LEU B 320     -31.838    1.888    2.337  1.00 50.47       B
ATOM   6673  CD2 LEU B 320     -34.295    2.129    2.052  1.00 50.70       B
ATOM   6674  C   LEU B 320     -31.965   -0.590   -0.198  1.00 51.86       B
ATOM   6675  O   LEU B 320     -32.782   -1.323   -0.755  1.00 50.20       B
ATOM   6676  N   VAL B 321     -31.201   -0.988    0.813  1.00 54.00       B
ATOM   6677  CA  VAL B 321     -31.277   -2.332    1.366  1.00 55.71       B
ATOM   6678  CB  VAL B 321     -30.287   -3.300    0.673  1.00 55.28       B
ATOM   6679  CG1 VAL B 321     -28.867   -2.810    0.842  1.00 55.80       B
ATOM   6680  CG2 VAL B 321     -30.442   -4.695    1.252  1.00 54.89       B
ATOM   6681  C   VAL B 321     -30.974   -2.272    2.863  1.00 56.98       B
ATOM   6682  O   VAL B 321     -29.889   -1.859    3.275  1.00 57.46       B
ATOM   6683  N   VAL B 322     -31.951   -2.678    3.668  1.00 57.72       B
ATOM   6684  CA  VAL B 322     -31.832   -2.675    5.121  1.00 58.29       B
ATOM   6685  CB  VAL B 322     -33.097   -2.076    5.757  1.00 58.30       B
ATOM   6686  CG1 VAL B 322     -32.953   -2.022    7.268  1.00 58.84       B
ATOM   6687  CG2 VAL B 322     -33.360   -0.700    5.180  1.00 59.90       B
ATOM   6688  C   VAL B 322     -31.644   -4.082    5.696  1.00 59.18       B
```

FIGURE 5- 89 -

```
ATOM   6689  O    VAL B 322     -32.225  -5.052   5.201  1.00 59.52      B
ATOM   6690  N    ILE B 323     -30.818  -4.188   6.732  1.00 59.31      B
ATOM   6691  CA   ILE B 323     -30.585  -5.458   7.407  1.00 60.14      B
ATOM   6692  CB   ILE B 323     -29.177  -6.012   7.108  1.00 58.68      B
ATOM   6693  CG2  ILE B 323     -28.857  -7.171   8.030  1.00 58.32      B
ATOM   6694  CG1  ILE B 323     -29.121  -6.484   5.655  1.00 57.63      B
ATOM   6695  CD1  ILE B 323     -27.765  -6.970   5.209  1.00 56.52      B
ATOM   6696  C    ILE B 323     -30.751  -5.152   8.888  1.00 62.05      B
ATOM   6697  O    ILE B 323     -30.038  -4.321   9.448  1.00 61.46      B
ATOM   6698  N    CYS B 324     -31.711  -5.807   9.523  1.00 64.40      B
ATOM   6699  CA   CYS B 324     -31.959  -5.530  10.926  1.00 67.52      B
ATOM   6700  CB   CYS B 324     -33.158  -4.600  11.054  1.00 68.94      B
ATOM   6701  SG   CYS B 324     -34.722  -5.387  10.612  1.00 72.71      B
ATOM   6702  C    CYS B 324     -32.197  -6.742  11.806  1.00 68.28      B
ATOM   6703  O    CYS B 324     -32.237  -7.882  11.342  1.00 67.82      B
ATOM   6704  N    GLU B 325     -32.368  -6.461  13.093  1.00 69.78      B
ATOM   6705  CA   GLU B 325     -32.609  -7.484  14.094  1.00 71.02      B
ATOM   6706  CB   GLU B 325     -32.296  -6.925  15.487  1.00 73.00      B
ATOM   6707  CG   GLU B 325     -32.157  -7.987  16.555  1.00 76.10      B
ATOM   6708  CD   GLU B 325     -31.185  -9.079  16.150  1.00 77.49      B
ATOM   6709  OE1  GLU B 325     -29.998  -8.763  15.906  1.00 78.15      B
ATOM   6710  OE2  GLU B 325     -31.615 -10.251  16.071  1.00 78.26      B
ATOM   6711  C    GLU B 325     -34.072  -7.902  13.999  1.00 69.81      B
ATOM   6712  O    GLU B 325     -34.968  -7.103  14.265  1.00 69.94      B
ATOM   6713  N    SER B 326     -34.315  -9.147  13.603  1.00 69.73      B
ATOM   6714  CA   SER B 326     -35.686  -9.625  13.477  1.00 69.75      B
ATOM   6715  CB   SER B 326     -35.738 -11.027  12.896  1.00 68.56      B
ATOM   6716  OG   SER B 326     -37.079 -11.473  12.895  1.00 68.85      B
ATOM   6717  C    SER B 326     -36.414  -9.644  14.804  1.00 69.80      B
ATOM   6718  O    SER B 326     -35.802  -9.785  15.861  1.00 69.86      B
ATOM   6719  N    ALA B 327     -37.731  -9.515  14.741  1.00 69.78      B
ATOM   6720  CA   ALA B 327     -38.540  -9.516  15.941  1.00 71.14      B
ATOM   6721  CB   ALA B 327     -39.148  -8.157  16.138  1.00 70.54      B
ATOM   6722  C    ALA B 327     -39.627 -10.581  15.854  1.00 71.98      B
ATOM   6723  O    ALA B 327     -40.538 -10.624  16.675  1.00 72.54      B
ATOM   6724  N    GLY B 328     -39.524 -11.446  14.853  1.00 72.74      B
ATOM   6725  CA   GLY B 328     -40.507 -12.499  14.698  1.00 73.79      B
ATOM   6726  C    GLY B 328     -41.334 -12.305  13.449  1.00 74.88      B
ATOM   6727  O    GLY B 328     -42.069 -11.325  13.350  1.00 74.53      B
ATOM   6728  N    THR B 329     -41.200 -13.238  12.506  1.00 75.86      B
ATOM   6729  CA   THR B 329     -41.921 -13.241  11.225  1.00 77.15      B
ATOM   6730  CB   THR B 329     -42.493 -14.645  10.963  1.00 76.75      B
ATOM   6731  OG1  THR B 329     -41.450 -15.614  11.122  1.00 77.44      B
ATOM   6732  CG2  THR B 329     -43.073 -14.751   9.565  1.00 75.74      B
ATOM   6733  C    THR B 329     -43.072 -12.243  11.170  1.00 78.11      B
ATOM   6734  O    THR B 329     -43.104 -11.327  10.345  1.00 78.21      B
ATOM   6735  N    GLN B 330     -44.010 -12.448  12.081  1.00 79.29      B
ATOM   6736  CA   GLN B 330     -45.202 -11.626  12.222  1.00 79.97      B
ATOM   6737  CB   GLN B 330     -45.963 -12.065  13.476  1.00 81.57      B
ATOM   6738  CG   GLN B 330     -45.938 -13.586  13.734  1.00 84.27      B
ATOM   6739  CD   GLN B 330     -44.712 -14.065  14.518  1.00 86.39      B
ATOM   6740  OE1  GLN B 330     -43.569 -13.709  14.212  1.00 87.74      B
ATOM   6741  NE2  GLN B 330     -44.952 -14.896  15.529  1.00 86.89      B
ATOM   6742  C    GLN B 330     -44.923 -10.130  12.311  1.00 78.95      B
ATOM   6743  O    GLN B 330     -45.351  -9.344  11.467  1.00 78.42      B
ATOM   6744  N    GLU B 331     -44.201  -9.756  13.358  1.00 78.80      B
ATOM   6745  CA   GLU B 331     -43.858  -8.368  13.619  1.00 78.74      B
ATOM   6746  CB   GLU B 331     -43.022  -8.275  14.899  1.00 82.43      B
ATOM   6747  CG   GLU B 331     -43.479  -9.211  16.017  1.00 87.90      B
ATOM   6748  CD   GLU B 331     -42.662  -9.052  17.306  1.00 91.82      B
ATOM   6749  OE1  GLU B 331     -41.653  -8.311  17.298  1.00 93.71      B
ATOM   6750  OE2  GLU B 331     -43.022  -9.677  18.331  1.00 93.68      B
ATOM   6751  C    GLU B 331     -43.105  -7.716  12.468  1.00 75.83      B
ATOM   6752  O    GLU B 331     -43.329  -6.547  12.160  1.00 74.76      B
ATOM   6753  N    ASP B 332     -42.213  -8.471  11.839  1.00 73.05      B
ATOM   6754  CA   ASP B 332     -41.447  -7.940  10.731  1.00 70.09      B
ATOM   6755  CB   ASP B 332     -40.505  -9.009  10.189  1.00 68.49      B
ATOM   6756  CG   ASP B 332     -39.536  -9.509  11.239  1.00 67.46      B
ATOM   6757  OD1  ASP B 332     -39.424  -8.872  12.315  1.00 66.03      B
ATOM   6758  OD2  ASP B 332     -38.878 -10.537  10.979  1.00 65.93      B
ATOM   6759  C    ASP B 332     -42.400  -7.470   9.649  1.00 68.98      B
ATOM   6760  O    ASP B 332     -42.316  -6.334   9.186  1.00 69.32      B
ATOM   6761  N    ALA B 333     -43.332  -8.338   9.274  1.00 67.91      B
ATOM   6762  CA   ALA B 333     -44.307  -8.006   8.237  1.00 66.61      B
ATOM   6763  CB   ALA B 333     -45.322  -9.142   8.073  1.00 65.97      B
ATOM   6764  C    ALA B 333     -45.026  -6.713   8.589  1.00 65.47      B
```

FIGURE 5- 90 -

```
ATOM   6765  O    ALA B 333     -45.269   -5.869    7.724  1.00 66.13      B
ATOM   6766  N    ALA B 334     -45.359   -6.564    9.865  1.00 63.03      B
ATOM   6767  CA   ALA B 334     -46.053   -5.382   10.333  1.00 61.96      B
ATOM   6768  CB   ALA B 334     -46.553   -5.603   11.751  1.00 59.82      B
ATOM   6769  C    ALA B 334     -45.126   -4.177   10.285  1.00 62.13      B
ATOM   6770  O    ALA B 334     -45.497   -3.119    9.775  1.00 62.59      B
ATOM   6771  N    ALA B 335     -43.919   -4.342   10.818  1.00 61.28      B
ATOM   6772  CA   ALA B 335     -42.942   -3.265   10.846  1.00 60.03      B
ATOM   6773  CB   ALA B 335     -41.680   -3.727   11.565  1.00 59.36      B
ATOM   6774  C    ALA B 335     -42.611   -2.808    9.428  1.00 59.94      B
ATOM   6775  O    ALA B 335     -42.536   -1.604    9.154  1.00 61.35      B
ATOM   6776  N    LEU B 336     -42.423   -3.763    8.522  1.00 57.46      B
ATOM   6777  CA   LEU B 336     -42.107   -3.418    7.147  1.00 55.67      B
ATOM   6778  CB   LEU B 336     -41.832   -4.672    6.321  1.00 53.65      B
ATOM   6779  CG   LEU B 336     -41.347   -4.404    4.894  1.00 54.41      B
ATOM   6780  CD1  LEU B 336     -40.074   -3.580    4.917  1.00 54.98      B
ATOM   6781  CD2  LEU B 336     -41.099   -5.715    4.183  1.00 55.57      B
ATOM   6782  C    LEU B 336     -43.267   -2.831    6.550  1.00 55.76      B
ATOM   6783  O    LEU B 336     -43.078   -1.813    5.648  1.00 56.53      B
ATOM   6784  N    ARG B 337     -44.471   -2.877    7.054  1.00 55.58      B
ATOM   6785  CA   ARG B 337     -45.633   -2.149    6.566  1.00 56.32      B
ATOM   6786  CB   ARG B 337     -46.940   -2.818    7.018  1.00 59.20      B
ATOM   6787  CG   ARG B 337     -47.369   -4.009    6.157  1.00 62.30      B
ATOM   6788  CD   ARG B 337     -48.879   -4.267    6.261  1.00 64.72      B
ATOM   6789  NE   ARG B 337     -49.275   -4.927    7.507  1.00 66.76      B
ATOM   6790  CZ   ARG B 337     -49.014   -6.201    7.797  1.00 67.09      B
ATOM   6791  NH1  ARG B 337     -48.354   -6.965    6.931  1.00 66.25      B
ATOM   6792  NH2  ARG B 337     -49.418   -6.713    8.952  1.00 65.39      B
ATOM   6793  C    ARG B 337     -45.550   -0.730    7.112  1.00 54.88      B
ATOM   6794  O    ARG B 337     -45.889    0.234    6.427  1.00 55.37      B
ATOM   6795  N    ALA B 338     -45.084   -0.609    8.351  1.00 53.13      B
ATOM   6796  CA   ALA B 338     -44.931    0.694    8.982  1.00 51.56      B
ATOM   6797  CB   ALA B 338     -44.455    0.532   10.422  1.00 51.54      B
ATOM   6798  C    ALA B 338     -43.901    1.474    8.179  1.00 50.30      B
ATOM   6799  O    ALA B 338     -44.142    2.606    7.773  1.00 49.57      B
ATOM   6800  N    PHE B 339     -42.754    0.846    7.946  1.00 48.51      B
ATOM   6801  CA   PHE B 339     -41.683    1.468    7.189  1.00 47.62      B
ATOM   6802  CB   PHE B 339     -40.598    0.449    6.878  1.00 46.01      B
ATOM   6803  CG   PHE B 339     -39.483    0.992    6.027  1.00 44.59      B
ATOM   6804  CD1  PHE B 339     -38.468    1.751    6.593  1.00 43.75      B
ATOM   6805  CD2  PHE B 339     -39.449    0.742    4.657  1.00 44.06      B
ATOM   6806  CE1  PHE B 339     -37.430    2.243    5.810  1.00 44.11      B
ATOM   6807  CE2  PHE B 339     -38.421    1.229    3.869  1.00 42.86      B
ATOM   6808  CZ   PHE B 339     -37.408    1.983    4.446  1.00 43.02      B
ATOM   6809  C    PHE B 339     -42.170    2.055    5.874  1.00 48.10      B
ATOM   6810  O    PHE B 339     -41.758    3.152    5.480  1.00 47.87      B
ATOM   6811  N    THR B 340     -43.045    1.318    5.196  1.00 47.15      B
ATOM   6812  CA   THR B 340     -43.552    1.755    3.906  1.00 47.55      B
ATOM   6813  CB   THR B 340     -44.270    0.611    3.189  1.00 48.63      B
ATOM   6814  OG1  THR B 340     -43.425   -0.551    3.163  1.00 46.75      B
ATOM   6815  CG2  THR B 340     -44.595    1.026    1.760  1.00 49.16      B
ATOM   6816  C    THR B 340     -44.485    2.960    3.971  1.00 47.41      B
ATOM   6817  O    THR B 340     -44.512    3.782    3.059  1.00 45.20      B
ATOM   6818  N    GLU B 341     -45.255    3.063    5.045  1.00 48.23      B
ATOM   6819  CA   GLU B 341     -46.167    4.186    5.206  1.00 48.64      B
ATOM   6820  CB   GLU B 341     -47.089    3.958    6.389  1.00 51.20      B
ATOM   6821  CG   GLU B 341     -48.041    2.808    6.241  1.00 55.87      B
ATOM   6822  CD   GLU B 341     -48.593    2.381    7.588  1.00 60.37      B
ATOM   6823  OE1  GLU B 341     -48.892    3.276    8.417  1.00 60.44      B
ATOM   6824  OE2  GLU B 341     -48.727    1.156    7.815  1.00 63.15      B
ATOM   6825  C    GLU B 341     -45.364    5.446    5.464  1.00 48.32      B
ATOM   6826  O    GLU B 341     -45.649    6.501    4.903  1.00 48.32      B
ATOM   6827  N    ALA B 342     -44.372    5.334    6.343  1.00 47.26      B
ATOM   6828  CA   ALA B 342     -43.517    6.464    6.674  1.00 46.62      B
ATOM   6829  CB   ALA B 342     -42.474    6.046    7.701  1.00 45.40      B
ATOM   6830  C    ALA B 342     -42.846    6.940    5.387  1.00 45.75      B
ATOM   6831  O    ALA B 342     -42.918    8.114    5.038  1.00 44.27      B
ATOM   6832  N    MET B 343     -42.200    6.018    4.681  1.00 45.42      B
ATOM   6833  CA   MET B 343     -41.544    6.357    3.425  1.00 44.86      B
ATOM   6834  CB   MET B 343     -40.979    5.102    2.756  1.00 42.63      B
ATOM   6835  CG   MET B 343     -39.730    4.549    3.410  1.00 41.37      B
ATOM   6836  SD   MET B 343     -38.277    5.622    3.209  1.00 39.76      B
ATOM   6837  CE   MET B 343     -37.607    4.980    1.709  1.00 39.75      B
ATOM   6838  C    MET B 343     -42.549    7.022    2.490  1.00 44.84      B
ATOM   6839  O    MET B 343     -42.216    7.961    1.764  1.00 46.09      B
ATOM   6840  N    THR B 344     -43.785    6.540    2.511  1.00 44.48      B
```

FIGURE 5- 91 -

```
ATOM   6841  CA   THR B 344     -44.809    7.110    1.650  1.00 44.53        B
ATOM   6842  CB   THR B 344     -46.073    6.254    1.642  1.00 43.66        B
ATOM   6843  OG1  THR B 344     -45.758    4.954    1.138  1.00 43.82        B
ATOM   6844  CG2  THR B 344     -47.127    6.882    0.757  1.00 43.18        B
ATOM   6845  C    THR B 344     -45.168    8.517    2.098  1.00 44.73        B
ATOM   6846  O    THR B 344     -45.489    9.381    1.277  1.00 45.47        B
ATOM   6847  N    ARG B 345     -45.115    8.743    3.403  1.00 44.23        B
ATOM   6848  CA   ARG B 345     -45.421   10.055    3.939  1.00 44.37        B
ATOM   6849  CB   ARG B 345     -45.512   10.010    5.469  1.00 45.54        B
ATOM   6850  CG   ARG B 345     -46.838    9.497    6.003  1.00 45.52        B
ATOM   6851  CD   ARG B 345     -47.009    9.864    7.465  1.00 47.56        B
ATOM   6852  NE   ARG B 345     -46.174    9.050    8.340  1.00 49.47        B
ATOM   6853  CZ   ARG B 345     -46.399    7.765    8.583  1.00 50.32        B
ATOM   6854  NH1  ARG B 345     -47.435    7.160    8.012  1.00 51.32        B
ATOM   6855  NH2  ARG B 345     -45.594    7.084    9.390  1.00 50.59        B
ATOM   6856  C    ARG B 345     -44.315   11.005    3.523  1.00 44.21        B
ATOM   6857  O    ARG B 345     -44.564   12.175    3.235  1.00 45.32        B
ATOM   6858  N    TYR B 346     -43.093   10.482    3.488  1.00 44.89        B
ATOM   6859  CA   TYR B 346     -41.914   11.261    3.126  1.00 45.25        B
ATOM   6860  CB   TYR B 346     -40.647   10.580    3.657  1.00 43.64        B
ATOM   6861  CG   TYR B 346     -40.635   10.406    5.160  1.00 42.93        B
ATOM   6862  CD1  TYR B 346     -41.370   11.256    5.979  1.00 42.72        B
ATOM   6863  CE1  TYR B 346     -41.352   11.116    7.364  1.00 44.70        B
ATOM   6864  CD2  TYR B 346     -39.873    9.403    5.765  1.00 43.31        B
ATOM   6865  CE2  TYR B 346     -39.846    9.256    7.152  1.00 42.25        B
ATOM   6866  CZ   TYR B 346     -40.590   10.117    7.945  1.00 43.59        B
ATOM   6867  OH   TYR B 346     -40.588    9.993    9.319  1.00 45.00        B
ATOM   6868  C    TYR B 346     -41.786   11.474    1.626  1.00 46.32        B
ATOM   6869  O    TYR B 346     -40.758   11.941    1.146  1.00 47.42        B
ATOM   6870  N    SER B 347     -42.840   11.135    0.895  1.00 47.40        B
ATOM   6871  CA   SER B 347     -42.864   11.287   -0.552  1.00 47.86        B
ATOM   6872  CB   SER B 347     -42.470   12.699   -0.952  1.00 46.71        B
ATOM   6873  OG   SER B 347     -42.319   12.768   -2.358  1.00 48.53        B
ATOM   6874  C    SER B 347     -41.954   10.303   -1.271  1.00 49.43        B
ATOM   6875  O    SER B 347     -41.115   10.700   -2.086  1.00 51.57        B
ATOM   6876  N    ALA B 348     -42.122    9.020   -0.969  1.00 48.73        B
ATOM   6877  CA   ALA B 348     -41.327    7.980   -1.603  1.00 48.26        B
ATOM   6878  CB   ALA B 348     -39.968    7.875   -0.943  1.00 47.75        B
ATOM   6879  C    ALA B 348     -42.055    6.648   -1.526  1.00 48.67        B
ATOM   6880  O    ALA B 348     -41.616    5.716   -0.850  1.00 48.19        B
ATOM   6881  N    PRO B 349     -43.201    6.549   -2.208  1.00 49.01        B
ATOM   6882  CD   PRO B 349     -43.873    7.585   -3.010  1.00 49.30        B
ATOM   6883  CA   PRO B 349     -43.968    5.302   -2.199  1.00 48.61        B
ATOM   6884  CB   PRO B 349     -45.266    5.687   -2.898  1.00 49.14        B
ATOM   6885  CG   PRO B 349     -44.815    6.762   -3.862  1.00 50.33        B
ATOM   6886  C    PRO B 349     -43.194    4.216   -2.937  1.00 48.67        B
ATOM   6887  O    PRO B 349     -42.321    4.500   -3.756  1.00 47.75        B
ATOM   6888  N    PRO B 350     -43.524    2.952   -2.670  1.00 49.35        B
ATOM   6889  CD   PRO B 350     -44.499    2.519   -1.650  1.00 48.81        B
ATOM   6890  CA   PRO B 350     -42.861    1.804   -3.292  1.00 49.29        B
ATOM   6891  CB   PRO B 350     -43.073    0.716   -2.260  1.00 50.21        B
ATOM   6892  CG   PRO B 350     -44.492    1.015   -1.805  1.00 49.84        B
ATOM   6893  C    PRO B 350     -43.336    1.365   -4.678  1.00 49.38        B
ATOM   6894  O    PRO B 350     -44.484    1.579   -5.060  1.00 47.79        B
ATOM   6895  N    GLY B 351     -42.421    0.755   -5.425  1.00 50.39        B
ATOM   6896  CA   GLY B 351     -42.754    0.240   -6.737  1.00 52.48        B
ATOM   6897  C    GLY B 351     -43.444   -1.064   -6.408  1.00 54.44        B
ATOM   6898  O    GLY B 351     -44.666   -1.147   -6.418  1.00 54.85        B
ATOM   6899  N    ASP B 352     -42.657   -2.084   -6.100  1.00 57.05        B
ATOM   6900  CA   ASP B 352     -43.217   -3.368   -5.702  1.00 60.80        B
ATOM   6901  CB   ASP B 352     -42.387   -4.517   -6.258  1.00 62.43        B
ATOM   6902  CG   ASP B 352     -41.886   -4.244   -7.653  1.00 65.46        B
ATOM   6903  OD1  ASP B 352     -42.714   -4.215   -8.592  1.00 65.92        B
ATOM   6904  OD2  ASP B 352     -40.660   -4.047   -7.805  1.00 66.24        B
ATOM   6905  C    ASP B 352     -43.095   -3.350   -4.180  1.00 62.41        B
ATOM   6906  O    ASP B 352     -42.071   -2.925   -3.639  1.00 62.65        B
ATOM   6907  N    PRO B 353     -44.137   -3.791   -3.467  1.00 63.25        B
ATOM   6908  CD   PRO B 353     -45.468   -4.220   -3.926  1.00 63.34        B
ATOM   6909  CA   PRO B 353     -44.061   -3.790   -2.003  1.00 63.27        B
ATOM   6910  CB   PRO B 353     -45.382   -4.432   -1.590  1.00 63.59        B
ATOM   6911  CG   PRO B 353     -46.310   -4.000   -2.689  1.00 64.35        B
ATOM   6912  C    PRO B 353     -42.853   -4.577   -1.507  1.00 62.68        B
ATOM   6913  O    PRO B 353     -42.527   -5.638   -2.042  1.00 62.92        B
ATOM   6914  N    PRO B 354     -42.165   -4.056   -0.485  1.00 61.54        B
ATOM   6915  CD   PRO B 354     -42.413   -2.793    0.227  1.00 60.98        B
ATOM   6916  CA   PRO B 354     -40.993   -4.735    0.062  1.00 61.82        B
```

FIGURE 5-92 -

```
ATOM   6917  CB   PRO B 354     -40.365   -3.665   0.942  1.00 61.12           B
ATOM   6918  CG   PRO B 354     -41.559   -2.954   1.462  1.00 61.56           B
ATOM   6919  C    PRO B 354     -41.390   -5.976   0.850  1.00 62.62           B
ATOM   6920  O    PRO B 354     -42.393   -5.980   1.564  1.00 62.55           B
ATOM   6921  N    GLN B 355     -40.593   -7.027   0.713  1.00 63.98           B
ATOM   6922  CA   GLN B 355     -40.850   -8.282   1.403  1.00 64.56           B
ATOM   6923  CB   GLN B 355     -41.117   -9.395   0.386  1.00 68.22           B
ATOM   6924  CG   GLN B 355     -42.333   -9.162  -0.502  1.00 72.29           B
ATOM   6925  CD   GLN B 355     -43.577   -8.770   0.293  1.00 75.55           B
ATOM   6926  OE1  GLN B 355     -43.832   -9.300   1.381  1.00 76.48           B
ATOM   6927  NE2  GLN B 355     -44.363   -7.845  -0.255  1.00 76.71           B
ATOM   6928  C    GLN B 355     -39.665   -8.676   2.267  1.00 62.84           B
ATOM   6929  O    GLN B 355     -38.527   -8.698   1.794  1.00 62.42           B
ATOM   6930  N    PRO B 356     -39.913   -8.990   3.549  1.00 61.44           B
ATOM   6931  CD   PRO B 356     -41.170   -8.924   4.312  1.00 60.36           B
ATOM   6932  CA   PRO B 356     -38.800   -9.379   4.415  1.00 60.86           B
ATOM   6933  CB   PRO B 356     -39.448   -9.473   5.799  1.00 59.74           B
ATOM   6934  CG   PRO B 356     -40.861   -9.793   5.497  1.00 59.80           B
ATOM   6935  C    PRO B 356     -38.160  -10.685   3.963  1.00 60.36           B
ATOM   6936  O    PRO B 356     -38.817  -11.551   3.395  1.00 60.01           B
ATOM   6937  N    GLU B 357     -36.862  -10.803   4.199  1.00 60.53           B
ATOM   6938  CA   GLU B 357     -36.114  -11.992   3.829  1.00 60.71           B
ATOM   6939  CB   GLU B 357     -35.159  -11.676   2.682  1.00 61.44           B
ATOM   6940  CG   GLU B 357     -35.848  -11.268   1.400  1.00 62.56           B
ATOM   6941  CD   GLU B 357     -36.806  -12.328   0.897  1.00 63.67           B
ATOM   6942  OE1  GLU B 357     -36.473  -13.528   0.988  1.00 64.17           B
ATOM   6943  OE2  GLU B 357     -37.888  -11.963   0.398  1.00 65.75           B
ATOM   6944  C    GLU B 357     -35.319  -12.455   5.039  1.00 60.32           B
ATOM   6945  O    GLU B 357     -35.030  -11.665   5.938  1.00 60.75           B
ATOM   6946  N    TYR B 358     -34.970  -13.735   5.067  1.00 59.52           B
ATOM   6947  CA   TYR B 358     -34.203  -14.276   6.180  1.00 59.27           B
ATOM   6948  CB   TYR B 358     -35.124  -15.108   7.061  1.00 56.71           B
ATOM   6949  CG   TYR B 358     -36.296  -14.304   7.598  1.00 54.43           B
ATOM   6950  CD1  TYR B 358     -36.170  -13.513   8.745  1.00 52.67           B
ATOM   6951  CE1  TYR B 358     -37.249  -12.759   9.229  1.00 51.10           B
ATOM   6952  CD2  TYR B 358     -37.527  -14.319   6.946  1.00 53.59           B
ATOM   6953  CE2  TYR B 358     -38.606  -13.569   7.421  1.00 52.92           B
ATOM   6954  CZ   TYR B 358     -38.461  -12.795   8.559  1.00 50.99           B
ATOM   6955  OH   TYR B 358     -39.539  -12.072   9.015  1.00 51.15           B
ATOM   6956  C    TYR B 358     -33.038  -15.096   5.639  1.00 60.08           B
ATOM   6957  O    TYR B 358     -32.375  -15.833   6.361  1.00 59.50           B
ATOM   6958  N    ASP B 359     -32.809  -14.924   4.342  1.00 61.96           B
ATOM   6959  CA   ASP B 359     -31.741  -15.564   3.585  1.00 63.20           B
ATOM   6960  CB   ASP B 359     -32.338  -16.517   2.542  1.00 65.72           B
ATOM   6961  CG   ASP B 359     -31.283  -17.175   1.656  1.00 68.36           B
ATOM   6962  OD1  ASP B 359     -30.329  -16.487   1.226  1.00 69.56           B
ATOM   6963  OD2  ASP B 359     -31.421  -18.387   1.372  1.00 69.26           B
ATOM   6964  C    ASP B 359     -31.102  -14.369   2.882  1.00 63.62           B
ATOM   6965  O    ASP B 359     -31.795  -13.611   2.200  1.00 62.55           B
ATOM   6966  N    LEU B 360     -29.797  -14.189   3.050  1.00 64.53           B
ATOM   6967  CA   LEU B 360     -29.117  -13.058   2.426  1.00 64.57           B
ATOM   6968  CB   LEU B 360     -27.695  -12.931   2.975  1.00 63.76           B
ATOM   6969  CG   LEU B 360     -26.922  -11.664   2.612  1.00 62.99           B
ATOM   6970  CD1  LEU B 360     -27.681  -10.459   3.126  1.00 63.70           B
ATOM   6971  CD2  LEU B 360     -25.526  -11.707   3.217  1.00 62.13           B
ATOM   6972  C    LEU B 360     -29.086  -13.153   0.899  1.00 65.41           B
ATOM   6973  O    LEU B 360     -29.127  -12.130   0.209  1.00 65.97           B
ATOM   6974  N    GLU B 361     -29.018  -14.374   0.371  1.00 65.66           B
ATOM   6975  CA   GLU B 361     -28.993  -14.572  -1.078  1.00 66.51           B
ATOM   6976  CB   GLU B 361     -28.643  -16.032  -1.418  1.00 67.73           B
ATOM   6977  CG   GLU B 361     -27.249  -16.477  -0.971  1.00 69.72           B
ATOM   6978  CD   GLU B 361     -26.883  -17.878  -1.445  1.00 70.10           B
ATOM   6979  OE1  GLU B 361     -26.766  -18.091  -2.672  1.00 69.79           B
ATOM   6980  OE2  GLU B 361     -26.710  -18.767  -0.585  1.00 70.78           B
ATOM   6981  C    GLU B 361     -30.348  -14.212  -1.693  1.00 66.20           B
ATOM   6982  O    GLU B 361     -30.456  -13.973  -2.899  1.00 65.46           B
ATOM   6983  N    LEU B 362     -31.374  -14.172  -0.847  1.00 66.51           B
ATOM   6984  CA   LEU B 362     -32.736  -13.860  -1.275  1.00 67.05           B
ATOM   6985  CB   LEU B 362     -33.745  -14.583  -0.382  1.00 66.82           B
ATOM   6986  CG   LEU B 362     -34.060  -16.027  -0.770  1.00 67.18           B
ATOM   6987  CD1  LEU B 362     -34.896  -16.673   0.325  1.00 66.95           B
ATOM   6988  CD2  LEU B 362     -34.793  -16.049  -2.117  1.00 66.26           B
ATOM   6989  C    LEU B 362     -33.043  -12.373  -1.272  1.00 67.38           B
ATOM   6990  O    LEU B 362     -34.169  -11.962  -0.999  1.00 67.26           B
ATOM   6991  N    ILE B 363     -32.036  -11.567  -1.568  1.00 67.94           B
ATOM   6992  CA   ILE B 363     -32.219  -10.131  -1.612  1.00 67.59           B
```

FIGURE 5- 93 -

```
ATOM   6993  CB   ILE B 363     -31.617   -9.449   -0.369  1.00 66.52      B
ATOM   6994  CG2  ILE B 363     -31.747   -7.940   -0.486  1.00 65.72      B
ATOM   6995  CG1  ILE B 363     -32.337   -9.934    0.889  1.00 66.50      B
ATOM   6996  CD1  ILE B 363     -31.865   -9.258    2.168  1.00 66.26      B
ATOM   6997  C    ILE B 363     -31.539   -9.595   -2.861  1.00 68.19      B
ATOM   6998  O    ILE B 363     -30.412   -9.976   -3.180  1.00 68.64      B
ATOM   6999  N    THR B 364     -32.237   -8.726   -3.581  1.00 69.17      B
ATOM   7000  CA   THR B 364     -31.670   -8.138   -4.779  1.00 70.03      B
ATOM   7001  CB   THR B 364     -32.488   -8.485   -6.012  1.00 68.67      B
ATOM   7002  OG1  THR B 364     -32.803   -9.882   -5.991  1.00 67.21      B
ATOM   7003  CG2  THR B 364     -31.682   -8.174   -7.263  1.00 68.72      B
ATOM   7004  C    THR B 364     -31.573   -6.621   -4.645  1.00 71.42      B
ATOM   7005  O    THR B 364     -32.577   -5.906   -4.635  1.00 70.58      B
ATOM   7006  N    SER B 365     -30.339   -6.151   -4.523  1.00 73.26      B
ATOM   7007  CA   SER B 365     -30.044   -4.740   -4.377  1.00 75.54      B
ATOM   7008  CB   SER B 365     -29.382   -4.486   -3.021  1.00 76.93      B
ATOM   7009  OG   SER B 365     -28.897   -3.157   -2.925  1.00 78.93      B
ATOM   7010  C    SER B 365     -29.103   -4.336   -5.496  1.00 76.48      B
ATOM   7011  O    SER B 365     -28.131   -5.039   -5.786  1.00 76.63      B
ATOM   7012  N    CYS B 366     -29.395   -3.195   -6.115  1.00 77.53      B
ATOM   7013  CA   CYS B 366     -28.595   -2.682   -7.223  1.00 77.75      B
ATOM   7014  CB   CYS B 366     -27.177   -2.341   -6.755  1.00 77.66      B
ATOM   7015  SG   CYS B 366     -27.077   -0.806   -5.804  1.00 79.00      B
ATOM   7016  C    CYS B 366     -28.549   -3.722   -8.330  1.00 77.63      B
ATOM   7017  O    CYS B 366     -27.512   -3.932   -8.964  1.00 77.31      B
ATOM   7018  N    SER B 367     -29.687   -4.374   -8.553  1.00 77.18      B
ATOM   7019  CA   SER B 367     -29.789   -5.398   -9.579  1.00 77.12      B
ATOM   7020  CB   SER B 367     -29.449   -4.798  -10.948  1.00 78.15      B
ATOM   7021  OG   SER B 367     -30.108   -3.556  -11.149  1.00 78.29      B
ATOM   7022  C    SER B 367     -28.809   -6.525   -9.255  1.00 76.56      B
ATOM   7023  O    SER B 367     -28.269   -7.162  -10.157  1.00 76.69      B
ATOM   7024  N    SER B 368     -28.576   -6.757   -7.965  1.00 75.22      B
ATOM   7025  CA   SER B 368     -27.654   -7.797   -7.523  1.00 73.84      B
ATOM   7026  CB   SER B 368     -26.287   -7.204   -7.184  1.00 72.94      B
ATOM   7027  OG   SER B 368     -25.476   -7.099   -8.331  1.00 73.86      B
ATOM   7028  C    SER B 368     -28.146   -8.545   -6.303  1.00 73.85      B
ATOM   7029  O    SER B 368     -28.896   -8.018   -5.489  1.00 74.42      B
ATOM   7030  N    ASN B 369     -27.701   -9.786   -6.187  1.00 73.49      B
ATOM   7031  CA   ASN B 369     -28.044  -10.629   -5.057  1.00 72.36      B
ATOM   7032  CB   ASN B 369     -29.078  -11.690   -5.449  1.00 71.93      B
ATOM   7033  CG   ASN B 369     -28.518  -12.722   -6.414  1.00 71.80      B
ATOM   7034  OD1  ASN B 369     -28.405  -12.477   -7.611  1.00 70.84      B
ATOM   7035  ND2  ASN B 369     -28.149  -13.881   -5.886  1.00 72.95      B
ATOM   7036  C    ASN B 369     -26.739  -11.310   -4.681  1.00 71.80      B
ATOM   7037  O    ASN B 369     -25.828  -11.414   -5.507  1.00 71.10      B
ATOM   7038  N    VAL B 370     -26.641  -11.754   -3.436  1.00 70.96      B
ATOM   7039  CA   VAL B 370     -25.444  -12.442   -2.987  1.00 69.88      B
ATOM   7040  CB   VAL B 370     -25.227  -12.262   -1.470  1.00 69.48      B
ATOM   7041  CG1  VAL B 370     -24.026  -13.072   -1.013  1.00 68.06      B
ATOM   7042  CG2  VAL B 370     -25.029  -10.800   -1.150  1.00 69.01      B
ATOM   7043  C    VAL B 370     -25.630  -13.923   -3.280  1.00 69.65      B
ATOM   7044  O    VAL B 370     -26.751  -14.430   -3.255  1.00 69.41      B
ATOM   7045  N    SER B 371     -24.534  -14.606   -3.580  1.00 69.39      B
ATOM   7046  CA   SER B 371     -24.574  -16.037   -3.838  1.00 69.57      B
ATOM   7047  CB   SER B 371     -24.836  -16.332   -5.320  1.00 70.41      B
ATOM   7048  OG   SER B 371     -25.075  -17.719   -5.528  1.00 70.15      B
ATOM   7049  C    SER B 371     -23.222  -16.585   -3.427  1.00 69.34      B
ATOM   7050  O    SER B 371     -22.266  -15.831   -3.260  1.00 68.88      B
ATOM   7051  N    VAL B 372     -23.140  -17.898   -3.260  1.00 69.63      B
ATOM   7052  CA   VAL B 372     -21.891  -18.520   -2.850  1.00 68.95      B
ATOM   7053  CB   VAL B 372     -22.117  -19.445   -1.637  1.00 67.07      B
ATOM   7054  CG1  VAL B 372     -20.805  -19.687   -0.922  1.00 66.05      B
ATOM   7055  CG2  VAL B 372     -23.159  -18.837   -0.701  1.00 66.38      B
ATOM   7056  C    VAL B 372     -21.279  -19.334   -3.984  1.00 70.07      B
ATOM   7057  O    VAL B 372     -21.879  -19.493   -5.052  1.00 70.45      B
ATOM   7058  N    ALA B 373     -20.075  -19.834   -3.734  1.00 71.09      B
ATOM   7059  CA   ALA B 373     -19.327  -20.657   -4.675  1.00 72.28      B
ATOM   7060  CB   ALA B 373     -18.809  -19.815   -5.836  1.00 71.73      B
ATOM   7061  C    ALA B 373     -18.167  -21.202   -3.849  1.00 74.00      B
ATOM   7062  O    ALA B 373     -18.151  -21.025   -2.626  1.00 74.39      B
ATOM   7063  N    HIS B 374     -17.199  -21.859   -4.488  1.00 75.04      B
ATOM   7064  CA   HIS B 374     -16.065  -22.409   -3.745  1.00 75.74      B
ATOM   7065  CB   HIS B 374     -16.278  -23.908   -3.508  1.00 74.40      B
ATOM   7066  CG   HIS B 374     -17.297  -24.213   -2.455  1.00 73.36      B
ATOM   7067  CD2  HIS B 374     -18.536  -24.747   -2.534  1.00 73.08      B
ATOM   7068  ND1  HIS B 374     -17.099  -23.906   -1.122  1.00 73.77      B
```

FIGURE 5- 94 -

```
ATCM   7069  CE1  HIS B 374    -18.171 -24.242  -0.431  1.00 72.72      B
ATCM   7070  NE2  HIS B 374    -19.061 -24.755  -1.263  1.00 72.56      B
ATCM   7071  C    HIS B 374    -14.728 -22.177  -4.426  1.00 77.20      B
ATCM   7072  O    HIS B 374    -14.628 -22.237  -5.651  1.00 77.29      B
ATCM   7073  N    ASP B 375    -13.702 -21.896  -3.626  1.00 79.85      B
ATCM   7074  CA   ASP B 375    -12.360 -21.673  -4.161  1.00 83.02      B
ATCM   7075  CB   ASP B 375    -11.572 -20.684  -3.285  1.00 84.25      B
ATCM   7076  CG   ASP B 375    -11.297 -21.222  -1.885  1.00 85.62      B
ATCM   7077  OD1  ASP B 375    -12.268 -21.582  -1.189  1.00 85.10      B
ATCM   7078  OD2  ASP B 375    -10.112 -21.286  -1.484  1.00 86.45      B
ATCM   7079  C    ASP B 375    -11.656 -23.022  -4.199  1.00 84.48      B
ATCM   7080  O    ASP B 375    -12.236 -24.029  -3.768  1.00 84.70      B
ATCM   7081  N    ALA B 376    -10.421 -23.049  -4.702  1.00 84.77      B
ATCM   7082  CA   ALA B 376     -9.686 -24.303  -4.793  1.00 85.31      B
ATCM   7083  CB   ALA B 376     -8.224 -24.043  -5.080  1.00 84.98      B
ATCM   7084  C    ALA B 376     -9.842 -25.076  -3.500  1.00 85.70      B
ATCM   7085  O    ALA B 376    -10.660 -25.990  -3.426  1.00 85.66      B
ATCM   7086  N    SER B 377     -9.068 -24.698  -2.486  1.00 85.85      B
ATCM   7087  CA   SER B 377     -9.131 -25.340  -1.178  1.00 85.80      B
ATCM   7088  CB   SER B 377     -8.856 -24.328  -0.076  1.00 86.08      B
ATCM   7089  OG   SER B 377     -7.836 -23.438  -0.456  1.00 87.27      B
ATCM   7090  C    SER B 377    -10.532 -25.875  -0.976  1.00 85.62      B
ATCM   7091  O    SER B 377    -10.728 -27.057  -0.709  1.00 86.15      B
ATCM   7092  N    GLY B 378    -11.506 -24.982  -1.109  1.00 84.53      B
ATCM   7093  CA   GLY B 378    -12.887 -25.381  -0.943  1.00 83.77      B
ATCM   7094  C    GLY B 378    -13.695 -24.583   0.064  1.00 83.39      B
ATCM   7095  O    GLY B 378    -14.724 -25.068   0.532  1.00 82.90      B
ATCM   7096  N    LYS B 379    -13.255 -23.376   0.419  1.00 82.70      B
ATCM   7097  CA   LYS B 379    -14.038 -22.591   1.365  1.00 81.80      B
ATCM   7098  CB   LYS B 379    -13.143 -21.642   2.184  1.00 81.89      B
ATCM   7099  CG   LYS B 379    -13.879 -20.949   3.352  1.00 82.38      B
ATCM   7100  CD   LYS B 379    -14.752 -21.940   4.139  1.00 82.96      B
ATCM   7101  CE   LYS B 379    -15.723 -21.254   5.111  1.00 83.84      B
ATCM   7102  NZ   LYS B 379    -16.692 -22.240   5.697  1.00 83.94      B
ATCM   7103  C    LYS B 379    -15.112 -21.804   0.604  1.00 80.86      B
ATCM   7104  O    LYS B 379    -14.926 -21.427  -0.553  1.00 79.72      B
ATCM   7105  N    ARG B 380    -16.248 -21.586   1.250  1.00 80.22      B
ATCM   7106  CA   ARG B 380    -17.340 -20.846   0.642  1.00 78.91      B
ATCM   7107  CB   ARG B 380    -18.493 -20.765   1.644  1.00 80.97      B
ATCM   7108  CG   ARG B 380    -18.831 -22.134   2.213  1.00 83.31      B
ATCM   7109  CD   ARG B 380    -19.479 -22.066   3.576  1.00 86.15      B
ATCM   7110  NE   ARG B 380    -20.763 -21.379   3.545  1.00 88.92      B
ATCM   7111  CZ   ARG B 380    -21.610 -21.343   4.570  1.00 90.41      B
ATCM   7112  NH1  ARG B 380    -21.311 -21.961   5.708  1.00 90.32      B
ATCM   7113  NH2  ARG B 380    -22.754 -20.677   4.462  1.00 90.74      B
ATCM   7114  C    ARG B 380    -16.843 -19.458   0.268  1.00 76.95      B
ATCM   7115  O    ARG B 380    -16.113 -18.827   1.030  1.00 77.01      B
ATCM   7116  N    VAL B 381    -17.202 -19.000  -0.923  1.00 74.60      B
ATCM   7117  CA   VAL B 381    -16.805 -17.671  -1.355  1.00 72.07      B
ATCM   7118  CB   VAL B 381    -15.846 -17.701  -2.570  1.00 72.29      B
ATCM   7119  CG1  VAL B 381    -15.535 -16.274  -3.034  1.00 69.81      B
ATCM   7120  CG2  VAL B 381    -14.558 -18.415  -2.194  1.00 73.41      B
ATCM   7121  C    VAL B 381    -18.062 -16.918  -1.736  1.00 70.29      B
ATCM   7122  O    VAL B 381    -18.790 -17.307  -2.650  1.00 70.35      B
ATCM   7123  N    TYR B 382    -18.332 -15.854  -1.000  1.00 66.01      B
ATCM   7124  CA   TYR B 382    -19.488 -15.036  -1.275  1.00 64.71      B
ATCM   7125  CB   TYR B 382    -19.916 -14.321  -0.008  1.00 64.51      B
ATCM   7126  CG   TYR B 382    -20.451 -15.264   1.037  1.00 64.55      B
ATCM   7127  CD1  TYR B 382    -21.724 -15.804   0.919  1.00 64.57      B
ATCM   7128  CE1  TYR B 382    -22.225 -16.677   1.868  1.00 66.07      B
ATCM   7129  CD2  TYR B 382    -19.682 -15.624   2.136  1.00 64.17      B
ATCM   7130  CE2  TYR B 382    -20.170 -16.498   3.093  1.00 66.06      B
ATCM   7131  CZ   TYR B 382    -21.445 -17.024   2.956  1.00 66.57      B
ATCM   7132  OH   TYR B 382    -21.943 -17.893   3.909  1.00 66.80      B
ATCM   7133  C    TYR B 382    -19.058 -14.048  -2.336  1.00 63.45      B
ATCM   7134  O    TYR B 382    -17.956 -13.506  -2.287  1.00 62.81      B
ATCM   7135  N    TYR B 383    -19.921 -13.844  -3.318  1.00 62.78      B
ATCM   7136  CA   TYR B 383    -19.634 -12.927  -4.404  1.00 61.72      B
ATCM   7137  CB   TYR B 383    -18.962 -13.675  -5.568  1.00 62.86      B
ATCM   7138  CG   TYR B 383    -19.820 -14.744  -6.221  1.00 63.98      B
ATCM   7139  CD1  TYR B 383    -20.414 -15.755  -5.460  1.00 63.75      B
ATCM   7140  CE1  TYR B 383    -21.238 -16.715  -6.047  1.00 63.71      B
ATCM   7141  CD2  TYR B 383    -20.065 -14.725  -7.598  1.00 64.02      B
ATCM   7142  CE2  TYR B 383    -20.889 -15.685  -8.199  1.00 64.78      B
ATCM   7143  CZ   TYR B 383    -21.474 -16.675  -7.414  1.00 64.14      B
ATCM   7144  OH   TYR B 383    -22.308 -17.610  -7.986  1.00 62.73      B
```

FIGURE 5- 95 -

```
ATOM   7145  C    TYR B 383     -20.951 -12.311  -4.842  1.00 61.13      B
ATOM   7146  O    TYR B 383     -22.024 -12.845  -4.552  1.00 60.54      B
ATOM   7147  N    LEU B 384     -20.873 -11.185  -5.537  1.00 60.05      B
ATOM   7148  CA   LEU B 384     -22.075 -10.507  -5.987  1.00 58.83      B
ATOM   7149  CB   LEU B 384     -21.835  -8.998  -5.874  1.00 59.99      B
ATOM   7150  CG   LEU B 384     -23.118  -8.249  -5.383  1.00 61.01      B
ATOM   7151  CD1  LEU B 384     -23.363  -8.597  -3.927  1.00 60.30      B
ATOM   7152  CD2  LEU B 384     -22.912  -6.755  -5.548  1.00 63.19      B
ATOM   7153  C    LEU B 384     -22.405 -10.883  -7.423  1.00 57.86      B
ATOM   7154  O    LEU B 384     -21.526 -10.872  -8.284  1.00 56.09      B
ATOM   7155  N    THR B 385     -23.676 -11.202  -7.677  1.00 57.28      B
ATOM   7156  CA   THR B 385     -24.133 -11.598  -9.014  1.00 56.46      B
ATOM   7157  CB   THR B 385     -24.199 -13.149  -9.138  1.00 55.01      B
ATOM   7158  OG1  THR B 385     -24.540 -13.518 -10.480  1.00 52.35      B
ATOM   7159  CG2  THR B 385     -25.248 -13.713  -8.188  1.00 53.66      B
ATOM   7160  C    THR B 385     -25.514 -11.025  -9.358  1.00 56.41      B
ATOM   7161  O    THR B 385     -26.072 -10.225  -8.603  1.00 55.54      B
ATOM   7162  N    ARG B 386     -26.056 -11.444 -10.502  1.00 56.42      B
ATOM   7163  CA   ARG B 386     -27.374 -10.992 -10.949  1.00 57.50      B
ATOM   7164  CB   ARG B 386     -27.339  -9.503 -11.279  1.00 57.49      B
ATOM   7165  CG   ARG B 386     -26.273  -9.111 -12.287  1.00 57.56      B
ATOM   7166  CD   ARG B 386     -26.570  -7.748 -12.874  1.00 58.19      B
ATOM   7167  NE   ARG B 386     -27.620  -7.818 -13.884  1.00 58.96      B
ATOM   7168  CZ   ARG B 386     -28.299  -6.769 -14.334  1.00 59.81      B
ATOM   7169  NH1  ARG B 386     -28.049  -5.556 -13.860  1.00 60.33      B
ATOM   7170  NH2  ARG B 386     -29.224  -6.932 -15.268  1.00 60.95      B
ATOM   7171  C    ARG B 386     -27.886 -11.741 -12.177  1.00 58.05      B
ATOM   7172  O    ARG B 386     -27.143 -12.479 -12.820  1.00 58.74      B
ATOM   7173  N    ASP B 387     -29.162 -11.553 -12.498  1.00 58.48      B
ATOM   7174  CA   ASP B 387     -29.726 -12.195 -13.672  1.00 58.89      B
ATOM   7175  CB   ASP B 387     -31.220 -11.917 -13.794  1.00 59.97      B
ATOM   7176  CG   ASP B 387     -31.857 -12.682 -14.942  1.00 61.58      B
ATOM   7177  OD1  ASP B 387     -31.378 -12.544 -16.089  1.00 61.31      B
ATOM   7178  OD2  ASP B 387     -32.835 -13.424 -14.695  1.00 62.24      B
ATOM   7179  C    ASP B 387     -28.994 -11.565 -14.846  1.00 58.89      B
ATOM   7180  O    ASP B 387     -29.170 -10.387 -15.142  1.00 58.86      B
ATOM   7181  N    PRO B 388     -28.173 -12.355 -15.540  1.00 58.67      B
ATOM   7182  CD   PRO B 388     -28.101 -13.813 -15.335  1.00 59.74      B
ATOM   7183  CA   PRO B 388     -27.362 -11.958 -16.693  1.00 58.74      B
ATOM   7184  CB   PRO B 388     -26.558 -13.218 -16.984  1.00 58.76      B
ATOM   7185  CG   PRO B 388     -27.532 -14.293 -16.653  1.00 59.53      B
ATOM   7186  C    PRO B 388     -28.073 -11.451 -17.940  1.00 59.12      B
ATOM   7187  O    PRO B 388     -27.421 -10.925 -18.849  1.00 59.74      B
ATOM   7188  N    THR B 389     -29.391 -11.595 -17.998  1.00 58.30      B
ATOM   7189  CA   THR B 389     -30.120 -11.166 -19.188  1.00 57.90      B
ATOM   7190  CB   THR B 389     -31.652 -11.289 -18.983  1.00 57.96      B
ATOM   7191  OG1  THR B 389     -31.990 -12.660 -18.724  1.00 58.67      B
ATOM   7192  CG2  THR B 389     -32.409 -10.832 -20.231  1.00 55.48      B
ATOM   7193  C    THR B 389     -29.774  -9.761 -19.693  1.00 57.92      B
ATOM   7194  O    THR B 389     -29.109  -9.619 -20.726  1.00 56.84      B
ATOM   7195  N    THR B 390     -30.207  -8.726 -18.980  1.00 57.32      B
ATOM   7196  CA   THR B 390     -29.928  -7.372 -19.435  1.00 58.15      B
ATOM   7197  CB   THR B 390     -30.328  -6.334 -18.379  1.00 58.29      B
ATOM   7198  OG1  THR B 390     -31.707  -6.517 -18.031  1.00 56.50      B
ATOM   7199  CG2  THR B 390     -30.143  -4.930 -18.930  1.00 57.12      B
ATOM   7200  C    THR B 390     -28.454  -7.198 -19.811  1.00 59.08      B
ATOM   7201  O    THR B 390     -28.131  -6.644 -20.858  1.00 58.83      B
ATOM   7202  N    PRO B 391     -27.537  -7.673 -18.962  1.00 60.12      B
ATOM   7203  CD   PRO B 391     -27.676  -8.203 -17.594  1.00 60.23      B
ATOM   7204  CA   PRO B 391     -26.127  -7.517 -19.323  1.00 61.25      B
ATOM   7205  CB   PRO B 391     -25.410  -8.265 -18.202  1.00 60.63      B
ATOM   7206  CG   PRO B 391     -26.291  -7.991 -17.024  1.00 60.48      B
ATOM   7207  C    PRO B 391     -25.819  -8.100 -20.712  1.00 62.47      B
ATOM   7208  O    PRO B 391     -25.436  -7.364 -21.642  1.00 63.06      B
ATOM   7209  N    LEU B 392     -25.947  -9.420 -20.843  1.00 63.40      B
ATOM   7210  CA   LEU B 392     -25.670 -10.125 -22.096  1.00 63.55      B
ATOM   7211  CB   LEU B 392     -26.077 -11.596 -21.977  1.00 63.42      B
ATOM   7212  CG   LEU B 392     -25.423 -12.426 -20.871  1.00 63.31      B
ATOM   7213  CD1  LEU B 392     -25.879 -13.868 -20.997  1.00 62.99      B
ATOM   7214  CD2  LEU B 392     -23.910 -12.341 -20.980  1.00 63.46      B
ATOM   7215  C    LEU B 392     -26.346  -9.528 -23.322  1.00 64.15      B
ATOM   7216  O    LEU B 392     -25.760  -9.497 -24.404  1.00 64.37      B
ATOM   7217  N    ALA B 393     -27.585  -9.076 -23.153  1.00 65.01      B
ATOM   7218  CA   ALA B 393     -28.343  -8.475 -24.246  1.00 65.58      B
ATOM   7219  CB   ALA B 393     -29.739  -8.087 -23.766  1.00 65.67      B
ATOM   7220  C    ALA B 393     -27.622  -7.247 -24.795  1.00 65.93      B
```

FIGURE 5- 96 -

```
ATOM   7221  O    ALA B 393     -27.442   -7.115  -26.001  1.00 65.99           B
ATOM   7222  N    ARG B 394     -27.212   -6.348  -23.907  1.00 66.53           B
ATOM   7223  CA   ARG B 394     -26.514   -5.142  -24.331  1.00 66.94           B
ATOM   7224  CB   ARG B 394     -26.349   -4.181  -23.149  1.00 66.35           B
ATOM   7225  CG   ARG B 394     -27.665   -3.675  -22.590  1.00 66.24           B
ATOM   7226  CD   ARG B 394     -27.466   -2.686  -21.454  1.00 67.17           B
ATOM   7227  NE   ARG B 394     -28.740   -2.295  -20.851  1.00 68.09           B
ATOM   7228  CZ   ARG B 394     -28.856   -1.449  -19.831  1.00 69.19           B
ATOM   7229  NH1  ARG B 394     -27.772   -0.898  -19.297  1.00 70.00           B
ATOM   7230  NH2  ARG B 394     -30.055   -1.154  -19.341  1.00 68.25           B
ATOM   7231  C    ARG B 394     -25.155   -5.498  -24.916  1.00 67.35           B
ATOM   7232  O    ARG B 394     -24.721   -4.907  -25.902  1.00 66.39           B
ATOM   7233  N    ALA B 395     -24.491   -6.473  -24.306  1.00 69.07           B
ATOM   7234  CA   ALA B 395     -23.182   -6.903  -24.771  1.00 71.58           B
ATOM   7235  CB   ALA B 395     -22.723   -8.115  -23.979  1.00 71.13           B
ATOM   7236  C    ALA B 395     -23.265   -7.245  -26.250  1.00 73.28           B
ATOM   7237  O    ALA B 395     -22.386   -6.892  -27.037  1.00 73.72           B
ATOM   7238  N    ALA B 396     -24.341   -7.932  -26.620  1.00 75.53           B
ATOM   7239  CA   ALA B 396     -24.570   -8.340  -28.007  1.00 77.92           B
ATOM   7240  CB   ALA B 396     -25.770   -9.265  -28.093  1.00 77.18           B
ATOM   7241  C    ALA B 396     -24.797   -7.131  -28.902  1.00 80.07           B
ATOM   7242  O    ALA B 396     -24.282   -7.061  -30.023  1.00 81.15           B
ATOM   7243  N    TRP B 397     -25.576   -6.180  -28.399  1.00 82.06           B
ATOM   7244  CA   TRP B 397     -25.902   -4.967  -29.131  1.00 83.47           B
ATOM   7245  CB   TRP B 397     -26.785   -4.087  -28.251  1.00 83.88           B
ATOM   7246  CG   TRP B 397     -27.346   -2.917  -28.974  1.00 85.99           B
ATOM   7247  CD2  TRP B 397     -28.591   -2.867  -29.689  1.00 86.57           B
ATOM   7248  CE2  TRP B 397     -28.688   -1.580  -30.264  1.00 86.58           B
ATOM   7249  CE3  TRP B 397     -29.629   -3.790  -29.910  1.00 86.01           B
ATOM   7250  CD1  TRP B 397     -26.761   -1.693  -29.134  1.00 86.09           B
ATOM   7251  NE1  TRP B 397     -27.561   -0.884  -29.907  1.00 87.01           B
ATOM   7252  CZ2  TRP B 397     -29.787   -1.134  -31.037  1.00 86.36           B
ATOM   7253  CZ3  TRP B 397     -30.725   -3.396  -30.682  1.00 85.51           B
ATOM   7254  CH2  TRP B 397     -30.790   -2.104  -31.239  1.00 85.90           B
ATOM   7255  C    TRP B 397     -24.677   -4.179  -29.592  1.00 84.70           B
ATOM   7256  O    TRP B 397     -24.621   -3.693  -30.721  1.00 84.36           B
ATOM   7257  N    GLU B 398     -23.697   -4.060  -28.706  1.00 86.32           B
ATOM   7258  CA   GLU B 398     -22.473   -3.321  -28.983  1.00 87.93           B
ATOM   7259  CB   GLU B 398     -21.742   -3.099  -27.673  1.00 87.39           B
ATOM   7260  CG   GLU B 398     -22.692   -2.669  -26.584  1.00 88.21           B
ATOM   7261  CD   GLU B 398     -22.076   -2.733  -25.216  1.00 89.25           B
ATOM   7262  OE1  GLU B 398     -21.461   -3.773  -24.894  1.00 90.26           B
ATOM   7263  OE2  GLU B 398     -22.214   -1.750  -24.459  1.00 88.66           B
ATOM   7264  C    GLU B 398     -21.572   -4.041  -29.972  1.00 89.67           B
ATOM   7265  O    GLU B 398     -20.694   -3.433  -30.587  1.00 90.07           B
ATOM   7266  N    THR B 399     -21.790   -5.341  -30.121  1.00 91.44           B
ATOM   7267  CA   THR B 399     -21.000   -6.142  -31.043  1.00 93.46           B
ATOM   7268  CB   THR B 399     -21.109   -7.635  -30.707  1.00 93.22           B
ATOM   7269  OG1  THR B 399     -20.534   -7.876  -29.417  1.00 93.89           B
ATOM   7270  CG2  THR B 399     -20.388   -8.473  -31.755  1.00 93.21           B
ATOM   7271  C    THR B 399     -21.516   -5.930  -32.452  1.00 94.86           B
ATOM   7272  O    THR B 399     -20.742   -5.763  -33.391  1.00 95.54           B
ATOM   7273  N    ALA B 400     -22.839   -5.924  -32.582  1.00 96.60           B
ATOM   7274  CA   ALA B 400     -23.482   -5.750  -33.879  1.00 98.29           B
ATOM   7275  CB   ALA B 400     -24.890   -6.354  -33.851  1.00 97.69           B
ATOM   7276  C    ALA B 400     -23.531   -4.296  -34.349  1.00 99.64           B
ATOM   7277  O    ALA B 400     -23.518   -4.037  -35.556  1.00 99.76           B
ATOM   7278  N    ARG B 401     -23.596   -3.351  -33.410  1.00101.32           B
ATOM   7279  CA   ARG B 401     -23.611   -1.942  -33.796  1.00103.68           B
ATOM   7280  CB   ARG B 401     -24.825   -1.199  -33.220  1.00103.96           B
ATOM   7281  CG   ARG B 401     -25.524   -0.342  -34.287  1.00104.49           B
ATOM   7282  CD   ARG B 401     -25.413   -1.047  -35.639  1.00105.47           B
ATOM   7283  NE   ARG B 401     -26.613   -0.928  -36.455  1.00106.20           B
ATOM   7284  CZ   ARG B 401     -26.892   -1.730  -37.477  1.00106.27           B
ATOM   7285  NH1  ARG B 401     -26.055   -2.709  -37.803  1.00106.62           B
ATOM   7286  NH2  ARG B 401     -28.007   -1.558  -38.174  1.00106.55           B
ATOM   7287  C    ARG B 401     -22.306   -1.210  -33.460  1.00105.27           B
ATOM   7288  O    ARG B 401     -21.258   -1.859  -33.276  1.00104.94           B
ATOM   7289  N    HIS B 402     -22.342    0.122  -33.367  1.00107.33           B
ATOM   7290  CA   HIS B 402     -21.088    0.854  -33.140  1.00109.33           B
ATOM   7291  CB   HIS B 402     -21.005    2.166  -33.987  1.00110.80           B
ATOM   7292  CG   HIS B 402     -22.318    2.712  -34.499  1.00112.82           B
ATOM   7293  CD2  HIS B 402     -23.088    3.732  -34.065  1.00113.05           B
ATOM   7294  ND1  HIS B 402     -22.874    2.298  -35.698  1.00113.95           B
ATOM   7295  CE1  HIS B 402     -23.921    3.052  -35.977  1.00113.87           B
ATOM   7296  NE2  HIS B 402     -24.080    3.933  -35.009  1.00113.47           B
```

FIGURE 5-97-

```
ATOM   7297  C    HIS B 402     -20.511   1.230 -31.781  1.00109.75      B
ATOM   7298  O    HIS B 402     -21.072   0.991 -30.720  1.00109.24      B
ATOM   7299  N    THR B 403     -19.309   1.787 -31.891  1.00110.80      B
ATOM   7300  CA   THR B 403     -18.522   2.375 -30.818  1.00111.38      B
ATOM   7301  CB   THR B 403     -18.406   3.827 -31.216  1.00111.71      B
ATOM   7302  OG1  THR B 403     -19.720   4.343 -31.485  1.00112.18      B
ATOM   7303  CG2  THR B 403     -17.620   3.905 -32.526  1.00111.60      B
ATOM   7304  C    THR B 403     -19.040   2.112 -29.375  1.00111.33      B
ATOM   7305  O    THR B 403     -19.227   0.947 -29.042  1.00111.74      B
ATOM   7306  N    PRO B 404     -19.305   3.144 -28.519  1.00111.00      B
ATOM   7307  CD   PRO B 404     -19.759   4.536 -28.738  1.00110.68      B
ATOM   7308  CA   PRO B 404     -19.771   2.733 -27.191  1.00110.61      B
ATOM   7309  CB   PRO B 404     -21.171   3.298 -27.162  1.00110.72      B
ATOM   7310  CG   PRO B 404     -20.848   4.735 -27.625  1.00110.64      B
ATOM   7311  C    PRO B 404     -19.628   1.268 -26.809  1.00110.33      B
ATOM   7312  O    PRO B 404     -20.529   0.434 -26.941  1.00110.48      B
ATOM   7313  N    ILE B 405     -18.405   1.023 -26.357  1.00109.55      B
ATOM   7314  CA   ILE B 405     -17.851  -0.245 -25.919  1.00108.14      B
ATOM   7315  CB   ILE B 405     -16.327  -0.215 -26.198  1.00109.22      B
ATOM   7316  CG2  ILE B 405     -15.669  -1.471 -25.640  1.00109.47      B
ATOM   7317  CG1  ILE B 405     -16.084   0.077 -27.693  1.00110.21      B
ATOM   7318  CD1  ILE B 405     -16.573  -1.013 -28.693  1.00110.34      B
ATOM   7319  C    ILE B 405     -18.118  -0.422 -24.414  1.00106.36      B
ATOM   7320  O    ILE B 405     -17.415  -1.156 -23.710  1.00105.70      B
ATOM   7321  N    ASN B 406     -19.143   0.268 -23.934  1.00104.60      B
ATOM   7322  CA   ASN B 406     -19.543   0.231 -22.538  1.00102.48      B
ATOM   7323  CB   ASN B 406     -20.689   1.232 -22.352  1.00103.82      B
ATOM   7324  CG   ASN B 406     -21.180   1.813 -23.683  1.00104.45      B
ATOM   7325  OD1  ASN B 406     -21.720   1.093 -24.525  1.00104.98      B
ATOM   7326  ND2  ASN B 406     -20.991   3.121 -23.872  1.00104.89      B
ATOM   7327  C    ASN B 406     -19.965  -1.166 -22.080  1.00100.23      B
ATOM   7328  O    ASN B 406     -19.452  -2.183 -22.547  1.00 99.36      B
ATOM   7329  N    SER B 407     -20.922  -1.176 -21.160  1.00 98.22      B
ATOM   7330  CA   SER B 407     -21.498  -2.378 -20.561  1.00 95.87      B
ATOM   7331  CB   SER B 407     -22.819  -2.735 -21.263  1.00 95.30      B
ATOM   7332  OG   SER B 407     -22.602  -3.202 -22.577  1.00 95.80      B
ATOM   7333  C    SER B 407     -20.626  -3.634 -20.424  1.00 94.34      B
ATOM   7334  O    SER B 407     -19.963  -3.817 -19.400  1.00 94.43      B
ATOM   7335  N    TRP B 408     -20.617  -4.489 -21.443  1.00 91.93      B
ATOM   7336  CA   TRP B 408     -19.848  -5.726 -21.369  1.00 89.51      B
ATOM   7337  CB   TRP B 408     -19.589  -6.309 -22.771  1.00 89.48      B
ATOM   7338  CG   TRP B 408     -18.498  -5.648 -23.586  1.00 89.37      B
ATOM   7339  CD2  TRP B 408     -17.093  -5.952 -23.552  1.00 89.18      B
ATOM   7340  CE2  TRP B 408     -16.457  -5.101 -24.485  1.00 88.78      B
ATOM   7341  CE3  TRP B 408     -16.311  -6.866 -22.830  1.00 89.25      B
ATOM   7342  CD1  TRP B 408     -18.648  -4.648 -24.508  1.00 88.86      B
ATOM   7343  NE1  TRP B 408     -17.428  -4.316 -25.051  1.00 88.74      B
ATOM   7344  CZ2  TRP B 408     -15.071  -5.129 -24.706  1.00 88.58      B
ATOM   7345  CZ3  TRP B 408     -14.930  -6.894 -23.051  1.00 88.95      B
ATOM   7346  CH2  TRP B 408     -14.330  -6.033 -23.985  1.00 88.63      B
ATOM   7347  C    TRP B 408     -18.533  -5.582 -20.609  1.00 87.89      B
ATOM   7348  O    TRP B 408     -18.260  -6.346 -19.682  1.00 88.13      B
ATOM   7349  N    LEU B 409     -17.727  -4.596 -20.986  1.00 85.84      B
ATOM   7350  CA   LEU B 409     -16.453  -4.381 -20.316  1.00 82.64      B
ATOM   7351  CB   LEU B 409     -15.743  -3.147 -20.895  1.00 81.93      B
ATOM   7352  CG   LEU B 409     -14.333  -2.870 -20.357  1.00 81.26      B
ATOM   7353  CD1  LEU B 409     -13.479  -4.121 -20.502  1.00 80.88      B
ATOM   7354  CD2  LEU B 409     -13.708  -1.700 -21.097  1.00 79.67      B
ATOM   7355  C    LEU B 409     -16.734  -4.189 -18.831  1.00 80.96      B
ATOM   7356  O    LEU B 409     -16.239  -4.941 -17.986  1.00 80.67      B
ATOM   7357  N    GLY B 410     -17.552  -3.188 -18.528  1.00 78.82      B
ATOM   7358  CA   GLY B 410     -17.902  -2.905 -17.151  1.00 76.75      B
ATOM   7359  C    GLY B 410     -18.412  -4.127 -16.415  1.00 75.08      B
ATOM   7360  O    GLY B 410     -17.979  -4.404 -15.293  1.00 74.93      B
ATOM   7361  N    ASN B 411     -19.330  -4.860 -17.045  1.00 73.62      B
ATOM   7362  CA   ASN B 411     -19.903  -6.060 -16.440  1.00 71.43      B
ATOM   7363  CB   ASN B 411     -20.912  -6.717 -17.381  1.00 69.06      B
ATOM   7364  CG   ASN B 411     -22.249  -6.002 -17.393  1.00 68.62      B
ATOM   7365  OD1  ASN B 411     -22.808  -5.685 -16.339  1.00 66.75      B
ATOM   7366  ND2  ASN B 411     -22.778  -5.757 -18.589  1.00 67.93      B
ATOM   7367  C    ASN B 411     -18.826  -7.063 -16.067  1.00 71.24      B
ATOM   7368  O    ASN B 411     -18.892  -7.683 -15.003  1.00 71.31      B
ATOM   7369  N    ILE B 412     -17.836  -7.225 -16.939  1.00 70.23      B
ATOM   7370  CA   ILE B 412     -16.751  -8.150 -16.658  1.00 69.84      B
ATOM   7371  CB   ILE B 412     -15.720  -8.180 -17.798  1.00 69.96      B
ATOM   7372  CG2  ILE B 412     -14.571  -9.121 -17.435  1.00 69.23      B
```

FIGURE 5- 98 -

```
ATOM   7373  CG1 ILE B 412     -16.388  -8.632 -19.093  1.00 69.67      B
ATOM   7374  CD1 ILE B 412     -15.419  -8.793 -20.247  1.00 69.13      B
ATOM   7375  C   ILE B 412     -16.036  -7.691 -15.394  1.00 70.24      B
ATOM   7376  O   ILE B 412     -15.977  -8.409 -14.392  1.00 69.77      B
ATOM   7377  N   ILE B 413     -15.499  -6.478 -15.455  1.00 69.31      B
ATOM   7378  CA  ILE B 413     -14.775  -5.906 -14.338  1.00 68.34      B
ATOM   7379  CB  ILE B 413     -14.396  -4.440 -14.638  1.00 68.01      B
ATOM   7380  CG2 ILE B 413     -13.305  -3.976 -13.683  1.00 66.44      B
ATOM   7381  CG1 ILE B 413     -13.888  -4.325 -16.080  1.00 67.68      B
ATOM   7382  CD1 ILE B 413     -13.712  -2.897 -16.560  1.00 66.93      B
ATOM   7383  C   ILE B 413     -15.605  -5.979 -13.057  1.00 68.74      B
ATOM   7384  O   ILE B 413     -15.109  -6.412 -12.023  1.00 69.65      B
ATOM   7385  N   MET B 414     -16.871  -5.583 -13.121  1.00 68.45      B
ATOM   7386  CA  MET B 414     -17.717  -5.606 -11.927  1.00 68.49      B
ATOM   7387  CB  MET B 414     -18.929  -4.671 -12.106  1.00 69.21      B
ATOM   7388  CG  MET B 414     -18.619  -3.163 -12.048  1.00 69.36      B
ATOM   7389  SD  MET B 414     -17.905  -2.573 -10.466  1.00 69.43      B
ATOM   7390  CE  MET B 414     -19.371  -2.466  -9.411  1.00 67.54      B
ATOM   7391  C   MET B 414     -18.216  -6.985 -11.493  1.00 67.92      B
ATOM   7392  O   MET B 414     -18.378  -7.233 -10.301  1.00 66.61      B
ATOM   7393  N   TYR B 415     -18.458  -7.880 -12.443  1.00 68.62      B
ATOM   7394  CA  TYR B 415     -18.969  -9.218 -12.130  1.00 68.48      B
ATOM   7395  CB  TYR B 415     -20.271  -9.472 -12.894  1.00 65.25      B
ATOM   7396  CG  TYR B 415     -21.432  -8.655 -12.381  1.00 62.58      B
ATOM   7397  CD1 TYR B 415     -22.012  -8.932 -11.145  1.00 61.38      B
ATOM   7398  CE1 TYR B 415     -23.072  -8.168 -10.659  1.00 59.39      B
ATOM   7399  CD2 TYR B 415     -21.942  -7.592 -13.123  1.00 62.06      B
ATOM   7400  CE2 TYR B 415     -23.003  -6.823 -12.643  1.00 59.42      B
ATOM   7401  CZ  TYR B 415     -23.563  -7.117 -11.418  1.00 58.55      B
ATOM   7402  OH  TYR B 415     -24.624  -6.372 -10.959  1.00 57.60      B
ATOM   7403  C   TYR B 415     -18.002 -10.365 -12.393  1.00 69.70      B
ATOM   7404  O   TYR B 415     -18.408 -11.530 -12.427  1.00 70.19      B
ATOM   7405  N   ALA B 416     -16.726 -10.031 -12.555  1.00 70.52      B
ATOM   7406  CA  ALA B 416     -15.677 -11.012 -12.820  1.00 70.75      B
ATOM   7407  CB  ALA B 416     -14.322 -10.423 -12.447  1.00 70.18      B
ATOM   7408  C   ALA B 416     -15.860 -12.371 -12.137  1.00 70.99      B
ATOM   7409  O   ALA B 416     -15.570 -13.408 -12.729  1.00 71.17      B
ATOM   7410  N   PRO B 417     -16.334 -12.386 -10.883  1.00 71.47      B
ATOM   7411  CD  PRO B 417     -16.368 -11.258  -9.941  1.00 71.75      B
ATOM   7412  CA  PRO B 417     -16.535 -13.652 -10.166  1.00 72.28      B
ATOM   7413  CB  PRO B 417     -16.731 -13.203  -8.716  1.00 72.51      B
ATOM   7414  CG  PRO B 417     -15.976 -11.926  -8.650  1.00 72.64      B
ATOM   7415  C   PRO B 417     -17.706 -14.519 -10.634  1.00 72.38      B
ATOM   7416  O   PRO B 417     -17.738 -15.714 -10.347  1.00 72.49      B
ATOM   7417  N   THR B 418     -18.665 -13.931 -11.344  1.00 72.16      B
ATOM   7418  CA  THR B 418     -19.829 -14.695 -11.785  1.00 72.52      B
ATOM   7419  CB  THR B 418     -20.986 -13.787 -12.236  1.00 72.42      B
ATOM   7420  OG1 THR B 418     -20.653 -13.185 -13.491  1.00 71.62      B
ATOM   7421  CG2 THR B 418     -21.262 -12.708 -11.199  1.00 72.94      B
ATOM   7422  C   THR B 418     -19.571 -15.674 -12.920  1.00 72.64      B
ATOM   7423  O   THR B 418     -18.638 -15.512 -13.711  1.00 72.12      B
ATOM   7424  N   LEU B 419     -20.433 -16.686 -12.987  1.00 72.35      B
ATOM   7425  CA  LEU B 419     -20.370 -17.729 -14.001  1.00 71.13      B
ATOM   7426  CB  LEU B 419     -21.543 -18.684 -13.807  1.00 71.55      B
ATOM   7427  CG  LEU B 419     -21.503 -20.024 -14.534  1.00 72.72      B
ATOM   7428  CD1 LEU B 419     -20.405 -20.888 -13.927  1.00 72.94      B
ATOM   7429  CD2 LEU B 419     -22.853 -20.717 -14.407  1.00 72.50      B
ATOM   7430  C   LEU B 419     -20.426 -17.137 -15.412  1.00 70.97      B
ATOM   7431  O   LEU B 419     -19.487 -17.283 -16.197  1.00 71.97      B
ATOM   7432  N   TRP B 420     -21.530 -16.464 -15.725  1.00 69.07      B
ATOM   7433  CA  TRP B 420     -21.727 -15.860 -17.043  1.00 67.67      B
ATOM   7434  CB  TRP B 420     -23.073 -15.126 -17.095  1.00 65.37      B
ATOM   7435  CG  TRP B 420     -23.420 -14.377 -15.846  1.00 62.32      B
ATOM   7436  CD2 TRP B 420     -23.330 -12.963 -15.639  1.00 60.66      B
ATOM   7437  CE2 TRP B 420     -23.792 -12.704 -14.329  1.00 61.29      B
ATOM   7438  CE3 TRP B 420     -22.912 -11.888 -16.433  1.00 59.42      B
ATOM   7439  CD1 TRP B 420     -23.908 -14.904 -14.688  1.00 61.73      B
ATOM   7440  NE1 TRP B 420     -24.136 -13.908 -13.771  1.00 61.58      B
ATOM   7441  CZ2 TRP B 420     -23.843 -11.411 -13.791  1.00 60.74      B
ATOM   7442  CZ3 TRP B 420     -22.961 -10.601 -15.900  1.00 58.54      B
ATOM   7443  CH2 TRP B 420     -23.427 -10.375 -14.592  1.00 60.00      B
ATOM   7444  C   TRP B 420     -20.631 -14.909 -17.519  1.00 67.55      B
ATOM   7445  O   TRP B 420     -20.233 -14.940 -18.687  1.00 67.86      B
ATOM   7446  N   ALA B 421     -20.156 -14.052 -16.625  1.00 67.06      B
ATOM   7447  CA  ALA B 421     -19.122 -13.099 -16.987  1.00 66.02      B
ATOM   7448  CB  ALA B 421     -18.813 -12.195 -15.809  1.00 66.00      B
```

FIGURE 5- 99 -

```
ATOM   7449  C    ALA B 421     -17.872 -13.836 -17.419  1.00 66.65      B
ATOM   7450  O    ALA B 421     -17.202 -13.422 -18.364  1.00 66.66      B
ATOM   7451  N    ARG B 422     -17.573 -14.936 -16.729  1.00 67.41      B
ATOM   7452  CA   ARG B 422     -16.389 -15.743 -17.016  1.00 67.84      B
ATOM   7453  CB   ARG B 422     -16.047 -16.616 -15.807  1.00 66.34      B
ATOM   7454  CG   ARG B 422     -15.778 -15.849 -14.524  1.00 66.37      B
ATOM   7455  CD   ARG B 422     -15.452 -16.798 -13.366  1.00 65.63      B
ATOM   7456  NE   ARG B 422     -14.162 -17.460 -13.546  1.00 64.34      B
ATOM   7457  CZ   ARG B 422     -13.741 -18.490 -12.820  1.00 63.97      B
ATOM   7458  NH1  ARG B 422     -14.508 -18.985 -11.858  1.00 62.23      B
ATOM   7459  NH2  ARG B 422     -12.550 -19.027 -13.059  1.00 64.45      B
ATOM   7460  C    ARG B 422     -16.535 -16.637 -18.248  1.00 69.25      B
ATOM   7461  O    ARG B 422     -15.790 -16.504 -19.225  1.00 68.98      B
ATOM   7462  N    MET B 423     -17.498 -17.551 -18.191  1.00 70.96      B
ATOM   7463  CA   MET B 423     -17.742 -18.485 -19.280  1.00 71.77      B
ATOM   7464  CB   MET B 423     -18.752 -19.544 -18.847  1.00 70.53      B
ATOM   7465  CG   MET B 423     -18.244 -20.480 -17.779  1.00 70.32      B
ATOM   7466  SD   MET B 423     -19.413 -21.798 -17.418  1.00 70.95      B
ATOM   7467  CE   MET B 423     -18.979 -23.003 -18.679  1.00 70.49      B
ATOM   7468  C    MET B 423     -18.231 -17.846 -20.568  1.00 73.05      B
ATOM   7469  O    MET B 423     -17.795 -18.220 -21.655  1.00 74.54      B
ATOM   7470  N    ILE B 424     -19.131 -16.878 -20.453  1.00 73.97      B
ATOM   7471  CA   ILE B 424     -19.695 -16.236 -21.633  1.00 75.33      B
ATOM   7472  CB   ILE B 424     -21.175 -15.901 -21.387  1.00 76.33      B
ATOM   7473  CG2  ILE B 424     -21.805 -15.328 -22.658  1.00 75.54      B
ATOM   7474  CG1  ILE B 424     -21.901 -17.169 -20.918  1.00 76.48      B
ATOM   7475  CD1  ILE B 424     -23.335 -16.953 -20.504  1.00 78.42      B
ATOM   7476  C    ILE B 424     -18.977 -14.983 -22.124  1.00 75.61      B
ATOM   7477  O    ILE B 424     -18.266 -15.019 -23.131  1.00 75.22      B
ATOM   7478  N    LEU B 425     -19.176 -13.874 -21.419  1.00 76.29      B
ATOM   7479  CA   LEU B 425     -18.557 -12.611 -21.802  1.00 76.20      B
ATOM   7480  CB   LEU B 425     -18.764 -11.560 -20.703  1.00 74.35      B
ATOM   7481  CG   LEU B 425     -20.190 -11.003 -20.632  1.00 72.93      B
ATOM   7482  CD1  LEU B 425     -20.294  -9.960 -19.531  1.00 71.58      B
ATOM   7483  CD2  LEU B 425     -20.561 -10.399 -21.978  1.00 71.25      B
ATOM   7484  C    LEU B 425     -17.076 -12.730 -22.147  1.00 76.77      B
ATOM   7485  O    LEU B 425     -16.675 -12.391 -23.257  1.00 77.67      B
ATOM   7486  N    MET B 426     -16.266 -13.225 -21.217  1.00 77.09      B
ATOM   7487  CA   MET B 426     -14.835 -13.356 -21.469  1.00 78.58      B
ATOM   7488  CB   MET B 426     -14.137 -13.949 -20.248  1.00 77.42      B
ATOM   7489  CG   MET B 426     -14.286 -13.093 -19.016  1.00 76.82      B
ATOM   7490  SD   MET B 426     -13.382 -13.737 -17.621  1.00 77.41      B
ATOM   7491  CE   MET B 426     -13.111 -12.241 -16.670  1.00 78.34      B
ATOM   7492  C    MET B 426     -14.524 -14.196 -22.704  1.00 79.95      B
ATOM   7493  O    MET B 426     -13.791 -13.760 -23.598  1.00 81.15      B
ATOM   7494  N    THR B 427     -15.077 -15.401 -22.757  1.00 80.55      B
ATOM   7495  CA   THR B 427     -14.842 -16.272 -23.899  1.00 80.71      B
ATOM   7496  CB   THR B 427     -15.720 -17.530 -23.840  1.00 79.84      B
ATOM   7497  OG1  THR B 427     -15.447 -18.252 -22.635  1.00 78.87      B
ATOM   7498  CG2  THR B 427     -15.438 -18.428 -25.035  1.00 80.01      B
ATOM   7499  C    THR B 427     -15.162 -15.534 -25.194  1.00 81.51      B
ATOM   7500  O    THR B 427     -14.294 -15.367 -26.050  1.00 81.26      B
ATOM   7501  N    HIS B 428     -16.408 -15.085 -25.314  1.00 82.55      B
ATOM   7502  CA   HIS B 428     -16.870 -14.390 -26.500  1.00 84.56      B
ATOM   7503  CB   HIS B 428     -18.308 -13.913 -26.324  1.00 83.89      B
ATOM   7504  CG   HIS B 428     -18.868 -13.251 -27.522  1.00 84.75      B
ATOM   7505  CD2  HIS B 428     -19.073 -11.946 -27.853  1.00 84.68      B
ATOM   7506  ND1  HIS B 428     -19.297 -13.954 -28.659  1.00 85.05      B
ATOM   7507  CE1  HIS B 428     -19.717 -13.128 -29.574  1.00 84.36      B
ATOM   7508  NE2  HIS B 428     -19.590 -11.875 -29.097  1.00 84.67      B
ATOM   7509  C    HIS B 428     -16.022 -13.201 -26.921  1.00 86.20      B
ATOM   7510  O    HIS B 428     -15.310 -13.265 -27.925  1.00 87.22      B
ATOM   7511  N    PHE B 429     -16.110 -12.112 -26.161  1.00 87.54      B
ATOM   7512  CA   PHE B 429     -15.367 -10.897 -26.477  1.00 88.07      B
ATOM   7513  CB   PHE B 429     -15.636  -9.821 -25.421  1.00 86.61      B
ATOM   7514  CG   PHE B 429     -16.900  -9.053 -25.675  1.00 85.67      B
ATOM   7515  CD1  PHE B 429     -17.015  -8.241 -26.802  1.00 84.73      B
ATOM   7516  CD2  PHE B 429     -17.995  -9.187 -24.834  1.00 84.75      B
ATOM   7517  CE1  PHE B 429     -18.202  -7.576 -27.091  1.00 84.07      B
ATOM   7518  CE2  PHE B 429     -19.188  -8.527 -25.114  1.00 84.96      B
ATOM   7519  CZ   PHE B 429     -19.290  -7.719 -26.249  1.00 84.74      B
ATOM   7520  C    PHE B 429     -13.876 -11.072 -26.698  1.00 89.08      B
ATOM   7521  O    PHE B 429     -13.308 -10.432 -27.585  1.00 89.38      B
ATOM   7522  N    PHE B 430     -13.228 -11.930 -25.918  1.00 89.85      B
ATOM   7523  CA   PHE B 430     -11.804 -12.127 -26.140  1.00 91.15      B
ATOM   7524  CB   PHE B 430     -11.194 -13.039 -25.073  1.00 92.08      B
```

FIGURE 5- 100 -

```
ATOM   7525  CG   PHE B 430     -10.521 -12.287 -23.956  1.00 92.74      B
ATOM   7526  CD1  PHE B 430     -11.265 -11.727 -22.923  1.00 93.05      B
ATOM   7527  CD2  PHE B 430      -9.140 -12.104 -23.961  1.00 92.99      B
ATOM   7528  CE1  PHE B 430     -10.644 -10.992 -21.909  1.00 93.73      B
ATOM   7529  CE2  PHE B 430      -8.509 -11.369 -22.953  1.00 93.60      B
ATOM   7530  CZ   PHE B 430      -9.263 -10.813 -21.926  1.00 93.87      B
ATOM   7531  C    PHE B 430     -11.590 -12.709 -27.534  1.00 91.15      B
ATOM   7532  O    PHE B 430     -10.607 -12.397 -28.202  1.00 91.03      B
ATOM   7533  N    SER B 431     -12.522 -13.542 -27.981  1.00 91.53      B
ATOM   7534  CA   SER B 431     -12.410 -14.127 -29.307  1.00 91.80      B
ATOM   7535  CB   SER B 431     -13.514 -15.159 -29.540  1.00 91.10      B
ATOM   7536  OG   SER B 431     -13.301 -16.308 -28.740  1.00 89.90      B
ATOM   7537  C    SER B 431     -12.495 -13.021 -30.345  1.00 92.40      B
ATOM   7538  O    SER B 431     -11.656 -12.943 -31.237  1.00 93.08      B
ATOM   7539  N    ILE B 432     -13.498 -12.158 -30.228  1.00 92.94      B
ATOM   7540  CA   ILE B 432     -13.639 -11.062 -31.180  1.00 94.23      B
ATOM   7541  CB   ILE B 432     -14.989 -10.311 -30.999  1.00 93.70      B
ATOM   7542  CG2  ILE B 432     -15.096  -9.169 -32.005  1.00 92.41      B
ATOM   7543  CG1  ILE B 432     -16.158 -11.275 -31.224  1.00 93.91      B
ATOM   7544  CD1  ILE B 432     -17.527 -10.614 -31.176  1.00 93.84      B
ATOM   7545  C    ILE B 432     -12.474 -10.081 -31.016  1.00 95.38      B
ATOM   7546  O    ILE B 432     -12.291  -9.180 -31.837  1.00 95.60      B
ATOM   7547  N    LEU B 433     -11.682 -10.266 -29.961  1.00 96.51      B
ATOM   7548  CA   LEU B 433     -10.534  -9.396 -29.711  1.00 97.32      B
ATOM   7549  CB   LEU B 433     -10.074  -9.488 -28.252  1.00 97.50      B
ATOM   7550  CG   LEU B 433     -10.710  -8.511 -27.258  1.00 97.70      B
ATOM   7551  CD1  LEU B 433     -10.036  -8.664 -25.904  1.00 98.08      B
ATOM   7552  CD2  LEU B 433     -10.557  -7.077 -27.759  1.00 97.02      B
ATOM   7553  C    LEU B 433      -9.368  -9.730 -30.628  1.00 97.78      B
ATOM   7554  O    LEU B 433      -9.187  -9.082 -31.658  1.00 97.91      B
ATOM   7555  N    LEU B 434      -8.574 -10.734 -30.256  1.00 98.21      B
ATOM   7556  CA   LEU B 434      -7.438 -11.131 -31.081  1.00 98.35      B
ATOM   7557  CB   LEU B 434      -6.773 -12.403 -30.534  1.00 97.58      B
ATOM   7558  CG   LEU B 434      -7.602 -13.415 -29.740  1.00 96.72      B
ATOM   7559  CD1  LEU B 434      -6.832 -14.718 -29.608  1.00 96.42      B
ATOM   7560  CD2  LEU B 434      -7.911 -12.848 -28.369  1.00 96.41      B
ATOM   7561  C    LEU B 434      -7.900 -11.352 -32.517  1.00 98.78      B
ATOM   7562  O    LEU B 434      -7.089 -11.394 -33.442  1.00 98.54      B
ATOM   7563  N    ALA B 435      -9.213 -11.483 -32.691  1.00 99.46      B
ATOM   7564  CA   ALA B 435      -9.807 -11.673 -34.008  1.00100.19      B
ATOM   7565  CB   ALA B 435     -11.270 -12.075 -33.872  1.00 99.60      B
ATOM   7566  C    ALA B 435      -9.697 -10.362 -34.781  1.00100.75      B
ATOM   7567  O    ALA B 435     -10.172 -10.250 -35.912  1.00100.72      B
ATOM   7568  N    GLN B 436      -9.074  -9.369 -34.152  1.00101.09      B
ATOM   7569  CA   GLN B 436      -8.885  -8.056 -34.756  1.00101.89      B
ATOM   7570  CB   GLN B 436     -10.119  -7.185 -34.521  1.00101.73      B
ATOM   7571  CG   GLN B 436     -11.433  -7.891 -34.823  1.00101.92      B
ATOM   7572  CD   GLN B 436     -12.629  -6.973 -34.725  1.00102.03      B
ATOM   7573  OE1  GLN B 436     -12.795  -6.259 -33.738  1.00101.66      B
ATOM   7574  NE2  GLN B 436     -13.477  -6.992 -35.750  1.00101.95      B
ATOM   7575  C    GLN B 436      -7.661  -7.401 -34.128  1.00102.61      B
ATOM   7576  O    GLN B 436      -7.324  -6.257 -34.438  1.00102.20      B
ATOM   7577  N    GLU B 437      -7.014  -8.145 -33.234  1.00104.10      B
ATOM   7578  CA   GLU B 437      -5.811  -7.703 -32.530  1.00105.52      B
ATOM   7579  CB   GLU B 437      -4.709  -7.373 -33.547  1.00106.11      B
ATOM   7580  CG   GLU B 437      -3.333  -7.153 -32.933  1.00106.76      B
ATOM   7581  CD   GLU B 437      -2.901  -8.309 -32.049  1.00107.17      B
ATOM   7582  OE1  GLU B 437      -2.804  -9.446 -32.562  1.00106.83      B
ATOM   7583  OE2  GLU B 437      -2.662  -8.077 -30.842  1.00107.10      B
ATOM   7584  C    GLU B 437      -6.045  -6.508 -31.601  1.00106.14      B
ATOM   7585  O    GLU B 437      -5.106  -5.795 -31.239  1.00106.39      B
ATOM   7586  N    GLN B 438      -7.295  -6.305 -31.197  1.00106.58      B
ATOM   7587  CA   GLN B 438      -7.642  -5.191 -30.319  1.00106.80      B
ATOM   7588  CB   GLN B 438      -9.132  -4.878 -30.438  1.00107.38      B
ATOM   7589  CG   GLN B 438      -9.567  -4.484 -31.835  1.00108.72      B
ATOM   7590  CD   GLN B 438     -11.054  -4.204 -31.918  1.00109.67      B
ATOM   7591  OE1  GLN B 438     -11.877  -5.065 -31.599  1.00109.69      B
ATOM   7592  NE2  GLN B 438     -11.408  -2.996 -32.348  1.00109.73      B
ATOM   7593  C    GLN B 438      -7.296  -5.429 -28.852  1.00106.54      B
ATOM   7594  O    GLN B 438      -7.737  -4.681 -27.980  1.00106.69      B
ATOM   7595  N    LEU B 439      -6.511  -6.466 -28.577  1.00106.14      B
ATOM   7596  CA   LEU B 439      -6.116  -6.775 -27.206  1.00105.76      B
ATOM   7597  CB   LEU B 439      -5.159  -7.969 -27.190  1.00106.63      B
ATOM   7598  CG   LEU B 439      -5.712  -9.285 -27.746  1.00107.32      B
ATOM   7599  CD1  LEU B 439      -4.597 -10.315 -27.838  1.00107.63      B
ATOM   7600  CD2  LEU B 439      -6.837  -9.787 -26.854  1.00107.20      B
```

FIGURE 5- 101 -

```
ATOM   7601  C   LEU B 439      -5.427  -5.556 -26.609  1.00104.98           B
ATOM   7602  O   LEU B 439      -5.100  -5.521 -25.422  1.00103.98           B
ATOM   7603  N   GLU B 440      -5.222  -4.553 -27.458  1.00104.78           B
ATOM   7604  CA  GLU B 440      -4.565  -3.313 -27.070  1.00104.49           B
ATOM   7605  CB  GLU B 440      -3.670  -2.828 -28.213  1.00105.85           B
ATOM   7606  CG  GLU B 440      -2.777  -3.904 -28.818  1.00108.03           B
ATOM   7607  CD  GLU B 440      -1.745  -4.436 -27.840  1.00108.88           B
ATOM   7608  OE1 GLU B 440      -0.935  -3.630 -27.330  1.00108.75           B
ATOM   7609  OE2 GLU B 440      -1.742  -5.661 -27.588  1.00109.77           B
ATOM   7610  C   GLU B 440      -5.565  -2.211 -26.726  1.00103.14           B
ATOM   7611  O   GLU B 440      -5.769  -1.880 -25.556  1.00102.98           B
ATOM   7612  N   LYS B 441      -6.180  -1.654 -27.764  1.00101.34           B
ATOM   7613  CA  LYS B 441      -7.143  -0.571 -27.624  1.00100.06           B
ATOM   7614  CB  LYS B 441      -8.197  -0.657 -28.728  1.00 99.46           B
ATOM   7615  CG  LYS B 441      -9.202   0.481 -28.682  1.00 99.72           B
ATOM   7616  CD  LYS B 441     -10.337   0.295 -29.682  1.00 99.95           B
ATOM   7617  CE  LYS B 441      -9.872   0.457 -31.119  1.00 99.99           B
ATOM   7618  NZ  LYS B 441     -11.008   0.298 -32.074  1.00100.39           B
ATOM   7619  C   LYS B 441      -7.844  -0.499 -26.269  1.00100.09           B
ATOM   7620  O   LYS B 441      -8.646  -1.369 -25.922  1.00 99.95           B
ATOM   7621  N   ALA B 442      -7.525   0.544 -25.504  1.00 99.48           B
ATOM   7622  CA  ALA B 442      -8.139   0.771 -24.200  1.00 97.72           B
ATOM   7623  CB  ALA B 442      -7.276   1.706 -23.367  1.00 97.13           B
ATOM   7624  C   ALA B 442      -9.493   1.413 -24.487  1.00 96.67           B
ATOM   7625  O   ALA B 442      -9.587   2.339 -25.294  1.00 95.81           B
ATOM   7626  N   LEU B 443     -10.542   0.923 -23.834  1.00 96.00           B
ATOM   7627  CA  LEU B 443     -11.880   1.453 -24.075  1.00 95.17           B
ATOM   7628  CB  LEU B 443     -12.725   0.384 -24.766  1.00 95.55           B
ATOM   7629  CG  LEU B 443     -12.191   0.084 -26.168  1.00 95.85           B
ATOM   7630  CD1 LEU B 443     -12.544  -1.328 -26.587  1.00 95.49           B
ATOM   7631  CD2 LEU B 443     -12.740   1.121 -27.137  1.00 95.29           B
ATOM   7632  C   LEU B 443     -12.598   1.972 -22.838  1.00 94.03           B
ATOM   7633  O   LEU B 443     -12.335   1.531 -21.718  1.00 93.37           B
ATOM   7634  N   ASP B 444     -13.512   2.913 -23.064  1.00 92.87           B
ATOM   7635  CA  ASP B 444     -14.286   3.533 -21.991  1.00 91.36           B
ATOM   7636  CB  ASP B 444     -14.971   4.815 -22.498  1.00 91.80           B
ATOM   7637  CG  ASP B 444     -14.055   5.679 -23.356  1.00 92.19           B
ATOM   7638  OD1 ASP B 444     -13.037   6.188 -22.836  1.00 92.09           B
ATOM   7639  OD2 ASP B 444     -14.360   5.849 -24.558  1.00 91.77           B
ATOM   7640  C   ASP B 444     -15.356   2.568 -21.438  1.00 89.29           B
ATOM   7641  O   ASP B 444     -15.860   1.713 -22.145  1.00 89.18           B
ATOM   7642  N   CYS B 445     -15.694   2.776 -20.168  1.00 86.83           B
ATOM   7643  CA  CYS B 445     -16.717   1.980 -19.501  1.00 84.10           B
ATOM   7644  CB  CYS B 445     -16.178   0.589 -19.145  1.00 83.26           B
ATOM   7645  SG  CYS B 445     -14.796   0.549 -17.983  1.00 82.66           B
ATOM   7646  C   CYS B 445     -17.167   2.723 -18.244  1.00 82.64           B
ATOM   7647  O   CYS B 445     -16.386   3.442 -17.626  1.00 82.14           B
ATOM   7648  N   GLN B 446     -18.428   2.554 -17.871  1.00 80.96           B
ATOM   7649  CA  GLN B 446     -18.970   3.237 -16.704  1.00 79.57           B
ATOM   7650  CB  GLN B 446     -20.453   3.524 -16.930  1.00 79.03           B
ATOM   7651  CG  GLN B 446     -20.719   4.387 -18.152  1.00 79.03           B
ATOM   7652  CD  GLN B 446     -20.753   5.868 -17.827  1.00 78.21           B
ATOM   7653  OE1 GLN B 446     -21.740   6.370 -17.284  1.00 77.02           B
ATOM   7654  NE2 GLN B 446     -19.673   6.574 -18.150  1.00 77.01           B
ATOM   7655  C   GLN B 446     -18.800   2.461 -15.407  1.00 78.95           B
ATOM   7656  O   GLN B 446     -18.798   1.235 -15.402  1.00 78.70           B
ATOM   7657  N   ILE B 447     -18.638   3.192 -14.308  1.00 78.49           B
ATOM   7658  CA  ILE B 447     -18.513   2.594 -12.982  1.00 77.95           B
ATOM   7659  CB  ILE B 447     -17.052   2.299 -12.595  1.00 77.57           B
ATOM   7660  CG2 ILE B 447     -16.984   1.858 -11.130  1.00 77.44           B
ATOM   7661  CG1 ILE B 447     -16.495   1.194 -13.497  1.00 77.28           B
ATOM   7662  CD1 ILE B 447     -15.131   0.682 -13.090  1.00 76.59           B
ATOM   7663  C   ILE B 447     -19.121   3.553 -11.969  1.00 78.43           B
ATOM   7664  O   ILE B 447     -18.445   4.430 -11.425  1.00 78.34           B
ATOM   7665  N   TYR B 448     -20.415   3.368 -11.728  1.00 79.39           B
ATOM   7666  CA  TYR B 448     -21.171   4.205 -10.811  1.00 80.06           B
ATOM   7667  CB  TYR B 448     -20.535   4.206  -9.414  1.00 79.44           B
ATOM   7668  CG  TYR B 448     -20.579   2.872  -8.692  1.00 79.30           B
ATOM   7669  CD1 TYR B 448     -21.759   2.125  -8.621  1.00 78.53           B
ATOM   7670  CE1 TYR B 448     -21.809   0.917  -7.922  1.00 78.16           B
ATOM   7671  CD2 TYR B 448     -19.446   2.374  -8.044  1.00 79.94           B
ATOM   7672  CE2 TYR B 448     -19.486   1.168  -7.342  1.00 79.72           B
ATOM   7673  CZ  TYR B 448     -20.667   0.446  -7.285  1.00 79.16           B
ATOM   7674  OH  TYR B 448     -20.696  -0.743  -6.589  1.00 79.10           B
ATOM   7675  C   TYR B 448     -21.200   5.619 -11.381  1.00 81.12           B
ATOM   7676  O   TYR B 448     -20.934   6.595 -10.678  1.00 82.55           B
```

FIGURE 5-102-

```
ATOM   7677  N    GLY B 449     -21.518   5.715 -12.669  1.00 81.43       B
ATOM   7678  CA   GLY B 449     -21.580   7.004 -13.330  1.00 81.63       B
ATOM   7679  C    GLY B 449     -20.225   7.525 -13.760  1.00 81.98       B
ATOM   7680  O    GLY B 449     -20.111   8.236 -14.755  1.00 82.58       B
ATOM   7681  N    ALA B 450     -19.192   7.172 -13.007  1.00 83.00       B
ATOM   7682  CA   ALA B 450     -17.845   7.618 -13.316  1.00 84.95       B
ATOM   7683  CB   ALA B 450     -16.923   7.362 -12.119  1.00 84.60       B
ATOM   7684  C    ALA B 450     -17.307   6.918 -14.561  1.00 86.53       B
ATOM   7685  O    ALA B 450     -17.162   5.695 -14.586  1.00 86.42       B
ATOM   7686  N    CYS B 451     -17.018   7.700 -15.596  1.00 88.72       B
ATOM   7687  CA   CYS B 451     -16.484   7.152 -16.834  1.00 91.25       B
ATOM   7688  CB   CYS B 451     -16.853   8.045 -18.020  1.00 91.85       B
ATOM   7689  SG   CYS B 451     -16.054   7.538 -19.568  1.00 94.32       B
ATOM   7690  C    CYS B 451     -14.966   7.011 -16.762  1.00 92.55       B
ATOM   7691  O    CYS B 451     -14.265   7.937 -16.357  1.00 92.79       B
ATOM   7692  N    TYR B 452     -14.469   5.844 -17.157  1.00 94.54       B
ATOM   7693  CA   TYR B 452     -13.038   5.562 -17.149  1.00 96.73       B
ATOM   7694  CB   TYR B 452     -12.732   4.409 -16.183  1.00 96.39       B
ATOM   7695  CG   TYR B 452     -12.915   4.768 -14.725  1.00 96.43       B
ATOM   7696  CD1  TYR B 452     -12.029   5.635 -14.081  1.00 97.26       B
ATOM   7697  CE1  TYR B 452     -12.212   5.995 -12.744  1.00 97.11       B
ATOM   7698  CD2  TYR B 452     -13.991   4.267 -13.995  1.00 96.63       B
ATOM   7699  CE2  TYR B 452     -14.186   4.621 -12.660  1.00 96.94       B
ATOM   7700  CZ   TYR B 452     -13.295   5.485 -12.042  1.00 96.99       B
ATOM   7701  OH   TYR B 452     -13.498   5.849 -10.731  1.00 95.77       B
ATOM   7702  C    TYR B 452     -12.562   5.209 -18.557  1.00 98.14       B
ATOM   7703  O    TYR B 452     -12.924   5.878 -19.525  1.00 98.89       B
ATOM   7704  N    SER B 453     -11.753   4.157 -18.657  1.00 99.52       B
ATOM   7705  CA   SER B 453     -11.204   3.684 -19.930  1.00100.89       B
ATOM   7706  CB   SER B 453     -10.675   4.859 -20.765  1.00101.59       B
ATOM   7707  OG   SER B 453     -10.414   4.462 -22.102  1.00102.06       B
ATOM   7708  C    SER B 453     -10.062   2.723 -19.600  1.00100.93       B
ATOM   7709  O    SER B 453      -8.981   3.148 -19.188  1.00100.33       B
ATOM   7710  N    ILE B 454     -10.303   1.431 -19.792  1.00101.12       B
ATOM   7711  CA   ILE B 454      -9.307   0.421 -19.462  1.00101.72       B
ATOM   7712  CB   ILE B 454      -9.874  -0.526 -18.369  1.00101.62       B
ATOM   7713  CG2  ILE B 454      -8.782  -1.445 -17.833  1.00101.36       B
ATOM   7714  CG1  ILE B 454     -10.450   0.315 -17.222  1.00102.07       B
ATOM   7715  CD1  ILE B 454     -11.130  -0.483 -16.126  1.00101.77       B
ATOM   7716  C    ILE B 454      -8.815  -0.409 -20.651  1.00102.09       B
ATOM   7717  O    ILE B 454      -9.372  -0.348 -21.748  1.00101.83       B
ATOM   7718  N    GLU B 455      -7.745  -1.165 -20.416  1.00102.80       B
ATOM   7719  CA   GLU B 455      -7.156  -2.044 -21.421  1.00103.61       B
ATOM   7720  CB   GLU B 455      -5.628  -1.998 -21.383  1.00103.97       B
ATOM   7721  CG   GLU B 455      -4.989  -0.660 -21.650  1.00103.67       B
ATOM   7722  CD   GLU B 455      -3.511  -0.811 -21.939  1.00103.37       B
ATOM   7723  OE1  GLU B 455      -2.828  -1.527 -21.174  1.00102.92       B
ATOM   7724  OE2  GLU B 455      -3.037  -0.219 -22.931  1.00102.99       B
ATOM   7725  C    GLU B 455      -7.575  -3.473 -21.098  1.00103.97       B
ATOM   7726  O    GLU B 455      -7.645  -3.861 -19.929  1.00104.63       B
ATOM   7727  N    PRO B 456      -7.835  -4.285 -22.130  1.00103.49       B
ATOM   7728  CD   PRO B 456      -7.822  -3.974 -23.570  1.00103.71       B
ATOM   7729  CA   PRO B 456      -8.241  -5.672 -21.894  1.00102.35       B
ATOM   7730  CB   PRO B 456      -8.375  -6.234 -23.307  1.00103.04       B
ATOM   7731  CG   PRO B 456      -8.751  -5.024 -24.121  1.00103.61       B
ATOM   7732  C    PRO B 456      -7.199  -6.430 -21.075  1.00101.43       B
ATOM   7733  O    PRO B 456      -7.523  -7.111 -20.103  1.00101.40       B
ATOM   7734  N    LEU B 457      -5.941  -6.286 -21.478  1.00100.22       B
ATOM   7735  CA   LEU B 457      -4.825  -6.964 -20.830  1.00 98.55       B
ATOM   7736  CB   LEU B 457      -3.506  -6.499 -21.453  1.00 98.81       B
ATOM   7737  CG   LEU B 457      -3.404  -6.569 -22.979  1.00 98.89       B
ATOM   7738  CD1  LEU B 457      -2.074  -5.980 -23.430  1.00 98.30       B
ATOM   7739  CD2  LEU B 457      -3.549  -8.012 -23.440  1.00 98.16       B
ATOM   7740  C    LEU B 457      -4.759  -6.762 -19.325  1.00 97.44       B
ATOM   7741  O    LEU B 457      -4.252  -7.620 -18.604  1.00 96.57       B
ATOM   7742  N    ASP B 458      -5.272  -5.634 -18.848  1.00 96.36       B
ATOM   7743  CA   ASP B 458      -5.225  -5.338 -17.420  1.00 95.94       B
ATOM   7744  CB   ASP B 458      -5.413  -3.835 -17.200  1.00 95.09       B
ATOM   7745  CG   ASP B 458      -4.233  -3.026 -17.695  1.00 94.14       B
ATOM   7746  OD1  ASP B 458      -3.116  -3.242 -17.181  1.00 92.54       B
ATOM   7747  OD2  ASP B 458      -4.420  -2.179 -18.595  1.00 93.49       B
ATOM   7748  C    ASP B 458      -6.213  -6.115 -16.545  1.00 95.60       B
ATOM   7749  O    ASP B 458      -5.979  -6.292 -15.345  1.00 95.42       B
ATOM   7750  N    LEU B 459      -7.303  -6.586 -17.143  1.00 94.50       B
ATOM   7751  CA   LEU B 459      -8.330  -7.321 -16.407  1.00 93.47       B
ATOM   7752  CB   LEU B 459      -9.252  -8.051 -17.386  1.00 93.29       B
```

FIGURE 5-103-

```
ATOM   7753  CG  LEU B 459     -10.126  -7.168 -18.278  1.00 93.20      3
ATOM   7754  CD1 LEU B 459     -10.890  -8.036 -19.261  1.00 92.93      3
ATOM   7755  CD2 LEU B 459     -11.088  -6.358 -17.420  1.00 92.95      3
ATOM   7756  C   LEU B 459      -7.828  -8.305 -15.347  1.00 93.01      3
ATOM   7757  O   LEU B 459      -8.230  -8.229 -14.185  1.00 92.77      3
ATOM   7758  N   PRO B 460      -6.948  -9.245 -15.730  1.00 92.52      3
ATOM   7759  CD  PRO B 460      -6.349  -9.466 -17.060  1.00 91.93      3
ATOM   7760  CA  PRO B 460      -6.434 -10.220 -14.761  1.00 91.71      3
ATOM   7761  CB  PRO B 460      -5.276 -10.871 -15.514  1.00 91.59      3
ATOM   7762  CG  PRO B 460      -5.772 -10.863 -16.925  1.00 91.82      3
ATOM   7763  C   PRO B 460      -5.996  -9.618 -13.422  1.00 91.32      3
ATOM   7764  O   PRO B 460      -6.369 -10.119 -12.360  1.00 90.66      3
ATOM   7765  N   GLN B 461      -5.210  -8.545 -13.475  1.00 90.89      3
ATOM   7766  CA  GLN B 461      -4.719  -7.899 -12.260  1.00 90.16      3
ATOM   7767  CB  GLN B 461      -3.615  -6.886 -12.595  1.00 90.92      3
ATOM   7768  CG  GLN B 461      -2.527  -7.398 -13.536  1.00 91.12      3
ATOM   7769  CD  GLN B 461      -2.836  -7.115 -15.000  1.00 92.02      3
ATOM   7770  OE1 GLN B 461      -2.952  -5.958 -15.413  1.00 91.70      3
ATOM   7771  NE2 GLN B 461      -2.971  -8.173 -15.792  1.00 92.34      3
ATOM   7772  C   GLN B 461      -5.842  -7.187 -11.509  1.00 89.36      3
ATOM   7773  O   GLN B 461      -6.075  -7.446 -10.324  1.00 88.88      3
ATOM   7774  N   ILE B 462      -6.528  -6.290 -12.214  1.00 88.39      3
ATOM   7775  CA  ILE B 462      -7.633  -5.512 -11.650  1.00 86.97      3
ATOM   7776  CB  ILE B 462      -8.407  -4.765 -12.758  1.00 86.44      3
ATOM   7777  CG2 ILE B 462      -9.543  -3.962 -12.141  1.00 86.36      3
ATOM   7778  CG1 ILE B 462      -7.453  -3.859 -13.542  1.00 85.91      3
ATOM   7779  CD1 ILE B 462      -8.115  -3.101 -14.675  1.00 85.30      3
ATOM   7780  C   ILE B 462      -8.627  -6.374 -10.879  1.00 85.83      3
ATOM   7781  O   ILE B 462      -8.973  -6.076  -9.733  1.00 85.08      3
ATOM   7782  N   ILE B 463      -9.084  -7.440 -11.526  1.00 84.53      3
ATOM   7783  CA  ILE B 463     -10.035  -8.356 -10.925  1.00 83.35      3
ATOM   7784  CB  ILE B 463     -10.311  -9.550 -11.861  1.00 81.85      3
ATOM   7785  CG2 ILE B 463     -11.156 -10.592 -11.146  1.00 81.19      3
ATOM   7786  CG1 ILE B 463     -11.010  -9.061 -13.132  1.00 80.09      3
ATOM   7787  CD1 ILE B 463     -11.314 -10.157 -14.125  1.00 77.96      3
ATOM   7788  C   ILE B 463      -9.535  -8.879  -9.585  1.00 84.07      3
ATOM   7789  O   ILE B 463     -10.330  -9.126  -8.680  1.00 84.16      3
ATOM   7790  N   GLU B 464      -8.222  -9.039  -9.451  1.00 85.19      3
ATOM   7791  CA  GLU B 464      -7.665  -9.548  -8.205  1.00 86.83      3
ATOM   7792  CB  GLU B 464      -6.229 -10.034  -8.404  1.00 87.75      3
ATOM   7793  CG  GLU B 464      -5.586 -10.525  -7.115  1.00 89.61      3
ATOM   7794  CD  GLU B 464      -4.144 -10.941  -7.298  1.00 91.25      3
ATOM   7795  OE1 GLU B 464      -3.904 -12.012  -7.893  1.00 91.53      3
ATOM   7796  OE2 GLU B 464      -3.247 -10.191  -6.853  1.00 93.21      3
ATOM   7797  C   GLU B 464      -7.699  -8.526  -7.077  1.00 87.30      3
ATOM   7798  O   GLU B 464      -7.960  -8.875  -5.930  1.00 86.64      3
ATOM   7799  N   ARG B 465      -7.431  -7.264  -7.381  1.00 88.16      3
ATOM   7800  CA  ARG B 465      -7.460  -6.269  -6.322  1.00 89.08      3
ATOM   7801  CB  ARG B 465      -6.755  -4.984  -6.761  1.00 90.95      3
ATOM   7802  CG  ARG B 465      -6.601  -3.967  -5.639  1.00 93.30      3
ATOM   7803  CD  ARG B 465      -5.676  -2.836  -6.042  1.00 95.37      3
ATOM   7804  NE  ARG B 465      -5.679  -1.750  -5.066  1.00 97.41      3
ATOM   7805  CZ  ARG B 465      -4.912  -0.668  -5.158  1.00 98.73      3
ATOM   7806  NH1 ARG B 465      -4.083  -0.538  -6.182  1.00 99.04      3
ATOM   7807  NH2 ARG B 465      -4.974   0.285  -4.235  1.00 98.85      3
ATOM   7808  C   ARG B 465      -8.905  -5.974  -5.936  1.00 88.45      3
ATOM   7809  O   ARG B 465      -9.196  -5.664  -4.778  1.00 88.71      3
ATOM   7810  N   LEU B 466      -9.808  -6.091  -6.908  1.00 87.10      3
ATOM   7811  CA  LEU B 466     -11.231  -5.836  -6.682  1.00 85.45      3
ATOM   7812  CB  LEU B 466     -11.937  -5.508  -7.998  1.00 85.51      3
ATOM   7813  CG  LEU B 466     -11.444  -4.322  -8.820  1.00 86.53      3
ATOM   7814  CD1 LEU B 466     -12.401  -4.100  -9.981  1.00 85.91      3
ATOM   7815  CD2 LEU B 466     -11.365  -3.078  -7.946  1.00 87.26      3
ATOM   7816  C   LEU B 466     -11.951  -7.015  -6.045  1.00 83.93      3
ATOM   7817  O   LEU B 466     -12.384  -6.941  -4.899  1.00 84.79      3
ATOM   7818  N   HIS B 467     -12.082  -8.094  -6.813  1.00 81.35      3
ATOM   7819  CA  HIS B 467     -12.762  -9.308  -6.372  1.00 78.89      3
ATOM   7820  CB  HIS B 467     -13.292 -10.047  -7.588  1.00 73.81      3
ATOM   7821  CG  HIS B 467     -14.114  -9.187  -8.492  1.00 68.83      3
ATOM   7822  CD2 HIS B 467     -13.830  -8.630  -9.692  1.00 66.49      3
ATOM   7823  ND1 HIS B 467     -15.399  -8.800  -8.183  1.00 67.24      3
ATOM   7824  CE1 HIS B 467     -15.874  -8.046  -9.158  1.00 66.13      3
ATOM   7825  NE2 HIS B 467     -14.942  -7.927 -10.085  1.00 65.11      3
ATOM   7826  C   HIS B 467     -11.840 -10.218  -5.568  1.00 80.41      3
ATOM   7827  O   HIS B 467     -12.295 -11.119  -4.854  1.00 79.96      3
ATOM   7828  N   GLY B 468     -10.539  -9.986  -5.712  1.00 81.75      3
```

FIGURE 5- 104 -

```
ATOM   7829  CA  GLY B 468      -9.547 -10.742  -4.971  1.00 82.79      B
ATOM   7830  C   GLY B 468      -9.389 -12.237  -5.152  1.00 83.47      B
ATOM   7831  O   GLY B 468     -10.315 -13.013  -4.929  1.00 84.23      B
ATOM   7832  N   LEU B 469      -8.186 -12.626  -5.559  1.00 84.16      B
ATOM   7833  CA  LEU B 469      -7.805 -14.023  -5.732  1.00 84.38      B
ATOM   7834  CB  LEU B 469      -7.321 -14.570  -4.370  1.00 86.37      B
ATOM   7835  CG  LEU B 469      -7.376 -13.653  -3.123  1.00 87.45      B
ATOM   7836  CD1 LEU B 469      -7.039 -14.455  -1.861  1.00 86.89      B
ATOM   7837  CD2 LEU B 469      -6.403 -12.480  -3.280  1.00 87.07      B
ATOM   7838  C   LEU B 469      -8.842 -14.986  -6.343  1.00 83.22      B
ATOM   7839  O   LEU B 469      -8.843 -15.227  -7.555  1.00 82.34      B
ATOM   7840  N   SER B 470      -9.709 -15.531  -5.489  1.00 81.75      B
ATOM   7841  CA  SER B 470     -10.744 -16.501  -5.867  1.00 80.56      B
ATOM   7842  CB  SER B 470     -11.683 -16.744  -4.680  1.00 80.17      B
ATOM   7843  OG  SER B 470     -12.503 -15.615  -4.428  1.00 77.77      B
ATOM   7844  C   SER B 470     -11.604 -16.243  -7.105  1.00 80.35      B
ATOM   7845  O   SER B 470     -12.302 -17.142  -7.564  1.00 80.38      B
ATOM   7846  N   ALA B 471     -11.580 -15.033  -7.646  1.00 80.22      B
ATOM   7847  CA  ALA B 471     -12.387 -14.736  -8.824  1.00 79.61      B
ATOM   7848  CB  ALA B 471     -12.376 -13.238  -9.095  1.00 79.64      B
ATOM   7849  C   ALA B 471     -11.892 -15.503 -10.056  1.00 80.31      B
ATOM   7850  O   ALA B 471     -12.358 -15.275 -11.180  1.00 79.87      B
ATOM   7851  N   PHE B 472     -10.948 -16.416  -9.839  1.00 80.07      B
ATOM   7852  CA  PHE B 472     -10.392 -17.214 -10.928  1.00 79.58      B
ATOM   7853  CB  PHE B 472      -8.917 -16.865 -11.146  1.00 79.72      B
ATOM   7854  CG  PHE B 472      -8.665 -15.415 -11.442  1.00 79.36      B
ATOM   7855  CD1 PHE B 472      -9.257 -14.798 -12.537  1.00 79.70      B
ATOM   7856  CD2 PHE B 472      -7.799 -14.675 -10.646  1.00 79.91      B
ATOM   7857  CE1 PHE B 472      -8.981 -13.463 -12.841  1.00 79.55      B
ATOM   7858  CE2 PHE B 472      -7.517 -13.341 -10.942  1.00 79.45      B
ATOM   7859  CZ  PHE B 472      -8.110 -12.736 -12.041  1.00 79.10      B
ATOM   7860  C   PHE B 472     -10.500 -18.706 -10.623  1.00 78.56      B
ATOM   7861  O   PHE B 472     -10.395 -19.543 -11.520  1.00 78.36      B
ATOM   7862  N   THR B 473     -10.708 -19.028  -9.352  1.00 77.22      B
ATOM   7863  CA  THR B 473     -10.805 -20.413  -8.922  1.00 75.89      B
ATOM   7864  CB  THR B 473      -9.714 -20.735  -7.871  1.00 76.42      B
ATOM   7865  OG1 THR B 473      -9.975 -20.015  -6.656  1.00 75.87      B
ATOM   7866  CG2 THR B 473      -8.350 -20.339  -8.398  1.00 76.17      B
ATOM   7867  C   THR B 473     -12.164 -20.748  -8.324  1.00 74.74      B
ATOM   7868  O   THR B 473     -12.264 -21.575  -7.420  1.00 74.72      B
ATOM   7869  N   LEU B 474     -13.219 -20.114  -8.814  1.00 73.42      B
ATOM   7870  CA  LEU B 474     -14.530 -20.410  -8.264  1.00 72.76      B
ATOM   7871  CB  LEU B 474     -15.433 -19.178  -8.293  1.00 71.50      B
ATOM   7872  CG  LEU B 474     -15.051 -18.074  -7.307  1.00 71.54      B
ATOM   7873  CD1 LEU B 474     -16.154 -17.025  -7.279  1.00 71.46      B
ATOM   7874  CD2 LEU B 474     -14.838 -18.665  -5.917  1.00 70.38      B
ATOM   7875  C   LEU B 474     -15.198 -21.550  -8.994  1.00 72.73      B
ATOM   7876  O   LEU B 474     -15.185 -21.610 -10.223  1.00 72.20      B
ATOM   7877  N   HIS B 475     -15.769 -22.463  -8.217  1.00 73.33      B
ATOM   7878  CA  HIS B 475     -16.469 -23.619  -8.760  1.00 74.01      B
ATOM   7879  CB  HIS B 475     -15.532 -24.814  -8.890  1.00 73.03      B
ATOM   7880  CG  HIS B 475     -15.144 -25.411  -7.577  1.00 72.65      B
ATOM   7881  CD2 HIS B 475     -15.483 -26.585  -6.996  1.00 73.11      B
ATOM   7882  ND1 HIS B 475     -14.336 -24.756  -6.673  1.00 73.86      B
ATOM   7883  CE1 HIS B 475     -14.194 -25.501  -5.592  1.00 73.88      B
ATOM   7884  NE2 HIS B 475     -14.881 -26.616  -5.761  1.00 73.77      B
ATOM   7885  C   HIS B 475     -17.587 -23.989  -7.802  1.00 74.94      B
ATOM   7886  O   HIS B 475     -17.718 -23.397  -6.724  1.00 74.98      B
ATOM   7887  N   SER B 476     -18.379 -24.982  -8.197  1.00 75.48      B
ATOM   7888  CA  SER B 476     -19.489 -25.455  -7.382  1.00 75.57      B
ATOM   7889  CB  SER B 476     -18.965 -25.957  -6.031  1.00 77.23      B
ATOM   7890  OG  SER B 476     -20.026 -26.377  -5.188  1.00 80.25      B
ATOM   7891  C   SER B 476     -20.508 -24.337  -7.179  1.00 74.76      B
ATOM   7892  O   SER B 476     -21.016 -24.128  -6.071  1.00 74.02      B
ATOM   7893  N   TYR B 477     -20.798 -23.617  -8.259  1.00 73.99      B
ATOM   7894  CA  TYR B 477     -21.758 -22.523  -8.205  1.00 73.42      B
ATOM   7895  CB  TYR B 477     -21.915 -21.858  -9.578  1.00 72.39      B
ATOM   7896  CG  TYR B 477     -20.792 -20.916  -9.972  1.00 71.96      B
ATOM   7897  CD1 TYR B 477     -19.616 -21.395 -10.548  1.00 71.31      B
ATOM   7898  CE1 TYR B 477     -18.594 -20.519 -10.934  1.00 70.06      B
ATOM   7899  CD2 TYR B 477     -20.917 -19.534  -9.786  1.00 71.89      B
ATOM   7900  CE2 TYR B 477     -19.902 -18.654 -10.166  1.00 70.18      B
ATOM   7901  CZ  TYR B 477     -18.749 -19.154 -10.741  1.00 69.33      B
ATOM   7902  OH  TYR B 477     -17.762 -18.292 -11.148  1.00 69.29      B
ATOM   7903  C   TYR B 477     -23.118 -23.025  -7.739  1.00 73.00      B
ATOM   7904  O   TYR B 477     -23.472 -24.180  -7.959  1.00 73.01      B
```

FIGURE 5-105-

```
ATOM   7905  N    SER B 478     -23.873 -22.145  -7.094  1.00 72.65      B
ATOM   7906  CA   SER B 478     -25.201 -22.481  -6.599  1.00 72.38      B
ATOM   7907  CB   SER B 478     -25.900 -21.213  -6.099  1.00 72.00      B
ATOM   7908  OG   SER B 478     -27.295 -21.417  -5.955  1.00 69.75      B
ATOM   7909  C    SER B 478     -26.073 -23.134  -7.668  1.00 72.95      B
ATOM   7910  O    SER B 478     -25.925 -22.857  -8.860  1.00 72.67      B
ATOM   7911  N    PRO B 479     -26.984 -24.033  -7.254  1.00 72.91      B
ATOM   7912  CD   PRO B 479     -27.082 -24.711  -5.951  1.00 73.50      B
ATOM   7913  CA   PRO B 479     -27.857 -24.681  -8.235  1.00 72.32      B
ATOM   7914  CB   PRO B 479     -28.647 -25.677  -7.390  1.00 72.02      B
ATOM   7915  CG   PRO B 479     -27.668 -26.057  -6.341  1.00 73.29      B
ATOM   7916  C    PRO B 479     -28.748 -23.605  -8.843  1.00 71.27      B
ATOM   7917  O    PRO B 479     -28.786 -23.431 -10.063  1.00 71.96      B
ATOM   7918  N    GLY B 480     -29.446 -22.873  -7.978  1.00 69.70      B
ATOM   7919  CA   GLY B 480     -30.322 -21.813  -8.446  1.00 69.00      B
ATOM   7920  C    GLY B 480     -29.607 -20.863  -9.388  1.00 68.19      B
ATOM   7921  O    GLY B 480     -30.151 -20.461 -10.421  1.00 67.47      B
ATOM   7922  N    GLU B 481     -28.374 -20.514  -9.030  1.00 67.55      B
ATOM   7923  CA   GLU B 481     -27.562 -19.610  -9.830  1.00 67.53      B
ATOM   7924  CB   GLU B 481     -26.261 -19.283  -9.090  1.00 66.90      B
ATOM   7925  CG   GLU B 481     -25.414 -18.200  -9.755  1.00 65.50      B
ATOM   7926  CD   GLU B 481     -26.196 -16.925 -10.021  1.00 64.93      B
ATOM   7927  OE1  GLU B 481     -26.889 -16.438  -9.096  1.00 64.06      B
ATOM   7928  OE2  GLU B 481     -26.109 -16.407 -11.155  1.00 64.41      B
ATOM   7929  C    GLU B 481     -27.252 -20.230 -11.189  1.00 68.36      B
ATOM   7930  O    GLU B 481     -27.503 -19.613 -12.232  1.00 68.65      B
ATOM   7931  N    ILE B 482     -26.709 -21.448 -11.170  1.00 68.26      B
ATOM   7932  CA   ILE B 482     -26.366 -22.168 -12.397  1.00 67.51      B
ATOM   7933  CB   ILE B 482     -25.894 -23.609 -12.102  1.00 66.45      B
ATOM   7934  CG2  ILE B 482     -25.658 -24.345 -13.404  1.00 65.37      B
ATOM   7935  CG1  ILE B 482     -24.617 -23.594 -11.262  1.00 65.57      B
ATOM   7936  CD1  ILE B 482     -24.141 -24.977 -10.846  1.00 63.74      B
ATOM   7937  C    ILE B 482     -27.595 -22.256 -13.295  1.00 67.84      B
ATOM   7938  O    ILE B 482     -27.498 -22.189 -14.522  1.00 67.40      B
ATOM   7939  N    ASN B 483     -28.756 -22.403 -12.666  1.00 68.34      B
ATOM   7940  CA   ASN B 483     -30.008 -22.505 -13.394  1.00 68.71      B
ATOM   7941  CB   ASN B 483     -31.119 -22.967 -12.453  1.00 71.66      B
ATOM   7942  CG   ASN B 483     -30.934 -24.405 -12.013  1.00 75.35      B
ATOM   7943  OD1  ASN B 483     -30.798 -25.312 -12.843  1.00 76.73      B
ATOM   7944  ND2  ASN B 483     -30.929 -24.625 -10.700  1.00 76.84      B
ATOM   7945  C    ASN B 483     -30.410 -21.210 -14.068  1.00 67.08      B
ATOM   7946  O    ASN B 483     -30.673 -21.194 -15.266  1.00 67.13      B
ATOM   7947  N    ARG B 484     -30.457 -20.125 -13.303  1.00 65.92      B
ATOM   7948  CA   ARG B 484     -30.834 -18.838 -13.866  1.00 64.77      B
ATOM   7949  CB   ARG B 484     -30.679 -17.728 -12.826  1.00 64.31      B
ATOM   7950  CG   ARG B 484     -31.011 -16.352 -13.381  1.00 64.57      B
ATOM   7951  CD   ARG B 484     -31.036 -15.290 -12.306  1.00 64.57      B
ATOM   7952  NE   ARG B 484     -29.793 -15.252 -11.549  1.00 65.45      B
ATOM   7953  CZ   ARG B 484     -29.520 -14.339 -10.627  1.00 66.17      B
ATOM   7954  NH1  ARG B 484     -30.405 -13.390 -10.355  1.00 65.59      B
ATOM   7955  NH2  ARG B 484     -28.369 -14.379  -9.971  1.00 67.27      B
ATOM   7956  C    ARG B 484     -30.001 -18.506 -15.101  1.00 64.29      B
ATOM   7957  O    ARG B 484     -30.490 -17.873 -16.039  1.00 62.98      B
ATOM   7958  N    VAL B 485     -28.743 -18.938 -15.097  1.00 64.51      B
ATOM   7959  CA   VAL B 485     -27.850 -18.686 -16.223  1.00 65.18      B
ATOM   7960  CB   VAL B 485     -26.398 -19.061 -15.881  1.00 64.00      B
ATOM   7961  CG1  VAL B 485     -25.472 -18.614 -17.003  1.00 63.14      B
ATOM   7962  CG2  VAL B 485     -25.996 -18.430 -14.562  1.00 63.10      B
ATOM   7963  C    VAL B 485     -28.285 -19.500 -17.440  1.00 66.92      B
ATOM   7964  O    VAL B 485     -28.561 -18.946 -18.505  1.00 66.67      B
ATOM   7965  N    ALA B 486     -28.345 -20.819 -17.268  1.00 68.91      B
ATOM   7966  CA   ALA B 486     -28.747 -21.730 -18.333  1.00 70.02      B
ATOM   7967  CB   ALA B 486     -28.867 -23.148 -17.791  1.00 69.56      B
ATOM   7968  C    ALA B 486     -30.065 -21.312 -18.995  1.00 70.66      B
ATOM   7969  O    ALA B 486     -30.156 -21.203 -20.224  1.00 70.35      B
ATOM   7970  N    SER B 487     -31.087 -21.080 -18.173  1.00 70.56      B
ATOM   7971  CA   SER B 487     -32.380 -20.686 -18.710  1.00 71.97      B
ATOM   7972  CB   SER B 487     -33.401 -20.543 -17.577  1.00 72.41      B
ATOM   7973  OG   SER B 487     -32.882 -19.784 -16.502  1.00 74.49      B
ATOM   7974  C    SER B 487     -32.287 -19.396 -19.515  1.00 72.76      B
ATOM   7975  O    SER B 487     -32.965 -19.253 -20.534  1.00 72.53      B
ATOM   7976  N    CYS B 488     -31.446 -18.463 -19.067  1.00 73.87      B
ATOM   7977  CA   CYS B 488     -31.280 -17.194 -19.773  1.00 73.63      B
ATOM   7978  CB   CYS B 488     -30.414 -16.225 -18.968  1.00 74.72      B
ATOM   7979  SG   CYS B 488     -30.089 -14.643 -19.822  1.00 77.83      B
ATOM   7980  C    CYS B 488     -30.635 -17.444 -21.126  1.00 73.01      B
```

FIGURE 5- 106 -

```
ATOM   7981  O    CYS B 488     -31.092 -16.921 -22.142  1.00 72.49      B
ATOM   7982  N    LEU B 489     -29.570 -18.241 -21.135  1.00 73.00      B
ATOM   7983  CA   LEU B 489     -28.885 -18.569 -22.380  1.00 73.88      B
ATOM   7984  CB   LEU B 489     -27.746 -19.562 -22.130  1.00 73.37      B
ATOM   7985  CG   LEU B 489     -26.479 -19.000 -21.480  1.00 72.81      B
ATOM   7986  CD1  LEU B 489     -25.500 -20.125 -21.218  1.00 72.58      B
ATOM   7987  CD2  LEU B 489     -25.850 -17.956 -22.393  1.00 72.55      B
ATOM   7988  C    LEU B 489     -29.908 -19.173 -23.334  1.00 74.86      B
ATOM   7989  O    LEU B 489     -29.860 -18.940 -24.547  1.00 74.75      B
ATOM   7990  N    ARG B 490     -30.838 -19.946 -22.777  1.00 75.17      B
ATOM   7991  CA   ARG B 490     -31.893 -20.549 -23.578  1.00 75.12      B
ATOM   7992  CB   ARG B 490     -32.718 -21.533 -22.742  1.00 75.56      B
ATOM   7993  CG   ARG B 490     -32.122 -22.933 -22.653  1.00 76.58      B
ATOM   7994  CD   ARG B 490     -33.117 -23.922 -22.044  1.00 76.42      B
ATOM   7995  NE   ARG B 490     -33.058 -24.011 -20.585  1.00 74.98      B
ATOM   7996  CZ   ARG B 490     -32.006 -24.465 -19.905  1.00 75.43      B
ATOM   7997  NH1  ARG B 490     -30.912 -24.864 -20.548  1.00 75.09      B
ATOM   7998  NH2  ARG B 490     -32.056 -24.550 -18.583  1.00 74.86      B
ATOM   7999  C    ARG B 490     -32.804 -19.454 -24.124  1.00 74.80      B
ATOM   8000  O    ARG B 490     -33.102 -19.431 -25.315  1.00 75.26      B
ATOM   8001  N    LYS B 491     -33.232 -18.539 -23.255  1.00 74.70      B
ATOM   8002  CA   LYS B 491     -34.116 -17.451 -23.667  1.00 74.24      B
ATOM   8003  CB   LYS B 491     -34.487 -16.557 -22.478  1.00 74.59      B
ATOM   8004  CG   LYS B 491     -35.309 -15.327 -22.889  1.00 74.82      B
ATOM   8005  CD   LYS B 491     -35.834 -14.520 -21.699  1.00 75.22      B
ATOM   8006  CE   LYS B 491     -34.716 -13.849 -20.916  1.00 74.96      B
ATOM   8007  NZ   LYS B 491     -35.249 -13.041 -19.778  1.00 74.30      B
ATOM   8008  C    LYS B 491     -33.522 -16.579 -24.763  1.00 74.21      B
ATOM   8009  O    LYS B 491     -34.191 -16.287 -25.757  1.00 74.28      B
ATOM   8010  N    LEU B 492     -32.275 -16.153 -24.580  1.00 73.51      B
ATOM   8011  CA   LEU B 492     -31.619 -15.300 -25.569  1.00 72.92      B
ATOM   8012  CB   LEU B 492     -30.470 -14.519 -24.928  1.00 71.01      B
ATOM   8013  CG   LEU B 492     -30.824 -13.154 -24.336  1.00 70.08      B
ATOM   8014  CD1  LEU B 492     -32.068 -13.244 -23.472  1.00 70.57      B
ATOM   8015  CD2  LEU B 492     -29.656 -12.661 -23.520  1.00 70.15      B
ATOM   8016  C    LEU B 492     -31.098 -16.084 -26.760  1.00 73.22      B
ATOM   8017  O    LEU B 492     -30.717 -15.502 -27.776  1.00 74.00      B
ATOM   8018  N    GLY B 493     -31.090 -17.406 -26.643  1.00 72.88      B
ATOM   8019  CA   GLY B 493     -30.602 -18.221 -27.738  1.00 72.96      B
ATOM   8020  C    GLY B 493     -29.092 -18.127 -27.861  1.00 73.33      B
ATOM   8021  O    GLY B 493     -28.564 -17.582 -28.830  1.00 73.38      B
ATOM   8022  N    VAL B 494     -28.395 -18.664 -26.867  1.00 72.78      B
ATOM   8023  CA   VAL B 494     -26.941 -18.653 -26.846  1.00 71.27      B
ATOM   8024  CB   VAL B 494     -26.413 -17.644 -25.792  1.00 70.89      B
ATOM   8025  CG1  VAL B 494     -24.891 -17.603 -25.811  1.00 69.50      B
ATOM   8026  CG2  VAL B 494     -26.990 -16.266 -26.064  1.00 69.98      B
ATOM   8027  C    VAL B 494     -26.451 -20.053 -26.488  1.00 70.64      B
ATOM   8028  O    VAL B 494     -27.005 -20.706 -25.602  1.00 69.33      B
ATOM   8029  N    PRO B 495     -25.417 -20.541 -27.189  1.00 70.77      B
ATOM   8030  CD   PRO B 495     -24.698 -19.898 -28.308  1.00 70.63      B
ATOM   8031  CA   PRO B 495     -24.874 -21.875 -26.909  1.00 71.19      B
ATOM   8032  CB   PRO B 495     -23.520 -21.832 -27.602  1.00 70.60      B
ATOM   8033  CG   PRO B 495     -23.828 -21.030 -28.844  1.00 70.94      B
ATOM   8034  C    PRO B 495     -24.761 -22.140 -25.399  1.00 71.64      B
ATOM   8035  O    PRO B 495     -24.247 -21.304 -24.651  1.00 71.90      B
ATOM   8036  N    PRO B 496     -25.242 -23.307 -24.933  1.00 71.33      B
ATOM   8037  CD   PRO B 496     -25.537 -24.515 -25.698  1.00 70.77      B
ATOM   8038  CA   PRO B 496     -25.166 -23.612 -23.503  1.00 71.95      B
ATOM   8039  CB   PRO B 496     -25.699 -25.038 -23.423  1.00 71.40      B
ATOM   8040  CG   PRO B 496     -25.249 -25.619 -24.715  1.00 71.67      B
ATOM   8041  C    PRO B 496     -23.743 -23.488 -22.987  1.00 72.58      B
ATOM   8042  O    PRO B 496     -22.785 -23.521 -23.760  1.00 72.79      B
ATOM   8043  N    LEU B 497     -23.613 -23.345 -21.676  1.00 73.44      B
ATOM   8044  CA   LEU B 497     -22.310 -23.191 -21.048  1.00 74.61      B
ATOM   8045  CB   LEU B 497     -22.435 -23.463 -19.547  1.00 73.00      B
ATOM   8046  CG   LEU B 497     -23.459 -22.570 -18.835  1.00 71.36      B
ATOM   8047  CD1  LEU B 497     -23.579 -22.977 -17.379  1.00 70.97      B
ATOM   8048  CD2  LEU B 497     -23.041 -21.112 -18.954  1.00 70.45      B
ATOM   8049  C    LEU B 497     -21.253 -24.094 -21.674  1.00 76.34      B
ATOM   8050  O    LEU B 497     -20.082 -23.723 -21.758  1.00 75.68      B
ATOM   8051  N    ARG B 498     -21.679 -25.268 -22.132  1.00 79.57      B
ATOM   8052  CA   ARG B 498     -20.784 -26.241 -22.753  1.00 82.14      B
ATOM   8053  CB   ARG B 498     -21.568 -27.496 -23.136  1.00 84.67      B
ATOM   8054  CG   ARG B 498     -22.159 -28.236 -21.948  1.00 89.32      B
ATOM   8055  CD   ARG B 498     -21.070 -28.881 -21.095  1.00 92.30      B
ATOM   8056  NE   ARG B 498     -21.623 -29.555 -19.923  1.00 94.50      B
```

FIGURE 5- 107 -

```
ATOM   8057  CZ   ARG B 498     -20.920 -30.334 -19.108  1.00 95.80      B
ATOM   8058  NH1  ARG B 498     -19.626 -30.545 -19.338  1.00 96.10      B
ATOM   8059  NH2  ARG B 498     -21.512 -30.895 -19.061  1.00 96.02      B
ATOM   8060  C    ARG B 498     -20.057 -25.703 -23.983  1.00 82.47      B
ATOM   8061  O    ARG B 498     -18.826 -25.678 -24.020  1.00 83.33      B
ATOM   8062  N    THR B 499     -20.815 -25.281 -24.990  1.00 82.15      B
ATOM   8063  CA   THR B 499     -20.220 -24.754 -26.212  1.00 82.80      B
ATOM   8064  CB   THR B 499     -21.287 -24.135 -27.137  1.00 84.30      B
ATOM   8065  OG1  THR B 499     -22.242 -25.140 -27.502  1.00 85.69      B
ATOM   8066  CG2  THR B 499     -20.640 -23.570 -28.408  1.00 84.87      B
ATOM   8067  C    THR B 499     -19.184 -23.691 -25.876  1.00 82.49      B
ATOM   8068  O    THR B 499     -18.182 -23.544 -26.573  1.00 82.67      B
ATOM   8069  N    TRP B 500     -19.436 -22.948 -24.804  1.00 82.14      B
ATOM   8070  CA   TRP B 500     -18.513 -21.907 -24.369  1.00 81.26      B
ATOM   8071  CB   TRP B 500     -19.181 -20.995 -23.336  1.00 78.17      B
ATOM   8072  CG   TRP B 500     -20.227 -20.111 -23.915  1.00 74.03      B
ATOM   8073  CD2  TRP B 500     -20.026 -19.070 -24.872  1.00 72.46      B
ATOM   8074  CE2  TRP B 500     -21.293 -18.517 -25.161  1.00 72.15      B
ATOM   8075  CE3  TRP B 500     -18.898 -18.558 -25.527  1.00 71.80      B
ATOM   8076  CD1  TRP B 500     -21.566 -20.144 -23.658  1.00 72.98      B
ATOM   8077  NE1  TRP B 500     -22.216 -19.188 -24.402  1.00 72.33      B
ATOM   8078  CZ2  TRP B 500     -21.465 -17.465 -26.072  1.00 72.05      B
ATOM   8079  CZ3  TRP B 500     -19.068 -17.514 -26.435  1.00 72.95      B
ATOM   8080  CH2  TRP B 500     -20.346 -16.982 -26.701  1.00 72.01      B
ATOM   8081  C    TRP B 500     -17.270 -22.549 -23.764  1.00 82.49      B
ATOM   8082  O    TRP B 500     -16.156 -22.056 -23.939  1.00 82.97      B
ATOM   8083  N    ARG B 501     -17.468 -23.649 -23.044  1.00 82.97      B
ATOM   8084  CA   ARG B 501     -16.359 -24.364 -22.424  1.00 84.35      B
ATOM   8085  CB   ARG B 501     -16.880 -25.548 -21.616  1.00 86.32      B
ATOM   8086  CG   ARG B 501     -15.788 -26.369 -20.966  1.00 89.56      B
ATOM   8087  CD   ARG B 501     -16.345 -27.551 -20.200  1.00 92.50      B
ATOM   8088  NE   ARG B 501     -15.256 -28.354 -19.656  1.00 96.10      B
ATOM   8089  CZ   ARG B 501     -14.359 -27.901 -18.783  1.00 97.87      B
ATOM   8090  NH1  ARG B 501     -14.427 -26.648 -18.351  1.00 99.31      B
ATOM   8091  NH2  ARG B 501     -13.387 -28.694 -18.349  1.00 98.43      B
ATOM   8092  C    ARG B 501     -15.388 -24.862 -23.495  1.00 84.07      B
ATOM   8093  O    ARG B 501     -14.182 -24.967 -23.257  1.00 82.93      B
ATOM   8094  N    HIS B 502     -15.917 -25.172 -24.674  1.00 84.94      B
ATOM   8095  CA   HIS B 502     -15.081 -25.632 -25.772  1.00 86.46      B
ATOM   8096  CB   HIS B 502     -15.953 -26.289 -26.858  1.00 88.93      B
ATOM   8097  CG   HIS B 502     -15.197 -27.202 -27.776  1.00 91.36      B
ATOM   8098  CD2  HIS B 502     -14.813 -27.045 -29.066  1.00 91.71      B
ATOM   8099  ND1  HIS B 502     -14.729 -28.440 -27.384  1.00 91.82      B
ATOM   8100  CE1  HIS B 502     -14.090 -29.005 -28.393  1.00 92.92      B
ATOM   8101  NE2  HIS B 502     -14.126 -28.180 -29.424  1.00 93.14      B
ATOM   8102  C    HIS B 502     -14.354 -24.409 -26.326  1.00 84.18      B
ATOM   8103  O    HIS B 502     -13.132 -24.400 -26.428  1.00 86.19      B
ATOM   8104  N    ARG B 503     -15.121 -23.371 -26.650  1.00 83.67      B
ATOM   8105  CA   ARG B 503     -14.581 -22.120 -27.195  1.00 83.11      B
ATOM   8106  CB   ARG B 503     -15.713 -21.125 -27.478  1.00 83.04      B
ATOM   8107  CG   ARG B 503     -16.868 -21.722 -28.282  1.00 82.21      B
ATOM   8108  CD   ARG B 503     -17.727 -20.632 -28.938  1.00 80.31      B
ATOM   8109  NE   ARG B 503     -18.761 -21.183 -29.824  1.00 83.81      B
ATOM   8110  CZ   ARG B 503     -19.869 -20.524 -30.189  1.00 85.06      B
ATOM   8111  NH1  ARG B 503     -20.092 -19.269 -29.741  1.00 87.36      B
ATOM   8112  NH2  ARG B 503     -20.775 -21.129 -30.981  1.00 86.65      B
ATOM   8113  C    ARG B 503     -13.582 -21.473 -26.241  1.00 83.92      B
ATOM   8114  O    ARG B 503     -12.610 -20.841 -26.666  1.00 86.22      B
ATOM   8115  N    ALA B 504     -13.832 -21.646 -24.946  1.00 83.39      B
ATOM   8116  CA   ALA B 504     -12.976 -21.096 -23.906  1.00 83.64      B
ATOM   8117  CB   ALA B 504     -13.555 -21.414 -22.529  1.00 81.76      B
ATOM   8118  C    ALA B 504     -11.579 -21.680 -24.029  1.00 84.78      B
ATOM   8119  O    ALA B 504     -10.589 -20.986 -23.813  1.00 85.07      B
ATOM   8120  N    ARG B 505     -11.497 -22.956 -24.385  1.00 87.13      B
ATOM   8121  CA   ARG B 505     -10.204 -23.602 -24.524  1.00 89.56      B
ATOM   8122  CB   ARG B 505     -10.386 -25.114 -24.649  1.00 90.38      B
ATOM   8123  CG   ARG B 505     -11.285 -25.709 -23.572  1.00 92.69      B
ATOM   8124  CD   ARG B 505     -11.028 -27.197 -23.372  1.00 94.57      B
ATOM   8125  NE   ARG B 505      -9.663 -27.454 -22.915  1.00 95.83      B
ATOM   8126  CZ   ARG B 505      -9.208 -28.643 -22.530  1.00 96.18      B
ATOM   8127  NH1  ARG B 505     -10.010 -29.698 -22.542  1.00 96.91      B
ATOM   8128  NH2  ARG B 505      -7.950 -28.778 -22.130  1.00 96.36      B
ATOM   8129  C    ARG B 505      -9.437 -23.059 -25.723  1.00 90.36      B
ATOM   8130  O    ARG B 505      -8.235 -22.825 -25.636  1.00 89.82      B
ATOM   8131  N    SER B 506     -10.137 -22.863 -26.837  1.00 92.31      B
ATOM   8132  CA   SER B 506      -9.531 -22.333 -28.058  1.00 95.20      B
```

FIGURE 5- 108 -

```
ATOM   8133  CB   SER B 506     -10.579 -22.273 -29.178  1.00  95.82      B
ATOM   8134  OG   SER B 506     -10.103 -21.557 -30.308  1.00  95.33      B
ATOM   8135  C    SER B 506      -8.971 -20.933 -27.797  1.00  96.86      B
ATOM   8136  O    SER B 506      -7.831 -20.623 -28.156  1.00  96.79      B
ATOM   8137  N    VAL B 507      -9.790 -20.090 -27.174  1.00  98.21      B
ATOM   8138  CA   VAL B 507      -9.387 -18.729 -26.848  1.00  98.94      B
ATOM   8139  CB   VAL B 507     -10.451 -18.028 -25.976  1.00  98.99      B
ATOM   8140  CG1  VAL B 507      -9.958 -16.652 -25.550  1.00  99.20      B
ATOM   8141  CG2  VAL B 507     -11.754 -17.911 -26.750  1.00  99.30      B
ATOM   8142  C    VAL B 507      -8.075 -18.773 -26.078  1.00  99.31      B
ATOM   8143  O    VAL B 507      -7.072 -18.201 -26.506  1.00  99.50      B
ATOM   8144  N    ARG B 508      -8.096 -19.466 -24.944  1.00  99.36      B
ATOM   8145  CA   ARG B 508      -6.926 -19.607 -24.088  1.00 100.11      B
ATOM   8146  CB   ARG B 508      -7.139 -20.748 -23.099  1.00 100.04      B
ATOM   8147  CG   ARG B 508      -5.946 -21.006 -22.206  1.00  99.64      B
ATOM   8148  CD   ARG B 508      -6.085 -22.329 -21.506  1.00  99.87      B
ATOM   8149  NE   ARG B 508      -5.710 -22.229 -20.103  1.00 101.37      B
ATOM   8150  CZ   ARG B 508      -5.675 -23.265 -19.275  1.00 102.69      B
ATOM   8151  NH1  ARG B 508      -5.990 -24.472 -19.724  1.00 102.59      B
ATOM   8152  NH2  ARG B 508      -5.339 -23.094 -18.001  1.00 103.01      B
ATOM   8153  C    ARG B 508      -5.652 -19.883 -24.876  1.00 100.72      B
ATOM   8154  O    ARG B 508      -4.641 -19.201 -24.699  1.00 100.94      B
ATOM   8155  N    ALA B 509      -5.709 -20.896 -25.735  1.00 101.06      B
ATOM   8156  CA   ALA B 509      -4.564 -21.293 -26.546  1.00 100.81      B
ATOM   8157  CB   ALA B 509      -4.918 -22.526 -27.373  1.00 100.74      B
ATOM   8158  C    ALA B 509      -4.081 -20.170 -27.457  1.00 100.51      B
ATOM   8159  O    ALA B 509      -2.914 -19.781 -27.404  1.00 100.26      B
ATOM   8160  N    LYS B 510      -4.978 -19.652 -28.291  1.00 100.52      B
ATOM   8161  CA   LYS B 510      -4.627 -18.579 -29.215  1.00 101.18      B
ATOM   8162  CB   LYS B 510      -5.886 -18.023 -29.885  1.00  99.96      B
ATOM   8163  CG   LYS B 510      -6.661 -19.052 -30.694  1.00  98.79      B
ATOM   8164  CD   LYS B 510      -7.673 -18.388 -31.619  1.00  98.12      B
ATOM   8165  CE   LYS B 510      -8.426 -19.420 -32.449  1.00  97.54      B
ATOM   8166  NZ   LYS B 510      -9.355 -18.781 -33.419  1.00  96.18      B
ATOM   8167  C    LYS B 510      -3.877 -17.454 -28.507  1.00 102.61      B
ATOM   8168  O    LYS B 510      -2.996 -16.816 -29.089  1.00 103.15      B
ATOM   8169  N    LEU B 511      -4.227 -17.220 -27.246  1.00 103.80      B
ATOM   8170  CA   LEU B 511      -3.599 -16.173 -26.444  1.00 104.18      B
ATOM   8171  CB   LEU B 511      -4.610 -15.618 -25.439  1.00 104.12      B
ATOM   8172  CG   LEU B 511      -5.750 -14.783 -26.027  1.00 104.75      B
ATOM   8173  CD1  LEU B 511      -6.829 -14.571 -24.978  1.00 104.68      B
ATOM   8174  CD2  LEU B 511      -5.200 -13.454 -26.522  1.00 104.45      B
ATOM   8175  C    LEU B 511      -2.365 -16.677 -25.702  1.00 104.54      B
ATOM   8176  O    LEU B 511      -1.372 -15.959 -25.564  1.00 104.39      B
ATOM   8177  N    LEU B 512      -2.440 -17.916 -25.225  1.00 105.14      B
ATOM   8178  CA   LEU B 512      -1.347 -18.547 -24.489  1.00 105.33      B
ATOM   8179  CB   LEU B 512      -1.789 -19.932 -24.008  1.00 104.22      B
ATOM   8180  CG   LEU B 512      -1.368 -20.366 -22.602  1.00 103.19      B
ATOM   8181  CD1  LEU B 512      -1.852 -19.355 -21.576  1.00 103.27      B
ATOM   8182  CD2  LEU B 512      -1.945 -21.734 -22.307  1.00 102.35      B
ATOM   8183  C    LEU B 512      -0.114 -18.673 -25.391  1.00 106.05      B
ATOM   8184  O    LEU B 512       0.979 -19.012 -24.933  1.00 105.74      B
ATOM   8185  N    SER B 513      -0.319 -18.384 -26.676  1.00 106.96      B
ATOM   8186  CA   SER B 513       0.710 -18.440 -27.714  1.00 107.38      B
ATOM   8187  CB   SER B 513       0.110 -19.066 -28.978  1.00 106.80      B
ATOM   8188  OG   SER B 513      -0.790 -18.144 -29.585  1.00 106.33      B
ATOM   8189  C    SER B 513       1.178 -17.021 -28.035  1.00 108.15      B
ATOM   8190  O    SER B 513       1.560 -16.740 -29.176  1.00 107.62      B
ATOM   8191  N    GLN B 514       1.137 -16.139 -27.034  1.00 109.03      B
ATOM   8192  CA   GLN B 514       1.528 -14.747 -27.241  1.00 110.18      B
ATOM   8193  CB   GLN B 514       0.441 -14.068 -28.102  1.00 110.89      B
ATOM   8194  CG   GLN B 514       0.563 -12.553 -28.319  1.00 111.98      B
ATOM   8195  CD   GLN B 514      -0.763 -11.890 -28.705  1.00 112.46      B
ATOM   8196  OE1  GLN B 514      -1.833 -12.514 -28.681  1.00 112.66      B
ATOM   8197  NE2  GLN B 514      -0.693 -10.609 -29.050  1.00 112.12      B
ATOM   8198  C    GLN B 514       1.832 -13.904 -25.977  1.00 110.70      B
ATOM   8199  O    GLN B 514       2.711 -14.247 -25.192  1.00 110.53      B
ATOM   8200  N    GLY B 515       1.091 -12.815 -25.790  1.00 111.65      B
ATOM   8201  CA   GLY B 515       1.304 -11.900 -24.679  1.00 112.64      B
ATOM   8202  C    GLY B 515       2.511 -12.006 -23.764  1.00 113.50      B
ATOM   8203  O    GLY B 515       3.680 -11.888 -24.134  1.00 113.46      B
ATOM   8204  N    GLY B 516       2.149 -12.224 -22.516  1.00 114.21      B
ATOM   8205  CA   GLY B 516       3.037 -12.338 -21.376  1.00 114.53      B
ATOM   8206  C    GLY B 516       1.818 -11.974 -20.587  1.00 115.04      B
ATOM   8207  O    GLY B 516       1.358 -12.663 -19.667  1.00 115.48      B
ATOM   8208  N    ARG B 517       1.248 -10.877 -21.082  1.00 115.12      B
```

FIGURE 5- 109 -

```
ATOM   8209  CA   ARG B 517    0.004 -10.318 -20.584  1.00114.63      B
ATOM   8210  CB   ARG B 517   -0.195  -8.865 -21.034  1.00114.87      B
ATOM   8211  CG   ARG B 517    0.560  -7.784 -20.234  1.00114.87      B
ATOM   8212  CD   ARG B 517    1.230  -6.863 -21.221  1.00114.05      B
ATOM   8213  NE   ARG B 517    1.926  -7.722 -22.166  1.00113.58      B
ATOM   8214  CZ   ARG B 517    2.113  -7.453 -23.449  1.00112.88      B
ATOM   8215  NH1  ARG B 517    1.668  -6.319 -23.975  1.00112.41      B
ATOM   8216  NH2  ARG B 517    2.700  -8.358 -24.217  1.00112.48      B
ATOM   8217  C    ARG B 517   -1.092 -11.159 -21.215  1.00114.19      B
ATOM   8218  O    ARG B 517   -1.787 -11.884 -20.513  1.00113.51      B
ATOM   8219  N    ALA B 518   -1.239 -11.086 -22.541  1.00113.95      B
ATOM   8220  CA   ALA B 518   -2.281 -11.879 -23.201  1.00113.99      B
ATOM   8221  CB   ALA B 518   -2.138 -11.832 -24.741  1.00113.75      B
ATOM   8222  C    ALA B 518   -2.277 -13.325 -22.696  1.00113.64      B
ATOM   8223  O    ALA B 518   -3.338 -13.937 -22.593  1.00113.37      B
ATOM   8224  N    ALA B 519   -1.113 -13.877 -22.362  1.00113.51      B
ATOM   8225  CA   ALA B 519   -1.111 -15.237 -21.827  1.00113.31      B
ATOM   8226  CB   ALA B 519    0.290 -15.771 -21.732  1.00113.23      B
ATOM   8227  C    ALA B 519   -1.759 -15.207 -20.442  1.00113.09      B
ATOM   8228  O    ALA B 519   -2.634 -16.025 -20.147  1.00113.26      B
ATOM   8229  N    THR B 520   -1.327 -14.256 -19.608  1.00112.98      B
ATOM   8230  CA   THR B 520   -1.863 -14.064 -18.253  1.00112.76      B
ATOM   8231  CB   THR B 520   -1.426 -12.703 -17.666  1.00113.19      B
ATOM   8232  OG1  THR B 520   -0.001 -12.588 -17.734  1.00113.76      B
ATOM   8233  CG2  THR B 520   -1.858 -12.574 -16.214  1.00113.19      B
ATOM   8234  C    THR B 520   -3.379 -14.073 -18.338  1.00112.02      B
ATOM   8235  O    THR B 520   -4.056 -14.729 -17.542  1.00111.98      B
ATOM   8236  N    CYS B 521   -3.894 -13.339 -19.324  1.00110.68      B
ATOM   8237  CA   CYS B 521   -5.328 -13.263 -19.567  1.00109.09      B
ATOM   8238  CB   CYS B 521   -5.613 -12.478 -20.857  1.00108.50      B
ATOM   8239  SG   CYS B 521   -5.586 -10.663 -20.714  1.00107.44      B
ATOM   8240  C    CYS B 521   -5.878 -14.683 -19.697  1.00108.40      B
ATOM   8241  O    CYS B 521   -6.872 -15.041 -19.061  1.00108.14      B
ATOM   8242  N    GLY B 522   -5.210 -15.484 -20.521  1.00107.33      B
ATOM   8243  CA   GLY B 522   -5.627 -16.855 -20.735  1.00106.33      B
ATOM   8244  C    GLY B 522   -5.361 -17.772 -19.558  1.00106.09      B
ATOM   8245  O    GLY B 522   -6.168 -18.648 -19.241  1.00106.07      B
ATOM   8246  N    ARG B 523   -4.227 -17.573 -18.896  1.00105.83      B
ATOM   8247  CA   ARG B 523   -3.859 -18.395 -17.735  1.00105.37      B
ATOM   8248  CB   ARG B 523   -2.461 -18.006 -17.231  1.00105.94      B
ATOM   8249  CG   ARG B 523   -1.967 -18.845 -16.044  1.00107.00      B
ATOM   8250  CD   ARG B 523   -0.661 -18.318 -15.437  1.00108.32      B
ATOM   8251  NE   ARG B 523   -0.438 -18.855 -14.090  1.00109.75      B
ATOM   8252  CZ   ARG B 523    0.504 -18.426 -13.251  1.00109.95      B
ATOM   8253  NH1  ARG B 523    1.325 -17.448 -13.616  1.00109.82      B
ATOM   8254  NH2  ARG B 523    0.615 -18.963 -12.040  1.00109.61      B
ATOM   8255  C    ARG B 523   -4.863 -18.294 -16.579  1.00104.82      B
ATOM   8256  O    ARG B 523   -5.425 -19.306 -16.161  1.00104.57      B
ATOM   8257  N    TYR B 524   -5.069 -17.078 -16.072  1.00103.92      B
ATOM   8258  CA   TYR B 524   -5.979 -16.821 -14.958  1.00102.61      B
ATOM   8259  CB   TYR B 524   -5.681 -15.428 -14.373  1.00102.63      B
ATOM   8260  CG   TYR B 524   -4.411 -15.367 -13.577  1.00103.39      B
ATOM   8261  CD1  TYR B 524   -3.165 -15.431 -14.201  1.00103.29      B
ATOM   8262  CE1  TYR B 524   -1.982 -15.490 -13.453  1.00103.72      B
ATOM   8263  CD2  TYR B 524   -4.453 -15.345 -12.189  1.00103.84      B
ATOM   8264  CE2  TYR B 524   -3.276 -15.404 -11.428  1.00104.45      B
ATOM   8265  CZ   TYR B 524   -2.046 -15.481 -12.069  1.00104.17      B
ATOM   8266  OH   TYR B 524   -0.887 -15.578 -11.329  1.00104.32      B
ATOM   8267  C    TYR B 524   -7.471 -16.946 -15.225  1.00101.55      B
ATOM   8268  O    TYR B 524   -8.171 -17.733 -14.591  1.00101.52      B
ATOM   8269  N    LEU B 525   -7.939 -16.152 -16.167  1.00 99.94      B
ATOM   8270  CA   LEU B 525   -9.342 -16.143 -16.523  1.00 98.45      B
ATOM   8271  CB   LEU B 525   -9.574 -15.177 -17.680  1.00 98.25      B
ATOM   8272  CG   LEU B 525   -8.938 -13.799 -17.521  1.00 98.40      B
ATOM   8273  CD1  LEU B 525   -9.289 -12.923 -18.712  1.00 98.03      B
ATOM   8274  CD2  LEU B 525   -9.415 -13.163 -16.230  1.00 98.79      B
ATOM   8275  C    LEU B 525   -9.909 -17.520 -16.897  1.00 97.68      B
ATOM   8276  O    LEU B 525  -10.867 -17.986 -16.283  1.00 97.40      B
ATOM   8277  N    PHE B 526   -9.297 -18.180 -17.878  1.00 96.48      B
ATOM   8278  CA   PHE B 526   -9.796 -19.454 -18.354  1.00 95.25      B
ATOM   8279  CB   PHE B 526   -9.607 -19.517 -19.872  1.00 93.24      B
ATOM   8280  CG   PHE B 526  -10.158 -18.307 -20.619  1.00 91.87      B
ATOM   8281  CD1  PHE B 526  -11.520 -18.027 -20.618  1.00 91.31      B
ATOM   8282  CD2  PHE B 526   -9.308 -17.440 -21.312  1.00 91.56      B
ATOM   8283  CE1  PHE B 526  -12.032 -16.895 -21.278  1.00 90.45      B
ATOM   8284  CE2  PHE B 526   -9.809 -16.307 -21.975  1.00 89.94      B
```

FIGURE 5- 110 -

```
ATOM   8285  CZ   PHE B 526     -11.165 -16.036 -21.962  1.00 89.60      B
ATOM   8286  C    PHE B 526      -9.244 -20.737 -17.711  1.00 95.68      B
ATOM   8287  O    PHE B 526      -9.032 -21.722 -18.424  1.00 95.51      B
ATOM   8288  N    ASN B 527      -9.031 -20.773 -16.395  1.00 96.21      B
ATOM   8289  CA   ASN B 527      -8.528 -22.019 -15.825  1.00 96.96      B
ATOM   8290  CB   ASN B 527      -7.641 -21.753 -14.603  1.00 97.03      B
ATOM   8291  CG   ASN B 527      -6.738 -22.937 -14.266  1.00 97.39      B
ATOM   8292  OD1  ASN B 527      -5.966 -23.396 -15.107  1.00 97.05      B
ATOM   8293  ND2  ASN B 527      -6.832 -23.432 -13.027  1.00 96.86      B
ATOM   8294  C    ASN B 527      -9.728 -22.899 -15.483  1.00 97.57      B
ATOM   8295  O    ASN B 527      -9.587 -23.969 -14.896  1.00 97.43      B
ATOM   8296  N    TRP B 528     -10.917 -22.422 -15.853  1.00 98.50      B
ATOM   8297  CA   TRP B 528     -12.160 -23.157 -15.602  1.00 99.78      B
ATOM   8298  CB   TRP B 528     -13.346 -22.199 -15.369  1.00 98.68      B
ATOM   8299  CG   TRP B 528     -13.592 -21.191 -16.509  1.00 97.44      B
ATOM   8300  CD2  TRP B 528     -14.409 -21.386 -17.676  1.00 96.97      B
ATOM   8301  CE2  TRP B 528     -14.291 -20.223 -18.475  1.00 96.60      B
ATOM   8302  CE3  TRP B 528     -15.227 -22.429 -18.123  1.00 97.20      B
ATOM   8303  CD1  TRP B 528     -13.031 -19.948 -16.649  1.00 97.02      B
ATOM   8304  NE1  TRP B 528     -13.446 -19.365 -17.826  1.00 96.54      B
ATOM   8305  CZ2  TRP B 528     -14.957 -20.079 -19.697  1.00 96.19      B
ATOM   8306  CZ3  TRP B 528     -15.887 -22.286 -19.336  1.00 97.26      B
ATOM   8307  CH2  TRP B 528     -15.749 -21.118 -20.108  1.00 96.69      B
ATOM   8308  C    TRP B 528     -12.478 -24.060 -16.782  1.00100.91      B
ATOM   8309  O    TRP B 528     -13.342 -24.940 -16.709  1.00100.56      B
ATOM   8310  N    ALA B 529     -11.758 -23.838 -17.872  1.00102.44      B
ATOM   8311  CA   ALA B 529     -11.955 -24.604 -19.091  1.00104.21      B
ATOM   8312  CB   ALA B 529     -11.729 -23.702 -20.293  1.00103.56      B
ATOM   8313  C    ALA B 529     -11.055 -25.849 -19.184  1.00105.46      B
ATOM   8314  O    ALA B 529     -11.047 -26.529 -20.223  1.00105.33      B
ATOM   8315  N    VAL B 530     -10.311 -26.130 -18.111  1.00107.06      B
ATOM   8316  CA   VAL B 530      -9.432 -27.326 -18.087  1.00108.47      B
ATOM   8317  CB   VAL B 530      -7.999 -26.983 -18.572  1.00107.95      B
ATOM   8318  CG1  VAL B 530      -8.029 -26.457 -19.989  1.00108.00      B
ATOM   8319  CG2  VAL B 530      -7.336 -25.993 -17.618  1.00107.65      B
ATOM   8320  C    VAL B 530      -9.266 -28.055 -16.745  1.00109.74      B
ATOM   8321  O    VAL B 530      -9.119 -27.429 -15.692  1.00109.56      B
ATOM   8322  N    ARG B 531      -9.275 -29.386 -16.805  1.00111.23      B
ATOM   8323  CA   ARG B 531      -9.071 -30.225 -15.626  1.00112.48      B
ATOM   8324  CB   ARG B 531      -9.754 -31.581 -15.796  1.00112.76      B
ATOM   8325  CG   ARG B 531     -11.253 -31.517 -15.976  1.00114.00      B
ATOM   8326  CD   ARG B 531     -11.806 -32.925 -16.048  1.00114.77      B
ATOM   8327  NE   ARG B 531     -13.228 -32.959 -16.366  1.00115.03      B
ATOM   8328  CZ   ARG B 531     -13.933 -34.080 -16.466  1.00114.80      B
ATOM   8329  NH1  ARG B 531     -13.340 -35.251 -16.270  1.00114.52      B
ATOM   8330  NH2  ARG B 531     -15.226 -34.036 -16.765  1.00114.27      B
ATOM   8331  C    ARG B 531      -7.564 -30.428 -15.538  1.00113.04      B
ATOM   8332  O    ARG B 531      -7.080 -31.419 -14.990  1.00113.32      B
ATOM   8333  N    THR B 532      -6.837 -29.489 -16.135  1.00113.71      B
ATOM   8334  CA   THR B 532      -5.374 -29.483 -16.155  1.00114.21      B
ATOM   8335  CB   THR B 532      -4.813 -28.780 -17.429  1.00114.07      B
ATOM   8336  OG1  THR B 532      -5.203 -29.504 -18.603  1.00114.24      B
ATOM   8337  CG2  THR B 532      -3.295 -28.674 -17.361  1.00112.75      B
ATOM   8338  C    THR B 532      -4.980 -28.620 -14.967  1.00114.38      B
ATOM   8339  O    THR B 532      -4.377 -29.087 -13.995  1.00114.87      B
ATOM   8340  N    LYS B 533      -5.359 -27.348 -15.082  1.00113.97      B
ATOM   8341  CA   LYS B 533      -5.099 -26.308 -14.090  1.00113.08      B
ATOM   8342  CB   LYS B 533      -4.984 -26.874 -12.669  1.00111.94      B
ATOM   8343  CG   LYS B 533      -6.229 -27.497 -12.074  1.00110.35      B
ATOM   8344  CD   LYS B 533      -5.879 -28.025 -10.686  1.00109.12      B
ATOM   8345  CE   LYS B 533      -7.021 -28.771 -10.024  1.00108.15      B
ATOM   8346  NZ   LYS B 533      -6.618 -29.203  -8.657  1.00106.78      B
ATOM   8347  C    LYS B 533      -3.799 -25.559 -14.369  1.00112.88      B
ATOM   8348  O    LYS B 533      -3.209 -25.626 -15.451  1.00112.22      B
ATOM   8349  N    LEU B 534      -3.392 -24.853 -13.327  1.00112.61      B
ATOM   8350  CA   LEU B 534      -2.193 -24.053 -13.225  1.00112.66      B
ATOM   8351  CB   LEU B 534      -1.989 -23.088 -14.411  1.00112.41      B
ATOM   8352  CG   LEU B 534      -0.651 -22.318 -14.314  1.00112.39      B
ATOM   8353  CD1  LEU B 534       0.447 -23.280 -13.871  1.00112.22      B
ATOM   8354  CD2  LEU B 534      -0.274 -21.670 -15.641  1.00112.05      B
ATOM   8355  C    LEU B 534      -2.549 -23.290 -11.973  1.00112.95      B
ATOM   8356  O    LEU B 534      -3.317 -22.325 -12.011  1.00113.59      B
ATOM   8357  N    LYS B 535      -2.060 -23.779 -10.845  1.00112.94      B
ATOM   8358  CA   LYS B 535      -2.326 -23.098  -9.599  1.00112.24      B
ATOM   8359  CB   LYS B 535      -1.654 -23.871  -8.470  1.00112.08      B
ATOM   8360  CG   LYS B 535      -2.117 -25.327  -8.482  1.00112.15      B
```

FIGURE 5- 111 -

```
ATOM   8361  CD   LYS B 535     -1.446 -26.202  -7.445  1.00113.11      B
ATOM   8362  CE   LYS B 535     -1.967 -27.636  -7.545  1.00112.92      B
ATOM   8363  NZ   LYS B 535     -1.355 -28.576  -6.563  1.00112.66      B
ATOM   8364  C    LYS B 535     -1.803 -21.671  -9.788  1.00112.04      B
ATOM   8365  O    LYS B 535     -0.674 -21.438 -10.235  1.00111.82      B
ATOM   8366  N    LEU B 536     -2.673 -20.722  -9.478  1.00111.85      B
ATOM   8367  CA   LEU B 536     -2.402 -19.309  -9.660  1.00111.31      B
ATOM   8368  CB   LEU B 536     -3.725 -18.610  -9.970  1.00111.28      B
ATOM   8369  CG   LEU B 536     -4.750 -19.551 -10.630  1.00110.94      B
ATOM   8370  CD1  LEU B 536     -5.299 -20.543  -9.595  1.00110.91      B
ATOM   8371  CD2  LEU B 536     -5.884 -18.756 -11.236  1.00110.52      B
ATOM   8372  C    LEU B 536     -1.712 -18.647  -8.474  1.00111.23      B
ATOM   8373  O    LEU B 536     -2.017 -18.922  -7.318  1.00111.12      B
ATOM   8374  N    THR B 537     -0.771 -17.765  -8.778  1.00110.74      B
ATOM   8375  CA   THR B 537     -0.043 -17.052  -7.741  1.00110.33      B
ATOM   8376  CB   THR B 537      1.451 -17.266  -7.872  1.00110.10      B
ATOM   8377  OG1  THR B 537      1.876 -16.804  -9.156  1.00109.95      B
ATOM   8378  CG2  THR B 537      1.766 -18.728  -7.726  1.00110.10      B
ATOM   8379  C    THR B 537     -0.322 -15.565  -7.805  1.00110.46      B
ATOM   8380  O    THR B 537     -0.101 -14.934  -8.829  1.00110.46      B
ATOM   8381  N    PRO B 538     -0.789 -14.982  -6.688  1.00110.53      B
ATOM   8382  CD   PRO B 538     -0.783 -15.542  -5.319  1.00110.62      B
ATOM   8383  CA   PRO B 538     -1.086 -13.545  -6.663  1.00110.59      B
ATOM   8384  CB   PRO B 538     -0.918 -13.204  -5.176  1.00110.43      B
ATOM   8385  CG   PRO B 538     -1.460 -14.462  -4.514  1.00110.20      B
ATOM   8386  C    PRO B 538     -0.130 -12.738  -7.570  1.00110.64      B
ATOM   8387  O    PRO B 538      0.968 -12.380  -7.155  1.00110.85      B
ATOM   8388  N    ILE B 539     -0.553 -12.471  -8.804  1.00111.07      B
ATOM   8389  CA   ILE B 539      0.208 -11.684  -9.783  1.00111.64      B
ATOM   8390  CB   ILE B 539     -0.639 -11.479 -11.080  1.00110.66      B
ATOM   8391  CG2  ILE B 539     -0.144 -12.408 -12.188  1.00110.48      B
ATOM   8392  CG1  ILE B 539     -2.117 -11.623 -10.751  1.00110.11      B
ATOM   8393  CD1  ILE B 539     -3.017 -11.465 -11.957  1.00109.34      B
ATOM   8394  C    ILE B 539      0.616 -10.299  -9.246  1.00112.77      B
ATOM   8395  O    ILE B 539      0.073  -9.847  -8.242  1.00112.88      B
ATOM   8396  N    PRO B 540      1.561  -9.605  -9.934  1.00113.70      B
ATOM   8397  CD   PRO B 540      2.098  -9.998 -11.244  1.00113.54      B
ATOM   8398  CA   PRO B 540      2.092  -8.272  -9.594  1.00114.42      B
ATOM   8399  CB   PRO B 540      2.971  -7.932 -10.809  1.00113.63      B
ATOM   8400  CG   PRO B 540      3.387  -9.252 -11.267  1.00113.07      B
ATOM   8401  C    PRO B 540      0.999  -7.224  -9.348  1.00115.16      B
ATOM   8402  O    PRO B 540      0.493  -7.156  -8.233  1.00115.09      B
ATOM   8403  N    ALA B 541      0.625  -6.421 -10.354  1.00116.02      B
ATOM   8404  CA   ALA B 541     -0.415  -5.387 -10.163  1.00116.71      B
ATOM   8405  CB   ALA B 541     -0.949  -4.934 -11.521  1.00116.26      B
ATOM   8406  C    ALA B 541     -1.591  -5.827  -9.263  1.00117.44      B
ATOM   8407  O    ALA B 541     -2.456  -6.583  -9.694  1.00117.45      B
ATOM   8408  N    ALA B 542     -1.625  -5.318  -8.033  1.00118.20      B
ATOM   8409  CA   ALA B 542     -2.672  -5.621  -7.046  1.00118.84      B
ATOM   8410  CB   ALA B 542     -2.773  -7.126  -6.788  1.00117.98      B
ATOM   8411  C    ALA B 542     -2.127  -4.921  -5.827  1.00119.02      B
ATOM   8412  O    ALA B 542     -2.853  -4.402  -4.983  1.00119.23      B
ATOM   8413  N    SER B 543     -0.804  -4.957  -5.764  1.00119.12      B
ATOM   8414  CA   SER B 543     -0.013  -4.304  -4.739  1.00118.74      B
ATOM   8415  CB   SER B 543      1.162  -5.199  -4.305  1.00118.26      B
ATOM   8416  OG   SER B 543      0.779  -6.550  -4.101  1.00117.48      B
ATOM   8417  C    SER B 543      0.521  -3.103  -5.533  1.00118.75      B
ATOM   8418  O    SER B 543      1.398  -2.374  -5.057  1.00119.15      B
ATOM   8419  N    GLN B 544     -0.013  -2.910  -6.746  1.00117.93      B
ATOM   8420  CA   GLN B 544      0.447  -1.838  -7.635  1.00117.19      B
ATOM   8421  CB   GLN B 544      1.587  -2.340  -8.504  1.00117.36      B
ATOM   8422  CG   GLN B 544      2.446  -3.362  -7.848  1.00117.41      B
ATOM   8423  CD   GLN B 544      3.318  -4.059  -8.843  1.00117.44      B
ATOM   8424  OE1  GLN B 544      2.871  -4.949  -9.570  1.00117.52      B
ATOM   8425  NE2  GLN B 544      4.579  -3.652  -8.899  1.00116.92      B
ATOM   8426  C    GLN B 544     -0.609  -1.290  -8.582  1.00117.01      B
ATOM   8427  O    GLN B 544     -0.290  -0.505  -9.481  1.00117.40      B
ATOM   8428  N    LEU B 545     -1.850  -1.728  -8.423  1.00116.05      B
ATOM   8429  CA   LEU B 545     -2.902  -1.227  -9.284  1.00114.80      B
ATOM   8430  CB   LEU B 545     -4.191  -2.011  -9.102  1.00114.30      B
ATOM   8431  CG   LEU B 545     -4.091  -3.224 -10.016  1.00113.72      B
ATOM   8432  CD1  LEU B 545     -5.389  -3.979 -10.030  1.00113.32      B
ATOM   8433  CD2  LEU B 545     -3.722  -2.742 -11.416  1.00113.20      B
ATOM   8434  C    LEU B 545     -3.164   0.236  -9.041  1.00114.62      B
ATOM   8435  O    LEU B 545     -3.256   0.700  -7.906  1.00114.68      B
ATOM   8436  N    ASP B 546     -3.262   0.985 -10.137  1.00114.31      B
```

FIGURE 5- 112 -

```
ATOM   8437  CA   ASP B 546      -3.514    2.391  -10.110  1.00 113.84      B
ATOM   8438  CB   ASP B 546      -3.219    2.938  -11.500  1.00 113.20      B
ATOM   8439  CG   ASP B 546      -3.668    1.985  -12.588  1.00 113.26      B
ATOM   8440  OD1  ASP B 546      -4.892    1.747  -12.691  1.00 113.02      B
ATOM   8441  OD2  ASP B 546      -2.802    1.465  -13.329  1.00 113.11      B
ATOM   8442  C    ASP B 546      -4.973    2.668   -9.720  1.00 113.70      B
ATOM   8443  O    ASP B 546      -5.638    3.503  -10.354  1.00 113.69      B
ATOM   8444  N    LEU B 547      -5.463    1.982   -8.685  1.00 113.09      B
ATOM   8445  CA   LEU B 547      -6.831    2.177   -8.249  1.00 112.33      B
ATOM   8446  CB   LEU B 547      -7.268    1.087   -7.235  1.00 111.81      B
ATOM   8447  CG   LEU B 547      -8.327    0.054   -7.684  1.00 111.43      B
ATOM   8448  CD1  LEU B 547      -7.891   -0.572   -8.989  1.00 111.17      B
ATOM   8449  CD2  LEU B 547      -8.528   -1.033   -6.617  1.00 111.08      B
ATOM   8450  C    LEU B 547      -7.001    3.576   -7.663  1.00 111.80      B
ATOM   8451  O    LEU B 547      -7.220    3.758   -6.455  1.00 112.18      B
ATOM   8452  N    SER B 548      -6.883    4.565   -8.545  1.00 110.46      B
ATOM   8453  CA   SER B 548      -7.064    5.965   -8.183  1.00 108.80      B
ATOM   8454  CB   SER B 548      -7.218    6.837   -9.449  1.00 108.89      B
ATOM   8455  OG   SER B 548      -8.220    6.338  -10.293  1.00 108.29      B
ATOM   8456  C    SER B 548      -8.257    6.202   -7.280  1.00 107.59      B
ATOM   8457  O    SER B 548      -8.190    5.911   -6.080  1.00 107.51      B
ATOM   8458  N    GLY B 549      -9.320    6.764   -7.845  1.00 105.79      B
ATOM   8459  CA   GLY B 549     -10.489    7.023   -7.022  1.00 103.10      B
ATOM   8460  C    GLY B 549     -11.649    6.211   -7.530  1.00 101.25      B
ATOM   8461  O    GLY B 549     -12.494    6.772   -8.252  1.00 101.46      B
ATOM   8462  N    TRP B 550     -11.643    4.907   -7.225  1.00  99.18      B
ATOM   8463  CA   TRP B 550     -12.670    4.019   -7.740  1.00  96.43      B
ATOM   8464  CB   TRP B 550     -12.169    2.563   -7.858  1.00  98.02      B
ATOM   8465  CG   TRP B 550     -11.082    2.407   -8.887  1.00 100.16      B
ATOM   8466  CD2  TRP B 550     -11.255    2.137  -10.294  1.00 100.80      B
ATOM   8467  CE2  TRP B 550     -10.007    2.349  -10.921  1.00 101.27      B
ATOM   8468  CE3  TRP B 550     -12.337    1.716  -11.077  1.00 100.89      B
ATOM   8469  CD1  TRP B 550      -9.781    2.755   -8.730  1.00 101.34      B
ATOM   8470  NE1  TRP B 550      -9.127    2.737   -9.945  1.00 102.07      B
ATOM   8471  CZ2  TRP B 550      -9.825    2.204  -12.305  1.00 101.45      B
ATOM   8472  CZ3  TRP B 550     -12.158    1.569  -12.447  1.00 101.03      B
ATOM   8473  CH2  TRP B 550     -10.908    1.799  -13.046  1.00 101.30      B
ATOM   8474  C    TRP B 550     -13.958    3.997   -6.970  1.00  93.40      B
ATOM   8475  O    TRP B 550     -14.994    4.514   -7.403  1.00  93.69      B
ATOM   8476  N    PHE B 551     -13.883    3.376   -5.811  1.00  89.39      B
ATOM   8477  CA   PHE B 551     -15.032    3.199   -4.976  1.00  86.07      B
ATOM   8478  CB   PHE B 551     -15.025    1.756   -4.461  1.00  86.86      B
ATOM   8479  CG   PHE B 551     -14.864    0.754   -5.584  1.00  87.25      B
ATOM   8480  CD1  PHE B 551     -15.802    0.677   -6.628  1.00  86.60      B
ATOM   8481  CD2  PHE B 551     -13.670    0.059   -5.716  1.00  87.96      B
ATOM   8482  CE1  PHE B 551     -15.525   -0.049   -7.772  1.00  86.63      B
ATOM   8483  CE2  PHE B 551     -13.391   -0.661   -6.846  1.00  88.09      B
ATOM   8484  CZ   PHE B 551     -14.316   -0.713   -7.881  1.00  87.37      B
ATOM   8485  C    PHE B 551     -14.908    4.242   -3.918  1.00  83.68      B
ATOM   8486  O    PHE B 551     -14.588    3.957   -2.766  1.00  83.36      B
ATOM   8487  N    VAL B 552     -15.141    5.476   -4.376  1.00  80.41      B
ATOM   8488  CA   VAL B 552     -15.123    6.705   -3.578  1.00  77.62      B
ATOM   8489  CB   VAL B 552     -14.197    7.754   -4.217  1.00  77.59      B
ATOM   8490  CG1  VAL B 552     -14.276    9.075   -3.464  1.00  76.99      B
ATOM   8491  CG2  VAL B 552     -12.795    7.210   -4.238  1.00  77.72      B
ATOM   8492  C    VAL B 552     -16.547    7.294   -3.553  1.00  75.16      B
ATOM   8493  O    VAL B 552     -17.135    7.524   -2.482  1.00  73.98      B
ATOM   8494  N    ALA B 553     -17.093    7.528   -4.748  1.00  72.62      B
ATOM   8495  CA   ALA B 553     -18.426    8.106   -4.889  1.00  70.99      B
ATOM   8496  CB   ALA B 553     -18.367    9.618   -4.609  1.00  70.65      B
ATOM   8497  C    ALA B 553     -19.085    7.863   -6.248  1.00  69.72      B
ATOM   8498  O    ALA B 553     -18.421    7.719   -7.277  1.00  68.91      B
ATOM   8499  N    GLY B 554     -20.412    7.833   -6.231  1.00  68.39      B
ATOM   8500  CA   GLY B 554     -21.165    7.639   -7.453  1.00  66.53      B
ATOM   8501  C    GLY B 554     -21.317    8.954   -8.191  1.00  65.92      B
ATOM   8502  O    GLY B 554     -21.428   10.010   -7.553  1.00  66.98      B
ATOM   8503  N    TYR B 555     -21.319    8.906   -9.519  1.00  64.15      B
ATOM   8504  CA   TYR B 555     -21.431   10.122  -10.320  1.00  63.08      B
ATOM   8505  CB   TYR B 555     -20.067   10.506  -10.868  1.00  62.47      B
ATOM   8506  CG   TYR B 555     -19.034   10.757   -9.802  1.00  61.36      B
ATOM   8507  CD1  TYR B 555     -19.099   11.888   -8.985  1.00  60.60      B
ATOM   8508  CE1  TYR B 555     -18.135   12.125   -8.010  1.00  60.10      B
ATOM   8509  CD2  TYR B 555     -17.986   9.869    -9.615  1.00  61.02      B
ATOM   8510  CE2  TYR B 555     -17.020   10.090   -8.649  1.00  61.25      B
ATOM   8511  CZ   TYR B 555     -17.094   11.218   -7.845  1.00  60.28      B
ATOM   8512  OH   TYR B 555     -16.134   11.432   -6.879  1.00  59.88      B
```

FIGURE 5- 113 -

```
ATOM   8513  C    TYR B 555     -22.382    9.910 -11.493  1.00 63.00      B
ATOM   8514  O    TYR B 555     -22.239   10.553 -12.546  1.00 62.03      B
ATOM   8515  N    SER B 556     -23.336    8.996 -11.312  1.00 63.58      B
ATOM   8516  CA   SER B 556     -24.347    8.661 -12.326  1.00 64.55      B
ATOM   8517  CB   SER B 556     -25.271    7.559 -11.793  1.00 65.50      B
ATOM   8518  OG   SER B 556     -26.276    7.216 -12.741  1.00 66.96      B
ATOM   8519  C    SER B 556     -25.206    9.844 -12.772  1.00 64.41      B
ATOM   8520  O    SER B 556     -26.146   10.225 -12.069  1.00 64.40      B
ATOM   8521  N    GLY B 557     -24.895   10.378 -13.956  1.00 64.09      B
ATOM   8522  CA   GLY B 557     -25.620   11.508 -14.525  1.00 63.06      B
ATOM   8523  C    GLY B 557     -24.850   12.793 -14.264  1.00 63.11      B
ATOM   8524  O    GLY B 557     -25.241   13.896 -14.699  1.00 62.87      B
ATOM   8525  N    GLY B 558     -23.729   12.647 -13.566  1.00 63.86      B
ATOM   8526  CA   GLY B 558     -22.921   13.809 -13.243  1.00 63.66      B
ATOM   8527  C    GLY B 558     -21.950   14.318 -14.297  1.00 63.75      B
ATOM   8528  O    GLY B 558     -21.207   15.243 -13.992  1.00 64.85      B
ATOM   8529  N    ASP B 559     -21.946   13.749 -15.505  1.00 62.92      B
ATOM   8530  CA   ASP B 559     -21.036   14.185 -16.565  1.00 62.32      B
ATOM   8531  CB   ASP B 559     -21.720   15.607 -17.022  1.00 60.64      B
ATOM   8532  CG   ASP B 559     -20.737   16.025 -18.292  1.00 61.51      B
ATOM   8533  OD1  ASP B 559     -20.653   15.203 -19.239  1.00 61.12      B
ATOM   8534  OD2  ASP B 559     -20.208   17.170 -18.343  1.00 62.02      B
ATOM   8535  C    ASP B 559     -19.595   14.139 -16.033  1.00 63.57      B
ATOM   8536  O    ASP B 559     -18.786   15.021 -16.315  1.00 64.24      B
ATOM   8537  N    ILE B 560     -19.290   13.096 -15.260  1.00 65.17      B
ATOM   8538  CA   ILE B 560     -17.957   12.908 -14.677  1.00 66.98      B
ATOM   8539  CB   ILE B 560     -18.042   12.393 -13.222  1.00 65.74      B
ATOM   8540  CG2  ILE B 560     -16.635   12.126 -12.667  1.00 63.77      B
ATOM   8541  CG1  ILE B 560     -18.817   13.409 -12.376  1.00 64.14      B
ATOM   8542  CD1  ILE B 560     -18.094   14.722 -12.171  1.00 62.47      B
ATOM   8543  C    ILE B 560     -17.092   11.936 -15.491  1.00 69.15      B
ATOM   8544  O    ILE B 560     -17.559   10.899 -15.955  1.00 68.35      B
ATOM   8545  N    TYR B 561     -15.821   12.292 -15.636  1.00 72.40      B
ATOM   8546  CA   TYR B 561     -14.852   11.521 -16.395  1.00 75.86      B
ATOM   8547  CB   TYR B 561     -14.553   12.231 -17.716  1.00 77.02      B
ATOM   8548  CG   TYR B 561     -13.543   11.535 -18.606  1.00 78.11      B
ATOM   8549  CD1  TYR B 561     -13.902   10.408 -19.347  1.00 78.78      B
ATOM   8550  CE1  TYR B 561     -12.971    9.736 -20.149  1.00 78.58      B
ATOM   8551  CD2  TYR B 561     -12.221   11.982 -18.687  1.00 78.14      B
ATOM   8552  CE2  TYR B 561     -11.277   11.313 -19.487  1.00 78.29      B
ATOM   8553  CZ   TYR B 561     -11.661   10.191 -20.213  1.00 78.39      B
ATOM   8554  OH   TYR B 561     -10.745    9.521 -20.995  1.00 78.15      B
ATOM   8555  C    TYR B 561     -13.556   11.400 -15.612  1.00 78.30      B
ATOM   8556  O    TYR B 561     -12.684   12.258 -15.722  1.00 78.54      B
ATOM   8557  N    HIS B 562     -13.421   10.355 -14.812  1.00 81.17      B
ATOM   8558  CA   HIS B 562     -12.192   10.185 -14.058  1.00 84.66      B
ATOM   8559  CB   HIS B 562     -12.432    9.325 -12.818  1.00 85.87      B
ATOM   8560  CG   HIS B 562     -13.082   10.048 -11.675  1.00 87.49      B
ATOM   8561  CD2  HIS B 562     -13.594   11.299 -11.567  1.00 87.60      B
ATOM   8562  ND1  HIS B 562     -13.304    9.438 -10.460  1.00 87.99      B
ATOM   8563  CE1  HIS B 562     -13.929   10.277  -9.653  1.00 88.67      B
ATOM   8564  NE2  HIS B 562     -14.118   11.412 -10.300  1.00 88.84      B
ATOM   8565  C    HIS B 562     -11.171    9.512 -14.983  1.00 86.29      B
ATOM   8566  O    HIS B 562     -11.486    8.547 -15.681  1.00 87.46      B
ATOM   8567  N    SER B 563      -9.953   10.046 -15.004  1.00 88.37      B
ATOM   8568  CA   SER B 563      -8.872    9.525 -15.848  1.00 90.00      B
ATOM   8569  CB   SER B 563      -8.665   10.438 -17.063  1.00 90.58      B
ATOM   8570  OG   SER B 563      -8.453   11.791 -16.668  1.00 91.63      B
ATOM   8571  C    SER B 563      -7.555    9.400 -15.088  1.00 90.53      B
ATOM   8572  O    SER B 563      -7.003    8.280 -15.029  1.00 90.35      B
ATOM   8573  OXT  SER B 563      -7.081   10.430 -14.556  1.00 91.06      B
ATOM   8574  OH2  WAT S   1     -23.007   47.531  46.796  1.00 33.88      S
ATOM   8575  OH2  WAT S   2     -20.799   30.948  51.047  1.00 27.44      S
ATOM   8576  OH2  WAT S   3     -16.674   26.956   8.438  1.00 25.70      S
ATOM   8577  OH2  WAT S   4     -28.139   24.481   6.790  1.00 24.30      S
ATOM   8578  OH2  WAT S   5      -9.675   38.172   6.844  1.00 28.11      S
ATOM   8579  OH2  WAT S   6     -47.868   21.895  -9.728  1.00 30.89      S
ATOM   8580  OH2  WAT S   7     -30.539   22.619  11.382  1.00 35.12      S
ATOM   8581  OH2  WAT S   8     -16.101   39.560  40.079  1.00 39.19      S
ATOM   8582  OH2  WAT S   9     -26.457   40.035  17.819  1.00 22.21      S
ATOM   8583  OH2  WAT S  10     -11.695   39.813  17.519  1.00 27.03      S
ATOM   8584  OH2  WAT S  11     -25.430   38.107  21.372  1.00 24.14      S
ATOM   8585  OH2  WAT S  12     -18.586   50.947  14.409  1.00 32.11      S
ATOM   8586  OH2  WAT S  13     -21.538   47.810   4.476  1.00 40.45      S
ATOM   8587  OH2  WAT S  14     -17.737   53.946  37.286  1.00 34.97      S
ATOM   8588  OH2  WAT S  15     -19.378   50.678   6.177  1.00 30.70      S
```

FIGURE 5- 114 -

```
ATOM   8589  OH2 WAT S   16     -36.200   15.273  -14.405  1.00 41.50      S
ATOM   8590  OH2 WAT S   17      -8.598   29.207  -28.468  1.00 37.95      S
ATOM   8591  OH2 WAT S   18     -21.213   26.211    7.010  1.00 35.57      S
ATOM   8592  OH2 WAT S   19     -15.258   33.187   -3.141  1.00 38.87      S
ATOM   8593  OH2 WAT S   20     -24.091   53.729   33.456  1.00 28.05      S
ATOM   8594  OH2 WAT S   21     -19.707   56.749    0.947  1.00 32.03      S
ATOM   8595  OH2 WAT S   22     -38.204   31.915    1.441  1.00 35.00      S
ATOM   8596  OH2 WAT S   23      -8.000   21.906   19.530  1.00 37.71      S
ATOM   8597  OH2 WAT S   24     -19.203   50.286   43.988  1.00 42.21      S
ATOM   8598  OH2 WAT S   25     -23.601   13.181   -6.781  1.00 34.44      S
ATOM   8599  OH2 WAT S   26     -17.655   28.714    4.618  1.00 34.75      S
ATOM   8600  OH2 WAT S   27     -28.970   77.396   35.376  1.00 38.44      S
ATOM   8601  OH2 WAT S   28     -31.918   21.716    7.737  1.00 33.48      S
ATOM   8602  OH2 WAT S   29     -38.551    9.600  -11.851  1.00 32.07      S
ATOM   8603  OH2 WAT S   30     -30.662   38.150   -8.701  1.00 30.35      S
ATOM   8604  OH2 WAT S   31     -12.216   60.697    6.346  1.00 42.87      S
ATOM   8605  OH2 WAT S   32     -35.753   48.538   12.334  1.00 40.01      S
ATOM   8606  OH2 WAT S   33     -38.189   17.510    2.560  1.00 35.01      S
ATOM   8607  OH2 WAT S   34     -33.744   24.006  -14.532  1.00 40.44      S
ATOM   8608  OH2 WAT S   35     -16.952   53.443   32.325  1.00 33.91      S
ATOM   8609  OH2 WAT S   36     -17.195   22.816    8.270  1.00 32.58      S
ATOM   8610  OH2 WAT S   37     -21.074   44.198   49.672  1.00 48.32      S
ATOM   8611  OH2 WAT S   38     -33.601   15.530    0.678  1.00 49.59      S
ATOM   8612  OH2 WAT S   39     -25.910   38.222  -14.976  1.00 34.72      S
ATOM   8613  OH2 WAT S   40     -17.577   49.735   12.319  1.00 50.70      S
ATOM   8614  OH2 WAT S   41     -20.727   43.840   26.202  1.00 30.63      S
ATOM   8615  OH2 WAT S   42     -27.697   38.355   19.737  1.00 34.94      S
ATOM   8616  OH2 WAT S   43     -28.305   46.877   -5.942  1.00 41.10      S
ATOM   8617  OH2 WAT S   44     -25.053   21.003  -23.297  1.00 45.38      S
ATOM   8618  OH2 WAT S   45       0.348   36.040   33.269  1.00 30.18      S
ATOM   8619  OH2 WAT S   46      -9.122   21.121   12.013  1.00 31.46      S
ATOM   8620  OH2 WAT S   47      -7.226   40.636   33.623  1.00 36.45      S
ATOM   8621  OH2 WAT S   48     -31.633    9.248  -11.810  1.00 25.08      S
ATOM   8622  OH2 WAT S   49     -23.958   70.422   39.996  1.00 30.28      S
ATOM   8623  OH2 WAT S   50     -17.315   45.015    1.270  1.00 32.58      S
ATOM   8624  OH2 WAT S   51     -16.148   29.892    6.664  1.00 34.61      S
ATOM   8625  OH2 WAT S   52     -11.151   61.919    9.090  1.00 44.06      S
ATOM   8626  OH2 WAT S   53     -34.330   25.740   16.513  1.00 34.99      S
ATOM   8627  OH2 WAT S   54     -29.229   32.889   21.925  1.00 47.98      S
ATOM   8628  OH2 WAT S   55     -35.774   26.764  -11.110  1.00 31.04      S
ATOM   8629  OH2 WAT S   56     -19.812   40.177   36.235  1.00 37.13      S
ATOM   8630  OH2 WAT S   57     -34.228   23.231    4.679  1.00 39.13      S
ATOM   8631  OH2 WAT S   58     -31.220   31.192  -16.468  1.00 40.61      S
ATOM   8632  OH2 WAT S   59     -37.582    8.562  -16.302  1.00 35.79      S
ATOM   8633  OH2 WAT S   60     -32.959   51.215    3.377  1.00 50.87      S
ATOM   8634  OH2 WAT S   61     -29.875   21.534   -3.886  1.00 30.44      S
ATOM   8635  OH2 WAT S   62     -28.763   21.054  -22.130  1.00 38.50      S
ATOM   8636  OH2 WAT S   63     -33.454   47.002   45.696  1.00 38.96      S
ATOM   8637  C1  BI  I    1     -23.739  -16.906  -30.458  1.00 73.98
ATOM   8638  C2  BI  I    1     -25.117  -16.400  -30.371  1.00 72.07
ATOM   8639  C3  BI  I    1     -25.436  -15.233  -29.541  1.00 71.20
ATOM   8640  C4  BI  I    1     -24.371  -14.579  -28.802  1.00 70.76
ATOM   8641  C5  BI  I    1     -22.984  -15.091  -28.891  1.00 71.21
ATOM   8642  C6  BI  I    1     -22.679  -16.242  -29.717  1.00 73.03
ATOM   8643  N7  BI  I    1     -26.668  -14.551  -29.271  1.00 71.58
ATOM   8644  C8  BI  I    1     -26.392  -13.459  -28.361  1.00 70.70
ATOM   8645  C9  BI  I    1     -24.970  -13.467  -28.054  1.00 69.44
ATOM   8646  C10 BI  I    1     -24.197  -12.470  -27.105  1.00 67.07
ATOM   8647  C11 BI  I    1     -23.628  -13.222  -25.840  1.00 65.96
ATOM   8648  C12 BI  I    1     -22.828  -12.287  -24.890  1.00 64.75
ATOM   8649  C13 BI  I    1     -21.707  -11.507  -25.638  1.00 65.13
ATOM   8650  C14 BI  I    1     -22.199  -10.785  -26.934  1.00 65.29
ATOM   8651  C15 BI  I    1     -23.031  -11.706  -27.875  1.00 65.39
ATOM   8652  C16 BI  I    1     -27.406  -12.522  -27.821  1.00 71.34
ATOM   8653  C17 BI  I    1     -28.303  -11.695  -28.560  1.00 71.32
ATOM   8654  C18 BI  I    1     -29.054  -11.002  -27.622  1.00 72.66
ATOM   8655  O19 BI  I    1     -28.670  -11.354  -26.347  1.00 73.48
ATOM   8656  C20 BI  I    1     -27.665  -12.281  -26.478  1.00 71.70
ATOM   8657  C21 BI  I    1     -23.412  -18.124  -31.329  1.00 75.70
ATOM   8658  O22 BI  I    1     -22.310  -18.734  -31.391  1.00 74.92
ATOM   8659  N23 BI  I    1     -24.652  -18.437  -32.105  1.00 78.93
ATOM   8660  C24 BI  I    1     -28.034  -14.901  -29.841  1.00 73.02
ATOM   8661  C25 BI  I    1     -28.164  -14.813  -31.412  1.00 74.25
ATOM   8662  O26 BI  I    1     -27.199  -14.368  -32.098  1.00 73.63
ATOM   8663  N27 BI  I    1     -29.401  -15.250  -32.085  1.00 75.29
ATOM   8664  C28 BI  I    1     -30.594  -15.792  -31.289  1.00 75.78
```

FIGURE 5- 115 -

```
ATOM   8665  C29  BI    I    1     -31.915  -15.064  -31.693  1.00  75.90
ATOM   8666  O30  BI    I    1     -32.085  -14.948  -33.258  1.00  77.06
ATOM   8667  C31  BI    I    1     -30.804  -14.442  -34.030  1.00  76.43
ATOM   8668  C32  BI    I    1     -29.508  -15.168  -33.585  1.00  76.39
ATOM   8669  S36  BI    I    1     -24.616  -19.616  -33.098  1.00  80.44
ATOM   8670  O37  BI    I    1     -23.948  -20.683  -32.577  1.00  79.05
ATOM   8671  O38  BI    I    1     -25.911  -19.961  -33.387  1.00  80.75
ATOM   8672  C39  BI    I    1     -23.777  -19.035  -34.606  1.00  81.96
ATOM   8673  C40  BI    I    1     -22.363  -18.791  -34.577  1.00  83.29
ATOM   8674  C41  BI    I    1     -21.683  -18.331  -35.747  1.00  84.19
ATOM   8675  C42  BI    I    1     -22.429  -18.114  -36.960  1.00  85.75
ATOM   8676  C43  BI    I    1     -23.852  -18.359  -36.996  1.00  84.71
ATOM   8677  C44  BI    I    1     -24.524  -18.818  -35.816  1.00  83.66
ATOM   8678  S    SO4   S  101     -11.156   50.084   23.370  1.00  95.46     S
ATOM   8679  O1   SO4   S  101     -10.227   51.190   23.052  1.00  95.17     S
ATOM   8680  O2   SO4   S  101     -11.904   50.403   24.599  1.00  95.39     S
ATOM   8681  O3   SO4   S  101     -12.095   49.887   22.248  1.00  95.49     S
ATOM   8682  O4   SO4   S  101     -10.388   48.844   23.588  1.00  96.50     S
ATOM   8683  S    SO4   S  102     -21.036   43.747   21.928  1.00  75.60     S
ATOM   8684  O1   SO4   S  102     -19.911   44.684   22.126  1.00  76.70     S
ATOM   8685  O2   SO4   S  102     -21.677   43.437   23.219  1.00  74.96     S
ATOM   8686  O3   SO4   S  102     -22.030   44.359   21.026  1.00  75.37     S
ATOM   8687  O4   SO4   S  102     -20.514   42.510   21.334  1.00  75.72     S
ATOM   8688  S    SO4   S  103     -38.819    3.029  -11.627  1.00 105.23     S
ATOM   8689  O1   SO4   S  103     -38.074    4.238  -11.235  1.00 105.17     S
ATOM   8690  O2   SO4   S  103     -39.565    2.525  -10.456  1.00 105.44     S
ATOM   8691  O3   SO4   S  103     -39.764    3.347  -12.718  1.00 104.81     S
ATOM   8692  O4   SO4   S  103     -37.868    2.000  -12.091  1.00 104.98     S
ATOM   8693  S    SO4   S  104     -28.262    7.505   -8.594  1.00 104.19     S
ATOM   8694  O1   SO4   S  104     -27.887    8.632   -9.470  1.00 103.70     S
ATOM   8695  O2   SO4   S  104     -29.269    7.950   -7.615  1.00 104.49     S
ATOM   8696  O3   SO4   S  104     -28.848    6.420   -9.408  1.00 104.74     S
ATOM   8697  O4   SO4   S  104     -27.060    7.015   -7.884  1.00 103.29     S
END
```

FIGURE 6-1-

| | | | | | | | | |
|---|---|---|---|---|---|---|---|---|
| ATOM | 1 | CB | SER | 1 | -46.252 | 21.241 | -6.638 | 23.68 | C |
| ATOM | 2 | HB2 | SER | 1 | -46.419 | 21.757 | -7.548 | 0.00 | H |
| ATOM | 3 | HB3 | SER | 1 | -46.246 | 21.932 | -5.836 | 0.00 | H |
| ATOM | 4 | OG | SER | 1 | -44.990 | 20.596 | -6.699 | 25.39 | O |
| ATOM | 5 | HG | SER | 1 | -44.297 | 21.256 | -6.837 | 0.00 | H |
| ATOM | 6 | C | SER | 1 | -47.210 | 19.096 | -7.447 | 25.25 | C |
| ATOM | 7 | O | SER | 1 | -46.899 | 17.956 | -7.087 | 27.50 | O |
| ATOM | 8 | N | SER | 1 | -47.301 | 19.671 | -5.029 | 22.50 | N |
| ATOM | 9 | H1 | SER | 1 | -47.410 | 20.424 | -4.366 | 0.00 | H |
| ATOM | 10 | H2 | SER | 1 | -48.041 | 18.998 | -4.898 | 0.00 | H |
| ATOM | 11 | CA | SER | 1 | -47.365 | 20.219 | -6.421 | 25.06 | C |
| ATOM | 12 | HA | SER | 1 | -48.302 | 20.690 | -6.572 | 0.00 | H |
| ATOM | 13 | N | MET | 2 | -47.420 | 19.415 | -8.722 | 23.80 | N |
| ATOM | 14 | HN | MET | 2 | -47.680 | 20.360 | -8.960 | 0.00 | H |
| ATOM | 15 | CA | MET | 2 | -47.277 | 18.411 | -9.771 | 23.17 | C |
| ATOM | 16 | HA | MET | 2 | -47.665 | 17.486 | -9.430 | 0.00 | H |
| ATOM | 17 | CB | MET | 2 | -48.037 | 18.828 | -11.034 | 21.26 | C |
| ATOM | 18 | HB2 | MET | 2 | -47.777 | 19.822 | -11.290 | 0.00 | H |
| ATOM | 19 | HB3 | MET | 2 | -47.780 | 18.180 | -11.831 | 0.00 | H |
| ATOM | 20 | CG | MET | 2 | -49.558 | 18.792 | -10.917 | 19.10 | C |
| ATOM | 21 | HG2 | MET | 2 | -49.874 | 19.505 | -10.201 | 0.00 | H |
| ATOM | 22 | HG3 | MET | 2 | -49.990 | 19.020 | -11.857 | 0.00 | H |
| ATOM | 23 | SD | MET | 2 | -50.256 | 17.199 | -10.401 | 21.33 | S |
| ATOM | 24 | CE | MET | 2 | -49.990 | 16.182 | -11.846 | 14.91 | C |
| ATOM | 25 | HE1 | MET | 2 | -50.496 | 16.606 | -12.674 | 0.00 | H |
| ATOM | 26 | HE2 | MET | 2 | -48.953 | 16.130 | -12.055 | 0.00 | H |
| ATOM | 27 | HE3 | MET | 2 | -50.363 | 15.207 | -11.665 | 0.00 | H |
| ATOM | 28 | C | MET | 2 | -45.810 | 18.178 | -10.130 | 23.48 | C |
| ATOM | 29 | O | MET | 2 | -45.031 | 19.117 | -10.289 | 23.98 | O |
| ATOM | 30 | N | SER | 3 | -45.436 | 16.915 | -10.257 | 22.87 | N |
| ATOM | 31 | HN | SER | 3 | -46.115 | 16.186 | -10.096 | 0.00 | H |
| ATOM | 32 | CA | SER | 3 | -44.075 | 16.570 | -10.621 | 22.79 | C |
| ATOM | 33 | HA | SER | 3 | -43.409 | 16.936 | -9.883 | 0.00 | H |
| ATOM | 34 | CB | SER | 3 | -43.947 | 15.050 | -10.717 | 22.98 | C |
| ATOM | 35 | HB2 | SER | 3 | -42.971 | 14.798 | -11.041 | 0.00 | H |
| ATOM | 36 | HB3 | SER | 3 | -44.126 | 14.620 | -9.766 | 0.00 | H |
| ATOM | 37 | OG | SER | 3 | -44.885 | 14.511 | -11.642 | 23.51 | O |
| ATOM | 38 | HG | SER | 3 | -44.782 | 13.550 | -11.683 | 0.00 | H |
| ATOM | 39 | C | SER | 3 | -43.719 | 17.204 | -11.972 | 23.87 | C |
| ATOM | 40 | O | SER | 3 | -42.605 | 17.700 | -12.169 | 25.36 | O |
| ATOM | 41 | N | TYR | 4 | -44.675 | 17.183 | -12.899 | 23.53 | N |
| ATOM | 42 | HN | TYR | 4 | -45.563 | 16.771 | -12.655 | 0.00 | H |
| ATOM | 43 | CA | TYR | 4 | -44.469 | 17.732 | -14.232 | 23.38 | C |
| ATOM | 44 | HA | TYR | 4 | -43.701 | 18.461 | -14.199 | 0.00 | H |
| ATOM | 45 | CB | TYR | 4 | -44.064 | 16.631 | -15.210 | 25.93 | C |
| ATOM | 46 | HB2 | TYR | 4 | -44.771 | 15.844 | -15.167 | 0.00 | H |
| ATOM | 47 | HB3 | TYR | 4 | -44.033 | 17.025 | -16.192 | 0.00 | H |
| ATOM | 48 | CG | TYR | 4 | -42.722 | 16.006 | -14.965 | 26.96 | C |
| ATOM | 49 | CD1 | TYR | 4 | -41.561 | 16.626 | -15.400 | 27.46 | C |
| ATOM | 50 | HD1 | TYR | 4 | -41.615 | 17.569 | -15.917 | 0.00 | H |
| ATOM | 51 | CE1 | TYR | 4 | -40.322 | 16.046 | -15.178 | 26.90 | C |
| ATOM | 52 | HE1 | TYR | 4 | -39.428 | 16.537 | -15.523 | 0.00 | H |
| ATOM | 53 | CD2 | TYR | 4 | -42.612 | 14.787 | -14.299 | 25.22 | C |
| ATOM | 54 | HD2 | TYR | 4 | -43.497 | 14.283 | -13.949 | 0.00 | H |
| ATOM | 55 | CE2 | TYR | 4 | -41.362 | 14.204 | -14.074 | 23.68 | C |
| ATOM | 56 | HE2 | TYR | 4 | -41.319 | 13.261 | -13.558 | 0.00 | H |
| ATOM | 57 | CZ | TYR | 4 | -40.243 | 14.839 | -14.514 | 24.59 | C |
| ATOM | 58 | OH | TYR | 4 | -39.015 | 14.277 | -14.274 | 25.80 | O |
| ATOM | 59 | HH | TYR | 4 | -38.323 | 14.850 | -14.632 | 0.00 | H |
| ATOM | 60 | C | TYR | 4 | -45.746 | 18.348 | -14.766 | 23.45 | C |
| ATOM | 61 | O | TYR | 4 | -46.842 | 18.026 | -14.301 | 23.88 | O |
| ATOM | 62 | N | THR | 5 | -45.577 | 19.221 | -15.758 | 21.84 | N |
| ATOM | 63 | HN | THR | 5 | -44.622 | 19.410 | -16.022 | 0.00 | H |
| ATOM | 64 | CA | THR | 5 | -46.667 | 19.887 | -16.450 | 20.28 | C |
| ATOM | 65 | HA | THR | 5 | -47.579 | 19.396 | -16.228 | 0.00 | H |
| ATOM | 66 | CB | THR | 5 | -46.818 | 21.361 | -16.045 | 17.90 | C |
| ATOM | 67 | HB | THR | 5 | -45.903 | 21.368 | -16.211 | 0.00 | H |
| ATOM | 68 | OG1 | THR | 5 | -47.167 | 21.455 | -14.660 | 14.79 | O |
| ATOM | 69 | HG1 | THR | 5 | -47.260 | 22.385 | -14.413 | 0.00 | H |
| ATOM | 70 | CG2 | THR | 5 | -47.915 | 22.010 | -16.878 | 15.45 | C |
| ATOM | 71 | HG21 | THR | 5 | -47.660 | 21.951 | -17.904 | 0.00 | H |
| ATOM | 72 | HG22 | THR | 5 | -48.830 | 21.504 | -16.712 | 0.00 | H |
| ATOM | 73 | HG23 | THR | 5 | -48.017 | 23.026 | -16.597 | 0.00 | H |
| ATOM | 74 | C | THR | 5 | -46.260 | 19.847 | -17.913 | 22.54 | C |
| ATOM | 75 | O | THR | 5 | -45.149 | 20.256 | -18.249 | 22.98 | O |
| ATOM | 76 | N | TRP | 6 | -47.158 | 19.367 | -18.775 | 23.48 | N |

FIGURE 6-2 -

```
ATOM     77  HN   TRP    6    -48.053  19.080 -18.407    0.00           H
ATOM     78  CA   TRP    6    -46.884  19.249 -20.207   22.07           C
ATOM     79  HA   TRP    6    -45.860  19.448 -20.388    0.00           H
ATOM     80  CB   TRP    6    -47.221  17.836 -20.657   21.29           C
ATOM     81  HB2  TRP    6    -48.269  17.692 -20.613    0.00           H
ATOM     82  HB3  TRP    6    -46.887  17.693 -21.652    0.00           H
ATOM     83  CG   TRP    6    -46.575  16.807 -19.799   22.80           C
ATOM     84  CD2  TRP    6    -45.175  16.515 -19.724   21.99           C
ATOM     85  CE2  TRP    6    -45.009  15.522 -18.737   20.81           C
ATOM     86  CE3  TRP    6    -44.044  17.002 -20.393   21.23           C
ATOM     87  HE3  TRP    6    -44.151  17.760 -21.150    0.00           H
ATOM     88  CD1  TRP    6    -47.184  16.000 -18.882   21.93           C
ATOM     89  HD1  TRP    6    -48.253  16.040 -18.755    0.00           H
ATOM     90  NE1  TRP    6    -46.252  15.226 -18.241   20.48           N
ATOM     91  HE1  TRP    6    -46.542  14.572 -17.530    0.00           H
ATOM     92  CZ2  TRP    6    -43.758  15.003 -18.399   19.87           C
ATOM     93  HZ2  TRP    6    -43.677  14.244 -17.639    0.00           H
ATOM     94  CZ3  TRP    6    -42.804  16.490 -20.059   21.71           C
ATOM     95  HZ3  TRP    6    -41.920  16.849 -20.559    0.00           H
ATOM     96  CH2  TRP    6    -42.671  15.497 -19.067   21.86           C
ATOM     97  HH2  TRP    6    -41.685  15.127 -18.839    0.00           H
ATOM     98  C    TRP    6    -47.655  20.249 -21.064   22.44           C
ATOM     99  O    TRP    6    -48.781  20.604 -20.736   24.31           O
ATOM    100  N    THR    7    -47.045  20.683 -22.166   22.20           N
ATOM    101  HN   THR    7    -46.118  20.329 -22.350    0.00           H
ATOM    102  CA   THR    7    -47.663  21.633 -23.092   23.11           C
ATOM    103  HA   THR    7    -48.446  22.148 -22.599    0.00           H
ATOM    104  CB   THR    7    -46.648  22.678 -23.609   21.59           C
ATOM    105  HB   THR    7    -47.158  23.418 -24.169    0.00           H
ATOM    106  OG1  THR    7    -45.697  22.031 -24.471   20.46           O
ATOM    107  HG1  THR    7    -45.061  22.683 -24.796    0.00           H
ATOM    108  CG2  THR    7    -45.931  23.347 -22.462   17.07           C
ATOM    109  HG21 THR    7    -46.636  23.836 -21.842    0.00           H
ATOM    110  HG22 THR    7    -45.410  22.618 -21.893    0.00           H
ATOM    111  HG23 THR    7    -45.243  24.057 -22.842    0.00           H
ATOM    112  C    THR    7    -48.216  20.916 -24.331   26.23           C
ATOM    113  O    THR    7    -48.843  21.538 -25.201   28.16           O
ATOM    114  N    GLY    8    -47.974  19.615 -24.421   27.43           N
ATOM    115  HN   GLY    8    -47.465  19.143 -23.683    0.00           H
ATOM    116  CA   GLY    8    -48.441  18.871 -25.573   29.43           C
ATOM    117  HA2  GLY    8    -48.787  17.920 -25.262    0.00           H
ATOM    118  HA3  GLY    8    -49.232  19.400 -26.038    0.00           H
ATOM    119  C    GLY    8    -47.322  18.678 -26.583   30.19           C
ATOM    120  O    GLY    8    -47.343  17.724 -27.361   30.13           O
ATOM    121  N    ALA    9    -46.351  19.588 -26.581   31.52           N
ATOM    122  HN   ALA    9    -46.409  20.359 -25.933    0.00           H
ATOM    123  CA   ALA    9    -45.216  19.486 -27.495   33.29           C
ATOM    124  HA   ALA    9    -45.566  19.491 -28.494    0.00           H
ATOM    125  CB   ALA    9    -44.264  20.658 -27.299   33.01           C
ATOM    126  HB1  ALA    9    -44.777  21.565 -27.483    0.00           H
ATOM    127  HB2  ALA    9    -43.904  20.658 -26.303    0.00           H
ATOM    128  HB3  ALA    9    -43.449  20.567 -27.969    0.00           H
ATOM    129  C    ALA    9    -44.504  18.164 -27.208   34.84           C
ATOM    130  O    ALA    9    -44.479  17.693 -26.068   33.96           O
ATOM    131  N    LEU   10    -43.901  17.582 -28.236   36.43           N
ATOM    132  HN   LEU   10    -43.889  18.045 -29.132    0.00           H
ATOM    133  CA   LEU   10    -43.262  16.290 -28.079   38.04           C
ATOM    134  HA   LEU   10    -43.749  15.746 -27.312    0.00           H
ATOM    135  CB   LEU   10    -43.354  15.513 -29.383   37.10           C
ATOM    136  HB2  LEU   10    -42.801  16.017 -30.137    0.00           H
ATOM    137  HB3  LEU   10    -42.957  14.541 -29.250    0.00           H
ATOM    138  CG   LEU   10    -44.746  15.305 -29.980   35.87           C
ATOM    139  HG   LEU   10    -45.153  16.241 -30.263    0.00           H
ATOM    140  CD1  LEU   10    -44.600  14.398 -31.200   33.63           C
ATOM    141  HD11 LEU   10    -43.963  14.860 -31.909    0.00           H
ATOM    142  HD12 LEU   10    -44.184  13.471 -30.903    0.00           H
ATOM    143  HD13 LEU   10    -45.552  14.234 -31.634    0.00           H
ATOM    144  CD2  LEU   10    -45.694  14.703 -28.942   33.10           C
ATOM    145  HD21 LEU   10    -45.317  13.767 -28.620    0.00           H
ATOM    146  HD22 LEU   10    -45.770  15.357 -28.112    0.00           H
ATOM    147  HD23 LEU   10    -46.651  14.568 -29.374    0.00           H
ATOM    148  C    LEU   10    -41.834  16.206 -27.590   39.68           C
ATOM    149  O    LEU   10    -41.045  17.145 -27.689   39.51           O
ATOM    150  N    ILE   11    -41.533  15.037 -27.049   42.07           N
ATOM    151  HN   ILE   11    -42.278  14.360 -26.983    0.00           H
ATOM    152  CA   ILE   11    -40.213  14.708 -26.565   45.11           C
```

FIGURE 6- 3 -

```
ATOM    153  HA   ILE   11     -39.744  15.583 -26.195    0.00           H
ATOM    154  CB   ILE   11     -40.305  13.671 -25.435   44.97           C
ATOM    155  HB   ILE   11     -40.935  12.875 -25.737    0.00           H
ATOM    156  CG2  ILE   11     -38.933  13.110 -25.104   45.15           C
ATOM    157  HG21 ILE   11     -38.526  12.643 -25.963    0.00           H
ATOM    158  HG22 ILE   11     -38.295  13.897 -24.794    0.00           H
ATOM    159  HG23 ILE   11     -39.021  12.399 -24.324    0.00           H
ATOM    160  CG1  ILE   11     -40.938  14.338 -24.214   43.81           C
ATOM    161  HG12 ILE   11     -40.292  15.095 -23.851    0.00           H
ATOM    162  HG13 ILE   11     -41.866  14.768 -24.488    0.00           H
ATOM    163  CD1  ILE   11     -41.206  13.409 -23.075   44.84           C
ATOM    164  HD11 ILE   11     -41.870  12.647 -23.390    0.00           H
ATOM    165  HD12 ILE   11     -40.296  12.974 -22.753    0.00           H
ATOM    166  HD13 ILE   11     -41.642  13.948 -22.275    0.00           H
ATOM    167  C    ILE   11     -39.628  14.108 -27.824   48.04           C
ATOM    168  O    ILE   11     -39.912  12.961 -28.174   46.13           O
ATOM    169  N    THR   12     -38.827  14.917 -28.507   52.66           N
ATOM    170  HN   THR   12     -38.639  15.828 -28.116    0.00           H
ATOM    171  CA   THR   12     -38.228  14.532 -29.776   57.14           C
ATOM    172  HA   THR   12     -38.818  13.779 -30.231    0.00           H
ATOM    173  CB   THR   12     -38.159  15.757 -30.698   56.47           C
ATOM    174  HB   THR   12     -37.635  15.504 -31.583    0.00           H
ATOM    175  OG1  THR   12     -37.473  16.819 -30.033   56.89           O
ATOM    176  HG1  THR   12     -37.431  17.590 -30.615    0.00           H
ATOM    177  CG2  THR   12     -39.571  16.226 -31.070   55.84           C
ATOM    178  HG21 THR   12     -40.082  15.445 -31.571    0.00           H
ATOM    179  HG22 THR   12     -40.100  16.486 -30.190    0.00           H
ATOM    180  HG23 THR   12     -39.506  17.071 -31.706    0.00           H
ATOM    181  C    THR   12     -36.857  13.820 -29.746   61.70           C
ATOM    182  O    THR   12     -36.089  13.958 -28.795   62.72           O
ATOM    183  N    PRO   13     -36.546  13.049 -30.809   66.15           N
ATOM    184  CD   PRO   13     -37.628  12.800 -31.769   66.95           C
ATOM    185  HD2  PRO   13     -38.561  12.996 -31.308    0.00           H
ATOM    186  HD3  PRO   13     -37.509  13.435 -32.608    0.00           H
ATOM    187  CA   PRO   13     -35.379  12.216 -31.162   69.56           C
ATOM    188  HA   PRO   13     -35.097  11.631 -30.326    0.00           H
ATOM    189  CB   PRO   13     -35.929  11.320 -32.276   69.01           C
ATOM    190  HB2  PRO   13     -35.640  11.709 -33.217    0.00           H
ATOM    191  HB3  PRO   13     -35.542  10.341 -32.165    0.00           H
ATOM    192  CG   PRO   13     -37.416  11.362 -32.083   67.51           C
ATOM    193  HG2  PRO   13     -37.897  11.051 -32.974    0.00           H
ATOM    194  HG3  PRO   13     -37.688  10.714 -31.291    0.00           H
ATOM    195  C    PRO   13     -34.066  12.876 -31.609   72.85           C
ATOM    196  O    PRO   13     -33.315  13.429 -30.798   73.19           O
ATOM    197  N    CYS   14     -33.809  12.741 -32.915   76.55           N
ATOM    198  HN   CYS   14     -34.522  12.228 -33.412    0.00           H
ATOM    199  CA   CYS   14     -32.637  13.253 -33.635   80.08           C
ATOM    200  HA   CYS   14     -32.951  13.725 -34.530    0.00           H
ATOM    201  CB   CYS   14     -31.921  14.345 -32.824   80.56           C
ATOM    202  HB2  CYS   14     -32.604  15.122 -32.598    0.00           H
ATOM    203  HB3  CYS   14     -31.549  13.929 -31.924    0.00           H
ATOM    204  SG   CYS   14     -30.508  15.104 -33.694   83.26           S
ATOM    205  HG   CYS   14     -29.989  15.976 -32.964    0.00           H
ATOM    206  C    CYS   14     -31.620  12.160 -34.026   81.54           C
ATOM    207  O    CYS   14     -30.530  12.477 -34.500   81.43           O
ATOM    208  N    ALA   15     -31.957  10.884 -33.835   83.75           N
ATOM    209  HN   ALA   15     -32.865  10.669 -33.452    0.00           H
ATOM    210  CA   ALA   15     -31.025   9.795 -34.175   85.61           C
ATOM    211  HA   ALA   15     -30.389  10.107 -34.962    0.00           H
ATOM    212  CB   ALA   15     -30.180   9.437 -32.957   84.97           C
ATOM    213  HB1  ALA   15     -29.628  10.286 -32.649    0.00           H
ATOM    214  HB2  ALA   15     -30.813   9.122 -32.169    0.00           H
ATOM    215  HB3  ALA   15     -29.513   8.654 -33.208    0.00           H
ATOM    216  C    ALA   15     -31.755   8.556 -34.676   86.89           C
ATOM    217  O    ALA   15     -31.143   7.526 -34.991   87.17           O
ATOM    218  N    ALA   16     -33.074   8.687 -34.743   88.12           N
ATOM    219  HN   ALA   16     -33.446   9.583 -34.466    0.00           H
ATOM    220  CA   ALA   16     -33.970   7.633 -35.182   89.15           C
ATOM    221  HA   ALA   16     -34.686   8.034 -35.851    0.00           H
ATOM    222  CB   ALA   16     -33.211   6.521 -35.895   89.34           C
ATOM    223  HB1  ALA   16     -32.718   6.918 -36.744    0.00           H
ATOM    224  HB2  ALA   16     -32.496   6.102 -35.235    0.00           H
ATOM    225  HB3  ALA   16     -33.891   5.770 -36.202    0.00           H
ATOM    226  C    ALA   16     -34.688   7.085 -33.966   90.09           C
ATOM    227  O    ALA   16     -34.910   5.879 -33.842   90.43           O
ATOM    228  N    GLU   17     -35.033   7.981 -33.052   90.35           N
```

FIGURE 6- 4 -

```
ATOM    229  HN   GLU   17     -34.787    8.950  -33.187    0.00        H
ATOM    230  CA   GLU   17     -35.759    7.576  -31.863   90.54        C
ATOM    231  HA   GLU   17     -35.349    6.674  -31.489    0.00        H
ATOM    232  CB   GLU   17     -35.654    8.657  -30.789   90.09        C
ATOM    233  HB2  GLU   17     -35.400    9.580  -31.241    0.00        H
ATOM    234  HB3  GLU   17     -36.584    8.752  -30.291    0.00        H
ATOM    235  CG   GLU   17     -34.620    8.409  -29.716   90.32        C
ATOM    236  HG2  GLU   17     -34.974    7.666  -29.050    0.00        H
ATOM    237  HG3  GLU   17     -33.718    8.081  -30.164    0.00        H
ATOM    238  CD   GLU   17     -34.325    9.672  -28.913   90.78        C
ATOM    239  OE1  GLU   17     -35.288   10.314  -28.434   91.95       O1-
ATOM    240  OE2  GLU   17     -33.134   10.028  -28.763   90.43        O
ATOM    241  C    GLU   17     -37.224    7.348  -32.259   91.03        C
ATOM    242  O    GLU   17     -38.078    8.157  -31.845   91.44        O
ATOM    243  OXT  GLU   17     -37.503    6.374  -32.998   91.22       O1-
ATOM    244  CB   MET   36     -36.911  -11.655  -28.617   76.38        C
ATOM    245  HB2  MET   36     -35.985  -12.190  -28.861    0.00        H
ATOM    246  HB3  MET   36     -37.002  -11.686  -27.527    0.00        H
ATOM    247  CG   MET   36     -38.121  -12.363  -29.228   78.04        C
ATOM    248  HG2  MET   36     -39.048  -11.924  -28.846    0.00        H
ATOM    249  HG3  MET   36     -38.139  -12.240  -30.313    0.00        H
ATOM    250  SD   MET   36     -38.172  -14.173  -28.930   81.54        S
ATOM    251  CE   MET   36     -38.091  -14.190  -27.116   79.74        C
ATOM    252  HE1  MET   36     -37.096  -13.906  -26.771    0.00        H
ATOM    253  HE2  MET   36     -38.839  -13.517  -26.692    0.00        H
ATOM    254  HE3  MET   36     -38.297  -15.201  -26.760    0.00        H
ATOM    255  C    MET   36     -35.879   -9.386  -28.122   73.65        C
ATOM    256  O    MET   36     -35.934   -9.543  -26.905   73.17        O
ATOM    257  N    MET   36     -36.328  -10.136  -30.476   74.87        N
ATOM    258  H1   MET   36     -37.022  -10.584  -31.085    0.00        H
ATOM    259  H2   MET   36     -36.410   -9.164  -30.798    0.00        H
ATOM    260  CA   MET   36     -36.795  -10.192  -29.081   74.97        C
ATOM    261  HA   MET   36     -37.776   -9.711  -29.025    0.00        H
ATOM    262  N    VAL   37     -35.079   -8.435  -28.712   71.96        N
ATOM    263  HN   VAL   37     -35.068   -8.383  -29.729    0.00        H
ATOM    264  CA   VAL   37     -34.197   -7.540  -27.948   70.93        C
ATOM    265  HA   VAL   37     -34.483   -7.573  -26.902    0.00        H
ATOM    266  CB   VAL   37     -32.728   -8.000  -28.105   70.57        C
ATOM    267  HB   VAL   37     -32.505   -8.126  -29.171    0.00        H
ATOM    268  CG1  VAL   37     -31.729   -6.988  -27.550   70.35        C
ATOM    269  HG11 VAL   37     -31.783   -6.033  -28.078    0.00        H
ATOM    270  HG12 VAL   37     -31.902   -6.802  -26.487    0.00        H
ATOM    271  HG13 VAL   37     -30.705   -7.357  -27.667    0.00        H
ATOM    272  CG2  VAL   37     -32.494   -9.349  -27.418   69.89        C
ATOM    273  HG21 VAL   37     -32.763   -9.307  -26.357    0.00        H
ATOM    274  HG22 VAL   37     -33.080  -10.144  -27.887    0.00        H
ATOM    275  HG23 VAL   37     -31.442   -9.643  -27.481    0.00        H
ATOM    276  C    VAL   37     -34.403   -6.116  -28.490   70.82        C
ATOM    277  O    VAL   37     -34.165   -5.839  -29.669   70.37        O
ATOM    278  N    TYR   38     -34.969   -5.198  -27.607   69.95        N
ATOM    279  HN   TYR   38     -35.196   -5.494  -26.669    0.00        H
ATOM    280  CA   TYR   38     -35.339   -3.850  -28.062   67.47        C
ATOM    281  HA   TYR   38     -35.085   -3.740  -29.084    0.00        H
ATOM    282  CB   TYR   38     -36.849   -3.636  -27.890   67.34        C
ATOM    283  HB2  TYR   38     -37.126   -2.710  -28.323    0.00        H
ATOM    284  HB3  TYR   38     -37.374   -4.421  -28.369    0.00        H
ATOM    285  CG   TYR   38     -37.290   -3.611  -26.440   66.87        C
ATOM    286  CD1  TYR   38     -37.326   -4.782  -25.679   66.84        C
ATOM    287  HD1  TYR   38     -37.069   -5.726  -26.130    0.00        H
ATOM    288  CE1  TYR   38     -37.692   -4.756  -24.332   66.72        C
ATOM    289  HE1  TYR   38     -37.714   -5.670  -23.762    0.00        H
ATOM    290  CD2  TYR   38     -37.637   -2.407  -25.815   66.52        C
ATOM    291  HD2  TYR   38     -37.625   -1.487  -26.375    0.00        H
ATOM    292  CE2  TYR   38     -38.003   -2.371  -24.464   66.30        C
ATOM    293  HE2  TYR   38     -38.263   -1.434  -24.001    0.00        H
ATOM    294  CZ   TYR   38     -38.027   -3.551  -23.731   66.70        C
ATOM    295  OH   TYR   38     -38.372   -3.537  -22.398   66.38        O
ATOM    296  HH   TYR   38     -38.328   -4.436  -22.044    0.00        H
ATOM    297  C    TYR   38     -34.614   -2.691  -27.373   65.44        C
ATOM    298  O    TYR   38     -34.145   -2.805  -26.238   63.71        O
ATOM    299  N    ALA   39     -34.548   -1.569  -28.082   64.00        N
ATOM    300  HN   ALA   39     -34.946   -1.583  -29.009    0.00        H
ATOM    301  CA   ALA   39     -33.931   -0.347  -27.570   63.10        C
ATOM    302  HA   ALA   39     -33.408   -0.564  -26.675    0.00        H
ATOM    303  CB   ALA   39     -32.952    0.220  -28.594   62.31        C
ATOM    304  HB1  ALA   39     -32.195   -0.494  -28.791    0.00        H
```

FIGURE 6- 5 -

```
ATOM    305  HB2  ALA    39     -33.469    0.443  -29.491    0.00    H
ATOM    306  HB3  ALA    39     -32.513    1.104  -28.211    0.00    H
ATOM    307  C    ALA    39     -35.065    0.642  -27.324   62.16    C
ATOM    308  O    ALA    39     -35.943    0.804  -28.170   61.83    C
ATOM    309  N    THR    40     -35.064    1.292  -26.167   61.50    N
ATOM    310  HN   THR    40     -34.327    1.122  -25.499    0.00    H
ATOM    311  CA   THR    40     -36.122    2.248  -25.859   61.45    C
ATOM    312  HA   THR    40     -37.065    1.776  -25.960    0.00    H
ATOM    313  CB   THR    40     -35.986    2.776  -24.420   60.62    C
ATOM    314  HB   THR    40     -36.627    3.608  -24.287    0.00    H
ATOM    315  OG1  THR    40     -34.632    3.186  -24.190   60.30    C
ATOM    316  HG1  THR    40     -34.545    3.518  -23.286    0.00    H
ATOM    317  CG2  THR    40     -36.365    1.694  -23.421   58.74    C
ATOM    318  HG21 THR    40     -37.368    1.397  -23.586    0.00    H
ATOM    319  HG22 THR    40     -35.725    0.860  -23.544    0.00    H
ATOM    320  HG23 THR    40     -36.266    2.072  -22.437    0.00    H
ATOM    321  C    THR    40     -36.109    3.414  -26.843   61.91    C
ATOM    322  O    THR    40     -35.057    3.809  -27.343   61.79    C
ATOM    323  N    THR    41     -37.287    3.958  -27.132   62.64    N
ATOM    324  HN   THR    41     -38.109    3.598  -26.672    0.00    H
ATOM    325  CA   THR    41     -37.407    5.054  -28.087   62.94    C
ATOM    326  HA   THR    41     -36.460    5.507  -28.225    0.00    H
ATOM    327  CB   THR    41     -37.915    4.524  -29.438   62.78    C
ATOM    328  HB   THR    41     -37.118    4.059  -29.957    0.00    H
ATOM    329  OG1  THR    41     -38.405    5.615  -30.226   62.93    C
ATOM    330  HG1  THR    41     -38.724    5.291  -31.075    0.00    H
ATOM    331  CG2  THR    41     -39.033    3.503  -29.220   62.23    C
ATOM    332  HG21 THR    41     -38.664    2.693  -28.647    0.00    H
ATOM    333  HG22 THR    41     -39.836    3.963  -28.705    0.00    H
ATOM    334  HG23 THR    41     -39.373    3.147  -30.157    0.00    H
ATOM    335  C    THR    41     -38.345    6.160  -27.607   62.85    C
ATOM    336  O    THR    41     -39.154    5.950  -26.697   62.90    C
ATOM    337  N    SER    42     -38.241    7.332  -28.235   61.86    N
ATOM    338  HN   SER    42     -37.565    7.413  -28.980    0.00    H
ATOM    339  CA   SER    42     -39.072    8.482  -27.872   61.44    C
ATOM    340  HA   SER    42     -39.000    8.655  -26.830    0.00    H
ATOM    341  CB   SER    42     -38.601    9.733  -28.621   59.62    C
ATOM    342  HB2  SER    42     -39.158   10.572  -28.293    0.00    H
ATOM    343  HB3  SER    42     -37.573    9.894  -28.427    0.00    H
ATOM    344  OG   SER    42     -38.780    9.589  -30.013   59.08    C
ATOM    345  HG   SER    42     -38.476   10.390  -30.462    0.00    H
ATOM    346  C    SER    42     -40.563    8.255  -28.142   61.79    C
ATOM    347  O    SER    42     -41.420    9.004  -27.659   61.78    C
ATOM    348  N    ARG    43     -40.865    7.213  -28.909   61.44    N
ATOM    349  HN   ARG    43     -40.111    6.642  -29.261    0.00    H
ATOM    350  CA   ARG    43     -42.243    6.887  -29.245   60.59    C
ATOM    351  HA   ARG    43     -42.751    7.767  -29.544    0.00    H
ATOM    352  CB   ARG    43     -42.254    5.869  -30.395   61.88    C
ATOM    353  HB2  ARG    43     -41.782    4.975  -30.080    0.00    H
ATOM    354  HB3  ARG    43     -43.255    5.661  -30.672    0.00    H
ATOM    355  CG   ARG    43     -41.514    6.380  -31.643   63.82    C
ATOM    356  HG2  ARG    43     -41.325    7.369  -31.858    0.00    H
ATOM    357  HG3  ARG    43     -40.470    6.370  -31.464    0.00    H
ATOM    358  CD   ARG    43     -41.763    5.545  -32.904   65.47    C
ATOM    359  HD2  ARG    43     -42.682    5.027  -32.809    0.00    H
ATOM    360  HD3  ARG    43     -41.303    6.134  -33.748    0.00    H
ATOM    361  NE   ARG    43     -40.721    4.551  -33.153   66.79    N1+
ATOM    362  HE   ARG    43     -40.034    4.711  -33.874    0.00    H
ATOM    363  CZ   ARG    43     -40.591    3.408  -32.488   68.42    C
ATOM    364  NH1  ARG    43     -41.447    3.100  -31.519   69.56    N
ATOM    365  HH11 ARG    43     -41.347    2.232  -31.015    0.00    H
ATOM    366  HH12 ARG    43     -42.197    3.734  -31.283    0.00    H
ATOM    367  NH2  ARG    43     -39.600    2.573  -32.793   68.06    N
ATOM    368  HH21 ARG    43     -39.499    1.704  -32.290    0.00    H
ATOM    369  HH22 ARG    43     -38.950    2.809  -33.528    0.00    H
ATOM    370  C    ARG    43     -43.007    6.367  -28.017   59.47    C
ATOM    371  O    ARG    43     -44.220    6.575  -27.892   59.27    C
ATOM    372  N    SER    44     -42.289    5.718  -27.101   57.37    N
ATOM    373  HN   SER    44     -41.301    5.594  -27.263    0.00    H
ATOM    374  CA   SER    44     -42.903    5.189  -25.880   54.99    C
ATOM    375  HA   SER    44     -43.935    5.023  -26.048    0.00    H
ATOM    376  CB   SER    44     -42.256    3.867  -25.466   55.14    C
ATOM    377  HB2  SER    44     -42.890    3.362  -24.785    0.00    H
ATOM    378  HB3  SER    44     -42.106    3.264  -26.323    0.00    H
ATOM    379  OG   SER    44     -41.001    4.093  -24.841   53.04    C
ATOM    380  HG   SER    44     -40.610    3.246  -24.588    0.00    H
```

FIGURE 6- 6 -

```
ATOM    381  C    SER   44    -42.722    6.186  -24.740   53.66      C
ATOM    382  O    SER   44    -43.037    5.886  -23.583   52.44      O
ATOM    383  N    ALA   45    -42.193    7.362  -25.076   51.08      N
ATOM    384  HN   ALA   45    -41.953    7.513  -26.044    0.00      H
ATOM    385  CA   ALA   45    -41.959    8.414  -24.095   49.14      C
ATOM    386  HA   ALA   45    -41.359    8.036  -23.308    0.00      H
ATOM    387  CB   ALA   45    -41.244    9.584  -24.755   49.11      C
ATOM    388  HB1  ALA   45    -40.316    9.256  -25.145    0.00      H
ATOM    389  HB2  ALA   45    -41.842    9.965  -25.541    0.00      H
ATOM    390  HB3  ALA   45    -41.077   10.345  -24.038    0.00      H
ATOM    391  C    ALA   45    -43.274    8.879  -23.464   47.72      C
ATOM    392  O    ALA   45    -43.375    9.033  -22.243   47.20      O
ATOM    393  N    SER   46    -44.278    9.106  -24.305   45.50      N
ATOM    394  HN   SER   46    -44.118    8.977  -25.293    0.00      H
ATOM    395  CA   SER   46    -45.585    9.531  -23.830   42.96      C
ATOM    396  HA   SER   46    -45.534   10.539  -23.510    0.00      H
ATOM    397  CB   SER   46    -46.606    9.409  -24.959   42.58      C
ATOM    398  HB2  SER   46    -46.481   10.213  -25.637    0.00      H
ATOM    399  HB3  SER   46    -46.461    8.492  -25.469    0.00      H
ATOM    400  OG   SER   46    -47.928    9.443  -24.454   41.61      O
ATOM    401  HG   SER   46    -48.555    9.364  -25.186    0.00      H
ATOM    402  C    SER   46    -45.992    8.627  -22.679   42.28      C
ATOM    403  O    SER   46    -46.386    9.084  -21.609   41.64      O
ATOM    404  N    LEU   47    -45.869    7.330  -22.918   41.74      N
ATOM    405  HN   LEU   47    -45.513    7.056  -23.822    0.00      H
ATOM    406  CA   LEU   47    -46.222    6.321  -21.944   41.12      C
ATOM    407  HA   LEU   47    -47.268    6.341  -21.779    0.00      H
ATOM    408  CB   LEU   47    -45.811    4.954  -22.476   43.20      C
ATOM    409  HB2  LEU   47    -46.204    4.822  -23.450    0.00      H
ATOM    410  HB3  LEU   47    -44.754    4.892  -22.510    0.00      H
ATOM    411  CG   LEU   47    -46.285    3.763  -21.656   44.36      C
ATOM    412  HG   LEU   47    -45.770    3.744  -20.731    0.00      H
ATOM    413  CD1  LEU   47    -47.781    3.879  -21.398   45.20      C
ATOM    414  HD11 LEU   47    -47.979    4.773  -20.865    0.00      H
ATOM    415  HD12 LEU   47    -48.298    3.897  -22.322    0.00      H
ATOM    416  HD13 LEU   47    -48.106    3.048  -20.827    0.00      H
ATOM    417  CD2  LEU   47    -45.954    2.483  -22.405   46.57      C
ATOM    418  HD21 LEU   47    -46.443    2.467  -23.344    0.00      H
ATOM    419  HD22 LEU   47    -44.907    2.421  -22.552    0.00      H
ATOM    420  HD23 LEU   47    -46.281    1.649  -21.840    0.00      H
ATOM    421  C    LEU   47    -45.583    6.560  -20.580   41.00      C
ATOM    422  O    LEU   47    -46.238    6.400  -19.542   41.61      O
ATOM    423  N    ARG   48    -44.312    6.950  -20.589   39.05      N
ATOM    424  HN   ARG   48    -43.870    7.069  -21.488    0.00      H
ATOM    425  CA   ARG   48    -43.557    7.205  -19.365   38.35      C
ATOM    426  HA   ARG   48    -43.734    6.424  -18.672    0.00      H
ATOM    427  CB   ARG   48    -42.063    7.265  -19.713   38.23      C
ATOM    428  HB2  ARG   48    -41.663    6.284  -19.722    0.00      H
ATOM    429  HB3  ARG   48    -41.941    7.705  -20.668    0.00      H
ATOM    430  CG   ARG   48    -41.173    8.060  -18.780   37.97      C
ATOM    431  HG2  ARG   48    -40.187    8.083  -19.167    0.00      H
ATOM    432  HG3  ARG   48    -41.543    9.049  -18.697    0.00      H
ATOM    433  CD   ARG   48    -41.091    7.491  -17.372   39.99      C
ATOM    434  HD2  ARG   48    -40.359    8.020  -16.819    0.00      H
ATOM    435  HD3  ARG   48    -42.032    7.589  -16.896    0.00      H
ATOM    436  NE   ARG   48    -40.729    6.080  -17.343   41.95      N1+
ATOM    437  HE   ARG   48    -40.798    5.524  -18.182    0.00      H
ATOM    438  CZ   ARG   48    -40.296    5.430  -16.262   44.71      C
ATOM    439  NH1  ARG   48    -40.144    6.055  -15.092   42.96      N
ATOM    440  HH11 ARG   48    -39.815    5.544  -14.286    0.00      H
ATOM    441  HH12 ARG   48    -40.358    7.038  -15.014    0.00      H
ATOM    442  NH2  ARG   48    -40.047    4.127  -16.346   47.12      N
ATOM    443  HH21 ARG   48    -39.719    3.623  -15.536    0.00      H
ATOM    444  HH22 ARG   48    -40.186    3.642  -17.220    0.00      H
ATOM    445  C    ARG   48    -44.004    8.474  -18.623   38.43      C
ATOM    446  O    ARG   48    -44.150    8.473  -17.387   37.38      O
ATOM    447  N    GLN   49    -44.233    9.544  -19.378   36.66      N
ATOM    448  HN   GLN   49    -44.107    9.465  -20.376    0.00      H
ATOM    449  CA   GLN   49    -44.657   10.810  -18.795   36.95      C
ATOM    450  HA   GLN   49    -43.896   11.178  -18.157    0.00      H
ATOM    451  CB   GLN   49    -44.922   11.826  -19.900   36.26      C
ATOM    452  HB2  GLN   49    -45.820   11.576  -20.402    0.00      H
ATOM    453  HB3  GLN   49    -45.012   12.793  -19.477    0.00      H
ATOM    454  CG   GLN   49    -43.834   11.898  -20.946   36.17      C
ATOM    455  HG2  GLN   49    -42.936   12.238  -20.499    0.00      H
ATOM    456  HG3  GLN   49    -43.679   10.936  -21.361    0.00      H
```

FIGURE 6-7 -

```
ATOM    457  CD   GLN    49     -44.178  12.840 -22.072  35.82      C
ATOM    458  OE1  GLN    49     -44.187  14.058 -21.897  35.28      O
ATOM    459  NE2  GLN    49     -44.476  12.280 -23.240  37.70      N
ATOM    460  HE21 GLN    49     -44.456  11.276 -23.338   0.00      H
ATOM    461  HE22 GLN    49     -44.723  12.859 -24.029   0.00      H
ATOM    462  C    GLN    49     -45.931  10.615 -17.979  37.70      C
ATOM    463  O    GLN    49     -46.189  11.332 -17.008  37.21      O
ATOM    464  N    LYS    50     -46.725   9.634 -18.383  37.26      N
ATOM    465  HN   LYS    50     -46.444   9.078 -19.177   0.00      H
ATOM    466  CA   LYS    50     -47.977   9.352 -17.708  38.38      C
ATOM    467  HA   LYS    50     -48.516  10.253 -17.573   0.00      H
ATOM    468  CB   LYS    50     -48.805   8.381 -18.559  39.51      C
ATOM    469  HB2  LYS    50     -48.705   8.635 -19.582   0.00      H
ATOM    470  HB3  LYS    50     -48.458   7.392 -18.405   0.00      H
ATOM    471  CG   LYS    50     -50.303   8.357 -18.269  38.95      C
ATOM    472  HG2  LYS    50     -50.629   9.332 -18.013   0.00      H
ATOM    473  HG3  LYS    50     -50.824   8.025 -19.129   0.00      H
ATOM    474  CD   LYS    50     -50.652   7.434 -17.127  39.43      C
ATOM    475  HD2  LYS    50     -50.186   6.495 -17.277   0.00      H
ATOM    476  HD3  LYS    50     -50.312   7.855 -16.217   0.00      H
ATOM    477  CE   LYS    50     -52.158   7.227 -17.041  40.33      C
ATOM    478  HE2  LYS    50     -52.623   8.133 -16.752   0.00      H
ATOM    479  HE3  LYS    50     -52.528   6.927 -17.987   0.00      H
ATOM    480  NZ   LYS    50     -52.512   6.172 -16.038  41.12      N1-
ATOM    481  HZ1  LYS    50     -52.085   5.298 -16.304   0.00      H
ATOM    482  HZ2  LYS    50     -52.175   6.447 -15.127   0.00      H
ATOM    483  HZ3  LYS    50     -53.514   6.061 -16.007   0.00      H
ATOM    484  C    LYS    50     -47.699   8.758 -16.340  38.93      C
ATOM    485  O    LYS    50     -48.416   9.033 -15.378  39.51      O
ATOM    486  N    LYS    51     -46.642   7.957 -16.248  39.27      N
ATOM    487  HN   LYS    51     -46.071   7.796 -17.064   0.00      H
ATOM    488  CA   LYS    51     -46.305   7.315 -14.985  38.26      C
ATOM    489  HA   LYS    51     -47.194   7.021 -14.490   0.00      H
ATOM    490  CB   LYS    51     -45.440   6.078 -15.216  39.35      C
ATOM    491  HB2  LYS    51     -45.909   5.446 -15.925   0.00      H
ATOM    492  HB3  LYS    51     -44.491   6.374 -15.581   0.00      H
ATOM    493  CG   LYS    51     -45.218   5.266 -13.940  41.97      C
ATOM    494  HG2  LYS    51     -44.908   5.912 -13.160   0.00      H
ATOM    495  HG3  LYS    51     -46.122   4.787 -13.664   0.00      H
ATOM    496  CD   LYS    51     -44.153   4.204 -14.134  44.95      C
ATOM    497  HD2  LYS    51     -44.413   3.583 -14.950   0.00      H
ATOM    498  HD3  LYS    51     -43.223   4.669 -14.332   0.00      H
ATOM    499  CE   LYS    51     -44.004   3.332 -12.889  46.29      C
ATOM    500  HE2  LYS    51     -43.827   3.948 -12.046   0.00      H
ATOM    501  HE3  LYS    51     -44.893   2.776 -12.739   0.00      H
ATOM    502  NZ   LYS    51     -42.861   2.360 -13.003  46.62      N1-
ATOM    503  HZ1  LYS    51     -43.015   1.751 -13.793   0.00      H
ATOM    504  HZ2  LYS    51     -41.999   2.868 -13.132   0.00      H
ATOM    505  HZ3  LYS    51     -42.803   1.809 -12.160   0.00      H
ATOM    506  C    LYS    51     -45.583   8.228 -14.018  37.15      C
ATOM    507  O    LYS    51     -45.754   8.108 -12.811  38.29      O
ATOM    508  N    VAL    52     -44.763   9.132 -14.538  35.50      N
ATOM    509  HN   VAL    52     -44.652   9.198 -15.539   0.00      H
ATOM    510  CA   VAL    52     -44.022  10.030 -13.662  33.88      C
ATOM    511  HA   VAL    52     -43.897   9.575 -12.714   0.00      H
ATOM    512  CB   VAL    52     -42.623  10.358 -14.234  32.97      C
ATOM    513  HB   VAL    52     -42.047  10.852 -13.496   0.00      H
ATOM    514  CG1  VAL    52     -41.893   9.075 -14.577  30.24      C
ATOM    515  HG11 VAL    52     -41.791   8.486 -13.704   0.00      H
ATOM    516  HG12 VAL    52     -42.455   8.537 -15.299   0.00      H
ATOM    517  HG13 VAL    52     -40.941   9.304 -14.968   0.00      H
ATOM    518  CG2  VAL    52     -42.748  11.258 -15.448  31.14      C
ATOM    519  HG21 VAL    52     -43.320  10.768 -16.193   0.00      H
ATOM    520  HG22 VAL    52     -43.228  12.160 -15.171   0.00      H
ATOM    521  HG23 VAL    52     -41.783  11.474 -15.828   0.00      H
ATOM    522  C    VAL    52     -44.743  11.340 -13.388  32.86      C
ATOM    523  O    VAL    52     -44.241  12.181 -12.653  33.41      O
ATOM    524  N    THR    53     -45.921  11.517 -13.968  31.49      N
ATOM    525  HN   THR    53     -46.307  10.794 -14.557   0.00      H
ATOM    526  CA   THR    53     -46.659  12.754 -13.756  31.20      C
ATOM    527  HA   THR    53     -46.004  13.495 -13.378   0.00      H
ATOM    528  CB   THR    53     -47.284  13.276 -15.082  31.07      C
ATOM    529  HB   THR    53     -47.957  12.553 -15.464   0.00      H
ATOM    530  OG1  THR    53     -46.251  13.505 -16.048  29.61      O
ATOM    531  HG1  THR    53     -46.644  13.829 -16.870   0.00      H
ATOM    532  CG2  THR    53     -48.039  14.573 -14.841  27.60      C
```

FIGURE 6- 8 -

```
ATOM    533  HG21 THR   53     -48.814  14.405 -14.139    0.00        H
ATOM    534  HG22 THR   53     -47.373  15.304 -14.464    0.00        H
ATOM    535  HG23 THR   53     -48.457  14.913 -15.753    0.00        H
ATOM    536  C    THR   53     -47.762  12.611 -12.710   30.92        C
ATOM    537  O    THR   53     -48.827  12.048 -12.972   31.76        O
ATOM    538  N    PHE   54     -47.501  13.133 -11.522   30.28        N
ATOM    539  HN   PHE   54     -46.608  13.577 -11.365    0.00        H
ATOM    540  CA   PHE   54     -48.479  13.073 -10.452   30.54        C
ATOM    541  HA   PHE   54     -49.446  13.245 -10.848    0.00        H
ATOM    542  CB   PHE   54     -48.445  11.693  -9.787   29.91        C
ATOM    543  HB2  PHE   54     -49.123  11.676  -8.974    0.00        H
ATOM    544  HB3  PHE   54     -48.722  10.954 -10.493    0.00        H
ATOM    545  CG   PHE   54     -47.098  11.304  -9.247   30.01        C
ATOM    546  CD1  PHE   54     -46.685  11.731  -7.996   30.41        C
ATOM    547  HD1  PHE   54     -47.326  12.362  -7.404    0.00        H
ATOM    548  CD2  PHE   54     -46.244  10.493  -9.992   31.37        C
ATOM    549  HD2  PHE   54     -46.542  10.152 -10.969    0.00        H
ATOM    550  CE1  PHE   54     -45.441  11.351  -7.490   31.08        C
ATOM    551  HE1  PHE   54     -45.131  11.687  -6.515    0.00        H
ATOM    552  CE2  PHE   54     -45.003  10.110  -9.498   29.95        C
ATOM    553  HE2  PHE   54     -44.358   9.482 -10.090    0.00        H
ATOM    554  CZ   PHE   54     -44.603  10.541  -8.242   30.74        C
ATOM    555  HZ   PHE   54     -43.644  10.248  -7.850    0.00        H
ATOM    556  C    PHE   54     -48.236  14.171  -9.426   30.76        C
ATOM    557  O    PHE   54     -47.271  14.928  -9.529   30.65        O
ATOM    558  N    ASP   55     -49.124  14.255  -8.442   31.19        N
ATOM    559  HN   ASP   55     -49.889  13.597  -8.436    0.00        H
ATOM    560  CA   ASP   55     -49.018  15.260  -7.389   29.85        C
ATOM    561  HA   ASP   55     -48.430  16.071  -7.733    0.00        H
ATOM    562  CB   ASP   55     -50.408  15.770  -7.013   29.64        C
ATOM    563  HB2  ASP   55     -50.966  15.955  -7.894    0.00        H
ATOM    564  HB3  ASP   55     -50.905  15.041  -6.427    0.00        H
ATOM    565  CG   ASP   55     -50.364  17.055  -6.214   30.60        C
ATOM    566  OD1  ASP   55     -49.253  17.541  -5.920   31.01        O
ATOM    567  OD2  ASP   55     -51.444  17.586  -5.881   30.97        O1-
ATOM    568  C    ASP   55     -48.354  14.675  -6.153   28.70        C
ATOM    569  O    ASP   55     -48.773  13.631  -5.657   26.99        O
ATOM    570  N    ARG   56     -47.303  15.336  -5.677   27.94        N
ATOM    571  HN   ARG   56     -46.983  16.160  -6.163    0.00        H
ATOM    572  CA   ARG   56     -46.620  14.889  -4.480   27.81        C
ATOM    573  HA   ARG   56     -46.680  13.834  -4.412    0.00        H
ATOM    574  CB   ARG   56     -45.146  15.285  -4.486   25.49        C
ATOM    575  HB2  ARG   56     -45.059  16.317  -4.706    0.00        H
ATOM    576  HB3  ARG   56     -44.724  15.090  -3.535    0.00        H
ATOM    577  CG   ARG   56     -44.289  14.562  -5.489   24.98        C
ATOM    578  HG2  ARG   56     -43.268  14.757  -5.287    0.00        H
ATOM    579  HG3  ARG   56     -44.469  13.521  -5.422    0.00        H
ATOM    580  CD   ARG   56     -44.604  15.022  -6.895   25.61        C
ATOM    581  HD2  ARG   56     -43.984  14.507  -7.582    0.00        H
ATOM    582  HD3  ARG   56     -45.620  14.818  -7.114    0.00        H
ATOM    583  NE   ARG   56     -44.386  16.454  -7.085   23.83        N1+
ATOM    584  HE   ARG   56     -45.175  17.080  -7.151    0.00        H
ATOM    585  CZ   ARG   56     -43.192  17.028  -7.183   23.65        C
ATOM    586  NH1  ARG   56     -42.085  16.294  -7.109   20.11        N
ATOM    587  HH11 ARG   56     -41.181  16.736  -7.184    0.00        H
ATOM    588  HH12 ARG   56     -42.149  15.296  -6.978    0.00        H
ATOM    589  NH2  ARG   56     -43.108  18.342  -7.364   22.84        N
ATOM    590  HH21 ARG   56     -42.204  18.784  -7.439    0.00        H
ATOM    591  HH22 ARG   56     -43.948  18.897  -7.426    0.00        H
ATOM    592  C    ARG   56     -47.321  15.636  -3.369   29.64        C
ATOM    593  O    ARG   56     -47.552  16.836  -3.492   30.86        O
ATOM    594  N    LEU   57     -47.674  14.931  -2.299   30.79        N
ATOM    595  HN   LEU   57     -47.470  13.943  -2.284    0.00        H
ATOM    596  CA   LEU   57     -48.342  15.554  -1.164   32.28        C
ATOM    597  HA   LEU   57     -48.267  16.607  -1.245    0.00        H
ATOM    598  CB   LEU   57     -49.817  15.145  -1.158   35.02        C
ATOM    599  HB2  LEU   57     -50.164  15.062  -2.155    0.00        H
ATOM    600  HB3  LEU   57     -49.922  14.212  -0.669    0.00        H
ATOM    601  CG   LEU   57     -50.823  16.071  -0.464   38.41        C
ATOM    602  HG   LEU   57     -50.595  16.129   0.569    0.00        H
ATOM    603  CD1  LEU   57     -50.763  17.486  -1.069   38.28        C
ATOM    604  HD11 LEU   57     -49.789  17.882  -0.944    0.00        H
ATOM    605  HD12 LEU   57     -50.995  17.439  -2.101    0.00        H
ATOM    606  HD13 LEU   57     -51.464  18.110  -0.578    0.00        H
ATOM    607  CD2  LEU   57     -52.223  15.477  -0.617   38.23        C
ATOM    608  HD21 LEU   57     -52.461  15.394  -1.646    0.00        H
```

FIGURE 6-9 -

```
ATOM    609  HD22 LEU   57    -52.250   14.517   -0.170    0.00    H
ATOM    610  HD23 LEU   57    -52.928   16.108   -0.141    0.00    H
ATOM    611  C    LEU   57    -47.612   15.070    0.097   32.21    C
ATOM    612  O    LEU   57    -48.102   14.229    0.857   33.45    O
ATOM    613  N    GLN   58    -46.425   15.630    0.299   30.76    N
ATOM    614  HN   GLN   58    -46.155   16.337   -0.368    0.00    H
ATOM    615  CA   GLN   58    -45.530   15.283    1.397   29.11    C
ATOM    616  HA   GLN   58    -45.560   14.237    1.560    0.00    H
ATOM    617  CB   GLN   58    -44.131   15.725    0.986   27.37    C
ATOM    618  HB2  GLN   58    -43.891   15.307    0.043    0.00    H
ATOM    619  HB3  GLN   58    -44.099   16.782    0.922    0.00    H
ATOM    620  CG   GLN   58    -42.999   15.347    1.888   26.33    C
ATOM    621  HG2  GLN   58    -43.133   15.805    2.833    0.00    H
ATOM    622  HG3  GLN   58    -42.977   14.295    2.005    0.00    H
ATOM    623  CD   GLN   58    -41.675   15.801    1.309   26.95    C
ATOM    624  OE1  GLN   58    -41.526   16.953    0.898   25.02    O
ATOM    625  NE2  GLN   58    -40.707   14.901    1.270   27.17    N
ATOM    626  HE21 GLN   58    -40.871   13.968    1.617    0.00    H
ATOM    627  HE22 GLN   58    -39.804   15.147    0.893    0.00    H
ATOM    628  C    GLN   58    -45.895   15.845    2.775   29.50    C
ATOM    629  O    GLN   58    -46.380   16.968    2.893   28.89    O
ATOM    630  N    VAL   59    -45.659   15.046    3.815   30.63    N
ATOM    631  HN   VAL   59    -45.270   14.136    3.617    0.00    H
ATOM    632  CA   VAL   59    -45.941   15.439    5.203   31.12    C
ATOM    633  HA   VAL   59    -46.014   16.494    5.263    0.00    H
ATOM    634  CB   VAL   59    -47.279   14.827    5.724   31.62    C
ATOM    635  HB   VAL   59    -47.214   13.770    5.707    0.00    H
ATOM    636  CG1  VAL   59    -47.507   15.258    7.168   27.78    C
ATOM    637  HG11 VAL   59    -46.705   14.916    7.769    0.00    H
ATOM    638  HG12 VAL   59    -47.560   16.315    7.217    0.00    H
ATOM    639  HG13 VAL   59    -48.415   14.843    7.521    0.00    H
ATOM    640  CG2  VAL   59    -48.465   15.264    4.841   30.48    C
ATOM    641  HG21 VAL   59    -48.545   16.320    4.855    0.00    H
ATOM    642  HG22 VAL   59    -48.305   14.936    3.847    0.00    H
ATOM    643  HG23 VAL   59    -49.359   14.837    5.214    0.00    H
ATOM    644  C    VAL   59    -44.822   14.937    6.119   30.90    C
ATOM    645  O    VAL   59    -44.660   13.736    6.280   31.76    O
ATOM    646  N    LEU   60    -44.077   15.848    6.737   31.05    N
ATOM    647  HN   LEU   60    -44.288   16.824    6.592    0.00    H
ATOM    648  CA   LEU   60    -42.971   15.461    7.612   32.69    C
ATOM    649  HA   LEU   60    -42.676   14.469    7.390    0.00    H
ATOM    650  CB   LEU   60    -41.788   16.405    7.391   32.81    C
ATOM    651  HB2  LEU   60    -41.999   17.345    7.831    0.00    H
ATOM    652  HB3  LEU   60    -40.920   15.994    7.837    0.00    H
ATOM    653  CG   LEU   60    -41.449   16.669    5.925   33.96    C
ATOM    654  HG   LEU   60    -42.344   16.792    5.372    0.00    H
ATOM    655  CD1  LEU   60    -40.608   17.934    5.809   32.41    C
ATOM    656  HD11 LEU   60    -41.152   18.756    6.196    0.00    H
ATOM    657  HD12 LEU   60    -39.711   17.813    6.359    0.00    H
ATOM    658  HD13 LEU   60    -40.376   18.112    4.791    0.00    H
ATOM    659  CD2  LEU   60    -40.743   15.458    5.343   33.11    C
ATOM    660  HD21 LEU   60    -39.851   15.275    5.884    0.00    H
ATOM    661  HD22 LEU   60    -41.377   14.613    5.412    0.00    H
ATOM    662  HD23 LEU   60    -40.508   15.641    4.327    0.00    H
ATOM    663  C    LEU   60    -43.312   15.438    9.103   33.75    C
ATOM    664  O    LEU   60    -44.287   16.050    9.531   34.37    O
ATOM    665  N    ASP   61    -42.491   14.730    9.883   34.83    N
ATOM    666  HN   ASP   61    -41.718   14.264    9.432    0.00    H
ATOM    667  CA   ASP   61    -42.672   14.613   11.331   34.33    C
ATOM    668  HA   ASP   61    -43.330   15.372   11.667    0.00    H
ATOM    669  CB   ASP   61    -43.263   13.251   11.697   34.68    C
ATOM    670  HB2  ASP   61    -43.189   13.104   12.743    0.00    H
ATOM    671  HB3  ASP   61    -44.281   13.218   11.407    0.00    H
ATOM    672  CG   ASP   61    -42.550   12.098   11.016   34.76    C
ATOM    673  OD1  ASP   61    -41.306   12.087   10.982   36.22    O
ATOM    674  OD2  ASP   61    -43.242   11.188   10.523   36.40    O1-
ATOM    675  C    ASP   61    -41.367   14.807   12.099   35.65    C
ATOM    676  O    ASP   61    -40.356   15.242   11.539   35.62    O
ATOM    677  N    ASP   62    -41.387   14.469   13.386   36.10    N
ATOM    678  HN   ASP   62    -42.231   14.090   13.789    0.00    H
ATOM    679  CA   ASP   62    -40.202   14.643   14.211   35.88    C
ATOM    680  HA   ASP   62    -39.761   15.583   14.002    0.00    H
ATOM    681  CB   ASP   62    -40.573   14.585   15.689   37.45    C
ATOM    682  HB2  ASP   62    -41.229   13.770   15.857    0.00    H
ATOM    683  HB3  ASP   62    -39.696   14.457   16.268    0.00    H
ATOM    684  CG   ASP   62    -41.263   15.846   16.155   39.44    C
```

FIGURE 6-10 -

```
ATOM    685  OD1 ASP    62     -40.739   16.942   15.872   40.87        O
ATOM    686  OD2 ASP    62     -42.322   15.748   16.808   41.78        O1-
ATOM    687  C   ASP    62     -39.065   13.676   13.930   35.08        C
ATOM    688  O   ASP    62     -37.906   13.994   14.196   34.94        O
ATOM    689  N   HIS    63     -39.382   12.498   13.405   33.62        N
ATOM    690  HN  HIS    63     -40.348   12.274   13.219    0.00        H
ATOM    691  CA  HIS    63     -38.339   11.532   13.098   32.66        C
ATOM    692  HA  HIS    63     -37.705   11.418   13.939    0.00        H
ATOM    693  CB  HIS    63     -38.945   10.179   12.751   34.03        C
ATOM    694  HB2 HIS    63     -39.809   10.321   12.155    0.00        H
ATOM    695  HB3 HIS    63     -38.237    9.602   12.214    0.00        H
ATOM    696  CG  HIS    63     -39.354    9.384   13.948   37.06        C
ATOM    697  CD2 HIS    63     -40.543    8.834   14.293   37.58        C
ATOM    698  HD2 HIS    63     -41.398    8.951   13.648    0.00        H
ATOM    699  ND1 HIS    63     -38.475    9.065   14.961   37.55        N1+
ATOM    700  HD1 HIS    63     -37.517    9.378   14.915    0.00        H
ATOM    701  CE1 HIS    63     -39.105    8.352   15.876   38.05        C
ATOM    702  HE1 HIS    63     -38.576    8.008   16.749    0.00        H
ATOM    703  NE2 HIS    63     -40.361    8.198   15.495   37.25        N
ATOM    704  HE2 HIS    63     -41.132    7.717   15.933    0.00        H
ATOM    705  C   HIS    63     -37.540   12.066   11.928   32.32        C
ATOM    706  O   HIS    63     -36.311   11.970   11.900   30.95        O
ATOM    707  N   TYR    64     -38.256   12.637   10.966   31.67        N
ATOM    708  HN  TYR    64     -39.259   12.658   11.074    0.00        H
ATOM    709  CA  TYR    64     -37.641   13.219    9.789   31.25        C
ATOM    710  HA  TYR    64     -37.073   12.480    9.286    0.00        H
ATOM    711  CB  TYR    64     -38.721   13.754    8.844   31.92        C
ATOM    712  HB2 TYR    64     -39.355   12.960    8.547    0.00        H
ATOM    713  HB3 TYR    64     -39.291   14.494    9.343    0.00        H
ATOM    714  CG  TYR    64     -38.195   14.393    7.569   32.70        C
ATOM    715  CD1 TYR    64     -37.919   13.626    6.439   31.62        C
ATOM    716  HD1 TYR    64     -38.079   12.561    6.459    0.00        H
ATOM    717  CE1 TYR    64     -37.435   14.214    5.273   31.89        C
ATOM    718  HE1 TYR    64     -37.228   13.605    4.409    0.00        H
ATOM    719  CD2 TYR    64     -37.968   15.770    7.497   32.60        C
ATOM    720  HD2 TYR    64     -38.168   16.394    8.352    0.00        H
ATOM    721  CE2 TYR    64     -37.482   16.367    6.330   31.73        C
ATOM    722  HE2 TYR    64     -37.315   17.430    6.299    0.00        H
ATOM    723  CZ  TYR    64     -37.220   15.587    5.226   31.56        C
ATOM    724  OH  TYR    64     -36.753   16.172    4.075   31.72        O
ATOM    725  HH  TYR    64     -36.627   15.494    3.397    0.00        H
ATOM    726  C   TYR    64     -36.761   14.368   10.262   31.03        C
ATOM    727  O   TYR    64     -35.573   14.422    9.960   31.87        O
ATOM    728  N   ARG    65     -37.351   15.282   11.022   30.80        N
ATOM    729  HN  ARG    65     -38.326   15.173   11.260    0.00        H
ATOM    730  CA  ARG    65     -36.608   16.431   11.511   31.18        C
ATOM    731  HA  ARG    65     -36.145   16.925   10.696    0.00        H
ATOM    732  CB  ARG    65     -37.553   17.410   12.221   31.44        C
ATOM    733  HB2 ARG    65     -38.192   16.874   12.873    0.00        H
ATOM    734  HB3 ARG    65     -36.984   18.108   12.779    0.00        H
ATOM    735  CG  ARG    65     -38.434   18.198   11.249   32.81        C
ATOM    736  HG2 ARG    65     -37.821   18.721   10.562    0.00        H
ATOM    737  HG3 ARG    65     -39.064   17.529   10.722    0.00        H
ATOM    738  CD  ARG    65     -39.309   19.207   11.969   36.41        C
ATOM    739  HD2 ARG    65     -38.709   19.802   12.607    0.00        H
ATOM    740  HD3 ARG    65     -39.791   19.827   11.258    0.00        H
ATOM    741  NE  ARG    65     -40.341   18.563   12.785   37.40        N1+
ATOM    742  HE  ARG    65     -40.137   18.293   13.736    0.00        H
ATOM    743  CZ  ARG    65     -41.575   18.291   12.367   36.96        C
ATOM    744  NH1 ARG    65     -41.950   18.608   11.132   35.51        N
ATOM    745  HH11 ARG   65     -42.887   18.400   10.820    0.00        H
ATOM    746  HH12 ARG   65     -41.298   19.057   10.506    0.00        H
ATOM    747  NH2 ARG    65     -42.433   17.697   13.189   36.42        N
ATOM    748  HH21 ARG   65     -43.370   17.489   12.876    0.00        H
ATOM    749  HH22 ARG   65     -42.148   17.454   14.126    0.00        H
ATOM    750  C   ARG    65     -35.474   16.001   12.420   30.65        C
ATOM    751  O   ARG    65     -34.445   16.668   12.509   32.22        O
ATOM    752  N   ASP    66     -35.656   14.871   13.082   29.93        N
ATOM    753  HN  ASP    66     -36.523   14.370   12.957    0.00        H
ATOM    754  CA  ASP    66     -34.638   14.348   13.974   30.36        C
ATOM    755  HA  ASP    66     -34.324   15.112   14.637    0.00        H
ATOM    756  CB  ASP    66     -35.208   13.185   14.776   32.50        C
ATOM    757  HB2 ASP    66     -36.024   12.761   14.251    0.00        H
ATOM    758  HB3 ASP    66     -34.458   12.451   14.915    0.00        H
ATOM    759  CG  ASP    66     -35.701   13.600   16.134   33.23        C
ATOM    760  OD1 ASP    66     -36.196   14.740   16.261   32.66        O
```

FIGURE 6-11-

```
ATOM    761  OD2 ASP    66     -35.600  12.768  17.066  35.13      O1-
ATOM    762  C   ASP    66     -33.405  13.869  13.213  30.24      C
ATOM    763  O   ASP    66     -32.275  14.188  13.592  30.89      O
ATOM    764  N   VAL    67     -33.625  13.099  12.147  28.50      N
ATOM    765  HN  VAL    67     -34.580  12.895  11.894   0.00      H
ATOM    766  CA  VAL    67     -32.525  12.554  11.351  25.20      C
ATOM    767  HA  VAL    67     -31.811  12.108  11.994   0.00      H
ATOM    768  CB  VAL    67     -33.034  11.473  10.348  24.83      C
ATOM    769  HB  VAL    67     -33.760  11.901   9.706   0.00      H
ATOM    770  CG1 VAL    67     -31.891  10.970   9.484  21.01      C
ATOM    771  HG11 VAL   67     -31.478  11.779   8.939   0.00      H
ATOM    772  HG12 VAL   67     -31.144  10.543  10.101   0.00      H
ATOM    773  HG13 VAL   67     -32.254  10.238   8.810   0.00      H
ATOM    774  CG2 VAL    67     -33.661  10.310  11.114  21.64      C
ATOM    775  HG21 VAL   67     -32.937   9.879  11.756   0.00      H
ATOM    776  HG22 VAL   67     -34.476  10.665  11.689   0.00      H
ATOM    777  HG23 VAL   67     -34.004   9.580  10.428   0.00      H
ATOM    778  C   VAL    67     -31.775  13.635  10.593  23.91      C
ATOM    779  O   VAL    67     -30.539  13.615  10.535  21.45      O
ATOM    780  N   LEU    68     -32.524  14.577  10.021  23.61      N
ATOM    781  HN  LEU    68     -33.527  14.523  10.121   0.00      H
ATOM    782  CA  LEU    68     -31.922  15.673   9.261  23.30      C
ATOM    783  HA  LEU    68     -31.430  15.283   8.408   0.00      H
ATOM    784  CB  LEU    68     -32.992  16.667   8.803  20.46      C
ATOM    785  HB2 LEU    68     -33.714  16.162   8.216   0.00      H
ATOM    786  HB3 LEU    68     -33.462  17.095   9.650   0.00      H
ATOM    787  CG  LEU    68     -32.598  17.879   7.946  17.31      C
ATOM    788  HG  LEU    68     -32.044  18.563   8.535   0.00      H
ATOM    789  CD1 LEU    68     -31.750  17.482   6.762  17.18      C
ATOM    790  HD11 LEU   68     -30.863  17.016   7.104   0.00      H
ATOM    791  HD12 LEU   68     -32.291  16.807   6.151   0.00      H
ATOM    792  HD13 LEU   68     -31.502  18.345   6.200   0.00      H
ATOM    793  CD2 LEU    68     -33.857  18.547   7.467  15.82      C
ATOM    794  HD21 LEU   68     -34.422  17.862   6.890   0.00      H
ATOM    795  HD22 LEU   68     -34.429  18.862   8.301   0.00      H
ATOM    796  HD23 LEU   68     -33.607  19.387   6.873   0.00      H
ATOM    797  C   LEU    68     -30.890  16.373  10.125  24.13      C
ATOM    798  O   LEU    68     -29.733  16.529   9.716  25.85      O
ATOM    799  N   LYS    69     -31.293  16.773  11.326  22.91      N
ATOM    800  HN  LYS    69     -32.248  16.620  11.612   0.00      H
ATOM    801  CA  LYS    69     -30.359  17.431  12.229  24.90      C
ATOM    802  HA  LYS    69     -30.043  18.348  11.804   0.00      H
ATOM    803  CB  LYS    69     -31.033  17.708  13.574  25.39      C
ATOM    804  HB2 LYS    69     -31.431  16.806  13.962   0.00      H
ATOM    805  HB3 LYS    69     -30.320  18.099  14.252   0.00      H
ATOM    806  CG  LYS    69     -32.164  18.698  13.493  25.72      C
ATOM    807  HG2 LYS    69     -31.795  19.629  13.148   0.00      H
ATOM    808  HG3 LYS    69     -32.900  18.339  12.821   0.00      H
ATOM    809  CD  LYS    69     -32.792  18.894  14.842  28.10      C
ATOM    810  HD2 LYS    69     -33.210  17.979  15.173   0.00      H
ATOM    811  HD3 LYS    69     -32.055  19.215  15.531   0.00      H
ATOM    812  CE  LYS    69     -33.891  19.939  14.783  30.95      C
ATOM    813  HE2 LYS    69     -33.495  20.847  14.408   0.00      H
ATOM    814  HE3 LYS    69     -34.665  19.601  14.145   0.00      H
ATOM    815  NZ  LYS    69     -34.476  20.203  16.133  32.44      N1+
ATOM    816  HZ1 LYS    69     -34.869  19.350  16.502   0.00      H
ATOM    817  HZ2 LYS    69     -33.753  20.537  16.753   0.00      H
ATOM    818  HZ3 LYS    69     -35.201  20.901  16.055   0.00      H
ATOM    819  C   LYS    69     -29.090  16.594  12.444  24.31      C
ATOM    820  O   LYS    69     -27.986  17.114  12.453  23.27      O
ATOM    821  N   GLU    70     -29.252  15.289  12.611  26.68      N
ATOM    822  HN  GLU    70     -30.186  14.908  12.588   0.00      H
ATOM    823  CA  GLU    70     -28.108  14.405  12.826  26.82      C
ATOM    824  HA  GLU    70     -27.532  14.764  13.639   0.00      H
ATOM    825  CB  GLU    70     -28.605  12.990  13.139  27.21      C
ATOM    826  HB2 GLU    70     -29.366  12.723  12.452   0.00      H
ATOM    827  HB3 GLU    70     -27.800  12.307  13.057   0.00      H
ATOM    828  CG  GLU    70     -29.186  12.848  14.545  29.10      C
ATOM    829  HG2 GLU    70     -28.402  12.879  15.256   0.00      H
ATOM    830  HG3 GLU    70     -29.862  13.642  14.730   0.00      H
ATOM    831  CD  GLU    70     -29.945  11.539  14.752  34.68      C
ATOM    832  OE1 GLU    70     -29.461  10.473  14.302  34.64      O1-
ATOM    833  OE2 GLU    70     -31.032  11.576  15.380  37.74      O
ATOM    834  C   GLU    70     -27.223  14.412  11.591  26.18      C
ATOM    835  O   GLU    70     -26.003  14.568  11.674  24.91      O
ATOM    836  N   MET    71     -27.851  14.261  10.436  26.47      N
```

FIGURE 6-12-

```
ATOM    837  HN   MET   71     -28.853   14.144   10.422    0.00           H
ATOM    838  CA   MET   71     -27.104   14.263    9.194   26.96           C
ATOM    839  HA   MET   71     -26.395   13.477    9.207    0.00           H
ATOM    840  CB   MET   71     -28.058   14.064    8.027   28.04           C
ATOM    841  HB2  MET   71     -28.834   14.783    8.079    0.00           H
ATOM    842  HB3  MET   71     -27.530   14.179    7.118    0.00           H
ATOM    843  CG   MET   71     -28.717   12.708    7.985   25.80           C
ATOM    844  HG2  MET   71     -27.983   11.964    7.812    0.00           H
ATOM    845  HG3  MET   71     -29.198   12.521    8.909    0.00           H
ATOM    846  SD   MET   71     -29.907   12.740    6.651   29.64           S
ATOM    847  CE   MET   71     -28.969   12.076    5.298   26.00           C
ATOM    848  HE1  MET   71     -28.127   12.692    5.118    0.00           H
ATOM    849  HE2  MET   71     -28.645   11.097    5.540    0.00           H
ATOM    850  HE3  MET   71     -29.576   12.043    4.431    0.00           H
ATOM    851  C    MET   71     -26.334   15.572    9.025   25.88           C
ATOM    852  O    MET   71     -25.175   15.570    8.614   25.19           O
ATOM    853  N    LYS   72     -26.987   16.685    9.351   24.73           N
ATOM    854  HN   LYS   72     -27.934   16.594    9.688    0.00           H
ATOM    855  CA   LYS   72     -26.378   18.009    9.234   23.10           C
ATOM    856  HA   LYS   72     -26.017   18.146    8.247    0.00           H
ATOM    857  CB   LYS   72     -27.413   19.092    9.550   19.09           C
ATOM    858  HB2  LYS   72     -27.803   18.934   10.522    0.00           H
ATOM    859  HB3  LYS   72     -26.953   20.045    9.505    0.00           H
ATOM    860  CG   LYS   72     -28.582   19.120    8.603   17.45           C
ATOM    861  HG2  LYS   72     -28.228   19.188    7.607    0.00           H
ATOM    862  HG3  LYS   72     -29.149   18.233    8.718    0.00           H
ATOM    863  CD   LYS   72     -29.502   20.312    8.866   15.87           C
ATOM    864  HD2  LYS   72     -30.402   20.190    8.322    0.00           H
ATOM    865  HD3  LYS   72     -29.720   20.368    9.901    0.00           H
ATOM    866  CE   LYS   72     -28.870   21.614    8.446   13.81           C
ATOM    867  HE2  LYS   72     -27.943   21.733    8.943    0.00           H
ATOM    868  HE3  LYS   72     -28.711   21.607    7.399    0.00           H
ATOM    869  NZ   LYS   72     -29.725   22.773    8.777   12.83           N1+
ATOM    870  HZ1  LYS   72     -30.611   22.684    8.302    0.00           H
ATOM    871  HZ2  LYS   72     -29.879   22.803    9.774    0.00           H
ATOM    872  HZ3  LYS   72     -29.263   23.623    8.481    0.00           H
ATOM    873  C    LYS   72     -25.138   18.221   10.126   22.74           C
ATOM    874  O    LYS   72     -24.137   18.770    9.680   20.94           O
ATOM    875  N    ALA   73     -25.211   17.800   11.386   23.48           N
ATOM    876  HN   ALA   73     -26.059   17.354   11.702    0.00           H
ATOM    877  CA   ALA   73     -24.092   17.974   12.305   24.20           C
ATOM    878  HA   ALA   73     -23.883   19.007   12.423    0.00           H
ATOM    879  CB   ALA   73     -24.429   17.379   13.650   21.16           C
ATOM    880  HB1  ALA   73     -25.283   17.864   14.046    0.00           H
ATOM    881  HB2  ALA   73     -24.630   16.345   13.538    0.00           H
ATOM    882  HB3  ALA   73     -23.611   17.511   14.309    0.00           H
ATOM    883  C    ALA   73     -22.842   17.315   11.731   26.33           C
ATOM    884  O    ALA   73     -21.727   17.812   11.912   27.33           O
ATOM    885  N    LYS   74     -23.034   16.197   11.033   27.26           N
ATOM    886  HN   LYS   74     -23.978   15.848   10.937    0.00           H
ATOM    887  CA   LYS   74     -21.928   15.481   10.418   27.24           C
ATOM    888  HA   LYS   74     -21.127   15.405   11.107    0.00           H
ATOM    889  CB   LYS   74     -22.348   14.080   10.000   29.34           C
ATOM    890  HB2  LYS   74     -23.293   14.119    9.539    0.00           H
ATOM    891  HB3  LYS   74     -21.633   13.688    9.318    0.00           H
ATOM    892  CG   LYS   74     -22.459   13.066   11.118   32.45           C
ATOM    893  HG2  LYS   74     -21.529   12.986   11.616    0.00           H
ATOM    894  HG3  LYS   74     -23.203   13.378   11.802    0.00           H
ATOM    895  CD   LYS   74     -22.841   11.734   10.488   38.25           C
ATOM    896  HD2  LYS   74     -23.818   11.801   10.088    0.00           H
ATOM    897  HD3  LYS   74     -22.157   11.499    9.715    0.00           H
ATOM    898  CE   LYS   74     -22.838   10.561   11.454   40.62           C
ATOM    899  HE2  LYS   74     -21.860   10.421   11.838    0.00           H
ATOM    900  HE3  LYS   74     -23.504   10.760   12.253    0.00           H
ATOM    901  NZ   LYS   74     -23.280    9.323   10.718   43.65           N1+
ATOM    902  HZ1  LYS   74     -24.210    9.463   10.353    0.00           H
ATOM    903  HZ2  LYS   74     -22.644    9.140    9.956    0.00           H
ATOM    904  HZ3  LYS   74     -23.281    8.538   11.351    0.00           H
ATOM    905  C    LYS   74     -21.443   16.222    9.184   27.72           C
ATOM    906  O    LYS   74     -20.257   16.195    8.871   29.65           O
ATOM    907  N    ALA   75     -22.359   16.874    8.473   27.55           N
ATOM    908  HN   ALA   75     -23.324   16.844    8.767    0.00           H
ATOM    909  CA   ALA   75     -21.983   17.626    7.280   27.08           C
ATOM    910  HA   ALA   75     -21.401   17.011    6.644    0.00           H
ATOM    911  CB   ALA   75     -23.229   18.079    6.533   27.92           C
ATOM    912  HB1  ALA   75     -23.798   17.232    6.248    0.00           H
```

FIGURE 6- 13 -

```
ATOM    913  HB2  ALA   75    -23.813   18.697    7.164    0.00    H
ATOM    914  HB3  ALA   75    -22.945   18.623    5.670    0.00    H
ATOM    915  C    ALA   75    -21.132   18.836    7.673   26.53    C
ATOM    916  O    ALA   75    -20.281   19.284    6.905   24.61    O
ATOM    917  N    SER   76    -21.369   19.335    8.885   27.44    N
ATOM    918  HN   SER   76    -22.082   18.866    9.423    0.00    H
ATOM    919  CA   SER   76    -20.666   20.493    9.450   29.73    C
ATOM    920  HA   SER   76    -20.874   21.352    8.866    0.00    H
ATOM    921  CB   SER   76    -21.132   20.737   10.888   31.51    C
ATOM    922  HB2  SER   76    -21.141   19.819   11.417    0.00    H
ATOM    923  HB3  SER   76    -20.469   21.412   11.364    0.00    H
ATOM    924  OG   SER   76    -22.438   21.289   10.914   37.18    O
ATOM    925  HG   SER   76    -22.709   21.433   11.831    0.00    H
ATOM    926  C    SER   76    -19.151   20.377    9.456   29.57    C
ATOM    927  O    SER   76    -18.437   21.378    9.304   29.39    O
ATOM    928  N    THR   77    -18.675   19.151    9.648   28.58    N
ATOM    929  HN   THR   77    -19.354   18.413    9.763    0.00    H
ATOM    930  CA   THR   77    -17.252   18.845    9.696   27.31    C
ATOM    931  HA   THR   77    -16.774   19.496   10.381    0.00    H
ATOM    932  CB   THR   77    -17.035   17.375   10.153   28.88    C
ATOM    933  HB   THR   77    -16.018   17.233   10.413    0.00    H
ATOM    934  OG1  THR   77    -17.404   16.482    9.092   30.52    O
ATOM    935  HG1  THR   77    -17.268   15.568    9.378    0.00    H
ATOM    936  CG2  THR   77    -17.902   17.049   11.365   27.22    C
ATOM    937  HG21 THR   77    -17.648   17.695   12.165    0.00    H
ATOM    938  HG22 THR   77    -18.923   17.181   11.115    0.00    H
ATOM    939  HG23 THR   77    -17.737   16.045   11.657    0.00    H
ATOM    940  C    THR   77    -16.559   19.031    8.336   26.88    C
ATOM    941  O    THR   77    -15.356   19.282    8.283   26.67    O
ATOM    942  N    VAL   78    -17.325   18.916    7.249   25.34    N
ATOM    943  HN   VAL   78    -18.309   18.754    7.403    0.00    H
ATOM    944  CA   VAL   78    -16.804   19.014    5.883   23.65    C
ATOM    945  HA   VAL   78    -15.908   18.456    5.806    0.00    H
ATOM    946  CB   VAL   78    -17.832   18.456    4.866   21.39    C
ATOM    947  HB   VAL   78    -18.703   19.058    4.879    0.00    H
ATOM    948  CG1  VAL   78    -17.260   18.500    3.478   18.26    C
ATOM    949  HG11 VAL   78    -17.028   19.501    3.224    0.00    H
ATOM    950  HG12 VAL   78    -16.380   17.913    3.440    0.00    H
ATOM    951  HG13 VAL   78    -17.970   18.117    2.792    0.00    H
ATOM    952  CG2  VAL   78    -18.206   17.048    5.219   19.38    C
ATOM    953  HG21 VAL   78    -17.340   16.438    5.204    0.00    H
ATOM    954  HG22 VAL   78    -18.634   17.029    6.187    0.00    H
ATOM    955  HG23 VAL   78    -18.908   16.682    4.515    0.00    H
ATOM    956  C    VAL   78    -16.371   20.389    5.372   25.42    C
ATOM    957  O    VAL   78    -17.095   21.368    5.526   26.26    O
ATOM    958  N    LYS   79    -15.185   20.447    4.756   26.69    N
ATOM    959  HN   LYS   79    -14.642   19.599    4.704    0.00    H
ATOM    960  CA   LYS   79    -14.670   21.686    4.168   27.82    C
ATOM    961  HA   LYS   79    -15.364   22.469    4.330    0.00    H
ATOM    962  CB   LYS   79    -13.334   22.102    4.780   28.45    C
ATOM    963  HB2  LYS   79    -13.465   22.299    5.812    0.00    H
ATOM    964  HB3  LYS   79    -12.630   21.320    4.656    0.00    H
ATOM    965  CG   LYS   79    -12.760   23.365    4.125   30.62    C
ATOM    966  HG2  LYS   79    -12.485   23.150    3.125    0.00    H
ATOM    967  HG3  LYS   79    -13.492   24.130    4.133    0.00    H
ATOM    968  CD   LYS   79    -11.531   23.881    4.851   32.68    C
ATOM    969  HD2  LYS   79    -11.785   24.117    5.852    0.00    H
ATOM    970  HD3  LYS   79    -10.778   23.136    4.844    0.00    H
ATOM    971  CE   LYS   79    -10.956   25.145    4.195   35.01    C
ATOM    972  HE2  LYS   79    -10.482   24.886    3.284    0.00    H
ATOM    973  HE3  LYS   79    -11.740   25.830    4.002    0.00    H
ATOM    974  NZ   LYS   79     -9.933   25.849    5.061   34.36    N1+
ATOM    975  HZ1  LYS   79    -10.362   26.124    5.932    0.00    H
ATOM    976  HZ2  LYS   79     -9.163   25.224    5.248    0.00    H
ATOM    977  HZ3  LYS   79     -9.592   26.668    4.580    0.00    H
ATOM    978  C    LYS   79    -14.479   21.471    2.673   27.52    C
ATOM    979  O    LYS   79    -13.413   21.069    2.219   26.91    O
ATOM    980  N    ALA   80    -15.532   21.738    1.914   28.65    N
ATOM    981  HN   ALA   80    -16.368   22.071    2.371    0.00    H
ATOM    982  CA   ALA   80    -15.512   21.566    0.472   28.61    C
ATOM    983  HA   ALA   80    -15.004   20.669    0.231    0.00    H
ATOM    984  CB   ALA   80    -16.934   21.496   -0.058   29.21    C
ATOM    985  HB1  ALA   80    -17.436   20.676    0.385    0.00    H
ATOM    986  HB2  ALA   80    -17.444   22.393    0.180    0.00    H
ATOM    987  HB3  ALA   80    -16.913   21.371   -1.109    0.00    H
ATOM    988  C    ALA   80    -14.775   22.710   -0.179   28.27    C
```

FIGURE 6-14-

```
ATOM    989  O    ALA   80     -14.859   23.843    0.275    29.25       O
ATOM    990  N    LYS   81     -14.066   22.401   -1.255    29.43       N
ATOM    991  HN   LYS   81     -14.070   21.439   -1.559     0.00       H
ATOM    992  CA   LYS   81     -13.301   23.392   -1.991    32.94       C
ATOM    993  HA   LYS   81     -13.232   24.281   -1.419     0.00       H
ATOM    994  CB   LYS   81     -11.895   22.876   -2.277    38.35       C
ATOM    995  HB2  LYS   81     -11.944   21.856   -2.559     0.00       H
ATOM    996  HB3  LYS   81     -11.466   23.439   -3.064     0.00       H
ATOM    997  CG   LYS   81     -10.910   22.948   -1.120    46.30       C
ATOM    998  HG2  LYS   81     -10.613   23.954   -0.971     0.00       H
ATOM    999  HG3  LYS   81     -11.372   22.582   -0.240     0.00       H
ATOM   1000  CD   LYS   81      -9.686   22.090   -1.460    50.65       C
ATOM   1001  HD2  LYS   81      -9.968   21.070   -1.491     0.00       H
ATOM   1002  HD3  LYS   81      -9.303   22.379   -2.404     0.00       H
ATOM   1003  CE   LYS   81      -8.557   22.223   -0.448    52.59       C
ATOM   1004  HE2  LYS   81      -8.185   23.214   -0.463     0.00       H
ATOM   1005  HE3  LYS   81      -8.922   21.998    0.520     0.00       H
ATOM   1006  NZ   LYS   81      -7.450   21.272   -0.794    53.97       N1+
ATOM   1007  HZ1  LYS   81      -7.802   20.326   -0.779     0.00       H
ATOM   1008  HZ2  LYS   81      -7.099   21.486   -1.716     0.00       H
ATOM   1009  HZ3  LYS   81      -6.705   21.364   -0.120     0.00       H
ATOM   1010  C    LYS   81     -13.938   23.758   -3.321    32.21       C
ATOM   1011  O    LYS   81     -14.729   23.012   -3.886    32.49       O
ATOM   1012  N    LEU   82     -13.553   24.924   -3.813    31.55       N
ATOM   1013  HN   LEU   82     -12.901   25.452   -3.253     0.00       H
ATOM   1014  CA   LEU   82     -14.016   25.455   -5.082    29.74       C
ATOM   1015  HA   LEU   82     -15.006   25.125   -5.263     0.00       H
ATOM   1016  CB   LEU   82     -13.977   26.983   -5.004    28.83       C
ATOM   1017  HB2  LEU   82     -14.548   27.309   -4.173     0.00       H
ATOM   1018  HB3  LEU   82     -12.974   27.305   -4.892     0.00       H
ATOM   1019  CG   LEU   82     -14.503   27.819   -6.160    28.44       C
ATOM   1020  HG   LEU   82     -13.891   27.669   -7.011     0.00       H
ATOM   1021  CD1  LEU   82     -15.924   27.404   -6.482    29.39       C
ATOM   1022  HD11 LEU   82     -15.940   26.380   -6.752     0.00       H
ATOM   1023  HD12 LEU   82     -16.537   27.554   -5.632     0.00       H
ATOM   1024  HD13 LEU   82     -16.288   27.987   -7.287     0.00       H
ATOM   1025  CD2  LEU   82     -14.439   29.283   -5.781    25.91       C
ATOM   1026  HD21 LEU   82     -15.033   29.451   -4.920     0.00       H
ATOM   1027  HD22 LEU   82     -13.435   29.551   -5.575     0.00       H
ATOM   1028  HD23 LEU   82     -14.804   29.871   -6.582     0.00       H
ATOM   1029  C    LEU   82     -13.061   24.940   -6.169    30.26       C
ATOM   1030  O    LEU   82     -11.841   25.021   -6.022    30.34       O
ATOM   1031  N    LEU   83     -13.606   24.396   -7.251    31.21       N
ATOM   1032  HN   LEU   83     -14.611   24.342   -7.317     0.00       H
ATOM   1033  CA   LEU   83     -12.776   23.882   -8.333    30.76       C
ATOM   1034  HA   LEU   83     -11.872   23.502   -7.934     0.00       H
ATOM   1035  CB   LEU   83     -13.493   22.761   -9.081    29.95       C
ATOM   1036  HB2  LEU   83     -14.521   22.768   -8.827     0.00       H
ATOM   1037  HB3  LEU   83     -13.386   22.908  -10.124     0.00       H
ATOM   1038  CG   LEU   83     -12.994   21.341   -8.798    30.62       C
ATOM   1039  HG   LEU   83     -11.944   21.302   -8.932     0.00       H
ATOM   1040  CD1  LEU   83     -13.337   20.968   -7.374    28.61       C
ATOM   1041  HD11 LEU   83     -12.871   21.648   -6.709     0.00       H
ATOM   1042  HD12 LEU   83     -14.387   21.009   -7.242     0.00       H
ATOM   1043  HD13 LEU   83     -12.994   19.986   -7.174     0.00       H
ATOM   1044  CD2  LEU   83     -13.619   20.356   -9.788    28.98       C
ATOM   1045  HD21 LEU   83     -14.673   20.379   -9.691     0.00       H
ATOM   1046  HD22 LEU   83     -13.349   20.629  -10.775     0.00       H
ATOM   1047  HD23 LEU   83     -13.267   19.378   -9.583     0.00       H
ATOM   1048  C    LEU   83     -12.418   24.975   -9.318    32.65       C
ATOM   1049  O    LEU   83     -13.195   25.895   -9.544    33.33       O
ATOM   1050  N    SER   84     -11.226   24.883   -9.898    34.61       N
ATOM   1051  HN   SER   84     -10.621   24.116   -9.645     0.00       H
ATOM   1052  CA   SER   84     -10.786   25.866  -10.885    34.90       C
ATOM   1053  HA   SER   84     -10.966   26.842  -10.515     0.00       H
ATOM   1054  CB   SER   84      -9.294   25.707  -11.165    34.73       C
ATOM   1055  HB2  SER   84      -8.994   26.415  -11.893     0.00       H
ATOM   1056  HB3  SER   84      -8.748   25.866  -10.272     0.00       H
ATOM   1057  OG   SER   84      -9.017   24.402  -11.649    33.52       O
ATOM   1058  HG   SER   84      -8.069   24.317  -11.822     0.00       H
ATOM   1059  C    SER   84     -11.550   25.571  -12.162    35.27       C
ATOM   1060  O    SER   84     -11.977   24.433  -12.382    34.32       O
ATOM   1061  N    ILE   85     -11.728   26.587  -12.996    35.62       N
ATOM   1062  HN   ILE   85     -11.380   27.502  -12.751     0.00       H
ATOM   1063  CA   ILE   85     -12.421   26.387  -14.258    37.18       C
ATOM   1064  HA   ILE   85     -13.442   26.177  -14.071     0.00       H
```

FIGURE 6-15-

```
ATOM   1065  CB   ILE    85    -12.335  27.639 -15.149   36.44    C
ATOM   1066  HB   ILE    85    -11.328  27.960 -15.210    0.00    H
ATOM   1067  CG2  ILE    85    -12.841  27.331 -16.549   34.24    C
ATOM   1068  HG21 ILE    85    -12.251  26.563 -16.977    0.00    H
ATOM   1069  HG22 ILE    85    -13.850  27.014 -16.498    0.00    H
ATOM   1070  HG23 ILE    85    -12.775  28.202 -17.148    0.00    H
ATOM   1071  CG1  ILE    85    -13.148  28.763 -14.504   38.37    C
ATOM   1072  HG12 ILE    85    -14.152  28.448 -14.384    0.00    H
ATOM   1073  HG13 ILE    85    -12.736  28.998 -13.557    0.00    H
ATOM   1074  CD1  ILE    85    -13.187  30.056 -15.296   39.76    C
ATOM   1075  HD11 ILE    85    -12.202  30.424 -15.419    0.00    H
ATOM   1076  HD12 ILE    85    -13.618  29.875 -16.246    0.00    H
ATOM   1077  HD13 ILE    85    -13.769  30.771 -14.775    0.00    H
ATOM   1078  C    ILE    85    -11.732  25.223 -14.956   38.34    C
ATOM   1079  O    ILE    85    -12.376  24.267 -15.403   38.17    O
ATOM   1080  N    GLU    86    -10.410  25.298 -15.020   39.25    N
ATOM   1081  HN   GLU    86     -9.944  26.096 -14.614    0.00    H
ATOM   1082  CA   GLU    86     -9.635  24.256 -15.661   40.68    C
ATOM   1083  HA   GLU    86     -9.861  24.233 -16.695    0.00    H
ATOM   1084  CB   GLU    86     -8.150  24.513 -15.488   43.54    C
ATOM   1085  HB2  GLU    86     -7.937  25.523 -15.723    0.00    H
ATOM   1086  HB3  GLU    86     -7.873  24.318 -14.485    0.00    H
ATOM   1087  CG   GLU    86     -7.312  23.635 -16.386   49.55    C
ATOM   1088  HG2  GLU    86     -7.499  22.618 -16.159    0.00    H
ATOM   1089  HG3  GLU    86     -7.563  23.823 -17.398    0.00    H
ATOM   1090  CD   GLU    86     -5.837  23.884 -16.220   51.64    C
ATOM   1091  OE1  GLU    86     -5.440  25.070 -16.243   52.11    O1-
ATOM   1092  OE2  GLU    86     -5.081  22.897 -16.073   53.55    O
ATOM   1093  C    GLU    86     -9.972  22.894 -15.095   40.25    C
ATOM   1094  O    GLU    86    -10.278  21.966 -15.841   40.24    O
ATOM   1095  N    GLU    87     -9.913  22.774 -13.772   40.65    N
ATOM   1096  HN   GLU    87     -9.645  23.579 -13.226    0.00    H
ATOM   1097  CA   GLU    87    -10.226  21.511 -13.106   41.01    C
ATOM   1098  HA   GLU    87     -9.512  20.780 -13.383    0.00    H
ATOM   1099  CB   GLU    87    -10.198  21.677 -11.591   43.30    C
ATOM   1100  HB2  GLU    87    -10.487  22.664 -11.339    0.00    H
ATOM   1101  HB3  GLU    87    -10.869  20.988 -11.148    0.00    H
ATOM   1102  CG   GLU    87     -8.839  21.438 -10.971   46.74    C
ATOM   1103  HG2  GLU    87     -8.433  20.536 -11.349    0.00    H
ATOM   1104  HG3  GLU    87     -8.195  22.243 -11.211    0.00    H
ATOM   1105  CD   GLU    87     -8.913  21.327  -9.460   48.00    C
ATOM   1106  OE1  GLU    87     -9.079  22.376  -8.787   48.92    O1-
ATOM   1107  OE2  GLU    87     -8.819  20.183  -8.957   46.45    O
ATOM   1108  C    GLU    87    -11.591  20.993 -13.507   40.01    C
ATOM   1109  O    GLU    87    -11.776  19.793 -13.711   39.44    O
ATOM   1110  N    ALA    88    -12.549  21.908 -13.601   38.77    N
ATOM   1111  HN   ALA    88    -12.314  22.869 -13.405    0.00    H
ATOM   1112  CA   ALA    88    -13.903  21.555 -13.974   36.80    C
ATOM   1113  HA   ALA    88    -14.250  20.776 -13.346    0.00    H
ATOM   1114  CB   ALA    88    -14.806  22.754 -13.825   37.58    C
ATOM   1115  HB1  ALA    88    -14.795  23.081 -12.818    0.00    H
ATOM   1116  HB2  ALA    88    -14.463  23.534 -14.453    0.00    H
ATOM   1117  HB3  ALA    88    -15.794  22.488 -14.099    0.00    H
ATOM   1118  C    ALA    88    -13.910  21.080 -15.410   36.48    C
ATOM   1119  O    ALA    88    -14.582  20.116 -15.755   36.99    O
ATOM   1120  N    CYS    89    -13.150  21.759 -16.254   35.91    N
ATOM   1121  HN   CYS    89    -12.599  22.537 -15.924    0.00    H
ATOM   1122  CA   CYS    89    -13.109  21.385 -17.650   35.51    C
ATOM   1123  HA   CYS    89    -14.088  21.418 -18.053    0.00    H
ATOM   1124  CB   CYS    89    -12.296  22.414 -18.436   34.24    C
ATOM   1125  HB2  CYS    89    -11.402  22.632 -17.912    0.00    H
ATOM   1126  HB3  CYS    89    -12.059  22.022 -19.391    0.00    H
ATOM   1127  SG   CYS    89    -13.192  23.993 -18.690   32.72    S
ATOM   1128  HG   CYS    89    -12.470  24.782 -19.337    0.00    H
ATOM   1129  C    CYS    89    -12.563  19.980 -17.866   36.05    C
ATOM   1130  O    CYS    89    -13.094  19.215 -18.676   36.23    O
ATOM   1131  N    LYS    90    -11.516  19.633 -17.126   37.07    N
ATOM   1132  HN   LYS    90    -11.150  20.297 -16.460    0.00    H
ATOM   1133  CA   LYS    90    -10.898  18.322 -17.262   37.97    C
ATOM   1134  HA   LYS    90    -10.682  18.138 -18.282    0.00    H
ATOM   1135  CB   LYS    90     -9.598  18.254 -16.460   40.61    C
ATOM   1136  HB2  LYS    90     -8.895  18.931 -16.870    0.00    H
ATOM   1137  HB3  LYS    90     -9.791  18.513 -15.452    0.00    H
ATOM   1138  CG   LYS    90     -8.995  16.865 -16.488   46.19    C
ATOM   1139  HG2  LYS    90     -9.534  16.233 -15.831    0.00    H
ATOM   1140  HG3  LYS    90     -9.047  16.477 -17.472    0.00    H
```

FIGURE 6- 16 -

| | | | | | | | | |
|---|---|---|---|---|---|---|---|---|
| ATOM | 1141 | CD   | LYS | 90 | -7.545  | 16.821 | -16.065 | 49.99 | C |
| ATOM | 1142 | HD2  | LYS | 90 | -7.010  | 17.591 | -16.557 | 0.00  | H |
| ATOM | 1143 | HD3  | LYS | 90 | -7.479  | 16.959 | -15.017 | 0.00  | H |
| ATOM | 1144 | CE   | LYS | 90 | -6.951  | 15.468 | -16.440 | 52.03 | C |
| ATOM | 1145 | HE2  | LYS | 90 | -7.506  | 14.697 | -15.972 | 0.00  | H |
| ATOM | 1146 | HE3  | LYS | 90 | -6.991  | 15.344 | -17.491 | 0.00  | H |
| ATOM | 1147 | NZ   | LYS | 90 | -5.531  | 15.336 | -16.015 | 55.58 | N1+ |
| ATOM | 1148 | HZ1  | LYS | 90 | -4.979  | 16.053 | -16.460 | 0.00  | H |
| ATOM | 1149 | HZ2  | LYS | 90 | -5.469  | 15.437 | -15.013 | 0.00  | H |
| ATOM | 1150 | HZ3  | LYS | 90 | -5.183  | 14.428 | -16.284 | 0.00  | H |
| ATOM | 1151 | C    | LYS | 90 | -11.803 | 17.161 | -16.855 | 37.76 | C |
| ATOM | 1152 | O    | LYS | 90 | -11.648 | 16.036 | -17.348 | 37.45 | O |
| ATOM | 1153 | N    | LEU | 91 | -12.744 | 17.431 | -15.954 | 36.83 | N |
| ATOM | 1154 | HN   | LEU | 91 | -12.803 | 18.371 | -15.592 | 0.00  | H |
| ATOM | 1155 | CA   | LEU | 91 | -13.675 | 16.411 | -15.489 | 34.41 | C |
| ATOM | 1156 | HA   | LEU | 91 | -13.146 | 15.515 | -15.290 | 0.00  | H |
| ATOM | 1157 | CB   | LEU | 91 | -14.364 | 16.880 | -14.218 | 32.72 | C |
| ATOM | 1158 | HB2  | LEU | 91 | -14.611 | 17.906 | -14.308 | 0.00  | H |
| ATOM | 1159 | HB3  | LEU | 91 | -15.248 | 16.316 | -14.067 | 0.00  | H |
| ATOM | 1160 | CG   | LEU | 91 | -13.591 | 16.768 | -12.913 | 31.33 | C |
| ATOM | 1161 | HG   | LEU | 91 | -12.629 | 17.194 | -13.035 | 0.00  | H |
| ATOM | 1162 | CD1  | LEU | 91 | -14.335 | 17.505 | -11.822 | 32.20 | C |
| ATOM | 1163 | HD11 | LEU | 91 | -14.432 | 18.525 | -12.088 | 0.00  | H |
| ATOM | 1164 | HD12 | LEU | 91 | -15.297 | 17.079 | -11.701 | 0.00  | H |
| ATOM | 1165 | HD13 | LEU | 91 | -13.797 | 17.427 | -10.913 | 0.00  | H |
| ATOM | 1166 | CD2  | LEU | 91 | -13.435 | 15.316 | -12.544 | 30.42 | C |
| ATOM | 1167 | HD21 | LEU | 91 | -14.391 | 14.877 | -12.426 | 0.00  | H |
| ATOM | 1168 | HD22 | LEU | 91 | -12.907 | 14.812 | -13.311 | 0.00  | H |
| ATOM | 1169 | HD23 | LEU | 91 | -12.897 | 15.239 | -11.635 | 0.00  | H |
| ATOM | 1170 | C    | LEU | 91 | -14.739 | 16.054 | -16.520 | 34.93 | C |
| ATOM | 1171 | O    | LEU | 91 | -15.380 | 15.020 | -16.406 | 36.25 | O |
| ATOM | 1172 | N    | THR | 92 | -14.915 | 16.905 | -17.526 | 36.09 | N |
| ATOM | 1173 | HN   | THR | 92 | -14.320 | 17.720 | -17.545 | 0.00  | H |
| ATOM | 1174 | CA   | THR | 92 | -15.916 | 16.704 | -18.578 | 36.82 | C |
| ATOM | 1175 | HA   | THR | 92 | -16.843 | 16.443 | -18.138 | 0.00  | H |
| ATOM | 1176 | CB   | THR | 92 | -16.095 | 17.994 | -19.399 | 35.48 | C |
| ATOM | 1177 | HB   | THR | 92 | -15.274 | 18.110 | -20.058 | 0.00  | H |
| ATOM | 1178 | OG1  | THR | 92 | -16.163 | 19.115 | -18.517 | 35.30 | O |
| ATOM | 1179 | HG1  | THR | 92 | -16.275 | 19.925 | -19.033 | 0.00  | H |
| ATOM | 1180 | CG2  | THR | 92 | -17.376 | 17.930 | -20.212 | 35.19 | C |
| ATOM | 1181 | HG21 | THR | 92 | -17.334 | 17.104 | -20.873 | 0.00  | H |
| ATOM | 1182 | HG22 | THR | 92 | -18.203 | 17.819 | -19.560 | 0.00  | H |
| ATOM | 1183 | HG23 | THR | 92 | -17.485 | 18.823 | -20.770 | 0.00  | H |
| ATOM | 1184 | C    | THR | 92 | -15.671 | 15.564 | -19.587 | 37.96 | C |
| ATOM | 1185 | O    | THR | 92 | -14.624 | 15.495 | -20.223 | 37.50 | O |
| ATOM | 1186 | N    | PRO | 93 | -16.650 | 14.660 | -19.753 | 39.82 | N |
| ATOM | 1187 | CD   | PRO | 93 | -17.925 | 14.514 | -19.029 | 40.47 | C |
| ATOM | 1188 | HD2  | PRO | 93 | -17.787 | 14.782 | -18.014 | 0.00  | H |
| ATOM | 1189 | HD3  | PRO | 93 | -18.653 | 15.147 | -19.466 | 0.00  | H |
| ATOM | 1190 | CA   | PRO | 93 | -16.468 | 13.566 | -20.712 | 40.62 | C |
| ATOM | 1191 | HA   | PRO | 93 | -15.630 | 12.984 | -20.429 | 0.00  | H |
| ATOM | 1192 | CB   | PRO | 93 | -17.792 | 12.807 | -20.630 | 40.73 | C |
| ATOM | 1193 | HB2  | PRO | 93 | -18.472 | 13.207 | -21.336 | 0.00  | H |
| ATOM | 1194 | HB3  | PRO | 93 | -17.625 | 11.783 | -20.841 | 0.00  | H |
| ATOM | 1195 | CG   | PRO | 93 | -18.227 | 13.039 | -19.219 | 41.32 | C |
| ATOM | 1196 | HG2  | PRO | 93 | -19.257 | 12.813 | -19.125 | 0.00  | H |
| ATOM | 1197 | HG3  | PRO | 93 | -17.668 | 12.416 | -18.570 | 0.00  | H |
| ATOM | 1198 | C    | PRO | 93 | -16.240 | 14.167 | -22.098 | 41.07 | C |
| ATOM | 1199 | O    | PRO | 93 | -16.809 | 15.207 | -22.430 | 41.72 | O |
| ATOM | 1200 | N    | PRO | 94 | -15.406 | 13.519 | -22.922 | 42.03 | N |
| ATOM | 1201 | CD   | PRO | 94 | -14.556 | 12.380 | -22.548 | 43.13 | C |
| ATOM | 1202 | HD2  | PRO | 94 | -14.330 | 12.432 | -21.515 | 0.00  | H |
| ATOM | 1203 | HD3  | PRO | 94 | -15.068 | 11.476 | -22.752 | 0.00  | H |
| ATOM | 1204 | CA   | PRO | 94 | -15.083 | 13.974 | -24.278 | 41.81 | C |
| ATOM | 1205 | HA   | PRO | 94 | -14.721 | 14.968 | -24.240 | 0.00  | H |
| ATOM | 1206 | CB   | PRO | 94 | -13.982 | 13.014 | -24.714 | 41.75 | C |
| ATOM | 1207 | HB2  | PRO | 94 | -14.411 | 12.200 | -25.238 | 0.00  | H |
| ATOM | 1208 | HB3  | PRO | 94 | -13.301 | 13.522 | -25.346 | 0.00  | H |
| ATOM | 1209 | CG   | PRO | 94 | -13.358 | 12.595 | -23.428 | 42.74 | C |
| ATOM | 1210 | HG2  | PRO | 94 | -12.794 | 11.712 | -23.581 | 0.00  | H |
| ATOM | 1211 | HG3  | PRO | 94 | -12.721 | 13.365 | -23.077 | 0.00  | H |
| ATOM | 1212 | C    | PRO | 94 | -16.249 | 13.975 | -25.257 | 41.63 | C |
| ATOM | 1213 | O    | PRO | 94 | -16.246 | 14.732 | -26.220 | 42.45 | O |
| ATOM | 1214 | N    | HIS | 95 | -17.244 | 13.129 | -25.037 | 41.33 | N |
| ATOM | 1215 | HN   | HIS | 95 | -17.231 | 12.501 | -24.247 | 0.00  | H |
| ATOM | 1216 | CA   | HIS | 95 | -18.369 | 13.115 | -25.958 | 42.66 | C |

FIGURE 6-17-

```
ATOM   1217  HA   HIS   95    -18.146  13.722 -26.797   0.00    H
ATOM   1218  CB   HIS   95    -18.658  11.689 -26.443  47.20    C
ATOM   1219  HB2  HIS   95    -18.631  11.024 -25.619   0.00    H
ATOM   1220  HB3  HIS   95    -19.616  11.656 -26.892   0.00    H
ATOM   1221  CG   HIS   95    -17.675  11.182 -27.456  51.67    C
ATOM   1222  CD2  HIS   95    -17.684  11.239 -28.811  52.41    C
ATOM   1223  HD2  HIS   95    -18.513  11.695 -29.325   0.00    H
ATOM   1224  ND1  HIS   95    -16.500  10.548 -27.107  52.93    N1+
ATOM   1225  HD1  HIS   95    -16.280  10.393 -26.135   0.00    H
ATOM   1226  CE1  HIS   95    -15.828  10.237 -28.203  54.09    C
ATOM   1227  HE1  HIS   95    -14.879   9.733 -28.128   0.00    H
ATOM   1228  NE2  HIS   95    -16.524  10.646 -29.249  54.00    N
ATOM   1229  HE2  HIS   95    -16.331  10.584 -30.237   0.00    H
ATOM   1230  C    HIS   95    -19.628  13.740 -25.358  41.73    C
ATOM   1231  O    HIS   95    -20.732  13.601 -25.902  40.85    O
ATOM   1232  N    SER   96    -19.448  14.433 -24.235  40.03    N
ATOM   1233  HN   SER   96    -18.513  14.475 -23.858   0.00    H
ATOM   1234  CA   SER   96    -20.543  15.118 -23.551  37.26    C
ATOM   1235  HA   SER   96    -21.203  14.401 -23.136   0.00    H
ATOM   1236  CB   SER   96    -19.960  15.998 -22.431  37.08    C
ATOM   1237  HB2  SER   96    -19.353  15.406 -21.797   0.00    H
ATOM   1238  HB3  SER   96    -19.376  16.772 -22.858   0.00    H
ATOM   1239  OG   SER   96    -20.971  16.599 -21.635  37.53    O
ATOM   1240  HG   SER   96    -20.560  17.140 -20.947   0.00    H
ATOM   1241  C    SER   96    -21.319  15.975 -24.574  35.94    C
ATOM   1242  O    SER   96    -20.764  16.377 -25.602  34.13    O
ATOM   1243  N    ALA   97    -22.596  16.242 -24.302  34.81    N
ATOM   1244  HN   ALA   97    -22.984  15.874 -23.447   0.00    H
ATOM   1245  CA   ALA   97    -23.435  17.046 -25.204  33.91    C
ATOM   1246  HA   ALA   97    -23.467  16.588 -26.158   0.00    H
ATOM   1247  CB   ALA   97    -24.845  17.149 -24.657  31.33    C
ATOM   1248  HB1  ALA   97    -25.261  16.179 -24.570   0.00    H
ATOM   1249  HB2  ALA   97    -24.821  17.610 -23.704   0.00    H
ATOM   1250  HB3  ALA   97    -25.437  17.730 -25.315   0.00    H
ATOM   1251  C    ALA   97    -22.867  18.441 -25.403  35.23    C
ATOM   1252  O    ALA   97    -22.623  19.164 -24.438  36.53    O
ATOM   1253  N    LYS   98    -22.663  18.828 -26.656  36.02    N
ATOM   1254  HN   LYS   98    -22.900  18.199 -27.409   0.00    H
ATOM   1255  CA   LYS   98    -22.105  20.141 -26.952  36.28    C
ATOM   1256  HA   LYS   98    -21.158  20.235 -26.488   0.00    H
ATOM   1257  CB   LYS   98    -21.941  20.319 -28.464  37.76    C
ATOM   1258  HB2  LYS   98    -21.448  21.236 -28.660   0.00    H
ATOM   1259  HB3  LYS   98    -21.367  19.519 -28.853   0.00    H
ATOM   1260  CG   LYS   98    -23.245  20.344 -29.238  36.35    C
ATOM   1261  HG2  LYS   98    -23.699  19.388 -29.196   0.00    H
ATOM   1262  HG3  LYS   98    -23.895  21.063 -28.811   0.00    H
ATOM   1263  CD   LYS   98    -23.003  20.705 -30.685  36.84    C
ATOM   1264  HD2  LYS   98    -22.480  21.624 -30.737   0.00    H
ATOM   1265  HD3  LYS   98    -22.428  19.945 -31.147   0.00    H
ATOM   1266  CE   LYS   98    -24.302  20.851 -31.446  37.33    C
ATOM   1267  HE2  LYS   98    -24.736  19.896 -31.590   0.00    H
ATOM   1268  HE3  LYS   98    -24.968  21.462 -30.894   0.00    H
ATOM   1269  NZ   LYS   98    -24.074  21.478 -32.781  40.20    N1+
ATOM   1270  HZ1  LYS   98    -23.687  22.393 -32.658   0.00    H
ATOM   1271  HZ2  LYS   98    -23.447  20.901 -33.321   0.00    H
ATOM   1272  HZ3  LYS   98    -24.954  21.564 -33.267   0.00    H
ATOM   1273  C    LYS   98    -22.990  21.248 -26.403  36.27    C
ATOM   1274  O    LYS   98    -24.138  21.004 -26.014  35.18    O
ATOM   1275  N    SER   99    -22.452  22.465 -26.372  35.46    N
ATOM   1276  HN   SER   99    -21.506  22.586 -26.702   0.00    H
ATOM   1277  CA   SER   99    -23.201  23.608 -25.875  35.08    C
ATOM   1278  HA   SER   99    -23.864  23.291 -25.113   0.00    H
ATOM   1279  CB   SER   99    -22.285  24.668 -25.301  33.25    C
ATOM   1280  HB2  SER   99    -21.877  24.324 -24.386   0.00    H
ATOM   1281  HB3  SER   99    -21.501  24.865 -25.985   0.00    H
ATOM   1282  OG   SER   99    -23.037  25.846 -25.079  26.89    O
ATOM   1283  HG   SER   99    -22.462  26.531 -24.712   0.00    H
ATOM   1284  C    SER   99    -24.023  24.274 -26.945  36.78    C
ATOM   1285  O    SER   99    -23.659  24.282 -28.116  38.66    O
ATOM   1286  N    LYS  100    -25.130  24.862 -26.523  37.62    N
ATOM   1287  HN   LYS  100    -25.350  24.811 -25.540   0.00    H
ATOM   1288  CA   LYS  100    -26.017  25.566 -27.429  37.92    C
ATOM   1289  HA   LYS  100    -26.286  24.925 -28.228   0.00    H
ATOM   1290  CB   LYS  100    -27.272  25.990 -26.652  41.32    C
ATOM   1291  HB2  LYS  100    -27.796  25.128 -26.331   0.00    H
ATOM   1292  HB3  LYS  100    -26.988  26.565 -25.809   0.00    H
```

FIGURE 6-18-

```
ATOM   1293  CG   LYS  100    -28.265  26.831 -27.429   46.05        C
ATOM   1294  HG2  LYS  100    -27.778  27.691 -27.809    0.00        H
ATOM   1295  HG3  LYS  100    -28.656  26.263 -28.233    0.00        H
ATOM   1296  CD   LYS  100    -29.435  27.289 -26.549   47.98        C
ATOM   1297  HD2  LYS  100    -29.906  26.443 -26.120    0.00        H
ATOM   1298  HD3  LYS  100    -29.072  27.919 -25.779    0.00        H
ATOM   1299  CE   LYS  100    -30.464  28.064 -27.389   50.56        C
ATOM   1300  HE2  LYS  100    -29.970  28.819 -27.943    0.00        H
ATOM   1301  HE3  LYS  100    -30.950  27.398 -28.054    0.00        H
ATOM   1302  NZ   LYS  100    -31.529  28.735 -26.579   51.75        N1+
ATOM   1303  HZ1  LYS  100    -32.037  28.041 -26.051    0.00        H
ATOM   1304  HZ2  LYS  100    -31.104  29.395 -25.945    0.00        H
ATOM   1305  HZ3  LYS  100    -32.164  29.221 -27.195    0.00        H
ATOM   1306  C    LYS  100    -25.282  26.798 -27.965   35.96        C
ATOM   1307  O    LYS  100    -25.691  27.400 -28.961   35.24        O
ATOM   1308  N    PHE  101    -24.178  27.142 -27.304   33.60        N
ATOM   1309  HN   PHE  101    -23.884  26.550 -26.542    0.00        H
ATOM   1310  CA   PHE  101    -23.403  28.325 -27.647   32.14        C
ATOM   1311  HA   PHE  101    -23.982  28.959 -28.267    0.00        H
ATOM   1312  CB   PHE  101    -23.025  29.066 -26.363   31.99        C
ATOM   1313  HB2  PHE  101    -22.501  28.410 -25.718    0.00        H
ATOM   1314  HB3  PHE  101    -22.408  29.893 -26.601    0.00        H
ATOM   1315  CG   PHE  101    -24.207  29.588 -25.611   32.25        C
ATOM   1316  CD1  PHE  101    -24.842  30.760 -26.017   32.51        C
ATOM   1317  HD1  PHE  101    -24.440  31.335 -26.834    0.00        H
ATOM   1318  CD2  PHE  101    -24.741  28.869 -24.547   31.29        C
ATOM   1319  HD2  PHE  101    -24.261  27.965 -24.213    0.00        H
ATOM   1320  CE1  PHE  101    -26.001  31.209 -25.379   32.41        C
ATOM   1321  HE1  PHE  101    -26.479  32.116 -25.707    0.00        H
ATOM   1322  CE2  PHE  101    -25.895  29.306 -23.905   32.16        C
ATOM   1323  HE2  PHE  101    -26.302  28.740 -23.084    0.00        H
ATOM   1324  CZ   PHE  101    -26.529  30.480 -24.323   31.71        C
ATOM   1325  HZ   PHE  101    -27.424  30.819 -23.829    0.00        H
ATOM   1326  C    PHE  101    -22.167  28.163 -28.503   31.13        C
ATOM   1327  O    PHE  101    -21.217  28.914 -28.343   30.92        O
ATOM   1328  N    GLY  102    -22.160  27.179 -29.391   31.25        N
ATOM   1329  HN   GLY  102    -22.944  26.546 -29.451    0.00        H
ATOM   1330  CA   GLY  102    -21.020  27.012 -30.280   30.89        C
ATOM   1331  HA2  GLY  102    -21.293  26.387 -31.090    0.00        H
ATOM   1332  HA3  GLY  102    -20.719  27.958 -30.649    0.00        H
ATOM   1333  C    GLY  102    -19.713  26.402 -29.809   30.80        C
ATOM   1334  O    GLY  102    -18.641  26.912 -30.136   30.69        O
ATOM   1335  N    TYR  103    -19.790  25.320 -29.046   30.89        N
ATOM   1336  HN   TYR  103    -20.702  24.980 -28.778    0.00        H
ATOM   1337  CA   TYR  103    -18.592  24.624 -28.595   32.66        C
ATOM   1338  HA   TYR  103    -17.978  24.402 -29.429    0.00        H
ATOM   1339  CB   TYR  103    -17.784  25.479 -27.610   33.88        C
ATOM   1340  HB2  TYR  103    -16.863  25.000 -27.400    0.00        H
ATOM   1341  HB3  TYR  103    -17.598  26.430 -28.038    0.00        H
ATOM   1342  CG   TYR  103    -18.439  25.737 -26.276   35.35        C
ATOM   1343  CD1  TYR  103    -18.321  24.820 -25.223   34.59        C
ATOM   1344  HD1  TYR  103    -17.741  23.922 -25.354    0.00        H
ATOM   1345  CE1  TYR  103    -18.945  25.050 -23.998   33.52        C
ATOM   1346  HE1  TYR  103    -18.843  24.335 -23.199    0.00        H
ATOM   1347  CD2  TYR  103    -19.196  26.890 -26.067   35.37        C
ATOM   1348  HD2  TYR  103    -19.301  27.616 -26.856    0.00        H
ATOM   1349  CE2  TYR  103    -19.826  27.125 -24.845   34.62        C
ATOM   1350  HE2  TYR  103    -20.410  28.019 -24.703    0.00        H
ATOM   1351  CZ   TYR  103    -19.695  26.204 -23.822   33.57        C
ATOM   1352  OH   TYR  103    -20.323  26.448 -22.626   34.71        O
ATOM   1353  HH   TYR  103    -20.144  25.721 -22.014    0.00        H
ATOM   1354  C    TYR  103    -19.008  23.299 -27.975   33.83        C
ATOM   1355  O    TYR  103    -20.183  23.113 -27.635   34.73        O
ATOM   1356  N    GLY  104    -18.061  22.373 -27.855   32.65        N
ATOM   1357  HN   GLY  104    -17.118  22.579 -28.150    0.00        H
ATOM   1358  CA   GLY  104    -18.380  21.071 -27.302   33.24        C
ATOM   1359  HA2  GLY  104    -19.333  21.107 -26.841    0.00        H
ATOM   1360  HA3  GLY  104    -18.390  20.351 -28.078    0.00        H
ATOM   1361  C    GLY  104    -17.405  20.573 -26.254   34.96        C
ATOM   1362  O    GLY  104    -16.492  21.290 -25.840   34.63        O
ATOM   1363  N    ALA  105    -17.603  19.334 -25.818   35.69        N
ATOM   1364  HN   ALA  105    -18.370  18.802 -26.202    0.00        H
ATOM   1365  CA   ALA  105    -16.739  18.740 -24.807   37.15        C
ATOM   1366  HA   ALA  105    -16.931  19.192 -23.869    0.00        H
ATOM   1367  CB   ALA  105    -17.006  17.249 -24.707   37.47        C
ATOM   1368  HB1  ALA  105    -18.018  17.089 -24.438    0.00        H
```

FIGURE 6- 19 -

```
ATOM   1369  HB2 ALA  105   -16.813  16.792 -25.643   0.00      H
ATOM   1370  HB3 ALA  105   -16.374  16.826 -23.970   0.00      H
ATOM   1371  C   ALA  105   -15.298  18.980 -25.201  38.12      C
ATOM   1372  O   ALA  105   -14.473  19.419 -24.389  36.56      O
ATOM   1373  N   LYS  106   -15.025  18.684 -26.470  39.44      N
ATOM   1374  HN  LYS  106   -15.797  18.337 -27.020   0.00      H
ATOM   1375  CA  LYS  106   -13.709  18.834 -27.075  39.87      C
ATOM   1376  HA  LYS  106   -13.061  18.085 -26.700   0.00      H
ATOM   1377  CB  LYS  106   -13.848  18.689 -28.593  43.35      C
ATOM   1378  HB2 LYS  106   -14.473  17.863 -28.813   0.00      H
ATOM   1379  HB3 LYS  106   -14.275  19.571 -28.994   0.00      H
ATOM   1380  CG  LYS  106   -12.559  18.458 -29.360  48.40      C
ATOM   1381  HG2 LYS  106   -12.677  18.793 -30.358   0.00      H
ATOM   1382  HG3 LYS  106   -11.772  18.996 -28.898   0.00      H
ATOM   1383  CD  LYS  106   -12.182  16.980 -29.388  53.86      C
ATOM   1384  HD2 LYS  106   -11.932  16.661 -28.410   0.00      H
ATOM   1385  HD3 LYS  106   -13.002  16.413 -29.746   0.00      H
ATOM   1386  CE  LYS  106   -10.972  16.731 -30.311  56.45      C
ATOM   1387  HE2 LYS  106   -10.635  15.713 -30.250   0.00      H
ATOM   1388  HE3 LYS  106   -11.236  16.964 -31.310   0.00      H
ATOM   1389  NZ  LYS  106    -9.780  17.573 -29.937  56.83     N1+
ATOM   1390  HZ1 LYS  106   -10.025  18.550 -30.001   0.00      H
ATOM   1391  HZ2 LYS  106    -9.500  17.358 -28.992   0.00      H
ATOM   1392  HZ3 LYS  106    -9.017  17.375 -30.567   0.00      H
ATOM   1393  C   LYS  106   -13.109  20.205 -26.726  38.97      C
ATOM   1394  O   LYS  106   -12.009  20.294 -26.173  37.11      O
ATOM   1395  N   ASP  107   -13.844  21.270 -27.038  37.48      N
ATOM   1396  HN  ASP  107   -14.744  21.125 -27.469   0.00      H
ATOM   1397  CA  ASP  107   -13.375  22.622 -26.770  37.46      C
ATOM   1398  HA  ASP  107   -12.333  22.728 -27.125   0.00      H
ATOM   1399  CB  ASP  107   -14.278  23.633 -27.479  37.38      C
ATOM   1400  HB2 ASP  107   -15.269  23.534 -27.119   0.00      H
ATOM   1401  HB3 ASP  107   -13.929  24.614 -27.286   0.00      H
ATOM   1402  CG  ASP  107   -14.303  23.431 -28.984  38.73      C
ATOM   1403  OD1 ASP  107   -13.210  23.412 -29.598  39.58      O
ATOM   1404  OD2 ASP  107   -15.409  23.286 -29.550  38.30     O1-
ATOM   1405  C   ASP  107   -13.259  22.957 -25.279  38.16      C
ATOM   1406  O   ASP  107   -12.438  23.796 -24.889  39.26      O
ATOM   1407  N   VAL  108   -14.069  22.306 -24.446  36.70      N
ATOM   1408  HN  VAL  108   -14.729  21.640 -24.820   0.00      H
ATOM   1409  CA  VAL  108   -14.011  22.545 -23.011  34.84      C
ATOM   1410  HA  VAL  108   -14.006  23.588 -22.827   0.00      H
ATOM   1411  CB  VAL  108   -15.233  21.922 -22.278  34.66      C
ATOM   1412  HB  VAL  108   -15.331  20.905 -22.557   0.00      H
ATOM   1413  CG1 VAL  108   -15.041  21.987 -20.765  32.96      C
ATOM   1414  HG11 VAL 108   -14.169  21.450 -20.496   0.00      H
ATOM   1415  HG12 VAL 108   -14.939  22.998 -20.465   0.00      H
ATOM   1416  HG13 VAL 108   -15.882  21.559 -20.284   0.00      H
ATOM   1417  CG2 VAL 108   -16.496  22.666 -22.655  33.23      C
ATOM   1418  HG21 VAL 108   -16.403  23.683 -22.376   0.00      H
ATOM   1419  HG22 VAL 108   -16.646  22.600 -23.701   0.00      H
ATOM   1420  HG23 VAL 108   -17.323  22.236 -22.152   0.00      H
ATOM   1421  C   VAL  108   -12.722  21.946 -22.452  34.78      C
ATOM   1422  O   VAL  108   -11.972  22.614 -21.738  34.85      O
ATOM   1423  N   ARG  109   -12.452  20.691 -22.791  34.71      N
ATOM   1424  HN  ARG  109   -13.086  20.190 -23.396   0.00      H
ATOM   1425  CA  ARG  109   -11.246  20.035 -22.294  35.52      C
ATOM   1426  HA  ARG  109   -11.256  20.034 -21.235   0.00      H
ATOM   1427  CB  ARG  109   -11.171  18.590 -22.788  34.00      C
ATOM   1428  HB2 ARG  109   -11.115  18.581 -23.845   0.00      H
ATOM   1429  HB3 ARG  109   -10.310  18.123 -22.385   0.00      H
ATOM   1430  CG  ARG  109   -12.357  17.738 -22.402  32.63      C
ATOM   1431  HG2 ARG  109   -12.437  17.702 -21.347   0.00      H
ATOM   1432  HG3 ARG  109   -13.240  18.157 -22.809   0.00      H
ATOM   1433  CD  ARG  109   -12.226  16.309 -22.919  35.36      C
ATOM   1434  HD2 ARG  109   -13.137  15.792 -22.763   0.00      H
ATOM   1435  HD3 ARG  109   -12.004  16.327 -23.954   0.00      H
ATOM   1436  NE  ARG  109   -11.166  15.565 -22.245  35.91     N1+
ATOM   1437  HE  ARG  109   -10.414  15.160 -22.782   0.00      H
ATOM   1438  CZ  ARG  109   -11.108  15.370 -20.932  37.85      C
ATOM   1439  NH1 ARG  109   -12.050  15.860 -20.139  39.67      N
ATOM   1440  HH11 ARG 109   -12.000  15.708 -19.143   0.00      H
ATOM   1441  HH12 ARG 109   -12.817  16.385 -20.532   0.00      H
ATOM   1442  NH2 ARG  109   -10.096  14.699 -20.405  39.48      N
ATOM   1443  HH21 ARG 109   -10.053  14.552 -19.408   0.00      H
ATOM   1444  HH22 ARG 109    -9.367  14.335 -21.001   0.00      H
```

FIGURE 6-20-

```
ATOM   1445  C    ARG  109    -9.985  20.784 -22.712  36.40           C
ATOM   1446  O    ARG  109    -9.044  20.886 -21.930  37.52           O
ATOM   1447  N    ASN  110    -9.967  21.312 -23.935  36.87           N
ATOM   1448  HN   ASN  110   -10.774  21.198 -24.530   0.00           H
ATOM   1449  CA   ASN  110    -8.800  22.049 -24.419  38.72           C
ATOM   1450  HA   ASN  110    -7.922  21.644 -23.987   0.00           H
ATOM   1451  CB   ASN  110    -8.693  21.950 -25.943  41.31           C
ATOM   1452  HB2  ASN  110    -9.616  22.230 -26.381   0.00           H
ATOM   1453  HB3  ASN  110    -7.928  22.598 -26.286   0.00           H
ATOM   1454  CG   ASN  110    -8.360  20.541 -26.413  45.36           C
ATOM   1455  OD1  ASN  110    -7.374  19.938 -25.963  47.58           O
ATOM   1456  ND2  ASN  110    -9.176  20.008 -27.324  45.14           N
ATOM   1457  HD21 ASN  110    -9.967  20.535 -27.663   0.00           H
ATOM   1458  HD22 ASN  110    -9.002  19.078 -27.674   0.00           H
ATOM   1459  C    ASN  110    -8.798  23.520 -24.007  38.21           C
ATOM   1460  O    ASN  110    -7.989  24.307 -24.497  37.99           O
ATOM   1461  N    LEU  111    -9.701  23.883 -23.104  36.54           N
ATOM   1462  HN   LEU  111   -10.332  23.179 -22.752   0.00           H
ATOM   1463  CA   LEU  111    -9.796  25.254 -22.620  34.98           C
ATOM   1464  HA   LEU  111   -10.693  25.373 -22.070   0.00           H
ATOM   1465  CB   LEU  111    -8.599  25.565 -21.714  35.04           C
ATOM   1466  HB2  LEU  111    -7.731  25.690 -22.307   0.00           H
ATOM   1467  HB3  LEU  111    -8.788  26.455 -21.173   0.00           H
ATOM   1468  CG   LEU  111    -8.210  24.528 -20.652  36.25           C
ATOM   1469  HG   LEU  111    -7.748  23.699 -21.121   0.00           H
ATOM   1470  CD1  LEU  111    -7.238  25.172 -19.666  35.28           C
ATOM   1471  HD11 LEU  111    -6.373  25.496 -20.134   0.00           H
ATOM   1472  HD12 LEU  111    -7.704  26.002 -19.202   0.00           H
ATOM   1473  HD13 LEU  111    -6.963  24.464 -18.928   0.00           H
ATOM   1474  CD2  LEU  111    -9.445  24.023 -19.912  36.53           C
ATOM   1475  HD21 LEU  111    -9.928  24.836 -19.435   0.00           H
ATOM   1476  HD22 LEU  111   -10.110  23.573 -20.602   0.00           H
ATOM   1477  HD23 LEU  111    -9.154  23.310 -19.185   0.00           H
ATOM   1478  C    LEU  111    -9.867  26.292 -23.747  33.52           C
ATOM   1479  O    LEU  111    -9.144  27.289 -23.723  32.20           O
ATOM   1480  N    SER  112   -10.751  26.077 -24.717  32.36           N
ATOM   1481  HN   SER  112   -11.346  25.263 -24.678   0.00           H
ATOM   1482  CA   SER  112   -10.863  27.009 -25.831  33.42           C
ATOM   1483  HA   SER  112    -9.900  27.366 -26.091   0.00           H
ATOM   1484  CB   SER  112   -11.482  26.318 -27.046  32.17           C
ATOM   1485  HB2  SER  112   -11.176  26.816 -27.929   0.00           H
ATOM   1486  HB3  SER  112   -11.161  25.310 -27.030   0.00           H
ATOM   1487  OG   SER  112   -12.895  26.337 -26.986  32.00           O
ATOM   1488  HG   SER  112   -13.257  25.894 -27.766   0.00           H
ATOM   1489  C    SER  112   -11.675  28.254 -25.484  35.61           C
ATOM   1490  O    SER  112   -12.908  28.232 -25.479  37.95           O
ATOM   1491  N    SER  113   -10.967  29.343 -25.208  36.15           N
ATOM   1492  HN   SER  113    -9.963  29.254 -25.256   0.00           H
ATOM   1493  CA   SER  113   -11.571  30.625 -24.849  37.97           C
ATOM   1494  HA   SER  113   -11.429  30.805 -23.815   0.00           H
ATOM   1495  CB   SER  113   -10.919  31.752 -25.651  37.97           C
ATOM   1496  HB2  SER  113   -11.309  32.684 -25.332   0.00           H
ATOM   1497  HB3  SER  113    -9.872  31.735 -25.496   0.00           H
ATOM   1498  OG   SER  113   -11.178  31.598 -27.029  40.79           O
ATOM   1499  HG   SER  113   -10.758  32.319 -27.518   0.00           H
ATOM   1500  C    SER  113   -13.090  30.730 -24.985  38.02           C
ATOM   1501  O    SER  113   -13.795  30.781 -23.977  39.50           O
ATOM   1502  N    ARG  114   -13.596  30.767 -26.216  37.69           N
ATOM   1503  HN   ARG  114   -12.974  30.714 -27.008   0.00           H
ATOM   1504  CA   ARG  114   -15.040  30.883 -26.426  38.12           C
ATOM   1505  HA   ARG  114   -15.330  31.897 -26.333   0.00           H
ATOM   1506  CB   ARG  114   -15.435  30.388 -27.815  35.36           C
ATOM   1507  HB2  ARG  114   -15.064  31.057 -28.547   0.00           H
ATOM   1508  HB3  ARG  114   -15.025  29.425 -27.976   0.00           H
ATOM   1509  CG   ARG  114   -16.950  30.288 -27.998  36.93           C
ATOM   1510  HG2  ARG  114   -17.287  29.349 -27.642   0.00           H
ATOM   1511  HG3  ARG  114   -17.423  31.063 -27.453   0.00           H
ATOM   1512  CD   ARG  114   -17.369  30.415 -29.455  37.09           C
ATOM   1513  HD2  ARG  114   -17.036  31.344 -29.838   0.00           H
ATOM   1514  HD3  ARG  114   -16.938  29.627 -30.016   0.00           H
ATOM   1515  NE   ARG  114   -18.815  30.351 -29.634  37.55           N1+
ATOM   1516  HE   ARG  114   -19.384  29.853 -28.967   0.00           H
ATOM   1517  CZ   ARG  114   -19.468  30.920 -30.647  39.74           C
ATOM   1518  NH1  ARG  114   -18.802  31.601 -31.569  39.37           N
ATOM   1519  HH11 ARG  114   -19.298  32.031 -32.335   0.00           H
ATOM   1520  HH12 ARG  114   -17.799  31.689 -31.505   0.00           H
```

FIGURE 6-21 -

```
ATOM   1521  NH2  ARG  114   -20.789  30.807 -30.749   39.54       N
ATOM   1522  HE21 ARG  114   -21.274  31.241 -31.520    0.00       H
ATOM   1523  HE22 ARG  114   -21.306  30.287 -30.056    0.00       H
ATOM   1524  C    ARG  114   -15.835  30.114 -25.374   39.60       C
ATOM   1525  O    ARG  114   -16.846  30.608 -24.864   39.60       O
ATOM   1526  N    ALA  115   -15.366  28.909 -25.056   39.72       N
ATOM   1527  HN   ALA  115   -14.533  28.591 -25.529    0.00       H
ATOM   1528  CA   ALA  115   -16.010  28.058 -24.065   39.27       C
ATOM   1529  HA   ALA  115   -17.062  28.138 -24.161    0.00       H
ATOM   1530  CB   ALA  115   -15.595  26.608 -24.278   39.55       C
ATOM   1531  HB1  ALA  115   -15.886  26.296 -25.248    0.00       H
ATOM   1532  HB2  ALA  115   -14.544  26.524 -24.180    0.00       H
ATOM   1533  HB3  ALA  115   -16.067  25.996 -23.554    0.00       H
ATOM   1534  C    ALA  115   -15.651  28.497 -22.647   38.61       C
ATOM   1535  O    ALA  115   -16.522  28.577 -21.774   38.06       O
ATOM   1536  N    VAL  116   -14.369  28.769 -22.417   37.22       N
ATOM   1537  HN   VAL  116   -13.701  28.675 -23.168    0.00       H
ATOM   1538  CA   VAL  116   -13.926  29.199 -21.098   36.81       C
ATOM   1539  HA   VAL  116   -14.188  28.465 -20.381    0.00       H
ATOM   1540  CB   VAL  116   -12.410  29.406 -21.034   35.64       C
ATOM   1541  HB   VAL  116   -12.138  30.220 -21.655    0.00       H
ATOM   1542  CG1  VAL  116   -12.000  29.742 -19.610   34.83       C
ATOM   1543  HG11 VAL  116   -12.489  30.629 -19.302    0.00       H
ATOM   1544  HG12 VAL  116   -12.274  28.946 -18.967    0.00       H
ATOM   1545  HG13 VAL  116   -10.951  29.885 -19.569    0.00       H
ATOM   1546  CG2  VAL  116   -11.700  28.167 -21.505   36.00       C
ATOM   1547  HG21 VAL  116   -11.966  27.351 -20.885    0.00       H
ATOM   1548  HG22 VAL  116   -11.981  27.958 -22.504    0.00       H
ATOM   1549  HG23 VAL  116   -10.653  28.320 -21.457    0.00       H
ATOM   1550  C    VAL  116   -14.581  30.522 -20.754   37.22       C
ATOM   1551  O    VAL  116   -15.062  30.730 -19.644   37.66       O
ATOM   1552  N    ASN  117   -14.602  31.426 -21.716   37.47       N
ATOM   1553  HN   ASN  117   -14.205  31.219 -22.620    0.00       H
ATOM   1554  CA   ASN  117   -15.197  32.717 -21.468   38.32       C
ATOM   1555  HA   ASN  117   -14.892  33.069 -20.517    0.00       H
ATOM   1556  CB   ASN  117   -14.747  33.710 -22.546   40.83       C
ATOM   1557  HB2  ASN  117   -15.035  33.351 -23.499    0.00       H
ATOM   1558  HB3  ASN  117   -15.201  34.651 -22.371    0.00       H
ATOM   1559  CG   ASN  117   -13.226  33.910 -22.553   41.85       C
ATOM   1560  OD1  ASN  117   -12.630  34.335 -21.551   42.11       O
ATOM   1561  ND2  ASN  117   -12.594  33.595 -23.682   41.57       N
ATOM   1562  HD21 ASN  117   -13.117  33.253 -24.474    0.00       H
ATOM   1563  HD22 ASN  117   -11.592  33.699 -23.745    0.00       H
ATOM   1564  C    ASN  117   -16.715  32.611 -21.377   37.58       C
ATOM   1565  O    ASN  117   -17.358  33.455 -20.755   39.64       O
ATOM   1566  N    HIS  118   -17.300  31.580 -21.978   35.65       N
ATOM   1567  HN   HIS  118   -16.758  30.912 -22.506    0.00       H
ATOM   1568  CA   HIS  118   -18.745  31.421 -21.867   34.73       C
ATOM   1569  HA   HIS  118   -19.214  32.363 -21.984    0.00       H
ATOM   1570  CB   HIS  118   -19.319  30.477 -22.926   34.90       C
ATOM   1571  HB2  HIS  118   -19.219  30.918 -23.884    0.00       H
ATOM   1572  HB3  HIS  118   -18.792  29.559 -22.904    0.00       H
ATOM   1573  CG   HIS  118   -20.772  30.170 -22.718   35.63       C
ATOM   1574  CD2  HIS  118   -21.879  30.935 -22.889   35.80       C
ATOM   1575  HD2  HIS  118   -21.790  31.928 -23.297    0.00       H
ATOM   1576  ND1  HIS  118   -21.213  28.974 -22.192   35.88       N1+
ATOM   1577  HD1  HIS  118   -20.552  28.240 -21.984    0.00       H
ATOM   1578  CE1  HIS  118   -22.527  29.016 -22.046   35.43       C
ATOM   1579  HE1  HIS  118   -23.052  28.166 -21.644    0.00       H
ATOM   1580  NE2  HIS  118   -22.955  30.195 -22.461   34.66       N
ATOM   1581  HE2  HIS  118   -23.884  30.586 -22.501    0.00       H
ATOM   1582  C    HIS  118   -19.040  30.850 -20.492   34.73       C
ATOM   1583  O    HIS  118   -20.007  31.246 -19.843   35.59       O
ATOM   1584  N    ILE  119   -18.209  29.909 -20.053   33.06       N
ATOM   1585  HN   ILE  119   -17.450  29.612 -20.648    0.00       H
ATOM   1586  CA   ILE  119   -18.380  29.309 -18.739   31.47       C
ATOM   1587  HA   ILE  119   -19.347  28.882 -18.669    0.00       H
ATOM   1588  CB   ILE  119   -17.351  28.215 -18.486   29.95       C
ATOM   1589  HB   ILE  119   -16.386  28.575 -18.730    0.00       H
ATOM   1590  CG2  ILE  119   -17.387  27.815 -17.018   27.71       C
ATOM   1591  HG21 ILE  119   -17.162  28.657 -16.417    0.00       H
ATOM   1592  HG22 ILE  119   -18.353  27.455 -16.774    0.00       H
ATOM   1593  HG23 ILE  119   -16.672  27.054 -16.842    0.00       H
ATOM   1594  CG1  ILE  119   -17.634  27.026 -19.413   29.32       C
ATOM   1595  HG12 ILE  119   -18.487  26.503 -19.066    0.00       H
ATOM   1596  HG13 ILE  119   -17.812  27.379 -20.396    0.00       H
```

FIGURE 6-22 -

```
ATOM   1597  CD1  ILE  119   -16.511  26.034 -19.496  27.36       C
ATOM   1598  HD11 ILE  119   -15.641  26.515 -19.862   0.00       H
ATOM   1599  HD12 ILE  119   -16.317  25.639 -18.533   0.00       H
ATOM   1600  HD13 ILE  119   -16.782  25.248 -20.152   0.00       H
ATOM   1601  C    ILE  119   -18.227  30.376 -17.670  31.91       C
ATOM   1602  O    ILE  119   -19.056  30.466 -16.768  33.88       O
ATOM   1603  N    ARG  120   -17.164  31.174 -17.782  31.22       N
ATOM   1604  HN   ARG  120   -16.503  31.022 -18.509   0.00       H
ATOM   1605  CA   ARG  120   -16.947  32.253 -16.805  30.11       C
ATOM   1606  HA   ARG  120   -16.718  31.842 -15.856   0.00       H
ATOM   1607  CB   ARG  120   -15.789  33.156 -17.235  33.89       C
ATOM   1608  HB2  ARG  120   -15.918  33.438 -18.248   0.00       H
ATOM   1609  HB3  ARG  120   -15.773  34.023 -16.627   0.00       H
ATOM   1610  CG   ARG  120   -14.388  32.581 -17.153  40.57       C
ATOM   1611  HG2  ARG  120   -14.317  31.942 -16.312   0.00       H
ATOM   1612  HG3  ARG  120   -14.180  32.030 -18.033   0.00       H
ATOM   1613  CD   ARG  120   -13.386  33.738 -17.014  44.87       C
ATOM   1614  HD2  ARG  120   -13.463  34.375 -17.857   0.00       H
ATOM   1615  HD3  ARG  120   -13.602  34.288 -16.135   0.00       H
ATOM   1616  NE   ARG  120   -11.996  33.299 -16.924  49.07       N1+
ATOM   1617  HE   ARG  120   -11.599  33.062 -16.027   0.00       H
ATOM   1618  CZ   ARG  120   -11.180  33.182 -17.969  52.73       C
ATOM   1619  NH1  ARG  120   -11.609  33.472 -19.195  53.89       N
ATOM   1620  HH11 ARG  120   -10.985  33.381 -19.983   0.00       H
ATOM   1621  HH12 ARG  120   -12.558  33.783 -19.337   0.00       H
ATOM   1622  NH2  ARG  120    -9.928  32.781 -17.789  53.49       N
ATOM   1623  HH21 ARG  120    -9.308  32.692 -18.580   0.00       H
ATOM   1624  HH22 ARG  120    -9.596  32.565 -16.861   0.00       H
ATOM   1625  C    ARG  120   -18.215  33.097 -16.812  28.34       C
ATOM   1626  O    ARG  120   -18.641  33.621 -15.782  27.11       O
ATOM   1627  N    SER  121   -18.795  33.223 -18.004  25.59       N
ATOM   1628  HN   SER  121   -18.346  32.745 -18.771   0.00       H
ATOM   1629  CA   SER  121   -20.003  33.992 -18.236  23.58       C
ATOM   1630  HA   SER  121   -19.865  34.981 -17.883   0.00       H
ATOM   1631  CB   SER  121   -20.308  34.022 -19.744  25.49       C
ATOM   1632  HB2  SER  121   -19.499  34.470 -20.259   0.00       H
ATOM   1633  HB3  SER  121   -20.446  33.033 -20.096   0.00       H
ATOM   1634  OG   SER  121   -21.481  34.759 -20.061  29.10       O
ATOM   1635  HG   SER  121   -21.623  34.744 -21.017   0.00       H
ATOM   1636  C    SER  121   -21.165  33.382 -17.470  22.60       C
ATOM   1637  O    SER  121   -21.856  34.071 -16.721  21.97       O
ATOM   1638  N    VAL  122   -21.374  32.082 -17.653  21.39       N
ATOM   1639  HN   VAL  122   -20.760  31.573 -18.271   0.00       H
ATOM   1640  CA   VAL  122   -22.464  31.393 -16.981  18.09       C
ATOM   1641  HA   VAL  122   -23.384  31.849 -17.241   0.00       H
ATOM   1642  CB   VAL  122   -22.531  29.906 -17.380  14.59       C
ATOM   1643  HB   VAL  122   -21.584  29.457 -17.230   0.00       H
ATOM   1644  CG1  VAL  122   -23.552  29.183 -16.532  12.51       C
ATOM   1645  HG11 VAL  122   -23.279  29.256 -15.512   0.00       H
ATOM   1646  HG12 VAL  122   -24.505  29.623 -16.675   0.00       H
ATOM   1647  HG13 VAL  122   -23.588  28.163 -16.816   0.00       H
ATOM   1648  CG2  VAL  122   -22.915  29.783 -18.831  10.21       C
ATOM   1649  HG21 VAL  122   -23.863  30.229 -18.984   0.00       H
ATOM   1650  HG22 VAL  122   -22.193  30.274 -19.430   0.00       H
ATOM   1651  HG23 VAL  122   -22.959  28.759 -19.099   0.00       H
ATOM   1652  C    VAL  122   -22.329  31.489 -15.481  19.39       C
ATOM   1653  O    VAL  122   -23.334  31.517 -14.766  20.60       O
ATOM   1654  N    TRP  123   -21.086  31.551 -15.007  20.44       N
ATOM   1655  HN   TRP  123   -20.327  31.540 -15.672   0.00       H
ATOM   1656  CA   TRP  123   -20.802  31.633 -13.571  20.42       C
ATOM   1657  HA   TRP  123   -21.445  30.975 -13.046   0.00       H
ATOM   1658  CB   TRP  123   -19.344  31.236 -13.310  20.13       C
ATOM   1659  HB2  TRP  123   -19.190  30.235 -13.620   0.00       H
ATOM   1660  HB3  TRP  123   -18.701  31.877 -13.855   0.00       H
ATOM   1661  CG   TRP  123   -18.924  31.320 -11.849  22.26       C
ATOM   1662  CD2  TRP  123   -18.945  30.264 -10.884  20.26       C
ATOM   1663  CE2  TRP  123   -18.454  30.795  -9.671  22.29       C
ATOM   1664  CE3  TRP  123   -19.330  28.921 -10.926  21.39       C
ATOM   1665  HE3  TRP  123   -19.709  28.498 -11.841   0.00       H
ATOM   1666  CD1  TRP  123   -18.437  32.420 -11.195  21.85       C
ATOM   1667  HD1  TRP  123   -18.329  33.354 -11.719   0.00       H
ATOM   1668  NE1  TRP  123   -18.152  32.112  -9.891  20.56       N
ATOM   1669  HE1  TRP  123   -17.781  32.820  -9.275   0.00       H
ATOM   1670  CZ2  TRP  123   -18.335  30.021  -8.501  24.67       C
ATOM   1671  HZ2  TRP  123   -17.955  30.466  -7.597   0.00       H
ATOM   1672  CZ3  TRP  123   -19.212  28.146  -9.761  22.73       C
```

FIGURE 6- 23 -

```
ATOM   1673  HZ3 TRP   123     -19.502  27.109  -9.773   0.00           H
ATOM   1674  CH2 TRP   123     -18.718  28.702  -8.567  23.61           C
ATOM   1675  HH2 TRP   123     -18.642  28.075  -7.695   0.00           H
ATOM   1676  C   TRP   123     -21.117  33.000 -12.955  19.63           C
ATOM   1677  O   TRP   123     -21.711  33.080 -11.880  18.48           O
ATOM   1678  N   GLU   124     -20.717  34.073 -13.626  20.42           N
ATOM   1679  HN  GLU   124     -20.204  33.965 -14.488   0.00           H
ATOM   1680  CA  GLU   124     -21.016  35.397 -13.122  21.19           C
ATOM   1681  HA  GLU   124     -20.552  35.529 -12.179   0.00           H
ATOM   1682  CB  GLU   124     -20.503  36.477 -14.075  26.21           C
ATOM   1683  HB2 GLU   124     -20.944  36.345 -15.029   0.00           H
ATOM   1684  HB3 GLU   124     -20.759  37.432 -13.697   0.00           H
ATOM   1685  CG  GLU   124     -18.992  36.497 -14.301  33.79           C
ATOM   1686  HG2 GLU   124     -18.712  35.662 -14.889   0.00           H
ATOM   1687  HG3 GLU   124     -18.722  37.389 -14.804   0.00           H
ATOM   1688  CD  GLU   124     -18.202  36.438 -13.005  38.82           C
ATOM   1689  OE1 GLU   124     -18.571  37.162 -12.046  41.01           O1-
ATOM   1690  OE2 GLU   124     -17.205  35.670 -12.953  42.18           O
ATOM   1691  C   GLU   124     -22.538  35.481 -13.021  20.62           C
ATOM   1692  O   GLU   124     -23.070  36.098 -12.101  20.82           O
ATOM   1693  N   ASP   125     -23.237  34.844 -13.958  18.69           N
ATOM   1694  HN  ASP   125     -22.739  34.345 -14.680   0.00           H
ATOM   1695  CA  ASP   125     -24.698  34.858 -13.955  17.87           C
ATOM   1696  HA  ASP   125     -25.041  35.859 -13.928   0.00           H
ATOM   1697  CB  ASP   125     -25.248  34.181 -15.210  18.11           C
ATOM   1698  HB2 ASP   125     -24.813  34.623 -16.069   0.00           H
ATOM   1699  HB3 ASP   125     -25.012  33.149 -15.186   0.00           H
ATOM   1700  CG  ASP   125     -26.759  34.315 -15.327  18.38           C
ATOM   1701  OD1 ASP   125     -27.225  35.399 -15.713  19.85           O
ATOM   1702  OD2 ASP   125     -27.489  33.346 -15.020  17.26           O1-
ATOM   1703  C   ASP   125     -25.294  34.178 -12.722  18.71           C
ATOM   1704  O   ASP   125     -26.365  34.549 -12.263  20.08           O
ATOM   1705  N   LEU   126     -24.624  33.163 -12.196  18.89           N
ATOM   1706  HN  LEU   126     -23.761  32.850 -12.615   0.00           H
ATOM   1707  CA  LEU   126     -25.137  32.501 -11.010  18.10           C
ATOM   1708  HA  LEU   126     -26.156  32.252 -11.158   0.00           H
ATOM   1709  CB  LEU   126     -24.350  31.227 -10.731  17.06           C
ATOM   1710  HB2 LEU   126     -23.313  31.435 -10.782   0.00           H
ATOM   1711  HB3 LEU   126     -24.591  30.868  -9.765   0.00           H
ATOM   1712  CG  LEU   126     -24.629  30.095 -11.713  17.30           C
ATOM   1713  HG  LEU   126     -24.386  30.411 -12.694   0.00           H
ATOM   1714  CD1 LEU   126     -23.790  28.884 -11.354  18.59           C
ATOM   1715  HD11 LEU  126     -22.763  29.140 -11.398   0.00           H
ATOM   1716  HD12 LEU  126     -24.032  28.565 -10.374   0.00           H
ATOM   1717  HD13 LEU  126     -23.988  28.101 -12.039   0.00           H
ATOM   1718  CD2 LEU   126     -26.116  29.755 -11.677  14.18           C
ATOM   1719  HD21 LEU  126     -26.385  29.451 -10.699   0.00           H
ATOM   1720  HD22 LEU  126     -26.680  30.609 -11.949   0.00           H
ATOM   1721  HD23 LEU  126     -26.315  28.969 -12.358   0.00           H
ATOM   1722  C   LEU   126     -25.030  33.445  -9.820  18.82           C
ATOM   1723  O   LEU   126     -25.820  33.368  -8.891  17.76           O
ATOM   1724  N   LEU   127     -24.052  34.343  -9.861  20.16           N
ATOM   1725  HN  LEU   127     -23.444  34.356 -10.666   0.00           H
ATOM   1726  CA  LEU   127     -23.847  35.294  -8.779  21.92           C
ATOM   1727  HA  LEU   127     -24.139  34.853  -7.861   0.00           H
ATOM   1728  CB  LEU   127     -22.370  35.695  -8.692  21.18           C
ATOM   1729  HB2 LEU   127     -22.127  36.325  -9.508   0.00           H
ATOM   1730  HB3 LEU   127     -22.197  36.211  -7.784   0.00           H
ATOM   1731  CG  LEU   127     -21.301  34.590  -8.721  22.83           C
ATOM   1732  HG  LEU   127     -21.405  34.021  -9.608   0.00           H
ATOM   1733  CD1 LEU   127     -19.900  35.206  -8.684  18.95           C
ATOM   1734  HD11 LEU  127     -19.769  35.836  -9.525   0.00           H
ATOM   1735  HD12 LEU  127     -19.787  35.773  -7.797   0.00           H
ATOM   1736  HD13 LEU  127     -19.175  34.435  -8.704   0.00           H
ATOM   1737  CD2 LEU   127     -21.505  33.646  -7.548  22.94           C
ATOM   1738  HD21 LEU  127     -21.425  34.187  -6.641   0.00           H
ATOM   1739  HD22 LEU  127     -22.466  33.206  -7.612   0.00           H
ATOM   1740  HD23 LEU  127     -20.767  32.887  -7.573   0.00           H
ATOM   1741  C   LEU   127     -24.694  36.541  -8.990  23.26           C
ATOM   1742  O   LEU   127     -25.059  37.220  -8.031  24.25           O
ATOM   1743  N   GLU   128     -25.015  36.839 -10.243  23.80           N
ATOM   1744  HN  GLU   128     -24.709  36.228 -10.986   0.00           H
ATOM   1745  CA  GLU   128     -25.796  38.026 -10.553  23.62           C
ATOM   1746  HA  GLU   128     -25.638  38.758  -9.804   0.00           H
ATOM   1747  CB  GLU   128     -25.364  38.584 -11.906  24.43           C
ATOM   1748  HB2 GLU   128     -25.352  37.804 -12.622   0.00           H
```

FIGURE 6-24 -

```
ATOM   1749  HB3  GLJ  128   -26.046  39.334 -12.213   0.00   H
ATOM   1750  CG   GLJ  128   -23.985  39.213 -11.919  25.59   C
ATOM   1751  HG2  GLJ  128   -23.287  38.542 -11.491   0.00   H
ATOM   1752  HG3  GLJ  128   -23.703  39.426 -12.917   0.00   H
ATOM   1753  CD   GLJ  128   -23.941  40.496 -11.137  28.52   C
ATOM   1754  OE1  GLJ  128   -24.973  41.195 -11.085  31.60   O1-
ATOM   1755  OE2  GLJ  128   -22.875  40.820 -10.583  31.09   O
ATOM   1756  C    GLJ  128   -27.300  37.809 -10.555  24.09   C
ATOM   1757  O    GLJ  128   -28.060  38.745 -10.305  26.52   O
ATOM   1758  N    ASP  129   -27.726  36.581 -10.840  24.11   N
ATOM   1759  HN   ASP  129   -27.023  35.878 -11.012   0.00   H
ATOM   1760  CA   ASP  129   -29.147  36.229 -10.910  22.46   C
ATOM   1761  HA   ASP  129   -29.732  37.064 -10.625   0.00   H
ATOM   1762  CB   ASP  129   -29.504  35.822 -12.342  22.05   C
ATOM   1763  HB2  ASP  129   -29.149  36.557 -13.017   0.00   H
ATOM   1764  HB3  ASP  129   -29.054  34.890 -12.567   0.00   H
ATOM   1765  CG   ASP  129   -30.999  35.679 -12.555  23.61   C
ATOM   1766  OD1  ASP  129   -31.698  35.150 -11.659  25.92   O
ATOM   1767  OD2  ASP  129   -31.480  36.086 -13.632  22.46   O1-
ATOM   1768  C    ASP  129   -29.471  35.073  -9.958  22.00   C
ATOM   1769  O    ASP  129   -28.911  33.980 -10.063  20.81   O
ATOM   1770  N    THR  130   -30.398  35.309  -9.040  20.99   N
ATOM   1771  HN   THR  130   -30.854  36.209  -9.026   0.00   H
ATOM   1772  CA   THR  130   -30.760  34.296  -8.065  21.00   C
ATOM   1773  HA   THR  130   -30.056  33.505  -8.100   0.00   H
ATOM   1774  CB   THR  130   -30.774  34.886  -6.642  20.41   C
ATOM   1775  HB   THR  130   -31.091  34.145  -5.956   0.00   H
ATOM   1776  OG1  THR  130   -31.694  35.983  -6.607  19.88   O
ATOM   1777  HG1  THR  130   -31.711  36.361  -5.717   0.00   H
ATOM   1778  CG2  THR  130   -29.386  35.372  -6.220  16.94   C
ATOM   1779  HG21 THR  130   -28.707  34.560  -6.238   0.00   H
ATOM   1780  HG22 THR  130   -29.056  36.123  -6.890   0.00   H
ATOM   1781  HG23 THR  130   -29.434  35.770  -5.240   0.00   H
ATOM   1782  C    THR  130   -32.132  33.686  -8.300  22.98   C
ATOM   1783  O    THR  130   -32.558  32.840  -7.520  24.88   O
ATOM   1784  N    GLJ  131   -32.832  34.077  -9.360  23.17   N
ATOM   1785  HN   GLJ  131   -32.463  34.735 -10.030   0.00   H
ATOM   1786  CA   GLJ  131   -34.166  33.527  -9.540  24.68   C
ATOM   1787  HA   GLJ  131   -34.317  32.735  -8.854   0.00   H
ATOM   1788  CB   GLJ  131   -35.212  34.613  -9.295  27.45   C
ATOM   1789  HB2  GLJ  131   -35.236  35.273 -10.123   0.00   H
ATOM   1790  HB3  GLJ  131   -36.164  34.165  -9.173   0.00   H
ATOM   1791  CG   GLJ  131   -34.974  35.468  -8.066  35.98   C
ATOM   1792  HG2  GLJ  131   -35.265  34.931  -7.201   0.00   H
ATOM   1793  HG3  GLJ  131   -33.946  35.713  -8.000   0.00   H
ATOM   1794  CD   GLJ  131   -35.773  36.775  -8.107  40.16   C
ATOM   1795  OE1  GLJ  131   -35.788  37.426  -9.184  42.18   O1-
ATOM   1796  OE2  GLJ  131   -36.375  37.153  -7.068  39.93   O
ATOM   1797  C    GLJ  131   -34.491  32.855 -10.861  23.94   C
ATOM   1798  O    GLJ  131   -35.004  31.738 -10.877  25.81   O
ATOM   1799  N    THR  132   -34.216  33.538 -11.964  21.89   N
ATOM   1800  HN   THR  132   -33.770  34.438 -11.872   0.00   H
ATOM   1801  CA   THR  132   -34.543  33.017 -13.289  20.25   C
ATOM   1802  HA   THR  132   -35.589  33.079 -13.445   0.00   H
ATOM   1803  CB   THR  132   -33.848  33.801 -14.403  17.61   C
ATOM   1804  HB   THR  132   -32.881  33.401 -14.566   0.00   H
ATOM   1805  OG1  THR  132   -33.745  35.181 -14.031  17.88   O
ATOM   1806  HG1  THR  132   -33.305  35.673 -14.738   0.00   H
ATOM   1807  CG2  THR  132   -34.661  33.695 -15.678  12.77   C
ATOM   1808  HG21 THR  132   -34.743  32.678 -15.961   0.00   H
ATOM   1809  HG22 THR  132   -35.628  34.095 -15.515   0.00   H
ATOM   1810  HG23 THR  132   -34.180  34.238 -16.450   0.00   H
ATOM   1811  C    THR  132   -34.239  31.549 -13.526  21.20   C
ATOM   1812  O    THR  132   -33.092  31.110 -13.396  22.45   O
ATOM   1813  N    PRO  133   -35.274  30.768 -13.878  19.95   N
ATOM   1814  CD   PRO  133   -36.705  31.113 -13.827  17.34   C
ATOM   1815  HD2  PRO  133   -36.881  31.768 -13.014   0.00   H
ATOM   1816  HD3  PRO  133   -36.986  31.589 -14.731   0.00   H
ATOM   1817  CA   PRO  133   -35.101  29.340 -14.141  19.10   C
ATOM   1818  HA   PRO  133   -34.733  28.863 -13.270   0.00   H
ATOM   1819  CB   PRO  133   -36.509  28.891 -14.510  18.63   C
ATOM   1820  HB2  PRO  133   -36.672  29.054 -15.544   0.00   H
ATOM   1821  HB3  PRO  133   -36.619  27.860 -14.294   0.00   H
ATOM   1822  CG   PRO  133   -37.353  29.758 -13.646  17.10   C
ATOM   1823  HG2  PRO  133   -38.355  29.729 -13.988   0.00   H
ATOM   1824  HG3  PRO  133   -37.311  29.409 -12.647   0.00   H
```

FIGURE 6- 25 -

```
ATOM   1825  C    PRO  133   -34.115  29.123 -15.276  18.79    C
ATOM   1826  O    PRO  133   -34.070  29.896 -16.232  17.29    O
ATOM   1827  N    ILE  134   -33.318  28.071 -15.152  19.03    N
ATOM   1828  HN   ILE  134   -33.415  27.499 -14.327   0.00    H
ATOM   1829  CA   ILE  134   -32.327  27.731 -16.160  19.71    C
ATOM   1830  HA   ILE  134   -32.071  28.599 -16.710   0.00    H
ATOM   1831  CB   ILE  134   -31.055  27.164 -15.485  20.61    C
ATOM   1832  HB   ILE  134   -31.333  26.489 -14.718   0.00    H
ATOM   1833  CG2  ILE  134   -30.196  26.431 -16.495  19.45    C
ATOM   1834  HG21 ILE  134   -30.748  25.630 -16.913   0.00    H
ATOM   1835  HG22 ILE  134   -29.907  27.099 -17.264   0.00    H
ATOM   1836  HG23 ILE  134   -29.332  26.051 -16.014   0.00    H
ATOM   1837  CG1  ILE  134   -30.302  28.318 -14.799  22.58    C
ATOM   1838  HG12 ILE  134   -29.843  28.926 -15.534   0.00    H
ATOM   1839  HG13 ILE  134   -30.985  28.899 -14.236   0.00    H
ATOM   1840  CD1  ILE  134   -29.198  27.902 -13.837  20.58    C
ATOM   1841  HD11 ILE  134   -29.610  27.312 -13.060   0.00    H
ATOM   1842  HD12 ILE  134   -28.469  27.339 -14.359   0.00    H
ATOM   1843  HD13 ILE  134   -28.747  28.766 -13.423   0.00    H
ATOM   1844  C    ILE  134   -32.929  26.714 -17.115  19.69    C
ATOM   1845  O    ILE  134   -33.637  25.802 -16.701  20.32    O
ATOM   1846  N    ASP  135   -32.665  26.869 -18.402  20.28    N
ATOM   1847  HN   ASP  135   -32.076  27.623 -18.723   0.00    H
ATOM   1848  CA   ASP  135   -33.235  25.938 -19.356  21.47    C
ATOM   1849  HA   ASP  135   -34.273  25.837 -19.174   0.00    H
ATOM   1850  CB   ASP  135   -33.033  26.434 -20.795  23.35    C
ATOM   1851  HB2  ASP  135   -33.289  27.460 -20.854   0.00    H
ATOM   1852  HB3  ASP  135   -32.019  26.307 -21.073   0.00    H
ATOM   1853  CG   ASP  135   -33.898  25.671 -21.795  29.12    C
ATOM   1854  OD1  ASP  135   -34.919  25.084 -21.357  30.20    O
ATOM   1855  OD2  ASP  135   -33.576  25.661 -23.009  30.84    O1-
ATOM   1856  C    ASP  135   -32.664  24.537 -19.202  20.18    C
ATOM   1857  O    ASP  135   -31.554  24.360 -18.698  19.94    O
ATOM   1858  N    THR  136   -33.466  23.552 -19.606  19.91    N
ATOM   1859  HN   THR  136   -34.375  23.830 -19.944   0.00    H
ATOM   1860  CA   THR  136   -33.096  22.133 -19.580  18.57    C
ATOM   1861  HA   THR  136   -32.041  22.043 -19.595   0.00    H
ATOM   1862  CB   THR  136   -33.608  21.384 -18.324  14.86    C
ATOM   1863  HB   THR  136   -33.437  20.345 -18.439   0.00    H
ATOM   1864  CG1  THR  136   -35.018  21.576 -18.196  13.45    O
ATOM   1865  HG1  THR  136   -35.337  21.108 -17.412   0.00    H
ATOM   1866  CG2  THR  136   -32.893  21.856 -17.075  14.33    C
ATOM   1867  HG21 THR  136   -31.854  21.678 -17.174   0.00    H
ATOM   1868  HG22 THR  136   -33.062  22.893 -16.942   0.00    H
ATOM   1869  HG23 THR  136   -33.263  21.327 -16.235   0.00    H
ATOM   1870  C    THR  136   -33.676  21.421 -20.804  19.76    C
ATOM   1871  O    THR  136   -34.744  21.776 -21.320  19.13    O
ATOM   1872  N    THR  137   -32.948  20.413 -21.259  20.66    N
ATOM   1873  HN   THR  137   -32.091  20.204 -20.769   0.00    H
ATOM   1874  CA   THR  137   -33.336  19.622 -22.409  20.93    C
ATOM   1875  HA   THR  137   -34.079  20.139 -22.959   0.00    H
ATOM   1876  CB   THR  137   -32.122  19.362 -23.333  20.28    C
ATOM   1877  HB   THR  137   -31.306  19.014 -22.754   0.00    H
ATOM   1878  CG1  THR  137   -31.737  20.584 -23.972  16.31    O
ATOM   1879  HG1  THR  137   -30.978  20.421 -24.549   0.00    H
ATOM   1880  CG2  THR  137   -32.461  18.313 -24.387  18.83    C
ATOM   1881  HG21 THR  137   -32.728  17.406 -23.909   0.00    H
ATOM   1882  HG22 THR  137   -33.272  18.654 -24.976   0.00    H
ATOM   1883  HG23 THR  137   -31.618  18.151 -25.007   0.00    H
ATOM   1884  C    THR  137   -33.845  18.290 -21.902  23.09    C
ATOM   1885  O    THR  137   -33.193  17.653 -21.070  22.58    O
ATOM   1886  N    ILE  138   -35.014  17.881 -22.382  25.15    N
ATOM   1887  HN   ILE  138   -35.513  18.471 -23.031   0.00    H
ATOM   1888  CA   ILE  138   -35.576  16.602 -21.983  28.09    C
ATOM   1889  HA   ILE  138   -35.016  16.207 -21.175   0.00    H
ATOM   1890  CB   ILE  138   -37.054  16.736 -21.531  26.41    C
ATOM   1891  HB   ILE  138   -37.101  17.313 -20.644   0.00    H
ATOM   1892  CG2  ILE  138   -37.864  17.409 -22.594  26.14    C
ATOM   1893  HG21 ILE  138   -37.471  18.375 -22.779   0.00    H
ATOM   1894  HG22 ILE  138   -37.825  16.835 -23.483   0.00    H
ATOM   1895  HG23 ILE  138   -38.869  17.493 -22.272   0.00    H
ATOM   1896  CG1  ILE  138   -37.629  15.353 -21.209  26.64    C
ATOM   1897  HG12 ILE  138   -37.755  14.805 -22.107   0.00    H
ATOM   1898  HG13 ILE  138   -36.963  14.834 -20.569   0.00    H
ATOM   1899  CD1  ILE  138   -38.978  15.389 -20.515  27.75    C
ATOM   1900  HD11 ILE  138   -38.889  15.911 -19.598   0.00    H
```

FIGURE 6-26-

```
ATOM   1901  HD12 ILE  138   -39.681  15.882 -21.135   0.00   H
ATOM   1902  HD13 ILE  138   -39.305  14.399 -20.328   0.00   H
ATOM   1903  C    ILE  138   -35.472  15.688 -23.189  29.97   C
ATOM   1904  O    ILE  138   -35.634  16.131 -24.314  31.27   O
ATOM   1905  N    MET  139   -35.172  14.418 -22.963  33.68   N
ATOM   1906  HN   MET  139   -35.031  14.102 -22.015   0.00   H
ATOM   1907  CA   MET  139   -35.046  13.481 -24.069  37.12   C
ATOM   1908  HA   MET  139   -35.667  13.792 -24.868   0.00   H
ATOM   1909  CB   MET  139   -33.600  13.418 -24.564  38.52   C
ATOM   1910  HB2  MET  139   -32.966  13.133 -23.765   0.00   H
ATOM   1911  HB3  MET  139   -33.525  12.707 -25.345   0.00   H
ATOM   1912  CG   MET  139   -33.051  14.713 -25.108  41.87   C
ATOM   1913  HG2  MET  139   -33.820  15.441 -25.129   0.00   H
ATOM   1914  HG3  MET  139   -32.262  15.050 -24.487   0.00   H
ATOM   1915  SD   MET  139   -32.421  14.473 -26.783  48.40   S
ATOM   1916  CE   MET  139   -31.113  13.199 -26.447  46.56   C
ATOM   1917  HE1  MET  139   -30.401  13.594 -25.770   0.00   H
ATOM   1918  HE2  MET  139   -31.560  12.337 -26.026   0.00   H
ATOM   1919  HE3  MET  139   -30.632  12.940 -27.354   0.00   H
ATOM   1920  C    MET  139   -35.457  12.094 -23.633  38.13   C
ATOM   1921  O    MET  139   -35.459  11.787 -22.443  37.58   O
ATOM   1922  N    ALA  140   -35.813  11.260 -24.601  39.79   N
ATOM   1923  HN   ALA  140   -35.828  11.590 -25.554   0.00   H
ATOM   1924  CA   ALA  140   -36.179   9.887 -24.302  40.58   C
ATOM   1925  HA   ALA  140   -36.683   9.851 -23.372   0.00   H
ATOM   1926  CB   ALA  140   -37.089   9.340 -25.378  38.74   C
ATOM   1927  HB1  ALA  140   -37.968   9.928 -25.430   0.00   H
ATOM   1928  HB2  ALA  140   -36.589   9.369 -26.311   0.00   H
ATOM   1929  HB3  ALA  140   -37.347   8.339 -25.147   0.00   H
ATOM   1930  C    ALA  140   -34.839   9.176 -24.319  41.38   C
ATOM   1931  O    ALA  140   -34.109   9.274 -25.300  41.74   O
ATOM   1932  N    LYS  141   -34.500   8.482 -23.239  43.66   N
ATOM   1933  HN   LYS  141   -35.135   8.431 -22.457   0.00   H
ATOM   1934  CA   LYS  141   -33.214   7.795 -23.181  47.34   C
ATOM   1935  HA   LYS  141   -32.457   8.429 -23.564   0.00   H
ATOM   1936  CB   LYS  141   -32.863   7.423 -21.740  47.41   C
ATOM   1937  HB2  LYS  141   -32.910   8.288 -21.131   0.00   H
ATOM   1938  HB3  LYS  141   -33.552   6.702 -21.384   0.00   H
ATOM   1939  CG   LYS  141   -31.475   6.840 -21.608  49.27   C
ATOM   1940  HG2  LYS  141   -31.317   6.127 -22.375   0.00   H
ATOM   1941  HG3  LYS  141   -30.757   7.614 -21.693   0.00   H
ATOM   1942  CD   LYS  141   -31.262   6.144 -20.265  52.61   C
ATOM   1943  HD2  LYS  141   -32.113   5.559 -20.032   0.00   H
ATOM   1944  HD3  LYS  141   -30.409   5.519 -20.323   0.00   H
ATOM   1945  CE   LYS  141   -31.041   7.119 -19.104  52.68   C
ATOM   1946  HE2  LYS  141   -30.211   7.741 -19.318   0.00   H
ATOM   1947  HE3  LYS  141   -31.906   7.716 -18.975   0.00   H
ATOM   1948  NZ   LYS  141   -30.773   6.378 -17.833  50.97   N1(
ATOM   1949  HZ1  LYS  141   -31.561   5.787 -17.616   0.00   H
ATOM   1950  HZ2  LYS  141   -29.946   5.810 -17.943   0.00   H
ATOM   1951  HZ3  LYS  141   -30.631   7.038 -17.083   0.00   H
ATOM   1952  C    LYS  141   -33.207   6.537 -24.035  48.91   C
ATOM   1953  O    LYS  141   -34.260   5.991 -24.350  49.74   O
ATOM   1954  N    SER  142   -32.016   6.076 -24.404  51.38   N
ATOM   1955  HN   SER  142   -31.194   6.580 -24.107   0.00   H
ATOM   1956  CA   SER  142   -31.879   4.871 -25.219  53.48   C
ATOM   1957  HA   SER  142   -32.837   4.546 -25.533   0.00   H
ATOM   1958  CB   SER  142   -31.018   5.162 -26.454  55.00   C
ATOM   1959  HB2  SER  142   -31.471   5.928 -27.028   0.00   H
ATOM   1960  HB3  SER  142   -30.054   5.474 -26.147   0.00   H
ATOM   1961  OG   SER  142   -30.880   4.008 -27.271  57.04   O
ATOM   1962  HG   SER  142   -30.334   4.221 -28.040   0.00   H
ATOM   1963  C    SER  142   -31.255   3.729 -24.422  53.98   C
ATOM   1964  O    SER  142   -30.069   3.758 -24.100  52.01   O
ATOM   1965  N    GLU  143   -32.069   2.727 -24.106  56.30   N
ATOM   1966  HN   GLU  143   -33.031   2.791 -24.403   0.00   H
ATOM   1967  CA   GLU  143   -31.613   1.561 -23.355  58.28   C
ATOM   1968  HA   GLU  143   -30.554   1.549 -23.331   0.00   H
ATOM   1969  CB   GLU  143   -32.144   1.612 -21.923  58.62   C
ATOM   1970  HB2  GLU  143   -33.202   1.574 -21.937   0.00   H
ATOM   1971  HB3  GLU  143   -31.768   0.786 -21.378   0.00   H
ATOM   1972  CG   GLU  143   -31.742   2.872 -21.179  59.54   C
ATOM   1973  HG2  GLU  143   -30.732   3.104 -21.397   0.00   H
ATOM   1974  HG3  GLU  143   -32.362   3.675 -21.484   0.00   H
ATOM   1975  CD   GLU  143   -31.866   2.747 -19.670  59.80   C
ATOM   1976  OE1  GLU  143   -32.983   2.482 -19.166  59.61   O1-
```

FIGURE 6-27-

```
ATOM   1977  OE2  GLU  143   -30.833   2.925 -18.990  60.17      O
ATOM   1978  C    GLU  143   -32.074   0.274 -24.029  59.73      C
ATOM   1979  O    GLU  143   -33.150   0.228 -24.630  59.94      O
ATOM   1980  N    VAL  144   -31.254  -0.768 -23.924  61.54      N
ATOM   1981  HN   VAL  144   -30.397  -0.648 -23.405   0.00      H
ATOM   1982  CA   VAL  144   -31.565  -2.061 -24.535  63.19      C
ATOM   1983  HA   VAL  144   -32.361  -1.944 -25.223   0.00      H
ATOM   1984  CB   VAL  144   -30.335  -2.616 -25.282  62.38      C
ATOM   1985  HB   VAL  144   -29.527  -2.717 -24.605   0.00      H
ATOM   1986  CG1  VAL  144   -30.643  -3.990 -25.833  62.08      C
ATOM   1987  HG11 VAL  144   -30.891  -4.642 -25.036   0.00      H
ATOM   1988  HG12 VAL  144   -31.459  -3.926 -26.504   0.00      H
ATOM   1989  HG13 VAL  144   -29.794  -4.364 -26.344   0.00      H
ATOM   1990  CG2  VAL  144   -29.936  -1.663 -26.403  61.96      C
ATOM   1991  HG21 VAL  144   -30.741  -1.561 -27.083   0.00      H
ATOM   1992  HG22 VAL  144   -29.698  -0.716 -25.993   0.00      H
ATOM   1993  HG23 VAL  144   -29.091  -2.050 -26.911   0.00      H
ATOM   1994  C    VAL  144   -32.060  -3.100 -23.524  64.36      C
ATOM   1995  O    VAL  144   -31.429  -3.325 -22.491  63.29      O
ATOM   1996  N    PHE  145   -33.194  -3.727 -23.840  66.57      N
ATOM   1997  HN   PHE  145   -33.634  -3.481 -24.714   0.00      H
ATOM   1998  CA   PHE  145   -33.803  -4.740 -22.972  68.60      C
ATOM   1999  HA   PHE  145   -33.081  -5.095 -22.283   0.00      H
ATOM   2000  CB   PHE  145   -34.986  -4.141 -22.192  67.54      C
ATOM   2001  HB2  PHE  145   -35.659  -3.683 -22.869   0.00      H
ATOM   2002  HB3  PHE  145   -35.486  -4.910 -21.663   0.00      H
ATOM   2003  CG   PHE  145   -34.587  -3.097 -21.186  67.89      C
ATOM   2004  CD1  PHE  145   -33.763  -3.424 -20.114  68.05      C
ATOM   2005  HD1  PHE  145   -33.417  -4.436 -19.990   0.00      H
ATOM   2006  CD2  PHE  145   -35.021  -1.779 -21.317  68.45      C
ATOM   2007  HD2  PHE  145   -35.662  -1.502 -22.137   0.00      H
ATOM   2008  CE1  PHE  145   -33.369  -2.450 -19.181  67.58      C
ATOM   2009  HE1  PHE  145   -32.729  -2.720 -18.358   0.00      H
ATOM   2010  CE2  PHE  145   -34.635  -0.796 -20.391  68.63      C
ATOM   2011  HE2  PHE  145   -34.979   0.218 -20.507   0.00      H
ATOM   2012  CZ   PHE  145   -33.806  -1.134 -19.321  67.71      C
ATOM   2013  HZ   PHE  145   -33.504  -0.387 -18.606   0.00      H
ATOM   2014  C    PHE  145   -34.289  -5.961 -23.755  70.05      C
ATOM   2015  O    PHE  145   -34.099  -6.060 -24.972  69.21      O
ATOM   2016  N    CYS  146   -34.932  -6.913 -23.001  71.90      N
ATOM   2017  HN   CYS  146   -35.033  -6.813 -21.991   0.00      H
ATOM   2018  CA   CYS  146   -35.450  -8.145 -23.594  73.93      C
ATOM   2019  HA   CYS  146   -35.357  -8.091 -24.675   0.00      H
ATOM   2020  CB   CYS  146   -34.634  -9.317 -23.072  74.26      C
ATOM   2021  HB2  CYS  146   -33.581  -9.175 -23.320   0.00      H
ATOM   2022  HB3  CYS  146   -34.698  -9.353 -21.984   0.00      H
ATOM   2023  SG   CYS  146   -35.137 -10.953 -23.689  75.43      S
ATOM   2024  HG   CYS  146   -34.322 -11.659 -22.891   0.00      H
ATOM   2025  C    CYS  146   -36.925  -8.275 -23.197  75.37      C
ATOM   2026  O    CYS  146   -37.323  -8.208 -22.034  75.25      O
ATOM   2027  N    VAL  147   -37.764  -8.444 -24.277  77.11      N
ATOM   2028  HN   VAL  147   -37.355  -8.530 -25.195   0.00      H
ATOM   2029  CA   VAL  147   -39.210  -8.548 -24.110  78.44      C
ATOM   2030  HA   VAL  147   -39.577  -7.665 -23.655   0.00      H
ATOM   2031  CB   VAL  147   -39.927  -8.734 -25.488  77.71      C
ATOM   2032  HB   VAL  147   -40.932  -8.411 -25.409   0.00      H
ATOM   2033  CG1  VAL  147   -39.258  -7.870 -26.543  77.21      C
ATOM   2034  HG11 VAL  147   -39.316  -6.853 -26.255   0.00      H
ATOM   2035  HG12 VAL  147   -38.242  -8.153 -26.638   0.00      H
ATOM   2036  HG13 VAL  147   -39.750  -8.002 -27.472   0.00      H
ATOM   2037  CG2  VAL  147   -39.915 -10.198 -25.915  76.79      C
ATOM   2038  HG21 VAL  147   -38.914 -10.531 -26.005   0.00      H
ATOM   2039  HG22 VAL  147   -40.418 -10.782 -25.188   0.00      H
ATOM   2040  HG23 VAL  147   -40.405 -10.297 -26.848   0.00      H
ATOM   2041  C    VAL  147   -39.644  -9.685 -23.186  79.91      C
ATOM   2042  O    VAL  147   -39.101 -10.787 -23.240  80.46      O
ATOM   2043  N    GLN  148   -40.614  -9.408 -22.319  81.30      N
ATOM   2044  HN   GLN  148   -40.979  -8.468 -22.302   0.00      H
ATOM   2045  CA   GLN  148   -41.152 -10.418 -21.407  82.55      C
ATOM   2046  HA   GLN  148   -40.426 -11.172 -21.247   0.00      H
ATOM   2047  CB   GLN  148   -41.516  -9.781 -20.059  83.10      C
ATOM   2048  HB2  GLN  148   -40.632  -9.595 -19.506   0.00      H
ATOM   2049  HB3  GLN  148   -42.027  -8.868 -20.226   0.00      H
ATOM   2050  CG   GLN  148   -42.415 -10.656 -19.200  85.08      C
ATOM   2051  HG2  GLN  148   -43.362 -10.752 -19.664   0.00      H
ATOM   2052  HG3  GLN  148   -41.976 -11.614 -19.091   0.00      H
```

FIGURE 6-28 -

```
ATOM   2053  CD   GLN  148   -42.637 -10.090 -17.812  86.57       C
ATOM   2054  OE1  GLN  148   -42.704  -8.869 -17.628  87.09       O
ATOM   2055  NE2  GLN  148   -42.771 -10.974 -16.825  86.79       N
ATOM   2056  HE21 GLN  148   -42.709 -11.962 -17.021   0.00       E
ATOM   2057  HE22 GLN  148   -42.934 -10.656 -15.882   0.00       E
ATOM   2058  C    GLN  148   -42.394 -11.086 -22.031  82.83       C
ATOM   2059  O    GLN  148   -42.296 -12.265 -22.442  82.28       O
ATOM   2060  OXT  GLN  148   -43.450 -10.418 -22.120  83.43       O1-
ATOM   2061  C    GLY  153   -43.550  -5.654 -21.797  66.26       C
ATOM   2062  O    GLY  153   -42.596  -6.427 -21.905  66.14       O
ATOM   2063  N    GLY  153   -44.930  -7.597 -20.945  67.21       N
ATOM   2064  H1   GLY  153   -44.232  -7.812 -20.249   0.00       E
ATOM   2065  H2   GLY  153   -45.843  -7.842 -20.593   0.00       E
ATOM   2066  CA   GLY  153   -44.891  -6.130 -21.256  66.70       C
ATOM   2067  HA2  GLY  153   -45.623  -5.905 -21.987   0.00       E
ATOM   2068  HA3  GLY  153   -45.089  -5.577 -20.375   0.00       E
ATOM   2069  N    ARG  154   -43.481  -4.371 -22.139  65.84       N
ATOM   2070  HN   ARG  154   -44.311  -3.810 -22.017   0.00       E
ATOM   2071  CA   ARG  154   -42.262  -3.766 -22.675  65.48       C
ATOM   2072  HA   ARG  154   -41.428  -4.366 -22.419   0.00       E
ATOM   2073  CB   ARG  154   -42.357  -3.660 -24.197  66.09       C
ATOM   2074  HB2  ARG  154   -42.347  -4.631 -24.620   0.00       E
ATOM   2075  HB3  ARG  154   -43.258  -3.169 -24.461   0.00       E
ATOM   2076  CG   ARG  154   -41.228  -2.887 -24.838  67.15       C
ATOM   2077  HG2  ARG  154   -41.295  -1.868 -24.559   0.00       E
ATOM   2078  HG3  ARG  154   -40.301  -3.281 -24.512   0.00       E
ATOM   2079  CD   ARG  154   -41.300  -2.988 -26.350  68.70       C
ATOM   2080  HD2  ARG  154   -42.285  -2.768 -26.672   0.00       E
ATOM   2081  HD3  ARG  154   -40.625  -2.296 -26.783   0.00       E
ATOM   2082  NE   ARG  154   -40.952  -4.324 -26.826  69.84       N1+
ATOM   2083  HE   ARG  154   -40.703  -5.046 -26.166   0.00       E
ATOM   2084  CZ   ARG  154   -40.936  -4.678 -28.107  70.58       C
ATOM   2085  NH1  ARG  154   -41.252  -3.792 -29.045  70.99       N
ATOM   2086  HH11 ARG  154   -41.240  -4.061 -30.017   0.00       E
ATOM   2087  HH12 ARG  154   -41.504  -2.850 -28.785   0.00       E
ATOM   2088  NH2  ARG  154   -40.596  -5.916 -28.448  70.79       N
ATOM   2089  HH21 ARG  154   -40.583  -6.186 -29.420   0.00       E
ATOM   2090  HH22 ARG  154   -40.350  -6.586 -27.735   0.00       E
ATOM   2091  C    ARG  154   -42.087  -2.379 -22.063  64.16       C
ATOM   2092  O    ARG  154   -42.971  -1.532 -22.179  65.49       O
ATOM   2093  N    LYS  155   -40.943  -2.138 -21.429  61.43       N
ATOM   2094  HN   LYS  155   -40.231  -2.852 -21.407   0.00       E
ATOM   2095  CA   LYS  155   -40.712  -0.857 -20.769  58.86       C
ATOM   2096  HA   LYS  155   -41.611  -0.525 -20.317   0.00       E
ATOM   2097  CB   LYS  155   -39.634  -1.010 -19.693  59.42       C
ATOM   2098  HB2  LYS  155   -39.390  -0.057 -19.300   0.00       E
ATOM   2099  HB3  LYS  155   -39.997  -1.630 -18.915   0.00       E
ATOM   2100  CG   LYS  155   -38.326  -1.630 -20.162  58.85       C
ATOM   2101  HG2  LYS  155   -38.532  -2.486 -20.751   0.00       E
ATOM   2102  HG3  LYS  155   -37.788  -0.924 -20.740   0.00       E
ATOM   2103  CD   LYS  155   -37.476  -2.043 -18.955  58.25       C
ATOM   2104  HD2  LYS  155   -36.584  -2.504 -19.292   0.00       E
ATOM   2105  HD3  LYS  155   -37.235  -1.185 -18.383   0.00       E
ATOM   2106  CE   LYS  155   -38.224  -3.033 -18.055  56.89       C
ATOM   2107  HE2  LYS  155   -39.092  -2.569 -17.664   0.00       E
ATOM   2108  HE3  LYS  155   -38.503  -3.883 -18.621   0.00       E
ATOM   2109  NZ   LYS  155   -37.403  -3.498 -16.911  55.27       N1+
ATOM   2110  HZ1  LYS  155   -36.575  -3.959 -17.257   0.00       E
ATOM   2111  HZ2  LYS  155   -37.136  -2.707 -16.345   0.00       E
ATOM   2112  HZ3  LYS  155   -37.940  -4.145 -16.353   0.00       E
ATOM   2113  C    LYS  155   -40.391   0.344 -21.648  56.97       C
ATOM   2114  O    LYS  155   -39.587   0.256 -22.576  56.93       O
ATOM   2115  N    PRO  156   -41.036   1.490 -21.361  54.85       N
ATOM   2116  CD   PRO  156   -42.048   1.659 -20.299  54.22       C
ATOM   2117  HD2  PRO  156   -42.935   1.149 -20.572   0.00       E
ATOM   2118  HD3  PRO  156   -41.677   1.260 -19.391   0.00       E
ATOM   2119  CA   PRO  156   -40.849   2.742 -22.097  52.43       C
ATOM   2120  HA   PRO  156   -40.824   2.540 -23.136   0.00       E
ATOM   2121  CB   PRO  156   -42.060   3.569 -21.684  52.61       C
ATOM   2122  HB2  PRO  156   -41.843   4.598 -21.807   0.00       E
ATOM   2123  HB3  PRO  156   -42.889   3.308 -22.289   0.00       E
ATOM   2124  CG   PRO  156   -42.229   3.170 -20.249  53.43       C
ATOM   2125  HG2  PRO  156   -41.493   3.652 -19.660   0.00       E
ATOM   2126  HG3  PRO  156   -43.192   3.456 -19.914   0.00       E
ATOM   2127  C    PRO  156   -39.538   3.386 -21.672  50.44       C
ATOM   2128  O    PRO  156   -39.022   3.106 -20.589  49.49       O
```

FIGURE 6-29-

```
ATOM   2129   N    ALA   157   -39.008    4.250  -22.527   48.15   N
ATOM   2130   HN   ALA   157   -39.497    4.439  -23.389    0.00   H
ATOM   2131   CA   ALA   157   -37.753    4.918  -22.245   45.54   C
ATOM   2132   HA   ALA   157   -37.001    4.195  -22.062    0.00   H
ATOM   2133   CB   ALA   157   -37.344    5.773  -23.426   44.84   C
ATOM   2134   HB1  ALA   157   -37.228    5.160  -24.282    0.00   H
ATOM   2135   HB2  ALA   157   -38.091    6.500  -23.611    0.00   H
ATOM   2136   HB3  ALA   157   -36.427    6.257  -23.211    0.00   H
ATOM   2137   C    ALA   157   -37.875    5.780  -21.014   43.96   C
ATOM   2138   O    ALA   157   -38.961    6.248  -20.681   44.16   O
ATOM   2139   N    ARG   158   -36.756    5.967  -20.327   42.63   N
ATOM   2140   HN   ARG   158   -35.915    5.498  -20.628    0.00   H
ATOM   2141   CA   ARG   158   -36.729    6.830  -19.159   40.97   C
ATOM   2142   HA   ARG   158   -37.645    6.743  -18.635    0.00   H
ATOM   2143   CB   ARG   158   -35.584    6.445  -18.213   41.89   C
ATOM   2144   HB2  ARG   158   -34.685    6.352  -18.766    0.00   H
ATOM   2145   HB3  ARG   158   -35.468    7.196  -17.475    0.00   H
ATOM   2146   CG   ARG   158   -35.806    5.120  -17.482   44.89   C
ATOM   2147   HG2  ARG   158   -36.844    4.958  -17.353    0.00   H
ATOM   2148   HG3  ARG   158   -35.394    4.329  -18.052    0.00   H
ATOM   2149   CD   ARG   158   -35.151    5.092  -16.099   48.00   C
ATOM   2150   HD2  ARG   158   -34.171    4.699  -16.180    0.00   H
ATOM   2151   HD3  ARG   158   -35.105    6.076  -15.710    0.00   H
ATOM   2152   NE   ARG   158   -35.908    4.257  -15.157   53.54   N1+
ATOM   2153   HE   ARG   158   -36.268    3.362  -15.453    0.00   H
ATOM   2154   CZ   ARG   158   -36.170    4.597  -13.891   56.32   C
ATOM   2155   NH1  ARG   158   -36.863    3.782  -13.100   55.72   N
ATOM   2156   HH11 ARG   158   -37.055    4.048  -12.146    0.00   H
ATOM   2157   HH12 ARG   158   -37.196    2.898  -13.454    0.00   H
ATOM   2158   NH2  ARG   158   -35.739    5.761  -13.414   58.30   N
ATOM   2159   HH21 ARG   158   -35.936    6.019  -12.459    0.00   H
ATOM   2160   HH22 ARG   158   -35.215    6.386  -14.007    0.00   H
ATOM   2161   C    ARG   158   -36.510    8.236  -19.717   39.30   C
ATOM   2162   O    ARG   158   -36.073    8.398  -20.857   40.08   O
ATOM   2163   N    LEU   159   -36.828    9.255  -18.934   36.65   N
ATOM   2164   HN   LEU   159   -37.196    9.085  -18.010    0.00   H
ATOM   2165   CA   LEU   159   -36.647   10.618  -19.404   34.09   C
ATOM   2166   HA   LEU   159   -36.543   10.617  -20.458    0.00   H
ATOM   2167   CB   LEU   159   -37.855   11.469  -19.020   34.00   C
ATOM   2168   HB2  LEU   159   -37.876   11.598  -17.969    0.00   H
ATOM   2169   HB3  LEU   159   -37.784   12.415  -19.491    0.00   H
ATOM   2170   CG   LEU   159   -39.206   10.865  -19.426   35.92   C
ATOM   2171   HG   LEU   159   -39.324    9.920  -18.962    0.00   H
ATOM   2172   CD1  LEU   159   -40.326   11.789  -18.985   35.85   C
ATOM   2173   HD11 LEU   159   -40.293   11.906  -17.933    0.00   H
ATOM   2174   HD12 LEU   159   -40.208   12.734  -19.449    0.00   H
ATOM   2175   HD13 LEU   159   -41.258   11.372  -19.265    0.00   H
ATOM   2176   CD2  LEU   159   -39.257   10.630  -20.935   33.47   C
ATOM   2177   HD21 LEU   159   -39.127   11.552  -21.440    0.00   H
ATOM   2178   HD22 LEU   159   -38.484    9.962  -21.215    0.00   H
ATOM   2179   HD23 LEU   159   -40.195   10.214  -21.196    0.00   H
ATOM   2180   C    LEU   159   -35.390   11.217  -18.803   32.39   C
ATOM   2181   O    LEU   159   -35.083   10.994  -17.637   33.19   O
ATOM   2182   N    ILE   160   -34.636   11.957  -19.600   30.75   N
ATOM   2183   HN   ILE   160   -34.887   12.084  -20.569    0.00   H
ATOM   2184   CA   ILE   160   -33.441   12.587  -19.072   29.74   C
ATOM   2185   HA   ILE   160   -33.357   12.373  -18.038    0.00   H
ATOM   2186   CB   ILE   160   -32.173   12.083  -19.772   30.65   C
ATOM   2187   HB   ILE   160   -31.334   12.617  -19.410    0.00   H
ATOM   2188   CG2  ILE   160   -31.989   10.599  -19.488   31.09   C
ATOM   2189   HG21 ILE   160   -31.898   10.448  -18.444    0.00   H
ATOM   2190   HG22 ILE   160   -32.828   10.064  -19.851    0.00   H
ATOM   2191   HG23 ILE   160   -31.113   10.253  -19.972    0.00   H
ATOM   2192   CG1  ILE   160   -32.275   12.324  -21.274   31.77   C
ATOM   2193   HG12 ILE   160   -33.108   11.797  -21.660    0.00   H
ATOM   2194   HG13 ILE   160   -32.397   13.360  -21.458    0.00   H
ATOM   2195   CD1  ILE   160   -31.056   11.868  -22.035   33.91   C
ATOM   2196   HD11 ILE   160   -30.205   12.392  -21.685    0.00   H
ATOM   2197   HD12 ILE   160   -30.916   10.829  -21.887    0.00   H
ATOM   2198   HD13 ILE   160   -31.191   12.063  -23.067    0.00   H
ATOM   2199   C    ILE   160   -33.576   14.089  -19.244   28.55   C
ATOM   2200   O    ILE   160   -33.916   14.575  -20.323   27.68   O
ATOM   2201   N    VAL   161   -33.341   14.814  -18.157   27.13   N
ATOM   2202   HN   VAL   161   -33.090   14.323  -17.312    0.00   H
ATOM   2203   CA   VAL   161   -33.435   16.267  -18.154   26.11   C
ATOM   2204   HA   VAL   161   -33.731   16.604  -19.114    0.00   H
```

FIGURE 6- 30 -

```
ATOM   2205  CB   VAL  161   -34.478  16.727 -17.110   26.01      C
ATOM   2206  HB   VAL  161   -34.212  16.351 -16.156    0.00      H
ATOM   2207  CG1  VAL  161   -34.494  18.244 -16.999   24.02      C
ATOM   2208 HG11  VAL  161   -33.537  18.586 -16.701    0.00      H
ATOM   2209 HG12  VAL  161   -34.742  18.664 -17.939    0.00      H
ATOM   2210 HG13  VAL  161   -35.214  18.538 -16.280    0.00      H
ATOM   2211  CG2  VAL  161   -35.353  16.197 -17.502   22.34      C
ATOM   2212 HG21  VAL  161   -36.117  16.573 -18.456    0.00      H
ATOM   2213 HG22  VAL  161   -35.827  15.139 -17.534    0.00      H
ATOM   2214 HG23  VAL  161   -36.569  16.511 -16.788    0.00      H
ATOM   2215  C    VAL  161   -32.059  16.816 -17.803   25.53      C
ATOM   2216  O    VAL  161   -31.492  16.470 -16.766   26.31      O
ATOM   2217  N    PHE  162   -31.508  17.657 -18.665   24.12      N
ATOM   2218  HN   PHE  162   -31.997  17.928 -19.505    0.00      H
ATOM   2219  CA   PHE  162   -30.183  18.191 -18.391   24.80      C
ATOM   2220  HA   PHE  162   -30.037  18.252 -17.344    0.00      H
ATOM   2221  CB   PHE  162   -29.126  17.263 -19.005   25.35      C
ATOM   2222  HB2  PHE  162   -28.161  17.581 -18.706    0.00      H
ATOM   2223  HB3  PHE  162   -29.290  16.271 -18.672    0.00      H
ATOM   2224  CG   PHE  162   -29.145  17.240 -20.504   25.50      C
ATOM   2225  CD1  PHE  162   -30.098  16.492 -21.193   28.29      C
ATOM   2226  HD1  PHE  162   -30.800  15.882 -20.649    0.00      H
ATOM   2227  CD2  PHE  162   -28.247  18.013 -21.233   23.95      C
ATOM   2228  HD2  PHE  162   -27.498  18.594 -20.722    0.00      H
ATOM   2229  CE1  PHE  162   -30.159  16.520 -22.593   26.60      C
ATOM   2230  HE1  PHE  162   -30.902  15.938 -23.111    0.00      H
ATOM   2231  CE2  PHE  162   -28.299  18.049 -22.621   24.80      C
ATOM   2232  HE2  PHE  162   -27.598  18.655 -23.171    0.00      H
ATOM   2233  CZ   PHE  162   -29.257  17.302 -23.302   25.92      C
ATOM   2234  HZ   PHE  162   -29.299  17.331 -24.378    0.00      H
ATOM   2235  C    PHE  162   -29.971  19.631 -18.892   23.35      C
ATOM   2236  O    PHE  162   -30.546  20.039 -19.906   24.26      O
ATOM   2237  N    PRO  163   -29.142  20.418 -18.176   20.01      N
ATOM   2238  CD   PRO  163   -28.505  20.110 -16.883   19.21      C
ATOM   2239  HD2  PRO  163   -29.252  19.910 -16.160    0.00      H
ATOM   2240  HD3  PRO  163   -27.881  19.261 -16.990    0.00      H
ATOM   2241  CA   PRO  163   -28.866  21.797 -18.559   17.37      C
ATOM   2242  HA   PRO  163   -29.726  22.216 -19.012    0.00      H
ATOM   2243  CB   PRO  163   -28.530  22.441 -17.233   16.01      C
ATOM   2244  HB2  PRO  163   -27.985  23.333 -17.402    0.00      H
ATOM   2245  HB3  PRO  163   -29.425  22.667 -16.714    0.00      H
ATOM   2246  CG   PRO  163   -27.727  21.374 -16.585   16.57      C
ATOM   2247  HG2  PRO  163   -26.756  21.357 -17.007    0.00      H
ATOM   2248  HG3  PRO  163   -27.657  21.567 -15.546    0.00      H
ATOM   2249  C    PRO  163   -27.707  21.849 -19.548   17.34      C
ATOM   2250  O    PRO  163   -27.001  20.851 -19.748   16.05      O
ATOM   2251  N    ASP  164   -27.523  23.017 -20.157   17.74      N
ATOM   2252  HN   ASP  164   -28.155  23.766 -19.915    0.00      H
ATOM   2253  CA   ASP  164   -26.469  23.242 -21.134   16.04      C
ATOM   2254  HA   ASP  164   -26.597  22.579 -21.950    0.00      H
ATOM   2255  CB   ASP  164   -26.534  24.681 -21.635   14.81      C
ATOM   2256  HB2  ASP  164   -27.535  24.924 -21.882    0.00      H
ATOM   2257  HB3  ASP  164   -26.189  25.335 -20.877    0.00      H
ATOM   2258  CG   ASP  164   -25.684  24.910 -22.866   18.32      C
ATOM   2259  OD1  ASP  164   -26.120  24.559 -23.986   19.54      O
ATOM   2260  OD2  ASP  164   -24.565  25.440 -22.719   21.33      O1-
ATOM   2261  C    ASP  164   -25.076  22.965 -20.552   17.90      C
ATOM   2262  O    ASP  164   -24.858  23.041 -19.333   14.62      O
ATOM   2263  N    LEU  165   -24.150  22.639 -21.452   19.75      N
ATOM   2264  HN   LEU  165   -24.458  22.607 -22.412    0.00      H
ATOM   2265  CA   LEU  165   -22.768  22.339 -21.122   19.73      C
ATOM   2266  HA   LEU  165   -22.719  21.408 -20.620    0.00      H
ATOM   2267  CB   LEU  165   -21.963  22.276 -22.419   20.30      C
ATOM   2268  HB2  LEU  165   -22.369  21.529 -23.050    0.00      H
ATOM   2269  HB3  LEU  165   -22.008  23.214 -22.908    0.00      H
ATOM   2270  CG   LEU  165   -20.476  21.949 -22.321   21.32      C
ATOM   2271  HG   LEU  165   -19.971  22.744 -21.837    0.00      H
ATOM   2272  CD1  LEU  165   -20.268  20.677 -21.528   20.22      C
ATOM   2273 HD11  LEU  165   -20.659  20.802 -20.552    0.00      H
ATOM   2274 HD12  LEU  165   -20.767  19.876 -22.009    0.00      H
ATOM   2275 HD13  LEU  165   -19.232  20.463 -21.469    0.00      H
ATOM   2276  CD2  LEU  165   -19.915  21.799 -23.712   22.12      C
ATOM   2277 HD21  LEU  165   -20.421  21.016 -24.214    0.00      H
ATOM   2278 HD22  LEU  165   -20.048  22.704 -24.246    0.00      H
ATOM   2279 HD23  LEU  165   -18.882  21.572 -23.654    0.00      H
ATOM   2280  C    LEU  165   -22.176  23.387 -20.176   20.10      C
```

FIGURE 6- 31 -

```
ATOM   2281   O     LEU  165   -21.595  23.051 -19.136  18.78    O
ATOM   2282   N     GLY  166   -22.323  24.655 -20.543  19.63    N
ATOM   2283   HN    GLY  166   -22.804  24.874 -21.403   0.00    H
ATOM   2284   CA    GLY  166   -21.796  25.723 -19.714  21.44    C
ATOM   2285   HA2   GLY  166   -20.738  25.723 -19.769   0.00    H
ATOM   2286   HA3   GLY  166   -22.168  26.653 -20.058   0.00    H
ATOM   2287   C     GLY  166   -22.185  25.579 -18.254  21.12    C
ATOM   2288   O     GLY  166   -21.338  25.642 -17.369  22.71    O
ATOM   2289   N     VAL  167   -23.473  25.398 -17.999  21.67    N
ATOM   2290   HN    VAL  167   -24.116  25.372 -18.776   0.00    H
ATOM   2291   CA    VAL  167   -23.968  25.238 -16.638  21.73    C
ATOM   2292   HA    VAL  167   -23.686  26.079 -16.059   0.00    H
ATOM   2293   CB    VAL  167   -25.517  25.117 -16.625  22.62    C
ATOM   2294   HB    VAL  167   -25.816  24.347 -17.287   0.00    H
ATOM   2295   CG1   VAL  167   -26.011  24.732 -15.227  21.35    C
ATOM   2296   HG11  VAL  167   -25.590  23.801 -14.948   0.00    H
ATOM   2297   HG12  VAL  167   -25.717  25.475 -14.532   0.00    H
ATOM   2298   HG13  VAL  167   -27.067  24.654 -15.235   0.00    H
ATOM   2299   CG2   VAL  167   -26.145  26.432 -17.068  21.41    C
ATOM   2300   HG21  VAL  167   -25.850  27.205 -16.407   0.00    H
ATOM   2301   HG22  VAL  167   -25.822  26.665 -18.049   0.00    H
ATOM   2302   HG23  VAL  167   -27.200  26.341 -17.056   0.00    H
ATOM   2303   C     VAL  167   -23.378  23.982 -16.000  22.00    C
ATOM   2304   O     VAL  167   -22.981  23.993 -14.831  22.57    O
ATOM   2305   N     ARG  168   -23.333  22.899 -16.774  21.24    N
ATOM   2306   HN    ARG  168   -23.673  22.973 -17.721   0.00    H
ATOM   2307   CA    ARG  168   -22.813  21.637 -16.287  20.12    C
ATOM   2308   HA    ARG  168   -23.405  21.301 -15.476   0.00    H
ATOM   2309   CB    ARG  168   -22.839  20.573 -17.393  20.89    C
ATOM   2310   HB2   ARG  168   -22.341  20.943 -18.251   0.00    H
ATOM   2311   HB3   ARG  168   -22.351  19.697 -17.052   0.00    H
ATOM   2312   CG    ARG  168   -24.238  20.140 -17.855  20.25    C
ATOM   2313   HG2   ARG  168   -24.887  20.092 -17.019   0.00    H
ATOM   2314   HG3   ARG  168   -24.613  20.843 -18.553   0.00    H
ATOM   2315   CD    ARG  168   -24.227  18.759 -18.529  16.92    C
ATOM   2316   HD2   ARG  168   -23.829  18.042 -17.859   0.00    H
ATOM   2317   HD3   ARG  168   -25.216  18.486 -18.791   0.00    H
ATOM   2318   NE    ARG  168   -23.427  18.693 -19.751  20.69    N1+
ATOM   2319   HE    ARG  168   -22.500  18.295 -19.726   0.00    H
ATOM   2320   CZ    ARG  168   -23.819  19.127 -20.953  23.69    C
ATOM   2321   NH1   ARG  168   -25.019  19.673 -21.132  22.83    N
ATOM   2322   HH11  ARG  168   -25.296  19.994 -22.048   0.00    H
ATOM   2323   HH12  ARG  168   -25.652  19.766 -20.352   0.00    H
ATOM   2324   NH2   ARG  168   -23.009  19.005 -21.994  21.32    N
ATOM   2325   HH21  ARG  168   -23.302  19.332 -22.902   0.00    H
ATOM   2326   HH22  ARG  168   -22.099  18.585 -21.878   0.00    H
ATOM   2327   C     ARG  168   -21.402  21.795 -15.753  21.57    C
ATOM   2328   O     ARG  168   -21.040  21.175 -14.750  21.28    O
ATOM   2329   N     VAL  169   -20.595  22.621 -16.409  21.71    N
ATOM   2330   HN    VAL  169   -20.920  23.112 -17.229   0.00    H
ATOM   2331   CA    VAL  169   -19.230  22.816 -15.936  22.68    C
ATOM   2332   HA    VAL  169   -18.791  21.875 -15.727   0.00    H
ATOM   2333   CB    VAL  169   -18.350  23.541 -16.994  22.41    C
ATOM   2334   HB    VAL  169   -18.762  24.494 -17.202   0.00    H
ATOM   2335   CG1   VAL  169   -16.939  23.732 -16.460  20.87    C
ATOM   2336   HG11  VAL  169   -16.972  24.316 -15.577   0.00    H
ATOM   2337   HG12  VAL  169   -16.513  22.787 -16.243   0.00    H
ATOM   2338   HG13  VAL  169   -16.350  24.226 -17.188   0.00    H
ATOM   2339   CG2   VAL  169   -18.298  22.725 -18.285  20.68    C
ATOM   2340   HG21  VAL  169   -17.883  21.772 -18.084   0.00    H
ATOM   2341   HG22  VAL  169   -19.278  22.610 -18.669   0.00    H
ATOM   2342   HG23  VAL  169   -17.697  23.228 -18.997   0.00    H
ATOM   2343   C     VAL  169   -19.246  23.630 -14.641  24.45    C
ATOM   2344   O     VAL  169   -18.508  23.331 -13.698  25.41    O
ATOM   2345   N     CYS  170   -20.093  24.653 -14.576  24.64    N
ATOM   2346   HN    CYS  170   -20.695  24.867 -15.357   0.00    H
ATOM   2347   CA    CYS  170   -20.149  25.467 -13.368  24.28    C
ATOM   2348   HA    CYS  170   -19.189  25.865 -13.165   0.00    H
ATOM   2349   CB    CYS  170   -21.062  26.666 -13.580  23.67    C
ATOM   2350   HB2   CYS  170   -22.002  26.335 -13.939   0.00    H
ATOM   2351   HB3   CYS  170   -21.195  27.175 -12.661   0.00    H
ATOM   2352   SG    CYS  170   -20.388  27.839 -14.776  25.50    S
ATOM   2353   HG    CYS  170   -21.178  28.799 -14.909   0.00    H
ATOM   2354   C     CYS  170   -20.592  24.669 -12.158  24.37    C
ATOM   2355   O     CYS  170   -20.152  24.931 -11.045  25.21    O
ATOM   2356   N     GLU  171   -21.458  23.687 -12.370  24.94    N
```

FIGURE 6- 32 -

```
ATOM   2357  HN   GLU   171    -21.799   23.519  -13.305    0.00      H
ATOM   2358  CA   GLU   171    -21.917   22.853  -11.266   25.39      C
ATOM   2359  HA   GLU   171    -22.401   23.458  -10.544    0.00      H
ATOM   2360  CB   GLU   171    -22.896   21.794  -11.745   27.25      C
ATOM   2361  HB2  GLU   171    -22.419   21.166  -12.452    0.00      H
ATOM   2362  HB3  GLU   171    -23.220   21.214  -10.920    0.00      H
ATOM   2363  CG   GLU   171    -24.155   22.267  -12.418   28.03      C
ATOM   2364  HG2  GLU   171    -24.659   22.949  -11.784    0.00      H
ATOM   2365  HG3  GLU   171    -23.909   22.747  -13.329    0.00      H
ATOM   2366  CD   GLU   171    -25.066   21.088  -12.706   29.13      C
ATOM   2367  OE1  GLU   171    -25.700   20.584  -11.755   29.71      O1-
ATOM   2368  OE2  GLU   171    -25.129   20.643  -13.873   28.59      O
ATOM   2369  C    GLU   171    -20.722   22.122  -10.673   25.78      C
ATOM   2370  O    GLU   171    -20.658   21.882   -9.468   25.23      O
ATOM   2371  N    LYS   172    -19.784   21.746  -11.539   26.83      N
ATOM   2372  HN   LYS   172    -19.916   21.966  -12.515    0.00      H
ATOM   2373  CA   LYS   172    -18.587   21.032  -11.107   27.54      C
ATOM   2374  HA   LYS   172    -18.867   20.197  -10.519    0.00      H
ATOM   2375  CB   LYS   172    -17.773   20.534  -12.308   28.00      C
ATOM   2376  HB2  LYS   172    -17.613   21.335  -12.982    0.00      H
ATOM   2377  HB3  LYS   172    -16.840   20.163  -11.972    0.00      H
ATOM   2378  CG   LYS   172    -18.416   19.414  -13.115   30.51      C
ATOM   2379  HG2  LYS   172    -18.583   18.578  -12.487    0.00      H
ATOM   2380  HG3  LYS   172    -19.340   19.749  -13.510    0.00      H
ATOM   2381  CD   LYS   172    -17.511   18.988  -14.273   32.25      C
ATOM   2382  HD2  LYS   172    -17.334   19.818  -14.906    0.00      H
ATOM   2383  HD3  LYS   172    -16.590   18.634  -13.889    0.00      H
ATOM   2384  CE   LYS   172    -18.124   17.873  -15.122   32.06      C
ATOM   2385  HE2  LYS   172    -17.376   17.446  -15.738    0.00      H
ATOM   2386  HE3  LYS   172    -18.527   17.127  -14.487    0.00      H
ATOM   2387  NZ   LYS   172    -19.217   18.373  -16.001   35.83      N1+
ATOM   2388  HZ1  LYS   172    -19.949   18.773  -15.433    0.00      H
ATOM   2389  HZ2  LYS   172    -18.852   19.077  -16.624    0.00      H
ATOM   2390  HZ3  LYS   172    -19.591   17.607  -16.541    0.00      H
ATOM   2391  C    LYS   172    -17.713   21.931  -10.247   27.87      C
ATOM   2392  O    LYS   172    -17.202   21.503   -9.209   29.34      O
ATOM   2393  N    MET   173    -17.544   23.179  -10.672   26.93      N
ATOM   2394  HN   MET   173    -17.995   23.481  -11.523    0.00      H
ATOM   2395  CA   MET   173    -16.715   24.108   -9.919   26.03      C
ATOM   2396  HA   MET   173    -15.742   23.704   -9.809    0.00      H
ATOM   2397  CB   MET   173    -16.610   25.453  -10.639   25.64      C
ATOM   2398  HB2  MET   173    -17.582   25.832  -10.823    0.00      H
ATOM   2399  HB3  MET   173    -16.073   26.136  -10.034    0.00      H
ATOM   2400  CG   MET   173    -15.895   25.372  -11.975   26.83      C
ATOM   2401  HG2  MET   173    -14.940   24.936  -11.838    0.00      H
ATOM   2402  HG3  MET   173    -16.462   24.777  -12.643    0.00      H
ATOM   2403  SD   MET   173    -15.637   26.965  -12.777   31.13      S
ATOM   2404  CE   MET   173    -17.207   27.219  -13.558   28.21      C
ATOM   2405  HE1  MET   173    -17.394   26.430  -14.240    0.00      H
ATOM   2406  HE2  MET   173    -17.968   27.237  -12.822    0.00      H
ATOM   2407  HE3  MET   173    -17.197   28.141  -14.079    0.00      H
ATOM   2408  C    MET   173    -17.261   24.326   -8.528   25.37      C
ATOM   2409  O    MET   173    -16.509   24.347   -7.549   25.31      O
ATOM   2410  N    ALA   174    -18.576   24.459   -8.433   24.41      N
ATOM   2411  HN   ALA   174    -19.144   24.379   -9.263    0.00      H
ATOM   2412  CA   ALA   174    -19.201   24.718   -7.146   23.26      C
ATOM   2413  HA   ALA   174    -18.499   25.175   -6.498    0.00      H
ATOM   2414  CB   ALA   174    -20.387   25.643   -7.348   21.85      C
ATOM   2415  HB1  ALA   174    -20.055   26.554   -7.773    0.00      H
ATOM   2416  HB2  ALA   174    -21.086   25.184   -7.998    0.00      H
ATOM   2417  HB3  ALA   174    -20.847   25.836   -6.414    0.00      H
ATOM   2418  C    ALA   174    -19.625   23.509   -6.308   23.27      C
ATOM   2419  O    ALA   174    -19.708   23.618   -5.087   23.92      O
ATOM   2420  N    LEU   175    -19.883   22.359   -6.926   21.07      N
ATOM   2421  HN   LEU   175    -19.770   22.262   -7.924    0.00      H
ATOM   2422  CA   LEU   175    -20.339   21.224   -6.129   21.17      C
ATOM   2423  HA   LEU   175    -20.137   21.407   -5.106    0.00      H
ATOM   2424  CB   LEU   175    -21.846   21.039   -6.329   16.83      C
ATOM   2425  HB2  LEU   175    -22.070   21.060   -7.364    0.00      H
ATOM   2426  HB3  LEU   175    -22.144   20.108   -5.922    0.00      H
ATOM   2427  CG   LEU   175    -22.786   22.064   -5.701   16.50      C
ATOM   2428  HG   LEU   175    -22.315   23.012   -5.687    0.00      H
ATOM   2429  CD1  LEU   175    -24.069   22.153   -6.511   14.62      C
ATOM   2430  HD11 LEU   175    -23.841   22.449   -7.502    0.00      H
ATOM   2431  HD12 LEU   175    -24.544   21.206   -6.526    0.00      H
ATOM   2432  HD13 LEU   175    -24.716   22.866   -6.070    0.00      H
```

FIGURE 6- 33 -

```
ATOM   2433  CD2  LEU  175   -23.064  21.674  -4.256  15.23  C
ATOM   2434  HD21 LEU  175   -23.515  20.716  -4.229   0.00  H
ATOM   2435  HD22 LEU  175   -22.154  21.650  -3.715   0.00  H
ATOM   2436  HD23 LEU  175   -23.716  22.384  -3.818   0.00  H
ATOM   2437  C    LEU  175   -19.645  19.873  -6.316  22.65  C
ATOM   2438  O    LEU  175   -20.034  18.896  -5.666  20.12  O
ATOM   2439  N    TYR  176   -18.636  19.805  -7.185  22.92  N
ATOM   2440  HN   TYR  176   -18.351  20.629  -7.692   0.00  H
ATOM   2441  CA   TYR  176   -17.947  18.544  -7.402  23.87  C
ATOM   2442  HA   TYR  176   -18.640  17.815  -7.733   0.00  H
ATOM   2443  CB   TYR  176   -16.848  18.672  -8.453  24.76  C
ATOM   2444  HB2  TYR  176   -17.273  18.984  -9.372   0.00  H
ATOM   2445  HB3  TYR  176   -16.135  19.387  -8.133   0.00  H
ATOM   2446  CG   TYR  176   -16.137  17.354  -8.677  27.26  C
ATOM   2447  CD1  TYR  176   -16.807  16.260  -9.239  27.46  C
ATOM   2448  HD1  TYR  176   -17.819  16.371  -9.590   0.00  H
ATOM   2449  CE1  TYR  176   -16.189  15.017  -9.356  27.58  C
ATOM   2450  HE1  TYR  176   -16.723  14.189  -9.790   0.00  H
ATOM   2451  CD2  TYR  176   -14.828  17.168  -8.247  26.97  C
ATOM   2452  HD2  TYR  176   -14.280  17.990  -7.818   0.00  H
ATOM   2453  CE2  TYR  176   -14.206  15.929  -8.361  27.41  C
ATOM   2454  HE2  TYR  176   -13.192  15.802  -8.021   0.00  H
ATOM   2455  CZ   TYR  176   -14.889  14.863  -8.910  27.80  C
ATOM   2456  OH   TYR  176   -14.271  13.640  -8.985  30.75  O
ATOM   2457  HH   TYR  176   -14.879  12.995  -9.372   0.00  H
ATOM   2458  C    TYR  176   -17.327  18.028  -6.116  24.46  C
ATOM   2459  O    TYR  176   -17.532  16.875  -5.735  24.67  O
ATOM   2460  N    ASP  177   -16.555  18.875  -5.449  25.12  N
ATOM   2461  HN   ASP  177   -16.406  19.804  -5.813   0.00  H
ATOM   2462  CA   ASP  177   -15.926  18.473  -4.202  25.18  C
ATOM   2463  HA   ASP  177   -15.257  17.673  -4.386   0.00  H
ATOM   2464  CB   ASP  177   -15.153  19.639  -3.601  27.06  C
ATOM   2465  HB2  ASP  177   -14.667  20.176  -4.374   0.00  H
ATOM   2466  HB3  ASP  177   -15.823  20.282  -3.091   0.00  H
ATOM   2467  CG   ASP  177   -14.101  19.190  -2.616  28.94  C
ATOM   2468  OD1  ASP  177   -14.025  17.971  -2.353  30.00  O
ATOM   2469  OD2  ASP  177   -13.346  20.055  -2.108  30.18  O1-
ATOM   2470  C    ASP  177   -17.025  18.031  -3.247  23.50  C
ATOM   2471  O    ASP  177   -16.955  16.962  -2.657  23.15  O
ATOM   2472  N    VAL  178   -18.059  18.848  -3.120  24.26  N
ATOM   2473  HN   VAL  178   -18.080  19.706  -3.650   0.00  H
ATOM   2474  CA   VAL  178   -19.157  18.518  -2.227  25.20  C
ATOM   2475  HA   VAL  178   -18.808  18.506  -1.227   0.00  H
ATOM   2476  CB   VAL  178   -20.301  19.541  -2.326  24.09  C
ATOM   2477  HB   VAL  178   -20.786  19.438  -3.262   0.00  H
ATOM   2478  CG1  VAL  178   -21.314  19.268  -1.236  22.00  C
ATOM   2479  HG11 VAL  178   -21.703  18.290  -1.352   0.00  H
ATOM   2480  HG12 VAL  178   -20.846  19.351  -0.290   0.00  H
ATOM   2481  HG13 VAL  178   -22.103  19.972  -1.303   0.00  H
ATOM   2482  CG2  VAL  178   -19.757  20.958  -2.202  24.11  C
ATOM   2483  HG21 VAL  178   -19.274  21.070  -1.266   0.00  H
ATOM   2484  HG22 VAL  178   -19.063  21.139  -2.981   0.00  H
ATOM   2485  HG23 VAL  178   -20.556  21.650  -2.272   0.00  H
ATOM   2486  C    VAL  178   -19.738  17.130  -2.484  27.82  C
ATOM   2487  O    VAL  178   -19.755  16.296  -1.571  29.73  O
ATOM   2488  N    VAL  179   -20.213  16.872  -3.708  27.78  N
ATOM   2489  HN   VAL  179   -20.157  17.590  -4.414   0.00  H
ATOM   2490  CA   VAL  179   -20.808  15.571  -4.031  26.64  C
ATOM   2491  HA   VAL  179   -21.551  15.335  -3.315   0.00  H
ATOM   2492  CB   VAL  179   -21.462  15.574  -5.425  26.91  C
ATOM   2493  HB   VAL  179   -22.010  14.678  -5.560   0.00  H
ATOM   2494  CG1  VAL  179   -22.464  16.705  -5.520  25.38  C
ATOM   2495  HG11 VAL  179   -23.213  16.576  -4.783   0.00  H
ATOM   2496  HG12 VAL  179   -21.970  17.628  -5.363   0.00  H
ATOM   2497  HG13 VAL  179   -22.910  16.702  -6.480   0.00  H
ATOM   2498  CG2  VAL  179   -20.394  15.674  -6.517  26.75  C
ATOM   2499  HG21 VAL  179   -19.845  16.571  -6.392   0.00  H
ATOM   2500  HG22 VAL  179   -19.733  14.846  -6.446   0.00  H
ATOM   2501  HG23 VAL  179   -20.860  15.675  -7.468   0.00  H
ATOM   2502  C    VAL  179   -19.852  14.376  -3.956  27.49  C
ATOM   2503  O    VAL  179   -20.290  13.226  -3.982  29.57  O
ATOM   2504  N    SER  180   -18.556  14.642  -3.850  26.99  N
ATOM   2505  HN   SER  180   -18.263  15.607  -3.827   0.00  H
ATOM   2506  CA   SER  180   -17.565  13.578  -3.767  27.55  C
ATOM   2507  HA   SER  180   -17.967  12.689  -4.178   0.00  H
ATOM   2508  CB   SER  180   -16.303  13.954  -4.541  25.84  C
```

FIGURE 6- 34 -

```
ATOM   2509  HB2  SER  180   -15.908  14.858  -4.155   0.00   H
ATOM   2510  HB3  SER  180   -15.584  13.183  -4.440   0.00   H
ATOM   2511  OG   SER  180   -16.582  14.133  -5.911  25.76   O
ATOM   2512  HG   SER  180   -15.769  14.370  -6.377   0.00   H
ATOM   2513  C    SER  180   -17.162  13.303  -2.335  29.14   C
ATOM   2514  O    SER  180   -16.592  12.250  -2.037  31.93   O
ATOM   2515  N    THR  181   -17.460  14.241  -1.443  29.19   N
ATOM   2516  HN   THR  181   -17.967  15.061  -1.742   0.00   H
ATOM   2517  CA   THR  181   -17.064  14.097  -0.046  28.69   C
ATOM   2518  HA   THR  181   -16.544  13.183   0.081   0.00   H
ATOM   2519  CB   THR  181   -16.144  15.267   0.366  29.09   C
ATOM   2520  HB   THR  181   -16.657  16.184   0.231   0.00   H
ATOM   2521  OG1  THR  181   -14.963  15.251  -0.439  28.37   O
ATOM   2522  HG1  THR  181   -14.387  15.984  -0.181   0.00   H
ATOM   2523  CG2  THR  181   -15.738  15.144   1.820  31.71   C
ATOM   2524  HG21 THR  181   -16.603  15.158   2.430   0.00   H
ATOM   2525  HG22 THR  181   -15.218  14.233   1.965   0.00   H
ATOM   2526  HG23 THR  181   -15.109  15.955   2.081   0.00   H
ATOM   2527  C    THR  181   -18.174  14.006   0.996  27.95   C
ATOM   2528  O    THR  181   -18.118  13.183   1.898  29.76   O
ATOM   2529  N    LEU  182   -19.173  14.865   0.880  26.54   N
ATOM   2530  HN   LEU  182   -19.175  15.501   0.097   0.00   H
ATOM   2531  CA   LEU  182   -20.251  14.905   1.849  23.31   C
ATOM   2532  HA   LEU  182   -19.852  15.077   2.815   0.00   H
ATOM   2533  CB   LEU  182   -21.202  16.041   1.465  18.68   C
ATOM   2534  HB2  LEU  182   -20.648  16.932   1.323   0.00   H
ATOM   2535  HB3  LEU  182   -21.706  15.792   0.567   0.00   H
ATOM   2536  CG   LEU  182   -22.297  16.406   2.447  15.69   C
ATOM   2537  HG   LEU  182   -21.968  16.205   3.433   0.00   H
ATOM   2538  CD1  LEU  182   -22.627  17.855   2.325  19.26   C
ATOM   2539  HD11 LEU  182   -21.764  18.432   2.534   0.00   H
ATOM   2540  HD12 LEU  182   -22.959  18.060   1.340   0.00   H
ATOM   2541  HD13 LEU  182   -23.392  18.102   3.014   0.00   H
ATOM   2542  CD2  LEU  182   -23.510  15.570   2.169  16.91   C
ATOM   2543  HD21 LEU  182   -23.845  15.751   1.181   0.00   H
ATOM   2544  HD22 LEU  182   -23.265  14.545   2.276   0.00   H
ATOM   2545  HD23 LEU  182   -24.277  15.823   2.854   0.00   H
ATOM   2546  C    LEU  182   -21.003  13.583   2.081  24.44   C
ATOM   2547  O    LEU  182   -21.200  13.178   3.230  24.14   O
ATOM   2548  N    PRO  183   -21.421  12.885   1.007  25.29   N
ATOM   2549  CD   PRO  183   -21.158  13.173  -0.415  25.94   C
ATOM   2550  HD2  PRO  183   -21.364  14.193  -0.612   0.00   H
ATOM   2551  HD3  PRO  183   -20.142  12.969  -0.635   0.00   H
ATOM   2552  CA   PRO  183   -22.150  11.612   1.160  26.00   C
ATOM   2553  HA   PRO  183   -23.140  11.808   1.482   0.00   H
ATOM   2554  CB   PRO  183   -22.118  11.019  -0.247  25.49   C
ATOM   2555  HB2  PRO  183   -21.243  10.433  -0.363   0.00   H
ATOM   2556  HB3  PRO  183   -22.972  10.410  -0.393   0.00   H
ATOM   2557  CG   PRO  183   -22.119  12.227  -1.123  27.26   C
ATOM   2558  HG2  PRO  183   -21.785  11.961  -2.092   0.00   H
ATOM   2559  HG3  PRO  183   -23.101  12.618  -1.184   0.00   H
ATOM   2560  C    PRO  183   -21.513  10.665   2.183  27.13   C
ATOM   2561  O    PRO  183   -22.178  10.160   3.087  26.75   O
ATOM   2562  N    GLN  184   -20.217  10.425   2.021  27.65   N
ATOM   2563  HN   GLN  184   -19.753  10.873   1.245   0.00   H
ATOM   2564  CA   GLN  184   -19.469   9.555   2.911  27.70   C
ATOM   2565  HA   GLN  184   -19.902   8.589   2.907   0.00   H
ATOM   2566  CB   GLN  184   -18.031   9.474   2.429  30.94   C
ATOM   2567  HB2  GLN  184   -18.000   8.978   1.494   0.00   H
ATOM   2568  HB3  GLN  184   -17.638  10.452   2.324   0.00   H
ATOM   2569  CG   GLN  184   -17.102   8.723   3.358  36.84   C
ATOM   2570  HG2  GLN  184   -16.157   9.201   3.374   0.00   H
ATOM   2571  HG3  GLN  184   -17.510   8.715   4.335   0.00   H
ATOM   2572  CD   GLN  184   -16.890   7.282   2.929  40.18   C
ATOM   2573  OE1  GLN  184   -16.645   7.002   1.745  42.24   O
ATOM   2574  NE2  GLN  184   -16.966   6.357   3.891  40.50   N
ATOM   2575  HE21 GLN  184   -17.168   6.632   4.841   0.00   H
ATOM   2576  HE22 GLN  184   -16.821   5.384   3.668   0.00   H
ATOM   2577  C    GLN  184   -19.490  10.101   4.330  26.82   C
ATOM   2578  O    GLN  184   -19.778   9.384   5.293  25.95   O
ATOM   2579  N    ALA  185   -19.173  11.383   4.439  25.08   N
ATOM   2580  HN   ALA  185   -18.958  11.877   3.586   0.00   H
ATOM   2581  CA   ALA  185   -19.126  12.081   5.716  25.79   C
ATOM   2582  HA   ALA  185   -18.415  11.615   6.347   0.00   H
ATOM   2583  CB   ALA  185   -18.725  13.536   5.478  25.38   C
ATOM   2584  HB1  ALA  185   -17.771  13.569   5.019   0.00   H
```

FIGURE 6-35-

```
ATOM   2585  HB2  ALA  185   -19.437  13.999   4.845   0.00   H
ATOM   2586  HB3  ALA  185   -18.689  14.048   6.404   0.00   H
ATOM   2587  C    ALA  185   -20.429  12.028   6.521  25.71   C
ATOM   2588  O    ALA  185   -20.407  11.973   7.752  25.06   O
ATOM   2589  N    VAL  186   -21.558  12.041   5.822  25.70   N
ATOM   2590  HN   VAL  186   -21.499  12.057   4.815   0.00   H
ATOM   2591  CA   VAL  186   -22.859  12.033   6.474  25.81   C
ATOM   2592  HA   VAL  186   -22.780  12.491   7.426   0.00   H
ATOM   2593  CB   VAL  186   -23.902  12.813   5.626  24.38   C
ATOM   2594  HB   VAL  186   -24.013  12.344   4.683   0.00   H
ATOM   2595  CG1  VAL  186   -25.257  12.802   6.300  19.98   C
ATOM   2596  HG11 VAL  186   -25.587  11.802   6.413   0.00   H
ATOM   2597  HG12 VAL  186   -25.181  13.258   7.253   0.00   H
ATOM   2598  HG13 VAL  186   -25.951  13.338   5.706   0.00   H
ATOM   2599  CG2  VAL  186   -23.432  14.246   5.423  23.87   C
ATOM   2600  HG21 VAL  186   -23.322  14.718   6.365   0.00   H
ATOM   2601  HG22 VAL  186   -22.501  14.244   4.918   0.00   H
ATOM   2602  HG23 VAL  186   -24.146  14.773   4.845   0.00   H
ATOM   2603  C    VAL  186   -23.407  10.643   6.757  27.72   C
ATOM   2604  O    VAL  186   -23.919  10.387   7.852  28.26   O
ATOM   2605  N    MET  187   -23.282   9.743   5.788  28.82   N
ATOM   2606  HN   MET  187   -22.808  10.007   4.937   0.00   H
ATOM   2607  CA   MET  187   -23.816   8.391   5.938  30.88   C
ATOM   2608  HA   MET  187   -24.447   8.353   6.788   0.00   H
ATOM   2609  CB   MET  187   -24.613   8.043   4.680  31.56   C
ATOM   2610  HB2  MET  187   -23.967   8.045   3.841   0.00   H
ATOM   2611  HB3  MET  187   -25.045   7.083   4.790   0.00   H
ATOM   2612  CG   MET  187   -25.747   9.028   4.390  32.91   C
ATOM   2613  HG2  MET  187   -26.612   8.740   4.929   0.00   H
ATOM   2614  HG3  MET  187   -25.454  10.001   4.687   0.00   H
ATOM   2615  SD   MET  187   -26.194   9.102   2.640  34.63   S
ATOM   2616  CE   MET  187   -26.578   7.404   2.322  36.55   C
ATOM   2617  HE1  MET  187   -25.725   6.807   2.517   0.00   H
ATOM   2618  HE2  MET  187   -27.374   7.098   2.950   0.00   H
ATOM   2619  HE3  MET  187   -26.864   7.291   1.309   0.00   H
ATOM   2620  C    MET  187   -22.793   7.284   6.241  31.86   C
ATOM   2621  O    MET  187   -23.166   6.139   6.512  32.58   O
ATOM   2622  N    GLY  188   -21.509   7.621   6.195  32.19   N
ATOM   2623  HN   GLY  188   -21.248   8.569   5.968   0.00   H
ATOM   2624  CA   GLY  188   -20.484   6.632   6.470  31.82   C
ATOM   2625  HA2  GLY  188   -19.548   6.989   6.127   0.00   H
ATOM   2626  HA3  GLY  188   -20.434   6.456   7.513   0.00   H
ATOM   2627  C    GLY  188   -20.704   5.283   5.811  32.13   C
ATOM   2628  O    GLY  188   -20.963   5.202   4.612  32.70   O
ATOM   2629  N    SER  189   -20.611   4.221   6.604  32.74   N
ATOM   2630  HN   SER  189   -20.426   4.384   7.582   0.00   H
ATOM   2631  CA   SER  189   -20.767   2.851   6.105  33.04   C
ATOM   2632  HA   SER  189   -19.934   2.598   5.503   0.00   H
ATOM   2633  CB   SER  189   -20.856   1.868   7.274  32.83   C
ATOM   2634  HB2  SER  189   -20.724   0.880   6.916   0.00   H
ATOM   2635  HB3  SER  189   -20.100   2.091   7.981   0.00   H
ATOM   2636  OG   SER  189   -22.121   1.960   7.910  34.06   O
ATOM   2637  HG   SER  189   -22.159   1.333   8.645   0.00   H
ATOM   2638  C    SER  189   -21.966   2.608   5.191  32.88   C
ATOM   2639  O    SER  189   -21.898   1.773   4.289  33.09   O
ATOM   2640  N    SER  190   -23.063   3.318   5.433  31.77   N
ATOM   2641  HN   SER  190   -23.053   3.986   6.189   0.00   H
ATOM   2642  CA   SER  190   -24.267   3.145   4.628  32.05   C
ATOM   2643  HA   SER  190   -24.441   2.112   4.470   0.00   H
ATOM   2644  CB   SER  190   -25.469   3.754   5.352  32.65   C
ATOM   2645  HB2  SER  190   -25.278   4.775   5.556   0.00   H
ATOM   2646  HB3  SER  190   -26.329   3.671   4.740   0.00   H
ATOM   2647  OG   SER  190   -25.716   3.084   6.576  35.24   O
ATOM   2648  HG   SER  190   -26.478   3.485   7.015   0.00   H
ATOM   2649  C    SER  190   -24.199   3.705   3.206  31.95   C
ATOM   2650  O    SER  190   -25.089   3.442   2.399  33.19   O
ATOM   2651  N    TYR  191   -23.169   4.482   2.891  30.96   N
ATOM   2652  HN   TYR  191   -22.466   4.692   3.584   0.00   H
ATOM   2653  CA   TYR  191   -23.053   5.031   1.548  31.78   C
ATOM   2654  HA   TYR  191   -24.002   5.367   1.221   0.00   H
ATOM   2655  CB   TYR  191   -22.076   6.209   1.534  32.80   C
ATOM   2656  HB2  TYR  191   -22.404   6.948   2.218   0.00   H
ATOM   2657  HB3  TYR  191   -21.112   5.872   1.815   0.00   H
ATOM   2658  CG   TYR  191   -21.920   6.899   0.190  31.97   C
ATOM   2659  CD1  TYR  191   -23.026   7.344  -0.520  31.58   C
ATOM   2660  HD1  TYR  191   -24.017   7.186  -0.128   0.00   H
```

FIGURE 6-36-

```
ATOM   2661  CE1 TYR 191    -22.885   7.996  -1.738  31.19      C
ATOM   2662  HE1 TYR 191    -23.757   8.330  -2.274   0.00      H
ATOM   2663  CD2 TYR 191    -20.656   7.128  -0.355  32.75      C
ATOM   2664  HD2 TYR 191    -19.776   6.793   0.167   0.00      H
ATOM   2665  CE2 TYR 191    -20.503   7.786  -1.571  31.65      C
ATOM   2666  HE2 TYR 191    -19.518   7.958  -1.970   0.00      H
ATOM   2667  CZ  TYR 191    -21.624   8.214  -2.258  32.67      C
ATOM   2668  OH  TYR 191    -21.489   8.849  -3.477  34.43      O
ATOM   2669  HH  TYR 191    -22.364   9.070  -3.824   0.00      H
ATOM   2670  C   TYR 191    -22.557   3.910   0.652  32.88      C
ATOM   2671  O   TYR 191    -21.431   3.432   0.804  34.60      O
ATOM   2672  N   GLY 192    -23.405   3.486  -0.279  33.27      N
ATOM   2673  HN  GLY 192    -24.308   3.927  -0.365   0.00      H
ATOM   2674  CA  GLY 192    -23.042   2.400  -1.167  34.02      C
ATOM   2675  HA2 GLY 192    -22.799   1.543  -0.595   0.00      H
ATOM   2676  HA3 GLY 192    -23.857   2.179  -1.805   0.00      H
ATOM   2677  C   GLY 192    -21.859   2.592  -2.101  35.29      C
ATOM   2678  O   GLY 192    -20.972   1.740  -2.164  35.24      O
ATOM   2679  N   PHE 193    -21.826   3.713  -2.813  36.35      N
ATOM   2680  HN  PHE 193    -22.552   4.398  -2.667   0.00      H
ATOM   2681  CA  PHE 193    -20.769   3.966  -3.791  37.03      C
ATOM   2682  HA  PHE 193    -20.721   3.159  -4.475   0.00      H
ATOM   2683  CB  PHE 193    -21.077   5.255  -4.543  35.55      C
ATOM   2684  HB2 PHE 193    -21.104   6.064  -3.860   0.00      H
ATOM   2685  HB3 PHE 193    -20.324   5.429  -5.267   0.00      H
ATOM   2686  CG  PHE 193    -22.391   5.226  -5.258  35.57      C
ATOM   2687  CD1 PHE 193    -22.611   4.322  -6.289  34.49      C
ATOM   2688  HD1 PHE 193    -21.833   3.636  -6.579   0.00      H
ATOM   2689  CD2 PHE 193    -23.415   6.099  -4.902  36.33      C
ATOM   2690  HD2 PHE 193    -23.266   6.807  -4.104   0.00      H
ATOM   2691  CE1 PHE 193    -23.827   4.286  -6.959  33.64      C
ATOM   2692  HE1 PHE 193    -23.981   3.580  -7.758   0.00      H
ATOM   2693  CE2 PHE 193    -24.639   6.072  -5.567  35.24      C
ATOM   2694  HE2 PHE 193    -25.422   6.755  -5.282   0.00      H
ATOM   2695  CZ  PHE 193    -24.843   5.161  -6.598  35.27      C
ATOM   2696  HZ  PHE 193    -25.787   5.133  -7.116   0.00      H
ATOM   2697  C   PHE 193    -19.325   3.981  -3.319  37.51      C
ATOM   2698  O   PHE 193    -18.411   4.127  -4.130  37.24      O
ATOM   2699  N   GLN 194    -19.101   3.822  -2.023  39.33      N
ATOM   2700  HN  GLN 194    -19.869   3.701  -1.380   0.00      H
ATOM   2701  CA  GLN 194    -17.729   3.823  -1.528  41.71      C
ATOM   2702  HA  GLN 194    -17.139   4.468  -2.126   0.00      H
ATOM   2703  CB  GLN 194    -17.671   4.306  -0.082  41.01      C
ATOM   2704  HB2 GLN 194    -16.674   4.564   0.164   0.00      H
ATOM   2705  HB3 GLN 194    -18.293   5.155   0.032   0.00      H
ATOM   2706  CG  GLN 194    -18.127   3.282   0.918  40.81      C
ATOM   2707  HG2 GLN 194    -19.167   3.116   0.804   0.00      H
ATOM   2708  HG3 GLN 194    -17.605   2.375   0.757   0.00      H
ATOM   2709  CD  GLN 194    -17.871   3.731   2.330  41.80      C
ATOM   2710  OE1 GLN 194    -16.751   4.104   2.674  41.98      O
ATOM   2711  NE2 GLN 194    -18.907   3.694   3.165  42.10      N
ATOM   2712 HE21 GLN 194    -19.808   3.380   2.837   0.00      H
ATOM   2713 HE22 GLN 194    -18.791   3.980   4.126   0.00      H
ATOM   2714  C   GLN 194    -17.163   2.415  -1.590  43.36      C
ATOM   2715  O   GLN 194    -15.988   2.192  -1.287  43.99      O
ATOM   2716  N   TYR 195    -18.011   1.471  -1.990  43.80      N
ATOM   2717  HN  TYR 195    -18.945   1.754  -2.245   0.00      H
ATOM   2718  CA  TYR 195    -17.630   0.070  -2.066  43.07      C
ATOM   2719  HA  TYR 195    -16.698  -0.069  -1.582   0.00      H
ATOM   2720  CB  TYR 195    -18.686  -0.783  -1.383  41.34      C
ATOM   2721  HB2 TYR 195    -19.607  -0.684  -1.897   0.00      H
ATOM   2722  HB3 TYR 195    -18.382  -1.798  -1.395   0.00      H
ATOM   2723  CG  TYR 195    -18.964  -0.442   0.053  41.20      C
ATOM   2724  CD1 TYR 195    -17.964  -0.534   1.020  40.19      C
ATOM   2725  HD1 TYR 195    -16.956  -0.777   0.730   0.00      H
ATOM   2726  CE1 TYR 195    -18.244  -0.316   2.363  40.01      C
ATOM   2727  HE1 TYR 195    -17.458  -0.391   3.096   0.00      H
ATOM   2728  CD2 TYR 195    -20.254  -0.111   0.463  41.91      C
ATOM   2729  HD2 TYR 195    -21.044  -0.021  -0.264   0.00      H
ATOM   2730  CE2 TYR 195    -20.549   0.108   1.803  42.56      C
ATOM   2731  HE2 TYR 195    -21.553   0.361   2.099   0.00      H
ATOM   2732  CZ  TYR 195    -19.540  -0.002   2.750  42.38      C
ATOM   2733  OH  TYR 195    -19.847   0.165   4.082  45.04      O
ATOM   2734  HH  TYR 195    -19.052   0.030   4.615   0.00      H
ATOM   2735  C   TYR 195    -17.428  -0.502  -3.461  44.56      C
ATOM   2736  O   TYR 195    -18.161  -0.184  -4.395  45.04      O
```

FIGURE 6- 37 -

```
ATOM   2737  N   SER  196   -16.428  -1.368  -3.588  46.44  N
ATOM   2738  HN  SER  196   -15.843  -1.548  -2.786   0.00  H
ATOM   2739  CA  SER  196   -16.167  -2.052  -4.850  46.37  C
ATOM   2740  HA  SER  196   -16.460  -1.430  -5.656   0.00  H
ATOM   2741  CB  SER  196   -14.681  -2.381  -5.002  44.33  C
ATOM   2742  HB2 SER  196   -14.491  -2.707  -5.991   0.00  H
ATOM   2743  HB3 SER  196   -14.105  -1.516  -4.799   0.00  H
ATOM   2744  OG  SER  196   -14.293  -3.404  -4.105  42.58  O
ATOM   2745  HG  SER  196   -13.352  -3.594  -4.220   0.00  H
ATOM   2746  C   SER  196   -16.981  -3.341  -4.698  47.90  C
ATOM   2747  O   SER  196   -17.306  -3.754  -3.572  47.07  O
ATOM   2748  N   PRO  197   -17.311  -4.002  -5.816  48.88  N
ATOM   2749  CD  PRO  197   -16.737  -3.805  -7.158  48.64  C
ATOM   2750  HD2 PRO  197   -16.796  -2.781  -7.420   0.00  H
ATOM   2751  HD3 PRO  197   -15.723  -4.111  -7.157   0.00  H
ATOM   2752  CA  PRO  197   -18.098  -5.241  -5.770  49.37  C
ATOM   2753  HA  PRO  197   -19.126  -5.003  -5.676   0.00  H
ATOM   2754  CB  PRO  197   -17.809  -5.875  -7.120  49.23  C
ATOM   2755  HB2 PRO  197   -16.940  -6.476  -7.049   0.00  H
ATOM   2756  HB3 PRO  197   -18.631  -6.476  -7.411   0.00  H
ATOM   2757  CG  PRO  197   -17.620  -4.684  -8.004  48.75  C
ATOM   2758  HG2 PRO  197   -17.161  -4.986  -8.909   0.00  H
ATOM   2759  HG3 PRO  197   -18.562  -4.247  -8.214   0.00  H
ATOM   2760  C   PRO  197   -17.739  -6.160  -4.605  50.27  C
ATOM   2761  O   PRO  197   -18.622  -6.636  -3.882  49.31  O
ATOM   2762  N   LYS  198   -16.443  -6.407  -4.425  51.39  N
ATOM   2763  HN  LYS  198   -15.771  -5.992  -5.054   0.00  H
ATOM   2764  CA  LYS  198   -15.990  -7.264  -3.337  52.32  C
ATOM   2765  HA  LYS  198   -16.466  -8.207  -3.409   0.00  H
ATOM   2766  CB  LYS  198   -14.477  -7.470  -3.400  53.33  C
ATOM   2767  HB2 LYS  198   -14.228  -7.984  -4.291   0.00  H
ATOM   2768  HB3 LYS  198   -13.992  -6.529  -3.388   0.00  H
ATOM   2769  CG  LYS  198   -13.936  -8.282  -2.233  55.35  C
ATOM   2770  HG2 LYS  198   -14.137  -7.773  -1.326   0.00  H
ATOM   2771  HG3 LYS  198   -14.405  -9.232  -2.216   0.00  H
ATOM   2772  CD  LYS  198   -12.432  -8.509  -2.314  57.91  C
ATOM   2773  HD2 LYS  198   -12.199  -9.015  -3.215   0.00  H
ATOM   2774  HD3 LYS  198   -11.933  -7.575  -2.295   0.00  H
ATOM   2775  CE  LYS  198   -11.948  -9.358  -1.125  59.42  C
ATOM   2776  HE2 LYS  198   -12.178  -8.860  -0.219   0.00  H
ATOM   2777  HE3 LYS  198   -12.432 -10.300  -1.143   0.00  H
ATOM   2778  NZ  LYS  198   -10.468  -9.625  -1.116  59.96  N1+
ATOM   2779  HZ1 LYS  198   -10.211 -10.121  -1.956   0.00  H
ATOM   2780  HZ2 LYS  198    -9.969  -8.749  -1.076   0.00  H
ATOM   2781  HZ3 LYS  198   -10.232 -10.184  -0.310   0.00  H
ATOM   2782  C   LYS  198   -16.344  -6.654  -1.986  52.07  C
ATOM   2783  O   LYS  198   -16.824  -7.340  -1.078  51.98  O
ATOM   2784  N   GLN  199   -16.110  -5.355  -1.864  50.73  N
ATOM   2785  HN  GLN  199   -15.743  -4.852  -2.658   0.00  H
ATOM   2786  CA  GLN  199   -16.372  -4.656  -0.620  50.55  C
ATOM   2787  HA  GLN  199   -15.950  -5.199   0.185   0.00  H
ATOM   2788  CB  GLN  199   -15.742  -3.270  -0.698  50.41  C
ATOM   2789  HB2 GLN  199   -16.318  -2.656  -1.341   0.00  H
ATOM   2790  HB3 GLN  199   -15.714  -2.840   0.269   0.00  H
ATOM   2791  CG  GLN  199   -14.325  -3.360  -1.240  49.93  C
ATOM   2792  HG2 GLN  199   -13.789  -4.100  -0.704   0.00  H
ATOM   2793  HG3 GLN  199   -14.355  -3.620  -2.266   0.00  H
ATOM   2794  CD  GLN  199   -13.551  -2.081  -1.128  48.80  C
ATOM   2795  OE1 GLN  199   -13.980  -1.031  -1.614  48.32  O
ATOM   2796  NE2 GLN  199   -12.386  -2.159  -0.493  48.71  N
ATOM   2797  HE21 GLN 199   -12.077  -3.041  -0.112   0.00  H
ATOM   2798  HE22 GLN 199   -11.810  -1.336  -0.392   0.00  H
ATOM   2799  C   GLN  199   -17.856  -4.581  -0.290  50.36  C
ATOM   2800  O   GLN  199   -18.249  -4.650   0.879  49.83  O
ATOM   2801  N   ARG  200   -18.685  -4.451  -1.319  49.54  N
ATOM   2802  HN  ARG  200   -18.315  -4.396  -2.256   0.00  H
ATOM   2803  CA  ARG  200   -20.119  -4.388  -1.099  48.82  C
ATOM   2804  HA  ARG  200   -20.340  -3.590  -0.439   0.00  H
ATOM   2805  CB  ARG  200   -20.856  -4.158  -2.423  48.43  C
ATOM   2806  HB2 ARG  200   -20.509  -3.262  -2.869   0.00  H
ATOM   2807  HB3 ARG  200   -20.672  -4.972  -3.075   0.00  H
ATOM   2808  CG  ARG  200   -22.361  -4.033  -2.273  47.04  C
ATOM   2809  HG2 ARG  200   -22.736  -4.878  -1.756   0.00  H
ATOM   2810  HG3 ARG  200   -22.590  -3.155  -1.727   0.00  H
ATOM   2811  CD  ARG  200   -23.055  -3.952  -3.619  47.60  C
ATOM   2812  HD2 ARG  200   -22.716  -3.094  -4.140   0.00  H
```

FIGURE 6- 38 -

```
ATOM   2813  HD3  ARG  2C0   -22.831   -4.819   -4.184    0.00  H
ATOM   2814  NE   ARG  2C0   -24.509   -3.859   -3.473   46.81  N1+
ATOM   2815  HE   ARG  2C0   -25.092   -4.646   -3.715    0.00  H
ATOM   2816  CZ   ARG  2C0   -25.158   -2.785   -3.032   45.14  C
ATOM   2817  NH1  ARG  2C0   -24.485   -1.693   -2.690   44.90  N
ATOM   2818  HH11 ARG  2C0   -24.980   -0.880   -2.356    0.00  H
ATOM   2819  HH12 ARG  2C0   -23.479   -1.676   -2.764    0.00  H
ATOM   2820  NH2  ARG  2C0   -26.480   -2.809   -2.928   43.45  N
ATOM   2821  HH21 ARG  2C0   -26.975   -1.996   -2.594    0.00  H
ATOM   2822  HH22 ARG  2C0   -26.991   -3.641   -3.183    0.00  H
ATOM   2823  C    ARG  2C0   -20.569   -5.706   -0.475   49.16  C
ATOM   2824  O    ARG  2C0   -21.197   -5.720    0.584   48.47  O
ATOM   2825  N    VAL  2C1   -20.232   -6.815   -1.130   49.79  N
ATOM   2826  HN   VAL  2C1   -19.700   -6.736   -1.984    0.00  H
ATOM   2827  CA   VAL  2C1   -20.620   -8.131   -0.630   51.03  C
ATOM   2828  HA   VAL  2C1   -21.667   -8.252   -0.731    0.00  H
ATOM   2829  CB   VAL  2C1   -19.928   -9.283   -1.402   52.26  C
ATOM   2830  HB   VAL  2C1   -18.881   -9.228   -1.253    0.00  H
ATOM   2831  CG1  VAL  2C1   -20.405  -10.620   -0.859   51.68  C
ATOM   2832  HG11 VAL  2C1   -20.162  -10.690    0.169    0.00  H
ATOM   2833  HG12 VAL  2C1   -21.454  -10.696   -0.980    0.00  H
ATOM   2834  HG13 VAL  2C1   -19.931  -11.405   -1.388    0.00  H
ATOM   2835  CG2  VAL  2C1   -20.220   -9.181   -2.889   54.03  C
ATOM   2836  HG21 VAL  2C1   -21.265   -9.241   -3.048    0.00  H
ATOM   2837  HG22 VAL  2C1   -19.859   -8.256   -3.257    0.00  H
ATOM   2838  HG23 VAL  2C1   -19.739   -9.975   -3.398    0.00  H
ATOM   2839  C    VAL  2C1   -20.232   -8.268    0.831   50.33  C
ATOM   2840  O    VAL  2C1   -21.037   -8.699    1.664   49.53  O
ATOM   2841  N    GLU  2C2   -18.990   -7.891    1.125   49.63  N
ATOM   2842  HN   GLU  2C2   -18.411   -7.535    0.379    0.00  H
ATOM   2843  CA   GLU  2C2   -18.463   -7.980    2.473   49.36  C
ATOM   2844  HA   GLU  2C2   -18.435   -8.995    2.775    0.00  H
ATOM   2845  CB   GLU  2C2   -17.049   -7.407    2.540   50.68  C
ATOM   2846  HB2  GLU  2C2   -16.376   -8.072    2.065    0.00  H
ATOM   2847  HB3  GLU  2C2   -17.024   -6.469    2.048    0.00  H
ATOM   2848  CG   GLU  2C2   -16.577   -7.201    3.972   52.88  C
ATOM   2849  HG2  GLU  2C2   -17.216   -6.510    4.458    0.00  H
ATOM   2850  HG3  GLU  2C2   -16.599   -8.126    4.488    0.00  H
ATOM   2851  CD   GLU  2C2   -15.163   -6.660    4.071   53.96  C
ATOM   2852  OE1  GLU  2C2   -14.827   -5.736    3.293   54.66  O1-
ATOM   2853  OE2  GLU  2C2   -14.399   -7.151    4.938   54.15  O
ATOM   2854  C    GLU  2C2   -19.340   -7.273    3.486   48.60  C
ATOM   2855  O    GLU  2C2   -19.740   -7.869    4.484   49.62  O
ATOM   2856  N    PHE  2C3   -19.646   -6.007    3.231   47.42  N
ATOM   2857  HN   PHE  2C3   -19.297   -5.576    2.388    0.00  H
ATOM   2858  CA   PHE  2C3   -20.475   -5.241    4.151   46.35  C
ATOM   2859  HA   PHE  2C3   -20.001   -5.193    5.097    0.00  H
ATOM   2860  CB   PHE  2C3   -20.679   -3.816    3.619   44.74  C
ATOM   2861  HB2  PHE  2C3   -19.736   -3.358    3.466    0.00  H
ATOM   2862  HB3  PHE  2C3   -21.206   -3.854    2.701    0.00  H
ATOM   2863  CG   PHE  2C3   -21.463   -2.925    4.547   43.64  C
ATOM   2864  CD1  PHE  2C3   -20.932   -2.530    5.766   42.59  C
ATOM   2865  HD1  PHE  2C3   -19.946   -2.853    6.054    0.00  H
ATOM   2866  CD2  PHE  2C3   -22.743   -2.491    4.200   42.83  C
ATOM   2867  HD2  PHE  2C3   -23.174   -2.785    3.258    0.00  H
ATOM   2868  CE1  PHE  2C3   -21.665   -1.714    6.630   43.44  C
ATOM   2869  HE1  PHE  2C3   -21.243   -1.413    7.574    0.00  H
ATOM   2870  CE2  PHE  2C3   -23.479   -1.680    5.052   41.55  C
ATOM   2871  HE2  PHE  2C3   -24.465   -1.355    4.767    0.00  H
ATOM   2872  CZ   PHE  2C3   -22.941   -1.290    6.270   42.42  C
ATOM   2873  HZ   PHE  2C3   -23.507   -0.661    6.936    0.00  H
ATOM   2874  C    PHE  2C3   -21.830   -5.922    4.371   46.20  C
ATOM   2875  O    PHE  2C3   -22.316   -6.003    5.496   47.19  O
ATOM   2876  N    LEU  2C4   -22.435   -6.425    3.303   45.21  N
ATOM   2877  HN   LEU  2C4   -21.998   -6.362    2.396    0.00  H
ATOM   2878  CA   LEU  2C4   -23.727   -7.067    3.442   44.39  C
ATOM   2879  HA   LEU  2C4   -24.384   -6.427    3.972    0.00  H
ATOM   2880  CB   LEU  2C4   -24.322   -7.365    2.066   41.98  C
ATOM   2881  HB2  LEU  2C4   -23.592   -7.834    1.460    0.00  H
ATOM   2882  HB3  LEU  2C4   -25.157   -8.007    2.174    0.00  H
ATOM   2883  CG   LEU  2C4   -24.814   -6.141    1.284   38.89  C
ATOM   2884  HG   LEU  2C4   -23.994   -5.505    1.072    0.00  H
ATOM   2885  CD1  LEU  2C4   -25.450   -6.588   -0.012   37.07  C
ATOM   2886  HD11 LEU  2C4   -24.737   -7.113   -0.593    0.00  H
ATOM   2887  HD12 LEU  2C4   -26.270   -7.224    0.198    0.00  H
ATOM   2888  HD13 LEU  2C4   -25.789   -5.741   -0.550    0.00  H
```

FIGURE 6- 39 -

```
ATOM   2889  CD2  LEU  204  -25.822   -5.359   2.107  36.00  C
ATOM   2890  HD21 LEU  204  -26.650   -5.979   2.334   0.00  H
ATOM   2891  HD22 LEU  204  -25.367   -5.034   3.007   0.00  H
ATOM   2892  HD23 LEU  204  -26.152   -4.518   1.555   0.00  H
ATOM   2893  C    LEU  204  -23.697   -8.329   4.301  45.84  C
ATOM   2894  O    LEU  204  -24.396   -8.405   5.313  46.38  O
ATOM   2895  N    VAL  205  -22.889   -9.317   3.926  47.11  N
ATOM   2896  HN   VAL  205  -22.316   -9.223   3.101   0.00  H
ATOM   2897  CA   VAL  205  -22.835  -10.548   4.720  47.44  C
ATOM   2898  HA   VAL  205  -23.788  -11.010   4.720   0.00  H
ATOM   2899  CB   VAL  205  -21.814  -11.562   4.163  47.02  C
ATOM   2900  HB   VAL  205  -20.888  -11.076   3.997   0.00  H
ATOM   2901  CG1  VAL  205  -21.590  -12.686   5.173  45.83  C
ATOM   2902  HG11 VAL  205  -21.219  -12.279   6.078   0.00  H
ATOM   2903  HG12 VAL  205  -22.507  -13.181   5.359   0.00  H
ATOM   2904  HG13 VAL  205  -20.888  -13.377   4.783   0.00  H
ATOM   2905  CG2  VAL  205  -22.328  -12.134   2.850  45.60  C
ATOM   2906  HG21 VAL  205  -23.254  -12.621   3.016   0.00  H
ATOM   2907  HG22 VAL  205  -22.462  -11.349   2.152   0.00  H
ATOM   2908  HG23 VAL  205  -21.626  -12.830   2.469   0.00  H
ATOM   2909  C    VAL  205  -22.484  -10.236   6.165  47.77  C
ATOM   2910  O    VAL  205  -23.148  -10.708   7.086  47.45  O
ATOM   2911  N    ASN  206  -21.437   -9.443   6.358  48.91  N
ATOM   2912  HN   ASN  206  -20.923   -9.107   5.557   0.00  H
ATOM   2913  CA   ASN  206  -21.028   -9.057   7.699  49.76  C
ATOM   2914  HA   ASN  206  -20.696   -9.913   8.227   0.00  H
ATOM   2915  CB   ASN  206  -19.892   -8.040   7.657  48.32  C
ATOM   2916  HB2  ASN  206  -20.016   -7.407   6.817   0.00  H
ATOM   2917  HB3  ASN  206  -19.906   -7.459   8.542   0.00  H
ATOM   2918  CG   ASN  206  -18.538   -8.692   7.551  48.00  C
ATOM   2919  OD1  ASN  206  -18.258   -9.668   8.245  48.00  O
ATOM   2920  ND2  ASN  206  -17.681   -8.151   6.693  47.49  N
ATOM   2921  HD21 ASN  206  -17.955   -7.350   6.144   0.00  H
ATOM   2922  HD22 ASN  206  -16.756   -8.541   6.590   0.00  H
ATOM   2923  C    ASN  206  -22.208   -8.442   8.428  51.49  C
ATOM   2924  O    ASN  206  -22.460   -8.752   9.594  51.95  O
ATOM   2925  N    THR  207  -22.935   -7.569   7.737  52.94  N
ATOM   2926  HN   THR  207  -22.683   -7.358   6.783   0.00  H
ATOM   2927  CA   THR  207  -24.084   -6.921   8.345  55.04  C
ATOM   2928  HA   THR  207  -23.779   -6.411   9.221   0.00  H
ATOM   2929  CB   THR  207  -24.744   -5.889   7.387  54.35  C
ATOM   2930  HB   THR  207  -25.014   -6.369   6.483   0.00  H
ATOM   2931  OG1  THR  207  -23.818   -4.833   7.109  51.78  O
ATOM   2932  HG1  THR  207  -24.229   -4.192   6.513   0.00  H
ATOM   2933  CG2  THR  207  -25.999   -5.290   8.025  52.83  C
ATOM   2934  HG21 THR  207  -26.694   -6.062   8.229   0.00  H
ATOM   2935  HG22 THR  207  -25.738   -4.802   8.928   0.00  H
ATOM   2936  HG23 THR  207  -26.434   -4.591   7.359   0.00  H
ATOM   2937  C    THR  207  -25.108   -7.977   8.728  57.28  C
ATOM   2938  O    THR  207  -25.731   -7.892   9.786  58.32  O
ATOM   2939  N    TRP  208  -25.271   -8.983   7.875  59.44  N
ATOM   2940  HN   TRP  208  -24.720   -9.012   7.030   0.00  H
ATOM   2941  CA   TRP  208  -26.236  -10.039   8.151  62.19  C
ATOM   2942  HA   TRP  208  -27.174   -9.607   8.385   0.00  H
ATOM   2943  CB   TRP  208  -26.395  -10.950   6.924  63.65  C
ATOM   2944  HB2  TRP  208  -26.563  -10.357   6.063   0.00  H
ATOM   2945  HB3  TRP  208  -25.513  -11.521   6.792   0.00  H
ATOM   2946  CG   TRP  208  -27.544  -11.909   7.047  65.34  C
ATOM   2947  CD2  TRP  208  -28.888  -11.695   6.600  66.17  C
ATOM   2948  CE2  TRP  208  -29.641  -12.824   6.992  66.42  C
ATOM   2949  CE3  TRP  208  -29.530  -10.656   5.914  65.83  C
ATOM   2950  HE3  TRP  208  -28.972   -9.786   5.610   0.00  H
ATOM   2951  CD1  TRP  208  -27.537  -13.123   7.667  65.67  C
ATOM   2952  HD1  TRP  208  -26.623  -13.507   8.088   0.00  H
ATOM   2953  NE1  TRP  208  -28.791  -13.679   7.641  65.58  N
ATOM   2954  HE1  TRP  208  -28.952  -14.581   8.063   0.00  H
ATOM   2955  CZ2  TRP  208  -31.006  -12.946   6.717  66.74  C
ATOM   2956  HZ2  TRP  208  -31.542  -13.825   7.032   0.00  H
ATOM   2957  CZ3  TRP  208  -30.887  -10.777   5.641  66.32  C
ATOM   2958  HZ3  TRP  208  -31.402   -9.992   5.113   0.00  H
ATOM   2959  CH2  TRP  208  -31.610  -11.916   6.044  67.04  C
ATOM   2960  HH2  TRP  208  -32.661  -11.967   5.812   0.00  H
ATOM   2961  C    TRP  208  -25.837  -10.862   9.379  63.29  C
ATOM   2962  O    TRP  208  -26.686  -11.187  10.219  63.76  O
ATOM   2963  N    LYS  209  -24.547  -11.185   9.488  63.69  N
ATOM   2964  HN   LYS  209  -23.918  -10.872   8.764   0.00  H
```

FIGURE 6-40-

| | | | | | | | | |
|---|---|---|---|---|---|---|---|---|
| ATOM | 2965 | CA | LYS | 209 | -24.035 | -11.969 | 10.614 | 63.64 | C |
| ATOM | 2966 | HA | LYS | 209 | -24.627 | -12.839 | 10.736 | 0.00 | H |
| ATOM | 2967 | CB | LYS | 209 | -22.588 | -12.383 | 10.358 | 63.58 | C |
| ATOM | 2968 | HB2 | LYS | 209 | -22.015 | -11.523 | 10.109 | 0.00 | H |
| ATOM | 2969 | HB3 | LYS | 209 | -22.190 | -12.833 | 11.230 | 0.00 | H |
| ATOM | 2970 | CG | LYS | 209 | -22.435 | -13.375 | 9.228 | 64.94 | C |
| ATOM | 2971 | HG2 | LYS | 209 | -23.072 | -14.204 | 9.397 | 0.00 | H |
| ATOM | 2972 | HG3 | LYS | 209 | -22.695 | -12.910 | 8.313 | 0.00 | H |
| ATOM | 2973 | CD | LYS | 209 | -21.007 | -13.874 | 9.129 | 65.83 | C |
| ATOM | 2974 | HD2 | LYS | 209 | -20.373 | -13.076 | 8.842 | 0.00 | H |
| ATOM | 2975 | HD3 | LYS | 209 | -20.698 | -14.249 | 10.070 | 0.00 | H |
| ATOM | 2976 | CE | LYS | 209 | -20.889 | -14.982 | 8.101 | 67.01 | C |
| ATOM | 2977 | HE2 | LYS | 209 | -21.519 | -15.787 | 8.376 | 0.00 | H |
| ATOM | 2978 | HE3 | LYS | 209 | -21.180 | -14.615 | 7.151 | 0.00 | H |
| ATOM | 2979 | NZ | LYS | 209 | -19.491 | -15.491 | 8.001 | 68.14 | N1+ |
| ATOM | 2980 | HZ1 | LYS | 209 | -18.877 | -14.738 | 7.729 | 0.00 | H |
| ATOM | 2981 | HZ2 | LYS | 209 | -19.201 | -15.855 | 8.896 | 0.00 | H |
| ATOM | 2982 | HZ3 | LYS | 209 | -19.449 | -16.225 | 7.310 | 0.00 | H |
| ATOM | 2983 | C | LYS | 209 | -24.114 | -11.232 | 11.946 | 63.56 | C |
| ATOM | 2984 | O | LYS | 209 | -24.517 | -11.806 | 12.959 | 64.18 | O |
| ATOM | 2985 | N | SER | 210 | -23.729 | -9.962 | 11.946 | 63.15 | N |
| ATOM | 2986 | HN | SER | 210 | -23.409 | -9.550 | 11.082 | 0.00 | H |
| ATOM | 2987 | CA | SER | 210 | -23.763 | -9.165 | 13.165 | 62.60 | C |
| ATOM | 2988 | HA | SER | 210 | -23.077 | -9.564 | 13.867 | 0.00 | H |
| ATOM | 2989 | CB | SER | 210 | -23.381 | -7.717 | 12.857 | 61.76 | C |
| ATOM | 2990 | HB2 | SER | 210 | -23.412 | -7.147 | 13.749 | 0.00 | H |
| ATOM | 2991 | HB3 | SER | 210 | -22.402 | -7.683 | 12.453 | 0.00 | H |
| ATOM | 2992 | OG | SER | 210 | -24.279 | -7.154 | 11.922 | 61.19 | O |
| ATOM | 2993 | HG | SER | 210 | -24.023 | -6.240 | 11.739 | 0.00 | H |
| ATOM | 2994 | C | SER | 210 | -25.134 | -9.194 | 13.841 | 62.80 | C |
| ATOM | 2995 | O | SER | 210 | -25.232 | -9.001 | 15.051 | 62.44 | O |
| ATOM | 2996 | N | LYS | 211 | -26.186 | -9.431 | 13.058 | 63.39 | N |
| ATOM | 2997 | HN | LYS | 211 | -26.020 | -9.579 | 12.074 | 0.00 | H |
| ATOM | 2998 | CA | LYS | 211 | -27.550 | -9.480 | 13.586 | 63.93 | C |
| ATOM | 2999 | HA | LYS | 211 | -27.667 | -8.737 | 14.332 | 0.00 | H |
| ATOM | 3000 | CB | LYS | 211 | -28.581 | -9.223 | 12.475 | 63.69 | C |
| ATOM | 3001 | HB2 | LYS | 211 | -28.620 | -10.069 | 11.833 | 0.00 | H |
| ATOM | 3002 | HB3 | LYS | 211 | -29.535 | -9.069 | 12.908 | 0.00 | H |
| ATOM | 3003 | CG | LYS | 211 | -28.305 | -8.016 | 11.583 | 62.95 | C |
| ATOM | 3004 | HG2 | LYS | 211 | -27.356 | -8.123 | 11.126 | 0.00 | H |
| ATOM | 3005 | HG3 | LYS | 211 | -29.052 | -7.951 | 10.835 | 0.00 | H |
| ATOM | 3006 | CD | LYS | 211 | -28.307 | -6.712 | 12.364 | 60.72 | C |
| ATOM | 3007 | HD2 | LYS | 211 | -29.251 | -6.579 | 12.826 | 0.00 | H |
| ATOM | 3008 | HD3 | LYS | 211 | -27.552 | -6.744 | 13.106 | 0.00 | H |
| ATOM | 3009 | CE | LYS | 211 | -28.043 | -5.531 | 11.458 | 57.48 | C |
| ATOM | 3010 | HE2 | LYS | 211 | -27.104 | -5.653 | 10.984 | 0.00 | H |
| ATOM | 3011 | HE3 | LYS | 211 | -28.804 | -5.472 | 10.724 | 0.00 | H |
| ATOM | 3012 | NZ | LYS | 211 | -28.028 | -4.267 | 12.236 | 56.63 | N1+ |
| ATOM | 3013 | HZ1 | LYS | 211 | -28.921 | -4.139 | 12.687 | 0.00 | H |
| ATOM | 3014 | HZ2 | LYS | 211 | -27.302 | -4.311 | 12.935 | 0.00 | H |
| ATOM | 3015 | HZ3 | LYS | 211 | -27.851 | -3.492 | 11.615 | 0.00 | H |
| ATOM | 3016 | C | LYS | 211 | -27.829 | -10.844 | 14.200 | 64.77 | C |
| ATOM | 3017 | O | LYS | 211 | -27.388 | -11.872 | 13.679 | 64.63 | O |
| ATOM | 3018 | N | LYS | 212 | -28.568 | -10.851 | 15.306 | 65.78 | N |
| ATOM | 3019 | HN | LYS | 212 | -28.890 | -9.972 | 15.682 | 0.00 | H |
| ATOM | 3020 | CA | LYS | 212 | -28.915 | -12.102 | 15.975 | 66.43 | C |
| ATOM | 3021 | HA | LYS | 212 | -28.032 | -12.651 | 16.177 | 0.00 | H |
| ATOM | 3022 | CB | LYS | 212 | -29.639 | -11.824 | 17.295 | 67.60 | C |
| ATOM | 3023 | HB2 | LYS | 212 | -30.504 | -11.242 | 17.108 | 0.00 | H |
| ATOM | 3024 | HB3 | LYS | 212 | -29.921 | -12.741 | 17.743 | 0.00 | H |
| ATOM | 3025 | CG | LYS | 212 | -28.799 | -11.063 | 18.309 | 68.84 | C |
| ATOM | 3026 | HG2 | LYS | 212 | -27.888 | -11.585 | 18.468 | 0.00 | H |
| ATOM | 3027 | HG3 | LYS | 212 | -28.594 | -10.096 | 17.943 | 0.00 | H |
| ATOM | 3028 | CD | LYS | 212 | -29.517 | -10.937 | 19.644 | 70.32 | C |
| ATOM | 3029 | HD2 | LYS | 212 | -30.385 | -10.342 | 19.521 | 0.00 | H |
| ATOM | 3030 | HD3 | LYS | 212 | -29.794 | -11.893 | 19.992 | 0.00 | H |
| ATOM | 3031 | CE | LYS | 212 | -28.617 | -10.279 | 20.691 | 70.76 | C |
| ATOM | 3032 | HE2 | LYS | 212 | -27.689 | -10.783 | 20.729 | 0.00 | H |
| ATOM | 3033 | HE3 | LYS | 212 | -28.453 | -9.266 | 20.429 | 0.00 | H |
| ATOM | 3034 | NZ | LYS | 212 | -29.221 | -10.312 | 22.059 | 70.84 | N1+ |
| ATOM | 3035 | HZ1 | LYS | 212 | -30.102 | -9.820 | 22.050 | 0.00 | H |
| ATOM | 3036 | HZ2 | LYS | 212 | -29.374 | -11.270 | 22.336 | 0.00 | H |
| ATOM | 3037 | HZ3 | LYS | 212 | -28.595 | -9.869 | 22.714 | 0.00 | H |
| ATOM | 3038 | C | LYS | 212 | -29.817 | -12.892 | 15.034 | 66.13 | C |
| ATOM | 3039 | O | LYS | 212 | -29.367 | -13.836 | 14.389 | 66.83 | O |
| ATOM | 3040 | N | CYS | 213 | -31.087 | -12.501 | 14.962 | 65.25 | N |

FIGURE 6-41 -

```
ATOM   3041  HN   CYS   213      -31.378 -11.736  15.553   0.00           H
ATOM   3042  CA   CYS   213      -32.049 -13.139  14.067  64.54           C
ATOM   3043  HA   CYS   213      -31.630 -14.029  13.675   0.00           H
ATOM   3044  CB   CYS   213      -33.350 -13.473  14.813  65.19           C
ATOM   3045  HB2  CYS   213      -33.119 -13.967  15.721   0.00           H
ATOM   3046  HB3  CYS   213      -33.877 -12.578  15.022   0.00           H
ATOM   3047  SG   CYS   213      -34.515 -14.562  13.913  65.25           S
ATOM   3048  HG   CYS   213      -35.529 -14.760  14.617   0.00           H
ATOM   3049  C    CYS   213      -32.318 -12.111  12.962  63.96           C
ATOM   3050  O    CYS   213      -33.255 -11.308  13.049  63.52           O
ATOM   3051  N    PRO   214      -31.484 -12.118  11.907  62.72           N
ATOM   3052  CD   PRO   214      -30.402 -13.077  11.630  61.97           C
ATOM   3053  HD2  PRO   214      -29.509 -12.746  12.094   0.00           H
ATOM   3054  HD3  PRO   214      -30.667 -14.028  12.013   0.00           H
ATOM   3055  CA   PRO   214      -31.638 -11.176  10.793  62.17           C
ATOM   3056  HA   PRO   214      -31.443 -10.192  11.133   0.00           H
ATOM   3057  CB   PRO   214      -30.535 -11.598   9.818  61.24           C
ATOM   3058  HB2  PRO   214      -30.862 -11.436   8.824   0.00           H
ATOM   3059  HB3  PRO   214      -29.664 -11.025  10.001   0.00           H
ATOM   3060  CG   PRO   214      -30.341 -13.037  10.123  61.80           C
ATOM   3061  HG2  PRO   214      -31.114 -13.601   9.670   0.00           H
ATOM   3062  HG3  PRO   214      -29.404 -13.355   9.745   0.00           H
ATOM   3063  C    PRO   214      -33.007 -11.121  10.131  61.17           C
ATOM   3064  O    PRO   214      -33.889 -11.939  10.399  62.40           O
ATOM   3065  N    MET   215      -33.159 -10.114   9.280  58.50           N
ATOM   3066  HN   MET   215      -32.362  -9.504   9.181   0.00           H
ATOM   3067  CA   MET   215      -34.369  -9.859   8.516  55.98           C
ATOM   3068  HA   MET   215      -34.664 -10.745   8.016   0.00           H
ATOM   3069  CB   MET   215      -35.511  -9.410   9.420  55.48           C
ATOM   3070  HB2  MET   215      -35.667 -10.133  10.178   0.00           H
ATOM   3071  HB3  MET   215      -35.265  -8.481   9.864   0.00           H
ATOM   3072  CG   MET   215      -36.830  -9.229   8.685  56.24           C
ATOM   3073  HG2  MET   215      -37.062 -10.114   8.152   0.00           H
ATOM   3074  HG3  MET   215      -37.599  -9.027   9.384   0.00           H
ATOM   3075  SD   MET   215      -36.854  -7.868   7.473  56.74           S
ATOM   3076  CE   MET   215      -37.925  -6.681   8.339  54.13           C
ATOM   3077  HE1  MET   215      -38.874  -7.120   8.509   0.00           H
ATOM   3078  HE2  MET   215      -37.486  -6.421   9.267   0.00           H
ATOM   3079  HE3  MET   215      -38.040  -5.811   7.746   0.00           H
ATOM   3080  C    MET   215      -33.975  -8.725   7.593  54.75           C
ATOM   3081  O    MET   215      -33.378  -7.743   8.032  54.19           O
ATOM   3082  N    GLY   216      -34.290  -8.862   6.314  52.92           N
ATOM   3083  HN   GLY   216      -34.783  -9.678   5.984   0.00           H
ATOM   3084  CA   GLY   216      -33.917  -7.820   5.386  51.38           C
ATOM   3085  HA2  GLY   216      -33.921  -6.886   5.884   0.00           H
ATOM   3086  HA3  GLY   216      -32.947  -8.015   5.008   0.00           H
ATOM   3087  C    GLY   216      -34.832  -7.685   4.196  49.83           C
ATOM   3088  O    GLY   216      -35.475  -8.642   3.775  50.03           O
ATOM   3089  N    PHE   217      -34.886  -6.477   3.653  47.80           N
ATOM   3090  HN   PHE   217      -34.335  -5.737   4.061   0.00           H
ATOM   3091  CA   PHE   217      -35.715  -6.209   2.495  44.94           C
ATOM   3092  HA   PHE   217      -35.800  -7.088   1.911   0.00           H
ATOM   3093  CB   PHE   217      -37.114  -5.763   2.927  44.79           C
ATOM   3094  HB2  PHE   217      -37.678  -5.493   2.072   0.00           H
ATOM   3095  HB3  PHE   217      -37.597  -6.558   3.433   0.00           H
ATOM   3096  CG   PHE   217      -37.116  -4.580   3.853  43.74           C
ATOM   3097  CD1  PHE   217      -36.900  -4.749   5.218  44.00           C
ATOM   3098  HD1  PHE   217      -36.743  -5.736   5.620   0.00           H
ATOM   3099  CD2  PHE   217      -37.316  -3.294   3.357  42.77           C
ATOM   3100  HD2  PHE   217      -37.485  -3.143   2.304   0.00           H
ATOM   3101  CE1  PHE   217      -36.884  -3.652   6.081  43.60           C
ATOM   3102  HE1  PHE   217      -36.717  -3.798   7.135   0.00           H
ATOM   3103  CE2  PHE   217      -37.301  -2.194   4.206  42.47           C
ATOM   3104  HE2  PHE   217      -37.456  -1.205   3.809   0.00           H
ATOM   3105  CZ   PHE   217      -37.085  -2.371   5.572  42.94           C
ATOM   3106  HZ   PHE   217      -37.073  -1.521   6.233   0.00           H
ATOM   3107  C    PHE   217      -35.082  -5.129   1.647  42.60           C
ATOM   3108  O    PHE   217      -34.128  -4.475   2.053  42.27           O
ATOM   3109  N    SER   218      -35.615  -4.968   0.451  40.67           N
ATOM   3110  HN   SER   218      -36.375  -5.575   0.181   0.00           H
ATOM   3111  CA   SER   218      -35.139  -3.957  -0.462  38.60           C
ATOM   3112  HA   SER   218      -34.279  -3.491  -0.055   0.00           H
ATOM   3113  CB   SER   218      -34.776  -4.588  -1.810  37.87           C
ATOM   3114  HB2  SER   218      -34.416  -3.838  -2.465   0.00           H
ATOM   3115  HB3  SER   218      -34.025  -5.321  -1.666   0.00           H
ATOM   3116  OG   SER   218      -35.903  -5.207  -2.408  37.63           O
```

FIGURE 6-42-

```
ATOM   3117  HG   SER  218   -35.646   -5.596   -3.255    0.00    H
ATOM   3118  C    SER  218   -36.343   -3.047   -0.598   38.39    C
ATOM   3119  O    SER  218   -37.478   -3.477   -0.375   38.14    O
ATOM   3120  N    TYR  219   -36.109   -1.785   -0.923   38.29    N
ATOM   3121  HN   TYR  219   -35.164   -1.461   -1.063    0.00    H
ATOM   3122  CA   TYR  219   -37.220   -0.867   -1.078   37.89    C
ATOM   3123  HA   TYR  219   -38.131   -1.405   -1.034    0.00    H
ATOM   3124  CB   TYR  219   -37.226    0.188    0.024   37.70    C
ATOM   3125  HB2  TYR  219   -37.067   -0.279    0.961    0.00    H
ATOM   3126  HB3  TYR  219   -36.454    0.890   -0.155    0.00    H
ATOM   3127  CG   TYR  219   -38.531    0.951    0.106   35.80    C
ATOM   3128  CD1  TYR  219   -39.648    0.399    0.733   34.33    C
ATOM   3129  HD1  TYR  219   -39.582   -0.572    1.194    0.00    H
ATOM   3130  CE1  TYR  219   -40.851    1.078    0.776   34.25    C
ATOM   3131  HE1  TYR  219   -41.701    0.637    1.268    0.00    H
ATOM   3132  CD2  TYR  219   -38.657    2.210   -0.475   34.79    C
ATOM   3133  HD2  TYR  219   -37.811    2.666   -0.961    0.00    H
ATOM   3134  CE2  TYR  219   -39.854    2.900   -0.444   34.57    C
ATOM   3135  HE2  TYR  219   -39.928    3.872   -0.903    0.00    H
ATOM   3136  CZ   TYR  219   -40.951    2.333    0.179   35.92    C
ATOM   3137  OH   TYR  219   -42.154    3.009    0.168   35.02    O
ATOM   3138  HH   TYR  219   -42.827    2.477    0.614    0.00    H
ATOM   3139  C    TYR  219   -37.117   -0.204   -2.430   39.14    C
ATOM   3140  O    TYR  219   -36.175    0.539   -2.723   40.22    O
ATOM   3141  N    ASP  220   -38.095   -0.500   -3.265   39.64    N
ATOM   3142  HN   ASP  220   -38.825   -1.122   -2.952    0.00    H
ATOM   3143  CA   ASP  220   -38.135    0.045   -4.599   39.75    C
ATOM   3144  HA   ASP  220   -37.170    0.385   -4.870    0.00    H
ATOM   3145  CB   ASP  220   -38.587   -1.039   -5.569   40.70    C
ATOM   3146  HB2  ASP  220   -37.772   -1.678   -5.789    0.00    H
ATOM   3147  HB3  ASP  220   -39.369   -1.602   -5.129    0.00    H
ATOM   3148  CG   ASP  220   -39.098   -0.475   -6.871   43.08    C
ATOM   3149  OD1  ASP  220   -38.275    0.070   -7.641   44.04    O
ATOM   3150  OD2  ASP  220   -40.323   -0.571   -7.115   43.48    O1-
ATOM   3151  C    ASP  220   -39.105    1.213   -4.607   39.95    C
ATOM   3152  O    ASP  220   -40.322    1.030   -4.520   40.51    O
ATOM   3153  N    THR  221   -38.564    2.421   -4.691   39.69    N
ATOM   3154  HN   THR  221   -37.561    2.520   -4.741    0.00    H
ATOM   3155  CA   THR  221   -39.410    3.597   -4.711   39.55    C
ATOM   3156  HA   THR  221   -40.213    3.465   -4.034    0.00    H
ATOM   3157  CB   THR  221   -38.642    4.856   -4.306   39.25    C
ATOM   3158  HB   THR  221   -37.985    5.136   -5.088    0.00    H
ATOM   3159  OG1  THR  221   -37.882    4.594   -3.118   40.22    O
ATOM   3160  HG1  THR  221   -37.397    5.391   -2.863    0.00    H
ATOM   3161  CG2  THR  221   -39.614    5.994   -4.038   37.95    C
ATOM   3162  HG21 THR  221   -40.174    6.194   -4.915    0.00    H
ATOM   3163  HG22 THR  221   -40.271    5.720   -3.254    0.00    H
ATOM   3164  HG23 THR  221   -39.074    6.861   -3.758    0.00    H
ATOM   3165  C    THR  221   -39.960    3.776   -6.114   40.79    C
ATOM   3166  O    THR  221   -39.237    3.653   -7.106   41.74    O
ATOM   3167  N    ARG  222   -41.252    4.058   -6.191   41.69    N
ATOM   3168  HN   ARG  222   -41.776    4.139   -5.332    0.00    H
ATOM   3169  CA   ARG  222   -41.917    4.249   -7.468   41.66    C
ATOM   3170  HA   ARG  222   -41.664    3.454   -8.120    0.00    H
ATOM   3171  CB   ARG  222   -43.430    4.271   -7.254   43.44    C
ATOM   3172  HB2  ARG  222   -43.747    3.333   -6.878    0.00    H
ATOM   3173  HB3  ARG  222   -43.677    5.032   -6.560    0.00    H
ATOM   3174  CG   ARG  222   -44.252    4.537   -8.495   44.74    C
ATOM   3175  HG2  ARG  222   -43.920    5.432   -8.953    0.00    H
ATOM   3176  HG3  ARG  222   -44.140    3.731   -9.172    0.00    H
ATOM   3177  CD   ARG  222   -45.702    4.676   -8.116   46.49    C
ATOM   3178  HD2  ARG  222   -46.053    3.758   -7.721    0.00    H
ATOM   3179  HD3  ARG  222   -45.805    5.437   -7.386    0.00    H
ATOM   3180  NE   ARG  222   -46.539    5.027   -9.255   51.07    N1+
ATOM   3181  HE   ARG  222   -47.304    4.426   -9.523    0.00    H
ATOM   3182  CZ   ARG  222   -46.373    6.115  -10.001   53.75    C
ATOM   3183  NH1  ARG  222   -45.386    6.964   -9.727   56.35    N
ATOM   3184  HH11 ARG  222   -45.259    7.790  -10.293    0.00    H
ATOM   3185  HH12 ARG  222   -44.764    6.782   -8.954    0.00    H
ATOM   3186  NH2  ARG  222   -47.202    6.361  -11.010   52.50    N
ATOM   3187  HH21 ARG  222   -47.076    7.187  -11.576    0.00    H
ATOM   3188  HH22 ARG  222   -47.957    5.722  -11.210    0.00    H
ATOM   3189  C    ARG  222   -41.463    5.554   -8.092   40.28    C
ATOM   3190  O    ARG  222   -41.810    6.620   -7.600   41.69    O
ATOM   3191  N    CYS  223   -40.683    5.468   -9.170   39.44    N
ATOM   3192  HN   CYS  223   -40.443    4.548   -9.504    0.00    H
```

FIGURE 6-43-

```
ATOM   3193  CA   CYS  223   -40.192   6.658  -9.869  38.34   C
ATOM   3194  HA   CYS  223   -39.425   6.377 -10.543   0.00   H
ATOM   3195  CB   CYS  223   -41.323   7.308 -10.656  40.10   C
ATOM   3196  HB2  CYS  223   -42.060   7.666  -9.985   0.00   H
ATOM   3197  HB3  CYS  223   -40.939   8.116 -11.223   0.00   H
ATOM   3198  SG   CYS  223   -42.138   6.199 -11.796  45.91   S
ATOM   3199  HG   CYS  223   -43.047   6.812 -12.396   0.00   H
ATOM   3200  C    CYS  223   -39.629   7.675  -8.887  36.65   C
ATOM   3201  O    CYS  223   -40.152   8.787  -8.765  36.22   O
ATOM   3202  N    PHE  224   -38.553   7.293  -8.204  34.12   N
ATOM   3203  HN   PHE  224   -38.168   6.382  -8.403   0.00   H
ATOM   3204  CA   PHE  224   -37.933   8.141  -7.199  31.58   C
ATOM   3205  HA   PHE  224   -38.550   8.179  -6.339   0.00   H
ATOM   3206  CB   PHE  224   -36.563   7.581  -6.808  31.66   C
ATOM   3207  HB2  PHE  224   -36.645   6.540  -6.629   0.00   H
ATOM   3208  HB3  PHE  224   -35.875   7.751  -7.595   0.00   H
ATOM   3209  CG   PHE  224   -35.990   8.209  -5.564  33.20   C
ATOM   3210  CD1  PHE  224   -35.458   9.503  -5.595  31.38   C
ATOM   3211  HD1  PHE  224   -35.398  10.038  -6.528   0.00   H
ATOM   3212  CD2  PHE  224   -36.047   7.535  -4.336  31.45   C
ATOM   3213  HD2  PHE  224   -36.446   6.536  -4.288   0.00   H
ATOM   3214  CE1  PHE  224   -34.998  10.119  -4.424  29.79   C
ATOM   3215  HE1  PHE  224   -34.592  11.116  -4.464   0.00   H
ATOM   3216  CE2  PHE  224   -35.589   8.145  -3.159  29.83   C
ATOM   3217  HE2  PHE  224   -35.640   7.615  -2.223   0.00   H
ATOM   3218  CZ   PHE  224   -35.067   9.439  -3.205  30.04   C
ATOM   3219  HZ   PHE  224   -34.718   9.913  -2.303   0.00   H
ATOM   3220  C    PHE  224   -37.797   9.609  -7.584  30.65   C
ATOM   3221  O    PHE  224   -38.241  10.490  -6.851  28.97   O
ATOM   3222  N    ASP  225   -37.193   9.878  -8.734  30.70   N
ATOM   3223  HN   ASP  225   -36.867   9.120  -9.315   0.00   H
ATOM   3224  CA   ASP  225   -37.000  11.252  -9.158  29.81   C
ATOM   3225  HA   ASP  225   -36.381  11.753  -8.460   0.00   H
ATOM   3226  CB   ASP  225   -36.335  11.299 -10.537  30.36   C
ATOM   3227  HB2  ASP  225   -36.862  10.668 -11.205   0.00   H
ATOM   3228  HB3  ASP  225   -36.351  12.293 -10.903   0.00   H
ATOM   3229  CG   ASP  225   -34.889  10.836 -10.494  33.85   C
ATOM   3230  OD1  ASP  225   -34.399  10.547  -9.381  35.25   O
ATOM   3231  OD2  ASP  225   -34.234  10.760 -11.558  34.98   O1-
ATOM   3232  C    ASP  225   -38.271  12.075  -9.149  28.41   C
ATOM   3233  O    ASP  225   -38.283  13.194  -8.633  29.04   O
ATOM   3234  N    SER  226   -39.348  11.537  -9.701  27.89   N
ATOM   3235  HN   SER  226   -39.320  10.611 -10.101   0.00   H
ATOM   3236  CA   SER  226   -40.585  12.303  -9.725  28.39   C
ATOM   3237  HA   SER  226   -40.400  13.259 -10.142   0.00   H
ATOM   3238  CB   SER  226   -41.651  11.597 -10.567  29.94   C
ATOM   3239  HB2  SER  226   -42.561  12.135 -10.507   0.00   H
ATOM   3240  HB3  SER  226   -41.332  11.553 -11.576   0.00   H
ATOM   3241  OG   SER  226   -41.878  10.277 -10.110  35.92   O
ATOM   3242  HG   SER  226   -42.554   9.857 -10.659   0.00   H
ATOM   3243  C    SER  226   -41.101  12.536  -8.320  27.25   C
ATOM   3244  O    SER  226   -41.823  13.495  -8.074  27.31   O
ATOM   3245  N    THR  227   -40.713  11.676  -7.387  27.68   N
ATOM   3246  HN   THR  227   -40.095  10.914  -7.622   0.00   H
ATOM   3247  CA   THR  227   -41.183  11.836  -6.022  27.79   C
ATOM   3248  HA   THR  227   -42.183  12.184  -6.032   0.00   H
ATOM   3249  CB   THR  227   -41.142  10.513  -5.243  29.27   C
ATOM   3250  HB   THR  227   -41.723  10.604  -4.362   0.00   H
ATOM   3251  OG1  THR  227   -39.792  10.207  -4.872  31.85   O
ATOM   3252  HG1  THR  227   -39.773   9.373  -4.382   0.00   H
ATOM   3253  CG2  THR  227   -41.702   9.339  -6.098  30.42   C
ATOM   3254  HG21 THR  227   -42.705   9.609  -6.358   0.00   H
ATOM   3255  HG22 THR  227   -41.122   9.293  -6.979   0.00   H
ATOM   3256  HG23 THR  227   -41.670   8.481  -5.553   0.00   H
ATOM   3257  C    THR  227   -40.398  12.874  -5.241  27.00   C
ATOM   3258  O    THR  227   -40.855  13.309  -4.188  28.47   O
ATOM   3259  N    VAL  228   -39.224  13.268  -5.737  26.42   N
ATOM   3260  HN   VAL  228   -38.896  12.860  -6.600   0.00   H
ATOM   3261  CA   VAL  228   -38.412  14.279  -5.048  25.54   C
ATOM   3262  HA   VAL  228   -38.336  14.031  -4.021   0.00   H
ATOM   3263  CB   VAL  228   -36.982  14.365  -5.635  25.62   C
ATOM   3264  HB   VAL  228   -37.038  14.471  -6.687   0.00   H
ATOM   3265  CG1  VAL  228   -36.245  15.567  -5.063  23.01   C
ATOM   3266  HG11 VAL  228   -36.772  16.453  -5.307   0.00   H
ATOM   3267  HG12 VAL  228   -36.180  15.473  -4.010   0.00   H
ATOM   3268  HG13 VAL  228   -35.270  15.612  -5.474   0.00   H
```

FIGURE 6- 44 -

```
ATOM   3269  CG2  VAL  228   -36.222  13.104  -5.295  24.29  C
ATOM   3270  HG21 VAL  228   -36.166  12.998  -4.243   0.00  H
ATOM   3271  HG22 VAL  228   -36.724  12.268  -5.708   0.00  H
ATOM   3272  HG23 VAL  228   -35.244  13.162  -5.696   0.00  H
ATOM   3273  C    VAL  228   -39.094  15.647  -5.135  25.24  C
ATOM   3274  O    VAL  228   -39.371  16.155  -6.227  25.50  O
ATOM   3275  N    TER  229   -39.348  16.233  -3.969  24.31  N
ATOM   3276  HN   TER  229   -39.033  15.750  -3.141   0.00  H
ATOM   3277  CA   TER  229   -40.047  17.515  -3.848  22.82  C
ATOM   3278  HA   TER  229   -40.637  17.678  -4.712   0.00  H
ATOM   3279  CB   TER  229   -40.947  17.494  -2.616  20.04  C
ATOM   3280  HB   TER  229   -41.564  18.355  -2.615   0.00  H
ATOM   3281  CG1  TER  229   -40.133  17.477  -1.437  16.03  O
ATOM   3282  HG1  TER  229   -40.700  17.464  -0.654   0.00  H
ATOM   3283  CG2  TER  229   -41.820  16.259  -2.629  17.89  C
ATOM   3284  HG21 TER  229   -42.423  16.262  -3.499   0.00  H
ATOM   3285  HG22 TER  229   -41.208  15.394  -2.627   0.00  H
ATOM   3286  HG23 TER  229   -42.439  16.256  -1.770   0.00  H
ATOM   3287  C    TER  229   -39.175  18.765  -3.744  24.33  C
ATOM   3288  O    TER  229   -37.989  18.697  -3.426  24.58  O
ATOM   3289  N    GLU  230   -39.779  19.917  -4.001  25.36  N
ATOM   3290  HN   GLU  230   -40.753  19.919  -4.266   0.00  H
ATOM   3291  CA   GLU  230   -39.049  21.171  -3.904  26.88  C
ATOM   3292  HA   GLU  230   -38.272  21.184  -4.624   0.00  H
ATOM   3293  CB   GLU  230   -39.981  22.363  -4.159  29.09  C
ATOM   3294  HB2  GLU  230   -40.742  22.380  -3.423   0.00  H
ATOM   3295  HB3  GLU  230   -39.424  23.263  -4.111   0.00  H
ATOM   3296  CG   GLU  230   -40.675  22.345  -5.511  32.43  C
ATOM   3297  HG2  GLU  230   -40.843  23.339  -5.835   0.00  H
ATOM   3298  HG3  GLU  230   -40.063  21.843  -6.215   0.00  H
ATOM   3299  CD   GLU  230   -42.017  21.634  -5.467  35.24  C
ATOM   3300  OE1  GLU  230   -42.103  20.532  -4.862  36.17  O1-
ATOM   3301  OE2  GLU  230   -42.982  22.183  -6.044  35.06  O
ATOM   3302  C    GLU  230   -38.480  21.259  -2.491  25.90  C
ATOM   3303  O    GLU  230   -37.381  21.772  -2.263  25.63  O
ATOM   3304  N    SER  231   -39.243  20.738  -1.541  24.29  N
ATOM   3305  HN   SER  231   -40.127  20.325  -1.799   0.00  H
ATOM   3306  CA   SER  231   -38.830  20.754  -0.156  22.81  C
ATOM   3307  HA   SER  231   -38.567  21.741   0.123   0.00  H
ATOM   3308  CB   SER  231   -39.977  20.267   0.719  20.49  C
ATOM   3309  HB2  SER  231   -40.806  20.917   0.609   0.00  H
ATOM   3310  HB3  SER  231   -40.254  19.288   0.425   0.00  H
ATOM   3311  OG   SER  231   -39.598  20.242   2.076  18.36  O
ATOM   3312  HG   SER  231   -40.340  19.930   2.612   0.00  H
ATOM   3313  C    SER  231   -37.595  19.873   0.029  24.01  C
ATOM   3314  O    SER  231   -36.629  20.290   0.665  25.37  O
ATOM   3315  N    ASP  232   -37.622  18.665  -0.534  22.90  N
ATOM   3316  HN   ASP  232   -38.446  18.388  -1.046   0.00  H
ATOM   3317  CA   ASP  232   -36.491  17.749  -0.421  22.68  C
ATOM   3318  HA   ASP  232   -36.327  17.515   0.599   0.00  H
ATOM   3319  CB   ASP  232   -36.757  16.450  -1.186  23.61  C
ATOM   3320  HB2  ASP  232   -37.018  16.677  -2.187   0.00  H
ATOM   3321  HB3  ASP  232   -35.885  15.849  -1.176   0.00  H
ATOM   3322  CG   ASP  232   -37.882  15.638  -0.590  26.72  C
ATOM   3323  OD1  ASP  232   -38.018  15.625   0.660  24.14  O
ATOM   3324  OD2  ASP  232   -38.616  14.995  -1.378  27.31  O1-
ATOM   3325  C    ASP  232   -35.201  18.361  -0.958  21.99  C
ATOM   3326  O    ASP  232   -34.133  18.228  -0.354  20.73  O
ATOM   3327  N    ILE  233   -35.313  19.020  -2.106  20.97  N
ATOM   3328  HN   ILE  233   -36.229  19.072  -2.526   0.00  H
ATOM   3329  CA   ILE  233   -34.178  19.653  -2.757  20.24  C
ATOM   3330  HA   ILE  233   -33.357  18.984  -2.765   0.00  H
ATOM   3331  CB   ILE  233   -34.581  20.015  -4.217  18.35  C
ATOM   3332  HB   ILE  233   -35.505  20.532  -4.210   0.00  H
ATOM   3333  CG2  ILE  233   -33.550  20.904  -4.903  14.51  C
ATOM   3334  HG21 ILE  233   -33.445  21.807  -4.360   0.00  H
ATOM   3335  HG22 ILE  233   -32.618  20.402  -4.937   0.00  H
ATOM   3336  HG23 ILE  233   -33.870  21.120  -5.889   0.00  H
ATOM   3337  CG1  ILE  233   -34.739  18.713  -5.001  14.92  C
ATOM   3338  HG12 ILE  233   -33.789  18.382  -5.331   0.00  H
ATOM   3339  HG13 ILE  233   -35.172  17.975  -4.377   0.00  H
ATOM   3340  CD1  ILE  233   -35.617  18.831  -6.224  12.96  C
ATOM   3341  HD11 ILE  233   -36.588  19.139  -5.933   0.00  H
ATOM   3342  HD12 ILE  233   -35.204  19.546  -6.887   0.00  H
ATOM   3343  HD13 ILE  233   -35.675  17.891  -6.709   0.00  H
ATOM   3344  C    ILE  233   -33.672  20.857  -1.933  21.80  C
```

FIGURE 6-45-

```
ATOM   3345  O    ILE  233   -32.468  21.134  -1.895  22.06   O
ATOM   3346  N    ARG  234   -34.573  21.548  -1.243  21.53   N
ATOM   3347  HN   ARG  234   -35.549  21.299  -1.303   0.00   H
ATOM   3348  CA   ARG  234   -34.155  22.665  -0.400  21.34   C
ATOM   3349  HA   ARG  234   -33.395  23.214  -0.893   0.00   H
ATOM   3350  CB   ARG  234   -35.335  23.598  -0.116  21.32   C
ATOM   3351  HB2  ARG  234   -36.239  23.050  -0.170   0.00   H
ATOM   3352  HB3  ARG  234   -35.231  24.013   0.853   0.00   H
ATOM   3353  CG   ARG  234   -35.420  24.737  -1.105  22.34   C
ATOM   3354  HG2  ARG  234   -34.691  25.467  -0.867   0.00   H
ATOM   3355  HG3  ARG  234   -35.245  24.369  -2.083   0.00   H
ATOM   3356  CD   ARG  234   -36.767  25.390  -1.080  26.50   C
ATOM   3357  HD2  ARG  234   -37.519  24.652  -1.182   0.00   H
ATOM   3358  HD3  ARG  234   -36.895  25.899  -0.161   0.00   H
ATOM   3359  NE   ARG  234   -36.926  26.358  -2.165  29.20   N1-
ATOM   3360  HE   ARG  234   -36.135  26.902  -2.475   0.00   H
ATOM   3361  CZ   ARG  234   -38.078  26.578  -2.792  27.52   C
ATOM   3362  NH1  ARG  234   -39.161  25.897  -2.441  29.98   N
ATOM   3363  HH11 ARG  234   -40.036  26.062  -2.915   0.00   H
ATOM   3364  HH12 ARG  234   -39.109  25.214  -1.700   0.00   H
ATOM   3365  NH2  ARG  234   -38.154  27.474  -3.762  26.45   N
ATOM   3366  HH21 ARG  234   -39.032  27.635  -4.233   0.00   H
ATOM   3367  HH22 ARG  234   -37.334  27.997  -4.031   0.00   H
ATOM   3368  C    ARG  234   -33.544  22.162   0.909  20.81   C
ATOM   3369  O    ARG  234   -32.665  22.807   1.481  21.08   O
ATOM   3370  N    VAL  235   -34.010  21.011   1.378  20.04   N
ATOM   3371  HN   VAL  235   -34.747  20.549   0.866   0.00   H
ATOM   3372  CA   VAL  235   -33.484  20.412   2.600  20.93   C
ATOM   3373  HA   VAL  235   -33.491  21.131   3.377   0.00   H
ATOM   3374  CB   VAL  235   -34.326  19.200   3.054  20.19   C
ATOM   3375  HB   VAL  235   -34.498  18.560   2.228   0.00   H
ATOM   3376  CG1  VAL  235   -33.576  18.410   4.099  21.38   C
ATOM   3377  HG11 VAL  235   -32.661  18.065   3.692   0.00   H
ATOM   3378  HG12 VAL  235   -33.379  19.029   4.935   0.00   H
ATOM   3379  HG13 VAL  235   -34.162  17.582   4.403   0.00   H
ATOM   3380  CG2  VAL  235   -35.650  19.660   3.603  19.54   C
ATOM   3381  HG21 VAL  235   -35.486  20.297   4.433   0.00   H
ATOM   3382  HG22 VAL  235   -36.179  20.187   2.852   0.00   H
ATOM   3383  HG23 VAL  235   -36.216  18.819   3.910   0.00   H
ATOM   3384  C    VAL  235   -32.089  19.924   2.263  21.75   C
ATOM   3385  O    VAL  235   -31.140  20.129   3.013  21.92   O
ATOM   3386  N    GLU  236   -31.981  19.264   1.120  22.70   N
ATOM   3387  HN   GLU  236   -32.816  19.116   0.573   0.00   H
ATOM   3388  CA   GLU  236   -30.707  18.759   0.649  23.77   C
ATOM   3389  HA   GLU  236   -30.369  17.993   1.298   0.00   H
ATOM   3390  CB   GLU  236   -30.904  18.205  -0.756  24.79   C
ATOM   3391  HB2  GLU  236   -31.407  17.275  -0.701   0.00   H
ATOM   3392  HB3  GLU  236   -31.481  18.886  -1.326   0.00   H
ATOM   3393  CG   GLU  236   -29.656  17.951  -1.559  25.93   C
ATOM   3394  HG2  GLU  236   -29.133  18.862  -1.696   0.00   H
ATOM   3395  HG3  GLU  236   -29.038  17.263  -1.043   0.00   H
ATOM   3396  CD   GLU  236   -29.985  17.374  -2.923  29.61   C
ATOM   3397  OE1  GLU  236   -29.102  17.423  -3.813  31.11   O1-
ATOM   3398  OE2  GLU  236   -31.125  16.866  -3.103  28.65   O
ATOM   3399  C    GLU  236   -29.725  19.937   0.654  25.12   C
ATOM   3400  O    GLU  236   -28.571  19.813   1.083  25.08   O
ATOM   3401  N    GLU  237   -30.198  21.092   0.200  23.15   N
ATOM   3402  HN   GLU  237   -31.150  21.148  -0.130   0.00   H
ATOM   3403  CA   GLU  237   -29.355  22.267   0.178  22.47   C
ATOM   3404  HA   GLU  237   -28.498  22.075  -0.413   0.00   H
ATOM   3405  CB   GLU  237   -30.085  23.464  -0.407  23.00   C
ATOM   3406  HB2  GLU  237   -30.679  23.150  -1.226   0.00   H
ATOM   3407  HB3  GLU  237   -30.706  23.896   0.334   0.00   H
ATOM   3408  CG   GLU  237   -29.135  24.529  -0.900  23.19   C
ATOM   3409  HG2  GLU  237   -28.247  24.504  -0.324   0.00   H
ATOM   3410  HG3  GLU  237   -28.901  24.350  -1.917   0.00   H
ATOM   3411  CD   GLU  237   -29.710  25.911  -0.797  25.59   C
ATOM   3412  OE1  GLU  237   -30.905  26.082  -1.111  25.15   O1-
ATOM   3413  OE2  GLU  237   -28.958  26.827  -0.409  26.48   O
ATOM   3414  C    GLU  237   -28.918  22.620   1.589  23.82   C
ATOM   3415  O    GLU  237   -27.742  22.902   1.816  24.75   O
ATOM   3416  N    SER  238   -29.852  22.624   2.537  21.97   N
ATOM   3417  HN   SER  238   -30.809  22.396   2.314   0.00   H
ATOM   3418  CA   SER  238   -29.486  22.958   3.896  20.50   C
ATOM   3419  HA   SER  238   -29.159  23.964   3.936   0.00   H
ATOM   3420  CB   SER  238   -30.676  22.790   4.831  21.00   C
```

FIGURE 6- 46 -

```
ATOM   3421  HB2  SER   238    -30.469   23.265    5.755    0.00       H
ATOM   3422  HB3  SER   238    -31.534   23.230    4.393    0.00       H
ATOM   3423  OG   SER   238    -30.947   21.425    5.078   20.61       O
ATOM   3424  HG   SER   238    -31.705   21.350    5.673    0.00       H
ATOM   3425  C    SER   238    -28.341   22.047    4.327   21.85       C
ATOM   3426  O    SER   238    -27.534   22.412    5.189   21.75       O
ATOM   3427  N    ILE   239    -28.258   20.861    3.734   20.90       N
ATOM   3428  HN   ILE   239    -28.938   20.574    3.046    0.00       H
ATOM   3429  CA   ILE   239    -27.164   19.971    4.092   22.90       C
ATOM   3430  HA   ILE   239    -27.015   19.999    5.140    0.00       H
ATOM   3431  CB   ILE   239    -27.435   18.502    3.691   21.00       C
ATOM   3432  HB   ILE   239    -27.623   18.449    2.650    0.00       H
ATOM   3433  CG2  ILE   239    -26.211   17.646    4.033   18.83       C
ATOM   3434  HG21 ILE   239    -25.368   18.007    3.503    0.00       H
ATOM   3435  HG22 ILE   239    -26.023   17.699    5.074    0.00       H
ATOM   3436  HG23 ILE   239    -26.396   16.640    3.759    0.00       H
ATOM   3437  CG1  ILE   239    -28.653   17.969    4.455   20.79       C
ATOM   3438  HG12 ILE   239    -28.424   17.910    5.487    0.00       H
ATOM   3439  HG13 ILE   239    -29.473   18.624    4.313    0.00       H
ATOM   3440  CD1  ILE   239    -29.107   16.593    4.024   18.82       C
ATOM   3441  HD11 ILE   239    -29.370   16.613    2.998    0.00       H
ATOM   3442  HD12 ILE   239    -28.321   15.899    4.173    0.00       H
ATOM   3443  HD13 ILE   239    -29.948   16.303    4.599    0.00       H
ATOM   3444  C    ILE   239    -25.876   20.457    3.428   24.22       C
ATOM   3445  O    ILE   239    -24.852   20.568    4.079   28.20       O
ATOM   3446  N    TYR   240    -25.915   20.759    2.138   24.26       N
ATOM   3447  HN   TYR   240    -26.770   20.648    1.614    0.00       H
ATOM   3448  CA   TYR   240    -24.717   21.253    1.478   23.43       C
ATOM   3449  HA   TYR   240    -23.957   20.517    1.529    0.00       H
ATOM   3450  CB   TYR   240    -25.002   21.569    0.011   23.86       C
ATOM   3451  HB2  TYR   240    -25.752   22.314   -0.050    0.00       H
ATOM   3452  HB3  TYR   240    -24.117   21.920   -0.453    0.00       H
ATOM   3453  CG   TYR   240    -25.493   20.397   -0.795   23.46       C
ATOM   3454  CD1  TYR   240    -24.992   19.117   -0.554   23.87       C
ATOM   3455  HD1  TYR   240    -24.291   18.951    0.246    0.00       H
ATOM   3456  CE1  TYR   240    -25.391   18.038   -1.331   26.60       C
ATOM   3457  HE1  TYR   240    -25.000   17.055   -1.129    0.00       H
ATOM   3458  CD2  TYR   240    -26.394   20.573   -1.836   24.06       C
ATOM   3459  HD2  TYR   240    -26.794   21.552   -2.042    0.00       H
ATOM   3460  CE2  TYR   240    -26.804   19.500   -2.626   24.86       C
ATOM   3461  HE2  TYR   240    -27.508   19.658   -3.426    0.00       H
ATOM   3462  CZ   TYR   240    -26.295   18.236   -2.368   27.01       C
ATOM   3463  OH   TYR   240    -26.657   17.177   -3.162   29.35       O
ATOM   3464  HH   TYR   240    -26.197   16.380   -2.866    0.00       H
ATOM   3465  C    TYR   240    -24.197   22.524    2.155   23.54       C
ATOM   3466  O    TYR   240    -22.995   22.663    2.356   23.83       O
ATOM   3467  N    GLN   241    -25.104   23.445    2.490   22.29       N
ATOM   3468  HN   GLN   241    -26.069   23.229    2.290    0.00       H
ATOM   3469  CA   GLN   241    -24.754   24.719    3.119   20.85       C
ATOM   3470  HA   GLN   241    -24.023   25.213    2.533    0.00       H
ATOM   3471  CB   GLN   241    -25.989   25.610    3.231   22.02       C
ATOM   3472  HB2  GLN   241    -26.778   25.065    3.680    0.00       H
ATOM   3473  HB3  GLN   241    -25.761   26.456    3.826    0.00       H
ATOM   3474  CG   GLN   241    -26.535   26.147    1.913   22.64       C
ATOM   3475  HG2  GLN   241    -26.657   25.347    1.229    0.00       H
ATOM   3476  HG3  GLN   241    -27.471   26.613    2.082    0.00       H
ATOM   3477  CD   GLN   241    -25.622   27.170    1.267   23.67       C
ATOM   3478  OE1  GLN   241    -24.658   27.627    1.874   25.29       O
ATOM   3479  NE2  GLN   241    -25.934   27.546    0.035   22.68       N
ATOM   3480  HE21 GLN   241    -26.736   27.144   -0.427    0.00       H
ATOM   3481  HE22 GLN   241    -25.370   28.234   -0.441    0.00       H
ATOM   3482  C    GLN   241    -24.114   24.587    4.500   22.39       C
ATOM   3483  O    GLN   241    -23.792   25.600    5.150   22.08       O
ATOM   3484  N    CYS   242    -23.937   23.352    4.958   20.83       N
ATOM   3485  HN   CYS   242    -24.250   22.568    4.405    0.00       H
ATOM   3486  CA   CYS   242    -23.299   23.125    6.244   19.52       C
ATOM   3487  HA   CYS   242    -23.536   23.921    6.901    0.00       H
ATOM   3488  CB   CYS   242    -23.814   21.840    6.875   18.89       C
ATOM   3489  HB2  CYS   242    -23.961   21.111    6.121    0.00       H
ATOM   3490  HB3  CYS   242    -23.106   21.484    7.578    0.00       H
ATOM   3491  SG   CYS   242    -25.372   22.063    7.732   24.51       S
ATOM   3492  HG   CYS   242    -25.736   20.973    8.225    0.00       H
ATOM   3493  C    CYS   242    -21.788   23.050    6.088   19.01       C
ATOM   3494  O    CYS   242    -21.054   23.205    7.061   18.68       O
ATOM   3495  N    CYS   243    -21.332   22.816    4.862   18.46       N
ATOM   3496  HN   CYS   243    -22.009   22.707    4.121    0.00       H
```

FIGURE 6- 47 -

```
ATOM   3497  CA   CYS  243   -19.909  22.715   4.569  21.22  C
ATOM   3498  HA   CYS  243   -19.448  22.074   5.275   0.00  H
ATOM   3499  CB   CYS  243   -19.689  22.152   3.160  20.34  C
ATOM   3500  HB2  CYS  243   -20.085  22.826   2.445   0.00  H
ATOM   3501  HB3  CYS  243   -18.652  22.025   2.989   0.00  H
ATOM   3502  SG   CYS  243   -20.460  20.556   2.841  24.56  S
ATOM   3503  HG   CYS  243   -20.213  20.201   1.668   0.00  H
ATOM   3504  C    CYS  243   -19.260  24.090   4.645  22.57  C
ATOM   3505  O    CYS  243   -19.955  25.102   4.674  23.21  C
ATOM   3506  N    ASP  244   -17.930  24.118   4.694  22.46  N
ATOM   3507  HN   ASP  244   -17.428  23.243   4.717   0.00  H
ATOM   3508  CA   ASP  244   -17.201  25.373   4.714  23.35  C
ATOM   3509  HA   ASP  244   -17.772  26.105   5.224   0.00  H
ATOM   3510  CB   ASP  244   -15.855  25.215   5.427  22.79  C
ATOM   3511  HB2  ASP  244   -16.018  24.888   6.421   0.00  H
ATOM   3512  HB3  ASP  244   -15.265  24.501   4.913   0.00  H
ATOM   3513  CG   ASP  244   -15.070  26.515   5.486  22.48  C
ATOM   3514  OD1  ASP  244   -14.469  26.923   4.469  22.31  O
ATOM   3515  OD2  ASP  244   -15.069  27.147   6.559  22.91  O1-
ATOM   3516  C    ASP  244   -16.989  25.681   3.233  24.69  C
ATOM   3517  O    ASP  244   -16.121  25.093   2.574  26.69  O
ATOM   3518  N    LEU  245   -17.786  26.607   2.714  24.38  N
ATOM   3519  HN   LEU  245   -18.439  27.075   3.324   0.00  H
ATOM   3520  CA   LEU  245   -17.734  26.952   1.302  24.07  C
ATOM   3521  HA   LEU  245   -17.109  26.265   0.794   0.00  H
ATOM   3522  CB   LEU  245   -19.144  26.889   0.726  21.21  C
ATOM   3523  HB2  LEU  245   -19.748  27.624   1.191   0.00  H
ATOM   3524  HB3  LEU  245   -19.108  27.070  -0.317   0.00  H
ATOM   3525  CG   LEU  245   -19.839  25.550   0.923  18.49  C
ATOM   3526  HG   LEU  245   -19.617  25.176   1.889   0.00  H
ATOM   3527  CD1  LEU  245   -21.320  25.728   0.786  21.24  C
ATOM   3528  HD11 LEU  245   -21.662  26.413   1.517   0.00  H
ATOM   3529  HD12 LEU  245   -21.543  26.102  -0.180   0.00  H
ATOM   3530  HD13 LEU  245   -21.802  24.795   0.923   0.00  H
ATOM   3531  CD2  LEU  245   -19.317  24.557  -0.072  18.12  C
ATOM   3532  HD21 LEU  245   -19.505  24.908  -1.053   0.00  H
ATOM   3533  HD22 LEU  245   -18.274  24.434   0.066   0.00  H
ATOM   3534  HD23 LEU  245   -19.803  23.627   0.069   0.00  H
ATOM   3535  C    LEU  245   -17.145  28.312   0.987  23.24  C
ATOM   3536  O    LEU  245   -17.162  29.219   1.811  23.79  C
ATOM   3537  N    ALA  246   -16.612  28.440  -0.219  22.79  N
ATOM   3538  HN   ALA  246   -16.583  27.642  -0.835   0.00  H
ATOM   3539  CA   ALA  246   -16.072  29.715  -0.657  23.23  C
ATOM   3540  HA   ALA  246   -15.430  30.102   0.091   0.00  H
ATOM   3541  CB   ALA  246   -15.284  29.538  -1.945  20.84  C
ATOM   3542  HB1  ALA  246   -14.486  28.862  -1.780   0.00  H
ATOM   3543  HB2  ALA  246   -15.921  29.155  -2.699   0.00  H
ATOM   3544  HB3  ALA  246   -14.896  30.474  -2.253   0.00  H
ATOM   3545  C    ALA  246   -17.291  30.629  -0.896  23.71  C
ATOM   3546  O    ALA  246   -18.365  30.164  -1.323  22.45  C
ATOM   3547  N    PRO  247   -17.151  31.936  -0.615  22.42  N
ATOM   3548  CD   PRO  247   -16.009  32.692  -0.079  21.06  C
ATOM   3549  HD2  PRO  247   -15.602  32.175   0.751   0.00  H
ATOM   3550  HD3  PRO  247   -15.269  32.793  -0.830   0.00  H
ATOM   3551  CA   PRO  247   -18.282  32.831  -0.829  22.25  C
ATOM   3552  HA   PRO  247   -18.976  32.719  -0.037   0.00  H
ATOM   3553  CB   PRO  247   -17.632  34.205  -0.765  20.76  C
ATOM   3554  HB2  PRO  247   -17.192  34.431  -1.701   0.00  H
ATOM   3555  HB3  PRO  247   -18.366  34.933  -0.535   0.00  H
ATOM   3556  CG   PRO  247   -16.655  34.013   0.302  19.17  C
ATOM   3557  HG2  PRO  247   -15.970  34.821   0.303   0.00  H
ATOM   3558  HG3  PRO  247   -17.155  33.973   1.235   0.00  H
ATOM   3559  C    PRO  247   -19.036  32.574  -2.129  22.43  C
ATOM   3560  O    PRO  247   -20.246  32.373  -2.108  24.40  C
ATOM   3561  N    GLU  248   -18.340  32.550  -3.257  22.02  N
ATOM   3562  HN   GLU  248   -17.339  32.677  -3.255   0.00  H
ATOM   3563  CA   GLU  248   -19.041  32.337  -4.508  22.69  C
ATOM   3564  HA   GLU  248   -19.913  32.937  -4.531   0.00  H
ATOM   3565  CB   GLU  248   -18.138  32.715  -5.673  23.99  C
ATOM   3566  HB2  GLU  248   -17.248  32.143  -5.630   0.00  H
ATOM   3567  HB3  GLU  248   -18.639  32.520  -6.585   0.00  H
ATOM   3568  CG   GLU  248   -17.750  34.176  -5.661  24.07  C
ATOM   3569  HG2  GLU  248   -18.616  34.770  -5.528   0.00  H
ATOM   3570  HG3  GLU  248   -17.074  34.355  -4.866   0.00  H
ATOM   3571  CD   GLU  248   -17.085  34.607  -6.941  26.12  C
ATOM   3572  OE1  GLU  248   -16.744  33.719  -7.756  25.39  O1-
```

FIGURE 6- 48 -

```
ATOM   3573  OE2  GLU  248   -16.901  35.833  -7.130  28.35   O
ATOM   3574  C    GLU  248   -19.588  30.920  -4.667  23.59   C
ATOM   3575  O    GLU  248   -20.535  30.693  -5.420  25.19   O
ATOM   3576  N    ALA  249   -19.005  29.965  -3.957  23.15   N
ATOM   3577  HN   ALA  249   -18.223  30.189  -3.360   0.00   H
ATOM   3578  CA   ALA  249   -19.489  28.599  -4.037  21.33   C
ATOM   3579  HA   ALA  249   -19.619  28.330  -5.053   0.00   H
ATOM   3580  CB   ALA  249   -18.498  27.664  -3.400  20.82   C
ATOM   3581  HB1  ALA  249   -17.570  27.735  -3.906   0.00   H
ATOM   3582  HB2  ALA  249   -18.367  27.928  -2.383   0.00   H
ATOM   3583  HB3  ALA  249   -18.859  26.670  -3.463   0.00   H
ATOM   3584  C    ALA  249   -20.807  28.571  -3.278  22.03   C
ATOM   3585  O    ALA  249   -21.816  28.051  -3.748  21.54   O
ATOM   3586  N    ARG  250   -20.804  29.160  -2.095  22.59   N
ATOM   3587  HN   ARG  250   -19.963  29.594  -1.744   0.00   H
ATOM   3588  CA   ARG  250   -22.014  29.181  -1.302  23.29   C
ATOM   3589  HA   ARG  250   -22.299  28.189  -1.067   0.00   H
ATOM   3590  CB   ARG  250   -21.776  29.955  -0.008  23.90   C
ATOM   3591  HB2  ARG  250   -20.878  29.621   0.443   0.00   H
ATOM   3592  HB3  ARG  250   -21.700  30.989  -0.224   0.00   H
ATOM   3593  CG   ARG  250   -22.879  29.790   1.013  26.71   C
ATOM   3594  HG2  ARG  250   -23.757  30.268   0.664   0.00   H
ATOM   3595  HG3  ARG  250   -23.072  28.759   1.160   0.00   H
ATOM   3596  CD   ARG  250   -22.503  30.402   2.355  25.86   C
ATOM   3597  HD2  ARG  250   -22.181  31.400   2.210   0.00   H
ATOM   3598  HD3  ARG  250   -23.346  30.393   2.996   0.00   H
ATOM   3599  NE   ARG  250   -21.427  29.684   3.029  24.74   N1+
ATOM   3600  HE   ARG  250   -20.476  30.013   2.953   0.00   H
ATOM   3601  CZ   ARG  250   -21.587  28.590   3.766  25.75   C
ATOM   3602  NH1  ARG  250   -22.791  28.059   3.939  24.65   N
ATOM   3603  HH11 ARG  250   -22.900  27.228   4.501   0.00   H
ATOM   3604  HH12 ARG  250   -23.597  28.486   3.509   0.00   H
ATOM   3605  NH2  ARG  250   -20.532  28.040   4.351  26.82   N
ATOM   3606  HH21 ARG  250   -20.643  27.209   4.913   0.00   H
ATOM   3607  HH22 ARG  250   -19.618  28.452   4.234   0.00   H
ATOM   3608  C    ARG  250   -23.162  29.802  -2.086  23.70   C
ATOM   3609  O    ARG  250   -24.294  29.338  -1.993  23.39   O
ATOM   3610  N    GLN  251   -22.873  30.836  -2.873  24.22   N
ATOM   3611  HN   GLN  251   -21.919  31.162  -2.927   0.00   H
ATOM   3612  CA   GLN  251   -23.918  31.504  -3.654  23.62   C
ATOM   3613  HA   GLN  251   -24.795  31.592  -3.067   0.00   H
ATOM   3614  CB   GLN  251   -23.482  32.899  -4.086  22.35   C
ATOM   3615  HB2  GLN  251   -23.279  33.487  -3.229   0.00   H
ATOM   3616  HB3  GLN  251   -22.608  32.828  -4.680   0.00   H
ATOM   3617  CG   GLN  251   -24.550  33.628  -4.911  22.28   C
ATOM   3618  HG2  GLN  251   -24.134  34.508  -5.328   0.00   H
ATOM   3619  HG3  GLN  251   -24.888  32.994  -5.689   0.00   H
ATOM   3620  CD   GLN  251   -25.758  34.032  -4.083  23.37   C
ATOM   3621  OE1  GLN  251   -26.901  33.740  -4.434  24.45   O
ATOM   3622  NE2  GLN  251   -25.509  34.710  -2.981  22.19   N
ATOM   3623  HE21 GLN  251   -24.557  34.930  -2.728   0.00   H
ATOM   3624  HE22 GLN  251   -26.270  35.010  -2.390   0.00   H
ATOM   3625  C    GLN  251   -24.329  30.720  -4.894  24.81   C
ATOM   3626  O    GLN  251   -25.510  30.693  -5.252  23.72   O
ATOM   3627  N    ALA  252   -23.353  30.103  -5.558  24.34   N
ATOM   3628  HN   ALA  252   -22.406  30.188  -5.221   0.00   H
ATOM   3629  CA   ALA  252   -23.634  29.315  -6.754  22.92   C
ATOM   3630  HA   ALA  252   -24.118  29.924  -7.472   0.00   H
ATOM   3631  CB   ALA  252   -22.339  28.777  -7.351  20.58   C
ATOM   3632  HB1  ALA  252   -21.707  29.586  -7.611   0.00   H
ATOM   3633  HB2  ALA  252   -21.851  28.163  -6.640   0.00   H
ATOM   3634  HB3  ALA  252   -22.559  28.208  -8.217   0.00   H
ATOM   3635  C    ALA  252   -24.566  28.164  -6.391  21.61   C
ATOM   3636  O    ALA  252   -25.487  27.836  -7.142  21.86   O
ATOM   3637  N    ILE  253   -24.322  27.558  -5.235  19.63   N
ATOM   3638  HN   ILE  253   -23.552  27.886  -4.672   0.00   H
ATOM   3639  CA   ILE  253   -25.139  26.442  -4.774  19.39   C
ATOM   3640  HA   ILE  253   -25.180  25.699  -5.528   0.00   H
ATOM   3641  CB   ILE  253   -24.523  25.825  -3.480  19.31   C
ATOM   3642  HB   ILE  253   -24.242  26.602  -2.818   0.00   H
ATOM   3643  CG2  ILE  253   -25.524  24.929  -2.785  18.94   C
ATOM   3644  HG21 ILE  253   -26.380  25.494  -2.520   0.00   H
ATOM   3645  HG22 ILE  253   -25.807  24.144  -3.437   0.00   H
ATOM   3646  HG23 ILE  253   -25.086  24.522  -1.911   0.00   H
ATOM   3647  CG1  ILE  253   -23.255  25.044  -3.844  18.20   C
ATOM   3648  HG12 ILE  253   -23.524  24.096  -4.232   0.00   H
```

FIGURE 6- 49 -

```
ATOM   3649  HG13 ILE   253    -22.706  25.582  -4.573   0.00      H
ATOM   3650  CD1  ILE   253    -22.313  24.791  -2.688  17.19      C
ATOM   3651  HD11 ILE   253    -21.996  25.716  -2.282   0.00      H
ATOM   3652  HD12 ILE   253    -22.813  24.231  -1.941   0.00      H
ATOM   3653  HD13 ILE   253    -21.471  24.249  -3.031   0.00      H
ATOM   3654  C    ILE   253    -26.576  26.908  -4.535  18.09      C
ATOM   3655  O    ILE   253    -27.530  26.216  -4.886  15.97      O
ATOM   3656  N    ARG   254    -26.707  28.096  -3.948  18.29      N
ATOM   3657  HN   ARG   254    -25.850  28.571  -3.708   0.00      H
ATOM   3658  CA   ARG   254    -28.000  28.720  -3.647  17.48      C
ATOM   3659  HA   ARG   254    -28.563  28.080  -3.019   0.00      H
ATOM   3660  CB   ARG   254    -27.736  30.049  -2.941  14.88      C
ATOM   3661  HB2  ARG   254    -27.165  29.876  -2.066   0.00      H
ATOM   3662  HB3  ARG   254    -27.201  30.693  -3.590   0.00      H
ATOM   3663  CG   ARG   254    -28.946  30.822  -2.498  17.07      C
ATOM   3664  HG2  ARG   254    -28.679  31.835  -2.339   0.00      H
ATOM   3665  HG3  ARG   254    -29.694  30.767  -3.246   0.00      H
ATOM   3666  CD   ARG   254    -29.520  30.271  -1.207  19.99      C
ATOM   3667  HD2  ARG   254    -28.731  29.945  -0.581   0.00      H
ATOM   3668  HD3  ARG   254    -30.071  31.029  -0.714   0.00      H
ATOM   3669  NE   ARG   254    -30.420  29.135  -1.397  18.20      N1-
ATOM   3670  HE   ARG   254    -30.100  28.199  -1.197   0.00      H
ATOM   3671  CZ   ARG   254    -31.671  29.247  -1.828  19.52      C
ATOM   3672  NH1  ARG   254    -32.130  30.443  -2.113  20.65      N
ATOM   3673  HH11 ARG   254    -33.131  30.522  -2.440   0.00      H
ATOM   3674  HH12 ARG   254    -31.615  31.271  -2.002   0.00      H
ATOM   3675  NH2  ARG   254    -32.416  28.162  -1.981  19.68      N
ATOM   3676  HH21 ARG   254    -33.367  28.245  -2.308   0.00      H
ATOM   3677  HH22 ARG   254    -32.033  27.253  -1.770   0.00      H
ATOM   3678  C    ARG   254    -28.807  28.953  -4.944  18.01      C
ATOM   3679  O    ARG   254    -29.986  28.607  -5.033  18.58      O
ATOM   3680  N    SER   255    -28.150  29.528  -5.947  17.36      N
ATOM   3681  HN   SER   255    -27.181  29.762  -5.789   0.00      H
ATOM   3682  CA   SER   255    -28.769  29.822  -7.230  15.85      C
ATOM   3683  HA   SER   255    -29.681  30.337  -7.072   0.00      H
ATOM   3684  CB   SER   255    -27.831  30.692  -8.059  14.50      C
ATOM   3685  HB2  SER   255    -26.882  30.227  -8.123   0.00      H
ATOM   3686  HB3  SER   255    -28.230  30.814  -9.032   0.00      H
ATOM   3687  OG   SER   255    -27.682  31.964  -7.459  14.64      O
ATOM   3688  HG   SER   255    -27.035  32.505  -7.994   0.00      H
ATOM   3689  C    SER   255    -29.155  28.586  -8.030  16.93      C
ATOM   3690  O    SER   255    -30.251  28.502  -8.576  16.90      O
ATOM   3691  N    LEU   256    -28.244  27.631  -8.117  17.49      N
ATOM   3692  HN   LEU   256    -27.350  27.759  -7.667   0.00      H
ATOM   3693  CA   LEU   256    -28.520  26.409  -8.850  17.00      C
ATOM   3694  HA   LEU   256    -28.774  26.647  -9.850   0.00      H
ATOM   3695  CB   LEU   256    -27.295  25.506  -8.850  15.32      C
ATOM   3696  HB2  LEU   256    -27.018  25.287  -7.852   0.00      H
ATOM   3697  HB3  LEU   256    -27.520  24.605  -9.360   0.00      H
ATOM   3698  CG   LEU   256    -26.057  26.089  -9.526  14.53      C
ATOM   3699  HG   LEU   256    -25.915  27.087  -9.202   0.00      H
ATOM   3700  CD1  LEU   256    -24.866  25.247  -9.142  12.79      C
ATOM   3701  HD11 LEU   256    -24.747  25.263  -8.090   0.00      H
ATOM   3702  HD12 LEU   256    -25.020  24.250  -9.464   0.00      H
ATOM   3703  HD13 LEU   256    -23.995  25.636  -9.602   0.00      H
ATOM   3704  CD2  LEU   256    -26.246  26.136 -11.026   8.28      C
ATOM   3705  HD21 LEU   256    -26.409  25.156 -11.392   0.00      H
ATOM   3706  HD22 LEU   256    -27.083  26.743 -11.258   0.00      H
ATOM   3707  HD23 LEU   256    -25.379  26.542 -11.478   0.00      H
ATOM   3708  C    LEU   256    -29.683  25.676  -8.212  19.19      C
ATOM   3709  O    LEU   256    -30.395  24.935  -8.890  22.16      O
ATOM   3710  N    THR   257    -29.875  25.877  -6.911  18.81      N
ATOM   3711  HN   THR   257    -29.253  26.499  -6.416   0.00      H
ATOM   3712  CA   THR   257    -30.958  25.219  -6.203  19.00      C
ATOM   3713  HA   THR   257    -30.926  24.178  -6.397   0.00      H
ATOM   3714  CB   THR   257    -30.843  25.441  -4.675  19.61      C
ATOM   3715  HB   THR   257    -30.750  26.477  -4.475   0.00      H
ATOM   3716  OG1  THR   257    -29.693  24.752  -4.171  19.75      O
ATOM   3717  HG1  THR   257    -29.625  24.893  -3.217   0.00      H
ATOM   3718  CG2  THR   257    -32.072  24.914  -3.960  17.63      C
ATOM   3719  HG21 THR   257    -32.931  25.421  -4.315   0.00      H
ATOM   3720  HG22 THR   257    -32.172  23.877  -4.148   0.00      H
ATOM   3721  HG23 THR   257    -31.971  25.076  -2.918   0.00      H
ATOM   3722  C    THR   257    -32.296  25.760  -6.690  21.08      C
ATOM   3723  O    THR   257    -33.163  25.000  -7.117  22.65      O
ATOM   3724  N    GLU   258    -32.461  27.077  -6.641  21.12      N
```

FIGURE 6- 50 -

```
ATOM   3725  HN   GLU  258   -31.705  27.652   -6.300    0.00        H
ATOM   3726  CA   GLU  258   -33.712  27.696   -7.071   21.71        C
ATOM   3727  HA   GLU  258   -34.530  27.136   -6.698    0.00        H
ATOM   3728  CB   GLU  258   -33.796  29.131   -6.535   21.80        C
ATOM   3729  HB2  GLU  258   -32.949  29.678   -6.857    0.00        H
ATOM   3730  HB3  GLU  258   -34.675  29.594   -6.901    0.00        H
ATOM   3731  CG   GLU  258   -33.841  29.260   -5.010   21.94        C
ATOM   3732  HG2  GLU  258   -32.948  28.368   -4.596    0.00        H
ATOM   3733  HG3  GLU  258   -33.935  30.281   -4.745    0.00        H
ATOM   3734  CD   GLU  258   -35.006  28.513   -4.375   21.31        C
ATOM   3735  OE1  GLU  258   -36.100  28.509   -4.966   20.92       O1-
ATOM   3736  OE2  GLU  258   -34.833  27.946   -3.275   21.93        O
ATOM   3737  C    GLU  258   -33.924  27.729   -8.585   21.79        C
ATOM   3738  O    GLU  258   -35.043  27.573   -9.064   22.13        O
ATOM   3739  N    ARG  259   -32.842  27.920   -9.334   22.11        N
ATOM   3740  HN   ARG  259   -31.951  27.980   -8.865    0.00        H
ATOM   3741  CA   ARG  259   -32.912  28.043  -10.788   21.26        C
ATOM   3742  HA   ARG  259   -33.871  28.397  -11.067    0.00        H
ATOM   3743  CB   ARG  259   -31.836  29.035  -11.255   20.53        C
ATOM   3744  HB2  ARG  259   -30.878  28.660  -11.005    0.00        H
ATOM   3745  HB3  ARG  259   -31.903  29.160  -12.304    0.00        H
ATOM   3746  CG   ARG  259   -31.956  30.418  -10.628   19.76        C
ATOM   3747  HG2  ARG  259   -32.845  30.883  -10.966    0.00        H
ATOM   3748  HG3  ARG  259   -31.985  30.326   -9.573    0.00        H
ATOM   3749  CD   ARG  259   -30.779  31.297  -11.004   19.00        C
ATOM   3750  HD2  ARG  259   -30.899  32.254  -10.567    0.00        H
ATOM   3751  HD3  ARG  259   -29.883  30.858  -10.650    0.00        H
ATOM   3752  NE   ARG  259   -30.677  31.457  -12.450   20.99       N1+
ATOM   3753  HE   ARG  259   -31.323  30.975  -13.058    0.00        H
ATOM   3754  CZ   ARG  259   -29.772  32.212  -13.064   19.53        C
ATOM   3755  NH1  ARG  259   -28.877  32.892  -12.364   19.84        N
ATOM   3756  HH11 ARG  259   -28.193  33.463  -12.838    0.00        H
ATOM   3757  HH12 ARG  259   -28.879  32.839  -11.356    0.00        H
ATOM   3758  NH2  ARG  259   -29.755  32.277  -14.383   18.70        N
ATOM   3759  HH21 ARG  259   -29.069  32.850  -14.851    0.00        H
ATOM   3760  HH22 ARG  259   -30.428  31.754  -14.923    0.00        H
ATOM   3761  C    ARG  259   -32.822  26.766  -11.627   22.01        C
ATOM   3762  O    ARG  259   -33.202  26.767  -12.811   22.35        O
ATOM   3763  N    LEU  260   -32.337  25.677  -11.036   20.38        N
ATOM   3764  HN   LEU  260   -32.063  25.705  -10.065    0.00        H
ATOM   3765  CA   LEU  260   -32.202  24.440  -11.796   19.20        C
ATOM   3766  HA   LEU  260   -32.785  24.502  -12.678    0.00        H
ATOM   3767  CB   LEU  260   -30.734  24.226  -12.170   18.83        C
ATOM   3768  HB2  LEU  260   -30.379  25.069  -12.703    0.00        H
ATOM   3769  HB3  LEU  260   -30.160  24.098  -11.289    0.00        H
ATOM   3770  CG   LEU  260   -30.378  23.023  -13.051   18.68        C
ATOM   3771  HG   LEU  260   -30.811  22.147  -12.643    0.00        H
ATOM   3772  CD1  LEU  260   -30.915  23.249  -14.453   19.35        C
ATOM   3773  HD11 LEU  260   -31.967  23.360  -14.414    0.00        H
ATOM   3774  HD12 LEU  260   -30.482  24.126  -14.860    0.00        H
ATOM   3775  HD13 LEU  260   -30.670  22.419  -15.063    0.00        H
ATOM   3776  CD2  LEU  260   -28.874  22.837  -13.081   16.29        C
ATOM   3777  HD21 LEU  260   -28.418  23.708  -13.476    0.00        H
ATOM   3778  HD22 LEU  260   -28.520  22.668  -12.097    0.00        H
ATOM   3779  HD23 LEU  260   -28.633  22.005  -13.691    0.00        H
ATOM   3780  C    LEU  260   -32.713  23.219  -11.047   19.95        C
ATOM   3781  O    LEU  260   -33.562  22.475  -11.548   19.96        O
ATOM   3782  N    TYR  261   -32.204  23.030   -9.833   18.71        N
ATOM   3783  HN   TYR  261   -31.550  23.716   -9.488    0.00        H
ATOM   3784  CA   TYR  261   -32.559  21.885   -9.010   15.35        C
ATOM   3785  HA   TYR  261   -32.455  20.997   -9.577    0.00        H
ATOM   3786  CB   TYR  261   -31.637  21.331   -7.806   13.81        C
ATOM   3787  HB2  TYR  261   -31.790  22.690   -7.205    0.00        H
ATOM   3788  HB3  TYR  261   -31.847  20.961   -7.239    0.00        H
ATOM   3789  CG   TYR  261   -30.171  21.790   -8.173   12.93        C
ATOM   3790  CD1  TYR  261   -29.743  21.181   -9.346   13.38        C
ATOM   3791  HD1  TYR  261   -30.462  20.748  -10.021    0.00        H
ATOM   3792  CE1  TYR  261   -28.388  21.118   -9.672   13.47        C
ATOM   3793  HE1  TYR  261   -28.076  20.644  -10.588    0.00        H
ATOM   3794  CD2  TYR  261   -29.206  22.336   -7.331   12.97        C
ATOM   3795  HD2  TYR  261   -29.502  22.318   -6.414    0.00        H
ATOM   3796  CE2  TYR  261   -27.857  22.274   -7.648   11.39        C
ATOM   3797  HE2  TYR  261   -27.127  22.702   -6.982    0.00        H
ATOM   3798  CZ   TYR  261   -27.452  21.665   -8.816   12.37        C
ATOM   3799  OH   TYR  261   -26.101  21.591   -9.115   14.01        O
ATOM   3800  HH   TYR  261   -25.982  21.127   -9.955    0.00        H
```

FIGURE 6- 51 -

```
ATOM   3801  C    TYR  261   -34.003  21.692  -8.564   15.77   C
ATOM   3802  O    TYR  261   -34.449  20.560  -8.539   17.32   O
ATOM   3803  N    ILE  262   -34.745  22.742  -8.208   16.34   N
ATOM   3804  HN   ILE  262   -34.360  23.675  -8.222    0.00   H
ATOM   3805  CA   ILE  262   -36.139  22.528  -7.792   18.02   C
ATOM   3806  HA   ILE  262   -36.212  21.617  -7.257    0.00   H
ATOM   3807  CB   ILE  262   -36.695  23.657  -6.869   18.41   C
ATOM   3808  HB   ILE  262   -37.733  23.511  -6.719    0.00   H
ATOM   3809  CG2  ILE  262   -36.001  23.642  -5.526   20.49   C
ATOM   3810  HG21 ILE  262   -36.162  22.707  -5.056    0.00   H
ATOM   3811  HG22 ILE  262   -34.962  23.794  -5.664    0.00   H
ATOM   3812  HG23 ILE  262   -36.393  24.415  -4.917    0.00   H
ATOM   3813  CG1  ILE  262   -36.556  25.003  -7.550   17.70   C
ATOM   3814  HG12 ILE  262   -35.542  25.163  -7.812    0.00   H
ATOM   3815  HG13 ILE  262   -37.153  25.020  -8.424    0.00   H
ATOM   3816  CD1  ILE  262   -36.984  26.147  -6.692   20.99   C
ATOM   3817  HD11 ILE  262   -38.002  26.028  -6.427    0.00   H
ATOM   3818  HD12 ILE  262   -36.391  26.171  -5.815    0.00   H
ATOM   3819  HD13 ILE  262   -36.862  27.054  -7.226    0.00   H
ATOM   3820  C    ILE  262   -37.075  22.426  -8.993   19.22   C
ATOM   3821  O    ILE  262   -38.282  22.198  -8.839   20.28   O
ATOM   3822  N    GLY  263   -36.529  22.602 -10.191   19.27   N
ATOM   3823  HN   GLY  263   -35.545  22.805 -10.283    0.00   H
ATOM   3824  CA   GLY  263   -37.362  22.500 -11.373   20.47   C
ATOM   3825  HA2  GLY  263   -37.208  21.559 -11.833    0.00   H
ATOM   3826  HA3  GLY  263   -38.380  22.595 -11.097    0.00   H
ATOM   3827  C    GLY  263   -37.034  23.582 -12.373   21.14   C
ATOM   3828  O    GLY  263   -36.065  24.309 -12.196   22.13   O
ATOM   3829  N    GLY  264   -37.847  23.695 -13.418   21.73   N
ATOM   3830  HN   GLY  264   -38.637  23.071 -13.492    0.00   H
ATOM   3831  CA   GLY  264   -37.614  24.694 -14.442   21.13   C
ATOM   3832  HA2  GLY  264   -38.072  25.605 -14.157    0.00   H
ATOM   3833  HA3  GLY  264   -36.572  24.843 -14.559    0.00   H
ATOM   3834  C    GLY  264   -38.206  24.216 -15.744   21.31   C
ATOM   3835  O    GLY  264   -38.713  23.102 -15.801   23.09   O
ATOM   3836  N    PRO  265   -38.137  25.016 -16.816   21.16   N
ATOM   3837  CD   PRO  265   -37.473  26.325 -16.873   20.26   C
ATOM   3838  HD2  PRO  265   -38.092  27.055 -16.419    0.00   H
ATOM   3839  HD3  PRO  265   -36.549  26.275 -16.358    0.00   H
ATOM   3840  CA   PRO  265   -38.681  24.662 -18.136   21.39   C
ATOM   3841  HA   PRO  265   -39.700  24.393 -18.037    0.00   H
ATOM   3842  CB   PRO  265   -38.559  25.965 -18.909   18.74   C
ATOM   3843  HB2  PRO  265   -38.504  25.757 -19.946    0.00   H
ATOM   3844  HB3  PRO  265   -39.406  26.571 -18.715    0.00   H
ATOM   3845  CG   PRO  265   -37.312  26.527 -18.367   20.47   C
ATOM   3846  HG2  PRO  265   -36.485  25.998 -18.764    0.00   H
ATOM   3847  HG3  PRO  265   -37.239  27.549 -18.635    0.00   H
ATOM   3848  C    PRO  265   -38.008  23.491 -18.864   21.74   C
ATOM   3849  O    PRO  265   -36.791  23.342 -18.840   21.67   O
ATOM   3850  N    LEU  266   -38.827  22.675 -19.524   23.36   N
ATOM   3851  HN   LEU  266   -39.813  22.889 -19.494    0.00   H
ATOM   3852  CA   LEU  266   -38.354  21.510 -20.270   23.52   C
ATOM   3853  HA   LEU  266   -37.354  21.297 -19.994    0.00   H
ATOM   3854  CB   LEU  266   -39.246  20.301 -19.945   23.76   C
ATOM   3855  HB2  LEU  266   -40.245  20.515 -20.223    0.00   H
ATOM   3856  HB3  LEU  266   -38.903  19.455 -20.482    0.00   H
ATOM   3857  CG   LEU  266   -39.316  19.854 -18.480   23.68   C
ATOM   3858  HG   LEU  266   -39.389  20.705 -17.854    0.00   H
ATOM   3859  CD1  LEU  266   -40.532  18.974 -18.279   24.97   C
ATOM   3860  HD11 LEU  266   -41.406  19.519 -18.524    0.00   H
ATOM   3861  HD12 LEU  266   -40.459  18.123 -18.905    0.00   H
ATOM   3862  HD13 LEU  266   -40.581  18.665 -17.267    0.00   H
ATOM   3863  CD2  LEU  266   -38.047  19.123 -18.089   21.73   C
ATOM   3864  HD21 LEU  266   -37.927  18.270 -18.704    0.00   H
ATOM   3865  HD22 LEU  266   -37.216  19.767 -18.213    0.00   H
ATOM   3866  HD23 LEU  266   -38.111  18.821 -17.076    0.00   H
ATOM   3867  C    LEU  266   -38.365  21.774 -21.782   22.57   C
ATOM   3868  O    LEU  266   -39.391  22.117 -22.347   21.55   O
ATOM   3869  N    THR  267   -37.221  21.611 -22.435   23.37   N
ATOM   3870  HN   THR  267   -36.400  21.327 -21.922    0.00   H
ATOM   3871  CA   THR  267   -37.140  21.837 -23.875   24.51   C
ATOM   3872  HA   THR  267   -38.088  22.137 -24.239    0.00   H
ATOM   3873  CB   THR  267   -36.112  22.940 -24.215   22.79   C
ATOM   3874  HB   THR  267   -35.147  22.630 -23.908    0.00   H
ATOM   3875  OG1  THR  267   -36.462  24.150 -23.531   23.41   O
ATOM   3876  HG1  THR  267   -35.813  24.839 -23.745    0.00   H
```

FIGURE 6- 52 -

```
ATOM   3877  CG2  THR  267  -36.098  23.200  -25.707  19.01       C
ATOM   3878  HG21 THR  267  -35.934  22.311  -26.218   0.00       H
ATOM   3879  HG22 THR  267  -37.060  23.514  -26.020   0.00       H
ATOM   3880  HG23 THR  267  -35.391  23.957  -25.927   0.00       H
ATOM   3881  C    THR  267  -36.755  20.584  -24.660  25.86       C
ATOM   3882  O    THR  267  -35.766  19.922  -24.329  25.31       O
ATOM   3883  N    ASN  268  -37.535  20.263  -25.696  26.77       N
ATOM   3884  HN   ASN  268  -38.342  20.831  -25.906   0.00       H
ATOM   3885  CA   ASN  268  -37.227  19.102  -26.520  28.74       C
ATOM   3886  HA   ASN  268  -36.939  18.294  -25.398   0.00       H
ATOM   3887  CB   ASN  268  -38.446  18.654  -27.364  28.44       C
ATOM   3888  HB2  ASN  268  -38.192  17.788  -27.919   0.00       H
ATOM   3889  HB3  ASN  268  -39.259  18.436  -26.722   0.00       H
ATOM   3890  CG   ASN  268  -38.925  19.718  -28.366  30.72       C
ATOM   3891  OD1  ASN  268  -38.165  20.591  -28.805  27.75       O
ATOM   3892  ND2  ASN  268  -40.197  19.622  -28.748  28.89       N
ATOM   3893  HD21 ASN  268  -40.785  18.896  -28.367   0.00       H
ATOM   3894  HD22 ASN  268  -40.573  20.275  -29.419   0.00       H
ATOM   3895  C    ASN  268  -36.036  19.438  -27.422  29.89       C
ATOM   3896  O    ASN  268  -35.627  20.592  -27.524  28.99       O
ATOM   3897  N    SER  269  -35.463  18.430  -28.060  32.11       N
ATOM   3898  HN   SER  269  -35.820  17.495  -27.933   0.00       H
ATOM   3899  CA   SER  269  -34.328  18.662  -28.938  33.36       C
ATOM   3900  HA   SER  269  -33.521  19.053  -28.375   0.00       H
ATOM   3901  CB   SER  269  -33.895  17.347  -29.593  34.42       C
ATOM   3902  HB2  SER  269  -33.089  17.531  -30.254   0.00       H
ATOM   3903  HB3  SER  269  -33.589  16.664  -28.844   0.00       H
ATOM   3904  OG   SER  269  -34.960  16.758  -30.333  36.37       O
ATOM   3905  HG   SER  269  -34.656  15.932  -30.733   0.00       H
ATOM   3906  C    SER  269  -34.625  19.707  -30.015  34.36       C
ATOM   3907  O    SER  269  -33.699  20.308  -30.551  35.83       O
ATOM   3908  N    LYS  270  -35.901  19.930  -30.335  34.96       N
ATOM   3909  HN   LYS  270  -36.619  19.403  -29.861   0.00       H
ATOM   3910  CA   LYS  270  -36.271  20.922  -31.357  35.75       C
ATOM   3911  HA   LYS  270  -35.586  20.871  -32.163   0.00       H
ATOM   3912  CB   LYS  270  -37.681  20.662  -31.897  38.44       C
ATOM   3913  HB2  LYS  270  -38.309  20.342  -31.106   0.00       H
ATOM   3914  HB3  LYS  270  -38.068  21.554  -32.317   0.00       H
ATOM   3915  CG   LYS  270  -37.828  19.610  -32.979  41.32       C
ATOM   3916  HG2  LYS  270  -37.102  19.775  -33.732   0.00       H
ATOM   3917  HG3  LYS  270  -37.688  18.648  -32.558   0.00       H
ATOM   3918  CD   LYS  270  -39.237  19.730  -33.567  45.92       C
ATOM   3919  HD2  LYS  270  -39.912  20.031  -32.808   0.00       H
ATOM   3920  HD3  LYS  270  -39.235  20.450  -34.344   0.00       H
ATOM   3921  CE   LYS  270  -39.757  18.412  -34.155  49.48       C
ATOM   3922  HE2  LYS  270  -39.288  18.232  -35.088   0.00       H
ATOM   3923  HE3  LYS  270  -39.536  17.618  -33.490   0.00       H
ATOM   3924  NZ   LYS  270  -41.250  18.435  -34.378  49.94      N1+
ATOM   3925  HZ1  LYS  270  -41.719  18.592  -33.499   0.00       H
ATOM   3926  HZ2  LYS  270  -41.483  19.178  -35.020   0.00       H
ATOM   3927  HZ3  LYS  270  -41.546  17.551  -34.764   0.00       H
ATOM   3928  C    LYS  270  -36.239  22.381  -30.882  34.49       C
ATOM   3929  O    LYS  270  -36.295  23.304  -31.692  34.31       O
ATOM   3930  N    GLY  271  -36.173  22.596  -29.577  33.27       N
ATOM   3931  HN   GLY  271  -36.125  21.821  -28.932   0.00       H
ATOM   3932  CA   GLY  271  -36.170  23.955  -29.077  30.61       C
ATOM   3933  HA2  GLY  271  -35.564  24.011  -28.210   0.00       H
ATOM   3934  HA3  GLY  271  -35.784  24.604  -29.320   0.00       H
ATOM   3935  C    GLY  271  -37.588  24.369  -28.731  29.80       C
ATOM   3936  O    GLY  271  -37.901  25.561  -28.640  29.25       O
ATOM   3937  N    GLN  272  -38.453  23.374  -28.550  28.56       N
ATOM   3938  HN   GLN  272  -38.124  22.426  -28.660   0.00       H
ATOM   3939  CA   GLN  272  -39.843  23.626  -28.202  26.99       C
ATOM   3940  HA   GLN  272  -40.068  24.648  -28.366   0.00       H
ATOM   3941  CB   GLN  272  -40.776  22.773  -29.055  25.18       C
ATOM   3942  HB2  GLN  272  -40.563  21.748  -28.394   0.00       H
ATOM   3943  HB3  GLN  272  -41.781  22.971  -28.785   0.00       H
ATOM   3944  CG   GLN  272  -40.653  23.027  -30.534  26.26       C
ATOM   3945  HG2  GLN  272  -40.938  24.025  -30.746   0.00       H
ATOM   3946  HG3  GLN  272  -39.650  22.874  -30.836   0.00       H
ATOM   3947  CD   GLN  272  -41.534  22.105  -31.352  27.88       C
ATOM   3948  OE1  GLN  272  -41.353  20.887  -31.355  27.17       O
ATOM   3949  NE2  GLN  272  -42.501  22.685  -32.050  29.85       N
ATOM   3950  HE21 GLN  272  -42.614  23.687  -32.019   0.00       H
ATOM   3951  HE22 GLN  272  -43.124  22.124  -32.612   0.00       H
ATOM   3952  C    GLN  272  -40.092  23.337  -26.728  26.39       C
```

FIGURE 6- 53 -

```
ATOM   3953  O    GLN  272   -39.530  22.408 -26.143  25.19    O
ATOM   3954  N    ASN  273   -40.946  24.156 -26.144  25.04    N
ATOM   3955  HN   ASN  273   -41.353  24.883 -26.714   0.00    H
ATOM   3956  CA   ASN  273   -41.305  24.045 -24.751  25.74    C
ATOM   3957  HA   ASN  273   -40.434  23.869 -24.175   0.00    H
ATOM   3958  CB   ASN  273   -41.960  25.345 -24.316  24.98    C
ATOM   3959  HB2  ASN  273   -41.303  26.153 -24.509   0.00    H
ATOM   3960  HB3  ASN  273   -42.860  25.485 -24.857   0.00    H
ATOM   3961  CG   ASN  273   -42.293  25.363 -22.861  26.05    C
ATOM   3962  OD1  ASN  273   -42.907  26.301 -22.388  29.10    O
ATOM   3963  ND2  ASN  273   -41.889  24.328 -22.132  26.07    N
ATOM   3964  HD21 ASN  273   -41.382  23.572 -22.567   0.00    H
ATOM   3965  HD22 ASN  273   -42.089  24.298 -21.143   0.00    H
ATOM   3966  C    ASN  273   -42.249  22.880 -24.499  26.42    C
ATOM   3967  O    ASN  273   -43.406  22.907 -24.898  30.01    O
ATOM   3968  N    CYS  274   -41.760  21.861 -23.820  26.33    N
ATOM   3969  HN   CYS  274   -40.803  21.895 -23.503   0.00    H
ATOM   3970  CA   CYS  274   -42.576  20.706 -23.528  27.22    C
ATOM   3971  HA   CYS  274   -43.258  20.545 -24.322   0.00    H
ATOM   3972  CB   CYS  274   -41.699  19.472 -23.397  28.13    C
ATOM   3973  HB2  CYS  274   -40.928  19.660 -22.696   0.00    H
ATOM   3974  HB3  CYS  274   -42.286  18.655 -23.066   0.00    H
ATOM   3975  SG   CYS  274   -40.959  19.036 -24.928  36.39    S
ATOM   3976  HG   CYS  274   -40.249  18.019 -24.773   0.00    H
ATOM   3977  C    CYS  274   -43.371  20.870 -22.260  26.82    C
ATOM   3978  O    CYS  274   -44.445  20.288 -22.121  29.77    O
ATOM   3979  N    GLY  275   -42.836  21.640 -21.325  25.99    N
ATOM   3980  HN   GLY  275   -41.949  22.093 -21.489   0.00    H
ATOM   3981  CA   GLY  275   -43.523  21.831 -20.071  25.48    C
ATOM   3982  HA2  GLY  275   -44.268  22.575 -20.186   0.00    H
ATOM   3983  HA3  GLY  275   -43.976  20.921 -19.774   0.00    H
ATOM   3984  C    GLY  275   -42.603  22.271 -18.959  26.18    C
ATOM   3985  O    GLY  275   -41.540  22.843 -19.203  26.76    O
ATOM   3986  N    TYR  276   -43.004  21.987 -17.727  25.21    N
ATOM   3987  HN   TYR  276   -43.861  21.471 -17.597   0.00    H
ATOM   3988  CA   TYR  276   -42.230  22.407 -16.577  23.92    C
ATOM   3989  HA   TYR  276   -41.325  22.849 -16.903   0.00    H
ATOM   3990  CB   TYR  276   -43.037  23.422 -15.777  23.19    C
ATOM   3991  HB2  TYR  276   -43.631  23.999 -16.437   0.00    H
ATOM   3992  HB3  TYR  276   -43.663  22.913 -15.091   0.00    H
ATOM   3993  CG   TYR  276   -42.188  24.374 -14.988  24.73    C
ATOM   3994  CD1  TYR  276   -41.657  25.519 -15.587  24.41    C
ATOM   3995  HD1  TYR  276   -41.896  25.751 -16.611   0.00    H
ATOM   3996  CE1  TYR  276   -40.819  26.376 -14.868  23.61    C
ATOM   3997  HE1  TYR  276   -40.416  27.249 -15.373   0.00    H
ATOM   3998  CD2  TYR  276   -41.866  24.109 -13.658  24.51    C
ATOM   3999  HD2  TYR  276   -42.265  23.235 -13.171   0.00    H
ATOM   4000  CE2  TYR  276   -41.032  24.961 -12.947  26.04    C
ATOM   4001  HE2  TYR  276   -40.791  24.745 -11.920   0.00    H
ATOM   4002  CZ   TYR  276   -40.511  26.093 -13.568  25.93    C
ATOM   4003  OH   TYR  276   -39.691  26.939 -12.859  25.73    O
ATOM   4004  HH   TYR  276   -39.420  27.675 -13.425   0.00    H
ATOM   4005  C    TYR  276   -41.889  21.227 -15.668  24.32    C
ATOM   4006  O    TYR  276   -42.556  20.199 -15.744  26.40    O
ATOM   4007  N    ARG  277   -40.860  21.387 -14.860  22.79    N
ATOM   4008  HN   ARG  277   -40.370  22.269 -14.879   0.00    H
ATOM   4009  CA   ARG  277   -40.434  20.337 -13.945  22.27    C
ATOM   4010  HA   ARG  277   -41.120  19.531 -13.988   0.00    H
ATOM   4011  CB   ARG  277   -39.039  19.827 -14.330  21.28    C
ATOM   4012  HB2  ARG  277   -39.091  19.325 -15.261   0.00    H
ATOM   4013  HB3  ARG  277   -38.373  20.646 -14.408   0.00    H
ATOM   4014  CG   ARG  277   -38.419  18.847 -13.333  23.15    C
ATOM   4015  HG2  ARG  277   -38.391  19.291 -12.372   0.00    H
ATOM   4016  HG3  ARG  277   -39.002  17.964 -13.297   0.00    H
ATOM   4017  CD   ARG  277   -36.992  18.466 -13.729  22.81    C
ATOM   4018  HD2  ARG  277   -36.539  17.924 -12.940   0.00    H
ATOM   4019  HD3  ARG  277   -37.016  17.865 -14.601   0.00    H
ATOM   4020  NE   ARG  277   -36.173  19.650 -14.006  23.96    N1+
ATOM   4021  HE   ARG  277   -36.146  20.038 -14.937   0.00    H
ATOM   4022  CZ   ARG  277   -35.425  20.298 -13.112  20.38    C
ATOM   4023  NH1  ARG  277   -35.356  19.899 -11.849  15.24    N
ATOM   4024  HH11 ARG  277   -34.783  20.405 -11.191   0.00    H
ATOM   4025  HH12 ARG  277   -35.876  19.089 -11.547   0.00    H
ATOM   4026  NH2  ARG  277   -34.754  21.367 -13.495  19.95    N
ATOM   4027  HH21 ARG  277   -34.183  21.869 -12.831   0.00    H
ATOM   4028  HH22 ARG  277   -34.811  21.683 -14.452   0.00    H
```

FIGURE 6- 54 -

```
ATOM   4029  C    ARG  277   -40.410  20.845 -12.506  23.13       C
ATOM   4030  O    ARG  277   -40.024  21.988 -12.250  21.86       O
ATOM   4031  N    ARG  278   -40.824  19.993 -11.570  23.45       N
ATOM   4032  HN   ARG  278   -41.140  19.078 -11.853   0.00       H
ATOM   4033  CA   ARG  278   -40.826  20.360 -10.163  24.13       C
ATOM   4034  HA   ARG  278   -40.199  21.201 -10.017   0.00       H
ATOM   4035  CB   ARG  278   -42.235  20.709  -9.703  23.92       C
ATOM   4036  HB2  ARG  278   -42.828  19.832  -9.687   0.00       H
ATOM   4037  HB3  ARG  278   -42.196  21.126  -8.730   0.00       H
ATOM   4038  CG   ARG  278   -42.902  21.710 -10.616  24.43       C
ATOM   4039  HG2  ARG  278   -42.196  22.440 -10.916   0.00       H
ATOM   4040  HG3  ARG  278   -43.279  21.212 -11.471   0.00       H
ATOM   4041  CD   ARG  278   -44.054  22.428  -9.956  21.15       C
ATOM   4042  HD2  ARG  278   -44.751  21.718  -9.592   0.00       H
ATOM   4043  HD3  ARG  278   -43.691  23.011  -9.150   0.00       H
ATOM   4044  NE   ARG  278   -44.700  23.290 -10.930  22.71       N1+
ATOM   4045  HE   ARG  278   -44.633  24.293 -10.839   0.00       H
ATOM   4046  CZ   ARG  278   -45.396  22.838 -11.967  22.25       C
ATOM   4047  NH1  ARG  278   -45.542  21.528 -12.156  22.00       N
ATOM   4048  HH11 ARG  278   -46.071  21.188 -12.945   0.00       H
ATOM   4049  HH12 ARG  278   -45.123  20.875 -11.510   0.00       H
ATOM   4050  NH2  ARG  278   -45.927  23.691 -12.828  20.10       N
ATOM   4051  HH21 ARG  278   -46.456  23.349 -13.616   0.00       H
ATOM   4052  HH22 ARG  278   -45.803  24.684 -12.696   0.00       H
ATOM   4053  C    ARG  278   -40.273  19.233  -9.311  25.29       C
ATOM   4054  O    ARG  278   -40.562  19.143  -8.115  26.28       O
ATOM   4055  N    CYS  279   -39.473  18.376  -9.936  24.56       N
ATOM   4056  HN   CYS  279   -39.291  18.521 -10.918   0.00       H
ATOM   4057  CA   CYS  279   -38.863  17.249  -9.240  24.76       C
ATOM   4058  HA   CYS  279   -38.889  17.423  -8.196   0.00       H
ATOM   4059  CB   CYS  279   -39.657  15.963  -9.518  25.76       C
ATOM   4060  HB2  CYS  279   -39.248  15.166  -8.952   0.00       H
ATOM   4061  HB3  CYS  279   -40.670  16.107  -9.244   0.00       H
ATOM   4062  SG   CYS  279   -39.654  15.431 -11.250  21.50       S
ATOM   4063  HG   CYS  279   -40.324  14.382 -11.365   0.00       H
ATOM   4064  C    CYS  279   -37.403  17.059  -9.670  24.32       C
ATOM   4065  O    CYS  279   -36.840  17.886 -10.362  24.59       O
ATOM   4066  N    ARG  280   -36.800  15.955  -9.248  22.33       N
ATOM   4067  HN   ARG  280   -37.322  15.302  -8.683   0.00       H
ATOM   4068  CA   ARG  280   -35.417  15.678  -9.584  21.95       C
ATOM   4069  HA   ARG  280   -34.801  16.455  -9.212   0.00       H
ATOM   4070  CB   ARG  280   -34.988  14.349  -8.959  21.54       C
ATOM   4071  HB2  ARG  280   -35.123  14.393  -7.910   0.00       H
ATOM   4072  HB3  ARG  280   -35.577  13.565  -9.359   0.00       H
ATOM   4073  CG   ARG  280   -33.530  13.986  -9.208  21.68       C
ATOM   4074  HG2  ARG  280   -33.374  12.966  -8.969   0.00       H
ATOM   4075  HG3  ARG  280   -33.295  14.149 -10.227   0.00       H
ATOM   4076  CD   ARG  280   -32.606  14.831  -8.355  21.63       C
ATOM   4077  HD2  ARG  280   -31.618  14.763  -8.731   0.00       H
ATOM   4078  HD3  ARG  280   -32.925  15.840  -8.382   0.00       H
ATOM   4079  NE   ARG  280   -32.593  14.395  -6.957  23.05       N1+
ATOM   4080  HE   ARG  280   -32.840  13.445  -6.722   0.00       H
ATOM   4081  CZ   ARG  280   -32.270  15.179  -5.930  23.57       C
ATOM   4082  NH1  ARG  280   -31.941  16.447  -6.152  21.43       N
ATOM   4083  HH11 ARG  280   -31.695  17.047  -5.379   0.00       H
ATOM   4084  HH12 ARG  280   -31.937  16.810  -7.094   0.00       H
ATOM   4085  NH2  ARG  280   -32.269  14.701  -4.686  19.94       N
ATOM   4086  HH21 ARG  280   -32.023  15.303  -3.914   0.00       H
ATOM   4087  HH22 ARG  280   -32.514  13.737  -4.516   0.00       H
ATOM   4088  C    ARG  280   -35.131  15.639 -11.082  22.64       C
ATOM   4089  O    ARG  280   -35.847  15.004 -11.851  23.36       O
ATOM   4090  N    ALA  281   -34.077  16.338 -11.489  22.89       N
ATOM   4091  HN   ALA  281   -33.576  16.882 -10.803   0.00       H
ATOM   4092  CA   ALA  281   -33.638  16.336 -12.880  23.18       C
ATOM   4093  HA   ALA  281   -34.465  16.135 -13.511   0.00       H
ATOM   4094  CB   ALA  281   -33.051  17.680 -13.253  22.22       C
ATOM   4095  HB1  ALA  281   -33.784  18.433 -13.125   0.00       H
ATOM   4096  HB2  ALA  281   -32.220  17.887 -12.630   0.00       H
ATOM   4097  HB3  ALA  281   -32.738  17.660 -14.265   0.00       H
ATOM   4098  C    ALA  281   -32.551  15.258 -12.917  24.11       C
ATOM   4099  O    ALA  281   -31.557  15.342 -12.199  24.21       O
ATOM   4100  N    SER  282   -32.749  14.237 -13.736  24.86       N
ATOM   4101  HN   SER  282   -33.584  14.234 -14.302   0.00       H
ATOM   4102  CA   SER  282   -31.798  13.135 -13.833  24.84       C
ATOM   4103  HA   SER  282   -31.678  12.688 -12.881   0.00       H
ATOM   4104  CB   SER  282   -32.322  12.099 -14.819  24.79       C
```

FIGURE 6- 55 -

```
ATOM   4105  HB2  SER  282   -31.604  11.329 -14.937   0.00  H
ATOM   4106  HB3  SER  282   -33.225  11.686 -14.451   0.00  H
ATOM   4107  OG   SER  282   -32.569  12.700 -16.083  28.64  C
ATOM   4108  HG   SER  282   -32.901  12.032 -16.698   0.00  H
ATOM   4109  C    SER  282   -30.390  13.530 -14.256  25.10  C
ATOM   4110  O    SER  282   -29.424  12.852 -13.899  25.61  C
ATOM   4111  N    GLY  283   -30.276  14.623 -15.007  24.69  N
ATOM   4112  HN   GLY  283   -31.100  15.160 -15.233   0.00  H
ATOM   4113  CA   GLY  283   -28.979  15.044 -15.499  24.86  C
ATOM   4114  HA2  GLY  283   -28.296  14.238 -15.428   0.00  H
ATOM   4115  HA3  GLY  283   -29.066  15.345 -16.511   0.00  H
ATOM   4116  C    GLY  283   -28.214  16.197 -14.865  26.23  C
ATOM   4117  O    GLY  283   -27.555  16.960 -15.583  27.70  C
ATOM   4118  N    VAL  284   -28.291  16.353 -13.547  24.35  N
ATOM   4119  HN   VAL  284   -28.879  15.738 -13.004   0.00  H
ATOM   4120  CA   VAL  284   -27.531  17.407 -12.886  24.40  C
ATOM   4121  HA   VAL  284   -27.057  18.011 -13.615   0.00  H
ATOM   4122  CB   VAL  284   -28.419  18.328 -12.012  25.38  C
ATOM   4123  HB   VAL  284   -27.807  19.014 -11.487   0.00  H
ATOM   4124  CG1  VAL  284   -29.321  19.151 -12.911  25.14  C
ATOM   4125  HG11 VAL  284   -28.728  19.741 -13.561   0.00  H
ATOM   4126  HG12 VAL  284   -29.935  18.504 -13.483   0.00  H
ATOM   4127  HG13 VAL  284   -29.930  19.782 -12.318   0.00  H
ATOM   4128  CG2  VAL  284   -29.225  17.508 -10.995  23.47  C
ATOM   4129  HG21 VAL  284   -29.848  16.822 -11.509   0.00  H
ATOM   4130  HG22 VAL  284   -28.561  16.977 -10.364   0.00  H
ATOM   4131  HG23 VAL  284   -29.823  18.159 -10.411   0.00  H
ATOM   4132  C    VAL  284   -26.487  16.713 -12.015  23.84  C
ATOM   4133  O    VAL  284   -26.622  15.529 -11.712  25.48  C
ATOM   4134  N    LEU  285   -25.452  17.435 -11.608  21.36  N
ATOM   4135  HN   LEU  285   -25.387  18.412 -11.852   0.00  H
ATOM   4136  CA   LEU  285   -24.415  16.818 -10.812  21.92  C
ATOM   4137  HA   LEU  285   -24.080  15.935 -11.292   0.00  H
ATOM   4138  CB   LEU  285   -23.245  17.776 -10.652  19.45  C
ATOM   4139  HB2  LEU  285   -23.040  18.242 -11.581   0.00  H
ATOM   4140  HB3  LEU  285   -23.489  18.514  -9.933   0.00  H
ATOM   4141  CG   LEU  285   -21.977  17.066 -10.189  18.93  C
ATOM   4142  HG   LEU  285   -22.017  16.920  -9.141   0.00  H
ATOM   4143  CD1  LEU  285   -21.875  15.724 -10.886  17.00  C
ATOM   4144  HD11 LEU  285   -22.721  15.135 -10.643   0.00  H
ATOM   4145  HD12 LEU  285   -21.837  15.872 -11.934   0.00  H
ATOM   4146  HD13 LEU  285   -20.996  15.227 -10.568   0.00  H
ATOM   4147  CD2  LEU  285   -20.764  17.925 -10.491  19.18  C
ATOM   4148  HD21 LEU  285   -20.706  18.099 -11.534   0.00  H
ATOM   4149  HD22 LEU  285   -20.851  18.850  -9.983   0.00  H
ATOM   4150  HD23 LEU  285   -19.888  17.426 -10.167   0.00  H
ATOM   4151  C    LEU  285   -24.876  16.349  -9.438  24.11  C
ATOM   4152  O    LEU  285   -24.231  15.506  -8.806  25.97  C
ATOM   4153  N    THR  286   -26.003  16.873  -8.976  23.58  N
ATOM   4154  HN   THR  286   -26.530  17.523  -9.540   0.00  H
ATOM   4155  CA   THR  286   -26.478  16.508  -7.655  23.12  C
ATOM   4156  HA   THR  286   -25.665  16.164  -7.070   0.00  H
ATOM   4157  CB   THR  286   -27.116  17.733  -6.966  23.82  C
ATOM   4158  HB   THR  286   -27.508  17.444  -6.026   0.00  H
ATOM   4159  OG1  THR  286   -28.174  18.256  -7.783  25.37  C
ATOM   4160  HG1  THR  286   -28.569  19.023  -7.346   0.00  H
ATOM   4161  CG2  THR  286   -26.073  18.811  -6.762  24.45  C
ATOM   4162  HG21 THR  286   -25.292  18.436  -6.153   0.00  H
ATOM   4163  HG22 THR  286   -25.680  19.104  -7.701   0.00  H
ATOM   4164  HG23 THR  286   -26.518  19.648  -6.289   0.00  H
ATOM   4165  C    THR  286   -27.446  15.335  -7.616  22.55  C
ATOM   4166  O    THR  286   -27.835  14.892  -6.534  20.46  C
ATOM   4167  N    THR  287   -27.824  14.824  -8.785  21.19  N
ATOM   4168  HN   THR  287   -27.457  15.214  -9.640   0.00  H
ATOM   4169  CA   THR  287   -28.762  13.708  -8.837  21.66  C
ATOM   4170  HA   THR  287   -29.705  14.022  -8.471   0.00  H
ATOM   4171  CB   THR  287   -28.948  13.188 -10.280  20.59  C
ATOM   4172  HB   THR  287   -28.009  12.897 -10.674   0.00  H
ATOM   4173  OG1  THR  287   -29.530  14.213 -11.088  24.14  C
ATOM   4174  HG1  THR  287   -29.645  13.885 -11.990   0.00  H
ATOM   4175  CG2  THR  287   -29.869  12.008 -10.299  18.91  C
ATOM   4176  HG21 THR  287   -29.461  11.232  -9.704   0.00  H
ATOM   4177  HG22 THR  287   -30.813  12.291  -9.911   0.00  H
ATOM   4178  HG23 THR  287   -29.984  11.666 -11.295   0.00  H
ATOM   4179  C    THR  287   -28.364  12.532  -7.936  21.38  C
ATOM   4180  O    THR  287   -29.161  12.075  -7.114  20.47  C
```

FIGURE 6-56-

```
ATOM   4181    N  SER 288   -27.138  12.044  -8.072  21.41  N
ATOM   4182   HN  SER 288   -26.495  12.449  -8.736   0.00  H
ATOM   4183   CA  SER 288   -26.723  10.916  -7.255  22.59  C
ATOM   4184   HA  SER 288   -27.463  10.160  -7.295   0.00  H
ATOM   4185   CB  SER 288   -25.408  10.344  -7.759  22.61  C
ATOM   4186  HB2  SER 288   -25.448  10.242  -8.812   0.00  H
ATOM   4187  HB3  SER 288   -24.616  10.997  -7.498   0.00  H
ATOM   4188   OG  SER 288   -25.192   9.078  -7.169  26.26  O
ATOM   4189   HG  SER 288   -24.356   8.712  -7.488   0.00  H
ATOM   4190    C  SER 288   -26.590  11.256  -5.776  23.28  C
ATOM   4191    O  SER 288   -27.174  10.588  -4.920  24.12  O
ATOM   4192    N  CYS 289   -25.828  12.293  -5.470  23.35  N
ATOM   4193   HN  CYS 289   -25.375  12.817  -6.204   0.00  H
ATOM   4194   CA  CYS 289   -25.642  12.679  -4.080  25.42  C
ATOM   4195   HA  CYS 289   -25.186  11.883  -3.551   0.00  H
ATOM   4196   CB  CYS 289   -24.689  13.861  -4.001  26.09  C
ATOM   4197  HB2  CYS 289   -23.735  13.570  -4.358   0.00  H
ATOM   4198  HB3  CYS 289   -25.061  14.655  -4.595   0.00  H
ATOM   4199   SG  CYS 289   -24.505  14.448  -2.341  30.73  S
ATOM   4200   HG  CYS 289   -23.715  15.417  -2.327   0.00  H
ATOM   4201    C  CYS 289   -26.949  13.021  -3.353  25.77  C
ATOM   4202    O  CYS 289   -27.177  12.583  -2.223  25.68  O
ATOM   4203    N  GLY 290   -27.797  13.810  -4.009  27.03  N
ATOM   4204   HN  GLY 290   -27.538  14.135  -4.928   0.00  H
ATOM   4205   CA  GLY 290   -29.069  14.204  -3.431  26.57  C
ATOM   4206  HA2  GLY 290   -28.906  14.630  -2.475   0.00  H
ATOM   4207  HA3  GLY 290   -29.537  14.916  -4.060   0.00  H
ATOM   4208    C  GLY 290   -30.032  13.047  -3.256  27.92  C
ATOM   4209    O  GLY 290   -30.747  12.972  -2.252  27.98  O
ATOM   4210    N  ASN 291   -30.069  12.141  -4.229  28.41  N
ATOM   4211   HN  ASN 291   -29.480  12.247  -5.041   0.00  H
ATOM   4212   CA  ASN 291   -30.961  10.995  -4.121  27.97  C
ATOM   4213   HA  ASN 291   -31.937  11.329  -3.891   0.00  H
ATOM   4214   CB  ASN 291   -31.016  10.223  -5.437  28.19  C
ATOM   4215  HB2  ASN 291   -30.032  10.075  -5.801   0.00  H
ATOM   4216  HB3  ASN 291   -31.478   9.284  -5.276   0.00  H
ATOM   4217   CG  ASN 291   -31.804  10.956  -6.505  30.30  C
ATOM   4218  OD1  ASN 291   -32.311  12.049  -6.269  31.35  O
ATOM   4219  ND2  ASN 291   -31.913  10.358  -7.683  29.72  N
ATOM   4220 HD21  ASN 291   -31.480   9.459  -7.834   0.00  H
ATOM   4221 HD22  ASN 291   -32.429  10.802  -8.428   0.00  H
ATOM   4222    C  ASN 291   -30.464  10.106  -3.001  27.26  C
ATOM   4223    O  ASN 291   -31.243   9.653  -2.167  27.38  O
ATOM   4224    N  THR 292   -29.162   9.868  -2.965  25.83  N
ATOM   4225   HN  THR 292   -28.551  10.262  -3.664   0.00  H
ATOM   4226   CA  THR 292   -28.615   9.034  -1.911  26.01  C
ATOM   4227   HA  THR 292   -29.059   8.074  -1.954   0.00  H
ATOM   4228   CB  THR 292   -27.102   8.872  -2.050  25.27  C
ATOM   4229   HB  THR 292   -26.642   9.826  -2.039   0.00  H
ATOM   4230  OG1  THR 292   -26.815   8.212  -3.286  26.62  O
ATOM   4231  HG1  THR 292   -25.858   8.106  -3.380   0.00  H
ATOM   4232  CG2  THR 292   -26.549   8.048  -0.910  23.00  C
ATOM   4233 HG21  THR 292   -26.760   8.530   0.009   0.00  H
ATOM   4234 HG22  THR 292   -26.999   7.089  -0.917   0.00  H
ATOM   4235 HG23  THR 292   -25.501   7.947  -1.024   0.00  H
ATOM   4236    C  THR 292   -28.920   9.637  -0.554  26.24  C
ATOM   4237    O  THR 292   -29.334   8.927   0.362  28.58  O
ATOM   4238    N  LEU 293   -28.727  10.948  -0.431  24.80  N
ATOM   4239   HN  LEU 293   -28.402  11.460  -1.237   0.00  H
ATOM   4240   CA  LEU 293   -28.972  11.646   0.826  23.19  C
ATOM   4241   HA  LEU 293   -28.488  11.132   1.615   0.00  H
ATOM   4242   CB  LEU 293   -28.433  13.075   0.760  22.68  C
ATOM   4243  HB2  LEU 293   -28.687  13.505  -0.174   0.00  H
ATOM   4244  HB3  LEU 293   -28.859  13.649   1.541   0.00  H
ATOM   4245   CG  LEU 293   -26.929  13.302   0.892  21.66  C
ATOM   4246   HG  LEU 293   -26.412  12.607   0.282   0.00  H
ATOM   4247  CD1  LEU 293   -26.591  14.711   0.451  22.16  C
ATOM   4248 HD11  LEU 293   -26.881  14.844  -0.559   0.00  H
ATOM   4249 HD12  LEU 293   -27.108  15.405   1.061   0.00  H
ATOM   4250 HD13  LEU 293   -25.548  14.869   0.542   0.00  H
ATOM   4251  CD2  LEU 293   -26.498  13.069   2.323  19.60  C
ATOM   4252 HD21  LEU 293   -27.010  13.742   2.960   0.00  H
ATOM   4253 HD22  LEU 293   -26.727  12.074   2.603   0.00  H
ATOM   4254 HD23  LEU 293   -25.454  13.228   2.408   0.00  H
ATOM   4255    C  LEU 293   -30.442  11.699   1.185  22.92  C
ATOM   4256    O  LEU 293   -30.805  11.555   2.343  23.37  O
```

FIGURE 6- 57 -

```
ATOM   4257  N    THR  294   -31.289  11.924   0.191  23.36   N
ATOM   4258  HN   THR  294   -30.923  12.034  -0.743   0.00   H
ATOM   4259  CA   THR  294   -32.721  12.014   0.425  22.82   C
ATOM   4260  HA   THR  294   -32.902  12.610   1.282   0.00   H
ATOM   4261  CB   THR  294   -33.408  12.651  -0.790  21.91   C
ATOM   4262  HB   THR  294   -33.219  12.063  -1.651   0.00   H
ATOM   4263  OG1  THR  294   -32.881  13.969  -0.966  24.42   O
ATOM   4264  HG1  THR  294   -33.304  14.386  -1.729   0.00   H
ATOM   4265  CG2  THR  294   -34.916  12.747  -0.593  19.62   C
ATOM   4266  HG21 THR  294   -35.316  11.777  -0.453   0.00   H
ATOM   4267  HG22 THR  294   -35.124  13.341   0.259   0.00   H
ATOM   4268  HG23 THR  294   -35.356  13.190  -1.448   0.00   H
ATOM   4269  C    THR  294   -33.340  10.655   0.744  23.43   C
ATOM   4270  O    THR  294   -34.251  10.560   1.571  22.13   O
ATOM   4271  N    CYS  295   -32.840   9.606   0.098  23.91   N
ATOM   4272  HN   CYS  295   -32.095   9.759  -0.565   0.00   H
ATOM   4273  CA   CYS  295   -33.344   8.256   0.330  24.88   C
ATOM   4274  HA   CYS  295   -34.397   8.248   0.215   0.00   H
ATOM   4275  CB   CYS  295   -32.710   7.292  -0.664  25.94   C
ATOM   4276  HB2  CYS  295   -32.885   7.636  -1.650   0.00   H
ATOM   4277  HB3  CYS  295   -31.667   7.240  -0.489   0.00   H
ATOM   4278  SG   CYS  295   -33.330   5.603  -0.590  25.59   S
ATOM   4279  HG   CYS  295   -32.742   4.906  -1.445   0.00   H
ATOM   4280  C    CYS  295   -32.961   7.864   1.748  25.68   C
ATOM   4281  O    CYS  295   -33.797   7.431   2.552  23.15   O
ATOM   4282  N    TYR  296   -31.681   8.034   2.052  26.30   N
ATOM   4283  HN   TYR  296   -31.057   8.389   1.343   0.00   H
ATOM   4284  CA   TYR  296   -31.172   7.720   3.375  26.20   C
ATOM   4285  HA   TYR  296   -31.265   6.680   3.551   0.00   H
ATOM   4286  CB   TYR  296   -29.697   8.127   3.453  25.82   C
ATOM   4287  HB2  TYR  296   -29.125   7.504   2.815   0.00   H
ATOM   4288  HB3  TYR  296   -29.593   9.136   3.148   0.00   H
ATOM   4289  CG   TYR  296   -29.087   8.022   4.825  29.06   C
ATOM   4290  CD1  TYR  296   -29.455   8.903   5.843  29.97   C
ATOM   4291  HD1  TYR  296   -30.186   9.671   5.652   0.00   H
ATOM   4292  CE1  TYR  296   -28.895   8.811   7.109  30.97   C
ATOM   4293  HE1  TYR  296   -29.194   9.499   7.881   0.00   H
ATOM   4294  CD2  TYR  296   -28.140   7.046   5.114  30.15   C
ATOM   4295  HD2  TYR  296   -27.835   6.349   4.352   0.00   H
ATOM   4296  CE2  TYR  296   -27.570   6.948   6.381  29.87   C
ATOM   4297  HE2  TYR  296   -26.836   6.187   6.584   0.00   H
ATOM   4298  CZ   TYR  296   -27.953   7.830   7.367  30.39   C
ATOM   4299  OH   TYR  296   -27.389   7.732   8.613  32.24   O
ATOM   4300  HH   TYR  296   -27.756   8.417   9.188   0.00   H
ATOM   4301  C    TYR  296   -32.019   8.429   4.439  26.10   C
ATOM   4302  O    TYR  296   -32.573   7.783   5.327  26.73   O
ATOM   4303  N    LEU  297   -32.140   9.748   4.335  25.57   N
ATOM   4304  HN   LEU  297   -31.681  10.221   3.571   0.00   H
ATOM   4305  CA   LEU  297   -32.921  10.511   5.302  26.99   C
ATOM   4306  HA   LEU  297   -32.450  10.467   6.249   0.00   H
ATOM   4307  CB   LEU  297   -33.032  11.983   4.869  25.10   C
ATOM   4308  HB2  LEU  297   -32.090  12.454   4.975   0.00   H
ATOM   4309  HB3  LEU  297   -33.339  12.031   3.856   0.00   H
ATOM   4310  CG   LEU  297   -34.015  12.907   5.617  23.84   C
ATOM   4311  HG   LEU  297   -35.006  12.571   5.457   0.00   H
ATOM   4312  CD1  LEU  297   -33.748  12.916   7.115  22.85   C
ATOM   4313  HD11 LEU  297   -33.855  11.935   7.499   0.00   H
ATOM   4314  HD12 LEU  297   -32.763  13.260   7.296   0.00   H
ATOM   4315  HD13 LEU  297   -34.440  13.559   7.593   0.00   H
ATOM   4316  CD2  LEU  297   -33.896  14.306   5.059  23.73   C
ATOM   4317  HD21 LEU  297   -32.905  14.656   5.192   0.00   H
ATOM   4318  HD22 LEU  297   -34.131  14.295   4.026   0.00   H
ATOM   4319  HD23 LEU  297   -34.568  14.947   5.568   0.00   H
ATOM   4320  C    LEU  297   -34.317   9.920   5.488  28.61   C
ATOM   4321  O    LEU  297   -34.713   9.573   6.607  31.00   O
ATOM   4322  N    LYS  298   -35.059   9.798   4.393  28.49   N
ATOM   4323  HN   LYS  298   -34.671  10.085   3.507   0.00   H
ATOM   4324  CA   LYS  298   -36.413   9.260   4.456  27.90   C
ATOM   4325  HA   LYS  298   -36.999   9.855   5.106   0.00   H
ATOM   4326  CB   LYS  298   -37.042   9.268   3.056  25.50   C
ATOM   4327  HB2  LYS  298   -36.408   8.753   2.381   0.00   H
ATOM   4328  HB3  LYS  298   -37.985   8.788   3.090   0.00   H
ATOM   4329  CG   LYS  298   -37.251  10.686   2.522  23.68   C
ATOM   4330  HG2  LYS  298   -37.839  11.238   3.208   0.00   H
ATOM   4331  HG3  LYS  298   -36.312  11.160   2.401   0.00   H
ATOM   4332  CD   LYS  298   -37.960  10.747   1.175  21.57   C
```

FIGURE 6- 58 -

```
ATOM   4333 HD2  LYS  298    -37.337  10.327   0.429   0.00      H
ATOM   4334 HD3  LYS  298    -38.866  10.201   1.228   0.00      H
ATOM   4335 CE   LYS  298    -38.274  12.188   0.801  18.55      C
ATOM   4336 HE2  LYS  298    -38.909  12.613   1.534   0.00      H
ATOM   4337 HE3  LYS  298    -37.374  12.743   0.749   0.00      H
ATOM   4338 NZ   LYS  298    -38.959  12.316  -0.517  18.43      N1+
ATOM   4339 HZ1  LYS  298    -38.369  11.935  -1.241   0.00      H
ATOM   4340 HZ2  LYS  298    -39.832  11.810  -0.493   0.00      H
ATOM   4341 HZ3  LYS  298    -39.140  13.290  -0.709   0.00      H
ATOM   4342 C    LYS  298    -36.446   7.359   5.065  27.99      C
ATOM   4343 O    LYS  298    -37.191   7.602   5.999  27.57      O
ATOM   4344 N    ALA  299    -35.621   6.961   4.551  29.28      N
ATOM   4345 HN   ALA  299    -35.011   7.231   3.794   0.00      H
ATOM   4346 CA   ALA  299    -35.586   5.595   5.065  31.37      C
ATOM   4347 HA   ALA  299    -36.547   5.159   4.975   0.00      H
ATOM   4348 CB   ALA  299    -34.581   4.764   4.271  31.80      C
ATOM   4349 HB1  ALA  299    -34.866   4.745   3.251   0.00      H
ATOM   4350 HB2  ALA  299    -33.618   5.195   4.361   0.00      H
ATOM   4351 HB3  ALA  299    -34.562   3.775   4.650   0.00      H
ATOM   4352 C    ALA  299    -35.249   5.545   6.559  32.34      C
ATOM   4353 O    ALA  299    -36.034   5.014   7.355  31.10      O
ATOM   4354 N    THR  300    -34.092   6.093   6.941  33.06      N
ATOM   4355 HN   THR  300    -33.492   6.514   6.248   0.00      H
ATOM   4356 CA   THR  300    -33.691   6.087   8.351  32.72      C
ATOM   4357 HA   THR  300    -33.449   5.099   8.645   0.00      H
ATOM   4358 CB   THR  300    -32.452   6.982   8.626  30.57      C
ATOM   4359 HB   THR  300    -32.616   7.946   8.221   0.00      H
ATOM   4360 OG1  THR  300    -31.287   6.407   8.029  30.14      O
ATOM   4361 HG1  THR  300    -30.522   6.972   8.206   0.00      H
ATOM   4362 CG2  THR  300    -32.217   7.104  10.118  27.43      C
ATOM   4363 HG21 THR  300    -33.068   7.539  10.575   0.00      H
ATOM   4364 HG22 THR  300    -32.049   6.142  10.529   0.00      H
ATOM   4365 HG23 THR  300    -31.371   7.716  10.293   0.00      H
ATOM   4366 C    THR  300    -34.834   6.584   9.237  33.73      C
ATOM   4367 O    THR  300    -35.110   6.000  10.285  33.54      O
ATOM   4368 N    ALA  301    -35.497   7.658   8.815  33.61      N
ATOM   4369 HN   ALA  301    -35.230   8.098   7.947   0.00      H
ATOM   4370 CA   ALA  301    -36.599   8.197   9.595  34.97      C
ATOM   4371 HA   ALA  301    -36.280   8.357  10.592   0.00      H
ATOM   4372 CB   ALA  301    -37.067   9.515   9.008  34.73      C
ATOM   4373 HB1  ALA  301    -36.267  10.209   9.016   0.00      H
ATOM   4374 HB2  ALA  301    -37.392   9.362   8.012   0.00      H
ATOM   4375 HB3  ALA  301    -37.869   9.894   9.587   0.00      H
ATOM   4376 C    ALA  301    -37.743   7.191   9.606  36.72      C
ATOM   4377 O    ALA  301    -38.314   6.893  10.661  37.61      O
ATOM   4378 N    ALA  302    -38.068   6.665   8.430  36.87      N
ATOM   4379 HN   ALA  302    -37.550   6.953   7.613   0.00      H
ATOM   4380 CA   ALA  302    -39.142   5.696   8.305  37.18      C
ATOM   4381 HA   ALA  302    -40.055   6.140   8.606   0.00      H
ATOM   4382 CB   ALA  302    -39.267   5.235   6.872  36.08      C
ATOM   4383 HB1  ALA  302    -39.477   6.066   6.251   0.00      H
ATOM   4384 HB2  ALA  302    -38.358   4.786   6.565   0.00      H
ATOM   4385 HB3  ALA  302    -40.053   4.529   6.795   0.00      H
ATOM   4386 C    ALA  302    -38.891   4.503   9.219  38.85      C
ATOM   4387 O    ALA  302    -39.832   3.973   9.820  40.89      O
ATOM   4388 N    CYS  303    -37.636   4.070   9.325  38.13      N
ATOM   4389 HN   CYS  303    -36.904   4.525   8.801   0.00      H
ATOM   4390 CA   CYS  303    -37.317   2.942  10.195  37.59      C
ATOM   4391 HA   CYS  303    -37.861   2.089   9.881   0.00      H
ATOM   4392 CB   CYS  303    -35.836   2.597  10.109  38.23      C
ATOM   4393 HB2  CYS  303    -35.263   3.486  10.163   0.00      H
ATOM   4394 HB3  CYS  303    -35.575   1.959  10.913   0.00      H
ATOM   4395 SG   CYS  303    -35.397   1.759   8.585  42.19      S
ATOM   4396 HG   CYS  303    -34.172   1.509   8.585   0.00      H
ATOM   4397 C    CYS  303    -37.687   3.264  11.639  37.91      C
ATOM   4398 O    CYS  303    -38.227   2.426  12.359  37.58      O
ATOM   4399 N    ARG  304    -37.401   4.487  12.064  37.69      N
ATOM   4400 HN   ARG  304    -36.950   5.140  11.441   0.00      H
ATOM   4401 CA   ARG  304    -37.733   4.888  13.416  38.03      C
ATOM   4402 HA   ARG  304    -37.341   4.181  14.100   0.00      H
ATOM   4403 CB   ARG  304    -37.140   6.263  13.730  36.02      C
ATOM   4404 HB2  ARG  304    -37.489   6.968  13.021   0.00      H
ATOM   4405 HB3  ARG  304    -37.438   6.562  14.701   0.00      H
ATOM   4406 CG   ARG  304    -35.630   6.279  13.688  33.31      C
ATOM   4407 HG2  ARG  304    -35.253   5.462  14.247   0.00      H
ATOM   4408 HG3  ARG  304    -35.304   6.200  12.684   0.00      H
```

FIGURE 6- 59 -

```
ATOM   4409  CD   ARG  304   -35.091   7.551  14.271  31.54      C
ATOM   4410  HD2  ARG  304   -35.563   8.379  13.809   0.00      H
ATOM   4411  HD3  ARG  304   -35.283   7.571  15.312   0.00      H
ATOM   4412  NE   ARG  304   -33.654   7.677  14.071  31.42     N1-
ATOM   4413  HE   ARG  304   -33.133   6.917  13.660   0.00      H
ATOM   4414  CZ   ARG  304   -32.961   8.761  14.405  32.28      C
ATOM   4415  NH1  ARG  304   -33.583   9.801  14.957  29.73      N
ATOM   4416  HH11 ARG  304   -33.059  10.625  15.211   0.00      H
ATOM   4417  HH12 ARG  304   -34.578   9.765  15.121   0.00      H
ATOM   4418  NH2  ARG  304   -31.653   8.812  14.178  31.08      N
ATOM   4419  HH21 ARG  304   -31.129   9.636  14.432   0.00      H
ATOM   4420  HH22 ARG  304   -31.184   8.027  13.751   0.00      H
ATOM   4421  C    ARG  304   -39.247   4.914  13.596  39.14      C
ATOM   4422  O    ARG  304   -39.745   4.674  14.690  41.50      O
ATOM   4423  N    ALA  305   -39.981   5.204  12.528  39.09      N
ATOM   4424  HN   ALA  305   -39.526   5.401  11.649   0.00      H
ATOM   4425  CA   ALA  305   -41.432   5.239  12.620  39.56      C
ATOM   4426  HA   ALA  305   -41.718   5.784  13.432   0.00      H
ATOM   4427  CB   ALA  305   -42.016   5.903  11.401  39.12      C
ATOM   4428  HB1  ALA  305   -41.650   6.894  11.329   0.00      H
ATOM   4429  HB2  ALA  305   -41.737   5.360  10.536   0.00      H
ATOM   4430  HB3  ALA  305   -43.072   5.922  11.481   0.00      H
ATOM   4431  C    ALA  305   -41.984   3.828  12.755  41.22      C
ATOM   4432  O    ALA  305   -43.004   3.617  13.403  41.68      O
ATOM   4433  N    ALA  306   -41.303   2.863  12.145  42.59      N
ATOM   4434  HN   ALA  306   -40.467   3.115  11.638   0.00      H
ATOM   4435  CA   ALA  306   -41.735   1.469  12.194  44.67      C
ATOM   4436  HA   ALA  306   -42.791   1.429  12.266   0.00      H
ATOM   4437  CB   ALA  306   -41.290   0.746  10.933  43.79      C
ATOM   4438  HB1  ALA  306   -41.720   1.216  10.087   0.00      H
ATOM   4439  HB2  ALA  306   -40.234   0.783  10.859   0.00      H
ATOM   4440  HB3  ALA  306   -41.606  -0.264  10.975   0.00      H
ATOM   4441  C    ALA  306   -41.181   0.757  13.424  47.00      C
ATOM   4442  O    ALA  306   -41.636  -0.325  13.799  48.06      O
ATOM   4443  N    LYS  307   -40.185   1.373  14.045  48.95      N
ATOM   4444  HN   LYS  307   -39.868   2.255  13.670   0.00      H
ATOM   4445  CA   LYS  307   -39.552   0.817  15.231  49.29      C
ATOM   4446  HA   LYS  307   -38.845   1.508  15.611   0.00      H
ATOM   4447  CB   LYS  307   -40.603   0.530  16.313  49.84      C
ATOM   4448  HB2  LYS  307   -41.189  -0.304  16.024   0.00      H
ATOM   4449  HB3  LYS  307   -40.117   0.319  17.230   0.00      H
ATOM   4450  CG   LYS  307   -41.570   1.685  16.576  50.58      C
ATOM   4451  HG2  LYS  307   -41.069   2.606  16.427   0.00      H
ATOM   4452  HG3  LYS  307   -42.390   1.618  15.909   0.00      H
ATOM   4453  CD   LYS  307   -42.105   1.656  17.997  49.75      C
ATOM   4454  HD2  LYS  307   -42.834   2.415  18.115   0.00      H
ATOM   4455  HD3  LYS  307   -42.544   0.712  18.190   0.00      H
ATOM   4456  CE   LYS  307   -40.970   1.892  18.985  50.48      C
ATOM   4457  HE2  LYS  307   -40.193   1.195  18.803   0.00      H
ATOM   4458  HE3  LYS  307   -40.597   2.876  18.865   0.00      H
ATOM   4459  NZ   LYS  307   -41.385   1.740  20.408  52.11     N1-
ATOM   4460  HZ1  LYS  307   -42.114   2.405  20.619   0.00      H
ATOM   4461  HZ2  LYS  307   -41.730   0.804  20.560   0.00      H
ATOM   4462  HZ3  LYS  307   -40.592   1.908  21.009   0.00      H
ATOM   4463  C    LYS  307   -38.746  -0.450  14.930  48.91      C
ATOM   4464  O    LYS  307   -38.642  -1.341  15.770  50.54      O
ATOM   4465  N    LEU  308   -38.179  -0.539  13.732  48.44      N
ATOM   4466  HN   LEU  308   -38.320   0.202  13.061   0.00      H
ATOM   4467  CA   LEU  308   -37.357  -1.697  13.381  49.62      C
ATOM   4468  HA   LEU  308   -37.909  -2.585  13.548   0.00      H
ATOM   4469  CB   LEU  308   -36.950  -1.630  11.907  47.59      C
ATOM   4470  HB2  LEU  308   -36.367  -0.762  11.741   0.00      H
ATOM   4471  HB3  LEU  308   -36.383  -2.489  11.658   0.00      H
ATOM   4472  CG   LEU  308   -38.098  -1.571  10.897  45.13      C
ATOM   4473  HG   LEU  308   -38.788  -0.824  11.191   0.00      H
ATOM   4474  CD1  LEU  308   -37.557  -1.241   9.531  43.55      C
ATOM   4475  HD11 LEU  308   -37.069  -0.302   9.562   0.00      H
ATOM   4476  HD12 LEU  308   -36.867  -1.988   9.235   0.00      H
ATOM   4477  HD13 LEU  308   -38.355  -1.201   8.836   0.00      H
ATOM   4478  CD2  LEU  308   -38.823  -2.894  10.872  45.24      C
ATOM   4479  HD21 LEU  308   -38.149  -3.661  10.592   0.00      H
ATOM   4480  HD22 LEU  308   -39.213  -3.101  11.835   0.00      H
ATOM   4481  HD23 LEU  308   -39.616  -2.849  10.172   0.00      H
ATOM   4482  C    LEU  308   -36.112  -1.632  14.279  50.98      C
ATOM   4483  O    LEU  308   -35.572  -0.550  14.515  51.35      O
ATOM   4484  N    GLN  309   -35.653  -2.771  14.736  51.64      N
```

FIGURE 6- 60 -

```
ATOM   4485  HN   GLN  309   -36.103   -3.646   14.564    0.00    H
ATOM   4486  CA   GLN  309   -34.493   -2.751   15.668   53.04    C
ATOM   4487  HA   GLN  309   -34.414   -1.799   16.126    0.00    H
ATOM   4488  CB   GLN  309   -34.639   -3.821   16.754   55.63    C
ATOM   4489  HB2  GLN  309   -34.805   -4.764   16.301    0.00    H
ATOM   4490  HB3  GLN  309   -33.753   -3.859   17.333    0.00    H
ATOM   4491  CG   GLN  309   -35.800   -3.551   17.700   58.79    C
ATOM   4492  HG2  GLN  309   -36.713   -3.624   17.168    0.00    H
ATOM   4493  HG3  GLN  309   -35.790   -4.263   18.483    0.00    H
ATOM   4494  CD   GLN  309   -35.737   -2.156   18.334   60.91    C
ATOM   4495  OE1  GLN  309   -35.685   -1.131   17.638   59.69    O
ATOM   4496  NE2  GLN  309   -35.751   -2.117   19.665   62.57    N
ATOM   4497  HE21 GLN  309   -35.794   -2.975   20.194    0.00    H
ATOM   4498  HE22 GLN  309   -35.719   -1.230   20.144    0.00    H
ATOM   4499  C    GLN  309   -33.171   -2.912   14.947   52.73    C
ATOM   4500  O    GLN  309   -33.095   -3.588   13.921   53.04    O
ATOM   4501  N    ASP  310   -32.135   -2.280   15.491   51.60    N
ATOM   4502  HN   ASP  310   -32.290   -1.748   16.334    0.00    H
ATOM   4503  CA   ASP  310   -30.803   -2.341   14.902   52.24    C
ATOM   4504  HA   ASP  310   -30.277   -1.450   15.126    0.00    H
ATOM   4505  CB   ASP  310   -30.035   -3.536   15.470   55.31    C
ATOM   4506  HB2  ASP  310   -30.654   -4.395   15.451    0.00    H
ATOM   4507  HB3  ASP  310   -29.170   -3.711   14.884    0.00    H
ATOM   4508  CG   ASP  310   -29.586   -3.317   16.910   59.11    C
ATOM   4509  OD1  ASP  310   -30.376   -2.749   17.702   59.24    O
ATOM   4510  OD2  ASP  310   -28.448   -3.730   17.248   60.51    O1-
ATOM   4511  C    ASP  310   -30.852   -2.453   13.380   50.77    C
ATOM   4512  O    ASP  310   -30.647   -3.537   12.835   50.77    O
ATOM   4513  N    CYS  311   -31.133   -1.343   12.699   48.73    N
ATOM   4514  HN   CYS  311   -31.305   -0.492   13.214    0.00    H
ATOM   4515  CA   CYS  311   -31.195   -1.339   11.236   46.63    C
ATOM   4516  HA   CYS  311   -31.431   -2.312   10.890    0.00    H
ATOM   4517  CB   CYS  311   -32.274   -0.366   10.729   44.67    C
ATOM   4518  HB2  CYS  311   -32.042    0.616   11.049    0.00    H
ATOM   4519  HB3  CYS  311   -32.305   -0.394    9.671    0.00    H
ATOM   4520  SG   CYS  311   -33.980   -0.665   11.274   43.18    S
ATOM   4521  HG   CYS  311   -34.733    0.203   10.782    0.00    H
ATOM   4522  C    CYS  311   -29.853   -0.914   10.644   45.93    C
ATOM   4523  O    CYS  311   -29.178   -0.055   11.191   46.22    O
ATOM   4524  N    THR  312   -29.464   -1.521    9.530   45.02    N
ATOM   4525  HN   THR  312   -30.040   -2.254    9.144    0.00    H
ATOM   4526  CA   THR  312   -28.224   -1.143    8.865   44.83    C
ATOM   4527  HA   THR  312   -27.879   -0.222    9.258    0.00    H
ATOM   4528  CB   THR  312   -27.117   -2.189    9.062   44.70    C
ATOM   4529  HB   THR  312   -27.509   -3.156    8.882    0.00    H
ATOM   4530  OG1  THR  312   -26.641   -2.114   10.409   46.49    O
ATOM   4531  HG1  THR  312   -25.943   -2.770   10.541    0.00    H
ATOM   4532  CG2  THR  312   -25.960   -1.938    8.097   41.78    C
ATOM   4533  HG21 THR  312   -26.313   -1.996    7.100    0.00    H
ATOM   4534  HG22 THR  312   -25.556   -0.975    8.273    0.00    H
ATOM   4535  HG23 THR  312   -25.209   -2.669    8.249    0.00    H
ATOM   4536  C    THR  312   -28.509   -0.987    7.382   45.05    C
ATOM   4537  O    THR  312   -28.683   -1.975    6.661   45.45    O
ATOM   4538  N    MET  313   -28.554    0.257    6.924   43.75    N
ATOM   4539  HN   MET  313   -28.384    1.033    7.547    0.00    H
ATOM   4540  CA   MET  313   -28.848    0.501    5.527   43.02    C
ATOM   4541  HA   MET  313   -29.349   -0.339    5.120    0.00    H
ATOM   4542  CB   MET  313   -29.738    1.731    5.386   44.77    C
ATOM   4543  HB2  MET  313   -29.206    2.590    5.704    0.00    H
ATOM   4544  HB3  MET  313   -30.022    1.847    4.372    0.00    H
ATOM   4545  CG   MET  313   -31.005    1.657    6.204   46.97    C
ATOM   4546  HG2  MET  313   -31.516    0.757    5.982    0.00    H
ATOM   4547  HG3  MET  313   -30.762    1.680    7.234    0.00    H
ATOM   4548  SD   MET  313   -32.070    3.042    5.825   49.75    S
ATOM   4549  CE   MET  313   -30.920    4.409    5.984   48.57    C
ATOM   4550  HE1  MET  313   -30.532    4.431    6.969    0.00    H
ATOM   4551  HE2  MET  313   -30.126    4.284    5.294    0.00    H
ATOM   4552  HE3  MET  313   -31.423    5.319    5.783    0.00    H
ATOM   4553  C    MET  313   -27.652    0.659    4.613   41.23    C
ATOM   4554  O    MET  313   -26.536    0.944    5.037   41.04    O
ATOM   4555  N    LEU  314   -27.921    0.444    3.337   40.03    N
ATOM   4556  HN   LEU  314   -28.864    0.164    3.113    0.00    H
ATOM   4557  CA   LEU  314   -26.943    0.591    2.285   39.23    C
ATOM   4558  HA   LEU  314   -26.120    1.152    2.644    0.00    H
ATOM   4559  CB   LEU  314   -26.443   -0.773    1.817   37.96    C
ATOM   4560  HB2  LEU  314   -26.067   -1.314    2.646    0.00    H
```

FIGURE 6- 61 -

```
ATOM   4561  HB3  LEU   314    -27.243   -1.311    1.378     0.00    H
ATOM   4562  CG   LEU   314    -25.322   -0.729    0.777    37.09    C
ATOM   4563  HG   LEU   314    -25.656   -0.203   -0.079     0.00    H
ATOM   4564  CD1  LEU   314    -24.122   -0.024    1.373    37.89    C
ATOM   4565  HD11 LEU   314    -24.393    0.962    1.648     0.00    H
ATOM   4566  HD12 LEU   314    -23.793   -0.551    2.230     0.00    H
ATOM   4567  HD13 LEU   314    -23.342    0.010    0.658     0.00    H
ATOM   4568  CD2  LEU   314    -24.945   -2.135    0.347    34.82    C
ATOM   4569  HD21 LEU   314    -24.613   -2.685    1.189     0.00    H
ATOM   4570  HD22 LEU   314    -25.790   -2.613   -0.076     0.00    H
ATOM   4571  HD23 LEU   314    -24.169   -2.088   -0.372     0.00    H
ATOM   4572  C    LEU   314    -27.757    1.287    1.192    39.71    C
ATOM   4573  O    LEU   314    -28.688    0.710    0.623    39.57    O
ATOM   4574  N    VAL   315    -27.429    2.546    0.937    39.35    N
ATOM   4575  HN   VAL   315    -26.666    2.962    1.449     0.00    H
ATOM   4576  CA   VAL   315    -28.145    3.324   -0.058    38.18    C
ATOM   4577  HA   VAL   315    -28.978    2.770   -0.407     0.00    H
ATOM   4578  CB   VAL   315    -28.647    4.655    0.551    39.01    C
ATOM   4579  HB   VAL   315    -27.817    5.257    0.817     0.00    H
ATOM   4580  CG1  VAL   315    -29.440    5.452   -0.480    37.93    C
ATOM   4581  HG11 VAL   315    -28.821    5.667   -1.312     0.00    H
ATOM   4582  HG12 VAL   315    -30.275    4.884   -0.799     0.00    H
ATOM   4583  HG13 VAL   315    -29.774    6.358   -0.045     0.00    H
ATOM   4584  CG2  VAL   315    -29.483    4.374    1.794    39.28    C
ATOM   4585  HG21 VAL   315    -30.315    3.774    1.531     0.00    H
ATOM   4586  HG22 VAL   315    -28.892    3.864    2.509     0.00    H
ATOM   4587  HG23 VAL   315    -29.823    5.289    2.205     0.00    H
ATOM   4588  C    VAL   315    -27.265    3.651   -1.250    38.40    C
ATOM   4589  O    VAL   315    -26.115    4.070   -1.092    38.30    O
ATOM   4590  N    ASN   316    -27.808    3.433   -2.442    37.37    N
ATOM   4591  HN   ASN   316    -28.734    3.033   -2.474     0.00    H
ATOM   4592  CA   ASN   316    -27.109    3.753   -3.680    37.79    C
ATOM   4593  HA   ASN   316    -26.208    4.263   -3.455     0.00    H
ATOM   4594  CB   ASN   316    -26.761    2.496   -4.480    38.31    C
ATOM   4595  HB2  ASN   316    -27.587    1.833   -4.472     0.00    H
ATOM   4596  HB3  ASN   316    -26.534    2.765   -5.479     0.00    H
ATOM   4597  CG   ASN   316    -25.569    1.756   -3.918    37.60    C
ATOM   4598  OD1  ASN   316    -25.652    1.100   -2.875    38.29    O
ATOM   4599  ND2  ASN   316    -24.446    1.862   -4.604    37.50    N
ATOM   4600  HD21 ASN   316    -24.422    2.409   -5.452     0.00    H
ATOM   4601  HD22 ASN   316    -23.611    1.396   -4.280     0.00    H
ATOM   4602  C    ASN   316    -28.080    4.602   -4.473    37.73    C
ATOM   4603  O    ASN   316    -28.958    4.079   -5.147    38.18    O
ATOM   4604  N    GLY   317    -27.933    5.916   -4.383    37.72    N
ATOM   4605  HN   GLY   317    -27.193    6.314   -3.824     0.00    H
ATOM   4606  CA   GLY   317    -28.845    6.781   -5.096    38.29    C
ATOM   4607  HA2  GLY   317    -28.565    7.791   -4.945     0.00    H
ATOM   4608  HA3  GLY   317    -28.810    6.556   -6.130     0.00    H
ATOM   4609  C    GLY   317    -30.237    6.537   -4.554    38.88    C
ATOM   4610  O    GLY   317    -30.516    6.820   -3.391    39.87    O
ATOM   4611  N    ASP   318    -31.115    5.991   -5.385    39.03    N
ATOM   4612  HN   ASP   318    -30.830    5.762   -6.325     0.00    H
ATOM   4613  CA   ASP   318    -32.479    5.722   -4.951    39.79    C
ATOM   4614  HA   ASP   318    -32.691    6.287   -4.081     0.00    H
ATOM   4615  CB   ASP   318    -33.469    6.109   -6.056    40.99    C
ATOM   4616  HB2  ASP   318    -34.440    6.202   -5.643     0.00    H
ATOM   4617  HB3  ASP   318    -33.177    7.033   -6.484     0.00    H
ATOM   4618  CG   ASP   318    -33.531    5.081   -7.166    41.99    C
ATOM   4619  OD1  ASP   318    -32.469    4.705   -7.700    41.08    O
ATOM   4620  OD2  ASP   318    -34.652    4.649   -7.503    45.00    O1-
ATOM   4621  C    ASP   318    -32.649    4.245   -4.609    38.36    C
ATOM   4622  O    ASP   318    -33.759    3.795   -4.331    37.19    O
ATOM   4623  N    ASP   319    -31.541    3.504   -4.629    38.16    N
ATOM   4624  HN   ASP   319    -30.676    3.973   -4.852     0.00    H
ATOM   4625  CA   ASP   319    -31.543    2.067   -4.344    37.61    C
ATOM   4626  HA   ASP   319    -32.509    1.673   -4.524     0.00    H
ATOM   4627  CB   ASP   319    -30.534    1.355   -5.244    39.96    C
ATOM   4628  HB2  ASP   319    -30.447    1.879   -6.160     0.00    H
ATOM   4629  HB3  ASP   319    -29.591    1.326   -4.763     0.00    H
ATOM   4630  CG   ASP   319    -30.942   -0.068   -5.558    43.16    C
ATOM   4631  OD1  ASP   319    -30.695   -0.970   -4.721    44.75    O
ATOM   4632  OD2  ASP   319    -31.529   -0.279   -6.643    45.55    O1-
ATOM   4633  C    ASP   319    -31.215    1.817   -2.884    36.10    C
ATOM   4634  O    ASP   319    -30.115    2.105   -2.419    36.05    O
ATOM   4635  N    LEU   320    -32.179    1.244   -2.180    34.82    N
ATOM   4636  HN   LEU   320    -33.018    0.969   -2.669     0.00    H
```

FIGURE 6- 62 -

```
ATOM   4637  CA   LEU  320   -32.060    1.008   -0.758   35.29      C
ATOM   4638  HA   LEU  320   -31.073    1.229   -0.445    0.00      H
ATOM   4639  CB   LEU  320   -33.057    1.920   -0.058   33.71      C
ATOM   4640  HB2  LEU  320   -32.677    2.908   -0.037    0.00      H
ATOM   4641  HB3  LEU  320   -33.977    1.907   -0.583    0.00      H
ATOM   4642  CG   LEU  320   -33.423    1.610    1.382   33.61      C
ATOM   4643  HG   LEU  320   -33.615    0.573    1.482    0.00      H
ATOM   4644  CD1  LEU  320   -32.280    2.000    2.285   32.82      C
ATOM   4645  HD11 LEU  320   -31.414    1.453    2.015    0.00      H
ATOM   4646  HD12 LEU  320   -32.088    3.037    2.184    0.00      H
ATOM   4647  HD13 LEU  320   -32.535    1.784    3.290    0.00      H
ATOM   4648  CD2  LEU  320   -34.687    2.374    1.737   34.61      C
ATOM   4649  HD21 LEU  320   -34.515    3.413    1.625    0.00      H
ATOM   4650  HD22 LEU  320   -35.473    2.075    1.093    0.00      H
ATOM   4651  HD23 LEU  320   -34.955    2.167    2.741    0.00      H
ATOM   4652  C    LEU  320   -32.272   -0.434   -0.306   36.54      C
ATOM   4653  O    LEU  320   -33.034   -1.187   -0.904   36.00      C
ATOM   4654  N    VAL  321   -31.594   -0.797    0.777   38.28      N
ATOM   4655  HN   VAL  321   -30.998   -0.105    1.207    0.00      H
ATOM   4656  CA   VAL  321   -31.686   -2.137    1.348   39.33      C
ATOM   4657  HA   VAL  321   -32.657   -2.526    1.182    0.00      H
ATOM   4658  CB   VAL  321   -30.656   -3.096    0.705   38.61      C
ATOM   4659  HB   VAL  321   -30.835   -3.160   -0.337    0.00      H
ATOM   4660  CG1  VAL  321   -29.249   -2.553    0.893   36.37      C
ATOM   4661  HG11 VAL  321   -29.173   -1.602    0.433    0.00      H
ATOM   4662  HG12 VAL  321   -29.041   -2.462    1.927    0.00      H
ATOM   4663  HG13 VAL  321   -28.553   -3.216    0.450    0.00      H
ATOM   4664  CG2  VAL  321   -30.784   -4.479    1.322   38.08      C
ATOM   4665  HG21 VAL  321   -30.603   -4.419    2.364    0.00      H
ATOM   4666  HG22 VAL  321   -31.761   -4.851    1.154    0.00      H
ATOM   4667  HG23 VAL  321   -30.077   -5.130    0.878    0.00      H
ATOM   4668  C    VAL  321   -31.434   -2.078    2.854   40.35      C
ATOM   4669  O    VAL  321   -30.407   -1.575    3.299   40.43      C
ATOM   4670  N    VAL  322   -32.375   -2.601    3.632   41.45      N
ATOM   4671  HN   VAL  322   -33.184   -3.009    3.188    0.00      H
ATOM   4672  CA   VAL  322   -32.265   -2.597    5.084   42.88      C
ATOM   4673  HA   VAL  322   -31.453   -1.983    5.375    0.00      H
ATOM   4674  CB   VAL  322   -33.552   -2.054    5.721   42.47      C
ATOM   4675  HB   VAL  322   -34.334   -2.757    5.591    0.00      H
ATOM   4676  CG1  VAL  322   -33.363   -1.894    7.218   42.45      C
ATOM   4677  HG11 VAL  322   -33.132   -2.834    7.647    0.00      H
ATOM   4678  HG12 VAL  322   -32.570   -1.217    7.403    0.00      H
ATOM   4679  HG13 VAL  322   -34.255   -1.519    7.648    0.00      H
ATOM   4680  CG2  VAL  322   -33.940   -0.756    5.069   42.74      C
ATOM   4681  HG21 VAL  322   -33.162   -0.049    5.199    0.00      H
ATOM   4682  HG22 VAL  322   -34.103   -0.915    4.035    0.00      H
ATOM   4683  HG23 VAL  322   -34.828   -0.389    5.514    0.00      H
ATOM   4684  C    VAL  322   -32.021   -3.988    5.673   44.44      C
ATOM   4685  O    VAL  322   -32.675   -4.955    5.287   45.88      C
ATOM   4686  N    ILE  323   -31.075   -4.087    6.598   45.27      N
ATOM   4687  HN   ILE  323   -30.543   -3.263    6.835    0.00      H
ATOM   4688  CA   ILE  323   -30.797   -5.353    7.268   47.01      C
ATOM   4689  HA   ILE  323   -31.484   -6.087    6.934    0.00      H
ATOM   4690  CB   ILE  323   -29.372   -5.859    6.976   45.60      C
ATOM   4691  HB   ILE  323   -28.693   -5.048    7.025    0.00      H
ATOM   4692  CG2  ILE  323   -28.960   -6.907    7.990   45.69      C
ATOM   4693  HG21 ILE  323   -28.982   -6.486    8.962    0.00      H
ATOM   4694  HG22 ILE  323   -29.631   -7.725    7.944    0.00      H
ATOM   4695  HG23 ILE  323   -27.979   -7.242    7.773    0.00      H
ATOM   4696  CG1  ILE  323   -29.339   -6.469    5.576   45.50      C
ATOM   4697  HG12 ILE  323   -30.039   -7.262    5.520    0.00      H
ATOM   4698  HG13 ILE  323   -29.588   -5.728    4.862    0.00      H
ATOM   4699  CD1  ILE  323   -27.999   -7.034    5.176   44.73      C
ATOM   4700  HD11 ILE  323   -27.271   -6.265    5.196    0.00      H
ATOM   4701  HD12 ILE  323   -27.722   -7.799    5.854    0.00      H
ATOM   4702  HD13 ILE  323   -28.063   -7.435    4.198    0.00      H
ATOM   4703  C    ILE  323   -30.982   -5.050    8.744   49.37      C
ATOM   4704  O    ILE  323   -30.327   -4.160    9.289   48.25      C
ATOM   4705  N    CYS  324   -31.885   -5.781    9.390   52.12      N
ATOM   4706  HN   CYS  324   -32.365   -6.523    8.903    0.00      H
ATOM   4707  CA   CYS  324   -32.183   -5.517   10.791   55.13      C
ATOM   4708  HA   CYS  324   -31.372   -4.999   11.233    0.00      H
ATOM   4709  CB   CYS  324   -33.398   -4.614   10.864   54.98      C
ATOM   4710  HB2  CYS  324   -33.664   -4.462   11.878    0.00      H
ATOM   4711  HB3  CYS  324   -33.173   -3.682   10.415    0.00      H
ATOM   4712  SG   CYS  324   -34.783   -5.357   10.002   56.13      S
```

FIGURE 6- 63 -

```
ATOM   4713  HG   CYS  324    -35.774   -4.598   10.073    0.00    H
ATOM   4714  C    CYS  324    -32.435   -6.713   11.697   56.90    C
ATOM   4715  O    CYS  324    -32.538   -7.854   11.253   57.77    O
ATOM   4716  N    GLU  325    -32.558   -6.406   12.985   59.16    N
ATOM   4717  HN   GLU  325    -32.470   -5.430   13.225    0.00    H
ATOM   4718  CA   GLU  325    -32.806   -7.392   14.027   60.53    C
ATOM   4719  HA   GLU  325    -32.238   -8.264   13.831    0.00    H
ATOM   4720  CB   GLU  325    -32.398   -6.809   15.384   61.11    C
ATOM   4721  HB2  GLU  325    -31.442   -6.361   15.303    0.00    H
ATOM   4722  HB3  GLU  325    -33.106   -6.080   15.682    0.00    H
ATOM   4723  CG   GLU  325    -32.319   -7.833   16.488   63.86    C
ATOM   4724  HG2  GLU  325    -32.043   -7.356   17.392    0.00    H
ATOM   4725  HG3  GLU  325    -33.263   -8.297   16.607    0.00    H
ATOM   4726  CD   GLU  325    -31.294   -8.912   16.187   64.68    C
ATOM   4727  OE1  GLU  325    -30.084   -8.584   16.105   65.21    O1-
ATOM   4728  OE2  GLU  325    -31.705  -10.083   16.024   64.48    O
ATOM   4729  C    GLU  325    -34.294   -7.756   14.028   60.40    C
ATOM   4730  O    GLU  325    -35.138   -6.961   14.438   59.45    O
ATOM   4731  N    SER  326    -34.605   -8.961   13.564   61.56    N
ATOM   4732  HN   SER  326    -33.860   -9.569   13.256    0.00    H
ATOM   4733  CA   SER  326    -35.990   -9.412   13.494   63.07    C
ATOM   4734  HA   SER  326    -36.569   -8.695   12.972    0.00    H
ATOM   4735  CB   SER  326    -36.094  -10.750   12.765   62.41    C
ATOM   4736  HB2  SER  326    -35.813  -10.623   11.752    0.00    H
ATOM   4737  HB3  SER  326    -35.449  -11.453   13.224    0.00    H
ATOM   4738  OG   SER  326    -37.424  -11.235   12.820   60.35    O
ATOM   4739  HG   SER  326    -37.478  -12.082   12.356    0.00    H
ATOM   4740  C    SER  326    -36.655   -9.560   14.847   63.98    C
ATOM   4741  O    SER  326    -35.987   -9.770   15.857   64.26    O
ATOM   4742  N    ALA  327    -37.981   -9.445   14.847   64.83    N
ATOM   4743  HN   ALA  327    -38.431   -9.249   13.965    0.00    H
ATOM   4744  CA   ALA  327    -38.780   -9.591   16.056   66.15    C
ATOM   4745  HA   ALA  327    -38.141   -9.756   16.884    0.00    H
ATOM   4746  CB   ALA  327    -39.599   -8.341   16.310   64.91    C
ATOM   4747  HB1  ALA  327    -38.951   -7.512   16.426    0.00    H
ATOM   4748  HB2  ALA  327    -40.247   -8.171   15.490    0.00    H
ATOM   4749  HB3  ALA  327    -40.172   -8.467   17.192    0.00    H
ATOM   4750  C    ALA  327    -39.699  -10.787   15.841   67.39    C
ATOM   4751  O    ALA  327    -40.135  -11.431   16.796   68.62    O
ATOM   4752  N    GLY  328    -39.982  -11.079   14.575   67.86    N
ATOM   4753  HN   GLY  328    -39.595  -10.507   13.840    0.00    H
ATOM   4754  CA   GLY  328    -40.835  -12.203   14.245   68.15    C
ATOM   4755  HA2  GLY  328    -40.237  -13.056   14.056    0.00    H
ATOM   4756  HA3  GLY  328    -41.487  -12.401   15.056    0.00    H
ATOM   4757  C    GLY  328    -41.707  -11.998   13.021   68.80    C
ATOM   4758  O    GLY  328    -42.329  -10.946   12.858   69.14    O
ATOM   4759  N    THR  329    -41.739  -13.017   12.164   68.76    N
ATOM   4760  HN   THR  329    -41.174  -13.819   12.400    0.00    H
ATOM   4761  CA   THR  329    -42.534  -13.019   10.937   68.90    C
ATOM   4762  HA   THR  329    -41.922  -12.738   10.120    0.00    H
ATOM   4763  CB   THR  329    -43.113  -14.426   10.670   68.20    C
ATOM   4764  HB   THR  329    -43.698  -14.730   11.499    0.00    H
ATOM   4765  OG1  THR  329    -42.045  -15.362   10.491   68.14    O
ATOM   4766  HG1  THR  329    -42.411  -16.241   10.324    0.00    H
ATOM   4767  CG2  THR  329    -43.985  -14.419    9.431   68.03    C
ATOM   4768  HG21 THR  329    -44.786  -13.739    9.567    0.00    H
ATOM   4769  HG22 THR  329    -43.407  -14.122    8.595    0.00    H
ATOM   4770  HG23 THR  329    -44.371  -15.391    9.266    0.00    H
ATOM   4771  C    THR  329    -43.706  -12.047   11.032   70.13    C
ATOM   4772  O    THR  329    -43.797  -11.060   10.299   70.39    O
ATOM   4773  N    GLN  330    -44.596  -12.349   11.967   70.84    N
ATOM   4774  HN   GLN  330    -44.407  -13.172   12.520    0.00    H
ATOM   4775  CA   GLN  330    -45.794  -11.565   12.217   70.90    C
ATOM   4776  HA   GLN  330    -46.446  -11.643   11.387    0.00    H
ATOM   4777  CB   GLN  330    -46.495  -12.099   13.474   72.81    C
ATOM   4778  HB2  GLN  330    -46.072  -11.646   14.333    0.00    H
ATOM   4779  HB3  GLN  330    -47.528  -11.870   13.426    0.00    H
ATOM   4780  CG   GLN  330    -46.374  -13.619   13.655   75.26    C
ATOM   4781  HG2  GLN  330    -47.152  -13.962   14.285    0.00    H
ATOM   4782  HG3  GLN  330    -46.448  -14.094   12.711    0.00    H
ATOM   4783  CD   GLN  330    -45.047  -14.056   14.285   76.24    C
ATOM   4784  OE1  GLN  330    -43.975  -13.562   13.925   77.75    O
ATOM   4785  NE2  GLN  330    -45.121  -15.001   15.223   75.86    N
ATOM   4786  HE21 GLN  330    -46.018  -15.379   15.489    0.00    H
ATOM   4787  HE22 GLN  330    -44.280  -15.338   15.667    0.00    H
ATOM   4788  C    GLN  330    -45.503  -10.080   12.391   69.09    C
```

FIGURE 6- 64 -

```
ATOM   4789  C    GLN  330   -46.145  -9.235  11.771  68.43  O
ATOM   4790  N    GLU  331   -44.529  -9.781  13.243  67.71  N
ATOM   4791  HN   GLU  331   -44.050 -10.552  13.685   0.00  H
ATOM   4792  CA   GLU  331   -44.141  -8.407  13.551  66.85  C
ATOM   4793  HA   GLU  331   -45.003  -7.843  13.797   0.00  H
ATOM   4794  CB   GLU  331   -43.176  -8.391  14.733  68.14  C
ATOM   4795  HB2  GLU  331   -42.317  -8.963  14.495   0.00  H
ATOM   4796  HB3  GLU  331   -42.889  -7.393  14.941   0.00  H
ATOM   4797  CG   GLU  331   -43.746  -8.962  16.014  69.90  C
ATOM   4798  HG2  GLU  331   -44.032  -8.170  16.657   0.00  H
ATOM   4799  HG3  GLU  331   -44.592  -9.558  15.789   0.00  H
ATOM   4800  CD   GLU  331   -42.729  -9.825  16.737  71.34  C
ATOM   4801  CE1  GLU  331   -42.419 -10.918  16.211  71.62  O1-
ATOM   4802  CE2  GLU  331   -42.234  -9.412  17.813  71.83  O
ATOM   4803  C    GLU  331   -43.501  -7.667  12.392  64.58  C
ATOM   4804  C    GLU  331   -43.902  -6.552  12.056  64.57  O
ATOM   4805  N    ASP  332   -42.488  -8.281  11.800  61.78  N
ATOM   4806  HN   ASP  332   -42.199  -9.187  12.138   0.00  H
ATOM   4807  CA   ASP  332   -41.798  -7.671  10.683  58.93  C
ATOM   4808  HA   ASP  332   -41.283  -6.808  11.015   0.00  H
ATOM   4809  CB   ASP  332   -40.799  -8.655  10.091  56.81  C
ATOM   4810  HB2  ASP  332   -41.321  -9.446   9.618   0.00  H
ATOM   4811  HB3  ASP  332   -40.193  -8.157   9.380   0.00  H
ATOM   4812  CG   ASP  332   -39.894  -9.253  11.139  55.71  C
ATOM   4813  CD1  ASP  332   -39.728  -8.626  12.213  53.76  O
ATOM   4814  CD2  ASP  332   -39.343 -10.344  10.884  54.93  O1-
ATOM   4815  C    ASP  332   -42.791  -7.222   9.618  58.69  C
ATOM   4816  C    ASP  332   -42.792  -6.058   9.215  58.62  O
ATOM   4817  N    ALA  333   -43.638  -8.140   9.163  58.10  N
ATOM   4818  HN   ALA  333   -43.592  -9.079   9.529   0.00  H
ATOM   4819  CA   ALA  333   -44.627  -7.801   8.145  57.41  C
ATOM   4820  HA   ALA  333   -44.144  -7.681   7.210   0.00  H
ATOM   4821  CB   ALA  333   -45.669  -8.909   8.028  57.52  C
ATOM   4822  HB1  ALA  333   -45.192  -9.815   7.758   0.00  H
ATOM   4823  HB2  ALA  333   -46.159  -9.032   8.958   0.00  H
ATOM   4824  HB3  ALA  333   -46.379  -8.649   7.286   0.00  H
ATOM   4825  C    ALA  333   -45.301  -6.493   8.533  55.87  C
ATOM   4826  C    ALA  333   -45.467  -5.593   7.701  57.63  O
ATOM   4827  N    ALA  334   -45.678  -6.403   9.808  55.18  N
ATOM   4828  HN   ALA  334   -45.489  -7.196  10.403   0.00  H
ATOM   4829  CA   ALA  334   -46.338  -5.223  10.353  53.89  C
ATOM   4830  HA   ALA  334   -47.202  -5.006   9.781   0.00  H
ATOM   4831  CB   ALA  334   -46.745  -5.477  11.803  52.09  C
ATOM   4832  HB1  ALA  334   -47.411  -6.299  11.844   0.00  H
ATOM   4833  HB2  ALA  334   -45.883  -5.692  12.379   0.00  H
ATOM   4834  HB3  ALA  334   -47.223  -4.616  12.191   0.00  H
ATOM   4835  C    ALA  334   -45.410  -4.016  10.273  53.27  C
ATOM   4836  C    ALA  334   -45.786  -2.962   9.760  53.15  O
ATOM   4837  N    ALA  335   -44.194  -4.184  10.780  52.80  N
ATOM   4838  HN   ALA  335   -43.966  -5.083  11.178   0.00  H
ATOM   4839  CA   ALA  335   -43.202  -3.117  10.773  53.17  C
ATOM   4840  HA   ALA  335   -43.589  -2.272  11.281   0.00  H
ATOM   4841  CB   ALA  335   -41.923  -3.584  11.475  52.01  C
ATOM   4842  HB1  ALA  335   -42.146  -3.845  12.477   0.00  H
ATOM   4843  HB2  ALA  335   -41.530  -4.427  10.969   0.00  H
ATOM   4844  HB3  ALA  335   -41.209  -2.802  11.465   0.00  H
ATOM   4845  C    ALA  335   -42.895  -2.664   9.344  53.56  C
ATOM   4846  C    ALA  335   -42.797  -1.460   9.075  53.64  O
ATOM   4847  N    LEU  336   -42.743  -3.623   8.430  52.90  N
ATOM   4848  HN   LEU  336   -42.824  -4.589   8.710   0.00  H
ATOM   4849  CA   LEU  336   -42.463  -3.288   7.039  52.43  C
ATOM   4850  HA   LEU  336   -41.585  -2.699   6.988   0.00  H
ATOM   4851  CB   LEU  336   -42.255  -4.551   6.199  52.91  C
ATOM   4852  HB2  LEU  336   -41.606  -5.213   6.711   0.00  H
ATOM   4853  HB3  LEU  336   -43.188  -5.025   6.038   0.00  H
ATOM   4854  CG   LEU  336   -41.638  -4.279   4.825  53.09  C
ATOM   4855  HG   LEU  336   -42.287  -3.660   4.263   0.00  H
ATOM   4856  CD1  LEU  336   -40.305  -3.585   5.011  53.97  C
ATOM   4857  HD11 LEU  336   -40.452  -2.670   5.524   0.00  H
ATOM   4858  HD12 LEU  336   -39.659  -4.206   5.575   0.00  H
ATOM   4859  HD13 LEU  336   -39.872  -3.393   4.064   0.00  H
ATOM   4860  CD2  LEU  336   -41.439  -5.565   4.067  53.44  C
ATOM   4861  HD21 LEU  336   -40.791  -6.200   4.613   0.00  H
ATOM   4862  HD22 LEU  336   -42.374  -6.044   3.934   0.00  H
ATOM   4863  HD23 LEU  336   -41.012  -5.355   3.121   0.00  H
ATOM   4864  C    LEU  336   -43.644  -2.486   6.498  52.04  C
```

FIGURE 6- 65 -

```
ATOM   4865  O    LEU  336   -43.472  -1.551   5.711  53.03  O
ATOM   4866  N    ARG  337   -44.848  -2.852   6.918  50.63  N
ATOM   4867  HN   ARG  337   -44.949  -3.642   7.538   0.00  H
ATOM   4868  CA   ARG  337   -46.021  -2.115   6.485  49.59  C
ATOM   4869  HA   ARG  337   -46.034  -2.061   5.427   0.00  H
ATOM   4870  CB   ARG  337   -47.306  -2.803   6.958  51.48  C
ATOM   4871  HB2  ARG  337   -47.146  -3.231   7.913   0.00  H
ATOM   4872  HB3  ARG  337   -48.087  -2.090   7.016   0.00  H
ATOM   4873  CG   ARG  337   -47.801  -3.931   6.043  52.40  C
ATOM   4874  HG2  ARG  337   -47.672  -3.647   5.031   0.00  H
ATOM   4875  HG3  ARG  337   -47.245  -4.812   6.236   0.00  H
ATOM   4876  CD   ARG  337   -49.299  -4.232   6.282  53.65  C
ATOM   4877  HD2  ARG  337   -49.844  -3.324   6.293   0.00  H
ATOM   4878  HD3  ARG  337   -49.663  -4.853   5.505   0.00  H
ATOM   4879  NE   ARG  337   -49.541  -4.916   7.554  53.55  N1-
ATOM   4880  HE   ARG  337   -50.066  -4.456   8.283   0.00  H
ATOM   4881  CZ   ARG  337   -49.108  -6.143   7.837  53.19  C
ATOM   4882  NH1  ARG  337   -48.412  -6.834   6.938  51.98  N
ATOM   4883  HH11 ARG  337   -48.086  -7.763   7.158   0.00  H
ATOM   4884  HH12 ARG  337   -48.210  -6.429   6.036   0.00  H
ATOM   4885  NH2  ARG  337   -49.363  -6.676   9.023  52.07  N
ATOM   4886  HH21 ARG  337   -49.036  -7.606   9.239   0.00  H
ATOM   4887  HH22 ARG  337   -49.884  -6.152   9.710   0.00  H
ATOM   4888  C    ARG  337   -45.931  -0.702   7.062  48.03  C
ATOM   4889  O    ARG  337   -46.303   0.270   6.406  49.32  O
ATOM   4890  N    ALA  338   -45.423  -0.594   8.287  45.72  N
ATOM   4891  HN   ALA  338   -45.144  -1.440   8.761   0.00  H
ATOM   4892  CA   ALA  338   -45.264   0.701   8.947  43.57  C
ATOM   4893  HA   ALA  338   -46.191   1.214   8.946   0.00  H
ATOM   4894  CB   ALA  338   -44.802   0.503  10.391  42.56  C
ATOM   4895  HB1  ALA  338   -45.522  -0.068  10.917   0.00  H
ATOM   4896  HB2  ALA  338   -43.874  -0.006  10.398   0.00  H
ATOM   4897  HB3  ALA  338   -44.690   1.447  10.858   0.00  H
ATOM   4898  C    ALA  338   -44.242   1.543   8.190  42.19  C
ATOM   4899  O    ALA  338   -44.453   2.726   7.935  41.35  O
ATOM   4900  N    PHE  339   -43.132   0.911   7.836  41.12  N
ATOM   4901  HN   PHE  339   -43.049  -0.062   8.088   0.00  H
ATOM   4902  CA   PHE  339   -42.058   1.567   7.112  41.04  C
ATOM   4903  HA   PHE  339   -41.669   2.359   7.698   0.00  H
ATOM   4904  CB   PHE  339   -40.956   0.559   6.823  40.16  C
ATOM   4905  HB2  PHE  339   -40.538   0.221   7.736   0.00  H
ATOM   4906  HB3  PHE  339   -41.361  -0.264   6.294   0.00  H
ATOM   4907  CG   PHE  339   -39.829   1.110   5.995  39.61  C
ATOM   4908  CD1  PHE  339   -38.757   1.754   6.601  38.10  C
ATOM   4909  HD1  PHE  339   -38.749   1.898   7.668   0.00  H
ATOM   4910  CD2  PHE  339   -39.822   0.946   4.609  38.78  C
ATOM   4911  HD2  PHE  339   -40.647   0.456   4.121   0.00  H
ATOM   4912  CE1  PHE  339   -37.688   2.219   5.846  38.43  C
ATOM   4913  HE1  PHE  339   -36.862   2.713   6.329   0.00  H
ATOM   4914  CE2  PHE  339   -38.760   1.408   3.842  38.97  C
ATOM   4915  HE2  PHE  339   -38.768   1.273   2.774   0.00  H
ATOM   4916  CZ   PHE  339   -37.685   2.047   4.465  39.28  C
ATOM   4917  HZ   PHE  339   -36.855   2.406   3.879   0.00  H
ATOM   4918  C    PHE  339   -42.527   2.163   5.790  41.72  C
ATOM   4919  O    PHE  339   -42.067   3.236   5.375  41.28  O
ATOM   4920  N    THR  340   -43.439   1.459   5.128  40.80  N
ATOM   4921  HN   THR  340   -43.784   0.602   5.533   0.00  H
ATOM   4922  CA   THR  340   -43.939   1.906   3.842  40.15  C
ATOM   4923  HA   THR  340   -43.132   2.256   3.252   0.00  H
ATOM   4924  CB   THR  340   -44.625   0.759   3.115  40.36  C
ATOM   4925  HB   THR  340   -45.552   0.549   3.582   0.00  H
ATOM   4926  OG1  THR  340   -43.784  -0.401   3.167  39.33  O
ATOM   4927  HG1  THR  340   -44.216  -1.133   2.706   0.00  H
ATOM   4928  CG2  THR  340   -44.874   1.132   1.661  40.53  C
ATOM   4929  HG21 THR  340   -45.494   1.990   1.618   0.00  H
ATOM   4930  HG22 THR  340   -43.950   1.340   1.187   0.00  H
ATOM   4931  HG23 THR  340   -45.351   0.326   1.167   0.00  H
ATOM   4932  C    THR  340   -44.896   3.085   3.961  40.09  C
ATOM   4933  O    THR  340   -45.005   3.903   3.048  39.21  O
ATOM   4934  N    GLU  341   -45.588   3.172   5.089  40.47  N
ATOM   4935  HN   GLU  341   -45.457   2.463   5.795   0.00  H
ATOM   4936  CA   GLU  341   -46.523   4.264   5.319  41.67  C
ATOM   4937  HA   GLU  341   -47.148   4.378   4.471   0.00  H
ATOM   4938  CB   GLU  341   -47.391   3.979   6.536  45.20  C
ATOM   4939  HB2  GLU  341   -46.772   3.777   7.371   0.00  H
ATOM   4940  HB3  GLU  341   -47.998   4.822   6.742   0.00  H
```

FIGURE 6- 66 -

```
ATOM   4941  CG   GLU   341   -48.322   2.805   6.398   50.58   C
ATOM   4942  HG2  GLU   341   -49.133   3.070   5.771   0.00    H
ATOM   4943  HG3  GLU   341   -47.799   1.988   5.973   0.00    H
ATOM   4944  CD   GLU   341   -48.872   2.380   7.752   55.00   C
ATOM   4945  OE1  GLU   341   -49.291   3.275   8.530   56.17   O1-
ATOM   4946  OE2  GLU   341   -48.886   1.158   8.038   56.57   O
ATOM   4947  C    GLU   341   -45.767   5.562   5.559   40.40   C
ATOM   4948  O    GLU   341   -46.177   6.629   5.091   40.72   O
ATOM   4949  N    ALA   342   -44.676   5.470   6.316   37.74   N
ATOM   4950  HN   ALA   342   -44.415   4.571   6.692   0.00    H
ATOM   4951  CA   ALA   342   -43.865   6.641   6.603   35.30   C
ATOM   4952  HA   ALA   342   -44.486   7.423   6.956   0.00    H
ATOM   4953  CB   ALA   342   -42.822   6.317   7.667   33.67   C
ATOM   4954  HB1  ALA   342   -43.308   6.008   8.556   0.00    H
ATOM   4955  HB2  ALA   342   -42.193   5.539   7.320   0.00    H
ATOM   4956  HB3  ALA   342   -42.240   7.179   7.865   0.00    H
ATOM   4957  C    ALA   342   -43.200   7.095   5.302   33.64   C
ATOM   4958  O    ALA   342   -43.316   8.255   4.922   32.14   O
ATOM   4959  N    MET   343   -42.518   6.183   4.613   32.38   N
ATOM   4960  HN   MET   343   -42.445   5.240   4.965   0.00    H
ATOM   4961  CA   MET   343   -41.878   6.543   3.353   32.61   C
ATOM   4962  HA   MET   343   -41.112   7.251   3.536   0.00    H
ATOM   4963  CB   MET   343   -41.260   5.316   2.679   31.87   C
ATOM   4964  HB2  MET   343   -41.959   4.521   2.684   0.00    H
ATOM   4965  HB3  MET   343   -41.003   5.554   1.680   0.00    H
ATOM   4966  CG   MET   343   -40.000   4.793   3.340   31.84   C
ATOM   4967  HG2  MET   343   -40.174   4.660   4.376   0.00    H
ATOM   4968  HG3  MET   343   -39.732   3.865   2.905   0.00    H
ATOM   4969  SD   MET   343   -39.579   5.884   3.177   31.20   S
ATOM   4970  CE   MET   343   -37.699   5.075   1.863   31.35   C
ATOM   4971  HE1  MET   343   -37.449   4.090   2.167   0.00    H
ATOM   4972  HE2  MET   343   -38.309   5.037   1.003   0.00    H
ATOM   4973  HE3  MET   343   -36.814   5.614   1.652   0.00    H
ATOM   4974  C    MET   343   -42.914   7.174   2.422   32.27   C
ATOM   4975  O    MET   343   -42.621   8.134   1.701   33.27   O
ATOM   4976  N    THR   344   -44.128   6.641   2.442   31.31   N
ATOM   4977  HN   THR   344   -44.316   5.853   3.043   0.00    H
ATOM   4978  CA   THR   344   -45.188   7.187   1.603   31.05   C
ATOM   4979  HA   THR   344   -44.845   7.259   0.604   0.00    H
ATOM   4980  CB   THR   344   -46.446   6.297   1.621   29.28   C
ATOM   4981  HB   THR   344   -46.755   6.142   2.622   0.00    H
ATOM   4982  OG1  THR   344   -46.140   5.030   1.022   26.09   O
ATOM   4983  HG1  THR   344   -46.928   4.470   1.032   0.00    H
ATOM   4984  CG2  THR   344   -47.579   6.960   0.851   25.39   C
ATOM   4985  HG21 THR   344   -47.811   7.892   1.297   0.00    H
ATOM   4986  HG22 THR   344   -47.281   7.114   -0.153  0.00    H
ATOM   4987  HG23 THR   344   -48.434   6.336   0.874   0.00    H
ATOM   4988  C    THR   344   -45.556   8.584   2.083   31.53   C
ATOM   4989  O    THR   344   -45.839   9.474   1.282   31.05   O
ATOM   4990  N    ARG   345   -45.549   8.781   3.394   32.53   N
ATOM   4991  HN   ARG   345   -45.319   8.026   4.023   0.00    H
ATOM   4992  CA   ARG   345   -45.874   10.091  3.923   34.25   C
ATOM   4993  HA   ARG   345   -46.791   10.421  3.509   0.00    H
ATOM   4994  CB   ARG   345   -46.010   10.048  5.443   34.73   C
ATOM   4995  HB2  ARG   345   -45.311   9.359   5.845   0.00    H
ATOM   4996  HB3  ARG   345   -45.822   11.011  5.846   0.00    H
ATOM   4997  CG   ARG   345   -47.378   9.625   5.933   35.98   C
ATOM   4998  HG2  ARG   345   -48.124   10.080  5.339   0.00    H
ATOM   4999  HG3  ARG   345   -47.466   8.572   5.872   0.00    H
ATOM   5000  CD   ARG   345   -47.603   10.040  7.391   37.77   C
ATOM   5001  HD2  ARG   345   -47.476   11.087  7.483   0.00    H
ATOM   5002  HD3  ARG   345   -48.586   9.776   7.685   0.00    H
ATOM   5003  NE   ARG   345   -46.664   9.386   8.300   38.88   N1+
ATOM   5004  HE   ARG   345   -45.954   9.929   8.763   0.00    H
ATOM   5005  CZ   ARG   345   -46.674   8.085   8.567   38.87   C
ATOM   5006  NH1  ARG   345   -47.580   7.298   7.997   38.81   N
ATOM   5007  HH11 ARG   345   -47.588   6.310   8.199   0.00    H
ATOM   5008  HH12 ARG   345   -48.260   7.689   7.362   0.00    H
ATOM   5009  NH2  ARG   345   -45.773   7.570   9.394   40.15   N
ATOM   5010  HH21 ARG   345   -45.781   6.582   9.597   0.00    H
ATOM   5011  HH22 ARG   345   -45.080   8.167   9.820   0.00    H
ATOM   5012  C    ARG   345   -44.792   11.088  3.531   35.53   C
ATOM   5013  O    ARG   345   -45.076   12.276  3.341   35.69   O
ATOM   5014  N    TYR   346   -43.559   10.594  3.405   35.60   N
ATOM   5015  HN   TYR   346   -43.438   9.605   3.566   0.00    H
ATOM   5016  CA   TYR   346   -42.409   11.423  3.050   35.67   C
```

FIGURE 6- 67 -

```
ATOM   5017  HA   TYR  346   -42.502   12.372    3.512    0.00   H
ATOM   5018  CB   TYR  346   -41.111   10.767    3.520   34.51   C
ATOM   5019  HB2  TYR  346   -40.996    9.830    3.041    0.00   H
ATOM   5020  HB3  TYR  346   -40.291   11.392    3.276    0.00   H
ATOM   5021  CG   TYR  346   -41.052   10.517    5.004   34.86   C
ATOM   5022  CD1  TYR  346   -41.867   11.233    5.883   33.80   C
ATOM   5023  HD1  TYR  346   -42.573   11.951    5.500    0.00   H
ATOM   5024  CE1  TYR  346   -41.788   11.039    7.256   34.94   C
ATOM   5025  HE1  TYR  346   -42.428   11.599    7.917    0.00   H
ATOM   5026  CD2  TYR  346   -40.150    9.594    5.541   34.09   C
ATOM   5027  HD2  TYR  346   -39.510    9.024    4.888    0.00   H
ATOM   5028  CE2  TYR  346   -40.061    9.394    6.918   33.51   C
ATOM   5029  HE2  TYR  346   -39.359    8.680    7.314    0.00   H
ATOM   5030  CZ   TYR  346   -40.883   10.122    7.768   34.49   C
ATOM   5031  OH   TYR  346   -40.802    9.952    9.133   35.99   O
ATOM   5032  HH   TYR  346   -41.434   10.540    9.569    0.00   H
ATOM   5033  C    TYR  346   -42.307   11.677    1.557   36.84   C
ATOM   5034  O    TYR  346   -41.334   12.267    1.089   37.54   O
ATOM   5035  N    SER  347   -43.304   11.220    0.814   36.47   N
ATOM   5036  HN   SER  347   -44.065   10.737    1.267    0.00   H
ATOM   5037  CA   SER  347   -43.315   11.402   -0.622   37.32   C
ATOM   5038  HA   SER  347   -44.287   11.207   -0.995    0.00   H
ATOM   5039  CB   SER  347   -42.924   12.831   -0.976   36.05   C
ATOM   5040  HB2  SER  347   -43.663   13.499   -0.617    0.00   H
ATOM   5041  HB3  SER  347   -41.992   13.063   -0.529    0.00   H
ATOM   5042  OG   SER  347   -42.812   12.930   -2.377   36.31   O
ATOM   5043  HG   SER  347   -42.564   13.891   -2.585    0.00   H
ATOM   5044  C    SER  347   -42.377   10.424   -1.324   39.79   C
ATOM   5045  O    SER  347   -41.557   10.817   -2.160   41.55   O
ATOM   5046  N    ALA  348   -42.497    9.147   -0.974   39.67   N
ATOM   5047  HN   ALA  348   -43.172    8.907   -0.263    0.00   H
ATOM   5048  CA   ALA  348   -41.685    8.107   -1.588   39.27   C
ATOM   5049  HA   ALA  348   -41.497    8.357   -2.600    0.00   H
ATOM   5050  CB   ALA  348   -40.360    7.971   -0.855   37.95   C
ATOM   5051  HB1  ALA  348   -39.836    8.890   -0.899    0.00   H
ATOM   5052  HB2  ALA  348   -40.541    7.716    0.157    0.00   H
ATOM   5053  HB3  ALA  348   -39.780    7.212   -1.312    0.00   H
ATOM   5054  C    ALA  348   -42.442    6.777   -1.578   39.91   C
ATOM   5055  O    ALA  348   -42.025    5.808   -0.940   39.91   O
ATOM   5056  N    PRO  349   -43.586    6.721   -2.273   39.96   N
ATOM   5057  CD   PRO  349   -44.265    7.800   -3.009   40.83   C
ATOM   5058  HD2  PRO  349   -44.795    8.413   -2.327    0.00   H
ATOM   5059  HD3  PRO  349   -43.546    8.383   -3.523    0.00   H
ATOM   5060  CA   PRO  349   -44.363    5.478   -2.312   39.80   C
ATOM   5061  HA   PRO  349   -44.589    5.172   -1.324    0.00   H
ATOM   5062  CB   PRO  349   -45.633    5.830   -3.066   40.61   C
ATOM   5063  HB2  PRO  349   -45.983    5.056   -3.632    0.00   H
ATOM   5064  HB3  PRO  349   -46.377    6.173   -2.372    0.00   H
ATOM   5065  CG   PRO  349   -45.172    7.025   -3.937   41.78   C
ATOM   5066  HG2  PRO  349   -44.663    6.642   -4.783    0.00   H
ATOM   5067  HG3  PRO  349   -46.011    7.587   -4.254    0.00   H
ATOM   5068  C    PRO  349   -43.585    4.361   -3.001   39.12   C
ATOM   5069  O    PRO  349   -42.697    4.616   -3.819   38.47   O
ATOM   5070  N    PRO  350   -43.913    3.103   -2.672   39.18   N
ATOM   5071  CD   PRO  350   -44.833    2.720   -1.584   38.40   C
ATOM   5072  HD2  PRO  350   -44.432    3.034   -0.656    0.00   H
ATOM   5073  HD3  PRO  350   -45.773    3.183   -1.737    0.00   H
ATOM   5074  CA   PRO  350   -43.256    1.919   -3.236   37.87   C
ATOM   5075  HA   PRO  350   -42.220    2.110   -3.348    0.00   H
ATOM   5076  CB   PRO  350   -43.507    0.866   -2.172   38.60   C
ATOM   5077  HB2  PRO  350   -43.443   -0.097   -2.607    0.00   H
ATOM   5078  HB3  PRO  350   -42.781    0.957   -1.407    0.00   H
ATOM   5079  CG   PRO  350   -44.895    1.216   -1.714   37.83   C
ATOM   5080  HG2  PRO  350   -45.597    0.897   -2.440    0.00   H
ATOM   5081  HG3  PRO  350   -45.095    0.733   -0.793    0.00   H
ATOM   5082  C    PRO  350   -43.739    1.454   -4.598   36.81   C
ATOM   5083  O    PRO  350   -44.919    1.544   -4.915   34.96   O
ATOM   5084  N    GLY  351   -42.806    0.951   -5.397   37.96   N
ATOM   5085  HN   GLY  351   -41.845    0.934   -5.091    0.00   H
ATOM   5086  CA   GLY  351   -43.160    0.429   -6.699   39.64   C
ATOM   5087  HA2  GLY  351   -43.804    1.112   -7.190    0.00   H
ATOM   5088  HA3  GLY  351   -42.282    0.295   -7.276    0.00   H
ATOM   5089  C    GLY  351   -43.848   -0.834   -6.398   41.24   C
ATOM   5090  O    GLY  351   -45.048   -1.038   -6.585   41.17   O
ATOM   5091  N    ASP  352   -43.080   -1.843   -5.911   43.92   N
ATOM   5092  HN   ASP  352   -42.091   -1.680   -5.793    0.00   H
```

FIGURE 6- 68 -

```
ATOM   5093  CA   ASP   352   -43.653   -3.128   -5.546   47.86   C
ATOM   5094  HA   ASP   352   -44.642   -3.192   -5.919    0.00   H
ATOM   5095  CB   ASP   352   -42.831   -4.270   -6.130   49.51   C
ATOM   5096  HB2  ASP   352   -41.935   -4.380   -5.576    0.00   H
ATOM   5097  HB3  ASP   352   -43.389   -5.168   -6.080    0.00   H
ATOM   5098  CG   ASP   352   -42.462   -4.032   -7.567   52.21   C
ATOM   5099  OD1  ASP   352   -43.391   -3.816   -8.380   53.29   O
ATOM   5100  OD2  ASP   352   -41.247   -4.055   -7.875   53.51   O1-
ATOM   5101  C    ASP   352   -43.595   -3.200   -4.033   48.54   C
ATOM   5102  O    ASP   352   -42.616   -2.766   -3.426   49.49   O
ATOM   5103  N    PRO   353   -44.641   -3.730   -3.395   48.96   N
ATOM   5104  CD   PRO   353   -45.936   -4.235   -3.877   49.37   C
ATOM   5105  HD2  PRO   353   -46.279   -3.625   -4.671    0.00   H
ATOM   5106  HD3  PRO   353   -45.821   -5.230   -4.221    0.00   H
ATOM   5107  CA   PRO   353   -44.561   -3.794   -1.935   49.07   C
ATOM   5108  HA   PRO   353   -44.530   -2.812   -1.540    0.00   H
ATOM   5109  CB   PRO   353   -45.842   -4.535   -1.553   49.14   C
ATOM   5110  HB2  PRO   353   -45.657   -5.578   -1.543    0.00   H
ATOM   5111  HB3  PRO   353   -46.157   -4.223   -0.591    0.00   H
ATOM   5112  CG   PRO   353   -46.794   -4.130   -2.630   49.18   C
ATOM   5113  HG2  PRO   353   -47.619   -4.794   -2.640    0.00   H
ATOM   5114  HG3  PRO   353   -47.136   -3.145   -2.447    0.00   H
ATOM   5115  C    PRO   353   -43.293   -4.550   -1.510   48.50   C
ATOM   5116  O    PRO   353   -42.936   -5.580   -2.099   47.47   O
ATOM   5117  N    PRO   354   -42.585   -4.032   -0.499   47.36   N
ATOM   5118  CD   PRO   354   -42.876   -2.822    0.284   46.87   C
ATOM   5119  HD2  PRO   354   -42.617   -1.965   -0.281    0.00   H
ATOM   5120  HD3  PRO   354   -43.909   -2.792    0.517    0.00   H
ATOM   5121  CA   PRO   354   -41.364   -4.677   -0.018   48.62   C
ATOM   5122  HA   PRO   354   -40.731   -4.892   -0.839    0.00   H
ATOM   5123  CB   PRO   354   -40.777   -3.637    0.916   47.77   C
ATOM   5124  HB2  PRO   354   -40.169   -4.115    1.639    0.00   H
ATOM   5125  HB3  PRO   354   -40.191   -2.953    0.359    0.00   H
ATOM   5126  CG   PRO   354   -42.000   -3.021    1.496   48.00   C
ATOM   5127  HG2  PRO   354   -42.426   -3.682    2.205    0.00   H
ATOM   5128  HG3  PRO   354   -41.745   -2.110    1.971    0.00   H
ATOM   5129  C    PRO   354   -41.698   -5.974    0.702   49.50   C
ATOM   5130  O    PRO   354   -42.726   -6.080    1.363   49.69   O
ATOM   5131  N    GLN   355   -40.826   -6.961    0.569   50.53   N
ATOM   5132  HN   GLN   355   -39.996   -6.805    0.017    0.00   H
ATOM   5133  CA   GLN   355   -41.047   -8.248    1.199   50.84   C
ATOM   5134  HA   GLN   355   -41.929   -8.208    1.784    0.00   H
ATOM   5135  CB   GLN   355   -41.200   -9.329    0.129   54.15   C
ATOM   5136  HB2  GLN   355   -40.366   -9.301   -0.523    0.00   H
ATOM   5137  HB3  GLN   355   -41.253  -10.280    0.593    0.00   H
ATOM   5138  CG   GLN   355   -42.444   -9.168   -0.719   59.06   C
ATOM   5139  HG2  GLN   355   -42.287   -8.403   -1.434    0.00   H
ATOM   5140  HG3  GLN   355   -42.652  -10.079   -1.217    0.00   H
ATOM   5141  CD   GLN   355   -43.660   -8.794    0.123   61.95   C
ATOM   5142  OE1  GLN   355   -43.946   -9.428    1.146   62.53   O
ATOM   5143  NE2  GLN   355   -44.380   -7.759   -0.303   63.47   N
ATOM   5144  HE21 GLN   355   -44.111   -7.269   -1.143    0.00   H
ATOM   5145  HE22 GLN   355   -45.195   -7.464    0.214    0.00   H
ATOM   5146  C    GLN   355   -39.910   -8.622    2.123   49.65   C
ATOM   5147  O    GLN   355   -38.762   -8.726    1.687   50.52   O
ATOM   5148  N    PRO   356   -40.206   -8.827    3.417   48.45   N
ATOM   5149  CD   PRO   356   -41.486   -8.699    4.132   47.66   C
ATOM   5150  HD2  PRO   356   -41.651   -7.683    4.381    0.00   H
ATOM   5151  HD3  PRO   356   -42.273   -9.043    3.512    0.00   H
ATOM   5152  CA   PRO   356   -39.129   -9.198    4.338   48.53   C
ATOM   5153  HA   PRO   356   -38.395   -8.435    4.348    0.00   H
ATOM   5154  CB   PRO   356   -39.839   -9.286    5.694   48.09   C
ATOM   5155  HB2  PRO   356   -39.408  -10.064    6.268    0.00   H
ATOM   5156  HB3  PRO   356   -39.732   -8.367    6.209    0.00   H
ATOM   5157  CG   PRO   356   -41.256   -9.570    5.330   47.83   C
ATOM   5158  HG2  PRO   356   -41.364  -10.600    5.108    0.00   H
ATOM   5159  HG3  PRO   356   -41.887   -9.316    6.142    0.00   H
ATOM   5160  C    PRO   356   -38.453  -10.505    3.930   48.13   C
ATOM   5161  O    PRO   356   -39.081  -11.404    3.389   47.78   O
ATOM   5162  N    GLU   357   -37.157  -10.588    4.172   49.09   N
ATOM   5163  HN   GLU   357   -36.692   -9.803    4.603    0.00   H
ATOM   5164  CA   GLU   357   -36.404  -11.779    3.830   50.66   C
ATOM   5165  HA   GLU   357   -37.073  -12.555    3.563    0.00   H
ATOM   5166  CB   GLU   357   -35.473  -11.493    2.653   52.19   C
ATOM   5167  HB2  GLU   357   -34.865  -10.656    2.879    0.00   H
ATOM   5168  HB3  GLU   357   -34.359  -12.337    2.475    0.00   H
```

FIGURE 6-69 -

```
ATOM   5169  CG   GLU  357   -36.200  -11.185   1.360  54.31      C
ATOM   5170  HG2  GLU  357   -36.734  -10.276   1.463   0.00      H
ATOM   5171  HG3  GLU  357   -35.497  -11.095   0.573   0.00      H
ATOM   5172  CD   GLU  357   -37.192  -12.270   0.980  54.95      C
ATOM   5173  OE1  GLU  357   -36.856  -13.470   1.108  55.71      O1-
ATOM   5174  OE2  GLU  357   -38.306  -11.919   0.542  56.29      O
ATOM   5175  C    GLU  357   -35.594  -12.258   5.030  50.70      C
ATOM   5176  O    GLU  357   -35.220  -11.468   5.907  50.70      O
ATOM   5177  N    TYR  358   -35.326  -13.557   5.064  49.65      N
ATOM   5178  HN   TYR  358   -35.655  -14.143   4.311   0.00      H
ATOM   5179  CA   TYR  358   -34.574  -14.138   6.159  49.66      C
ATOM   5180  HA   TYR  358   -34.187  -13.365   6.771   0.00      H
ATOM   5181  CB   TYR  358   -35.503  -15.024   6.974  47.09      C
ATOM   5182  HB2  TYR  358   -35.881  -15.799   6.359   0.00      H
ATOM   5183  HB3  TYR  358   -34.968  -15.446   7.785   0.00      H
ATOM   5184  CG   TYR  358   -36.676  -14.248   7.533  44.64      C
ATOM   5185  CD1  TYR  358   -36.537  -13.455   8.672  43.62      C
ATOM   5186  HD1  TYR  358   -35.590  -13.407   9.182   0.00      H
ATOM   5187  CE1  TYR  358   -37.611  -12.712   9.173  42.52      C
ATOM   5188  HE1  TYR  358   -37.482  -12.107  10.054   0.00      H
ATOM   5189  CD2  TYR  358   -37.919  -14.280   6.906  44.38      C
ATOM   5190  HD2  TYR  358   -38.063  -14.883   6.025   0.00      H
ATOM   5191  CE2  TYR  358   -38.996  -13.540   7.398  43.27      C
ATOM   5192  HE2  TYR  358   -39.949  -13.577   6.897   0.00      H
ATOM   5193  CZ   TYR  358   -38.835  -12.762   8.528  42.53      C
ATOM   5194  OH   TYR  358   -39.897  -12.036   9.008  43.88      O
ATOM   5195  HH   TYR  358   -39.624  -11.548   9.797   0.00      H
ATOM   5196  C    TYR  358   -33.391  -14.905   5.599  50.85      C
ATOM   5197  O    TYR  358   -32.605  -15.504   6.328  50.46      O
ATOM   5198  N    ASP  359   -33.281  -14.846   4.279  52.12      N
ATOM   5199  HN   ASP  359   -34.004  -14.331   3.798   0.00      H
ATOM   5200  CA   ASP  359   -32.205  -15.467   3.523  53.94      C
ATOM   5201  HA   ASP  359   -31.606  -16.049   4.174   0.00      H
ATOM   5202  CB   ASP  359   -32.791  -16.366   2.436  56.63      C
ATOM   5203  HB2  ASP  359   -33.386  -17.119   2.884   0.00      H
ATOM   5204  HB3  ASP  359   -33.388  -15.786   1.782   0.00      H
ATOM   5205  CG   ASP  359   -31.729  -17.056   1.599  58.73      C
ATOM   5206  OD1  ASP  359   -30.614  -16.500   1.447  60.55      O
ATOM   5207  OD2  ASP  359   -32.027  -18.155   1.078  59.74      O1-
ATOM   5208  C    ASP  359   -31.539  -14.258   2.878  54.43      C
ATOM   5209  O    ASP  359   -32.231  -13.371   2.390  54.30      O
ATOM   5210  N    LEU  360   -30.213  -14.208   2.868  55.08      N
ATOM   5211  HN   LEU  360   -29.678  -14.962   3.272   0.00      H
ATOM   5212  CA   LEU  360   -29.527  -13.063   2.273  55.15      C
ATOM   5213  HA   LEU  360   -30.016  -12.169   2.563   0.00      H
ATOM   5214  CB   LEU  360   -28.072  -13.008   2.741  55.17      C
ATOM   5215  HB2  LEU  360   -28.038  -13.072   3.798   0.00      H
ATOM   5216  HB3  LEU  360   -27.535  -13.819   2.321   0.00      H
ATOM   5217  CG   LEU  360   -27.313  -11.740   2.358  54.70      C
ATOM   5218  HG   LEU  360   -27.392  -11.583   1.314   0.00      H
ATOM   5219  CD1  LEU  360   -27.937  -10.589   3.112  55.46      C
ATOM   5220  HD11 LEU  360   -28.958  -10.503   2.844   0.00      H
ATOM   5221  HD12 LEU  360   -27.859  -10.766   4.153   0.00      H
ATOM   5222  HD13 LEU  360   -27.431   -9.691   2.867   0.00      H
ATOM   5223  CD2  LEU  360   -25.835  -11.859   2.697  54.32      C
ATOM   5224  HD21 LEU  360   -25.723  -12.018   3.738   0.00      H
ATOM   5225  HD22 LEU  360   -25.416  -12.676   2.168   0.00      H
ATOM   5226  HD23 LEU  360   -25.336  -10.967   2.420   0.00      H
ATOM   5227  C    LEU  360   -29.564  -13.119   0.751  55.50      C
ATOM   5228  O    LEU  360   -29.749  -12.102   0.078  55.66      O
ATOM   5229  N    GLU  361   -29.383  -14.318   0.215  55.85      N
ATOM   5230  HN   GLU  361   -29.240  -15.101   0.835   0.00      H
ATOM   5231  CA   GLU  361   -29.387  -14.521  -1.225  55.77      C
ATOM   5232  HA   GLU  361   -28.613  -13.947  -1.665   0.00      H
ATOM   5233  CB   GLU  361   -29.161  -16.000  -1.547  56.94      C
ATOM   5234  HB2  GLU  361   -29.982  -16.568  -1.193   0.00      H
ATOM   5235  HB3  GLU  361   -29.072  -16.124  -2.595   0.00      H
ATOM   5236  CG   GLU  361   -27.916  -16.608  -0.932  59.09      C
ATOM   5237  HG2  GLU  361   -27.097  -15.951  -1.070   0.00      H
ATOM   5238  HG3  GLU  361   -28.074  -16.763   0.104   0.00      H
ATOM   5239  CD   GLU  361   -27.558  -17.949  -1.563  59.95      C
ATOM   5240  OE1  GLU  361   -27.407  -18.001  -2.807  59.04      O1-
ATOM   5241  OE2  GLU  361   -27.422  -18.945  -0.819  60.29      O
ATOM   5242  C    GLU  361   -30.704  -14.073  -1.858  55.09      C
ATOM   5243  O    GLU  361   -30.742  -13.691  -3.029  53.73      O
ATOM   5244  N    LEU  362   -31.776  -14.117  -1.070  54.70      N
```

FIGURE 6-70 -

```
ATOM   5245  HN   LEU  362   -31.642 -14.410  -0.114   0.00    H
ATOM   5246  CA   LEU  362   -33.112 -13.760  -1.545  55.02    C
ATOM   5247  HA   LEU  362   -33.186 -13.970  -2.580   0.00    H
ATOM   5248  CB   LEU  362   -34.167 -14.568  -0.790  55.14    C
ATOM   5249  HB2  LEU  362   -33.893 -14.640   0.230   0.00    H
ATOM   5250  HB3  LEU  362   -35.106 -14.085  -0.870   0.00    H
ATOM   5251  CG   LEU  362   -34.351 -15.992  -1.306  54.72    C
ATOM   5252  HG   LEU  362   -33.415 -16.487  -1.317   0.00    H
ATOM   5253  CD1  LEU  362   -35.306 -16.756  -0.409  55.40    C
ATOM   5254  HD11 LEU  362   -34.914 -16.792   0.574   0.00    H
ATOM   5255  HD12 LEU  362   -36.246 -16.268  -0.397   0.00    H
ATOM   5256  HD13 LEU  362   -35.425 -17.742  -0.778   0.00    H
ATOM   5257  CD2  LEU  362   -34.872 -15.933  -2.729  53.93    C
ATOM   5258  HD21 LEU  362   -35.800 -15.423  -2.744   0.00    H
ATOM   5259  HD22 LEU  362   -34.176 -15.418  -3.339   0.00    H
ATOM   5260  HD23 LEU  362   -35.004 -16.917  -3.098   0.00    H
ATOM   5261  C    LEU  362   -33.482 -12.290  -1.489  55.20    C
ATOM   5262  O    LEU  362   -34.647 -11.940  -1.297  55.62    O
ATOM   5263  N    ILE  363   -32.488 -11.433  -1.656  54.87    N
ATOM   5264  HN   ILE  363   -31.557 -11.800  -1.787   0.00    H
ATOM   5265  CA   ILE  363   -32.708  -9.999  -1.654  53.74    C
ATOM   5266  HA   ILE  363   -33.748  -9.801  -1.682   0.00    H
ATOM   5267  CB   ILE  363   -32.114  -9.344  -0.383  52.76    C
ATOM   5268  HB   ILE  363   -31.083  -9.575  -0.316   0.00    H
ATOM   5269  CG2  ILE  363   -32.283  -7.832  -0.442  52.15    C
ATOM   5270  HG21 ILE  363   -31.780  -7.454  -1.294   0.00    H
ATOM   5271  HG22 ILE  363   -33.313  -7.594  -0.505   0.00    H
ATOM   5272  HG23 ILE  363   -31.873  -7.397   0.432   0.00    H
ATOM   5273  CG1  ILE  363   -32.797  -9.912   0.864  52.10    C
ATOM   5274  HG12 ILE  363   -33.825  -9.659   0.849   0.00    H
ATOM   5275  HG13 ILE  363   -32.692 -10.966   0.875   0.00    H
ATOM   5276  CD1  ILE  363   -32.227  -9.392   2.174  50.97    C
ATOM   5277  HD11 ILE  363   -31.201  -9.645   2.238   0.00    H
ATOM   5278  HD12 ILE  363   -32.334  -8.339   2.212   0.00    H
ATOM   5279  HD13 ILE  363   -32.750  -9.829   2.985   0.00    H
ATOM   5280  C    ILE  363   -32.002  -9.454  -2.888  54.14    C
ATOM   5281  O    ILE  363   -30.848  -9.797  -3.146  54.06    O
ATOM   5282  N    THR  364   -32.698  -8.636  -3.670  54.86    N
ATOM   5283  HN   THR  364   -33.657  -8.418  -3.445   0.00    H
ATOM   5284  CA   THR  364   -32.077  -8.055  -4.851  56.10    C
ATOM   5285  HA   THR  364   -31.093  -8.434  -4.955   0.00    H
ATOM   5286  CB   THR  364   -32.860  -8.388  -6.134  56.48    C
ATOM   5287  HB   THR  364   -33.806  -7.913  -6.104   0.00    H
ATOM   5288  OG1  THR  364   -33.027  -9.808  -6.231  57.50    O
ATOM   5289  HG1  THR  364   -33.519 -10.020  -7.036   0.00    H
ATOM   5290  CG2  THR  364   -32.094  -7.898  -7.369  55.82    C
ATOM   5291  HG21 THR  364   -31.961  -6.849  -7.308   0.00    H
ATOM   5292  HG22 THR  364   -31.148  -8.372  -7.409   0.00    H
ATOM   5293  HG23 THR  364   -32.644  -8.134  -8.242   0.00    H
ATOM   5294  C    THR  364   -31.928  -6.538  -4.727  56.40    C
ATOM   5295  O    THR  364   -32.905  -5.786  -4.774  56.52    O
ATOM   5296  N    SER  365   -30.683  -6.107  -4.551  56.19    N
ATOM   5297  HN   SER  365   -29.953  -6.802  -4.503   0.00    H
ATOM   5298  CA   SER  365   -30.354  -4.699  -4.429  57.01    C
ATOM   5299  HA   SER  365   -31.243  -4.125  -4.462   0.00    H
ATOM   5300  CB   SER  365   -29.639  -4.435  -3.106  57.43    C
ATOM   5301  HB2  SER  365   -30.279  -4.691  -2.302   0.00    H
ATOM   5302  HB3  SER  365   -28.759  -5.022  -3.057   0.00    H
ATOM   5303  OG   SER  365   -29.285  -3.067  -2.992  59.50    O
ATOM   5304  HG   SER  365   -28.834  -2.920  -2.149   0.00    H
ATOM   5305  C    SER  365   -29.454  -4.295  -5.595  57.18    C
ATOM   5306  O    SER  365   -28.552  -5.040  -5.988  56.99    O
ATOM   5307  N    CYS  366   -29.703  -3.110  -6.142  57.22    N
ATOM   5308  HN   CYS  366   -30.454  -2.555  -5.759   0.00    H
ATOM   5309  CA   CYS  366   -28.925  -2.606  -7.266  56.84    C
ATOM   5310  HA   CYS  366   -29.374  -1.722  -7.638   0.00    H
ATOM   5311  CB   CYS  366   -27.509  -2.250  -6.817  56.38    C
ATOM   5312  HB2  CYS  366   -27.104  -3.052  -6.256   0.00    H
ATOM   5313  HB3  CYS  366   -26.903  -2.073  -7.667   0.00    H
ATOM   5314  SG   CYS  366   -27.460  -0.782  -5.791  57.69    S
ATOM   5315  HG   CYS  366   -26.279  -0.545  -5.458   0.00    H
ATOM   5316  C    CYS  366   -28.864  -3.629  -8.382  56.34    C
ATOM   5317  O    CYS  366   -27.810  -3.849  -8.985  55.72    O
ATOM   5318  N    SER  367   -29.997  -4.264  -8.651  55.39    N
ATOM   5319  HN   SER  367   -30.828  -4.056  -8.119   0.00    H
ATOM   5320  CA   SER  367   -30.042  -5.254  -9.706  56.17    C
```

FIGURE 6- 71 -

| | | | | | | | | |
|---|---|---|---|---|---|---|---|---|
| ATOM | 5321 | HA | SER | 367 | -31.028 | -5.629 | -9.797 | 0.00 | H |
| ATOM | 5322 | CB | SER | 367 | -29.616 | -4.606 | -11.029 | 55.61 | C |
| ATOM | 5323 | HB2 | SER | 367 | -28.592 | -4.340 | -10.978 | 0.00 | H |
| ATOM | 5324 | HB3 | SER | 367 | -29.764 | -5.292 | -11.822 | 0.00 | H |
| ATOM | 5325 | OG | SER | 367 | -30.369 | -3.438 | -11.301 | 54.28 | O |
| ATOM | 5326 | HG | SER | 367 | -30.077 | -3.054 | -12.139 | 0.00 | H |
| ATOM | 5327 | C | SER | 367 | -29.089 | -6.403 | -9.368 | 56.49 | C |
| ATOM | 5328 | O | SER | 367 | -28.519 | -7.029 | -10.262 | 56.52 | O |
| ATOM | 5329 | N | SER | 368 | -28.905 | -6.667 | -8.078 | 55.80 | N |
| ATOM | 5330 | HN | SER | 368 | -29.396 | -6.118 | -7.388 | 0.00 | H |
| ATOM | 5331 | CA | SER | 368 | -28.006 | -7.735 | -7.655 | 55.45 | C |
| ATOM | 5332 | HA | SER | 368 | -27.952 | -8.472 | -8.414 | 0.00 | H |
| ATOM | 5333 | CB | SER | 368 | -26.603 | -7.185 | -7.397 | 54.39 | C |
| ATOM | 5334 | HB2 | SER | 368 | -26.670 | -6.315 | -6.797 | 0.00 | H |
| ATOM | 5335 | HB3 | SER | 368 | -26.024 | -7.916 | -6.896 | 0.00 | H |
| ATOM | 5336 | OG | SER | 368 | -25.955 | -6.849 | -8.606 | 54.11 | O |
| ATOM | 5337 | HG | SER | 368 | -25.072 | -6.505 | -8.414 | 0.00 | H |
| ATOM | 5338 | C | SER | 368 | -28.468 | -8.471 | -6.411 | 56.02 | C |
| ATOM | 5339 | O | SER | 368 | -29.051 | -7.886 | -5.503 | 56.24 | O |
| ATOM | 5340 | N | ASN | 369 | -28.204 | -9.770 | -6.388 | 56.73 | N |
| ATOM | 5341 | HN | ASN | 369 | -27.753 | -10.172 | -7.196 | 0.00 | H |
| ATOM | 5342 | CA | ASN | 369 | -28.543 | -10.611 | -5.249 | 56.39 | C |
| ATOM | 5343 | HA | ASN | 369 | -29.018 | -10.025 | -4.506 | 0.00 | H |
| ATOM | 5344 | CB | ASN | 369 | -29.494 | -11.750 | -5.650 | 56.26 | C |
| ATOM | 5345 | HB2 | ASN | 369 | -29.794 | -12.281 | -4.784 | 0.00 | H |
| ATOM | 5346 | HB3 | ASN | 369 | -30.347 | -11.345 | -6.129 | 0.00 | H |
| ATOM | 5347 | CG | ASN | 369 | -28.851 | -12.749 | -6.610 | 56.64 | C |
| ATOM | 5348 | OD1 | ASN | 369 | -28.733 | -12.495 | -7.809 | 56.13 | O |
| ATOM | 5349 | ND2 | ASN | 369 | -28.424 | -13.890 | -6.076 | 57.25 | N |
| ATOM | 5350 | HD21 | ASN | 369 | -28.540 | -14.059 | -5.088 | 0.00 | H |
| ATOM | 5351 | HD22 | ASN | 369 | -27.984 | -14.586 | -6.659 | 0.00 | H |
| ATOM | 5352 | C | ASN | 369 | -27.211 | -11.196 | -4.824 | 56.15 | C |
| ATOM | 5353 | O | ASN | 369 | -26.232 | -11.120 | -5.571 | 55.96 | O |
| ATOM | 5354 | N | VAL | 370 | -27.165 | -11.760 | -3.626 | 56.12 | N |
| ATOM | 5355 | HN | VAL | 370 | -27.991 | -11.760 | -3.047 | 0.00 | H |
| ATOM | 5356 | CA | VAL | 370 | -25.938 | -12.375 | -3.143 | 55.70 | C |
| ATOM | 5357 | HA | VAL | 370 | -25.108 | -11.949 | -3.644 | 0.00 | H |
| ATOM | 5358 | CB | VAL | 370 | -25.748 | -12.162 | -1.620 | 55.79 | C |
| ATOM | 5359 | HB | VAL | 370 | -26.590 | -12.543 | -1.103 | 0.00 | H |
| ATOM | 5360 | CG1 | VAL | 370 | -24.516 | -12.911 | -1.137 | 55.60 | C |
| ATOM | 5361 | HG11 | VAL | 370 | -24.633 | -13.945 | -1.331 | 0.00 | H |
| ATOM | 5362 | HG12 | VAL | 370 | -23.661 | -12.551 | -1.648 | 0.00 | H |
| ATOM | 5363 | HG13 | VAL | 370 | -24.396 | -12.759 | -0.096 | 0.00 | H |
| ATOM | 5364 | CG2 | VAL | 370 | -25.603 | -10.683 | -1.317 | 54.73 | C |
| ATOM | 5365 | HG21 | VAL | 370 | -24.760 | -10.298 | -1.830 | 0.00 | H |
| ATOM | 5366 | HG22 | VAL | 370 | -26.474 | -10.171 | -1.634 | 0.00 | H |
| ATOM | 5367 | HG23 | VAL | 370 | -25.474 | -10.547 | -0.275 | 0.00 | H |
| ATOM | 5368 | C | VAL | 370 | -26.058 | -13.864 | -3.435 | 55.36 | C |
| ATOM | 5369 | O | VAL | 370 | -27.155 | -14.425 | -3.397 | 54.64 | O |
| ATOM | 5370 | N | SER | 371 | -24.932 | -14.496 | -3.746 | 55.43 | N |
| ATOM | 5371 | HN | SER | 371 | -24.074 | -13.966 | -3.776 | 0.00 | H |
| ATOM | 5372 | CA | SER | 371 | -24.918 | -15.923 | -4.040 | 55.11 | C |
| ATOM | 5373 | HA | SER | 371 | -25.709 | -16.398 | -3.520 | 0.00 | H |
| ATOM | 5374 | CB | SER | 371 | -25.096 | -16.153 | -5.551 | 55.65 | C |
| ATOM | 5375 | HB2 | SER | 371 | -25.916 | -15.581 | -5.901 | 0.00 | H |
| ATOM | 5376 | HB3 | SER | 371 | -24.216 | -15.856 | -6.059 | 0.00 | H |
| ATOM | 5377 | OG | SER | 371 | -25.345 | -17.520 | -5.847 | 55.49 | O |
| ATOM | 5378 | HG | SER | 371 | -25.452 | -17.629 | -6.802 | 0.00 | H |
| ATOM | 5379 | C | SER | 371 | -23.594 | -16.518 | -3.559 | 54.32 | C |
| ATOM | 5380 | O | SER | 371 | -22.639 | -15.793 | -3.285 | 53.16 | O |
| ATOM | 5381 | N | VAL | 372 | -23.535 | -17.840 | -3.466 | 54.30 | N |
| ATOM | 5382 | HN | VAL | 372 | -24.341 | -18.392 | -3.717 | 0.00 | H |
| ATOM | 5383 | CA | VAL | 372 | -22.318 | -18.495 | -3.005 | 54.17 | C |
| ATOM | 5384 | HA | VAL | 372 | -21.616 | -17.762 | -2.701 | 0.00 | H |
| ATOM | 5385 | CB | VAL | 372 | -22.629 | -19.418 | -1.814 | 51.56 | C |
| ATOM | 5386 | HB | VAL | 372 | -23.061 | -20.318 | -2.168 | 0.00 | H |
| ATOM | 5387 | CG1 | VAL | 372 | -21.345 | -19.803 | -1.104 | 49.18 | C |
| ATOM | 5388 | HG11 | VAL | 372 | -20.707 | -20.310 | -1.780 | 0.00 | H |
| ATOM | 5389 | HG12 | VAL | 372 | -20.862 | -18.930 | -0.750 | 0.00 | H |
| ATOM | 5390 | HG13 | VAL | 372 | -21.570 | -20.438 | -0.287 | 0.00 | H |
| ATOM | 5391 | CG2 | VAL | 372 | -23.606 | -18.724 | -0.869 | 49.14 | C |
| ATOM | 5392 | HG21 | VAL | 372 | -23.175 | -17.825 | -0.514 | 0.00 | H |
| ATOM | 5393 | HG22 | VAL | 372 | -24.503 | -18.505 | -1.387 | 0.00 | H |
| ATOM | 5394 | HG23 | VAL | 372 | -23.818 | -19.361 | -0.050 | 0.00 | H |
| ATOM | 5395 | C | VAL | 372 | -21.623 | -19.302 | -4.105 | 55.82 | C |
| ATOM | 5396 | O | VAL | 372 | -22.167 | -19.491 | -5.199 | 55.88 | O |

FIGURE 6-72-

```
ATOM   5397  N    ALA  373   -20.410 -19.755  -3.803  57.11   N
ATOM   5398  HN   ALA  373   -20.054 -19.521  -2.888   0.00   H
ATOM   5399  CA   ALA  373   -19.601 -20.554  -4.719  58.88   C
ATOM   5400  HA   ALA  373   -20.188 -21.342  -5.113   0.00   H
ATOM   5401  CB   ALA  373   -19.086 -19.693  -5.878  58.56   C
ATOM   5402  HB1  ALA  373   -19.908 -19.289  -6.410   0.00   H
ATOM   5403  HB2  ALA  373   -18.492 -18.905  -5.495   0.00   H
ATOM   5404  HB3  ALA  373   -18.503 -20.290  -6.529   0.00   H
ATOM   5405  C    ALA  373   -18.428 -21.139  -3.931  60.35   C
ATOM   5406  O    ALA  373   -18.381 -21.027  -2.702  60.01   O
ATOM   5407  N    HIS  374   -17.482 -21.756  -4.634  61.79   N
ATOM   5408  HN   HIS  374   -17.572 -21.807  -5.638   0.00   H
ATOM   5409  CA   HIS  374   -16.328 -22.353  -3.974  62.54   C
ATOM   5410  HA   HIS  374   -16.186 -21.896  -3.029   0.00   H
ATOM   5411  CB   HIS  374   -16.553 -23.851  -3.778  60.90   C
ATOM   5412  HB2  HIS  374   -16.954 -24.267  -4.665   0.00   H
ATOM   5413  HB3  HIS  374   -15.630 -24.320  -3.554   0.00   H
ATOM   5414  CG   HIS  374   -17.500 -24.171  -2.665  59.94   C
ATOM   5415  CD2  HIS  374   -18.792 -24.577  -2.678  59.79   C
ATOM   5416  HD2  HIS  374   -19.295 -24.743  -3.616   0.00   H
ATOM   5417  ND1  HIS  374   -17.150 -24.052  -1.337  59.81   N1+
ATOM   5418  HD1  HIS  374   -16.218 -23.758  -1.085   0.00   H
ATOM   5419  CE1  HIS  374   -18.185 -24.371  -0.579  59.49   C
ATOM   5420  HE1  HIS  374   -18.098 -24.336   0.494   0.00   H
ATOM   5421  NE2  HIS  374   -19.195 -24.693  -1.368  59.42   N
ATOM   5422  HE2  HIS  374   -20.137 -24.986  -1.154   0.00   H
ATOM   5423  C    HIS  374   -15.047 -22.127  -4.741  64.61   C
ATOM   5424  O    HIS  374   -15.025 -22.194  -5.969  65.37   O
ATOM   5425  N    ASP  375   -13.979 -21.852  -4.002  66.74   N
ATOM   5426  HN   ASP  375   -14.095 -21.808  -3.001   0.00   H
ATOM   5427  CA   ASP  375   -12.669 -21.617  -4.594  69.27   C
ATOM   5428  HA   ASP  375   -12.788 -21.256  -5.583   0.00   H
ATOM   5429  CB   ASP  375   -11.893 -20.585  -3.778  71.15   C
ATOM   5430  HB2  ASP  375   -11.014 -20.301  -4.301   0.00   H
ATOM   5431  HB3  ASP  375   -12.496 -19.728  -3.628   0.00   H
ATOM   5432  CG   ASP  375   -11.479 -21.115  -2.407  72.56   C
ATOM   5433  OD1  ASP  375   -12.343 -21.657  -1.673  71.33   O
ATOM   5434  OD2  ASP  375   -10.281 -20.980  -2.069  73.97   O1-
ATOM   5435  C    ASP  375   -11.907 -22.930  -4.583  70.41   C
ATOM   5436  O    ASP  375   -12.416 -23.947  -4.097  70.19   O
ATOM   5437  N    ALA  376   -10.686 -22.902  -5.109  71.29   N
ATOM   5438  HN   ALA  376   -10.339 -22.030  -5.478   0.00   H
ATOM   5439  CA   ALA  376    -9.853 -24.098  -5.159  72.41   C
ATOM   5440  HA   ALA  376   -10.202 -24.740  -5.926   0.00   H
ATOM   5441  CB   ALA  376    -8.400 -23.717  -5.448  72.80   C
ATOM   5442  HB1  ALA  376    -8.345 -23.217  -6.380   0.00   H
ATOM   5443  HB2  ALA  376    -8.044 -23.078  -4.682   0.00   H
ATOM   5444  HB3  ALA  376    -7.806 -24.593  -5.482   0.00   H
ATOM   5445  C    ALA  376    -9.963 -24.810  -3.817  73.03   C
ATOM   5446  O    ALA  376   -10.486 -25.926  -3.731  72.87   O
ATOM   5447  N    SER  377    -9.484 -24.136  -2.774  73.74   N
ATOM   5448  HN   SER  377    -9.084 -23.229  -2.964   0.00   H
ATOM   5449  CA   SER  377    -9.516 -24.649  -1.405  73.94   C
ATOM   5450  HA   SER  377    -8.700 -25.307  -1.255   0.00   H
ATOM   5451  CB   SER  377    -9.418 -23.485  -0.409  74.45   C
ATOM   5452  HB2  SER  377   -10.364 -23.017  -0.319   0.00   H
ATOM   5453  HB3  SER  377    -9.115 -23.854   0.536   0.00   H
ATOM   5454  OG   SER  377    -8.473 -22.514  -0.838  74.76   O
ATOM   5455  HG   SER  377    -8.434 -21.795  -0.192   0.00   H
ATOM   5456  C    SER  377   -10.623 -25.399  -1.157  73.96   C
ATOM   5457  O    SER  377   -10.834 -26.510  -0.614  74.50   O
ATOM   5458  N    GLY  378   -11.924 -24.777  -1.568  73.06   N
ATOM   5459  HN   GLY  378   -11.844 -23.874  -2.012   0.00   H
ATOM   5460  CA   GLY  378   -13.228 -25.381  -1.385  72.07   C
ATOM   5461  HA2  GLY  378   -13.758 -25.360  -2.301   0.00   H
ATOM   5462  HA3  GLY  378   -13.111 -26.384  -1.068   0.00   H
ATOM   5463  C    GLY  378   -14.020 -24.624  -0.341  71.07   C
ATOM   5464  O    GLY  378   -15.039 -25.107   0.153  70.67   O
ATOM   5465  N    LYS  379   -13.548 -23.429   0.001  70.50   N
ATOM   5466  HN   LYS  379   -12.702 -23.100  -0.439   0.00   H
ATOM   5467  CA   LYS  379   -14.226 -22.599   0.990  68.86   C
ATOM   5468  HA   LYS  379   -14.689 -23.219   1.713   0.00   H
ATOM   5469  CB   LYS  379   -13.218 -21.678   1.690  69.09   C
ATOM   5470  HB2  LYS  379   -12.498 -22.265   2.199   0.00   H
ATOM   5471  HB3  LYS  379   -12.734 -21.072   0.969   0.00   H
ATOM   5472  CG   LYS  379   -13.831 -20.739   2.718  69.21   C
```

FIGURE 6- 73 -

```
ATOM   5473  HG2 LYS 379    -13.095 -20.056  3.056   0.00       H
ATOM   5474  HG3 LYS 379    -14.631 -20.205  2.275   0.00       H
ATOM   5475  CD  LYS 379    -14.373 -21.486  3.928  69.90       C
ATOM   5476  HD2 LYS 379    -15.160 -22.126  3.624   0.00       H
ATOM   5477  HD3 LYS 379    -13.598 -22.061  4.364   0.00       H
ATOM   5478  CE  LYS 379    -14.907 -20.504  4.969  71.11       C
ATOM   5479  HE2 LYS 379    -14.140 -19.826  5.240   0.00       H
ATOM   5480  HE3 LYS 379    -15.725 -19.968  4.562   0.00       H
ATOM   5481  NZ  LYS 379    -15.387 -21.155  6.227  71.82       N1+
ATOM   5482  HZ1 LYS 379    -16.136 -21.796  6.010   0.00       H
ATOM   5483  HZ2 LYS 379    -14.626 -21.660  6.656   0.00       H
ATOM   5484  HZ3 LYS 379    -15.723 -20.449  6.864   0.00       H
ATOM   5485  C   LYS 379    -15.316 -21.767  0.310  67.43       C
ATOM   5486  O   LYS 379    -15.180 -21.366 -0.852  65.77       O
ATOM   5487  N   ARG 380    -16.399 -21.526  1.043  66.88       N
ATOM   5488  HN  ARG 380    -16.424 -21.907  1.977   0.00       H
ATOM   5489  CA  ARG 380    -17.526 -20.743  0.544  65.90       C
ATOM   5490  HA  ARG 380    -17.918 -21.203 -0.326   0.00       H
ATOM   5491  CB  ARG 380    -18.625 -20.664  1.610  67.93       C
ATOM   5492  HB2 ARG 380    -18.277 -20.098  2.434   0.00       H
ATOM   5493  HB3 ARG 380    -19.483 -20.199  1.199   0.00       H
ATOM   5494  CG  ARG 380    -19.059 -22.014  2.144  71.41       C
ATOM   5495  HG2 ARG 380    -19.753 -22.452  1.474   0.00       H
ATOM   5496  HG3 ARG 380    -18.213 -22.644  2.239   0.00       H
ATOM   5497  CD  ARG 380    -19.720 -21.892  3.505  75.22       C
ATOM   5498  HD2 ARG 380    -19.664 -22.822  4.009   0.00       H
ATOM   5499  HD3 ARG 380    -19.222 -21.151  4.074   0.00       H
ATOM   5500  NE  ARG 380    -21.129 -21.516  3.424  78.35       N1+
ATOM   5501  HE  ARG 380    -21.551 -21.331  2.526   0.00       H
ATOM   5502  CZ  ARG 380    -21.934 -21.393  4.479  79.46       C
ATOM   5503  NH1 ARG 380    -21.469 -21.612  5.707  78.96       N
ATOM   5504 HH11 ARG 380    -22.082 -21.518  6.503   0.00       H
ATOM   5505 HH12 ARG 380    -20.504 -21.872  5.842   0.00       H
ATOM   5506  NH2 ARG 380    -23.211 -21.068  4.306  79.52       N
ATOM   5507 HH21 ARG 380    -23.321 -20.975  5.105   0.00       H
ATOM   5508 HH22 ARG 380    -23.571 -20.914  3.376   0.00       H
ATOM   5509  C   ARG 380    -17.044 -19.337  0.215  64.30       C
ATOM   5510  O   ARG 380    -16.448 -18.666  1.058  64.44       O
ATOM   5511  N   VAL 381    -17.293 -18.895 -1.011  62.12       N
ATOM   5512  HN  VAL 381    -17.772 -19.504 -1.657   0.00       H
ATOM   5513  CA  VAL 381    -16.889 -17.559 -1.432  58.77       C
ATOM   5514  HA  VAL 381    -16.477 -17.038 -0.607   0.00       H
ATOM   5515  CB  VAL 381    -15.830 -17.608 -2.552  58.49       C
ATOM   5516  HB  VAL 381    -16.215 -18.148 -3.378   0.00       H
ATOM   5517  CG1 VAL 381    -15.508 -16.196 -3.048  55.90       C
ATOM   5518 HG11 VAL 381    -16.388 -15.746 -3.427   0.00       H
ATOM   5519 HG12 VAL 381    -15.133 -15.617 -2.245   0.00       H
ATOM   5520 HG13 VAL 381    -14.780 -16.249 -3.816   0.00       H
ATOM   5521  CG2 VAL 381    -14.577 -18.298 -2.034  58.07       C
ATOM   5522 HG21 VAL 381    -14.193 -17.758 -1.208   0.00       H
ATOM   5523 HG22 VAL 381    -14.817 -19.284 -1.731   0.00       H
ATOM   5524 HG23 VAL 381    -13.849 -18.332 -2.803   0.00       H
ATOM   5525  C   VAL 381    -18.106 -16.813 -1.936  57.06       C
ATOM   5526  O   VAL 381    -18.680 -17.161 -2.967  56.79       O
ATOM   5527  N   TYR 382    -18.510 -15.797 -1.189  55.52       N
ATOM   5528  HN  TYR 382    -18.006 -15.580 -0.342   0.00       H
ATOM   5529  CA  TYR 382    -19.659 -15.001 -1.572  53.75       C
ATOM   5530  HA  TYR 382    -20.424 -15.637 -1.936   0.00       H
ATOM   5531  CB  TYR 382    -20.176 -14.232 -0.371  51.09       C
ATOM   5532  HB2 TYR 382    -19.391 -13.653  0.042   0.00       H
ATOM   5533  HB3 TYR 382    -20.965 -13.593 -0.674   0.00       H
ATOM   5534  CG  TYR 382    -20.702 -15.133  0.711  49.77       C
ATOM   5535  CD1 TYR 382    -22.032 -15.533  0.720  48.76       C
ATOM   5536  HD1 TYR 382    -22.700 -15.200 -0.057   0.00       H
ATOM   5537  CE1 TYR 382    -22.524 -16.362  1.721  49.40       C
ATOM   5538  HE1 TYR 382    -23.559 -16.659  1.714   0.00       H
ATOM   5539  CD2 TYR 382    -19.869 -15.589  1.728  49.68       C
ATOM   5540  HD2 TYR 382    -18.832 -15.298  1.746   0.00       H
ATOM   5541  CE2 TYR 382    -20.350 -16.420  2.730  49.84       C
ATOM   5542  HE2 TYR 382    -19.689 -16.764  3.507   0.00       H
ATOM   5543  CZ  TYR 382    -21.678 -16.803  2.726  49.63       C
ATOM   5544  OH  TYR 382    -22.156 -17.617  3.731  50.39       O
ATOM   5545  HH  TYR 382    -23.097 -17.786  3.589   0.00       H
ATOM   5546  C   TYR 382    -19.247 -14.047 -2.677  53.82       C
ATOM   5547  O   TYR 382    -18.097 -13.605 -2.733  53.69       O
ATOM   5548  N   TYR 383    -20.188 -13.756 -3.566  53.80       N
```

FIGURE 6- 74 -

```
ATOM   5549   HN    TYR  383   -21.097  -14.178   -3.447    0.00    H
ATOM   5550   CA    TYR  383   -19.944  -12.862   -4.682   53.65    C
ATOM   5551   HA    TYR  383   -19.276  -12.097   -4.382    0.00    H
ATOM   5552   CB    TYR  383   -19.327  -13.622   -5.862   54.98    C
ATOM   5553   HB2   TYR  383   -19.113  -12.943   -6.646    0.00    H
ATOM   5554   HB3   TYR  383   -18.432  -14.093   -5.549    0.00    H
ATOM   5555   CG    TYR  383   -20.205  -14.712   -6.459   56.20    C
ATOM   5556   CD1   TYR  383   -20.666  -15.774   -5.675   56.67    C
ATOM   5557   HD1   TYR  383   -20.406  -15.825   -4.631    0.00    H
ATOM   5558   CE1   TYR  383   -21.466  -16.784   -6.218   55.99    C
ATOM   5559   HE1   TYR  383   -21.810  -17.592   -5.595    0.00    H
ATOM   5560   CD2   TYR  383   -20.566  -14.686   -7.811   56.16    C
ATOM   5561   HD2   TYR  383   -20.228  -13.882   -8.443    0.00    H
ATOM   5562   CE2   TYR  383   -21.366  -15.694   -8.365   56.64    C
ATOM   5563   HE2   TYR  383   -21.632  -15.658   -9.408    0.00    H
ATOM   5564   CZ    TYR  383   -21.811  -16.737   -7.559   55.69    C
ATOM   5565   OH    TYR  383   -22.607  -17.722   -8.093   54.62    O
ATOM   5566   HH    TYR  383   -22.834  -18.362   -7.404    0.00    H
ATOM   5567   C     TYR  383   -21.265  -12.243   -5.097   53.44    C
ATOM   5568   O     TYR  383   -22.337  -12.757   -4.756   53.58    O
ATOM   5569   N     LEU  384   -21.184  -11.137   -5.827   51.37    N
ATOM   5570   HN    LEU  384   -20.272  -10.779   -6.069    0.00    H
ATOM   5571   CA    LEU  384   -22.375  -10.446   -6.275   49.25    C
ATOM   5572   HA    LEU  384   -23.198  -10.736   -5.675    0.00    H
ATOM   5573   CB    LEU  384   -22.175   -8.940   -6.159   50.20    C
ATOM   5574   HB2   LEU  384   -21.532   -8.731   -5.344    0.00    H
ATOM   5575   HB3   LEU  384   -21.743   -8.571   -7.053    0.00    H
ATOM   5576   CG    LEU  384   -23.483   -8.194   -5.928   51.36    C
ATOM   5577   HG    LEU  384   -24.247   -8.631   -6.517    0.00    H
ATOM   5578   CD1   LEU  384   -23.833   -8.301   -4.449   52.23    C
ATOM   5579   HD11  LEU  384   -23.943   -9.321   -4.185    0.00    H
ATOM   5580   HD12  LEU  384   -23.059   -7.868   -3.871    0.00    H
ATOM   5581   HD13  LEU  384   -24.741   -7.789   -4.263    0.00    H
ATOM   5582   CD2   LEU  384   -23.346   -6.738   -6.342   52.86    C
ATOM   5583   HD21  LEU  384   -22.582   -6.279   -5.770    0.00    H
ATOM   5584   HD22  LEU  384   -23.097   -6.685   -7.370    0.00    H
ATOM   5585   HD23  LEU  384   -24.263   -6.236   -6.175    0.00    H
ATOM   5586   C     LEU  384   -22.704  -10.810   -7.718   47.89    C
ATOM   5587   O     LEU  384   -21.831  -10.785   -8.589   46.57    O
ATOM   5588   N     THR  385   -23.972  -11.133   -7.967   46.20    N
ATOM   5589   HN    THR  385   -24.626  -11.111   -7.199    0.00    H
ATOM   5590   CA    THR  385   -24.427  -11.511   -9.304   44.71    C
ATOM   5591   HA    THR  385   -23.795  -11.069  -10.030    0.00    H
ATOM   5592   CB    THR  385   -24.391  -13.056   -9.479   43.67    C
ATOM   5593   HB    THR  385   -23.388  -13.394   -9.430    0.00    H
ATOM   5594   OG1   THR  385   -24.939  -13.415  -10.753   42.91    O
ATOM   5595   HG1   THR  385   -24.914  -14.376  -10.855    0.00    H
ATOM   5596   CG2   THR  385   -25.194  -13.729   -8.382   42.52    C
ATOM   5597   HG21  THR  385   -24.783  -13.478   -7.439    0.00    H
ATOM   5598   HG22  THR  385   -26.199  -13.399   -8.428    0.00    H
ATOM   5599   HG23  THR  385   -25.161  -14.779   -8.514    0.00    H
ATOM   5600   C     THR  385   -25.847  -11.004   -9.590   43.55    C
ATOM   5601   O     THR  385   -26.417  -10.258   -8.793   42.03    O
ATOM   5602   N     ARG  386   -26.404  -11.419  -10.729   43.20    N
ATOM   5603   HN    ARG  386   -25.860  -12.030  -11.319    0.00    H
ATOM   5604   CA    ARG  386   -27.751  -11.020  -11.134   43.34    C
ATOM   5605   HA    ARG  386   -28.431  -11.227  -10.349    0.00    H
ATOM   5606   CB    ARG  386   -27.784   -9.523  -11.445   43.77    C
ATOM   5607   HB2   ARG  386   -28.754   -9.252  -11.773    0.00    H
ATOM   5608   HB3   ARG  386   -27.541   -8.976  -10.572    0.00    H
ATOM   5609   CG    ARG  386   -26.805   -9.080  -12.535   44.27    C
ATOM   5610   HG2   ARG  386   -25.826   -9.034  -12.133    0.00    H
ATOM   5611   HG3   ARG  386   -26.826   -9.776  -13.333    0.00    H
ATOM   5612   CD    ARG  386   -27.170   -7.707  -13.080   44.60    C
ATOM   5613   HD2   ARG  386   -27.291   -7.029  -12.276    0.00    H
ATOM   5614   HD3   ARG  386   -26.398   -7.364  -13.718    0.00    H
ATOM   5615   NE    ARG  386   -28.417   -7.739  -13.845   45.20    N1+
ATOM   5616   HE    ARG  386   -28.848   -8.623  -14.070    0.00    H
ATOM   5617   CZ    ARG  386   -29.059   -6.660  -14.289   44.92    C
ATOM   5618   NH1   ARG  386   -28.587   -5.446  -14.049   43.80    N
ATOM   5619   HH11  ARG  386   -29.082   -4.636  -14.390    0.00    H
ATOM   5620   HH12  ARG  386   -27.732   -5.331  -13.525    0.00    H
ATOM   5621   NH2   ARG  386   -30.176   -6.796  -14.989   45.23    N
ATOM   5622   HH21  ARG  386   -30.663   -5.979  -15.326    0.00    H
ATOM   5623   HH22  ARG  386   -30.539   -7.717  -15.185    0.00    H
ATOM   5624   C     ARG  386   -28.239  -11.773  -12.363   43.36    C
```

FIGURE 6- 75 -

```
ATOM   5625  O    ARG  386   -27.466 -12.467 -13.024   43.38        O
ATOM   5626  N    ASP  387   -29.529 -11.630 -12.674   42.64        N
ATOM   5627  HN   ASP  387   -30.102 -11.072 -12.058    0.00        H
ATOM   5628  CA   ASP  387   -30.118 -12.249 -13.855   42.39        C
ATOM   5629  HA   ASP  387   -29.983 -13.298 -13.808    0.00        H
ATOM   5630  CB   ASP  387   -31.614 -11.943 -13.928   44.89        C
ATOM   5631  HB2  ASP  387   -32.074 -12.209 -13.012    0.00        H
ATOM   5632  HB3  ASP  387   -31.754 -10.909 -14.107    0.00        H
ATOM   5633  CG   ASP  387   -32.318 -12.711 -15.045   48.22        C
ATOM   5634  OD1  ASP  387   -31.804 -12.703 -16.187   49.38        O
ATOM   5635  OD2  ASP  387   -33.387 -13.318 -14.780   47.83        O1-
ATOM   5636  C    ASP  387   -29.403 -11.592 -15.034   42.07        C
ATOM   5637  O    ASP  387   -29.631 -10.425 -15.339   41.36        O
ATOM   5638  N    PRO  388   -28.545 -12.348 -15.724   41.73        N
ATOM   5639  CD   PRO  388   -28.438 -13.806 -15.546   42.32        C
ATOM   5640  HD2  PRO  388   -27.850 -14.015 -14.690    0.00        H
ATOM   5641  HD3  PRO  388   -29.405 -14.218 -15.419    0.00        H
ATOM   5642  CA   PRO  388   -27.746 -11.915 -16.874   42.19        C
ATOM   5643  HA   PRO  388   -27.157 -11.079 -16.600    0.00        H
ATOM   5644  CB   PRO  388   -26.852 -13.118 -17.125   41.82        C
ATOM   5645  HB2  PRO  388   -26.513 -13.103 -18.128    0.00        H
ATOM   5646  HB3  PRO  388   -26.020 -13.082 -16.471    0.00        H
ATOM   5647  CG   PRO  388   -27.776 -14.243 -16.836   41.95        C
ATOM   5648  HG2  PRO  388   -28.464 -14.349 -17.634    0.00        H
ATOM   5649  HG3  PRO  388   -27.220 -15.138 -16.728    0.00        H
ATOM   5650  C    PRO  388   -28.462 -11.478 -18.148   43.54        C
ATOM   5651  O    PRO  388   -27.802 -11.076 -19.112   44.59        O
ATOM   5652  N    THR  389   -29.791 -11.544 -18.166   43.35        N
ATOM   5653  HN   THR  389   -30.287 -11.853 -17.344    0.00        H
ATOM   5654  CA   THR  389   -30.531 -11.172 -19.368   43.07        C
ATOM   5655  HA   THR  389   -30.291 -11.843 -20.152    0.00        H
ATOM   5656  CB   THR  389   -32.054 -11.219 -19.140   43.08        C
ATOM   5657  HB   THR  389   -32.331 -10.464 -18.451    0.00        H
ATOM   5658  OG1  THR  389   -32.415 -12.506 -18.626   44.14        O
ATOM   5659  HG1  THR  389   -33.371 -12.539 -18.482    0.00        H
ATOM   5660  CG2  THR  389   -32.801 -10.990 -20.455   40.77        C
ATOM   5661  HG21 THR  389   -32.542 -10.041 -20.848    0.00        H
ATOM   5662  HG22 THR  389   -32.534 -11.744 -21.149    0.00        H
ATOM   5663  HG23 THR  389   -33.845 -11.026 -20.279    0.00        H
ATOM   5664  C    THR  389   -30.161  -9.796 -19.906   43.81        C
ATOM   5665  O    THR  389   -29.480  -9.687 -20.932   43.75        O
ATOM   5666  N    THR  390   -30.605  -8.748 -19.218   43.71        N
ATOM   5667  HN   THR  390   -31.145  -8.904 -18.380    0.00        H
ATOM   5668  CA   THR  390   -30.321  -7.391 -19.659   43.31        C
ATOM   5669  HA   THR  390   -30.857  -7.190 -20.550    0.00        H
ATOM   5670  CB   THR  390   -30.735  -6.360 -18.596   42.97        C
ATOM   5671  HB   THR  390   -30.119  -6.468 -17.741    0.00        H
ATOM   5672  OG1  THR  390   -32.103  -6.579 -18.220   41.31        O
ATOM   5673  HG1  THR  390   -32.361  -5.930 -17.552    0.00        H
ATOM   5674  CG2  THR  390   -30.581  -4.951 -19.148   39.81        C
ATOM   5675  HG21 THR  390   -29.570  -4.786 -19.411    0.00        H
ATOM   5676  HG22 THR  390   -31.197  -4.837 -20.002    0.00        H
ATOM   5677  HG23 THR  390   -30.868  -4.249 -18.409    0.00        H
ATOM   5678  C    THR  390   -28.833  -7.243 -19.965   44.33        C
ATOM   5679  O    THR  390   -28.451  -6.724 -21.012   44.12        O
ATOM   5680  N    PRO  391   -27.884  -7.682 -19.045   44.79        N
ATOM   5681  CD   PRO  391   -28.014  -8.025 -17.633   44.15        C
ATOM   5682  HD2  PRO  391   -28.543  -7.266 -17.080    0.00        H
ATOM   5683  HD3  PRO  391   -28.539  -8.960 -17.518    0.00        H
ATOM   5684  CA   PRO  391   -26.461  -7.679 -19.434   45.70        C
ATOM   5685  HA   PRO  391   -26.157  -6.639 -19.421    0.00        H
ATOM   5686  CB   PRO  391   -25.782  -8.459 -18.314   44.67        C
ATOM   5687  HB2  PRO  391   -25.829  -9.539 -18.489    0.00        H
ATOM   5688  HB3  PRO  391   -24.726  -8.210 -18.203    0.00        H
ATOM   5689  CG   PRO  391   -26.600  -8.106 -17.098   44.54        C
ATOM   5690  HG2  PRO  391   -26.502  -8.828 -16.284    0.00        H
ATOM   5691  HG3  PRO  391   -26.292  -7.127 -16.715    0.00        H
ATOM   5692  C    PRO  391   -25.951  -8.260 -20.773   47.47        C
ATOM   5693  O    PRO  391   -24.931  -7.821 -21.304   48.24        O
ATOM   5694  N    LEU  392   -26.581  -9.400 -21.187   48.83        N
ATOM   5695  HN   LEU  392   -27.459  -9.672 -20.732    0.00        H
ATOM   5696  CA   LEU  392   -26.129 -10.182 -22.322   50.06        C
ATOM   5697  HA   LEU  392   -25.096  -9.962 -22.553    0.00        H
ATOM   5698  CB   LEU  392   -26.344 -11.689 -22.094   50.29        C
ATOM   5699  HB2  LEU  392   -27.410 -11.866 -21.913    0.00        H
ATOM   5700  HB3  LEU  392   -26.119 -12.223 -23.022    0.00        H
```

FIGURE 6- 76 -

```
ATOM   5701  CG   LEU   392    -25.542 -12.354 -20.969   50.05      C
ATOM   5702  HG   LEU   392    -25.771 -11.870 -20.018    0.00      H
ATOM   5703  CD1  LEU   392    -25.922 -13.831 -20.862   48.80      C
ATOM   5704  HD11 LEU   392    -26.993 -13.947 -20.668    0.00      H
ATOM   5705  HD12 LEU   392    -25.686 -14.373 -21.783    0.00      H
ATOM   5706  HD13 LEU   392    -25.384 -14.315 -20.040    0.00      H
ATOM   5707  CD2  LEU   392    -24.048 -12.225 -21.182   51.21      C
ATOM   5708  HD21 LEU   392    -23.747 -12.563 -22.178    0.00      H
ATOM   5709  HD22 LEU   392    -23.759 -11.181 -21.060    0.00      H
ATOM   5710  HD23 LEU   392    -23.497 -12.811 -20.439    0.00      H
ATOM   5711  C    LEU   392    -26.978  -9.861 -23.566   51.23      C
ATOM   5712  O    LEU   392    -26.801 -10.419 -24.646   50.97      O
ATOM   5713  N    ALA   393    -27.932  -8.921 -23.342   52.75      N
ATOM   5714  HN   ALA   393    -28.030  -8.591 -22.381    0.00      H
ATOM   5715  CA   ALA   393    -28.883  -8.424 -24.341   53.52      C
ATOM   5716  HA   ALA   393    -28.782  -9.021 -25.242    0.00      H
ATOM   5717  CB   ALA   393    -30.315  -8.481 -23.863   52.90      C
ATOM   5718  HB1  ALA   393    -30.598  -9.504 -23.605    0.00      H
ATOM   5719  HB2  ALA   393    -30.473  -7.848 -22.986    0.00      H
ATOM   5720  HB3  ALA   393    -30.996  -8.130 -24.642    0.00      H
ATOM   5721  C    ALA   393    -28.519  -6.998 -24.705   53.80      C
ATOM   5722  O    ALA   393    -28.763  -6.534 -25.816   53.81      O
ATOM   5723  N    ARG   394    -27.948  -6.287 -23.684   54.52      N
ATOM   5724  HN   ARG   394    -27.871  -6.724 -22.762    0.00      H
ATOM   5725  CA   ARG   394    -27.295  -5.025 -23.929   56.11      C
ATOM   5726  HA   ARG   394    -27.902  -4.422 -24.590    0.00      H
ATOM   5727  CB   ARG   394    -26.934  -4.276 -22.648   54.59      C
ATOM   5728  HB2  ARG   394    -26.489  -4.959 -21.917    0.00      H
ATOM   5729  HB3  ARG   394    -26.171  -3.524 -22.866    0.00      H
ATOM   5730  CG   ARG   394    -28.127  -3.558 -22.039   53.18      C
ATOM   5731  HG2  ARG   394    -28.512  -2.834 -22.759    0.00      H
ATOM   5732  HG3  ARG   394    -28.937  -4.261 -21.833    0.00      H
ATOM   5733  CD   ARG   394    -27.762  -2.808 -20.767   52.91      C
ATOM   5734  HD2  ARG   394    -27.483  -3.507 -19.978    0.00      H
ATOM   5735  HD3  ARG   394    -26.924  -2.138 -20.972    0.00      H
ATOM   5736  NE   ARG   394    -28.906  -2.008 -20.300   53.19      N1+
ATOM   5737  HE   ARG   394    -29.812  -2.204 -20.712    0.00      H
ATOM   5738  CZ   ARG   394    -28.815  -0.933 -19.499   53.10      C
ATOM   5739  NH1  ARG   394    -27.680  -0.596 -18.889   53.23      N
ATOM   5740  HH11 ARG   394    -27.640   0.237 -18.308    0.00      H
ATOM   5741  HH12 ARG   394    -26.840  -1.151 -18.971    0.00      H
ATOM   5742  NH2  ARG   394    -29.893  -0.177 -19.315   52.78      N
ATOM   5743  HH21 ARG   394    -29.871   0.709 -18.814    0.00      H
ATOM   5744  HH22 ARG   394    -30.775  -0.447 -19.723    0.00      H
ATOM   5745  C    ARG   394    -26.016  -5.333 -24.657   57.71      C
ATOM   5746  O    ARG   394    -25.433  -4.477 -25.319   58.08      O
ATOM   5747  N    ALA   395    -25.550  -6.598 -24.445   59.20      N
ATOM   5748  HN   ALA   395    -26.101  -7.223 -23.855    0.00      H
ATOM   5749  CA   ALA   395    -24.338  -7.039 -25.068   60.51      C
ATOM   5750  HA   ALA   395    -23.605  -6.242 -25.020    0.00      H
ATOM   5751  CB   ALA   395    -23.774  -8.283 -24.432   60.81      C
ATOM   5752  HB1  ALA   395    -23.610  -8.138 -23.365    0.00      H
ATOM   5753  HB2  ALA   395    -24.426  -9.145 -24.576    0.00      H
ATOM   5754  HB3  ALA   395    -22.811  -8.534 -24.870    0.00      H
ATOM   5755  C    ALA   395    -24.609  -7.320 -26.535   61.55      C
ATOM   5756  O    ALA   395    -23.710  -7.219 -27.369   61.71      O
ATOM   5757  N    ALA   396    -25.833  -7.849 -26.858   62.92      N
ATOM   5758  HN   ALA   396    -26.550  -7.875 -26.139    0.00      H
ATOM   5759  CA   ALA   396    -26.083  -8.343 -28.207   64.22      C
ATOM   5760  HA   ALA   396    -25.223  -8.945 -28.501    0.00      H
ATOM   5761  CB   ALA   396    -27.324  -9.223 -28.239   63.65      C
ATOM   5762  HB1  ALA   396    -27.243 -10.043 -27.521    0.00      H
ATOM   5763  HB2  ALA   396    -28.223  -8.650 -27.994    0.00      H
ATOM   5764  HB3  ALA   396    -27.471  -9.659 -29.231    0.00      H
ATOM   5765  C    ALA   396    -26.215  -7.257 -29.302   65.65      C
ATOM   5766  O    ALA   396    -26.273  -7.553 -30.495   66.69      O
ATOM   5767  N    TRP   397    -26.362  -5.974 -28.827   67.00      N
ATOM   5768  HN   TRP   397    -26.273  -5.848 -27.820    0.00      H
ATOM   5769  CA   TRP   397    -26.501  -4.799 -29.678   68.53      C
ATOM   5770  HA   TRP   397    -27.091  -5.103 -30.541    0.00      H
ATOM   5771  CB   TRP   397    -27.203  -3.661 -28.931   68.71      C
ATOM   5772  HB2  TRP   397    -27.923  -4.076 -28.223    0.00      H
ATOM   5773  HB3  TRP   397    -26.486  -3.097 -28.332    0.00      H
ATOM   5774  CG   TRP   397    -27.955  -2.708 -29.830   69.95      C
ATOM   5775  CD2  TRP   397    -29.253  -2.914 -30.412   70.00      C
ATOM   5776  CE2  TRP   397    -29.547  -1.791 -31.193   69.38      C
```

FIGURE 6- 77 -

```
ATOM   5777  CE3  TRP   397    -30.201   -3.954  -30.345   69.70      C
ATOM   5778  HE3  TRP   397    -30.016   -4.824  -29.728    0.00      H
ATOM   5779  CD1  TRP   397    -27.527   -1.452  -30.241   69.15      C
ATOM   5780  HD1  TRP   397    -26.614   -0.913  -30.032    0.00      H
ATOM   5781  NE1  TRP   397    -28.486   -0.918  -31.068   69.60      N
ATOM   5782  HE1  TRP   397    -28.425   -0.009  -31.521    0.00      H
ATOM   5783  CZ2  TRP   397    -30.734   -1.668  -31.930   69.28      C
ATOM   5784  HZ2  TRP   397    -30.943   -0.785  -32.526    0.00      H
ATOM   5785  CZ3  TRP   397    -31.398   -3.843  -31.067   70.13      C
ATOM   5786  HZ3  TRP   397    -32.134   -4.637  -30.997    0.00      H
ATOM   5787  CH2  TRP   397    -31.657   -2.717  -31.853   69.88      C
ATOM   5788  HH2  TRP   397    -32.593   -2.647  -32.400    0.00      H
ATOM   5789  C    TRP   397    -25.168   -4.290  -30.241   69.95      C
ATOM   5790  O    TRP   397    -25.146   -3.568  -31.235   70.03      O
ATOM   5791  N    GLU   398    -24.052   -4.564  -29.485   71.41      N
ATOM   5792  HN   GLU   398    -24.124   -5.254  -28.735    0.00      H
ATOM   5793  CA   GLU   398    -22.805   -3.820  -29.662   72.92      C
ATOM   5794  HA   GLU   398    -22.875   -3.264  -30.594    0.00      H
ATOM   5795  CB   GLU   398    -22.624   -2.792  -28.539   71.82      C
ATOM   5796  HB2  GLU   398    -22.939   -3.231  -27.589    0.00      H
ATOM   5797  HB3  GLU   398    -21.568   -2.534  -28.422    0.00      H
ATOM   5798  CG   GLU   398    -23.406   -1.503  -28.849   72.08      C
ATOM   5799  HG2  GLU   398    -22.757   -0.843  -29.434    0.00      H
ATOM   5800  HG3  GLU   398    -24.259   -1.733  -29.495    0.00      H
ATOM   5801  CD   GLU   398    -24.038   -0.650  -27.763   72.38      C
ATOM   5802  OE1  GLU   398    -24.117   -1.108  -26.591   72.90      O1-
ATOM   5803  OE2  GLU   398    -24.497    0.463  -28.174   72.87      O
ATOM   5804  C    GLU   398    -21.604   -4.738  -29.945   74.71      C
ATOM   5805  O    GLU   398    -20.435   -4.357  -29.979   74.48      O
ATOM   5806  N    THR   399    -22.000   -5.979  -30.399   77.06      N
ATOM   5807  HN   THR   399    -22.977   -6.211  -30.212    0.00      H
ATOM   5808  CA   THR   399    -21.382   -6.609  -31.557   79.31      C
ATOM   5809  HA   THR   399    -20.316   -6.373  -31.562    0.00      H
ATOM   5810  CB   THR   399    -21.627   -8.136  -31.634   79.04      C
ATOM   5811  HB   THR   399    -22.699   -8.349  -31.688    0.00      H
ATOM   5812  OG1  THR   399    -21.136   -8.819  -30.475   79.59      O
ATOM   5813  HG1  THR   399    -21.517   -8.324  -29.718    0.00      H
ATOM   5814  CG2  THR   399    -20.953   -8.780  -32.841   78.69      C
ATOM   5815 HG21  THR   399    -21.388   -8.437  -33.784    0.00      H
ATOM   5816 HG22  THR   399    -19.881   -8.561  -32.850    0.00      H
ATOM   5817 HG23  THR   399    -21.054   -9.869  -32.801    0.00      H
ATOM   5818  C    THR   399    -22.046   -5.979  -32.795   81.00      C
ATOM   5819  O    THR   399    -21.380   -5.724  -33.801   81.00      O
ATOM   5820  N    ALA   400    -23.430   -5.921  -32.784   82.55      N
ATOM   5821  HN   ALA   400    -23.964   -6.202  -31.975    0.00      H
ATOM   5822  CA   ALA   400    -24.102   -5.701  -34.061   84.33      C
ATOM   5823  HA   ALA   400    -23.534   -6.141  -34.839    0.00      H
ATOM   5824  CB   ALA   400    -25.494   -6.337  -34.024   83.77      C
ATOM   5825  HB1  ALA   400    -25.402   -7.377  -33.849    0.00      H
ATOM   5826  HB2  ALA   400    -26.063   -5.897  -33.246    0.00      H
ATOM   5827  HB3  ALA   400    -25.980   -6.177  -34.951    0.00      H
ATOM   5828  C    ALA   400    -24.208   -4.242  -34.546   85.80      C
ATOM   5829  O    ALA   400    -24.488   -4.007  -35.721   85.49      O
ATOM   5830  N    ARG   401    -23.990   -3.266  -33.663   87.49      N
ATOM   5831  HN   ARG   401    -23.762   -3.499  -32.708    0.00      H
ATOM   5832  CA   ARG   401    -24.080   -1.860  -34.073   89.65      C
ATOM   5833  HA   ARG   401    -24.193   -1.805  -35.125    0.00      H
ATOM   5834  CB   ARG   401    -25.279   -1.178  -33.412   89.41      C
ATOM   5835  HB2  ARG   401    -26.116   -1.826  -33.445    0.00      H
ATOM   5836  HB3  ARG   401    -25.046   -0.954  -32.404    0.00      H
ATOM   5837  CG   ARG   401    -25.680    0.128  -34.093   89.92      C
ATOM   5838  HG2  ARG   401    -26.094    0.787  -33.375    0.00      H
ATOM   5839  HG3  ARG   401    -24.825    0.575  -34.531    0.00      H
ATOM   5840  CD   ARG   401    -26.721   -0.068  -35.200   90.25      C
ATOM   5841  HD2  ARG   401    -27.621   -0.434  -34.778    0.00      H
ATOM   5842  HD3  ARG   401    -26.906    0.859  -35.678    0.00      H
ATOM   5843  NE   ARG   401    -26.321   -1.016  -36.243   90.69      N1+
ATOM   5844  HE   ARG   401    -25.406   -1.439  -36.216    0.00      H
ATOM   5845  CZ   ARG   401    -27.099   -1.378  -37.264   90.66      C
ATOM   5846  NH1  ARG   401    -28.323   -0.872  -37.388   91.04      N
ATOM   5847 HH11  ARG   401    -28.907   -1.149  -38.162    0.00      H
ATOM   5848 HH12  ARG   401    -28.667   -0.211  -36.708    0.00      H
ATOM   5849  NH2  ARG   401    -26.659   -2.251  -38.162   90.28      N
ATOM   5850 HH21  ARG   401    -27.250   -2.523  -38.933    0.00      H
ATOM   5851 HH22  ARG   401    -25.733   -2.643  -38.073    0.00      H
ATOM   5852  C    ARG   401    -22.800   -1.051  -33.809   91.44      C
```

FIGURE 6-78 -

```
ATOM   5853  O    ARG  401   -21.700   -1.621  -33.851   91.69   O
ATOM   5854  N    HIS  402   -22.910    0.254  -33.512   93.22   N
ATOM   5855  HN   HIS  402   -23.809    0.704  -33.422    0.00   H
ATOM   5856  CA   HIS  402   -21.676    1.031  -33.317   94.63   C
ATOM   5857  HA   HIS  402   -20.867    0.530  -33.781    0.00   H
ATOM   5858  CB   HIS  402   -21.763    2.461  -33.925   95.62   C
ATOM   5859  HB2  HIS  402   -20.908    3.018  -33.642    0.00   H
ATOM   5860  HB3  HIS  402   -21.806    2.394  -34.981    0.00   H
ATOM   5861  CG   HIS  402   -22.949    3.276  -33.509   96.97   C
ATOM   5862  CD2  HIS  402   -23.049    4.332  -32.665   97.09   C
ATOM   5863  HD2  HIS  402   -22.198    4.636  -32.079    0.00   H
ATOM   5864  ND1  HIS  402   -24.192    3.134  -34.091   97.25   N1+
ATOM   5865  HD1  HIS  402   -24.356    2.394  -34.757    0.00   H
ATOM   5866  CE1  HIS  402   -25.003    4.070  -33.631   96.83   C
ATOM   5867  HE1  HIS  402   -26.021    4.120  -33.980    0.00   H
ATOM   5868  NE2  HIS  402   -24.334    4.811  -32.765   97.03   N
ATOM   5869  HE2  HIS  402   -24.619    5.610  -32.218    0.00   H
ATOM   5870  C    HIS  402   -20.841    1.079  -32.026   95.15   C
ATOM   5871  O    HIS  402   -20.796    0.090  -31.291   94.77   O
ATOM   5872  N    THR  403   -20.218    2.222  -31.718   95.80   N
ATOM   5873  HN   THR  403   -20.430    3.093  -32.182    0.00   H
ATOM   5874  CA   THR  403   -19.200    2.181  -30.671   95.95   C
ATOM   5875  HA   THR  403   -19.133    1.198  -30.282    0.00   H
ATOM   5876  CB   THR  403   -17.868    2.607  -31.349   96.29   C
ATOM   5877  HB   THR  403   -17.206    2.991  -30.617    0.00   H
ATOM   5878  OG1  THR  403   -18.120    3.630  -32.328   96.12   O
ATOM   5879  HG1  THR  403   -17.287    3.889  -32.745    0.00   H
ATOM   5880  CG2  THR  403   -17.227    1.381  -32.032   95.84   C
ATOM   5881  HG21 THR  403   -17.032    0.635  -31.307    0.00   H
ATOM   5882  HG22 THR  403   -17.890    0.998  -32.764    0.00   H
ATOM   5883  HG23 THR  403   -16.319    1.669  -32.495    0.00   H
ATOM   5884  C    THR  403   -19.025    2.548  -29.194   95.76   C
ATOM   5885  O    THR  403   -18.031    3.187  -28.813   94.88   O
ATOM   5886  N    PRO  404   -20.009    2.229  -28.353   96.04   N
ATOM   5887  CD   PRO  404   -21.472    2.334  -28.494   95.80   C
ATOM   5888  HD2  PRO  404   -21.706    2.776  -29.428    0.00   H
ATOM   5889  HD3  PRO  404   -21.902    1.367  -28.443    0.00   H
ATOM   5890  CA   PRO  404   -19.593    2.596  -26.998   95.70   C
ATOM   5891  HA   PRO  404   -18.906    3.400  -27.045    0.00   H
ATOM   5892  CB   PRO  404   -20.906    2.796  -26.251   95.83   C
ATOM   5893  HB2  PRO  404   -21.192    1.886  -25.791    0.00   H
ATOM   5894  HB3  PRO  404   -20.780    3.542  -25.510    0.00   H
ATOM   5895  CG   PRO  404   -21.845    3.210  -27.315   95.52   C
ATOM   5896  HG2  PRO  404   -22.840    3.043  -26.993    0.00   H
ATOM   5897  HG3  PRO  404   -21.710    4.239  -27.524    0.00   H
ATOM   5898  C    PRO  404   -19.012    1.184  -26.720   95.57   C
ATOM   5899  O    PRO  404   -18.963    0.357  -27.638   95.83   O
ATOM   5900  N    ILE  405   -18.568    0.876  -25.512   95.00   N
ATOM   5901  HN   ILE  405   -18.572    1.567  -24.776    0.00   H
ATOM   5902  CA   ILE  405   -18.068   -0.478  -25.245   94.18   C
ATOM   5903  HA   ILE  405   -18.507   -1.158  -25.928    0.00   H
ATOM   5904  CB   ILE  405   -16.523   -0.562  -25.397   94.87   C
ATOM   5905  HB   ILE  405   -16.080    0.307  -24.984    0.00   H
ATOM   5906  CG2  ILE  405   -15.963   -1.778  -24.679   95.04   C
ATOM   5907  HG21 ILE  405   -16.197   -1.718  -23.648    0.00   H
ATOM   5908  HG22 ILE  405   -16.390   -2.657  -25.088    0.00   H
ATOM   5909  HG23 ILE  405   -14.911   -1.807  -24.801    0.00   H
ATOM   5910  CG1  ILE  405   -16.169   -0.702  -26.887   95.76   C
ATOM   5911  HG12 ILE  405   -16.542    0.134  -27.419    0.00   H
ATOM   5912  HG13 ILE  405   -15.117   -0.749  -26.997    0.00   H
ATOM   5913  CD1  ILE  405   -16.749   -1.966  -27.574   95.79   C
ATOM   5914  HD11 ILE  405   -16.380   -2.832  -27.089    0.00   H
ATOM   5915  HD12 ILE  405   -17.806   -1.949  -27.510    0.00   H
ATOM   5916  HD13 ILE  405   -16.457   -1.980  -28.592    0.00   H
ATOM   5917  C    ILE  405   -18.530   -0.808  -23.842   93.47   C
ATOM   5918  O    ILE  405   -18.144   -1.801  -23.211   93.15   O
ATOM   5919  N    ASN  406   -19.400    0.074  -23.383   92.25   N
ATOM   5920  HN   ASN  406   -19.627    0.840  -24.000    0.00   H
ATOM   5921  CA   ASN  406   -20.016   -0.011  -22.084   90.48   C
ATOM   5922  HA   ASN  406   -19.275    0.095  -21.335    0.00   H
ATOM   5923  CB   ASN  406   -21.048    1.121  -21.975   92.23   C
ATOM   5924  HB2  ASN  406   -21.766    0.874  -21.237    0.00   H
ATOM   5925  HB3  ASN  406   -20.558    2.020  -21.705    0.00   H
ATOM   5926  CG   ASN  406   -21.784    1.357  -23.297   93.06   C
ATOM   5927  OD1  ASN  406   -21.916    0.433  -24.109   92.92   O
ATOM   5928  ND2  ASN  406   -22.265    2.584  -23.517   93.57   N
```

FIGURE 6- 79 -

```
ATOM   5929 HD21 ASN  406   -22.134   3.308 -22.827    0.00    H
ATOM   5930 HD22 ASN  406   -22.759   2.736 -24.373    0.00    H
ATOM   5931 C    ASN  406   -20.684  -1.379 -21.874   88.20    C
ATOM   5932 O    ASN  406   -20.509  -2.323 -22.656   87.43    O
ATOM   5933 N    SER  407   -21.455  -1.448 -20.797   85.57    N
ATOM   5934 HN   SER  407   -21.514  -0.607 -20.243    0.00    H
ATOM   5935 CA   SER  407   -22.188  -2.633 -20.396   82.51    C
ATOM   5936 HA   SER  407   -22.503  -2.530 -19.390    0.00    H
ATOM   5937 CB   SER  407   -23.419  -2.824 -21.288   81.67    C
ATOM   5938 HB2  SER  407   -24.069  -3.534 -20.846    0.00    H
ATOM   5939 HB3  SER  407   -23.925  -1.900 -21.393    0.00    H
ATOM   5940 OG   SER  407   -23.060  -3.285 -22.570   81.72    O
ATOM   5941 HG   SER  407   -23.856  -3.395 -23.108    0.00    H
ATOM   5942 C    SER  407   -21.308  -3.893 -20.394   80.84    C
ATOM   5943 O    SER  407   -20.692  -4.192 -19.375   80.63    O
ATOM   5944 N    TRP  408   -21.112  -4.591 -21.570   77.93    N
ATOM   5945 HN   TRP  408   -21.433  -4.146 -22.432    0.00    H
ATOM   5946 CA   TRP  408   -20.410  -5.869 -21.555   74.87    C
ATOM   5947 HA   TRP  408   -20.965  -6.482 -20.862    0.00    H
ATOM   5948 CB   TRP  408   -20.386  -6.655 -22.847   74.84    C
ATOM   5949 HB2  TRP  408   -20.078  -7.671 -22.611    0.00    H
ATOM   5950 HB3  TRP  408   -21.403  -6.737 -23.224    0.00    H
ATOM   5951 CG   TRP  408   -19.485  -6.161 -23.940   75.03    C
ATOM   5952 CD2  TRP  408   -18.057  -6.372 -24.085   74.79    C
ATOM   5953 CE2  TRP  408   -17.660  -5.742 -25.273   74.66    C
ATOM   5954 CE3  TRP  408   -17.066  -7.031 -23.315   74.82    C
ATOM   5955 HE3  TRP  408   -17.345  -7.525 -22.408    0.00    H
ATOM   5956 CD1  TRP  408   -19.895  -5.427 -25.051   74.67    C
ATOM   5957 HD1  TRP  408   -20.870  -5.066 -25.337    0.00    H
ATOM   5958 NE1  TRP  408   -18.791  -5.183 -25.839   74.50    N
ATOM   5959 HE1  TRP  408   -18.806  -4.665 -26.712    0.00    H
ATOM   5960 CZ2  TRP  408   -16.317  -5.714 -25.707   74.27    C
ATOM   5961 HZ2  TRP  408   -16.034  -5.220 -26.628    0.00    H
ATOM   5962 CZ3  TRP  408   -15.721  -7.016 -23.727   74.20    C
ATOM   5963 HZ3  TRP  408   -14.976  -7.528 -23.133    0.00    H
ATOM   5964 CH2  TRP  408   -15.356  -6.362 -24.908   74.04    C
ATOM   5965 HH2  TRP  408   -14.320  -6.367 -25.216    0.00    H
ATOM   5966 C    TRP  408   -19.026  -5.804 -20.963   72.68    C
ATOM   5967 O    TRP  408   -18.585  -6.758 -20.341   73.02    O
ATOM   5968 N    LEU  409   -18.267  -4.669 -21.189   70.17    N
ATOM   5969 HN   LEU  409   -18.526  -4.118 -21.994    0.00    H
ATOM   5970 CA   LEU  409   -16.999  -4.425 -20.518   67.26    C
ATOM   5971 HA   LEU  409   -16.380  -5.279 -20.612    0.00    H
ATOM   5972 CB   LEU  409   -16.284  -3.220 -21.143   66.67    C
ATOM   5973 HB2  LEU  409   -16.106  -3.409 -22.170    0.00    H
ATOM   5974 HB3  LEU  409   -16.891  -2.358 -21.043    0.00    H
ATOM   5975 CG   LEU  409   -14.927  -2.860 -20.533   65.53    C
ATOM   5976 HG   LEU  409   -15.071  -2.455 -19.565    0.00    H
ATOM   5977 CD1  LEU  409   -14.055  -4.106 -20.431   65.82    C
ATOM   5978 HD11 LEU  409   -14.534  -4.823 -19.816    0.00    H
ATOM   5979 HD12 LEU  409   -13.906  -4.513 -21.397    0.00    H
ATOM   5980 HD13 LEU  409   -13.119  -3.848 -20.008    0.00    H
ATOM   5981 CD2  LEU  409   -14.254  -1.799 -21.382   65.42    C
ATOM   5982 HD21 LEU  409   -14.112  -2.170 -22.364    0.00    H
ATOM   5983 HD22 LEU  409   -14.865  -0.935 -21.417    0.00    H
ATOM   5984 HD23 LEU  409   -13.315  -1.551 -20.959    0.00    H
ATOM   5985 C    LEU  409   -17.263  -4.179 -19.040   65.13    C
ATOM   5986 O    LEU  409   -16.772  -4.908 -18.176   64.95    O
ATOM   5987 N    GLY  410   -18.059  -3.156 -18.758   62.91    N
ATOM   5988 HN   GLY  410   -18.441  -2.597 -19.506    0.00    H
ATOM   5989 CA   GLY  410   -18.381  -2.840 -17.381   60.37    C
ATOM   5990 HA2  GLY  410   -17.511  -2.495 -16.885    0.00    H
ATOM   5991 HA3  GLY  410   -19.124  -2.036 -17.356    0.00    H
ATOM   5992 C    GLY  410   -18.903  -4.055 -16.647   58.65    C
ATOM   5993 O    GLY  410   -18.412  -4.395 -15.567   58.33    O
ATOM   5994 N    ASN  411   -19.896  -4.713 -17.244   57.09    N
ATOM   5995 HN   ASN  411   -20.227  -4.363 -18.130    0.00    H
ATOM   5996 CA   ASN  411   -20.502  -5.902 -16.658   55.21    C
ATOM   5997 HA   ASN  411   -21.024  -5.634 -15.776    0.00    H
ATOM   5998 CB   ASN  411   -21.487  -6.555 -17.631   53.99    C
ATOM   5999 HB2  ASN  411   -21.168  -6.382 -18.626    0.00    H
ATOM   6000 HB3  ASN  411   -21.525  -7.598 -17.449    0.00    H
ATOM   6001 CG   ASN  411   -22.902  -6.009 -17.496   53.04    C
ATOM   6002 OD1  ASN  411   -23.403  -5.785 -16.381   49.12    O
ATOM   6003 ND2  ASN  411   -23.564  -5.813 -18.636   52.85    N
ATOM   6004 HD21 ASN  411   -23.117  -6.009 -19.519    0.00    H
```

FIGURE 6- 80 -

```
ATOM   6005  HD22 ASN   411   -24.512   -5.469  -18.616    0.00        H
ATOM   6006  C    ASN   411   -19.451   -6.919  -16.254   54.81        C
ATOM   6007  O    ASN   411   -19.511   -7.471  -15.155   54.28        O
ATOM   6008  N    ILE   412   -18.493   -7.169  -17.142   54.35        N
ATOM   6009  HN   ILE   412   -18.511   -6.690  -18.030    0.00        H
ATOM   6010  CA   ILE   412   -17.428   -8.119  -16.848   55.05        C
ATOM   6011  HA   ILE   412   -17.849   -9.070  -16.649    0.00        H
ATOM   6012  CB   ILE   412   -16.449   -8.257  -18.032   55.58        C
ATOM   6013  HB   ILE   412   -16.168   -7.294  -18.372    0.00        H
ATOM   6014  CG2  ILE   412   -15.201   -9.018  -17.593   55.35        C
ATOM   6015  HG21 ILE   412   -14.725   -8.492  -16.807    0.00        H
ATOM   6016  HG22 ILE   412   -15.477   -9.983  -17.255    0.00        H
ATOM   6017  HG23 ILE   412   -14.536   -9.107  -18.412    0.00        H
ATOM   6018  CG1  ILE   412   -17.121   -8.994  -19.191   56.05        C
ATOM   6019  HG12 ILE   412   -17.487   -9.928  -18.851    0.00        H
ATOM   6020  HG13 ILE   412   -17.925   -8.413  -19.560    0.00        H
ATOM   6021  CD1  ILE   412   -16.179   -9.265  -20.352   54.75        C
ATOM   6022  HD11 ILE   412   -15.809   -8.347  -20.728    0.00        H
ATOM   6023  HD12 ILE   412   -15.370   -9.862  -20.018    0.00        H
ATOM   6024  HD13 ILE   412   -16.702   -9.775  -21.119    0.00        H
ATOM   6025  C    ILE   412   -16.645   -7.638  -15.629   56.10        C
ATOM   6026  O    ILE   412   -16.544   -8.335  -14.614   55.34        O
ATOM   6027  N    ILE   413   -16.089   -6.437  -15.741   56.54        N
ATOM   6028  HN   ILE   413   -16.213   -5.926  -16.602    0.00        H
ATOM   6029  CA   ILE   413   -15.316   -5.857  -14.658   56.44        C
ATOM   6030  HA   ILE   413   -14.403   -6.383  -14.555    0.00        H
ATOM   6031  CB   ILE   413   -14.999   -4.378  -14.926   56.67        C
ATOM   6032  HB   ILE   413   -15.903   -3.835  -15.020    0.00        H
ATOM   6033  CG2  ILE   413   -14.187   -3.808  -13.771   56.48        C
ATOM   6034  HG21 ILE   413   -14.744   -3.890  -12.874    0.00        H
ATOM   6035  HG22 ILE   413   -13.282   -4.349  -13.675    0.00        H
ATOM   6036  HG23 ILE   413   -13.971   -2.789  -13.960    0.00        H
ATOM   6037  CG1  ILE   413   -14.229   -4.242  -16.243   57.44        C
ATOM   6038  HG12 ILE   413   -13.309   -4.761  -16.169    0.00        H
ATOM   6039  HG13 ILE   413   -14.804   -4.653  -17.032    0.00        H
ATOM   6040  CD1  ILE   413   -13.909   -2.810  -16.618   56.20        C
ATOM   6041  HD11 ILE   413   -14.810   -2.263  -16.722    0.00        H
ATOM   6042  HD12 ILE   413   -13.315   -2.371  -15.859    0.00        H
ATOM   6043  HD13 ILE   413   -13.379   -2.795  -17.535    0.00        H
ATOM   6044  C    ILE   413   -16.073   -5.949  -13.343   56.43        C
ATOM   6045  O    ILE   413   -15.525   -6.389  -12.338   57.02        O
ATOM   6046  N    MET   414   -17.340   -5.548  -13.362   55.71        N
ATOM   6047  HN   MET   414   -17.730   -5.229  -14.236    0.00        H
ATOM   6048  CA   MET   414   -18.164   -5.562  -12.156   55.50        C
ATOM   6049  HA   MET   414   -17.582   -5.253  -11.327    0.00        H
ATOM   6050  CB   MET   414   -19.355   -4.603  -12.325   55.92        C
ATOM   6051  HB2  MET   414   -19.915   -4.882  -13.180    0.00        H
ATOM   6052  HB3  MET   414   -19.973   -4.653  -11.467    0.00        H
ATOM   6053  CG   MET   414   -18.969   -3.122  -12.510   56.41        C
ATOM   6054  HG2  MET   414   -18.418   -3.010  -13.408    0.00        H
ATOM   6055  HG3  MET   414   -19.847   -2.532  -12.559    0.00        H
ATOM   6056  SD   MET   414   -17.937   -2.429  -11.164   56.10        S
ATOM   6057  CE   MET   414   -19.152   -2.328   -9.810   52.43        C
ATOM   6058  HE1  MET   414   -19.950   -1.695  -10.099    0.00        H
ATOM   6059  HE2  MET   414   -19.527   -3.296   -9.599    0.00        H
ATOM   6060  HE3  MET   414   -18.685   -1.934   -8.945    0.00        H
ATOM   6061  C    MET   414   -18.679   -6.931  -11.704   55.03        C
ATOM   6062  O    MET   414   -18.881   -7.152  -10.512   54.02        O
ATOM   6063  N    TYR   415   -18.892   -7.852  -12.639   55.20        N
ATOM   6064  HN   TYR   415   -18.698   -7.631  -13.604    0.00        H
ATOM   6065  CA   TYR   415   -19.403   -9.177  -12.280   55.03        C
ATOM   6066  HA   TYR   415   -19.536   -9.232  -11.231    0.00        H
ATOM   6067  CB   TYR   415   -20.744   -9.424  -12.971   52.56        C
ATOM   6068  HB2  TYR   415   -20.650   -9.222  -14.006    0.00        H
ATOM   6069  HB3  TYR   415   -21.032  -10.434  -12.833    0.00        H
ATOM   6070  CG   TYR   415   -21.865   -8.556  -12.439   50.60        C
ATOM   6071  CD1  TYR   415   -22.502   -8.859  -11.235   50.04        C
ATOM   6072  HD1  TYR   415   -22.194   -9.719  -10.664    0.00        H
ATOM   6073  CE1  TYR   415   -23.544   -8.061  -10.748   48.86        C
ATOM   6074  HE1  TYR   415   -24.023   -8.310   -9.816    0.00        H
ATOM   6075  CD2  TYR   415   -22.292   -7.433  -13.143   50.20        C
ATOM   6076  HD2  TYR   415   -21.819   -7.169  -14.074    0.00        H
ATOM   6077  CE2  TYR   415   -23.329   -6.631  -12.668   49.24        C
ATOM   6078  HE2  TYR   415   -23.642   -5.767  -13.230    0.00        H
ATOM   6079  CZ   TYR   415   -23.952   -6.950  -11.475   48.82        C
ATOM   6080  OH   TYR   415   -25.001   -6.174  -11.036   48.10        O
```

FIGURE 6-81-

```
ATOM   6081  HH   TYR 415     -25.345  -6.536 -10.208   0.00    H
ATOM   6082  C    TYR 415     -18.448 -10.317 -12.601  55.84    C
ATOM   6083  O    TYR 415     -18.854 -11.480 -12.648  55.75    O
ATOM   6084  N    ALA 416     -17.179  -9.966 -12.797  56.91    N
ATOM   6085  HN   ALA 416     -16.971  -8.982 -12.711   0.00    H
ATOM   6086  CA   ALA 416     -16.113 -10.913 -13.120  57.29    C
ATOM   6087  HA   ALA 416     -16.139 -11.133 -14.155   0.00    H
ATOM   6088  CB   ALA 416     -14.766 -10.299 -12.764  57.66    C
ATOM   6089  HB1  ALA 416     -14.627  -9.407 -13.318   0.00    H
ATOM   6090  HB2  ALA 416     -14.741 -10.078 -11.729   0.00    H
ATOM   6091  HB3  ALA 416     -13.993 -10.984 -12.998   0.00    H
ATOM   6092  C    ALA 416     -16.246 -12.287 -12.458  58.01    C
ATOM   6093  O    ALA 416     -15.929 -13.311 -13.067  57.96    O
ATOM   6094  N    PRO 417     -16.699 -12.328 -11.195  58.65    N
ATOM   6095  CD   PRO 417     -16.762 -11.207 -10.246  58.48    C
ATOM   6096  HD2  PRO 417     -16.107 -10.438 -10.564   0.00    H
ATOM   6097  HD3  PRO 417     -17.752 -10.834 -10.206   0.00    H
ATOM   6098  CA   PRO 417     -16.861 -13.605 -10.483  59.41    C
ATOM   6099  HA   PRO 417     -15.994 -14.198 -10.620   0.00    H
ATOM   6100  CB   PRO 417     -17.033 -13.171  -9.026  59.87    C
ATOM   6101  HB2  PRO 417     -18.065 -13.081  -8.804   0.00    H
ATOM   6102  HB3  PRO 417     -16.596 -13.895  -8.388   0.00    H
ATOM   6103  CG   PRO 417     -16.326 -11.868  -8.974  59.80    C
ATOM   6104  HG2  PRO 417     -16.630 -11.336  -8.110   0.00    H
ATOM   6105  HG3  PRO 417     -15.281 -12.035  -8.936   0.00    H
ATOM   6106  C    PRO 417     -18.052 -14.451 -10.944  59.08    C
ATOM   6107  O    PRO 417     -18.083 -15.660 -10.716  58.54    O
ATOM   6108  N    THR 418     -19.032 -13.821 -11.583  58.59    N
ATOM   6109  HN   THR 418     -18.953 -12.832 -11.768   0.00    H
ATOM   6110  CA   THR 418     -20.216 -14.551 -12.016  58.58    C
ATOM   6111  HA   THR 418     -20.580 -15.140 -11.215   0.00    H
ATOM   6112  CB   THR 418     -21.343 -13.615 -12.468  58.29    C
ATOM   6113  HB   THR 418     -22.262 -14.141 -12.462   0.00    H
ATOM   6114  OG1  THR 418     -21.080 -13.175 -13.804  58.02    O
ATOM   6115  HG1  THR 418     -21.788 -12.584 -14.094   0.00    H
ATOM   6116  CG2  THR 418     -21.458 -12.413 -11.535  59.42    C
ATOM   6117  HG21 THR 418     -21.667 -12.748 -10.552   0.00    H
ATOM   6118  HG22 THR 418     -20.546 -11.875 -11.539   0.00    H
ATOM   6119  HG23 THR 418     -22.241 -11.782 -11.867   0.00    H
ATOM   6120  C    THR 418     -19.969 -15.531 -13.149  58.38    C
ATOM   6121  O    THR 418     -19.133 -15.305 -14.027  57.95    O
ATOM   6122  N    LEU 419     -20.728 -16.623 -13.105  57.99    N
ATOM   6123  HN   LEU 419     -21.367 -16.687 -12.327   0.00    H
ATOM   6124  CA   LEU 419     -20.677 -17.690 -14.095  56.46    C
ATOM   6125  HA   LEU 419     -19.771 -18.228 -13.988   0.00    H
ATOM   6126  CB   LEU 419     -21.859 -18.635 -13.884  57.18    C
ATOM   6127  HB2  LEU 419     -21.891 -18.939 -12.870   0.00    H
ATOM   6128  HB3  LEU 419     -22.759 -18.135 -14.132   0.00    H
ATOM   6129  CG   LEU 419     -21.889 -19.931 -14.689  57.91    C
ATOM   6130  HG   LEU 419     -21.641 -19.726 -15.698   0.00    H
ATOM   6131  CD1  LEU 419     -20.873 -20.907 -14.095  58.86    C
ATOM   6132  HD11 LEU 419     -19.905 -20.480 -14.140   0.00    H
ATOM   6133  HD12 LEU 419     -21.124 -21.107 -13.086   0.00    H
ATOM   6134  HD13 LEU 419     -20.887 -21.810 -14.648   0.00    H
ATOM   6135  CD2  LEU 419     -23.285 -20.526 -14.639  57.17    C
ATOM   6136  HD21 LEU 419     -23.546 -20.729 -13.633   0.00    H
ATOM   6137  HD22 LEU 419     -23.977 -19.838 -15.051   0.00    H
ATOM   6138  HD23 LEU 419     -23.306 -21.425 -15.198   0.00    H
ATOM   6139  C    LEU 419     -20.759 -17.094 -15.499  55.65    C
ATOM   6140  O    LEU 419     -19.809 -17.180 -16.277  56.46    O
ATOM   6141  N    TRP 420     -21.900 -16.484 -15.808  53.54    N
ATOM   6142  HN   TRP 420     -22.624 -16.448 -15.106   0.00    H
ATOM   6143  CA   TRP 420     -22.121 -15.878 -17.114  52.71    C
ATOM   6144  HA   TRP 420     -22.151 -16.635 -17.854   0.00    H
ATOM   6145  CB   TRP 420     -23.450 -15.104 -17.147  50.60    C
ATOM   6146  HB2  TRP 420     -23.427 -14.397 -17.935   0.00    H
ATOM   6147  HB3  TRP 420     -24.249 -15.781 -17.303   0.00    H
ATOM   6148  CG   TRP 420     -23.768 -14.346 -15.900  46.84    C
ATOM   6149  CD2  TRP 420     -23.717 -12.929 -15.722  44.98    C
ATOM   6150  CE2  TRP 420     -24.092 -12.664 -14.388  44.82    C
ATOM   6151  CE3  TRP 420     -23.390 -11.856 -16.559  43.60    C
ATOM   6152  HE3  TRP 420     -23.102 -12.038 -17.581   0.00    H
ATOM   6153  CD1  TRP 420     -24.160 -14.868 -14.702  46.11    C
ATOM   6154  HD1  TRP 420     -24.271 -15.933 -14.589   0.00    H
ATOM   6155  NE1  TRP 420     -24.357 -13.866 -13.788  44.70    N
ATOM   6156  HE1  TRP 420     -24.651 -14.090 -12.849   0.00    H
```

FIGURE 6- 82 -

| | | | | | | | |
|---|---|---|---|---|---|---|---|
| ATOM | 6157 | CZ2 | TRP | 420 | -24.149 -11.365 -13.869 | 44.91 | C |
| ATOM | 6158 | HZ2 | TRP | 420 | -24.441 -11.207 -12.845 | 0.00 | H |
| ATOM | 6159 | CZ3 | TRP | 420 | -23.446 -10.565 -16.043 | 42.93 | C |
| ATOM | 6160 | HZ3 | TRP | 420 | -23.199  -9.724 -16.668 | 0.00 | H |
| ATOM | 6161 | CH2 | TRP | 420 | -23.822 -10.333 -14.711 | 43.75 | C |
| ATOM | 6162 | HH2 | TRP | 420 | -23.850  -9.317 -14.354 | 0.00 | H |
| ATOM | 6163 | C | TRP | 420 | -21.001 -14.961 -17.579 | 53.47 | C |
| ATOM | 6164 | O | TRP | 420 | -20.485 -15.119 -18.687 | 54.31 | O |
| ATOM | 6165 | N | ALA | 421 | -20.628 -14.002 -16.740 | 53.92 | N |
| ATOM | 6166 | HN | ALA | 421 | -21.089 -13.932 -15.845 | 0.00 | H |
| ATOM | 6167 | CA | ALA | 421 | -19.574 -13.061 -17.092 | 53.80 | C |
| ATOM | 6168 | HA | ALA | 421 | -19.886 -12.473 -17.916 | 0.00 | H |
| ATOM | 6169 | CB | ALA | 421 | -19.273 -12.151 -15.919 | 53.88 | C |
| ATOM | 6170 | HB1 | ALA | 421 | -20.146 -11.612 -15.657 | 0.00 | H |
| ATOM | 6171 | HB2 | ALA | 421 | -18.957 -12.733 -15.093 | 0.00 | H |
| ATOM | 6172 | HB3 | ALA | 421 | -18.506 -11.472 -16.187 | 0.00 | H |
| ATOM | 6173 | C | ALA | 421 | -18.307 -13.785 -17.519 | 54.77 | C |
| ATOM | 6174 | O | ALA | 421 | -17.627 -13.354 -18.453 | 55.06 | O |
| ATOM | 6175 | N | ARG | 422 | -18.003 -14.892 -16.841 | 54.99 | N |
| ATOM | 6176 | HN | ARG | 422 | -18.630 -15.184 -16.106 | 0.00 | H |
| ATOM | 6177 | CA | ARG | 422 | -16.804 -15.676 -17.134 | 55.58 | C |
| ATOM | 6178 | HA | ARG | 422 | -15.991 -15.023 -17.317 | 0.00 | H |
| ATOM | 6179 | CB | ARG | 422 | -16.460 -16.582 -15.950 | 54.06 | C |
| ATOM | 6180 | HB2 | ARG | 422 | -17.206 -17.327 -15.847 | 0.00 | H |
| ATOM | 6181 | HB3 | ARG | 422 | -15.522 -17.043 -16.119 | 0.00 | H |
| ATOM | 6182 | CG | ARG | 422 | -16.359 -15.892 -14.602 | 53.26 | C |
| ATOM | 6183 | HG2 | ARG | 422 | -15.618 -15.137 -14.647 | 0.00 | H |
| ATOM | 6184 | HG3 | ARG | 422 | -17.293 -15.457 -14.357 | 0.00 | H |
| ATOM | 6185 | CD | ARG | 422 | -15.979 -16.899 -13.517 | 51.34 | C |
| ATOM | 6186 | HD2 | ARG | 422 | -16.021 -16.429 -12.569 | 0.00 | H |
| ATOM | 6187 | HD3 | ARG | 422 | -16.656 -17.713 -13.538 | 0.00 | H |
| ATOM | 6188 | NE | ARG | 422 | -14.628 -17.409 -13.727 | 50.48 | N1+ |
| ATOM | 6189 | HE | ARG | 422 | -14.036 -16.995 -14.432 | 0.00 | H |
| ATOM | 6190 | CZ | ARG | 422 | -14.084 -18.411 -13.046 | 49.83 | C |
| ATOM | 6191 | NH1 | ARG | 422 | -14.779 -19.025 -12.099 | 48.20 | N |
| ATOM | 6192 | HH11 | ARG | 422 | -14.365 -19.786 -11.582 | 0.00 | H |
| ATOM | 6193 | HH12 | ARG | 422 | -15.722 -18.731 -11.895 | 0.00 | H |
| ATOM | 6194 | NH2 | ARG | 422 | -12.838 -18.795 -13.313 | 49.74 | N |
| ATOM | 6195 | HH21 | ARG | 422 | -12.423 -19.556 -12.797 | 0.00 | H |
| ATOM | 6196 | HH22 | ARG | 422 | -12.308 -18.325 -14.032 | 0.00 | H |
| ATOM | 6197 | C | ARG | 422 | -16.929 -16.543 -18.392 | 56.87 | C |
| ATOM | 6198 | O | ARG | 422 | -16.231 -16.328 -19.390 | 56.58 | O |
| ATOM | 6199 | N | MET | 423 | -17.823 -17.525 -18.328 | 57.78 | N |
| ATOM | 6200 | HN | MET | 423 | -18.358 -17.615 -17.477 | 0.00 | H |
| ATOM | 6201 | CA | MET | 423 | -18.044 -18.452 -19.428 | 58.71 | C |
| ATOM | 6202 | HA | MET | 423 | -17.122 -18.888 -19.713 | 0.00 | H |
| ATOM | 6203 | CB | MET | 423 | -19.010 -19.556 -18.996 | 59.28 | C |
| ATOM | 6204 | HB2 | MET | 423 | -19.892 -19.120 -18.605 | 0.00 | H |
| ATOM | 6205 | HB3 | MET | 423 | -19.255 -20.158 -19.832 | 0.00 | H |
| ATOM | 6206 | CG | MET | 423 | -18.470 -20.484 -17.931 | 59.44 | C |
| ATOM | 6207 | HG2 | MET | 423 | -17.572 -20.928 -18.273 | 0.00 | H |
| ATOM | 6208 | HG3 | MET | 423 | -18.278 -19.933 -17.047 | 0.00 | H |
| ATOM | 6209 | SD | MET | 423 | -19.643 -21.801 -17.537 | 61.94 | S |
| ATOM | 6210 | CE | MET | 423 | -19.084 -23.146 -18.655 | 59.81 | C |
| ATOM | 6211 | HE1 | MET | 423 | -19.147 -22.819 -19.660 | 0.00 | H |
| ATOM | 6212 | HE2 | MET | 423 | -18.081 -23.399 -18.428 | 0.00 | H |
| ATOM | 6213 | HE3 | MET | 423 | -19.702 -23.996 -18.521 | 0.00 | H |
| ATOM | 6214 | C | MET | 423 | -18.558 -17.836 -20.722 | 59.21 | C |
| ATOM | 6215 | O | MET | 423 | -18.086 -18.179 -21.804 | 60.06 | O |
| ATOM | 6216 | N | ILE | 424 | -19.386 -16.696 -20.593 | 58.89 | N |
| ATOM | 6217 | HN | ILE | 424 | -19.489 -16.230 -19.685 | 0.00 | H |
| ATOM | 6218 | CA | ILE | 424 | -20.109 -16.162 -21.772 | 59.05 | C |
| ATOM | 6219 | HA | ILE | 424 | -19.993 -16.884 -22.574 | 0.00 | H |
| ATOM | 6220 | CB | ILE | 424 | -21.629 -16.010 -21.493 | 59.75 | C |
| ATOM | 6221 | HB | ILE | 424 | -21.771 -15.156 -20.825 | 0.00 | H |
| ATOM | 6222 | CG2 | ILE | 424 | -22.404 -15.692 -22.781 | 58.18 | C |
| ATOM | 6223 | HG21 | ILE | 424 | -22.122 -14.717 -23.188 | 0.00 | H |
| ATOM | 6224 | HG22 | ILE | 424 | -22.219 -16.448 -23.549 | 0.00 | H |
| ATOM | 6225 | HG23 | ILE | 424 | -23.482 -15.644 -22.613 | 0.00 | H |
| ATOM | 6226 | CG1 | ILE | 424 | -22.234 -17.257 -20.820 | 59.19 | C |
| ATOM | 6227 | HG12 | ILE | 424 | -22.355 -18.067 -21.547 | 0.00 | H |
| ATOM | 6228 | HG13 | ILE | 424 | -21.574 -17.641 -20.038 | 0.00 | H |
| ATOM | 6229 | CD1 | ILE | 424 | -23.570 -16.941 -20.163 | 60.36 | C |
| ATOM | 6230 | HD11 | ILE | 424 | -23.481 -16.073 -19.516 | 0.00 | H |
| ATOM | 6231 | HD12 | ILE | 424 | -24.340 -16.680 -20.883 | 0.00 | H |
| ATOM | 6232 | HD13 | ILE | 424 | -23.920 -17.787 -19.568 | 0.00 | H |

FIGURE 6- 83 -

```
ATOM   6233  C    ILE   424   -19.608 -14.818 -22.367   59.14   C
ATOM   6234  O    ILE   424   -19.581 -14.654 -23.589   58.46   O
ATOM   6235  N    LEU   425   -19.427 -13.784 -21.488   59.84   N
ATOM   6236  HN   LEU   425   -19.316 -14.039 -20.503    0.00   H
ATOM   6237  CA   LEU   425   -19.024 -12.455 -21.932   60.45   C
ATOM   6238  HA   LEU   425   -19.473 -12.275 -22.891    0.00   H
ATOM   6239  CB   LEU   425   -19.375 -11.355 -20.952   59.95   C
ATOM   6240  HB2  LEU   425   -19.034 -11.634 -19.954    0.00   H
ATOM   6241  HB3  LEU   425   -18.829 -10.447 -21.217    0.00   H
ATOM   6242  CG   LEU   425   -20.859 -11.003 -20.910   59.95   C
ATOM   6243  HG   LEU   425   -21.413 -11.899 -20.624    0.00   H
ATOM   6244  CD1  LEU   425   -21.110  -9.932 -19.849   59.10   C
ATOM   6245  HD11 LEU   425   -20.749 -10.258 -18.868    0.00   H
ATOM   6246  HD12 LEU   425   -20.603  -8.995 -20.101    0.00   H
ATOM   6247  HD13 LEU   425   -22.179  -9.717 -19.752    0.00   H
ATOM   6248  CD2  LEU   425   -21.342 -10.521 -22.280   59.06   C
ATOM   6249  HD21 LEU   425   -20.621  -9.837 -22.733    0.00   H
ATOM   6250  HD22 LEU   425   -21.475 -11.365 -22.963    0.00   H
ATOM   6251  HD23 LEU   425   -22.298  -9.996 -22.217    0.00   H
ATOM   6252  C    LEU   425   -17.540 -12.371 -22.198   61.19   C
ATOM   6253  O    LEU   425   -17.100 -11.578 -23.021   61.23   O
ATOM   6254  N    MET   426   -16.726 -13.171 -21.420   62.15   N
ATOM   6255  HN   MET   426   -17.080 -13.556 -20.557    0.00   H
ATOM   6256  CA   MET   426   -15.294 -13.186 -21.691   63.41   C
ATOM   6257  HA   MET   426   -14.954 -12.196 -21.849    0.00   H
ATOM   6258  CB   MET   426   -14.530 -13.787 -20.517   62.81   C
ATOM   6259  HB2  MET   426   -14.771 -14.814 -20.428    0.00   H
ATOM   6260  HB3  MET   426   -13.489 -13.681 -20.682    0.00   H
ATOM   6261  CG   MET   426   -14.854 -13.126 -19.202   62.93   C
ATOM   6262  HG2  MET   426   -14.827 -12.074 -19.320    0.00   H
ATOM   6263  HG3  MET   426   -15.821 -13.421 -18.888    0.00   H
ATOM   6264  SD   MET   426   -13.693 -13.574 -17.926   63.00   S
ATOM   6265  CE   MET   426   -13.706 -12.100 -16.912   63.19   C
ATOM   6266  HE1  MET   426   -13.395 -11.270 -17.492    0.00   H
ATOM   6267  HE2  MET   426   -14.686 -11.930 -16.549    0.00   H
ATOM   6268  HE3  MET   426   -13.044 -12.228 -16.095    0.00   H
ATOM   6269  C    MET   426   -15.032 -13.999 -22.951   64.59   C
ATOM   6270  O    MET   426   -14.516 -13.484 -23.944   65.44   O
ATOM   6271  N    THR   427   -15.400 -15.272 -22.909   65.21   N
ATOM   6272  HN   THR   427   -15.819 -15.634 -22.065    0.00   H
ATOM   6273  CA   THR   427   -15.208 -16.142 -24.055   65.69   C
ATOM   6274  HA   THR   427   -14.186 -16.408 -24.129    0.00   H
ATOM   6275  CB   THR   427   -16.041 -17.419 -23.916   64.79   C
ATOM   6276  HB   THR   427   -17.071 -17.172 -23.928    0.00   H
ATOM   6277  OG1  THR   427   -15.718 -18.064 -22.679   64.39   O
ATOM   6278  HG1  THR   427   -16.243 -18.871 -22.589    0.00   H
ATOM   6279  CG2  THR   427   -15.745 -18.370 -25.066   65.10   C
ATOM   6280  HG21 THR   427   -15.984 -17.899 -25.984    0.00   H
ATOM   6281  HG22 THR   427   -14.717 -18.625 -25.058    0.00   H
ATOM   6282  HG23 THR   427   -16.327 -19.248 -24.957    0.00   H
ATOM   6283  C    THR   427   -15.599 -15.450 -25.358   66.93   C
ATOM   6284  O    THR   427   -14.790 -15.343 -26.278   66.78   O
ATOM   6285  N    HID   428   -16.901 -14.998 -25.533   68.01   N
ATOM   6286  HN   HID   428   -17.487 -14.892 -24.704    0.00   H
ATOM   6287  CA   HID   428   -17.397 -14.502 -26.831   70.25   C
ATOM   6288  HA   HID   428   -17.052 -15.219 -27.581    0.00   H
ATOM   6289  CB   HID   428   -18.925 -14.468 -26.838   71.72   C
ATOM   6290  HB2  HID   428   -19.335 -15.412 -26.478    0.00   H
ATOM   6291  HB3  HID   428   -19.284 -13.689 -26.158    0.00   H
ATOM   6292  CG   HID   428   -19.528 -14.200 -28.168   73.09   C
ATOM   6293  CD2  HID   428   -20.547 -13.302 -28.513   73.35   C
ATOM   6294  HD2  HID   428   -21.093 -12.608 -27.900    0.00   H
ATOM   6295  ND1  HID   428   -19.125 -14.825 -29.366   73.29   N1+
ATOM   6296  HD1  HID   428   -18.370 -15.501 -29.481    0.00   H
ATOM   6297  CE1  HID   428   -19.868 -14.321 -30.360   73.27   C
ATOM   6298  HE1  HID   428   -19.829 -14.565 -31.413    0.00   H
ATOM   6299  NE2  HID   428   -20.746 -13.406 -29.869   73.74   N
ATOM   6300  C    HID   428   -16.917 -13.126 -27.343   71.06   C
ATOM   6301  O    HID   428   -17.032 -12.843 -28.538   71.05   O
ATOM   6302  N    PHE   429   -16.582 -12.207 -26.381   72.30   N
ATOM   6303  HN   PHE   429   -16.418 -12.549 -25.433    0.00   H
ATOM   6304  CA   PHE   429   -16.072 -10.910 -26.754   73.46   C
ATOM   6305  HA   PHE   429   -16.345 -10.736 -27.795    0.00   H
ATOM   6306  CB   PHE   429   -16.662  -9.760 -25.951   73.24   C
ATOM   6307  HB2  PHE   429   -16.518  -9.924 -24.884    0.00   H
ATOM   6308  HB3  PHE   429   -16.111  -8.850 -26.181    0.00   H
```

FIGURE 6-84-

```
ATOM    6309  CG  PHE   429     -18.131   -9.526 -26.253  72.71      C
ATOM    6310  CD1 PHE   429     -18.531   -8.559 -27.194  71.34      C
ATOM    6311  HD1 PHE   429     -17.790   -7.959 -27.703   0.00      H
ATOM    6312  CD2 PHE   429     -19.123  -10.276 -25.590  72.72      C
ATOM    6313  HD2 PHE   429     -18.829  -11.032 -24.883   0.00      H
ATOM    6314  CE1 PHE   429     -19.890   -8.322 -27.435  71.11      C
ATOM    6315  HE1 PHE   429     -20.194   -7.532 -28.112   0.00      H
ATOM    6316  CE2 PHE   429     -20.480  -10.056 -25.848  72.50      C
ATOM    6317  HE2 PHE   429     -21.230  -10.624 -25.331   0.00      H
ATOM    6318  CZ  PHE   429     -20.859   -9.080 -26.773  71.91      C
ATOM    6319  HZ  PHE   429     -21.903   -8.877 -26.951   0.00      H
ATOM    6320  C   PHE   429     -14.540  -10.873 -26.788  74.33      C
ATOM    6321  O   PHE   429     -14.006   -9.933 -27.371  74.17      O
ATOM    6322  N   PHE   430     -13.810  -11.882 -26.142  75.25      N
ATOM    6323  HN  PHE   430     -14.320  -12.434 -25.469   0.00      H
ATOM    6324  CA  PHE   430     -12.384  -12.104 -26.336  77.04      C
ATOM    6325  HA  PHE   430     -11.875  -11.176 -26.304   0.00      H
ATOM    6326  CB  PHE   430     -11.804  -13.013 -25.248  78.01      C
ATOM    6327  HB2 PHE   430     -12.586  -13.564 -24.794   0.00      H
ATOM    6328  HB3 PHE   430     -11.107  -13.682 -25.682   0.00      H
ATOM    6329  CG  PHE   430     -11.086  -12.266 -24.151  78.63      C
ATOM    6330  CD1 PHE   430     -11.796  -11.612 -23.146  78.99      C
ATOM    6331  HD1 PHE   430     -12.873  -11.642 -23.140   0.00      H
ATOM    6332  CD2 PHE   430      -9.696  -12.207 -24.132  78.46      C
ATOM    6333  HD2 PHE   430      -9.125  -12.704 -24.898   0.00      H
ATOM    6334  CE1 PHE   430     -11.129  -10.911 -22.136  78.96      C
ATOM    6335  HE1 PHE   430     -11.692  -10.411 -21.365   0.00      H
ATOM    6336  CE2 PHE   430      -9.019  -11.509 -23.129  78.62      C
ATOM    6337  HE2 PHE   430      -7.943  -11.473 -23.130   0.00      H
ATOM    6338  CZ  PHE   430      -9.737  -10.860 -22.128  78.91      C
ATOM    6339  HZ  PHE   430      -9.222  -10.321 -21.351   0.00      H
ATOM    6340  C   PHE   430     -12.166  -12.729 -27.715  77.50      C
ATOM    6341  O   PHE   430     -11.103  -12.581 -28.317  78.00      O
ATOM    6342  N   SER   431     -13.181  -13.429 -28.214  77.63      N
ATOM    6343  HN  SER   431     -14.021  -13.533 -27.665   0.00      H
ATOM    6344  CA  SER   431     -13.093  -14.040 -29.532  77.21      C
ATOM    6345  HA  SER   431     -12.214  -14.628 -29.590   0.00      H
ATOM    6346  CB  SER   431     -14.304  -14.938 -29.803  76.60      C
ATOM    6347  HB2 SER   431     -15.194  -14.391 -29.631   0.00      H
ATOM    6348  HB3 SER   431     -14.281  -15.268 -30.809   0.00      H
ATOM    6349  OG  SER   431     -14.296  -16.072 -28.953  76.92      O
ATOM    6350  HG  SER   431     -15.068  -16.622 -29.142   0.00      H
ATOM    6351  C   SER   431     -13.070  -12.900 -30.529  77.68      C
ATOM    6352  O   SER   431     -12.081  -12.696 -31.232  78.15      O
ATOM    6353  N   ILE   432     -14.191  -12.098 -30.502  78.34      N
ATOM    6354  HN  ILE   432     -14.804  -12.164 -29.691   0.00      H
ATOM    6355  CA  ILE   432     -14.351  -10.995 -31.440  78.96      C
ATOM    6356  HA  ILE   432     -14.106  -11.394 -32.420   0.00      H
ATOM    6357  CB  ILE   432     -15.837  -10.536 -31.491  78.65      C
ATOM    6358  HB  ILE   432     -16.152  -10.262 -30.477   0.00      H
ATOM    6359  CG2 ILE   432     -16.060   -9.314 -32.391  78.17      C
ATOM    6360  HG21 ILE  432     -15.585   -8.422 -31.978   0.00      H
ATOM    6361  HG22 ILE  432     -15.670   -9.487 -33.400   0.00      H
ATOM    6362  HG23 ILE  432     -17.118   -9.055 -32.478   0.00      H
ATOM    6363  CG1 ILE   432     -16.716  -11.716 -31.981  79.11      C
ATOM    6364  HG12 ILE  432     -16.408  -12.014 -32.990   0.00      H
ATOM    6365  HG13 ILE  432     -16.557  -12.592 -31.344   0.00      H
ATOM    6366  CD1 ILE   432     -18.211  -11.433 -31.994  79.44      C
ATOM    6367  HD11 ILE  432     -18.553  -11.056 -31.025   0.00      H
ATOM    6368  HD12 ILE  432     -18.480  -10.711 -32.768   0.00      H
ATOM    6369  HD13 ILE  432     -18.762  -12.351 -32.217   0.00      H
ATOM    6370  C   ILE   432     -13.294   -9.886 -31.168  79.71      C
ATOM    6371  O   ILE   432     -13.287   -8.822 -31.789  79.20      O
ATOM    6372  N   LEU   433     -12.343  -10.223 -30.229  80.77      N
ATOM    6373  HN  LEU   433     -12.548  -10.998 -29.617   0.00      H
ATOM    6374  CA  LEU   433     -11.198   -9.358 -29.954  81.81      C
ATOM    6375  HA  LEU   433     -11.471   -8.348 -30.119   0.00      H
ATOM    6376  CB  LEU   433     -10.723   -9.505 -28.500  81.61      C
ATOM    6377  HB2 LEU   433     -11.032  -10.444 -28.121   0.00      H
ATOM    6378  HB3 LEU   433      -9.667   -9.441 -28.466   0.00      H
ATOM    6379  CG  LEU   433     -11.236   -8.463 -27.499  81.77      C
ATOM    6380  HG  LEU   433     -12.288   -8.545 -27.412   0.00      H
ATOM    6381  CD1 LEU   433     -10.588   -8.714 -26.145  81.95      C
ATOM    6382  HD11 LEU  433     -10.839   -9.686 -25.808   0.00      H
ATOM    6383  HD12 LEU  433      -9.536   -8.633 -26.237   0.00      H
ATOM    6384  HD13 LEU  433     -10.938   -7.998 -25.448   0.00      H
```

FIGURE 6- 85 -

```
ATOM   6385  CD2  LEU  433   -10.902   -7.048  -27.986  81.01   C
ATOM   6386  HD21 LEU  433    -9.852   -6.947  -28.083   0.00   H
ATOM   6387  HD22 LEU  433   -11.361   -6.880  -28.925   0.00   H
ATOM   6388  HD23 LEU  433   -11.262   -6.340  -27.286   0.00   H
ATOM   6389  C    LEU  433   -10.051   -9.681  -30.902  82.16   C
ATOM   6390  O    LEU  433    -9.899   -9.026  -31.936  82.37   O
ATOM   6391  N    LEU  434    -9.252  -10.691  -30.554  82.40   N
ATOM   6392  HN   LEU  434    -9.440  -11.183  -29.693   0.00   H
ATOM   6393  CA   LEU  434    -8.123  -11.089  -31.392  82.45   C
ATOM   6394  HA   LEU  434    -7.382  -10.333  -31.368   0.00   H
ATOM   6395  CB   LEU  434    -7.498  -12.404  -30.897  81.58   C
ATOM   6396  HB2  LEU  434    -7.299  -13.034  -31.725   0.00   H
ATOM   6397  HB3  LEU  434    -6.594  -12.195  -30.387   0.00   H
ATOM   6398  CG   LEU  434    -8.252  -13.317  -29.927  80.64   C
ATOM   6399  HG   LEU  434    -9.214  -13.528  -30.316   0.00   H
ATOM   6400  CD1  LEU  434    -7.481  -14.623  -29.747  80.32   C
ATOM   6401  HD11 LEU  434    -7.385  -15.108  -30.683   0.00   H
ATOM   6402  HD12 LEU  434    -6.519  -14.414  -29.357   0.00   H
ATOM   6403  HD13 LEU  434    -8.005  -15.253  -29.076   0.00   H
ATOM   6404  CD2  LEU  434    -8.412  -12.617  -28.589  80.17   C
ATOM   6405  HD21 LEU  434    -7.456  -12.393  -28.191   0.00   H
ATOM   6406  HD22 LEU  434    -8.957  -11.719  -28.723   0.00   H
ATOM   6407  HD23 LEU  434    -8.934  -13.250  -27.920   0.00   H
ATOM   6408  C    LEU  434    -8.595  -11.246  -32.832  82.73   C
ATOM   6409  O    LEU  434    -7.811  -11.123  -33.774  82.60   O
ATOM   6410  N    ALA  435    -9.891  -11.499  -32.990  83.07   N
ATOM   6411  HN   ALA  435   -10.463  -11.581  -32.163   0.00   H
ATOM   6412  CA   ALA  435   -10.489  -11.657  -34.306  83.67   C
ATOM   6413  HA   ALA  435    -9.980  -12.420  -34.836   0.00   H
ATOM   6414  CB   ALA  435   -11.965  -12.038  -34.168  83.18   C
ATOM   6415  HB1  ALA  435   -12.046  -12.951  -33.637   0.00   H
ATOM   6416  HB2  ALA  435   -12.478  -11.276  -33.641   0.00   H
ATOM   6417  HB3  ALA  435   -12.392  -12.151  -35.131   0.00   H
ATOM   6418  C    ALA  435   -10.353  -10.351  -35.087  84.15   C
ATOM   6419  O    ALA  435   -10.781  -10.261  -36.236  84.01   O
ATOM   6420  N    GLN  436    -9.760   -9.341  -34.455  84.93   N
ATOM   6421  HN   GLN  436    -9.442   -9.502  -33.511   0.00   H
ATOM   6422  CA   GLN  436    -9.563   -8.034  -35.080  86.13   C
ATOM   6423  HA   GLN  436    -9.395   -8.161  -36.118   0.00   H
ATOM   6424  CB   GLN  436   -10.803   -7.159  -34.875  86.06   C
ATOM   6425  HB2  GLN  436   -10.809   -6.782  -33.886   0.00   H
ATOM   6426  HB3  GLN  436   -10.783   -6.352  -35.560   0.00   H
ATOM   6427  CG   GLN  436   -12.119   -7.893  -35.084  87.44   C
ATOM   6428  HG2  GLN  436   -12.103   -8.387  -36.020   0.00   H
ATOM   6429  HG3  GLN  436   -12.253   -8.605  -34.311   0.00   H
ATOM   6430  CD   GLN  436   -13.319   -6.968  -35.072  88.34   C
ATOM   6431  OE1  GLN  436   -13.368   -6.011  -34.296  88.86   O
ATOM   6432  NE2  GLN  436   -14.305   -7.256  -35.926  88.89   N
ATOM   6433  HE21 GLN  436   -14.221   -8.052  -36.543   0.00   H
ATOM   6434  HE22 GLN  436   -15.134   -6.683  -35.954   0.00   H
ATOM   6435  C    GLN  436    -8.341   -7.344  -34.469  86.81   C
ATOM   6436  O    GLN  436    -8.031   -6.196  -34.791  86.38   O
ATOM   6437  N    GLU  437    -7.665   -8.063  -33.579  88.42   N
ATOM   6438  HN   GLU  437    -8.018   -8.988  -33.386   0.00   H
ATOM   6439  CA   GLU  437    -6.468   -7.579  -32.891  90.23   C
ATOM   6440  HA   GLU  437    -6.085   -8.345  -32.268   0.00   H
ATOM   6441  CB   GLU  437    -5.399   -7.181  -33.924  90.76   C
ATOM   6442  HB2  GLU  437    -5.291   -7.957  -34.637   0.00   H
ATOM   6443  HB3  GLU  437    -5.696   -6.291  -34.414   0.00   H
ATOM   6444  CG   GLU  437    -4.013   -6.923  -33.330  91.27   C
ATOM   6445  HG2  GLU  437    -3.310   -6.806  -34.113   0.00   H
ATOM   6446  HG3  GLU  437    -4.039   -6.041  -32.744   0.00   H
ATOM   6447  CD   GLU  437    -3.543   -8.070  -32.439  91.82   C
ATOM   6448  OE1  GLU  437    -3.438   -9.213  -32.940  91.66   O1-
ATOM   6449  OE2  GLU  437    -3.286   -7.829  -31.236  92.11   O
ATOM   6450  C    GLU  437    -6.733   -6.411  -31.926  91.14   C
ATOM   6451  O    GLU  437    -5.821   -5.647  -31.595  91.19   O
ATOM   6452  N    GLN  438    -7.975   -6.285  -31.460  92.03   N
ATOM   6453  HN   GLN  438    -8.665   -6.962  -31.749   0.00   H
ATOM   6454  CA   GLN  438    -8.350   -5.199  -30.551  92.20   C
ATOM   6455  HA   GLN  438    -7.807   -4.325  -30.802   0.00   H
ATOM   6456  CB   GLN  438    -9.846   -4.914  -30.670  92.42   C
ATOM   6457  HB2  GLN  438   -10.393   -5.780  -30.401   0.00   H
ATOM   6458  HB3  GLN  438   -10.106   -4.117  -30.023   0.00   H
ATOM   6459  CG   GLN  438   -10.269   -4.522  -32.073  93.31   C
ATOM   6460  HG2  GLN  438    -9.693   -3.695  -32.397   0.00   H
```

FIGURE 6-86 -

```
ATOM   6461  HG3  GLN  438   -10.115  -5.339 -32.729   0.00   H
ATOM   6462  CD   GLN  438   -11.733  -4.128 -32.161  93.66   C
ATOM   6463  OE1  GLN  438   -12.625  -4.912 -31.817  92.67   O
ATOM   6464  NE2  GLN  438   -11.988  -2.905 -32.627  93.99   N
ATOM   6465  HE21 GLN  438   -11.228  -2.299 -32.896   0.00   H
ATOM   6466  HE22 GLN  438   -12.941  -2.586 -32.711   0.00   H
ATOM   6467  C    GLN  438    -7.996  -5.422 -29.082  92.49   C
ATOM   6468  O    GLN  438    -8.536  -4.750 -28.200  92.71   O
ATOM   6469  N    LEU  439    -7.084  -6.355 -28.819  92.58   N
ATOM   6470  HN   LEU  439    -6.682  -6.865 -29.591   0.00   H
ATOM   6471  CA   LEU  439    -6.662  -6.649 -27.449  92.23   C
ATOM   6472  HA   LEU  439    -7.510  -6.895 -26.864   0.00   H
ATOM   6473  CB   LEU  439    -5.684  -7.831 -27.433  92.43   C
ATOM   6474  HB2  LEU  439    -4.854  -7.611 -28.052   0.00   H
ATOM   6475  HB3  LEU  439    -5.350  -8.000 -26.442   0.00   H
ATOM   6476  CG   LEU  439    -6.222  -9.180 -27.925  92.83   C
ATOM   6477  HG   LEU  439    -6.730  -9.043 -28.844   0.00   H
ATOM   6478  CD1  LEU  439    -5.067 -10.160 -28.130  92.84   C
ATOM   6479  HD11 LEU  439    -4.396  -9.769 -28.850   0.00   H
ATOM   6480  HD12 LEU  439    -4.557 -10.302 -27.213   0.00   H
ATOM   6481  HD13 LEU  439    -5.448 -11.088 -28.470   0.00   H
ATOM   6482  CD2  LEU  439    -7.235  -9.722 -26.919  92.22   C
ATOM   6483  HD21 LEU  439    -6.765  -9.851 -25.979   0.00   H
ATOM   6484  HD22 LEU  439    -8.037  -9.037 -26.821   0.00   H
ATOM   6485  HD23 LEU  439    -7.606 -10.654 -27.259   0.00   H
ATOM   6486  C    LEU  439    -5.986  -5.415 -26.876  91.93   C
ATOM   6487  O    LEU  439    -5.645  -5.357 -25.692  91.24   O
ATOM   6488  N    GLU  440    -5.809  -4.421 -27.737  92.26   N
ATOM   6489  HN   GLU  440    -6.138  -4.551 -28.682   0.00   H
ATOM   6490  CA   GLU  440    -5.164  -3.173 -27.357  92.85   C
ATOM   6491  HA   GLU  440    -4.570  -3.331 -26.495   0.00   H
ATOM   6492  CB   GLU  440    -4.277  -2.688 -28.509  93.72   C
ATOM   6493  HB2  GLU  440    -4.882  -2.256 -29.263   0.00   H
ATOM   6494  HB3  GLU  440    -3.593  -1.964 -28.148   0.00   H
ATOM   6495  CG   GLU  440    -3.454  -3.796 -29.170  95.11   C
ATOM   6496  HG2  GLU  440    -4.069  -4.642 -29.334   0.00   H
ATOM   6497  HG3  GLU  440    -3.076  -3.450 -30.097   0.00   H
ATOM   6498  CD   GLU  440    -2.261  -4.248 -28.323  95.84   C
ATOM   6499  OE1  GLU  440    -1.293  -3.459 -28.175  95.34   O1-
ATOM   6500  OE2  GLU  440    -2.296  -5.391 -27.808  96.31   O
ATOM   6501  C    GLU  440    -6.189  -2.091 -27.011  92.60   C
ATOM   6502  O    GLU  440    -6.427  -1.787 -25.836  92.29   O
ATOM   6503  N    LYS  441    -6.790  -1.529 -28.056  92.13   N
ATOM   6504  HN   LYS  441    -6.528  -1.881 -28.964   0.00   H
ATOM   6505  CA   LYS  441    -7.778  -0.461 -27.945  92.33   C
ATOM   6506  HA   LYS  441    -7.299   0.476 -28.060   0.00   H
ATOM   6507  CB   LYS  441    -8.844  -0.623 -29.036  92.62   C
ATOM   6508  HB2  LYS  441    -8.380  -0.609 -29.988   0.00   H
ATOM   6509  HB3  LYS  441    -9.349  -1.544 -28.902   0.00   H
ATOM   6510  CG   LYS  441    -9.899   0.484 -29.024  93.71   C
ATOM   6511  HG2  LYS  441   -10.300   0.579 -28.048   0.00   H
ATOM   6512  HG3  LYS  441    -9.453   1.400 -29.313   0.00   H
ATOM   6513  CD   LYS  441   -11.067   0.211 -29.984  94.26   C
ATOM   6514  HD2  LYS  441   -11.435  -0.769 -29.823   0.00   H
ATOM   6515  HD3  LYS  441   -11.841   0.912 -29.807   0.00   H
ATOM   6516  CE   LYS  441   -10.669   0.321 -31.457  94.82   C
ATOM   6517  HE2  LYS  441   -10.327   1.303 -31.658   0.00   H
ATOM   6518  HE3  LYS  441    -9.896  -0.372 -31.667   0.00   H
ATOM   6519  NZ   LYS  441   -11.832   0.027 -32.360  93.96   N1+
ATOM   6520  HZ1  LYS  441   -12.164  -0.910 -32.186   0.00   H
ATOM   6521  HZ2  LYS  441   -12.574   0.686 -32.178   0.00   H
ATOM   6522  HZ3  LYS  441   -11.539   0.107 -33.322   0.00   H
ATOM   6523  C    LYS  441    -8.466  -0.310 -26.580  92.69   C
ATOM   6524  O    LYS  441    -9.360  -1.088 -26.228  93.03   O
ATOM   6525  N    ALA  442    -8.040   0.698 -25.816  92.16   N
ATOM   6526  HN   ALA  442    -7.285   1.267 -26.170   0.00   H
ATOM   6527  CA   ALA  442    -8.627   0.992 -24.508  90.52   C
ATOM   6528  HA   ALA  442    -8.697   0.099 -23.943   0.00   H
ATOM   6529  CB   ALA  442    -7.762   1.992 -23.750  90.17   C
ATOM   6530  HB1  ALA  442    -6.794   1.586 -23.610   0.00   H
ATOM   6531  HB2  ALA  442    -7.691   2.890 -24.306   0.00   H
ATOM   6532  HB3  ALA  442    -8.200   2.194 -22.807   0.00   H
ATOM   6533  C    ALA  442    -9.998   1.592 -24.804  89.48   C
ATOM   6534  O    ALA  442   -10.121   2.470 -25.657  89.23   O
ATOM   6535  N    LEU  443   -11.027   1.119 -24.107  88.22   N
ATOM   6536  HN   LEU  443   -10.861   0.419 -23.400   0.00   H
```

FIGURE 6- 87 -

```
ATOM   6537  CA   LEU  443   -12.384   1.600 -24.354   86.51   C
ATOM   6538  HA   LEU  443   -12.343   2.507 -24.899    0.00   H
ATOM   6539  CB   LEU  443   -13.139   0.546 -25.158   87.12   C
ATOM   6540  HB2  LEU  443   -13.165  -0.362 -24.613    0.00   H
ATOM   6541  HB3  LEU  443   -14.128   0.880 -25.336    0.00   H
ATOM   6542  CG   LEU  443   -12.458   0.291 -26.503   88.00   C
ATOM   6543  HG   LEU  443   -11.416   0.453 -26.407    0.00   H
ATOM   6544  CD1  LEU  443   -12.696  -1.148 -26.961   88.16   C
ATOM   6545  HD11 LEU  443   -12.299  -1.817 -26.243    0.00   H
ATOM   6546  HD12 LEU  443   -13.736  -1.318 -27.065    0.00   H
ATOM   6547  HD13 LEU  443   -12.218  -1.306 -27.893    0.00   H
ATOM   6548  CD2  LEU  443   -12.973   1.311 -27.518   88.39   C
ATOM   6549  HD21 LEU  443   -14.022   1.207 -27.622    0.00   H
ATOM   6550  HD22 LEU  443   -12.747   2.289 -27.181    0.00   H
ATOM   6551  HD23 LEU  443   -12.507   1.143 -28.454    0.00   H
ATOM   6552  C    LEU  443   -13.183   1.991 -23.115   84.73   C
ATOM   6553  O    LEU  443   -13.142   1.319 -22.085   84.70   O
ATOM   6554  N    ASP  444   -13.921   3.090 -23.253   82.70   N
ATOM   6555  HN   ASP  444   -13.883   3.526 -24.162    0.00   H
ATOM   6556  CA   ASP  444   -14.750   3.673 -22.195   80.10   C
ATOM   6557  HA   ASP  444   -14.145   3.897 -21.355    0.00   H
ATOM   6558  CB   ASP  444   -15.403   4.963 -22.721   80.28   C
ATOM   6559  HB2  ASP  444   -16.312   4.725 -23.209    0.00   H
ATOM   6560  HB3  ASP  444   -15.598   5.616 -21.910    0.00   H
ATOM   6561  CG   ASP  444   -14.517   5.706 -23.719   80.39   C
ATOM   6562  OD1  ASP  444   -13.522   6.345 -23.299   80.09   O
ATOM   6563  OD2  ASP  444   -14.814   5.633 -24.932   79.76   O1-
ATOM   6564  C    ASP  444   -15.843   2.758 -21.637   77.56   C
ATOM   6565  O    ASP  444   -16.463   1.987 -22.368   77.80   O
ATOM   6566  N    CYS  445   -16.073   2.856 -20.333   74.33   N
ATOM   6567  HN   CYS  445   -15.504   3.491 -19.794    0.00   H
ATOM   6568  CA   CYS  445   -17.114   2.076 -19.678   71.51   C
ATOM   6569  HA   CYS  445   -17.920   1.929 -20.349    0.00   H
ATOM   6570  CB   CYS  445   -16.601   0.677 -19.306   70.49   C
ATOM   6571  HB2  CYS  445   -17.419   0.061 -19.036    0.00   H
ATOM   6572  HB3  CYS  445   -16.099   0.253 -20.136    0.00   H
ATOM   6573  SG   CYS  445   -15.437   0.569 -17.928   67.13   S
ATOM   6574  HG   CYS  445   -15.114  -0.625 -17.748    0.00   H
ATOM   6575  C    CYS  445   -17.608   2.829 -18.441   70.43   C
ATOM   6576  O    CYS  445   -16.877   3.632 -17.855   70.20   O
ATOM   6577  N    GLN  446   -18.852   2.573 -18.056   68.63   N
ATOM   6578  HN   GLN  446   -19.385   1.895 -18.580    0.00   H
ATOM   6579  CA   GLN  446   -19.452   3.243 -16.910   67.70   C
ATOM   6580  HA   GLN  446   -18.978   4.178 -16.760    0.00   H
ATOM   6581  CB   GLN  446   -20.945   3.465 -17.169   67.78   C
ATOM   6582  HB2  GLN  446   -21.398   2.545 -17.433    0.00   H
ATOM   6583  HB3  GLN  446   -21.403   3.845 -16.293    0.00   H
ATOM   6584  CG   GLN  446   -21.249   4.450 -18.293   68.61   C
ATOM   6585  HG2  GLN  446   -20.457   4.439 -18.996    0.00   H
ATOM   6586  HG3  GLN  446   -22.151   4.171 -18.773    0.00   H
ATOM   6587  CD   GLN  446   -21.410   5.883 -17.792   68.51   C
ATOM   6588  OE1  GLN  446   -22.389   6.213 -17.113   67.99   O
ATOM   6589  NE2  GLN  446   -20.445   6.739 -18.123   68.43   N
ATOM   6590  HE21 GLN  446   -19.663   6.427 -18.679    0.00   H
ATOM   6591  HE22 GLN  446   -20.496   7.699 -17.818    0.00   H
ATOM   6592  C    GLN  446   -19.285   2.494 -15.594   66.52   C
ATOM   6593  O    GLN  446   -19.274   1.266 -15.563   66.87   O
ATOM   6594  N    ILE  447   -19.143   3.248 -14.509   64.93   N
ATOM   6595  HN   ILE  447   -19.114   4.248 -14.637    0.00   H
ATOM   6596  CA   ILE  447   -19.030   2.680 -13.167   63.80   C
ATOM   6597  HA   ILE  447   -19.555   1.761 -13.127    0.00   H
ATOM   6598  CB   ILE  447   -17.578   2.405 -12.751   63.49   C
ATOM   6599  HB   ILE  447   -16.995   3.275 -12.907    0.00   H
ATOM   6600  CG2  ILE  447   -17.531   2.022 -11.272   63.10   C
ATOM   6601  HG21 ILE  447   -17.919   2.816 -10.689    0.00   H
ATOM   6602  HG22 ILE  447   -18.113   1.151 -11.114    0.00   H
ATOM   6603  HG23 ILE  447   -16.528   1.833 -10.988    0.00   H
ATOM   6604  CG1  ILE  447   -17.004   1.267 -13.596   63.31   C
ATOM   6605  HG12 ILE  447   -17.612   0.407 -13.490    0.00   H
ATOM   6606  HG13 ILE  447   -16.981   1.560 -14.613    0.00   H
ATOM   6607  CD1  ILE  447   -15.595   0.866 -13.216   62.22   C
ATOM   6608  HD11 ILE  447   -14.948   1.697 -13.331    0.00   H
ATOM   6609  HD12 ILE  447   -15.580   0.544 -12.207    0.00   H
ATOM   6610  HD13 ILE  447   -15.271   0.077 -13.844    0.00   H
ATOM   6611  C    ILE  447   -19.648   3.669 -12.189   63.76   C
ATOM   6612  O    ILE  447   -18.987   4.596 -11.713   62.56   O
```

FIGURE 6- 88 -

```
ATOM   6613  N    TYR  448   -20.927   3.456 -11.894   64.18   N
ATOM   6614  HN   TYR  448   -21.382   2.654 -12.304    0.00   H
ATOM   6615  CA   TYR  448   -21.668   4.338 -11.011   65.16   C
ATOM   6616  HA   TYR  448   -22.661   3.984 -10.910    0.00   H
ATOM   6617  CB   TYR  448   -21.016   4.388  -9.626   64.06   C
ATOM   6618  HB2  TYR  448   -20.000   4.672  -9.724    0.00   H
ATOM   6619  HB3  TYR  448   -21.523   5.095  -9.022    0.00   H
ATOM   6620  CG   TYR  448   -21.033   3.073  -8.870   63.93   C
ATOM   6621  CD1  TYR  448   -22.163   2.243  -8.886   62.94   C
ATOM   6622  HD1  TYR  448   -23.023   2.515  -9.475    0.00   H
ATOM   6623  CE1  TYR  448   -22.202   1.055  -8.147   61.25   C
ATOM   6624  HE1  TYR  448   -23.082   0.434  -8.172    0.00   H
ATOM   6625  CD2  TYR  448   -19.938   2.678  -8.095   64.34   C
ATOM   6626  HD2  TYR  448   -19.053   3.291  -8.062    0.00   H
ATOM   6627  CE2  TYR  448   -19.968   1.493  -7.355   63.51   C
ATOM   6628  HE2  TYR  448   -19.115   1.206  -6.763    0.00   H
ATOM   6629  CZ   TYR  448   -21.099   0.687  -7.385   62.47   C
ATOM   6630  OH   TYR  448   -21.108  -0.482  -6.653   62.71   O
ATOM   6631  HH   TYR  448   -21.955  -0.933  -6.776    0.00   H
ATOM   6632  C    TYR  448   -21.675   5.730 -11.657   66.44   C
ATOM   6633  O    TYR  448   -21.286   6.728 -11.046   66.64   O
ATOM   6634  N    GLY  449   -22.107   5.770 -12.914   67.27   N
ATOM   6635  HN   GLY  449   -22.397   4.909 -13.353    0.00   H
ATOM   6636  CA   GLY  449   -22.166   7.016 -13.653   68.44   C
ATOM   6637  HA2  GLY  449   -22.709   6.869 -14.550    0.00   H
ATOM   6638  HA3  GLY  449   -22.649   7.753 -13.065    0.00   H
ATOM   6639  C    GLY  449   -20.808   7.568 -14.036   69.58   C
ATOM   6640  O    GLY  449   -20.685   8.318 -15.003   70.29   O
ATOM   6641  N    ALA  450   -19.784   7.192 -13.279   70.95   N
ATOM   6642  HN   ALA  450   -19.962   6.560 -12.513    0.00   H
ATOM   6643  CA   ALA  450   -18.431   7.669 -13.531   72.87   C
ATOM   6644  HA   ALA  450   -18.463   8.691 -13.908    0.00   H
ATOM   6645  CB   ALA  450   -17.574   7.515 -12.263   72.46   C
ATOM   6646  HB1  ALA  450   -18.002   8.081 -11.477    0.00   H
ATOM   6647  HB2  ALA  450   -17.537   6.494 -11.984    0.00   H
ATOM   6648  HB3  ALA  450   -16.593   7.864 -12.456    0.00   H
ATOM   6649  C    ALA  450   -17.765   6.956 -14.703   74.06   C
ATOM   6650  O    ALA  450   -17.371   5.797 -14.594   74.30   O
ATOM   6651  N    CYS  451   -17.637   7.666 -15.819   75.97   N
ATOM   6652  HN   CYS  451   -17.995   8.609 -15.819    0.00   H
ATOM   6653  CA   CYS  451   -17.005   7.126 -17.017   78.30   C
ATOM   6654  HA   CYS  451   -17.408   6.170 -17.228    0.00   H
ATOM   6655  CB   CYS  451   -17.286   8.026 -18.224   78.74   C
ATOM   6656  HB2  CYS  451   -18.306   7.943 -18.496    0.00   H
ATOM   6657  HB3  CYS  451   -17.068   9.031 -17.973    0.00   H
ATOM   6658  SG   CYS  451   -16.290   7.596 -19.686   81.84   S
ATOM   6659  HG   CYS  451   -16.573   8.370 -20.626    0.00   H
ATOM   6660  C    CYS  451   -15.491   6.975 -16.862   79.05   C
ATOM   6661  O    CYS  451   -14.827   7.798 -16.233   78.93   O
ATOM   6662  N    TYR  452   -14.958   5.907 -17.444   80.42   N
ATOM   6663  HN   TYR  452   -15.583   5.274 -17.920    0.00   H
ATOM   6664  CA   TYR  452   -13.529   5.632 -17.413   81.95   C
ATOM   6665  HA   TYR  452   -13.014   6.482 -17.048    0.00   H
ATOM   6666  CB   TYR  452   -13.230   4.437 -16.496   80.30   C
ATOM   6667  HB2  TYR  452   -13.891   3.642 -16.725    0.00   H
ATOM   6668  HB3  TYR  452   -12.231   4.119 -16.645    0.00   H
ATOM   6669  CG   TYR  452   -13.390   4.743 -15.019   79.28   C
ATOM   6670  CD1  TYR  452   -12.585   5.697 -14.388   79.27   C
ATOM   6671  HD1  TYR  452   -11.828   6.219 -14.949    0.00   H
ATOM   6672  CE1  TYR  452   -12.744   5.993 -13.024   78.87   C
ATOM   6673  HE1  TYR  452   -12.114   6.731 -12.556    0.00   H
ATOM   6674  CD2  TYR  452   -14.356   4.090 -14.254   79.21   C
ATOM   6675  HD2  TYR  452   -14.992   3.349 -14.708    0.00   H
ATOM   6676  CE2  TYR  452   -14.524   4.375 -12.896   78.48   C
ATOM   6677  HE2  TYR  452   -15.277   3.857 -12.326    0.00   H
ATOM   6678  CZ   TYR  452   -13.719   5.325 -12.289   78.43   C
ATOM   6679  OH   TYR  452   -13.399   5.610 -10.956   77.41   O
ATOM   6680  HH   TYR  452   -13.271   6.294 -10.685    0.00   H
ATOM   6681  C    TYR  452   -13.078   5.344 -18.846   83.63   C
ATOM   6682  O    TYR  452   -13.442   6.073 -19.770   83.99   O
ATOM   6683  N    SER  453   -12.292   4.284 -19.021   85.29   N
ATOM   6684  HN   SER  453   -12.056   3.759 -18.193    0.00   H
ATOM   6685  CA   SER  453   -11.773   3.864 -20.331   87.20   C
ATOM   6686  HA   SER  453   -12.535   3.362 -20.868    0.00   H
ATOM   6687  CB   SER  453   -11.308   5.076 -21.153   87.34   C
ATOM   6688  HB2  SER  453   -12.082   5.798 -21.186    0.00   H
```

FIGURE 6- 89 -

```
ATOM   6689  HB3  SER  453   -10.449   5.500  -20.702   0.00      H
ATOM   6690  OG   SER  453   -10.983   4.696  -22.482  87.59      O
ATOM   6691  HG   SER  453   -10.694   5.474  -22.978   0.00      H
ATOM   6692  C    SER  453   -10.598   2.903  -20.098  87.90      C
ATOM   6693  O    SER  453    -9.445   3.320  -19.969  88.72      O
ATOM   6694  N    ILE  454   -10.901   1.610  -20.062  87.73      N
ATOM   6695  HN   ILE  454   -11.859   1.341  -20.231   0.00      H
ATOM   6696  CA   ILE  454    -9.896   0.592  -19.789  87.99      C
ATOM   6697  HA   ILE  454    -9.003   1.057  -19.462   0.00      H
ATOM   6698  CB   ILE  454   -10.425  -0.354  -18.688  87.97      C
ATOM   6699  HB   ILE  454   -11.229  -0.927  -19.071   0.00      H
ATOM   6700  CG2  ILE  454    -9.322  -1.302  -18.216  87.56      C
ATOM   6701  HG21 ILE  454    -8.983  -1.883  -19.033   0.00      H
ATOM   6702  HG22 ILE  454    -8.515  -0.738  -17.825   0.00      H
ATOM   6703  HG23 ILE  454    -9.704  -1.941  -17.463   0.00      H
ATOM   6704  CG1  ILE  454   -10.959   0.484  -17.520  88.19      C
ATOM   6705  HG12 ILE  454   -10.146   0.858  -16.953   0.00      H
ATOM   6706  HG13 ILE  454   -11.528   1.293  -17.897   0.00      H
ATOM   6707  CD1  ILE  454   -11.852  -0.272  -16.562  88.38      C
ATOM   6708  HD11 ILE  454   -12.695  -0.644  -17.084   0.00      H
ATOM   6709  HD12 ILE  454   -11.313  -1.080  -16.140   0.00      H
ATOM   6710  HD13 ILE  454   -12.174   0.379  -15.791   0.00      H
ATOM   6711  C    ILE  454    -9.453  -0.235  -20.992  88.52      C
ATOM   6712  O    ILE  454   -10.061  -0.188  -22.063  88.65      O
ATOM   6713  N    GLU  455    -8.369  -0.982  -20.794  88.76      N
ATOM   6714  HN   GLU  455    -7.929  -0.921  -19.888   0.00      H
ATOM   6715  CA   GLU  455    -7.814  -1.860  -21.815  89.23      C
ATOM   6716  HA   GLU  455    -8.161  -1.556  -22.768   0.00      H
ATOM   6717  CB   GLU  455    -6.285  -1.814  -21.816  89.91      C
ATOM   6718  HB2  GLU  455    -5.922  -2.114  -20.867   0.00      H
ATOM   6719  HB3  GLU  455    -5.913  -2.469  -22.560   0.00      H
ATOM   6720  CG   GLU  455    -5.633  -0.472  -22.094  90.37      C
ATOM   6721  HG2  GLU  455    -6.074  -0.036  -22.953   0.00      H
ATOM   6722  HG3  GLU  455    -5.774   0.168  -21.262   0.00      H
ATOM   6723  CD   GLU  455    -4.133  -0.625  -22.342  90.96      C
ATOM   6724  OE1  GLU  455    -3.487  -1.404  -21.600  91.32      O1-
ATOM   6725  OE2  GLU  455    -3.601   0.026  -23.272  90.79      O
ATOM   6726  C    GLU  455    -8.242  -3.283  -21.473  89.28      C
ATOM   6727  O    GLU  455    -8.422  -3.619  -20.302  89.47      O
ATOM   6728  N    PRO  456    -8.409  -4.142  -22.486  89.24      N
ATOM   6729  CD   PRO  456    -8.444  -3.871  -23.933  89.70      C
ATOM   6730  HD2  PRO  456    -8.802  -2.888  -24.100   0.00      H
ATOM   6731  HD3  PRO  456    -7.468  -3.963  -24.333   0.00      H
ATOM   6732  CA   PRO  456    -8.818  -5.520  -22.200  88.73      C
ATOM   6733  HA   PRO  456    -9.722  -5.513  -21.649   0.00      H
ATOM   6734  CB   PRO  456    -9.000  -6.125  -23.591  89.34      C
ATOM   6735  HB2  PRO  456    -8.089  -6.561  -23.908   0.00      H
ATOM   6736  HB3  PRO  456    -9.754  -6.868  -23.557   0.00      H
ATOM   6737  CG   PRO  456    -9.394  -4.943  -24.428  89.74      C
ATOM   6738  HG2  PRO  456    -9.259  -5.175  -25.452   0.00      H
ATOM   6739  HG3  PRO  456   -10.411  -4.708  -24.251   0.00      H
ATOM   6740  C    PRO  456    -7.769  -6.274  -21.383  88.02      C
ATOM   6741  O    PRO  456    -8.095  -6.972  -20.422  87.96      O
ATOM   6742  N    LEU  457    -6.507  -6.118  -21.770  87.33      N
ATOM   6743  HN   LEU  457    -6.325  -5.506  -22.551   0.00      H
ATOM   6744  CA   LEU  457    -5.399  -6.801  -21.102  86.52      C
ATOM   6745  HA   LEU  457    -5.511  -7.848  -21.214   0.00      H
ATOM   6746  CB   LEU  457    -4.070  -6.369  -21.719  87.00      C
ATOM   6747  HB2  LEU  457    -3.890  -5.350  -21.492   0.00      H
ATOM   6748  HB3  LEU  457    -3.287  -6.962  -21.323   0.00      H
ATOM   6749  CG   LEU  457    -4.004  -6.504  -23.239  88.05      C
ATOM   6750  HG   LEU  457    -4.788  -5.944  -23.678   0.00      H
ATOM   6751  CD1  LEU  457    -2.656  -5.974  -23.729  88.70      C
ATOM   6752  HD11 LEU  457    -2.557  -4.955  -23.457   0.00      H
ATOM   6753  HD12 LEU  457    -1.874  -6.535  -23.287   0.00      H
ATOM   6754  HD13 LEU  457    -2.603  -6.064  -24.783   0.00      H
ATOM   6755  CD2  LEU  457    -4.212  -7.965  -23.641  87.60      C
ATOM   6756  HD21 LEU  457    -3.455  -8.563  -23.204   0.00      H
ATOM   6757  HD22 LEU  457    -5.160  -8.293  -23.302   0.00      H
ATOM   6758  HD23 LEU  457    -4.165  -8.051  -24.695   0.00      H
ATOM   6759  C    LEU  457    -5.327  -6.614  -19.591  85.41      C
ATOM   6760  O    LEU  457    -4.876  -7.509  -18.876  84.58      O
ATOM   6761  N    ASP  458    -5.775  -5.460  -19.107  84.06      N
ATOM   6762  HN   ASP  458    -6.150  -4.781  -19.753   0.00      H
ATOM   6763  CA   ASP  458    -5.734  -5.163  -17.677  83.56      C
ATOM   6764  HA   ASP  458    -4.785  -5.428  -17.289   0.00      H
```

FIGURE 6- 90 -

```
ATOM   6765  CB   ASP  458   -5.975  -3.667 -17.452  83.76    C
ATOM   6766  HB2  ASP  458   -6.803  -3.352 -18.032   0.00    H
ATOM   6767  HB3  ASP  458   -6.175  -3.492 -16.427   0.00    H
ATOM   6768  CG   ASP  458   -4.780  -2.820 -17.846  84.39    C
ATOM   6769  OD1  ASP  458   -3.697  -3.013 -17.241  83.42    O
ATOM   6770  OD2  ASP  458   -4.919  -1.969 -18.755  84.16    O1-
ATOM   6771  C    ASP  458   -6.695  -5.961 -16.791  83.07    C
ATOM   6772  O    ASP  458   -6.401  -6.221 -15.616  83.02    O
ATOM   6773  N    LEU  459   -7.835  -6.350 -17.359  81.68    N
ATOM   6774  HN   LEU  459   -7.976  -6.112 -18.329   0.00    H
ATOM   6775  CA   LEU  459   -8.863  -7.094 -16.632  79.74    C
ATOM   6776  HA   LEU  459   -9.444  -6.422 -16.055   0.00    H
ATOM   6777  CB   LEU  459   -9.778  -7.831 -17.618  79.57    C
ATOM   6778  HB2  LEU  459   -9.218  -8.562 -18.141   0.00    H
ATOM   6779  HB3  LEU  459  -10.564  -8.302 -17.086   0.00    H
ATOM   6780  CG   LEU  459  -10.461  -6.992 -18.697  79.20    C
ATOM   6781  HG   LEU  459   -9.726  -6.496 -19.276   0.00    H
ATOM   6782  CD1  LEU  459  -11.282  -7.913 -19.584  78.67    C
ATOM   6783  HD11 LEU  459  -10.645  -8.629 -20.035   0.00    H
ATOM   6784  HD12 LEU  459  -12.012  -8.409 -18.998   0.00    H
ATOM   6785  HD13 LEU  459  -11.761  -7.343 -20.337   0.00    H
ATOM   6786  CD2  LEU  459  -11.346  -5.923 -18.064  79.68    C
ATOM   6787  HD21 LEU  459  -12.089  -6.387 -17.468   0.00    H
ATOM   6788  HD22 LEU  459  -10.754  -5.288 -17.458   0.00    H
ATOM   6789  HD23 LEU  459  -11.810  -5.352 -18.826   0.00    H
ATOM   6790  C    LEU  459   -8.354  -8.091 -15.588  78.71    C
ATOM   6791  O    LEU  459   -8.785  -8.062 -14.436  78.25    O
ATOM   6792  N    PRO  460   -7.433  -8.990 -15.976  77.48    N
ATOM   6793  CD   PRO  460   -6.814  -9.153 -17.304  76.53    C
ATOM   6794  HD2  PRO  460   -7.556  -9.057 -18.053   0.00    H
ATOM   6795  HD3  PRO  460   -6.074  -8.408 -17.442   0.00    H
ATOM   6796  CA   PRO  460   -6.904  -9.982 -15.030  76.88    C
ATOM   6797  HA   PRO  460   -7.647 -10.709 -14.828   0.00    H
ATOM   6798  CB   PRO  460   -5.746 -10.605 -15.806  76.31    C
ATOM   6799  HB2  PRO  460   -4.869 -10.031 -15.653   0.00    H
ATOM   6800  HB3  PRO  460   -5.584 -11.594 -15.464   0.00    H
ATOM   6801  CG   PRO  460   -6.239 -10.550 -17.214  76.12    C
ATOM   6802  HG2  PRO  460   -5.429 -10.705 -17.878   0.00    H
ATOM   6803  HG3  PRO  460   -6.967 -11.305 -17.363   0.00    H
ATOM   6804  C    PRO  460   -6.465  -9.414 -13.674  76.79    C
ATOM   6805  O    PRO  460   -6.901  -9.882 -12.619  76.06    O
ATOM   6806  N    GLN  461   -5.600  -8.404 -13.715  76.49    N
ATOM   6807  HN   GLN  461   -5.298  -8.078 -14.621   0.00    H
ATOM   6808  CA   GLN  461   -5.089  -7.770 -12.502  75.93    C
ATOM   6809  HA   GLN  461   -4.715  -8.513 -11.846   0.00    H
ATOM   6810  CB   GLN  461   -3.959  -6.793 -12.855  76.81    C
ATOM   6811  HB2  GLN  461   -4.370  -5.925 -13.301   0.00    H
ATOM   6812  HB3  GLN  461   -3.437  -6.524 -11.974   0.00    H
ATOM   6813  CG   GLN  461   -2.919  -7.352 -13.838  77.75    C
ATOM   6814  HG2  GLN  461   -1.952  -7.030 -13.550   0.00    H
ATOM   6815  HG3  GLN  461   -2.957  -8.410 -13.828   0.00    H
ATOM   6816  CD   GLN  461   -3.150  -6.893 -15.283  78.15    C
ATOM   6817  OE1  GLN  461   -2.967  -5.712 -15.619  77.64    O
ATOM   6818  NE2  GLN  461   -3.559  -7.827 -16.141  77.45    N
ATOM   6819  HE21 GLN  461   -3.696  -8.776 -15.826   0.00    H
ATOM   6820  HE22 GLN  461   -3.732  -7.585 -17.105   0.00    H
ATOM   6821  C    GLN  461   -6.206  -7.031 -11.766  75.29    C
ATOM   6822  O    GLN  461   -6.411  -7.224 -10.561  74.84    O
ATOM   6823  N    ILE  462   -6.926  -6.186 -12.501  74.68    N
ATOM   6824  HN   ILE  462   -6.681  -6.089 -13.475   0.00    H
ATOM   6825  CA   ILE  462   -8.039  -5.412 -11.944  73.38    C
ATOM   6826  HA   ILE  462   -7.662  -4.682 -11.276   0.00    H
ATOM   6827  CB   ILE  462   -8.834  -4.698 -13.048  72.41    C
ATOM   6828  HB   ILE  462   -9.201  -5.413 -13.737   0.00    H
ATOM   6829  CG2  ILE  462  -10.000  -3.947 -12.431  71.66    C
ATOM   6830  HG21 ILE  462  -10.633  -4.630 -11.927   0.00    H
ATOM   6831  HG22 ILE  462   -9.634  -3.231 -11.742   0.00    H
ATOM   6832  HG23 ILE  462  -10.547  -3.456 -13.193   0.00    H
ATOM   6833  CG1  ILE  462   -7.912  -3.767 -13.838  71.82    C
ATOM   6834  HG12 ILE  462   -7.545  -3.007 -13.198   0.00    H
ATOM   6835  HG13 ILE  462   -7.099  -4.323 -14.228   0.00    H
ATOM   6836  CD1  ILE  462   -8.594  -3.085 -15.005  72.01    C
ATOM   6837  HD11 ILE  462   -8.957  -3.817 -15.679   0.00    H
ATOM   6838  HD12 ILE  462   -9.403  -2.501 -14.649   0.00    H
ATOM   6839  HD13 ILE  462   -7.900  -2.460 -15.503   0.00    H
ATOM   6840  C    ILE  462   -9.013  -6.306 -11.186  72.95    C
```

FIGURE 6-91-

```
ATOM   6841   O     ILE   462    -9.348  -6.040 -10.029   73.12        O
ATOM   6842   N     ILE   463    -9.466  -7.364 -11.855   71.90        N
ATOM   6843   HN    ILE   463    -9.142  -7.503 -12.800    0.00        H
ATOM   6844   CA    ILE   463   -10.403  -8.307 -11.260   70.84        C
ATOM   6845   HA    ILE   463   -11.329  -7.823 -11.088    0.00        H
ATOM   6846   CB    ILE   463   -10.648  -9.519 -12.184   69.91        C
ATOM   6847   HB    ILE   463    -9.719  -9.949 -12.456    0.00        H
ATOM   6848   CG2   ILE   463   -11.495 -10.570 -11.463   68.70        C
ATOM   6849   HC21  ILE   463   -10.988 -10.895 -10.592    0.00        H
ATOM   6850   HG22  ILE   463   -12.427 -10.147 -11.192    0.00        H
ATOM   6851   HG23  ILE   463   -11.656 -11.396 -12.106    0.00        H
ATOM   6852   CG1   ILE   463   -11.344  -9.051 -13.465   68.40        C
ATOM   6853   HG12  ILE   463   -12.268  -8.597 -13.219    0.00        H
ATOM   6854   HG13  ILE   463   -10.728  -8.350 -13.965    0.00        H
ATOM   6855   CD1   ILE   463   -11.640 -10.156 -14.441   67.56        C
ATOM   6856   HD11  ILE   463   -10.735 -10.623 -14.731    0.00        H
ATOM   6857   HD12  ILE   463   -12.275 -10.870 -13.984    0.00        H
ATOM   6858   HD13  ILE   463   -12.119  -9.753 -15.295    0.00        H
ATOM   6859   C     ILE   463    -9.931  -8.801  -9.902   71.13        C
ATOM   6860   O     ILE   463   -10.734  -8.925  -8.976   71.03        O
ATOM   6861   N     GLU   464    -8.636  -9.072  -9.772   72.24        N
ATOM   6862   HN    GLU   464    -8.015  -8.951 -10.558    0.00        H
ATOM   6863   CA    GLU   464    -8.113  -9.544  -8.496   74.07        C
ATOM   6864   HA    GLU   464    -8.694 -10.362  -8.158    0.00        H
ATOM   6865   CB    GLU   464    -6.660 -10.001  -8.619   75.20        C
ATOM   6866   HB2   GLU   464    -6.617 -10.888  -9.195    0.00        H
ATOM   6867   HB3   GLU   464    -6.091  -9.244  -9.093    0.00        H
ATOM   6868   CG    GLU   464    -6.036 -10.285  -7.258   77.24        C
ATOM   6869   HG2   GLU   464    -6.114  -9.424  -6.647    0.00        H
ATOM   6870   HG3   GLU   464    -6.545 -11.092  -6.798    0.00        H
ATOM   6871   CD    GLU   464    -4.566 -10.658  -7.327   79.19        C
ATOM   6872   OE1   GLU   464    -4.257 -11.843  -7.590   79.90        O1-
ATOM   6873   OE2   GLU   464    -3.718  -9.760  -7.120   80.78        O
ATOM   6874   C     GLU   464    -8.196  -8.473  -7.409   74.83        C
ATOM   6875   O     GLU   464    -8.683  -8.734  -6.312   74.50        O
ATOM   6876   N     ARG   465    -7.719  -7.266  -7.700   75.19        N
ATOM   6877   HN    ARG   465    -7.325  -7.071  -8.608    0.00        H
ATOM   6878   CA    ARG   465    -7.771  -6.221  -6.691   75.15        C
ATOM   6879   HA    ARG   465    -7.270  -6.549  -5.817    0.00        H
ATOM   6880   CB    ARG   465    -7.101  -4.941  -7.184   76.83        C
ATOM   6881   HB2   ARG   465    -6.149  -5.173  -7.586    0.00        H
ATOM   6882   HB3   ARG   465    -7.701  -4.494  -7.933    0.00        H
ATOM   6883   CG    ARG   465    -6.903  -3.919  -6.072   79.32        C
ATOM   6884   HG2   ARG   465    -7.841  -3.515  -5.793    0.00        H
ATOM   6885   HG3   ARG   465    -6.459  -4.391  -5.234    0.00        H
ATOM   6886   CD    ARG   465    -6.000  -2.769  -6.503   80.92        C
ATOM   6887   HD2   ARG   465    -5.049  -3.149  -6.773    0.00        H
ATOM   6888   HD3   ARG   465    -6.431  -2.274  -7.334    0.00        H
ATOM   6889   NE    ARG   465    -5.816  -1.792  -5.433   82.69        N1-
ATOM   6890   HE    ARG   465    -6.279  -1.922  -4.546    0.00        H
ATOM   6891   CZ    ARG   465    -5.060  -0.702  -5.534   84.08        C
ATOM   6892   NH1   ARG   465    -4.414  -0.450  -6.664   84.40        N
ATOM   6893   HH11  ARG   465    -3.840   0.376  -6.744    0.00        H
ATOM   6894   HH12  ARG   465    -4.496  -1.084  -7.444    0.00        H
ATOM   6895   NH2   ARG   465    -4.954   0.137  -4.507   84.57        N
ATOM   6896   HH21  ARG   465    -4.380   0.963  -4.567    0.00        H
ATOM   6897   HH22  ARG   465    -5.448  -0.052  -3.648    0.00        H
ATOM   6898   C     ARG   465    -9.219  -5.942  -6.302   74.69        C
ATOM   6899   O     ARG   465    -9.513  -5.668  -5.133   75.31        O
ATOM   6900   N     LEU   466   -10.122  -6.029  -7.279   73.00        N
ATOM   6901   HN    LEU   466    -9.799  -6.259  -8.207    0.00        H
ATOM   6902   CA    LEU   466   -11.547  -5.802  -7.036   70.49        C
ATOM   6903   HA    LEU   466   -11.668  -4.957  -6.409    0.00        H
ATOM   6904   CB    LEU   466   -12.297  -5.550  -8.350   70.13        C
ATOM   6905   HB2   LEU   466   -12.089  -6.334  -9.031    0.00        H
ATOM   6906   HB3   LEU   466   -13.338  -5.514  -8.161    0.00        H
ATOM   6907   CG    LEU   466   -12.015  -4.275  -9.145   70.46        C
ATOM   6908   HG    LEU   466   -11.018  -4.294  -9.500    0.00        H
ATOM   6909   CD1   LEU   466   -12.970  -4.181 -10.331   69.00        C
ATOM   6910   HD11  LEU   466   -12.835  -5.022 -10.960    0.00        H
ATOM   6911   HD12  LEU   466   -13.969  -4.160  -9.979    0.00        H
ATOM   6912   HD13  LEU   466   -12.769  -3.296 -10.877    0.00        H
ATOM   6913   CD2   LEU   466   -12.192  -3.071  -8.240   71.19        C
ATOM   6914   HD21  LEU   466   -13.185  -3.048  -7.873    0.00        H
ATOM   6915   HD22  LEU   466   -11.517  -3.138  -7.427    0.00        H
ATOM   6916   HD23  LEU   466   -11.997  -2.186  -8.788    0.00        H
```

FIGURE 6- 92 -

```
ATOM   6917  C    LEU  466  -12.205   -6.985   -6.326  69.36  C
ATOM   6918  O    LEU  466  -12.363   -6.980   -5.101  69.54  O
ATOM   6919  N    HIS  467  -12.572   -7.994   -7.117  67.27  N
ATOM   6920  HN   HIS  467  -12.360   -7.890   -6.098   0.00  H
ATOM   6921  CA   HIS  467  -13.246   -9.203   -6.638  64.65  C
ATOM   6922  HA   HIS  467  -14.013   -8.934   -5.960   0.00  H
ATOM   6923  CB   HIS  467  -13.843   -9.935   -7.820  59.18  C
ATOM   6924  HB2  HIS  467  -13.066  -10.354   -8.405   0.00  H
ATOM   6925  HB3  HIS  467  -14.479  -10.707   -7.472   0.00  H
ATOM   6926  CG   HIS  467  -14.649   -9.048   -8.705  54.08  C
ATOM   6927  CD2  HIS  467  -14.329   -8.413   -9.856  51.76  C
ATOM   6928  HD2  HIS  467  -13.354   -8.548  -10.292   0.00  H
ATOM   6929  ND1  HIS  467  -15.942   -8.681   -8.407  50.90  N1+
ATOM   6930  HD1  HIS  467  -16.390   -9.041   -7.578   0.00  H
ATOM   6931  CE1  HIS  467  -16.386   -7.859   -9.340  50.98  C
ATOM   6932  HE1  HIS  467  -17.386   -7.464   -9.278   0.00  H
ATOM   6933  NE2  HIS  467  -15.426   -7.679  -10.229  51.31  N
ATOM   6934  HE2  HIS  467  -15.398   -7.122  -11.070   0.00  H
ATOM   6935  C    HIS  467  -12.318  -10.126   -5.883  66.20  C
ATOM   6936  O    HIS  467  -12.751  -11.106   -5.269  65.92  O
ATOM   6937  N    GLY  468  -11.032   -9.812   -5.958  67.95  N
ATOM   6938  HN   GLY  468  -10.756   -9.021   -6.521   0.00  H
ATOM   6939  CA   GLY  468  -10.030  -10.581   -5.250  69.16  C
ATOM   6940  HA2  GLY  468   -9.075  -10.153   -5.414   0.00  H
ATOM   6941  HA3  GLY  468  -10.247  -10.574   -4.213   0.00  H
ATOM   6942  C    GLY  468   -9.836  -12.046   -5.575  69.41  C
ATOM   6943  O    GLY  468  -10.788  -12.821   -5.681  70.73  O
ATOM   6944  N    LEU  469   -8.569  -12.398   -5.755  68.97  N
ATOM   6945  HN   LEU  469   -7.899  -11.645   -5.708   0.00  H
ATOM   6946  CA   LEU  469   -8.116  -13.762   -6.007  68.37  C
ATOM   6947  HA   LEU  469   -7.353  -13.751   -6.741   0.00  H
ATOM   6948  CB   LEU  469   -7.579  -14.317   -4.679  69.43  C
ATOM   6949  HB2  LEU  469   -8.131  -15.179   -4.408   0.00  H
ATOM   6950  HB3  LEU  469   -6.557  -14.572   -4.791   0.00  H
ATOM   6951  CG   LEU  469   -7.661  -13.346   -3.477  69.74  C
ATOM   6952  HG   LEU  469   -8.622  -12.901   -3.448   0.00  H
ATOM   6953  CD1  LEU  469   -7.420  -14.092   -2.154  69.22  C
ATOM   6954  HD11 LEU  469   -8.155  -14.845   -2.035   0.00  H
ATOM   6955  HD12 LEU  469   -6.459  -14.536   -2.169   0.00  H
ATOM   6956  HD13 LEU  469   -7.481  -13.409   -1.347   0.00  H
ATOM   6957  CD2  LEU  469   -6.636  -12.214   -3.656  69.02  C
ATOM   6958  HD21 LEU  469   -5.662  -12.625   -3.710   0.00  H
ATOM   6959  HD22 LEU  469   -6.846  -11.686   -4.550   0.00  H
ATOM   6960  HD23 LEU  469   -6.695  -11.551   -2.832   0.00  H
ATOM   6961  C    LEU  469   -9.119  -14.760   -6.615  67.41  C
ATOM   6962  O    LEU  469   -9.114  -15.015   -7.825  65.99  O
ATOM   6963  N    SER  470   -9.961  -15.319   -5.744  66.45  N
ATOM   6964  HN   SER  470   -9.851  -15.005   -4.791   0.00  H
ATOM   6965  CA   SER  470  -10.988  -16.316   -6.075  65.82  C
ATOM   6966  HA   SER  470  -10.522  -17.233   -6.325   0.00  H
ATOM   6967  CB   SER  470  -11.907  -16.521   -4.864  66.14  C
ATOM   6968  HB2  SER  470  -12.524  -17.366   -5.028   0.00  H
ATOM   6969  HB3  SER  470  -11.319  -16.676   -3.997   0.00  H
ATOM   6970  OG   SER  470  -12.736  -15.388   -4.654  64.51  O
ATOM   6971  HG   SER  470  -13.304  -15.542   -3.887   0.00  H
ATOM   6972  C    SER  470  -11.877  -16.098   -7.304  65.13  C
ATOM   6973  O    SER  470  -12.650  -16.980   -7.671  64.05  O
ATOM   6974  N    ALA  471  -11.784  -14.937   -7.936  64.95  N
ATOM   6975  HN   ALA  471  -11.136  -14.239   -7.602   0.00  H
ATOM   6976  CA   ALA  471  -12.611  -14.664   -9.107  64.29  C
ATOM   6977  HA   ALA  471  -13.605  -14.976   -8.918   0.00  H
ATOM   6978  CB   ALA  471  -12.601  -13.167   -9.410  64.98  C
ATOM   6979  HB1  ALA  471  -12.985  -12.636   -8.578   0.00  H
ATOM   6980  HB2  ALA  471  -11.608  -12.852   -9.601   0.00  H
ATOM   6981  HB3  ALA  471  -13.202  -12.975  -10.260   0.00  H
ATOM   6982  C    ALA  471  -12.163  -15.459  -10.340  63.95  C
ATOM   6983  O    ALA  471  -12.658  -15.239  -11.449  64.07  O
ATOM   6984  N    PHE  472  -11.226  -16.381  -10.142  62.82  N
ATOM   6985  HN   PHE  472  -10.866  -16.503   -9.207   0.00  H
ATOM   6986  CA   PHE  472  -10.716  -17.207  -11.235  62.09  C
ATOM   6987  HA   PHE  472  -11.308  -17.053  -12.100   0.00  H
ATOM   6988  CB   PHE  472   -9.267  -16.845  -11.559  62.16  C
ATOM   6989  HB2  PHE  472   -8.646  -17.107  -10.742   0.00  H
ATOM   6990  HB3  PHE  472   -8.956  -17.373  -12.423   0.00  H
ATOM   6991  CG   PHE  472   -9.038  -15.391  -11.831  62.18  C
ATOM   6992  CD1  PHE  472   -9.653  -14.762  -12.906  62.70  C
```

FIGURE 6-93 -

```
ATOM   6993  HD1  PHE  472   -10.345 -15.308 -13.525    0.00   H
ATOM   6994  CD2  PHE  472    -8.154 -14.661 -11.044   62.65   C
ATOM   6995  HD2  PHE  472    -7.670 -15.128 -10.203    0.00   H
ATOM   6996  CE1  PHE  472    -9.337 -13.424 -13.200   61.93   C
ATOM   6997  HE1  PHE  472    -9.870 -12.951 -14.038    0.00   H
ATOM   6998  CE2  PHE  472    -7.882 -13.325 -11.328   62.39   C
ATOM   6999  HE2  PHE  472    -7.194 -12.772 -10.710    0.00   H
ATOM   7000  CZ   PHE  472    -8.499 -12.707 -12.409   62.14   C
ATOM   7001  HZ   PHE  472    -8.290 -11.675 -12.634    0.00   H
ATOM   7002  C    PHE  472   -10.751 -18.687 -10.859   61.28   C
ATOM   7003  O    PHE  472   -10.478 -19.557 -11.686   60.97   O
ATOM   7004  N    THR  473   -11.077 -18.972  -9.607   60.27   N
ATOM   7005  HN   THR  473   -11.305 -18.226  -8.967    0.00   H
ATOM   7006  CA   THR  473   -11.107 -20.350  -9.155   59.72   C
ATOM   7007  HA   THR  473   -10.995 -20.997  -9.986    0.00   H
ATOM   7008  CB   THR  473    -9.952 -20.615  -8.147   60.34   C
ATOM   7009  HB   THR  473    -9.804 -21.659  -8.046    0.00   H
ATOM   7010  OG1  THR  473   -10.282 -20.063  -6.865   59.58   O
ATOM   7011  HG1  THR  473    -9.559 -20.232  -6.245    0.00   H
ATOM   7012  CG2  THR  473    -8.651 -19.968  -8.649   59.51   C
ATOM   7013  HG21 THR  473    -8.392 -20.380  -9.589    0.00   H
ATOM   7014  HG22 THR  473    -8.792 -18.923  -8.748    0.00   H
ATOM   7015  HG23 THR  473    -7.873 -20.155  -7.955    0.00   H
ATOM   7016  C    THR  473   -12.443 -20.707  -8.516   59.19   C
ATOM   7017  O    THR  473   -12.511 -21.547  -7.617   58.71   O
ATOM   7018  N    LEU  474   -13.514 -20.069  -8.970   58.64   N
ATOM   7019  HN   LEU  474   -13.432 -19.377  -9.699    0.00   H
ATOM   7020  CA   LEU  474   -14.814 -20.377  -8.405   58.64   C
ATOM   7021  HA   LEU  474   -14.691 -20.767  -7.428    0.00   H
ATOM   7022  CB   LEU  474   -15.696 -19.125  -8.324   58.11   C
ATOM   7023  HB2  LEU  474   -15.714 -18.644  -9.268    0.00   H
ATOM   7024  HB3  LEU  474   -16.680 -19.404  -8.051    0.00   H
ATOM   7025  CG   LEU  474   -15.222 -18.084  -7.298   58.99   C
ATOM   7026  HG   LEU  474   -14.268 -17.720  -7.579    0.00   H
ATOM   7027  CD1  LEU  474   -16.200 -16.915  -7.235   58.97   C
ATOM   7028  HD11 LEU  474   -16.264 -16.456  -8.187    0.00   H
ATOM   7029  HD12 LEU  474   -17.156 -17.270  -6.950    0.00   H
ATOM   7030  HD13 LEU  474   -15.859 -16.208  -6.524    0.00   H
ATOM   7031  CD2  LEU  474   -15.088 -18.737  -5.926   58.15   C
ATOM   7032  HD21 LEU  474   -16.027 -19.123  -5.626    0.00   H
ATOM   7033  HD22 LEU  474   -14.382 -19.525  -5.978    0.00   H
ATOM   7034  HD23 LEU  474   -14.761 -18.016  -5.222    0.00   H
ATOM   7035  C    LEU  474   -15.491 -21.462  -9.216   59.08   C
ATOM   7036  O    LEU  474   -15.437 -21.473 -10.445   58.38   O
ATOM   7037  N    HIS  475   -16.104 -22.392  -8.500   59.65   N
ATOM   7038  HN   HIS  475   -16.066 -22.304  -7.496    0.00   H
ATOM   7039  CA   HIS  475   -16.812 -23.507  -9.105   60.96   C
ATOM   7040  HA   HIS  475   -17.182 -23.217 -10.054    0.00   H
ATOM   7041  CB   HIS  475   -15.881 -24.705  -9.283   60.06   C
ATOM   7042  HB2  HIS  475   -16.332 -25.464  -9.826    0.00   H
ATOM   7043  HB3  HIS  475   -15.015 -24.404  -9.813    0.00   H
ATOM   7044  CG   HIS  475   -15.434 -25.297  -7.986   60.11   C
ATOM   7045  CD2  HIS  475   -15.838 -26.408  -7.327   60.01   C
ATOM   7046  HD2  HIS  475   -16.549 -27.076  -7.783    0.00   H
ATOM   7047  ND1  HIS  475   -14.532 -24.667  -7.156   60.62   N1+
ATOM   7048  HD1  HIS  475   -14.092 -23.808  -7.449    0.00   H
ATOM   7049  CE1  HIS  475   -14.401 -25.362  -6.041   61.48   C
ATOM   7050  HE1  HIS  475   -13.734 -25.019  -5.268    0.00   H
ATOM   7051  NE2  HIS  475   -15.184 -26.423  -6.118   61.76   N
ATOM   7052  HE2  HIS  475   -15.349 -27.174  -5.464    0.00   H
ATOM   7053  C    HIS  475   -17.887 -23.874  -8.091   62.46   C
ATOM   7054  O    HIS  475   -17.963 -23.277  -7.009   62.89   O
ATOM   7055  N    SER  476   -18.697 -24.871  -8.435   63.25   N
ATOM   7056  HN   SER  476   -18.554 -25.310  -9.332    0.00   H
ATOM   7057  CA   SER  476   -19.766 -25.334  -7.559   63.84   C
ATOM   7058  HA   SER  476   -20.268 -26.148  -8.014    0.00   H
ATOM   7059  CB   SER  476   -19.189 -25.790  -6.212   64.65   C
ATOM   7060  HB2  SER  476   -18.429 -26.509  -6.379    0.00   H
ATOM   7061  HB3  SER  476   -18.781 -24.956  -5.703    0.00   H
ATOM   7062  OG   SER  476   -20.190 -26.373  -5.393   65.62   O
ATOM   7063  HG   SER  476   -19.798 -26.650  -4.553    0.00   H
ATOM   7064  C    SER  476   -20.730 -24.210  -7.351   63.62   C
ATOM   7065  O    SER  476   -21.253 -23.962  -6.232   63.18   O
ATOM   7066  N    TYR  477   -21.097 -23.521  -8.442   62.69   N
ATOM   7067  HN   TYR  477   -20.661 -23.760  -9.320    0.00   H
ATOM   7068  CA   TYR  477   -22.058 -22.436  -8.381   62.18   C
```

FIGURE 6- 94 -

| | | | | | | | | |
|---|---|---|---|---|---|---|---|---|
| ATOM | 7069 | HA | TYR | 477 | -21.725 | -21.708 | -7.688 | 0.00 | H |
| ATOM | 7070 | CB | TYR | 477 | -22.219 | -21.776 | -9.751 | 63.07 | C |
| ATOM | 7071 | HB2 | TYR | 477 | -22.303 | -22.524 | -10.496 | 0.00 | H |
| ATOM | 7072 | HB3 | TYR | 477 | -23.092 | -21.176 | -9.753 | 0.00 | H |
| ATOM | 7073 | CG | TYR | 477 | -21.066 | -20.880 | -10.153 | 63.76 | C |
| ATOM | 7074 | CD1 | TYR | 477 | -19.916 | -21.404 | -10.745 | 63.32 | C |
| ATOM | 7075 | HD1 | TYR | 477 | -19.838 | -22.463 | -10.926 | 0.00 | H |
| ATOM | 7076 | CE1 | TYR | 477 | -18.853 | -20.574 | -11.111 | 63.11 | C |
| ATOM | 7077 | HE1 | TYR | 477 | -17.973 | -20.995 | -11.568 | 0.00 | H |
| ATOM | 7078 | CD2 | TYR | 477 | -21.127 | -19.500 | -9.933 | 64.21 | C |
| ATOM | 7079 | HD2 | TYR | 477 | -22.001 | -19.065 | -9.479 | 0.00 | H |
| ATOM | 7080 | CE2 | TYR | 477 | -20.074 | -18.662 | -10.290 | 63.96 | C |
| ATOM | 7081 | HE2 | TYR | 477 | -20.143 | -17.603 | -10.107 | 0.00 | H |
| ATOM | 7082 | CZ | TYR | 477 | -18.943 | -19.205 | -10.880 | 63.97 | C |
| ATOM | 7083 | OH | TYR | 477 | -17.915 | -18.373 | -11.247 | 64.44 | O |
| ATOM | 7084 | HH | TYR | 477 | -17.207 | -18.894 | -11.651 | 0.00 | H |
| ATOM | 7085 | C | TYR | 477 | -23.403 | -22.973 | -7.913 | 61.42 | C |
| ATOM | 7086 | O | TYR | 477 | -23.732 | -24.133 | -8.140 | 60.81 | O |
| ATOM | 7087 | N | SER | 478 | -24.175 | -22.116 | -7.254 | 61.02 | N |
| ATOM | 7088 | HN | SER | 478 | -23.824 | -21.182 | -7.102 | 0.00 | H |
| ATOM | 7089 | CA | SER | 478 | -25.492 | -22.489 | -6.756 | 58.36 | C |
| ATOM | 7090 | HA | SER | 478 | -25.389 | -23.230 | -6.007 | 0.00 | H |
| ATOM | 7091 | CB | SER | 478 | -26.192 | -21.274 | -6.163 | 58.05 | C |
| ATOM | 7092 | HB2 | SER | 478 | -25.744 | -21.026 | -5.236 | 0.00 | H |
| ATOM | 7093 | HB3 | SER | 478 | -26.103 | -20.455 | -6.829 | 0.00 | H |
| ATOM | 7094 | OG | SER | 478 | -27.565 | -21.558 | -5.955 | 57.45 | O |
| ATOM | 7095 | HG | SER | 478 | -28.001 | -20.781 | -5.579 | 0.00 | H |
| ATOM | 7096 | C | SER | 478 | -26.406 | -23.081 | -7.825 | 58.21 | C |
| ATOM | 7097 | O | SER | 478 | -26.325 | -22.721 | -9.001 | 57.33 | O |
| ATOM | 7098 | N | PRO | 479 | -27.295 | -24.003 | -7.425 | 57.33 | N |
| ATOM | 7099 | CD | PRO | 479 | -27.409 | -24.685 | -6.125 | 56.98 | C |
| ATOM | 7100 | HD2 | PRO | 479 | -26.448 | -24.777 | -5.689 | 0.00 | H |
| ATOM | 7101 | HD3 | PRO | 479 | -28.035 | -24.121 | -5.484 | 0.00 | H |
| ATOM | 7102 | CA | PRO | 479 | -28.204 | -24.598 | -8.405 | 56.72 | C |
| ATOM | 7103 | HA | PRO | 479 | -27.641 | -25.045 | -9.182 | 0.00 | H |
| ATOM | 7104 | CB | PRO | 479 | -28.996 | -25.603 | -7.575 | 56.52 | C |
| ATOM | 7105 | HB2 | PRO | 479 | -29.853 | -25.130 | -7.171 | 0.00 | H |
| ATOM | 7106 | HB3 | PRO | 479 | -29.297 | -26.410 | -8.191 | 0.00 | H |
| ATOM | 7107 | CG | PRO | 479 | -28.009 | -26.011 | -6.525 | 56.67 | C |
| ATOM | 7108 | HG2 | PRO | 479 | -28.518 | -26.493 | -5.731 | 0.00 | H |
| ATOM | 7109 | HG3 | PRO | 479 | -27.301 | -26.677 | -6.946 | 0.00 | H |
| ATOM | 7110 | C | PRO | 479 | -29.083 | -23.487 | -8.963 | 55.96 | C |
| ATOM | 7111 | O | PRO | 479 | -29.059 | -23.200 | -10.160 | 55.56 | O |
| ATOM | 7112 | N | GLY | 480 | -29.842 | -22.852 | -8.074 | 55.09 | N |
| ATOM | 7113 | HN | GLY | 480 | -29.807 | -23.130 | -7.105 | 0.00 | H |
| ATOM | 7114 | CA | GLY | 480 | -30.714 | -21.769 | -8.487 | 55.08 | C |
| ATOM | 7115 | HA2 | GLY | 480 | -31.564 | -22.168 | -8.978 | 0.00 | H |
| ATOM | 7116 | HA3 | GLY | 480 | -31.023 | -21.220 | -7.636 | 0.00 | H |
| ATOM | 7117 | C | GLY | 480 | -30.020 | -20.815 | -9.440 | 55.12 | C |
| ATOM | 7118 | O | GLY | 480 | -30.607 | -20.392 | -10.438 | 56.07 | O |
| ATOM | 7119 | N | GLU | 481 | -28.762 | -20.496 | -9.131 | 54.64 | N |
| ATOM | 7120 | HN | GLU | 481 | -28.383 | -20.922 | -8.299 | 0.00 | H |
| ATOM | 7121 | CA | GLU | 481 | -27.939 | -19.583 | -9.926 | 53.53 | C |
| ATOM | 7122 | HA | GLU | 481 | -28.484 | -18.696 | -10.121 | 0.00 | H |
| ATOM | 7123 | CB | GLU | 481 | -26.657 | -19.234 | -9.153 | 51.57 | C |
| ATOM | 7124 | HB2 | GLU | 481 | -26.913 | -18.817 | -8.214 | 0.00 | H |
| ATOM | 7125 | HB3 | GLU | 481 | -26.084 | -20.112 | -9.005 | 0.00 | H |
| ATOM | 7126 | CG | GLU | 481 | -25.731 | -18.219 | -9.844 | 49.77 | C |
| ATOM | 7127 | HG2 | GLU | 481 | -24.904 | -18.012 | -9.216 | 0.00 | H |
| ATOM | 7128 | HG3 | GLU | 481 | -25.386 | -18.623 | -10.760 | 0.00 | H |
| ATOM | 7129 | CD | GLU | 481 | -26.409 | -16.890 | -10.158 | 47.32 | C |
| ATOM | 7130 | OE1 | GLU | 481 | -27.220 | -16.419 | -9.328 | 45.91 | O1- |
| ATOM | 7131 | OE2 | GLU | 481 | -26.113 | -16.311 | -11.226 | 44.38 | O |
| ATOM | 7132 | C | GLU | 481 | -27.582 | -20.166 | -11.295 | 53.90 | C |
| ATOM | 7133 | O | GLU | 481 | -27.709 | -19.486 | -12.322 | 51.78 | O |
| ATOM | 7134 | N | ILE | 482 | -27.130 | -21.423 | -11.294 | 54.76 | N |
| ATOM | 7135 | HN | ILE | 482 | -27.045 | -21.888 | -10.402 | 0.00 | H |
| ATOM | 7136 | CA | ILE | 482 | -26.763 | -22.127 | -12.524 | 54.19 | C |
| ATOM | 7137 | HA | ILE | 482 | -25.957 | -21.624 | -12.992 | 0.00 | H |
| ATOM | 7138 | CB | ILE | 482 | -26.328 | -23.584 | -12.250 | 53.97 | C |
| ATOM | 7139 | HB | ILE | 482 | -27.079 | -24.077 | -11.689 | 0.00 | H |
| ATOM | 7140 | CG2 | ILE | 482 | -26.123 | -24.313 | -13.565 | 53.24 | C |
| ATOM | 7141 | HG21 | ILE | 482 | -27.029 | -24.315 | -14.113 | 0.00 | H |
| ATOM | 7142 | HG22 | ILE | 482 | -25.372 | -23.822 | -14.127 | 0.00 | H |
| ATOM | 7143 | HG23 | ILE | 482 | -25.825 | -25.311 | -13.373 | 0.00 | H |
| ATOM | 7144 | CG1 | ILE | 482 | -25.047 | -23.615 | -11.413 | 54.10 | C |

FIGURE 6-95-

```
ATOM   7145  HG12 ILE  482    -24.261 -23.157 -11.954   0.00    H
ATOM   7146  HG13 ILE  482    -25.205 -23.090 -10.507   0.00    H
ATOM   7147  CD1  ILE  482    -24.593 -25.019 -11.052  53.46    C
ATOM   7148  HD11 ILE  482    -25.350 -25.501 -10.491   0.00    H
ATOM   7149  HD12 ILE  482    -24.406 -25.568 -11.938   0.00    H
ATOM   7150  HD13 ILE  482    -23.706 -24.966 -10.476   0.00    H
ATOM   7151  C    ILE  482    -27.978 -22.178 -13.435  54.14    C
ATOM   7152  O    ILE  482    -27.867 -22.034 -14.653  53.51    O
ATOM   7153  N    ASN  483    -29.138 -22.387 -12.826  54.46    N
ATOM   7154  HN   ASN  483    -29.142 -22.495 -11.823   0.00    H
ATOM   7155  CA   ASN  483    -30.381 -22.461 -13.568  55.76    C
ATOM   7156  HA   ASN  483    -30.283 -23.166 -14.352   0.00    H
ATOM   7157  CB   ASN  483    -31.519 -22.893 -12.648  58.31    C
ATOM   7158  HB2  ASN  483    -31.580 -22.228 -11.826   0.00    H
ATOM   7159  HB3  ASN  483    -32.432 -22.876 -13.184   0.00    H
ATOM   7160  CG   ASN  483    -31.319 -24.289 -12.108  60.48    C
ATOM   7161  OD1  ASN  483    -30.986 -25.212 -12.862  60.53    O
ATOM   7162  ND2  ASN  483    -31.522 -24.461 -10.796  61.82    N
ATOM   7163  HD21 ASN  483    -31.793 -23.678 -10.220   0.00    H
ATOM   7164  HD22 ASN  483    -31.404 -25.374 -10.383   0.00    H
ATOM   7165  C    ASN  483    -30.723 -21.138 -14.220  55.29    C
ATOM   7166  O    ASN  483    -30.885 -21.072 -15.438  56.09    O
ATOM   7167  N    ARG  484    -30.825 -20.084 -13.418  53.93    N
ATOM   7168  HN   ARG  484    -30.672 -20.190 -12.426   0.00    H
ATOM   7169  CA   ARG  484    -31.156 -18.778 -13.967  52.54    C
ATOM   7170  HA   ARG  484    -32.177 -18.762 -14.249   0.00    H
ATOM   7171  CB   ARG  484    -30.910 -17.680 -12.928  51.98    C
ATOM   7172  HB2  ARG  484    -31.492 -17.874 -12.065   0.00    H
ATOM   7173  HB3  ARG  484    -29.884 -17.666 -12.666   0.00    H
ATOM   7174  CG   ARG  484    -31.278 -16.286 -13.430  52.49    C
ATOM   7175  HG2  ARG  484    -30.548 -15.956 -14.122   0.00    H
ATOM   7176  HG3  ARG  484    -32.224 -16.320 -13.904   0.00    H
ATOM   7177  CD   ARG  484    -31.354 -15.263 -12.307  52.75    C
ATOM   7178  HD2  ARG  484    -31.489 -14.297 -12.718   0.00    H
ATOM   7179  HD3  ARG  484    -32.171 -15.494 -11.674   0.00    H
ATOM   7180  NE   ARG  484    -30.145 -15.239 -11.490  53.88    N1+
ATOM   7181  HE   ARG  484    -29.435 -15.944 -11.619   0.00    H
ATOM   7182  CZ   ARG  484    -29.898 -14.326 -10.555  55.13    C
ATOM   7183  NH1  ARG  484    -30.779 -13.360 -10.321  55.20    N
ATOM   7184  HH11 ARG  484    -30.592 -12.667  -9.612   0.00    H
ATOM   7185  HH12 ARG  484    -31.636 -13.319 -10.853   0.00    H
ATOM   7186  NH2  ARG  484    -28.773 -14.378  -9.853  55.85    N
ATOM   7187  HH21 ARG  484    -28.588 -13.684  -9.144   0.00    H
ATOM   7188  HH22 ARG  484    -28.103 -15.111 -10.028   0.00    H
ATOM   7189  C    ARG  484    -30.358 -18.499 -15.245  51.58    C
ATOM   7190  O    ARG  484    -30.898 -17.956 -16.213  51.70    O
ATOM   7191  N    VAL  485    -29.086 -18.895 -15.260  50.36    N
ATOM   7192  HN   VAL  485    -28.710 -19.355 -14.444   0.00    H
ATOM   7193  CA   VAL  485    -28.236 -18.674 -16.433  49.80    C
ATOM   7194  HA   VAL  485    -28.271 -17.652 -16.706   0.00    H
ATOM   7195  CB   VAL  485    -26.750 -19.053 -16.153  48.53    C
ATOM   7196  HB   VAL  485    -26.675 -20.101 -16.008   0.00    H
ATOM   7197  CG1  VAL  485    -25.874 -18.692 -17.356  45.56    C
ATOM   7198  HG11 VAL  485    -26.212 -19.219 -18.210   0.00    H
ATOM   7199  HG12 VAL  485    -25.936 -17.650 -17.536   0.00    H
ATOM   7200  HG13 VAL  485    -24.869 -18.956 -17.153   0.00    H
ATOM   7201  CG2  VAL  485    -26.255 -18.343 -14.907  46.99    C
ATOM   7202  HG21 VAL  485    -26.325 -17.296 -15.048   0.00    H
ATOM   7203  HG22 VAL  485    -26.849 -18.628 -14.078   0.00    H
ATOM   7204  HG23 VAL  485    -25.246 -18.608 -14.726   0.00    H
ATOM   7205  C    VAL  485    -28.733 -19.485 -17.628  50.27    C
ATOM   7206  O    VAL  485    -29.118 -18.918 -18.652  49.51    O
ATOM   7207  N    ALA  486    -28.726 -20.810 -17.490  51.48    N
ATOM   7208  HN   ALA  486    -28.399 -21.193 -16.616   0.00    H
ATOM   7209  CA   ALA  486    -29.174 -21.705 -18.560  51.98    C
ATOM   7210  HA   ALA  486    -28.484 -21.669 -19.362   0.00    H
ATOM   7211  CB   ALA  486    -29.265 -23.128 -18.044  50.32    C
ATOM   7212  HB1  ALA  486    -28.312 -23.442 -17.704   0.00    H
ATOM   7213  HB2  ALA  486    -29.957 -23.170 -17.243   0.00    H
ATOM   7214  HB3  ALA  486    -29.589 -23.766 -18.824   0.00    H
ATOM   7215  C    ALA  486    -30.522 -21.259 -19.136  52.94    C
ATOM   7216  O    ALA  486    -30.680 -21.145 -20.358  53.11    O
ATOM   7217  N    SER  487    -31.489 -21.001 -18.261  53.10    N
ATOM   7218  HN   SER  487    -31.315 -21.120 -17.274   0.00    H
ATOM   7219  CA   SER  487    -32.791 -20.549 -18.720  54.33    C
ATOM   7220  HA   SER  487    -33.265 -21.327 -19.260   0.00    H
```

FIGURE 6- 96 -

```
ATOM   7221  CB   SER  487   -33.674 -20.160 -17.536  54.70       C
ATOM   7222  HB2  SER  487   -34.001 -19.159 -17.653   0.00       H
ATOM   7223  HB3  SER  487   -34.514 -20.803 -17.496   0.00       H
ATOM   7224  OG   SER  487   -32.960 -20.267 -16.318  55.70       O
ATOM   7225  HG   SER  487   -33.537 -20.017 -15.583   0.00       H
ATOM   7226  C    SER  487   -32.587 -19.342 -19.625  56.00       C
ATOM   7227  O    SER  487   -33.024 -19.344 -20.775  56.68       O
ATOM   7228  N    CYS  488   -31.905 -18.324 -19.102  56.95       N
ATOM   7229  HN   CYS  488   -31.567 -18.419 -18.156   0.00       H
ATOM   7230  CA   CYS  488   -31.642 -17.100 -19.852  57.23       C
ATOM   7231  HA   CYS  488   -32.554 -16.590 -20.026   0.00       H
ATOM   7232  CB   CYS  488   -30.743 -16.161 -19.040  57.99       C
ATOM   7233  HB2  CYS  488   -31.174 -15.997 -18.087   0.00       H
ATOM   7234  HB3  CYS  488   -29.786 -16.601 -18.924   0.00       H
ATOM   7235  SG   CYS  488   -30.476 -14.509 -19.788  60.12       S
ATOM   7236  HG   CYS  488   -29.733 -13.831 -19.046   0.00       H
ATOM   7237  C    CYS  488   -30.992 -17.400 -21.197  57.24       C
ATOM   7238  O    CYS  488   -31.393 -16.841 -22.219  57.03       O
ATOM   7239  N    LEU  489   -30.000 -18.350 -21.216  57.47       N
ATOM   7240  HN   LEU  489   -29.807 -18.864 -20.352   0.00       H
ATOM   7241  CA   LEU  489   -29.294 -18.588 -22.453  57.35       C
ATOM   7242  HA   LEU  489   -28.952 -17.636 -22.859   0.00       H
ATOM   7243  CB   LEU  489   -28.153 -19.591 -22.257  56.47       C
ATOM   7244  HB2  LEU  489   -28.504 -20.420 -21.633   0.00       H
ATOM   7245  HB3  LEU  489   -27.885 -20.046 -23.218   0.00       H
ATOM   7246  CG   LEU  489   -26.900 -18.966 -21.625  56.40       C
ATOM   7247  HG   LEU  489   -27.185 -18.327 -20.782   0.00       H
ATOM   7248  CD1  LEU  489   -25.978 -20.058 -21.089  56.21       C
ATOM   7249  HD11 LEU  489   -26.489 -20.684 -20.352   0.00       H
ATOM   7250  HD12 LEU  489   -25.612 -20.703 -21.891   0.00       H
ATOM   7251  HD13 LEU  489   -25.109 -19.613 -20.598   0.00       H
ATOM   7252  CD2  LEU  489   -26.147 -18.123 -22.650  56.49       C
ATOM   7253  HD21 LEU  489   -25.929 -18.702 -23.548   0.00       H
ATOM   7254  HD22 LEU  489   -26.713 -17.232 -22.934   0.00       H
ATOM   7255  HD23 LEU  489   -25.181 -17.797 -22.276   0.00       H
ATOM   7256  C    LEU  489   -30.304 -19.179 -23.425  58.04       C
ATOM   7257  O    LEU  489   -30.183 -19.026 -24.639  57.53       O
ATOM   7258  N    ARG  490   -31.274 -19.970 -22.852  58.58       N
ATOM   7259  HN   ARG  490   -31.246 -20.147 -21.859   0.00       H
ATOM   7260  CA   ARG  490   -32.334 -20.543 -23.662  59.05       C
ATOM   7261  HA   ARG  490   -31.913 -21.015 -24.512   0.00       H
ATOM   7262  CB   ARG  490   -33.122 -21.577 -22.860  59.79       C
ATOM   7263  HB2  ARG  490   -33.129 -21.300 -21.838   0.00       H
ATOM   7264  HB3  ARG  490   -34.117 -21.620 -23.221   0.00       H
ATOM   7265  CG   ARG  490   -32.546 -22.976 -22.948  59.87       C
ATOM   7266  HG2  ARG  490   -32.388 -23.229 -23.964   0.00       H
ATOM   7267  HG3  ARG  490   -31.624 -23.012 -22.427   0.00       H
ATOM   7268  CD   ARG  490   -33.501 -23.991 -22.330  60.22       C
ATOM   7269  HD2  ARG  490   -34.499 -23.721 -22.558   0.00       H
ATOM   7270  HD3  ARG  490   -33.297 -24.953 -22.723   0.00       H
ATOM   7271  NE   ARG  490   -33.392 -24.080 -20.874  58.66       N1+
ATOM   7272  HE   ARG  490   -34.172 -23.813 -20.292   0.00       H
ATOM   7273  CZ   ARG  490   -32.303 -24.502 -20.232  57.37       C
ATOM   7274  NH1  ARG  490   -31.221 -24.865 -20.914  55.70       N
ATOM   7275  HH11 ARG  490   -30.399 -25.184 -20.424   0.00       H
ATOM   7276  HH12 ARG  490   -31.222 -24.822 -21.922   0.00       H
ATOM   7277  NH2  ARG  490   -32.307 -24.593 -18.911  56.48       N
ATOM   7278  HH21 ARG  490   -31.483 -24.912 -18.425   0.00       H
ATOM   7279  HH22 ARG  490   -33.134 -24.343 -18.391   0.00       H
ATOM   7280  C    ARG  490   -33.270 -19.442 -24.160  59.14       C
ATOM   7281  O    ARG  490   -33.455 -19.286 -25.368  59.56       O
ATOM   7282  N    LYS  491   -33.847 -18.676 -23.234  58.71       N
ATOM   7283  HN   LYS  491   -33.647 -18.855 -22.261   0.00       H
ATOM   7284  CA   LYS  491   -34.754 -17.594 -23.605  58.52       C
ATOM   7285  HA   LYS  491   -35.651 -18.003 -23.992   0.00       H
ATOM   7286  CB   LYS  491   -35.103 -16.713 -22.400  59.15       C
ATOM   7287  HB2  LYS  491   -35.745 -17.246 -21.747   0.00       H
ATOM   7288  HB3  LYS  491   -34.215 -16.451 -21.886   0.00       H
ATOM   7289  CG   LYS  491   -35.819 -15.404 -22.796  59.76       C
ATOM   7290  HG2  LYS  491   -35.156 -14.742 -23.351   0.00       H
ATOM   7291  HG3  LYS  491   -36.668 -15.631 -23.387   0.00       H
ATOM   7292  CD   LYS  491   -36.303 -14.581 -21.592  59.46       C
ATOM   7293  HD2  LYS  491   -36.881 -13.762 -21.934   0.00       H
ATOM   7294  HD3  LYS  491   -36.895 -15.192 -20.962   0.00       H
ATOM   7295  CE   LYS  491   -35.149 -14.027 -20.760  58.88       C
ATOM   7296  HE2  LYS  491   -34.565 -14.829 -20.388   0.00       H
```

FIGURE 6-97-

```
ATOM   7297  HE3 LYS  491   -34.546 -13.402 -21.365   0.00    H
ATOM   7298  NZ  LYS  491   -35.638 -13.226 -19.600  57.41    N1+
ATOM   7299  HZ1 LYS  491   -36.188 -12.450 -19.935   0.00    H
ATOM   7300  HZ2 LYS  491   -36.207 -13.809 -19.005   0.00    H
ATOM   7301  HZ3 LYS  491   -34.850 -12.878 -19.076   0.00    H
ATOM   7302  C   LYS  491   -34.156 -16.716 -24.688  58.45    C
ATOM   7303  O   LYS  491   -34.812 -16.411 -25.682  58.19    O
ATOM   7304  N   LEU  492   -32.880 -16.267 -24.431  58.71    N
ATOM   7305  HN  LEU  492   -32.366 -16.646 -23.626   0.00    H
ATOM   7306  CA  LEU  492   -32.220 -15.373 -25.372  59.49    C
ATOM   7307  HA  LEU  492   -32.918 -14.569 -25.602   0.00    H
ATOM   7308  CB  LEU  492   -30.878 -14.803 -24.888  58.41    C
ATOM   7309  HB2 LEU  492   -30.504 -15.362 -24.027   0.00    H
ATOM   7310  HB3 LEU  492   -30.136 -14.929 -25.679   0.00    H
ATOM   7311  CG  LEU  492   -30.883 -13.301 -24.569  56.75    C
ATOM   7312  HG  LEU  492   -31.128 -12.754 -25.486   0.00    H
ATOM   7313  CD1 LEU  492   -31.914 -12.939 -23.515  57.22    C
ATOM   7314  HD11 LEU 492   -32.925 -13.196 -23.838   0.00    H
ATOM   7315  HD12 LEU 492   -31.722 -13.464 -22.576   0.00    H
ATOM   7316  HD13 LEU 492   -31.890 -11.862 -23.322   0.00    H
ATOM   7317  CD2 LEU  492   -29.495 -12.852 -24.100  55.72    C
ATOM   7318  HD21 LEU 492   -29.217 -13.335 -23.158   0.00    H
ATOM   7319  HD22 LEU 492   -28.722 -13.097 -24.833   0.00    H
ATOM   7320  HD23 LEU 492   -29.468 -11.770 -23.942   0.00    H
ATOM   7321  C   LEU  492   -32.002 -16.087 -26.700  60.41    C
ATOM   7322  O   LEU  492   -31.930 -15.465 -27.762  61.14    O
ATOM   7323  N   GLY  493   -31.797 -17.434 -26.610  60.81    N
ATOM   7324  HN  GLY  493   -31.776 -17.873 -25.689   0.00    H
ATOM   7325  CA  GLY  493   -31.690 -18.265 -27.790  61.41    C
ATOM   7326  HA2 GLY  493   -32.123 -19.242 -27.577   0.00    H
ATOM   7327  HA3 GLY  493   -32.225 -17.813 -28.626   0.00    H
ATOM   7328  C   GLY  493   -30.241 -18.465 -28.185  61.35    C
ATOM   7329  O   GLY  493   -29.893 -18.739 -29.334  61.68    O
ATOM   7330  N   VAL  494   -29.398 -18.437 -27.113  60.36    N
ATOM   7331  HN  VAL  494   -29.845 -18.489 -26.189   0.00    H
ATOM   7332  CA  VAL  494   -27.968 -18.604 -27.186  59.49    C
ATOM   7333  HA  VAL  494   -27.635 -18.258 -28.163   0.00    H
ATOM   7334  CB  VAL  494   -27.265 -17.813 -26.057  59.21    C
ATOM   7335  HB  VAL  494   -27.320 -18.410 -25.145   0.00    H
ATOM   7336  CG1 VAL  494   -25.800 -17.550 -26.364  57.90    C
ATOM   7337  HG11 VAL 494   -25.253 -18.483 -26.428   0.00    H
ATOM   7338  HG12 VAL 494   -25.679 -17.019 -27.311   0.00    H
ATOM   7339  HG13 VAL 494   -25.322 -16.962 -25.575   0.00    H
ATOM   7340  CG2 VAL  494   -27.926 -16.475 -25.750  58.15    C
ATOM   7341  HG21 VAL 494   -28.034 -15.864 -26.651   0.00    H
ATOM   7342  HG22 VAL 494   -28.909 -16.638 -25.310   0.00    H
ATOM   7343  HG23 VAL 494   -27.356 -15.903 -25.011   0.00    H
ATOM   7344  C   VAL  494   -27.683 -20.112 -27.037  59.53    C
ATOM   7345  O   VAL  494   -28.454 -20.921 -26.517  58.97    O
ATOM   7346  N   PRO  495   -26.456 -20.545 -27.504  59.73    N
ATOM   7347  CD  PRO  495   -25.752 -20.047 -28.674  60.00    C
ATOM   7348  HD2 PRO  495   -26.450 -19.704 -29.440   0.00    H
ATOM   7349  HD3 PRO  495   -25.110 -19.215 -28.395   0.00    H
ATOM   7350  CA  PRO  495   -25.954 -21.851 -27.105  60.72    C
ATOM   7351  HA  PRO  495   -26.683 -22.593 -27.427   0.00    H
ATOM   7352  CB  PRO  495   -24.657 -22.007 -27.873  60.13    C
ATOM   7353  HB2 PRO  495   -23.809 -21.583 -27.325   0.00    H
ATOM   7354  HB3 PRO  495   -24.437 -23.055 -28.076   0.00    H
ATOM   7355  CG  PRO  495   -24.914 -21.221 -29.146  60.25    C
ATOM   7356  HG2 PRO  495   -23.996 -20.908 -29.650   0.00    H
ATOM   7357  HG3 PRO  495   -25.493 -21.833 -29.846   0.00    H
ATOM   7358  C   PRO  495   -25.739 -21.937 -25.584  61.69    C
ATOM   7359  O   PRO  495   -25.503 -20.942 -24.905  61.74    O
ATOM   7360  N   PRO  496   -25.842 -23.205 -25.031  62.10    N
ATOM   7361  CD  PRO  496   -26.094 -24.462 -25.712  61.71    C
ATOM   7362  HD2 PRO  496   -27.115 -24.438 -26.104   0.00    H
ATOM   7363  HD3 PRO  496   -25.407 -24.602 -26.548   0.00    H
ATOM   7364  CA  PRO  496   -25.692 -23.401 -23.590  62.31    C
ATOM   7365  HA  PRO  496   -26.234 -22.633 -23.038   0.00    H
ATOM   7366  CB  PRO  496   -26.284 -24.789 -23.357  62.46    C
ATOM   7367  HB2 PRO  496   -25.895 -25.304 -22.474   0.00    H
ATOM   7368  HB3 PRO  496   -27.373 -24.715 -23.254   0.00    H
ATOM   7369  CG  PRO  496   -25.944 -25.528 -24.643  62.92    C
ATOM   7370  HG2 PRO  496   -24.907 -25.875 -24.611   0.00    H
ATOM   7371  HG3 PRO  496   -26.584 -26.396 -24.822   0.00    H
ATOM   7372  C   PRO  496   -24.210 -23.373 -23.166  62.31    C
```

FIGURE 6-98 -

```
ATOM   7373  O    PRO  496    -23.301 -23.451 -23.984   62.60      O
ATOM   7374  N    LEU  497    -23.998 -23.385 -21.793   62.33      N
ATOM   7375  HN   LEU  497    -24.834 -23.372 -21.229    0.00      H
ATOM   7376  CA   LEU  497    -22.690 -23.271 -21.160   62.18      C
ATOM   7377  HA   LEU  497    -22.333 -22.279 -21.263    0.00      H
ATOM   7378  CB   LEU  497    -22.799 -23.617 -19.669   60.19      C
ATOM   7379  HB2  LEU  497    -23.231 -24.578 -19.560    0.00      H
ATOM   7380  HB3  LEU  497    -21.833 -23.612 -19.234    0.00      H
ATOM   7381  CG   LEU  497    -23.659 -22.653 -18.839   58.93      C
ATOM   7382  HG   LEU  497    -24.665 -22.708 -19.165    0.00      H
ATOM   7383  CD1  LEU  497    -23.593 -23.024 -17.362   56.95      C
ATOM   7384  HD11 LEU  497    -23.954 -24.011 -17.229    0.00      H
ATOM   7385  HD12 LEU  497    -22.590 -22.967 -17.028    0.00      H
ATOM   7386  HD13 LEU  497    -24.190 -22.352 -16.802    0.00      H
ATOM   7387  CD2  LEU  497    -23.161 -21.230 -19.037   58.12      C
ATOM   7388  HD21 LEU  497    -22.152 -21.162 -18.723    0.00      H
ATOM   7389  HD22 LEU  497    -23.230 -20.971 -20.062    0.00      H
ATOM   7390  HD23 LEU  497    -23.754 -20.565 -18.464    0.00      H
ATOM   7391  C    LEU  497    -21.639 -24.149 -21.827   63.20      C
ATOM   7392  O    LEU  497    -20.499 -23.725 -22.032   62.06      O
ATOM   7393  N    ARG  498    -22.011 -25.472 -22.091   65.17      N
ATOM   7394  HN   ARG  498    -22.995 -25.702 -21.965    0.00      H
ATOM   7395  CA   ARG  498    -21.074 -26.551 -22.457   66.71      C
ATOM   7396  HA   ARG  498    -20.339 -26.605 -21.645    0.00      H
ATOM   7397  CB   ARG  498    -21.810 -27.910 -22.613   69.19      C
ATOM   7398  HB2  ARG  498    -21.075 -28.714 -22.485    0.00      H
ATOM   7399  HB3  ARG  498    -22.551 -28.037 -21.815    0.00      H
ATOM   7400  CG   ARG  498    -22.481 -28.096 -23.989   72.91      C
ATOM   7401  HG2  ARG  498    -23.222 -27.309 -24.157    0.00      H
ATOM   7402  HG3  ARG  498    -21.733 -27.996 -24.780    0.00      H
ATOM   7403  CD   ARG  498    -23.128 -29.455 -24.202   75.95      C
ATOM   7404  HD2  ARG  498    -22.463 -30.243 -23.833    0.00      H
ATOM   7405  HD3  ARG  498    -24.088 -29.499 -23.677    0.00      H
ATOM   7406  NE   ARG  498    -23.356 -29.692 -25.636   77.45      N1+
ATOM   7407  HE   ARG  498    -23.124 -28.964 -26.308    0.00      H
ATOM   7408  CZ   ARG  498    -23.810 -30.843 -26.158   78.58      C
ATOM   7409  NH1  ARG  498    -24.170 -31.868 -25.376   79.84      N
ATOM   7410  HH11 ARG  498    -24.513 -32.733 -25.780    0.00      H
ATOM   7411  HH12 ARG  498    -24.128 -31.806 -24.368    0.00      H
ATOM   7412  NH2  ARG  498    -23.919 -31.002 -27.475   78.74      N
ATOM   7413  HH21 ARG  498    -24.264 -31.858 -27.884    0.00      H
ATOM   7414  HH22 ARG  498    -23.653 -30.275 -28.157    0.00      H
ATOM   7415  C    ARG  498    -20.317 -26.293 -23.777   66.42      C
ATOM   7416  O    ARG  498    -19.310 -26.912 -24.117   67.11      O
ATOM   7417  N    THR  499    -21.017 -25.454 -24.584   65.91      N
ATOM   7418  HN   THR  499    -21.811 -24.976 -24.154    0.00      H
ATOM   7419  CA   THR  499    -20.756 -25.096 -25.965   66.07      C
ATOM   7420  HA   THR  499    -20.084 -25.853 -26.378    0.00      H
ATOM   7421  CB   THR  499    -22.096 -25.066 -26.739   67.34      C
ATOM   7422  HB   THR  499    -22.850 -24.515 -26.173    0.00      H
ATOM   7423  OG1  THR  499    -22.598 -26.412 -26.915   68.02      O
ATOM   7424  HG1  THR  499    -23.506 -26.330 -27.274    0.00      H
ATOM   7425  CG2  THR  499    -21.982 -24.439 -28.115   68.08      C
ATOM   7426  HG21 THR  499    -21.830 -23.358 -28.063    0.00      H
ATOM   7427  HG22 THR  499    -21.150 -24.887 -28.664    0.00      H
ATOM   7428  HG23 THR  499    -22.893 -24.618 -28.690    0.00      H
ATOM   7429  C    THR  499    -20.029 -23.732 -25.998   65.70      C
ATOM   7430  O    THR  499    -19.516 -23.284 -27.025   66.01      O
ATOM   7431  N    TRP  500    -20.020 -23.057 -24.797   65.06      N
ATOM   7432  HN   TRP  500    -20.501 -23.494 -24.013    0.00      H
ATOM   7433  CA   TRP  500    -19.148 -21.923 -24.516   64.75      C
ATOM   7434  HA   TRP  500    -18.819 -21.526 -25.470    0.00      H
ATOM   7435  CB   TRP  500    -19.804 -20.823 -23.694   61.72      C
ATOM   7436  HB2  TRP  500    -20.236 -21.235 -22.781    0.00      H
ATOM   7437  HB3  TRP  500    -19.055 -20.097 -23.378    0.00      H
ATOM   7438  CG   TRP  500    -20.859 -20.108 -24.485   58.55      C
ATOM   7439  CD2  TRP  500    -20.639 -19.265 -25.625   56.88      C
ATOM   7440  CE2  TRP  500    -21.895 -18.892 -26.109   56.47      C
ATOM   7441  CE3  TRP  500    -19.488 -18.813 -26.303   56.23      C
ATOM   7442  HE3  TRP  500    -18.506 -19.094 -25.952    0.00      H
ATOM   7443  CD1  TRP  500    -22.225 -20.146 -24.259   57.62      C
ATOM   7444  HD1  TRP  500    -22.805 -20.653 -23.504    0.00      H
ATOM   7445  NE1  TRP  500    -22.833 -19.440 -25.260   56.28      N
ATOM   7446  HE1  TRP  500    -23.838 -19.373 -25.361    0.00      H
ATOM   7447  CZ2  TRP  500    -22.051 -18.119 -27.263   56.36      C
ATOM   7448  HZ2  TRP  500    -23.034 -17.860 -27.631    0.00      H
```

FIGURE 6- 99 -

```
ATOM   7449  CZ3  TRP  500   -19.629 -18.013 -27.439  56.74   C
ATOM   7450  HZ3  TRP  500   -18.738 -17.657 -27.940   0.00   H
ATOM   7451  CH2  TRP  500   -20.895 -17.682 -27.918  55.82   C
ATOM   7452  HH2  TRP  500   -20.990 -17.073 -28.808   0.00   H
ATOM   7453  C    TRP  500   -17.897 -22.411 -23.831  66.62   C
ATOM   7454  O    TRP  500   -16.849 -21.792 -23.891  67.38   O
ATOM   7455  N    ARG  501   -18.022 -23.589 -23.163  67.71   N
ATOM   7456  HN   ARG  501   -18.962 -23.929 -23.023   0.00   H
ATOM   7457  CA   ARG  501   -16.895 -24.284 -22.547  68.98   C
ATOM   7458  HA   ARG  501   -16.380 -23.620 -21.902   0.00   H
ATOM   7459  CB   ARG  501   -17.392 -25.486 -21.735  69.07   C
ATOM   7460  HB2  ARG  501   -18.028 -25.149 -20.958   0.00   H
ATOM   7461  HB3  ARG  501   -17.928 -26.143 -22.369   0.00   H
ATOM   7462  CG   ARG  501   -16.288 -26.294 -21.087  68.65   C
ATOM   7463  HG2  ARG  501   -15.683 -26.732 -21.838   0.00   H
ATOM   7464  HG3  ARG  501   -15.695 -25.659 -20.482   0.00   H
ATOM   7465  CD   ARG  501   -16.833 -27.412 -20.208  69.86   C
ATOM   7466  HD2  ARG  501   -17.375 -26.993 -19.400   0.00   H
ATOM   7467  HD3  ARG  501   -17.474 -28.030 -20.781   0.00   H
ATOM   7468  NE   ARG  501   -15.742 -28.228 -19.674  71.52   N1+
ATOM   7469  HE   ARG  501   -15.665 -29.200 -19.934   0.00   H
ATOM   7470  CZ   ARG  501   -14.803 -27.783 -18.841  72.06   C
ATOM   7471  NH1  ARG  501   -14.815 -26.521 -18.432  72.77   N
ATOM   7472  HH11 ARG  501   -14.101 -26.188 -17.801   0.00   H
ATOM   7473  HH12 ARG  501   -15.538 -25.894 -18.752   0.00   H
ATOM   7474  NH2  ARG  501   -13.840 -28.596 -18.424  71.86   N
ATOM   7475  HH21 ARG  501   -13.130 -28.255 -17.793   0.00   H
ATOM   7476  HH22 ARG  501   -13.818 -29.555 -18.738   0.00   H
ATOM   7477  C    ARG  501   -15.947 -24.755 -23.646  70.27   C
ATOM   7478  O    ARG  501   -14.730 -24.826 -23.461  70.44   O
ATOM   7479  N    HID  502   -16.579 -25.153 -24.796  71.71   N
ATOM   7480  HN   HID  502   -17.583 -24.966 -24.832   0.00   H
ATOM   7481  CA   HID  502   -15.929 -25.797 -25.928  73.75   C
ATOM   7482  HA   HID  502   -15.183 -26.493 -25.533   0.00   H
ATOM   7483  CB   HID  502   -17.005 -26.493 -26.761  75.28   C
ATOM   7484  HB2  HID  502   -17.774 -26.921 -26.111   0.00   H
ATOM   7485  HB3  HID  502   -17.520 -25.782 -27.418   0.00   H
ATOM   7486  CG   HID  502   -16.493 -27.612 -27.589  76.78   C
ATOM   7487  CD2  HID  502   -16.004 -27.640 -28.902  77.01   C
ATOM   7488  HD2  HID  502   -15.850 -26.837 -29.607   0.00   H
ATOM   7489  ND1  HID  502   -16.507 -28.950 -27.134  77.42   N1+
ATOM   7490  HD1  HID  502   -16.848 -29.288 -26.229   0.00   H
ATOM   7491  CE1  HID  502   -16.033 -29.722 -28.120  77.99   C
ATOM   7492  HE1  HID  502   -15.901 -30.799 -28.128   0.00   H
ATOM   7493  NE2  HID  502   -15.714 -28.952 -29.200  78.05   N
ATOM   7494  C    HID  502   -15.213 -24.763 -26.811  74.30   C
ATOM   7495  O    HID  502   -14.389 -25.079 -27.669  73.94   O
ATOM   7496  N    ARG  503   -15.739 -23.506 -26.655  74.81   N
ATOM   7497  HN   ARG  503   -16.372 -23.395 -25.863   0.00   H
ATOM   7498  CA   ARG  503   -15.315 -22.299 -27.338  75.92   C
ATOM   7499  HA   ARG  503   -14.799 -22.614 -28.248   0.00   H
ATOM   7500  CB   ARG  503   -16.515 -21.411 -27.693  75.87   C
ATOM   7501  HB2  ARG  503   -17.393 -21.735 -27.132   0.00   H
ATOM   7502  HB3  ARG  503   -16.332 -20.374 -27.391   0.00   H
ATOM   7503  CG   ARG  503   -16.855 -21.408 -29.192  76.55   C
ATOM   7504  HG2  ARG  503   -16.056 -20.911 -29.751   0.00   H
ATOM   7505  HG3  ARG  503   -16.929 -22.431 -29.577   0.00   H
ATOM   7506  CD   ARG  503   -18.181 -20.687 -29.407  76.56   C
ATOM   7507  HD2  ARG  503   -18.987 -21.334 -29.051   0.00   H
ATOM   7508  HD3  ARG  503   -18.172 -19.762 -28.835   0.00   H
ATOM   7509  NE   ARG  503   -18.458 -20.306 -30.805  76.45   N1+
ATOM   7510  HE   ARG  503   -17.741 -20.361 -31.519   0.00   H
ATOM   7511  CZ   ARG  503   -19.673 -19.826 -31.175  77.30   C
ATOM   7512  NH1  ARG  503   -20.701 -19.783 -30.334  76.96   N
ATOM   7513  HH11 ARG  503   -21.624 -19.516 -30.690   0.00   H
ATOM   7514  HH12 ARG  503   -20.647 -20.093 -29.376   0.00   H
ATOM   7515  NH2  ARG  503   -19.875 -19.376 -32.404  77.67   N
ATOM   7516  HH21 ARG  503   -20.778 -18.979 -32.649   0.00   H
ATOM   7517  HH22 ARG  503   -19.138 -19.369 -33.099   0.00   H
ATOM   7518  C    ARG  503   -14.272 -21.504 -26.518  76.59   C
ATOM   7519  O    ARG  503   -13.424 -20.867 -27.136  75.80   O
ATOM   7520  N    ALA  504   -14.402 -21.557 -25.135  77.96   N
ATOM   7521  HN   ALA  504   -15.253 -22.041 -24.890   0.00   H
ATOM   7522  CA   ALA  504   -13.548 -21.008 -24.087  79.04   C
ATOM   7523  HA   ALA  504   -13.436 -19.965 -24.233   0.00   H
ATOM   7524  CB   ALA  504   -14.170 -21.256 -22.726  78.41   C
```

FIGURE 6- 100 -

```
ATOM   7525  HB1  ALA  504   -15.119 -20.789 -22.681    0.00    H
ATOM   7526  HB2  ALA  504   -14.282 -22.298 -22.574    0.00    H
ATOM   7527  HB3  ALA  504   -13.543 -20.854 -21.973    0.00    H
ATOM   7528  C    ALA  504   -12.147 -21.605 -24.136   80.09    C
ATOM   7529  O    ALA  504   -11.185 -20.991 -23.672   80.59    O
ATOM   7530  N    ARG  505   -12.035 -22.803 -24.703   80.90    N
ATOM   7531  HN   ARG  505   -12.866 -23.250 -25.060    0.00    H
ATOM   7532  CA   ARG  505   -10.746 -23.469 -24.814   80.62    C
ATOM   7533  HA   ARG  505   -10.176 -23.282 -23.941    0.00    H
ATOM   7534  CB   ARG  505   -10.947 -24.979 -24.970   80.81    C
ATOM   7535  HB2  ARG  505   -11.372 -25.182 -25.918    0.00    H
ATOM   7536  HB3  ARG  505   -10.012 -25.470 -24.890    0.00    H
ATOM   7537  CG   ARG  505   -11.874 -25.582 -23.912   81.50    C
ATOM   7538  HG2  ARG  505   -11.741 -25.072 -22.994    0.00    H
ATOM   7539  HG3  ARG  505   -12.880 -25.484 -24.227    0.00    H
ATOM   7540  CD   ARG  505   -11.590 -27.069 -23.677   82.40    C
ATOM   7541  HD2  ARG  505   -12.253 -27.443 -22.941    0.00    H
ATOM   7542  HD3  ARG  505   -11.729 -27.602 -24.581    0.00    H
ATOM   7543  NE   ARG  505   -10.216 -27.297 -23.216   82.81    N1+
ATOM   7544  HE   ARG  505    -9.533 -26.557 -23.279    0.00    H
ATOM   7545  CZ   ARG  505    -9.770 -28.441 -22.701   82.74    C
ATOM   7546  NH1  ARG  505   -10.587 -29.479 -22.572   83.25    N
ATOM   7547  HH11 ARG  505   -10.245 -30.344 -22.181    0.00    H
ATOM   7548  HH12 ARG  505   -11.550 -29.403 -22.865    0.00    H
ATOM   7549  NH2  ARG  505    -8.504 -28.550 -22.312   82.33    N
ATOM   7550  HH21 ARG  505    -8.169 -29.418 -21.922    0.00    H
ATOM   7551  HH22 ARG  505    -7.878 -27.765 -22.407    0.00    H
ATOM   7552  C    ARG  505    -9.944 -22.900 -25.989   80.86    C
ATOM   7553  O    ARG  505    -8.754 -22.628 -25.850   80.64    O
ATOM   7554  N    SER  506   -10.604 -22.711 -27.132   81.73    N
ATOM   7555  HN   SER  506   -11.579 -22.968 -27.154    0.00    H
ATOM   7556  CA   SER  506    -9.966 -22.153 -28.328   82.50    C
ATOM   7557  HA   SER  506    -9.139 -22.756 -28.601    0.00    H
ATOM   7558  CB   SER  506   -10.956 -22.108 -29.502   82.50    C
ATOM   7559  HB2  SER  506   -10.960 -23.044 -29.996    0.00    H
ATOM   7560  HB3  SER  506   -11.927 -21.898 -29.137    0.00    H
ATOM   7561  OG   SER  506   -10.602 -21.101 -30.447   80.81    O
ATOM   7562  HG   SER  506   -11.243 -21.099 -31.171    0.00    H
ATOM   7563  C    SER  506    -9.460 -20.739 -28.061   83.68    C
ATOM   7564  O    SER  506    -8.373 -20.360 -28.504   83.87    O
ATOM   7565  N    VAL  507   -10.266 -19.955 -27.352   84.69    N
ATOM   7566  HN   VAL  507   -11.151 -20.327 -27.040    0.00    H
ATOM   7567  CA   VAL  507    -9.895 -18.586 -27.024   85.35    C
ATOM   7568  HA   VAL  507    -9.807 -18.021 -27.915    0.00    H
ATOM   7569  CB   VAL  507   -10.957 -17.907 -26.116   85.86    C
ATOM   7570  HB   VAL  507   -11.008 -18.417 -25.190    0.00    H
ATOM   7571  CG1  VAL  507   -10.549 -16.458 -25.822   86.23    C
ATOM   7572  HG11 VAL  507    -9.612 -16.448 -25.328    0.00    H
ATOM   7573  HG12 VAL  507   -10.474 -15.921 -26.732    0.00    H
ATOM   7574  HG13 VAL  507   -11.279 -16.004 -25.203    0.00    H
ATOM   7575  CG2  VAL  507   -12.327 -17.954 -26.793   85.83    C
ATOM   7576  HG21 VAL  507   -12.281 -17.442 -27.719    0.00    H
ATOM   7577  HG22 VAL  507   -12.604 -18.962 -26.960    0.00    H
ATOM   7578  HG23 VAL  507   -13.045 -17.490 -26.169    0.00    H
ATOM   7579  C    VAL  507    -8.556 -18.624 -26.298   84.95    C
ATOM   7580  O    VAL  507    -7.569 -18.045 -26.760   85.25    O
ATOM   7581  N    ARG  508    -8.533 -19.325 -25.170   84.53    N
ATOM   7582  HN   ARG  508    -9.390 -19.768 -24.875    0.00    H
ATOM   7583  CA   ARG  508    -7.326 -19.466 -24.367   84.90    C
ATOM   7584  HA   ARG  508    -7.154 -18.571 -23.828    0.00    H
ATOM   7585  CB   ARG  508    -7.489 -20.625 -23.381   84.51    C
ATOM   7586  HB2  ARG  508    -8.321 -20.439 -22.752    0.00    H
ATOM   7587  HB3  ARG  508    -7.646 -21.525 -23.917    0.00    H
ATOM   7588  CG   ARG  508    -6.289 -20.849 -22.477   84.40    C
ATOM   7589  HG2  ARG  508    -5.402 -20.817 -23.054    0.00    H
ATOM   7590  HG3  ARG  508    -6.257 -20.091 -21.738    0.00    H
ATOM   7591  CD   ARG  508    -6.395 -22.199 -21.801   84.93    C
ATOM   7592  HD2  ARG  508    -7.372 -22.584 -21.934    0.00    H
ATOM   7593  HD3  ARG  508    -5.692 -22.865 -22.230    0.00    H
ATOM   7594  NE   ARG  508    -6.130 -22.124 -20.368   85.10    N1+
ATOM   7595  HE   ARG  508    -5.776 -21.270 -19.964    0.00    H
ATOM   7596  CZ   ARG  508    -6.327 -23.132 -19.525   85.39    C
ATOM   7597  NH1  ARG  508    -6.789 -24.287 -19.983   84.44    N
ATOM   7598  HH11 ARG  508    -6.941 -25.057 -19.349    0.00    H
ATOM   7599  HH12 ARG  508    -6.989 -24.396 -20.966    0.00    H
ATOM   7600  NH2  ARG  508    -6.075 -22.980 -18.227   86.34    N
```

FIGURE 6- 101 -

```
ATOM    7601  HH21 ARG   508      -6.226 -23.748 -17.590   0.00           H
ATOM    7602  HH22 ARG   508      -5.733 -22.097 -17.880   0.00           H
ATOM    7603  C    ARG   508      -6.106 -19.729 -25.251  85.26           C
ATOM    7604  O    ARG   508      -5.188 -18.904 -25.330  85.54           O
ATOM    7605  N    ALA   509      -6.116 -20.895 -25.913  84.74           N
ATOM    7606  HN   ALA   509      -6.920 -21.482 -25.787   0.00           H
ATOM    7607  CA   ALA   509      -5.030 -21.302 -26.790  83.86           C
ATOM    7608  HA   ALA   509      -4.187 -21.568 -26.206   0.00           H
ATOM    7609  CB   ALA   509      -5.470 -22.500 -27.615  83.57           C
ATOM    7610  HB1  ALA   509      -5.726 -23.299 -26.969   0.00           H
ATOM    7611  HB2  ALA   509      -6.312 -22.236 -28.200   0.00           H
ATOM    7612  HB3  ALA   509      -4.678 -22.800 -28.251   0.00           H
ATOM    7613  C    ALA   509      -4.553 -20.179 -27.706  83.69           C
ATOM    7614  O    ALA   509      -3.398 -19.757 -27.627  83.40           O
ATOM    7615  N    LYS   510      -5.444 -19.694 -28.566  83.73           N
ATOM    7616  HN   LYS   510      -6.373 -20.088 -28.565   0.00           H
ATOM    7617  CA   LYS   510      -5.108 -18.619 -29.496  84.36           C
ATOM    7618  HA   LYS   510      -4.438 -18.984 -30.231   0.00           H
ATOM    7619  CB   LYS   510      -6.372 -18.098 -30.187  83.14           C
ATOM    7620  HB2  LYS   510      -7.057 -17.753 -29.457   0.00           H
ATOM    7621  HB3  LYS   510      -6.117 -17.301 -30.836   0.00           H
ATOM    7622  CG   LYS   510      -7.092 -19.144 -31.021  81.26           C
ATOM    7623  HG2  LYS   510      -6.382 -19.719 -31.556   0.00           H
ATOM    7624  HG3  LYS   510      -7.653 -19.778 -30.385   0.00           H
ATOM    7625  CD   LYS   510      -8.043 -18.506 -32.021  79.65           C
ATOM    7626  HD2  LYS   510      -8.788 -17.962 -31.502   0.00           H
ATOM    7627  HD3  LYS   510      -7.503 -17.850 -32.653   0.00           H
ATOM    7628  CE   LYS   510      -8.724 -19.559 -32.884  78.22           C
ATOM    7629  HE2  LYS   510      -7.995 -20.220 -33.275   0.00           H
ATOM    7630  HE3  LYS   510      -9.416 -20.104 -32.296   0.00           H
ATOM    7631  NZ   LYS   510      -9.466 -18.959 -34.031  76.74           N1+
ATOM    7632  HZ1  LYS   510     -10.177 -18.334 -33.682   0.00           H
ATOM    7633  HZ2  LYS   510      -8.824 -18.445 -34.615   0.00           H
ATOM    7634  HZ3  LYS   510      -9.899 -19.692 -34.572   0.00           H
ATOM    7635  C    LYS   510      -4.383 -17.458 -28.809  85.94           C
ATOM    7636  O    LYS   510      -3.453 -16.871 -29.375  86.20           O
ATOM    7637  N    LEU   511      -4.809 -17.145 -27.586  87.27           N
ATOM    7638  HN   LEU   511      -5.568 -17.690 -27.205   0.00           H
ATOM    7639  CA   LEU   511      -4.221 -16.060 -26.800  88.20           C
ATOM    7640  HA   LEU   511      -3.964 -15.258 -27.442   0.00           H
ATOM    7641  CB   LEU   511      -5.222 -15.564 -25.755  87.87           C
ATOM    7642  HB2  LEU   511      -5.714 -16.393 -25.316   0.00           H
ATOM    7643  HB3  LEU   511      -4.709 -15.020 -25.005   0.00           H
ATOM    7644  CG   LEU   511      -6.346 -14.637 -26.218  88.26           C
ATOM    7645  HG   LEU   511      -6.894 -15.106 -26.993   0.00           H
ATOM    7646  CD1  LEU   511      -7.255 -14.362 -25.022  88.09           C
ATOM    7647  HD11 LEU   511      -7.657 -15.275 -24.667   0.00           H
ATOM    7648  HD12 LEU   511      -6.694 -13.900 -24.251   0.00           H
ATOM    7649  HD13 LEU   511      -8.044 -13.720 -25.318   0.00           H
ATOM    7650  CD2  LEU   511      -5.772 -13.329 -26.781  87.68           C
ATOM    7651  HD21 LEU   511      -5.210 -12.838 -26.030   0.00           H
ATOM    7652  HD22 LEU   511      -5.144 -13.545 -27.606   0.00           H
ATOM    7653  HD23 LEU   511      -6.565 -12.702 -27.096   0.00           H
ATOM    7654  C    LEU   511      -2.917 -16.438 -26.098  89.05           C
ATOM    7655  O    LEU   511      -2.012 -15.609 -25.961  89.25           O
ATOM    7656  N    LEU   512      -2.830 -17.687 -25.645  89.71           N
ATOM    7657  HN   LEU   512      -3.618 -18.301 -25.784   0.00           H
ATOM    7658  CA   LEU   512      -1.639 -18.174 -24.964  89.67           C
ATOM    7659  HA   LEU   512      -1.409 -17.532 -24.154   0.00           H
ATOM    7660  CB   LEU   512      -1.877 -19.589 -24.431  88.12           C
ATOM    7661  HB2  LEU   512      -2.915 -19.797 -24.433   0.00           H
ATOM    7662  HB3  LEU   512      -1.376 -20.238 -25.049   0.00           H
ATOM    7663  CG   LEU   512      -1.373 -19.798 -23.005  86.90           C
ATOM    7664  HG   LEU   512      -0.322 -19.674 -22.981   0.00           H
ATOM    7665  CD1  LEU   512      -2.024 -18.779 -22.074  86.47           C
ATOM    7666  HD11 LEU   512      -1.776 -17.800 -22.394   0.00           H
ATOM    7667  HD12 LEU   512      -3.076 -18.902 -22.096   0.00           H
ATOM    7668  HD13 LEU   512      -1.672 -18.928 -21.086   0.00           H
ATOM    7669  CD2  LEU   512      -1.684 -21.210 -22.564  85.84           C
ATOM    7670  HD21 LEU   512      -2.731 -21.367 -22.596   0.00           H
ATOM    7671  HD22 LEU   512      -1.204 -21.896 -23.213   0.00           H
ATOM    7672  HD23 LEU   512      -1.335 -21.356 -21.575   0.00           H
ATOM    7673  C    LEU   512      -0.469 -18.163 -25.948  90.79           C
ATOM    7674  O    LEU   512       0.688 -18.036 -25.546  90.71           O
ATOM    7675  N    SER   513      -0.792 -18.290 -27.238  91.95           N
ATOM    7676  HN   SER   513      -1.771 -18.404 -27.454   0.00           H
```

FIGURE 6- 102 -

```
ATOM   7677  CA   SER  513    0.198 -18.270 -28.317   92.92   C
ATOM   7678  HA   SER  513    0.911 -19.036 -28.156    0.00   H
ATOM   7679  CB   SER  513   -0.491 -18.499 -29.672   92.90   C
ATOM   7680  HB2  SER  513   -0.841 -17.574 -30.051    0.00   H
ATOM   7681  HB3  SER  513    0.202 -18.920 -30.353    0.00   H
ATOM   7682  OG   SER  513   -1.600 -19.382 -29.565   93.37   O
ATOM   7683  HG   SER  513   -2.004 -19.499 -30.436    0.00   H
ATOM   7684  C    SER  513    0.835 -16.875 -28.292   94.09   C
ATOM   7685  O    SER  513    1.986 -16.681 -28.694   93.91   O
ATOM   7686  N    GLN  514    0.055 -15.911 -27.804   95.50   N
ATOM   7687  HN   GLN  514   -0.873 -16.177 -27.509    0.00   H
ATOM   7688  CA   GLN  514    0.488 -14.524 -27.687   95.98   C
ATOM   7689  HA   GLN  514    1.057 -14.259 -28.540    0.00   H
ATOM   7690  CB   GLN  514   -0.723 -13.589 -27.587   96.02   C
ATOM   7691  HB2  GLN  514   -1.421 -13.833 -28.345    0.00   H
ATOM   7692  HB3  GLN  514   -1.179 -13.702 -26.638    0.00   H
ATOM   7693  CG   GLN  514   -0.396 -12.115 -27.747   95.77   C
ATOM   7694  HG2  GLN  514   -0.840 -11.567 -26.957    0.00   H
ATOM   7695  HG3  GLN  514    0.654 -11.982 -27.722    0.00   H
ATOM   7696  CD   GLN  514   -0.911 -11.542 -29.063   95.50   C
ATOM   7697  OE1  GLN  514   -1.499 -12.256 -29.880   94.97   O
ATOM   7698  NE2  GLN  514   -0.693 -10.245 -29.269   95.06   N
ATOM   7699 HE21  GLN  514   -0.208  -9.698 -28.574    0.00   H
ATOM   7700 HE22  GLN  514   -1.013  -9.809 -30.121    0.00   H
ATOM   7701  C    GLN  514    1.357 -14.400 -26.445   96.50   C
ATOM   7702  O    GLN  514    1.063 -14.962 -25.388   95.97   O
ATOM   7703  N    GLY  515    2.434 -13.646 -26.594   97.50   N
ATOM   7704  HN   GLY  515    2.606 -13.190 -27.477    0.00   H
ATOM   7705  CA   GLY  515    3.361 -13.474 -25.500   98.39   C
ATOM   7706  HA2  GLY  515    3.338 -14.332 -24.880    0.00   H
ATOM   7707  HA3  GLY  515    4.339 -13.342 -25.884    0.00   H
ATOM   7708  C    GLY  515    3.068 -12.287 -24.621   98.87   C
ATOM   7709  O    GLY  515    2.838 -11.177 -25.096   99.23   O
ATOM   7710  N    GLY  516    3.069 -12.518 -23.319   98.98   N
ATOM   7711  HN   GLY  516    3.232 -13.444 -22.953    0.00   H
ATOM   7712  CA   GLY  516    2.831 -11.418 -22.418   98.92   C
ATOM   7713  HA2  GLY  516    3.442 -11.526 -21.560    0.00   H
ATOM   7714  HA3  GLY  516    3.064 -10.507 -22.904    0.00   H
ATOM   7715  C    GLY  516    1.405 -11.315 -21.939   98.80   C
ATOM   7716  O    GLY  516    0.867 -12.271 -21.378   98.84   O
ATOM   7717  N    ARG  517    0.807 -10.144 -22.169   98.49   N
ATOM   7718  HN   ARG  517    1.357  -9.457 -22.662    0.00   H
ATOM   7719  CA   ARG  517   -0.563  -9.825 -21.752   97.94   C
ATOM   7720  HA   ARG  517   -0.585  -9.662 -20.706    0.00   H
ATOM   7721  CB   ARG  517   -1.071  -8.554 -22.464   98.39   C
ATOM   7722  HB2  ARG  517   -1.502  -8.819 -23.395    0.00   H
ATOM   7723  HB3  ARG  517   -1.800  -8.079 -21.860    0.00   H
ATOM   7724  CG   ARG  517   -0.008  -7.502 -22.765   98.55   C
ATOM   7725  HG2  ARG  517   -0.478  -6.588 -23.019    0.00   H
ATOM   7726  HG3  ARG  517    0.601  -7.360 -21.910    0.00   H
ATOM   7727  CD   ARG  517    0.882  -7.933 -23.931   98.25   C
ATOM   7728  HD2  ARG  517    0.616  -8.912 -24.235    0.00   H
ATOM   7729  HD3  ARG  517    0.751  -7.264 -24.741    0.00   H
ATOM   7730  NE   ARG  517    2.291  -7.932 -23.554   97.92   N1+
ATOM   7731  HE   ARG  517    2.819  -8.792 -23.572    0.00   H
ATOM   7732  CZ   ARG  517    2.958  -6.847 -23.175   98.16   C
ATOM   7733  NH1  ARG  517    2.342  -5.672 -23.124   97.97   N
ATOM   7734 HH11  ARG  517    2.849  -4.849 -22.836    0.00   H
ATOM   7735 HH12  ARG  517    1.367  -5.602 -23.373    0.00   H
ATOM   7736  NH2  ARG  517    4.242  -6.939 -22.854   98.37   N
ATOM   7737 HH21  ARG  517    4.750  -6.116 -22.566    0.00   H
ATOM   7738 HH22  ARG  517    4.710  -7.832 -22.898    0.00   H
ATOM   7739  C    ARG  517   -1.559 -10.958 -21.998   97.33   C
ATOM   7740  O    ARG  517   -2.063 -11.576 -21.053   96.34   O
ATOM   7741  N    ALA  518   -1.850 -11.206 -23.273   97.02   N
ATOM   7742  HN   ALA  518   -1.398 -10.643 -23.978    0.00   H
ATOM   7743  CA   ALA  518   -2.788 -12.252 -23.666   96.70   C
ATOM   7744  HA   ALA  518   -3.778 -11.927 -23.477    0.00   H
ATOM   7745  CB   ALA  518   -2.640 -12.563 -25.154   96.44   C
ATOM   7746  HB1  ALA  518   -2.839 -11.690 -25.719    0.00   H
ATOM   7747  HB2  ALA  518   -1.653 -12.892 -25.349    0.00   H
ATOM   7748  HB3  ALA  518   -3.326 -13.323 -25.426    0.00   H
ATOM   7749  C    ALA  518   -2.560 -13.513 -22.842   96.29   C
ATOM   7750  O    ALA  518   -3.469 -13.991 -22.160   96.39   O
ATOM   7751  N    ALA  519   -1.338 -14.040 -22.904   96.05   N
ATOM   7752  HN   ALA  519   -0.656 -13.578 -23.488    0.00   H
```

FIGURE 6- 103 -

```
ATOM   7753  CA   ALA   519     -0.969 -15.246 -22.162   95.95   C
ATOM   7754  HA   ALA   519     -1.334 -16.100 -22.672    0.00   H
ATOM   7755  CB   ALA   519      0.563 -15.351 -22.039   95.69   C
ATOM   7756  HB1  ALA   519      0.993 -15.395 -23.006    0.00   H
ATOM   7757  HB2  ALA   519      0.935 -14.502 -21.526    0.00   H
ATOM   7758  HB3  ALA   519      0.815 -16.227 -21.500    0.00   H
ATOM   7759  C    ALA   519     -1.606 -15.190 -20.779   95.48   C
ATOM   7760  O    ALA   519     -2.203 -16.163 -20.312   95.11   O
ATOM   7761  N    THR   520     -1.487 -14.025 -20.146   95.48   N
ATOM   7762  HN   THR   520     -0.991 -13.288 -20.624    0.00   H
ATOM   7763  CA   THR   520     -2.040 -13.789 -18.814   95.49   C
ATOM   7764  HA   THR   520     -1.663 -14.515 -18.141    0.00   H
ATOM   7765  CB   THR   520     -1.659 -12.386 -18.288   95.89   C
ATOM   7766  HB   THR   520     -2.324 -11.666 -18.690    0.00   H
ATOM   7767  OG1  THR   520     -0.319 -12.072 -18.690   96.10   O
ATOM   7768  HG1  THR   520     -0.081 -11.194 -18.361    0.00   H
ATOM   7769  CG2  THR   520     -1.747 -12.348 -16.751   95.97   C
ATOM   7770  HG21 THR   520     -2.737 -12.573 -16.448    0.00   H
ATOM   7771  HG22 THR   520     -1.081 -13.063 -16.342    0.00   H
ATOM   7772  HG23 THR   520     -1.484 -11.382 -16.406    0.00   H
ATOM   7773  C    THR   520     -3.566 -13.897 -18.846   95.07   C
ATOM   7774  O    THR   520     -4.161 -14.671 -18.089   94.91   O
ATOM   7775  N    CYS   521     -4.193 -13.108 -19.717   93.90   N
ATOM   7776  HN   CYS   521     -3.643 -12.483 -20.288    0.00   H
ATOM   7777  CA   CYS   521     -5.644 -13.135 -19.855   92.35   C
ATOM   7778  HA   CYS   521     -6.087 -12.666 -19.015    0.00   H
ATOM   7779  CB   CYS   521     -6.082 -12.366 -21.119   91.99   C
ATOM   7780  HB2  CYS   521     -5.501 -12.685 -21.945    0.00   H
ATOM   7781  HB3  CYS   521     -7.105 -12.558 -21.312    0.00   H
ATOM   7782  SG   CYS   521     -5.911 -10.541 -21.051   90.89   S
ATOM   7783  HG   CYS   521     -6.298 -10.046 -22.131    0.00   H
ATOM   7784  C    CYS   521     -6.093 -14.596 -19.938   92.03   C
ATOM   7785  O    CYS   521     -6.820 -15.085 -19.074   92.13   O
ATOM   7786  N    GLY   522     -5.631 -15.291 -20.973   91.57   N
ATOM   7787  HN   GLY   522     -5.024 -14.828 -21.633    0.00   H
ATOM   7788  CA   GLY   522     -5.982 -16.687 -21.164   91.25   C
ATOM   7789  HA2  GLY   522     -7.006 -16.761 -21.422    0.00   H
ATOM   7790  HA3  GLY   522     -5.392 -17.096 -21.942    0.00   H
ATOM   7791  C    GLY   522     -5.773 -17.573 -19.946   91.07   C
ATOM   7792  O    GLY   522     -6.646 -18.368 -19.590   91.64   O
ATOM   7793  N    ARG   523     -4.616 -17.439 -19.303   90.45   N
ATOM   7794  HN   ARG   523     -3.960 -16.757 -19.653    0.00   H
ATOM   7795  CA   ARG   523     -4.280 -18.241 -18.124   89.80   C
ATOM   7796  HA   ARG   523     -4.311 -19.269 -18.376    0.00   H
ATOM   7797  CB   ARG   523     -2.872 -17.888 -17.628   90.91   C
ATOM   7798  HB2  ARG   523     -2.160 -18.162 -18.363    0.00   H
ATOM   7799  HB3  ARG   523     -2.812 -16.846 -17.449    0.00   H
ATOM   7800  CG   ARG   523     -2.486 -18.593 -16.338   91.87   C
ATOM   7801  HG2  ARG   523     -3.260 -18.473 -15.625    0.00   H
ATOM   7802  HG3  ARG   523     -2.339 -19.624 -16.530    0.00   H
ATOM   7803  CD   ARG   523     -1.198 -18.023 -15.753   92.43   C
ATOM   7804  HD2  ARG   523     -0.396 -18.207 -16.419    0.00   H
ATOM   7805  HD3  ARG   523     -1.306 -16.979 -15.611    0.00   H
ATOM   7806  NE   ARG   523     -0.859 -18.621 -14.462   92.96   N1+
ATOM   7807  HE   ARG   523     -1.344 -19.447 -14.146    0.00   H
ATOM   7808  CZ   ARG   523      0.073 -18.147 -13.637   93.37   C
ATOM   7809  NH1  ARG   523      0.763 -17.064 -13.967   93.56   N
ATOM   7810  HH11 ARG   523      1.469 -16.706 -13.341    0.00   H
ATOM   7811  HH12 ARG   523      0.582 -16.598 -14.844    0.00   H
ATOM   7812  NH2  ARG   523      0.313 -18.749 -12.477   93.43   N
ATOM   7813  HH21 ARG   523      1.020 -18.385 -11.856    0.00   H
ATOM   7814  HH22 ARG   523     -0.212 -19.570 -12.217    0.00   H
ATOM   7815  C    ARG   523     -5.265 -18.106 -16.959   88.74   C
ATOM   7816  O    ARG   523     -5.867 -19.096 -16.534   87.87   O
ATOM   7817  N    TYR   524     -5.417 -16.880 -16.452   87.68   N
ATOM   7818  HN   TYR   524     -4.888 -16.136 -16.882    0.00   H
ATOM   7819  CA   TYR   524     -6.304 -16.590 -15.321   86.39   C
ATOM   7820  HA   TYR   524     -6.197 -17.345 -14.586    0.00   H
ATOM   7821  CB   TYR   524     -5.951 -15.229 -14.696   87.00   C
ATOM   7822  HB2  TYR   524     -5.830 -14.509 -15.463    0.00   H
ATOM   7823  HB3  TYR   524     -6.731 -14.926 -14.047    0.00   H
ATOM   7824  CG   TYR   524     -4.675 -15.244 -13.889   88.62   C
ATOM   7825  CD1  TYR   524     -3.426 -15.256 -14.514   88.97   C
ATOM   7826  HD1  TYR   524     -3.361 -15.213 -15.588    0.00   H
ATOM   7827  CE1  TYR   524     -2.250 -15.323 -13.768   89.27   C
ATOM   7828  HE1  TYR   524     -1.296 -15.331 -14.267    0.00   H
```

FIGURE 6- 104 -

```
ATOM   7829  CD2  TYR  524   -4.717 -15.294 -12.495   89.23   C
ATOM   7830  HD2  TYR  524   -5.665 -15.280 -11.984    0.00   H
ATOM   7831  CE2  TYR  524   -3.551 -15.362 -11.742   89.61   C
ATOM   7832  HE2  TYR  524   -3.606 -15.401 -10.667    0.00   H
ATOM   7833  CZ   TYR  524   -2.319 -15.379 -12.381   89.48   C
ATOM   7834  OH   TYR  524   -1.163 -15.471 -11.635   89.62   O
ATOM   7835  HH   TYR  524   -0.398 -15.485 -12.226    0.00   H
ATOM   7836  C    TYR  524   -7.797 -16.607 -15.632   84.89   C
ATOM   7837  O    TYR  524   -8.577 -17.287 -14.953   84.89   O
ATOM   7838  N    LEU  525   -8.194 -15.853 -16.650   82.70   N
ATOM   7839  HN   LEU  525   -7.499 -15.333 -17.164    0.00   H
ATOM   7840  CA   LEU  525   -9.598 -15.766 -17.031   80.88   C
ATOM   7841  HA   LEU  525  -10.165 -15.408 -16.211    0.00   H
ATOM   7842  CB   LEU  525   -9.770 -14.810 -18.211   79.90   C
ATOM   7843  HB2  LEU  525   -9.246 -15.187 -19.050    0.00   H
ATOM   7844  HB3  LEU  525  -10.799 -14.723 -18.448    0.00   H
ATOM   7845  CG   LEU  525   -9.273 -13.379 -18.033   79.56   C
ATOM   7846  HG   LEU  525   -8.221 -13.383 -17.912    0.00   H
ATOM   7847  CD1  LEU  525   -9.649 -12.579 -19.269   79.57   C
ATOM   7848 HD11  LEU  525   -9.197 -13.014 -20.122    0.00   H
ATOM   7849 HD12  LEU  525  -10.702 -12.584 -19.386    0.00   H
ATOM   7850 HD13  LEU  525   -9.310 -11.582 -19.160    0.00   H
ATOM   7851  CD2  LEU  525   -9.889 -12.753 -16.786   80.27   C
ATOM   7852 HD21  LEU  525  -10.944 -12.742 -16.881    0.00   H
ATOM   7853 HD22  LEU  525   -9.617 -13.321 -15.935    0.00   H
ATOM   7854 HD23  LEU  525   -9.534 -11.761 -16.677    0.00   H
ATOM   7855  C    LEU  525  -10.222 -17.105 -17.399   80.39   C
ATOM   7856  O    LEU  525  -11.326 -17.425 -16.952   80.15   O
ATOM   7857  N    PHE  526   -9.504 -17.889 -18.200   79.14   N
ATOM   7858  HN   PHE  526   -8.587 -17.576 -18.481    0.00   H
ATOM   7859  CA   PHE  526  -10.013 -19.172 -18.670   77.69   C
ATOM   7860  HA   PHE  526  -11.028 -19.275 -18.386    0.00   H
ATOM   7861  CB   PHE  526   -9.888 -19.205 -20.189   75.14   C
ATOM   7862  HB2  PHE  526   -8.869 -19.310 -20.457    0.00   H
ATOM   7863  HB3  PHE  526  -10.439 -20.025 -20.571    0.00   H
ATOM   7864  CG   PHE  526  -10.407 -17.958 -20.860   73.19   C
ATOM   7865  CD1  PHE  526  -11.738 -17.578 -20.721   71.88   C
ATOM   7866  HD1  PHE  526  -12.409 -18.175 -20.126    0.00   H
ATOM   7867  CD2  PHE  526   -9.566 -17.164 -21.634   71.86   C
ATOM   7868  HD2  PHE  526   -8.531 -17.436 -21.756    0.00   H
ATOM   7869  CE1  PHE  526  -12.223 -16.429 -21.343   70.78   C
ATOM   7870  HE1  PHE  526  -13.256 -16.149 -21.226    0.00   H
ATOM   7871  CE2  PHE  526  -10.045 -16.011 -22.260   70.31   C
ATOM   7872  HE2  PHE  526   -9.382 -15.407 -22.856    0.00   H
ATOM   7873  CZ   PHE  526  -11.374 -15.644 -22.115   70.02   C
ATOM   7874  HZ   PHE  526  -11.750 -14.757 -22.596    0.00   H
ATOM   7875  C    PHE  526   -9.365 -20.409 -18.055   78.36   C
ATOM   7876  O    PHE  526   -9.079 -21.386 -18.744   78.60   O
ATOM   7877  N    ASN  527   -9.156 -20.366 -16.746   79.30   N
ATOM   7878  HN   ASN  527   -9.427 -19.531 -16.248    0.00   H
ATOM   7879  CA   ASN  527   -8.554 -21.480 -16.026   80.29   C
ATOM   7880  HA   ASN  527   -7.923 -22.023 -16.680    0.00   H
ATOM   7881  CB   ASN  527   -7.730 -20.943 -14.850   79.83   C
ATOM   7882  HB2  ASN  527   -6.966 -20.308 -15.216    0.00   H
ATOM   7883  HB3  ASN  527   -8.361 -20.397 -14.197    0.00   H
ATOM   7884  CG   ASN  527   -7.069 -22.042 -14.041   79.24   C
ATOM   7885  OD1  ASN  527   -6.264 -22.825 -14.563   78.09   O
ATOM   7886  ND2  ASN  527   -7.407 -22.106 -12.750   78.48   N
ATOM   7887 HD21  ASN  527   -8.068 -21.446 -12.368    0.00   H
ATOM   7888 HD22  ASN  527   -7.001 -22.814 -12.157    0.00   H
ATOM   7889  C    ASN  527   -9.663 -22.414 -15.530   81.29   C
ATOM   7890  O    ASN  527   -9.429 -23.323 -14.731   81.47   O
ATOM   7891  N    TRP  528  -10.875 -22.182 -16.021   82.58   N
ATOM   7892  HN   TRP  528  -10.986 -21.421 -16.674    0.00   H
ATOM   7893  CA   TRP  528  -12.031 -22.994 -15.641   83.86   C
ATOM   7894  HA   TRP  528  -11.783 -23.591 -14.802    0.00   H
ATOM   7895  CB   TRP  528  -13.218 -22.096 -15.281   83.49   C
ATOM   7896  HB2  TRP  528  -14.071 -22.696 -15.096    0.00   H
ATOM   7897  HB3  TRP  528  -12.986 -21.535 -14.413    0.00   H
ATOM   7898  CG   TRP  528  -13.576 -21.118 -16.374   83.05   C
ATOM   7899  CD2  TRP  528  -14.427 -21.361 -17.503   82.62   C
ATOM   7900  CE2  TRP  528  -14.459 -20.170 -18.267   82.28   C
ATOM   7901  CE3  TRP  528  -15.165 -22.469 -17.946   82.03   C
ATOM   7902  HE3  TRP  528  -15.153 -23.385 -17.380    0.00   H
ATOM   7903  CD1  TRP  528  -13.138 -19.828 -16.497   82.73   C
ATOM   7904  HD1  TRP  528  -12.475 -19.412 -15.758    0.00   H
```

FIGURE 6- 105 -

```
ATOM   7905  NE1 TRP   528   -13.665 -19.252 -17.631   81.88        N
ATOM   7906  HE1 TRP   528   -13.437 -18.297 -17.864    0.00        H
ATOM   7907  CZ2 TRP   528   -15.201 -20.056 -19.447   81.90        C
ATOM   7908  HZ2 TRP   528   -15.198 -19.130 -19.998    0.00        H
ATOM   7909  CZ3 TRP   528   -15.903 -22.354 -19.122   81.78        C
ATOM   7910  HZ3 TRP   528   -16.477 -23.191 -19.482    0.00        H
ATOM   7911  CH2 TRP   528   -15.915 -21.154 -19.858   81.66        C
ATOM   7912  HH2 TRP   528   -16.500 -21.109 -20.761    0.00        H
ATOM   7913  C   TRP   528   -12.449 -23.929 -16.776   84.63        C
ATOM   7914  O   TRP   528   -13.127 -24.938 -16.551   84.38        O
ATOM   7915  N   ALA   529   -12.038 -23.583 -17.995   85.60        N
ATOM   7916  HN  ALA   529   -11.480 -22.748 -18.086    0.00        H
ATOM   7917  CA  ALA   529   -12.372 -24.372 -19.179   87.13        C
ATOM   7918  HA  ALA   529   -13.359 -24.744 -19.088    0.00        H
ATOM   7919  CB  ALA   529   -12.275 -23.499 -20.435   86.82        C
ATOM   7920  HB1 ALA   529   -12.951 -22.688 -20.354    0.00        H
ATOM   7921  HB2 ALA   529   -11.288 -23.127 -20.531    0.00        H
ATOM   7922  HB3 ALA   529   -12.518 -24.078 -21.287    0.00        H
ATOM   7923  C   ALA   529   -11.502 -25.617 -19.348   87.98        C
ATOM   7924  O   ALA   529   -11.416 -26.168 -20.446   87.83        O
ATOM   7925  N   VAL   530   -10.867 -26.057 -18.262   89.33        N
ATOM   7926  HN  VAL   530   -10.994 -25.551 -17.398    0.00        H
ATOM   7927  CA  VAL   530   -10.005 -27.238 -18.298   90.37        C
ATOM   7928  HA  VAL   530   -10.417 -27.956 -18.958    0.00        H
ATOM   7929  CB  VAL   530    -8.577 -26.887 -18.787   89.51        C
ATOM   7930  HB  VAL   530    -7.988 -27.766 -18.816    0.00        H
ATOM   7931  CG1 VAL   530    -8.626 -26.342 -20.199   89.36        C
ATOM   7932 HG11 VAL   530    -9.044 -27.070 -20.844    0.00        H
ATOM   7933 HG12 VAL   530    -9.224 -25.468 -20.219    0.00        H
ATOM   7934 HG13 VAL   530    -7.645 -26.106 -20.521    0.00        H
ATOM   7935  CG2 VAL   530    -7.933 -25.884 -17.839   88.82        C
ATOM   7936 HG21 VAL   530    -8.517 -25.001 -17.809    0.00        H
ATOM   7937 HG22 VAL   530    -7.875 -26.303 -16.868    0.00        H
ATOM   7938 HG23 VAL   530    -6.958 -25.650 -18.181    0.00        H
ATOM   7939  C   VAL   530    -9.840 -27.975 -16.963   91.75        C
ATOM   7940  O   VAL   530    -9.836 -27.363 -15.890   91.60        O
ATOM   7941  N   ARG   531    -9.715 -29.299 -17.050   93.34        N
ATOM   7942  HN  ARG   531    -9.788 -29.713 -17.967    0.00        H
ATOM   7943  CA  ARG   531    -9.482 -30.145 -15.885   94.20        C
ATOM   7944  HA  ARG   531    -9.888 -29.680 -15.024    0.00        H
ATOM   7945  CB  ARG   531   -10.145 -31.514 -16.065   94.81        C
ATOM   7946  HB2 ARG   531    -9.807 -31.954 -16.967    0.00        H
ATOM   7947  HB3 ARG   531    -9.890 -32.140 -15.250    0.00        H
ATOM   7948  CG  ARG   531   -11.663 -31.441 -16.130   96.79        C
ATOM   7949  HG2 ARG   531   -12.033 -30.991 -15.245    0.00        H
ATOM   7950  HG3 ARG   531   -11.953 -30.862 -16.968    0.00        H
ATOM   7951  CD  ARG   531   -12.303 -32.821 -16.263   98.50        C
ATOM   7952  HD2 ARG   531   -11.886 -33.325 -17.096    0.00        H
ATOM   7953  HD3 ARG   531   -12.120 -33.381 -15.383    0.00        H
ATOM   7954  NE  ARG   531   -13.751 -32.726 -16.458  100.24        N1+
ATOM   7955  HE  ARG   531   -14.200 -31.822 -16.474    0.00        H
ATOM   7956  CZ  ARG   531   -14.564 -33.769 -16.623  101.18        C
ATOM   7957  NH1 ARG   531   -14.080 -35.006 -16.614  101.18        N
ATOM   7958 HH11 ARG   531   -14.701 -35.792 -16.739    0.00        H
ATOM   7959 HH12 ARG   531   -13.092 -35.160 -16.482    0.00        H
ATOM   7960  NH2 ARG   531   -15.866 -33.575 -16.810  101.96        N
ATOM   7961 HH21 ARG   531   -16.481 -34.365 -16.935    0.00        H
ATOM   7962 HH22 ARG   531   -16.239 -32.638 -16.827    0.00        H
ATOM   7963  C   ARG   531    -7.965 -30.278 -15.896   94.23        C
ATOM   7964  O   ARG   531    -7.403 -31.340 -15.633   94.04        O
ATOM   7965  N   THR   532    -7.326 -29.162 -16.241   94.66        N
ATOM   7966  HN  THR   532    -7.911 -28.365 -16.440    0.00        H
ATOM   7967  CA  THR   532    -5.874 -29.045 -16.340   94.90        C
ATOM   7968  HA  THR   532    -5.441 -30.011 -16.330    0.00        H
ATOM   7969  CB  THR   532    -5.465 -28.322 -17.666   94.13        C
ATOM   7970  HB  THR   532    -5.972 -27.395 -17.734    0.00        H
ATOM   7971  OG1 THR   532    -5.839 -29.128 -18.794   93.57        O
ATOM   7972  HG1 THR   532    -5.584 -28.677 -19.611    0.00        H
ATOM   7973  CG2 THR   532    -3.962 -28.063 -17.702   93.46        C
ATOM   7974 HG21 THR   532    -3.690 -27.451 -16.882    0.00        H
ATOM   7975 HG22 THR   532    -3.444 -28.984 -17.642    0.00        H
ATOM   7976 HG23 THR   532    -3.710 -27.574 -18.607    0.00        H
ATOM   7977  C   THR   532    -5.334 -28.249 -15.152   95.09        C
ATOM   7978  O   THR   532    -4.598 -28.783 -14.319   95.50        O
ATOM   7979  N   LYS   533    -5.715 -26.975 -15.092   94.88        N
ATOM   7980  HN  LYS   533    -6.319 -26.654 -15.833    0.00        H
```

FIGURE 6- 106 -

```
ATOM   7981   CA   LYS  533    -5.306 -26.054 -14.030   93.94   C
ATOM   7982   HA   LYS  533    -6.011 -25.268 -13.954    0.00   H
ATOM   7983   CB   LYS  533    -5.226 -26.780 -12.677   92.53   C
ATOM   7984   HB2  LYS  533    -4.484 -27.535 -12.725    0.00   H
ATOM   7985   HB3  LYS  533    -4.975 -26.085 -11.918    0.00   H
ATOM   7986   CG   LYS  533    -6.516 -27.458 -12.243   91.29   C
ATOM   7987   HG2  LYS  533    -7.277 -26.730 -12.130    0.00   H
ATOM   7988   HG3  LYS  533    -6.808 -28.163 -12.977    0.00   H
ATOM   7989   CD   LYS  533    -6.335 -28.182 -10.918   90.13   C
ATOM   7990   HD2  LYS  533    -5.626 -28.960 -11.035    0.00   H
ATOM   7991   HD3  LYS  533    -5.991 -27.498 -10.186    0.00   H
ATOM   7992   CE   LYS  533    -7.637 -28.801 -10.411   88.90   C
ATOM   7993   HE2  LYS  533    -8.360 -28.040 -10.275    0.00   H
ATOM   7994   HE3  LYS  533    -7.993 -29.504 -11.119    0.00   H
ATOM   7995   NZ   LYS  533    -7.453 -29.510  -9.101   86.66   N1-
ATOM   7996   HZ1  LYS  533    -6.776 -30.250  -9.211    0.00   H
ATOM   7997   HZ2  LYS  533    -7.126 -28.855  -8.407    0.00   H
ATOM   7998   HZ3  LYS  533    -8.334 -29.902  -8.804    0.00   H
ATOM   7999   C    LYS  533    -3.970 -25.351 -14.304   93.73   C
ATOM   8000   O    LYS  533    -3.342 -25.542 -15.349   92.81   O
ATOM   8001   N    LEU  534    -3.563 -24.531 -13.340   93.80   N
ATOM   8002   HN   LEU  534    -4.174 -24.450 -12.541    0.00   H
ATOM   8003   CA   LEU  534    -2.317 -23.772 -13.386   94.20   C
ATOM   8004   HA   LEU  534    -1.496 -24.439 -13.343    0.00   H
ATOM   8005   CB   LEU  534    -2.216 -22.954 -14.678   93.30   C
ATOM   8006   HB2  LEU  534    -2.242 -23.606 -15.512    0.00   H
ATOM   8007   HB3  LEU  534    -3.030 -22.279 -14.733    0.00   H
ATOM   8008   CG   LEU  534    -0.938 -22.114 -14.817   93.20   C
ATOM   8009   HG   LEU  534    -0.903 -21.394 -14.041    0.00   H
ATOM   8010   CD1  LEU  534     0.308 -23.008 -14.724   92.26   C
ATOM   8011   HD11 LEU  534     0.320 -23.500 -13.736    0.00   H
ATOM   8012   HD12 LEU  534     0.284 -23.728 -15.500    0.00   H
ATOM   8013   HD13 LEU  534     1.178 -22.412 -14.822    0.00   H
ATOM   8014   CD2  LEU  534    -0.964 -21.374 -16.144   92.87   C
ATOM   8015   HD21 LEU  534    -1.016 -22.074 -16.937    0.00   H
ATOM   8016   HD22 LEU  534    -1.811 -20.739 -16.177    0.00   H
ATOM   8017   HD23 LEU  534    -0.083 -20.794 -16.242    0.00   H
ATOM   8018   C    LEU  534    -2.269 -22.835 -12.180   94.51   C
ATOM   8019   O    LEU  534    -2.792 -21.720 -12.230   94.58   O
ATOM   8020   N    LYS  535    -1.646 -23.309 -11.101   94.86   N
ATOM   8021   HN   LYS  535    -1.259 -24.238 -11.180    0.00   H
ATOM   8022   CA   LYS  535    -1.506 -22.560  -9.848   94.79   C
ATOM   8023   HA   LYS  535    -2.397 -22.647  -9.283    0.00   H
ATOM   8024   CB   LYS  535    -0.332 -23.120  -9.030   94.66   C
ATOM   8025   HB2  LYS  535     0.553 -23.081  -9.610    0.00   H
ATOM   8026   HB3  LYS  535    -0.205 -22.540  -8.153    0.00   H
ATOM   8027   CG   LYS  535    -0.523 -24.571  -8.591   94.27   C
ATOM   8028   HG2  LYS  535    -1.403 -24.650  -8.007    0.00   H
ATOM   8029   HG3  LYS  535    -0.610 -25.190  -9.446    0.00   H
ATOM   8030   CD   LYS  535     0.641 -25.084  -7.758   93.40   C
ATOM   8031   HD2  LYS  535     1.537 -25.003  -8.316    0.00   H
ATOM   8032   HD3  LYS  535     0.723 -24.508  -6.873    0.00   H
ATOM   8033   CE   LYS  535     0.432 -26.539  -7.376   92.66   C
ATOM   8034   HE2  LYS  535    -0.454 -26.630  -6.804    0.00   H
ATOM   8035   HE3  LYS  535     0.347 -27.126  -8.254    0.00   H
ATOM   8036   NZ   LYS  535     1.558 -27.085  -6.567   92.00   N1-
ATOM   8037   HZ1  LYS  535     2.414 -27.023  -7.097    0.00   H
ATOM   8038   HZ2  LYS  535     1.651 -26.551  -5.716    0.00   H
ATOM   8039   HZ3  LYS  535     1.372 -28.050  -6.340    0.00   H
ATOM   8040   C    LYS  535    -1.344 -21.047 -10.036   94.73   C
ATOM   8041   O    LYS  535    -0.236 -20.532 -10.219   94.43   O
ATOM   8042   N    LEU  536    -2.476 -20.349  -9.974   94.29   N
ATOM   8043   HN   LEU  536    -3.326 -20.867  -9.810    0.00   H
ATOM   8044   CA   LEU  536    -2.524 -18.901 -10.131   93.62   C
ATOM   8045   HA   LEU  536    -2.000 -18.624 -11.008    0.00   H
ATOM   8046   CB   LEU  536    -3.979 -18.427 -10.245   93.90   C
ATOM   8047   HB2  LEU  536    -4.339 -18.158  -9.236    0.00   H
ATOM   8048   HB3  LEU  536    -4.027 -17.587 -10.889    0.00   H
ATOM   8049   CG   LEU  536    -5.051 -19.379 -10.792   93.95   C
ATOM   8050   HG   LEU  536    -4.721 -19.792 -11.710    0.00   H
ATOM   8051   CD1  LEU  536    -5.305 -20.513  -9.791   94.35   C
ATOM   8052   HD11 LEU  536    -4.407 -21.052  -9.633    0.00   H
ATOM   8053   HD12 LEU  536    -5.637 -20.105  -8.872    0.00   H
ATOM   8054   HD13 LEU  536    -6.046 -21.165 -10.176    0.00   H
ATOM   8055   CD2  LEU  536    -6.340 -18.600 -11.023   93.57   C
ATOM   8056   HD21 LEU  536    -6.669 -18.182 -10.107    0.00   H
```

FIGURE 6-107 -

```
ATOM   3C57  HD22  LEU  536    -6.163  -17.824  -11.722   0.00    H
ATOM   3C58  HD23  LEU  536    -7.084  -19.252  -11.401   0.00    H
ATOM   3C59  C     LEU  536    -1.878  -18.255   -8.913  93.36    C
ATOM   3C60  O     LEU  536    -2.278  -18.525   -7.782  93.08    O
ATOM   3C61  N     THR  537    -0.881  -17.405   -9.149  92.90    N
ATOM   3C62  HN    THR  537    -0.617  -17.240  -10.109   0.00    H
ATOM   3C63  CA    THR  537    -0.175  -16.719   -8.069  92.13    C
ATOM   3C64  HA    THR  537    -0.555  -17.045   -7.136   0.00    H
ATOM   3C65  CB    THR  537     1.344  -17.020   -8.118  92.08    C
ATOM   3C66  HB    THR  537     1.818  -16.582   -7.278   0.00    H
ATOM   3C67  OG1   THR  537     1.909  -16.471   -9.316  91.76    O
ATOM   3C68  HG1   THR  537     2.857  -16.661   -9.342   0.00    H
ATOM   3C69  CG2   THR  537     1.584  -18.529   -8.097  91.85    C
ATOM   3C70  HG21  THR  537     1.178  -18.939   -7.209   0.00    H
ATOM   3C71  HG22  THR  537     1.116  -18.973   -8.937   0.00    H
ATOM   3C72  HG23  THR  537     2.625  -18.721   -8.131   0.00    H
ATOM   3C73  C     THR  537    -0.393  -15.206   -8.161  92.10    C
ATOM   3C74  O     THR  537    -0.061  -14.583   -9.172  91.91    O
ATOM   3C75  N     PRO  538    -0.953  -14.598   -7.099  91.80    N
ATOM   3C76  CD    PRO  538    -1.140  -15.222   -5.775  91.43    C
ATOM   3C77  HD2   PRO  538    -1.767  -16.070   -5.870   0.00    H
ATOM   3C78  HD3   PRO  538    -0.200  -15.520   -5.389   0.00    H
ATOM   3C79  CA    PRO  538    -1.232  -13.157   -7.033  91.50    C
ATOM   3C80  HA    PRO  538    -2.208  -12.969   -7.400   0.00    H
ATOM   3C81  CB    PRO  538    -1.163  -12.871   -5.540  91.36    C
ATOM   3C82  HB2   PRO  538    -0.152  -12.740   -5.252   0.00    H
ATOM   3C83  HB3   PRO  538    -1.709  -11.990   -5.324   0.00    H
ATOM   3C84  CG    PRO  538    -1.782  -14.100   -4.965  91.09    C
ATOM   3C85  HG2   PRO  538    -1.552  -14.161   -3.933   0.00    H
ATOM   3C86  HG3   PRO  538    -2.833  -14.058   -5.091   0.00    H
ATOM   3C87  C     PRO  538    -0.272  -12.291   -7.852  91.79    C
ATOM   3C88  O     PRO  538     0.748  -11.818   -7.356  91.78    O
ATOM   3C89  N     ILE  539    -0.627  -12.098   -9.116  92.21    N
ATOM   3C90  HN    ILE  539    -1.492  -12.530   -9.406   0.00    H
ATOM   3C91  CA    ILE  539     0.154  -11.315  -10.070  92.85    C
ATOM   3C92  HA    ILE  539     1.091  -11.783  -10.228   0.00    H
ATOM   3C93  CB    ILE  539    -0.613  -11.227  -11.410  92.35    C
ATOM   3C94  HB    ILE  539    -0.543  -10.242  -11.793   0.00    H
ATOM   3C95  CG2   ILE  539    -0.012  -12.200  -12.412  92.28    C
ATOM   3C96  HG21  ILE  539     1.006  -11.956  -12.574   0.00    H
ATOM   3C97  HG22  ILE  539    -0.082  -13.186  -12.032   0.00    H
ATOM   3C98  HG23  ILE  539    -0.541  -12.136  -13.327   0.00    H
ATOM   3C99  CG1   ILE  539    -2.102  -11.515  -11.172  91.65    C
ATOM   3100  HG12  ILE  539    -2.203  -12.388  -10.582   0.00    H
ATOM   3101  HG13  ILE  539    -2.544  -10.695  -10.668   0.00    H
ATOM   3102  CD1   ILE  539    -2.913  -11.743  -12.436  91.82    C
ATOM   3103  HD11  ILE  539    -2.862  -10.881  -13.049   0.00    H
ATOM   3104  HD12  ILE  539    -2.520  -12.574  -12.962   0.00    H
ATOM   3105  HD13  ILE  539    -3.922  -11.933  -12.178   0.00    H
ATOM   3106  C     ILE  539     0.561   -9.902   -9.615  94.12    C
ATOM   3107  O     ILE  539     0.132   -9.430   -8.558  94.24    O
ATOM   3108  N     PRO  540     1.413   -9.216  -10.410  95.43    N
ATOM   3109  CD    PRO  540     2.145   -9.739  -11.580  95.56    C
ATOM   3110  HD2   PRO  540     2.388  -10.757  -11.418   0.00    H
ATOM   3111  HD3   PRO  540     1.538   -9.654  -12.443   0.00    H
ATOM   3112  CA    PRO  540     1.880   -7.858  -10.089  95.65    C
ATOM   3113  HA    PRO  540     2.437   -7.880   -9.189   0.00    H
ATOM   3114  CB    PRO  540     2.776   -7.514  -11.279  95.39    C
ATOM   3115  HB2   PRO  540     2.186   -7.109  -12.060   0.00    H
ATOM   3116  HB3   PRO  540     3.502   -6.803  -10.980   0.00    H
ATOM   3117  CG    PRO  540     3.366   -8.838  -11.623  95.06    C
ATOM   3118  HG2   PRO  540     3.813   -8.787  -12.581   0.00    H
ATOM   3119  HG3   PRO  540     4.100   -9.095  -10.904   0.00    H
ATOM   3120  C     PRO  540     0.748   -6.849   -9.900  95.96    C
ATOM   3121  O     PRO  540     0.202   -6.729   -8.803  95.57    O
ATOM   3122  N     ALA  541     0.405   -6.136  -10.973  96.80    N
ATOM   3123  HN    ALA  541     0.914   -6.310  -11.827   0.00    H
ATOM   3124  CA    ALA  541    -0.662   -5.133  -10.948  97.53    C
ATOM   3125  HA    ALA  541    -0.278   -4.218  -10.578   0.00    H
ATOM   3126  CB    ALA  541    -1.210   -4.914  -12.365  97.21    C
ATOM   3127  HB1   ALA  541    -0.430   -4.577  -12.997   0.00    H
ATOM   3128  HB2   ALA  541    -1.598   -5.826  -12.738   0.00    H
ATOM   3129  HB3   ALA  541    -1.980   -4.188  -12.337   0.00    H
ATOM   3130  C     ALA  541    -1.788   -5.533   -9.986  98.10    C
ATOM   3131  O     ALA  541    -2.712   -6.272  -10.340  97.78    O
ATOM   3132  N     ALA  542    -1.675   -5.026   -8.762  98.65    N
```

FIGURE 6- 108 -

```
ATOM   8133  HN   ALA  542   -0.880  -4.423  -8.616    0.00   H
ATOM   8134  CA   ALA  542   -2.606  -5.288  -7.664   99.00   C
ATOM   8135  HA   ALA  542   -3.589  -5.035  -7.966    0.00   H
ATOM   8136  CB   ALA  542   -2.564  -6.768  -7.282   98.50   C
ATOM   8137  HB1  ALA  542   -2.839  -7.356  -8.119    0.00   H
ATOM   8138  HB2  ALA  542   -1.584  -7.026  -6.976    0.00   H
ATOM   8139  HB3  ALA  542   -3.241  -6.947  -6.487    0.00   H
ATOM   8140  C    ALA  542   -2.053  -4.422  -6.534   99.32   C
ATOM   8141  O    ALA  542   -2.739  -3.549  -5.999  100.12   O
ATOM   8142  N    SER  543   -0.787  -4.663  -6.201   99.14   N
ATOM   8143  HN   SER  543   -0.317  -5.413  -6.685    0.00   H
ATOM   8144  CA   SER  543   -0.077  -3.893  -5.181   98.80   C
ATOM   8145  HA   SER  543   -0.753  -3.613  -4.416    0.00   H
ATOM   8146  CB   SER  543    1.053  -4.729  -4.566   98.65   C
ATOM   8147  HB2  SER  543    1.845  -4.819  -5.263    0.00   H
ATOM   8148  HB3  SER  543    1.407  -4.253  -3.689    0.00   H
ATOM   8149  OG   SER  543    0.602  -6.029  -4.224   98.64   O
ATOM   8150  HG   SER  543    1.332  -6.533  -3.840    0.00   H
ATOM   8151  C    SER  543    0.529  -2.712  -5.948   98.57   C
ATOM   8152  O    SER  543    1.411  -1.999  -5.449   98.33   O
ATOM   8153  N    GLN  544    0.039  -2.523  -7.173   97.79   N
ATOM   8154  HN   GLN  544   -0.695  -3.143  -7.482    0.00   H
ATOM   8155  CA   GLN  544    0.524  -1.468  -8.058   97.23   C
ATOM   8156  HA   GLN  544    0.893  -0.662  -7.478    0.00   H
ATOM   8157  CB   GLN  544    1.648  -2.012  -8.942   97.15   C
ATOM   8158  HB2  GLN  544    1.242  -2.674  -9.662    0.00   H
ATOM   8159  HB3  GLN  544    2.131  -1.208  -9.434    0.00   H
ATOM   8160  CG   GLN  544    2.730  -2.783  -8.205   96.56   C
ATOM   8161  HG2  GLN  544    3.282  -2.119  -7.592    0.00   H
ATOM   8162  HG3  GLN  544    2.283  -3.530  -7.602    0.00   H
ATOM   8163  CD   GLN  544    3.689  -3.455  -9.156   96.06   C
ATOM   8164  OE1  GLN  544    3.277  -4.225 -10.024   96.25   O
ATOM   8165  NE2  GLN  544    4.978  -3.172  -8.999   95.86   N
ATOM   8166  HE21 GLN  544    5.270  -2.535  -8.273    0.00   H
ATOM   8167  HE22 GLN  544    5.665  -3.595  -9.605    0.00   H
ATOM   8168  C    GLN  544   -0.556  -0.878  -8.970   96.81   C
ATOM   8169  O    GLN  544   -0.270   0.016  -9.773   96.80   O
ATOM   8170  N    LEU  545   -1.787  -1.371  -8.856   95.73   N
ATOM   8171  HN   LEU  545   -1.969  -2.097  -8.180    0.00   H
ATOM   8172  CA   LEU  545   -2.870  -0.870  -9.699   94.51   C
ATOM   8173  HA   LEU  545   -2.565  -0.888 -10.713    0.00   H
ATOM   8174  CB   LEU  545   -4.128  -1.739  -9.544   93.92   C
ATOM   8175  HB2  LEU  545   -4.248  -2.009  -8.527    0.00   H
ATOM   8176  HB3  LEU  545   -4.976  -1.193  -9.867    0.00   H
ATOM   8177  CG   LEU  545   -4.123  -3.050 -10.345   93.73   C
ATOM   8178  HG   LEU  545   -3.243  -3.596 -10.123    0.00   H
ATOM   8179  CD1  LEU  545   -5.342  -3.896  -9.979   92.94   C
ATOM   8180  HD11 LEU  545   -5.317  -4.121  -8.945    0.00   H
ATOM   8181  HD12 LEU  545   -6.226  -3.357 -10.202    0.00   H
ATOM   8182  HD13 LEU  545   -5.327  -4.796 -10.537    0.00   H
ATOM   8183  CD2  LEU  545   -4.119  -2.732 -11.845   93.12   C
ATOM   8184  HD21 LEU  545   -4.984  -2.172 -12.089    0.00   H
ATOM   8185  HD22 LEU  545   -3.255  -2.169 -12.084    0.00   H
ATOM   8186  HD23 LEU  545   -4.116  -3.636 -12.397    0.00   H
ATOM   8187  C    LEU  545   -3.217   0.598  -9.466   94.11   C
ATOM   8188  O    LEU  545   -3.390   1.052  -8.335   93.76   O
ATOM   8189  N    ASP  546   -3.309   1.333 -10.567   93.66   N
ATOM   8190  HN   ASP  546   -3.142   0.868 -11.447    0.00   H
ATOM   8191  CA   ASP  546   -3.635   2.755 -10.544   93.29   C
ATOM   8192  HA   ASP  546   -3.078   3.233  -9.781    0.00   H
ATOM   8193  CB   ASP  546   -3.284   3.371 -11.899   92.39   C
ATOM   8194  HB2  ASP  546   -3.862   4.245 -12.050    0.00   H
ATOM   8195  HB3  ASP  546   -2.255   3.621 -11.917    0.00   H
ATOM   8196  CG   ASP  546   -3.559   2.418 -13.053   92.34   C
ATOM   8197  OD1  ASP  546   -4.732   2.014 -13.225   91.99   O
ATOM   8198  OD2  ASP  546   -2.604   2.061 -13.781   92.64   O1-
ATOM   8199  C    ASP  546   -5.118   2.972 -10.228   93.19   C
ATOM   8200  O    ASP  546   -5.795   3.777 -10.873   92.88   O
ATOM   8201  N    LEU  547   -5.611   2.244  -9.227   92.88   N
ATOM   8202  HN   LEU  547   -4.976   1.619  -8.755    0.00   H
ATOM   8203  CA   LEU  547   -7.010   2.323  -8.804   92.31   C
ATOM   8204  HA   LEU  547   -7.640   2.227  -9.649    0.00   H
ATOM   8205  CB   LEU  547   -7.327   1.199  -7.811   91.51   C
ATOM   8206  HB2  LEU  547   -6.476   0.579  -7.696    0.00   H
ATOM   8207  HB3  LEU  547   -7.587   1.619  -6.874    0.00   H
ATOM   8208  CG   LEU  547   -8.483   0.281  -8.213   91.07   C
```

FIGURE 6- 109 -

```
ATOM   8209  HG   LEU  547    -9.390   0.627  -8.195    0.00   H
ATOM   8210  CD1  LEU  547    -8.232  -0.253  -9.624   91.49   C
ATOM   8211  HD11 LEU  547    -8.169   0.558 -10.302    0.00   H
ATOM   8212  HD12 LEU  547    -7.324  -0.797  -9.639    0.00   H
ATOM   8213  HD13 LEU  547    -9.030  -0.889  -9.908    0.00   H
ATOM   8214  CD2  LEU  547    -8.615  -0.862  -7.215   90.68   C
ATOM   8215  HD21 LEU  547    -7.716  -1.422  -7.199    0.00   H
ATOM   8216  HD22 LEU  547    -8.803  -0.468  -6.250    0.00   H
ATOM   8217  HD23 LEU  547    -9.417  -1.491  -7.502    0.00   H
ATOM   8218  C    LEU  547    -7.370   3.670  -8.178   92.13   C
ATOM   8219  O    LEU  547    -7.711   3.746  -6.993   92.33   O
ATOM   8220  N    SER  548    -7.294   4.722  -8.992   91.48   N
ATOM   8221  HN   SER  548    -7.011   4.534  -9.942    0.00   H
ATOM   8222  CA   SER  548    -7.596   6.096  -8.574   90.53   C
ATOM   8223  HA   SER  548    -6.816   6.456  -7.956    0.00   H
ATOM   8224  CB   SER  548    -7.724   7.003  -9.813   90.16   C
ATOM   8225  HB2  SER  548    -7.986   7.983  -9.508    0.00   H
ATOM   8226  HB3  SER  548    -6.799   7.029 -10.328    0.00   H
ATOM   8227  OG   SER  548    -8.724   6.525 -10.704   89.28   O
ATOM   8228  HG   SER  548    -8.781   7.113 -11.470    0.00   H
ATOM   8229  C    SER  548    -8.861   6.221  -7.707   89.84   C
ATOM   8230  O    SER  548    -8.901   5.764  -6.558   89.81   O
ATOM   8231  N    GLY  549    -9.885   6.864  -8.260   88.50   N
ATOM   8232  HN   GLY  549    -9.738   7.234  -9.194    0.00   H
ATOM   8233  CA   GLY  549   -11.132   7.037  -7.537   86.79   C
ATOM   8234  HA2  GLY  549   -11.002   6.733  -6.531    0.00   H
ATOM   8235  HA3  GLY  549   -11.417   8.057  -7.564    0.00   H
ATOM   8236  C    GLY  549   -12.241   6.208  -8.153   85.59   C
ATOM   8237  O    GLY  549   -13.234   6.749  -8.655   85.81   O
ATOM   8238  N    TRP  550   -12.072   4.888  -8.118   83.54   N
ATOM   8239  HN   TRP  550   -11.240   4.512  -7.689    0.00   H
ATOM   8240  CA   TRP  550   -13.068   3.989  -8.688   81.50   C
ATOM   8241  HA   TRP  550   -13.386   4.364  -9.626    0.00   H
ATOM   8242  CB   TRP  550   -12.496   2.585  -8.893   83.10   C
ATOM   8243  HB2  TRP  550   -12.094   2.231  -7.980    0.00   H
ATOM   8244  HB3  TRP  550   -13.266   1.934  -9.215    0.00   H
ATOM   8245  CG   TRP  550   -11.407   2.496  -9.905   84.51   C
ATOM   8246  CD2  TRP  550   -11.522   2.008 -11.243   85.05   C
ATOM   8247  CE2  TRP  550   -10.236   2.076 -11.822   85.62   C
ATOM   8248  CE3  TRP  550   -12.587   1.518 -12.010   85.56   C
ATOM   8249  HE3  TRP  550   -13.575   1.460 -11.585    0.00   H
ATOM   8250  CD1  TRP  550   -10.099   2.836  -9.731   85.17   C
ATOM   8251  HD1  TRP  550    -9.768   3.238  -8.788    0.00   H
ATOM   8252  NE1  TRP  550    -9.337   2.585 -10.877   85.93   N
ATOM   8253  HE1  TRP  550    -8.398   2.782 -10.910    0.00   H
ATOM   8254  CZ2  TRP  550    -9.983   1.672 -13.135   86.64   C
ATOM   8255  HZ2  TRP  550    -8.936   1.741 -13.537    0.00   H
ATOM   8256  CZ3  TRP  550   -12.335   1.114 -13.319   86.52   C
ATOM   8257  HZ3  TRP  550   -13.137   0.733 -13.929    0.00   H
ATOM   8258  CH2  TRP  550   -11.040   1.195 -13.867   86.81   C
ATOM   8259  HH2  TRP  550   -10.889   0.873 -14.883    0.00   H
ATOM   8260  C    TRP  550   -14.237   3.877  -7.799   79.06   C
ATOM   8261  O    TRP  550   -15.430   4.010  -8.257   78.64   O
ATOM   8262  N    PHE  551   -14.037   3.631  -6.521   75.36   N
ATOM   8263  HN   PHE  551   -13.083   3.560  -6.201    0.00   H
ATOM   8264  CA   PHE  551   -15.127   3.465  -5.587   72.43   C
ATOM   8265  HA   PHE  551   -16.045   3.659  -6.078    0.00   H
ATOM   8266  CB   PHE  551   -15.104   2.034  -5.073   71.51   C
ATOM   8267  HB2  PHE  551   -14.198   1.860  -4.554    0.00   H
ATOM   8268  HB3  PHE  551   -15.921   1.881  -4.417    0.00   H
ATOM   8269  CG   PHE  551   -15.204   1.029  -6.180   70.21   C
ATOM   8270  CD1  PHE  551   -16.417   0.792  -6.812   69.89   C
ATOM   8271  HD1  PHE  551   -17.317   1.253  -6.441    0.00   H
ATOM   8272  CD2  PHE  551   -14.065   0.412  -6.676   70.27   C
ATOM   8273  HD2  PHE  551   -13.114   0.573  -6.198    0.00   H
ATOM   8274  CE1  PHE  551   -16.493  -0.040  -7.929   69.54   C
ATOM   8275  HE1  PHE  551   -17.442  -0.212  -8.409    0.00   H
ATOM   8276  CE2  PHE  551   -14.130  -0.420  -7.791   69.98   C
ATOM   8277  HE2  PHE  551   -13.236  -0.889  -8.165    0.00   H
ATOM   8278  CZ   PHE  551   -15.346  -0.644  -8.419   69.30   C
ATOM   8279  HZ   PHE  551   -15.402  -1.284  -9.284    0.00   H
ATOM   8280  C    PHE  551   -15.104   4.495  -4.483   70.65   C
ATOM   8281  O    PHE  551   -14.835   4.210  -3.313   70.47   O
ATOM   8282  N    VAL  552   -15.409   5.713  -4.913   68.31   N
ATOM   8283  HN   VAL  552   -15.614   5.796  -5.897    0.00   H
ATOM   8284  CA   VAL  552   -15.458   6.886  -4.060   66.24   C
```

FIGURE 6- 110 -

```
ATOM   8285  HA   VAL  552   -15.146   6.625  -3.082   0.00          H
ATOM   8286  CB   VAL  552   -14.528   7.981  -4.611  66.11          C
ATOM   8287  HB   VAL  552   -14.815   8.222  -5.602   0.00          H
ATOM   8288  CG1  VAL  552   -14.667   9.262  -3.795  65.46          C
ATOM   8289  HG11 VAL  552   -15.668   9.605  -3.844   0.00          H
ATOM   8290  HG12 VAL  552   -14.409   9.068  -2.786   0.00          H
ATOM   8291  HG13 VAL  552   -14.021  10.003  -4.188   0.00          H
ATOM   8292  CG2  VAL  552   -13.100   7.475  -4.605  66.76          C
ATOM   8293  HG21 VAL  552   -12.815   7.234  -3.614   0.00          H
ATOM   8294  HG22 VAL  552   -13.029   6.611  -5.213   0.00          H
ATOM   8295  HG23 VAL  552   -12.458   8.227  -4.984   0.00          H
ATOM   8296  C    VAL  552   -16.878   7.437  -3.980  64.27          C
ATOM   8297  O    VAL  552   -17.439   7.571  -2.889  63.37          O
ATOM   8298  N    ALA  553   -17.459   7.743  -5.137  61.84          N
ATOM   8299  HN   ALA  553   -16.952   7.581  -5.994   0.00          H
ATOM   8300  CA   ALA  553   -18.801   8.302  -5.181  60.06          C
ATOM   8301  HA   ALA  553   -19.413   7.806  -4.473   0.00          H
ATOM   8302  CB   ALA  553   -18.734   9.784  -4.850  59.96          C
ATOM   8303  HB1  ALA  553   -18.327   9.911  -3.881   0.00          H
ATOM   8304  HB2  ALA  553   -18.120  10.276  -5.558   0.00          H
ATOM   8305  HB3  ALA  553   -19.709  10.197  -4.880   0.00          H
ATOM   8306  C    ALA  553   -19.508   8.102  -6.524  59.20          C
ATOM   8307  O    ALA  553   -18.870   8.079  -7.581  58.67          O
ATOM   8308  N    GLY  554   -20.832   7.969  -6.470  57.32          N
ATOM   8309  HN   GLY  554   -21.294   7.995  -5.573   0.00          H
ATOM   8310  CA   GLY  554   -21.610   7.789  -7.682  55.92          C
ATOM   8311  HA2  GLY  554   -21.118   7.101  -8.319   0.00          H
ATOM   8312  HA3  GLY  554   -22.569   7.416  -7.433   0.00          H
ATOM   8313  C    GLY  554   -21.774   9.103  -8.419  55.32          C
ATOM   8314  O    GLY  554   -21.833  10.162  -7.795  56.25          O
ATOM   8315  N    TYR  555   -21.842   9.041  -9.744  54.09          N
ATOM   8316  HN   TYR  555   -21.785   8.134 -10.182   0.00          H
ATOM   8317  CA   TYR  555   -21.995  10.240 -10.565  52.91          C
ATOM   8318  HA   TYR  555   -22.371  11.030  -9.969   0.00          H
ATOM   8319  CB   TYR  555   -20.645  10.659 -11.155  52.19          C
ATOM   8320  HB2  TYR  555   -20.276   9.885 -11.776   0.00          H
ATOM   8321  HB3  TYR  555   -20.768  11.542 -11.727   0.00          H
ATOM   8322  CG   TYR  555   -19.588  10.942 -10.115  52.52          C
ATOM   8323  CD1  TYR  555   -19.686  12.056  -9.275  51.51          C
ATOM   8324  HD1  TYR  555   -20.512  12.739  -9.381   0.00          H
ATOM   8325  CE1  TYR  555   -18.725  12.302  -8.292  51.35          C
ATOM   8326  HE1  TYR  555   -18.816  13.165  -7.654   0.00          H
ATOM   8327  CD2  TYR  555   -18.501  10.080  -9.949  51.60          C
ATOM   8328  HD2  TYR  555   -18.397   9.216 -10.584   0.00          H
ATOM   8329  CE2  TYR  555   -17.538  10.314  -8.971  51.64          C
ATOM   8330  HE2  TYR  555   -16.709   9.635  -8.858   0.00          H
ATOM   8331  CZ   TYR  555   -17.654  11.426  -8.145  51.53          C
ATOM   8332  OH   TYR  555   -16.703  11.652  -7.174  49.78          O
ATOM   8333  HH   TYR  555   -16.926  12.456  -6.685   0.00          H
ATOM   8334  C    TYR  555   -22.968   9.971 -11.701  52.49          C
ATOM   8335  O    TYR  555   -22.874  10.585 -12.767  51.73          O
ATOM   8336  N    SER  556   -23.903   9.054 -11.475  52.23          N
ATOM   8337  HN   SER  556   -23.943   8.597 -10.576   0.00          H
ATOM   8338  CA   SER  556   -24.866   8.706 -12.512  52.19          C
ATOM   8339  HA   SER  556   -24.355   8.303 -13.347   0.00          H
ATOM   8340  CB   SER  556   -25.866   7.666 -11.992  52.55          C
ATOM   8341  HB2  SER  556   -25.344   6.898 -11.483   0.00          H
ATOM   8342  HB3  SER  556   -26.546   8.132 -11.327   0.00          H
ATOM   8343  OG   SER  556   -26.594   7.093 -13.069  50.11          O
ATOM   8344  HG   SER  556   -27.219   6.441 -12.725   0.00          H
ATOM   8345  C    SER  556   -25.602   9.947 -12.990  51.51          C
ATOM   8346  O    SER  556   -26.379  10.534 -12.241  50.33          O
ATOM   8347  N    GLY  557   -25.345  10.339 -14.238  51.42          N
ATOM   8348  HN   GLY  557   -24.693   9.804 -14.792   0.00          H
ATOM   8349  CA   GLY  557   -25.986  11.516 -14.804  51.55          C
ATOM   8350  HA2  GLY  557   -26.001  11.436 -15.860   0.00          H
ATOM   8351  HA3  GLY  557   -26.978  11.586 -14.441   0.00          H
ATOM   8352  C    GLY  557   -25.270  12.809 -14.447  52.06          C
ATOM   8353  O    GLY  557   -25.729  13.908 -14.765  51.65          O
ATOM   8354  N    GLY  558   -24.128  12.674 -13.787  52.55          N
ATOM   8355  HN   GLY  558   -23.790  11.749 -13.565   0.00          H
ATOM   8356  CA   GLY  558   -23.367  13.838 -13.385  53.96          C
ATOM   8357  HA2  GLY  558   -24.030  14.627 -13.144   0.00          H
ATOM   8358  HA3  GLY  558   -22.779  13.600 -12.537   0.00          H
ATOM   8359  C    GLY  558   -22.411  14.387 -14.428  55.08          C
ATOM   8360  O    GLY  558   -21.687  15.338 -14.146  56.32          O
```

FIGURE 6-111-

```
ATOM   8361   N    ASP 559   -22.384  13.800 -15.621  55.28  N
ATOM   8362   HN   ASP 559   -22.983  13.008 -15.802   0.00  H
ATOM   8363   CA   ASP 559   -21.493  14.296 -16.666  55.18  C
ATOM   8364   HA   ASP 559   -21.562  13.668 -17.516   0.00  H
ATOM   8365   CB   ASP 559   -21.920  15.731 -17.037  54.15  C
ATOM   8366   HB2  ASP 559   -22.955  15.744 -17.262   0.00  H
ATOM   8367   HB3  ASP 559   -21.728  16.378 -16.221   0.00  H
ATOM   8368   CG   ASP 559   -21.181  16.285 -18.245  54.33  C
ATOM   8369   OD1  ASP 559   -21.128  15.596 -19.287  54.53  O
ATOM   8370   OD2  ASP 559   -20.666  17.422 -18.158  54.95  O1-
ATOM   8371   C    ASP 559   -20.038  14.259 -16.170  55.99  C
ATOM   8372   O    ASP 559   -19.261  15.187 -16.416  57.34  O
ATOM   8373   N    ILE 560   -19.675  13.164 -15.471  56.04  N
ATOM   8374   HN   ILE 560   -20.367  12.467 -15.315   0.00  H
ATOM   8375   CA   ILE 560   -18.322  13.024 -14.936  56.21  C
ATOM   8376   HA   ILE 560   -17.816  13.954 -14.972   0.00  H
ATOM   8377   CB   ILE 560   -18.357  12.534 -13.461  55.22  C
ATOM   8378   HB   ILE 560   -18.910  11.633 -13.402   0.00  H
ATOM   8379   CG2  ILE 560   -16.944  12.281 -12.942  54.41  C
ATOM   8380   HG21 ILE 560   -16.477  11.540 -13.537   0.00  H
ATOM   8381   HG22 ILE 560   -16.384  13.178 -12.991   0.00  H
ATOM   8382   HG23 ILE 560   -16.991  11.949 -11.938   0.00  H
ATOM   8383   CG1  ILE 560   -19.048  13.581 -12.584  52.99  C
ATOM   8384   HG12 ILE 560   -20.019  13.771 -12.960   0.00  H
ATOM   8385   HG13 ILE 560   -19.118  13.219 -11.591   0.00  H
ATOM   8386   CD1  ILE 560   -18.335  14.906 -12.519  52.03  C
ATOM   8387   HD11 ILE 560   -17.363  14.765 -12.124   0.00  H
ATOM   8388   HD12 ILE 560   -18.264  15.317 -13.493   0.00  H
ATOM   8389   HD13 ILE 560   -18.877  15.568 -11.895   0.00  H
ATOM   8390   C    ILE 560   -17.473  12.066 -15.776  57.61  C
ATOM   8391   O    ILE 560   -17.961  11.067 -16.297  55.46  O
ATOM   8392   N    TYR 561   -16.188  12.392 -15.883  61.19  N
ATOM   8393   HN   TYR 561   -15.886  13.217 -15.386   0.00  H
ATOM   8394   CA   TYR 561   -15.231  11.623 -16.669  64.69  C
ATOM   8395   HA   TYR 561   -15.613  10.650 -16.837   0.00  H
ATOM   8396   CB   TYR 561   -14.996  12.321 -18.018  66.59  C
ATOM   8397   HB2  TYR 561   -15.914  12.398 -18.540   0.00  H
ATOM   8398   HB3  TYR 561   -14.603  13.290 -17.850   0.00  H
ATOM   8399   CG   TYR 561   -14.026  11.616 -18.950  69.59  C
ATOM   8400   CD1  TYR 561   -14.445  10.545 -19.747  70.33  C
ATOM   8401   HD1  TYR 561   -15.470  10.216 -19.712   0.00  H
ATOM   8402   CE1  TYR 561   -13.554   9.882 -20.599  71.19  C
ATOM   8403   HE1  TYR 561   -13.898   9.061 -21.205   0.00  H
ATOM   8404   CD2  TYR 561   -12.686  12.010 -19.028  70.57  C
ATOM   8405   HD2  TYR 561   -12.331  12.832 -18.430   0.00  H
ATOM   8406   CE2  TYR 561   -11.785  11.355 -19.873  71.96  C
ATOM   8407   HE2  TYR 561   -10.757  11.674 -19.915   0.00  H
ATOM   8408   CZ   TYR 561   -12.224  10.292 -20.656  72.68  C
ATOM   8409   OH   TYR 561   -11.335   9.643 -21.489  74.04  O
ATOM   8410   HH   TYR 561   -11.793   8.933 -21.959   0.00  H
ATOM   8411   C    TYR 561   -13.895  11.501 -15.946  66.57  C
ATOM   8412   O    TYR 561   -12.951  12.221 -16.266  67.40  O
ATOM   8413   N    HIS 562   -13.802  10.603 -14.973  68.65  N
ATOM   8414   HN   HIS 562   -14.600  10.038 -14.724   0.00  H
ATOM   8415   CA   HIS 562   -12.540  10.434 -14.263  71.28  C
ATOM   8416   HA   HIS 562   -12.178  11.381 -13.957   0.00  H
ATOM   8417   CB   HIS 562   -12.732   9.555 -13.029  71.94  C
ATOM   8418   HB2  HIS 562   -13.334   8.721 -13.280   0.00  H
ATOM   8419   HB3  HIS 562   -11.789   9.218 -12.685   0.00  H
ATOM   8420   CG   HIS 562   -13.398  10.257 -11.885  72.11  C
ATOM   8421   CD2  HIS 562   -13.869  11.521 -11.768  72.16  C
ATOM   8422   HD2  HIS 562   -13.804  12.199 -12.602   0.00  H
ATOM   8423   ND1  HIS 562   -13.625   9.650 -10.669  72.31  N1+
ATOM   8424   HD1  HIS 562   -13.352   8.689 -10.526   0.00  H
ATOM   8425   CE1  HIS 562   -14.205  10.510  -9.851  72.54  C
ATOM   8426   HE1  HIS 562   -14.458  10.212  -8.848   0.00  H
ATOM   8427   NE2  HIS 562   -14.365  11.652 -10.493  71.74  N
ATOM   8428   HE2  HIS 562   -14.767  12.528 -10.196   0.00  H
ATOM   8429   C    HIS 562   -11.505   9.812 -15.195  72.97  C
ATOM   8430   O    HIS 562   -11.797   8.840 -15.888  73.36  O
ATOM   8431   N    SER 563   -10.299  10.378 -15.214  75.53  N
ATOM   8432   HN   SER 563   -10.138  11.172 -14.612   0.00  H
ATOM   8433   CA   SER 563    -9.219   9.879 -16.077  77.13  C
ATOM   8434   HA   SER 563    -9.483   8.927 -16.459   0.00  H
ATOM   8435   CB   SER 563    -8.992  10.851 -17.250  77.92  C
ATOM   8436   HB2  SER 563    -8.185  10.506 -17.843   0.00  H
```

FIGURE 6-112 -

```
ATOM    8437  HB3 SER   563      -9.869  10.901 -17.842  0.00           H
ATOM    8438  OG  SER   563      -8.684  12.163 -16.796 77.68           O
ATOM    8439  HG  SER   563      -8.548  12.744 -17.557  0.00           H
ATOM    8440  C   SER   563      -7.887   9.640 -15.345 77.50           C
ATOM    8441  O   SER   563      -7.469   8.462 -15.238 77.02           O
ATOM    8442  OXT SER   563      -7.277  10.633 -14.889 78.15           O1-
TER     8443      SER   563
HETATM  8444  C1  BI      1     -24.458 -17.285 -31.257  0.00           C
HETATM  8445  C2  BI      1     -25.788 -16.854 -31.304  0.00           C
HETATM  8446  H   BI      1     -26.535 -17.336 -31.922  0.00           H
HETATM  8447  C3  BI      1     -26.182 -15.759 -30.516  0.00           C
HETATM  8448  C4  BI      1     -25.274 -15.153 -29.656  0.00           C
HETATM  8449  C5  BI      1     -23.937 -15.553 -29.603  0.00           C
HETATM  8450  H   BI      1     -23.212 -15.070 -28.957  0.00           H
HETATM  8451  C6  BI      1     -23.551 -16.613 -30.431  0.00           C
HETATM  8452  H   BI      1     -22.509 -16.919 -30.429  0.00           H
HETATM  8453  N7  BI      1     -27.402 -15.128 -30.462  0.00           N
HETATM  8454  C8  BI      1     -27.277 -14.208 -29.522  0.00           C
HETATM  8455  C16 BI      1     -28.388 -13.349 -29.238  0.00           C
HETATM  8456  N9  BI      1     -26.011 -14.193 -28.984  0.00           N
HETATM  8457  C10 BI      1     -25.545 -13.310 -27.908  0.00           C
HETATM  8458  H   BI      1     -26.405 -12.721 -27.597  0.00           H
HETATM  8459  C11 BI      1     -25.090 -14.090 -26.676  0.00           C
HETATM  8460  H   BI      1     -25.907 -14.724 -26.335  0.00           H
HETATM  8461  H   BI      1     -24.251 -14.751 -26.910  0.00           H
HETATM  8462  C12 BI      1     -24.687 -13.168 -25.538  0.00           C
HETATM  8463  H   BI      1     -25.574 -12.634 -25.190  0.00           H
HETATM  8464  H   BI      1     -24.317 -13.756 -24.692  0.00           H
HETATM  8465  C13 BI      1     -23.630 -12.166 -25.976  0.00           C
HETATM  8466  H   BI      1     -23.430 -11.469 -25.155  0.00           H
HETATM  8467  H   BI      1     -22.694 -12.694 -26.181  0.00           H
HETATM  8468  C14 BI      1     -24.069 -11.390 -27.214  0.00           C
HETATM  8469  H   BI      1     -24.908 -10.744 -26.940  0.00           H
HETATM  8470  H   BI      1     -23.263 -10.734 -27.550  0.00           H
HETATM  8471  C15 BI      1     -24.493 -12.301 -28.363  0.00           C
HETATM  8472  H   BI      1     -23.611 -12.812 -28.756  0.00           H
HETATM  8473  H   BI      1     -24.889 -11.695 -29.185  0.00           H
HETATM  8474  C20 BI      1     -28.938 -13.155 -27.994  0.00           C
HETATM  8475  H   BI      1     -28.727 -13.542 -27.018  0.00           H
HETATM  8476  O19 BI      1     -29.979 -12.273 -28.073  0.00           O
HETATM  8477  C18 BI      1     -30.095 -11.927 -29.390  0.00           C
HETATM  8478  H   BI      1     -30.880 -11.220 -29.617  0.00           H
HETATM  8479  C17 BI      1     -29.152 -12.586 -30.151  0.00           C
HETATM  8480  H   BI      1     -29.021 -12.505 -31.221  0.00           H
HETATM  8481  C21 BI      1     -23.934 -18.442 -32.042  0.00           C
HETATM  8482  O22 BI      1     -22.361 -18.946 -31.720  0.00           O
HETATM  8483  N23 BI      1     -24.667 -18.870 -33.117  0.00           N
HETATM  8484  H   BI      1     -25.517 -18.362 -33.353  0.00           H
HETATM  8485  C24 BI      1     -24.326 -19.993 -34.019  0.00           C
HETATM  8486  C25 BI      1     -22.961 -19.818 -34.728  0.00           C
HETATM  8487  H   BI      1     -22.164 -19.598 -34.019  0.00           H
HETATM  8488  H   BI      1     -22.677 -20.760 -35.215  0.00           H
HETATM  8489  C26 BI      1     -22.967 -18.710 -35.778  0.00           C
HETATM  8490  H   BI      1     -23.109 -17.733 -35.301  0.00           H
HETATM  8491  H   BI      1     -21.985 -18.670 -36.262  0.00           H
HETATM  8492  N27 BI      1     -23.987 -18.918 -36.809  0.00           N
HETATM  8493  H   BI      1     -23.302 -19.820 -37.283  0.00           H
HETATM  8494  C28 BI      1     -25.309 -18.982 -36.179  0.00           C
HETATM  8495  H   BI      1     -25.556 -18.010 -35.736  0.00           H
HETATM  8496  H   BI      1     -26.059 -19.156 -36.958  0.00           H
HETATM  8497  C29 BI      1     -25.407 -20.091 -35.132  0.00           C
HETATM  8498  H   BI      1     -25.320 -21.058 -35.645  0.00           H
HETATM  8499  H   BI      1     -26.415 -20.070 -34.700  0.00           H
HETATM  8500  C30 BI      1     -24.456 -21.331 -33.193  0.00           C
HETATM  8501  O31 BI      1     -25.568 -21.805 -32.947  0.00           O
HETATM  8502  N32 BI      1     -23.267 -21.871 -32.743  0.00           N
HETATM  8503  H   BI      1     -22.448 -21.265 -32.778  0.00           H
HETATM  8504  C33 BI      1     -23.045 -23.178 -32.259  0.00           C
HETATM  8505  C34 BI      1     -24.045 -24.147 -32.136  0.00           C
HETATM  8506  H   BI      1     -25.071 -23.937 -32.398  0.00           H
HETATM  8507  C35 BI      1     -23.737 -25.422 -31.623  0.00           C
HETATM  8508  C36 BI      1     -22.416 -25.719 -31.272  0.00           C
HETATM  8509  C37 BI      1     -21.386 -24.782 -31.455  0.00           C
HETATM  8510  H   BI      1     -20.358 -24.997 -31.183  0.00           H
HETATM  8511  C38 BI      1     -21.727 -23.511 -31.928  0.00           C
HETATM  8512  H   BI      1     -20.936 -22.772 -32.028  0.00           H
```

FIGURE 6- 113 -

```
HETATM 8513  C39  BI  1   -24.518 -26.576 -31.338  0.00    C
HETATM 8514  H    BI  1   -25.581 -26.694 -31.500  0.00    H
HETATM 8515  C40  BI  1   -23.689 -27.511 -30.755  0.00    C
HETATM 8516  N41  BI  1   -22.421 -26.987 -30.703  0.00    N
HETATM 8517  C42  BI  1   -21.270 -27.637 -30.091  0.00    C
HETATM 8518  H    BI  1   -20.374 -27.032 -30.231  0.00    H
HETATM 8519  H    BI  1   -21.459 -27.754 -29.023  0.00    H
HETATM 8520  H    BI  1   -21.119 -28.602 -30.579  0.00    H
HETATM 8521  C43  BI  1   -24.133 -28.804 -30.274  0.00    C
HETATM 8522  O44  BI  1   -23.381 -29.470 -29.493  0.00    O
HETATM 8523  O45  BI  1   -25.272 -29.218 -30.664  0.00    O1-
END
```

HEPATITIS C VIRUS NS5B POLYMERASE INHIBITOR BINDING POCKET

This application claims the benefit of U.S. Provisional Application No. 60/469,604, filed on May 9, 2003, which application is herein incorporated by reference in its entirety.

FIELD OF THE INVENTION

The present invention relates to Hepatitis C Virus NS5B polymerase (HCV NS5B), and in particular, to a novel HCV NS5B inhibitor binding pocket. The crystal structure of HCV NS5B is provided including the coordinates that define the novel inhibitor-binding pocket and 3-dimensional models for use in inhibitor screening. Methods of designing and screening NS5B inhibitors are also provided utilizing the crystal structure and inhibitor-binding information.

BACKGROUND OF THE INVENTION

Hepatitis C virus (HCV) is the major etiological agent of post-transfusion and community-acquired non-A non-B hepatitis worldwide. It is estimated that over 200 million people worldwide are infected by the virus. A high percentage of carriers become chronically infected and many progress to chronic liver disease, so called chronic hepatitis C. This group is in turn at high risk for serious liver disease such as liver cirrhosis, hepatocellular carcinoma and terminal liver disease leading to death.

The mechanism by which HCV establishes viral persistence and causes a high rate of chronic liver disease has not been thoroughly elucidated. It is not known how HCV interacts with and evades the host immune system. In addition, the roles of cellular and humoral immune responses in protecting against HCV infection and disease have yet to be established.

HCV is an enveloped positive strand RNA virus in the *Flaviviridae* family. The single strand HCV RNA genome is of positive polarity and comprises one open reading frame (ORF) of approximately 9600 nucleotides in length, which encodes a linear polyprotein of approx. 3010 amino acids. In infected cells, this polyprotein is cleaved at multiple sites by cellular and viral proteases to produce structural and non-structural (NS) proteins. The structural proteins (C, E1, E2 and E2-p7) comprise polypeptides that constitute the virus particle. The non-structural proteins (NS2, NS3, NS4A, NS4B, NS5A, NS5B) encode for enzymes or accessory factors that catalyze and regulate the replication of the HCV RNA genome. Processing of the structural proteins is catalyzed by host cell proteases. The generation of the mature non-structural proteins is catalyzed by two virally encoded proteases. The first is the NS2/3 zinc-dependent metalloprotease which auto-catalyzes the release of the NS3 protein from the polyprotein. The released NS3 protein contains an N-terminal serine protease domain and catalyzes the remaining cleavages from the polyprotein. The released NS4A protein has at least two roles. The first role is forming a stable complex with NS3 protein and assisting in the membrane localization of the NS3/NS4A complex; the second is acting as a cofactor for NS3 protease activity. This membrane-associated complex, in turn catalyzes the cleavage of the remaining sites on the polyprotein, thus effecting the release of NS4B, NS5A and NS5B. The C-terminal segment of the NS3 protein also harbors nucleoside triphosphatase and RNA helicase activity. The function of the protein NS4B is unknown. NS5A is a highly phosphorylated protein that appears to be responsible for the interferon resistance of various HCV genotypes. NS5B is an RNA-dependent RNA polymerase (RdRp) that is involved in the replication of HCV.

The open reading frame of the HCV RNA genome is flanked on its 5' end by a non-translated region (NTR) of approx. 340 nucleotides that functions as the internal ribosome entry site (IRES), and on its 3' end by an NTR of approximately 230 nucleotides. Both the 5' and 3' NTRs are important for RNA genome replication. The genomic sequence variance is not evenly distributed over the genome and the 5'NTR and parts of the 3'NTR are the most highly conserved portions.

The cloned and characterized partial and complete sequences of the HCV genome have been analyzed with regard to appropriate targets for a prospective antiviral therapy. The following four viral enzyme activities provide possible targets: (1) the NS2/3 protease; (2) the NS3/4A protease complex, (3) the NS3 helicase and (4) the NS5B RNA-dependent RNA polymerase (NS5B RdRp). The NS5B RNA dependent RNA polymerase has also been crystallized to reveal a structure reminiscent of other nucleic acid polymerases (Ago et al. 1999; Bressanelli et al. 1999; Lesburg et al. 1999) with an enclosed active site.

Virus-specific functions essential for replication are the most attractive targets for drug development. The absence of RNA dependent RNA polymerases in mammals, and the fact that this enzyme appears to be essential to viral replication, would suggest that the HCV NS5B polymerase is an ideal target for anti-HCV therapeutics. It has recently been demonstrated that mutations destroying NS5B activity abolish infectivity of HCV RNA in a chimp model (Kolykhalov, A. A. et al. 2000). The initial step of viral RNA replication is recognition of the 3'-end of RNA template by NS5B (RdRp), which may occur directly or indirectly with the help of cellular proteins (Lai, 1998; Strauss et al., 1999). HCV polymerase then proceeds to elongate this template and form a complementary RNA product.

Several groups have described the crystal structure of HCV NS5B polymerase (Ago et al. 1999 supra; Bressanelli et al. 1999 supra; Lesburg et al. 1999 supra). It resembles a flattened sphere with the approximate dimensions 70 Å×60 Å×40 Å. The polypeptide chain encircles the active site, forming a cavity at the center of the molecule, and resulting in an appearance that is very different from other U-shaped polymerases. The domain organization of NS5B is consistent with other polymerases in that it is subdivided into finger, palm and thumb domains in which the palm domain, i.e. residues 188-225 and 287-370, is conserved. In contrast to other polymerases, extensive thumb and finger domain contacts result in a globular-shaped HCV polymerase. These contacts are mediated, in part, by loops that extend from the finger to the thumb domain. Knowledge of the crystal structure of NS5B is useful for structure-based drug design and, indeed, structures of NS5B polymerase/inhibitor complexes have been reported recently (Wang et al. 2003; Love et al, 2003; EP 1 256 628). Non-nucleoside analogue inhibitors were found to bind in a wedge-like fashion to a hydrophobic binding pocket located near the C-terminal region of the polymerase thumb domain. In this study, the enzyme was determined to undergo only minor conformational changes in the enzyme/inhibitor complex. At least two NTP binding sites have been characterized on NS5B, one in the active site palm and a second potential allosteric site on the thumb (O'Farrell et al. 2003; Bressanelli et al. 2002).

Interestingly, Labonté et al. 2002 have reported that a mutation of Leu30 in the N-terminal finger loop of the NS5B affects its polymerase activity and speculate that a local alteration in the structure of the Leu30 mutant is responsible for this decrease in activity. However, the authors are silent on the presence of a binding pocket that is "masked" by the finger loop in its native state and becomes exposed by a mutation or displacement of the Leu30 residue. The discovery of this peculiar binding pocket is the subject-matter of the present invention.

Accordingly, the effort to develop effective treatments to HCV infection can be facilitated by increased knowledge of the structure of enzymes critical to HCV replication, most notably, the NS5B polymerase. An increased knowledge of enzyme structure, particularly when complexed with specific inhibitors, will lead to a means of identifying binding sites in the enzyme, as well as the conformation of enzyme/inhibitor complexes and susceptible residues in the enzyme, knowledge of each of which is critical to the process of drug design and optimization.

SUMMARY OF THE INVENTION

It has now been found that the HCV polymerase, when complexed with certain inhibitors, adopts a conformation in which the finger loop region defined by amino acid residues 18 to 35 is displaced to expose a binding pocket defined generally by amino acid residues 392, 393, 395, 396, 399, 424, 425, 428, 429, 492, 493, 494, 495, 500 and 503. This is in contrast to NS5B crystal structures disclosed in the prior art in which the finger loop defined by amino acid residues 18 to 35 conceals this binding pocket in its native state. This newly "exposed" binding pocket defines a novel target in the search of further chemical entities which are capable of binding to HCV NS5B and modulating, or preferably inhibiting, the polymerase activity of HCV NS5B.

Thus, in one aspect, the present invention provides an isolated and purified polypeptide comprising an HCV NS5B inhibitor binding pocket defined by at least amino acid residues 392, 393, 395, 396, 399, 424, 425, 428, 429, 492, 493, 494, 495, 500 and 503 of native HCV NS5B, or defined by a functionally equivalent analog thereof, wherein said binding pocket is exposed by displacement of a finger loop chain defined by at least amino acid residues 18 to 35 and said binding pocket retains its native functional configuration.

In a second aspect of the present invention, there is provided an isolated and purified HCV NS5B polypeptide analog comprising an HCV NS5B binding pocket defined by at least amino acid residues 392, 393, 395, 396, 399, 424, 425, 428, 429, 492, 493, 494, 495, 500 and 503 of native HCV NS5B, or defined by a functionally equivalent analog thereof, wherein said binding pocket retains its native functional configuration and wherein said binding pocket is exposable.

In a further aspect, there is provided an isolated and purified HCV NS5B polypeptide consisting of an HCV NS5B binding pocket defined by at least amino acid residues 392, 393, 395, 396, 399, 424,425, 428, 429, 492, 493, 494, 495, 500 and 503 of native HCV NS5B, or defined by a functionally equivalent analog thereof, wherein said binding pocket retains its native functional configuration.

In another aspect, there is provided an HCV NS5B polypeptide variant comprising at least one amino acid mutation within a finger loop defined by amino acid residues 18 to 35 of an HCV NS5B, wherein said mutation provokes displacement of said finger loop to expose a binding pocket essentially defined by amino acid residues 392, 393, 395, 396, 399, 424, 425, 428, 429, 492, 493, 494, 495, 500 and 503 of native HCV NS5B, or defined by a functionally equivalent analog thereof, and wherein said binding pocket retains its native functional configuration.

In another aspect of the present invention, there is provided an HCV NS5B polypeptide, or a functionally equivalent analog thereof, characterized by displacement of amino acid residues 18 to 35.

In another aspect of the present invention, there is provided an HCV NS5B polypeptide, or a functionally equivalent analog thereof, in which at least amino acid residues 18 to 35 have been deleted.

In another aspect of the invention, there is provided an HCV NS5B crystal structure comprising a binding pocket defined by the structural coordinates of at least amino acid residues 392, 393, 395, 396, 399, 424, 425, 428, 429, 492, 493, 494, 495, 500 and 503 of a native HCV NS5B, or defined by the structural coordinates of a functionally equivalent analog thereof, wherein a native finger loop chain defined by the structural coordinates of at least amino acids 18 to 35 is displaced to expose said binding pocket.

In another aspect of the present invention, there is provided a complex comprising an HCV NS5B polypeptide, polypeptide variant or polypeptide analog as defined above and a compound, wherein the compound associates with a binding pocket within the NS5B polypeptide, polypeptide variant or polypeptide analog, said binding pocket being defined by amino acid residues 392, 393, 395, 396, 399, 424, 425, 428, 429, 492, 493, 494, 495, 500 and 503 of native HCV NS5B, or defined by a functionally equivalent analog thereof.

In further aspects of the present invention, a method of producing a crystallized HCV NS5B complex is provided, comprising an NS5B polypeptide, polypeptide variant or polypeptide analog as defined above and a compound binding to said polypeptide, polypeptide variant or polypeptide analog, wherein said compound is associated with an NS5B binding pocket defined by at least amino acid residues 392, 393, 395, 396, 399, 424, 425, 428, 429, 492, 493, 494, 495, 500 and 503 of a native HCV NS5B, or defined by a functionally equivalent analog thereof. This method comprises the steps of:
  a) incubating a purified HCV NS5B polypeptide in a crystallization buffer to obtain a crystallized NS5B polypeptide;
  b) solubilizing the compound; and
  c) soaking the crystallized NS5B polypeptide with the solubilized compound in a soaking buffer for a suitable soaking period to generate the HCV NS5B complex.

In an alternative method of preparing a crystallized HCV NS5B complex as defined above, the compound is added to a crystallization buffer containing crystallized HCV NS5B.

Another alternative method of preparing a crystallized HCV NS5B complex as defined above comprises the steps of:
  a) combining purified HCV NS5B with the compound in solubilized form to form an NS5B complex; and
  b) crystallizing the complex in a crystallization buffer.

In another aspect of the present invention, there is provided X-ray crystal structure coordinates of a complex comprising an HCV NS5B polypeptide, polypeptide variant or polypeptide analog as defined above and a compound, wherein the compound associates with a binding pocket within the NS5B polypeptide, polypeptide variant or polypeptide analog, said binding pocket being defined by amino acid residues 392, 393, 395, 396, 399, 424, 425, 428, 429, 492, 493, 494, 495, 500 and 503 of native HCV NS5B, or defined by a functionally equivalent analog thereof.

In another aspect of the present invention, there is provided a computer-readable storage medium having stored thereon a model of the crystal structure of a complex comprising an HCV NS5B polypeptide, polypeptide variant or polypeptide analog as defined above and a compound, wherein said compound associates with an NS5B binding pocket defined by the structural coordinates of at least amino acid residues 392, 393, 395, 396, 399, 424, 425, 428, 429, 492, 493, 494, 495, 500 and 503 of a native HCV NS5B, or defined by structural coordinates of a functionally equivalent analog thereof.

In a further aspect of the present invention, there is provided a method of identifying a compound that may bind to HCV NS5B, comprising the steps of:
a) applying a 3-dimensional molecular modeling algorithm to the structural coordinates of an HCV NS5B binding pocket defined by the structural coordinates of at least amino acid residues 392, 393, 395, 396, 399, 424, 425, 428, 429, 492, 493, 494, 495, 500 and 503 of native HCV NS5B, or defined by the structural coordinates of a functionally equivalent analog thereof, to determine the spatial coordinates of the binding pocket of HCV NS5B; and
b) electronically screening stored spatial coordinates of the compound against the spatial coordinates of the HCV NS5B binding pocket to determine whether the compound may bind within the HCV NS5B binding pocket.

In another aspect of the present invention, there is provided a virtual screening method to identify potential HCV inhibitors comprising the steps of:
a) constructing a computer model of an HCV NS5B binding pocket defined by the structural coordinates of at least amino acid residues 392, 393, 395, 396, 399, 424, 425, 428, 429, 492, 493, 494, 495, 500 and 503 of a native HCV NS5B, or defined by the structural coordinates of a functionally equivalent analog thereof;
b) employing computational means to perform a fitting program operation between computer models of the compound to be evaluated and the NS5B binding pocket to provide an energy-minimized configuration of the compound in the binding pocket; and
c) evaluating the results of the filting operation to quantify the association between the compound and the binding pocket, wherein a compound that associates with the binding pocket to yield a low energy, stable complex is a potential NS5B inhibitor.

In yet another aspect of the present invention, a method of screening candidate HCV NS5B inhibitor compounds is provided comprising the steps of:
a) incubating an HCV NS5B polypeptide, polypeptide variant or polypeptide analog as defined above with a candidate inhibitor compound under conditions suitable for binding; and
b) determining whether or not the candidate inhibitor compound binds to the polypeptide, wherein a compound that binds to the polypeptide is a potential HCV NS5B inhibitor.

In another aspect of the invention, a method of designing a compound which binds to an NS5B polypeptide, polypeptide variant or polypeptide analog as defined above is provided which comprises the step of: assessing the complementarity, i.e. the "fit", between the compound and a binding pocket in the NS5B polypeptide defined by at least amino acid residues 392, 393, 395, 396, 399, 424, 425, 428, 429, 492, 493, 494, 495, 500 and 503 of a native HCV NS5B, or defined by a functionally equivalent analog thereof.

In another aspect of the invention, a method of producing a drug which inhibits RNA replication activity of HCV NS5B is provided which comprises identifying or designing a compound which fits into an NS5B binding pocket as defined by at least amino acid residues 392, 393, 395, 396, 399, 424, 425, 428, 429, 492, 493, 494, 495, 500 and 503 of a native HCV NS5B, or defined by a functionally equivalent analog thereof, wherein said binding pocket is exposed by displacement of a finger loop chain defined by at least amino acid residues 18 to 35.

Aspects and embodiments of the present invention are described in more detail herein by reference to the accompanying drawings in which:

BRIEF DESCRIPTION OF THE DRAWINGS

FIG. 4 shows the atomic structure coordinates of the HCV NS5B of SEQ ID No. 1 complexed with the compound A;

FIG. 5 shows the atomic structure coordinates of the HCV NS5B of SEQ ID No.1 complexed with the compound B FIG. 6 shows the atomic structure coordinates of the HCV NS5B of SEQ ID No.1 complexed with the compound C

DETAILED DESCRIPTION OF THE INVENTION

Definitions

Figures 1A, 1B:
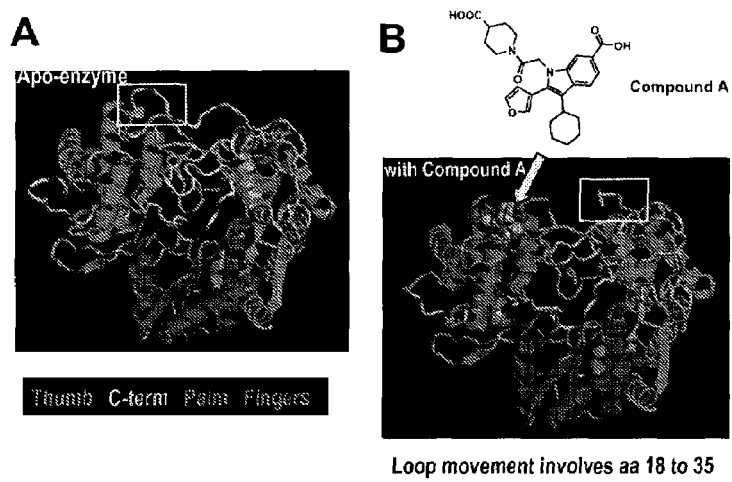
FIG. 1A depicts the NS5B apo-enzyme structure without compound.
FIG. 1B depicts compound A bound to the NS5B where amino acids 18-35 are displaced and not seen in the structure.
Figure 1C:
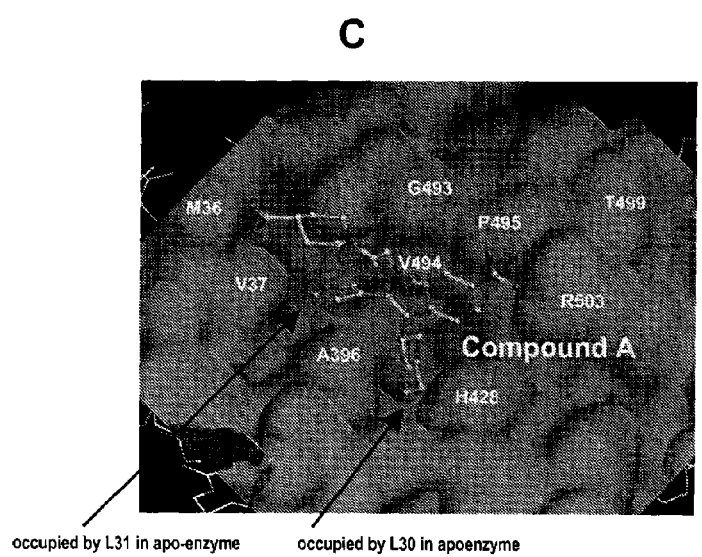
FIG. 1C depicts compound A bound within a solvent accessible surface representation of the binding pocket of the present invention.
Figure 2:
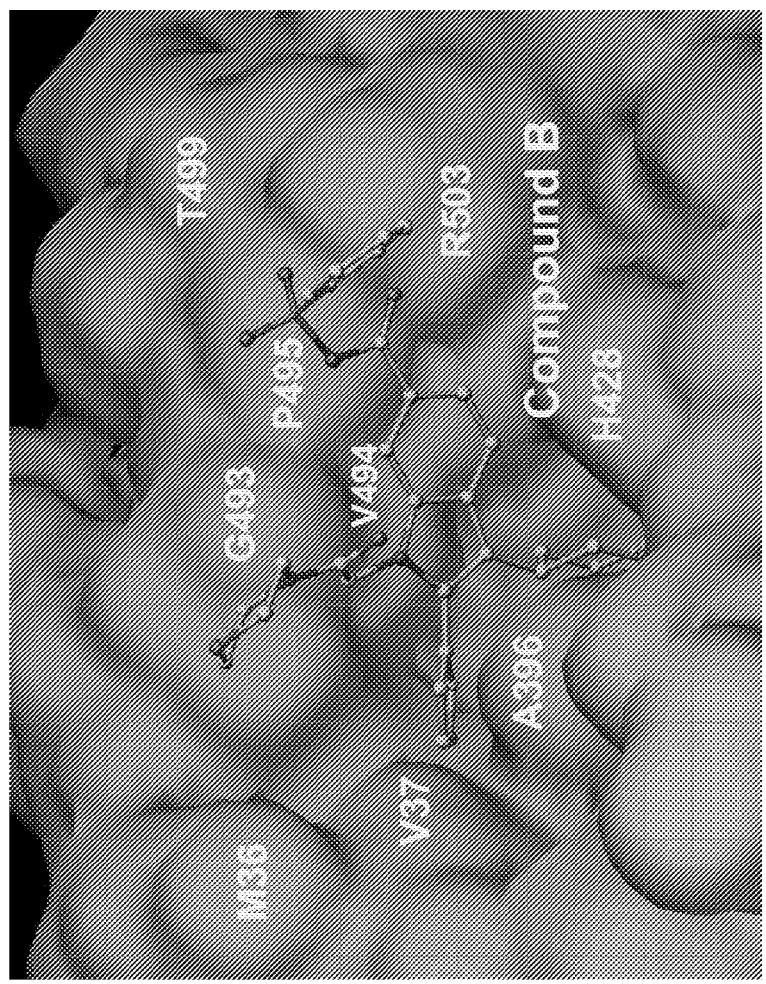
FIG. 2 depicts compound B bound within a solvent accessible surface representation of the binding pocket of the present invention.
Figure 2:
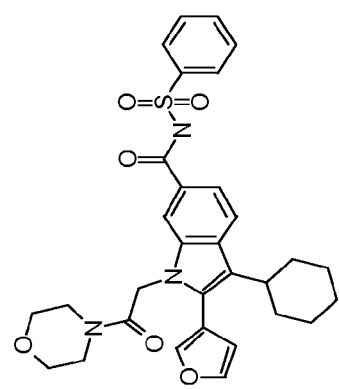
Figure 3:
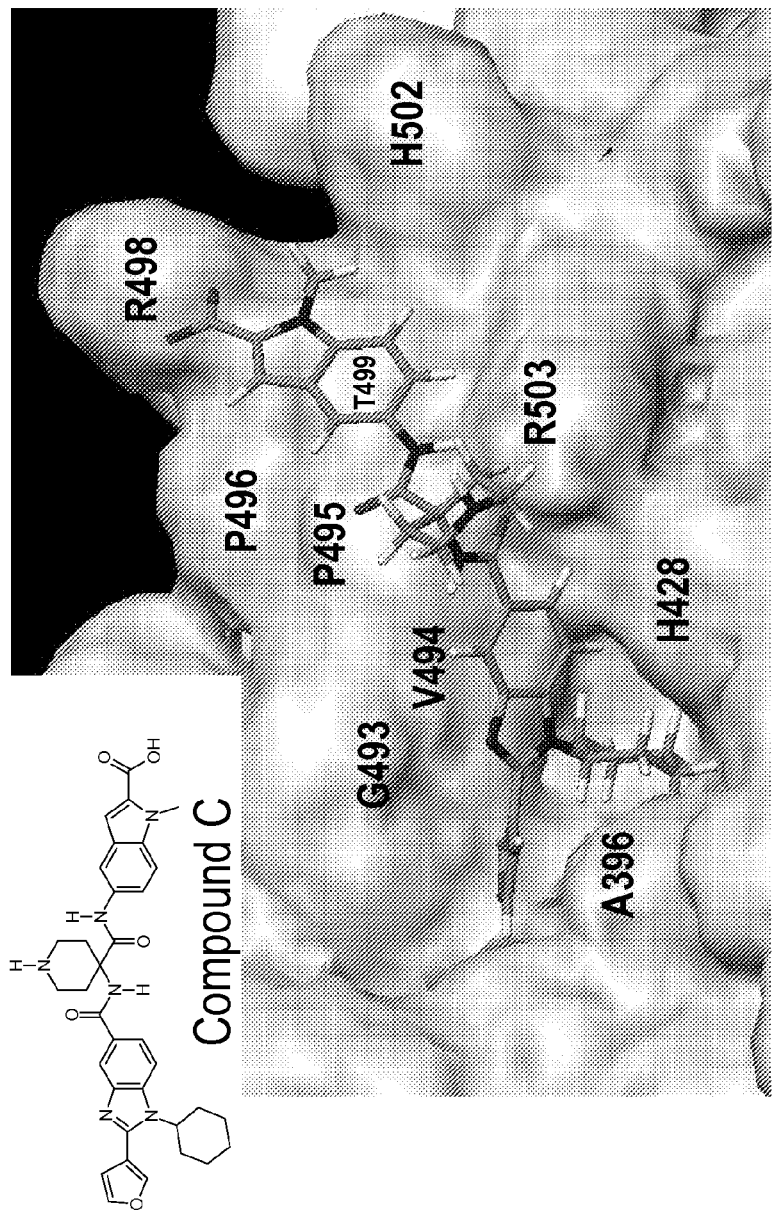
FIG. 3 depicts a docked model of the NMR derived bound conformation of compound C bound within the accessible representation of the binding pocket of the present invention.

Unless defined otherwise, the scientific and technological terms and nomenclature used herein have the same meaning as commonly understood by a person of ordinary skill to which this invention pertains. Generally, the procedures for cell culture, infection, molecular biology methods and the like are well-known to those of skill in the art. Such standard techniques can be found in reference manuals such as for example Sambrook et al. (1989) and Ausubel et al. (1994).

The term "HCV NS5B" refers to the RNA-dependent RNA polymerase (RdRp) of a Hepatitis C virus (HCV) that is involved in the replication of HCV. As one of skill in the art is well aware, the term HCV encompasses a viral family including many different strains, isolates and subtypes. Moreover, the NS5B polymerase of each member of this family, although functionally equivalent and highly homologous structurally, will vary somewhat in amino acid sequence. The amino acid sequence of one HCV NS5B polymerase, NS5B from HCV genotype 1b, is shown in SEQ ID No: 1. The sequences of other isolated HCV NS5B polymerases may be accessed in publicly available sequence databases.

The term "binding pocket", as used herein, refers to a region of a molecule or molecular complex, that, as a result of its configuration, favorably associates with or is occupied by an entity or region of the same molecule or molecular complex, or an entity or region of a different molecule, molecular complex, chemical compound or other compound. In accordance with the present invention, the NS5B binding pocket defined herein becomes exposed by displacement of the finger loop domain of residues 18-35 thereby allowing binding of a compound that is capable of affecting NS5B activity, for example, inhibiting NS5B activity. Typically, a binding pocket, or at least a portion thereof, comprises a cavity which is the site of interaction with an entity of the same or different molecule. As will be appreciated by those of skill in the art, the nature of the cavity within a binding pocket will vary from molecule to molecule.

The term "isolated and purified" as it is used with respect to polypeptides according to the present invention refers to a polypeptide that is substantially free from other components.

The term "native HCV NS5B", as it is used herein with respect to the amino acid sequence of the binding pocket of the present invention, refers to the natural amino acid sequence of the binding pocket in a given HCV NS5B.

The term "native functional configuration" as it is used with respect to the binding pocket of the present invention refers to the natural arrangement, including spatial arrangement, of amino acids that form a pocket that can associate with or be occupied by certain compounds/entities.

As used herein the term "complex" refers to the combination of two or more entities, at least one of which is a protein or enzyme. In particular, complexes in accordance with the present invention are formed between an NS5B protein, including analogs thereof which may include amino acid substitutions, truncations or insertions, and another compound. The combination or "complexing" of a compound or chemical entity with a protein refers to the nature of the association/binding between the compound or chemical entity and the protein. The association between the components of the complex is the condition of proximity therebetween and may be non-covalent in nature, wherein the juxtaposition is energetically favored by hydrogen bonding, van der Waals forces or electrostatic interactions, or it may be covalent.

The term "analog" as used herein denotes, with respect to a molecular compound, a sequence of amino acids modified from the native or natural sequence of amino acids that retains the biological activity (either functional or structural) of the native sequence of amino acids. This analog may be from the same or different species and may be a natural analog or may be prepared synthetically. Such analogs include amino acid sequences having substitutions, deletions, or additions of one or more amino acids, provided that the biological activity of the protein is conserved. In particular, the term "conservative analog" denotes an analog having amino acid modifications that retain biological activity. Analogs including amino acid substitutions may include substitutions having either strong or weak similarity (see, for example, Dayhoff, M. O., (1978), Atlas of Protein Sequence and Structure, 5, suppl. 3, National Biomedical Research Foundation, Washington, D.C.) as defined according to the following "Table of Amino Acid Similarity":

| Amino acid | Strong | Weak |
|---|---|---|
| A | G, S | C, T, V |
| C | | A, S |
| D | E | G, H, K, N, Q, R, S |

-continued

| Amino acid | Strong | Weak |
|---|---|---|
| E | D | H, K, N, Q, R, S |
| F | W, Y | H, I, L, M |
| G | A | D, N, S |
| H | Y | D, E, F, K, N, Q, R |
| I | L, M, V | F |
| K | R | D, E, H, N, Q, S, T |
| L | I, M, V | F |
| M | I, L, V | F |
| N | Q | D, E, G, H, K, R, S, T |
| P | | S, T |
| Q | N | D, E, H, K, R, S |
| R | K | D, E, H, N, Q |
| S | A, T | C, D, E, G, K, N, P, Q |
| T | S | A, K, N, P, V |
| V | I, L, M | A, T |
| W | F, Y | |
| Y | F, H, W | |

The meaning of the term "functionally equivalent analog" as it is used herein with respect to the binding pocket polypeptide of the invention refers to substitutions, deletions or insertions of one or more of the amino acids of the binding pocket. Substitutions may be made as set out above, for example, with an appropriate conservative amino acid or conservative synthetic amino acid analog. In essence, the term "analog" corresponds with the foregoing definition. The phrase "functionally equivalent" indicates that the analog retains the biological activity of the native molecule.

The term "side chain" with reference to an amino acid or amino acid residue means a group attached to the α-carbon atom of the α-amino acid. For example, the R-group side chain for glycine is hydrogen, for alanine it is methyl, for valine it is isopropyl. For the specific R-groups or side chains of the α-amino acids reference is made to A. L. Lehninger's text on Biochemistry (see chapter 4).

The term "truncation" refers to any shortened or abbreviated segment of a molecule which, for the purposes of the present invention, retains its biological activity. Truncation may refer to the shortening of a native protein molecule, or to an analog thereof.

The term "root mean square deviation" or "rms deviation" or "rmsd" means the square root of the arithmetic mean of the square of the deviations from the mean. In the context of atomic objects, the numbers are given in angstroms (Å). It is a way to express the deviation or variation from a trend or object.

The following abbreviations are used herein:
DLB: differential line broadening;
DMSO: dimethyl sulfoxide;
DTT: dithiothreitol;
EDTA: ethylenediaminetetraacetic acid;
FID: free induction decay
IPTG: isopropyl-beta-D-thiogalactopyranoside
HEPES: 4-(2-hydroxyethyl)-1-piperazineethanesulfonic acid
MES: 2-(N-morpholino)ethanesulfonic acid,
MPD: 2-methyl-2,4-pentanediol
NMR: nuclear magnetic resonance;
NOESY: Nuclear Overhauser Effect Spectroscopy
PEG: polyethylene glycol;
PEG5k mme: monomethyl ether polyethylene glycol 5000;
Tris: tris(hydroxymethyl)aminomethane;
TSP: sodium 3-trimethylsilyltetradeuteriopropionate.

Preferred Embodiments

HCV NS5B Polypeptide

In a first aspect, the present invention provides an isolated and purified polypeptide comprising a functional HCV NS5B binding pocket defined by at least amino acid residues 392, 393, 395, 396, 399, 424, 425, 428, 429, 492, 493, 494, 495, 500 and 503 (and optionally one or more of: amino acid residues 37 and 496) of a native HCV NS5B, wherein said binding pocket is exposed by displacement of a finger loop chain defined by at least amino acid residues 18 to 35 and wherein said binding pocket retains its native functional configuration.

Within this aspect of this invention, there is also provided an isolated and purified HCV NS5B polypeptide consisting of an exposed HCV NS5B binding pocket defined by at least amino acid residues 392, 393, 395, 396, 399, 424, 425, 428, 429, 492, 493, 494, 495, 500 and 503 (and optionally one or more of: amino acid residues 37 and 496 ) of a native HCV NS5B, wherein said binding pocket retains its native functional configuration.

In this aspect of the invention, it is important that the present polypeptide incorporates a binding pocket that assumes its native configuration, i.e. the natural configuration that it assumes in the native HCV NS5B polymerase, in order for it to properly mimic the binding pocket and be a useful HCV NS5B inhibitor screening tool.

Further, in order for the polypeptide to function effectively as an HCV NS5B inhibitor screening tool, it is also important that the inhibitor binding pocket be exposed, or at least exposable, in order to allow inhibitor access to the binding pocket. In HCV NS5B, the inventors have determined that the binding pocket defined herein is exposed when at least amino acid residues 18 to 35 of an NS5B finger loop chain are displaced. Accordingly, in this aspect, a polypeptide is provided in which the binding pocket is in an exposed configuration.

The binding pocket of the present invention is defined herein by reference to amino acids by their position in the HCV NS5B protein due to expected sequence similarity from one HCV genotype or strain to another. The displaced or displaceable finger loop region is also defined by reference to amino acid positions, i.e. amino acids 18 to 35. It will be readily apparent to those of skill in the art that the numbering of amino acids in all HCV NS5B may be slightly different from that of the HCV NS5B exemplified herein due to amino acid insertions or deletions. The amino acid numbering presented herein is based on native HCV 1b NS5B polymerase sequence as shown SEQ ID NO: 1. However, corresponding amino acids in other HCV NS5B can be identified by visual inspection of the amino acid sequences or by using commercially available homology software programs such as Vector NTI (provided by InfoMax Inc.). In this regard, in order to identify the NS5B protein, it is notable that the first four amino acids of the HCV NS5B sequence are typically, -SMSY-(SEQ ID NO: 2), which are conserved from one variant to the next.

In one embodiment of the present invention, the binding pocket is defined by amino acid sequence as follows:

| (37)* | 392-393 | 395-396 | 399 | 424-425 | 428-429 | 492-495 | (496)* | 500 | 503 |
|---|---|---|---|---|---|---|---|---|---|
| (V) | L-A | A-A | T | I-L | H-F | L-G-V-P (SEQ ID NO: 3) | (P) | W | R |

*(the brackets identifying optional amino acid residues)

or, alternatively, (V37), L392, A393, A395, A396, T399, I424, L425, H428, F429, L492, G493, V494, P495, (P496), W500 and R503.

As will be appreciated by one of skill in the art, a functionally equivalent analog of the polypeptide is also within the scope of this aspect of the invention. One or more of the amino acid residues of the present polypeptide, either within the binding pocket or outside of the binding pocket domain, may be substituted with a functionally equivalent amino acid, generally a conservative amino acid replacement as set out in the 'Table of Amino Acid Similarity' above, a synthetic amino acid analog thereof or a naturally occurring amino acid substitution as found in other HCV genotypes while still retaining the binding pocket in functional form or configuration. Amino acid deletions and/or insertions may also be made to the polypeptide. Such amino acid substitutions, insertions or deletions may render a polypeptide that is more practical for use in a screening assay, or a polypeptide that is more readily prepared. Cursory examples of naturally occurring amino acids substitutions within the binding pocket among different HCV genotypes include, but are in no way limited to, HCV genotype 1b NS5B has a T499V substitution; HCV genotype 1a NS5B has M36L, I424V and T499A substitutions; HCV genotype 3a NS5B has M36L, I424V, L425M, and V494C substitutions; HCV genotype 2b NS5B has M36K, L392I, A393S, I424V, L425I and V494A substitutions; HCV genotype 2a, 2k, 6b have a V494A substitution; HCV genotype 3b has a V494l substitution; HCV genotype 6a has a P495L substitution; and HCV genotype 4a has an A396V substitution.

It is notable that a binding pocket is generally defined by atoms of any amino acid of a polypeptide, e.g. NS5B, that are within 5 Å of any atom of an inhibitor when the inhibitor is complexed with the polypeptide. Various computational analyses may be used to determine whether a polypeptide comprising a binding pocket as defined herein is sufficiently similar to the HCV NS5B binding pocket described above so as to be functional. Such analyses may be carried out in well known software applications, such as the Molecular Similarity applications of QUANTA [Molecular Simulations Inc, San Diego, Calif.], Sybyl [Tripos Associates, St. Louis, Mo.], InsightII [Accelrys], and MOE [Chemical Computing Group Inc., Montreal, Quebec, Canada].

There are a number of embodiments that stem from this aspect of the invention. For example, in addition to the amino acids set out above to define the binding pocket of the present invention, the binding pocket may additionally include one or more of amino acid residues 36, 426, 498 or 499 of the HCV NS5B. Preferably, each of these positions is occupied as follows: M36, M426, R498 and T/V499.

In another embodiment of this aspect, the polypeptide may contain the amino acid cluster of residues 36 and 37 of HCV NS5B in their native configuration. It is preferred that positions 36 and 37 are occupied by the following amino acids: M36, and V37, or has the amino acid sequence M-V.

In another embodiment, the polypeptide may contain the amino acid cluster of residues 392 to 399 of HCV NS5B in their native configuration. It is preferred that positions 392 to 399 are occupied by the following amino acids: L392, A393, R394, A395, A396, W397, E398 and T399, or has the amino acid sequence L-A-R-A-A-W-E-T (SEQ ID NO: 4).

In another embodiment, the polypeptide may contain the amino acid cluster of residues 424 to 429 of the HCV NS5B in their native configuration. It is preferred that positions 424 to 429 are occupied by the following amino acids: I424, L425, M426, T427, H428 and F429, or has the amino acid sequence, I-L-M-T-H-F (SEQ ID NO: 5).

In another embodiment, the polypeptide may contain the amino acid cluster of residues 492 to 503 of the HCV NS5B in their native NS5B configuration. In this regard, it is preferred that positions 492 to 503 are occupied by the following amino acids: L492, G493, V494, P495, P496, L497, R498, T499, W500, R501, H502 and R503, or has the amino acid sequence, L-G-V-P-P-L-R-T-W-R-H-R (SEQ ID NO: 6).

HCV NS5B Polypeptide Analog

In a second aspect, the present invention provides an isolated and purified HCV NS5B polypeptide analog comprising an HCV NS5B binding pocket defined by at least amino acid residues 392, 393, 395, 396, 399, 424, 425, 428, 429, 492, 493, 494, 495, 500 and 503 (and optionally one of: amino acid residues 37 and 496) of a native HCV NS5B, or defined by a functionally equivalent analog thereof, wherein said binding pocket retains its native functional configuration and wherein said binding pocket is exposable.

An NS5B polypeptide analog as defined above which retains the functional configuration of the native binding pocket disclosed herein advantageously provides a mimic of the native NS5B polypeptide which can be designed to be superior to the native NS5B polypeptide for use in inhibitor screening assays. For example, the polypeptide analog can be designed such that it is more readily made and used, or is more stable. It can also be designed in order to provide a binding pocket that is more readily accessible.

The NS5B polypeptide may be altered to provide an NS5B polypeptide analog by amino acid substitution, deletion or insertion as described in more detail in the definitions set out above, and in particular, the definition of the term "analog". In this regard, it may be particularly desirable to modify the finger loop chain defined by amino acid residues 18 to 35 to provide a finger loop chain that is more readily displaced to expose the binding pocket of the present invention, or to provide a finger loop chain that is displaced or deleted to expose the binding pocket.

As set out above, the present HCV NS5B binding pocket is exposed when at least amino acid residues 18 to 35 of an NS5B finger loop chain are displaced. It has also been determined that certain compounds are capable of displacing the finger loop in order to access the binding pocket. Accordingly, a polypeptide analog is provided in which the binding pocket is exposable, i.e. concealed in its native NS5B configuration by a segment of the NS5B protein, such as the finger loop defined by amino acids 18 to 35, which can be displaced to expose the binding pocket, for example, by a compound with a propensity for the binding pocket.

There are a number of embodiments that stem from this aspect of the invention. For example, in addition to the amino acids set out above to define the binding pocket of the present invention, the binding pocket may additionally include one or more of amino acids residues 36, 426, 498 or 499 of the HCV NS5B. Preferably, the binding pocket includes all of these amino acid residues. Also preferably, each of these positions is occupied as follows: M36, M426, R498 and TN499.

In another embodiment of this aspect, the binding pocket of the polypeptide may contain amino acid residues 36 and 37 of HCV NS5B in their native configuration. It is preferred that positions 36 and 37 are occupied by the following amino acids: M36, and V37, or has the amino acid sequence M-V.

In another embodiment of this aspect, the binding pocket of the polypeptide may contain amino acid residues 392 to 399 of HCV NS5B in their native configuration. It is preferred that positions 392 to 399 are occupied by the following amino acids: L392, A393, R394, A395, A396, W397, E398 and T399, or has the amino acid sequence

```
L-A-R-A-A-W-E-T.        (SEQ ID NO: 4)
```

In another embodiment, the binding pocket of the polypeptide may contain the amino acid residues 424 to 429 of the HCV NS5B in their native configuration. It is preferred that positions 424 to 429 are occupied by the following amino acids: I424, L425, M426, T427, H428 and F429, or has the amino acid sequence, I-L-M-T-H-F (SEQ ID NO: 5).

In another embodiment, the binding pocket of the polypeptide may contain the amino acid residues 492 to 503 of the HCV NS5B in their native NS5B configuration. In this regard, it is preferred that positions 492 to 503 are occupied by the following amino acids: L492, G493, V494, P495, P496, L497, R498, T499, W500, R501, H502 and R503, or has the amino acid sequence,

```
L-G-V-P-P-L-R-T-W-R-H-R.    (SEQ ID NO: 6)
```

In further embodiments, the preferred sequence of the binding pocket residues is in accordance with the sequence set out in SEQ ID NO: 1.

As set out above, the binding pocket and displaceable/displaced finger loop region are defined herein by reference to amino acid positions based on the HCV genotype 1b NS5B sequence shown in SEQ ID NO: 1 due to the high level of sequence homology that exists between HCV genotypes. However, one of skill in the art will appreciate that a slight variation in the position of one or more of the amino acid residues of the binding pocket or finger loop, for example a shift in position of each of the amino acids in the pocket by 1 or 2 (which may occur due to the insertion or deletion of one or more N-terminal amino acids) or a shift in a single amino acid elsewhere in the NS5B protein (e.g. a region which has no impact on binding pocket configuration), may still yield a binding pocket in accordance with the present invention and a finger loop that functions to expose the binding pocket. Accordingly, such position discrepancies are within the scope of the present invention.

HCV NS5B Polypeptide Variants

In another aspect, there is provided an HCV NS5B polypeptide variant comprising at least one amino acid mutation within a finger loop defined by amino acid residues 18 to 35, wherein said mutation provokes a displacement of said finger loop to expose a binding pocket essentially defined by amino acid residues 392, 393, 395, 396, 399, 424, 425, 428, 429, 492, 493, 494, 495, 500 and 503 (and optionally one of: amino acid residues 37 and 496) of native HCV NS5B, or defined by a functionally equivalent analog thereof, wherein said binding pocket retains its native functional configuration.

An NS5B variant in accordance with this aspect of the invention may include any mutation which causes the finger loop defined by amino acids 18 to 35 to become displaced. For example, mutation of an amino acid which forms an association with one or more residues within the binding pocket as defined herein, may prevent such an association and thereby trigger the displacement or "opening" of the finger loop to expose the binding pocket.

In one embodiment of the present invention, at least one of the amino acid residues at positions 30 and 31 of HCV NS5B is mutated to provoke displacement of the finger loop. In a preferred embodiment, amino acid residue 30 is mutated to an amino acid residue other than leucine. More preferably, amino acid residue 30 is selected from: P, F, W, M, G, S, T, C, Y, N, Q, D, E, K, R and H.

Embodiments with respect to the binding pocket, and the additional amino acid residues that may comprise the binding pocket, as well as the specific sequences of the pocket residues, are set out above with respect to the NS5B polypeptides and analogs.

In another aspect of the present invention, there is provided an HCV NS5B polypeptide, or functionally equivalent analog thereof, characterized by displacement of amino acid residues 18 to 35.

In another aspect of the present invention, there is provided an HCV NS5B polypeptide, or functionally equivalent analog thereof, in which at least amino acid residues 18 to 35 have been deleted.

As previously set out, displacement or deletion of amino acid residues 18 to 35 exposes a novel binding pocket as defined herein which has significance in the development of HCV therapeutics.

HCV NS5B Crystal Structure

In a further aspect of the invention, there is provided an HCV NS5B crystal structure comprising a binding pocket defined by the structural coordinates of at least amino acid residues 392, 393, 395, 396, 399, 424, 425, 428, 429, 492, 493, 494, 495, 500 and 503 (and optionally one of: amino acid residues 37 and 496) of a native HCV NS5B, or defined by the structural coordinates of a functionally equivalent analog thereof, wherein a native finger loop chain defined by the structural coordinates of at least amino acids 18 to 35 is displaced to expose said binding pocket. Preferably, the structural coordinates are as set forth in any one of FIG. 4, 5 or 6.

A structure in which an inhibitor binding pocket is exposed is a valuable tool for the design and development of candidate NS5B inhibitors because it provides a means to more clearly understand the configuration and overall nature of the binding pocket, knowledge that is crucial to guide the development of therapeutic NS5B inhibitors.

In a preferred embodiment, an HCV NS5B crystal structure is provided in which the binding pocket is additionally defined by amino acid residues 36, 426, 498 and 499. In a further preferred embodiment, an HCV NS5B crystal structure is provided in which the binding pocket is defined by clusters of amino acid residues 36-37, 392-399, 424-429 and 492-503.

HCV NS5B Complex

In another aspect of the present invention, there is provided a complex comprising an HCV NS5B polypeptide and a compound, wherein the compound associates with a binding pocket within the NS5B polypeptide which is defined by amino acid residues 392, 393, 395, 396, 399, 424, 425, 428, 429, 492, 493, 494, 495, 500 and 503 (and optionally one of: amino acid residues 37 and 496) of native HCV NS5B, or defined by a functionally equivalent analog thereof.

The NS5B inhibitor-binding pocket of the present invention is exposed on displacement of the finger loop region defined by amino acid residues 18 to 35. The binding pocket itself is defined by at least the amino acid residues 392, 393, 395, 396, 399, 424, 425, 428, 429, 492, 493, 494, 495, 500 and 503 (and optionally one of: amino acid residues 37 and 496) of the HCV NS5B. However, it can further be defined by the addition of one or more of amino acid residues 36, 426, 498 and 499, or even further defined by the following clusters of amino acid residues: 36-37, 392-399, 424-429 and 492-503.

In accordance with this aspect of the invention, thus, the HCV NS5B polypeptide may be a native NS5B polypeptide, or it may be an HCV NS5B polypeptide, variant or analog selected from the group consisting of:

i) an isolated and purified polypeptide comprising a functional HCV NS5B binding pocket defined by at least amino acid residues 392, 393, 395, 396, 399, 424, 425, 428, 429, 492, 493, 494, 495, 500 and 503 (and optionally one of: amino acid residues 37 and 496) of a native HCV NS5B, or defined by a functionally equivalent analog thereof, wherein said binding pocket is exposed by displacement of a finger loop chain defined by at least amino acid residues 18 to 35 and wherein said binding pocket retains its native functional configuration;

ii) an isolated and purified HCV NS5B polypeptide consisting of an HCV NS5B binding pocket defined by at least amino acid residues 392, 393, 395, 396, 399, 424, 425, 428, 429, 492, 493, 494, 495, 500 and 503 (and optionally one of: amino acid residues 37 and 496) of a native HCV NS5B, or defined by a functionally equivalent analog thereof, wherein said binding pocket retains its native functional configuration;

iii) an isolated and purified HCV NS5B polypeptide analog comprising an HCV NS5B binding pocket defined by at least amino acid residues 392, 393, 395, 396, 399, 424, 425, 428, 429, 492, 493, 494, 495, 500 and 503 (and optionally one of: amino acid residues 37 and 496) of a native HCV NS5B, or defined by a functionally equivalent analog thereof, wherein said binding pocket retains its native functional configuration and wherein said binding pocket is exposable;

iv) an HCV NS5B polypeptide variant comprising at least one amino acid mutation within a finger loop defined by amino acid residues 18 to 35, wherein said mutation provokes a displacement of said finger loop to expose a binding pocket essentially defined by amino acid residues 392, 393, 395, 396, 399, 424, 425, 428, 429, 492, 493, 494, 495, 500 and 503 (and optionally one of: amino acid residues 37 and 496) of native HCV NS5B, or defined by a functionally equivalent analog thereof, wherein said binding pocket retains its native functional configuration;

v) an HCV NS5B polypeptide, or a functionally equivalent analog thereof, characterized by displacement of amino acid residues 18 to 35; and vi) an HCV NS5B polypeptide, or a functionally equivalent analog thereof, in which at least amino acid residues 18 to 35 have been deleted.

In a preferred embodiment of this aspect, the complex comprises an HCV NS5B polypeptide, analog or variant as defined above, associated with a compound selected from the compound families described in the following patent documents: WO 01/047883, WO 02/004425, WO 03/000254, WO 03/007945, WO 03/010140, WO 03/010141 and WO 03/026587. In an alternative preferred embodiment of this aspect, the complex comprises an HCV NS5B polypeptide, analog or variant as defined above, associated with a compound selected from the compound families described in the U.S. co-pending applications Ser. Nos. 10/755,256, 10/755,544 and 60/546,213, herein incorporated by reference. Such compounds have not previously been shown to associate with the presently claimed binding pocket of NS5B to form an NS5B complex in accordance with the present invention.

In more preferred embodiments, the HCV NS5B complex comprises NS5B polypeptide, analog or variant associated with one of compounds A, B or C as set out below:

and their utility in understanding the protein structure and specifically the binding pocket as described herein, will be understood by those of skill in the art. Reference may also be made to standard texts such as Crystal Structure Analysis, Jenny Pickworth Glusker and Kenneth N. Trueblood, 2nd Ed. Oxford University Press, 1985, New York; and Principles of Protein Structure, G. E. Schulz and R. H. Schirmer, Springer-Verlag, 1985, New York which provide further guidance in this regard.

Moreover, as is appreciated by one of skill in the art, a set of structure coordinates for an enzyme-complex, as set out in FIGS. 4, 5 and 6, is a relative set of points that define a three-dimensional shape. It is possible, thus, that an entirely different set of coordinates could define a similar or identical shape, i.e. a functionally equivalent analog of the native Compound A

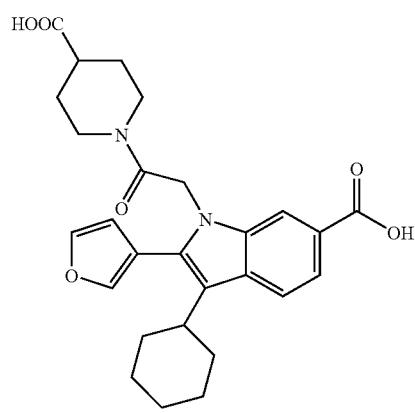

Compound B

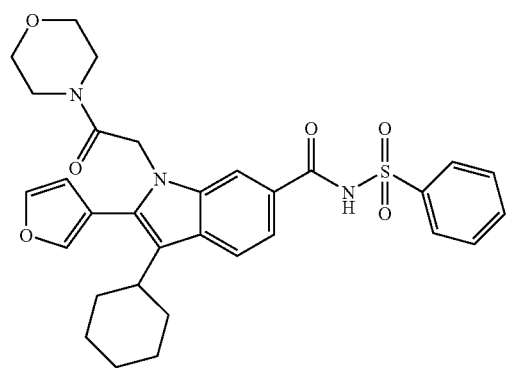

Compound C

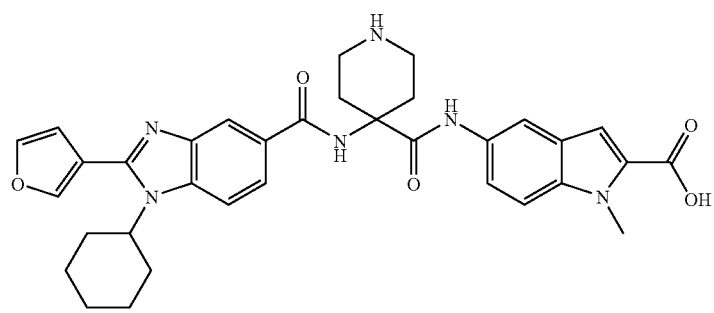

FIGS. 4, 5 and 6 show the structure coordinates of the HCV NS5B of SEQ ID No: 1 complexed with the compounds A, B and C, respectively. The manner of obtaining these structure coordinates, interpretation of the coordinates NS5B binding pocket, and thus, be within the scope of the present invention. Moreover, slight variations in the individual coordinates will have little effect on overall shape. In terms of binding pockets, these variations would not be expected to significantly alter the nature of compounds that could associate with those pockets.

It is also noteworthy that modifications in the crystal structure due to mutations, additions, substitutions, and/or deletions of amino acids, or other changes in any of the components that make up the crystal could also account for variations in structure coordinates. If such variations are within an acceptable standard of error such as a rmsd<1.0 Å for the alpha carbons that comprise the binding pocket, as compared to the original coordinates, the resulting three-dimensional shape is considered to be the same. Thus, for example, a compound that bound to the active site binding pocket of NS5B described herein would also be expected to bind to another binding pocket whose structure coordinates defined a shape that fell within the acceptable error.

Method of Crystallizing

In another aspect of the present invention, there is provided a method for producing a crystallized HCV NS5B complex comprising an HCV NS5B polypeptide and a compound, wherein said compound forms an association within an NS5B binding pocket defined by the structural coordinates of at least amino acid residues 392, 393, 395, 396, 399, 424, 425, 428, 429, 492, 493, 494, 495, 500 and 503 (and optionally one of: amino acid residues 37 and 496) of the HCV NS5B, or defined by a functionally equivalent analog thereof.

A preferred crystallization method comprises the steps of:
a) incubating a purified HCV NS5B polypeptide in a crystallization buffer to obtain a crystallized NS5B polypeptide;
b) solubilizing the compound; and
c) soaking the crystallized polypeptide with the solubilized compound in a soaking buffer for a suitable soaking period to yield a crystallized NS5B complex.

In an alternative method of preparing a crystallized HCV NS5B complex as defined above, the compound is added directly to a crystallization buffer containing crystallized HCV NS5B.

In another alternative method, a crystallized HCV NS5B complex as defined above is prepared by co-crystallizing the NS5B protein with the compound. This method comprises the steps of:
a) combining purified HCV NS5B polypeptide with the compound in solubilized form to form an NS5B complex; and
b) crystallizing the complex in a crystallization buffer.

In a preferred embodiment of this aspect, the NS5B is complexed with a compound selected from the compound families identified above. More preferably, the compound is selected from one of Compounds A, B or C, as set out above, or a related compound thereof. As set out above, the crystallization method may involve direct addition of the compound to a crystallization buffer containing crystallized HCV NS5B or combining purified HCV NS5B polypeptide with the compound in solubilized form. When the solubilized form of the compound is used, the compound is preferably solubilized in 100% DMSO at a concentration of about 25 mM.

NS5B is admixed with the purification buffer at a concentration of about 5 mg/mL to about 15 mg/mL. Preferably, the NS5B is used at a concentration of about 7 to about 10 mg/mL in the purification buffer. The purification buffer, the nature of which is generally known in the art and which may include a salt and/or glycerol to stabilize the HCV NS5B, is used at a pH of between about 6 and about 9. The preferred pH of the purification buffer is about 7.5. A buffer such as, but not limited to, Tris-HCl, HEPES or bis-Tris can be used at a concentration of between about 0 mM and about 50 mM. Preferably, the buffer is Tris-HCl at a concentration of about 20 mM.

In order to stabilize the HCV NS5B, a salt such as NaCl, $(NH_4)_2SO_4$, or KCl can be added to the buffer at a concentration of about 200 mM to about 800 mM. Preferably, the salt is NaCl at a concentration of about 300 mM.

To further stabilize the HCV NS5B, glycerol can be added at a concentration of between about 0% and about 30%. Preferably, glycerol is at a concentration of about 10%.

More preferably, the purification buffer is at about pH 7.5 and contains Tris-HCl at a concentration of about 20 mM, glycerol at a concentration of about 10%, DTT at a concentration of about 5 mM, and NaCl at a concentration of about 300 mM.

The NS5B polypeptide can be crystallized using any one of various techniques known in the art, including for example, batch crystallization under oil, hanging drop vapor diffusion and sifting drop vapor diffusion techniques. The hanging drop vapor diffusion technique, as described in McPherson et al. (Preparation and Analysis of Protein Crystals, Krieger Pub. 1989) is the preferred method of crystallization for the purposes of the present invention. Briefly, this method of crystallization involves placing a droplet containing purified NS5B in a crystallization buffer over a reservoir solution. Vapor diffusion from the droplet increases protein concentration thereby promoting crystallization.

The crystallization buffer used may be selected from any one of a number of buffers known by those of skill in the art to be suitable for this purpose, including, but not limited to, MES, sodium phosphate, potassium phosphate, sodium acetate or sodium succinate at a concentration of about 50 mM to about 0.2 M. Preferably, the crystallization buffer is MES at a concentration of about 0.1 M.

The pH of the crystallization buffer is typically between about 4.5 and about 6.5, and preferably, the crystallization buffer is used at a pH of about 5.4.

The crystallization buffer may additionally contain at least one precipitating agent which facilitates crystallization of the NS5B. Examples of appropriate precipitating agents include, but are not limited to, PEG, PEG5K mme (monomethyl ether polyethylene glycol 5000), ammonium sulfate, MPD, isopropanol, ethanol, or tertiary butanol. The precipitating agent is generally used at a concentration of about 30% to about 40%. In a preferred embodiment, the precipitating agent is PEG5K mme at a concentration of about 21% and ammonium sulfate at a concentration of about 0.4 mM.

The crystallization of NS5B is conducted under standard conditions of crystallization. For example, the crystallization is carried out at a temperature of between about 0° C. and about 22° C. The preferred temperature under which to conduct the crystallization is between about 4° C. and about 11° C.

In the preferred crystallization method, solubilized compound is soaked into crystallized NS5B polypeptide in the presence of a soaking buffer. The soaking buffer can comprise any one of a number of standard buffers including, but not limited to, MES, Tris, sodium phosphate, sodium acetate and sodium succinate at a concentration of between about 50 mM to about 0.2 M. Preferably, the soaking buffer is used at a concentration of about 0.1 M. The pH of the soaking buffer is typically between about 5 and about 8, and preferably, the soaking buffer is used at a pH of about 7.0.

The protein content of the soaking buffer is supplemented to a concentration of up to about 10 mg/mL by addition of any suitable protein including, but not limited to, lysozyme, BSA or even additional NS5B.

The soaking buffer may contain additional agents which function as NS5B stabilizers. One or more salts such as NaCl, $(NH_4)_2SO_4$ or KCl can be added to the buffer at a concentration of about 100 mM to about 500 mM. Preferably, the salt is added at a concentration of between about 150 mM and about 300 nM. More preferably, NaCl and $(NH_4)_2SO_4$ are both added at concentration of about 210 mM and about 280 mM, respectively.

To further stabilize the HCV NS5B, glycerol can be added to the soaking buffer at a concentration of between about 10 and about 20%. Preferably, glycerol is added at a concentration of about 14%.

The soaking buffer may additionally contain at least one precipitating agent which facilitates crystallization. Examples of appropriate precipitating agents include, but are not limited to, PEG, PEG5K mme (monomethyl ether polyethylene glycol 5000), ammonium sulfate, MPD, isopropanol, ethanol, or tertiary butanol. The precipitating agent is generally used at a concentration of about 10% to about 18%. In a preferred embodiment, the precipitating agent is PEG5K mme at a concentration of about 14% and ammonium sulfate at a concentration of about 0.4 mM.

Crystallized NS5B is soaked with solubilized compound in a soaking buffer for a suitable soaking period of about 1 to about 12 hours, preferably about 3 to about 8 hours and most preferably for about 5 to about 6 hours. Soaking occurs at a temperature of between about 5 and about 15° C., and preferably at a temperature of about 11° C.

In one alternative crystallization method, the compound is added to crystallization buffer containing crystallized NS5B. In this method, the compound is simply sprinkled onto the buffer and allowed to solubilize and crystallize following a suitable period of incubation.

In another alternative crystallization method, NS5B and compound are co-crystallized in a crystallization buffer as described above for NS5B alone. In this method, the NS5B and solubilized compound are combined in a crystallization buffer and allowed to crystallize under crystallization conditions such as those described above.

In accordance with the present invention, it is important that the crystallized NS5B complex be amenable to X-ray crystallography. Using X-ray crystallography analysis, the crystals of the NS5B complex obtained belong to space group P2(1)2(1)2(1) with unit cell dimension of a=105.1, b=106.6 and c=133.5 and contain two molecules per asymmetric unit. Diffraction data were measured using a MicroMax007 home source x-ray generator equipped with a R-axis IV++ image plate area detector (Rigaku, Japan). Preferably, data to a resolution of 2.8 Å were collected on a single crystal of the complex.

X-ray Coordinates

According to yet another aspect, there is provided X-ray crystal structure coordinates of an NS5B complex as defined above. Even more preferably, the set of structure coordinates for the NS5B complex are defined according to one of FIG. 4, FIG. 5 and FIG. 6.

The three-dimensional structure of an NS5B complex of this invention is defined by a set of structure coordinates as set forth in any one of FIG. 4, FIG. 5 and FIG. 6. The term "structure coordinates" refers to Cartesian coordinates derived from mathematical operations related to the patterns obtained on diffraction of a monochromatic beam of X-rays by the atoms (scaltering centers) of the complex in crystal form. The diffraction data are used to calculate an electron density map of the repeating unit of the crystal. The electron density maps are then used to establish the positions of the individual atoms of the binding pocket known as the structure coordinates.

Those of skill in the art will understand that a set of structure coordinates for a protein or protein-inhibitor complex or a portion thereof, is a relative set of points that define a shape in three dimensions. Thus, it is possible that an entirely different set of coordinates could define a similar or identical shape.

The variations in coordinates may be generated by mathematical manipulations of the structure coordinates. For example, the structure coordinates set forth in FIG. 4, 5 or 6 could be manipulated by crystallographic permutations of the structure coordinates, fractionalization or matrix operations to sets of the structure coordinates or any combination of the above.

Various computational analyses are necessary to determine whether a molecule or molecular complex or a portion thereof is sufficiently similar to all or parts of the HCV NS5B protein or the NS5B complex described herein to be considered equivalent. Such analyses may be carried out using current software applications, such as the Molecular Similarity applications of QUANTA [Molecular Simulations Inc, San Diego, Calif.], Sybyl [Tripos Associates, St. Louis, Mo.], InsightII [Accelrys], and MOE [Chemical Computing Group Inc., Montreal, Quebec, Canada].

The Molecular Similarity application permits comparisons between different structures, different conformations of the same structure, and different parts of the same structure. The procedure used in Molecular Similarity to compare structures is divided into four steps: 1) load the structures to be compared; 2) define the atom equivalence in these structures; 3) perform a fitting (superposition) operation; and 4) analyze the results.

Computer-readable Storage Medium

Still, in another aspect of the present invention, there is provided a computer-readable storage medium having stored thereon a model of the crystal structure of an HCV NS5B complex comprising an HCV NS5B polypeptide and a compound, wherein said compound associates with an NS5B binding pocket defined by the structural coordinates of at least amino acid residues 392, 393, 395, 396, 399, 424, 425, 428, 429, 492, 493, 494, 495, 500 and 503 (and optionally one of: amino acid residues 37 and 496) of a native HCV NS5B as set forth in FIGS. 4, 5 and 6, or defined by structural coordinates of a functionally equivalent analog thereof.

Computer readable data storage media are well known to those skilled in the art and include, for example, hard-disk, CD-ROM, diskette ("floppy disks") and DVD.

In accordance with this aspect of the present invention, the structure coordinates of an NS5B complex, and portions thereof, can be stored in a machine-readable storage medium. Such data can be used for a variety of purposes, such as drug discovery and X-ray crystallographic analysis of the protein crystal.

In a preferred embodiment of this aspect, the HCV NS5B complex comprises NS5B complexed with a compound of a compound family identified above. More preferably, the NS5B complex comprises NS5B complexed with one of Compounds A, B or C.

As set out previously, the binding pocket may be additionally defined by the addition of one or more of the amino acid residues selected from 36, 426, 498 and 499, or even further defined by the amino acid clusters, 36-37, 392-399, 424-429 and 492-503.

The coordinate data of an NS5B complex, such as that set out in FIGS. 4, 5 and 6, when used in conjunction with a computer programmed with software to translate those coordinates into a 3-dimensional structure, may be used for a variety of purposes, especially for purposes relating to drug discovery. Software for generating such three-dimensional graphical representations are known and commercially available. Examples include Quanta and WebLite Viewer. The ready use of the coordinate data requires that it be stored in a computer-readable format. Thus, in accordance with the present invention, data capable of being displayed as a three dimensional structure is stored in a computer-readable storage medium which is capable of displaying a graphical three-dimensional representation of an HCV NS5B complex or of an HCV NS5B binding pocket as defined herein when used by a machine programmed with instructions for using said data.

The HCV NS5B X-ray coordinate data is useful for screening compounds for potential NS5B inhibitory activity. For example, the polypeptide NS5B binding pocket structure encoded by the data may be computationally evaluated for its ability to associate or bind with a given compound. Compounds determined to "fit" into the binding pocket defined herein via some type of association or bonding may also impede the biological activity of the HCV NS5B polymerase and, thus, represent a potential drug candidate. In addition, the data may be displayed in a graphical three-dimensional representation on a computer screen which allows visual examination of the HCV NS5B binding pocket as well as the association of compounds within the binding pocket in an NS5B complex.

Virtual Methods of Identifying Compounds that Associate/Bind HCV NS5B

In further aspects, the present invention provides virtual methods to evaluate the potential of a compound to complex with HCV NS5B. These methods represent a first screen in the search for compounds that can associate or bind to the binding pocket of the present invention, and ultimately in the search for a compound that has therapeutic effects due to an association/binding with the binding pocket that results in HCV inhibition.

Thus, in a further aspect of the present invention, a virtual screening method is provided to identify potential HCV inhibitors comprising the steps of:
  a) constructing a computer model of an HCV NS5B binding pocket defined by the structural coordinates of at least amino acid residues 392, 393, 395, 396, 399, 424, 425, 428, 429, 492, 493, 494, 495, 500 and 503 (and optionally one of: amino acid residues 37 and 496) of a native HCV NS5B, or defined by a functionally equivalent analog thereof;
  b) employing computational means to perform a filtering program operation between computer models of the compound to be evaluated and the NS5B binding pocket to provide an energy-minimized configuration of the compound in the binding pocket; and
  c) evaluating the results of the fitting operation to quantify the association between the compound and the binding pocket, wherein a compound that associates with the binding pocket to yield a low energy, stable complex is a potential NS5B inhibitor.

In addition, the present invention provides a method of identifying compounds that can bind to HCV NS5B, comprising the steps of:
  a) applying a 3-dimensional molecular modeling algorithm to the structural coordinates of an HCV NS5B binding pocket defined by at least amino acid residues 392, 393, 395, 396, 399, 424, 425, 428, 429, 492, 493, 494, 495, 500 and 503 (and optionally one of: amino acid residues 37 and 496) of a native HCV NS5B to determine the spatial coordinates of the binding pocket of HCV NS5B; and
  b) electronically screening stored spatial coordinates of candidate compounds against the spatial coordinates of the HCV NS5B binding pocket to identify compounds that can bind within the HCV NS5B binding pocket.

In preferred embodiments of this aspect of the invention, the binding pocket may be defined additionally by one or more of amino acid residues 36, 426, 498 and 499, or by one or more of the amino acid clusters defined by amino acid residues 36-37, 392-399, 424-429 and 492-503.

In another preferred embodiment of the invention, the structural coordinates of the binding pocket are those set out in any one of FIGS. 4, 5 and 6, or functionally equivalent structural coordinates as would be appreciated by one of skill in the art.

According to this aspect of the invention, any given compound may be computationally evaluated for its ability to associate with the HCV NS5B binding pocket defined herein, and thus, its potential as an NS5B inhibitor determined. As alluded to above, a computer model of a polypeptide consisting of an HCV NS5B binding pocket as defined herein is constructed using well-known software such as QUANTA [Molecular Simulations Inc, San Diego, Calif.], Sybyl [Tripos Associates, St. Louis, Mo.], InsightII [Accelrys], MOE [Chemical Computing Group Inc., Montreal, Quebec, Canada]. Selected compounds to be evaluated may then be positioned in a variety of orientations, or docked, within the binding pocket. Docking may be accomplished using software such as GRID, DOCK, AUTODOCK, FlexX, and GOLD. When a compound is docked within the binding pocket to form a "virtual" representation of an NS5B complex, computational means may be further employed to generate quantitative and qualitative maps of the complex, including for example, pharmacophore maps, surface property maps (which map Conolly, Gaussian and van der Waals surfaces) and maps of Probabilistic Receptor Potentials using software such as QUANTA, Sybyl, InsightII, and MOE.

The efficiency with which a selected compound binds to the present HCV NS5B binding pocket may be tested and optimized by computational evaluation. The quality of the fit of a given compound within the NS5B binding pocket may be evaluated, for example, by shape, size and electrostatic complementarity as determined qualitatively by visual inspection or as determined quantitatively by the use of scoring functions such as LUDI, PLP, PMF, SCORE, GOLD and FlexX. These methods of qualitative and quantitative evaluation may be employed individually or in combination, for example, as in a consensus scoring manner.

Alternatively, binding efficiency can be determined based on the interaction energy of a complex formed by the binding or association of a compound with the HCV NS5B. For example, a compound determined to form a "low energy, stable complex" with NS5B, in the manner described herein, warrants further analysis as a potential NS5B inhibitor. The term "low energy, stable complex" as used herein is defined as an NS5B complex in which the van der Waals interaction energy value, i.e. the van der Waals energy of interaction between the compound and NS5B, is less than about 8000 kcal/mol. Van der Waals interaction energy value can be determined using the software MOE, and is based on the MMFF94 force field. Accordingly, a compound determined to form a complex having a van der Waals interaction energy value of less than about 8000 kcal/mol is a potential NS5B inhibitor. Preferably, a low energy, stable complex in accordance with the present invention will have a van der Waals interaction energy value of less than about 6000 kcal/mol, and more preferably, a value of less than about 4000 kcal/mol.

Method of Using the NS5B Polypeptide Variants/Analogs of the Invention

Once a series of compounds has been screened using virtual methods such as those described above, compounds determined to be potential HCV inhibitors can be further evaluated to determine the actual propensity of each to interact with the binding pocket of the present invention and to inhibit HCV.

Thus, in still another aspect of the invention, a method of screening candidate HCV NS5B inhibitor compounds is provided comprising the steps of:

a) incubating a candidate inhibitor compound under conditions suitable for binding with a polypeptide selected from the group consisting of:
  i) an isolated and purified polypeptide comprising a functional HCV NS5B binding pocket defined by at least amino acid residues 392, 393, 395, 396, 399, 424, 425, 428, 429, 492, 493, 494, 495, 500 and 503 (and optionally one of: amino acid residues 37 and 496) of a native HCV NS5B, or defined by a functionally equivalent analog thereof, wherein said binding pocket is exposed by displacement of a finger loop chain defined by at least amino acid residues 18 to 35 and wherein said binding pocket retains its native functional configuration;
   ii) an isolated and purified HCV NS5B polypeptide consisting of an HCV NS5B binding pocket defined by at least amino acid residues 392, 393, 395, 396, 399, 424, 425, 428, 429, 492, 493, 494, 495, 500 and 503 (and optionally one of: amino acid residues 37 and 496) of a native HCV NS5B, or defined by a functionally equivalent analog thereof, wherein said binding pocket retains its native functional configuration;
   iii) an isolated and purified HCV NS5B polypeptide analog comprising an HCV NS5B binding pocket defined by at least amino acid residues 392, 393, 395, 396, 399, 424, 425, 428, 429, 492, 493, 494, 495, 500 and 503 (and optionally one of: amino acid residues 37 and 496) of a native HCV NS5B, or defined by a functionally equivalent analog thereof, wherein said binding pocket retains its native functional configuration and wherein said binding pocket is exposable;
   iv) an HCV NS5B polypeptide variant comprising at least one amino acid mutation within a finger loop defined by amino acid residues 18 to 35, wherein said mutation provokes a displacement of said finger loop to expose a binding pocket essentially defined by amino acid residues 392, 393, 395, 396, 399, 424, 425, 428, 429, 492, 493, 494, 495, 500 and 503 (and optionally one of: amino acid residues 37 and 496) of native HCV NS5B, or defined by a functionally equivalent analog thereof, wherein said binding pocket retains its native functional configuration;
   v) an HCV NS5B polypeptide, or a functionally equivalent analog thereof, characterized by displacement of amino acid residues 18 to 35; and
   vi) an HCV NS5B polypeptide, or a functionally equivalent analog thereof, in which at least amino acid residues 18 to 35 have been deleted; and
b) determining whether or not the candidate inhibitor compound binds to the polypeptide, wherein a compound that binds to the polypeptide is a potential HCV NS5B inhibitor.

Binding of the candidate compound within the defined HCV NS5B binding pocket can be determined using methods well-established in the art. For example, binding assays may be used in which the candidate compound is exposed to a polypeptide containing the NS5B binding pocket of the invention under conditions suitable for association or binding to occur. Binding is then assessed, for example using NMR or other known detection techniques.

Method of Designing an HCV NS5B Inhibitor

In further aspects of the present invention, there is provided methods of designing compounds which associate with the NS5B binding pocket defined herein. The present invention, thus, provides the opportunity to use molecular design techniques to identify, select or design potential inhibitors of HCV NS5B based on the structure of a novel binding pocket in NS5B. Such a predictive model is valuable in light of the high costs associated with the preparation and testing of many diverse compounds that may or may not bind to the HCV NS5B protein.

According to this invention, a potential NS5B inhibitor may be evaluated for its ability to bind an NS5B binding pocket as defined herein prior to its actual synthesis and testing. If a proposed compound is predicted to have insufficient interaction or association with the binding pocket, preparation and testing of the compound is obviated. However, if the computer modeling indicates a strong interaction, the compound may then be obtained and physically tested for its ability to bind. Testing to confirm binding may be performed using conventional assays within the purview of one of skill in the art.

In this regard, a method of designing a compound which binds to an NS5B polypeptide as defined above is provided which comprises the step of: assessing the complementarity, i.e. the "fit", between the compound and a binding pocket in the NS5B polypeptide defined by at least amino acid residues 392, 393, 395, 396, 399, 424, 425, 428, 429, 492, 493, 494, 495, 500 and 503 (and optionally one of: amino acid residues 37 and 496) of a native HCV NS5B, or defined by a functionally equivalent analog thereof.

Similarly, a method of producing a drug which inhibits RNA replication activity of HCV NS5B is also provided which comprises identifying or designing a compound which fits into an NS5B binding pocket as defined by at least amino acid residues 392, 393, 395, 396, 399, 424, 425, 428, 429, 492, 493, 494, 495, 500 and 503 (and optionally one of: amino acid residues 37 and 496) of a native HCV NS5B, or defined by a functionally equivalent analog thereof, wherein said binding pocket is exposed by displacement of a finger loop chain defined by at least amino acid residues 18 to 35.

For the first time, the present invention permits the use of structure-based or rational drug design techniques to design, select, and synthesize chemical entities, including inhibitory compounds, that are capable of filting into and/or binding with the novel NS5B binding pocket defined herein.

One particularly useful drug design technique enabled by this invention is iterative drug design. Iterative drug design is a method for optimizing associations between a protein and a compound by determining and evaluating the three-dimensional structures of successive sets of protein/compound complexes.

Those of skill in the art will realize that association of natural ligands or substrates with the binding pocket of their corresponding receptors or enzymes is the basis of many biological mechanisms of action. Similarly, many drugs exert their biological effects through association with the binding cavities of receptors and enzymes. Such associations may occur with all or any part of the binding pocket. An understanding of such associations will help lead to the design of drugs having more favorable associations with their target receptor or enzyme, and thus, improved biological effects. Therefore, this information is valuable in designing potential ligands or inhibitors of receptors or enzymes, such as inhibitors of HCV NS5B-like polypeptides, and more importantly, HCV NS5B.

In iterative drug design, crystals of a series of protein/compound complexes are obtained and then the three-dimensional structure of each complex is solved. Such an approach provides insight into the association between the proteins and compounds of each complex. This is accomplished by selecting compounds with inhibitory activity, obtaining crystals of this new protein/compound complex, solving the three-dimensional structure of the complex, and comparing the associations between the new protein/compound complex and previously solved protein/compound complexes. By observing how changes in the compound affected the protein/compound associations, these associations may be optimized.

Embodiments of the present invention are described in the following specific examples which are not to be construed as limiting.

EXAMPLES

Example 1

Expression and Purification of HVC NS5B

The recombinant HCV genotype 1b (J4 strain) NS5B polymerase (the amino acid sequence of which is shown in SEQ ID NO: 1) was produced in soluble form by expression of a variant that lacks the C-terminal 21 amino acids normally found on the mature NS5B. For the purposes of the present invention, this NS5BΔ21 was expressed with a C-terminal hexa-histidine sequence. Expression of the NS5B from a pET vector in *E. coli* strain JM109 (DE3) was induced with 0.4 mM IPTG for 3 hours at 24° C. Cells were harvested (in 25 mM Tris pH 7.5, 10% glycerol, 1 mM EDTA, 500 mM NaCl, 2 mM 2-mercaptoethanol and cocktail of protease inhibitors (standard cocktail that can be purchased from Roche Biochemicals Inc.) and lysed in a microfluidizer. The lysate, after centrifugation (30,000×), was purified according to the following sequential chromatographic steps that are known to one skilled in the art: (i) metal affinity using Ni-NTA resin (Qiagen) and elution with a buffer containing increasing concentration of imidazole (from 10 mM to 500 mM); (ii) DEAE-Sepharose chromatography wherein the NS5B flowed through the column in a buffered solution containing 300 mM NaCl; (iii) Heparin Sepharose chromatography wherein the NS5B was in a buffered solution with 200 mM NaCl, and then bound NS5B was then eluted with a buffer containing a gradient up to 1 M NaCl. Eluted fractions, enriched with the NS5B protein were concentrated on a Resource S column, and then applied to a Superdex 200 column in 20 mM Tris-HCl pH 7.5, 10% glycerol, 5 mM DTT, 300 mM NaCl. Peak fractions containing highly pure His-tag NS5B were stored at −80° C. until use.

Example 2

Crystallization of HCV NS5B

HCV polymerase NS5B strain 1b/J4 (SEQ. ID NO: 1), obtained as described in detail in Example 1, was crystallized in its apo form using monomethyl ether polyethylene glycol 5000 (PEG5Kmme) as a precipitant agent. Large single crystals were obtained by the hanging drop vapor diffusion technique (McPherson, supra). In particular, 1 μL of NS5B (7.66 mg/mL in purification buffer containing 20 mM Tris, pH 7.3, 300 mM NaCl, 10% glycerol) was added to 1 μL of a solution made of 21% PEG5Kmme, 0.1 M MES, pH 5.4, 10% glycerol and 0.4 M ammonium sulfate. The resulting 2 μL drop was suspended above a 1 mL reservoir solution of 21% PEG5Kmme, 0.1 M MES, pH 5.4, 20% glycerol and 0.4 M ammonium sulfate. The crystals of the NS5B complex obtained belong to space group P2(1)2(1)2(1) with unit cell dimension of a=105.1, b=106.6 and c=133.5 and contain two molecules per asymmetric unit. The crystals were shown to diffract to a resolution of up to 2 Å using X-rays from a regular rotating anode source.

Example 3

Preparation of Inhibitor Compounds A, B and C

Inhibitor compound A was made as described in detail in co-pending application U.S. Ser. No. 10/755,256 filed Jan. 12, 2004.

Inhibitor compound B was made as described in detail in co-pending application U.S. Ser. No. 10/755,256 filed Jan. 12, 2004.

Inhibitor compound C was made as described in detail in WO 03/007945 published Jan. 22, 2003.

Example 4

Formation of NS5B-Inhibitor Complex

Inhibitor Soaking

Crystals were transferred in a 5 μL drop of a soaking solution made of 14% PEG5Kmme, 14 mM Tris, pH 7.5, 70 mM MES, pH 7.0, 14% glycerol, 210 mM NaCl, 10 mg/mL lysozyme and 280 mM ammonium sulfate. The inhibitor molecule was dissolved in DMSO to a concentration of 25 mM. Inhibitor solution (0.2 μL) was added to the 5 μL NS5B crystal drop and incubated for 5-6 hours at 11° C. Following incubation, the crystals of the NS5B-inhibitor complex were transferred from the solution with a cryoloop (Hampton Research, California, USA) and cryo-cooled in liquid nitrogen. NS5B complexes were prepared using Compounds A and B.

Data Collection

Diffraction data were collected on a MicroMax-007 rotating anode x-ray generator equipped with an Raxis-IV++ Image plate detector (Rigaku/MSC, Texas, USA). Data to a resolution of 2.8 Å was collected on a single crystal cryo-cooled at −180° C. for NS5B complexes prepared with Compound A and Compound B.

Phasing, Model Building and Refinement

The diffraction data were phased by Molecular Replacement (MR) using the publicly available structure of HCV NS5B (pdb code: 1C2J). Rotation and translation search were done using the program CNX (Accelrys). Model building was carried out with the software O (Alwyn Jones, Upsala University, Sweden) and model refinement was performed with the CNX software (Accelrys). The model was improved by repetition of the procedure of model building and refinement until a desirable result was obtained. The final model in each case included two molecules of NS5B, identified as NS5B A and NS5B B, (i.e. residue A1 to A149, A154 to A563, B1 to B17, B36 to B148 and B153 to B563) and one molecule of compound A or B associated with NS5B molecule B. The resulting atomic structure coordinates of the compound A and compound B NS5B complexes are shown in FIG. 4 and FIG. 5, respectively. The final crystallographic R factor the NS5B-Compound A complex was 21.9% and $R_{free}$ factor was 28.0% to a resolution of 2.8 Å. For the NS5B-Compound B complex, the final crystallographic R factor was 21.9% and $R_{free}$ factor was 25.7% to a resolution of 2.7 Å.

Example 5

Model of NS5B-Compound C Complex Based on an NMR Bound Conformation

The binding site of Compound C on HCV polymerase was determined by several steps which are described herein in detail. Initially, NMR spectroscopic methods (transferred NOESY) were applied to determine the structure of Compound C when bound to HCV polymerase. Another NMR technique, differential line-broadening (DLB), helped to identify the segments of Compound C which come into contact with the polymerase versus those that are solvent exposed in the bound state. The bound structure was then docked onto the X-ray-derived structure of the NS5B-Compound A complex. The docking procedure began by overlaying the common feature of the 5/6 aromatic rings of the indole and benzimidazole of Compound A and Compound C. All the differential line-broadening data were then accounted for and the complex was energy minimized using MOE.

The transferred NOESY and DLB data were acquired as follows. A sample tube (5 mm) containing Compound C was prepared by adding 15 μL of concentrated solution in DMSO-$d_6$ (containing 0.31 mg of Compound C) to an aqueous buffer composed of 20 mM Tris-$d_{11}$, 2 mM DTT-$d_{10}$, 1 mM EDTA-$d_{12}$, 300 mM NaCl, and 10% (v/v) $D_2O$ spiked with TSP-2,2,3,3-$d_4$. Buffer was added to a final volume of 600 μL, and the pH was adjusted to 6.0. Spectra of free Compound C were taken. A concentrated stock solution of HCV polymerase was added twice to the NMR tube and spectra were acquired. The concentrated stock contained 21.7 mg/mL of HCV polymerase (NS5BΔ21C-His$_6$) in buffer consisting of 20 mM Tris-$d_{11}$, 2 mM DTT-$d_{10}$, 1 mM EDTA-$d_{12}$, 300 mM NaCl, and 10% (v/v) glycerol-$d_8$.

NMR spectra were acquired on Bruker AVANCE 600 and 800 MHz NMR spectrometers at 22 and 27° C. Suppression of the solvent signal was achieved by the use of pre-saturation or by inserting a 3-9-19 WATERGATE module prior to data acquisition. One-dimensional spectra were collected on both sample tubes for DLB comparisons, and 128 scans were collected for each spectrum. NOESY experiments on a sample tube containing no polymerase resulted in the observation of no significant cross-peaks, as expected. On the other hand, NOESY spectra on a sample tube containing polymerase resulted in the observation of many cross-peaks which contained the valuable inter-hydrogen distance information of the inhibitor C when bound to HCV polymerase. A series of NOESY mixing times including 75, 100, 150, 200 and 300 msec (at 600 and 800 MHz fields) was recorded. Two-dimensional data sets were typically acquired with 2048 points in $t_2$ and 512 points in $t_1$. 128 scans were averaged for NOESY FIDs. The data were processed and analyzed using Bruker's XWinNMR and WinNMR software (Bruker Canada, 555 Steeles Ave. East, Milton, Ontario). Data sets were zero-filled to yield 2048 by 2048 real points after transformation using a phase-shifted sinebell window function.

The structure of Compound C was calculated by a custom simulated annealing protocol that was implemented in the MOE molecular modeling program (CCG, Montreal, Qc, Canada). All calculations were performed using the mmff94 forcefield as implemented in MOE version 2202.03. NMR-derived flat-bottomed restraints were generated from the series of NOESY data. The relative intensity of NOESY cross-peaks was classified into three categories which were then used as restraints, strong (1.8-2.7 Å), medium (1.8-3.5 Å) or weak (1.8-5.0 Å). The force constants in the NMR-derived flat-bottomed restraints were gradually increased during the cooling stages. A single, high temperature unrestrained dynamics run was performed at 1000 K, with 100 structures collected at 10 psec intervals to generate a starting set of conformations. Each structure was cooled and minimized using the following simulated annealing protocol. During the simulations the temperature and restraint weights were changed from 1000K to 50K, and from 1/10000000 to 20, respectively. The final structures were energy minimized, the total energies were calculated, the restraint energies were calculated, and the restraint violations were determined. NMR-consistent structures were isolated, and two families of structures were identified.

One representative from each family of NMR-derived structures was then docked onto the X-ray-derived structure of the NS5B-Compound A complex. The docking procedure began by overlaying the common 5/6 aromatic rings of the indole and benzimidazole scaffolds of Compounds A and C. Only one structure of Compound C simultaneously matched the DLB data and the shape of the binding pocket. In this complex, the right-hand side of Compound C lies over or in the vicinity of Pro 495 and Pro 496. Using the MOE molecular modeling program, the side-chain orientations of amino acids at positions 503, 498, and 499 were slightly re-adjusted to improve the inhibitor-polymerase fit. His 428 and 502 were protonated. A combination of steepest descent, conjugate gradient and truncated Newton algorithms was used to minimize the energy of the complex which resulted in only minor changes to the structure. The protocol was set up such that the inhibitor and polymerase residues within 6 Å of the inhibitor were allowed to move during the minimization whereas all other residues were fixed, and a cutoff of long-range forces at 9.5-10 Å was used. The mmff94s forcefield as implemented in the MOE molecular modeling program version 2002.03 was applied for the calculations which included solvation. Visualization of the complex was performed using the MOE molecular modeling program.

The structural coordinates of the NS5B-Compound C complex were generated from the final minimization and are shown in FIG. 6.

REFERENCES

Ago et al. 1999, Structure 7(11): 1417-1426
Ausubel et al., 1994, Current Protocols in Molecular Biology, Wiley, N.Y.
Bressanelli et al. 1999, Proc. Natl. Acad. Sci, USA 96(23): 13034-13039.
Bressanelli et al., 2002, J. Virol. 76: 3482-3492.
Dayhoff, M. O., 1978, Atlas of Protein Sequence and Structure, 5, suppl. 3, National Biomedical Research Foundation, Washington, D.C.
Kolykhalov, A. A. et al., 2000; J. Virol. 74: 2046-2051.
Labonté et al., 2002, J. Biol. Chem. 277(41): 38838-38846.
Lai, M. M. C., 1998, Virology 244, 1-12.
Lehninger, A. L., et al., 1993, Principles of Biochemistry (2nd edn.) Worth, New York.
Lesburg et al. 1999, Nat. Struct. Biol. 6: 937-943.
Love et al., 2003, J. Virol. 77: 7575-7581.
McPherson et al., 1989, Preparation and Analysis of Protein Crystals, Krieger Pub.
O'Farrell et al., 2003, J. Mol. Biol. 326: 1025-1035.
Pickworth-Glusker J., Trueblood K. N., Crystal Structure Analysis, 2nd Ed. Oxford University Press, 1985, New York.
Sambrook et al., 1989, Molecular Cloning—A Laboratory Manual, Cold Spring Harbor Labs.
Schulz G. E. and Schirmer R. H., 1985, Principles of Protein Structure, Springer-Verlag, New York
Stauss, J. H., and Strauss, E. G. 1999, *Science* 283, 802-804.
Wang et al., 2003, J. Biol. Chem. 278(11): 9485-9495.
WO 01/047883.
WO 02/004425.
WO 03/000254.
WO 03/007945.
WO 03/010140.
WO 03/010141.
WO 03/026587.
EP 1 256 628.
U.S. Ser. No. 10/755256.
U.S. Ser. No. 10/755544.
U.S. Ser. No. 60/546213.

---

What is claimed is:

1. A method of identifying a compound that may bind to HCV NS5B, comprising the steps of:
   a) obtaining the structural coordinates of one of FIGS. 4 through 6;
   b) applying a 3-dimensional molecular modeling algorithm to the structural coordinates of an HCV NS5B binding pocket defined by the structural coordinates of at least amino acid residues 392, 393, 395, 396, 399, 424, 425, 428, 429, 492, 493, 494, 495, 500 and 503, and optionally one of: amino acid residues 37 and 496, of native HCV NS5B as shown in said Figure to determine the spatial coordinates of the binding pocket of HCV NS5B; and
   c) electronically screening stored spatial coordinates of the compound against the spatial coordinates of the HCV NS5B binding pocket to determine if the compound binds within the HCV NS5B binding pocket, wherein a compound identified by the electronic screening as a compound that binds to NS5B is identified as a compound that may bind to HCV NS5B.

2. A virtual screening method to identify potential HCV inhibitors comprising the steps of:
   a) obtaining the structural coordinates of one of FIGS. 4 through 6;
   b) constructing a computer model of an HCV NS5B binding pocket defined by the structural coordinates of at least amino acid residues 392, 393, 395, 396, 399, 424, 425, 428, 429, 492, 493, 494, 495, 500 and 503, and optionally one of: amino acid residues 37 and 496, of the HCV NS5B as shown in said Figure;
   c) employing computational means to perform a fitting program operation between computer models of the compound to be evaluated and the NS5B binding pocket to provide an energy-minimized configuration of the compound in the binding pocket; and
   d) evaluating the results of the fitting operation to quantify the association between the compound and the binding pocket, wherein a compound that associates with the binding pocket to yield a low energy, stable complex is a potential NS5B inhibitor.

3. The method as defined in claim 2, wherein the complex has a van der Waals interaction energy value of less than about 8000 kcal/mol.

4. The method as defined in claim 3, wherein the complex has a van der Waals interaction energy value of less than about 6000 kcal/mol.

5. The method as defined in claim 4, wherein the complex has a van der Waals interaction energy value of less than about 4000 kcal/mol.

6. A method of evaluating the potential of a compound to bind to a NS5B polypeptide comprising the steps of:
   a) obtaining the structural coordinates of one of FIGS. 4 through 6;
   b) constructing a computer model of an HCV NS5B binding pocket defined by the structure coordinates of at least amino acid residues 392, 393, 395, 396, 399, 424, 425, 428, 429, 492, 493, 494, 495, 500 and 503 of SEQ ID NO: 1 as shown in said Figure;
   c) supplying the computer model with structure coordinates of the compound to be evaluated;
   d) employing computational means to perform a fitting program operation between structure coordinates of the compound to be evaluated and the structure coordinates of the binding pocket; and
   e) evaluating the results of the fitting operation to quantify the association between the compound and the binding pocket.

7. The method claim 6 wherein the binding pocket is further defined by one or both of amino acid residues 37 and 496 of SEQ ID NO: 1.

8. The method of claim 6 wherein step d) involves determining the binding efficiency by calculating the van der Waals interaction energy between the compound and the binding pocket.

9. A method of selecting a compound to evaluate for potential to inhibit HCV NS5B polymerase activity, which method comprises the steps of:
   a) obtaining the structural coordinates of one of FIGS. 4 through 6;
   b) supplying a computer modeling application with structure coordinates of a HCV NS5B binding pocket defined by at least amino acid residues 392, 393, 395, 396, 399, 424, 425, 428, 429, 492, 493, 494, 495, 500 and 503 SEQ ID NO: 1 as shown in said Figure, and structure coordinates of a compound known to bind to the binding pocket;
   c) assessing fit of the compound of paragraph b) to the binding pocket;
   d) supplying the computer modeling application with coordinates of a second compound to be evaluated for ability to bind with the binding pocket;
   e) assessing fit of the compound of paragraph d) to the binding pocket;
   f) comparing the fit of the compound of paragraph b) and the fit of the compound of paragraph d), wherein the compound with the better fit is the compound to evaluate for potential to inhibit HCV NS5B polymerase activity.

10. The method of claim 9 wherein the binding pocket is further defined by one or both of the amino acid residues 37 and 496 of SEQ ID NO: 1.

11. A method of identifying an inhibitor of polymerase activity of a native HCV NS5B polypeptide of SEQ ID NO: 1, which method comprises the steps of:
   a) obtaining the structural coordinates of one of FIGS. 4 through 6;
   b) selecting a potential inhibitor by applying a 3-dimensional molecular modeling algorithm to structural coordinates of a HCV NS5B binding pocket defined by at least amino acid residues 392, 393, 395, 396, 399, 424, 425, 428, 429, 492, 493, 494, 495, 500 and 503 of SEQ ID NO: 1 as shown in said Figure to determine the spatial coordinates of the binding pocket, and electronically screening stored spatial coordinates of a candidate compound against the spatial coordinates of the binding pocket, wherein a potential inhibitor is a compound that fits the binding pocket;
   c) incubating the polypeptide with the potential inhibitor under conditions suitable for binding;
   d) detecting the ability of the potential inhibitor to inhibit the polymerase activity of HCV NS5B, wherein a compound that inhibits NS5B Polymerase activity is identified as an NS5B inhibitor.

12. The method of claim 11 wherein the binding pocket is further defined by one or both of the amino acid residues 37 and 496 of SEQ ID NO: 1.

13. The method of claim 11 wherein step b) further involves employing computational means to perform a fitting program operation between the spatial coordinates of the candidate compound and the spatial coordinates of the binding pocket to provide an energy-minimized configuration of the compound in the binding pocket, and a potential inhibitor is a candidate compound that associates with the binding pocket to yield a low energy, stable complex having a van der Waals interaction energy value of less than about 8000 kcal/mol.

14. The method of claim 13 wherein the complex has a van der Waals interaction energy value of less than about 6000 kcal/mol.

15. The method of claim 13 wherein the complex has a van der Waals interaction energy value of less than about 4000 kcal/mol.

* * * * *

SEQUENCE LISTING

<160> NUMBER OF SEQ ID NOS: 6

<210> SEQ ID NO 1
<211> LENGTH: 576
<212> TYPE: PRT
<213> ORGANISM: Hepatitis C virus

<400> SEQUENCE: 1

```
Ser Met Ser Tyr Thr Trp Thr Gly Ala Leu Ile Thr Pro Cys Ala Ala
1               5                   10                  15

Glu Glu Ser Lys Leu Pro Ile Asn Pro Leu Ser Asn Ser Leu Leu Arg
            20                  25                  30

His His Asn Met Val Tyr Ala Thr Thr Ser Arg Ser Ala Ser Leu Arg
        35                  40                  45

Gln Lys Lys Val Thr Phe Asp Arg Leu Gln Val Leu Asp Asp His Tyr
    50                  55                  60

Arg Asp Val Leu Lys Glu Met Lys Ala Lys Ala Ser Thr Val Lys Ala
65                  70                  75                  80

Lys Leu Leu Ser Ile Glu Glu Ala Cys Lys Leu Thr Pro Pro His Ser
                85                  90                  95

Ala Lys Ser Lys Phe Gly Tyr Gly Ala Lys Asp Val Arg Asn Leu Ser
            100                 105                 110

Ser Arg Ala Val Asn His Ile Arg Ser Val Trp Glu Asp Leu Leu Glu
        115                 120                 125

Asp Thr Glu Thr Pro Ile Asp Thr Thr Ile Met Ala Lys Ser Glu Val
    130                 135                 140

Phe Cys Val Gln Pro Glu Lys Gly Gly Arg Lys Pro Ala Arg Leu Ile
145                 150                 155                 160

Val Phe Pro Asp Leu Gly Val Arg Val Cys Glu Lys Met Ala Leu Tyr
                165                 170                 175

Asp Val Val Ser Thr Leu Pro Gln Ala Val Met Gly Ser Ser Tyr Gly
            180                 185                 190

Phe Gln Tyr Ser Pro Lys Gln Arg Val Glu Phe Leu Val Asn Thr Trp
        195                 200                 205
```

```
Lys Ser Lys Lys Cys Pro Met Gly Phe Ser Tyr Asp Thr Arg Cys Phe
    210                 215                 220

Asp Ser Thr Val Thr Glu Ser Asp Ile Arg Val Glu Glu Ser Ile Tyr
225                 230                 235                 240

Gln Cys Cys Asp Leu Ala Pro Glu Ala Arg Gln Ala Ile Arg Ser Leu
                245                 250                 255

Thr Glu Arg Leu Tyr Ile Gly Gly Pro Leu Thr Asn Ser Lys Gly Gln
            260                 265                 270

Asn Cys Gly Tyr Arg Arg Cys Arg Ala Ser Gly Val Leu Thr Thr Ser
        275                 280                 285

Cys Gly Asn Thr Leu Thr Cys Tyr Leu Lys Ala Thr Ala Ala Cys Arg
    290                 295                 300

Ala Ala Lys Leu Gln Asp Cys Thr Met Leu Val Asn Gly Asp Asp Leu
305                 310                 315                 320

Val Val Ile Cys Glu Ser Ala Gly Thr Gln Glu Asp Ala Ala Ala Leu
                325                 330                 335

Arg Ala Phe Thr Glu Ala Met Thr Arg Tyr Ser Ala Pro Pro Gly Asp
            340                 345                 350

Pro Pro Gln Pro Glu Tyr Asp Leu Glu Leu Ile Thr Ser Cys Ser Ser
        355                 360                 365

Asn Val Ser Val Ala His Asp Ala Ser Gly Lys Arg Val Tyr Tyr Leu
    370                 375                 380

Thr Arg Asp Pro Thr Thr Pro Leu Ala Arg Ala Ala Trp Glu Thr Ala
385                 390                 395                 400

Arg His Thr Pro Ile Asn Ser Trp Leu Gly Asn Ile Ile Met Tyr Ala
                405                 410                 415

Pro Thr Leu Trp Ala Arg Met Ile Leu Met Thr His Phe Phe Ser Ile
            420                 425                 430

Leu Leu Ala Gln Glu Gln Leu Glu Lys Ala Leu Asp Cys Gln Ile Tyr
        435                 440                 445

Gly Ala Cys Tyr Ser Ile Glu Pro Leu Asp Leu Pro Gln Ile Ile Glu
    450                 455                 460

Arg Leu His Gly Leu Ser Ala Phe Thr Leu His Ser Tyr Ser Pro Gly
465                 470                 475                 480

Glu Ile Asn Arg Val Ala Ser Cys Leu Arg Lys Leu Gly Val Pro Pro
                485                 490                 495

Leu Arg Thr Trp Arg His Arg Ala Arg Ser Val Arg Ala Lys Leu Leu
            500                 505                 510

Ser Gln Gly Gly Arg Ala Ala Thr Cys Gly Arg Tyr Leu Phe Asn Trp
        515                 520                 525

Ala Val Arg Thr Lys Leu Lys Leu Thr Pro Ile Pro Ala Ala Ser Gln
    530                 535                 540

Leu Asp Leu Ser Gly Trp Phe Val Ala Gly Tyr Ser Gly Gly Asp Ile
545                 550                 555                 560

Tyr His Ser Leu Ser Arg Ala Arg Pro Arg His His His His His His
                565                 570                 575

<210> SEQ ID NO 2
<211> LENGTH: 4
<212> TYPE: PRT
<213> ORGANISM: Hepatitis C virus

<400> SEQUENCE: 2

Ser Met Ser Tyr
```

```
<210> SEQ ID NO 3
<211> LENGTH: 4
<212> TYPE: PRT
<213> ORGANISM: Hepatitis C virus

<400> SEQUENCE: 3

Leu Gly Val Pro
1

<210> SEQ ID NO 4
<211> LENGTH: 8
<212> TYPE: PRT
<213> ORGANISM: Hepatitis C virus

<400> SEQUENCE: 4

Leu Ala Arg Ala Ala Trp Glu Thr
1               5

<210> SEQ ID NO 5
<211> LENGTH: 6
<212> TYPE: PRT
<213> ORGANISM: Hepatitis C virus

<400> SEQUENCE: 5

Ile Leu Met Thr His Phe
1               5

<210> SEQ ID NO 6
<211> LENGTH: 12
<212> TYPE: PRT
<213> ORGANISM: Hepatitis C virus

<400> SEQUENCE: 6

Leu Gly Val Pro Pro Leu Arg Thr Trp Arg His Arg
1               5                   10
```